(12) United States Patent
Alessi et al.

(10) Patent No.: US 7,792,665 B2
(45) Date of Patent: Sep. 7, 2010

(54) METHOD FOR DESIGNING A COMPOUND BASED ON THE THREE DIMENSIONAL STRUCTURE OF PHOSPHOINOSITIDE DEPENDENT PROTEIN KINASE 1 (PDK1)

(75) Inventors: Dario Alessi, Dundee (GB); Ricardo Biondi, Homburg (GB); David Komander, London (GB); Daan Van Aalten, Dundee (GB)

(73) Assignee: Medical Research Council, London (GB)

( * ) Notice: Subject to any disclaimer, the term of this patent is extended or adjusted under 35 U.S.C. 154(b) by 1490 days.

(21) Appl. No.: 10/517,225

(22) PCT Filed: Jun. 9, 2003

(86) PCT No.: PCT/GB03/02509

§ 371 (c)(1),
(2), (4) Date: Jun. 9, 2005

(87) PCT Pub. No.: WO03/104481

PCT Pub. Date: Dec. 18, 2003

(65) Prior Publication Data

US 2005/0232804 A1      Oct. 20, 2005

(30) Foreign Application Priority Data

Jun. 8, 2002    (GB) ................................. 0213186.0

(51) Int. Cl.
G01N 31/00    (2006.01)
G06F 19/00    (2006.01)
G06G 7/48    (2006.01)

(52) U.S. Cl. .......................................... 703/11; 702/27
(58) Field of Classification Search ........................ None
See application file for complete search history.

(56) References Cited

U.S. PATENT DOCUMENTS

| 5,854,992 A | 12/1998 | Shakhnovich et al. |
| 6,387,641 B1 | 5/2002 | Bellon et al. |
| 2004/0137518 A1* | 7/2004 | Lambert et al. .............. 435/7.1 |

FOREIGN PATENT DOCUMENTS

| EP | 1 096 014 | 5/2001 |
| WO | WO 98/41638 | 9/1998 |
| WO | WO 00/35946 | 6/2000 |
| WO | WO 00/36135 | 6/2000 |
| WO | WO 00/56864 | 9/2000 |
| WO | WO 00/70030 | 11/2000 |
| WO | WO 01/35316 | 5/2001 |
| WO | WO 01/44497 | 6/2001 |
| WO | WO 01/71347 | 9/2001 |
| WO | WO 02/22793 | 3/2002 |

OTHER PUBLICATIONS

Godden et al. (Evaluation of docking strategies for virtual screening of compound databases: cAMP-dependent serine/threonine kinase as an example, Journal of Molecular Graphics and Modelling, vol. 16, Issue 3, Jun. 1998, pp. 139-143.*
Giege et al. Crystallogenesis of Biological Macromolecules: Facts and Perspectives. Acta Cryst., 1994, D50: 339-350.*
Branden et al., "Introduction to Protein Structure Second Edition", Garland Publishing Inc., New York, 1999.*
Drenth, "Principles of X-ray Crystallography," Springer, New York, 1995.*
Kierzek et al., Biophys Chem 91:1-20, 2001.*
Wiencek (Ann Rev Biomed Eng, 1999, 1:505-534).*
Biondi et al. (2002) EMBO J. 21: 4219-4228.
Alessi & Cohen (1998) Curr. Opin. Genetics. Develop. 8: 55-62.
Alessi et al. (1997) Curr. Biol. 7: 261-269.
Alessi et al. (1998) Curr. Biol. 8: 69-81.
Alessi et al. (1997) Curr. Biol. 7: 776-789.
Alessi (2001) Biochem. Soc. Trans. 29: 1-14.
Bain et al. (2003) Biochem. J. 371: 199-204.
Balendran et al. (1999) Curr. Biol. 9: 393-404.
Balendran et al. (1999) J. Biol. Chem. 274: 37400-37406.
Balendran et al. (2000) J. Biol. Chem. 275: 20806-20813.
Battistutta et al. (2000) J. Biol. Chem. 275: 29618-29622.
Bellon et al. (1999) Struct. Fold. Des. 7: 1057-1065.
Biondi and Nebreda (2003) Biochem. J. 372: 1-13.
Biondi et al. (2000) EMBO J. 19: 979-988.
Biondi et al. (2001) EMBO J. 20: 4380-4390.
Brazil and Hemmings (2001) Trends Biochem. Sci. 26: 657-664.
Casamayor et al. (1999) Curr. Biol. 9: 186-197.
Cheng et al. (1998) Proc. Natl. Acad. Sci. USA 95: 9849-9854.
Chou et al. (1998) Curr. Biol. 8: 1069-1077.
Couldwell et al.(1994) FEBS Lett. 345: 43-46.
Cross et al. (1995) Nature 378: 785-789.
Currie et al. (1999) Biochem. J. 337: 575-583.
Davies et al. (2000) Biochem. J. 351: 95-105.
De Groot et al. (1998) Proteins 31: 116-127.
Dutil et al. (1998) Curr. Biol. 8: 1366-1375.
Etchebehere et al. (1997) Eur. J. Biochem. 248: 820-826.
Frodin and Gammeltoft (1999) Mol. Cell. Endocrinol. 151: 65-77.

(Continued)

*Primary Examiner*—Suzanne M. Noakes
*Assistant Examiner*—Jae W Lee
(74) *Attorney, Agent, or Firm*—Knobbe Martens Olson & Bear LLP

(57) ABSTRACT

A method for selecting a compound for modulating the activity of phosphoinositide dependent protein kinase 1 (PDK1) is provided. The method may comprise modelling a three dimensional structure of a plurality of molecules in a computer, comparing with the three dimensional structure of the compounds with that of a reference structure such as at least part of a protein kinase catalytic domain of PDK1, and selecting the compound based on a predicted interacting ability of the molecules to the protein kinase catalytic domain. Also a method for selecting a compound for modulating the activity of hydrophobic pocket containing protein kinase is provided. In this method, the reference structures may be one or more of a phosphate binding pocket of PDK1, a hydrophobic pocket of PDK1, and αC helix or region interacting therewith of PDK1.

14 Claims, 21 Drawing Sheets

OTHER PUBLICATIONS

Frodin et al. (2000) EMBO J. 19: 2924-2934.
Gescher (2000) Crit. Rev. Oncol. Hematol. 34: 127-133.
Graves et al. (2000) J. Biol. Chem. 275: 5600-5605.
Husen and Kuriyan (2002) Cell 109: 275-282.
Johnson and Pinto (2002) Aust. J. Chem. 55: 13-25.
Johnson et al. (1996) Cell 85: 149-158.
Johnson et al. (2001) Chem. Rev. 101: 2243-2270.
Knighton et al. (1991) Science 253: 407-414.
Kobayashi et al. (1999) Biochem. J. 339: 319-328.
Lamers, et al. (1999) J. Mol. Biol. 285: 713-725.
Lang and Cohen (2001) Sci. STKE RE17.
Lawrie et al. (1997) Nat. Struct. Biol. 4: 796-801.
LeGood et al. (1998) Science 281: 2042-2045.
Leslie and Downes (2002) Cell. Signal. 14: 285-295.
Narayana et al. (1997) Structure 5: 921-935.
Narayana et al. (1999) Biochemistry 38: 2367-2376.
Navaza (1994) Acta Cryst. A50: 157-163.
Owen et al. (1995) Structure, 3, 467-482.
Perrakis et al. (1999) Nature Struct. Biol. 6: 458-463.
Prade et al. (1997) Structure 5: 1627-1637.
Pullen et al. (1998) Science 279: 707-710.
Ruegg and Burgess (1989) Trends Pharmacol. Sci. 10: 218-220.
Sato et al. (2002) Oncogene 21: 1727-1738.
Scheid and Woodgett (2001) Nat. Rev. Mol. Cell Biol. 2:760-768.
Senderowicz (2002) Oncologist 7(3): 9-12.
Smith et al. (1997) Trends Biochem. Sci. 22: 444-446.
Stephens et al. (1998) Science 279: 710-714.
Stokoe et al. (1997) Science 277: 567-570.
Takahashi et al. (1987) J. Antibiot. 40: 1782-1784.
Takahashi et al. (1989) J. Antibiot. 42: 571-576.
Taylor and Radzio-Andzelm (1994) Structure 2: 345-355.
Taylor et al. (1992) Annu. Rev. Cell Biol. 8: 429-462.
ter Haar et al. (2001) Nat. Struct. Biol. 8: 593-596.
Tian et al. (2002) EMBO J. 21: 1327-1338.
Toker and Newton (2000) Cell 103: 185-188.
Tsai et al. (1999) J. Mol. Biol. 290: 253-266.
van Aalten et al. (1997) Biophys. J. 73: 2891-2896.
van Aalten et al. (2000) Biochemistry 39: 10082-10089.
Vanhaesebroeck and Alessi (2000) Biochem. J. 346: 561-576.
Volarevic and Thomas (2001) Prog. Nucl. Acid Res. Mol. Biol. 65: 101-127.
Wang et al. (1997) Proc. Natl. Acad. Sci. USA 94: 2327-2332.
Webster et al. (1993) Mol. Cell. Biol. 13: 2031-2040.
Yang et al. (2002) Nat. Struct. Biol. 9: 940-944.
Zhai et al. (1995) J. Biol. Chem. 270: 12717-12724.
Zhang et al. (1994) Nature 367: 704-711.
Zhao et al. (2002) J. Biol. Chem. 277: 46609-46615.
Zheng et al. (1993) Protein Sci. 2: 1559-1573.
Zhu et al. (1999) Struct. Fold. Des. 7: 651-661.

* cited by examiner

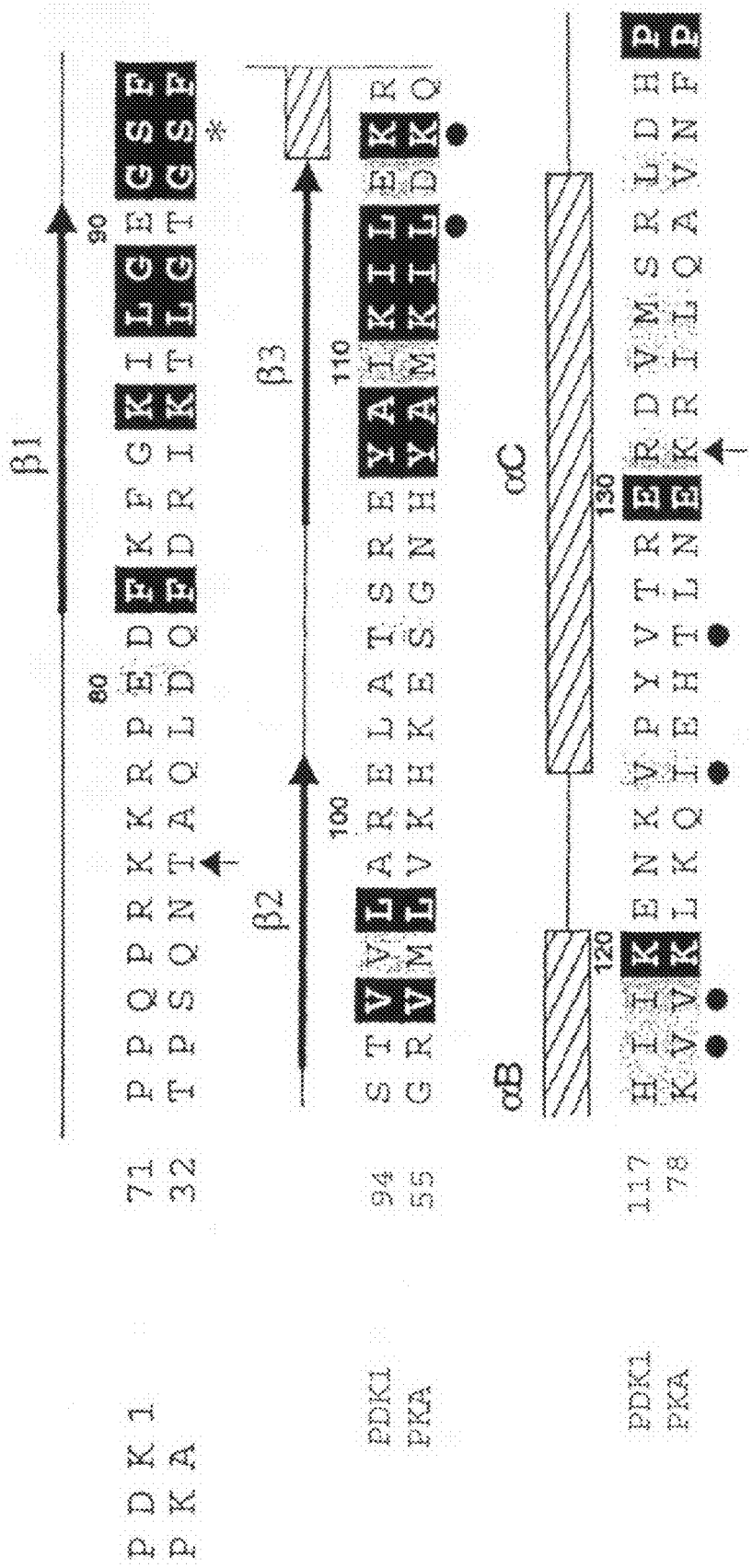
Figure 3: page 1

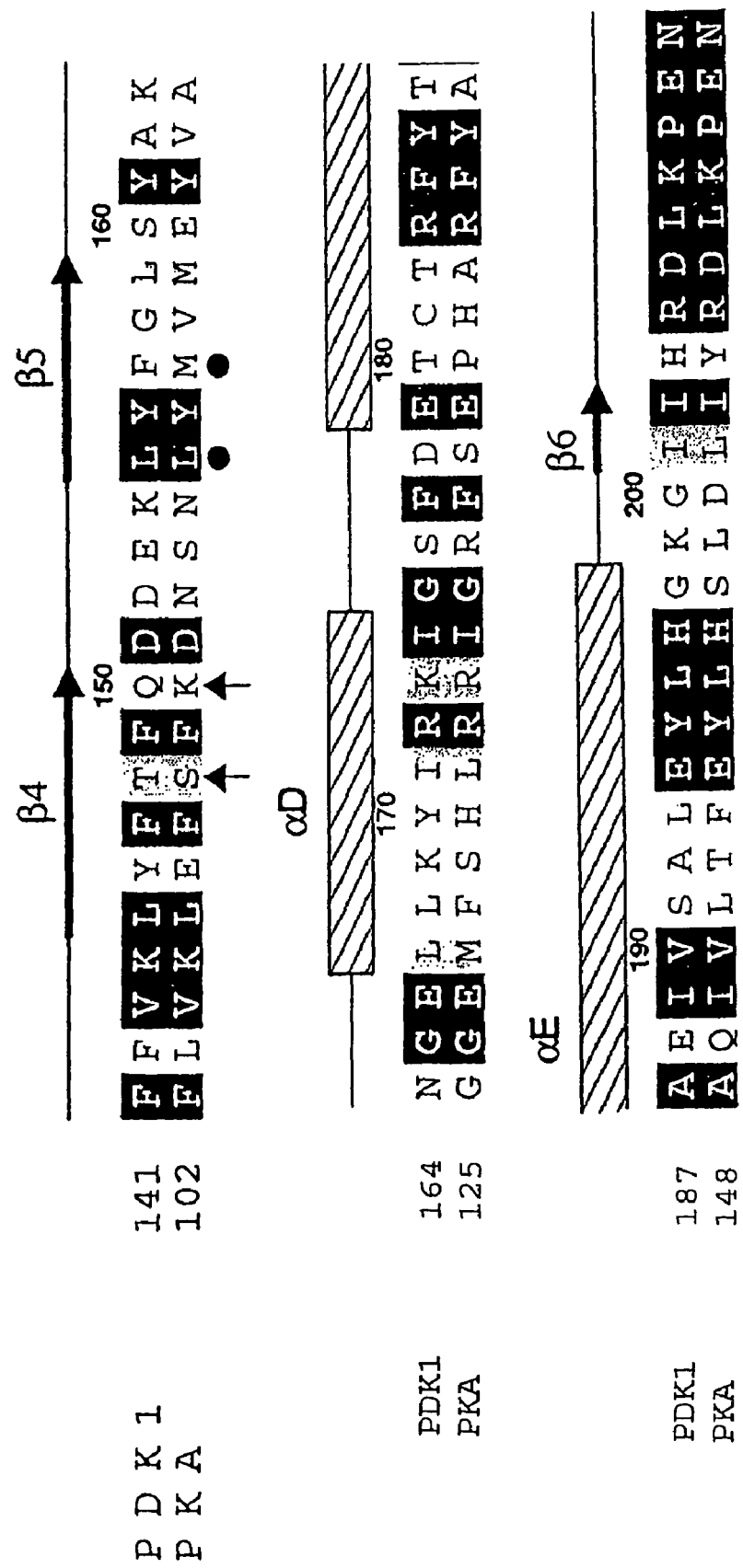
Figure 3 page 2

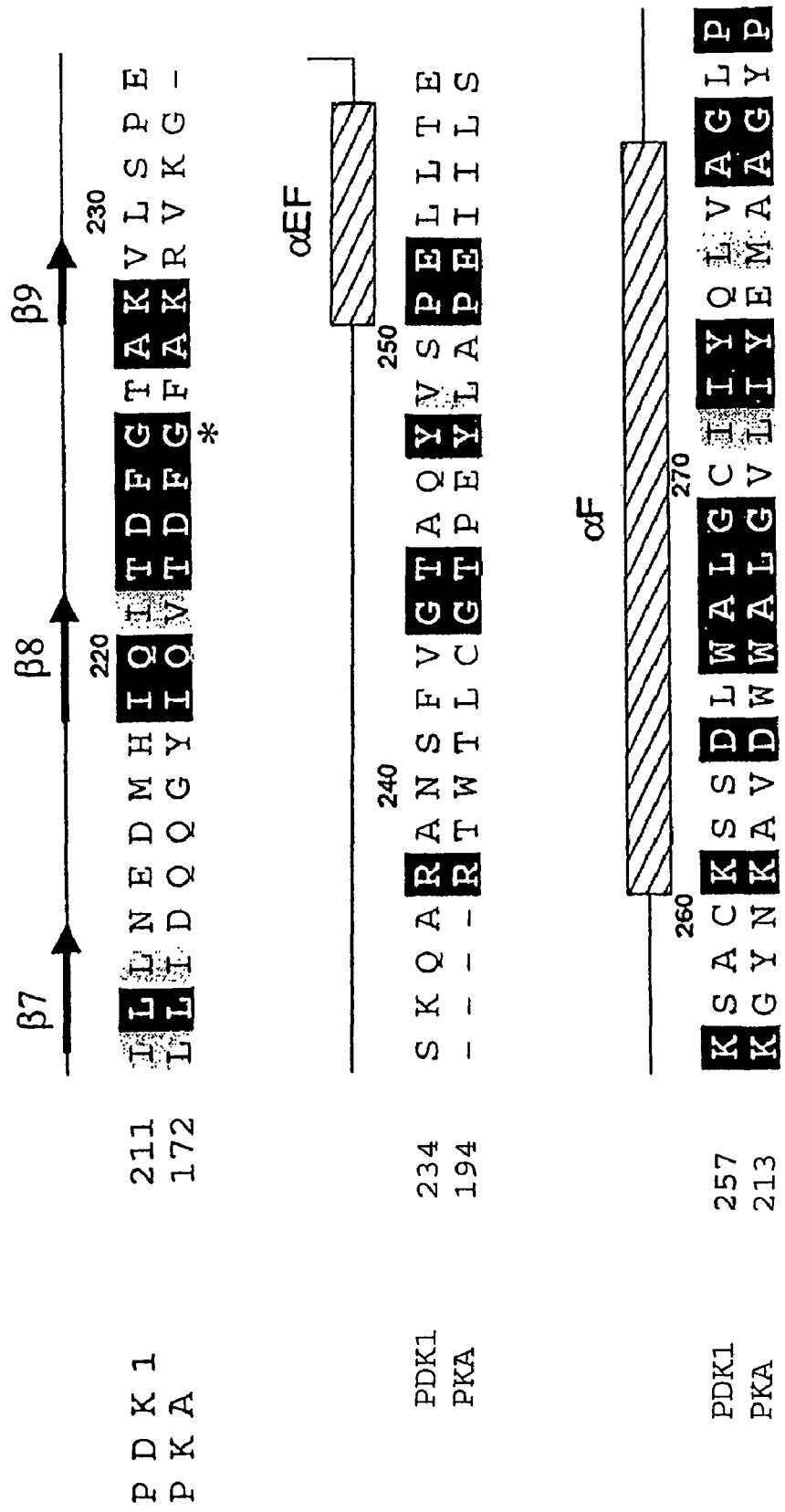
Figure 3: page 3

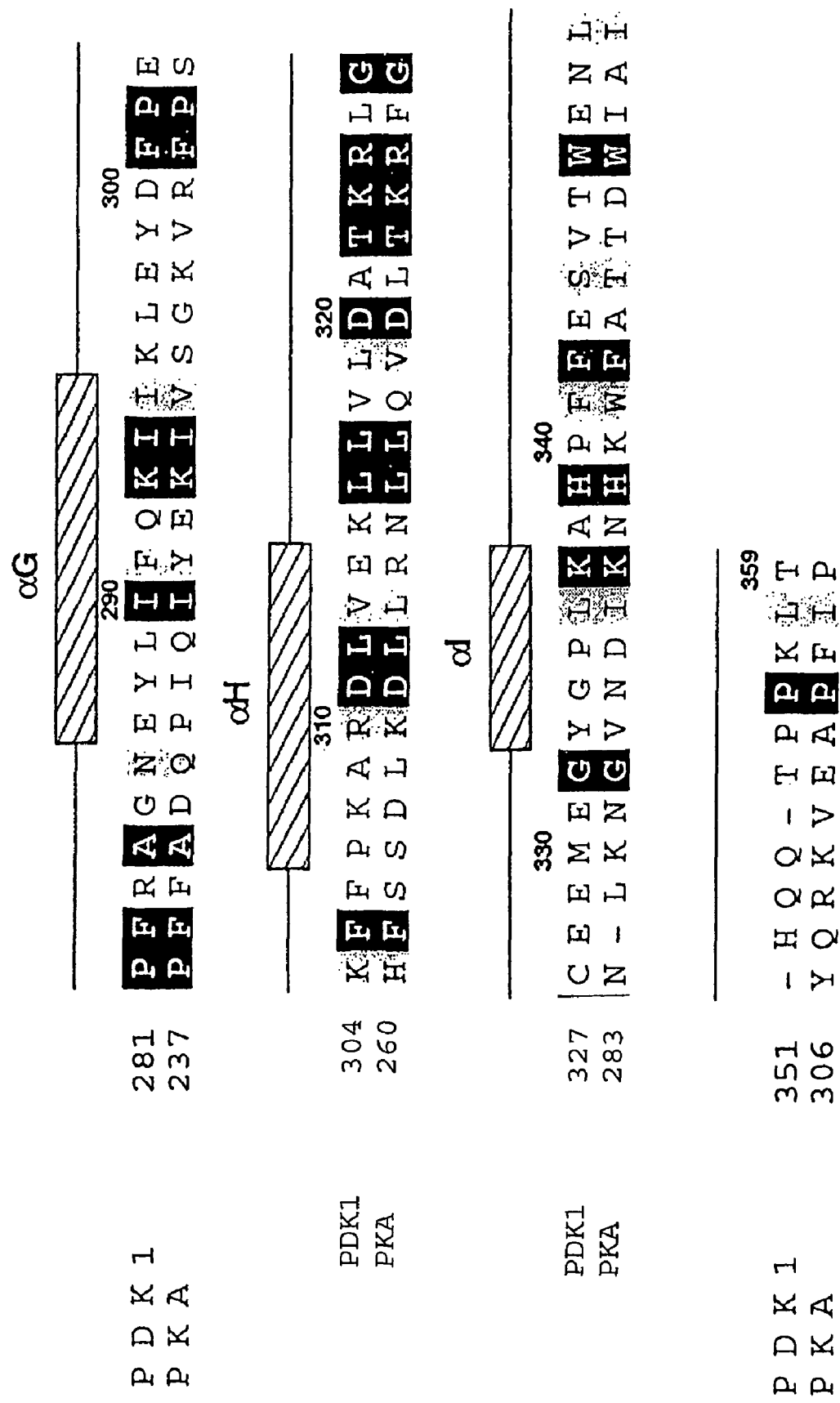
Figure 3:page 4

Figure 4: page 1
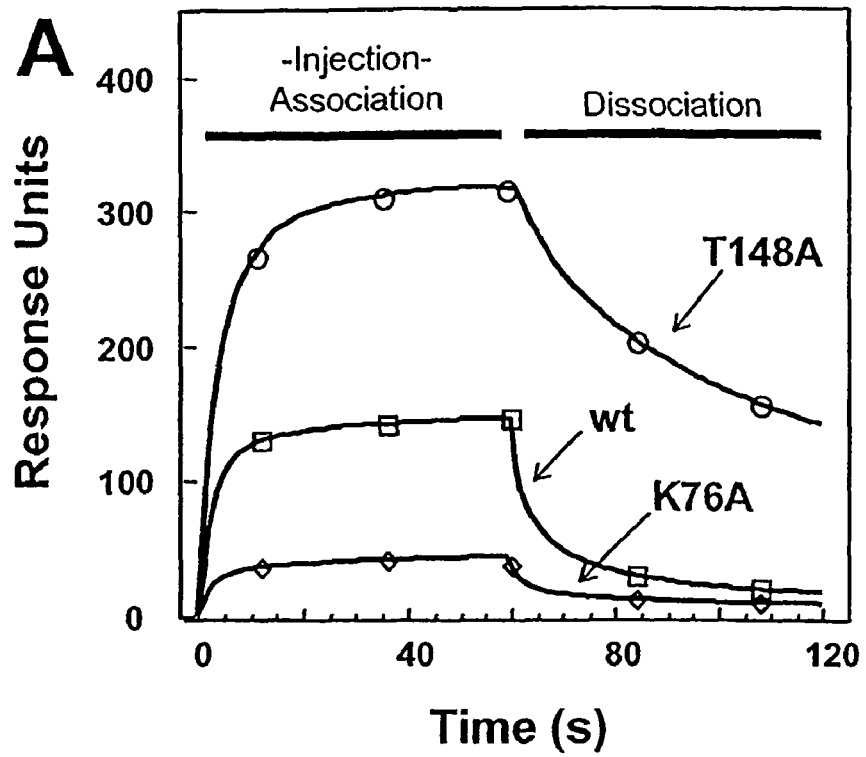
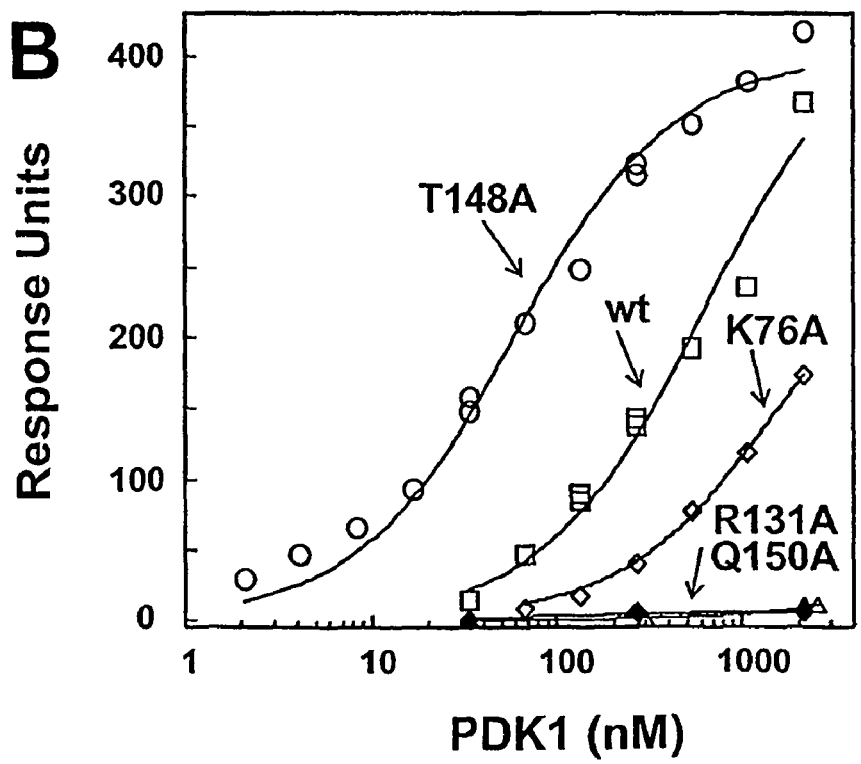

Figure 4: page 2
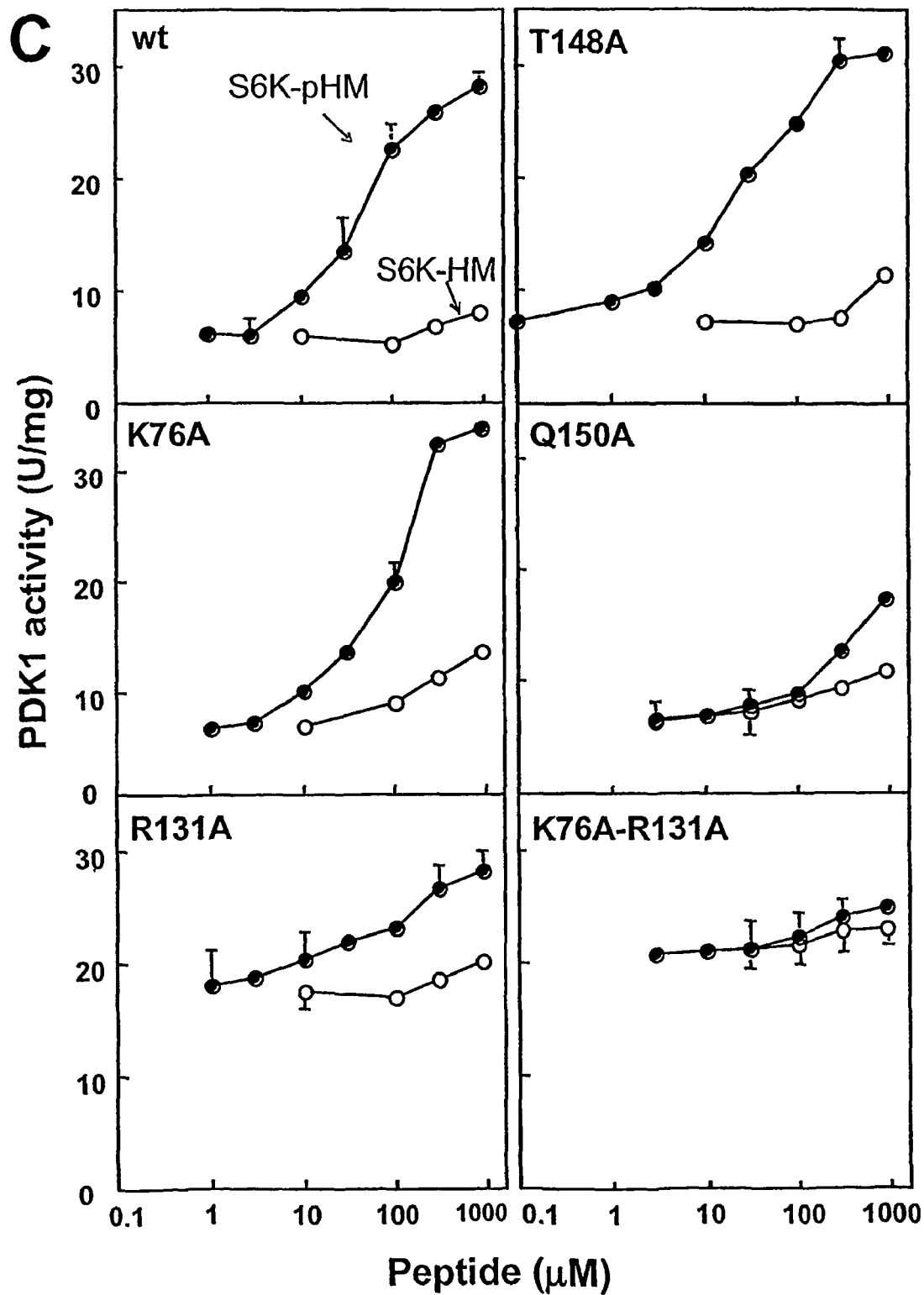

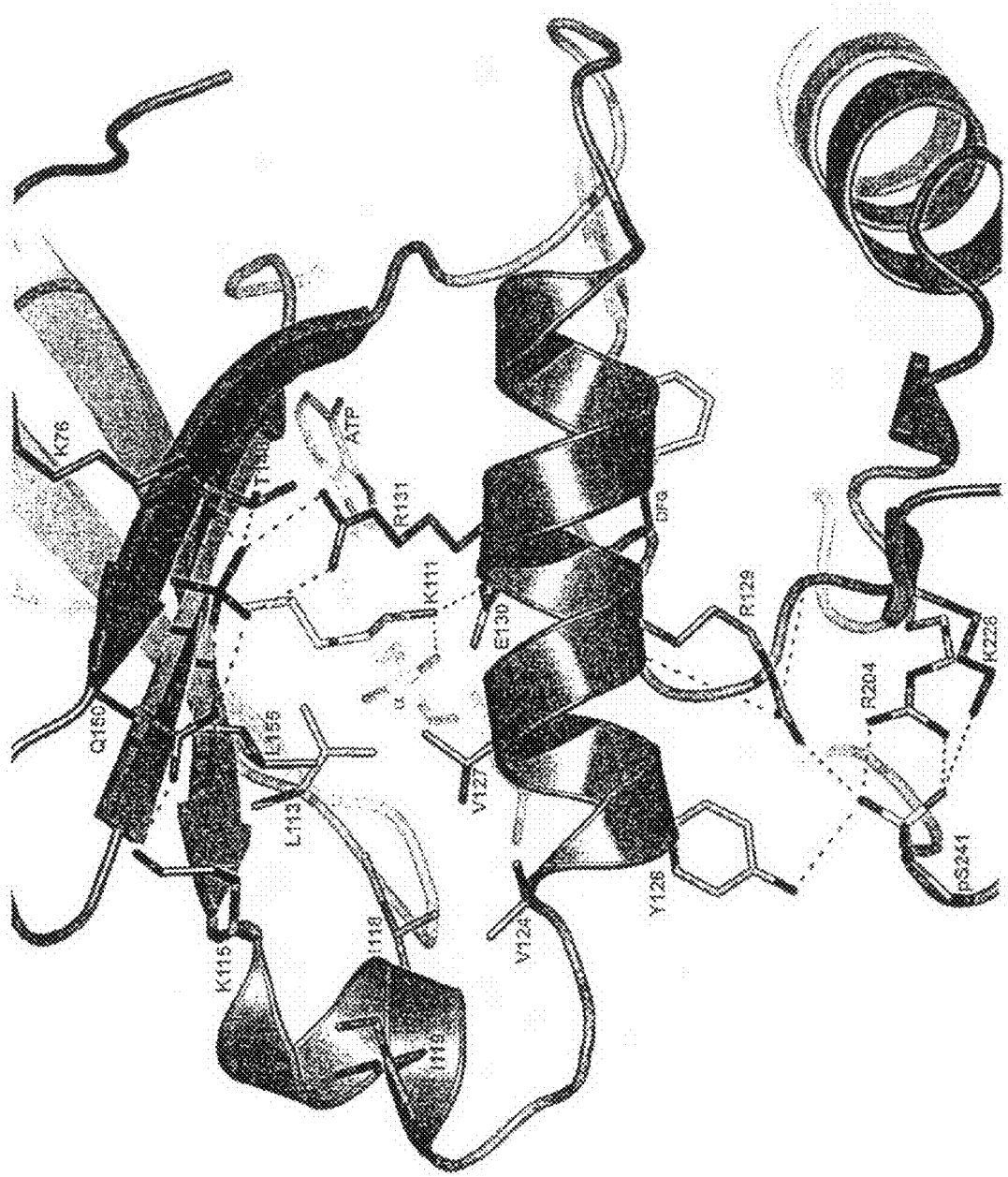
Figure 5:page 1

Figure 5: page 2

Figure 6: page 1
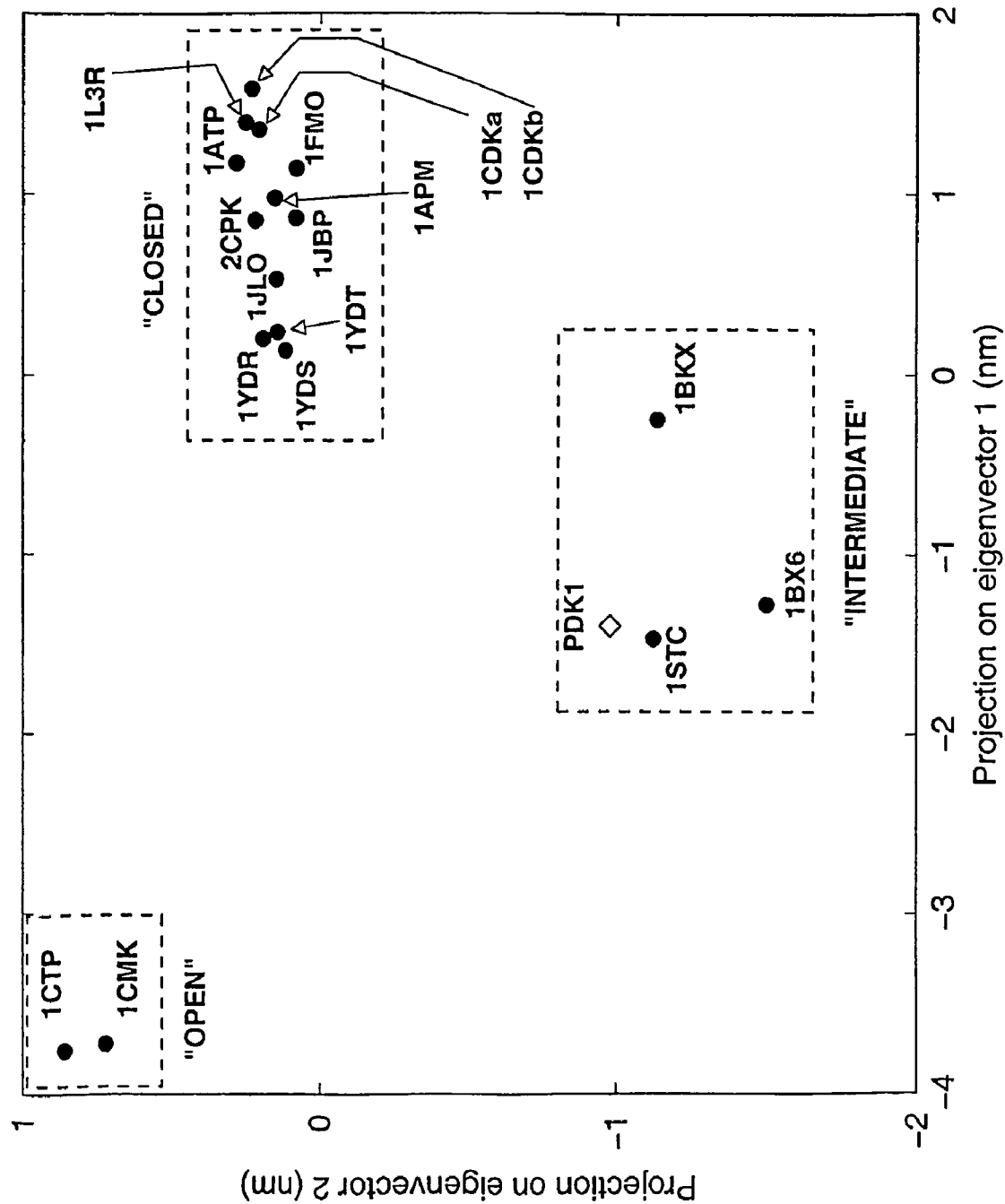

Figure 6: page 2

Figure 7: page 1

```
                         Lys 115    Ile 119
                            ↓         ↓
p70S6Kalpha  104  KVFQVRKVTGANTGKIFAMKVLKKAMIVRNAKDTAHTKAERNILEEVK--H-P------FI
p70S6Kbeta    93  KVFQVRKVQGTNLGKIYAMKVLRKAKIVRNAKDTAHTRAERNILESVK--H-P------FI
p90RSK1       81  KVFLVKKISGSDARQLYAMKVLKKATLKVRDRVR--TKMERDILVEVN--H-P------FI
p90RSK2       81  KVFLVKKISGSDARQLYAMKVLKKATLKVRDRVR--TKMERDILVEVN--H-P------FI
p90RSK3       72  KVFLVRKVKGSDAGQLYAMKVLKKATLKVRDRVR---SKMERDILAEVN--H-P------FI
MSK1          62  KVFLVRKISGHDTGKLYAMKVLKKATIVQKAKTTEHTRTERQVLEHIR---QSP------FL
MSK2          30  KVFLVRKAGGHDAGKLYAMKVLRKAALVQRAKTQEHTRTERSVLELVR---QAP------FL
PKBalpha     163  KVILVKEK----ATGRYYAMKILKKEVIVAKDEVA-HTLTENRVLQNS----RHP------FL
PKBbeta      165  KVILVREK----ATGRYYAMKILRKEVIIAKDEVA-HTVTESRVLQNT----RHP------FL
PKBgamma     161  KVILVREK----ASGKYYAMKILKKEVIAKDEVA-HTLTESRVLKNT----RHP------FL
PRK1         628  KVLLSEFR----PSGELFAIKALKKGDIVARDEVE-SLMCEKRILAAVTSAGHP------FL
PRK2         670  KVLLAEYK----NTNEMFAIKALKKGDIVARDEVD-SLMCEKRIFETVNSVRHP------FL
SGK1         111  KVLLARHK----AEEVFYAVKVLQKKAILKKKEEK-HIMSERNVLLKN---VKHP------FL
SGK2         108  KVLLAKRK----LDGKFYAVKVLQKKIVLNRKEQK-HIMAERNVLLKN---VKHP------FL
SGK3         108  KVLLAKRK----SDGAFYAVKVLQKKSILKKEQS-HIMAERSVLLKN---VRHP------FL
PKCbeta      355  KVMLSERK----GTDELYAVKILKDVVIQDDDVE-CTMVEKRVLALP--GKPP------FL
PKCbetaII    355  KVMLSERK----GTDELYAVKILKDVVIQDDDVE-CTMVEKRVLALP--GKPP------FL
PKCalpha     352  KVMLADRK----GTEELYAIKILKDVVIQDDDVE-CTMVEKRVLALL--DKPP------FL
PKCgamma     364  KVMLAERR----GSDELYAIKILKDVIVQDDDVD-CTLVEKRVLALG--GRGPGGRPHFL
PKCzeta      257  KVLLVRLK----KNDQIYAMKVVKKELVHDDEDID-WVQTEKHVFEQA--SSNP------FL
PKCiota      258  KVLLVRLK----KTDRIYAMKVVKKELVNDDEDID-WVQTEKHVFEQA--SNHP------FL
PKCdelta     362  KVLLGELK----GRGEYSAIKALKKDVVLIDDDVE-CTMVEKRVLTLAA--ENP------FL
PKAgamma      57  RVMLVRHQ----ETGGHYAMKILNKQKVVKMKQVE-HILNEKRILQAI----DFP------PL
PDK1          95  TVVLAREL----ATSREYAIKILEKRHIIKENKVP-YVTRERDVMSRL----DHP------FF
```

Figure 7: page 2

```
                      Gln 150        Leu 155
                         ↓              ↓
p70S6Kalpha   156  VDLIYAFQTGGKLYLILEYLSGGELFMQLEREGIFMEDTACFYLAEISMALGHLHQ-KGI
p70S6Kbeta    145  VELAYAFQTGGKLYLILECLSGGELFTHLEREGIFLEDTACFYLAEITLALGHLHS-QGI
p90RSK1       131  VKLHYAFQTEGKLYLILDFLRGGDLFTRLSKEVMFTEEDVKFYLAELALALDHLHS-LGI
p90RSK2       131  VKLHYAFQTEGKLYLILDFLRGGDLFTRLSKEVMFTEEDVKFYLAELALALDHLHS-LGI
p90RSK3       122  VKLHYAFQTEGKLYLILDFLRGGDLFTRLSKEVMFTEEDVKFYLAELALALDHLHS-LGI
MSK1          115  VTLHYAFQTETKLHLILDYINGGELFTHLSQRERFTEHEVQIYVGEIVLALEHLHK-LGI
MSK2           83  VTLHYAFQTDAKLHLILDVVSGGEMFTHLYQRQYFKEAEVRVYGGEIVLALEHLHK-LGI
PKBalpha      211  TALKYSFQTHDRLCFVMEYANGGELFFHLSRERVFSEDRARFYGAEIVSALDYLHSEKNV
PKBbeta       213  TALKYAFQTHDRLCFVMEYANGGELFFHLSRERVFTEERARFYGAEIVSALEYLHS-RDV
PKBgamma      209  TSLKYSFQTKDRLCFVMEYVNGGELFFHLSRERVFSEDRTRFYGAEIVSALDYLHS-GKI
PRK1          679  VNLFGCFQTPEHVCFVMEYSAGGDLMLHIHSD-VFSEPRAIFYSACVVLGLQFLHE-HKI
PRK2          721  VNLFACFQTKEHVCFVMEYAAGGDLMHIHTD-VFSEPRAVFYAACVVLGLQYLHE-HKI
SGK1          160  VGLHFSFQTADKLYFVLDYINGGELFYHLQRERCFLEPRARFYAAEIASALGYLHS-LNI
SGK3          157  VGLHYSFQTTEKLYFVLDFVNGGELFFHLQRERSFPEHRARFYAAEIASALGYLHS-IKI
SGK2          157  VGLRYSFQTPEKLYFVLDYVNGGELFFHLQRERRFLEPRARFYAAEVASAIGYLHS-LNI
PKCbeta       404  TQLHSCFQTMDRLYFVMEYVNGGDLMYHIQQVGRFKEPHAVFYAAEIAIGLFFLQS-KGI
PKCbetaII     404  TQLHSCFQTMDRLYFVMEYVNGGDLMYHIQQVGRFKEPHAVFYAAEIAIGLFFLQS-KGI
PKCalpha      401  TQLHSCFQTVDRLYFVMEYVNGGDLMYHIQQVGKFKEPQAVFYAAEISIGLFFLHK-RGI
PKCgamma      418  TQLHSTFQTPDRLYFVMEYVTGGDLMYHIQQLGKFKEPHAAFYAAEIAIGLFFLHN-QGI
PKCzeta       306  VGLHSCFQTTSRLFLVIEYVNGGDLMFHMQRQRKLPEEHARFYAAEICIALNFLHE-RGI
PKCiota       307  VGLHSCFQTESRLFLFFVMEFLNGGDLMYHIQDKGRFELYRATFYAAEIMCGLQFLHS-KGI
PKCdelta      411  THLICTFQTKDHLFFVMEYVNGGDLMYHIQDKGRFELYRATFYAAEIMCGLQFLHS-KGI
PKAgamma      105  VKLQFSFKDNSYLYLVMEYVPGGEMFSRLQRVGRFSEPHACFYAAQVVLAVQYLHS-LDL
PDK1          143  VKLYFTFQDDEKLYFGLSYAKNGELLKYIRKIGSFDETCTRFYTAEIVSALEYLHG-KGI
```

Figure 7: page 3

```
p70S6Kalpha  215  IYRDLKPENIMLNHQGHVKLTDFGLCKESIHDGT----VTHTFCGTIEYMAPEILM--RSG
p70S6Kbeta   204  IYRDLKPENIMLSSQGHIKLTDFGLCKESIHEGA----VTHTFCGTIEYMAPEILV--RSG
p90RSK1      190  IYRDLKPENILLDEEGHIKLTDFGLSKESIDHEK----KAYSFCGTVEYMAPEVVN--RRG
p90RSK2      190  IYRDLKPENILLDEEGHIKLTDFGLSKESIDHEK----KAYSFCGTVEYMAPEVVN--RRG
p90RSK3      181  IYRDLKPENILLDEEGHIKLTDFGLSKEAIDHDK----RAYSFCGTIEYMAPEVVN--RRG
MSK1         174  IYRDIKLENILLDSNGHVVLTDFGLSKEFVADET----ERAYSFCGTIEYMAPDIVRGGDSG
MSK2         142  IYRDLKLENVLLDSEGHIVLTDFGLSKEFLTEEK----ERTFSFCGTIEYMAPEIIR--SKTG
PKBalpha     271  VYRDLKLENLMLDKDGHIKITDFGLCKEGIKDGA----TMKTFCGTPEYLAPEVLE--DND
PKBbeta      272  VYRDIKLENLMLDKDGHIKITDFGLCKEGISDGA----TMKTFCGTPEYLAPEVLE--DND
PKBgamma     268  VYRDLKLENLMLDKDGHIKITDFGLCKEGITDAA----TMKTFCGTPEYLAPEVLE--DND
PRK1         737  VYRDLKPENLLLDHTGYVKIADFGLCKEGMYGD----RTSTFCGTPEFLAPEVLT--DTS
PRK2         779  VYRDLKDNLLLDTEGFVKIADFGLCKEGMYGD----RTSTFCGTPEFLAPEVLT--ETS
SGK1         219  VYRDLKPENILLDSQGHIVLTDFGLCKENIEHNS----TTSTFCGTPEYLAPEVLH--KQP
SGK3         216  VYRDLKPENILLDSVGHVVLTDFGLCKEGIAISD----TTTFFCGTPEYLAPEVIR--KQP
SGK2         216  IYRDLKPENILLDCQGHVVLTDFGLCKEGVEPED----TTSTFCGTPEYLAPEVLR--KEP
PKCbeta      463  IYRDLKLDNVMLDSEGHIKIADFGMCKENIWDGV----TTKTFCGTPDYIAPEIIA--YQP
PKCbetaII    463  IYRDLKLDNVMLDSEGHIKIADFGMCKENIWDGV----TTKTFCGTPDYIAPEIIA--YQP
PKCalpha     460  IYRDLKLDNVMLDSEGHIKIADFGMCKEHMMDGV----TTRTFCGTPDYIAPEIIA--YQP
PKCgamma     477  IYRDLKLDNVMLDAEGHIKITDFGMCKENVFPGT----TTRTFCGTPDYIAPEIIA--YQP
PKCzeta      365  IYRDLKLDNVLLDADGHIKLTDYGMCKEGLGPGD----TTSTFCGTPNYIAPEILR--GEE
PKCiota      366  IYRDLKLDNVLLDSEGHIKLTDYGMCKEGLRPGD----TTSTFCGTPNYIAPEILR--GED
PKCdelta     470  IYRDLKLDNVLLDRDGHIKIADFGMCKENIFGES----RASTFCGTPDYIAPEILQ--GLK
PKAgamma     164  IHRDLKPENLLIDQQGYLQVTDFGFAKRVKG------RTWTLCGTPEYLAPEIIL--SKG
PDK1         202  IHRDLKPENILLNEDMHIQITDFGTAKVLSPESKQA-RANSFVGTAQYVSPELLT--EKS
```

Figure 7: page 4

```
p70S6Kalpha  270  HNRAVDWWSLGALMYDMLTGAPPFTGE------NRK---KTIDKILKCKLNLPPYLTQEA
p70S6Kbeta   259  HNRAVDWWSLGALMYDMLTGSPPFTAE------NRK---KTMDKIIRGKLALPPYLTPDA
p90RSK1      245  HTQSADWWSFGVLMFEMLTGTLPFQGK------DRK---ETMTMILKAKLGMPQFLSPEA
p90RSK2      245  HTQSADWWSFGVLMFEMLTGTLPFQGK------DRK---ETMTMILKAKLGMPQFLSPEA
p90RSK3      236  HTQSADWWSFGVLMFEMLTGSLPFQGK------DRK---ETMALILKAKLGMPQFLSGEA
MSK1         232  HDKAVDWWSLGVLMYELLTGASPFTVDG------EKNSQAEISRRILKSEPPYPQEMSALA
MSK2         199  HGKAVDWWSLGILLFELLTGASPFTLEG------ERNTQAEVSRRILKCSPPFPPRIGPVA
PKBalpha     326  YGRAVDWWGLGVVMYEMMCGRLPFYNQD------HEKLFELILMEEIRFPRTLGPEA
PKBbeta      327  YGRAVDWWGLGVVMYEMMCGRLPFYNQD------HERLFELILMEEIRFPRTLSPEA
PKBgamma     323  YGRAVDWWGLGVVMYEMMCGRLPFYNQD------HEKLFELILMEDIKFPRTLSSDA
PRK1         792  YTRAVDWWGLGVLLYEMLVGESPFPGDD------EEEVFDSIVNDEVRYPRFLSAEA
PRK2         834  YTRAVDWWGLGVLLIYEMLVGESPFPGDD------EEEVFDSIVNDEVRYPRFLSTEA
SGK1         274  YDRTVDWWCLGAVLYEMLYGLPPFYSRN------TAEMYDNILNKPLQLKPNITNSA
SGK3         271  YDNTVDWWCLGAVLYEMLYGLPPFYCRD------VAEMYDNILHKPLSLRPGVSLTA
SGK2         271  YDRAVDWWCLGAVLYEMLYGLPPFYSQD------VSQMYENILHQPLQIPGGRTVAA
PKCbeta      518  YGKSVDWWAFGVLLYEMLAGQAPFEGED------EDELFQSIMEHNVAYPKSMSKEA
PKCbetaII    518  YGKSVDWWAFGVLLYEMLAGQAPFEGED------EDELFQSIMEHNVAYPKSMSKEA
PKCalpha     515  YGKSVDWWAYGVLLYEMLAGQPPFDGED------EDELFQSIMEHNVSYPKSLSKEA
PKCgamma     532  YGKSVDWWSFGVLLYEMLAGQPPFDGED------EEELFQAIMEQTVTYPKSLSREA
PKCzeta      420  YGFSVDWWALGVLMFEMMAGRSPFDIT--DNPDMNTEDYLFQVILEKPIRIPRFLSVKA
PKCiota      421  YGFSVDWWALGVLMFEMMAGRSPFDIVGSSDNPDQNTEDYLFQVILEKQIRIPRSLSVKA
PKCdelta     525  YTFSVDWWSFGVLMLIGQSPFHGDD------EDELFESIRVDTPHYPRWITKES
PKAgamma     216  YNKAVDWWALGVLIYEMAVGFPPFYADQ------PIQIYEKIVSGRVRFPSKLSSDL
PDK1         259  ACKSSDLWALGCIIYQLVAGLPPFRAGN------EYLIFQKIIKLEYDFPEKFFPKA
```

| | | | |
|---|---|---|---|
| p70S6Kalpha | 321 | RDLLKKLLLKRNAASRLGAGPG-DAGEVQAHPFFRHINWEELLAR-- | KVEPPFKPLLQSE- |
| p70S6Kbeta | 310 | RDLVKKFLKRNPSQRIGGGPG-DAADVQRHPFFRHMNWDDLLAW-- | RVDPPFRPCLQSE- |
| p90RSK1 | 296 | QSLLRMLFKRNPANRLGAGPD-GVEEIKRHSFFSTIDWNKLYRR-- | EIHPPFKPATGRP- |
| p90RSK2 | 296 | QSLLRMLFKRNPANRLGAGPD-GVEEIKRHSFFSTIDWNKLYRR-- | EIHPPFKPATGRP- |
| p90RSK3 | 287 | QSLLRALFKRNPCNRLGAGID-GVEEIKRHPFFVTIDWNTLYRK-- | EIKPPFKPALGRP- |
| MSK1 | 287 | KDLIQRLLMKDPKKRLGCGPR-DADEIKEHLFFQKINWDDLAAK-- | KVPAPFKPVIRDE- |
| MSK2 | 254 | QDLLQRLLCKDPKKRLGAGPQ-GAQEVRNHPFFQGLDWVALAAR-- | KIPAPFRPQIRSE- |
| PKBalpha | 377 | KSLLSGLLKKDPKQRLGGGSE-DAKEIMQHRFFAGIVWQHVYEK-- | KLSPPFKPQVTSE- |
| PKBbeta | 378 | KSLLAGLLKKDPKQRLGGGPS-DAKEVMEHRFFLSINWQDVVQK-- | KLLPPFKPQVTSE- |
| PKBgamma | 374 | KSLLSGLLIKDPNKRLGGGPD-DAKEIMRHSFFSGVNWQDVYDK-- | KLVPPFKPQVTSE- |
| PRK1 | 843 | IGIMRRLLRRNPERRLGSSER-DAEDVKKQPFFRTLGWEALLAR-- | RLPPPFVPTLSGR- |
| PRK2 | 885 | ISIMRRLLRRNPERRLGASEK-DAEDVKKHPFFRLIDWSALMDK-- | KVKPFFIPTIRGR- |
| SGK1 | 325 | RHLLEGLLQKDRTKRLGAKDD-FMEIKSHVFFSLINWDDLINK-- | KITPPFNPNVSGP- |
| SGK3 | 322 | WSILEELLEKDRQNRLGAKED-FLEIQNHPFFESLSWADLVQK-- | KIPPPFNPNVAGP- |
| SGK2 | 322 | CDLLQSLLHKDQRQRLGSKAD-FLEIKNHVFFSPINWDDLYHK-- | RLTPPFNPNVTGP- |
| PKCbeta | 569 | VAICKGLMTKHPGKRLGCGPE-GERDIKEHAFFRYIDWEKLERK-- | EIQPPYKPKARDK- |
| PKCbetaII | 569 | VAICKGLMTKHPGKRLGCGPE-GERDIKEHAFFRYIDWEKLERK-- | EIQPPYKPKACG-- |
| PKCalpha | 566 | VSICKGLMTKHPAKRLGCGPE-GERDVREHAFFRRIDWEKLENR-- | EIQPPFKPKVCG-- |
| PKCgamma | 583 | VAICKGFLTKHPGKRLGSGPD-GEPTIRAHGFFRWIDWERLERL-- | EIPPPFRPRPCG-- |
| PKCzeta | 478 | SHVLKGFLNKDPKERLGCRPQTGFSDIKSHAFFRSIDWDLLEKK-- | QALPPFQPQITDD- |
| PKCiota | 481 | ASVLKSFLNKDPKERLGCHPQTGFADIQGHPFFRNVDWDMMEQK-- | QVVPPFKPNISGE- |
| PKCdelta | 576 | KDILEKLFEREPTKRLGMTGN-----IKIHPFFKTINWTLLEKR-- | RLEPPFRPKVKSP- |
| PKAgamma | 267 | KDLLRSLLQVDLTKRFGNLRN-GVGDIKNHKWFATTSWIAIYEK-- | KVEAPFIPKYTGP- |
| PDK1 | 310 | RDLVEKLLVLDATKRLGCEEMEGYGPLKAHPFFESVTWENLHQQTPPKLTAYLPAMSEDD |

Figure 7: page 5

Figure 7: page 6

```
p70S6Kalpha 377 -----EDVSQFDSKFTRQTPVDSPDDSTLSESA------------------NQVFLGFTYVAPSVLES-
p70S6Kbeta  366 -----EDVSQFDTRFTRQTPVDSPDDTALSESA------------------NQAFLGFTYVAPSVLDS-
p90RSK1     352 -----EDTFYFDPEFTAKTPKDSP-GIPPSANA------------------HQLFRGFSFVAITSDDE-
p90RSK2     352 -----EDTFYFDPEFTAKTPKDSP-GIPPSANA------------------HQLFRGFSFVAITSDDE-
p90RSK3     343 -----EDTFHFDPEFTARTPTDSP-GVPPSANA------------------HHLFRGFSFVASSLIQEP
MSK1        343 -----LDVSNFAEEFTEMDPTYSPAALPQSSE-------------------KLFQGYSFVAPSILFKR
MSK2        310 -----LDVGNFAEEFTRLEPVYSPPGSPPPGDP------------------RIFQGYSFVAPSILFDH
PKBalpha    433 -----TDTRYFDEEFTAQMITITP----PDQDDS--MECVDSERRPHPQFSYSASSTA---------
PKBbeta     434 -----VDTRYFDDEFTAQSITITP----PDRYDS--LGLLELDQRTHFPQFSYSASIRE---------
PKBgamma    430 -----TDTRYFDEEFTAQTITITP----PEKYDEDGMDCMDNERRPHFPQFSYSASGRE---------
PRK1        899 -----TDVSNFDEEFTGEAPTLSP----PRD--A---R-PLTAAEQAAFLDFDFVAGGC---------
PRK2        941 -----EDVSNFDDEFTSEAPILTP----PRE--P---R-ILSEEEQEMFRDFDYIADWC---------
SGK1        380 -----NDLRHFDPEFTEEPVPNSIGKSPDSVLVT----ASVKEAAEAFLGFSYAPPT-DSFL------
SGK3        377 -----DDIRNFDTAFTEETVPYSVCVSSDYSIVN----ASVLEADDAFVGFSYAPPSEDLFL------
SGK2        377 -----ADLKHFDPEFTQEAVSKSIGCTPDTVAS----SS--GASSAFLGFSYAPEDDDILD-------
PKCbeta     625 -----RDTSNFDKEFTRQPVELTP----TDKLFIM----NLD----QNEFAGFSYTNPEFVINV----
PKCbetaII   624 -----RNAENFDRFFTRHPPVLTP----PDQEVIR----NID----QSEFEGFSFVNSEFLKPE----
PKCalpha    621 -----KGAENFDKFFTRGQPVLTP----PDQLVIA----NID----QSDFEGFSYVNPQFVHPI----
PKCgamma    638 -----RSGENFDKFFTRAAPALTP----PDRLVLA----SID----QADFQGFTYVNPDFVHPD----
PKCzeta     535 -----YGLDNFDTQFTSEPVQLTP----DDEDAIK----RID----QSEFEGFEYINPLLLSTE----
PKCiota     538 -----FGLDNFDSQFTNEPVQLTP----DDDDIVR----KID----QSEFEGFEYINPLLMSAE----
PKCdelta    628 -----RDYSNFDQEFLNEKARLSY----SDKNLID----SMD----QSAFAGFSFVNPKFEHLL----
PKAgamma    323 -----GDASNFDDYEE--EELRISI---NEK-CA-------------------KEFSEF--------
PDK1        370 EDCYGNYDNLLSQFGCMQVSSSSSHSLSASDTGLPQRSGSNIEQYIHDLDSNSFELDLQ
```

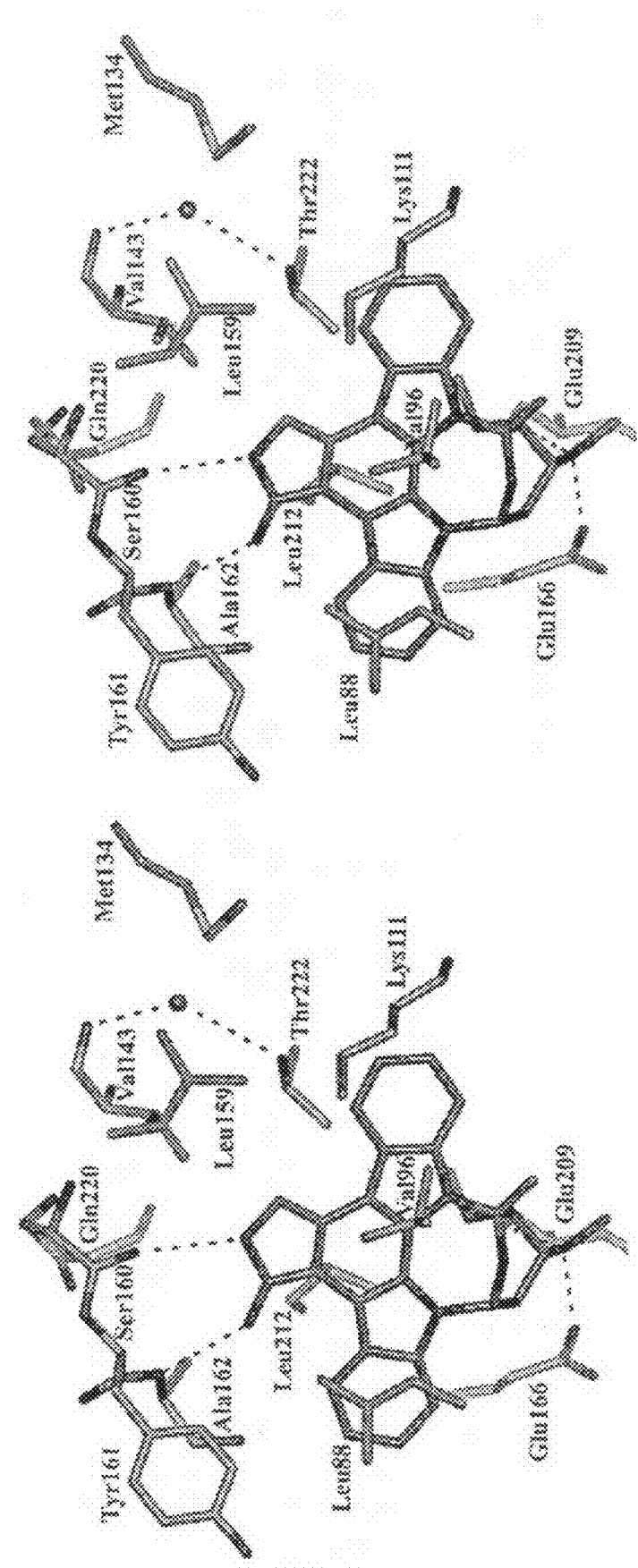
Figure 9: page 1

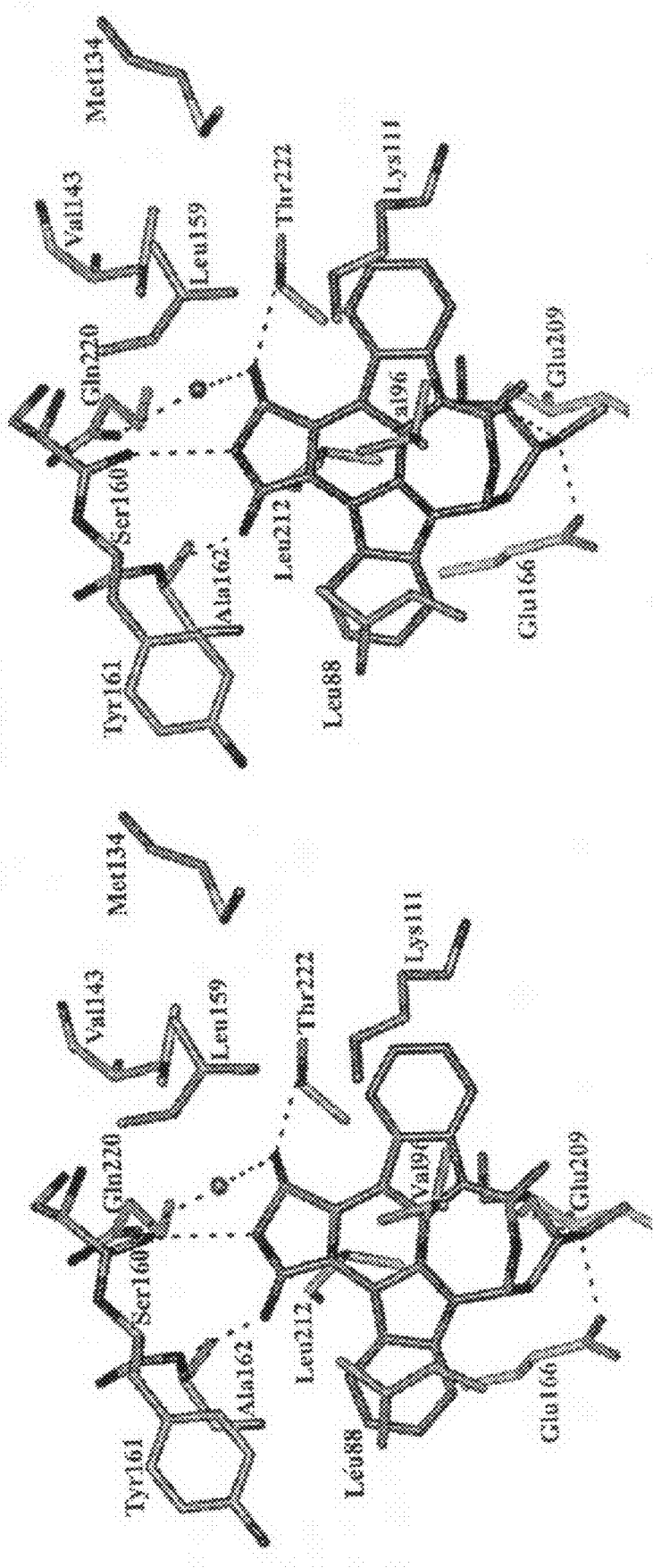
Figure 9; page 2

SEQUENCE LISTING

<160> NUMBER OF SEQ ID NOS: 148

<210> SEQ ID NO 1
<211> LENGTH: 4
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: Any amino acid residue

<400> SEQUENCE: 1

Phe Xaa Xaa Phe
1

<210> SEQ ID NO 2
<211> LENGTH: 6
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (5)..(5)
<223> OTHER INFORMATION: S or T

<400> SEQUENCE: 2

Phe Xaa Xaa Phe Xaa Tyr
1               5

<210> SEQ ID NO 3
<211> LENGTH: 556
<212> TYPE: PRT
<213> ORGANISM: Homo sapiens

<400> SEQUENCE: 3

Met Ala Arg Thr Thr Ser Gln Leu Tyr Asp Ala Val Pro Ile Gln Ser
1               5                   10                  15

-continued

```
Ser Val Val Leu Cys Ser Cys Pro Ser Pro Ser Met Val Arg Thr Gln
            20                  25                  30

Thr Glu Ser Ser Thr Pro Pro Gly Ile Pro Gly Gly Ser Arg Gln Gly
        35                  40                  45

Pro Ala Met Asp Gly Thr Ala Ala Glu Pro Arg Pro Gly Ala Gly Ser
    50                  55                  60

Leu Gln His Ala Gln Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
            100                 105                 110

Leu Glu Lys Arg His Ile Ile Lys Glu Asn Lys Val Pro Tyr Val Thr
        115                 120                 125

Arg Glu Arg Asp Val Met Ser Arg Leu Asp His Pro Phe Phe Val Lys
    130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
    210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
        275                 280                 285

Leu Ile Phe Gln Lys Ile Ile Lys Leu Glu Tyr Asp Phe Pro Glu Lys
    290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
            340                 345                 350

Gln Thr Pro Pro Lys Leu Thr Ala Tyr Leu Pro Ala Met Ser Glu Asp
        355                 360                 365

Asp Glu Asp Cys Tyr Gly Asn Tyr Asp Asn Leu Leu Ser Gln Phe Gly
    370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
            420                 425                 430

Asp Glu Lys Arg Leu Leu Leu Glu Lys Gln Ala Gly Gly Asn Pro Trp
```

```
                      435                 440                 445
His Gln Phe Val Glu Asn Asn Leu Ile Leu Lys Met Gly Pro Val Asp
    450                 455                 460

Lys Arg Lys Gly Leu Phe Ala Arg Arg Gln Leu Leu Leu Thr Glu
465                 470                 475                 480

Gly Pro His Leu Tyr Tyr Val Asp Pro Val Asn Lys Val Leu Lys Gly
                    485                 490                 495

Glu Ile Pro Trp Ser Gln Glu Leu Arg Pro Glu Ala Lys Asn Phe Lys
                500                 505                 510

Thr Phe Phe Val His Thr Pro Asn Arg Thr Tyr Tyr Leu Met Asp Pro
            515                 520                 525

Ser Gly Asn Ala His Lys Trp Cys Arg Lys Ile Gln Glu Val Trp Arg
    530                 535                 540

Gln Arg Tyr Gln Ser His Pro Asp Ala Ala Val Gln
545                 550                 555

<210> SEQ ID NO 4
<211> LENGTH: 249
<212> TYPE: PRT
<213> ORGANISM: Homo sapiens

<400> SEQUENCE: 4

Met Asp Gly Thr Ala Ala Glu Pro Arg Pro Gly Ala Gly Ser Leu Gln
1               5                   10                  15

His Ala Gln Pro Pro Pro Gln Pro Arg Lys Lys Arg Pro Glu Asp Phe
            20                  25                  30

Lys Phe Gly Lys Ile Leu Gly Glu Gly Ser Phe Ser Thr Val Val Leu
        35                  40                  45

Ala Arg Glu Leu Ala Thr Ser Arg Glu Tyr Ala Ile Lys Ile Leu Glu
    50                  55                  60

Lys Arg His Ile Ile Lys Glu Asn Lys Val Pro Tyr Val Thr Arg Glu
65                  70                  75                  80

Arg Asp Val Met Ser Arg Leu Asp His Pro Phe Phe Val Lys Leu Tyr
                85                  90                  95

Phe Thr Phe Gln Asp Asp Glu Lys Leu Tyr Phe Gly Leu Ser Tyr Ala
            100                 105                 110

Lys Asn Gly Glu Leu Leu Lys Tyr Ile Arg Lys Ile Gly Ser Phe Asp
        115                 120                 125

Glu Thr Cys Thr Arg Phe Tyr Thr Ala Glu Ile Val Ser Ala Leu Glu
130                 135                 140

Tyr Leu His Gly Lys Gly Ile Ile His Arg Asp Leu Lys Pro Glu Asn
145                 150                 155                 160

Ile Leu Leu Asn Glu Asp Met His Ile Gln Ile Thr Asp Phe Gly Thr
                165                 170                 175

Ala Lys Val Leu Ser Pro Glu Ser Lys Gln Ala Arg Ala Asn Ser Phe
            180                 185                 190

Val Gly Thr Ala Gln Tyr Val Ser Pro Glu Leu Leu Thr Glu Lys Ser
        195                 200                 205

Ala Cys Lys Ser Ser Asp Leu Trp Ala Leu Gly Cys Ile Ile Tyr Gln
210                 215                 220

Leu Val Ala Gly Leu Pro Pro Phe Arg Ala Gly Asn Glu Tyr Leu Ile
225                 230                 235                 240

Phe Gln Lys Ile Ile Lys Leu Glu Tyr
                245
```

```
<210> SEQ ID NO 5
<211> LENGTH: 8
<212> TYPE: PRT
<213> ORGANISM: Artificial Sequence
<220> FEATURE:
<223> OTHER INFORMATION: Phosphorylation consensus motif
<220> FEATURE:
<221> NAME/KEY: MISC_FEATURE
<222> LOCATION: (6)..(6)
<223> OTHER INFORMATION: Any amino acid

<400> SEQUENCE: 5
```

Thr Phe Cys Gly Thr Xaa Glu Leu
1               5

```
<210> SEQ ID NO 6
<211> LENGTH: 229
<212> TYPE: PRT
<213> ORGANISM: Homo sapiens

<400> SEQUENCE: 6
```

Pro Pro Gln Pro Arg Lys Lys Arg Pro Glu Asp Phe Lys Phe Gly Lys
1               5                   10                  15

Ile Leu Gly Glu Gly Ser Phe Ser Thr Val Val Leu Ala Arg Glu Leu
            20                  25                  30

Ala Thr Ser Arg Glu Tyr Ala Ile Lys Ile Leu Glu Lys Arg His Ile
        35                  40                  45

Ile Lys Glu Asn Lys Val Pro Tyr Val Thr Arg Glu Arg Asp Val Met
    50                  55                  60

Ser Arg Leu Asp His Pro Phe Phe Val Lys Leu Tyr Phe Thr Phe Gln
65                  70                  75                  80

Asp Asp Glu Lys Leu Tyr Phe Gly Leu Ser Tyr Ala Lys Asn Gly Glu
                85                  90                  95

Leu Leu Lys Tyr Ile Arg Lys Ile Gly Ser Phe Asp Glu Thr Cys Thr
            100                 105                 110

Arg Phe Tyr Thr Ala Glu Ile Val Ser Ala Leu Glu Tyr Leu His Gly
        115                 120                 125

Lys Gly Ile Ile His Arg Asp Leu Lys Pro Glu Asn Ile Leu Leu Asn
    130                 135                 140

Glu Asp Met His Ile Gln Ile Thr Asp Phe Gly Thr Ala Lys Val Leu
145                 150                 155                 160

Ser Pro Glu Ser Lys Gln Ala Arg Ala Asn Ser Phe Val Gly Thr Ala
                165                 170                 175

Gln Tyr Val Ser Pro Glu Leu Leu Thr Glu Lys Ser Ala Cys Lys Ser
            180                 185                 190

Ser Asp Leu Trp Ala Leu Gly Cys Ile Ile Tyr Gln Leu Val Ala Gly
        195                 200                 205

Leu Pro Pro Phe Arg Ala Gly Asn Glu Tyr Leu Ile Phe Gln Lys Ile
    210                 215                 220

Ile Lys Leu Glu Tyr
225

```
<210> SEQ ID NO 7
<211> LENGTH: 251
<212> TYPE: PRT
<213> ORGANISM: Artificial Sequence
<220> FEATURE:
<223> OTHER INFORMATION: Modified PDK1

<400> SEQUENCE: 7
```

```
Gly Pro Met Asp Gly Thr Ala Ala Glu Pro Arg Pro Gly Ala Gly Ser
1               5                   10                  15

Leu Gln His Ala Gln Pro Pro Gln Pro Arg Lys Lys Arg Pro Glu
            20                  25                  30

Asp Phe Lys Phe Gly Lys Ile Leu Gly Glu Gly Ser Phe Ser Thr Val
            35                  40                  45

Val Leu Ala Arg Glu Leu Ala Thr Ser Arg Glu Tyr Ala Ile Lys Ile
    50                  55                  60

Leu Glu Lys Arg His Ile Ile Lys Glu Asn Lys Val Pro Tyr Val Thr
65                  70                  75                  80

Arg Glu Arg Asp Val Met Ser Arg Leu Asp His Pro Phe Phe Val Lys
                85                  90                  95

Leu Tyr Phe Thr Phe Gln Asp Asp Glu Lys Leu Tyr Phe Gly Leu Ser
            100                 105                 110

Tyr Ala Lys Asn Gly Glu Leu Leu Lys Tyr Ile Arg Lys Ile Gly Ser
            115                 120                 125

Phe Asp Glu Thr Cys Thr Arg Phe Tyr Thr Ala Glu Ile Val Ser Ala
130                 135                 140

Leu Glu Tyr Leu His Gly Lys Gly Ile Ile His Arg Asp Leu Lys Pro
145                 150                 155                 160

Glu Asn Ile Leu Leu Asn Glu Asp Met His Ile Gln Ile Thr Asp Phe
                165                 170                 175

Gly Thr Ala Lys Val Leu Ser Pro Glu Ser Lys Gln Ala Arg Ala Asn
            180                 185                 190

Ser Phe Val Gly Thr Ala Gln Tyr Val Ser Pro Glu Leu Leu Thr Glu
            195                 200                 205

Lys Ser Ala Cys Lys Ser Ser Asp Leu Trp Ala Leu Gly Cys Ile Ile
            210                 215                 220

Tyr Gln Leu Val Ala Gly Leu Pro Pro Phe Arg Ala Gly Asn Glu Tyr
225                 230                 235                 240

Leu Ile Phe Gln Lys Ile Ile Lys Leu Glu Tyr
                245                 250

<210> SEQ ID NO 8
<211> LENGTH: 14
<212> TYPE: PRT
<213> ORGANISM: Homo sapiens

<400> SEQUENCE: 8

Lys Val Pro Tyr Val Thr Arg Glu Arg Asp Val Met Ser Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: PDK1 activity
<220> FEATURE:
<221> NAME/KEY: MISC_FEATURE
<222> LOCATION: (1)..(1)
<223> OTHER INFORMATION: T or S
<220> FEATURE:
<221> NAME/KEY: MISC_FEATURE
<222> LOCATION: (6)..(6)
<223> OTHER INFORMATION: Any amino acid residue

<400> SEQUENCE: 9

Xaa Phe Cys Gly Thr Xaa Glu Leu
```

```
<210> SEQ ID NO 10
<211> LENGTH: 6
<212> TYPE: PRT
<213> ORGANISM: Artificial Sequence
<220> FEATURE:
<223> OTHER INFORMATION: PDK2 activity
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (5)..(5)
<223> OTHER INFORMATION: S or T
<220> FEATURE:
<221> NAME/KEY: MISC_FEATURE
<222> LOCATION: (6)..(6)
<223> OTHER INFORMATION: P or Y

<400> SEQUENCE: 10

Pro Xaa Xaa Pro Xaa Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: Phosphorylated hydrophobic motif
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (5)..(5)
<223> OTHER INFORMATION: Any negatively charged residue

<400> SEQUENCE: 11

Phe Xaa Xaa Phe Xaa Tyr
1               5

<210> SEQ ID NO 12
<211> LENGTH: 26
<212> TYPE: PRT
<213> ORGANISM: Homo sapiens

<400> SEQUENCE: 12

Gln Pro Arg Lys Lys Arg Pro Glu Asp Phe Lys Phe Gly Lys Ile Leu
1               5                   10                  15

Gly Glu Gly Ser Phe Ser Thr Val Val Leu
            20                  25

<210> SEQ ID NO 13
<211> LENGTH: 26
<212> TYPE: PRT
<213> ORGANISM: Homo sapiens

<400> SEQUENCE: 13

Pro Lys His Arg Val Thr Met Asn Glu Phe Glu Tyr Leu Lys Leu Leu
1               5                   10                  15

Gly Lys Gly Thr Phe Gly Lys Val Ile Leu
            20                  25

<210> SEQ ID NO 14
<211> LENGTH: 26
```

```
<212> TYPE: PRT
<213> ORGANISM: Homo sapiens

<400> SEQUENCE: 14

Gly Pro Glu Lys Ile Arg Pro Glu Cys Phe Glu Leu Leu Arg Val Leu
1               5                   10                  15

Gly Lys Gly Gly Tyr Gly Lys Val Phe Gln
            20                  25

<210> SEQ ID NO 15
<211> LENGTH: 26
<212> TYPE: PRT
<213> ORGANISM: Homo sapiens

<400> SEQUENCE: 15

Ser Asn Pro His Ala Lys Pro Ser Asp Phe His Phe Leu Lys Val Ile
1               5                   10                  15

Gly Lys Gly Ser Phe Gly Lys Val Leu Leu
            20                  25

<210> SEQ ID NO 16
<211> LENGTH: 26
<212> TYPE: PRT
<213> ORGANISM: Homo sapiens

<400> SEQUENCE: 16

Gly Ser Glu Lys Ala Asp Pro Ser His Phe Glu Leu Leu Lys Val Leu
1               5                   10                  15

Gly Gln Gly Ser Phe Gly Lys Val Phe Leu
            20                  25

<210> SEQ ID NO 17
<211> LENGTH: 318
<212> TYPE: PRT
<213> ORGANISM: Homo sapiens

<400> SEQUENCE: 17

Lys Val Phe Gln Val Arg Lys Val Thr Gly Ala Asn Thr Gly Lys Ile
1               5                   10                  15

Phe Ala Met Lys Val Leu Lys Lys Ala Met Ile Val Arg Asn Ala Lys
                20                  25                  30

Asp Thr Ala His Thr Lys Ala Glu Arg Asn Ile Leu Glu Glu Val Lys
            35                  40                  45

His Pro Phe Ile Val Asp Leu Ile Tyr Ala Phe Gln Thr Gly Gly Lys
        50                  55                  60

Leu Tyr Leu Ile Leu Glu Tyr Leu Ser Gly Gly Glu Leu Phe Met Gln
65                  70                  75                  80

Leu Glu Arg Glu Gly Ile Phe Met Glu Asp Thr Ala Cys Phe Tyr Leu
                85                  90                  95

Ala Glu Ile Ser Met Ala Leu Gly His Leu His Gln Lys Gly Ile Ile
            100                 105                 110

Tyr Arg Asp Leu Lys Pro Glu Asn Ile Met Leu Asn His Gln Gly His
        115                 120                 125

Val Lys Leu Thr Asp Phe Gly Leu Cys Lys Glu Ser Ile His Asp Gly
    130                 135                 140

Thr Val Thr His Thr Phe Cys Gly Thr Ile Glu Tyr Met Ala Pro Glu
145                 150                 155                 160

Ile Leu Met Arg Ser Gly His Asn Arg Ala Val Asp Trp Trp Ser Leu
                165                 170                 175
```

Gly Ala Leu Met Tyr Asp Met Leu Thr Gly Ala Pro Pro Phe Thr Gly
            180                 185                 190

Glu Asn Arg Lys Lys Thr Ile Asp Lys Ile Leu Lys Cys Lys Leu Asn
            195                 200                 205

Leu Pro Pro Tyr Leu Thr Gln Glu Ala Arg Asp Leu Leu Lys Lys Leu
210                 215                 220

Leu Lys Arg Asn Ala Ala Ser Arg Leu Gly Ala Gly Pro Gly Asp Ala
225                 230                 235                 240

Gly Glu Val Gln Ala His Pro Phe Phe Arg His Ile Asn Trp Glu Glu
                245                 250                 255

Leu Leu Ala Arg Lys Val Glu Pro Pro Phe Lys Pro Leu Leu Gln Ser
            260                 265                 270

Glu Glu Asp Val Ser Gln Phe Asp Ser Lys Phe Thr Arg Gln Thr Pro
            275                 280                 285

Val Asp Ser Pro Asp Asp Ser Thr Leu Ser Glu Ser Ala Asn Gln Val
            290                 295                 300

Phe Leu Gly Phe Thr Tyr Val Ala Pro Ser Val Leu Glu Ser
305                 310                 315

<210> SEQ ID NO 18
<211> LENGTH: 318
<212> TYPE: PRT
<213> ORGANISM: Homo sapiens

<400> SEQUENCE: 18

Lys Val Phe Gln Val Arg Lys Val Gln Gly Thr Asn Leu Gly Lys Ile
1               5                   10                  15

Tyr Ala Met Lys Val Leu Arg Lys Ala Lys Ile Val Arg Asn Ala Lys
            20                  25                  30

Asp Thr Ala His Thr Arg Ala Glu Arg Asn Ile Leu Glu Ser Val Lys
            35                  40                  45

His Pro Phe Ile Val Glu Leu Ala Tyr Ala Phe Gln Thr Gly Gly Lys
50                  55                  60

Leu Tyr Leu Ile Leu Glu Cys Leu Ser Gly Gly Glu Leu Phe Thr His
65                  70                  75                  80

Leu Glu Arg Glu Gly Ile Phe Leu Glu Asp Thr Ala Cys Phe Tyr Leu
            85                  90                  95

Ala Glu Ile Thr Leu Ala Leu Gly His Leu His Ser Gln Gly Ile Ile
            100                 105                 110

Tyr Arg Asp Leu Lys Pro Glu Asn Ile Met Leu Ser Ser Gln Gly His
            115                 120                 125

Ile Lys Leu Thr Asp Phe Gly Leu Cys Lys Glu Ser Ile His Glu Gly
            130                 135                 140

Ala Val Thr His Thr Phe Cys Gly Thr Ile Glu Tyr Met Ala Pro Glu
145                 150                 155                 160

Ile Leu Val Arg Ser Gly His Asn Arg Ala Val Asp Trp Trp Ser Leu
            165                 170                 175

Gly Ala Leu Met Tyr Asp Met Leu Thr Gly Ser Pro Pro Phe Thr Ala
            180                 185                 190

Glu Asn Arg Lys Lys Thr Met Asp Lys Ile Ile Arg Gly Lys Leu Ala
            195                 200                 205

Leu Pro Pro Tyr Leu Thr Pro Asp Ala Arg Asp Leu Val Lys Lys Phe
210                 215                 220

Leu Lys Arg Asn Pro Ser Gln Arg Ile Gly Gly Gly Pro Gly Asp Ala

```
                225                 230                 235                 240
Ala Asp Val Gln Arg His Pro Phe Phe Arg His Met Asn Trp Asp Asp
                    245                 250                 255

Leu Leu Ala Trp Arg Val Asp Pro Pro Phe Arg Pro Cys Leu Gln Ser
                260                 265                 270

Glu Glu Asp Val Ser Gln Phe Asp Thr Arg Phe Thr Arg Gln Thr Pro
            275                 280                 285

Val Asp Ser Pro Asp Asp Thr Ala Leu Ser Glu Ser Ala Asn Gln Ala
        290                 295                 300

Phe Leu Gly Phe Thr Tyr Val Ala Pro Ser Val Leu Asp Ser
305                 310                 315

<210> SEQ ID NO 19
<211> LENGTH: 315
<212> TYPE: PRT
<213> ORGANISM: Homo sapiens

<400> SEQUENCE: 19

Lys Val Phe Leu Val Lys Lys Ile Ser Gly Ser Asp Ala Arg Gln Leu
1               5                   10                  15

Tyr Ala Met Lys Val Leu Lys Lys Ala Thr Leu Lys Val Arg Asp Arg
            20                  25                  30

Val Arg Thr Lys Met Glu Arg Asp Ile Leu Val Glu Val Asn His Pro
        35                  40                  45

Phe Ile Val Lys Leu His Tyr Ala Phe Gln Thr Glu Gly Lys Leu Tyr
    50                  55                  60

Leu Ile Leu Asp Phe Leu Arg Gly Gly Asp Leu Phe Thr Arg Leu Ser
65                  70                  75                  80

Lys Glu Val Met Phe Thr Glu Glu Asp Val Lys Phe Tyr Leu Ala Glu
                85                  90                  95

Leu Ala Leu Ala Leu Asp His Leu His Ser Leu Gly Ile Ile Tyr Arg
            100                 105                 110

Asp Leu Lys Pro Glu Asn Ile Leu Leu Asp Glu Glu Gly His Ile Lys
        115                 120                 125

Leu Thr Asp Phe Gly Leu Ser Lys Glu Ser Ile Asp His Glu Lys Lys
    130                 135                 140

Ala Tyr Ser Phe Cys Gly Thr Val Glu Tyr Met Ala Pro Glu Val Val
145                 150                 155                 160

Asn Arg Arg Gly His Thr Gln Ser Ala Asp Trp Trp Ser Phe Gly Val
                165                 170                 175

Leu Met Phe Glu Met Leu Thr Gly Thr Leu Pro Phe Gln Gly Lys Asp
            180                 185                 190

Arg Lys Glu Thr Met Thr Met Ile Leu Lys Ala Lys Leu Gly Met Pro
        195                 200                 205

Gln Phe Leu Ser Pro Glu Ala Gln Ser Leu Leu Arg Met Leu Phe Lys
    210                 215                 220

Arg Asn Pro Ala Asn Arg Leu Gly Ala Gly Pro Asp Gly Val Glu Glu
225                 230                 235                 240

Ile Lys Arg His Ser Phe Phe Ser Thr Ile Asp Trp Asn Lys Leu Tyr
                245                 250                 255

Arg Arg Glu Ile His Pro Pro Phe Lys Pro Ala Thr Gly Arg Pro Glu
            260                 265                 270

Asp Thr Phe Tyr Phe Asp Pro Glu Phe Thr Ala Lys Thr Pro Lys Asp
        275                 280                 285
```

-continued

Ser Pro Gly Ile Pro Pro Ser Ala Asn Ala His Gln Leu Phe Arg Gly
        290                 295                 300

Phe Ser Phe Val Ala Ile Thr Ser Asp Asp Glu
305                 310                 315

<210> SEQ ID NO 20
<211> LENGTH: 315
<212> TYPE: PRT
<213> ORGANISM: Homo sapiens

<400> SEQUENCE: 20

Lys Val Phe Leu Val Lys Lys Ile Ser Gly Ser Asp Ala Arg Gln Leu
1               5                   10                  15

Tyr Ala Met Lys Val Leu Lys Lys Ala Thr Leu Lys Val Arg Asp Arg
                20                  25                  30

Val Arg Thr Lys Met Glu Arg Asp Ile Leu Val Glu Val Asn His Pro
            35                  40                  45

Phe Ile Val Lys Leu His Tyr Ala Phe Gln Thr Glu Gly Lys Leu Tyr
        50                  55                  60

Leu Ile Leu Asp Phe Leu Arg Gly Gly Asp Leu Phe Thr Arg Leu Ser
65                  70                  75                  80

Lys Glu Val Met Phe Thr Glu Glu Asp Val Lys Phe Tyr Leu Ala Glu
                85                  90                  95

Leu Ala Leu Ala Leu Asp His Leu His Ser Leu Gly Ile Ile Tyr Arg
            100                 105                 110

Asp Leu Lys Pro Glu Asn Ile Leu Leu Asp Glu Glu Gly His Ile Lys
        115                 120                 125

Leu Thr Asp Phe Gly Leu Ser Lys Glu Ser Ile Asp His Glu Lys Lys
130                 135                 140

Ala Tyr Ser Phe Cys Gly Thr Val Glu Tyr Met Ala Pro Glu Val Val
145                 150                 155                 160

Asn Arg Arg Gly His Thr Gln Ser Ala Asp Trp Trp Ser Phe Gly Val
                165                 170                 175

Leu Met Phe Glu Met Leu Thr Gly Thr Leu Pro Phe Gln Gly Lys Asp
            180                 185                 190

Arg Lys Glu Thr Met Thr Met Ile Leu Lys Ala Lys Leu Gly Met Pro
        195                 200                 205

Gln Phe Leu Ser Pro Glu Ala Gln Ser Leu Leu Arg Met Leu Phe Lys
210                 215                 220

Arg Asn Pro Ala Asn Arg Leu Gly Ala Gly Pro Asp Gly Val Glu Glu
225                 230                 235                 240

Ile Lys Arg His Ser Phe Phe Ser Thr Ile Asp Trp Asn Lys Leu Tyr
                245                 250                 255

Arg Arg Glu Ile His Pro Pro Phe Lys Pro Ala Thr Gly Arg Pro Glu
            260                 265                 270

Asp Thr Phe Tyr Phe Asp Pro Glu Phe Thr Ala Lys Thr Pro Lys Asp
        275                 280                 285

Ser Pro Gly Ile Pro Pro Ser Ala Asn Ala His Gln Leu Phe Arg Gly
290                 295                 300

Phe Ser Phe Val Ala Ile Thr Ser Asp Asp Glu
305                 310                 315

<210> SEQ ID NO 21
<211> LENGTH: 316
<212> TYPE: PRT
<213> ORGANISM: Homo sapiens

<400> SEQUENCE: 21

```
Lys Val Phe Leu Val Arg Lys Val Lys Gly Ser Asp Ala Gly Gln Leu
1               5                   10                  15
Tyr Ala Met Lys Val Leu Lys Lys Ala Thr Leu Lys Val Arg Asp Arg
            20                  25                  30
Val Arg Ser Lys Met Glu Arg Asp Ile Leu Ala Glu Val Asn His Pro
        35                  40                  45
Phe Ile Val Lys Leu His Tyr Ala Phe Gln Thr Glu Gly Lys Leu Tyr
    50                  55                  60
Leu Ile Leu Asp Phe Leu Arg Gly Gly Asp Leu Phe Thr Arg Leu Ser
65                  70                  75                  80
Lys Glu Val Met Phe Thr Glu Glu Asp Val Lys Phe Tyr Leu Ala Glu
                85                  90                  95
Leu Ala Leu Ala Leu Asp His Leu His Ser Leu Gly Ile Ile Tyr Arg
            100                 105                 110
Asp Leu Lys Pro Glu Asn Ile Leu Leu Asp Glu Glu Gly His Ile Lys
        115                 120                 125
Ile Thr Asp Phe Gly Leu Ser Lys Glu Ala Ile Asp His Asp Lys Arg
    130                 135                 140
Ala Tyr Ser Phe Cys Gly Thr Ile Glu Tyr Met Ala Pro Glu Val Val
145                 150                 155                 160
Asn Arg Arg Gly His Thr Gln Ser Ala Asp Trp Trp Ser Phe Gly Val
                165                 170                 175
Leu Met Phe Glu Met Leu Thr Gly Ser Leu Pro Phe Gln Gly Lys Asp
            180                 185                 190
Arg Lys Glu Thr Met Ala Leu Ile Leu Lys Ala Lys Leu Gly Met Pro
        195                 200                 205
Gln Phe Leu Ser Gly Glu Ala Gln Ser Leu Leu Arg Ala Leu Phe Lys
    210                 215                 220
Arg Asn Pro Cys Asn Arg Leu Gly Ala Gly Ile Asp Gly Val Glu Glu
225                 230                 235                 240
Ile Lys Arg His Pro Phe Phe Val Thr Ile Asp Trp Asn Thr Leu Tyr
                245                 250                 255
Arg Arg Glu Ile Lys Pro Pro Phe Lys Pro Ala Leu Gly Arg Pro Glu
            260                 265                 270
Asp Thr Phe His Phe Asp Pro Glu Phe Thr Ala Arg Thr Pro Thr Asp
        275                 280                 285
Ser Pro Gly Val Pro Pro Ser Ala Asn Ala His His Leu Phe Arg Gly
    290                 295                 300
Phe Ser Phe Val Ala Ser Ser Leu Ile Gln Glu Pro
305                 310                 315
```

<210> SEQ ID NO 22
<211> LENGTH: 325
<212> TYPE: PRT
<213> ORGANISM: Homo sapiens

<400> SEQUENCE: 22

```
Lys Val Phe Leu Val Arg Lys Ile Ser Gly His Asp Thr Gly Lys Leu
1               5                   10                  15
Tyr Ala Met Lys Val Leu Lys Lys Ala Thr Ile Val Gln Lys Ala Lys
            20                  25                  30
Thr Thr Glu His Thr Arg Thr Glu Arg Gln Val Leu Glu His Ile Arg
        35                  40                  45
```

```
Gln Ser Pro Phe Leu Val Thr Leu His Tyr Ala Phe Gln Thr Glu Thr
     50                  55                  60

Lys Leu His Leu Ile Leu Asp Tyr Ile Asn Gly Gly Glu Leu Phe Thr
 65                  70                  75                  80

His Leu Ser Gln Arg Glu Arg Phe Thr Glu His Glu Val Gln Ile Tyr
             85                  90                  95

Val Gly Glu Ile Val Leu Ala Leu Glu His Leu His Lys Leu Gly Ile
            100                 105                 110

Ile Tyr Arg Asp Ile Lys Leu Glu Asn Ile Leu Leu Asp Ser Asn Gly
        115                 120                 125

His Val Val Leu Thr Asp Phe Gly Leu Ser Lys Glu Phe Val Ala Asp
    130                 135                 140

Glu Thr Glu Arg Ala Tyr Ser Phe Cys Gly Thr Ile Glu Tyr Met Ala
145                 150                 155                 160

Pro Asp Ile Val Arg Gly Gly Asp Ser Gly His Asp Lys Ala Val Asp
                165                 170                 175

Trp Trp Ser Leu Gly Val Leu Met Tyr Glu Leu Leu Thr Gly Ala Ser
            180                 185                 190

Pro Phe Thr Val Asp Gly Glu Lys Asn Ser Gln Ala Glu Ile Ser Arg
        195                 200                 205

Arg Ile Leu Lys Ser Glu Pro Pro Tyr Pro Gln Glu Met Ser Ala Leu
    210                 215                 220

Ala Lys Asp Leu Ile Gln Arg Leu Leu Met Lys Asp Pro Lys Lys Arg
225                 230                 235                 240

Leu Gly Cys Gly Pro Arg Asp Ala Asp Glu Ile Lys Glu His Leu Phe
                245                 250                 255

Phe Gln Lys Ile Asn Trp Asp Asp Leu Ala Ala Lys Lys Val Pro Ala
            260                 265                 270

Pro Phe Lys Pro Val Ile Arg Asp Glu Leu Asp Val Ser Asn Phe Ala
        275                 280                 285

Glu Glu Phe Thr Glu Met Asp Pro Thr Tyr Ser Pro Ala Ala Leu Pro
    290                 295                 300

Gln Ser Ser Glu Lys Leu Phe Gln Gly Tyr Ser Phe Val Ala Pro Ser
305                 310                 315                 320

Ile Leu Phe Lys Arg
                325

<210> SEQ ID NO 23
<211> LENGTH: 325
<212> TYPE: PRT
<213> ORGANISM: Homo sapiens

<400> SEQUENCE: 23

Lys Val Phe Leu Val Arg Lys Ala Gly Gly His Asp Ala Gly Lys Leu
 1               5                  10                  15

Tyr Ala Met Lys Val Leu Arg Lys Ala Ala Leu Val Gln Arg Ala Lys
            20                  25                  30

Thr Gln Glu His Thr Arg Thr Glu Arg Ser Val Leu Glu Leu Val Arg
        35                  40                  45

Gln Ala Pro Phe Leu Val Thr Leu His Tyr Ala Phe Gln Thr Asp Ala
    50                  55                  60

Lys Leu His Leu Ile Leu Asp Tyr Val Ser Gly Gly Glu Met Phe Thr
 65                  70                  75                  80

His Leu Tyr Gln Arg Gln Tyr Phe Lys Glu Ala Glu Val Arg Val Tyr
```

```
                  85                  90                  95
Gly Gly Glu Ile Val Leu Ala Leu Glu His Leu His Lys Leu Gly Ile
            100                 105                 110
Ile Tyr Arg Asp Leu Lys Leu Glu Asn Val Leu Leu Asp Ser Glu Gly
            115                 120                 125
His Ile Val Leu Thr Asp Phe Gly Leu Ser Lys Glu Phe Leu Thr Glu
            130                 135                 140
Glu Lys Glu Arg Thr Phe Ser Phe Cys Gly Thr Ile Glu Tyr Met Ala
145                 150                 155                 160
Pro Glu Ile Ile Arg Ser Lys Thr Gly His Gly Lys Ala Val Asp Trp
            165                 170                 175
Trp Ser Leu Gly Ile Leu Leu Phe Glu Leu Leu Thr Gly Ala Ser Pro
            180                 185                 190
Phe Thr Leu Glu Gly Glu Arg Asn Thr Gln Ala Glu Val Ser Arg Arg
            195                 200                 205
Ile Leu Lys Cys Ser Pro Pro Phe Pro Pro Arg Ile Gly Pro Val Ala
            210                 215                 220
Gln Asp Leu Leu Gln Arg Leu Leu Cys Lys Asp Pro Lys Lys Arg Leu
225                 230                 235                 240
Gly Ala Gly Pro Gln Gly Ala Gln Glu Val Arg Asn His Pro Phe Phe
            245                 250                 255
Gln Gly Leu Asp Trp Val Ala Leu Ala Ala Arg Lys Ile Pro Ala Pro
            260                 265                 270
Phe Arg Pro Gln Ile Arg Ser Glu Leu Asp Val Gly Asn Phe Ala Glu
            275                 280                 285
Glu Phe Thr Arg Leu Glu Pro Val Tyr Ser Pro Pro Gly Ser Pro Pro
            290                 295                 300
Pro Gly Asp Pro Arg Ile Phe Gln Gly Tyr Ser Phe Val Ala Pro Ser
305                 310                 315                 320
Ile Leu Phe Asp His
            325

<210> SEQ ID NO 24
<211> LENGTH: 318
<212> TYPE: PRT
<213> ORGANISM: Homo sapiens

<400> SEQUENCE: 24

Lys Val Ile Leu Val Lys Glu Lys Ala Thr Gly Arg Tyr Tyr Ala Met
1               5                   10                  15
Lys Ile Leu Lys Lys Glu Val Ile Val Ala Lys Asp Glu Val Ala His
            20                  25                  30
Thr Leu Thr Glu Asn Arg Val Leu Gln Asn Ser Arg His Pro Phe Leu
            35                  40                  45
Thr Ala Leu Lys Tyr Ser Phe Gln Thr His Asp Arg Leu Cys Phe Val
            50                  55                  60
Met Glu Tyr Ala Asn Gly Gly Glu Leu Phe Phe His Leu Ser Arg Glu
65                  70                  75                  80
Arg Val Phe Ser Glu Asp Arg Ala Arg Phe Tyr Gly Ala Glu Ile Val
            85                  90                  95
Ser Ala Leu Asp Tyr Leu His Ser Glu Lys Asn Val Val Tyr Arg Asp
            100                 105                 110
Leu Lys Leu Glu Asn Leu Met Leu Asp Lys Asp Gly His Ile Lys Ile
            115                 120                 125
```

```
Thr Asp Phe Gly Leu Cys Lys Glu Gly Ile Lys Asp Gly Ala Thr Met
    130                 135                 140

Lys Thr Phe Cys Gly Thr Pro Glu Tyr Leu Ala Pro Glu Val Leu Glu
145                 150                 155                 160

Asp Asn Asp Tyr Gly Arg Ala Val Asp Trp Trp Gly Leu Gly Val Val
                165                 170                 175

Met Tyr Glu Met Met Cys Gly Arg Leu Pro Phe Tyr Asn Gln Asp His
            180                 185                 190

Glu Lys Leu Phe Glu Leu Ile Leu Met Glu Glu Ile Arg Phe Pro Arg
        195                 200                 205

Thr Leu Gly Pro Glu Ala Lys Ser Leu Leu Ser Gly Leu Leu Lys Lys
    210                 215                 220

Asp Pro Lys Gln Arg Leu Gly Gly Gly Ser Glu Asp Ala Lys Glu Ile
225                 230                 235                 240

Met Gln His Arg Phe Phe Ala Gly Ile Val Trp Gln His Val Tyr Glu
                245                 250                 255

Lys Lys Leu Ser Pro Pro Phe Lys Pro Gln Val Thr Ser Glu Val Asp
            260                 265                 270

Thr Arg Tyr Phe Asp Asp Glu Phe Thr Ala Gln Ser Ile Thr Ile Thr
        275                 280                 285

Pro Pro Asp Arg Tyr Asp Ser Leu Gly Leu Leu Glu Leu Asp Gln Arg
    290                 295                 300

Thr His Phe Pro Gln Phe Ser Tyr Ser Ala Ser Ile Arg Glu
305                 310                 315

<210> SEQ ID NO 25
<211> LENGTH: 317
<212> TYPE: PRT
<213> ORGANISM: Homo sapiens

<400> SEQUENCE: 25

Lys Val Ile Leu Val Arg Glu Lys Ala Thr Gly Arg Tyr Tyr Ala Met
1               5                   10                  15

Lys Ile Leu Arg Lys Glu Val Ile Ile Ala Lys Asp Glu Val Ala His
            20                  25                  30

Thr Val Thr Glu Ser Arg Val Leu Gln Asn Thr Arg His Pro Phe Leu
        35                  40                  45

Thr Ala Leu Lys Tyr Ala Phe Gln Thr His Asp Arg Leu Cys Phe Val
    50                  55                  60

Met Glu Tyr Ala Asn Gly Gly Glu Leu Phe Phe His Leu Ser Arg Glu
65                  70                  75                  80

Arg Val Phe Thr Glu Glu Arg Ala Arg Phe Tyr Gly Ala Glu Ile Val
                85                  90                  95

Ser Ala Leu Glu Tyr Leu His Ser Arg Asp Val Val Tyr Arg Asp Ile
            100                 105                 110

Lys Leu Glu Asn Leu Met Leu Asp Lys Asp Gly His Ile Lys Ile Thr
        115                 120                 125

Asp Phe Gly Leu Cys Lys Glu Gly Ile Ser Asp Gly Ala Thr Met Lys
    130                 135                 140

Thr Phe Cys Gly Thr Pro Glu Tyr Leu Ala Pro Glu Val Leu Glu Asp
145                 150                 155                 160

Asn Asp Tyr Gly Arg Ala Val Asp Trp Trp Gly Leu Gly Val Val Met
                165                 170                 175

Tyr Glu Met Met Cys Gly Arg Leu Pro Phe Tyr Asn Gln Asp His Glu
            180                 185                 190
```

-continued

Arg Leu Phe Glu Leu Ile Leu Met Glu Glu Ile Arg Phe Pro Arg Thr
            195                 200                 205

Leu Ser Pro Glu Ala Lys Ser Leu Leu Ala Gly Leu Leu Lys Lys Asp
    210                 215                 220

Pro Lys Gln Arg Leu Gly Gly Pro Ser Asp Ala Lys Glu Val Met
225                 230                 235                 240

Glu His Arg Phe Phe Leu Ser Ile Asn Trp Gln Asp Val Val Gln Lys
                245                 250                 255

Lys Leu Leu Pro Pro Phe Lys Pro Gln Val Thr Ser Glu Val Asp Thr
            260                 265                 270

Arg Tyr Phe Asp Asp Glu Phe Thr Ala Gln Ser Ile Thr Ile Thr Pro
        275                 280                 285

Pro Asp Arg Tyr Asp Ser Leu Gly Leu Leu Glu Leu Asp Gln Arg Thr
    290                 295                 300

His Phe Pro Gln Phe Ser Tyr Ser Ala Ser Ile Arg Glu
305                 310                 315

<210> SEQ ID NO 26
<211> LENGTH: 306
<212> TYPE: PRT
<213> ORGANISM: Homo sapiens

<400> SEQUENCE: 26

Lys Lys Val Ile Leu Val Arg Glu Lys Ala Ser Gly Lys Tyr Tyr Ala
1               5                   10                  15

Met Lys Ile Leu Lys Lys Glu Val Ile Ile Ala Lys Asp Glu Val Ala
            20                  25                  30

His Thr Leu Thr Glu Ser Arg Val Leu Lys Asn Thr Arg His Pro Phe
        35                  40                  45

Leu Thr Ser Leu Lys Tyr Ser Phe Gln Thr Lys Asp Arg Leu Cys Phe
    50                  55                  60

Val Met Glu Tyr Val Asn Gly Gly Glu Leu Phe Phe His Leu Ser Arg
65                  70                  75                  80

Glu Arg Val Phe Ser Glu Asp Arg Thr Arg Phe Tyr Gly Ala Glu Ile
                85                  90                  95

Val Ser Ala Leu Asp Tyr Leu His Ser Gly Lys Ile Val Tyr Arg Asp
            100                 105                 110

Leu Lys Leu Glu Asn Leu Met Leu Asp Lys Asp Gly His Ile Lys Ile
        115                 120                 125

Thr Asp Phe Gly Leu Cys Lys Glu Gly Ile Thr Asp Ala Ala Thr Met
130                 135                 140

Lys Thr Phe Cys Gly Thr Pro Glu Tyr Leu Ala Pro Glu Val Leu Glu
145                 150                 155                 160

Asp Asn Asp Tyr Gly Arg Ala Val Asp Trp Trp Gly Leu Gly Val Val
                165                 170                 175

Met Tyr Glu Met Met Cys Gly Arg Leu Pro Phe Tyr Asn Gln Asp His
            180                 185                 190

Glu Lys Leu Phe Glu Leu Ile Leu Met Glu Asp Ile Lys Phe Pro Arg
        195                 200                 205

Thr Leu Ser Ser Asp Ala Lys Ser Leu Leu Ser Gly Leu Leu Ile Lys
    210                 215                 220

Asp Pro Asn Lys Arg Leu Gly Gly Gly Pro Asp Asp Ala Lys Glu Ile
225                 230                 235                 240

Met Arg His Ser Phe Phe Ser Gly Val Asn Trp Gln Asp Val Tyr Asp

```
                    245                 250                 255
Lys Lys Leu Val Pro Pro Phe Lys Pro Gln Val Thr Ser Glu Thr Asp
            260                 265                 270

Thr Arg Tyr Phe Asp Glu Glu Phe Thr Ala Gln Thr Ile Thr Ile Thr
            275                 280                 285

Pro Pro Glu Lys Cys Gln Gln Ser Asp Cys Gly Met Leu Gly Asn Trp
            290                 295                 300

Lys Lys
305

<210> SEQ ID NO 27
<211> LENGTH: 315
<212> TYPE: PRT
<213> ORGANISM: Homo sapiens

<400> SEQUENCE: 27

Lys Val Leu Leu Ser Glu Phe Arg Pro Ser Gly Glu Leu Phe Ala Ile
1               5                   10                  15

Lys Ala Leu Lys Lys Gly Asp Ile Val Ala Arg Asp Glu Val Glu Ser
            20                  25                  30

Leu Met Cys Glu Lys Arg Ile Leu Ala Ala Val Thr Ser Ala Gly His
        35                  40                  45

Pro Phe Leu Val Asn Leu Phe Gly Cys Phe Gln Thr Pro Glu His Val
    50                  55                  60

Cys Phe Val Met Glu Tyr Ser Ala Gly Gly Asp Leu Met Leu His Ile
65                  70                  75                  80

His Ser Asp Val Phe Ser Glu Pro Arg Ala Ile Phe Tyr Ser Ala Cys
                85                  90                  95

Val Val Leu Gly Leu Gln Phe Leu His Glu His Lys Ile Val Tyr Arg
            100                 105                 110

Asp Leu Lys Leu Asp Asn Leu Leu Leu Asp Thr Glu Gly Tyr Val Lys
        115                 120                 125

Ile Ala Asp Phe Gly Leu Cys Lys Glu Gly Met Gly Tyr Gly Asp Arg
    130                 135                 140

Thr Ser Thr Phe Cys Gly Thr Pro Glu Phe Leu Ala Pro Glu Val Leu
145                 150                 155                 160

Thr Asp Thr Ser Tyr Thr Arg Ala Val Asp Trp Trp Gly Leu Gly Val
                165                 170                 175

Leu Leu Tyr Glu Met Leu Val Gly Glu Ser Pro Phe Pro Gly Asp Asp
            180                 185                 190

Glu Glu Glu Val Phe Asp Ser Ile Val Asn Asp Glu Val Arg Tyr Pro
        195                 200                 205

Arg Phe Leu Ser Ala Glu Ala Ile Gly Ile Met Arg Arg Leu Leu Arg
    210                 215                 220

Arg Asn Pro Glu Arg Arg Leu Gly Ser Ser Glu Arg Asp Ala Glu Asp
225                 230                 235                 240

Val Lys Lys Gln Pro Phe Phe Arg Thr Leu Gly Trp Glu Ala Leu Leu
                245                 250                 255

Ala Arg Arg Leu Pro Pro Pro Phe Val Pro Thr Leu Ser Gly Arg Thr
            260                 265                 270

Asp Val Ser Asn Phe Asp Glu Glu Phe Thr Gly Glu Ala Pro Thr Leu
        275                 280                 285

Ser Pro Pro Arg Asp Ala Arg Pro Leu Thr Ala Ala Glu Gln Ala Ala
    290                 295                 300
```

Phe Leu Asp Phe Asp Phe Val Ala Gly Gly Cys
305                 310                 315

<210> SEQ ID NO 28
<211> LENGTH: 315
<212> TYPE: PRT
<213> ORGANISM: Homo sapiens

<400> SEQUENCE: 28

Lys Val Leu Leu Ala Glu Tyr Lys Asn Thr Asn Glu Met Phe Ala Ile
1               5                   10                  15

Lys Ala Leu Lys Lys Gly Asp Ile Val Ala Arg Asp Glu Val Asp Ser
            20                  25                  30

Leu Met Cys Glu Lys Arg Ile Phe Glu Thr Val Asn Ser Val Arg His
        35                  40                  45

Pro Phe Leu Val Asn Leu Phe Ala Cys Phe Gln Thr Lys Glu His Val
    50                  55                  60

Cys Phe Val Met Glu Tyr Ala Ala Gly Gly Asp Leu Met Met His Ile
65                  70                  75                  80

His Thr Asp Val Phe Ser Glu Pro Arg Ala Val Phe Tyr Ala Ala Cys
                85                  90                  95

Val Val Leu Gly Leu Gln Tyr Leu His Glu His Lys Ile Val Tyr Arg
            100                 105                 110

Asp Leu Lys Leu Asp Asn Leu Leu Leu Asp Thr Glu Gly Phe Val Lys
        115                 120                 125

Ile Ala Asp Phe Gly Leu Cys Lys Glu Gly Met Gly Tyr Gly Asp Arg
    130                 135                 140

Thr Ser Thr Phe Cys Gly Thr Pro Glu Phe Leu Ala Pro Glu Val Leu
145                 150                 155                 160

Thr Glu Thr Ser Tyr Thr Arg Ala Val Asp Trp Trp Gly Leu Gly Val
                165                 170                 175

Leu Ile Tyr Glu Met Leu Val Gly Glu Ser Pro Phe Pro Gly Asp Asp
            180                 185                 190

Glu Glu Glu Val Phe Asp Ser Ile Val Asn Asp Glu Val Arg Tyr Pro
        195                 200                 205

Arg Phe Leu Ser Thr Glu Ala Ile Ser Ile Met Arg Arg Leu Leu Arg
    210                 215                 220

Arg Asn Pro Glu Arg Arg Leu Gly Ala Ser Glu Lys Asp Ala Glu Asp
225                 230                 235                 240

Val Lys Lys His Pro Phe Phe Arg Leu Ile Asp Trp Ser Ala Leu Met
                245                 250                 255

Asp Lys Lys Val Lys Pro Pro Phe Ile Pro Thr Ile Arg Gly Arg Glu
            260                 265                 270

Asp Val Ser Asn Phe Asp Asp Glu Phe Thr Ser Glu Ala Pro Ile Leu
        275                 280                 285

Thr Pro Pro Arg Glu Pro Arg Ile Leu Ser Glu Glu Glu Gln Glu Met
    290                 295                 300

Phe Arg Asp Phe Asp Tyr Ile Ala Asp Trp Cys
305                 310                 315

<210> SEQ ID NO 29
<211> LENGTH: 321
<212> TYPE: PRT
<213> ORGANISM: Homo sapiens

<400> SEQUENCE: 29

Lys Val Leu Leu Ala Arg His Lys Ala Glu Glu Val Phe Tyr Ala Val
1               5                   10                  15

Lys Val Leu Gln Lys Lys Ala Ile Leu Lys Lys Lys Glu Glu Lys His
                20                  25                  30

Ile Met Ser Glu Arg Asn Val Leu Leu Lys Asn Val Lys His Pro Phe
            35                  40                  45

Leu Val Gly Leu His Phe Ser Phe Gln Thr Ala Asp Lys Leu Tyr Phe
        50                  55                  60

Val Leu Asp Tyr Ile Asn Gly Gly Glu Leu Phe Tyr His Leu Gln Arg
65                  70                  75                  80

Glu Arg Cys Phe Leu Glu Pro Arg Ala Arg Phe Tyr Ala Ala Glu Ile
                85                  90                  95

Ala Ser Ala Leu Gly Tyr Leu His Ser Leu Asn Ile Val Tyr Arg Asp
            100                 105                 110

Leu Lys Pro Glu Asn Ile Leu Leu Asp Ser Gln Gly His Ile Val Leu
        115                 120                 125

Thr Asp Phe Gly Leu Cys Lys Glu Asn Ile Glu His Asn Ser Thr Thr
130                 135                 140

Ser Thr Phe Cys Gly Thr Pro Glu Tyr Leu Ala Pro Glu Val Leu His
145                 150                 155                 160

Lys Gln Pro Tyr Asp Arg Thr Val Asp Trp Trp Cys Leu Gly Ala Val
                165                 170                 175

Leu Tyr Glu Met Leu Tyr Gly Leu Pro Pro Phe Tyr Ser Arg Asn Thr
            180                 185                 190

Ala Glu Met Tyr Asp Asn Ile Leu Asn Lys Pro Leu Gln Leu Lys Pro
        195                 200                 205

Asn Ile Thr Asn Ser Ala Arg His Leu Leu Glu Gly Leu Leu Gln Lys
210                 215                 220

Asp Arg Thr Lys Arg Leu Gly Ala Lys Asp Asp Phe Met Glu Ile Lys
225                 230                 235                 240

Ser His Val Phe Phe Ser Leu Ile Asn Trp Asp Asp Leu Ile Asn Lys
                245                 250                 255

Lys Ile Thr Pro Pro Phe Asn Pro Asn Val Ser Gly Pro Asn Asp Leu
            260                 265                 270

Arg His Phe Asp Pro Glu Phe Thr Glu Glu Pro Val Pro Asn Ser Ile
        275                 280                 285

Gly Lys Ser Pro Asp Ser Val Leu Val Thr Ala Ser Val Lys Glu Ala
290                 295                 300

Ala Glu Ala Phe Leu Gly Phe Ser Tyr Ala Pro Pro Thr Asp Ser Phe
305                 310                 315                 320

Leu

<210> SEQ ID NO 30
<211> LENGTH: 322
<212> TYPE: PRT
<213> ORGANISM: Homo sapiens

<400> SEQUENCE: 30

Lys Val Leu Leu Ala Lys Arg Lys Leu Asp Gly Lys Phe Tyr Ala Val
1               5                   10                  15

Lys Val Leu Gln Lys Lys Ile Val Leu Asn Arg Lys Glu Gln Lys His
                20                  25                  30

Ile Met Ala Glu Arg Asn Val Leu Leu Lys Asn Val Lys His Pro Phe
            35                  40                  45

Leu Val Gly Leu His Tyr Ser Phe Gln Thr Thr Glu Lys Leu Tyr Phe
            50                  55                  60

Val Leu Asp Phe Val Asn Gly Gly Glu Leu Phe His Leu Gln Arg
65                  70                  75                  80

Glu Arg Ser Phe Pro Glu His Arg Ala Arg Phe Tyr Ala Ala Glu Ile
                    85                  90                  95

Ala Ser Ala Leu Gly Tyr Leu His Ser Ile Lys Ile Val Tyr Arg Asp
                100                 105                 110

Leu Lys Pro Glu Asn Ile Leu Leu Asp Ser Val Gly His Val Val Leu
            115                 120                 125

Thr Asp Phe Gly Leu Cys Lys Glu Gly Ile Ala Ile Ser Asp Thr Thr
130                 135                 140

Thr Thr Phe Cys Gly Thr Pro Glu Tyr Leu Ala Pro Glu Val Ile Arg
145                 150                 155                 160

Lys Gln Pro Tyr Asp Asn Thr Val Asp Trp Trp Cys Leu Gly Ala Val
                165                 170                 175

Leu Tyr Glu Met Leu Tyr Gly Leu Pro Pro Phe Tyr Cys Arg Asp Val
                180                 185                 190

Ala Glu Met Tyr Asp Asn Ile Leu His Lys Pro Leu Ser Leu Arg Pro
            195                 200                 205

Gly Val Ser Leu Thr Ala Trp Ser Ile Leu Glu Glu Leu Leu Glu Lys
210                 215                 220

Asp Arg Gln Asn Arg Leu Gly Ala Lys Glu Asp Phe Leu Glu Ile Gln
225                 230                 235                 240

Asn His Pro Phe Phe Glu Ser Leu Ser Trp Ala Asp Leu Val Gln Lys
                245                 250                 255

Lys Ile Pro Pro Pro Phe Asn Pro Asn Val Ala Gly Pro Asp Asp Ile
                260                 265                 270

Arg Asn Phe Asp Thr Ala Phe Thr Glu Glu Thr Val Pro Tyr Ser Val
            275                 280                 285

Cys Val Ser Ser Asp Tyr Ser Ile Val Asn Ala Ser Val Leu Glu Ala
290                 295                 300

Asp Asp Ala Phe Val Gly Phe Ser Tyr Ala Pro Pro Ser Glu Asp Leu
305                 310                 315                 320

Phe Leu

<210> SEQ ID NO 31
<211> LENGTH: 319
<212> TYPE: PRT
<213> ORGANISM: Homo sapiens

<400> SEQUENCE: 31

Lys Val Leu Leu Ala Lys Arg Lys Ser Asp Gly Ala Phe Tyr Ala Val
1               5                   10                  15

Lys Val Leu Gln Lys Lys Ser Ile Leu Lys Lys Glu Gln Ser His
            20                  25                  30

Ile Met Ala Glu Arg Ser Val Leu Leu Lys Asn Val Arg His Pro Phe
                35                  40                  45

Leu Val Gly Leu Arg Tyr Ser Phe Gln Thr Pro Glu Lys Leu Tyr Phe
            50                  55                  60

Val Leu Asp Tyr Val Asn Gly Gly Glu Leu Phe His Leu Gln Arg
65                  70                  75                  80

Glu Arg Arg Phe Leu Glu Pro Arg Ala Arg Phe Tyr Ala Ala Glu Val
                85                  90                  95

```
Ala Ser Ala Ile Gly Tyr Leu His Ser Leu Asn Ile Ile Tyr Arg Asp
            100                 105                 110

Leu Lys Pro Glu Asn Ile Leu Leu Asp Cys Gln Gly His Val Val Leu
        115                 120                 125

Thr Asp Phe Gly Leu Cys Lys Glu Gly Val Pro Glu Asp Thr Thr
    130                 135                 140

Ser Thr Phe Cys Gly Thr Pro Glu Tyr Leu Ala Pro Glu Val Leu Arg
145                 150                 155                 160

Lys Glu Pro Tyr Asp Arg Ala Val Asp Trp Trp Cys Leu Gly Ala Val
                165                 170                 175

Leu Tyr Glu Met Leu His Gly Leu Pro Pro Phe Tyr Ser Gln Asp Val
            180                 185                 190

Ser Gln Met Tyr Glu Asn Ile Leu His Gln Pro Leu Gln Ile Pro Gly
        195                 200                 205

Gly Arg Thr Val Ala Ala Cys Asp Leu Leu Gln Ser Leu Leu His Lys
    210                 215                 220

Asp Gln Arg Gln Arg Leu Gly Ser Lys Ala Asp Phe Leu Glu Ile Lys
225                 230                 235                 240

Asn His Val Phe Phe Ser Pro Ile Asn Trp Asp Asp Leu Tyr His Lys
                245                 250                 255

Arg Leu Thr Pro Pro Phe Asn Pro Asn Val Thr Gly Pro Ala Asp Leu
            260                 265                 270

Lys His Phe Asp Pro Glu Phe Thr Gln Glu Ala Val Ser Lys Ser Ile
        275                 280                 285

Gly Cys Thr Pro Asp Thr Val Ala Ser Ser Ser Gly Ala Ser Ser Ala
    290                 295                 300

Phe Leu Gly Phe Ser Tyr Ala Pro Glu Asp Asp Ile Leu Asp
305                 310                 315

<210> SEQ ID NO 32
<211> LENGTH: 317
<212> TYPE: PRT
<213> ORGANISM: Homo sapiens

<400> SEQUENCE: 32

Lys Val Met Leu Ser Glu Arg Lys Gly Thr Asp Glu Leu Tyr Ala Val
1               5                   10                  15

Lys Ile Leu Lys Lys Asp Val Val Ile Gln Asp Asp Val Glu Cys
        20                  25                  30

Thr Met Val Glu Lys Arg Val Leu Ala Leu Pro Gly Lys Pro Pro Phe
    35                  40                  45

Leu Thr Gln Leu His Ser Cys Phe Gln Thr Met Asp Arg Leu Tyr Phe
50                  55                  60

Val Met Glu Tyr Val Asn Gly Gly Asp Leu Met Tyr His Ile Gln Gln
65                  70                  75                  80

Val Gly Arg Phe Lys Glu Pro His Ala Val Phe Tyr Ala Ala Glu Ile
                85                  90                  95

Ala Ile Gly Leu Phe Phe Leu Gln Ser Lys Gly Ile Ile Tyr Arg Asp
            100                 105                 110

Leu Lys Leu Asp Asn Val Met Leu Asp Ser Glu Gly His Ile Lys Ile
        115                 120                 125

Ala Asp Phe Gly Met Cys Lys Glu Asn Ile Trp Asp Gly Val Thr Thr
    130                 135                 140

Lys Thr Phe Cys Gly Thr Pro Asp Tyr Ile Ala Pro Glu Ile Ile Ala
145                 150                 155                 160
```

```
Tyr Gln Pro Tyr Gly Lys Ser Val Asp Trp Trp Ala Phe Gly Val Leu
            165                 170                 175

Leu Tyr Glu Met Leu Ala Gly Gln Ala Pro Phe Glu Gly Glu Asp Glu
        180                 185                 190

Asp Glu Leu Phe Gln Ser Ile Met Glu His Asn Val Ala Tyr Pro Lys
    195                 200                 205

Ser Met Ser Lys Glu Ala Val Ala Ile Cys Lys Gly Leu Met Thr Lys
210                 215                 220

His Pro Gly Lys Arg Leu Gly Cys Gly Pro Glu Gly Glu Arg Asp Ile
225                 230                 235                 240

Lys Glu His Ala Phe Phe Arg Tyr Ile Asp Trp Glu Lys Leu Glu Arg
                245                 250                 255

Lys Glu Ile Gln Pro Pro Tyr Lys Pro Lys Ala Arg Asp Lys Arg Asp
            260                 265                 270

Thr Ser Asn Phe Asp Lys Glu Phe Thr Arg Gln Pro Val Glu Leu Thr
        275                 280                 285

Pro Thr Asp Lys Leu Phe Ile Met Asn Leu Asp Gln Asn Glu Phe Ala
    290                 295                 300

Gly Phe Ser Tyr Thr Asn Pro Glu Phe Val Ile Asn Val
305                 310                 315

<210> SEQ ID NO 33
<211> LENGTH: 316
<212> TYPE: PRT
<213> ORGANISM: Homo sapiens

<400> SEQUENCE: 33

Lys Val Met Leu Ser Glu Arg Lys Gly Thr Asp Glu Leu Tyr Ala Val
1               5                   10                  15

Lys Ile Leu Lys Lys Asp Val Val Ile Gln Asp Asp Asp Val Glu Cys
            20                  25                  30

Thr Met Val Glu Lys Arg Val Leu Ala Leu Pro Gly Lys Pro Pro Phe
        35                  40                  45

Leu Thr Gln Leu His Ser Cys Phe Gln Thr Met Asp Arg Leu Tyr Phe
    50                  55                  60

Val Met Glu Tyr Val Asn Gly Gly Asp Leu Met Tyr His Ile Gln Gln
65                  70                  75                  80

Val Gly Arg Phe Lys Glu Pro His Ala Val Phe Tyr Ala Ala Glu Ile
                85                  90                  95

Ala Ile Gly Leu Phe Phe Leu Gln Ser Lys Gly Ile Ile Tyr Arg Asp
            100                 105                 110

Leu Lys Leu Asp Asn Val Met Leu Asp Ser Glu Gly His Ile Lys Ile
        115                 120                 125

Ala Asp Phe Gly Met Cys Lys Glu Asn Ile Trp Asp Gly Val Thr Thr
    130                 135                 140

Lys Thr Phe Cys Gly Thr Pro Asp Tyr Ile Ala Pro Glu Ile Ile Ala
145                 150                 155                 160

Tyr Gln Pro Tyr Gly Lys Ser Val Asp Trp Trp Ala Phe Gly Val Leu
                165                 170                 175

Leu Tyr Glu Met Leu Ala Gly Gln Ala Pro Phe Glu Gly Glu Asp Glu
            180                 185                 190

Asp Glu Leu Phe Gln Ser Ile Met Glu His Asn Val Ala Tyr Pro Lys
        195                 200                 205

Ser Met Ser Lys Glu Ala Val Ala Ile Cys Lys Gly Leu Met Thr Lys
```

```
                210                 215                 220
His Pro Gly Lys Arg Leu Gly Cys Gly Pro Glu Gly Glu Arg Asp Ile
225                 230                 235                 240

Lys Glu His Ala Phe Phe Arg Tyr Ile Asp Trp Glu Lys Leu Glu Arg
                245                 250                 255

Lys Glu Ile Gln Pro Pro Tyr Lys Pro Lys Ala Cys Gly Arg Asn Ala
            260                 265                 270

Glu Asn Phe Asp Arg Phe Phe Thr Arg His Pro Pro Val Leu Thr Pro
        275                 280                 285

Pro Asp Gln Glu Val Ile Arg Asn Ile Asp Gln Ser Glu Phe Glu Gly
290                 295                 300

Phe Ser Phe Val Asn Ser Glu Phe Leu Lys Pro Glu
305                 310                 315

<210> SEQ ID NO 34
<211> LENGTH: 316
<212> TYPE: PRT
<213> ORGANISM: Homo sapiens

<400> SEQUENCE: 34

Lys Val Met Leu Ala Asp Arg Lys Gly Thr Glu Glu Leu Tyr Ala Ile
1               5                   10                  15

Lys Ile Leu Lys Lys Asp Val Val Ile Gln Asp Asp Val Glu Cys
            20                  25                  30

Thr Met Val Glu Lys Arg Val Leu Ala Leu Leu Asp Lys Pro Pro Phe
        35                  40                  45

Leu Thr Gln Leu His Ser Cys Phe Gln Thr Val Asp Arg Leu Tyr Phe
    50                  55                  60

Val Met Glu Tyr Val Asn Gly Gly Asp Leu Met Tyr His Ile Gln Gln
65                  70                  75                  80

Val Gly Lys Phe Lys Glu Pro Gln Ala Val Phe Tyr Ala Ala Glu Ile
                85                  90                  95

Ser Ile Gly Leu Phe Phe Leu His Lys Arg Gly Ile Ile Tyr Arg Asp
            100                 105                 110

Leu Lys Leu Asp Asn Val Met Leu Asp Ser Glu Gly His Ile Lys Ile
        115                 120                 125

Ala Asp Phe Gly Met Cys Lys Glu His Met Met Asp Gly Val Thr Thr
    130                 135                 140

Arg Thr Phe Cys Gly Thr Pro Asp Tyr Ile Ala Pro Glu Ile Ile Ala
145                 150                 155                 160

Tyr Gln Pro Tyr Gly Lys Ser Val Asp Trp Trp Ala Tyr Gly Val Leu
                165                 170                 175

Leu Tyr Glu Met Leu Ala Gly Gln Pro Pro Phe Asp Gly Glu Asp Glu
            180                 185                 190

Asp Glu Leu Phe Gln Ser Ile Met Glu His Asn Val Ser Tyr Pro Lys
        195                 200                 205

Ser Leu Ser Lys Glu Ala Val Ser Ile Cys Lys Gly Leu Met Thr Lys
    210                 215                 220

His Pro Ala Lys Arg Leu Gly Cys Gly Pro Glu Gly Glu Arg Asp Val
225                 230                 235                 240

Arg Glu His Ala Phe Phe Arg Arg Ile Asp Trp Glu Lys Leu Glu Asn
                245                 250                 255

Arg Glu Ile Gln Pro Pro Phe Lys Pro Lys Val Cys Gly Lys Gly Ala
            260                 265                 270
```

```
Glu Asn Phe Asp Lys Phe Phe Thr Arg Gly Gln Pro Val Leu Thr Pro
        275                 280                 285

Pro Asp Gln Leu Val Ile Ala Asn Ile Asp Gln Ser Asp Phe Glu Gly
    290                 295                 300

Phe Ser Tyr Val Asn Pro Gln Phe Val His Pro Ile
305                 310                 315

<210> SEQ ID NO 35
<211> LENGTH: 321
<212> TYPE: PRT
<213> ORGANISM: Homo sapiens

<400> SEQUENCE: 35

Lys Val Met Leu Ala Glu Arg Arg Gly Ser Asp Glu Leu Tyr Ala Ile
1               5                   10                  15

Lys Ile Leu Lys Lys Asp Val Ile Val Gln Asp Asp Val Asp Cys
            20                  25                  30

Thr Leu Val Glu Lys Arg Val Leu Ala Leu Gly Gly Arg Gly Pro Gly
            35                  40                  45

Gly Arg Pro His Phe Leu Thr Gln Leu His Ser Thr Phe Gln Thr Pro
        50                  55                  60

Asp Arg Leu Tyr Phe Val Met Glu Tyr Val Thr Gly Gly Asp Leu Met
65                  70                  75                  80

Tyr His Ile Gln Gln Leu Gly Lys Phe Lys Glu Pro His Ala Ala Phe
                85                  90                  95

Tyr Ala Ala Glu Ile Ala Ile Gly Leu Phe Phe Leu His Asn Gln Gly
            100                 105                 110

Ile Ile Tyr Arg Asp Leu Lys Leu Asp Asn Val Met Leu Asp Ala Glu
        115                 120                 125

Gly His Ile Lys Ile Thr Asp Phe Gly Met Cys Lys Glu Asn Val Phe
    130                 135                 140

Pro Gly Thr Thr Thr Arg Thr Phe Cys Gly Thr Pro Asp Tyr Ile Ala
145                 150                 155                 160

Pro Glu Ile Ile Ala Tyr Gln Pro Tyr Gly Lys Ser Val Asp Trp Trp
                165                 170                 175

Ser Phe Gly Val Leu Leu Tyr Glu Met Leu Ala Gly Gln Pro Pro Phe
            180                 185                 190

Asp Gly Glu Asp Glu Glu Leu Phe Gln Ala Ile Met Glu Gln Thr
        195                 200                 205

Val Thr Tyr Pro Lys Ser Leu Ser Arg Glu Ala Val Ala Ile Cys Lys
    210                 215                 220

Gly Phe Leu Thr Lys His Pro Gly Lys Arg Leu Gly Ser Gly Pro Asp
225                 230                 235                 240

Gly Glu Pro Thr Ile Arg Ala His Gly Phe Phe Arg Trp Ile Asp Trp
                245                 250                 255

Glu Arg Leu Glu Arg Leu Glu Ile Pro Pro Pro Phe Arg Pro Arg Pro
            260                 265                 270

Cys Gly Arg Ser Gly Glu Asn Phe Asp Lys Phe Phe Thr Arg Ala Ala
        275                 280                 285

Pro Ala Leu Thr Pro Pro Asp Arg Leu Val Leu Ala Ser Ile Asp Gln
    290                 295                 300

Ala Asp Phe Gln Gly Phe Thr Tyr Val Asn Pro Asp Phe Val His Pro
305                 310                 315                 320

Asp
```

<210> SEQ ID NO 36
<211> LENGTH: 325
<212> TYPE: PRT
<213> ORGANISM: Homo sapiens

<400> SEQUENCE: 36

```
Lys Val Leu Val Arg Leu Lys Lys Asn Asp Gln Ile Tyr Ala Met
1               5                   10                  15

Lys Val Val Lys Glu Leu Val His Asp Asp Glu Asp Ile Asp Trp
            20                  25                  30

Val Gln Thr Glu Lys His Val Phe Glu Gln Ala Ser Ser Asn Pro Phe
        35                  40                  45

Leu Val Gly Leu His Ser Cys Phe Gln Thr Thr Ser Arg Leu Phe Leu
    50                  55                  60

Val Ile Glu Tyr Val Asn Gly Gly Asp Leu Met Phe His Met Gln Arg
65                  70                  75                  80

Gln Arg Lys Leu Pro Glu Glu His Ala Arg Phe Tyr Ala Ala Glu Ile
                85                  90                  95

Cys Ile Ala Leu Asn Phe Leu His Glu Arg Gly Ile Ile Tyr Arg Asp
                100                 105                 110

Leu Lys Leu Asp Asn Val Leu Leu Asp Ala Asp Gly His Ile Lys Leu
            115                 120                 125

Thr Asp Tyr Gly Met Cys Lys Glu Gly Leu Gly Pro Gly Asp Thr Thr
130                 135                 140

Ser Thr Phe Cys Gly Thr Pro Asn Tyr Ile Ala Pro Glu Ile Leu Arg
145                 150                 155                 160

Gly Glu Glu Tyr Gly Phe Ser Val Asp Trp Trp Ala Leu Gly Val Leu
                165                 170                 175

Met Phe Glu Met Met Ala Gly Arg Ser Pro Phe Asp Ile Ile Thr Asp
            180                 185                 190

Asn Pro Asp Met Asn Thr Glu Asp Tyr Leu Phe Gln Val Ile Leu Glu
        195                 200                 205

Lys Pro Ile Arg Ile Pro Arg Phe Leu Ser Val Lys Ala Ser His Val
    210                 215                 220

Leu Lys Gly Phe Leu Asn Lys Asp Pro Lys Glu Arg Leu Gly Cys Arg
225                 230                 235                 240

Pro Gln Thr Gly Phe Ser Asp Ile Lys Ser His Ala Phe Phe Arg Ser
                245                 250                 255

Ile Asp Trp Asp Leu Leu Glu Lys Lys Gln Ala Leu Pro Pro Phe Gln
            260                 265                 270

Pro Gln Ile Thr Asp Asp Tyr Gly Leu Asp Asn Phe Asp Thr Gln Phe
        275                 280                 285

Thr Ser Glu Pro Val Gln Leu Thr Pro Asp Asp Glu Asp Ala Ile Lys
    290                 295                 300

Arg Ile Asp Gln Ser Glu Phe Glu Gly Phe Glu Tyr Ile Asn Pro Leu
305                 310                 315                 320

Leu Leu Ser Thr Glu
                325
```

<210> SEQ ID NO 37
<211> LENGTH: 327
<212> TYPE: PRT
<213> ORGANISM: Homo sapiens

<400> SEQUENCE: 37

-continued

```
Lys Val Leu Leu Val Arg Leu Lys Lys Thr Asp Arg Ile Tyr Ala Met
1               5                   10                  15

Lys Val Val Lys Glu Leu Val Asn Asp Glu Asp Ile Asp Trp
            20                  25                  30

Val Gln Thr Glu Lys His Val Phe Glu Gln Ala Ser Asn His Pro Phe
        35                  40                  45

Leu Val Gly Leu His Ser Cys Phe Gln Thr Glu Ser Arg Leu Phe Phe
    50                  55                  60

Val Ile Glu Tyr Val Asn Gly Gly Asp Leu Met Phe His Met Gln Arg
65                  70                  75                  80

Gln Arg Lys Leu Pro Glu Glu His Ala Arg Phe Tyr Ser Ala Glu Ile
                85                  90                  95

Ser Leu Ala Leu Asn Tyr Leu His Glu Arg Gly Ile Ile Tyr Arg Asp
            100                 105                 110

Leu Lys Leu Asp Asn Val Leu Leu Asp Ser Glu Gly His Ile Lys Leu
        115                 120                 125

Thr Asp Tyr Gly Met Cys Lys Glu Gly Leu Arg Pro Gly Asp Thr Thr
    130                 135                 140

Ser Thr Phe Cys Gly Thr Pro Asn Tyr Ile Ala Pro Glu Ile Leu Arg
145                 150                 155                 160

Gly Glu Asp Tyr Gly Phe Ser Val Asp Trp Trp Ala Leu Gly Val Leu
                165                 170                 175

Met Phe Glu Met Met Ala Gly Arg Ser Pro Phe Asp Ile Val Gly Ser
            180                 185                 190

Ser Asp Asn Pro Asp Gln Asn Thr Glu Asp Tyr Leu Phe Gln Val Ile
        195                 200                 205

Leu Glu Lys Gln Ile Arg Ile Pro Arg Ser Met Ser Val Lys Ala Ala
    210                 215                 220

Ser Val Leu Lys Ser Phe Leu Asn Lys Asp Pro Lys Glu Arg Leu Gly
225                 230                 235                 240

Cys Leu Pro Gln Thr Gly Phe Ala Asp Ile Gln Gly His Pro Phe Phe
                245                 250                 255

Arg Asn Val Asp Trp Asp Met Met Glu Gln Lys Gln Val Val Pro Pro
            260                 265                 270

Phe Lys Pro Asn Ile Ser Gly Glu Phe Gly Leu Asp Asn Phe Asp Ser
        275                 280                 285

Gln Phe Thr Asn Glu Arg Val Gln Leu Thr Pro Asp Asp Asp Asp Ile
    290                 295                 300

Val Arg Lys Ile Asp Gln Ser Glu Phe Glu Gly Phe Glu Tyr Ile Asn
305                 310                 315                 320

Pro Leu Leu Met Ser Ala Glu
                325
```

<210> SEQ ID NO 38
<211> LENGTH: 313
<212> TYPE: PRT
<213> ORGANISM: Homo sapiens

<400> SEQUENCE: 38

```
Lys Val Leu Leu Gly Glu Leu Lys Gly Arg Gly Glu Tyr Ser Ala Ile
1               5                   10                  15

Lys Ala Leu Lys Lys Asp Val Val Leu Ile Asp Asp Asp Val Glu Cys
            20                  25                  30

Thr Met Val Glu Lys Arg Val Leu Thr Leu Ala Ala Glu Asn Pro Phe
        35                  40                  45
```

Leu Thr His Leu Ile Cys Thr Phe Gln Thr Lys Asp His Leu Phe Phe
            50                  55                  60

Val Met Glu Phe Leu Asn Gly Gly Asp Leu Met Tyr His Ile Gln Asp
65                  70                  75                  80

Lys Gly Arg Phe Glu Leu Tyr Arg Ala Thr Phe Tyr Ala Ala Glu Ile
                85                  90                  95

Met Cys Gly Leu Gln Phe Leu His Ser Lys Gly Ile Ile Tyr Arg Asp
            100                 105                 110

Leu Lys Leu Asp Asn Val Leu Leu Asp Arg Asp Gly His Ile Lys Ile
        115                 120                 125

Ala Asp Phe Gly Met Cys Lys Glu Asn Ile Phe Gly Glu Ser Arg Ala
    130                 135                 140

Ser Thr Phe Cys Gly Thr Pro Asp Tyr Ile Ala Pro Glu Ile Leu Gln
145                 150                 155                 160

Gly Leu Lys Tyr Thr Phe Ser Val Asp Trp Trp Ser Phe Gly Val Leu
                165                 170                 175

Leu Tyr Glu Met Leu Ile Gly Gln Ser Pro Phe His Gly Asp Asp Glu
            180                 185                 190

Asp Glu Leu Phe Glu Ser Ile Arg Val Asp Thr Pro His Tyr Pro Arg
        195                 200                 205

Trp Ile Thr Lys Glu Ser Lys Asp Ile Leu Glu Lys Leu Phe Glu Arg
    210                 215                 220

Glu Pro Thr Lys Arg Leu Gly Val Thr Gly Asn Ile Lys Ile His Pro
225                 230                 235                 240

Phe Phe Lys Thr Ile Asn Trp Thr Leu Leu Glu Lys Arg Arg Leu Glu
                245                 250                 255

Pro Pro Phe Arg Pro Lys Val Lys Ser Pro Arg Asp Tyr Ser Asn Phe
            260                 265                 270

Asp Gln Glu Phe Leu Asn Glu Lys Ala Arg Leu Ser Tyr Ser Asp Lys
        275                 280                 285

Asn Leu Ile Asp Ser Met Asp Gln Ser Ala Phe Ala Gly Phe Ser Phe
    290                 295                 300

Val Asn Pro Lys Phe Glu His Leu Leu
305                 310

<210> SEQ ID NO 39
<211> LENGTH: 295
<212> TYPE: PRT
<213> ORGANISM: Homo sapiens

<400> SEQUENCE: 39

Arg Val Met Leu Val Arg His Gln Glu Thr Gly Gly His Tyr Ala Met
1               5                   10                  15

Lys Ile Leu Asn Lys Gln Lys Val Val Lys Met Lys Gln Val Glu His
            20                  25                  30

Ile Leu Asn Glu Lys Arg Ile Leu Gln Ala Ile Asp Phe Pro Phe Leu
        35                  40                  45

Val Lys Leu Gln Phe Ser Phe Lys Asp Asn Ser Tyr Leu Tyr Leu Val
    50                  55                  60

Met Glu Tyr Val Pro Gly Gly Glu Met Phe Ser Arg Leu Gln Arg Val
65                  70                  75                  80

Gly Arg Phe Ser Glu Pro His Ala Cys Phe Tyr Ala Ala Gln Val Val
                85                  90                  95

Leu Ala Val Gln Tyr Leu His Ser Leu Asp Leu Ile His Arg Asp Leu

-continued

```
                100                 105                 110
Lys Pro Glu Asn Leu Leu Ile Asp Gln Gln Gly Tyr Leu Gln Val Thr
            115                 120                 125
Asp Phe Gly Phe Ala Lys Arg Val Lys Gly Arg Thr Trp Thr Leu Cys
        130                 135                 140
Gly Thr Pro Glu Tyr Leu Ala Pro Glu Ile Ile Leu Ser Lys Gly Tyr
145                 150                 155                 160
Asn Lys Ala Val Asp Trp Trp Ala Leu Gly Val Leu Ile Tyr Glu Met
                165                 170                 175
Ala Val Gly Phe Pro Pro Phe Tyr Ala Asp Gln Pro Ile Gln Ile Tyr
            180                 185                 190
Glu Lys Ile Val Ser Gly Arg Val Arg Phe Pro Ser Lys Leu Ser Ser
        195                 200                 205
Asp Leu Lys His Leu Leu Arg Ser Leu Leu Gln Val Asp Leu Thr Lys
    210                 215                 220
Arg Phe Gly Asn Leu Arg Asn Gly Val Gly Asp Ile Lys Asn His Lys
225                 230                 235                 240
Trp Phe Ala Thr Thr Ser Trp Ile Ala Ile Tyr Glu Lys Lys Val Glu
                245                 250                 255
Ala Pro Phe Ile Pro Lys Tyr Thr Gly Pro Gly Asp Ala Ser Asn Phe
            260                 265                 270
Asp Asp Tyr Glu Glu Glu Leu Arg Ile Ser Ile Asn Glu Lys Cys
        275                 280                 285
Ala Lys Glu Phe Ser Glu Phe
    290                 295

<210> SEQ ID NO 40
<211> LENGTH: 335
<212> TYPE: PRT
<213> ORGANISM: Homo sapiens

<400> SEQUENCE: 40

Thr Val Val Leu Ala Arg Glu Leu Ala Thr Ser Arg Glu Tyr Ala Ile
1               5                  10                  15
Lys Ile Leu Glu Lys Arg His Ile Ile Lys Glu Asn Lys Val Pro Tyr
            20                  25                  30
Val Thr Arg Glu Arg Asp Val Met Ser Arg Leu Asp His Pro Phe Phe
        35                  40                  45
Val Lys Leu Tyr Phe Thr Phe Gln Asp Asp Glu Lys Leu Tyr Phe Gly
    50                  55                  60
Leu Ser Tyr Ala Lys Asn Gly Glu Leu Leu Lys Tyr Ile Arg Lys Ile
65                  70                  75                  80
Gly Ser Phe Asp Glu Thr Cys Thr Arg Phe Tyr Thr Ala Glu Ile Val
                85                  90                  95
Ser Ala Leu Glu Tyr Leu His Gly Lys Gly Ile Ile His Arg Asp Leu
            100                 105                 110
Lys Pro Glu Asn Ile Leu Leu Asn Glu Asp Met His Ile Gln Ile Thr
        115                 120                 125
Asp Phe Gly Thr Ala Lys Val Leu Ser Pro Glu Ser Lys Gln Ala Arg
    130                 135                 140
Ala Asn Ser Phe Val Gly Thr Ala Gln Tyr Val Ser Pro Glu Leu Leu
145                 150                 155                 160
Thr Glu Lys Ser Ala Cys Lys Ser Ser Asp Leu Trp Ala Leu Gly Cys
                165                 170                 175
```

```
Ile Ile Tyr Gln Leu Val Ala Gly Leu Pro Pro Phe Arg Ala Gly Asn
            180                 185                 190

Glu Tyr Leu Ile Phe Gln Lys Ile Lys Leu Glu Tyr Asp Phe Pro
        195                 200                 205

Glu Lys Phe Phe Pro Lys Ala Arg Asp Leu Val Glu Lys Leu Leu Val
    210                 215                 220

Leu Asp Ala Thr Lys Arg Leu Gly Cys Glu Glu Met Glu Gly Tyr Gly
225                 230                 235                 240

Pro Leu Lys Ala His Pro Phe Phe Glu Ser Val Thr Trp Glu Asn Leu
                245                 250                 255

His Gln Gln Thr Pro Pro Lys Leu Thr Ala Tyr Leu Pro Ala Met Ser
            260                 265                 270

Glu Asp Asp Glu Asp Cys Tyr Gly Asn Tyr Asp Asn Leu Leu Ser Gln
        275                 280                 285

Phe Gly Cys Met Gln Val Ser Ser Ser Ser Ser His Ser Leu Ser
    290                 295                 300

Ala Ser Asp Thr Gly Leu Pro Gln Arg Ser Gly Ser Asn Ile Glu Gln
305                 310                 315                 320

Tyr Ile His Asp Leu Asp Ser Asn Ser Phe Glu Leu Asp Leu Gln
                325                 330                 335

<210> SEQ ID NO 41
<211> LENGTH: 12
<212> TYPE: PRT
<213> ORGANISM: Artificial Sequence
<220> FEATURE:
<223> OTHER INFORMATION: Consensus activation or T-loop
<220> FEATURE:
<221> NAME/KEY: MISC_FEATURE
<222> LOCATION: (6)..(7)
<223> OTHER INFORMATION: Any amino acid residue
<220> FEATURE:
<221> NAME/KEY: MISC_FEATURE
<222> LOCATION: (9)..(9)
<223> OTHER INFORMATION: Any amino acid residue

<400> SEQUENCE: 41

Thr Phe Cys Gly Thr Xaa Xaa Tyr Xaa Ala Pro Asp
1               5                   10

<210> SEQ ID NO 42
<211> LENGTH: 6
<212> TYPE: PRT
<213> ORGANISM: Artificial Sequence
<220> FEATURE:
<223> OTHER INFORMATION: Consensus hydrophobic motif
<220> FEATURE:
<221> NAME/KEY: MISC_FEATURE
<222> LOCATION: (2)..(3)
<223> OTHER INFORMATION: Any amino acid residue

<400> SEQUENCE: 42

Phe Xaa Xaa Phe Ser Tyr
1               5

<210> SEQ ID NO 43
<211> LENGTH: 12
<212> TYPE: PRT
<213> ORGANISM: Artificial Sequence
<220> FEATURE:
<223> OTHER INFORMATION: Second consensus activation or T-loop
<220> FEATURE:
<221> NAME/KEY: MISC_FEATURE
<222> LOCATION: (6)..(7)
<223> OTHER INFORMATION: Any amino acid residue
```

```
<220> FEATURE:
<221> NAME/KEY: MISC_FEATURE
<222> LOCATION: (9)..(9)
<223> OTHER INFORMATION: Any amino acid residue

<400> SEQUENCE: 43

Thr Leu Cys Gly Thr Xaa Xaa Tyr Xaa Ala Pro Glu
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Second consensus hydrophobic motif
<220> FEATURE:
<221> NAME/KEY: MISC_FEATURE
<222> LOCATION: (2)..(3)
<223> OTHER INFORMATION: Any amino acid residue

<400> SEQUENCE: 44

Phe Xaa Xaa Tyr Thr Phe
1               5

<210> SEQ ID NO 45
<211> LENGTH: 12
<212> TYPE: PRT
<213> ORGANISM: Homo sapiens

<400> SEQUENCE: 45

Thr Phe Cys Gly Thr Pro Glu Tyr Leu Ala Pro Glu
1               5                   10

<210> SEQ ID NO 46
<211> LENGTH: 6
<212> TYPE: PRT
<213> ORGANISM: Homo sapiens

<400> SEQUENCE: 46

Phe Pro Gln Phe Ser Tyr
1               5

<210> SEQ ID NO 47
<211> LENGTH: 12
<212> TYPE: PRT
<213> ORGANISM: Homo sapiens

<400> SEQUENCE: 47

Thr Phe Cys Gly Thr Pro Glu Tyr Leu Ala Pro Glu
1               5                   10

<210> SEQ ID NO 48
<211> LENGTH: 6
<212> TYPE: PRT
<213> ORGANISM: Homo sapiens

<400> SEQUENCE: 48

Phe Pro Gln Phe Ser Tyr
1               5

<210> SEQ ID NO 49
<211> LENGTH: 12
<212> TYPE: PRT
<213> ORGANISM: Homo sapiens

<400> SEQUENCE: 49
```

-continued

Thr Phe Cys Gly Thr Pro Glu Tyr Leu Ala Pro Glu
1               5                   10

<210> SEQ ID NO 50
<211> LENGTH: 6
<212> TYPE: PRT
<213> ORGANISM: Homo sapiens

<400> SEQUENCE: 50

Phe Pro Gln Phe Ser Tyr
1               5

<210> SEQ ID NO 51
<211> LENGTH: 12
<212> TYPE: PRT
<213> ORGANISM: Homo sapiens

<400> SEQUENCE: 51

Thr Phe Cys Gly Thr Pro Glu Tyr Leu Ala Pro Glu
1               5                   10

<210> SEQ ID NO 52
<211> LENGTH: 6
<212> TYPE: PRT
<213> ORGANISM: Homo sapiens

<400> SEQUENCE: 52

Phe Leu Gly Phe Ser Tyr
1               5

<210> SEQ ID NO 53
<211> LENGTH: 12
<212> TYPE: PRT
<213> ORGANISM: Homo sapiens

<400> SEQUENCE: 53

Thr Phe Cys Gly Thr Pro Glu Tyr Leu Ala Pro Glu
1               5                   10

<210> SEQ ID NO 54
<211> LENGTH: 6
<212> TYPE: PRT
<213> ORGANISM: Homo sapiens

<400> SEQUENCE: 54

Phe Leu Gly Phe Ser Tyr
1               5

<210> SEQ ID NO 55
<211> LENGTH: 12
<212> TYPE: PRT
<213> ORGANISM: Homo sapiens

<400> SEQUENCE: 55

Thr Phe Cys Gly Thr Pro Glu Tyr Leu Ala Pro Glu
1               5                   10

<210> SEQ ID NO 56
<211> LENGTH: 6
<212> TYPE: PRT
<213> ORGANISM: Homo sapiens

<400> SEQUENCE: 56

Phe Leu Gly Phe Ser Tyr
1               5

```
<210> SEQ ID NO 57
<211> LENGTH: 12
<212> TYPE: PRT
<213> ORGANISM: Homo sapiens

<400> SEQUENCE: 57

Thr Phe Cys Gly Thr Pro Asp Tyr Ile Ala Pro Glu
1               5                   10

<210> SEQ ID NO 58
<211> LENGTH: 6
<212> TYPE: PRT
<213> ORGANISM: Homo sapiens

<400> SEQUENCE: 58

Phe Glu Gly Phe Ser Tyr
1               5

<210> SEQ ID NO 59
<211> LENGTH: 12
<212> TYPE: PRT
<213> ORGANISM: Homo sapiens

<400> SEQUENCE: 59

Thr Phe Cys Gly Thr Pro Asp Tyr Ile Ala Pro Glu
1               5                   10

<210> SEQ ID NO 60
<211> LENGTH: 6
<212> TYPE: PRT
<213> ORGANISM: Homo sapiens

<400> SEQUENCE: 60

Phe Ala Gly Phe Ser Tyr
1               5

<210> SEQ ID NO 61
<211> LENGTH: 12
<212> TYPE: PRT
<213> ORGANISM: Homo sapiens

<400> SEQUENCE: 61

Thr Phe Cys Gly Thr Pro Asp Tyr Ile Ala Pro Glu
1               5                   10

<210> SEQ ID NO 62
<211> LENGTH: 6
<212> TYPE: PRT
<213> ORGANISM: Homo sapiens

<400> SEQUENCE: 62

Phe Glu Gly Phe Ser Phe
1               5

<210> SEQ ID NO 63
<211> LENGTH: 12
<212> TYPE: PRT
<213> ORGANISM: Homo sapiens

<400> SEQUENCE: 63

Thr Phe Cys Gly Thr Pro Asp Tyr Ile Ala Pro Glu
1               5                   10
```

```
<210> SEQ ID NO 64
<211> LENGTH: 6
<212> TYPE: PRT
<213> ORGANISM: Homo sapiens

<400> SEQUENCE: 64

Phe Gly Gly Phe Thr Tyr
1               5

<210> SEQ ID NO 65
<211> LENGTH: 12
<212> TYPE: PRT
<213> ORGANISM: Homo sapiens

<400> SEQUENCE: 65

Thr Phe Cys Gly Thr Pro Asp Tyr Ile Ala Pro Glu
1               5                   10

<210> SEQ ID NO 66
<211> LENGTH: 6
<212> TYPE: PRT
<213> ORGANISM: Homo sapiens

<400> SEQUENCE: 66

Phe Ala Gly Phe Ser Phe
1               5

<210> SEQ ID NO 67
<211> LENGTH: 12
<212> TYPE: PRT
<213> ORGANISM: Homo sapiens

<400> SEQUENCE: 67

Thr Phe Cys Gly Thr Pro Asn Tyr Ile Ala Pro Glu
1               5                   10

<210> SEQ ID NO 68
<211> LENGTH: 6
<212> TYPE: PRT
<213> ORGANISM: Homo sapiens

<400> SEQUENCE: 68

Phe Glu Gly Phe Glu Tyr
1               5

<210> SEQ ID NO 69
<211> LENGTH: 12
<212> TYPE: PRT
<213> ORGANISM: Homo sapiens

<400> SEQUENCE: 69

Thr Phe Cys Gly Thr Pro Asn Tyr Ile Ala Pro Glu
1               5                   10

<210> SEQ ID NO 70
<211> LENGTH: 6
<212> TYPE: PRT
<213> ORGANISM: Homo sapiens

<400> SEQUENCE: 70

Phe Glu Gly Phe Glu Tyr
1               5

<210> SEQ ID NO 71
<211> LENGTH: 12
```

```
<212> TYPE: PRT
<213> ORGANISM: Homo sapiens

<400> SEQUENCE: 71

Thr Phe Cys Gly Thr Pro Glu Phe Leu Ala Pro Glu
1               5                   10

<210> SEQ ID NO 72
<211> LENGTH: 6
<212> TYPE: PRT
<213> ORGANISM: Homo sapiens

<400> SEQUENCE: 72

Phe Leu Asp Phe Asp Phe
1               5

<210> SEQ ID NO 73
<211> LENGTH: 12
<212> TYPE: PRT
<213> ORGANISM: Homo sapiens

<400> SEQUENCE: 73

Thr Phe Cys Gly Thr Pro Glu Phe Leu Ala Pro Glu
1               5                   10

<210> SEQ ID NO 74
<211> LENGTH: 6
<212> TYPE: PRT
<213> ORGANISM: Homo sapiens

<400> SEQUENCE: 74

Phe Arg Asp Phe Asp Tyr
1               5

<210> SEQ ID NO 75
<211> LENGTH: 12
<212> TYPE: PRT
<213> ORGANISM: Homo sapiens

<400> SEQUENCE: 75

Thr Phe Cys Gly Thr Ile Glu Tyr Met Ala Pro Glu
1               5                   10

<210> SEQ ID NO 76
<211> LENGTH: 6
<212> TYPE: PRT
<213> ORGANISM: Homo sapiens

<400> SEQUENCE: 76

Phe Leu Gly Phe Thr Tyr
1               5

<210> SEQ ID NO 77
<211> LENGTH: 12
<212> TYPE: PRT
<213> ORGANISM: Homo sapiens

<400> SEQUENCE: 77

Thr Phe Cys Gly Thr Ile Glu Tyr Met Ala Pro Glu
1               5                   10

<210> SEQ ID NO 78
<211> LENGTH: 6
<212> TYPE: PRT
<213> ORGANISM: Homo sapiens
```

```
<400> SEQUENCE: 78

Phe Leu Gly Phe Thr Tyr
1               5

<210> SEQ ID NO 79
<211> LENGTH: 12
<212> TYPE: PRT
<213> ORGANISM: Homo sapiens

<400> SEQUENCE: 79

Ser Phe Cys Gly Thr Val Glu Tyr Met Ala Pro Glu
1               5                   10

<210> SEQ ID NO 80
<211> LENGTH: 6
<212> TYPE: PRT
<213> ORGANISM: Homo sapiens

<400> SEQUENCE: 80

Phe Arg Gly Phe Ser Phe
1               5

<210> SEQ ID NO 81
<211> LENGTH: 12
<212> TYPE: PRT
<213> ORGANISM: Homo sapiens

<400> SEQUENCE: 81

Ser Phe Cys Gly Thr Val Glu Tyr Met Ala Pro Glu
1               5                   10

<210> SEQ ID NO 82
<211> LENGTH: 6
<212> TYPE: PRT
<213> ORGANISM: Homo sapiens

<400> SEQUENCE: 82

Phe Arg Asp Phe Ser Phe
1               5

<210> SEQ ID NO 83
<211> LENGTH: 12
<212> TYPE: PRT
<213> ORGANISM: Homo sapiens

<400> SEQUENCE: 83

Ser Phe Cys Gly Thr Ile Glu Tyr Met Ala Pro Glu
1               5                   10

<210> SEQ ID NO 84
<211> LENGTH: 6
<212> TYPE: PRT
<213> ORGANISM: Homo sapiens

<400> SEQUENCE: 84

Phe Arg Gly Phe Ser Phe
1               5

<210> SEQ ID NO 85
<211> LENGTH: 12
<212> TYPE: PRT
<213> ORGANISM: Homo sapiens

<400> SEQUENCE: 85
```

-continued

Ser Phe Cys Gly Thr Ile Glu Tyr Met Ala Pro Asp
1               5                  10

<210> SEQ ID NO 86
<211> LENGTH: 6
<212> TYPE: PRT
<213> ORGANISM: Homo sapiens

<400> SEQUENCE: 86

Phe Gln Gly Tyr Ser Phe
1               5

<210> SEQ ID NO 87
<211> LENGTH: 12
<212> TYPE: PRT
<213> ORGANISM: Homo sapiens

<400> SEQUENCE: 87

Ser Phe Cys Gly Thr Ile Glu Tyr Met Ala Pro Glu
1               5                  10

<210> SEQ ID NO 88
<211> LENGTH: 6
<212> TYPE: PRT
<213> ORGANISM: Homo sapiens

<400> SEQUENCE: 88

Phe Gln Gly Tyr Ser Phe
1               5

<210> SEQ ID NO 89
<211> LENGTH: 12
<212> TYPE: PRT
<213> ORGANISM: Homo sapiens

<400> SEQUENCE: 89

Ser Phe Val Gly Thr Ala Gln Tyr Val Ser Pro Glu
1               5                  10

<210> SEQ ID NO 90
<211> LENGTH: 354
<212> TYPE: PRT
<213> ORGANISM: Homo sapiens

<400> SEQUENCE: 90

Met Asp Gly Thr Ala Ala Glu Pro Arg Pro Gly Ala Gly Ser Leu Gln
1               5                  10                  15

His Ala Gln Pro Pro Pro Gln Pro Arg Lys Lys Arg Pro Glu Asp Phe
            20                  25                  30

Lys Phe Gly Lys Ile Leu Gly Glu Gly Ser Phe Ser Thr Val Val Leu
        35                  40                  45

Ala Arg Glu Leu Ala Thr Ser Arg Glu Tyr Ala Ile Lys Ile Leu Glu
    50                  55                  60

Lys Arg His Ile Ile Lys Glu Asn Lys Val Pro Tyr Val Thr Arg Glu
65                  70                  75                  80

Arg Asp Val Met Ser Arg Leu Asp His Pro Phe Phe Val Lys Leu Tyr
                85                  90                  95

Phe Thr Phe Gln Asp Asp Glu Lys Leu Tyr Phe Gly Leu Ser Tyr Ala
            100                 105                 110

Lys Asn Gly Glu Leu Leu Lys Tyr Ile Arg Lys Ile Gly Ser Phe Asp
        115                 120                 125

```
Glu Thr Cys Thr Arg Phe Tyr Thr Ala Glu Ile Val Ser Ala Leu Glu
    130                 135                 140

Tyr Leu His Gly Lys Gly Ile Ile His Arg Asp Leu Lys Pro Glu Asn
145                 150                 155                 160

Ile Leu Leu Asn Glu Asp Met His Ile Gln Ile Thr Asp Phe Gly Thr
                165                 170                 175

Ala Lys Val Leu Ser Pro Glu Ser Lys Gln Ala Arg Ala Asn Ser Phe
            180                 185                 190

Val Gly Thr Ala Gln Tyr Val Ser Pro Glu Leu Leu Thr Glu Lys Ser
        195                 200                 205

Ala Cys Lys Ser Ser Asp Leu Trp Ala Leu Gly Cys Ile Ile Tyr Gln
    210                 215                 220

Leu Val Ala Gly Leu Pro Pro Phe Arg Ala Gly Asn Glu Tyr Leu Ile
225                 230                 235                 240

Phe Gln Lys Ile Ile Lys Leu Glu Tyr Asp Phe Pro Glu Lys Phe Phe
                245                 250                 255

Pro Lys Ala Arg Asp Leu Val Glu Lys Leu Leu Val Leu Asp Ala Thr
            260                 265                 270

Lys Arg Leu Gly Cys Glu Glu Met Glu Gly Tyr Gly Pro Leu Lys Ala
        275                 280                 285

His Pro Phe Phe Glu Ser Val Thr Trp Glu Asn Leu His Gln Gln Thr
    290                 295                 300

Pro Pro Lys Leu Thr Ala Tyr Leu Pro Ala Met Ser Glu Asp Asp Glu
305                 310                 315                 320

Asp Cys Tyr Gly Asn Tyr Asp Asn Leu Leu Ser Gln Phe Gly Cys Met
                325                 330                 335

Gln Val Ser Ser Ser Ser Ser His Ser Leu Ser Ala Ser Asp Thr
            340                 345                 350

Gly Leu

<210> SEQ ID NO 91
<211> LENGTH: 215
<212> TYPE: PRT
<213> ORGANISM: Homo sapiens

<400> SEQUENCE: 91

Lys Val Phe Gln Val Arg Lys Val Thr Gly Ala Asn Thr Gly Lys Ile
1               5                   10                  15

Phe Ala Met Lys Val Leu Lys Lys Ala Met Ile Val Arg Asn Ala Lys
                20                  25                  30

Asp Thr Ala His Thr Lys Ala Glu Arg Asn Ile Leu Glu Glu Val Lys
            35                  40                  45

His Pro Phe Ile Val Asp Leu Ile Tyr Ala Phe Gln Thr Gly Gly Lys
        50                  55                  60

Leu Tyr Leu Ile Leu Glu Tyr Leu Ser Gly Gly Glu Leu Phe Met Gln
65                  70                  75                  80

Leu Glu Arg Glu Gly Ile Phe Met Glu Asp Thr Ala Cys Phe Tyr Leu
                85                  90                  95

Ala Glu Ile Ser Met Ala Leu Gly His Leu His Gln Lys Gly Ile Ile
            100                 105                 110

Tyr Arg Asp Leu Lys Pro Glu Asn Ile Met Leu Asn His Gln Gly His
        115                 120                 125

Val Lys Leu Thr Asp Phe Gly Leu Cys Lys Glu Ser Ile His Asp Gly
    130                 135                 140
```

```
Thr Val Thr His Thr Phe Cys Gly Thr Ile Glu Tyr Met Ala Pro Glu
145                 150                 155                 160

Ile Leu Met Arg Ser Gly His Asn Arg Ala Val Asp Trp Trp Ser Leu
            165                 170                 175

Gly Ala Leu Met Tyr Asp Met Leu Thr Gly Ala Pro Pro Phe Thr Gly
                180                 185                 190

Glu Asn Arg Lys Lys Thr Ile Asp Lys Ile Leu Lys Cys Lys Leu Asn
            195                 200                 205

Leu Pro Pro Tyr Leu Thr Gln
        210             215

<210> SEQ ID NO 92
<211> LENGTH: 4
<212> TYPE: PRT
<213> ORGANISM: Artificial Sequence
<220> FEATURE:
<223> OTHER INFORMATION: Interacting peptide I
<220> FEATURE:
<221> NAME/KEY: MISC_FEATURE
<222> LOCATION: (1)..(1)
<223> OTHER INFORMATION: Phe or Tyr
<220> FEATURE:
<221> NAME/KEY: MISC_FEATURE
<222> LOCATION: (4)..(4)
<223> OTHER INFORMATION: Phe or Tyr
<220> FEATURE:
<221> NAME/KEY: MISC_FEATURE
<222> LOCATION: (2)..(3)
<223> OTHER INFORMATION: Any amino acid residue

<400> SEQUENCE: 92

Xaa Xaa Xaa Xaa
1

<210> SEQ ID NO 93
<211> LENGTH: 6
<212> TYPE: PRT
<213> ORGANISM: Artificial Sequence
<220> FEATURE:
<223> OTHER INFORMATION: Interacting polypeptide II
<220> FEATURE:
<221> NAME/KEY: MISC_FEATURE
<222> LOCATION: (1)..(1)
<223> OTHER INFORMATION: Phe or Tyr
<220> FEATURE:
<221> NAME/KEY: MISC_FEATURE
<222> LOCATION: (4)..(4)
<223> OTHER INFORMATION: Phe or Tyr
<220> FEATURE:
<221> NAME/KEY: MISC_FEATURE
<222> LOCATION: (6)..(6)
<223> OTHER INFORMATION: Phe or Tyr
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (5)..(5)
<223> OTHER INFORMATION: Any amino acid residue

<400> SEQUENCE: 93

Xaa Xaa Xaa Xaa Xaa Xaa
1               5

<210> SEQ ID NO 94
<211> LENGTH: 6
<212> TYPE: PRT
<213> ORGANISM: Artificial Sequence
```

```
<220> FEATURE:
<223> OTHER INFORMATION: Interacting polypeptide III
<220> FEATURE:
<221> NAME/KEY: MISC_FEATURE
<222> LOCATION: (1)..(1)
<223> OTHER INFORMATION: Phe or Tyr
<220> FEATURE:
<221> NAME/KEY: MISC_FEATURE
<222> LOCATION: (4)..(4)
<223> OTHER INFORMATION: Phe or Tyr
<220> FEATURE:
<221> NAME/KEY: MISC_FEATURE
<222> LOCATION: (6)..(6)
<223> OTHER INFORMATION: Phe or Tyr
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (5)..(5)
<223> OTHER INFORMATION: Asp or Glu

<400> SEQUENCE: 94

Xaa Xaa Xaa Xaa Xaa Xaa
1               5

<210> SEQ ID NO 95
<211> LENGTH: 6
<212> TYPE: PRT
<213> ORGANISM: Artificial Sequence
<220> FEATURE:
<223> OTHER INFORMATION: Interacting polypeptide IV
<220> FEATURE:
<221> NAME/KEY: MISC_FEATURE
<222> LOCATION: (1)..(1)
<223> OTHER INFORMATION: Phe or Tyr
<220> FEATURE:
<221> NAME/KEY: MISC_FEATURE
<222> LOCATION: (4)..(4)
<223> OTHER INFORMATION: Phe or Tyr
<220> FEATURE:
<221> NAME/KEY: MISC_FEATURE
<222> LOCATION: (6)..(6)
<223> OTHER INFORMATION: Phe or Tyr
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (5)..(5)
<223> OTHER INFORMATION: Phospho Ser or Phospho Thr

<400> SEQUENCE: 95

Xaa Xaa Xaa Xaa Xaa Xaa
1               5

<210> SEQ ID NO 96
<211> LENGTH: 11
<212> TYPE: PRT
<213> ORGANISM: Artificial Sequence
<220> FEATURE:
<223> OTHER INFORMATION: peptide substrate Crosstide

<400> SEQUENCE: 96

Gly Arg Pro Arg Thr Ser Ser Phe Ala Glu Gly
1               5                   10

<210> SEQ ID NO 97
<211> LENGTH: 7
<212> TYPE: PRT
<213> ORGANISM: Artificial Sequence
```

```
<220> FEATURE:
<223> OTHER INFORMATION: Peptide substrate Kemptide

<400> SEQUENCE: 97

Leu Arg Arg Ala Ser Leu Gly
1               5

<210> SEQ ID NO 98
<211> LENGTH: 11
<212> TYPE: PRT
<213> ORGANISM: Artificial Sequence
<220> FEATURE:
<223> OTHER INFORMATION: Peptide substrate CREBtide

<400> SEQUENCE: 98

Glu Ile Leu Ser Arg Arg Pro Ser Tyr Arg Lys
1               5                   10

<210> SEQ ID NO 99
<211> LENGTH: 4
<212> TYPE: PRT
<213> ORGANISM: Artificial Sequence
<220> FEATURE:
<223> OTHER INFORMATION: Preferred interaction motif I
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (4)..(4)
<223> OTHER INFORMATION: Phe or Tyr

<400> SEQUENCE: 99

Phe Xaa Xaa Xaa
1

<210> SEQ ID NO 100
<211> LENGTH: 6
<212> TYPE: PRT
<213> ORGANISM: Artificial Sequence
<220> FEATURE:
<223> OTHER INFORMATION: Phosphorylation site
<220> FEATURE:
<221> NAME/KEY: MISC_FEATURE
<222> LOCATION: (2)..(2)
<223> OTHER INFORMATION: Any amino acid residue
<220> FEATURE:
<221> NAME/KEY: MISC_FEATURE
<222> LOCATION: (4)..(4)
<223> OTHER INFORMATION: Any amino acid residue
<220> FEATURE:
<221> NAME/KEY: MISC_FEATURE
<222> LOCATION: (5)..(5)
<223> OTHER INFORMATION: Any amino acid residue
<220> FEATURE:
<221> NAME/KEY: MISC_FEATURE
<222> LOCATION: (6)..(6)
<223> OTHER INFORMATION: Ser or Thr

<400> SEQUENCE: 100

Arg Xaa Arg Xaa Xaa Xaa
1               5

<210> SEQ ID NO 101
<211> LENGTH: 4
<212> TYPE: PRT
<213> ORGANISM: Artificial Sequence
<220> FEATURE:
<223> OTHER INFORMATION: Interaction motif for large hyrophobic pocket
      protein kinases
```

```
<220> FEATURE:
<221> NAME/KEY: MISC_FEATURE
<222> LOCATION: (2)..(2)
<223> OTHER INFORMATION: Any amino acid residue

<400> SEQUENCE: 101

Phe Xaa Phe Pro
1

<210> SEQ ID NO 102
<211> LENGTH: 289
<212> TYPE: PRT
<213> ORGANISM: Homo sapiens

<400> SEQUENCE: 102

Pro Pro Gln Pro Arg Lys Lys Arg Pro Glu Asp Phe Lys Phe Gly Lys
1               5                   10                  15

Ile Leu Gly Glu Gly Ser Phe Ser Thr Val Val Leu Ala Arg Glu Leu
            20                  25                  30

Ala Thr Ser Arg Glu Tyr Ala Ile Lys Ile Leu Glu Lys Arg His Ile
        35                  40                  45

Ile Lys Glu Asn Lys Val Pro Tyr Val Thr Arg Glu Arg Asp Val Met
50                  55                  60

Ser Arg Leu Asp His Pro Phe Phe Val Lys Leu Tyr Phe Thr Phe Gln
65                  70                  75                  80

Asp Asp Glu Lys Leu Tyr Phe Gly Leu Ser Tyr Ala Lys Asn Gly Glu
                85                  90                  95

Leu Leu Lys Tyr Ile Arg Lys Ile Gly Ser Phe Asp Glu Thr Cys Thr
            100                 105                 110

Arg Phe Tyr Thr Ala Glu Ile Val Ser Ala Leu Glu Tyr Leu His Gly
        115                 120                 125

Lys Gly Ile Ile His Arg Asp Leu Lys Pro Glu Asn Ile Leu Leu Asn
    130                 135                 140

Glu Asp Met His Ile Gln Ile Thr Asp Phe Gly Thr Ala Lys Val Leu
145                 150                 155                 160

Ser Pro Glu Ser Lys Gln Ala Arg Ala Asn Ser Phe Val Gly Thr Ala
                165                 170                 175

Gln Tyr Val Ser Pro Glu Leu Leu Thr Glu Lys Ser Ala Cys Lys Ser
            180                 185                 190

Ser Asp Leu Trp Ala Leu Gly Cys Ile Ile Tyr Gln Leu Val Ala Gly
        195                 200                 205

Leu Pro Pro Phe Arg Ala Gly Asn Glu Tyr Leu Ile Phe Gln Lys Ile
    210                 215                 220

Ile Lys Leu Glu Tyr Asp Phe Pro Glu Lys Phe Phe Pro Lys Ala Arg
225                 230                 235                 240

Asp Leu Val Glu Lys Leu Leu Val Leu Asp Ala Thr Lys Arg Leu Gly
                245                 250                 255

Cys Glu Glu Met Glu Gly Tyr Gly Pro Leu Lys Ala His Pro Phe Phe
            260                 265                 270

Glu Ser Val Thr Trp Glu Asn Leu His Gln Gln Thr Pro Pro Lys Leu
        275                 280                 285

Thr

<210> SEQ ID NO 103
<211> LENGTH: 286
<212> TYPE: PRT
<213> ORGANISM: Homo sapiens
```

-continued

<400> SEQUENCE: 103

Thr Pro Ser Gln Asn Thr Ala Gln Leu Asp Gln Phe Asp Arg Ile Lys
1               5                   10                  15

Thr Leu Gly Thr Gly Ser Phe Gly Arg Val Met Leu Val Lys His Lys
            20                  25                  30

Glu Ser Gly Asn His Tyr Ala Met Lys Ile Leu Asp Lys Gln Lys Val
        35                  40                  45

Val Lys Leu Lys Gln Ile Glu His Thr Leu Asn Glu Lys Arg Ile Leu
    50                  55                  60

Gln Ala Val Asn Phe Pro Phe Leu Val Lys Leu Glu Phe Ser Phe Lys
65                  70                  75                  80

Asp Asn Ser Asn Leu Tyr Met Val Met Glu Tyr Val Ala Gly Gly Glu
                85                  90                  95

Met Phe Ser His Leu Arg Arg Ile Gly Arg Phe Ser Glu Pro His Ala
            100                 105                 110

Arg Phe Tyr Ala Ala Gln Ile Val Leu Thr Phe Glu Tyr Leu His Ser
        115                 120                 125

Leu Asp Leu Ile Tyr Arg Asp Leu Lys Pro Glu Asn Ile Leu Leu Ile
    130                 135                 140

Asp Gln Gln Gly Tyr Ile Gln Val Thr Asp Phe Gly Phe Ala Lys Arg
145                 150                 155                 160

Val Lys Gly Arg Thr Trp Thr Leu Cys Gly Thr Pro Glu Tyr Leu Ala
                165                 170                 175

Pro Glu Ile Ile Leu Ser Lys Gly Tyr Asn Lys Ala Val Asp Trp Trp
            180                 185                 190

Ala Leu Gly Val Leu Ile Tyr Glu Met Ala Ala Gly Tyr Pro Pro Phe
        195                 200                 205

Phe Ala Asp Gln Pro Ile Gln Ile Tyr Glu Lys Ile Val Ser Gly Lys
    210                 215                 220

Val Arg Phe Pro Ser His Phe Ser Ser Asp Leu Lys Asp Leu Leu Arg
225                 230                 235                 240

Asn Leu Leu Gln Val Asp Leu Thr Lys Arg Phe Gly Asn Leu Lys Asn
                245                 250                 255

Gly Val Asn Asp Ile Lys Asn His Lys Trp Phe Ala Thr Thr Asp Trp
            260                 265                 270

Ile Ala Ile Tyr Gln Arg Lys Val Glu Ala Pro Phe Ile Pro
        275                 280                 285

<210> SEQ ID NO 104
<211> LENGTH: 18
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: Phospho threonine

<400> SEQUENCE: 104

Ser Glu Ser Ala Asn Gln Val Phe Leu Gly Phe Xaa Tyr Val Ala Pro
1               5                   10                  15

Ser Val

<210> SEQ ID NO 105
<211> LENGTH: 18
<212> TYPE: PRT
<213> ORGANISM: Homo sapiens -continued

<400> SEQUENCE: 105

Ser Glu Ser Ala Asn Gln Val Phe Leu Gly Phe Thr Tyr Val Ala Pro
1               5                   10                  15

Ser Val

<210> SEQ ID NO 106
<211> LENGTH: 88
<212> TYPE: DNA
<213> ORGANISM: Artificial Sequence
<220> FEATURE:
<223> OTHER INFORMATION: PCR primer 5'

<400> SEQUENCE: 106
ggatcctata aatatggcac atcatcatca tcatcatctg gaagttctgt tccaggggcc       60
catggacggc actgcagccg agcctcgg                                          88

<210> SEQ ID NO 107
<211> LENGTH: 36
<212> TYPE: DNA
<213> ORGANISM: Artificial Sequence
<220> FEATURE:
<223> OTHER INFORMATION: PCR primer 3'

<400> SEQUENCE: 107
ggatcctcag gtgagcttcg gaggcgtctg ctggtg                                 36

<210> SEQ ID NO 108
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 108

Lys Thr Phe Cys Gly Thr Pro Glu Tyr Leu Ala Pro Glu Val Arg Arg
1               5                   10                  15

<210> SEQ ID NO 109
<211> LENGTH: 506
<212> TYPE: PRT
<213> ORGANISM: Homo sapiens

<400> SEQUENCE: 109

Met Asp Gly Thr Ala Ala Glu Pro Arg Pro Gly Ala Gly Ser Leu Gln
1               5                   10                  15

His Ala Gln Pro Pro Pro Gln Pro Arg Lys Lys Arg Pro Glu Asp Phe
                20                  25                  30

Lys Phe Gly Lys Ile Leu Gly Glu Gly Ser Phe Ser Thr Val Val Leu
        35                  40                  45

Ala Arg Glu Leu Ala Thr Ser Arg Glu Tyr Ala Ile Lys Ile Leu Glu
    50                  55                  60

Lys Arg His Ile Ile Lys Glu Asn Lys Val Pro Tyr Val Thr Arg Glu
65                  70                  75                  80

Arg Asp Val Met Ser Arg Leu Asp His Pro Phe Phe Val Lys Leu Tyr
                85                  90                  95

Phe Thr Phe Gln Asp Asp Glu Lys Leu Tyr Phe Gly Leu Ser Tyr Ala
                100                 105                 110

Lys Asn Gly Glu Leu Leu Lys Tyr Ile Arg Lys Ile Gly Ser Phe Asp
        115                 120                 125

-continued

```
Glu Thr Cys Thr Arg Phe Tyr Thr Ala Glu Ile Val Ser Ala Leu Glu
    130                 135                 140
Tyr Leu His Gly Lys Gly Ile Ile His Arg Asp Leu Lys Pro Glu Asn
145                 150                 155                 160
Ile Leu Leu Asn Glu Asp Met His Ile Gln Ile Thr Asp Phe Gly Thr
                165                 170                 175
Ala Lys Val Leu Ser Pro Glu Ser Lys Gln Ala Arg Ala Asn Ser Phe
            180                 185                 190
Val Gly Thr Ala Gln Tyr Val Ser Pro Glu Leu Leu Thr Glu Lys Ser
        195                 200                 205
Ala Cys Lys Ser Ser Asp Leu Trp Ala Leu Gly Cys Ile Ile Tyr Gln
    210                 215                 220
Leu Val Ala Gly Leu Pro Pro Phe Arg Ala Gly Asn Glu Tyr Leu Ile
225                 230                 235                 240
Phe Gln Lys Ile Ile Lys Leu Glu Tyr Asp Phe Pro Glu Lys Phe Phe
                245                 250                 255
Pro Lys Ala Arg Asp Leu Val Glu Lys Leu Leu Val Leu Asp Ala Thr
            260                 265                 270
Lys Arg Leu Gly Cys Glu Glu Met Glu Gly Tyr Gly Pro Leu Lys Ala
        275                 280                 285
His Pro Phe Phe Glu Ser Val Thr Trp Glu Asn Leu His Gln Gln Thr
    290                 295                 300
Pro Pro Lys Leu Thr Ala Tyr Leu Pro Ala Met Ser Glu Asp Asp Glu
305                 310                 315                 320
Asp Cys Tyr Gly Asn Tyr Asp Asn Leu Leu Ser Gln Phe Gly Cys Met
                325                 330                 335
Gln Val Ser Ser Ser Ser Ser His Ser Leu Ser Ala Ser Asp Thr
            340                 345                 350
Gly Leu Pro Gln Arg Ser Gly Ser Asn Ile Glu Gln Tyr Ile His Asp
        355                 360                 365
Leu Asp Ser Asn Ser Phe Glu Leu Asp Leu Gln Phe Ser Glu Asp Glu
    370                 375                 380
Lys Arg Leu Leu Leu Glu Lys Gln Ala Gly Gly Asn Pro Trp His Gln
385                 390                 395                 400
Phe Val Glu Asn Asn Leu Ile Leu Lys Met Gly Pro Val Asp Lys Arg
                405                 410                 415
Lys Gly Leu Phe Ala Arg Arg Arg Gln Leu Leu Leu Thr Glu Gly Pro
            420                 425                 430
His Leu Tyr Tyr Val Asp Pro Val Asn Lys Val Leu Lys Gly Glu Ile
        435                 440                 445
Pro Trp Ser Gln Glu Leu Arg Pro Glu Ala Lys Asn Phe Lys Thr Phe
    450                 455                 460
Phe Val His Thr Pro Asn Arg Thr Tyr Tyr Leu Met Asp Pro Ser Gly
465                 470                 475                 480
Asn Ala His Lys Trp Cys Arg Lys Ile Gln Glu Val Trp Arg Gln Arg
                485                 490                 495
Tyr Gln Ser His Pro Asp Ala Ala Val Gln
            500                 505
```

<210> SEQ ID NO 110
<211> LENGTH: 360
<212> TYPE: PRT
<213> ORGANISM: Homo sapiens

<400> SEQUENCE: 110

```
Met Ala Arg Thr Thr Ser Gln Leu Tyr Asp Ala Val Pro Ile Gln Ser
1               5                   10                  15

Ser Val Val Leu Cys Ser Cys Pro Ser Pro Met Val Arg Thr Gln
            20                  25                  30

Thr Glu Ser Ser Thr Pro Pro Gly Ile Pro Gly Ser Arg Gln Gly
        35                  40                  45

Pro Ala Met Asp Gly Thr Ala Ala Glu Pro Arg Pro Gly Ala Gly Ser
    50                  55                  60

Leu Gln His Ala Gln Pro Pro Gln Pro Arg Lys Lys Arg Pro Glu
65              70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
            100                 105                 110

Leu Glu Lys Arg His Ile Ile Lys Glu Asn Lys Val Pro Tyr Val Thr
            115                 120                 125

Arg Glu Arg Asp Val Met Ser Arg Leu Asp His Pro Phe Phe Val Lys
130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
            195                 200                 205

Glu Asn Ile Leu Leu Asn Glu Asp Met His Ile Gln Ile Thr Asp Phe
210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
            245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
            275                 280                 285

Leu Ile Phe Gln Lys Ile Ile Lys Leu Glu Tyr Asp Phe Pro Glu Lys
            290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
            325                 330                 335

Lys Ala His Pro Phe Phe Glu Ser Val Thr Trp Glu Asn Leu His Gln
                340                 345                 350

Gln Thr Pro Pro Lys Leu Thr Ala
            355                 360

<210> SEQ ID NO 111
<211> LENGTH: 337
<212> TYPE: PRT
<213> ORGANISM: Homo sapiens

<400> SEQUENCE: 111

Met Asp Gly Thr Ala Ala Glu Pro Arg Pro Gly Ala Gly Ser Leu Gln
```

```
                1               5                  10                 15
            His Ala Gln Pro Pro Gln Pro Arg Lys Lys Arg Pro Glu Asp Phe
                            20                  25                  30

Lys Phe Gly Lys Ile Leu Gly Glu Gly Ser Phe Ser Thr Val Val Leu
                            35                  40                  45

Ala Arg Glu Leu Ala Thr Ser Arg Glu Tyr Ala Ile Lys Ile Leu Glu
            50                  55                  60

Lys Arg His Ile Ile Lys Glu Asn Lys Val Pro Tyr Val Thr Arg Glu
            65                  70                  75                  80

Arg Asp Val Met Ser Arg Leu Asp His Pro Phe Phe Val Lys Leu Tyr
                            85                  90                  95

Phe Thr Phe Gln Asp Asp Glu Lys Leu Tyr Phe Gly Leu Ser Tyr Ala
                            100                 105                 110

Lys Asn Gly Glu Leu Leu Lys Tyr Ile Arg Lys Ile Gly Ser Phe Asp
                            115                 120                 125

Glu Thr Cys Thr Arg Phe Tyr Thr Ala Glu Ile Val Ser Ala Leu Glu
                            130                 135                 140

Tyr Leu His Gly Lys Gly Ile Ile His Arg Asp Leu Lys Pro Glu Asn
            145                 150                 155                 160

Ile Leu Leu Asn Glu Asp Met His Ile Gln Ile Thr Asp Phe Gly Thr
                            165                 170                 175

Ala Lys Val Leu Ser Pro Glu Ser Lys Gln Ala Arg Ala Asn Ser Phe
                            180                 185                 190

Val Gly Thr Ala Gln Tyr Val Ser Pro Glu Leu Leu Thr Glu Lys Ser
                            195                 200                 205

Ala Cys Lys Ser Ser Asp Leu Trp Ala Leu Gly Cys Ile Ile Tyr Gln
                            210                 215                 220

Leu Val Ala Gly Leu Pro Pro Phe Arg Ala Gly Asn Glu Tyr Leu Ile
            225                 230                 235                 240

Phe Gln Lys Ile Ile Lys Leu Glu Tyr Asp Phe Pro Glu Lys Phe Phe
                            245                 250                 255

Pro Lys Ala Arg Asp Leu Val Glu Lys Leu Leu Val Leu Asp Ala Thr
                            260                 265                 270

Lys Arg Leu Gly Cys Glu Glu Met Glu Gly Tyr Gly Pro Leu Lys Ala
                            275                 280                 285

His Pro Phe Phe Glu Ser Val Thr Trp Glu Asn Leu His Gln Gln Thr
                            290                 295                 300

Pro Pro Lys Leu Thr Ala Tyr Leu Pro Ala Met Ser Glu Asp Asp Glu
            305                 310                 315                 320

Asp Cys Tyr Gly Asn Tyr Asp Asn Leu Leu Ser Gln Phe Gly Cys Met
                            325                 330                 335

Gln

<210> SEQ ID NO 112
<211> LENGTH: 39
<212> TYPE: PRT
<213> ORGANISM: Artificial Sequence
<220> FEATURE:
<223> OTHER INFORMATION: PDK1tide substrate peptide

<400> SEQUENCE: 112

Lys Thr Phe Cys Gly Thr Pro Glu Tyr Leu Ala Pro Glu Val Arg Arg
            1               5                   10                  15

Glu Pro Arg Ile Leu Ser Glu Glu Glu Gln Glu Met Phe Arg Asp Phe
                            20                  25                  30
```

Asp Tyr Ile Ala Asp Trp Cys
        35

<210> SEQ ID NO 113
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: Lys76 mutated to Ala

<400> SEQUENCE: 113

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
50                  55                  60

Leu Gln His Ala Gln Pro Pro Pro Gln Pro Arg Ala Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
            100                 105                 110

Leu Glu Lys Arg His Ile Ile Lys Glu Asn Lys Val Pro Tyr Val Thr
        115                 120                 125

Arg Glu Arg Asp Val Met Ser Arg Leu Asp His Pro Phe Phe Val Lys
130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
        275                 280                 285

Leu Ile Phe Gln Lys Ile Ile Lys Leu Glu Tyr Asp Phe Pro Glu Lys
290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

```
Lys Ala His Pro Phe Phe Glu Ser Val Thr Trp Glu Asn Leu His Gln
            340                 345                 350

Gln Thr Pro Pro Lys Leu Thr Ala Tyr Leu Pro Ala Met Ser Glu Asp
        355                 360                 365

Asp Glu Asp Cys Tyr Gly Asn Tyr Asp Asn Leu Leu Ser Gln Phe Gly
    370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
            420                 425                 430

Asp Glu Lys Arg Leu Leu Leu Glu Lys Gln Ala Gly Gly Asn Pro Trp
        435                 440                 445

His Gln Phe Val Glu Asn Asn Leu Ile Leu Lys Met Gly Pro Val Asp
    450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
            500                 505                 510

Thr Phe Phe Val His Thr Pro Asn Arg Thr Tyr Tyr Leu Met Asp Pro
        515                 520                 525

Ser Gly Asn Ala His Lys Trp Cys Arg Lys Ile Gln Glu Val Trp Arg
    530                 535                 540

Gln Arg Tyr Gln Ser His Pro Asp Ala Ala Val Gln
545                 550                 555

<210> SEQ ID NO 114
<211> LENGTH: 431
<212> TYPE: PRT
<213> ORGANISM: Homo sapiens

<400> SEQUENCE: 114

Met Thr Val Lys Thr Glu Ala Ala Lys Gly Thr Leu Thr Tyr Ser Arg
1               5                   10                  15

Met Arg Gly Met Val Ala Ile Leu Ile Ala Phe Met Lys Gln Arg Arg
            20                  25                  30

Met Gly Leu Asn Asp Phe Ile Gln Lys Ile Ala Asn Asn Ser Tyr Ala
        35                  40                  45

Cys Lys His Pro Glu Val Gln Ser Ile Leu Lys Ile Ser Gln Pro Gln
    50                  55                  60

Glu Pro Glu Leu Met Asn Ala Asn Pro Ser Pro Pro Pro Ser Pro Ser
65                  70                  75                  80

Gln Gln Ile Asn Leu Gly Pro Ser Ser Asn Pro His Ala Lys Pro Ser
                85                  90                  95

Asp Phe His Phe Leu Lys Val Ile Gly Lys Gly Ser Phe Gly Lys Val
            100                 105                 110

Leu Leu Ala Arg His Lys Ala Glu Glu Val Phe Tyr Ala Val Lys Val
        115                 120                 125

Leu Gln Lys Lys Ala Ile Leu Lys Lys Lys Glu Glu Lys His Ile Met
    130                 135                 140

Ser Glu Arg Asn Val Leu Leu Lys Asn Val Lys His Pro Phe Leu Val
145                 150                 155                 160
```

```
Gly Leu His Phe Ser Phe Gln Thr Ala Asp Lys Leu Tyr Phe Val Leu
                165                 170                 175

Asp Tyr Ile Asn Gly Gly Glu Leu Phe Tyr His Leu Gln Arg Glu Arg
            180                 185                 190

Cys Phe Leu Glu Pro Arg Ala Arg Phe Tyr Ala Ala Glu Ile Ala Ser
        195                 200                 205

Ala Leu Gly Tyr Leu His Ser Leu Asn Ile Val Tyr Arg Asp Leu Lys
    210                 215                 220

Pro Glu Asn Ile Leu Leu Asp Ser Gln Gly His Ile Val Leu Thr Asp
225                 230                 235                 240

Phe Gly Leu Cys Lys Glu Asn Ile Glu His Asn Ser Thr Thr Ser Thr
                245                 250                 255

Phe Cys Gly Thr Pro Glu Tyr Leu Ala Pro Glu Val Leu His Lys Gln
            260                 265                 270

Pro Tyr Asp Arg Thr Val Asp Trp Trp Cys Leu Gly Ala Val Leu Tyr
        275                 280                 285

Glu Met Leu Tyr Gly Leu Pro Pro Phe Tyr Ser Arg Asn Thr Ala Glu
    290                 295                 300

Met Tyr Asp Asn Ile Leu Asn Lys Pro Leu Gln Leu Lys Pro Asn Ile
305                 310                 315                 320

Thr Asn Ser Ala Arg His Leu Leu Glu Gly Leu Leu Gln Lys Asp Arg
                325                 330                 335

Thr Lys Arg Leu Gly Ala Lys Asp Asp Phe Met Glu Ile Lys Ser His
            340                 345                 350

Val Phe Phe Ser Leu Ile Asn Trp Asp Asp Leu Ile Asn Lys Lys Ile
        355                 360                 365

Thr Pro Pro Phe Asn Pro Asn Val Ser Gly Pro Asn Asp Leu Arg His
    370                 375                 380

Phe Asp Pro Glu Phe Thr Glu Glu Pro Val Pro Asn Ser Ile Gly Lys
385                 390                 395                 400

Ser Pro Asp Ser Val Leu Val Thr Ala Ser Val Lys Glu Ala Ala Glu
                405                 410                 415

Ala Phe Leu Gly Phe Ser Tyr Ala Pro Pro Thr Asp Ser Phe Leu
            420                 425                 430

<210> SEQ ID NO 115
<211> LENGTH: 367
<212> TYPE: PRT
<213> ORGANISM: Homo sapiens

<400> SEQUENCE: 115

Met Asn Ser Ser Pro Ala Gly Thr Pro Ser Gln Pro Ser Arg Ala
1               5                   10                  15

Asn Gly Asn Ile Asn Leu Gly Pro Ser Ala Asn Pro Asn Ala Gln Pro
            20                  25                  30

Thr Asp Phe Asp Phe Leu Lys Val Ile Gly Lys Gly Asn Tyr Gly Lys
        35                  40                  45

Val Leu Leu Ala Lys Arg Lys Ser Asp Gly Ala Phe Tyr Ala Val Lys
    50                  55                  60

Val Leu Gln Lys Lys Ser Ile Leu Lys Lys Lys Glu Gln Ser His Ile
65                  70                  75                  80

Met Ala Glu Arg Ser Val Leu Leu Lys Asn Val Arg His Pro Phe Leu
                85                  90                  95

Val Gly Leu Arg Tyr Ser Phe Gln Thr Pro Glu Lys Leu Tyr Phe Val
```

```
                100                 105                 110
Leu Asp Tyr Val Asn Gly Gly Glu Leu Phe Phe His Leu Gln Arg Glu
            115                 120                 125
Arg Arg Phe Leu Glu Pro Arg Ala Arg Phe Tyr Ala Ala Glu Val Ala
        130                 135                 140
Ser Ala Ile Gly Tyr Leu His Ser Leu Asn Ile Ile Tyr Arg Asp Leu
145                 150                 155                 160
Lys Pro Glu Asn Ile Leu Leu Asp Cys Gln Gly His Val Val Leu Thr
                165                 170                 175
Asp Phe Gly Leu Cys Lys Glu Gly Val Glu Pro Glu Asp Thr Thr Ser
            180                 185                 190
Thr Phe Cys Gly Thr Pro Glu Tyr Leu Ala Pro Glu Val Leu Arg Lys
        195                 200                 205
Glu Pro Tyr Asp Arg Ala Val Asp Trp Trp Cys Leu Gly Ala Val Leu
    210                 215                 220
Tyr Glu Met Leu His Gly Leu Pro Pro Phe Tyr Ser Gln Asp Val Ser
225                 230                 235                 240
Gln Met Tyr Glu Asn Ile Leu His Gln Pro Leu Gln Ile Pro Gly Gly
                245                 250                 255
Arg Thr Val Ala Ala Cys Asp Leu Leu Gln Ser Leu Leu His Lys Asp
            260                 265                 270
Gln Arg Gln Arg Leu Gly Ser Lys Ala Asp Phe Leu Glu Ile Lys Asn
        275                 280                 285
His Val Phe Phe Ser Pro Ile Asn Trp Asp Asp Leu Tyr His Lys Arg
    290                 295                 300
Leu Thr Pro Pro Phe Asn Pro Asn Val Thr Gly Pro Ala Asp Leu Lys
305                 310                 315                 320
His Phe Asp Pro Glu Phe Thr Gln Glu Ala Val Ser Lys Ser Ile Gly
                325                 330                 335
Cys Thr Pro Asp Thr Val Ala Ser Ser Ser Gly Ala Ser Ser Ala Phe
            340                 345                 350
Leu Gly Phe Ser Tyr Ala Pro Glu Asp Asp Asp Ile Leu Asp Cys
        355                 360                 365

<210> SEQ ID NO 116
<211> LENGTH: 429
<212> TYPE: PRT
<213> ORGANISM: Homo sapiens

<400> SEQUENCE: 116

Met Ala Leu Lys Ile Pro Ala Lys Arg Ile Phe Gly Asp Asn Phe Asp
1               5                   10                  15
Pro Asp Phe Ile Lys Gln Arg Arg Ala Gly Leu Asn Glu Phe Ile Gln
                20                  25                  30
Asn Leu Val Arg Tyr Pro Glu Leu Tyr Asn His Pro Asp Val Arg Ala
            35                  40                  45
Phe Leu Gln Met Asp Ser Pro Lys His Gln Ser Asp Pro Ser Glu Asp
        50                  55                  60
Glu Asp Glu Arg Ser Ser Gln Lys Leu His Ser Thr Ser Gln Asn Ile
65                  70                  75                  80
Asn Leu Gly Pro Ser Gly Asn Pro His Ala Lys Pro Thr Asp Phe Asp
                85                  90                  95
Phe Leu Lys Val Ile Gly Lys Gly Ser Phe Gly Lys Val Leu Leu Ala
                100                 105                 110
```

```
Lys Arg Lys Leu Asp Gly Lys Phe Tyr Ala Val Lys Val Leu Gln Lys
            115                 120                 125

Lys Ile Val Leu Asn Arg Lys Glu Gln Lys His Ile Met Ala Glu Arg
        130                 135                 140

Asn Val Leu Leu Lys Asn Val Lys His Pro Phe Leu Val Gly Leu His
145                 150                 155                 160

Tyr Ser Phe Gln Thr Thr Glu Lys Leu Tyr Phe Val Leu Asp Phe Val
                165                 170                 175

Asn Gly Gly Glu Leu Phe Phe His Leu Gln Arg Glu Arg Ser Phe Pro
            180                 185                 190

Glu His Arg Ala Arg Phe Tyr Ala Ala Glu Ile Ala Ser Ala Leu Gly
        195                 200                 205

Tyr Leu His Ser Ile Lys Ile Val Tyr Arg Asp Leu Lys Pro Glu Asn
    210                 215                 220

Ile Leu Leu Asp Ser Val Gly His Val Val Leu Thr Asp Phe Gly Leu
225                 230                 235                 240

Cys Lys Glu Gly Ile Ala Ile Ser Asp Thr Thr Thr Thr Phe Cys Gly
                245                 250                 255

Thr Pro Glu Tyr Leu Ala Pro Glu Val Ile Arg Lys Gln Pro Tyr Asp
            260                 265                 270

Asn Thr Val Asp Trp Trp Cys Leu Gly Ala Val Leu Tyr Glu Met Leu
        275                 280                 285

Tyr Gly Leu Pro Pro Phe Tyr Cys Arg Asp Val Ala Glu Met Tyr Asp
    290                 295                 300

Asn Ile Leu His Lys Pro Leu Ser Leu Arg Pro Gly Val Ser Leu Thr
305                 310                 315                 320

Ala Trp Ser Ile Leu Glu Glu Leu Leu Glu Lys Asp Arg Gln Asn Arg
                325                 330                 335

Leu Gly Ala Lys Glu Asp Phe Leu Glu Ile Gln Asn His Pro Phe Phe
            340                 345                 350

Glu Ser Leu Ser Trp Ala Asp Leu Val Gln Lys Lys Ile Pro Pro Pro
        355                 360                 365

Phe Asn Pro Asn Val Ala Gly Pro Asp Asp Ile Arg Asn Phe Asp Thr
    370                 375                 380

Ala Phe Thr Glu Glu Thr Val Pro Tyr Ser Val Cys Val Ser Ser Asp
385                 390                 395                 400

Tyr Ser Ile Val Asn Ala Ser Val Leu Glu Ala Asp Asp Ala Phe Val
                405                 410                 415

Gly Phe Ser Tyr Ala Pro Pro Ser Glu Asp Leu Phe Leu
            420                 425

<210> SEQ ID NO 117
<211> LENGTH: 556
<212> TYPE: PRT
<213> ORGANISM: Homo sapiens

<400> SEQUENCE: 117

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60
```

-continued

```
Leu Gln His Ala Gln Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
                100                 105                 110

Leu Glu Lys Arg His Ile Ile Lys Glu Asn Lys Val Pro Tyr Val Thr
                115                 120                 125

Arg Glu Arg Asp Val Met Ser Arg Leu Asp His Pro Phe Phe Val Lys
130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
                180                 185                 190

Leu Glu Tyr Leu His Gly Lys Gly Ile Ile His Arg Asp Leu Lys Pro
                195                 200                 205

Glu Asn Ile Leu Leu Asn Glu Asp Met His Ile Gln Ile Thr Asp Phe
210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
                260                 265                 270

Tyr Gln Leu Val Ala Gly Leu Pro Pro Phe Arg Ala Gly Asn Glu Tyr
                275                 280                 285

Leu Ile Phe Gln Lys Ile Ile Lys Leu Glu Tyr Asp Phe Pro Glu Lys
                290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
                355                 360                 365

Asp Glu Asp Cys Tyr Gly Asn Tyr Asp Asn Leu Leu Ser Gln Phe Gly
370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Trp
                435                 440                 445

His Gln Phe Val Glu Asn Asn Leu Ile Leu Lys Met Gly Pro Val Asp
450                 455                 460

Lys Arg Lys Gly Leu Phe Ala Arg Arg Arg Gln Leu Leu Leu Thr Glu
465                 470                 475                 480
```

```
Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
            500                 505                 510

Thr Phe Phe Val His Thr Pro Asn Arg Thr Tyr Tyr Leu Met Asp Pro
        515                 520                 525

Ser Gly Asn Ala His Lys Trp Cys Arg Lys Ile Gln Glu Val Trp Arg
    530                 535                 540

Gln Arg Tyr Gln Ser His Pro Asp Ala Ala Val Gln
545                 550                 555

<210> SEQ ID NO 118
<211> LENGTH: 481
<212> TYPE: PRT
<213> ORGANISM: Homo sapiens

<400> SEQUENCE: 118

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
    290                 295                 300
```

```
Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445

Thr Ile Thr Pro Pro Asp Arg Tyr Asp Ser Leu Gly Leu Leu Glu Leu
    450                 455                 460

Asp Gln Arg Thr His Phe Pro Gln Phe Ser Tyr Ser Ala Ser Ile Arg
465                 470                 475                 480

Glu
```

<210> SEQ ID NO 119
<211> LENGTH: 479
<212> TYPE: PRT
<213> ORGANISM: Homo sapiens

<400> SEQUENCE: 119

```
Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
    130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190
```

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
        210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
    290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
    370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
    450                 455                 460

Arg Pro His Phe Pro Gln Phe Ser Tyr Ser Ala Ser Gly Arg Glu
465                 470                 475

<210> SEQ ID NO 120
<211> LENGTH: 672
<212> TYPE: PRT
<213> ORGANISM: Homo sapiens

<400> SEQUENCE: 120

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp

-continued

```
                   85                  90                  95
Asp Pro Arg Ser Lys His Lys Phe Lys Ile His Thr Tyr Gly Ser Pro
            100                 105                 110
Thr Phe Cys Asp His Cys Gly Ser Leu Leu Tyr Gly Leu Ile His Gln
        115                 120                 125
Gly Met Lys Cys Asp Thr Cys Asp Met Asn Val His Lys Gln Cys Val
    130                 135                 140
Ile Asn Val Pro Ser Leu Cys Gly Met Asp His Thr Glu Lys Arg Gly
145                 150                 155                 160
Arg Ile Tyr Leu Lys Ala Glu Val Ala Asp Glu Lys Leu His Val Thr
                165                 170                 175
Val Arg Asp Ala Lys Asn Leu Ile Pro Met Asp Pro Asn Gly Leu Ser
            180                 185                 190
Asp Pro Tyr Val Lys Leu Lys Leu Ile Pro Asp Pro Lys Asn Glu Ser
        195                 200                 205
Lys Gln Lys Thr Lys Thr Ile Arg Ser Thr Leu Asn Pro Gln Trp Asn
    210                 215                 220
Glu Ser Phe Thr Phe Lys Leu Lys Pro Ser Asp Lys Asp Arg Arg Leu
225                 230                 235                 240
Ser Val Glu Ile Trp Asp Trp Asp Arg Thr Thr Arg Asn Asp Phe Met
                245                 250                 255
Gly Ser Leu Ser Phe Gly Val Ser Glu Leu Met Lys Met Pro Ala Ser
            260                 265                 270
Gly Trp Tyr Lys Leu Leu Asn Gln Glu Glu Gly Glu Tyr Tyr Asn Val
        275                 280                 285
Pro Ile Pro Glu Gly Asp Glu Glu Gly Asn Met Glu Leu Arg Gln Lys
    290                 295                 300
Phe Glu Lys Ala Lys Leu Gly Pro Ala Gly Asn Lys Val Ile Ser Pro
305                 310                 315                 320
Ser Glu Asp Arg Lys Gln Pro Ser Asn Asn Leu Asp Arg Val Lys Leu
                325                 330                 335
Thr Asp Phe Asn Phe Leu Met Val Leu Gly Lys Gly Ser Phe Gly Lys
            340                 345                 350
Val Met Leu Ala Asp Arg Lys Gly Thr Glu Glu Leu Tyr Ala Ile Lys
        355                 360                 365
Ile Leu Lys Lys Asp Val Val Ile Gln Asp Asp Asp Val Glu Cys Thr
    370                 375                 380
Met Val Glu Lys Arg Val Leu Ala Leu Leu Asp Lys Pro Pro Phe Leu
385                 390                 395                 400
Thr Gln Leu His Ser Cys Phe Gln Thr Val Asp Arg Leu Tyr Phe Val
                405                 410                 415
Met Glu Tyr Val Asn Gly Gly Asp Leu Met Tyr His Ile Gln Gln Val
            420                 425                 430
Gly Lys Phe Lys Glu Pro Gln Ala Val Phe Tyr Ala Ala Glu Ile Ser
        435                 440                 445
Ile Gly Leu Phe Phe Leu His Lys Arg Gly Ile Ile Tyr Arg Asp Leu
    450                 455                 460
Lys Leu Asp Asn Val Met Leu Asp Ser Glu Gly His Ile Lys Ile Ala
465                 470                 475                 480
Asp Phe Gly Met Cys Lys Glu His Met Met Asp Gly Val Thr Thr Arg
                485                 490                 495
Thr Phe Cys Gly Thr Pro Asp Tyr Ile Ala Pro Glu Ile Ile Ala Tyr
            500                 505                 510
```

```
Gln Pro Tyr Gly Lys Ser Val Asp Trp Trp Ala Tyr Gly Val Leu Leu
                515                 520                 525

Tyr Glu Met Leu Ala Gly Gln Pro Pro Phe Asp Gly Glu Asp Glu Asp
530                 535                 540

Glu Leu Phe Gln Ser Ile Met Glu His Asn Val Ser Tyr Pro Lys Ser
545                 550                 555                 560

Leu Ser Lys Glu Ala Val Ser Ile Cys Lys Gly Leu Met Thr Lys His
                565                 570                 575

Pro Ala Lys Arg Leu Gly Cys Gly Pro Glu Gly Glu Arg Asp Val Arg
                580                 585                 590

Glu His Ala Phe Phe Arg Arg Ile Asp Trp Glu Lys Leu Glu Asn Arg
                595                 600                 605

Glu Ile Gln Pro Pro Phe Lys Pro Lys Val Cys Gly Lys Gly Ala Glu
                610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
                660                 665                 670

<210> SEQ ID NO 121
<211> LENGTH: 671
<212> TYPE: PRT
<213> ORGANISM: Homo sapiens

<400> SEQUENCE: 121

Met Ala Asp Pro Ala Ala Gly Pro Pro Ser Glu Gly Glu Glu Ser
1               5                   10                  15

Thr Val Arg Phe Ala Arg Lys Gly Ala Leu Arg Gln Lys Asn Val His
                20                  25                  30

Glu Val Lys Asn His Lys Phe Thr Ala Arg Phe Phe Lys Gln Pro Thr
            35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Ala Ser Asp
                85                  90                  95

Asp Pro Arg Ser Lys His Lys Phe Lys Ile His Thr Tyr Ser Ser Pro
                100                 105                 110

Thr Phe Cys Asp His Cys Gly Ser Leu Leu Tyr Gly Leu Ile His Gln
            115                 120                 125

Gly Met Lys Cys Asp Thr Cys Met Met Asn Val His Lys Arg Cys Val
130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
                180                 185                 190

Asp Pro Tyr Val Lys Leu Lys Leu Ile Pro Asp Pro Lys Ser Glu Ser
            195                 200                 205

Lys Gln Lys Thr Lys Thr Ile Lys Cys Ser Leu Asn Pro Glu Trp Asn
```

```
          210                 215                 220
Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
            260                 265                 270

Gly Trp Phe Lys Leu Leu Ser Gln Glu Gly Glu Tyr Phe Asn Val
        275                 280                 285

Pro Val Pro Pro Glu Gly Ser Glu Ala Asn Glu Leu Arg Gln Lys
290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
                325                 330                 335

Met Lys Leu Thr Asp Phe Asn Phe Leu Met Val Leu Gly Lys Gly Ser
            340                 345                 350

Phe Gly Lys Val Met Leu Ser Glu Arg Lys Gly Thr Asp Glu Leu Tyr
        355                 360                 365

Ala Val Lys Ile Leu Lys Lys Asp Val Val Ile Gln Asp Asp Asp Val
    370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
                405                 410                 415

Tyr Phe Val Met Glu Tyr Val Asn Gly Gly Asp Leu Met Tyr His Ile
            420                 425                 430

Gln Gln Val Gly Arg Phe Lys Glu Pro His Ala Val Phe Tyr Ala Ala
        435                 440                 445

Glu Ile Ala Ile Gly Leu Phe Phe Leu Gln Ser Lys Gly Ile Ile Tyr
    450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
                485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
        515                 520                 525

Val Leu Leu Tyr Glu Met Leu Ala Gly Gln Ala Pro Phe Glu Gly Glu
    530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
                565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
        595                 600                 605

Glu Arg Lys Glu Ile Gln Pro Pro Tyr Lys Pro Lys Ala Arg Asp Lys
    610                 615                 620

Arg Asp Thr Ser Asn Phe Asp Lys Glu Phe Thr Arg Gln Pro Val Glu
625                 630                 635                 640
```

Leu Thr Pro Thr Asp Lys Leu Phe Ile Met Asn Leu Asp Gln Asn Glu
                645                 650                 655

Phe Ala Gly Phe Ser Tyr Thr Asn Pro Glu Phe Val Ile Asn Val
            660                 665                 670

<210> SEQ ID NO 122
<211> LENGTH: 673
<212> TYPE: PRT
<213> ORGANISM: Homo sapiens

<400> SEQUENCE: 122

Met Ala Asp Pro Ala Gly Pro Pro Ser Glu Gly Glu Glu Ser
1               5                   10                  15

Thr Val Arg Phe Ala Arg Lys Gly Ala Leu Arg Gln Lys Asn Val His
            20                  25                  30

Glu Val Lys Asn His Lys Phe Thr Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Ala Ser Asp
                85                  90                  95

Asp Pro Arg Ser Lys His Lys Phe Lys Ile His Thr Tyr Ser Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Met Met Asn Val His Lys Arg Cys Val
    130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
            180                 185                 190

Asp Pro Tyr Val Lys Leu Lys Leu Ile Pro Asp Pro Lys Ser Glu Ser
        195                 200                 205

Lys Gln Lys Thr Lys Thr Ile Lys Cys Ser Leu Asn Pro Glu Trp Asn
    210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
            260                 265                 270

Gly Trp Phe Lys Leu Leu Ser Gln Glu Glu Gly Glu Tyr Phe Asn Val
        275                 280                 285

Pro Val Pro Pro Glu Gly Ser Glu Ala Asn Glu Glu Leu Arg Gln Lys
    290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
                325                 330                 335

Met Lys Leu Thr Asp Phe Asn Phe Leu Met Val Leu Gly Lys Gly Ser

```
                340             345                 350
Phe Gly Lys Val Met Leu Ser Glu Arg Lys Gly Thr Asp Glu Leu Tyr
        355                 360                 365

Ala Val Lys Ile Leu Lys Lys Asp Val Val Ile Gln Asp Asp Asp Val
    370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
                405                 410                 415

Tyr Phe Val Met Glu Tyr Val Asn Gly Gly Asp Leu Met Tyr His Ile
            420                 425                 430

Gln Gln Val Gly Arg Phe Lys Glu Pro His Ala Val Phe Tyr Ala Ala
        435                 440                 445

Glu Ile Ala Ile Gly Leu Phe Phe Leu Gln Ser Lys Gly Ile Ile Tyr
    450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
                485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
        515                 520                 525

Val Leu Leu Tyr Glu Met Leu Ala Gly Gln Ala Pro Phe Glu Gly Glu
    530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
                565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
        595                 600                 605

Glu Arg Lys Glu Ile Gln Pro Pro Tyr Lys Pro Lys Ala Cys Gly Arg
    610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
                645                 650                 655

Glu Gly Phe Ser Phe Val Asn Ser Glu Phe Leu Lys Pro Glu Val Lys
            660                 665                 670

Ser

<210> SEQ ID NO 123
<211> LENGTH: 697
<212> TYPE: PRT
<213> ORGANISM: Homo sapiens

<400> SEQUENCE: 123

Met Ala Gly Leu Gly Pro Gly Val Gly Asp Ser Glu Gly Gly Pro Arg
1               5                   10                  15

Pro Leu Phe Cys Arg Lys Gly Ala Leu Arg Gln Lys Val Val His Glu
            20                  25                  30

Val Lys Ser His Lys Phe Thr Ala Arg Phe Phe Lys Gln Pro Thr Phe
```

-continued

```
                35                  40                  45
Cys Ser His Cys Thr Asp Phe Ile Trp Gly Ile Gly Lys Gln Gly Leu
 50                  55                  60

Gln Cys Gln Val Cys Ser Phe Val Val His Arg Arg Cys His Glu Phe
 65                  70                  75                  80

Val Thr Phe Glu Cys Pro Gly Ala Gly Lys Gly Pro Gln Thr Asp Asp
                 85                  90                  95

Pro Arg Asn Lys His Lys Phe Arg Leu His Ser Tyr Ser Ser Pro Thr
                100                 105                 110

Phe Cys Asp His Cys Gly Ser Leu Leu Tyr Gly Leu Val His Gln Gly
                115                 120                 125

Met Lys Cys Ser Cys Cys Glu Met Asn Val His Arg Arg Cys Val Arg
        130                 135                 140

Ser Val Pro Ser Leu Cys Gly Val Asp His Thr Glu Arg Arg Gly Arg
145                 150                 155                 160

Leu Gln Leu Glu Ile Arg Ala Pro Thr Ala Asp Glu Ile His Val Thr
                165                 170                 175

Val Gly Glu Ala Arg Asn Leu Ile Pro Met Asp Pro Asn Gly Leu Ser
            180                 185                 190

Asp Pro Tyr Val Lys Leu Lys Leu Ile Pro Asp Pro Arg Asn Leu Thr
            195                 200                 205

Lys Gln Lys Thr Arg Thr Val Lys Ala Thr Leu Asn Pro Val Trp Asn
210                 215                 220

Glu Thr Phe Val Phe Asn Leu Lys Pro Gly Asp Val Glu Arg Arg Leu
225                 230                 235                 240

Ser Val Glu Val Trp Asp Trp Asp Arg Thr Ser Arg Asn Asp Phe Met
                245                 250                 255

Gly Ala Met Ser Phe Gly Val Ser Glu Leu Leu Lys Ala Pro Val Asp
                260                 265                 270

Gly Trp Tyr Lys Leu Leu Asn Gln Glu Glu Gly Glu Tyr Tyr Asn Val
            275                 280                 285

Pro Val Ala Asp Ala Asp Asn Cys Ser Leu Leu Gln Lys Phe Glu Ala
        290                 295                 300

Cys Asn Tyr Pro Leu Glu Leu Tyr Glu Arg Val Arg Met Gly Pro Ser
305                 310                 315                 320

Ser Ser Pro Ile Pro Ser Pro Ser Pro Thr Asp Pro Lys Arg
                325                 330                 335

Cys Phe Phe Gly Ala Ser Pro Gly Arg Leu His Ile Ser Asp Phe Ser
            340                 345                 350

Phe Leu Met Val Leu Gly Lys Gly Ser Phe Gly Lys Val Met Leu Ala
            355                 360                 365

Glu Arg Arg Gly Ser Asp Glu Leu Tyr Ala Ile Lys Ile Leu Lys Lys
        370                 375                 380

Asp Val Ile Val Gln Asp Asp Val Asp Cys Thr Leu Val Glu Lys
385                 390                 395                 400

Arg Val Leu Ala Leu Gly Gly Arg Gly Pro Gly Gly Arg Pro His Phe
                405                 410                 415

Leu Thr Gln Leu His Ser Thr Phe Gln Thr Pro Asp Arg Leu Tyr Phe
            420                 425                 430

Val Met Glu Tyr Val Thr Gly Gly Asp Leu Met Tyr His Ile Gln Gln
        435                 440                 445

Leu Gly Lys Phe Lys Glu Pro His Ala Ala Phe Tyr Ala Ala Glu Ile
    450                 455                 460
```

```
Ala Ile Gly Leu Phe Phe Leu His Asn Gln Gly Ile Ile Tyr Arg Asp
465                 470                 475                 480

Leu Lys Leu Asp Asn Val Met Leu Asp Ala Glu Gly His Ile Lys Ile
                485                 490                 495

Thr Asp Phe Gly Met Cys Lys Glu Asn Val Phe Pro Gly Thr Thr Thr
            500                 505                 510

Arg Thr Phe Cys Gly Thr Pro Asp Tyr Ile Ala Pro Glu Ile Ile Ala
        515                 520                 525

Tyr Gln Pro Tyr Gly Lys Ser Val Asp Trp Trp Ser Phe Gly Val Leu
    530                 535                 540

Leu Tyr Glu Met Leu Ala Gly Gln Pro Pro Phe Asp Gly Glu Asp Glu
545                 550                 555                 560

Glu Glu Leu Phe Gln Ala Ile Met Glu Gln Thr Val Thr Tyr Pro Lys
                565                 570                 575

Ser Leu Ser Arg Glu Ala Val Ala Ile Cys Lys Gly Phe Leu Thr Lys
            580                 585                 590

His Pro Gly Lys Arg Leu Gly Ser Gly Pro Asp Gly Glu Pro Thr Ile
        595                 600                 605

Arg Ala His Gly Phe Phe Arg Trp Ile Asp Trp Glu Arg Leu Glu Arg
    610                 615                 620

Leu Glu Ile Pro Pro Pro Phe Arg Pro Arg Pro Cys Gly Arg Ser Gly
625                 630                 635                 640

Glu Asn Phe Asp Lys Phe Phe Thr Arg Ala Ala Pro Ala Leu Thr Pro
                645                 650                 655

Pro Asp Arg Leu Val Leu Ala Ser Ile Asp Gln Ala Asp Phe Gln Gly
            660                 665                 670

Phe Thr Tyr Val Asn Pro Asp Phe Val His Pro Asp Ala Arg Ser Pro
        675                 680                 685

Thr Ser Pro Val Pro Val Pro Val Met
    690                 695

<210> SEQ ID NO 124
<211> LENGTH: 676
<212> TYPE: PRT
<213> ORGANISM: Homo sapiens

<400> SEQUENCE: 124

Met Ala Pro Phe Leu Arg Ile Ala Phe Asn Ser Tyr Glu Leu Gly Ser
1               5                   10                  15

Leu Gln Ala Glu Asp Glu Ala Asn Gln Pro Phe Cys Ala Val Lys Met
                20                  25                  30

Lys Glu Ala Leu Ser Thr Glu Arg Gly Lys Thr Leu Val Gln Lys Lys
            35                  40                  45

Pro Thr Met Tyr Pro Glu Trp Lys Ser Thr Phe Asp Ala His Ile Tyr
        50                  55                  60

Glu Gly Arg Val Ile Gln Ile Val Leu Met Arg Ala Ala Glu Glu Pro
65                  70                  75                  80

Val Ser Glu Val Thr Val Gly Val Ser Val Leu Ala Glu Arg Cys Lys
                85                  90                  95

Lys Asn Asn Gly Lys Ala Glu Phe Trp Leu Asp Leu Gln Pro Gln Ala
            100                 105                 110

Lys Val Leu Met Ser Val Gln Tyr Phe Leu Glu Asp Val Asp Cys Lys
        115                 120                 125

Gln Ser Met Arg Ser Glu Asp Glu Ala Lys Phe Pro Thr Met Asn Arg
```

-continued

```
            130                 135                 140
Arg Gly Ala Ile Lys Gln Ala Lys Ile His Tyr Ile Lys Asn His Glu
145                 150                 155                 160

Phe Ile Ala Thr Phe Phe Gly Gln Pro Thr Phe Cys Ser Val Cys Lys
                165                 170                 175

Asp Phe Val Trp Gly Leu Asn Lys Gln Gly Tyr Lys Cys Arg Gln Cys
                180                 185                 190

Asn Ala Ala Ile His Lys Lys Cys Ile Asp Lys Ile Gly Arg Cys
                195                 200                 205

Thr Gly Thr Ala Ala Asn Ser Arg Asp Thr Ile Phe Gln Lys Glu Arg
210                 215                 220

Phe Asn Ile Asp Met Pro His Arg Phe Lys Val His Asn Tyr Met Ser
225                 230                 235                 240

Pro Thr Phe Cys Asp His Cys Gly Ser Leu Leu Trp Gly Leu Val Lys
                245                 250                 255

Gln Gly Leu Lys Cys Glu Asp Cys Gly Met Asn Val His His Lys Cys
                260                 265                 270

Arg Glu Lys Val Ala Asn Leu Cys Gly Ile Asn Gln Lys Leu Leu Ala
                275                 280                 285

Glu Ala Leu Asn Gln Val Thr Gln Arg Ala Ser Arg Arg Ser Asp Ser
290                 295                 300

Ala Ser Ser Glu Pro Val Gly Ile Tyr Gln Gly Phe Glu Lys Lys Thr
305                 310                 315                 320

Gly Val Ala Gly Glu Asp Met Gln Asp Asn Ser Gly Thr Tyr Gly Lys
                325                 330                 335

Ile Trp Glu Gly Ser Ser Lys Cys Asn Ile Asn Asn Phe Ile Phe His
                340                 345                 350

Lys Val Leu Gly Lys Gly Ser Phe Gly Lys Val Leu Leu Gly Glu Leu
                355                 360                 365

Lys Gly Arg Gly Glu Tyr Ser Ala Ile Lys Ala Leu Lys Lys Asp Val
                370                 375                 380

Val Leu Ile Asp Asp Val Glu Cys Thr Met Val Glu Lys Arg Val
385                 390                 395                 400

Leu Thr Leu Ala Ala Glu Asn Pro Phe Leu Thr His Leu Ile Cys Thr
                405                 410                 415

Phe Gln Thr Lys Asp His Leu Phe Phe Val Met Glu Phe Leu Asn Gly
                420                 425                 430

Gly Asp Leu Met Tyr His Ile Gln Asp Lys Gly Arg Phe Glu Leu Tyr
                435                 440                 445

Arg Ala Thr Phe Tyr Ala Ala Glu Ile Met Cys Gly Leu Gln Phe Leu
450                 455                 460

His Ser Lys Gly Ile Ile Tyr Arg Asp Leu Lys Leu Asp Asn Val Leu
465                 470                 475                 480

Leu Asp Arg Asp Gly His Ile Lys Ile Ala Asp Phe Gly Met Cys Lys
                485                 490                 495

Glu Asn Ile Phe Gly Glu Ser Arg Ala Ser Thr Phe Cys Gly Thr Pro
                500                 505                 510

Asp Tyr Ile Ala Pro Glu Ile Leu Gln Gly Leu Lys Tyr Thr Phe Ser
                515                 520                 525

Val Asp Trp Trp Ser Phe Gly Val Leu Leu Tyr Glu Met Leu Ile Gly
                530                 535                 540

Gln Ser Pro Phe His Gly Asp Asp Glu Asp Leu Phe Glu Ser Ile
545                 550                 555                 560
```

Arg Val Asp Thr Pro His Tyr Pro Arg Trp Ile Thr Lys Glu Ser Lys
            565                 570                 575

Asp Ile Leu Glu Lys Leu Phe Glu Arg Glu Pro Thr Lys Arg Leu Gly
            580                 585                 590

Met Thr Gly Asn Ile Lys Ile His Pro Phe Phe Lys Thr Ile Asn Trp
            595                 600                 605

Thr Leu Leu Glu Lys Arg Arg Leu Glu Pro Pro Phe Arg Pro Lys Val
            610                 615                 620

Lys Ser Pro Arg Asp Tyr Ser Asn Phe Asp Gln Glu Phe Leu Asn Glu
625                 630                 635                 640

Lys Ala Arg Leu Ser Tyr Ser Asp Lys Asn Leu Ile Asp Ser Met Asp
            645                 650                 655

Gln Ser Ala Phe Ala Gly Phe Ser Phe Val Asn Pro Lys Phe Glu His
            660                 665                 670

Leu Leu Glu Asp
        675

<210> SEQ ID NO 125
<211> LENGTH: 584
<212> TYPE: PRT
<213> ORGANISM: Homo sapiens

<400> SEQUENCE: 125

Met Glu Gly Ser Gly Gly Arg Val Arg Leu Lys Ala His Tyr Gly Gly
1               5                   10                  15

Asp Ile Phe Ile Thr Ser Val Asp Ala Ala Thr Thr Phe Glu Glu Leu
            20                  25                  30

Cys Glu Glu Val Arg Asp Met Cys Arg Leu His Gln Gln His Pro Leu
        35                  40                  45

Thr Leu Lys Trp Val Asp Ser Glu Gly Asp Pro Cys Thr Val Ser Ser
    50                  55                  60

Gln Met Glu Leu Glu Glu Ala Phe Arg Leu Ala Arg Gln Cys Arg Asp
65              70                  75                  80

Glu Gly Leu Ile Ile His Val Phe Pro Ser Thr Pro Glu Gln Pro Gly
                85                  90                  95

Leu Pro Cys Pro Gly Glu Asp Lys Ser Ile Tyr Arg Arg Gly Ala Arg
            100                 105                 110

Arg Trp Arg Lys Leu Tyr Arg Ala Asn Gly His Leu Phe Gln Ala Lys
        115                 120                 125

Arg Phe Asn Arg Arg Ala Tyr Cys Gly Gln Cys Ser Glu Arg Ile Trp
    130                 135                 140

Gly Leu Ala Arg Gln Gly Tyr Arg Cys Ile Asn Cys Lys Leu Leu Val
145                 150                 155                 160

His Lys Arg Cys His Gly Leu Val Pro Leu Thr Cys Arg Lys His Met
                165                 170                 175

Asp Ser Val Met Pro Ser Gln Glu Pro Pro Val Asp Asp Lys Asn Glu
            180                 185                 190

Asp Ala Asp Leu Pro Ser Glu Glu Thr Asp Gly Ile Ala Tyr Ile Ser
        195                 200                 205

Ser Ser Arg Lys His Asp Ser Ile Lys Asp Asp Ser Glu Asp Leu Lys
    210                 215                 220

Pro Val Ile Asp Gly Met Asp Gly Ile Lys Ile Ser Gln Gly Leu Gly
225                 230                 235                 240

Leu Gln Asp Phe Asp Leu Ile Arg Val Ile Gly Arg Gly Ser Tyr Ala

```
                245                 250                 255
Lys Val Leu Leu Val Arg Leu Lys Lys Asn Asp Gln Ile Tyr Ala Met
            260                 265                 270

Lys Val Val Lys Lys Glu Leu Val His Asp Asp Glu Asp Ile Asp Trp
            275                 280                 285

Val Gln Thr Glu Lys His Val Phe Glu Gln Ala Ser Ser Asn Pro Phe
            290                 295                 300

Leu Val Gly Leu His Ser Cys Phe Gln Thr Thr Ser Arg Leu Phe Leu
305                 310                 315                 320

Val Ile Glu Tyr Val Asn Gly Gly Asp Leu Met Phe His Met Gln Arg
                325                 330                 335

Gln Arg Lys Leu Pro Glu Glu His Ala Arg Phe Tyr Ala Ala Glu Ile
            340                 345                 350

Cys Ile Ala Leu Asn Phe Leu His Glu Arg Gly Ile Ile Tyr Arg Asp
            355                 360                 365

Leu Lys Leu Asp Asn Val Leu Leu Asp Ala Asp Gly His Ile Lys Leu
            370                 375                 380

Thr Asp Tyr Gly Met Cys Lys Glu Gly Leu Gly Pro Gly Asp Thr Thr
385                 390                 395                 400

Ser Thr Phe Cys Gly Thr Pro Asn Tyr Ile Ala Pro Glu Ile Leu Arg
                405                 410                 415

Gly Glu Glu Tyr Gly Phe Ser Val Asp Trp Trp Ala Leu Gly Val Leu
                420                 425                 430

Met Phe Glu Met Met Ala Gly Arg Ser Pro Phe Asp Ile Ile Thr Asp
            435                 440                 445

Asn Pro Asp Met Asn Thr Glu Asp Tyr Leu Phe Gln Val Ile Leu Glu
450                 455                 460

Lys Pro Ile Arg Ile Pro Arg Phe Leu Ser Val Lys Ala Ser His Val
465                 470                 475                 480

Leu Lys Gly Phe Leu Asn Lys Asp Pro Lys Glu Arg Leu Gly Cys Arg
                485                 490                 495

Pro Gln Thr Gly Phe Ser Asp Ile Lys Ser His Ala Phe Phe Arg Ser
            500                 505                 510

Ile Asp Trp Asp Leu Leu Glu Lys Lys Gln Ala Leu Pro Pro Phe Gln
            515                 520                 525

Pro Gln Ile Thr Asp Asp Tyr Gly Leu Asp Asn Phe Asp Thr Gln Phe
            530                 535                 540

Thr Ser Glu Pro Val Gln Leu Thr Pro Asp Asp Glu Asp Ala Ile Lys
545                 550                 555                 560

Arg Ile Asp Gln Ser Glu Phe Glu Gly Phe Glu Tyr Ile Asn Pro Leu
                565                 570                 575

Leu Leu Ser Thr Glu Glu Ser Val
            580

<210> SEQ ID NO 126
<211> LENGTH: 587
<212> TYPE: PRT
<213> ORGANISM: Homo sapiens

<400> SEQUENCE: 126

Met Ser His Thr Val Ala Gly Gly Ser Gly Asp His Ser His Gln
1               5                   10                  15

Val Arg Val Lys Ala Tyr Tyr Arg Gly Asp Ile Met Ile Thr His Phe
            20                  25                  30
```

-continued

```
Glu Pro Ser Ile Ser Phe Glu Gly Leu Cys Asn Glu Val Arg Asp Met
            35                  40                  45
Cys Ser Phe Asp Asn Glu Gln Leu Phe Thr Met Lys Trp Ile Asp Glu
 50                  55                  60
Glu Gly Asp Pro Cys Thr Val Ser Ser Gln Leu Glu Leu Glu Glu Ala
 65                  70                  75                  80
Phe Arg Leu Tyr Glu Leu Asn Lys Asp Ser Glu Leu Leu Ile His Val
                85                  90                  95
Phe Pro Cys Val Pro Glu Arg Pro Gly Met Pro Cys Pro Gly Glu Asp
               100                 105                 110
Lys Ser Ile Tyr Arg Arg Gly Ala Arg Arg Trp Arg Lys Leu Tyr Cys
               115                 120                 125
Ala Asn Gly His Thr Phe Gln Ala Lys Arg Phe Asn Arg Arg Ala His
130                 135                 140
Cys Ala Ile Cys Thr Asp Arg Ile Trp Gly Leu Gly Arg Gln Gly Tyr
145                 150                 155                 160
Lys Cys Ile Asn Cys Lys Leu Leu Val His Lys Lys Cys His Lys Leu
                165                 170                 175
Val Thr Ile Glu Cys Gly Arg His Ser Leu Pro Gln Glu Pro Val Met
               180                 185                 190
Pro Met Asp Gln Ser Ser Met His Ser Asp His Ala Gln Thr Val Ile
               195                 200                 205
Pro Tyr Asn Pro Ser Ser His Glu Ser Leu Asp Gln Val Gly Glu Glu
               210                 215                 220
Lys Glu Ala Met Asn Thr Arg Glu Ser Gly Lys Ala Ser Ser Ser Leu
225                 230                 235                 240
Gly Leu Gln Asp Phe Asp Leu Leu Arg Val Ile Gly Arg Gly Ser Tyr
                245                 250                 255
Ala Lys Val Leu Leu Val Arg Leu Lys Lys Thr Asp Arg Ile Tyr Ala
                260                 265                 270
Met Lys Val Val Lys Lys Glu Leu Val Asn Asp Asp Glu Asp Ile Asp
            275                 280                 285
Trp Val Gln Thr Glu Lys His Val Phe Glu Gln Ala Ser Asn His Pro
290                 295                 300
Phe Leu Val Gly Leu His Ser Cys Phe Gln Thr Glu Ser Arg Leu Phe
305                 310                 315                 320
Phe Val Ile Glu Tyr Val Asn Gly Gly Asp Leu Met Phe His Met Gln
                325                 330                 335
Arg Gln Arg Lys Leu Pro Glu Glu His Ala Arg Phe Tyr Ser Ala Glu
                340                 345                 350
Ile Ser Leu Ala Leu Asn Tyr Leu His Glu Arg Gly Ile Ile Tyr Arg
                355                 360                 365
Asp Leu Lys Leu Asp Asn Val Leu Leu Asp Ser Glu Gly His Ile Lys
            370                 375                 380
Leu Thr Asp Tyr Gly Met Cys Lys Glu Gly Leu Arg Pro Gly Asp Thr
385                 390                 395                 400
Thr Ser Thr Phe Cys Gly Thr Pro Asn Tyr Ile Ala Pro Glu Ile Leu
                405                 410                 415
Arg Gly Glu Asp Tyr Gly Phe Ser Val Asp Trp Trp Ala Leu Gly Val
                420                 425                 430
Leu Met Phe Glu Met Met Ala Gly Arg Ser Pro Phe Asp Ile Val Gly
                435                 440                 445
Ser Ser Asp Asn Pro Asp Gln Asn Thr Glu Asp Tyr Leu Phe Gln Val
```

```
               450                 455                 460
Ile Leu Glu Lys Gln Ile Arg Ile Pro Arg Ser Leu Ser Val Lys Ala
465                 470                 475                 480

Ala Ser Val Leu Lys Ser Phe Leu Asn Lys Asp Pro Lys Glu Arg Leu
                485                 490                 495

Gly Cys His Pro Gln Thr Gly Phe Ala Asp Ile Gln Gly His Pro Phe
            500                 505                 510

Phe Arg Asn Val Asp Trp Asp Met Met Glu Gln Lys Gln Val Val Pro
            515                 520                 525

Pro Phe Lys Pro Asn Ile Ser Gly Glu Phe Gly Leu Asp Asn Phe Asp
        530                 535                 540

Ser Gln Phe Thr Asn Glu Pro Val Gln Leu Thr Pro Asp Asp Asp Asp
545                 550                 555                 560

Ile Val Arg Lys Ile Asp Gln Ser Glu Phe Glu Gly Phe Glu Tyr Ile
                565                 570                 575

Asn Pro Leu Leu Met Ser Ala Glu Glu Cys Val
            580                 585

<210> SEQ ID NO 127
<211> LENGTH: 942
<212> TYPE: PRT
<213> ORGANISM: Homo sapiens

<400> SEQUENCE: 127

Met Ala Ser Asp Ala Val Gln Ser Glu Pro Arg Ser Trp Ser Leu Leu
1               5                   10                  15

Glu Gln Leu Gly Leu Ala Gly Ala Asp Leu Ala Ala Pro Gly Val Gln
                20                  25                  30

Gln Gln Leu Glu Leu Glu Arg Glu Arg Leu Arg Arg Glu Ile Arg Lys
            35                  40                  45

Glu Leu Lys Leu Lys Glu Gly Ala Glu Asn Leu Arg Arg Ala Thr Thr
        50                  55                  60

Asp Leu Gly Arg Ser Leu Gly Pro Val Glu Leu Leu Leu Arg Gly Ser
65                  70                  75                  80

Ser Arg Arg Leu Asp Leu Leu His Gln Gln Leu Gln Glu Leu His Ala
                85                  90                  95

His Val Val Leu Pro Asp Pro Ala Thr His Asp Gly Pro Gln Ser
            100                 105                 110

Pro Gly Ala Gly Gly Pro Thr Cys Ser Ala Thr Asn Leu Ser Arg Val
        115                 120                 125

Ala Gly Leu Glu Lys Gln Leu Ala Ile Glu Leu Lys Val Lys Gln Gly
    130                 135                 140

Ala Glu Asn Met Ile Gln Thr Tyr Ser Asn Gly Ser Thr Lys Asp Arg
145                 150                 155                 160

Lys Leu Leu Leu Thr Ala Gln Gln Met Leu Gln Asp Ser Lys Thr Lys
                165                 170                 175

Ile Asp Ile Ile Arg Met Gln Leu Arg Arg Ala Leu Gln Ala Asp Gln
            180                 185                 190

Leu Glu Asn Gln Ala Ala Pro Asp Asp Thr Gln Gly Ser Pro Asp Leu
        195                 200                 205

Gly Ala Val Glu Leu Arg Ile Glu Glu Leu Arg His His Phe Arg Val
    210                 215                 220

Glu His Ala Val Ala Glu Gly Ala Lys Asn Val Leu Arg Leu Leu Ser
225                 230                 235                 240
```

-continued

```
Ala Ala Lys Ala Pro Asp Arg Lys Ala Val Ser Glu Ala Gln Glu Lys
            245                 250                 255
Leu Thr Glu Ser Asn Gln Lys Leu Gly Leu Leu Arg Glu Ala Leu Glu
        260                 265                 270
Arg Arg Leu Gly Glu Leu Pro Ala Asp His Pro Lys Gly Arg Leu Leu
    275                 280                 285
Arg Glu Glu Leu Ala Ala Ala Ser Ser Ala Ala Phe Ser Thr Arg Leu
290                 295                 300
Ala Gly Pro Phe Pro Ala Thr His Tyr Ser Thr Leu Cys Lys Pro Ala
305                 310                 315                 320
Pro Leu Thr Gly Thr Leu Glu Val Arg Val Gly Cys Arg Asp Leu
            325                 330                 335
Pro Glu Thr Ile Pro Trp Asn Pro Thr Pro Ser Met Gly Gly Pro Gly
        340                 345                 350
Thr Pro Asp Ser Arg Pro Pro Phe Leu Ser Arg Pro Ala Arg Gly Leu
    355                 360                 365
Tyr Ser Arg Ser Gly Ser Leu Ser Gly Arg Ser Ser Leu Lys Ala Glu
    370                 375                 380
Ala Glu Asn Thr Ser Glu Val Ser Thr Val Leu Lys Leu Asp Asn Thr
385                 390                 395                 400
Val Val Gly Gln Thr Ser Trp Lys Pro Cys Gly Pro Asn Ala Trp Asp
            405                 410                 415
Gln Ser Phe Thr Leu Glu Leu Glu Arg Ala Arg Glu Leu Glu Leu Ala
        420                 425                 430
Val Phe Trp Arg Asp Gln Arg Gly Leu Cys Ala Leu Lys Phe Leu Lys
    435                 440                 445
Leu Glu Asp Phe Leu Asp Asn Glu Arg His Glu Val Gln Leu Asp Met
    450                 455                 460
Glu Pro Gln Gly Cys Leu Val Ala Glu Val Thr Phe Arg Asn Pro Val
465                 470                 475                 480
Ile Glu Arg Ile Pro Arg Leu Arg Arg Gln Lys Lys Ile Phe Ser Lys
            485                 490                 495
Gln Gln Gly Lys Ala Phe Gln Arg Ala Arg Gln Met Asn Ile Asp Val
        500                 505                 510
Ala Thr Trp Val Arg Leu Leu Arg Arg Leu Ile Pro Asn Ala Thr Gly
    515                 520                 525
Thr Gly Thr Phe Ser Pro Gly Ala Ser Pro Gly Ser Glu Ala Arg Thr
    530                 535                 540
Thr Gly Asp Ile Ser Val Glu Lys Leu Asn Leu Gly Thr Asp Ser Asp
545                 550                 555                 560
Ser Ser Pro Gln Lys Ser Ser Arg Asp Pro Ser Ser Pro Ser Ser
            565                 570                 575
Leu Ser Ser Pro Ile Gln Glu Ser Thr Ala Pro Glu Leu Pro Ser Glu
        580                 585                 590
Thr Gln Glu Thr Pro Gly Pro Ala Leu Cys Ser Pro Leu Arg Lys Ser
    595                 600                 605
Pro Leu Thr Leu Glu Asp Phe Lys Phe Leu Ala Val Leu Gly Arg Gly
    610                 615                 620
His Phe Gly Lys Val Leu Leu Ser Glu Phe Arg Pro Ser Gly Glu Leu
625                 630                 635                 640
Phe Ala Ile Lys Ala Leu Lys Lys Gly Asp Ile Val Ala Arg Asp Glu
            645                 650                 655
Val Glu Ser Leu Met Cys Glu Lys Arg Ile Leu Ala Ala Val Thr Ser
```

```
                    660                 665                 670
Ala Gly His Pro Phe Leu Val Asn Leu Phe Gly Cys Phe Gln Thr Pro
            675                 680                 685

Glu His Val Cys Phe Val Met Glu Tyr Ser Ala Gly Gly Asp Leu Met
            690                 695                 700

Leu His Ile His Ser Asp Val Phe Ser Glu Pro Arg Ala Ile Phe Tyr
705                 710                 715                 720

Ser Ala Cys Val Val Leu Gly Leu Gln Phe Leu His Glu His Lys Ile
                725                 730                 735

Val Tyr Arg Asp Leu Lys Leu Asp Asn Leu Leu Leu Asp Thr Glu Gly
            740                 745                 750

Tyr Val Lys Ile Ala Asp Phe Gly Leu Cys Lys Glu Gly Met Gly Tyr
            755                 760                 765

Gly Asp Arg Thr Ser Thr Phe Cys Gly Thr Pro Glu Phe Leu Ala Pro
            770                 775                 780

Glu Val Leu Thr Asp Thr Ser Tyr Thr Arg Ala Val Asp Trp Trp Gly
785                 790                 795                 800

Leu Gly Val Leu Leu Tyr Glu Met Leu Val Gly Glu Ser Pro Phe Pro
                805                 810                 815

Gly Asp Asp Glu Glu Glu Val Phe Asp Ser Ile Val Asn Asp Glu Val
            820                 825                 830

Arg Tyr Pro Arg Phe Leu Ser Ala Glu Ala Ile Gly Ile Met Arg Arg
            835                 840                 845

Leu Leu Arg Arg Asn Pro Glu Arg Arg Leu Gly Ser Ser Glu Arg Asp
850                 855                 860

Ala Glu Asp Val Lys Lys Gln Pro Phe Phe Arg Thr Leu Gly Trp Glu
865                 870                 875                 880

Ala Leu Leu Ala Arg Arg Leu Pro Pro Pro Phe Val Pro Thr Leu Ser
                885                 890                 895

Gly Arg Thr Asp Val Ser Asn Phe Asp Glu Glu Phe Thr Gly Glu Ala
            900                 905                 910

Pro Thr Leu Ser Pro Pro Arg Asp Ala Arg Pro Leu Thr Ala Ala Glu
            915                 920                 925

Gln Ala Ala Phe Leu Asp Phe Asp Phe Val Ala Gly Gly Cys
            930                 935                 940

<210> SEQ ID NO 128
<211> LENGTH: 984
<212> TYPE: PRT
<213> ORGANISM: Homo sapiens

<400> SEQUENCE: 128

Met Ala Ser Asn Pro Glu Arg Gly Glu Ile Leu Leu Thr Glu Leu Gln
1               5                   10                  15

Gly Asp Ser Arg Ser Leu Pro Phe Ser Glu Asn Val Ser Ala Val Gln
                20                  25                  30

Lys Leu Asp Phe Ser Asp Thr Met Val Gln Gln Lys Leu Asp Asp Ile
            35                  40                  45

Lys Asp Arg Ile Lys Arg Glu Ile Arg Lys Glu Leu Lys Ile Lys Glu
        50                  55                  60

Gly Ala Glu Asn Leu Arg Lys Val Thr Thr Asp Lys Lys Ser Leu Ala
65                  70                  75                  80

Tyr Val Asp Asn Ile Leu Lys Lys Ser Asn Lys Lys Leu Glu Glu Leu
                85                  90                  95
```

-continued

```
His His Lys Leu Gln Glu Leu Asn Ala His Ile Val Val Ser Asp Pro
            100                 105                 110
Glu Asp Ile Thr Asp Cys Pro Arg Thr Pro Asp Thr Pro Asn Asn Asp
        115                 120                 125
Pro Arg Cys Ser Thr Ser Asn Asn Arg Leu Lys Ala Leu Gln Lys Gln
    130                 135                 140
Leu Asp Ile Glu Leu Lys Val Lys Gln Gly Ala Glu Asn Met Ile Gln
145                 150                 155                 160
Met Tyr Ser Asn Gly Ser Ser Lys Asp Arg Lys Leu His Gly Thr Ala
                165                 170                 175
Gln Gln Leu Leu Gln Asp Ser Lys Thr Lys Ile Glu Val Ile Arg Met
            180                 185                 190
Gln Ile Leu Gln Ala Val Gln Thr Asn Glu Leu Ala Phe Asp Asn Ala
        195                 200                 205
Lys Pro Val Ile Ser Pro Leu Glu Leu Arg Met Glu Glu Leu Arg His
    210                 215                 220
His Phe Arg Ile Glu Phe Ala Val Ala Glu Gly Ala Lys Asn Val Met
225                 230                 235                 240
Lys Leu Leu Gly Ser Gly Lys Val Thr Asp Arg Lys Ala Leu Ser Glu
                245                 250                 255
Ala Gln Ala Arg Phe Asn Glu Ser Ser Gln Lys Leu Asp Leu Leu Lys
            260                 265                 270
Tyr Ser Leu Glu Gln Arg Leu Asn Glu Val Pro Lys Asn His Pro Lys
        275                 280                 285
Ser Arg Ile Ile Ile Glu Glu Leu Ser Leu Val Ala Ala Ser Pro Thr
    290                 295                 300
Leu Ser Pro Arg Gln Ser Met Ile Ser Thr Gln Asn Gln Tyr Ser Thr
305                 310                 315                 320
Leu Ser Lys Pro Ala Ala Leu Thr Gly Thr Leu Glu Val Arg Leu Met
                325                 330                 335
Gly Cys Gln Asp Ile Leu Glu Asn Val Pro Gly Arg Ser Lys Ala Thr
            340                 345                 350
Ser Val Ala Leu Pro Gly Trp Ser Pro Ser Glu Thr Arg Ser Ser Phe
        355                 360                 365
Met Ser Arg Thr Ser Lys Ser Lys Ser Gly Ser Ser Arg Asn Leu Leu
    370                 375                 380
Lys Thr Asp Asp Leu Ser Asn Asp Val Cys Ala Val Leu Lys Leu Asp
385                 390                 395                 400
Asn Thr Val Val Gly Gln Thr Ser Trp Lys Pro Ile Ser Asn Gln Ser
                405                 410                 415
Trp Asp Gln Lys Phe Thr Leu Glu Leu Asp Arg Ser Arg Glu Leu Glu
            420                 425                 430
Ile Ser Val Tyr Trp Arg Asp Trp Arg Ser Leu Cys Ala Val Lys Phe
        435                 440                 445
Leu Arg Leu Glu Asp Phe Leu Asp Asn Gln Arg His Gly Met Cys Leu
    450                 455                 460
Tyr Leu Glu Pro Gln Gly Thr Leu Phe Ala Glu Val Thr Phe Phe Asn
465                 470                 475                 480
Pro Val Ile Glu Arg Arg Pro Lys Leu Gln Arg Gln Lys Lys Ile Phe
                485                 490                 495
Ser Lys Gln Gln Gly Lys Thr Phe Leu Arg Ala Pro Gln Met Asn Ile
            500                 505                 510
Asn Ile Ala Thr Trp Gly Arg Leu Val Arg Arg Ala Ile Pro Thr Val
```

-continued

```
            515                 520                 525
Asn His Ser Gly Thr Phe Ser Pro Gln Ala Pro Val Pro Thr Thr Val
        530                 535                 540

Pro Val Val Asp Val Arg Ile Pro Gln Leu Ala Pro Pro Ala Ser Asp
545                 550                 555                 560

Ser Thr Val Thr Lys Leu Asp Phe Asp Leu Glu Pro Glu Pro Pro Pro
                565                 570                 575

Ala Pro Pro Arg Ala Ser Ser Leu Gly Glu Ile Asp Glu Ser Ser Glu
            580                 585                 590

Leu Arg Val Leu Asp Ile Pro Gly Gln Asp Ser Glu Thr Val Phe Asp
        595                 600                 605

Ile Gln Asn Asp Arg Asn Ser Ile Leu Pro Lys Ser Gln Ser Glu Tyr
    610                 615                 620

Lys Pro Asp Thr Pro Gln Ser Gly Leu Glu Tyr Ser Gly Ile Gln Glu
625                 630                 635                 640

Leu Glu Asp Arg Arg Ser Gln Gln Arg Phe Gln Phe Asn Leu Gln Asp
                645                 650                 655

Phe Arg Cys Cys Ala Val Leu Gly Arg Gly His Phe Gly Lys Val Leu
            660                 665                 670

Leu Ala Glu Tyr Lys Asn Thr Asn Glu Met Phe Ala Ile Lys Ala Leu
        675                 680                 685

Lys Lys Gly Asp Ile Val Ala Arg Asp Glu Val Asp Ser Leu Met Cys
    690                 695                 700

Glu Lys Arg Ile Phe Glu Thr Val Asn Ser Val Arg His Pro Phe Leu
705                 710                 715                 720

Val Asn Leu Phe Ala Cys Phe Gln Thr Lys Glu His Val Cys Phe Val
                725                 730                 735

Met Glu Tyr Ala Ala Gly Gly Asp Leu Met Met His Ile His Thr Asp
            740                 745                 750

Val Phe Ser Glu Pro Arg Ala Val Phe Tyr Ala Ala Cys Val Val Leu
        755                 760                 765

Gly Leu Gln Tyr Leu His Glu His Lys Ile Val Tyr Arg Asp Leu Lys
    770                 775                 780

Leu Asp Asn Leu Leu Leu Asp Thr Glu Gly Phe Val Lys Ile Ala Asp
785                 790                 795                 800

Phe Gly Leu Cys Lys Glu Gly Met Gly Tyr Gly Asp Arg Thr Ser Thr
                805                 810                 815

Phe Cys Gly Thr Pro Glu Phe Leu Ala Pro Glu Val Leu Thr Glu Thr
            820                 825                 830

Ser Tyr Thr Arg Ala Val Asp Trp Trp Gly Leu Gly Val Leu Ile Tyr
        835                 840                 845

Glu Met Leu Val Gly Glu Ser Pro Phe Pro Gly Asp Asp Glu Glu Glu
    850                 855                 860

Val Phe Asp Ser Ile Val Asn Asp Glu Val Arg Tyr Pro Arg Phe Leu
865                 870                 875                 880

Ser Thr Glu Ala Ile Ser Ile Met Arg Arg Leu Leu Arg Arg Asn Pro
                885                 890                 895

Glu Arg Arg Leu Gly Ala Ser Glu Lys Asp Ala Glu Asp Val Lys Lys
            900                 905                 910

His Pro Phe Phe Arg Leu Ile Asp Trp Ser Ala Leu Met Asp Lys Lys
        915                 920                 925

Val Lys Pro Pro Phe Ile Pro Thr Ile Arg Gly Arg Glu Asp Val Ser
    930                 935                 940
```

```
Asn Phe Asp Asp Glu Phe Thr Ser Glu Ala Pro Ile Leu Thr Pro Pro
945                 950                 955                 960

Arg Glu Pro Arg Ile Leu Ser Glu Glu Gln Glu Met Phe Arg Asp
            965                 970                 975

Phe Asp Tyr Ile Ala Asp Trp Cys
            980

<210> SEQ ID NO 129
<211> LENGTH: 525
<212> TYPE: PRT
<213> ORGANISM: Homo sapiens

<400> SEQUENCE: 129

Met Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
                20                  25                  30

Asp Gln Pro Glu Asp Ala Gly Ser Glu Asp Glu Leu Glu Glu Gly Gly
            35                  40                  45

Gln Leu Asn Glu Ser Met Asp His Gly Val Gly Pro Tyr Glu Leu
        50                  55                  60

Gly Met Glu His Cys Glu Lys Phe Glu Ile Ser Glu Thr Ser Val Asn
65              70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
                100                 105                 110

Gly Ala Asn Thr Gly Lys Ile Phe Ala Met Lys Val Leu Lys Lys Ala
            115                 120                 125

Met Ile Val Arg Asn Ala Lys Asp Thr Ala His Thr Lys Ala Glu Arg
130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
        195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
        275                 280                 285

Gly Ala Pro Pro Phe Thr Gly Glu Asn Arg Lys Lys Thr Ile Asp Lys
    290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
```

-continued

```
                325                 330                 335
Gly Ala Gly Pro Gly Asp Ala Gly Glu Val Gln Ala His Pro Phe Phe
            340                 345                 350

Arg His Ile Asn Trp Glu Glu Leu Leu Ala Arg Lys Val Glu Pro Pro
            355                 360                 365

Phe Lys Pro Leu Leu Gln Ser Glu Asp Val Ser Gln Phe Asp Ser
            370                 375                 380

Lys Phe Thr Arg Gln Thr Pro Val Asp Ser Pro Asp Asp Ser Thr Leu
385                 390                 395                 400

Ser Glu Ser Ala Asn Gln Val Phe Leu Gly Phe Thr Tyr Val Ala Pro
            405                 410                 415

Ser Val Leu Glu Ser Val Lys Glu Lys Phe Ser Phe Glu Pro Lys Ile
            420                 425                 430

Arg Ser Pro Arg Arg Phe Ile Gly Ser Pro Arg Thr Pro Val Ser Pro
            435                 440                 445

Val Lys Phe Ser Pro Gly Asp Phe Trp Gly Arg Gly Ala Ser Ala Ser
            450                 455                 460

Thr Ala Asn Pro Gln Thr Pro Val Glu Tyr Pro Met Glu Thr Ser Gly
465                 470                 475                 480

Ile Glu Gln Met Asp Val Thr Met Ser Gly Glu Ala Ser Ala Pro Leu
            485                 490                 495

Pro Ile Arg Gln Pro Asn Ser Gly Pro Tyr Lys Lys Gln Ala Phe Pro
            500                 505                 510

Met Ile Ser Lys Arg Pro Glu His Leu Arg Met Asn Leu
            515                 520                 525

<210> SEQ ID NO 130
<211> LENGTH: 495
<212> TYPE: PRT
<213> ORGANISM: Homo sapiens

<400> SEQUENCE: 130

Met Ala Arg Gly Arg Ala Arg Gly Ala Gly Ala Ala Met Ala Ala
1               5                   10                  15

Val Phe Asp Leu Asp Leu Glu Thr Glu Glu Gly Ser Glu Gly Glu Gly
            20                  25                  30

Glu Pro Glu Leu Ser Pro Ala Asp Ala Cys Pro Leu Ala Glu Leu Arg
        35                  40                  45

Ala Ala Gly Leu Glu Pro Val Gly His Tyr Glu Glu Val Glu Leu Thr
    50                  55                  60

Glu Thr Ser Val Asn Val Gly Pro Glu Arg Ile Gly Pro His Cys Phe
65                  70                  75                  80

Glu Leu Leu Arg Val Leu Gly Lys Gly Gly Tyr Gly Lys Val Phe Gln
            85                  90                  95

Val Arg Lys Val Gln Gly Thr Asn Leu Gly Lys Ile Tyr Ala Met Lys
            100                 105                 110

Val Leu Arg Lys Ala Lys Ile Val Arg Asn Ala Lys Asp Thr Ala His
        115                 120                 125

Thr Arg Ala Glu Arg Asn Ile Leu Glu Ser Val Lys His Pro Phe Ile
    130                 135                 140

Val Glu Leu Ala Tyr Ala Phe Gln Thr Gly Gly Lys Leu Tyr Leu Ile
145                 150                 155                 160

Leu Glu Cys Leu Ser Gly Gly Glu Leu Phe Thr His Leu Glu Arg Glu
            165                 170                 175
```

```
Gly Ile Phe Leu Glu Asp Thr Ala Cys Phe Tyr Leu Ala Glu Ile Thr
            180                 185                 190

Leu Ala Leu Gly His Leu His Ser Gln Gly Ile Ile Tyr Arg Asp Leu
        195                 200                 205

Lys Pro Glu Asn Ile Met Leu Ser Ser Gln Gly His Ile Lys Leu Thr
    210                 215                 220

Asp Phe Gly Leu Cys Lys Glu Ser Ile His Glu Gly Ala Val Thr His
225                 230                 235                 240

Thr Phe Cys Gly Thr Ile Glu Tyr Met Ala Pro Glu Ile Leu Val Arg
                245                 250                 255

Ser Gly His Asn Arg Ala Val Asp Trp Trp Ser Leu Gly Ala Leu Met
            260                 265                 270

Tyr Asp Met Leu Thr Gly Ser Pro Pro Phe Thr Ala Glu Asn Arg Lys
        275                 280                 285

Lys Thr Met Asp Lys Ile Ile Arg Gly Lys Leu Ala Leu Pro Pro Tyr
    290                 295                 300

Leu Thr Pro Asp Ala Arg Asp Leu Val Lys Lys Phe Leu Lys Arg Asn
305                 310                 315                 320

Pro Ser Gln Arg Ile Gly Gly Gly Pro Gly Asp Ala Ala Asp Val Gln
                325                 330                 335

Arg His Pro Phe Phe Arg His Met Asn Trp Asp Asp Leu Leu Ala Trp
            340                 345                 350

Arg Val Asp Pro Pro Phe Arg Pro Cys Leu Gln Ser Glu Glu Asp Val
        355                 360                 365

Ser Gln Phe Asp Thr Arg Phe Thr Arg Gln Thr Pro Val Asp Ser Pro
    370                 375                 380

Asp Asp Thr Ala Leu Ser Glu Ser Ala Asn Gln Ala Phe Leu Gly Phe
385                 390                 395                 400

Thr Tyr Val Ala Pro Ser Val Leu Asp Ser Ile Lys Glu Gly Phe Ser
                405                 410                 415

Phe Gln Pro Lys Leu Arg Ser Pro Arg Arg Leu Asn Ser Ser Pro Arg
            420                 425                 430

Val Pro Val Ser Pro Leu Lys Phe Ser Pro Phe Glu Gly Phe Arg Pro
        435                 440                 445

Ser Pro Ser Leu Pro Glu Pro Thr Glu Leu Pro Leu Pro Pro Leu Leu
    450                 455                 460

Pro Pro Pro Pro Pro Ser Thr Thr Ala Pro Leu Pro Ile Arg Pro Pro
465                 470                 475                 480

Ser Gly Thr Lys Lys Ser Lys Arg Gly Arg Gly Arg Pro Gly Arg
                485                 490                 495

<210> SEQ ID NO 131
<211> LENGTH: 740
<212> TYPE: PRT
<213> ORGANISM: Homo sapiens

<400> SEQUENCE: 131

Met Pro Leu Ala Gln Leu Ala Asp Pro Trp Gln Lys Met Ala Val Glu
1               5                   10                  15

Ser Pro Ser Asp Ser Ala Glu Asn Gly Gln Gln Ile Met Asp Glu Pro
            20                  25                  30

Met Gly Glu Glu Glu Ile Asn Pro Gln Thr Glu Glu Val Ser Ile Lys
        35                  40                  45

Glu Ile Ala Ile Thr His His Val Lys Glu Gly His Glu Lys Ala Asp
    50                  55                  60
```

```
Pro Ser Gln Phe Glu Leu Leu Lys Val Leu Gly Gln Gly Ser Phe Gly
 65                  70                  75                  80

Lys Val Phe Leu Val Lys Lys Ile Ser Gly Ser Asp Ala Arg Gln Leu
                 85                  90                  95

Tyr Ala Met Lys Val Leu Lys Lys Ala Thr Leu Lys Val Arg Asp Arg
            100                 105                 110

Val Arg Thr Lys Met Glu Arg Asp Ile Leu Val Glu Val Asn His Pro
        115                 120                 125

Phe Ile Val Lys Leu His Tyr Ala Phe Gln Thr Glu Gly Lys Leu Tyr
130                 135                 140

Leu Ile Leu Asp Phe Leu Arg Gly Gly Asp Leu Phe Thr Arg Leu Ser
145                 150                 155                 160

Lys Glu Val Met Phe Thr Glu Glu Asp Val Lys Phe Tyr Leu Ala Glu
                165                 170                 175

Leu Ala Leu Ala Leu Asp His Leu His Ser Leu Gly Ile Ile Tyr Arg
            180                 185                 190

Asp Leu Lys Pro Glu Asn Ile Leu Leu Asp Glu Glu Gly His Ile Lys
        195                 200                 205

Leu Thr Asp Phe Gly Leu Ser Lys Glu Ser Ile Asp His Glu Lys Lys
    210                 215                 220

Ala Tyr Ser Phe Cys Gly Thr Val Glu Tyr Met Ala Pro Glu Val Val
225                 230                 235                 240

Asn Arg Arg Gly His Thr Gln Ser Ala Asp Trp Trp Ser Phe Gly Val
                245                 250                 255

Leu Met Phe Glu Met Leu Thr Gly Thr Leu Pro Phe Gln Gly Lys Asp
            260                 265                 270

Arg Lys Glu Thr Met Thr Met Ile Leu Lys Ala Lys Leu Gly Met Pro
        275                 280                 285

Gln Phe Leu Ser Pro Glu Ala Gln Ser Leu Leu Arg Met Leu Phe Lys
    290                 295                 300

Arg Asn Pro Ala Asn Arg Leu Gly Ala Gly Pro Asp Gly Val Glu Glu
305                 310                 315                 320

Ile Lys Arg His Ser Phe Phe Ser Thr Ile Asp Trp Asn Lys Leu Tyr
                325                 330                 335

Arg Arg Glu Ile His Pro Pro Phe Lys Pro Ala Thr Gly Arg Pro Glu
            340                 345                 350

Asp Thr Phe Tyr Phe Asp Pro Glu Phe Thr Ala Lys Thr Pro Lys Asp
        355                 360                 365

Ser Pro Gly Ile Pro Pro Ser Ala Asn Ala His Gln Leu Phe Arg Gly
    370                 375                 380

Phe Ser Phe Val Ala Ile Thr Ser Asp Asp Glu Ser Gln Ala Met Gln
385                 390                 395                 400

Thr Val Gly Val His Ser Ile Val Gln Gln Leu His Arg Asn Ser Ile
                405                 410                 415

Gln Phe Thr Asp Gly Tyr Glu Val Lys Glu Asp Ile Gly Val Gly Ser
            420                 425                 430

Tyr Ser Val Cys Lys Arg Cys Ile His Lys Ala Thr Asn Met Glu Phe
        435                 440                 445

Ala Val Lys Ile Ile Asp Lys Ser Lys Arg Asp Pro Thr Glu Glu Ile
    450                 455                 460

Glu Ile Leu Leu Arg Tyr Gly Gln His Pro Asn Ile Ile Thr Leu Lys
465                 470                 475                 480
```

-continued

```
Asp Val Tyr Asp Asp Gly Lys Tyr Val Tyr Val Thr Glu Leu Met
            485                 490                 495
Lys Gly Gly Glu Leu Leu Asp Lys Ile Leu Arg Gln Lys Phe Phe Ser
        500                 505                 510
Glu Arg Glu Ala Ser Ala Val Leu Phe Thr Ile Thr Lys Thr Val Glu
        515                 520                 525
Tyr Leu His Ala Gln Gly Val Val His Arg Asp Leu Lys Pro Ser Asn
    530                 535                 540
Ile Leu Tyr Val Asp Glu Ser Gly Asn Pro Glu Ser Ile Arg Ile Cys
545                 550                 555                 560
Asp Phe Gly Phe Ala Lys Gln Leu Arg Ala Glu Asn Gly Leu Leu Met
            565                 570                 575
Thr Pro Cys Tyr Thr Ala Asn Phe Val Ala Pro Glu Val Leu Lys Arg
        580                 585                 590
Gln Gly Tyr Asp Ala Ala Cys Asp Ile Trp Ser Leu Gly Val Leu Leu
        595                 600                 605
Tyr Thr Met Leu Thr Gly Tyr Thr Pro Phe Ala Asn Gly Pro Asp Asp
    610                 615                 620
Thr Pro Glu Glu Ile Leu Ala Arg Ile Gly Ser Gly Lys Phe Ser Leu
625                 630                 635                 640
Ser Gly Gly Tyr Trp Asn Ser Val Ser Asp Thr Ala Lys Asp Leu Val
            645                 650                 655
Ser Lys Met Leu His Val Asp Pro His Gln Arg Leu Thr Ala Ala Leu
        660                 665                 670
Val Leu Arg His Pro Trp Ile Val His Trp Asp Gln Leu Pro Gln Tyr
        675                 680                 685
Gln Leu Asn Arg Gln Asp Ala Pro His Leu Val Lys Gly Ala Met Ala
    690                 695                 700
Ala Thr Tyr Ser Ala Leu Asn Arg Asn Gln Ser Pro Val Leu Glu Pro
705                 710                 715                 720
Val Gly Arg Ser Thr Leu Ala Gln Arg Arg Gly Ile Lys Lys Ile Thr
            725                 730                 735
Ser Thr Ala Leu
            740

<210> SEQ ID NO 132
<211> LENGTH: 740
<212> TYPE: PRT
<213> ORGANISM: Homo sapiens

<400> SEQUENCE: 132

Met Pro Leu Ala Gln Leu Ala Asp Pro Trp Gln Lys Met Ala Val Glu
1               5                   10                  15
Ser Pro Ser Asp Ser Ala Glu Asn Gly Gln Gln Ile Met Asp Glu Pro
            20                  25                  30
Met Gly Glu Glu Glu Ile Asn Pro Gln Thr Glu Glu Val Ser Ile Lys
        35                  40                  45
Glu Ile Ala Ile Thr His His Val Lys Glu Gly His Glu Lys Ala Asp
    50                  55                  60
Pro Ser Gln Phe Glu Leu Leu Lys Val Leu Gly Gln Gly Ser Phe Gly
65                  70                  75                  80
Lys Val Phe Leu Val Lys Lys Ile Ser Gly Ser Asp Ala Arg Gln Leu
            85                  90                  95
Tyr Ala Met Lys Val Leu Lys Lys Ala Thr Leu Lys Val Arg Asp Arg
        100                 105                 110
```

```
Val Arg Thr Lys Met Glu Arg Asp Ile Leu Val Glu Val Asn His Pro
        115                 120                 125

Phe Ile Val Lys Leu His Tyr Ala Phe Gln Thr Glu Gly Lys Leu Tyr
        130                 135                 140

Leu Ile Leu Asp Phe Leu Arg Gly Gly Asp Leu Phe Thr Arg Leu Ser
145                 150                 155                 160

Lys Glu Val Met Phe Thr Glu Asp Val Lys Phe Tyr Leu Ala Glu
                165                 170                 175

Leu Ala Leu Ala Leu Asp His Leu His Ser Leu Gly Ile Ile Tyr Arg
                180                 185                 190

Asp Leu Lys Pro Glu Asn Ile Leu Leu Asp Glu Gly His Ile Lys
        195                 200                 205

Leu Thr Asp Phe Gly Leu Ser Lys Glu Ser Ile Asp His Glu Lys Lys
        210                 215                 220

Ala Tyr Ser Phe Cys Gly Thr Val Glu Tyr Met Ala Pro Glu Val Val
225                 230                 235                 240

Asn Arg Arg Gly His Thr Gln Ser Ala Asp Trp Trp Ser Phe Gly Val
                245                 250                 255

Leu Met Phe Glu Met Leu Thr Gly Thr Leu Pro Phe Gln Gly Lys Asp
                260                 265                 270

Arg Lys Glu Thr Met Thr Met Ile Leu Lys Ala Lys Leu Gly Met Pro
        275                 280                 285

Gln Phe Leu Ser Pro Glu Ala Gln Ser Leu Leu Arg Met Leu Phe Lys
        290                 295                 300

Arg Asn Pro Ala Asn Arg Leu Gly Ala Gly Pro Asp Gly Val Glu Glu
305                 310                 315                 320

Ile Lys Arg His Ser Phe Phe Ser Thr Ile Asp Trp Asn Lys Leu Tyr
                325                 330                 335

Arg Arg Glu Ile His Pro Pro Phe Lys Pro Ala Thr Gly Arg Pro Glu
                340                 345                 350

Asp Thr Phe Tyr Phe Asp Pro Glu Phe Thr Ala Lys Thr Pro Lys Asp
        355                 360                 365

Ser Pro Gly Ile Pro Pro Ser Ala Asn Ala His Gln Leu Phe Arg Gly
        370                 375                 380

Phe Ser Phe Val Ala Ile Thr Ser Asp Asp Glu Ser Gln Ala Met Gln
385                 390                 395                 400

Thr Val Gly Val His Ser Ile Val Gln Gln Leu His Arg Asn Ser Ile
                405                 410                 415

Gln Phe Thr Asp Gly Tyr Glu Val Lys Glu Asp Ile Gly Val Gly Ser
                420                 425                 430

Tyr Ser Val Cys Lys Arg Cys Ile His Lys Ala Thr Asn Met Glu Phe
        435                 440                 445

Ala Val Lys Ile Ile Asp Lys Ser Lys Arg Asp Pro Thr Glu Ile
        450                 455                 460

Glu Ile Leu Leu Arg Tyr Gly Gln His Pro Asn Ile Ile Thr Leu Lys
465                 470                 475                 480

Asp Val Tyr Asp Asp Gly Lys Tyr Val Tyr Val Thr Glu Leu Met
                485                 490                 495

Lys Gly Gly Glu Leu Leu Asp Lys Ile Leu Arg Gln Lys Phe Ser
        500                 505                 510

Glu Arg Glu Ala Ser Ala Val Leu Phe Thr Ile Thr Lys Thr Val Glu
        515                 520                 525
```

-continued

```
Tyr Leu His Ala Gln Gly Val His Arg Asp Leu Lys Pro Ser Asn
530                 535                 540

Ile Leu Tyr Val Asp Glu Ser Gly Asn Pro Glu Ser Ile Arg Ile Cys
545                 550                 555                 560

Asp Phe Gly Phe Ala Lys Gln Leu Arg Ala Glu Asn Gly Leu Leu Met
                565                 570                 575

Thr Pro Cys Tyr Thr Ala Asn Phe Val Ala Pro Glu Val Leu Lys Arg
            580                 585                 590

Gln Gly Tyr Asp Ala Ala Cys Asp Ile Trp Ser Leu Gly Val Leu Leu
        595                 600                 605

Tyr Thr Met Leu Thr Gly Tyr Thr Pro Phe Ala Asn Gly Pro Asp Asp
610                 615                 620

Thr Pro Glu Glu Ile Leu Ala Arg Ile Gly Ser Gly Lys Phe Ser Leu
625                 630                 635                 640

Ser Gly Gly Tyr Trp Asn Ser Val Ser Asp Thr Ala Lys Asp Leu Val
                645                 650                 655

Ser Lys Met Leu His Val Asp Pro His Gln Arg Leu Thr Ala Ala Leu
            660                 665                 670

Val Leu Arg His Pro Trp Ile Val His Trp Asp Gln Leu Pro Gln Tyr
        675                 680                 685

Gln Leu Asn Arg Gln Asp Ala Pro His Leu Val Lys Gly Ala Met Ala
690                 695                 700

Ala Thr Tyr Ser Ala Leu Asn Arg Asn Gln Ser Pro Val Leu Glu Pro
705                 710                 715                 720

Val Gly Arg Ser Thr Leu Ala Gln Arg Arg Gly Ile Lys Lys Ile Thr
                725                 730                 735

Ser Thr Ala Leu
            740

<210> SEQ ID NO 133
<211> LENGTH: 733
<212> TYPE: PRT
<213> ORGANISM: Homo sapiens

<400> SEQUENCE: 133

Met Asp Leu Ser Met Lys Lys Phe Ala Val Arg Arg Phe Phe Ser Val
1               5                   10                  15

Tyr Leu Arg Arg Lys Ser Arg Ser Lys Ser Ser Ser Leu Ser Arg Leu
                20                  25                  30

Glu Glu Glu Gly Val Val Lys Glu Ile Asp Ile Ser His His Val Lys
            35                  40                  45

Glu Gly Phe Glu Lys Ala Asp Pro Ser Gln Phe Glu Leu Leu Lys Val
        50                  55                  60

Leu Gly Gln Gly Ser Tyr Gly Lys Val Phe Leu Val Arg Lys Val Lys
65                  70                  75                  80

Gly Ser Asp Ala Gly Gln Leu Tyr Ala Met Lys Val Leu Lys Lys Ala
                85                  90                  95

Thr Leu Lys Val Arg Asp Arg Val Arg Ser Lys Met Glu Arg Asp Ile
            100                 105                 110

Leu Ala Glu Val Asn His Pro Phe Ile Val Lys Leu His Tyr Ala Phe
        115                 120                 125

Gln Thr Glu Gly Lys Leu Tyr Leu Ile Leu Asp Phe Leu Arg Gly Gly
    130                 135                 140

Asp Leu Phe Thr Arg Leu Ser Lys Glu Val Met Phe Thr Glu Glu Asp
145                 150                 155                 160
```

Val Lys Phe Tyr Leu Ala Glu Leu Ala Leu Ala Leu Asp His Leu His
            165                 170                 175

Ser Leu Gly Ile Ile Tyr Arg Asp Leu Lys Pro Glu Asn Ile Leu Leu
        180                 185                 190

Asp Glu Glu Gly His Ile Lys Ile Thr Asp Phe Gly Leu Ser Lys Glu
    195                 200                 205

Ala Ile Asp His Asp Lys Arg Ala Tyr Ser Phe Cys Gly Thr Ile Glu
210                 215                 220

Tyr Met Ala Pro Glu Val Val Asn Arg Arg Gly His Thr Gln Ser Ala
225                 230                 235                 240

Asp Trp Trp Ser Phe Gly Val Leu Met Phe Glu Met Leu Thr Gly Ser
                245                 250                 255

Leu Pro Phe Gln Gly Lys Asp Arg Lys Glu Thr Met Ala Leu Ile Leu
            260                 265                 270

Lys Ala Lys Leu Gly Met Pro Gln Phe Leu Ser Gly Glu Ala Gln Ser
        275                 280                 285

Leu Leu Arg Ala Leu Phe Lys Arg Asn Pro Cys Asn Arg Leu Gly Ala
    290                 295                 300

Gly Ile Asp Gly Val Glu Glu Ile Lys Arg His Pro Phe Phe Val Thr
305                 310                 315                 320

Ile Asp Trp Asn Thr Leu Tyr Arg Lys Glu Ile Lys Pro Pro Phe Lys
                325                 330                 335

Pro Ala Leu Gly Arg Pro Glu Asp Thr Phe His Phe Asp Pro Glu Phe
            340                 345                 350

Thr Ala Arg Thr Pro Thr Asp Ser Pro Gly Val Pro Pro Ser Ala Asn
        355                 360                 365

Ala His His Leu Phe Arg Gly Phe Ser Phe Val Ala Ser Ser Leu Ile
    370                 375                 380

Gln Glu Pro Ser Gln Gln Asp Leu His Lys Val Pro Val His Pro Ile
385                 390                 395                 400

Val Gln Gln Leu His Gly Asn Asn Ile His Phe Thr Asp Gly Tyr Glu
                405                 410                 415

Ile Lys Glu Asp Ile Gly Val Gly Ser Tyr Ser Val Cys Lys Arg Cys
            420                 425                 430

Val His Lys Ala Thr Asp Thr Glu Tyr Ala Val Lys Ile Ile Asp Lys
        435                 440                 445

Ser Lys Arg Asp Pro Ser Glu Glu Ile Glu Ile Leu Leu Arg Tyr Gly
    450                 455                 460

Gln His Pro Asn Ile Ile Thr Leu Lys Asp Val Tyr Asp Asp Gly Lys
465                 470                 475                 480

Phe Val Tyr Leu Val Met Glu Leu Met Arg Gly Gly Glu Leu Leu Asp
                485                 490                 495

Arg Ile Leu Arg Gln Arg Tyr Phe Ser Glu Arg Glu Ala Ser Asp Val
            500                 505                 510

Leu Cys Thr Ile Thr Lys Thr Met Asp Tyr Leu His Ser Gln Gly Val
        515                 520                 525

Val His Arg Asp Leu Lys Pro Ser Asn Ile Leu Tyr Arg Asp Glu Ser
    530                 535                 540

Gly Ser Pro Glu Ser Ile Arg Val Cys Asp Phe Gly Phe Ala Lys Gln
545                 550                 555                 560

Leu Arg Ala Gly Asn Gly Leu Leu Met Thr Pro Cys Tyr Thr Ala Asn
                565                 570                 575

```
Phe Val Ala Pro Glu Val Leu Lys Arg Gln Gly Tyr Asp Ala Ala Cys
            580                 585                 590

Asp Ile Trp Ser Leu Gly Ile Leu Leu Tyr Thr Met Leu Ala Gly Phe
            595                 600                 605

Thr Pro Phe Ala Asn Gly Pro Asp Asp Thr Pro Glu Glu Ile Leu Ala
            610                 615                 620

Arg Ile Gly Ser Gly Lys Tyr Ala Leu Ser Gly Gly Asn Trp Asp Ser
625                 630                 635                 640

Ile Ser Asp Ala Ala Lys Asp Val Val Ser Lys Met Leu His Val Asp
                    645                 650                 655

Pro His Gln Arg Leu Thr Ala Met Gln Val Leu Lys His Pro Trp Val
                660                 665                 670

Val Asn Arg Glu Tyr Leu Ser Pro Asn Gln Leu Ser Arg Gln Asp Val
            675                 680                 685

His Leu Val Lys Gly Ala Met Ala Ala Thr Tyr Phe Ala Leu Asn Arg
        690                 695                 700

Thr Pro Gln Ala Pro Arg Leu Glu Pro Val Leu Ser Ser Asn Leu Ala
705                 710                 715                 720

Gln Arg Arg Gly Met Lys Arg Leu Thr Ser Thr Arg Leu
                    725                 730
```

<210> SEQ ID NO 134
<211> LENGTH: 802
<212> TYPE: PRT
<213> ORGANISM: Homo sapiens

<400> SEQUENCE: 134

```
Met Glu Glu Glu Gly Gly Ser Ser Gly Gly Ala Ala Gly Thr Ser Ala
1               5                   10                  15

Asp Gly Gly Asp Gly Gly Glu Gln Leu Leu Thr Val Lys His Glu Leu
                20                  25                  30

Arg Thr Ala Asn Leu Thr Gly His Ala Glu Lys Val Gly Ile Glu Asn
            35                  40                  45

Phe Glu Leu Leu Lys Val Leu Gly Thr Gly Ala Tyr Gly Lys Val Phe
        50                  55                  60

Leu Val Arg Lys Ile Ser Gly His Asp Thr Gly Lys Leu Tyr Ala Met
65                  70                  75                  80

Lys Val Leu Lys Lys Ala Thr Ile Val Gln Lys Ala Lys Thr Thr Glu
                85                  90                  95

His Thr Arg Thr Glu Arg Gln Val Leu Glu His Ile Arg Gln Ser Pro
            100                 105                 110

Phe Leu Val Thr Leu His Tyr Ala Phe Gln Thr Glu Thr Lys Leu His
        115                 120                 125

Leu Ile Leu Asp Tyr Ile Asn Gly Gly Glu Leu Phe Thr His Leu Ser
130                 135                 140

Gln Arg Glu Arg Phe Thr Glu His Glu Val Gln Ile Tyr Val Gly Glu
145                 150                 155                 160

Ile Val Leu Ala Leu Glu His Leu His Lys Leu Gly Ile Ile Tyr Arg
                165                 170                 175

Asp Ile Lys Leu Glu Asn Ile Leu Leu Asp Ser Asn Gly His Val Val
            180                 185                 190

Leu Thr Asp Phe Gly Leu Ser Lys Glu Phe Val Ala Asp Glu Thr Glu
        195                 200                 205

Arg Ala Tyr Ser Phe Cys Gly Thr Ile Glu Tyr Met Ala Pro Asp Ile
    210                 215                 220
```

-continued

```
Val Arg Gly Gly Asp Ser Gly His Asp Lys Ala Val Asp Trp Trp Ser
225                 230                 235                 240

Leu Gly Val Leu Met Tyr Glu Leu Leu Thr Gly Ala Ser Pro Phe Thr
            245                 250                 255

Val Asp Gly Glu Lys Asn Ser Gln Ala Glu Ile Ser Arg Arg Ile Leu
        260                 265                 270

Lys Ser Glu Pro Pro Tyr Pro Gln Glu Met Ser Ala Leu Ala Lys Asp
    275                 280                 285

Leu Ile Gln Arg Leu Leu Met Lys Asp Pro Lys Lys Arg Leu Gly Cys
290                 295                 300

Gly Pro Arg Asp Ala Asp Glu Ile Lys Glu His Leu Phe Phe Gln Lys
305                 310                 315                 320

Ile Asn Trp Asp Asp Leu Ala Ala Lys Lys Val Pro Ala Pro Phe Lys
                325                 330                 335

Pro Val Ile Arg Asp Glu Leu Asp Val Ser Asn Phe Ala Glu Glu Phe
            340                 345                 350

Thr Glu Met Asp Pro Thr Tyr Ser Pro Ala Ala Leu Pro Gln Ser Ser
        355                 360                 365

Glu Lys Leu Phe Gln Gly Tyr Ser Phe Val Ala Pro Ser Ile Leu Phe
    370                 375                 380

Lys Arg Asn Ala Ala Val Ile Asp Pro Leu Gln Phe His Met Gly Val
385                 390                 395                 400

Glu Arg Pro Gly Val Thr Asn Val Ala Arg Ser Ala Met Met Lys Asp
                405                 410                 415

Ser Pro Phe Tyr Gln His Tyr Asp Leu Asp Leu Lys Asp Lys Pro Leu
            420                 425                 430

Gly Glu Gly Ser Phe Ser Ile Cys Arg Lys Cys Val His Lys Lys Ser
        435                 440                 445

Asn Gln Ala Phe Ala Val Lys Ile Ile Ser Lys Arg Met Glu Ala Asn
    450                 455                 460

Thr Gln Lys Glu Ile Thr Ala Leu Lys Leu Cys Glu Gly His Pro Asn
465                 470                 475                 480

Ile Val Lys Leu His Glu Val Phe His Asp Gln Leu His Thr Phe Leu
                485                 490                 495

Val Met Glu Leu Leu Asn Gly Gly Glu Leu Phe Glu Arg Ile Lys Lys
            500                 505                 510

Lys Lys His Phe Ser Glu Thr Glu Ala Ser Tyr Ile Met Arg Lys Leu
        515                 520                 525

Val Ser Ala Val Ser His Met His Asp Val Gly Val Val His Arg Asp
    530                 535                 540

Leu Lys Pro Glu Asn Leu Leu Phe Thr Asp Glu Asn Asp Asn Leu Glu
545                 550                 555                 560

Ile Lys Ile Ile Asp Phe Gly Phe Ala Arg Leu Lys Pro Pro Asp Asn
                565                 570                 575

Gln Pro Leu Lys Thr Pro Cys Phe Thr Leu His Tyr Ala Ala Pro Glu
            580                 585                 590

Leu Leu Asn Gln Asn Gly Tyr Asp Glu Ser Cys Asp Leu Trp Ser Leu
        595                 600                 605

Gly Val Ile Leu Tyr Thr Met Leu Ser Gly Gln Val Pro Phe Gln Ser
    610                 615                 620

His Asp Arg Ser Leu Thr Cys Thr Ser Ala Val Glu Ile Met Lys Lys
625                 630                 635                 640
```

```
Ile Lys Lys Gly Asp Phe Ser Phe Glu Gly Glu Ala Trp Lys Asn Val
                645                 650                 655

Ser Gln Glu Ala Lys Asp Leu Ile Gln Gly Leu Leu Thr Val Asp Pro
            660                 665                 670

Asn Lys Arg Leu Lys Met Ser Gly Leu Arg Tyr Asn Glu Trp Leu Gln
        675                 680                 685

Asp Gly Ser Gln Leu Ser Ser Asn Pro Leu Met Thr Pro Asp Ile Leu
    690                 695                 700

Gly Ser Ser Gly Ala Ala Val His Thr Cys Val Lys Ala Thr Phe His
705                 710                 715                 720

Ala Phe Asn Lys Tyr Lys Arg Glu Gly Phe Cys Leu Gln Asn Val Asp
                725                 730                 735

Lys Ala Pro Leu Ala Lys Arg Lys Met Lys Lys Thr Ser Thr Ser
            740                 745                 750

Thr Glu Thr Arg Ser Ser Ser Glu Ser Ser His Ser Ser Ser Ser
        755                 760                 765

His Ser His Gly Lys Thr Thr Pro Thr Lys Thr Leu Gln Pro Ser Asn
    770                 775                 780

Pro Ala Asp Ser Asn Asn Pro Glu Thr Leu Phe Gln Phe Ser Asp Ser
785                 790                 795                 800

Val Ala

<210> SEQ ID NO 135
<211> LENGTH: 705
<212> TYPE: PRT
<213> ORGANISM: Homo sapiens

<400> SEQUENCE: 135

Thr Glu Ala Asn Leu Thr Gly His Glu Glu Lys Val Ser Val Glu Asn
1               5                   10                  15

Phe Glu Leu Leu Lys Val Leu Gly Thr Gly Ala Tyr Gly Lys Val Phe
            20                  25                  30

Leu Val Arg Lys Ala Gly Gly His Asp Ala Gly Lys Leu Tyr Ala Met
        35                  40                  45

Lys Val Leu Arg Lys Ala Ala Leu Val Gln Arg Ala Lys Thr Gln Glu
    50                  55                  60

His Thr Arg Thr Glu Arg Ser Val Leu Glu Leu Val Arg Gln Ala Pro
65                  70                  75                  80

Phe Leu Val Thr Leu His Tyr Ala Phe Gln Thr Asp Ala Lys Leu His
                85                  90                  95

Leu Ile Leu Asp Tyr Val Ser Gly Gly Glu Met Phe Thr His Leu Tyr
            100                 105                 110

Gln Arg Gln Tyr Phe Lys Glu Ala Glu Val Arg Val Tyr Gly Gly Glu
        115                 120                 125

Ile Val Leu Ala Leu Glu His Leu His Lys Leu Gly Ile Ile Tyr Arg
    130                 135                 140

Asp Leu Lys Leu Glu Asn Val Leu Leu Asp Ser Glu Gly His Ile Val
145                 150                 155                 160

Leu Thr Asp Phe Gly Leu Ser Lys Glu Phe Leu Thr Glu Glu Lys Glu
                165                 170                 175

Arg Thr Phe Ser Phe Cys Gly Thr Ile Glu Tyr Met Ala Pro Glu Ile
            180                 185                 190

Ile Arg Ser Lys Thr Gly His Gly Lys Ala Val Asp Trp Trp Ser Leu
        195                 200                 205
```

```
Gly Ile Leu Leu Phe Glu Leu Leu Thr Gly Ala Ser Pro Phe Thr Leu
            210                 215                 220

Glu Gly Glu Arg Asn Thr Gln Ala Glu Val Ser Arg Arg Ile Leu Lys
225                 230                 235                 240

Cys Ser Pro Pro Phe Pro Pro Arg Ile Gly Pro Val Ala Gln Asp Leu
                245                 250                 255

Leu Gln Arg Leu Leu Cys Lys Asp Pro Lys Arg Leu Gly Ala Gly
            260                 265                 270

Pro Gln Gly Ala Gln Glu Val Arg Asn His Pro Phe Phe Gln Gly Leu
            275                 280                 285

Asp Trp Val Ala Leu Ala Ala Arg Lys Ile Pro Ala Pro Phe Arg Pro
290                 295                 300

Gln Ile Arg Ser Glu Leu Asp Val Gly Asn Phe Ala Glu Glu Phe Thr
305                 310                 315                 320

Arg Leu Glu Pro Val Tyr Ser Pro Pro Gly Ser Pro Pro Gly Asp
                325                 330                 335

Pro Arg Ile Phe Gln Gly Tyr Ser Phe Val Ala Pro Ser Ile Leu Phe
            340                 345                 350

Asp His Asn Asn Ala Val Met Thr Asp Gly Leu Glu Ala Pro Gly Ala
            355                 360                 365

Gly Asp Arg Pro Gly Arg Ala Ala Val Ala Arg Ser Ala Met Met Gln
370                 375                 380

Gln Tyr Glu Leu Asp Leu Arg Glu Pro Ala Leu Gly Gln Gly Ser Phe
385                 390                 395                 400

Ser Val Cys Arg Arg Cys Arg Gln Arg Gln Ser Gly Gln Glu Phe Ala
                405                 410                 415

Val Lys Ile Leu Ser Arg Arg Leu Glu Ala Asn Thr Gln Arg Glu Val
            420                 425                 430

Ala Ala Leu Arg Leu Cys Gln Ser His Pro Asn Val Val Asn Leu His
            435                 440                 445

Glu Val His His Asp Gln Leu His Thr Tyr Leu Val Leu Glu Leu Leu
450                 455                 460

Arg Gly Gly Glu Leu Leu Glu His Ile Arg Lys Lys Arg His Phe Ser
465                 470                 475                 480

Glu Ser Glu Ala Ser Gln Ile Leu Arg Ser Leu Val Ser Ala Val Ser
                485                 490                 495

Phe Met His Glu Glu Ala Gly Val Val His Arg Asp Leu Lys Pro Glu
            500                 505                 510

Asn Ile Leu Tyr Ala Asp Asp Thr Pro Gly Ala Pro Val Lys Ile Ile
            515                 520                 525

Asp Phe Gly Phe Ala Arg Leu Arg Pro Gln Ser Pro Gly Val Pro Met
530                 535                 540

Gln Thr Pro Cys Phe Thr Leu Gln Tyr Ala Ala Pro Glu Leu Leu Ala
545                 550                 555                 560

Gln Gln Gly Tyr Asp Glu Ser Cys Asp Leu Trp Ser Leu Gly Val Ile
                565                 570                 575

Leu Tyr Met Met Leu Ser Gly Gln Val Pro Phe Gln Gly Ala Ser Gly
            580                 585                 590

Gln Gly Gly Gln Ser Gln Ala Ala Glu Ile Met Cys Lys Ile Arg Glu
            595                 600                 605

Gly Arg Phe Ser Leu Asp Gly Glu Ala Trp Gln Gly Val Ser Glu Glu
610                 615                 620

Ala Lys Glu Leu Val Arg Gly Leu Leu Thr Val Asp Pro Ala Lys Arg
```

```
                625                 630                 635                 640
Leu Lys Leu Glu Gly Leu Arg Gly Ser Ser Trp Leu Gln Asp Gly Ser
                    645                 650                 655
Ala Arg Ser Ser Pro Pro Leu Arg Thr Pro Asp Val Leu Glu Ser Ser
                660                 665                 670
Gly Pro Ala Val Arg Ser Gly Leu Asn Ala Thr Phe Met Ala Phe Asn
            675                 680                 685
Arg Gly Lys Arg Glu Gly Phe Phe Leu Lys Ser Val Glu Asn Ala Pro
        690                 695                 700
Leu
705

<210> SEQ ID NO 136
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: Lys115, Ile119, Gln150, and Leu155 to Ala

<400> SEQUENCE: 136

Met Ala Arg Thr Thr Ser Gln Leu Tyr Asp Ala Val Pro Ile Gln Ser
1               5                   10                  15
Ser Val Val Leu Cys Ser Cys Pro Ser Pro Ser Met Val Arg Thr Gln
                20                  25                  30
Thr Glu Ser Ser Thr Pro Pro Gly Ile Pro Gly Gly Ser Arg Gln Gly
            35                  40                  45
Pro Ala Met Asp Gly Thr Ala Ala Glu Pro Arg Pro Gly Ala Gly Ser
        50                  55                  60
Leu Gln His Ala Gln Pro Pro Pro Gln Pro Arg Lys Lys Arg Pro Glu
65                  70                  75                  80
Asp Phe Lys Phe Gly Lys Ile Leu Gly Glu Gly Ser Phe Ser Thr Val
                85                  90                  95
Val Leu Ala Arg Glu Leu Ala Thr Ser Arg Glu Tyr Ala Ile Lys Ile
                100                 105                 110
Leu Glu Ala Arg His Ile Ala Lys Glu Asn Lys Val Pro Tyr Val Thr
            115                 120                 125
Arg Glu Arg Asp Val Met Ser Arg Leu Asp His Pro Phe Phe Val Lys
        130                 135                 140
Leu Tyr Phe Thr Phe Ala Asp Asp Glu Lys Ala Tyr Phe Gly Leu Ser
145                 150                 155                 160
Tyr Ala Lys Asn Gly Glu Leu Leu Lys Tyr Ile Arg Lys Ile Gly Ser
                165                 170                 175
Phe Asp Glu Thr Cys Thr Arg Phe Tyr Thr Ala Glu Ile Val Ser Ala
                180                 185                 190
Leu Glu Tyr Leu His Gly Lys Gly Ile Ile His Arg Asp Leu Lys Pro
            195                 200                 205
Glu Asn Ile Leu Leu Asn Glu Asp Met His Ile Gln Ile Thr Asp Phe
        210                 215                 220
Gly Thr Ala Lys Val Leu Ser Pro Glu Ser Lys Gln Ala Arg Ala Asn
225                 230                 235                 240
Ser Phe Val Gly Thr Ala Gln Tyr Val Ser Pro Glu Leu Leu Thr Glu
                245                 250                 255
Lys Ser Ala Cys Lys Ser Ser Asp Leu Trp Ala Leu Gly Cys Ile Ile
                260                 265                 270
```

```
Tyr Gln Leu Val Ala Gly Leu Pro Pro Phe Arg Ala Gly Asn Glu Tyr
        275                 280                 285

Leu Ile Phe Gln Lys Ile Ile Lys Leu Glu Tyr Asp Phe Pro Glu Lys
        290                 295                 300

Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
        355                 360                 365

Asp Glu Asp Cys Tyr Gly Asn Tyr Asp Asn Leu Leu Ser Gln Phe Gly
        370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Trp
        435                 440                 445

His Gln Phe Val Glu Asn Asn Leu Ile Leu Lys Met Gly Pro Val Asp
        450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
                500                 505                 510

Thr Phe Phe Val His Thr Pro Asn Arg Thr Tyr Tyr Leu Met Asp Pro
        515                 520                 525

Ser Gly Asn Ala His Lys Trp Cys Arg Lys Ile Gln Glu Val Trp Arg
        530                 535                 540

Gln Arg Tyr Gln Ser His Pro Asp Ala Ala Val Gln
545                 550                 555

<210> SEQ ID NO 137
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: lys76 to ala

<400> SEQUENCE: 137

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60
```

```
Leu Gln His Ala Gln Pro Pro Gln Pro Arg Ala Lys Arg Pro Glu
65                  70                  75                  80

Asp Phe Lys Phe Gly Ala Ile Leu Gly Glu Gly Ser Phe Ser Thr Val
                85                  90                  95

Val Leu Ala Arg Glu Leu Ala Thr Ser Arg Glu Tyr Ala Ile Lys Ile
                100                 105                 110

Leu Glu Lys Arg His Ile Ile Lys Glu Asn Lys Val Pro Tyr Val Thr
                115                 120                 125

Arg Glu Arg Asp Val Met Ser Arg Leu Asp His Pro Phe Phe Val Lys
130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
                180                 185                 190

Leu Glu Tyr Leu His Gly Lys Gly Ile Ile His Arg Asp Leu Lys Pro
                195                 200                 205

Glu Asn Ile Leu Leu Asn Glu Asp Met His Ile Gln Ile Thr Asp Phe
210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
                260                 265                 270

Tyr Gln Leu Val Ala Gly Leu Pro Pro Phe Arg Ala Gly Asn Glu Tyr
                275                 280                 285

Leu Ile Phe Gln Lys Ile Ile Lys Leu Glu Tyr Asp Phe Pro Glu Lys
                290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
                355                 360                 365

Asp Glu Asp Cys Tyr Gly Asn Tyr Asp Asn Leu Leu Ser Gln Phe Gly
                370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Trp
                435                 440                 445

His Gln Phe Val Glu Asn Asn Leu Ile Leu Lys Met Gly Pro Val Asp
                450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
```

```
                  485                 490                 495
Glu Ile Pro Trp Ser Gln Glu Leu Arg Pro Glu Ala Lys Asn Phe Lys
            500                 505                 510

Thr Phe Phe Val His Thr Pro Asn Arg Thr Tyr Tyr Leu Met Asp Pro
            515                 520                 525

Ser Gly Asn Ala His Lys Trp Cys Arg Lys Ile Gln Glu Val Trp Arg
            530                 535                 540

Gln Arg Tyr Gln Ser His Pro Asp Ala Ala Val Gln
545                 550                 555

<210> SEQ ID NO 138
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: Arg131 changed to alanine

<400> SEQUENCE: 138

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
            20                  25                  30

Thr Glu Ser Ser Thr Pro Pro Gly Ile Pro Gly Gly Ser Arg Gln Gly
        35                  40                  45

Pro Ala Met Asp Gly Thr Ala Ala Glu Pro Arg Pro Gly Ala Gly Ser
    50                  55                  60

Leu Gln His Ala Gln Pro Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
            100                 105                 110

Leu Glu Lys Arg His Ile Ile Lys Glu Asn Lys Val Pro Tyr Val Thr
        115                 120                 125

Arg Glu Ala Asp Val Met Ser Arg Leu Asp His Pro Phe Phe Val Lys
    130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
    210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
        275                 280                 285
```

```
Leu Ile Phe Gln Lys Ile Ile Lys Leu Glu Tyr Asp Phe Pro Glu Lys
    290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
            340                 345                 350

Gln Thr Pro Pro Lys Leu Thr Ala Tyr Leu Pro Ala Met Ser Glu Asp
        355                 360                 365

Asp Glu Asp Cys Tyr Gly Asn Tyr Asp Asn Leu Leu Ser Gln Phe Gly
    370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
            420                 425                 430

Asp Glu Lys Arg Leu Leu Leu Glu Lys Gln Ala Gly Gly Asn Pro Trp
        435                 440                 445

His Gln Phe Val Glu Asn Asn Leu Ile Leu Lys Met Gly Pro Val Asp
    450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
            500                 505                 510

Thr Phe Phe Val His Thr Pro Asn Arg Thr Tyr Tyr Leu Met Asp Pro
        515                 520                 525

Ser Gly Asn Ala His Lys Trp Cys Arg Lys Ile Gln Glu Val Trp Arg
    530                 535                 540

Gln Arg Tyr Gln Ser His Pro Asp Ala Ala Val Gln
545                 550                 555

<210> SEQ ID NO 139
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: Thr148 changed to alanine

<400> SEQUENCE: 139

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60

Leu Gln His Ala Gln Pro Pro Pro Gln Pro Arg Lys Lys Arg Pro Glu
65                  70                  75                  80
```

-continued

```
Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
            100                 105                 110

Leu Glu Lys Arg His Ile Ile Lys Glu Asn Lys Val Pro Tyr Val Thr
        115                 120                 125

Arg Glu Arg Asp Val Met Ser Arg Leu Asp His Pro Phe Phe Val Lys
    130                 135                 140

Leu Tyr Phe Ala Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
    210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
        275                 280                 285

Leu Ile Phe Gln Lys Ile Ile Lys Leu Glu Tyr Asp Phe Pro Glu Lys
    290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
            340                 345                 350

Gln Thr Pro Pro Lys Leu Thr Ala Tyr Leu Pro Ala Met Ser Glu Asp
        355                 360                 365

Asp Glu Asp Cys Tyr Gly Asn Tyr Asp Asn Leu Leu Ser Gln Phe Gly
    370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
            420                 425                 430

Asp Glu Lys Arg Leu Leu Leu Glu Lys Gln Ala Gly Gly Asn Pro Trp
        435                 440                 445

His Gln Phe Val Glu Asn Asn Leu Ile Leu Lys Met Gly Pro Val Asp
    450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
```

-continued

```
                500             505              510
Thr Phe Phe Val His Thr Pro Asn Arg Thr Tyr Tyr Leu Met Asp Pro
        515                 520                 525
Ser Gly Asn Ala His Lys Trp Cys Arg Lys Ile Gln Glu Val Trp Arg
    530                 535                 540
Gln Arg Tyr Gln Ser His Pro Asp Ala Ala Val Gln
545                 550                 555

<210> SEQ ID NO 140
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: Gln150 changed to alanine

<400> SEQUENCE: 140

Met Ala Arg Thr Thr Ser Gln Leu Tyr Asp Ala Val Pro Ile Gln Ser
1               5                   10                  15
Ser Val Val Leu Cys Ser Cys Pro Ser Pro Ser Met Val Arg Thr Gln
            20                  25                  30
Thr Glu Ser Ser Thr Pro Pro Gly Ile Pro Gly Gly Ser Arg Gln Gly
        35                  40                  45
Pro Ala Met Asp Gly Thr Ala Ala Glu Pro Arg Pro Gly Ala Gly Ser
    50                  55                  60
Leu Gln His Ala Gln Pro Pro Pro Gln Pro Arg Lys Lys Arg Pro Glu
65                  70                  75                  80
Asp Phe Lys Phe Gly Lys Ile Leu Gly Glu Gly Ser Phe Ser Thr Val
                85                  90                  95
Val Leu Ala Arg Glu Leu Ala Thr Ser Arg Glu Tyr Ala Ile Lys Ile
            100                 105                 110
Leu Glu Lys Arg His Ile Ile Lys Glu Asn Lys Val Pro Tyr Val Thr
        115                 120                 125
Arg Glu Arg Asp Val Met Ser Arg Leu Asp His Pro Phe Phe Val Lys
    130                 135                 140
Leu Tyr Phe Thr Phe Ala Asp Asp Glu Lys Leu Tyr Phe Gly Leu Ser
145                 150                 155                 160
Tyr Ala Lys Asn Gly Glu Leu Leu Lys Tyr Ile Arg Lys Ile Gly Ser
                165                 170                 175
Phe Asp Glu Thr Cys Thr Arg Phe Tyr Thr Ala Glu Ile Val Ser Ala
            180                 185                 190
Leu Glu Tyr Leu His Gly Lys Gly Ile Ile His Arg Asp Leu Lys Pro
        195                 200                 205
Glu Asn Ile Leu Leu Asn Glu Asp Met His Ile Gln Ile Thr Asp Phe
    210                 215                 220
Gly Thr Ala Lys Val Leu Ser Pro Glu Ser Lys Gln Ala Arg Ala Asn
225                 230                 235                 240
Ser Phe Val Gly Thr Ala Gln Tyr Val Ser Pro Glu Leu Leu Thr Glu
                245                 250                 255
Lys Ser Ala Cys Lys Ser Ser Asp Leu Trp Ala Leu Gly Cys Ile Ile
            260                 265                 270
Tyr Gln Leu Val Ala Gly Leu Pro Pro Phe Arg Ala Gly Asn Glu Tyr
        275                 280                 285
Leu Ile Phe Gln Lys Ile Ile Lys Leu Glu Tyr Asp Phe Pro Glu Lys
    290                 295                 300
```

```
Phe Phe Pro Lys Ala Arg Asp Leu Val Glu Lys Leu Val Leu Asp
305                 310                 315                 320

Ala Thr Lys Arg Leu Gly Cys Glu Glu Met Glu Gly Tyr Gly Pro Leu
            325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
            355                 360                 365

Asp Glu Asp Cys Tyr Gly Asn Tyr Asp Asn Leu Leu Ser Gln Phe Gly
        370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Trp
            435                 440                 445

His Gln Phe Val Glu Asn Asn Leu Ile Leu Lys Met Gly Pro Val Asp
        450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
                500                 505                 510

Thr Phe Phe Val His Thr Pro Asn Arg Thr Tyr Tyr Leu Met Asp Pro
            515                 520                 525

Ser Gly Asn Ala His Lys Trp Cys Arg Lys Ile Gln Glu Val Trp Arg
        530                 535                 540

Gln Arg Tyr Gln Ser His Pro Asp Ala Ala Val Gln
545                 550                 555

<210> SEQ ID NO 141
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: Lys115 to alanine

<400> SEQUENCE: 141

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
            20                  25                  30

Thr Glu Ser Ser Thr Pro Pro Gly Ile Pro Gly Gly Ser Arg Gln Gly
        35                  40                  45

Pro Ala Met Asp Gly Thr Ala Ala Glu Pro Arg Pro Gly Ala Gly Ser
    50                  55                  60

Leu Gln His Ala Gln Pro Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95
```

```
Val Leu Ala Arg Glu Leu Ala Thr Ser Arg Glu Tyr Ala Ile Lys Ile
            100                 105                 110

Leu Glu Ala Arg His Ile Ile Lys Glu Asn Lys Val Pro Tyr Val Thr
            115                 120                 125

Arg Glu Arg Asp Val Met Ser Arg Leu Asp His Pro Phe Phe Val Lys
            130                 135                 140

Leu Tyr Phe Thr Phe Gln Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
            195                 200                 205

Glu Asn Ile Leu Leu Asn Glu Asp Met His Ile Gln Ile Thr Asp Phe
            210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
            275                 280                 285

Leu Ile Phe Gln Lys Ile Ile Lys Leu Glu Tyr Asp Phe Pro Glu Lys
            290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
            325                 330                 335

Lys Ala His Pro Phe Phe Glu Ser Val Thr Trp Glu Asn Leu His Gln
            340                 345                 350

Gln Thr Pro Pro Lys Leu Thr Ala Tyr Leu Pro Ala Met Ser Glu Asp
            355                 360                 365

Asp Glu Asp Cys Tyr Gly Asn Tyr Asp Asn Leu Leu Ser Gln Phe Gly
            370                 375                 380

Cys Met Gln Val Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
            405                 410                 415

His Asp Leu Asp Ser Asn Ser Phe Glu Leu Asp Leu Gln Phe Ser Glu
            420                 425                 430

Asp Glu Lys Arg Leu Leu Leu Glu Lys Gln Ala Gly Gly Asn Pro Trp
            435                 440                 445

His Gln Phe Val Glu Asn Asn Leu Ile Leu Lys Met Gly Pro Val Asp
            450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
            500                 505                 510

Thr Phe Phe Val His Thr Pro Asn Arg Thr Tyr Tyr Leu Met Asp Pro
```

```
                    515                 520                 525
Ser Gly Asn Ala His Lys Trp Cys Arg Lys Ile Gln Glu Val Trp Arg
    530                 535                 540

Gln Arg Tyr Gln Ser His Pro Asp Ala Ala Val Gln
545                 550                 555

<210> SEQ ID NO 142
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: Leu155 changed to Glu

<400> SEQUENCE: 142

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
    50                  55                  60

Leu Gln His Ala Gln Pro Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
            100                 105                 110

Leu Glu Lys Arg His Ile Ile Lys Glu Asn Lys Val Pro Tyr Val Thr
        115                 120                 125

Arg Glu Arg Asp Val Met Ser Arg Leu Asp His Pro Phe Phe Val Lys
    130                 135                 140

Leu Tyr Phe Thr Phe Gln Asp Asp Glu Lys Glu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
    210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
        275                 280                 285

Leu Ile Phe Gln Lys Ile Ile Lys Leu Glu Tyr Asp Phe Pro Glu Lys
    290                 295                 300

Phe Phe Pro Lys Ala Arg Asp Leu Val Glu Lys Leu Leu Val Leu Asp
305                 310                 315                 320
```

```
Ala Thr Lys Arg Leu Gly Cys Glu Glu Met Glu Gly Tyr Gly Pro Leu
            325                 330                 335

Lys Ala His Pro Phe Phe Glu Ser Val Thr Trp Glu Asn Leu His Gln
        340                 345                 350

Gln Thr Pro Pro Lys Leu Thr Ala Tyr Leu Pro Ala Met Ser Glu Asp
        355                 360                 365

Asp Glu Asp Cys Tyr Gly Asn Tyr Asp Asn Leu Leu Ser Gln Phe Gly
        370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Trp
                435                 440                 445

His Gln Phe Val Glu Asn Asn Leu Ile Leu Lys Met Gly Pro Val Asp
            450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
                500                 505                 510

Thr Phe Phe Val His Thr Pro Asn Arg Thr Tyr Tyr Leu Met Asp Pro
            515                 520                 525

Ser Gly Asn Ala His Lys Trp Cys Arg Lys Ile Gln Glu Val Trp Arg
                530                 535                 540

Gln Arg Tyr Gln Ser His Pro Asp Ala Ala Val Gln
545                 550                 555

<210> SEQ ID NO 143
<211> LENGTH: 556
<212> TYPE: PRT
<213> ORGANISM: Artificial Sequence
<220> FEATURE:
<223> OTHER INFORMATION: modified PDK1 of Homo sapiens
<220> FEATURE:
<223> OTHER INFORMATION: Lys76 and Arg131 changed to Ala

<400> SEQUENCE: 143

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60

Leu Gln His Ala Gln Pro Pro Pro Gln Pro Arg Ala Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
                100                 105                 110
```

-continued

```
Leu Glu Lys Arg His Ile Ile Lys Glu Asn Lys Val Pro Tyr Val Thr
        115                 120                 125

Arg Glu Ala Asp Val Met Ser Arg Leu Asp His Pro Phe Phe Val Lys
        130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
                180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
                260                 265                 270

Tyr Gln Leu Val Ala Gly Leu Pro Pro Phe Arg Ala Gly Asn Glu Tyr
        275                 280                 285

Leu Ile Phe Gln Lys Ile Ile Lys Leu Glu Tyr Asp Phe Pro Glu Lys
        290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
        355                 360                 365

Asp Glu Asp Cys Tyr Gly Asn Tyr Asp Asn Leu Leu Ser Gln Phe Gly
        370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Trp
        435                 440                 445

His Gln Phe Val Glu Asn Asn Leu Ile Leu Lys Met Gly Pro Val Asp
        450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
                500                 505                 510

Thr Phe Phe Val His Thr Pro Asn Arg Thr Tyr Tyr Leu Met Asp Pro
        515                 520                 525

Ser Gly Asn Ala His Lys Trp Cys Arg Lys Ile Gln Glu Val Trp Arg
```

```
                530             535             540
Gln Arg Tyr Gln Ser His Pro Asp Ala Ala Val Gln
545             550             555

<210> SEQ ID NO 144
<211> LENGTH: 25
<212> TYPE: PRT
<213> ORGANISM: Homo sapiens

<400> SEQUENCE: 144

Arg Glu Arg Asp Val Met Ser Arg Leu Asp His Pro Phe Phe Val Lys
1               5                   10                  15

Leu Tyr Phe Thr Phe Gln Asp Asp Glu
            20                  25

<210> SEQ ID NO 145
<211> LENGTH: 25
<212> TYPE: PRT
<213> ORGANISM: Homo sapiens

<400> SEQUENCE: 145

Thr Glu Asn Arg Val Leu Gln Asn Ser Arg His Pro Phe Leu Thr Ala
1               5                   10                  15

Leu Lys Tyr Ser Phe Gln Thr His Asp
            20                  25

<210> SEQ ID NO 146
<211> LENGTH: 25
<212> TYPE: PRT
<213> ORGANISM: Homo sapiens

<400> SEQUENCE: 146

Ala Glu Arg Asn Ile Leu Glu Glu Val Lys His Pro Phe Ile Val Asp
1               5                   10                  15

Leu Ile Tyr Ala Phe Gln Thr Gly Gly
            20                  25

<210> SEQ ID NO 147
<211> LENGTH: 26
<212> TYPE: PRT
<213> ORGANISM: Homo sapiens

<400> SEQUENCE: 147

Ser Glu Arg Asn Val Leu Leu Lys Asn Val Lys His Pro Phe Leu Val
1               5                   10                  15

Gly Leu His Phe Ser Phe Gln Thr Ala Asp
            20                  25

<210> SEQ ID NO 148
<211> LENGTH: 25
<212> TYPE: PRT
<213> ORGANISM: Homo sapiens

<400> SEQUENCE: 148

Met Glu Arg Asp Ile Leu Ala Asp Val Asn His Pro Phe Val Val Lys
1               5                   10                  15

Leu His Tyr Ala Phe Gln Thr Glu Gly
            20                  25
```

METHOD FOR DESIGNING A COMPOUND BASED ON THE THREE DIMENSIONAL STRUCTURE OF PHOSPHOINOSITIDE DEPENDENT PROTEIN KINASE 1 (PDK1)

CROSS-REFERENCE TO RELATED APPLICATION

The present application is the US national phase under 35 USC 371 of International Application No. PCT/GB03/02509, filed Jun. 9, 2003, and published in the English language as WO 03/104481.

REFERENCE TO SEQUENCE LISTING

The present application incorporates by reference the sequence listing submitted as an ASCII text filed via EFS-Web on Feb. 5, 2010. The Sequence Listing is provided as a file entitled 8506534.1.txt, created on-Feb. 5, 2010, which is 4 Kb in size.

FIELD OF THE INVENTION

The present invention relates to protein kinase catalytic domain structures and mutants and screening assays making use thereof.

BACKGROUND OF THE INVENTION

The 3-Phosphoinositide Dependent Protein Kinase-1 (PDK1) is a key protein kinase, regulating activity of a group of related protein kinases through phosphorylation. These kinases include isoforms of Protein Kinase B (also known as Akt) [Brazil and Hemmings, 2001, Scheid and Woodgett, 2001], p70 ribosomal S6 kinase (S6K) [Alessi et al., 1997, Volarevic and Thomas, 2001], p90 ribosomal S6 Kinase (RSK) [Frodin and Gammeltoft, 1999] and the serum and glucocorticoid induced-protein kinase (SGK) [Lang and Cohen, 2001]. These enzymes are stimulated by hormones and growth factors and phosphorylate regulatory proteins mediating the various physiological effects of these agonists.

PDK1 possesses an N-terminal kinase catalytic domain and a C-terminal pleckstrin homology (PH) domain [Alessi et al., 1997, Stephens et al., 1998]. PDK1 activates its substrates by phosphorylating these kinases at their activation loop (reviewed in [Alessi, 2001, Toker and Newton, 2000]). The phosphorylation of PKB by PDK1 is dependent upon prior activation of the phosphoinositide 3-kinase (PI-3-kinase) and the production of the second messenger, phosphatidylinositol 3,4,5-trisphosphate (PtdIns(3,4,5)$P_3$) which binds to the PH domains of PDK1 and PKB. This does not activate either PKB or PDK1 but instead recruits and co-localises these enzymes at the plasma membrane.

Unlike PKB, the other PDK1 substrates described thus far do not interact with PtdIns(3,4,5)$P_3$ nor is the rate at which they are phosphorylated by PDK1 further enhanced by the binding of PDK1 to PtdIns(3,4,5)$P_3$. Instead the ability of PDK1 to phosphorylate S6K, SGK and RSK is promoted by phosphorylation of these enzymes at a residue located C-terminal to the kinase catalytic domain in a region known as the hydrophobic motif [Alessi et al., 1997, Kobayashi and Cohen, 1999, Pullen et al., 1998]. The kinases that phosphorylate the hydrophobic motif of S6K and SGK are unknown but as the phosphorylation of this residue in vivo is dependent on PI-3-kinase activation, the hydrophobic motif kinases and/or the hydrophobic motif phosphatases may be regulated by PtdIns (3,4,5)$P_3$. In the case of RSK isoforms, phosphorylation by the ERK1/ERK2 MAP kinases induce phosphorylation of the hydrophobic motif (reviewed in Frodin and Gammeltoft, 1999).

PDK1 belongs to the same subfamily of protein kinases as its substrates, termed the AGC protein kinases as they are related to the cAMP dependent protein kinase (PKA)/cGMP dependent protein kinase/Protein kinase C (PKC). PKA is the only AGC kinase whose crystal structure has been solved. Like all protein kinases, its catalytic core possesses an N-terminal lobe consisting mainly of β-sheet and a predominantly α-helical C-terminal lobe [Taylor et al., 1992, Husen and Kuriyan, 2002]. The ATP binding site is located in between the 2 lobes [Johnson et al., 2001, Knighton et al., 1991]. At the very C-terminus, PKA possesses an extended loop that terminates in the sequence FXXF (SEQ ID NO:1) which resembles the first part of the hydrophobic motif phosphorylation site of S6K and SGK (FXXFS/TY, SEQ ID NO:2) in which the Ser/Thr is the phosphorylated residue [Biondi et al., 2000]. In the structure of PKA, the FXXF motif (SEQ ID NO:1) is buried in a hydrophobic pocket in the small lobe of the PKA catalytic domain [Knighton et al., 1991] and mutation of either of the Phe residues drastically reduces PKA activity towards a peptide substrate [Etchebehere et al., 1997]. Unlike other AGC kinases, PDK1 does not possess a hydrophobic motif C-terminal to its catalytic domain. However, there is evidence that PDK1 possesses a hydrophobic pocket in the small lobe of its catalytic domain similar to that in PKA. We have biochemically demonstrated that the interaction of PDK1 with four of its substrates (S6K1, SGK1, PKζ and PKC related kinase-2 (PRK2)) is reduced or abolished by mutation of residues predicted to form part of this pocket [Balendran et al., 2000, Biondi et al., 2000]. Furthermore, mutation of a central residue in the predicted pocket, Leu 155, prevented PDK1 from phosphorylating and activating S6K1 and SGK1 without affecting its ability to phosphorylate either PKB or a short peptide substrate that encompasses the activation loop of PKB (T308tide) [Biondi et al., 2000]. The hydrophobic pocket on the kinase domain of PDK1 has been termed the "PIF-pocket" after the name of the first AGC-kinase hydrophobic motif-containing peptide (PDK1 Interacting Fragment) that was found to bind PDK1 [Balendran et al., 1999a]. It has been suggested that the PIF-pocket in PDK1 functions as a docking site, enabling PDK1 to interact with some of its physiological substrates. Furthermore, there is evidence that phosphorylation of the hydrophobic motif of S6K1, SGK and RSK2 [Balendran et al., 1999b, Biondi et al., 2001, Frodin et al., 2000] promotes the interaction of these enzymes with PDK1. These findings suggest that the PIF-pocket on PDK1 could contain a phosphate binding site promoting the binding of PDK1 to a subset of substrates (S6K, SGK and RSK) once these enzymes have been phosphorylated at their hydrophobic motif. This would result in a physiological phosphate dependent interaction. In addition there is evidence that occupancy of the PIF-pocket activates PDK1 as peptides that encompass the hydrophobic motif of PRK2 [Biondi et al., 2000] and RSK [Frodin et al., 2000] induce a 4-6-fold activation of PDK1.

Previous predicted structures PDK1 catalytic domain were obtained using homology modelling methods based upon structural information available from the catalytic domain of PKA (Biondi et al., 2000). These predictions of the PDK1 catalytic domain structure were thus biased towards the catalytic domain from which the structural information was obtained.

SUMMARY OF THE INVENTION

We have determined a crystal structure for the kinase domain of the AGC family protein kinase PDK. The structure defines the PIF-pocket and reveals an adjacent possible phosphate binding site. Furthermore, we have performed structure-based mutagenesis and biochemical analysis which support the existence of such a phosphate-binding site. This may mediate the phosphate dependent docking interaction with substrates such as (for PDK1) S6K and SGK. We have used a novel algorithm to define the conformational state of the crystallised PDK1 relative to all the reported structures of PKA, which shows that while PDK1 has all the signs of being in an active form in the crystal, its overall conformation is in-between and 'open' and 'closed' state. We have also determined crystal structures for the kinase domain of PDK1 in complex with modulators of PDK1 activity.

On the basis of this work we provide drug screening methods and mutated protein kinase molecules (which are useful in, for example, drug screening methods).

A first aspect of the invention provides a method for selecting or designing a compound for modulating the activity of phosphoinositide dependent protein kinase 1 (PDK1), the method comprising the step of using molecular modelling means to select or design a compound that is predicted to interact with the protein kinase catalytic domain of PDK1, wherein a three-dimensional structure of at least a part of the protein kinase catalytic domain of PDK1 is compared with a three-dimensional structure of a compound, and a compound that is predicted to interact with the said protein kinase catalytic domain is selected, wherein the three-dimensional structure of at least a part of the protein kinase catalytic domain of PDK1 is a three-dimensional structure (or part thereof) determined for a polypeptide consisting of residues equivalent to residues 51 to 359 of full length human PDK1, or a fragment or fusion thereof.

BRIEF DESCRIPTION OF THE DRAWINGS

FIG. 3 shows a structure-based sequence alignment
FIGS. 4A-C show PDK1 binding & activation studies.
FIGS. 5A and 5B show interactions of regulatory phosphates with the αC helix.
FIGS. 6A and 6B show essential dynamics.
FIG. 7 shows alignment of AGC protein kinase family members.
FIG. 9 shows details of the inhibitor binding sites.

DETAILED DESCRIPTION OF THE INVENTION

Figure 1:
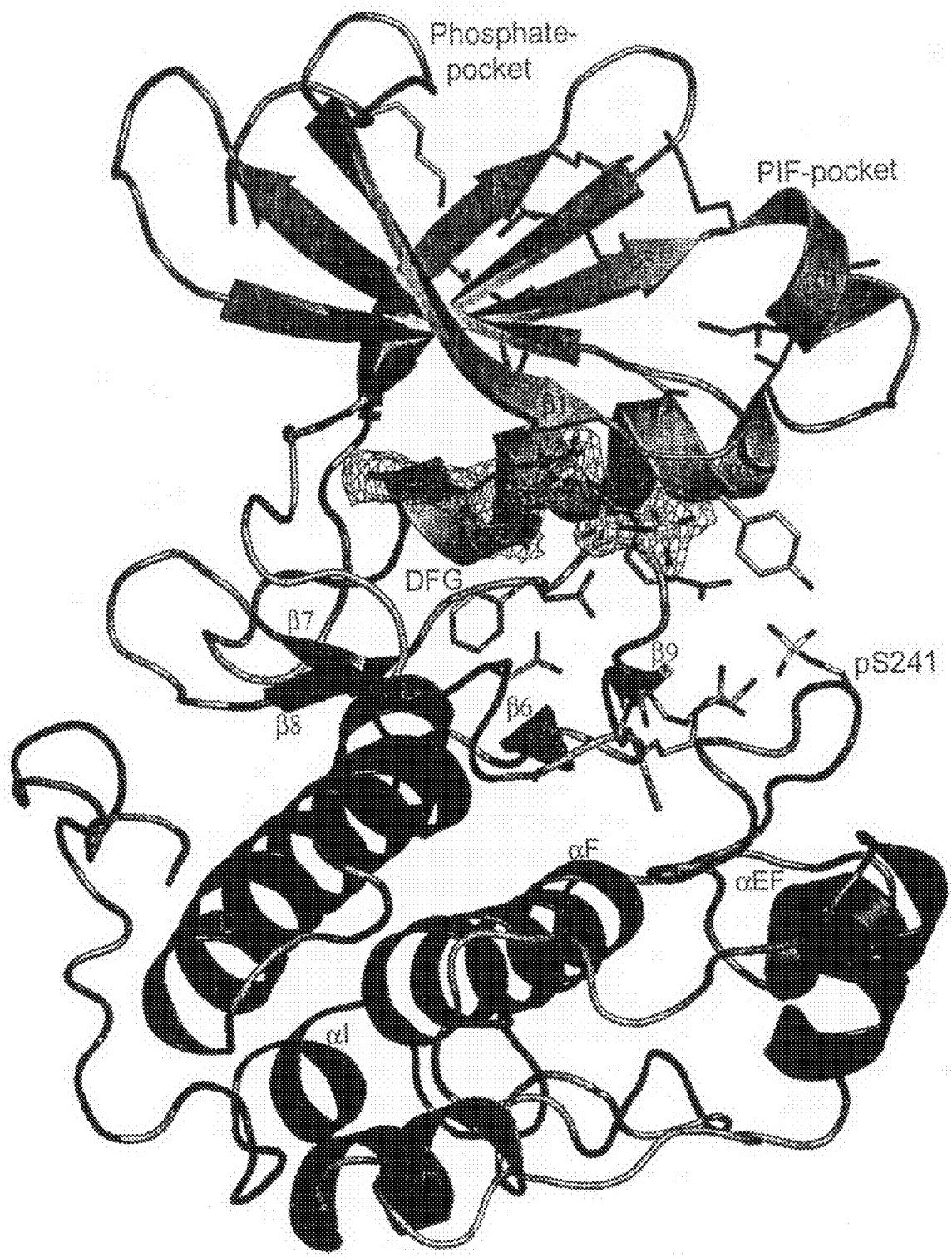
FIG. 1 provides an overview of the PDK1 structure.

The term PDK1 as used herein includes a polypeptide (a PDK1 polypeptide) comprising the amino acid sequence identified as PDK1 in Alessi D. R et al (1997) Curr. Biol. 7: 261-269, Alessi D. R et al (1997) Curr. Biol. 7: 776-789, Stokoe D et al (1997) Science 277: 567-570 or Stephens L et al (1998) Science 279: 710-714, or a variant, fragment, fusion or derivative thereof, or a fusion of a said variant or fragment or derivative, for example as described in WO98/41638, incorporated herein by reference. It is preferred that the said PDK1 polypeptide is a protein kinase. It is preferred that the said PDK1 polypeptide is a protein kinase that is capable of phosphorylating a threonine residue that lies in a Thr-Phe-Cys-Gly-Thr-Xaa-Glu-Leu consensus motif (where the underlined Thr corresponds to the threonine that is phosphorylated by PDK1 and Xaa is a variable residue, SEQ ID NO:9), and preferably that is capable of phosphorylating PKB, for example PKBα, at residue Thr308. The rate at which the said PDK1 polypeptide is capable of phosphorylating a threonine residue as described above may be increased in the presence of PtdIns(3,4,5)$P_3$ or PtdIns(3,4)$P_2$ but it will be appreciated that this is not essential. The said polypeptide may be capable of phosphorylating the equivalent residues to Thr308 of PKBα on PKC isoforms (LeGood et al (1998) Science 281: 2042-2045; et al (1998) Curr. Biol. 8: 1069-1077; Dutil et al (1998) Curr. Biol. 8:1366-1375), p70 S6 kinase (Alessi et al (1998) Curr. Biol. 8: 69-81; Pullen et al (1998) Science 279, 707-710), SGK (sequence given in Webster et al (1993) Mol. Cell. Biol. 13, 1031-2040; equivalent residues identified in US application no 112217 filed on 14 Dec. 1998; GB 9919676.8, filed on 19 Aug. 1999, and Kobayashi & Cohen (1999)) and PKA (Cheng et al (1998) Proc. Natl. Acad. Sci. USA 95: 9849-9854). It may further be preferred that the substrate specificity and/or other characteristics of the said PDK1 polypeptide in vitro may be substantially as reported in Alessi D. R et al (1997) Curr. Biol. 7: 261-269, Alessi D. R et al (1997) Curr. Biol. 7: 776-789, Stokoe D et al (1997) Science 277: 567-570 or Stephens L et al (1998) Science 279: 710-714.

We have found that a fragment of PDK1 consisting essentially of residues equivalent to residues 51 to 359 of full length human PDK1 is particularly beneficial for determining a structure for the catalytic domain of PDK1. This fragment has, for example, protein kinase activity and surprisingly beneficial solubility and stability characteristics which make it particularly suitable for structural studies, for example formation of crystals which may be analysed by X-ray crystallography methods. Other fragments of PDK1 were surprisingly found to be unsuitable for crystallisation, as discussed in Example 5.

It is particularly preferred that the structure is one determined for the fragment consisting of residues 51 to 359 of full length human PDK1. The fragment may comprise an N-terminal or C-terminal fusion polypeptide (ie amino acid sequence not derived from PDK1), though this is preferably of less than or equal to about 10, 5, 4, 3, 2 or 1 amino acids. For example, it is particularly preferred that the structure is one determined for a polypeptide consisting residues 51 to 359 of full length human PDK1 and the amino acid sequence Gly-Pro (or less preferably other sequence forming part of a protease cleavage site) preceding the methionine corresponding to Met51 of human PDK1. A further preferred structure is one determined for the fragment consisting essentially of residues 71 to 359 of full length human PDK1 (or residues equivalent thereto), which also has protein kinase activity.

It is particularly preferred that the structure is one determinable by a method as described in Example 1, for example a structure obtainable by X-ray analysis from a crystal obtainable using a mother liquor solution comprising ammonium sulphate, preferably between 1.8 and 2.2M. It is particularly preferred that the mother liquor solution is of pH 7 to 9, preferably 7 to 8.5, most preferably pH8.5, and comprises ammonium sulphate and preferably ATP. Crystals may form in the absence of ATP but better crystals may be obtained in the presence of ATP. Preferably the crystal is obtainable using a mother liquor solution containing 0.1M Tris/HCl pH 8.5, 2.0 M ammonium sulphate, 16.6 mM ATP. Further preferred details of the crystallisation and X-ray analysis are described in Example 1, for example as partially summarised in Table 1 (shown in Example 1).

It is particularly preferred that the structure is that represented by the structure co-ordinates shown in Examples 2, 3 or 4, or a structure based or modelled on such a structure or co-ordinates. The co-ordinates shown in Example 2 are for the PDK1 fragment (SEQ ID NO:102) with all alternate side chains. The co-ordinates shown in Example 3 are for the PDK1 fragment (SEQ ID NO:102) without alternate side chains. The co-ordinates shown in Example 4 are for the dimer of the PDK1 fragment (SEQ ID NO:102), without alternate side chains; chain A is the molecule for which co-ordinates are given in Examples 2 and 3, and chain B is the symmetry-related molecule.

The structure may be one determined following crystallisation in the presence of a known or potential interactor with PDK1 or modulator of PDK1 activity (as discussed further below), for example a known or potential inhibitor of PDK1 activity. For example, the structure may be one determined following crystallisation in the presence of a known protein kinase inhibitor, for example an inhibitor that binds at the ATP binding site, for example an ATP-competitive inhibitor, for example staurosporine or a staurosporine derivative, for example UCN-01. Examples of such crystallisation techniques and analysis are given in Example 6, and examples of co-ordinates are given in Examples 7 and 8. Example 7 represents the co-ordinates of PDK1 fragment (SEQ ID NO:102) co-crystallised with Staurosporine, whereas in Example 8, the co-ordinates of PDK1 fragment (SEQ ID NO:102) co-crystallised with UCN-01.

It will be appreciated that some variation in crystallisation conditions (for example different mother liquors) may be required for co-crystallisation with different molecules. Techniques for investigating suitable crystallisation conditions in each case will be well known to those skilled in the art.

A further aspect of the invention provides a crystalline form of a polypeptide as defined in any of the preceding aspects of the invention, for example a polypeptide consisting of residues equivalent to residues 51 to 359 of full length human PDK1, or a fragment or fusion thereof; a polypeptide consisting of residues 51 to 359 of full length human PDK1 or a fusion thereof; a polypeptide consisting of residues 51 to 359 of full length human PDK1 and the amino acid sequence Gly-Pro preceding the methionine corresponding to Met51 of human PDK1; a polypeptide consisting of residues 71 to 359 of full length human PDK1 or a fusion thereof.

The crystalline form may further comprise co-crystallised molecule, for example a known or potential interactor with PDK1 or modulator of PDK1 activity, or a test compound whose properties vis a vis PDK1 may not be known. For example, the co-crystallised molecule, for example test compound, may be a molecule that is known to modulate protein kinase activity, or may already be known to modulate PDK1 protein kinase activity. For example, the co-crystallised molecule may be staurosporine, the staurosporine derivative UCN-01 (7-hydroxyl staurosporine) or other staurosporine derivative.

Such co-crystallisation and structures determined from co-crystallised molecules may be useful in molecular modelling and in determining features of the polypeptide and compound that are important for interaction. This may be useful in designing or selecting further test compounds, for example as discussed in Example 6.

In one embodiment it is preferred that the modelled molecule is predicted to bind to a region of the structure termed the "PIF binding pocket", the "phosphate binding pocket" and/or the α C helix (residues equivalent to 123-136 of full length human PDK1), particularly the residue equivalent to Arg 131 of full length human PDK1, or interacting regions. As discussed in Example 1, the PIF binding pocket is considered to be formed by residues including Lys115, Ile118, Ile119 on the αB helix, Val124, Val127 on the αC helix and Leu 155 on 13-sheet 5. The phosphate binding pocket is considered to be formed by residues including Lys76, Arg 131, Thr 148 and Gln150. Residues of the αC helix that are considered to interact either with phosphate bound in the phosphate binding site or intermolecularly with phosphorylated Ser241 of PDK1 include Arg131 (phosphate binding site) and Arg 129 and His126 (phosphorylated Ser241). Glu 130 is involved in binding the α-phosphate of the bound ATP, and Val124 and Val127 form part of the PIF binding pocket, as discussed in Example 1.

It is preferred that the compound is for modulating the protein kinase activity of PDK1. The protein kinase activity of PDK1 that is modulated may be phosphorylation of the underlined residue in a polypeptide with the amino acid sequence Thr/Ser-Phe-Cys-Gly-Thr-Xaa-Glu-Leu ("PDK1" activity, SEQ ID NO:9). Alternatively or in addition, the modulated activity may be phosphorylation of the underlined residue in a polypeptide with the amino acid sequence Phe-Xaa-Xaa-Phe-Ser/Thr-Phe/Tyr ("PDK2" activity, SEQ ID NO:11). The substrate polypeptide may be, for example, a PKB, SGK, p70 S6 kinase, PKC or (in relation only to phosphorylation of the underlined residue in a polypeptide with the amino acid sequence Thr/Ser-Phe-Cys-Gly-Thr-Xaa-Glu-Leu (SEQ ID NO:9) PKA polypeptide. The modulated protein kinase activity may be towards PKB or other PH-domain-comprising/phosphoinositide-binding substrate of PDK1; or SGK, S6K or other substrate of PDK1 whose phosphorylation by PDK1 is promoted by phosphorylation of the substrate on the Ser/Thr of the "hydrophobic motif" FXXFS/TY (SEQ ID NO:2); or an artificial substrate such as T308tide (which comprises the sequence of PKB which is phosphorylated by PDK1) or PDKtide (which comprises the sequence of PKB which is phosphorylated by PDK1 (eg T308tide) fused to a sequence mimicking a phosphorylated hydrophobic motif ie FXXFZY (SEQ ID NO: 2), in which Z is a negatively charged (for example acidic) residue (eg PIFtide)). Such substrates for PDK1 are discussed, for example, in WO 01/44497. Other activities of PDK1 that may be modulated include interactions with other polypeptides or phosphoinositides and/or intramolecular interactions.

It is preferred that the three-dimensional structure of at least a part of the protein kinase catalytic domain of the PDK1 is a three-dimensional structure of at least a part of the PIF binding pocket, the phosphate binding pocket and/or the α C helix, or interacting regions of PDK1, and a compound that is predicted to interact with the said PIF binding pocket, the phosphate binding pocket and/or the α C helix, or interacting regions of PDK1 is selected. Alternatively, the compound may bind to a portion of said PDK1 polypeptide that is not the PIF binding pocket, the phosphate binding pocket and/or the α C helix, or interacting regions of PDK1, for example so as to interfere with the binding of the ATP or substrate polypeptide or their access to the catalytic site. In a still further example, the compound may bind to a portion of PDK1 so as to decrease said polypeptide's activity by an allosteric effect. This allosteric effect may be an allosteric effect that is involved in the natural regulation of PDK1's activity.

It is further preferred that the three-dimensional structure of at least a part of the protein kinase catalytic domain of PDK1 is a three-dimensional structure of the part of the protein kinase catalytic domain of PDK1 that is defined by residues Lys115, Ile118, Ile119 (on the αB helix), Val124, Val127 (on the αC helix) and Leu 155 (on 13-sheet 50 and/or residues Lys76, Arg 131, Thr 148 and Gln150 and/or residues Arg131, Arg 129, His126, Glu 130 of full-length human PDK1 and a compound that is predicted to interact with the said part of the protein kinase catalytic domain is selected.

Figure 2:
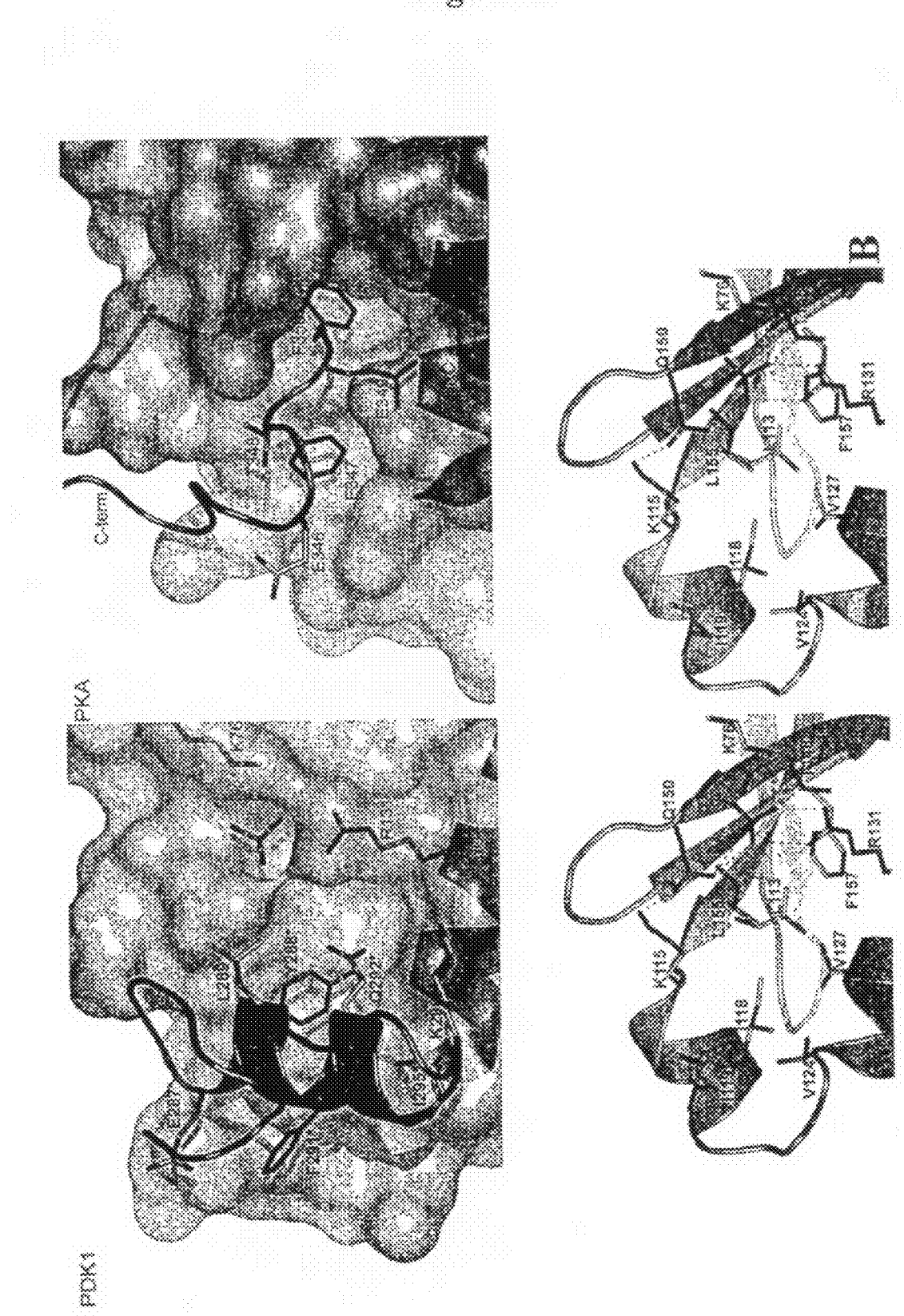
FIGS. 2A and 2B show the PIF-pocket.

For example, it is preferred if the portions of the structure of PDK1 shown in FIGS. 1 and 2 as forming the PIF binding pocket and/or phosphate binding pocket and/or αC helix interactions (for example with phosphoserine241) are compared with the structure of the candidate compound.

A further aspect of the invention provides a method for selecting or designing a compound for modulating the activity of a hydrophobic pocket (PIF binding pocket)-containing protein kinase having a hydrophobic pocket in the position equivalent to the hydrophobic pocket of human PDK1 that is defined by residues including Lys115, Ile118, Ile119, Val124, Val127 and/or Leu155 of full-length human PDK1 and further having a phosphate binding pocket in the position equivalent to the phosphate binding pocket of human PDK1 that is defined by residues including Lys76, Arg131, Thr148 and/or Gln150, the method comprising the step of using molecular modelling means to select or design a compound that is predicted to interact with the said hydrophobic pocket-containing protein kinase, wherein a three-dimensional structure of a compound is compared with a three-dimensional structure of the said phosphate binding pocket and optionally also the hydrophobic pocket and/or αC helix or region interacting therewith, and a compound that is predicted to interact with the said phosphate binding pocket and optionally also the hydrophobic pocket and/or αC helix or region interacting therewith, is selected.

The three-dimensional structure of a compound may be compared with the three-dimensional structure of the hydrophobic and/or phosphate binding pocket and/or αC helix or region interacting therewith, as appropriate. A compound that can interact with the hydrophobic pocket and/or phosphate binding pocket, in particular residues noted above as defining such regions, in a similar manner (for example similar separation and/or type of interaction ie hydrophobic or ionic, and/or similar cumulative energy of interaction) to an interacting polypeptide such as S6K-pHM may be selected. Methods of assessing the interaction are well known to those skilled in the art and are discussed further below.

The three-dimensional structures that are compared may be, as appropriate, predicted or modelled three-dimensional structures (for example on the basis of a PDK1 structure as referred to above, for example as represented by the co-ordinates given in Examples 2, 3 or 4 or 6 or 7) or may be three-dimensional structures that have been determined, for example by techniques such as X-ray crystallography, as well known to those skilled in the art. The three-dimensional structures may be displayed by a computer in a two-dimensional form, for example on a computer screen. The comparison may be performed using such two-dimensional displays.

The following relate to molecular modelling techniques: Blundell et al (1996) Structure-based drug design *Nature* 384, 23-26; Bohm (1996) Computational tools for structure-based ligand design *Prog Biophys Mol Biol* 66(3), 197-210; Cohen et al (1990) *J Med Chem* 33, 883-894; Navia et al (1992) *Curr Opin Struct Biol* 2, 202-210.

The following computer programs, for example, may be useful in carrying out the method of this aspect of the invention: GRID (Goodford (1985) *J Med Chem* 28, 849-857; available from Oxford University, Oxford, UK); MCSS (Miranker et al (1991) *Proteins: Structure, Function and Genetics* 11, 29-34; available from Molecular Simulations, Burlington, Mass.); AUTODOCK (Goodsell et al (1990) *Proteins: Structure, Function and Genetics* 8, 195-202; available from Scripps Research Institute, La Jolla, Calif.); DOCK (Kuntz et al (1982) *J Mol Biol* 161, 269-288; available from the University of California, San Francisco, Calif.); LUDI (Bohm (1992) *J Comp Aid Molec Design* 6, 61-78; available from Biosym Technologies, San Diego, Calif.); LEGEND (Nishibata et al (1991) *Tetrahedron* 47, 8985; available from Molecular Simulations, Burlington, Mass.); LeapFrog (available from Tripos Associates, St Louis, Mo.); Gaussian 92, for example revision C (M J Frisch, Gaussian, Inc., Pittsburgh, Pa. ©1992); AMBER, version 4.0 (P A Kollman, University of California at San Francisco, ©1994); QUANTA/CHARMM (Molecular Simulations, Inc., Burlington, Mass. ©1994); and Insight II/Discover (Biosym Technologies Inc., San Diego, Calif. ©1994). Programs may be run on, for example, a Silicon Graphics™ workstation, Indigo$^2$™ or IBM RISC/6000™ workstation model 550.

Several in silico methods could be employed, for example, via a substructure search for new ligands using programmes such as CHEM DRAW or CHEM FINDER. The basic structure of the natural ligand (for example a phosphorylated hydrophobic motif peptide such as 56K-pHM) capable of binding to PDK1 (or other protein kinase) is taken (or predicted) and various structural features of it (for example the hydrophobic and negatively charged entities) are submitted to a programme which will searches a set of chemical company catalogues for chemicals containing this substructure.

These compounds are then screened by eye for groups that could not interact with the PIF/phosphate binding pockets (or the αC residues/interacting region) because, for example, they are too large or have steric or charge hindrance, and those are discarded. The remaining chemicals are submitted to a PRODRG server and topologies/co-ordinates for these chemicals are created. These chemicals are modelled into the structure, from which chemicals that are possibly able to bind to the PIF/phosphate binding site domain/αC helix/interacting region are selected. Further details of the PRODRG programme are available in the art, for example, from Daan van Aalten Laboratory.

These compounds may then be ordered or synthesised and assessed, for one or more of ability to bind to and/or modulate PDK1 (or other protein kinase) activity. The compounds may be crystallised with the PDK1 or other protein kinase protein and the structure of any complex determined, as illustrated in Examples 6 to 8.

An alternative approach is to use PRODRG: a tool for generating GROMOS/MOL2/WHATIF topologies and hydrogen atom positions from small molecule PDB files. We take the natural ligand and computationally vary all possible groups at each site on the ligand, with a variety of new groups while the protein co-ordinates and the ligand back-bone co-ordinates remain fixed the results can then be screened for hindrance and repulsion, and the molecules are obtained either through catalogues or made.

As noted above, the selected or designed compound may be synthesised (if not already synthesised) or purified and tested for its effect on the relevant hydrophobic/phosphate pocket-containing protein kinase, for example its effect on the protein kinase activity. The compound may be tested in a screening method of the invention or other screening method. The compound may be formulated for pharmaceutical use, for example for use in in vivo trials in animals or humans, or for use in agriculture, for example as an antifungal agent.

It may be useful to analyse a protein kinase structure (for example a structure determined or predicted for a complex of the protein kinase with a binding partner) in order to determine the activation state of the structure. This may be useful in further modelling binding of the binding partner to the protein kinase in other activation states, and in predicting how the binding partner may affect the activation state of the protein kinase or compete with other potential binding partners. It may also be useful in designing and assessing derivatives of the binding partner.

Thus, a further aspect of the invention provides a method for assessing the activation state of a structure for a protein kinase, wherein the structure is analysed using principle component analysis of the structure co-ordinates. The method may further comprise the step of classifying the activation state of the structure as "open", "closed" or "intermediate". Details of the analysis, which involves the generation of eigenvectors and associated eigenvalues are given in Example 1. The analysis makes use of techniques described in Amadei et al (1993) Essential dynamics of proteins. *Proteins* 17, 412-425.

Figure 5:
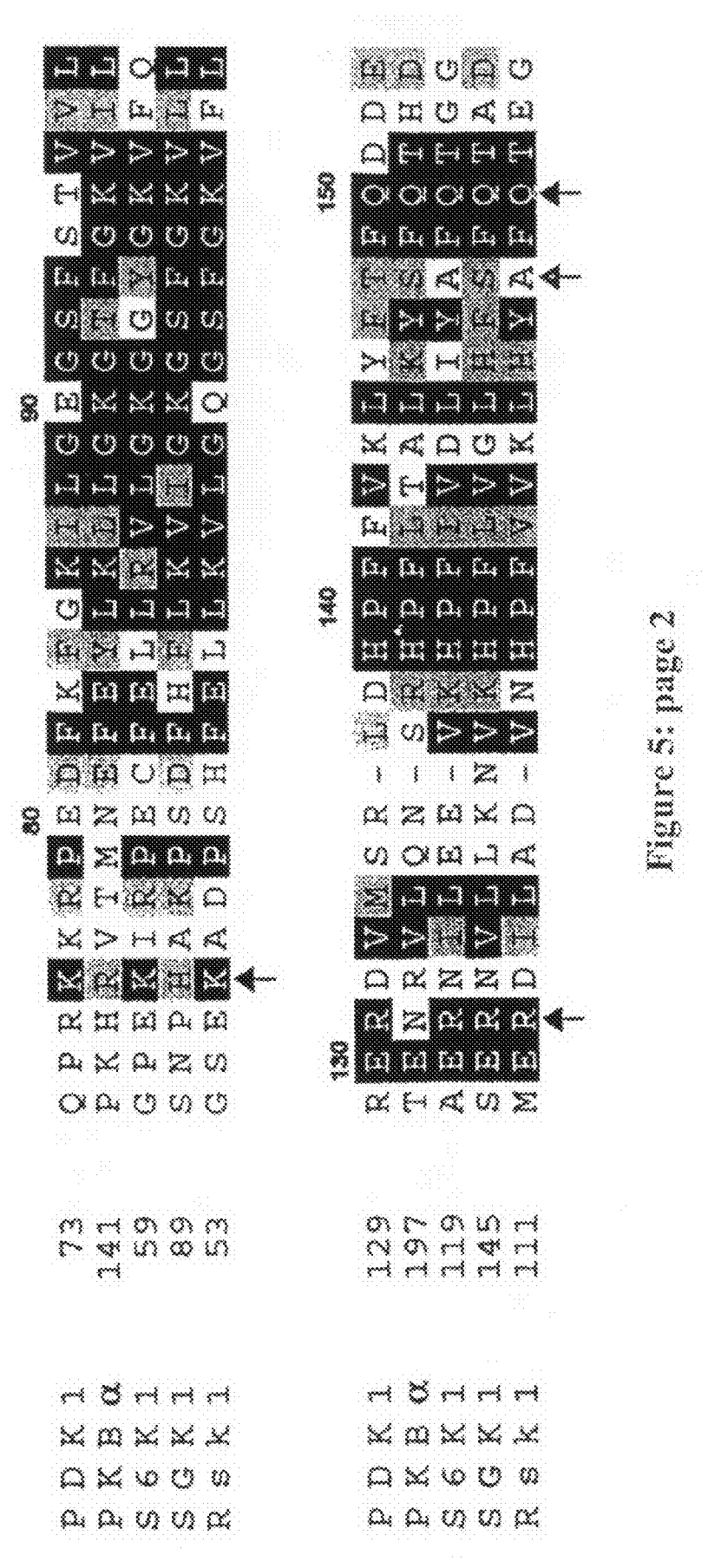

The hydrophobic/phosphate pocket-containing protein kinase may be PDK1. Alternatively, it may be an isoform of Serum and Glucocorticoid stimulated protein kinase (SGK), Protein Kinase B (PKB), p70 S6 kinase, p90 RSK, PKC isoforms (for example PKCα, PKCδ, PKCζ), PRK1, PRK2, MSK1 or MSK2. Hydrophobic/phosphate pocket-containing protein kinases and their EMBL database accession numbers are listed in Table I. Sequences considered to form the phosphate binding pocket from representative hydrophobic/phosphate pocket-containing protein kinases are shown in FIG. 5. All AGC family protein kinases other than PKA may be hydrophobic/phosphate pocket-containing protein kinases, as defined above. In addition to the protein kinases shown in FIG. 7, rhodopsin and G-protein coupled receptor protein kinases, for example, may possibly also have a hydrophobic/phosphate pocket as defined above.

The terms SGK, PKB, p70 S6 kinase, p90 RSK, PKCα, PKCδ, PKCζ or PRK2, for example, as used herein include a polypeptide (a SGK, PKB, PKA, p70S6 kinase, p90 RSK, PKCα, PKCδ, PKCζ or PRK2 polypeptide) comprising the amino acid sequence identified as a SGK, PKB, p70 S6 kinase, p90 RSK, PKCα, PKCδ, PKCζ or PRK2, respectively, in the relevant EMBL database records indicated in Table 2.

TABLE 2

| | Activation or T-Loop | AGC Hydrophobic Motif | Accession number |
|---|---|---|---|
| consensus: | TFCGTxxYxAPD (SEQ ID NO:41) L E | FxxFSY (SEQ ID NO:42) YTF | |
| PKBα | TFCGTPEYLAPE (SEQ ID NO:45) | FPQFSY (SEQ ID NO:46) | (Y15056) |
| PKBβ | TFCGTPEYLAPE (SEQ ID NO:47) | FPQFSY (SEQ ID NO:48) | (P31751) |
| PKBγ | TFCGTPEYLAPE (SEQ ID NO:49) | FPQFSY (SEQ ID NO:50) | (AF135794) |
| SGK1 | TFCGTPEYLAPE (SEQ ID NO:51) | FLGFSY (SEQ ID NO:52) | (AAD41091) |
| SGK2 | TFCGTPEYLAPE (SEQ ID NO:53) | FLGFSY (SEQ ID NO:54) | (AF169034) |
| SGK3 | TFCGTPEYLAPE (SEQ ID NO:55) | FLGFSY (SEQ ID NO:56) | (AF169035) |
| PKCα | TFCGTPDYIAPE (SEQ ID NO:57) | FEGFSY (SEQ ID NO:58) | (4506067) |
| PKCβI | TFCGTPDYIAPE (SEQ ID NO:59) | FAGFSY (SEQ ID NO:60) | (4506069) |
| PKCβII | TFCGTPDYIAPE (SEQ ID NO:61) | FEGFSF (SEQ ID NO:62) | (P05127) |

TABLE 2-continued

| | Activation or T-Loop | AGC Hydrophobic Motif | Accession number |
|---|---|---|---|
| PKCγ | TFCGTPDYIAPE (SEQ ID NO:63) | FGGFTY (SEQ ID NO:64) | (P05129) |
| PKCδ | TFCGTPDYIAPE (SEQ ID NO:65) | FAGFSF (SEQ ID NO:66) | (5453970) |
| PCKζ | TFCGTPNYIAPE (SEQ ID NO:67) | FEGFEY (SEQ ID NO:68) | (4506079) |
| PKCι | TFCGTPNYIAPE (SEQ ID NO:69) | FEGFEY (SEQ ID NO:68) | (4506071) |
| PRK1 | TFCGTPEFLAPE (SEQ ID NO:71) | FLDFDF (SEQ ID NO:72) | (AAC50209) |
| PRK2 | TFCGTPEFLAPE (SEQ ID NO:73) | FRDFDY (SEQ ID NO:74) | (AAC50208) |
| p70-S6Kα | TFCGTIEYMAiPE (SEQ ID NO:75) | FLGFTY (SEQ ID NO:76) | (AAA36410) |
| p70-S6Kβ | TFCGTIEYMAPE (SEQ ID NO:77) | FLGFTY (SEQ ID NO:78) | (4506739) |
| p90-RSK1 | SFCGTVEYMAPE (SEQ ID NO:79) | FRGFSF (SEQ ID NO:80) | (I38556) |
| p90-RSK2 | SFCGTVEYMAPE (SEQ ID NO:81) | FRDFSF (SEQ ID NO:82) | (P51812) |
| p90-RSK3 | SFCGTIEYMAPE (SEQ ID NO:83) | FRGFSF (SEQ ID NO:84) | (CAA59427) |
| MSK1 | SFCGTIEYMAPD (SEQ ID NO:85) | FQGYSF (SEQ ID NO:86) | (AAC31171) |
| MSK2 | SFCGTIEYMAPE (SEQ ID NO:87) | FQGYSF (SEQ ID NO:88) | (AAC67395) |
| PDK1 | SFVGTAQYVSPE (SEQ ID NO:89) | (1) | (AF017995) |

Table 2. Alignment of the amino acid sequences surrounding the T-loop and the hydrophobic motif of AGC kinases. All the sequences and accession numbers are from human proteins. The underlined residues correspond to those that become phosphorylated. Footnotes: (1) PDK1 does not possess a hydrophobic motif.

It is preferred that the PDK1 (or, for example, SGK, PKB, PKA or p70 S6 kinase) is a polypeptide which consists of the amino acid sequence of the protein kinase PDK1 (or, for example, SGK, PKB, PKA or p70 S6 kinase as the case may be) sequence referred to above or naturally occurring allelic variants thereof. It is preferred that the naturally occurring allelic variants are mammalian, preferably human, but may alternatively be homologues from parasitic or pathogenic or potentially pathogenic organisms. Examples of such organisms and homologues, and of uses of modulators of such homologues are given in U.S. patent application No. 60/112, 114, filed on 14 Dec. 1998, and applications claiming priority therefrom, or in Casamayor et al (1999) *Curr Biol* 9, 186-197.

The PDK1 may also be a polypeptide with the amino acid sequence of residues 51 to 359 or 404 (or 71 to 360) of full-length human PDK1; this may comprise the protein kinase domain of PDK1, as described in Example 2. The PDK1 (or SGK, PKB, PKA or p70 S6 kinase) may also be Myc epitope-tagged or His-tagged, as described in Example 1. The p70 S6 kinase, for example, may have a His tag at its N-terminus and/or may lack the carboxy terminal 104 residues (p70 S6K-T2). The PDK1 or SGK may be a *Saccharomyces cerevisiae* homologue, for example Pkh1 or Pkh2 (PDK1 homologues) or Ypk1 or Yrk2 (SGK homologues), as described in Casamayor et al (1999) *Curr Biol* 9, 186-197.

It is particularly preferred, although not essential, that the variant or fragment or derivative or fusion of the PDK1, or the fusion of the variant or fragment or derivative has at least 30% of the enzyme activity of full-length human PDK1 with respect to the phosphorylation of full-length human PKBα on residue Thr308 or SGK1 on residue Thr 256 in either the presence or absence of PtdIns(3,4,5)P$_3$ or PtdIns(3,4)P$_2$. It is more preferred if the variant or fragment or derivative or fusion of the said protein kinase, or the fusion of the variant or fragment or derivative has at least 50%, preferably at least 70% and more preferably at least 90% of the enzyme activity of PDK1 with respect to the phosphorylation of PKBα or SGK1. However, it will be appreciated that variants or fusions or derivatives or fragments which are devoid of enzymatic activity may nevertheless be useful, for example by interacting with another polypeptide. Thus, variants or fusions or derivatives or fragments which are devoid of enzymatic activity may be useful in a binding assay, which may be used, for example, in a method of the invention in which modulation of an interaction of a mutated PDK1 of the invention and optionally also PDK1 with a interacting polypeptide or compound, for example an interacting polypeptide comprising the amino acid sequence motif Phe/Tyr-Xaa-Xaa-Phe/Tyr (SEQ ID NO:92), for example Phe/Tyr-Xaa-Xaa-Phe/Tyr-Zaa-Phe/Tyr (SEQ ID NO:93), for example Phe/Tyr-Xaa-Xaa-Phe/Tyr-Asp/Glu-Phe/Tyr (SEQ ID NO:94) or Phe/Tyr-Xaa-Xaa-Phe/Tyr-PhosphoSer/PhosphoThr-Phe/Tyr (SEQ ID NO: 95) is measured.

It is preferred that the variant or fragment or derivative or fusion of the said hydrophobic/phosphate binding pocket-containing protein kinase, or the fusion of the variant or fragment or derivative comprises a hydrophobic pocket and a phosphate binding pocket in the position equivalent to the hydrophobic and phosphate binding pocket of human PDK1, as discussed further below.

Equivalent preferences apply to a variant or fragment or derivative or fusion of the SGK, PKB, p70 S6 kinase, p90 RSK, PKCα, PKCδ, PKCζ or PRK2 (for example), or the fusion of the variant or fragment or derivative, with the substitution in relation to SGK, PKB and p70S6 kinase of the peptide substrate Crosstide (GRPRTSSFAEG, SEQ ID NO:96), or for PKB and SGK of the peptide substrate RPRAATF; the substitution in relation to PKA of the peptide substrate Kemptide (LRRASLG, SEQ ID NO:97); the substitution in relation to PKC isoforms and PRK1/2 of histone H1; and the substitution in relation to MSK1/2 or p90-RSK1/2/3 of CREBtide (EILSRRPSYRK, SEQ ID NO:98).

By "variants" of a polypeptide we include insertions, deletions and substitutions, either conservative or non-conservative. In particular we include variants of the polypeptide where such changes do not substantially alter the activity of the said polypeptide, for example the protein kinase activity of PDK1, as described above.

By "conservative substitutions" is intended combinations such as Gly, Ala; Val, Ile, Leu; Asp, Glu; Asn, Gln; Ser, Thr; Lys, Arg; and Phe, Tyr.

The three-letter amino acid code of the IUPAC-IUB Biochemical Nomenclature Commission is used herein, with the exception of the symbol Zaa (negatively charged amino acid). In particular, Xaa represents any amino acid. It is preferred that Xaa and Zaa represent a naturally occurring amino acid. It is preferred that at least the amino acids corresponding to the consensus sequences defined above are L-amino acids.

It is particularly preferred if the PDK1 (or SGK, PKB, PKA or p70 S6 kinase or other hydrophobic/phosphate binding pocket-containing kinase as defined above) variant has an amino acid sequence which has at least 65% identity with the amino acid sequence of PDK1 referred to above (or the sequence for SGK (including SGK1, 2 and 3), PKB, PKA or p70 S6 kinase, for example, as appropriate, referred to above), more preferably at least 70%, 71%, 72%, 73% or 74%, still more preferably at least 75%, yet still more preferably at least 80%, in further preference at least 85%, in still further preference at least 90% and most preferably at least 95% or 97% identity with the amino acid sequence defined above.

It is still further preferred if the PDK1 (or SGK, PKB, PKA or p70 S6 kinase or other hydrophobic/phosphate binding pocket-containing kinase, as defined above) variant has an amino acid sequence which has at least 65% identity with the amino acid sequence of the catalytic domain, particularly the residues forming the hydrophobic pocket, of PDK1 (or, for example, SGK, PKB, PKA or p70 S6 kinase) in the appropriate sequence referred to above, more preferably at least 70%, 71%, 72%, 73% or 74%, still more preferably at least 75%, yet still more preferably at least 80%, in further preference at least 83 or 85%, in still further preference at least 90% and most preferably at least 95% or 97% identity with the amino acid sequence defined above. It will be appreciated that the catalytic domain of a protein kinase-related polypeptide may be readily identified by a person skilled in the art, for example using sequence comparisons as described below.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al (1994) *Nucl Acid Res* 22, 4673-4680). The parameters used may be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

It is preferred that the PDK1 (or, for example, SGK, PKB, PKA or p70 S6 kinase) is a polypeptide which consists of the amino acid sequence of the protein kinase PDK1 (or, for example, SGK, PKB, PKA or p70 S6 kinase as the case may be) sequence referred to above or naturally occurring allelic variants thereof. It is preferred that the naturally occurring allelic variants are mammalian, preferably human, but may alternatively be homologues from parasitic or pathogenic or potentially pathogenic organisms. Examples of such organisms and homologues, and of uses of modulators of such homologues are given in U.S. patent application No. 60/112, 114, filed on 14 Dec. 1998, and applications claiming priority therefrom, or in Casamayor et al (1999) *Curr Biol* 9, 186-197.

It is preferred that the PDK1 (or, for example, SGK, PKB, PKA or p70 S6 kinase) is a polypeptide that is capable of interacting with a polypeptide comprising the amino acid sequence motif Phe/Tyr-Xaa-Xaa-Phe/Tyr (SEQ ID NO:92), preferably Phe-Xaa-Xaa-Phe/Tyr, more preferably Phe-Xaa-Xaa-Phe, still more preferably Phe/Tyr-Xaa-Xaa-Phe/Tyr-Xaa-Phe/Tyr (SEQ ID NO:93) or Phe/Tyr-Xaa-Xaa-Phe/Tyr-COOH, for example the polypeptide PIF or PIFtide, as defined below. Further preferences for the said polypeptide are as given above.

The protein kinase activity of PKB, SGK or p70 S6 kinase that is modulated may be phosphorylation of the underlined residue in a polypeptide with the amino acid sequence Arg-Xaa-Arg-Xaa-Xaa-Ser/Thr(SEQ ID NO:100). The polypeptide may be Glycogen Synthase Kinase 3 (GSK3), 40 S ribosomal subunit S6, BAD, 6-phosphofructo-2-kinase, phosphodiesterase 3b, human caspase 9, endothelial nitric oxide synthase or BRCA1.

A compound identified by a method of the invention may modulate the ability of the protein kinase to phosphorylate different substrates, for example different naturally occurring polypeptides, to different extents. The compound may inhibit the protein kinase activity in relation to one substrate but may increase the protein kinase activity in relation to a second substrate. For example, the protein kinase activity of PDK1 may be modulated to a different extent for PKB when compared with SGK, p70 S6 kinase and/or PKC.

It will be appreciated that the modulatory, for example inhibitory action of a compound found to bind (or inhibit binding of a polypeptide or compound) to the protein kinase may be confirmed by performing an assay of enzymic activity (for example PDK1 and/or PDK2 protein kinase activity) in the presence of the compound.

By "hydrophobic pocket-containing protein kinase having a hydrophobic pocket (PIF binding pocket) in the position equivalent to the hydrophobic pocket of human PDK1 that is defined by residues including Lys115, Ile118, Ile119, Val124, Val127 and/or Leu155 of full-length human PDK1 and further having a phosphate binding pocket in the position equivalent to the phosphate binding pocket of human PDK1 that is defined by residues including Lys76, Arg131, Thr148 and/or Gln150," is meant a polypeptide having an amino acid sequence identifiable as that of a protein kinase catalytic domain, and further having a predicted or determined three-dimensional structure that includes a hydrophobic pocket corresponding to the region indicated in Example 1 as the PIF binding pocket, and a pocket corresponding to the region indicated in Example 1 as the phosphate binding pocket. The hydrophobic pocket and phosphate binding pockets in PDK1 do not overlap with the ATP or phosphorylation site binding sites on PDK1.

It is preferred that the protein kinase has identical or conserved residues that are equivalent to Lys 115, Ile118, Ile119, Val124, Val127 and/or Leu 155 of human PDK1, more preferably at least Lys115 and Leu155 of human PDK1, most preferably an identical residue equivalent to Leu155. Thus, for example, the protein kinase may have a Lys residue at the position equivalent to Lys115 of PDK1 and/or a Leu residue at the position equivalent to Leu155 of PDK1. It is preferred that the protein kinase does not have an Ala at the position equivalent to Lys115 and/or a Ser, Asp or Glu at the position equivalent to Leu155 of PDK1.

It is further preferred that the protein kinase has identical or conserved residues that are equivalent to Lys76, Arg131, Thr148 and/or Gln 150 of human PDK1, more preferably at least Lys76 and Gln150 of human PDK1, most preferably an identical residue equivalent to Gln150. FIG. 5B shows an alignment of examples of protein kinases considered to have a phosphate binding pocket at the position equivalent to the said phosphate binding pocket of PDK1. Sequence conservation/preferred residues at the positions identified are discussed further in Example 1.

An amino acid sequence may be identifiable as that of a protein kinase catalytic domain by reference to sequence identity or similarities of three dimensional structure with known protein kinase domains, as known to those skilled in the art.

Protein kinases show a conserved catalytic core, as reviewed in Johnson et al (1996) *Cell*, 85, 149-158 and Taylor & Radzio-Andzelm (1994) *Structure* 2, 345-355. This core folds into a small N-terminal lobe largely comprising anti-parallel β-sheet, and a large C-terminal lobe which is mostly α-helical.

A deep cleft at the interface between these lobes is the site of ATP binding, with the phosphate groups near the opening of the cleft.

Protein kinases also show conserved sequences within this catalytic core, and the residue equivalent to a given residue of, for example, PDK1, may be identified by alignment of the sequence of the kinase with that of known kinases in such a way as to maximise the match between the sequences. The alignment may be carried out by visual inspection and/or by the use of suitable computer programs, for example the GAP program of the University of Wisconsin Genetic Computing Group, which will also allow the percent identity of the polypeptides to be calculated. The Align program (Pearson (1994) in: Methods in Molecular Biology, Computer Analysis of Sequence Data, Part II (Griffin, A M and Griffin, H G eds) pp 365-389, Humana Press, Clifton).

The comparison of amino acid sequences or three dimension structure (for example from crystallography or computer modelling based on a known structure) may be carried out using methods well known to the skilled man, for example as described in WO 01/44497.

MAP kinase, MEK1, Cdk2 and Erk2 (for example) are not protein kinases having a hydrophobic pocket in the position equivalent to the hydrophobic (PIF binding) pocket of PDK1. MEK1, Cdk2 and ERK2 may have a larger hydrophobic pocket which interacts with an amino acid sequence motif (which may be Phe-Xaa-Phe-Pro, SEQ ID NO:101) which is not Phe-Xaa-Xaa-Phe (SEQ ID NO:99). Thus, these protein kinases do not have a hydrophobic pocket in the position equivalent to the said hydrophobic (PIF-binding) pocket of PDK1.

A further aspect of the invention provides a mutated protein kinase, wherein the protein kinase before mutation has a hydrophobic pocket in the position equivalent to the hydrophobic pocket (PIF-binding pocket) of human PDK1 that is defined by residues including Lys115, Ile118, Ile119, Val124, Val127 and/or Leu155 of full-length human PDK1 and further has a phosphate binding pocket in the position equivalent to the phosphate binding pocket of human PDK1 that is defined by residues including Lys76, Arg131, Thr148 and/or Gln150, and wherein one or more residues equivalent to Ile118, Val124, Val127, Lys76 or Thr148 forming part of the hydrophobic pocket or phosphate binding pocket of the protein kinase is mutated. It is preferred that the said protein kinase is PDK1. The said protein kinase may alternatively be, for example, SGK, PKB or p70 S6 kinase. It is particularly preferred that the residue at the position equivalent to residue Lys76 of PDK1 is mutated to an Ala. The mutated protein kinase may be useful in determining whether a polypeptide or compound interacts with the hydrophobic (PIF binding) pocket or phosphate binding pocket of the unmutated protein kinase. For example, the abilities of a compound (including polypeptide) to bind to the mutated and unmutated protein kinase, or to modulate the activity of the protein kinase towards one or more substrates of the protein kinase, may be measured and compared.

The mutated protein kinase may alternatively or in addition be mutated at a residue forming part of the "hydroxyl-pocket" discussed in Example 6, for example the residue equivalent to Thr222 and/or Gln 220 of full length human PDK1. These residues are involved in the binding of the UCN-01 7-hydroxyl group.

A further aspect of the invention provides a polynucleotide encoding a mutated protein kinase of the invention. A still further aspect of the invention provides a recombinant polynucleotide suitable for expressing a mutated protein kinase of the invention. A yet further aspect of the invention provides a host cell comprising a polynucleotide of the invention.

A further aspect of the invention provides a method of making a mutated protein kinase of the invention, the method comprising culturing a host cell of the invention which expresses said mutated protein kinase and isolating said mutated protein kinase.

A further aspect of the invention provides a mutated protein kinase obtainable by the above method.

Examples of these aspects of the invention are provided in Example 1, and may be prepared using routine methods by those skilled in the art, for example as described in WO 00/35946.

For example, the above mutated protein kinase may be made by methods well known in the art and as described below and in Example 1 or 2, for example using molecular biology methods or automated chemical peptide synthesis methods.

It will be appreciated that peptidomimetic compounds may also be useful. Thus, by "polypeptide" or "peptide" we include not only molecules in which amino acid residues are joined by peptide (—CO—NH—) linkages but also molecules in which the peptide bond is reversed. Such retro-inverso peptidomimetics may be made using methods known in the art, for example such as those described in Mézière et al (1997) *J. Immunol.* 159, 3230-3237, incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the Ca atoms of the amino acid residues is used; it is particularly preferred if the linker moiety has substantially the same charge distribution and substantially the same planarity as a peptide bond.

It will be appreciated that the peptide may conveniently be blocked at its N- or C-terminus so as to help reduce susceptibility to exoproteolytic digestion.

The invention further provides a method of identifying a compound that modulates the protein kinase activity of a protein kinase having a hydrophobic pocket and phosphate binding pocket in the positions equivalent to the hydrophobic (PIF binding) pocket and phosphate binding pocket of PDK1, as defined above (for example PDK1), comprising the step of determining the effect of the compound on the protein kinase activity of, or ability of the compound to bind to the said mutated protein kinase of the invention.

The method may further comprise determining the effect of the compound on the protein kinase activity of, or ability of the compound to bind to, the protein kinase (for example PDK1) which is not mutated at the said residue. When the protein kinase is PDK1, it may lack a functional PH domain (ie it may lack a PH domain capable of binding a phosphoinositide).

It will be appreciated that the protein kinase or mutated protein kinase may be a fusion protein comprising a tag, for example to aid purification, for example a GST tag, as described in Example 1.

The capability of the said PDK1 (or, for example, SGK, PKB, PKA or p70 S6 kinase) polypeptide with regard to interacting with or binding to a polypeptide or other compound may be measured by any method of detecting/measuring a protein/protein interaction or other compound/protein interaction, as discussed further below. Suitable methods include methods analagous to those described in Example 1, as well as other methods, for example yeast two-hybrid interactions, co-purification, ELISA, co-immunoprecipitation and surface plasmon resonance methods. Thus, the said PDK1 (or SGK, PKB, PKA or p70 S6 kinase) may be considered capable of binding to or interacting with a polypeptide or other compound If an interaction may be detected between the said PDK1 polypeptide and the said interacting polypeptide by ELISA, co-immunoprecipitation or surface plasmon resonance methods or by a yeast two-hybrid interaction or copurification method, for example as described in Example 1.

It is preferred that the interaction can be detected using a surface plasmon resonance method, as described in Example 1. The interacting polypeptide (for example a polypeptide comprising a phosphorylated "hydrophobic motif", for example 56K-pHM; see example 1) may be immobilised on the test surface, for example it can be coupled through amino groups to a Sensor Chip CM5™, according to the manufacturer's instructions, or a biotinylated polypeptide can be bound to an avidin coated Sensor Chip SA. The protein kinase (at concentrations between, for example 0 and between 10 µM and 1.0 µM, for example 2 µM) is then injected over the surface and steady state binding determined in each case. From these measurements a $K_d$ can be determined. It is preferred that the interaction has a $K_d$ of less than 8 µM, more preferably less than 5 µM, 2 µM, 1 µM, 500 nM, 300 nM, 200 nM or 100 nM, for example about 150 nM. Alternatively, a $K_d$ can be determined for a polypeptide or other compound in competition with the immobilised polypeptide (or other compound). The protein kinase (for example at a concentration of 0.5 µM) is mixed with free polypeptide (for example, at concentrations between 0 and 3 µM) and the mixture injected over the immobilised polypeptides. The steady state binding is determined in each case, from which the $K_d$ of the interaction can be determined using the Cheng-Prescott relationship. Alternatively, the interaction may be expressed in terms of an observed response or relative observed responses, measured in terms of mass of protein bound to the surface, as described in Example 2. For example, the polypeptide may be immobilised by amino coupling to a Sensor Chip CM5 and each protein kinase (for example different mutated protein kinases, as discussed below) for example at a concentration of 1.0 µM or a range of concentrations, injected over the immobilised polypeptide. Alternatively, the polypeptide may be immobilised on a SA Sensor Chip and each protein kinase, for example at a concentration of 40 nM or a range of concentrations injected over the immobilised polypeptide. The steady state response for each protein kinase is determined, for example expressed in Response Units (RU). 1000 RU corresponds to 1 ng/mm$^2$ of protein bound to the surface. A response of less than 10 RU may indicate that no interaction has taken place. A response of at least 10 RU may indicate that the immobilised and injected molecules interact with each other.

It will be appreciated that the above methods may be used to determine whether a particular polypeptide or compound interacts with a protein kinase or mutated protein kinase.

The effect of the compound on the rate or degree of phosphorylation of a hydrophobic pocket and/or phosphate binding pocket-dependent substrate may be determined. A compound may be selected that decreases the protein kinase activity of the said protein kinase, for example PDK1, towards a hydrophobic pocket-dependent substrate or a phosphate binding pocket-dependent substrate and does not affect or increases the protein kinase activity towards a hydrophobic pocket or phosphate binding pocket-independent substrate, for example PKB when the kinase is PDK1. An activator of PDK1 may mimic insulin and may be useful in treating diabetes or obesity, and may protect cells from apoptosis.

Compounds that bind specifically to the phosphate binding site may activate PDK1 (or other AGK kinase having a phosphate binding site). Also compounds that bind to the residues forming part of the phosphate binding site might transduce the negative effect and inhibit the kinase activity. A compound interacting with the phosphate binding site of PDK1 may be an activator, but only of a subset of substrates. Some substrates of PDK1 require the interaction with the phosphate binding site, such as S6K and SGK.

To generate a specific molecule that could bind to the phosphate and/or PIF-binding pocket of PDK1 a anti-idiotype strategy using combinatorial RNA libraries could be employed. Previous studies have established that Combinatorial RNA libraries can be used to isolate specific ligands, called aptamers, for virtually any target molecule by a procedure probably best known as SELEX (Ellington, A. D., and Szostak, J. W. (1990) Nature 346, 818-822; Tuerk, C., and Gold, L. (1990) Science 249, 505-510). Using this approach RNA molecules that interact with antibodies raised against PIFtide or peptides that encompass the hydrophobic motif of AGC kinases which are phosphorylated at their hydrophobic motif would be selected (preferably antibodies that are specific for the phosphorylated form ie bind the phosphorylated form but not the non-phosphorylated form). These RNA species then may have the intrinsic conformation to interact with the phosphate binding (and possibly also the PIF-binding) pocket(s) of PDK1. Antibodies to the phosphate binding pocket may be produced. For example, animals could be immunised with wild type PDK1. Serum could then be purified with a column where the resin is coated with wild type PDK1 used for the immunisation. Specific antibodies could then be passed through columns coated with mutant PDK1 molecules differing only in that they have specific mutations in the phosphate binding pocket, such as Arg131, Lys76 or Gln150, for example mutated to Ala. Antibodies that don't bind to this mutant will either be specific antibodies that recognise the specific motifs or antibodies that are sensitive to the conformational changes associated with these mutations. The opposite development could also be performed: antibodies against a mutant PDK1 having a specific mutation(s) in the phosphate binding pocket, such as Arg131, Lys76 or Gln150, for example mutated to Ala, could be produced and the serum further purified through columns coated with wild type PDK1.

Thus, a further aspect of the invention provides an antibody reactive with the phosphate binding pocket of PDK1 or other hydrophobic pocket (PIF binding pocket)-containing protein kinase having a hydrophobic pocket in the position equivalent to the hydrophobic pocket of human PDK1 that is defined by residues including Lys115, Ile118, Ile119, Val124, Val127 and/or Leu155 of full-length human PDK1 and further having a phosphate binding pocket in the position equivalent to the phosphate binding pocket of human PDK1 that is defined by residues including Lys76, Arg131, Thr148 and/or Gln150. A further aspect of the invention provides an antibody reactive with PDK1 or other phosphate-binding pocket-containing protein kinase as defined above but not with the said protein kinase mutated at the phosphate binding site, or vice versa. A further aspect of the invention provides a method for preparing or selecting an antibody wherein the antibody is prepared or selected against a said protein kinase (for example PDK1) unmutated at the phosphate binding site and a said protein kinase mutated at the phosphate binding site.

By the term "antibody" is included synthetic antibodies and fragments and variants (for example as discussed above) of whole antibodies which retain the antigen binding site. The antibody may be a monoclonal antibody, but may also be a polyclonal antibody preparation, a part or parts thereof (for example an $F_{ab}$ fragment or $F(ab)_2$) or a synthetic antibody or part thereof. Fab, Fv, ScFv and dAb antibody fragments can all be expressed in and secreted from *E. coli*, thus allowing the facile production of large amounts of the said fragments. By "ScFv molecules" is meant molecules wherein the $V_H$ and $V_L$ partner domains are linked via a flexible oligopeptide. IgG class antibodies are preferred.

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: techniques and Applications", JGR Hurrell (CRC Press, 1982), modified as indicated above. Bispecific antibodies may be prepared by cell fusion, by reassociation of monovalent fragments or by chemical cross-linking of whole antibodies. Methods for preparing bispecific antibodies are disclosed in Corvalen et al, (1987) *Cancer Immunol. Immunother.* 24, 127-132 and 133-137 and 138-143.

A general review of the techniques involved in the synthesis of antibody fragments which retain their specific binding sites is to be found in Winter & Milstein (1991) *Nature* 349, 293-299.

For example, an antibody that does not bind PDK1 Arg131Ala could be specifically recognising this residue in the phosphate binding site, but could also be recognising specifically the inactive conformation of PDK1, which is stabilised by Arg 131. The opposite development could also be performed: antibodies against a mutant PDK1 Arg131Ala could be produced and the serum further purified through columns coated with wild type PDK1. In this way, antibodies may be prepared that would either not be able to interact with the phosphate binding site Arg 131 but only when a small residue is in its place, or antibodies that are probes for the active conformation of PDK1. These conformational probes could be used in high throughoutput screenings, HTS, in the search of compounds that are capable of modifying the conformation of the given protein kinase. Antibodies could have been produced with previous knowledge to detect active protein kinases by immunising with active protein kinases, but in those cases, the antibodies would have recognised also the phosphorylation events that make a protein kinase be active. In the methodology here described using antibodies, the conformational probes could be easily isolated. Furthermore, antibodies obtained from an active protein kinase (with overall modifications that make it active) could be further purified through a column coated with the inactive protein kinase (keeping the non bound fraction) and then further purified on a column coated with a protein kinase consisting of an activating mutation (such as R131A in the case of PDK1), retaining the specifically bound fraction, which could be an active conformation probe. This type of approach could also allow the development of conformation specific probes by the use of activating or inhibiting mutations.

A further aspect of the invention provides a kit of parts useful in carrying out a method according to the preceding aspect of the invention, comprising (1) a mutated protein kinase of the invention and (2) the protein kinase which is not a mutated said protein kinase as defined above.

The protein structures described herein (for example with the co-ordinates shown in Examples 2, 3 or 4, or structures modelled thereon) may be useful in designing further reagents that may be useful in drug screening assays or characterisation of protein kinase activity or regulation. For example, such structures may be useful in designing mutants that may be useful in FRET-based activities, for example in which surface residues near to binding sites are mutated to cysteines to allow coupling of chromophores. For example, the cysteine residue may be fluorescently-labelled, and a change in fluorescence intensity or frequency may be detected in an assay. Any thiol-reactive fluorophore, for example BADAN (see, for example, Wadum et al Fluorescently labeled bovine acyl-CoA binding protein—an acyl-CoA sensor. Interaction with CoA and acyl-CoA esters and its use in measuring free acyl CoA esters and non-esterified fatty acids (NEFA); Hammarstrom et al (2001) *Biophys J* 80(6), 2867-2885; Schindel et al (2001) *Eur J Biochem* 268(3), 800-808), could be used to label the cysteine. An alternative suitable fluorophore is Acrylodan (Richieri et al (1992) *J Biol Chem* 267(33), 23495-23501).

It will be appreciated that the invention provides screening assays for drugs which may be useful in modulating, for example either enhancing or inhibiting, the protein kinase activity of a protein kinase (for example, the protein kinase activity towards a particular substrate) having a hydrophobic pocket in the position equivalent to the hydrophobic pocket of Protein Kinase A (PKA) that is defined by residues including Lys76, Leu116, Val80 and/or Lys111 of full-length mouse PKA, for example PDK1, SGK, PKB, PKA or p70 S6 kinase, for example the PDK1 or PDK2 activity (as discussed above) of PDK1. The compounds identified in the methods may themselves be useful as a drug or they may represent lead compounds for the design and synthesis of more efficacious compounds.

The compound may be a drug-like compound or lead compound for the development of a drug-like compound for each of the above methods of identifying a compound. It will be appreciated that the said methods may be useful as screening assays in the development of pharmaceutical compounds or drugs, as well known to those skilled in the art.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons. A drug-like compound may additionally exhibit features of selective interaction with a particular protein or proteins and be bioavailable and/or able to penetrate cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, difficult to synthesise or has poor bioavailability) may provide a starting-point for the design of other compounds that may have more desirable characteristics.

It is appreciated that screening assays which are capable of high throughput operation are particularly preferred. Examples may include cell based assays and protein-protein binding assays. An SPA-based (Scintillation Proximity Assay; Amersham International) system may be used. For example, beads comprising scintillant and a substrate polypeptide or interacting polypeptide may be prepared. The beads may be mixed with a sample comprising $^{32}$P- or $^{33}$P-γ-labelled PDK1 or other protein kinase or mutated protein kinase (as defined above) and with the test compound. Conveniently this is done in a 96-well or 384-well format. The plate is then counted using a suitable scintillation counter, using known parameters for $^{32}$P or $^{33}$P SPA assays. Only $^{32}$P or $^{33}$P that is in proximity to the scintillant, i.e. only that bound to the substrate or interacting polypeptide that is bound to the beads, is detected. Variants of such an assay, for example in which the substrate or interacting polypeptide is immobilised on the scintillant beads via binding to an antibody or antibody fragment, may also be used.

It will be understood that it will be desirable to identify compounds that may modulate the activity of the protein kinase in vivo. Thus it will be understood that reagents and conditions used in the method may be chosen such that the interactions between, for example, the said protein kinase and the interacting polypeptide, are substantially the same as between the human protein kinase and a naturally occurring interacting polypeptide comprising the said amino acid sequence. It will be appreciated that the compound may bind to the protein kinase, or may bind to the interacting polypeptide.

The compounds that are tested in the screening methods of the assay or in other assays in which the ability of a compound to modulate the protein kinase activity of a protein kinase, for example a hydrophobic pocket-containing protein kinase, as defined above, may be measured, may be compounds that have been selected and/or designed (including modified) using molecular modelling techniques, for example using computer techniques.

A further aspect of the invention is a compound identified or identifiable by the above selection/design methods of the invention, for example an RNA molecule or antibody identifiable as defined above.

A still further aspect of the invention is a compound (or polypeptide or polynucleotide) of the invention or identified or identifiable by the above selection/design methods of the invention, for use in medicine. Conditions or diseases in which such compounds, polypeptides or polynucleotides may be useful are indicated below.

The compound (or polypeptide or polynucleotide) may be administered in any suitable way, usually parenterally, for example intravenously, intraperitoneally or intravesically, in standard sterile, non-pyrogenic formulations of diluents and carriers. The compound (or polypeptide or polynucleotide) may also be administered topically, which may be of particular benefit for treatment of surface wounds. The compound (or polypeptide or polynucleotide) may also be administered in a localised manner, for example by injection. The compound may be useful as an antifungal (or other parasitic, pathogenic or potentially parasitic or pathogenic organism) agent.

A further aspect of the invention is the use of a compound (or polypeptide or polynucleotide) as defined above in the manufacture of a medicament for the treatment of a patient in need of modulation of signalling by a protein kinase having a hydrophobic/phosphate binding pocket, as defined above, for example PDK1, SGK, PKB or p70 S6 kinase, for example insulin signalling pathway and/or PDK1/PDK2/SGK/PKB/p70 S6 kinase/PRK2/PKC signalling. The patient may be in need of inhibition of a said hydrophobic/phosphate binding pocket-containing kinase in an infecting organism, for example the patient may have a fungal infection for which treatment is required. The compound may inhibit the infecting organism's (for example fungal) hydrophobic/phosphate binding pocket-containing protein kinase, but may not inhibit the patient's equivalent hydrophobic/phosphate binding pocket-containing protein kinase.

A further aspect of the invention is a method of treating a patient in need of modulation of signalling by a protein kinase having a hydrophobic/phosphate binding pocket as defined above, for example PDK1, SGK, PKB or p70 S6 kinase, for example insulin signalling pathway and/or PDK1/PDK2/SGK/PKB/p70 S6 kinase/PRK2/PKC signalling, wherein the patient is administered an effective amount of a compound (or polypeptide or polynucleotide) as defined above.

A compound that is capable of reducing the activity of PKC, for example PKCβ, PRK1 or 2, PDK1 (ie the PDK1 and/or the PDK2 activity), PKB, SGK or p70 S6 kinase may be useful in treating cancer. PDK1, for example via PKB and/or SGK, may be capable of providing a survival signal that protects cells from apoptosis induced in a variety of ways (reviewed in Cross et al (1995) Nature 378, 785-789 and Alessi & Cohen (1998) *Curr. Opin. Genetics. Develop.* 8, 55-62). Thus, such compounds may aid apoptosis. Reduction of the activity of PDK1, PKB, SGK and/or p70 S6 kinase may promote apoptosis and may therefore be useful in treating cancer. Conditions in which aiding apoptosis may be of benefit may also include resolution of inflammation.

A compound is capable of increasing the activity of PDK1, PKB, SGK or p70 S6 kinase may be useful in treating diabetes or obesity, or may be useful in inhibiting apoptosis. Increased activity of PDK1, PKB, SGK or p70 S6 kinase may lead to increased levels of leptin, as discussed above, which may lead to weight loss; thus such compounds may lead to weight loss. For example, such compounds may suppress apoptosis, which may aid cell survival during or following cell damaging processes. It is believed that such compounds are useful in treating disease in which apoptosis is involved. Examples of such diseases include, but are not limited to, mechanical (including heat) tissue injury or ischaemic disease, for example stroke and myocardial infarction, neural injury and myocardial infarction. Thus the patient in need of modulation of the activity of PDK1, PKB, SGK or p70 S6 kinase may be a patient with cancer or with diabetes, or a patient in need of inhibition of apoptosis, for example a patient suffering from tissue injury or ischaemic injury, including stroke.

Thus, a further aspect of the invention provides a method of treating a patient with an ischaemic disease the method comprising administering to the patient an effective amount of a compound identified or identifiable by the screening methods of the invention.

A still further invention provides a use of a compound identifiable by the screening methods of the invention in the manufacture of a medicament for treating an ischaemic disease in a patient.

Thus, a further aspect of the invention provides a method of treating a patient with an ischaemic disease the method comprising administering to the patient an effective amount of a compound identifiable by the screening methods of the invention.

If the patient is a patient in need of promotion of apoptosis, for example a patient with cancer, it is preferred that the compound of the invention that is used in the preparation of the medicament is capable of reducing the activity of PDK1, PKB, SGK or p70 S6 kinase. If the patient is a patient with diabetes or a patient in need of inhibition of apoptosis, for example a patient with ischaemic disease, it is preferred that the compound of the invention that is used in the preparation of the medicament is capable of increasing the activity of PDK1, PKB, SGK or p70 S6 kinase.

All documents referred to herein are hereby incorporated by reference.

The invention is now described in more detail by reference to the following, non-limiting, Figures and Examples.

Figure Legends

1. Overview of the PDK1 Structure.

The PDK1 kinase domain backbone is shown in a ribbon representation, with the secondary structure elements for residues 74-163 in the lower half of the Figure and for residues 164-358 in the upper part of the Figure. Helix αG, encompassing residues 287-295 (which makes a crystal contact to a symmetry related PDK1 molecule, FIG. 2), is at the bottom right of the Figure. Key residues discussed in the text are shown as a sticks model. ATP is shown as a sticks model. A simulated annealing |Fo−|Fc', φ calc map is shown in black, contoured at 3σ. The phosphoserine and the sulphate discussed in the text are also shown.

2. The PIF-Pocket

A. A surface representation of the putative PIF binding pocket is shown and compared to the pocket interacting with the C-terminal FXXF (SEQ ID NO: 1) motif in PKA. For PDK1, the αG helix of a symmetry-related molecule is shown as a ribbon, in PKA the C-terminus is also shown as a ribbon. Aromatic amino acids buried in the pocket are shown as sticks; further side chains interacting with the pocket are also shown as sticks. Helix αC is also shown as a ribbon in both PDK1 and PKA (at bottom of images). In PDK1, the ordered sulphate ion and basic residues interacting with it are also shown.

B. A stereo image of the residues lining the PIF-pocket is shown. The PDK1 backbone is shown as a grey ribbon. Side chains are shown as sticks. Hydrogen bonds to the sulphate ion are shown as black dotted lines.

3. Structure-Based Sequence Alignment

The sequences of PKA (SEQ ID NO: 103) and PDK1 (SEQ ID NO:102) are aligned according to a structural superposition performed in WHAT IF [Vriend, 1990]. Sequence numbering is according to PDK1. 13-strands (arrows) and α-helices (bars) are shown for the PDK1 structure according to a DSSP [Kabsch and Sander, 1983] secondary structure assignment, and labelled consistent with the secondary structure element names proposed for PKA [Taylor and Radzioandzelm, 1994]. Residues lining the PIF-pocket are indicated with a black dot. Residues hydrogen bonding the sulphate ion are indicated by arrows. The PDK1 residues equivalent to Ser53 and Gly186 in PKA, are labelled with an asterisk.

4. PDK1 Binding & Activation Studies

Binding and activation of wild type and mutant forms of PDK1 to a phosphopeptide derived from the hydrophobic motif of S6K1. The binding of the wild type (wt) PDK1 and indicated mutants to a phosphopeptide comprising the hydrophobic motif of S6K1 (S6K-pHM: SESANQVFLGFT*YVAPSV, where T* indicates phosphothreonine, SEQ ID NO:104) was analysed by surface plasmon resonance as described in the Materials and Methods.

A. The sensor chip SA was coated with 12RUs of the biotinylated S6K-pHM peptide and the binding was analysed following injection of 270 nM wild type PDK1, PDK1 [T148A] and PDK1 [K76A]. No detectable binding to S6K-pHM was observed using PDK1 [R131A] or PDK1 [Q150] (data not shown).

B. As in A. except that binding was analysed over a range of PDK1 concentrations (2-2150 nM). The response level at the steady state binding is plotted versus the log of the PDK1 concentration. The estimated Kd was obtained by fitting the data to a sigmoid curve using Kaleidagraph software. Kd for wild type PDK1 was 642-131 nM, PDK1 [T148A] was 64-7 nM and PDK1 [K76A] was 1744-167 nM. No detectable binding of PDK1 to the non-phosphorylated S6K-HM peptide (SESANQVFLGFTYVAPSV, SEQ ID NO:105) was detected with wild type PDK1 or any of the mutants (data not shown).

C. Activation of the indicated forms of PDK1 by 56K-pHM and S6K-HM. PDK1 activity was measured using the peptide substrate (T308tide) in the presence of the indicated concentrations of 56K-pHM (closed circles) and S6K-HM (open circles) as described in the methods. Assays were performed in triplicate and similar results obtained in 2 separate experiments. The results are the average—SD for a single experiment.

5. Interactions of Regulatory Phosphates with the αC Helix

A. The PDK1 backbone is shown as a ribbon, with helix a C in the centre of the view. Key residues are shown as sticks. The sulphate ion and the phosphate on the activation loop are also shown. A sticks model of ATP is shown. Hydrogen bonds are shown as black dotted lines.

B. Alignment of the amino acid sequence forming part of the phosphate pocket on PDK1 with the equivalent region of the indicated AGC kinases. Identical residues are denoted by white letters on a black background and similar residues by gray boxes. Arrows indicate the residues corresponding to Lys 76, Arg131, Thr148 and Gln150 of PDK1 (SEQ ID NOs: 12 and 144). The aligned amino acid sequences are as follows: PKBα (SEQ ID NOs: 13 and 145), S6K1 (SEQ ID NOs: 14 and 146), SGK1 (SEQ ID NOs: 15 and 147), and Rsk1 (SEQ ID NOs: 16 and 148).

6. Essential Dynamics

A. Projection of all available PKA crystal structures (labelled dots) and the PDK1 structure (diamond) onto the first two eigenvectors (i.e. the ones with the two largest eigenvalues) calculated from the PKA structures.

B. Graphic representation of the motion along the first eigenvector, generated by projecting two structures at −4 nm (black) and +4 nm (grey).

7. Alignment of AGC Protein Kinase Family Members.

The aligned amino acid sequences and their respective corresponding sequence identifier are as follows:

P70S6Kalpha (SEQ ID NO: 17), P70S6 Kbeta (SEQ ID NO: 18), P90RSK1 (SEQ ID NO: 19), P90RSK2 (SEQ ID NO: 20), P90RSK3 (SEQ ID NO: 21), MSK1 (SEQ ID NO: 22), MSK2 (SEQ ID NO: 23), PKBalpha (SEQ ID NO: 24), PKBbeta (SEQ ID NO: 25), PKBgamma (SEQ ID NO: 26), PRK1 (SEQ ID NO: 27), PRK2 (SEQ ID NO: 28), SGK1 (SEQ ID NO: 29), SGK3 (SEQ ID NO: 30), SGK2 (SEQ ID NO: 31), PKCbeta (SEQ ID NO: 32), PKCbetaII (SEQ ID NO: 33), PKCalpha (SEQ ID NO: 34), PKCgamma (SEQ ID NO: 35), PKCzeta (SEQ ID NO: 36), PKCiota (SEQ ID NO: 37), PKCdelta (SEQ ID NO: 38), PKAgamma (SEQ ID NO: 39), and PDK1 (SEQ ID NO: 40).

8. Staurosporine and UCN-01 Electron Density.

The staurosporine and UCN-01 molecules are shown in a stick representation. Hydrogen bonding atoms (Table 4) are labelled according to [49]. The unbiased $|F_o|-|F_c|$, $\phi_{calc}$ maps are contoured at 2.5σ.

9. Details of the Inhibitor Binding Sites.

The bridging water molecule is shown as a sphere. Hydrogen bonds are indicated by black dotted lines. Labelled residues hydrogen-bond the inhibitor molecules.

Example 1

High Resolution Crystal Structure of the Human PDK1 Catalytic Domain Defines the Regulatory Phosphopeptide Docking Site The 3-Phosphoinositide Dependent Protein Kinase-1 (PDK1) plays a key role in insulin/growth factor induced signalling pathways through phosphorylation of downstream AGC-kinases such as Protein Kinase B/Akt and p70 ribosomal S6 kinase (S6K1). Here we describe the 2.0 Å crystal structure of the PDK1 kinase domain in complex with ATP. The structure defines the hydrophobic pocket termed the 'PIF-pocket' which plays a key role in mediating the interaction and phosphorylation of certain substrates such as S6K1. In the PDK1 structure, this pocket is occupied by an extensive crystallographic contact with another molecule of PDK1, reminiscent of the interaction of Protein Kinase A with the hydrophobic motif at its C-terminus. Previous studies have shown that phosphorylation of S6K1 at its C-terminal PIF-pocket-interacting motif, promotes the binding of S6K1 with PDK1, suggesting that there may be a phosphate docking site located nearby the PIF-pocket. Interestingly, close to the PIF-pocket on the PDK1 structure, there is an ordered sulphate ion, interacting tightly with four surrounding side chains. The roles of these residues were investigated through a combination of site directed mutagenesis and kinetic studies, the results of which suggest that this region of PDK1 does indeed represent a phosphate dependent docking site. An analogous phosphate binding regulatory motif may participate in the activation of other AGC kinases.

Results & Discussion

Overall Structure

The structure of the catalytic domain of PDK1 was solved by molecular replacement and refined to an R-factor of 0.19 (Rfree=0.22). PDK1 assumes the classic bilobal kinase fold (FIG. 1) and is similar to the only other AGC kinase structure solved, that of PKA (RMSD of 1.0 Å on C α atoms with PDB entry 1STC [Prade et al., 1997]). The form of PDK1 that was crystallized comprised residues 51 to 359. The tip of the activation loop (residues 233-236) is disordered, as observed in other kinase structures [Johnson et al., 1996]. The N-terminus (residue 51-70), which is pointing into a large void generated by the crystallographic symmetry, is also disordered. In contrast, the N-terminal extension to the kinase domain of PKA assumes an amphipathic α-helix (termed αA-helix), and packs against the kinase core [Knighton et al., 1991]. The cluster of hydrophobic residues that mediates this interaction in PKA is not present in PDK1, suggesting that the N-terminus of PDK1 could have a different function from that of PKA. Interestingly, it has recently been shown that the N-terminus of PDK1 (residues 1-50) interacts with Ral guanine nucleotide exchange factors [Tian et al., 2002]. Thus, this region may assume a unique conformation in PDK1, which is not defined by the structure described here.

PDK1 was crystallised in the presence of ATP but in the absence of any divalent cations. In the early stages of the refinement well-defined density for the entire ATP molecule could be observed. ATP adopts a different conformation to that observed in other kinase-ATP complexes (FIG. 1). Perhaps due to the absence of divalent cations, the generally observed kink between the β and γ phosphate caused by the interaction with such an ion, is not seen in the PDK1 structure.

It is known that PDK1 can phosphorylate itself on residue Ser 241 in the activation loop and that this phosphorylation is required for PDK1 activity [Alessi et al., 1997]. Indeed, we observed density for a phosphate attached to this residue (FIG. 1), and extensive interactions are observed between this phosphoserine and residues from the C-terminal lobe and αC-helix (FIG. 1). The interaction between Ser241 and the C-terminal lobe is similar to the equivalent interactions in PKA but as discussed below the binding to the αC-helix differs.

The PIF-Pocket

As outlined in the introduction, PDK1 was postulated to possess a pocket (the 'PIF-pocket') in the small lobe of its catalytic domain, required for the binding of PDK1 to the hydrophobic motif of its substrates [Biondi et al., 2000]. The PDK1 structure described here indeed reveals such a pocket, and shows that it lies in a location similar to the FXXF (SEQ ID NO:1)-binding pocket in PKA (FIG. 2). PDK1 residues Lys115, Ile118, Ile119 on the αB helix (FIG. 2), Val124, Val127 on the αC helix and Leu155 on β-sheet 5 form an approximately 5 Å deep pocket. Previous work has shown that mutation of Leu155 to Glu abolishes the ability of PDK1 to interact with a peptide that encompasses the hydrophobic motif of PRK2 (PIFtide) [Biondi et al., 2000] as well as with S6K1, SGK1, PKCζ and PRK2 [Balendran et al., 2000, Biondi et al., 2000]. In addition, mutation of Lys115, Ile119, Glu150, and Leu155 to alanine, reduced the affinity of PDK1 for PIFtide approximately 10-fold, but did not affect the ability to phosphorylate and activate S6K1 and SGK1 [Biondi et al., 2001]. These results are in agreement with the crystal structure of the PIF-pocket, since Leu155 is located at the center and the other residues line the wall of the pocket (FIG. 2). Interestingly, in our structure, the PIF-pocket is occupied by helix αG of a symmetry related molecule (FIG. 2). Tyr288 and Phe291 make hydrophobic contacts in this pocket with almost all pocket-lining residues, remarkably reminiscent of the interactions of the phenylalanines in the FXXF motif in PKA and their hydrophobic docking site in the equivalent region of the kinase domain (FIG. 2). In addition, residues Glu287, Gln292, Ile295 and Lys296 on the symmetry related loop also form contacts with residues lining the PIF-pocket. In total, 244$^2$ Å of accessible surface is buried by this contact, suggesting this is a tight interaction. However, the significance of this interaction is not clear as an oligomerisation event for PDK1 has not been demonstrated in solution previously. Indeed both the isolated catalytic domain of PDK1 that was crystallised and full length PDK1 migrate in gel filtration chromatography as apparent monomeric species (data not shown).

The Phosphate Pocket

As outlined in the introduction, substrates of PDK1, such as S6K1, interact with the PIF-pocket of PDK1 with higher affinity when they are phosphorylated at their hydrophobic motif. This suggested that a regulatory phosphate binding site may be located close to the PIF-pocket. During refinement of the PDK1 structure, it became clear that next to the PIF-pocket another small pocket was present, occupied by a tetrahedral oxy-anion (FIG. 2). As 2.0 M of sulphate was present in the crystallisation conditions, this was assigned as a sulphate ion. The ion interacts with four residues lining the pocket, namely Lys76, Arg131, Thr148 and Gln150.

Because of its close proximity to the PIF-pocket (approximately 5A) it is possible that this sulphate-occupied pocket could represent the binding site for the phosphate on the phosphopeptide. To investigate this further, we mutated Lys76, Arg131, Thr148 and Gln150 to Ala, in order to verify the contribution of each of these residues in enabling PDK1 to interact with a peptide encompassing the hydrophobic motif of S6K1, in which the residue equivalent to Thr412 was phosphorylated (termed S6K-pHM). A quantitative surface plasmon resonance based binding assay (FIG. 4A) showed that wild type PDK1 interacted with S6K-pHM, with a Kd of 0.6 μM with S6K-pHM but not detectably to the non-phosphorylated form of this peptide (S6K-HM). The PDK1 [R131A] and PDK1[Q150A] mutants did not detectably interact with S6K-pHM in this assay (FIG. 4B), confirming that the interactions these residues make in the PDK1 structure are of key importance. The PDK1 [K76A] mutant interacted with 3-fold lower affinity (Kd 1.7 μM) with S6K-pHM. The PDK1[T148A] mutant however possessed about 10-fold higher (Kd 0.06 μM) affinity for S6K-pHM than wild type PDK1. Moreover, the dissociation of PDK1[T148A] from S6K-pHM is markedly slower than that of wild type PDK1 or PDK1[K76A] (FIG. 4A). These findings are unexpected as Thr148 is within hydrogen bonding distance of the sulphate (FIG. 2), but indicate that this residue may play a role in enabling the dissociation of PDK1 from S6K-pHM.

The binding of PDK1 to PIFtide stimulates up to 4-fold the rate at which PDK1 phosphorylates a small peptide that encompasses the activation loop motif of PKB (termed T308tide) [Biondi et al., 2000], indicating that occupancy of the PIF-pocket of PDK1 activates the enzyme. Similarly, the binding of a phosphopeptide corresponding to the hydrophobic motif of RSK stimulated PDK1 activity 6-fold [Frodin et al., 2000]. We have now also found that the binding of 56K-pHM to wild type PDK1 induces a maximal 5-fold activation, with a half maximal activation occurring at a concentration of approximately 50 μM S6K-pHM (FIG. 4C). We next assayed the specific activities of PDK1 [K76A], PDK1[R131A], PDK1[T148A] and PDK1[Q150A] mutants in the absence and presence of increasing concentrations of S6K-pHM (FIG. 4C). The PDK1[K76A] possessed the same specific activity towards T308tide in the absence of S6K-pHM as wild type PDK1, but an approximately 3-fold higher concentration of S6K-pHM was required to half maximally activate PDK1 [K76A], consistent with the reduced affinity of this form of PDK1 for S6K-pHM (FIG. 4A,B). The PDK1[R131A] mutant possessed a 3-fold higher specific activity towards Thr308tide in the absence of S6K-pHM (FIG. 4C), as has been observed previously with certain other PIF-pocket mutants of PDK1(PDK1[K115A] and PDK1[L155E]) [Biondi et al., 2000]. However, in accordance with the inability of PDK1[R131A] to bind S6K-pHM in the Biacore assay (FIG. 4B), it was not significantly activated by concentrations of S6K-pHM below 0.1 mM and its activity was only moderately further increased by the addition of high concentrations (0.3 and 1 mM) of S6K-pHM (FIG. 4C). The activity of a mutant of PDK1 in which both Lys76 and Arg131 were changed to Ala was activated even less significantly by these high concentrations of S6K-pHM. The PDK1[T148A] and PDK1[Q150A] mutants possessed similar specific activity towards T308tide as wild type PDK1 in the absence of S6K-pHM. The PDK1[T148A] mutant was activated similarly as wild type PDK1 by S6K-pHM and consistent with the inability of PDK1[Q150A] to interact with S6K-pHM, this mutant of PDK1 was not significantly activated by concentrations of S6K-pHM below 0.1 mM but at 0.3 and 1 mM peptide a 2-3 fold activation was observed (FIG. 4).

At very high peptide concentrations (0.3-1 mM) the non-phosphorylated S6K-HM peptide induced a small (<2-fold) activation of PDK1 (FIG. 4C). Interestingly, despite the PDK1 [K76A] and PDK1[R131A] mutants being markedly less able to interact with the phosphorylated S6K-pHM peptide, than wild type PDK1, high concentrations of the S6K-HM peptide activated PDK1[K76A] and PDK1[R131A] to a similar extent as wild type PDK1, indicating that the ability of these mutants to interact weakly with the S6K-HM peptide was not affected.

We evaluated the sequence conservation in the phosphate pocket of the insulin/growth factor-activated AGC family kinases (PKBα, S6K1, SGK1 and RSK1). Sequence alignments indicate that this pocket is conserved amongst these kinases (FIG. 5A). The most conserved residue is Gln150 which is found in all of these AGC kinases and the residue equivalent to Lys76 is always a basic residue (FIG. 5A). Arg131 is conserved in S6K1, SGK1 and RSK1 but not in PKBα, or PKBβ or PKBγ, where it is an Asn or Ser. Thr148 is conserved in PKBα and SGK1 but is an Ala in S6K1 and RSK1. Interestingly, we have found the Thr 148Ala mutation in PDK1 did not disrupt the phosphate pocket (FIG. 4). As PKBα, S6K1, SGK1 and RSK1 require to be phosphorylated at their hydrophobic motif to be maximally activated, it is tempting to speculate that the C-terminal hydrophobic motifs of these enzymes, when phosphorylated, bind to their own PIF/phosphate pockets, thereby generating a network of interactions similar to that of PDK1. In support of this, PKBα, S6K1, SGK1 and RSK1 also require phosphorylation of their activation loop at the position equivalent to Ser241 for activity. Consistent with PKA not possessing a phosphate pocket, Lys76 and Gln150 are not conserved in PKA (FIG. 3), and indeed such a pocket is not observed in the PKA structure (FIG. 2).

The αC Helix

The PDK1 structure shows that, as in other protein kinases [Johnson et al., 2001, Husen and Kuriyan, 2002], the αC helix (residues 124-136) is a key signal integration motif in the kinase core. One turn of the PDK1 αC helix (residues 129-131, FIGS. 3, 5) links together the N-terminal lobe, the C-terminal lobe and the active site. Arg129 points towards the activation loop and forms two hydrogen bonds with the phosphorylated Ser241, whereas Arg131 forms two hydrogen bonds with the sulphate in the phosphate pocket (FIG. 5). Glu130 coordinates Lys111 which forms a hydrogen bond with the α-phosphate of the bound ATP. This interaction is conserved in all protein kinases and shown to be crucial for activation [Johnson et al., 2001, Husen and Kuriyan, 2002]. An additional residue, His126, forms a third hydrogen bond with the phosphorylated Ser241. Val124 and Val127 on the αC helix are involved in formation of the PIF-pocket (FIG. 5).

The αC helix provides a structural link between the putative phosphopeptide binding pocket and the phosphoserine in the activation loop. The fact that R131A has higher basal activity than wild type PDK1 may indicate that this residue plays tuning role in the PDK1 structure, not only participating in the activation of PDK1 in the presence of a phosphate ion, but also on keeping the equilibrium of the enzyme towards an inactive conformation in the absence of S6K-pHM. To our knowledge this is the first report of a kinase structure in which the αC helix is positioned by 2 regulatory phosphate binding sites on either side of the helix (FIG. 5). This provides a possible sensor-mechanism for linking the phosphorylation-state of the activation loop and the phosphopeptide binding event in the PIF-pocket to PDK1 activity.

Activation State

All structures of PKA solved to date show a phosphorylated T-loop and are therefore assumed to be in an active state. In addition to the unphosphorylated versus phosphorylated states of PKA, there appear to be two main conformational states possible for the latter [Zheng et al., 1993, Johnson et al., 2001]. In the active, closed conformation, all residues are positioned to facilitate phosphoryl transfer. In contrast, the inactive, open conformation is seen in absence of a nucleotide, and differs from the closed conformation by conformational changes of the N-terminal and C-terminal domains with respect to each other. In addition, three 'intermediate' structures were described from PKA, having either adenosine (PDB entry 1BKX [Narayana et al., 1997]) or the inhibitors staurosporine (PDB entry 1STC [Prade et al., 1997]) and balanol (PDB entry 1BX6 [Narayana et al., 1999]) in the ATP-binding site. Taylor and colleagues have described a method to distinguish between the active and inactive conformations, based on three distances: His87-pThr197 (αC helix positioning), Ser53-Gly186 (opening of the glycine-rich loop) and Glu170-Tyr330 (C-terminal tail distance to active site) [Johnson et al., 2001]. In PDK1, only one of these distances, the opening state of the glycine rich loop, can be measured due to sequence conservation (FIG. 3). This distance is 12.4 Å, similar to a PKA intermediate conformation (this distance in PKA is 14.2 Å for the open, 11.8 Å for intermediate and 10.0 Å for the closed conformation [Johnson et al., 2001]). To allow a more direct comparison of the PDK1 structure with the available PKA structures, we have analysed the conformational state of PDK1 in detail using a novel approach, which involves a principal component analysis (also called "essential dynamics" [Amadei et al., 1993]) of the crystallographic coordinates. In short, this involves the construction of a covariance matrix containing the correlations between atomic shifts (with respect to an average structure) in the ensemble of all available PKA crystal structures. Diagonalisation of this matrix gives eigenvector/eigenvalue sets which describe concerted shifts of atoms (eigenvectors) together with the corresponding mean square fluctuation of the structures (eigenvalues). This approach allows a condensed description of PKA conformational states using only a few degrees of freedom, as shown previously for a range of other proteins [van Aalten et al., 1997, van Aalten et al., 2000, deGroot et al., 1998]. Diagonalisation of a covariance matrix built from the backbone atoms of residues 37-196, 198-283 and 286-305 results in a set of eigenvectors that describe concerted motions of the PKA backbone. In FIG. 6A, all PKA structures are projected on a subspace spanned by the first two eigenvectors (i.e. those with the two largest eigenvalues). It appears that the PKA structures cluster in three main areas along the first eigenvector. On the left of the average structure (which by definition has a projection of 0.0 on all eigenvectors) are the structures that are known to be in the "open" conformation (FIG. 6A). Around the average structure lie the structures that have been shown to be in an "intermediate" conformation (complexes with the inhibitors staurosporine, balanol and adenosine). More to the right of the average structure are the PKA structures that are known to be in the "closed" conformation. Thus, we have captured the conformational state of PKA in a single variable, the translation along the first eigenvector. This is further clarified by investigation of the atomic shifts described by this eigenvector in Cartesian space (FIG. 6B). A hinge-bending motion is observed between the N-terminal and C-terminal lobes, opening and closing the active site. It is now possible directly to compare the PDK1 conformational state by projecting the structure (backbone atoms only) onto the PKA eigenvectors. FIG. 6A shows that the conformation of PDK1 is close to the PKA structures that are in an "intermediate" conformation, consistent with the other structural analyses described above.

Conclusions

We have reported the structure of the PDK1 catalytic domain, which, although similar to PKA, has revealed important features that increase our understanding of the mechanism by which PDK1 is regulated. The structure, together with mutational analyses, defines a phosphopeptide binding pocket, consisting of a separate hydrophobic PIF-pocket and a phosphate binding site, which mediates the interaction of PDK1 with the phosphorylated hydrophobic motif of S6K. This is consistent with the previous hypothesis that phosphorylation of S6K and SGK [Biondi et al., 2001] as well as RSK [Frodin et al., 2000] at their FXXFS/T hydrophobic motif (SEQ ID NO:2) is the trigger for their interaction and phosphorylation by PDK1. In this mechanism the PIF-pocket would physiologically only interact with the Phe residues when the Ser/Thr residue is phosphorylated. Furthermore, as the phosphate pocket is conserved in other AGC kinases, the structural features and network of interaction of the phosphate pocket with the αC-helix on PDK1, could provide insight into the mode of activation of other AGC kinases.

EXPERIMENTAL PROCEDURES

Materials

Mammalian and Insect cells culture reagents were from Life Technologies. Sensor Chips SA were from BiaCore AB. Glutathione Sepharose, as well as pre-packed HiTrap Q HP and Hiload Superdex 200 prep grade columns were from Amersham Biosciences. Dialysis cassettes were from the Slide-A-Lyzer series (Pierce). Ni-NTA Agarose was from Qiagen. Disposable ultrafiltration devices (polyethersulfone membranes) were from Vivascience. Crystallisation research tools (primary screens, additive screens and crystallisation plates) were from Hampton Research. Peptides were synthesised by Dr G. Blomberg (University of Bristol, UK).

General Methods

Molecular biology techniques were performed using standard protocols. Site directed mutagenesis was performed using a QuickChange kit (Stratagene) following instructions provided by the manufacturer. DNA constructs used for transfection were purified from bacteria using Qiagen plasmid Mega kit according to the manufacturer's protocol, and their sequence verified. Human kidney embryonic 293 cells were cultured on 10 cm diameter dishes in Dulbecco's modified Eagle's medium containing 10% foetal bovine serum.

Buffers

Low Salt Buffer: 25 mM Tris-HCl pH 7.5, 150 mM NaCl; High Salt Buffer: 25 mM Tris-HCl pH 7.5, 500 mM NaCl. Lysis Buffer: 25 mM Tris-HCl pH 7.5, 150 mM NaCl 0.07% β-mercaptoethanol, 1 mM Benzamidine, and 20 μg/ml PMSF. Buffer A: 50 mM Tris-HCl pH 7.5, 1 mM EGTA, 1 mM EDTA, 1% (by mass) Triton-X 100, 1 mM sodium orthovanadate, 50 mM sodium fluoride, 5 mM sodium pyrophosphate, 0.27 M sucrose, 1 μM microcystin-LR, 0.1% (by vol)-mercaptoethanol and "complete" proteinase inhibitor cocktail (one tablet per 50 ml, Roche). Buffer B: 50 mM Tris/HCl pH 7.5, 0.1 mM EGTA, 10 mM β-mercaptoethanol and 0.27 M sucrose.

Expression, Purification and Characterisation of the Kinase Domain of PDK1

A cDNA encoding for human PDK1 amino acid residues 51-359 with a stop codon inserted at position 360, was amplified by PCR reaction using full length human PDK1 cDNA in the pCMV5 vector [Alessi et al., 1997] as a template a 5' primer, which incorporates a BamHI restriction site, an initiating methionine, a hexahistidine tag followed by a PreScission protease recognition sequence prior to the residue equivalent to Met51 of PDK1 (ggatcctataaatatggcacatcatcatcatcatcatctggaagttctgttccaggggcccatggacggcact gcagccgagc-ctcgg) (SEQ ID NO:106) and the 3' primer applied in this reaction was: 5'-ggatcctcaggtgagcttcggaggcgtctgctggtg-3' (SEQ ID NO: 107). The resulting PCR product was ligated into pCR 2.1 TOPO vector (Invitrogen) and then subcloned as a BamHI-BamHI fragment into pFastbac1 vector (Life Technologies) for baculovirus protein expression. The resulting construct was then used to generate recombinant baculovirus using the Bac-to-Bac system (Life Technologies) following the manufacturer's protocol. The resulting baculoviruses were used to infect Sf21 cells at 1.5×106/ml. The infected cells were harvested by centrifugation 72 hours post infection. Cell pellets corresponding to 7 l of culture were resuspended in 900 ml of Lysis Buffer and cells lysed in nitrogen cavitation chamber. Cell debris was then pelleted by centrifugation, the supernatant made 0.5 M NaCl by addition of 4M NaCl and then incubated with Ni-NTA-Agarose (10 ml resin) for one hour. The resin was then washed in 10 times with 40 ml of Lysis Buffer containing 0.5M NaCl and then placed in a disposable Econo-Pac column (BioRad), where the resin was further washed with 700 ml of high salt buffer and then with 100 ml of low salt buffer, both supplemented with 10 mM imidazole. Elution was performed with 200 mM imidazole in high salt buffer and 2 ml fractions were collected. Fractions containing protein were pooled, diluted to 200 mM NaCl with 25 mM Tris/HCl pH 7.5, and loaded onto a 5 ml Hi-trap Q sepharose column. The flow-through from this step, containing PDK1, was concentrated to 4 ml and then chromatographed on a 16/60 Superdex 200 gel filtration column using an AKTA Explorer system (Amersham Biosciences) equilibrated with high salt buffer with the addition of 1 mM DTT. PDK1 eluted in a large symmetric peak at the expected size for a monomer. The PDK1 containing peak was again pooled, concentrated and incubated with 300 μg GST-PreScission protease (expression construct kindly provided by John Heath, University of Birmingham, UK) on ice for 4 h. In order to eliminate the cleaved His-tag sequences as well as any remaining uncleaved His-PDK1 and the GST-PreScission protease, the mixture was incubated with a mixture of 200 μl glutathione-Sepharose and 200 μl Ni-NTA agarose resin for 15 minutes and the PDK1 protein that did not bind was collected. The resulting protein consists of PDK1 (51-359) preceded by a Gly-Pro at the N-terminus. The protein at this stage of the purification was apparently homogeneous as revealed by a single band after electrophoresis of 20 μg of protein on SDS-PAGE and staining with Coomasie Brilliant Blue 8250 (data not shown).

Electrospray mass spectrometry revealed a main peak mass close to the expected size of this fragment of PDK1. The specific activity of PDK1 (51-359) towards the peptide T308tide and its activation in the presence of PIFtide was identical to wild type full length PDK1 [Biondi et al., 2000], and tryptic peptide mass finger printing indicated that PDK1 was quantitatively phosphorylated at Ser241 (data not shown). In BiaCore experiments, the steady state binding of PDK1 (51-359) to the peptide PIFtide was similar to that of the His-tag PDK1 (51-556) protein characterised previously [Balendran et al., 1999a].

Crystallisation and Data Collection

The PDK1 (51-359) protein was concentrated to a final concentration of 8.5 mg/ml (as determined by a Bradford assay using bovine serum albumin as a standard). The sitting drop vapour diffusion method was used for producing crystals. Sitting drops were formed by mixing 1 μl of protein solution with 1 μl of a mother liquor solution (0.1 M Tris/HCl pH 8.5, 2.0 M ammonium sulphate, 16.6 mM ATP) with the addition of 0.2 μl EDTA (100 mM). Hexagonal crystals (Table I) of PDK1 were grown at 20° C. from a mother liquor containing 0.1M Tris/HCl pH 8.5, 2.0 M ammonium sulphate, 16.6 mM ATP). Crystals appeared after one day, growing to 0.05×0.05×0.2 mm over 20 days. Crystals were frozen in a nitrogen gas stream after being soaked in 0.075 M Tris 8.5, 1.5M ammonium sulphate, 25% (v/v) glycerol.

Expression and Purification of Wild Type and Mutant Forms of GST-PDK1.

Wild type-PDK1 [Alessi et al., 1997], PDK1[R76A], PDK1[R131A], PDK1[R76A,R131A], PDK1[T148A] and PDK1[Q150A] in the pEBG2T vector were used to express the wild type and indicated mutants of PDK1 fused through their N-terminus to glutathione S-transferase (GST). The GST fusion proteins were expressed in human embryonic kidney 293 cells. For the expression of each construct, twenty 10 cm diameter dishes of 293 cells were cultured and each dish transfected with 10 μg of the pEBG-2T construct, using a modified calcium phosphate method. 36 h post-transfection, the cells were lysed in 0.6 ml of ice-cold Buffer A, the lysates pooled, centrifuged at 4° C. for 10 min at 13000 g and the GST-fusion proteins were purified by affinity chromatography on glutathione-Sepharose and eluted in Buffer B supplemented with 20 mM glutathione as described previously [Alessi et al., 1997]. Typically between 1 and 2 mg of each GST-fusion protein was obtained and each protein was more than 75 judged by SDS polyacrylamide gel electrophoresis (data not shown).

PDK1 Catalytic Activity Measurements

The ability of wild type and mutant PDK1 to phosphorylate the synthetic peptide T308tide (KTFCGTPEYLAPEVRR ([Biondi et al., 2000]) (SEQ ID NO:108) was carried out in 30 μl assays containing 100 ng of wild type or mutant PDK1, 50 mM Tris/HCl pH 7.5, 0.1% 13-mercaptoethanol, 10 mM $MgCl_2$, 100 μM [32γ P]ATP (200 cpm/pmol), 0.5 μM microcystin-LR, 1 mM T308tide in the presence or absence of the indicated concentrations of the 56K-pHM peptide (SESANQVFLGFT(P)YVAPSV) (SEQ ID NO:104) or 56K-HM. peptide (SESANQVFLGFTYVAPSV) (SEQ ID NO:105). After incubation for 10 min at 30° C., 25 μl of the resultant mixture was spotted into P81 phosphocellulose paper (2×2 cm) and the papers washed and analysed as described previously for assays of MAP kinase. Control assays were carried out in parallel in which either PDK1, or peptide substrate were omitted; these values were always less than 5% of the activity measured in the presence of these reagents. One Unit of PDK1 activity was defined as that amount required to catalyse the phosphorylation of 1 nmol of the T308tide in 1 min.

Biacore Analysis

Binding was analysed in a BiaCore 3000 system (BiaCore AB, Stevenage, UK). Biotinylated S6K-pHM (Biotin-$C_{12}$-SESANQVFLGFT(P)YVAPSV) (SEQ ID NO:104) or the non-phosphorylated form of this peptide S6K-HM was bound to an streptavidin-coated Sensor chip (SA) (12 response units, RU). 30 μl of wild type or the indicated mutant GST-PDK1 were injected at a flow rate of 30 μl/min, in buffer HBS-P (10 mM HEPES pH 7.4, 0.15M NaCl, 0.005% (by vol) polysorbate-20) supplemented with 1 mM DTT. Specific interactions between 56K-pHM and PDK1 proteins were obtained between the concentration range of 2-2150 nM PDK1. Steady state binding was determined at each concentration. Dissociation of PDK1 from the phospho-peptide was monitored over a 1 min period. Regeneration of the sensor chip surface was performed with 10 μl injections of 0.05% SDS. As previously found for PDK1 binding to PIFtide [Biondi et al., 2000], the interaction data obtained using BiaCore did not fit to simple 1:1 interaction model. Apparent Kd values were estimated from the concentration of PDK1 which gives 50% of maximal response, which was obtained empirically using GST-PDK1[T148A] (RUmax=435). For all PDK1 construct tested, the off rates for S6Kp-HM were high in comparison to those of PIFtide binding with the time taken for 50% dissociation to occur for 56K-pHM is 30s compared to 1000s for PIFtide. This could account for the overall approximately 100-fold lower affinity of wild type PDK1 for 56K-pHM in comparison to PIFtide.

Data Collection, Structure Solution, and Refinement

Data on PDK1 crystals were collected at the European Synchrotron Radiation Facility (Grenoble, France) beamline ID14-EH1, using an ADSC Q4 CCD detector. The temperature of the crystals was maintained at 100K using a nitrogen cryostream. Data were processed using the HKL package [Otwinowski and Minor, 1997], statistics are shown in Table I.

The structure of PDK1 was solved by molecular replacement with AMoRe [Navaza, 1994] using the structure of PKA in complex with an inhibitory peptide as a search model (PDB entry 1YDB), against 8-4 Å data. A single, well separated solution was found with an R-factor of 0.479 (correlation coefficient=0.428). The structure was automatically built using warpNtrace [Perrakis et al., 1999], which found 262 of a possible 309 residues, giving an initial protein model with R=0.293 (Rfree=0.318) after simulated annealing in CNS [Brunger et al., 1998]. Iterative protein building in 0 [Jones et al., 1991] together with refinement in CNS, which included incorporation of a model for ATP, the phosphoserine in the activation loop, solvent molecules and a key sulphate molecule, resulted in a final model with R=0.195 (Rfree=0.222). No electron density was observed for residues 51-70 (the N-terminus of the construct) and 233-236 (the tip of the activation loop). All figures were made with PyMOL.

TABLE I

Details of data collection & structure refinement for the PDK1 kinase domain. Values between brackets are for the highest resolution shell. All measured data were included in structure refinement.

| | |
|---|---|
| Wave length ( ) | 0.933 |
| Space group | $P3_221$ |
| Unit cell ( ) | a = 123.01, b = 123.01, c = 47.62 |
| Resolution ( ) | 25-2.0 (2.07-1.0) |
| Observed reflections | 77315 |
| Unique reflections | 27643 |
| Redundancy | 2.8 (2.5) |
| Completeness (%) | 98.0 (93.5) |
| Rmerge | 0.091 (0.454) |
| I/sigma I | 7.3 (2.0) |
| $R_{free}$ reflections | 579 |
| $R_{cryst}$ | 0.195 |
| $R_{free}$ | 0.222 |
| Number of groups | |
| °°Protein residues | 71-359 |
| °°Water | 200 |
| ATP | 1 |
| $SO_4$ | 5 |
| Glycerol | 8 |
| Wilson B ($^2$) | 22.4 |
| <B> Protein | 25.6 |
| <B> Water | 35.7 |
| <B> ATP | 38.8 |
| RMSD from ideal geometry | |
| Bond lengths ( ) | 0.005 |
| Bond angles (°) | 1.34 |
| Main chain B ($^2$) | 1.5. |

REFERENCES

Alessi, D. R. (2001). Discovery of PDK1, one of the missing links in insulin signal transduction. Biochem. Soc. Trans. 29, 1-14.

Alessi, D. R., Deak, M., Casamayor, A., Caudwell, F. B., Morrice, N., Norman, D. G., Gaffney, P., Reese, C. B., MacDougall, C. N., Harbison, D., Ashworth, A., and Bownes, M. (1997). 3-phosphoinositide-dependent protein kinase-1 (PDK1): structural and functional homology with the *drosophila* DSTPK61 kinase. Curr. Biol. 7, 776-789.

Amadei, A., Linssen, A. B. M., and Berendsen, H. J. C. (1993). Essential dynamics of proteins. Proteins 17, 412-425.

Balendran, A., Biondi, R. M., Cheung, P. C. F., Casamayor, A., Deak, M., and Alessi, D. R. (2000). A 3-phosphoinositide-dependent protein kinase-1 (PDK1) docking site is required for the phosphorylation of protein kinase c zeta (pkc zeta) and pkc-related kinase 2 by PDK1. J. Biol. Chem. 275, 20806-20813.

Balendran, A., Casamayor, A., Deak, M., Paterson, A., Gaffney, P., Currie, R., Downes, C. P., and Alessi, D. R. (1999a). PDK1 acquires PDK2 activity in the presence of a synthetic peptide derived from the carboxyl terminus of PRK2. Curr. Biol. 9, 393-404.

Balendran, A., Currie, R., Armstrong, C. G., Avruch, J., and Alessi, D. R. (1999b). Evidence that 3-phosphoinositide-dependent protein kinase-1 mediatesphosphorylation of p70 56 kinase in vivo at thr-412 as well as thr-252. J. Biol. Chem. 274, 37400-37406.

Biondi, R. M., Cheung, P. C. F., Casamayor, A., Deak, M., Currie, R. A., and Alessi, D. R. (2000). Identification of a pocket in the pdk1 kinase domain that interacts with pif and the c-terminal residues of pka. Embo J. 19, 979-988.

Biondi, R. M., Kieloch, A., Currie, R. A., Deak, M., and Alessi, D. R. (2001). The PIF-binding pocket in PDK1 is essential for activation of S6K and SGK, but not PKB. EMBO J. 20, 4380-4390.

Brazil, D. P. and Hemmings, B. A. (2001). Ten years of protein kinase B signalling: a hard Akt to follow. Trends Biochem. Sci. 26, 657-664.

Brunger, A. T., Adams, P. D., Clore, G. M., Gros, P., Grosse-Kunstleve, R. W., Jiang, J.-S., Kuszewski, J., Nilges, M., Pannu, N. S., Read, R. J., Rice, L. M., Simonson, T., and Warren, G. L. (1998). Crystallography and NMR system: A new software system for macromolecular structure determination. Acta Cryst. D54, 905-921.

De Groot, B. L., Hayward, S., van Aalten, D. M. F., Amadei, A., and Berendsen, H. J. C. (1998). Domain motions in bacteriophage t4 lysozyme: A comparison between molecular dynamics and crystallographic data. Proteins 31, 116-127.

Etchebehere, L. C., VanBemmelen, M. X. P., Anjard, C., Traincard, F., Assemat, K., Reymond, C., and Veron, M. (1997). The catalytic subunit of dictyostelium cAMP-dependent protein kinase-role of the n-terminal domain and of the c-terminal residues in catalytic activity and stability. Eur. J. Biochem. 248, 820-826.

Frodin, M. and Gammeltoft, S. (1999). Role and regulation of 90 kda ribosomal s6 kinase (rsk) in signal transduction. Mol. Cell. Endocrinol. 151, 65-77.

Frodin, M., Jensen, C. J., Merienne, K., and Gammeltoft, S. (2000). A phosphoserine-regulated docking site in the protein kinase rsk2 that recruits and activates PDK1. EMBO J. 19, 2924-2934.

Husen, M. and Kuriyan, J. (2002). The conformational plasticity of protein kinases. Cell 109 (275-282).

Johnson, D. A., Akamine, P., Radzio-Andzelm, E., Madhusudan, and Taylor, S. S. (2001). Dynamics of camp-dependent protein kinase. Chem. Rev. 101, 2243-2270.

Johnson, L. N., Noble, M. E. M., and Owen, D. J. (1996). Active and inactive protein kinases: Structural basis for regulation. Cell 85, 149-158.

Jones, T. A., Zou, J. Y., Cowan, S. W., and Kjeldgaard, M. (1991). Improved methods for building protein models in electron density maps and the location of errors in these models. Acta Cryst. A47, 110-119.

Kabsch, W. and Sander, C. (1983). Dictionary of protein secondary structure: pattern recognition of hydrogen-bonded and geometrical features. Biopolymers 22, 2577-2637.

Knighton, D. R., Zheng, J. H., Teneyck, L. F., Ashford, V. A., Xuong, N. H., Taylor, S. S., and Sowadski, J. M. (1991). Crystal-structure of the catalytic subunit of cyclic adenosinemonophosphate dependent protein-kinase. Science 253, 407-414.

Kobayashi, T. and Cohen, P. (1999). Activation of serum- and glucocorticoid-regulated protein kinase by agonists that activate phosphatidylinositide 3-kinase is mediated by 3-phosphoinositide-dependent protein kinase-1 (pdk1) and pdk2. Biochem. J. 339, 319-328.

Lang, F. and Cohen, P. (2001). Regulation and physiological roles of serum- and glucocorticoid-induced protein kinase isoforms. Sci. STKE RE17.

Narayana, N., Cox, S., Xuong, N. H., TenEyck, L. F., and Taylor, S. S. (1997). A binary complex of the catalytic subunit of camp-dependent protein kinase and adenosine further defines conformational flexibility. Structure 5, 921-935.

Narayana, N., Diller, T. C., Koide, K., Bunnage, M. E., Nicolaou, K. C., Brunton, L. L., Xuong, N. H., Ten Eyck, L. F., and Taylor, S. S. (1999). Crystal structure of the potent natural product inhibitor balanol in complex with the catalytic subunit of camp-dependent protein kinase. Biochemistry 38, 2367-2376.

Navaza, J. (1994). AMoRe: an automated package for molecular replacement. Acta Cryst. A50, 157-163.

Otwinowski, Z. and Minor, W. (1997). Processing of X-ray diffraction data collected in oscillation mode. Methods in Enzymology 276, 307-326.

Perrakis, A., Morris, R., and Lamzin, V. S. (1999). Automated protein model building combined with iterative structure refinement. Nature Struct. Biol. 6, 458-463.

Prade, L., Engh, R. A., Girod, A., Kinzel, V., Huber, R., and Bossemeyer, D. (1997). Staurosporine-induced conformational changes of camp-dependent protein kinase catalytic subunit explain inhibitory potential. Structure 5, 1627-1637.

Pullen, N., Dennis, P. B., Andjelkovic, M., Dufner, A., Kozma, S. C., Hemmings, B. A., and Thomas, G. (1998). Phosphorylation and activation of p70(s6k) by pdk1. Science 279, 707-710.

Scheid, M. P. and Woodgett, J. R. (2001). Pkb/akt: Functional insights from genetic models. Nat. Rev. Mol. Cell. Biol. 2, 760-768.

Stephens, L., Anderson, K., Stokoe, D., Erdjument-Bromage, H., Painter, G. F., Holmes, A. B., Gaffney, P. R. J., Reese, C. B., McCormick, F., Tempst, P., Coadwell, J., and Hawkins, P. T. (1998). Protein kinase b kinases that mediate phosphatidylinositol 3,4,5-trisphosphate-dependent activation of protein kinase b. Science 279, 710-714.

Taylor, S. S., Knighton, D. R., Zheng, J. H., Teneyck, L. F., and Sowadski, J. M. (1992). Structural framework for the protein-kinase family. Annu. Rev. Cell Biol. 8, 429-462.

Taylor, S. S. and Radzioandzelm, E. (1994). 3 protein-kinase structures define a common motif. Structure 2, 345-355.

Tian, X. J., Rusanescu, G., Hou, W. M., Schaffhausen, B., and Feig, L. A. (2002). Pdk1 mediates growth factor-induced ral-gef activation by a kinase-independent mechanism. Embo J. 21, 1327-1338.

Toker, A. and Newton, A. C. (2000). Cellular signaling: Pivoting around pdk-1. Cell 103, 185-188.

van Aalten, D. M. F., Chong, C. R., and Joshua-Tor, L. (2000). Crystal structure of carboxypeptidase a complexed with d-cysteine at 1.75 Å-inhibitor-induced conformational changes. Biochemistry 39, 10082-10089.

van Aalten, D. M. F., Conn, D. A., de Groot, B. L., Berendsen, H. J. C., Findlay, J. B. C., and Amadei, A. (1997). Protein dynamics derived from clusters of crystal structures. Biophys. J. 73, 2891-2896.

Volarevic, S, and Thomas, G. (2001). Role of s6 phosphorylation and s6 kinase in cell growth. Prog Nucl Acid Res Mol Biol 65, 101-127.

Vriend, G. (1990). WHAT IF: a molecular modeling and drug design program. J. Mol. Graph. 8, 52-56.

Zheng, J. H., Knighton, D. R., Xuong, N. H., Taylor, S. S., Sowadski, J. M., and Teneyck, L. F. (1993). Crystal-structures of the myristylated catalytic subunit of camp-dependent protein-kinase reveal open and closed conformations. Protein Sci. 2, 1559-1573.

Example 2

Co-Ordinates for PDK1Fragment with All Alternate Side Chains

```
REMARK coordinates from restrained individual B-factor refinement
REMARK refinement resolution: 25.0 - 2.0 A
REMARK starting r= 0.1972 free_r= 0.2220
REMARK final r= 0.1954 free_r= 0.2224
REMARK B rmsd for bonded mainchain atoms= 1.501 target= 1.5
REMARK B rmsd for bonded sidechain atoms= 2.235 target= 2.0
REMARK B rmsd for angle mainchain atoms= 2.347 target= 2.0
REMARK B rmsd for angle sidechain atoms= 3.302 target= 2.5
REMARK rweight= 0.0900 (with wa= 1.29263)
REMARK target= mlf steps= 30
REMARK sg= P3(2)21 a= 123.013 b= 123.013 c= 47.624 alpha= 90 beta= 90
gamma= 120
REMARK parameter file 1 : /dd1/david/projects/PDK1_new/CNS/prot.par
REMARK parameter file 2 : /dd1/david/projects/PDK1_new/CNS/atp.par
REMARK parameter file 3 : CNS_TOPPAR:water_rep.param
REMARK parameter file 4 : CNS_TOPPAR:ion.param
REMARK parameter file 5 : /dd1/david/projects/PDK1_new/CNS/glycerol.par
REMARK molecular structure file: ../generate/alternate.mtf
REMARK input coordinates: ../minimize/minimize.pdb
REMARK reflection file=. ./. ./1/hkl/cns.hkl
REMARK ncs= none
REMARK B-correction resolution: 6.0 - 2.0
REMARK initial B-factor correction applied to fobs :
REMARK B11= -2.766 B22= -2.766 B33= 5.532
REMARK B12= -0.375 B13= 0.000 B23= 0.000
REMARK B-factor correction applied to coordinate array B: 0.031 0.031
REMARK bulk solvent: density level= 0.378441 e/A^3, B-factor= 52.6885 A^2
REMARK reflections with |Fobs|/sigma_F < 0.0 rejected
REMARK reflections with |Fobs|> 10000 * rms(Fobs) rejected
REMARK theoretical total number of refl. in resol. range: 28210 ( 100.0% )
REMARK number of unobserved reflections (no entry or |F|= 0): 568 ( 2.0% )
REMARK number of reflections rejected: 0 ( 0.0% )
REMARK total number of reflections used: 27642 ( 98.0% )
REMARK number of reflections in working set: 27063 ( 95.9% )
REMARK number of reflections in test set: 579 ( 2.1% )
CRYST1 123.013 123.013 47.624 90.00 90.00 120.00 P 32 2 1
REMARK FILENAME="bindividual.pdb"
REMARK DATE:Apr. 16, 2002 18:31:12 created by user: david
REMARK VERSTON:1.0
ATOM      1  CB   PRO  A   71    58.912   -7.251    8.216  1.00  67.78 A
ATOM      2  CC   PRO  A   71    59.621   -6.941    9.534  1.00  69.16 A
ATOM      3  C    PRO  A   71    59.493   -6.506    5.894  1.00  67.06 A
ATOM      4  O    PRO  A   71    59.196   -5.318    5.766  1.00  66.66 A
ATOM      5  N    PRO  A   71    60.984   -6.073    7.833  1.00  67.86 A
ATOM      6  CD   PRO  A   71    60.554   -5.762    9.207  1.00  68.24 A
ATOM      7  CA   PRO  A   71    60.040   -7.03S    7.217  1.00  67.75 A
ATOM      8  N    PRO  A   72    59.356   -7.38S    4.890  1.00  66.32 A
ATOM      9  CD   PRO  A   72    59.712   -8.816    4.898  1.00  67.17 A
ATOM     10  CA   PRO  A   72    58.840   -6.986    3.S78  1.00  65.61 A
ATOM     11  CB   PRO  A   72    58.672   -8.321    2.8S8  1.00  66.47 A
ATOM     12  CG   PRO  A   72    59.796   -9.133    3.419  1.00  67.57 A
ATOM     13  C    PRO  A   72    57.527   -6.208    3.673  1.00  63.94 A
ATOM     14  O    PRO  A   72    56.710   -6.451    4.561  1.00  64.11 A
ATOM     15  N    ALA  A   73    57.341   -5.268    2.753  1.00  61.57 A
ATOM     16  CA   ALA  A   73    56.133   -4.454    2.708  1.00  58.74 A
ATOM     17  CB   ALA  A   73    56.438   -3.030    3.165  1.00  58.05 A
ATOM     18  C    ALA  A   73    55.626   -4.448    1.271  1.00  56.78 A
ATOM     19  O    ALA  A   73    56.347   -4.834    0.349  1.00  56.95 A
ATOM     20  N    PRO  A   74    54.372   -4.024    1.057  1.00  54.15 A
ATOM     21  CD   PRO  A   74    53.335   -3.610    2.018  1.00  53.31 A
```

-continued

| | | | | | | | | | | |
|---|---|---|---|---|---|---|---|---|---|---|
| ATOM | 22 | CA | PRO | A | 74 | 53.856 | −4.003 | −0.314 | 1.00 | 52.54 A |
| ATOM | 23 | CB | PRO | A | 74 | 52.474 | −3.375 | −0.148 | 1.00 | 52.86 A |
| ATOM | 24 | CG | PRO | A | 74 | 52.067 | −3.824 | 1.226 | 1.00 | 52.88 A |
| ATOM | 25 | C | PRO | A | 74 | 54.772 | −3.167 | −1.204 | 1.00 | 50.08 A |
| ATOM | 26 | O | PRO | A | 74 | 55.559 | −2.361 | −0.708 | 1.00 | 49.96 A |
| ATOM | 27 | N | ALA | A | 75 | 54.680 | −3.366 | −2.514 | 1.00 | 47.58 A |
| ATOM | 28 | CA | ALA | A | 75 | 55.503 | −2.602 | −3.446 | 1.00 | 44.69 A |
| ATOM | 29 | CB | ALA | A | 75 | 55.312 | −3.121 | −4.870 | 1.00 | 46.14 A |
| ATOM | 30 | C | ALA | A | 75 | 55.100 | −1.134 | −3.371 | 1.00 | 41.55 A |
| ATOM | 31 | O | ALA | A | 75 | 53.947 | −0.813 | −3.086 | 1.00 | 41.01 A |
| ATOM | 32 | N | LYS | A | 76 | 56.053 | −0.245 | −3.619 | 1.00 | 38.31 A |
| ATOM | 33 | CA | LYS | A | 76 | 55.781 | 1.184 | −3.588 | 1.00 | 35.72 A |
| ATOM | 34 | CB | LYS | A | 76 | 57.053 | 1.957 | −3.930 | 1.00 | 37.70 A |
| ATOM | 35 | CG | LYS | A | 76 | 57.123 | 3.356 | −3.350 | 1.00 | 40.99 A |
| ATOM | 36 | CD | LYS | A | 76 | 57.262 | 3.316 | −1.836 | 1.00 | 40.04 A |
| ATOM | 37 | CE | LYS | A | 76 | 57.511 | 4.705 | −1.277 | 1.00 | 42.08 A |
| ATOM | 38 | NZ | LYS | A | 76 | 57.681 | 4.695 | 0.202 | 1.00 | 42.99 A |
| ATOM | 39 | C | LYS | A | 76 | 54.708 | 1.467 | −4.638 | 1.00 | 32.65 A |
| ATOM | 40 | O | LYS | A | 76 | 54.814 | 1.005 | −5.770 | 1.00 | 31.41 A |
| ATOM | 41 | N | LYS | A | 77 | 53.668 | 2.207 | −4.270 | 1.00 | 28.59 A |
| ATOM | 42 | CA | LYS | A | 77 | 52.619 | 2.517 | −5.232 | 1.00 | 25.72 A |
| ATOM | 43 | CB | LYS | A | 77 | 51.316 | 2.865 | −4.509 | 1.00 | 26.22 A |
| ATOM | 44 | CG | LYS | A | 77 | 50.796 | 1.731 | −3.631 | 1.00 | 27.15 A |
| ATOM | 45 | CD | LYS | A | 77 | 49.487 | 2.089 | −2.967 | 1.00 | 26.80 A |
| ATOM | 46 | CE | LYS | A | 77 | 49.136 | 1.091 | −1.870 | 1.00 | 27.31 A |
| ATOM | 47 | NZ | LYS | A | 77 | 48.998 | −0.296 | −2.380 | 1.00 | 27.17 A |
| ATOM | 48 | C | LYS | A | 77 | 53.053 | 3.668 | −6.137 | 1.00 | 24.67 A |
| ATOM | 49 | O | LYS | A | 77 | 54.010 | 4.377 | −5.829 | 1.00 | 21.60 A |
| ATOM | 50 | N | ARG | A | 78 | 52.351 | 3.838 | −7.254 | 1.00 | 23.66 A |
| ATOM | 51 | CA | ARG | A | 78 | 52.662 | 4.897 | −8.211 | 1.00 | 26.14 A |
| ATOM | 52 | CB | ARG | A | 78 | 53.574 | 4.344 | −9.318 | 1.00 | 28.57 A |
| ATOM | 53 | CG | ARG | A | 78 | 53.017 | 3.139 | −10.050 | 1.00 | 34.78 A |
| ATOM | 54 | CD | ARG | A | 78 | 54.092 | 2.465 | −10.896 | 1.00 | 40.96 A |
| ATOM | 55 | NE | ARG | A | 78 | 53.560 | 1.364 | −11.700 | 1.00 | 48.93 A |
| ATOM | 56 | CZ | ARG | A | 78 | 52.985 | 0.270 | −11.203 | 1.00 | 52.58 A |
| ATOM | 57 | NH1 | ARG | A | 78 | 52.860 | 0.113 | −9.889 | 1.00 | 54.60 A |
| ATOM | 58 | NH2 | ARG | A | 78 | 52.530 | −0.672 | −12.022 | 1.00 | 54.09 A |
| ATOM | 59 | C | ARG | A | 78 | 51.382 | 5.488 | −8.803 | 1.00 | 23.76 A |
| ATOM | 60 | O | ARG | A | 78 | 50.311 | 4.888 | −8.706 | 1.00 | 24.25 A |
| ATOM | 61 | N | PRO | A | 79 | 51.475 | 6.676 | −9.428 | 1.00 | 21.76 A |
| ATOM | 62 | CD | PRO | A | 79 | 52.691 | 7.475 | −9.668 | 1.00 | 20.82 A |
| ATOM | 63 | CA | PRO | A | 79 | 50.301 | 7.325 | −10.021 | 1.00 | 21.96 A |
| ATOM | 64 | CB | PRO | A | 79 | 50.910 | 8.481 | −10.816 | 1.00 | 22.27 A |
| ATOM | 65 | CG | PRO | A | 79 | 52.124 | 8.831 | −10.014 | 1.00 | 22.12 A |
| ATOM | 66 | C | PRO | A | 79 | 49.446 | 6.413 | −10.903 | 1.00 | 22.86 A |
| ATOM | 67 | O | PRO | A | 79 | 48.213 | 6.461 | −10.842 | 1.00 | 20.52 A |
| ATOM | 68 | N | GLU | A | 80 | 50.103 | 5.586 | −11.714 | 1.00 | 21.87 A |
| ATOM | 69 | CA | GLU | A | 80 | 49.403 | 4.685 | −12.628 | 1.00 | 22.99 A |
| ATOM | 70 | CB | GLU | | 80 | 50.393 | 3.994 | −13.571 | 0.50 | 25.24 AC1 |
| ATOM | 71 | CG | GLU | | 80 | 51.230 | 2.907 | −12.925 | 0.50 | 28.75 AC1 |
| ATOM | 72 | CD | GLU | | 80 | 52.157 | 2.224 | −13.913 | 0.50 | 31.99 AC1 |
| ATOM | 73 | OE1 | GLU | | 80 | 53.072 | 2.897 | −14.433 | 0.50 | 34.34 AC1 |
| ATOM | 74 | OE2 | GLU | | 80 | 51.969 | 1.015 | −14.172 | 0.50 | 32.83 AC1 |
| ATOM | 75 | C | GLU | A | 80 | 48.556 | 3.631 | −11.912 | 1.00 | 22.09 A |
| ATOM | 76 | O | GLU | A | 80 | 47.692 | 3.013 | −12.530 | 1.00 | 22.37 A |
| ATOM | 77 | N | ASP | A | 81 | 48.804 | 3.413 | −10.622 | 1.00 | 19.97 A |
| ATOM | 78 | CA | ASP | A | 81 | 48.026 | 2.423 | −9.874 | 1.00 | 19.93 A |
| ATOM | 79 | CB | ASP | A | 81 | 48.736 | 2.029 | −8.571 | 1.00 | 21.19 A |
| ATOM | 80 | CG | ASP | A | 81 | 50.089 | 1.380 | −8.807 | 1.00 | 22.46 A |
| ATOM | 81 | OD1 | ASP | A | 81 | 50.195 | 0.554 | −9.731 | 1.00 | 24.22 A |
| ATOM | 82 | OD2 | ASP | A | 81 | 51.043 | 1.685 | −8.058 | 1.00 | 23.33 A |
| ATOM | 83 | C | ASP | A | 81 | 46.652 | 2.975 | −9.518 | 1.00 | 20.85 A |
| ATOM | 84 | O | ASP | A | 81 | 45.793 | 2.246 | −9.015 | 1.00 | 19.96 A |
| ATOM | 85 | N | PHE | A | 82 | 46.445 | 4.258 | −9.804 | 1.00 | 18.91 A |
| ATOM | 86 | CA | PHE | A | 82 | 45.200 | 4.934 | −9.465 | 1.00 | 19.30 A |
| ATOM | 87 | CB | PHE | A | 82 | 45.475 | 6.027 | −8.427 | 1.00 | 18.43 A |
| ATOM | 88 | CG | PHE | A | 82 | 46.134 | 5.531 | −7.175 | 1.00 | 18.01 A |
| ATOM | 89 | CD1 | PHE | A | 82 | 45.371 | 5.136 | −6.084 | 1.00 | 17.19 A |
| ATOM | 90 | CD2 | PHE | A | 82 | 47.520 | 5.460 | −7.086 | 1.00 | 18.99 A |
| ATOM | 91 | CE1 | PHE | A | 82 | 45.977 | 4.676 | −4.918 | 1.00 | 17.12 A |
| ATOM | 92 | CE2 | PHE | A | 82 | 48.137 | 5.000 | −5.925 | 1.00 | 19.64 A |
| ATOM | 93 | CZ | PHE | A | 82 | 47.361 | 4.607 | −4.838 | 1.00 | 18.00 A |
| ATOM | 94 | C | PHE | A | 82 | 44.476 | 5.596 | −10.621 | 1.00 | 20.81 A |
| ATOM | 95 | O | PHE | A | 82 | 45.066 | 5.933 | −11.649 | 1.00 | 20.34 A |
| ATOM | 96 | N | LYS | A | 83 | 43.182 | 5.792 | −10.411 | 1.00 | 19.80 A |
| ATOM | 97 | CA | LYS | A | 83 | 42.321 | 6.478 | −11.353 | 1.00 | 21.65 A |
| ATOM | 98 | CB | LYS | A | 83 | 41.096 | 5.625 | −11.687 | 1.00 | 22.02 A |
| ATOM | 99 | CG | LYS | A | 83 | 40.062 | 6.326 | −12.550 | 1.00 | 28.93 A |
| ATOM | 100 | CD | LYS | A | 83 | 38.974 | 5.355 | −12.981 | 1.00 | 34.20 A |

-continued

| | | | | | | | | | | | |
|---|---|---|---|---|---|---|---|---|---|---|---|
| ATOM | 101 | CE | LYS | A | 83 | 37.909 | 6.042 | −13.824 | 1.00 | 38.10 | A |
| ATOM | 102 | NZ | LYS | A | 83 | 37.179 | 7.086 | −13.043 | 1.00 | 43.33 | A |
| ATOM | 103 | C | LYS | A | 83 | 41.913 | 7.702 | −10.541 | 1.00 | 20.74 | A |
| ATOM | 104 | O | LYS | A | 83 | 41.084 | 7.606 | −9.635 | 1.00 | 20.98 | A |
| ATOM | 105 | N | PHE | A | 84 | 42.513 | 8.848 | −10.835 | 1.00 | 19.99 | A |
| ATOM | 106 | CA | PHE | A | 84 | 42.188 | 10.049 | −10.083 | 1.00 | 18.63 | A |
| ATOM | 107 | CB | PHE | A | 84 | 43.279 | 11.103 | −10.258 | 1.00 | 18.95 | A |
| ATOM | 108 | CG | PHE | A | 84 | 44.571 | 10.741 | −9.587 | 1.00 | 17.68 | A |
| ATOM | 109 | CD1 | PHE | A | 84 | 45.498 | 9.926 | −10.224 | 1.00 | 18.16 | A |
| ATOM | 110 | CD2 | PHE | A | 84 | 44.843 | 11.183 | −8.299 | 1.00 | 19.66 | A |
| ATOM | 111 | CE1 | PHE | A | 84 | 46.676 | 9.556 | −9.589 | 1.00 | 18.09 | A |
| ATOM | 112 | CE2 | PHE | A | 84 | 46.021 | 10.816 | −7.653 | 1.00 | 18.89 | A |
| ATOM | 113 | CZ | PHE | A | 84 | 46.936 | 10.002 | −8.301 | 1.00 | 17.33 | A |
| ATOM | 114 | C | PHE | A | 84 | 40.834 | 10.617 | −10.460 | 1.00 | 19.69 | A |
| ATOM | 115 | O | PHE | A | 84 | 40.391 | 10.489 | −11.601 | 1.00 | 20.72 | A |
| ATOM | 116 | N | GLY | A | 85 | 40.178 | 11.233 | −9.484 | 1.00 | 16.80 | A |
| ATOM | 117 | CA | GLY | A | 85 | 38.872 | 11.810 | −9.716 | 1.00 | 17.73 | A |
| ATOM | 118 | C | GLY | A | 85 | 38.819 | 13.280 | −9.346 | 1.00 | 18.75 | A |
| ATOM | 119 | O | GLY | A | 85 | 39.740 | 14.043 | −9.650 | 1.00 | 18.45 | A |
| ATOM | 120 | N | LYS | A | 86 | 37.753 | 13.673 | −8.659 | 1.00 | 16.00 | A |
| ATOM | 121 | CA | LYS | A | 86 | 37.571 | 15.064 | −8.278 | 1.00 | 18.26 | A |
| ATOM | 122 | CB | LYS | A | 86 | 36.133 | 15.302 | −7.812 | 1.00 | 19.00 | A |
| ATOM | 123 | CG | LYS | A | 86 | 35.793 | 14.660 | −6.481 | 1.00 | 21.55 | A |
| ATOM | 124 | CD | LYS | A | 86 | 34.368 | 14.981 | −6.066 | 1.00 | 26.48 | A |
| ATOM | 125 | CE | LYS | A | 86 | 33.994 | 14.239 | −4.793 | 1.00 | 31.92 | A |
| ATOM | 126 | NZ | LYS | A | 86 | 32.568 | 14.457 | −4.412 | 1.00 | 35.36 | A |
| ATOM | 127 | C | LYS | A | 86 | 38.523 | 15.571 | −7.202 | 1.00 | 18.57 | A |
| ATOM | 128 | O | LYS | A | 86 | 39.045 | 14.807 | −6.385 | 1.00 | 16.77 | A |
| ATOM | 129 | N | ILE | A | 87 | 38.737 | 16.881 | −7.227 | 1.00 | 17.88 | A |
| ATOM | 130 | CA | ILE | A | 87 | 39.577 | 17.554 | −6.256 | 1.00 | 18.26 | A |
| ATOM | 131 | CB | ILE | A | 87 | 39.994 | 18.952 | −6.772 | 1.00 | 19.60 | A |
| ATOM | 132 | CG2 | ILE | A | 87 | 40.593 | 19.786 | −5.628 | 1.00 | 18.73 | A |
| ATOM | 133 | CG1 | ILE | A | 87 | 40.968 | 18.786 | −7.945 | 1.00 | 21.16 | A |
| ATOM | 134 | CD1 | ILE | A | 87 | 41.412 | 20.087 | −8.588 | 1.00 | 25.26 | A |
| ATOM | 135 | C | ILE | A | 87 | 38.731 | 17.709 | −4.997 | 1.00 | 19.67 | A |
| ATOM | 136 | O | ILE | A | 87 | 37.628 | 18.249 | −5.052 | 1.00 | 20.41 | A |
| ATOM | 137 | N | LEU | A | 88 | 39.240 | 17.229 | −3.867 | 1.00 | 19.15 | A |
| ATOM | 138 | CA | LEU | A | 88 | 38.508 | 17.324 | −2.611 | 1.00 | 20.68 | A |
| ATOM | 139 | CB | LEU | A | 88 | 38.870 | 16.151 | −1.700 | 1.00 | 19.97 | A |
| ATOM | 140 | CG | LEU | A | 88 | 38.529 | 14.759 | −2.237 | 1.00 | 19.24 | A |
| ATOM | 141 | CD1 | LEU | A | 88 | 39.090 | 13.692 | −1.311 | 1.00 | 21.41 | A |
| ATOM | 142 | CD2 | LEU | A | 88 | 37.029 | 14.622 | −2.359 | 1.00 | 18.84 | A |
| ATOM | 143 | C | LEU | A | 88 | 38.815 | 18.632 | −1.901 | 1.00 | 23.11 | A |
| ATOM | 144 | O | LEU | A | 88 | 37.999 | 19.146 | −1.139 | 1.00 | 25.10 | A |
| ATOM | 145 | N | GLY | A | 89 | 39.997 | 19.174 | −2.149 | 1.00 | 24.09 | A |
| ATOM | 146 | CA | GLY | A | 89 | 40.367 | 20.418 | −1.507 | 1.00 | 24.27 | A |
| ATOM | 147 | C | GLY | A | 89 | 41.658 | 20.954 | −2.078 | 1.00 | 25.47 | A |
| ATOM | 148 | O | GLY | A | 89 | 42.445 | 20.202 | −2.666 | 1.00 | 22.19 | A |
| ATOM | 149 | N | GLU | A | 90 | 41.870 | 22.254 | −1.906 | 1.00 | 26.22 | A |
| ATOM | 150 | CA | GLU | A | 90 | 43.064 | 22.924 | −2.404 | 1.00 | 29.96 | A |
| ATOM | 151 | CB | GLU | A | 90 | 42.698 | 23.814 | −3.596 | 1.00 | 30.75 | A |
| ATOM | 152 | CG | GLU | A | 90 | 42.267 | 23.038 | −4.831 | 1.00 | 34.32 | A |
| ATOM | 153 | CD | GLU | A | 90 | 41.711 | 23.930 | −5.927 | 1.00 | 38.27 | A |
| ATOM | 154 | OE1 | GLU | A | 90 | 40.590 | 24.456 | −5.764 | 1.00 | 40.57 | A |
| ATOM | 155 | OE2 | GLU | A | 90 | 42.398 | 24.110 | −6.952 | 1.00 | 40.90 | A |
| ATOM | 156 | C | GLU | A | 90 | 43.711 | 23.768 | −1.313 | 1.00 | 30.68 | A |
| ATOM | 157 | O | GLU | A | 90 | 43.049 | 24.574 | −0.668 | 1.00 | 32.83 | A |
| ATOM | 158 | N | GLY | A | 91 | 45.006 | 23.566 | −1.104 | 1.00 | 29.66 | A |
| ATOM | 159 | CA | GLY | A | 91 | 45.724 | 24.332 | −0.104 | 1.00 | 29.40 | A |
| ATOM | 160 | C | GLY | A | 91 | 46.795 | 25.151 | −0.798 | 1.00 | 29.98 | A |
| ATOM | 161 | O | GLY | A | 91 | 46.894 | 25.130 | −2.028 | 1.00 | 28.16 | A |
| ATOM | 162 | N | SER | A | 92 | 47.605 | 25.870 | −0.029 | 1.00 | 28.30 | A |
| ATOM | 163 | CA | SER | A | 92 | 48.653 | 26.681 | −0.633 | 1.00 | 30.50 | A |
| ATOM | 164 | CB | SER | A | 92 | 49.165 | 27.717 | −0.370 | 1.00 | 32.43 | A |
| ATOM | 165 | OG | SER | A | 92 | 49.520 | 27.099 | −1.593 | 1.00 | 40.94 | A |
| ATOM | 166 | C | SER | A | 92 | 49.815 | 25.843 | −1.164 | 1.00 | 29.77 | A |
| ATOM | 167 | O | SER | A | 92 | 50.456 | 26.221 | −2.143 | 1.00 | 30.46 | A |
| ATOM | 168 | N | PHE | A | 93 | 50.087 | 24.703 | −0.536 | 1.00 | 27.65 | A |
| ATOM | 169 | CA | PHE | A | 93 | 51.185 | 23.855 | −0.995 | 1.00 | 26.34 | A |
| ATOM | 170 | CB | PHE | A | 93 | 52.281 | 23.785 | −0.068 | 1.00 | 27.95 | A |
| ATOM | 171 | CG | PHE | A | 93 | 52.861 | 25.117 | −0.406 | 1.00 | 31.06 | A |
| ATOM | 172 | CD1 | PHE | A | 93 | 52.283 | 25.909 | −1.392 | 1.00 | 29.96 | A |
| ATOM | 173 | CD2 | PHE | A | 93 | 53.949 | 25.613 | −0.308 | 1.00 | 31.38 | A |
| ATOM | 174 | CE1 | PHE | A | 93 | 52.779 | 27.181 | −1.665 | 1.00 | 32.69 | A |
| ATOM | 175 | CE2 | PHE | A | 93 | 54.452 | 26.883 | −0.044 | 1.00 | 32.63 | A |
| ATOM | 176 | CZ | PHE | A | 93 | 53.864 | 27.670 | −0.945 | 1.00 | 31.81 | A |
| ATOM | 177 | C | PHE | A | 93 | 50.759 | 22.445 | −1.365 | 1.00 | 25.39 | A |
| ATOM | 178 | O | PHE | A | 93 | 51.601 | 21.559 | −1.522 | 1.00 | 24.59 | A |
| ATOM | 179 | N | SER | A | 94 | 49.457 | 22.235 | −1.519 | 1.00 | 23.63 | A |

-continued

| | | | | | | | | | | |
|---|---|---|---|---|---|---|---|---|---|---|
| ATOM | 180 | CA | SER | A | 94 | 48.965 | 20.912 | −1.860 | 1.00 | 21.43 A |
| ATOM | 181 | CB | SER | A | 94 | 49.017 | 20.013 | −0.628 | 1.00 | 21.42 A |
| ATOM | 182 | OG | SER | A | 94 | 48.091 | 20.475 | −0.340 | 1.00 | 21.19 A |
| ATOM | 183 | C | SER | A | 94 | 47.539 | 20.925 | −2.378 | 1.00 | 19.82 A |
| ATOM | 184 | O | SER | A | 94 | 46.795 | 21.882 | −2.173 | 1.00 | 18.76 A |
| ATOM | 185 | N | THR | A | 95 | 47.174 | 19.832 | −3.038 | 1.00 | 19.38 A |
| ATOM | 186 | CA | THR | A | 95 | 45.840 | 19.637 | −3.580 | 1.00 | 17.98 A |
| ATOM | 187 | CB | THR | A | 95 | 45.818 | 19.818 | −5.110 | 1.00 | 19.25 A |
| ATOM | 188 | OG1 | THR | A | 95 | 46.196 | 21.162 | −5.434 | 1.00 | 22.04 A |
| ATOM | 189 | CG2 | THR | A | 95 | 44.421 | 19.549 | −5.661 | 1.00 | 17.61 A |
| ATOM | 190 | C | THR | A | 95 | 45.455 | 18.201 | −3.243 | 1.00 | 18.61 A |
| ATOM | 191 | O | THR | A | 95 | 46.212 | 17.264 | −3.524 | 1.00 | 17.10 A |
| ATOM | 192 | N | VAL | A | 96 | 44.295 | 18.024 | −2.623 | 1.00 | 16.53 A |
| ATOM | 193 | CA | VAL | A | 96 | 43.845 | 16.685 | −2.266 | 1.00 | 16.05 A |
| ATOM | 194 | CB | VAL | A | 96 | 43.170 | 16.672 | −0.886 | 1.00 | 16.32 A |
| ATOM | 195 | CG1 | VAL | A | 96 | 42.741 | 15.249 | −0.532 | 1.00 | 18.02 A |
| ATOM | 196 | CG2 | VAL | A | 96 | 44.145 | 17.206 | −0.168 | 1.00 | 16.69 A |
| ATOM | 197 | C | VAL | A | 96 | 42.875 | 16.207 | −3.335 | 1.00 | 16.42 A |
| ATOM | 198 | O | VAL | A | 96 | 41.906 | 16.892 | −3.665 | 1.00 | 16.47 A |
| ATOM | 199 | N | VAL | A | 97 | 43.157 | 15.033 | −3.888 | 1.00 | 16.80 A |
| ATOM | 200 | CA | VAL | A | 97 | 42.338 | 14.471 | −4.949 | 1.00 | 16.72 A |
| ATOM | 201 | CB | VAL | A | 97 | 43.153 | 14.354 | −6.255 | 1.00 | 18.43 A |
| ATOM | 202 | CG1 | VAL | A | 97 | 42.249 | 13.927 | −7.404 | 1.00 | 19.69 A |
| ATOM | 203 | CG2 | VAL | A | 97 | 43.831 | 15.685 | −6.569 | 1.00 | 17.84 A |
| ATOM | 204 | C | VAL | A | 97 | 41.812 | 13.091 | −4.583 | 1.00 | 16.77 A |
| ATOM | 205 | O | VAL | A | 97 | 42.532 | 12.270 | −4.014 | 1.00 | 17.13 A |
| ATOM | 206 | N | LEU | A | 98 | 40.545 | 12.845 | −4.895 | 1.00 | 16.62 A |
| ATOM | 207 | CA | LEU | A | 98 | 39.947 | 11.548 | −4.624 | 1.00 | 17.04 A |
| ATOM | 208 | CB | LEU | A | 98 | 38.424 | 11.633 | −4.743 | 1.00 | 16.89 A |
| ATOM | 209 | CG | LEU | A | 98 | 37.635 | 10.342 | −4.508 | 1.00 | 19.46 A |
| ATOM | 210 | CD1 | LEU | A | 98 | 37.990 | 9.762 | −3.146 | 1.00 | 20.07 A |
| ATOM | 211 | CD2 | LEU | A | 98 | 36.143 | 10.627 | −4.588 | 1.00 | 17.93 A |
| ATOM | 212 | C | LEU | A | 98 | 40.512 | 10.597 | −5.677 | 1.00 | 17.38 A |
| ATOM | 213 | O | LEU | A | 98 | 40.527 | 10.920 | −6.863 | 1.00 | 18.60 A |
| ATOM | 214 | N | ALA | A | 99 | 40.995 | 9.438 | −5.246 | 1.00 | 17.13 A |
| ATOM | 215 | CA | ALA | A | 99 | 41.570 | 8.466 | −6.168 | 1.00 | 18.42 A |
| ATOM | 216 | CB | ALA | A | 99 | 43.090 | 8.524 | −6.105 | 1.00 | 14.76 A |
| ATOM | 217 | C | ALA | A | 99 | 41.102 | 7.055 | −5.848 | 1.00 | 21.40 A |
| ATOM | 218 | O | ALA | A | 99 | 40.941 | 6.691 | −4.679 | 1.00 | 22.52 A |
| ATOM | 219 | N | ARG | A | 100 | 40.878 | 6.261 | −6.888 | 1.00 | 19.77 A |
| ATOM | 220 | CA | ARG | A | 100 | 40.459 | 4.884 | −6.693 | 1.00 | 20.85 A |
| ATOM | 221 | CB | ARG | A | 100 | 39.202 | 4.585 | −7.518 | 1.00 | 24.22 A |
| ATOM | 222 | CG | ARG | A | 100 | 38.608 | 3.205 | −7.256 | 1.00 | 31.78 A |
| ATOM | 223 | CD | ARG | A | 100 | 37.326 | 2.979 | −8.048 | 1.00 | 36.24 A |
| ATOM | 224 | NE | ARG | A | 100 | 36.213 | 3.818 | −7.594 | 1.00 | 41.40 A |
| ATOM | 225 | CZ | ARG | A | 100 | 35.566 | 3.662 | −6.439 | 1.00 | 42.05 A |
| ATOM | 226 | NH1 | ARG | A | 100 | 35.912 | 2.696 | −5.598 | 1.00 | 40.67 A |
| ATOM | 227 | NH2 | ARG | A | 100 | 34.559 | 4.468 | −6.128 | 1.00 | 43.65 A |
| ATOM | 228 | C | ARG | A | 100 | 41.613 | 3.985 | −7.129 | 1.00 | 18.63 A |
| ATOM | 229 | O | ARG | A | 100 | 42.078 | 4.065 | −8.271 | 1.00 | 19.49 A |
| ATOM | 230 | N | GLU | A | 101 | 42.102 | 3.157 | −6.212 | 1.00 | 16.43 A |
| ATOM | 231 | CA | GLU | A | 101 | 43.196 | 2.246 | −6.533 | 1.00 | 16.11 A |
| ATOM | 232 | CB | GLU | A | 101 | 43.774 | 1.637 | −5.248 | 1.00 | 16.79 A |
| ATOM | 233 | CG | GLU | A | 101 | 44.917 | 0.657 | −5.488 | 1.00 | 16.51 A |
| ATOM | 234 | CD | GLU | A | 101 | 45.501 | 0.115 | −4.200 | 1.00 | 18.20 A |
| ATOM | 235 | OE1 | GLU | A | 101 | 44.733 | −0.081 | −3.239 | 1.00 | 18.32 A |
| ATOM | 236 | OE2 | GLU | A | 101 | 46.725 | −0.132 | −4.150 | 1.00 | 17.14 A |
| ATOM | 237 | C | GLU | A | 101 | 42.625 | 1.152 | −7.442 | 1.00 | 17.92 A |
| ATOM | 238 | O | GLU | A | 101 | 41.681 | 0.462 | −7.069 | 1.00 | 18.02 A |
| ATOM | 239 | N | LEU | A | 102 | 43.198 | 1.002 | −8.632 | 1.00 | 19.06 A |
| ATOM | 240 | CA | LEU | A | 102 | 42.718 | 0.025 | −9.607 | 1.00 | 20.71 A |
| ATOM | 241 | CB | LEU | A | 102 | 43.569 | 0.097 | −10.878 | 1.00 | 23.42 A |
| ATOM | 242 | CG | LEU | A | 102 | 43.531 | 1.426 | −11.642 | 1.00 | 25.30 A |
| ATOM | 243 | CD1 | LEU | A | 102 | 44.577 | 1.414 | −12.748 | 1.00 | 27.88 A |
| ATOM | 244 | CD2 | LEU | A | 102 | 42.140 | 1.647 | −12.214 | 1.00 | 26.79 A |
| ATOM | 245 | C | LEU | A | 102 | 42.671 | −1.418 | −9.125 | 1.00 | 21.62 A |
| ATOM | 246 | O | LEU | A | 102 | 41.668 | −2.103 | −9.305 | 1.00 | 21.09 A |
| ATOM | 247 | N | ALA | A | 103 | 43.753 | −1.874 | −8.507 | 1.00 | 19.38 A |
| ATOM | 248 | CA | ALA | A | 103 | 43.836 | −3.249 | −8.035 | 1.00 | 20.87 A |
| ATOM | 249 | CB | ALA | A | 103 | 45.284 | −3.571 | −7.671 | 1.00 | 19.23 A |
| ATOM | 250 | C | ALA | A | 103 | 42.919 | −3.629 | −6.872 | 1.00 | 19.92 A |
| ATOM | 251 | O | ALA | A | 103 | 42.703 | −4.815 | −6.628 | 1.00 | 20.38 A |
| ATOM | 252 | N | THR | A | 104 | 42.361 | −2.643 | −6.175 | 1.00 | 18.12 A |
| ATOM | 253 | CA | THR | A | 104 | 41.517 | −2.927 | −5.018 | 1.00 | 17.15 A |
| ATOM | 254 | CB | THR | A | 104 | 42.212 | −2.484 | −3.717 | 1.00 | 19.54 A |
| ATOM | 255 | CC1 | THR | A | 104 | 42.456 | −1.070 | −3.773 | 1.00 | 19.26 A |
| ATOM | 256 | CC2 | THR | A | 104 | 43.536 | −3.219 | −3.529 | 1.00 | 17.02 A |
| ATOM | 257 | C | THR | A | 104 | 40.159 | −2.247 | −5.026 | 1.00 | 19.44 A |
| ATOM | 258 | O | THR | A | 104 | 39.259 | −2.648 | −4.285 | 1.00 | 18.70 A |

-continued

| | | | | | | | | | | |
|---|---|---|---|---|---|---|---|---|---|---|
| ATOM | 259 | N | SER | A | 105 | 40.034 | −1.207 | −5.847 | 1.00 | 19.65 A |
| ATOM | 260 | CA | SER | A | 105 | 38.819 | −0.400 | −5.967 | 1.00 | 19.37 A |
| ATOM | 261 | CB | SER | | 105 | 37.598 | −1.304 | −6.173 | 0.50 | 21.81 AC1 |
| ATOM | 262 | OG | SER | | 105 | 36.431 | −0.539 | −6.412 | 0.50 | 23.01 AC1 |
| ATOM | 263 | C | SER | A | 105 | 38.644 | 0.447 | −4.701 | 1.00 | 18.99 A |
| ATOM | 264 | O | SER | A | 105 | 37.602 | 1.070 | −4.488 | 1.00 | 18.66 A |
| ATOM | 265 | N | ARC | A | 106 | 39.674 | 0.468 | −3.861 | 1.00 | 16.84 A |
| ATOM | 266 | CA | ARC | A | 106 | 39.655 | 1.267 | −2.634 | 1.00 | 16.21 A |
| ATOM | 267 | CB | ARC | A | 106 | 40.827 | 0.886 | −1.723 | 1.00 | 16.41 A |
| ATOM | 268 | CC | ARC | A | 106 | 40.619 | −0.367 | −0.906 | 1.00 | 15.49 A |
| ATOM | 269 | CD | ARC | A | 106 | 41.887 | −0.755 | −0.170 | 1.00 | 17.43 A |
| ATOM | 270 | NE | ARC | A | 106 | 41.620 | −1.792 | 0.824 | 1.00 | 20.47 A |
| ATOM | 271 | CZ | ARC | A | 106 | 42.548 | −2.568 | 1.371 | 1.00 | 20.24 A |
| ATOM | 272 | NH1 | ARC | A | 106 | 43.821 | −2.433 | 1.017 | 1.00 | 17.80 A |
| ATOM | 273 | NH2 | ARC | A | 106 | 42.198 | −3.468 | 2.285 | 1.00 | 20.14 A |
| ATOM | 274 | C | ARC | A | 106 | 39.785 | 2.746 | −2.981 | 1.00 | 17.37 A |
| ATOM | 275 | O | ARC | A | 106 | 40.514 | 3.103 | −3.902 | 1.00 | 17.75 A |
| ATOM | 276 | N | CLU | A | 107 | 39.085 | 3.599 | −2.240 | 1.00 | 16.06 A |
| ATOM | 277 | CA | CLU | A | 107 | 39.156 | 5.039 | −2.461 | 1.00 | 20.80 A |
| ATOM | 278 | CB | CLU | A | 107 | 37.779 | 5.694 | −2.337 | 1.00 | 22.93 A |
| ATOM | 279 | CC | CLU | A | 107 | 36.711 | 5.171 | −3.269 | 1.00 | 30.87 A |
| ATOM | 280 | CD | CLU | A | 107 | 35.431 | 5.975 | −3.148 | 1.00 | 32.40 A |
| ATOM | 281 | OE1 | CLU | A | 107 | 35.262 | 6.939 | −3.923 | 1.00 | 33.74 A |
| ATOM | 282 | OE2 | CLU | A | 107 | 34.608 | 5.654 | −2.263 | 1.00 | 36.00 A |
| ATOM | 283 | C | CLU | A | 107 | 40.053 | 5.678 | −1.410 | 1.00 | 18.93 A |
| ATOM | 284 | O | CLU | A | 107 | 39.891 | 5.427 | −0.220 | 1.00 | 19.21 A |
| ATOM | 285 | N | TYR | A | 108 | 40.988 | 6.507 | −1.852 | 1.00 | 16.70 A |
| ATOM | 286 | CA | TYR | A | 108 | 41.883 | 7.209 | −0.942 | 1.00 | 15.86 A |
| ATOM | 287 | CB | TYR | A | 108 | 43.325 | 6.728 | −1.104 | 1.00 | 15.30 A |
| ATOM | 288 | CC | TYR | A | 108 | 43.593 | 5.328 | −0.612 | 1.00 | 16.33 A |
| ATOM | 289 | CD1 | TYR | A | 108 | 43.765 | 5.066 | 0.746 | 1.00 | 16.36 A |
| ATOM | 290 | CE1 | TYR | A | 108 | 44.046 | 3.769 | 1.201 | 1.00 | 18.48 A |
| ATOM | 291 | CD2 | TYR | A | 108 | 43.701 | 4.268 | −1.511 | 1.00 | 13.25 A |
| ATOM | 292 | CE2 | TYR | A | 108 | 43.980 | 2.981 | −1.075 | 1.00 | 17.28 A |
| ATOM | 293 | CZ | TYR | A | 108 | 44.152 | 2.736 | 0.276 | 1.00 | 19.17 A |
| ATOM | 294 | OH | TYR | A | 108 | 44.440 | 1.461 | 0.688 | 1.00 | 19.38 A |
| ATOM | 295 | C | TYR | A | 108 | 41.850 | 8.687 | −1.292 | 1.00 | 16.80 A |
| ATOM | 296 | O | TYR | A | 108 | 41.560 | 9.058 | −2.431 | 1.00 | 15.22 A |
| ATOM | 297 | N | ALA | A | 109 | 42.132 | 9.528 | −0.306 | 1.00 | 14.61 A |
| ATOM | 298 | CA | ALA | A | 109 | 42.207 | 10.957 | −0.539 | 1.00 | 14.30 A |
| ATOM | 299 | CB | ALA | A | 109 | 41.671 | 11.726 | 0.661 | 1.00 | 14.78 A |
| ATOM | 300 | C | ALA | A | 109 | 43.713 | 11.136 | −0.667 | 1.00 | 16.79 A |
| ATOM | 301 | O | ALA | A | 109 | 44.450 | 10.983 | 0.317 | 1.00 | 16.52 A |
| ATOM | 302 | N | ILE | A | 110 | 44.182 | 11.410 | −1.881 | 1.00 | 14.80 A |
| ATOM | 303 | CA | ILE | A | 110 | 45.609 | 11.574 | −2.093 | 1.00 | 15.80 A |
| ATOM | 304 | CB | ILE | A | 110 | 46.065 | 10.863 | −3.396 | 1.00 | 16.85 A |
| ATOM | 305 | CC2 | ILE | A | 110 | 47.550 | 11.098 | −3.632 | 1.00 | 16.80 A |
| ATOM | 306 | CC1 | ILE | A | 110 | 45.774 | 9.358 | −3.284 | 1.00 | 17.76 A |
| ATOM | 307 | CD1 | ILE | A | 110 | 46.308 | 8.513 | −4.437 | 1.00 | 16.07 A |
| ATOM | 308 | C | ILE | A | 110 | 46.004 | 13.045 | −2.129 | 1.00 | 17.78 A |
| ATOM | 309 | O | ILE | A | 110 | 45.534 | 13.813 | −2.976 | 1.00 | 16.24 A |
| ATOM | 310 | N | LYS | A | 111 | 46.846 | 13.435 | −1.177 | 1.00 | 16.15 A |
| ATOM | 311 | CA | LYS | A | 111 | 47.326 | 14.808 | −1.100 | 1.00 | 17.20 A |
| ATOM | 312 | CB | LYS | A | 111 | 47.700 | 15.176 | 0.344 | 1.00 | 17.41 A |
| ATOM | 313 | CG | LYS | A | 111 | 48.350 | 16.547 | 0.464 | 1.00 | 20.71 A |
| ATOM | 314 | CD | LYS | A | 111 | 48.585 | 16.971 | 1.910 | 1.00 | 24.25 A |
| ATOM | 315 | CE | LYS | A | 111 | 47.288 | 17.381 | 2.598 | 1.00 | 29.46 A |
| ATOM | 316 | NZ | LYS | A | 111 | 47.516 | 17.866 | 4.000 | 1.00 | 30.50 A |
| ATOM | 317 | C | LYS | A | 111 | 48.551 | 14.890 | −1.994 | 1.00 | 16.41 A |
| ATOM | 318 | O | LYS | A | 111 | 49.509 | 14.137 | −1.813 | 1.00 | 18.20 A |
| ATOM | 319 | N | ILE | A | 112 | 48.509 | 15.798 | −2.963 | 1.00 | 15.87 A |
| ATOM | 320 | CA | ILE | A | 112 | 49.606 | 15.967 | −3.907 | 1.00 | 17.28 A |
| ATOM | 321 | CB | ILE | A | 112 | 49.079 | 15.911 | −5.358 | 1.00 | 16.43 A |
| ATOM | 322 | CG2 | ILE | A | 112 | 50.235 | 15.998 | −6.341 | 1.00 | 15.12 A |
| ATOM | 323 | CG1 | ILE | A | 112 | 48.293 | 14.609 | −5.565 | 1.00 | 16.82 A |
| ATOM | 324 | CD1 | ILE | A | 112 | 47.580 | 14.511 | −6.904 | 1.00 | 18.47 A |
| ATOM | 325 | C | ILE | A | 112 | 50.307 | 17.301 | −3.663 | 1.00 | 19.03 A |
| ATOM | 326 | O | ILE | A | 112 | 49.669 | 18.350 | −3.635 | 1.00 | 19.15 A |
| ATOM | 327 | N | LEU | A | 113 | 51.622 | 17.245 | −3.472 | 1.00 | 20.22 A |
| ATOM | 328 | CA | LEU | A | 113 | 52.416 | 18.442 | −3.214 | 1.00 | 22.36 A |
| ATOM | 329 | CB | LEU | A | 113 | 52.995 | 18.397 | −1.794 | 1.00 | 22.13 A |
| ATOM | 330 | CG | LEU | A | 113 | 52.042 | 18.063 | −0.646 | 1.00 | 22.46 A |
| ATOM | 331 | CD1 | LEU | A | 113 | 51.866 | 16.557 | −0.553 | 1.00 | 23.81 A |
| ATOM | 332 | CD2 | LEU | A | 113 | 52.603 | 18.595 | 0.660 | 1.00 | 23.68 A |
| ATOM | 333 | C | LEU | A | 113 | 53.560 | 18.547 | −4.215 | 1.00 | 23.37 A |
| ATOM | 334 | O | LEU | A | 113 | 54.300 | 17.586 | −4.424 | 1.00 | 23.11 A |
| ATOM | 335 | N | GLU | A | 114 | 53.706 | 19.714 | −4.834 | 1.00 | 23.88 A |
| ATOM | 336 | CA | GLU | A | 114 | 54.771 | 19.920 | −5.806 | 1.00 | 26.00 A |
| ATOM | 337 | CB | GLU | A | 114 | 54.435 | 21.111 | −6.706 | 1.00 | 27.74 A |

-continued

| | | | | | | | | | | |
|---|---|---|---|---|---|---|---|---|---|---|
| ATOM | 338 | CG | GLU | A | 114 | 55.533 | 21.452 | −7.696 | 1.00 | 35.07 A |
| ATOM | 339 | CD | GLU | A | 114 | 55.220 | 22.696 | −8.497 | 1.00 | 39.24 A |
| ATOM | 340 | OE1 | GLU | A | 114 | 54.808 | 23.703 | −7.885 | 1.00 | 41.45 A |
| ATOM | 341 | OE2 | GLU | A | 114 | 55.395 | 22.670 | −9.736 | 1.00 | 44.05 A |
| ATOM | 342 | C | GLU | A | 114 | 56.087 | 20.163 | −5.067 | 1.00 | 24.37 A |
| ATOM | 343 | O | GLU | A | 114 | 56.186 | 21.071 | −4.238 | 1.00 | 24.43 A |
| ATOM | 344 | N | LYS | A | 115 | 57.096 | 19.350 | −5.360 | 1.00 | 24.10 A |
| ATOM | 345 | CA | LYS | A | 115 | 58.376 | 19.493 | −4.678 | 1.00 | 24.93 A |
| ATOM | 346 | CB | LYS | A | 115 | 59.339 | 18.373 | −5.103 | 1.00 | 23.72 A |
| ATOM | 347 | CG | LYS | A | 115 | 59.139 | 17.080 | −4.308 | 1.00 | 23.09 A |
| ATOM | 348 | CD | LYS | A | 115 | 60.064 | 15.944 | −4.743 | 1.00 | 21.92 A |
| ATOM | 349 | CE | LYS | A | 115 | 59.691 | 15.400 | −6.117 | 1.00 | 22.42 A |
| ATOM | 350 | NZ | LYS | A | 115 | 60.447 | 14.150 | −6.448 | 1.00 | 19.71 A |
| ATOM | 351 | C | LYS | A | 115 | 59.031 | 20.858 | −4.868 | 1.00 | 26.87 A |
| ATOM | 352 | O | LYS | A | 115 | 59.492 | 21.469 | −3.903 | 1.00 | 26.17 A |
| ATOM | 353 | N | ARG | A | 116 | 59.058 | 21.348 | −6.102 | 1.00 | 28.73 A |
| ATOM | 354 | CA | ARG | A | 116 | 59.678 | 22.638 | −6.380 | 1.00 | 29.66 A |
| ATOM | 355 | CB | ARG | | 116 | 59.533 | 22.980 | −7.868 | 0.50 | 31.29 AC1 |
| ATOM | 356 | CG | ARG | | 116 | 60.047 | 24.361 | −8.267 | 0.50 | 33.19 AC1 |
| ATOM | 357 | CD | ARG | | 116 | 61.368 | 24.710 | −7.590 | 0.50 | 35.13 AC1 |
| ATOM | 358 | NE | ARG | | 116 | 62.329 | 23.612 | −7.618 | 0.50 | 36.42 AC1 |
| ATOM | 359 | CZ | ARG | | 116 | 63.510 | 23.648 | −7.009 | 0.50 | 36.18 AC1 |
| ATOM | 360 | NH1 | ARG | | 116 | 63.871 | 24.729 | −6.332 | 0.50 | 36.12 AC1 |
| ATOM | 361 | NH2 | ARG | | 116 | 64.324 | 22.602 | −7.067 | 0.50 | 35.77 AC1 |
| ATOM | 362 | C | ARG | A | 116 | 59.097 | 23.761 | −5.519 | 1.00 | 29.70 A |
| ATOM | 363 | O | ARG | A | 116 | 59.843 | 24.515 | −4.889 | 1.00 | 29.16 A |
| ATOM | 364 | N | HIS | A | 117 | 57.773 | 23.862 | −5.472 | 1.00 | 27.22 A |
| ATOM | 365 | CA | HIS | A | 117 | 57.126 | 24.903 | −4.681 | 1.00 | 26.33 A |
| ATOM | 366 | CB | HIS | A | 117 | 55.606 | 24.835 | −4.848 | 1.00 | 28.41 A |
| ATOM | 367 | CG | HIS | A | 117 | 54.881 | 26.00 | −54.258 | 1.00 | 31.82 A |
| ATOM | 368 | CD2 | HIS | A | 117 | 55.309 | 27.24 | −93.935 | 1.00 | 33.19 A |
| ATOM | 369 | ND1 | HIS | A | 117 | 53.536 | 25.97 | −43.961 | 1.00 | 34.30 A |
| ATOM | 370 | CE1 | HIS | A | 117 | 53.165 | 27.14 | −83.480 | 1.00 | 34.58 A |
| ATOM | 371 | NE2 | HIS | A | 117 | 54.222 | 27.94 | −03.455 | 1.00 | 35.18 A |
| ATOM | 372 | C | HIS | A | 117 | 57.477 | 24.78 | −03.202 | 1.00 | 26.22 A |
| ATOM | 373 | O | HIS | A | 117 | 57.737 | 25.77 | −62.534 | 1.00 | 25.67 A |
| ATOM | 374 | N | ILE | A | 118 | 57.469 | 23.554 | −2.689 | 1.00 | 24.94 A |
| ATOM | 375 | CA | ILE | A | 118 | 57.792 | 23.315 | −1.285 | 1.00 | 23.94 A |
| ATOM | 376 | CB | ILE | A | 118 | 57.711 | 21.812 | −0.952 | 1.00 | 23.50 A |
| ATOM | 377 | CG2 | ILE | A | 118 | 58.374 | 21.533 | 0.389 | 1.00 | 23.76 A |
| ATOM | 378 | CG1 | ILE | A | 118 | 56.246 | 21.362 | −0.959 | 1.00 | 24.42 A |
| ATOM | 379 | CD1 | ILE | A | 118 | 56.066 | 19.858 | −0.834 | 1.00 | 28.06 A |
| ATOM | 380 | C | ILE | A | 118 | 59.195 | 23.821 | −0.958 | 1.00 | 23.78 A |
| ATOM | 381 | O | ILE | A | 118 | 59.402 | 24.495 | −0.048 | 1.00 | 23.49 A |
| ATOM | 382 | N | ILE | A | 119 | 60.153 | 23.489 | −1.815 | 1.00 | 23.46 A |
| ATOM | 383 | CA | ILE | A | 119 | 61.534 | 23.913 | −1.619 | 1.00 | 25.13 A |
| ATOM | 384 | CB | ILE | A | 119 | 62.467 | 23.250 | −2.664 | 1.00 | 24.25 A |
| ATOM | 385 | CG2 | ILE | A | 119 | 63.858 | 23.890 | −2.617 | 1.00 | 22.47 A |
| ATOM | 386 | CG1 | ILE | A | 119 | 62.540 | 21.738 | −2.395 | 1.00 | 25.05 A |
| ATOM | 387 | CD1 | ILE | A | 119 | 63.327 | 20.945 | −3.439 | 1.00 | 24.62 A |
| ATOM | 388 | C | ILE | A | 119 | 61.667 | 25.435 | −1.705 | 1.00 | 25.96 A |
| ATOM | 389 | O | ILE | A | 119 | 62.330 | 26.051 | −0.872 | 1.00 | 24.78 A |
| ATOM | 390 | N | LYS | A | 120 | 61.028 | 26.039 | −2.704 | 1.00 | 27.67 A |
| ATOM | 391 | CA | LYS | A | 120 | 61.100 | 27.489 | −2.879 | 1.00 | 30.29 A |
| ATOM | 392 | CB | LYS | A | 120 | 60.242 | 27.940 | −4.060 | 1.00 | 32.34 A |
| ATOM | 393 | CG | LYS | A | 120 | 60.674 | 27.407 | −5.409 | 1.00 | 39.30 A |
| ATOM | 394 | CD | LYS | A | 120 | 59.765 | 27.950 | −6.512 | 1.00 | 45.19 A |
| ATOM | 395 | CE | LYS | A | 120 | 58.294 | 27.636 | −6.218 | 1.00 | 46.48 A |
| ATOM | 396 | NZ | LYS | A | 120 | 57.363 | 28.155 | −7.252 | 1.00 | 46.49 A |
| ATOM | 397 | C | LYS | A | 120 | 60.647 | 28.247 | −1.638 | 1.00 | 30.89 A |
| ATOM | 398 | O | LYS | A | 120 | 61.303 | 29.198 | −1.217 | 1.00 | 32.48 A |
| ATOM | 399 | N | GLU | A | 121 | 59.527 | 27.825 | −1.055 | 1.00 | 29.82 A |
| ATOM | 400 | CA | GLU | A | 121 | 58.986 | 28.488 | 0.128 | 1.00 | 30.33 A |
| ATOM | 401 | CB | GLU | A | 121 | 57.455 | 28.416 | 0.117 | 1.00 | 33.04 A |
| ATOM | 402 | CG | GLU | A | 121 | 56.794 | 29.021 | −1.120 | 1.00 | 36.45 A |
| ATOM | 403 | CD | GLU | A | 121 | 57.221 | 30.456 | −1.373 | 1.00 | 39.88 A |
| ATOM | 404 | OE1 | GLU | A | 121 | 57.200 | 31.264 | −0.420 | 1.00 | 40.53 A |
| ATOM | 405 | OE2 | GLU | A | 121 | 57.573 | 30.778 | −2.529 | 1.00 | 43.24 A |
| ATOM | 406 | C | GLU | A | 121 | 59.511 | 27.930 | 1.451 | 1.00 | 30.37 A |
| ATOM | 407 | O | GLU | A | 121 | 58.946 | 28.204 | 2.513 | 1.00 | 31.24 A |
| ATOM | 408 | N | ASN | A | 122 | 60.588 | 27.151 | 1.390 | 1.00 | 29.03 A |
| ATOM | 409 | CA | ASN | A | 122 | 61.183 | 26.573 | 2.594 | 1.00 | 28.46 A |
| ATOM | 410 | CB | ASN | A | 122 | 61.836 | 27.673 | 3.436 | 1.00 | 31.28 A |
| ATOM | 411 | CG | ASN | A | 122 | 62.945 | 28.395 | 2.698 | 1.00 | 34.12 A |
| ATOM | 412 | OD1 | ASN | A | 122 | 62.697 | 29.143 | 1.754 | 1.00 | 35.57 A |
| ATOM | 413 | ND2 | ASN | A | 122 | 64.181 | 28.169 | 3.127 | 1.00 | 35.73 A |
| ATOM | 414 | C | ASN | A | 122 | 60.157 | 25.835 | 3.456 | 1.00 | 26.89 A |
| ATOM | 415 | O | ASN | A | 122 | 60.085 | 26.055 | 4.663 | 1.00 | 27.23 A |
| ATOM | 416 | N | LYS | A | 123 | 59.375 | 24.955 | 2.842 | 1.00 | 23.99 A |

-continued

| | | | | | | | | | | |
|---|---|---|---|---|---|---|---|---|---|---|
| ATOM | 417 | CA | LYS | A | 123 | 58.358 | 24.210 | 3.574 | 1.00 | 22.43 A |
| ATOM | 418 | CB | LYS | A | 123 | 57.031 | 24.248 | 2.810 | 1.00 | 21.97 A |
| ATOM | 419 | CG | LYS | A | 123 | 56.475 | 25.645 | 2.599 | 1.00 | 25.68 A |
| ATOM | 420 | CD | LYS | A | 123 | 56.253 | 26.354 | 3.927 | 1.00 | 27.54 A |
| ATOM | 421 | CE | LYS | A | 123 | 55.822 | 27.796 | 3.716 | 1.00 | 31.30 A |
| ATOM | 422 | NZ | LYS | A | 123 | 55.756 | 28.540 | 5.004 | 1.00 | 33.21 A |
| ATOM | 423 | C | LYS | A | 123 | 58.748 | 22.759 | 3.821 | 1.00 | 22.20 A |
| ATOM | 424 | O | LYS | A | 123 | 57.924 | 21.960 | 4.264 | 1.00 | 22.50 A |
| ATOM | 425 | N | VAL | A | 124 | 59.997 | 22.412 | 3.535 | 1.00 | 20.59 A |
| ATOM | 426 | CA | VAL | A | 124 | 60.439 | 21.039 | 3.730 | 1.00 | 20.25 A |
| ATOM | 427 | CB | VAL | A | 124 | 61.922 | 20.850 | 3.328 | 1.00 | 19.43 A |
| ATOM | 428 | CG1 | VAL | A | 124 | 62.346 | 19.407 | 3.573 | 1.00 | 18.69 A |
| ATOM | 429 | CG2 | VAL | A | 124 | 62.104 | 21.195 | 1.853 | 1.00 | 18.21 A |
| ATOM | 430 | C | VAL | A | 124 | 60.236 | 20.561 | 5.163 | 1.00 | 19.53 A |
| ATOM | 431 | O | VAL | A | 124 | 59.841 | 19.418 | 5.385 | 1.00 | 20.02 A |
| ATOM | 432 | N | PRO | A | 125 | 60.513 | 21.422 | 6.159 | 1.00 | 20.01 A |
| ATOM | 433 | CD | PRO | A | 125 | 61.178 | 22.738 | 6.118 | 1.00 | 18.69 A |
| ATOM | 434 | CA | PRO | A | 125 | 60.318 | 20.979 | 7.544 | 1.00 | 19.88 A |
| ATOM | 435 | CB | PRO | A | 125 | 60.793 | 22.180 | 8.363 | 1.00 | 19.95 A |
| ATOM | 436 | CG | PRO | A | 125 | 61.839 | 22.805 | 7.479 | 1.00 | 18.85 A |
| ATOM | 437 | C | PRO | A | 125 | 58.848 | 20.642 | 7.824 | 1.00 | 19.76 A |
| ATOM | 438 | O | PRO | A | 125 | 58.544 | 19.700 | 8.550 | 1.00 | 16.99 A |
| ATOM | 439 | N | TYR | A | 126 | 57.947 | 21.418 | 7.235 | 1.00 | 18.98 A |
| ATOM | 440 | CA | TYR | A | 126 | 56.516 | 21.220 | 7.435 | 1.00 | 21.97 A |
| ATOM | 441 | CB | TYR | A | 126 | 55.752 | 22.448 | 6.933 | 1.00 | 25.17 A |
| ATOM | 442 | CG | TYR | A | 126 | 56.040 | 23.690 | 7.748 | 1.00 | 30.98 A |
| ATOM | 443 | CD1 | TYR | A | 126 | 55.438 | 23.886 | 8.991 | 1.00 | 33.95 A |
| ATOM | 444 | CE1 | TYR | A | 126 | 55.721 | 25.015 | 9.763 | 1.00 | 36.60 A |
| ATOM | 445 | CD2 | TYR | A | 126 | 56.938 | 24.657 | 7.292 | 1.00 | 35.43 A |
| ATOM | 446 | CE2 | TYR | A | 126 | 57.231 | 25.792 | 8.058 | 1.00 | 37.20 A |
| ATOM | 447 | CZ | TYR | A | 126 | 56.618 | 25.962 | 9.291 | 1.00 | 37.40 A |
| ATOM | 448 | OH | TYR | A | 126 | 56.903 | 27.073 | 10.052 | 1.00 | 40.85 A |
| ATOM | 449 | C | TYR | A | 126 | 55.990 | 19.956 | 6.762 | 1.00 | 21.35 A |
| ATOM | 450 | O | TYR | A | 126 | 55.265 | 19.175 | 7.383 | 1.00 | 20.49 A |
| ATOM | 451 | N | VAL | A | 127 | 56.354 | 19.746 | 5.501 | 1.00 | 18.16 A |
| ATOM | 452 | CA | VAL | A | 127 | 55.892 | 18.562 | 4.790 | 1.00 | 17.58 A |
| ATOM | 453 | CB | VAL | A | 127 | 56.308 | 18.596 | 3.308 | 1.00 | 17.45 A |
| ATOM | 454 | CG1 | VAL | A | 127 | 55.786 | 17.350 | 2.600 | 1.00 | 17.97 A |
| ATOM | 455 | CG2 | VAL | A | 127 | 55.751 | 19.850 | 2.641 | 1.00 | 14.90 A |
| ATOM | 456 | C | VAL | A | 127 | 56.459 | 17.306 | 5.448 | 1.00 | 18.39 A |
| ATOM | 457 | O | VAL | A | 127 | 55.769 | 16.298 | 5.583 | 1.00 | 18.14 A |
| ATOM | 458 | N | THR | A | 128 | 57.716 | 17.381 | 5.869 | 1.00 | 17.50 A |
| ATOM | 459 | CA | THR | A | 128 | 58.375 | 16.260 | 6.530 | 1.00 | 18.54 A |
| ATOM | 460 | CB | THR | A | 128 | 59.861 | 16.586 | 6.805 | 1.00 | 18.01 A |
| ATOM | 461 | OG1 | THR | A | 128 | 60.537 | 16.804 | 5.559 | 1.00 | 21.14 A |
| ATOM | 462 | CG2 | THR | A | 128 | 60.536 | 15.446 | 7.545 | 1.00 | 17.95 A |
| ATOM | 463 | C | THR | A | 128 | 57.676 | 15.941 | 7.856 | 1.00 | 19.49 A |
| ATOM | 464 | O | THR | A | 128 | 57.438 | 14.776 | 8.179 | 1.00 | 18.76 A |
| ATOM | 465 | N | ARG | A | 129 | 57.345 | 16.981 | 8.619 | 1.00 | 19.60 A |
| ATOM | 466 | CA | ARG | A | 129 | 56.673 | 16.804 | 9.904 | 1.00 | 20.12 A |
| ATOM | 467 | CB | ARG | A | 129 | 56.534 | 18.144 | 10.621 | 1.00 | 21.33 A |
| ATOM | 468 | CG | ARG | A | 129 | 55.948 | 18.029 | 12.023 | 1.00 | 28.02 A |
| ATOM | 469 | CD | ARG | A | 129 | 55.721 | 19.404 | 12.597 | 1.00 | 31.25 A |
| ATOM | 470 | NE | ARG | A | 129 | 56.940 | 20.205 | 12.560 | 1.00 | 37.78 A |
| ATOM | 471 | CZ | ARG | A | 129 | 56.962 | 21.524 | 12.391 | 1.00 | 40.10 A |
| ATOM | 472 | NH1 | ARG | A | 129 | 55.828 | 22.197 | 12.239 | 1.00 | 40.03 A |
| ATOM | 473 | NH2 | ARG | A | 129 | 58.119 | 22.170 | 12.374 | 1.00 | 44.58 A |
| ATOM | 474 | C | ARG | A | 129 | 55.288 | 16.186 | 9.729 | 1.00 | 20.08 A |
| ATOM | 475 | O | ARG | A | 129 | 54.891 | 15.305 | 10.496 | 1.00 | 20.40 A |
| ATOM | 476 | N | GLU | A | 130 | 54.553 | 16.654 | 8.724 | 1.00 | 18.79 A |
| ATOM | 477 | CA | GLU | A | 130 | 53.222 | 16.125 | 8.454 | 1.00 | 20.10 A |
| ATOM | 478 | CB | GLU | A | 130 | 52.638 | 16.749 | 7.183 | 1.00 | 19.92 A |
| ATOM | 479 | CG | GLU | A | 130 | 51.350 | 16.087 | 6.708 | 1.00 | 27.85 A |
| ATOM | 480 | CD | GLU | A | 130 | 50.581 | 16.933 | 5.707 | 1.00 | 29.72 A |
| ATOM | 481 | OE1 | GLU | A | 130 | 51.216 | 17.528 | 4.814 | 1.00 | 33.46 A |
| ATOM | 482 | OE2 | GLU | A | 130 | 49.339 | 16.996 | 5.807 | 1.00 | 30.74 A |
| ATOM | 483 | C | GLU | A | 130 | 53.301 | 14.615 | 8.295 | 1.00 | 19.81 A |
| ATOM | 484 | O | GLU | A | 130 | 52.553 | 13.875 | 8.935 | 1.00 | 18.37 A |
| ATOM | 485 | N | ARG | A | 131 | 54.219 | 14.162 | 7.447 | 1.00 | 20.41 A |
| ATOM | 486 | CA | ARG | A | 131 | 54.397 | 12.735 | 7.202 | 1.00 | 22.45 A |
| ATOM | 487 | CB | ARG | A | 131 | 55.442 | 12.511 | 6.098 | 1.00 | 25.16 A |
| ATOM | 488 | CG | ARG | A | 131 | 55.742 | 11.043 | 5.840 | 1.00 | 28.75 A |
| ATOM | 489 | CD | ARG | A | 131 | 56.736 | 10.837 | 4.708 | 1.00 | 33.75 A |
| ATOM | 490 | NE | ARG | A | 131 | 57.020 | 9.415 | 4.520 | 1.00 | 40.07 A |
| ATOM | 491 | CZ | ARG | A | 131 | 57.756 | 8.915 | 3.532 | 1.00 | 43.07 A |
| ATOM | 492 | NH1 | ARG | A | 131 | 58.293 | 9.721 | 2.625 | 1.00 | 44.91 A |
| ATOM | 493 | NH2 | ARG | A | 131 | 57.955 | 7.606 | 3.449 | 1.00 | 44.45 A |
| ATOM | 494 | C | ARG | A | 131 | 54.820 | 11.982 | 8.466 | 1.00 | 23.24 A |
| ATOM | 495 | O | ARG | A | 131 | 54.241 | 10.948 | 8.804 | 1.00 | 23.86 A |

-continued

| | | | | | | | | | | |
|---|---|---|---|---|---|---|---|---|---|---|
| ATOM | 496 | N | ASP | A | 132 | 55.831 | 12.497 | 9.160 | 1.00 | 21.99 A |
| ATOM | 497 | CA | ASP | A | 132 | 56.318 | 11.850 | 10.370 | 1.00 | 22.04 A |
| ATOM | 498 | CB | ASP | A | 132 | 57.570 | 12.564 | 10.888 | 1.00 | 23.72 A |
| ATOM | 499 | CG | ASP | A | 132 | 58.750 | 12.442 | 9.932 | 1.00 | 27.77 A |
| ATOM | 500 | OD1 | ASP | A | 132 | 58.681 | 11.620 | 8.989 | 1.00 | 27.34 A |
| ATOM | 501 | OD2 | ASP | A | 132 | 59.753 | 13.163 | 10.128 | 1.00 | 28.70 A |
| ATOM | 502 | C | ASP | A | 132 | 55.258 | 11.772 | 11.474 | 1.00 | 21.69 A |
| ATOM | 503 | O | ASP | A | 132 | 55.077 | 10.723 | 12.092 | 1.00 | 22.75 A |
| ATOM | 504 | N | VAL | A | 133 | 54.551 | 12.868 | 11.725 | 1.00 | 19.54 A |
| ATOM | 505 | CA | VAL | A | 133 | 53.525 | 12.843 | 12.759 | 1.00 | 18.52 A |
| ATOM | 506 | CB | VAL | A | 133 | 52.908 | 14.244 | 12.990 | 1.00 | 19.26 A |
| ATOM | 507 | CG1 | VAL | A | 133 | 51.708 | 14.135 | 13.918 | 1.00 | 18.79 A |
| ATOM | 508 | CG2 | VAL | A | 133 | 53.953 | 15.180 | 13.604 | 1.00 | 18.80 A |
| ATOM | 509 | C | VAL | A | 133 | 52.419 | 11.854 | 12.398 | 1.00 | 19.46 A |
| ATOM | 510 | O | VAL | A | 133 | 52.073 | 10.991 | 13.200 | 1.00 | 19.94 A |
| ATOM | 511 | N | MET | A | 134 | 51.878 | 11.957 | 11.187 | 1.00 | 19.15 A |
| ATOM | 512 | CA | MET | A | 134 | 50.807 | 11.052 | 10.792 | 1.00 | 21.25 A |
| ATOM | 513 | CB | MET | A | 134 | 50.309 | 11.381 | 9.383 | 1.00 | 17.34 A |
| ATOM | 514 | CG | MET | A | 134 | 49.615 | 12.730 | 9.302 | 1.00 | 20.00 A |
| ATOM | 515 | SD | MET | A | 134 | 48.643 | 12.952 | 7.798 | 1.00 | 24.21 A |
| ATOM | 516 | CE | MET | A | 134 | 47.033 | 12.434 | 8.400 | 1.00 | 23.20 A |
| ATOM | 517 | C | MET | A | 134 | 51.203 | 9.582 | 10.881 | 1.00 | 22.43 A |
| ATOM | 518 | O | MET | A | 134 | 50.384 | 8.741 | 11.249 | 1.00 | 23.82 A |
| ATOM | 519 | N | SER | A | 135 | 52.454 | 9.273 | 10.556 | 1.00 | 23.09 A |
| ATOM | 520 | CA | SER | A | 135 | 52.939 | 7.895 | 10.615 | 1.00 | 26.13 A |
| ATOM | 521 | CB | SER | A | 135 | 54.356 | 7.798 | 10.039 | 1.00 | 26.17 A |
| ATOM | 522 | OG | SER | A | 135 | 54.383 | 8.177 | 8.673 | 1.00 | 31.91 A |
| ATOM | 523 | C | SER | A | 135 | 52.957 | 7.358 | 12.045 | 1.00 | 26.58 A |
| ATOM | 524 | O | SER | A | 135 | 52.926 | 6.148 | 12.261 | 1.00 | 26.42 A |
| ATOM | 525 | N | ARG | A | 136 | 53.014 | 8.261 | 13.018 | 1.00 | 25.65 A |
| ATOM | 526 | CA | ARG | A | 136 | 53.056 | 7.870 | 14.425 | 1.00 | 27.47 A |
| ATOM | 527 | CB | ARG | A | 136 | 53.823 | 8.914 | 15.238 | 1.00 | 27.97 A |
| ATOM | 528 | CG | ARG | A | 136 | 55.283 | 9.082 | 14.857 | 1.00 | 32.00 A |
| ATOM | 529 | CD | ARG | A | 136 | 55.904 | 10.218 | 15.664 | 1.00 | 33.03 A |
| ATOM | 530 | NE | ARG | A | 136 | 55.602 | 10.073 | 17.084 | 1.00 | 36.11 A |
| ATOM | 531 | CZ | ARG | A | 136 | 55.867 | 10.990 | 18.007 | 1.00 | 39.74 A |
| ATOM | 532 | NH1 | ARG | A | 136 | 56.449 | 12.132 | 17.661 | 1.00 | 40.55 A |
| ATOM | 533 | NH2 | ARG | A | 136 | 55.540 | 10.769 | 19.276 | 1.00 | 36.72 A |
| ATOM | 534 | C | ARG | A | 136 | 51.667 | 7.709 | 15.036 | 1.00 | 26.38 A |
| ATOM | 535 | O | ARG | A | 136 | 51.516 | 7.121 | 16.106 | 1.00 | 27.06 A |
| ATOM | 536 | N | LEU | A | 137 | 50.655 | 8.235 | 14.360 | 1.00 | 24.77 A |
| ATOM | 537 | CA | LEU | A | 137 | 49.294 | 8.162 | 14.870 | 1.00 | 24.70 A |
| ATOM | 538 | CB | LEU | A | 137 | 48.483 | 9.363 | 14.371 | 1.00 | 24.52 A |
| ATOM | 539 | CG | LEU | A | 137 | 49.050 | 10.760 | 14.662 | 1.00 | 26.67 A |
| ATOM | 540 | CD1 | LEU | A | 137 | 48.075 | 11.813 | 14.141 | 1.00 | 27.25 A |
| ATOM | 541 | CD2 | LEU | A | 137 | 49.279 | 10.945 | 16.155 | 1.00 | 27.09 A |
| ATOM | 542 | C | LEU | A | 137 | 48.592 | 6.868 | 14.473 | 1.00 | 25.20 A |
| ATOM | 543 | O | LEU | A | 137 | 48.619 | 6.469 | 13.309 | 1.00 | 25.99 A |
| ATOM | 544 | N | ASP | A | 138 | 47.971 | 6.218 | 15.451 | 1.00 | 21.89 A |
| ATOM | 545 | CA | ASP | A | 138 | 47.239 | 4.977 | 15.219 | 1.00 | 21.35 A |
| ATOM | 546 | CB | ASP | A | 138 | 48.124 | 3.761 | 15.523 | 1.00 | 22.14 A |
| ATOM | 547 | CC | ASP | A | 138 | 47.432 | 2.448 | 15.201 | 1.00 | 24.90 A |
| ATOM | 548 | OD1 | ASP | A | 138 | 46.631 | 2.423 | 14.241 | 1.00 | 24.78 A |
| ATOM | 549 | OD2 | ASP | A | 138 | 47.691 | 1.443 | 15.897 | 1.00 | 25.39 A |
| ATOM | 550 | C | ASP | A | 138 | 46.031 | 4.991 | 16.138 | 1.00 | 20.47 A |
| ATOM | 551 | O | ASP | A | 138 | 45.967 | 4.248 | 17.118 | 1.00 | 19.06 A |
| ATOM | 552 | N | HIS | A | 139 | 45.075 | 5.852 | 15.810 | 1.00 | 18.27 A |
| ATOM | 553 | CA | HIS | A | 139 | 43.869 | 6.016 | 16.606 | 1.00 | 18.21 A |
| ATOM | 554 | CB | HIS | A | 139 | 44.096 | 7.157 | 17.612 | 1.00 | 15.84 A |
| ATOM | 555 | CC | HIS | A | 139 | 42.985 | 7.332 | 18.600 | 1.00 | 15.24 A |
| ATOM | 556 | CD2 | HIS | A | 139 | 42.884 | 6.964 | 19.900 | 1.00 | 13.97 A |
| ATOM | 557 | ND1 | HIS | A | 139 | 41.791 | 7.943 | 18.280 | 1.00 | 14.74 A |
| ATOM | 558 | CE1 | HIS | A | 139 | 41.002 | 7.944 | 19.341 | 1.00 | 14.19 A |
| ATOM | 559 | NE2 | HIS | A | 139 | 41.641 | 7.356 | 20.336 | 1.00 | 14.15 A |
| ATOM | 560 | C | HIS | A | 139 | 42.715 | 6.330 | 15.654 | 1.00 | 18.50 A |
| ATOM | 561 | O | HIS | A | 139 | 42.879 | 7.080 | 14.693 | 1.00 | 20.80 A |
| ATOM | 562 | N | PRO | A | 140 | 41.527 | 5.767 | 15.913 | 1.00 | 18.32 A |
| ATOM | 563 | CD | PRO | A | 140 | 41.143 | 4.984 | 17.100 | 1.00 | 16.71 A |
| ATOM | 564 | CA | PRO | A | 140 | 40.367 | 6.001 | 15.048 | 1.00 | 17.43 A |
| ATOM | 565 | CB | PRO | A | 140 | 39.273 | 5.157 | 15.704 | 1.00 | 16.64 A |
| ATOM | 566 | CC | PRO | A | 140 | 39.643 | 5.204 | 17.152 | 1.00 | 18.43 A |
| ATOM | 567 | C | PRO | A | 140 | 39.914 | 7.441 | 14.803 | 1.00 | 18.77 A |
| ATOM | 568 | O | PRO | A | 140 | 39.207 | 7.695 | 13.831 | 1.00 | 19.88 A |
| ATOM | 569 | N | PHE | A | 141 | 40.301 | 8.381 | 15.664 | 1.00 | 17.14 A |
| ATOM | 570 | CA | PHE | A | 141 | 39.874 | 9.767 | 15.477 | 1.00 | 16.42 A |
| ATOM | 571 | CB | PHE | A | 141 | 39.568 | 10.422 | 16.836 | 1.00 | 14.60 A |
| ATOM | 572 | CC | PHE | A | 141 | 38.386 | 9.817 | 17.556 | 1.00 | 15.26 A |
| ATOM | 573 | CD1 | PHE | A | 141 | 37.335 | 9.234 | 16.842 | 1.00 | 14.78 A |
| ATOM | 574 | CD2 | PHE | A | 141 | 38.297 | 9.880 | 18.942 | 1.00 | 13.70 A |

-continued

| | | | | | | | | | | |
|---|---|---|---|---|---|---|---|---|---|---|
| ATOM | 575 | CE1 | PHE | A | 141 | 36.215 | 8.727 | 17.502 | 1.00 | 16.94 A |
| ATOM | 576 | CE2 | PHE | A | 141 | 37.178 | 9.375 | 19.615 | 1.00 | 15.75 A |
| ATOM | 577 | CZ | PHE | A | 141 | 36.135 | 8.799 | 18.893 | 1.00 | 16.89 A |
| ATOM | 578 | C | PHE | A | 141 | 40.857 | 10.641 | 14.694 | 1.00 | 16.15 A |
| ATOM | 579 | O | PHE | A | 141 | 40.799 | 11.871 | 14.761 | 1.00 | 17.35 A |
| ATOM | 580 | N | PHE | A | 142 | 41.748 | 10.011 | 13.941 | 1.00 | 15.88 A |
| ATOM | 581 | CA | PHE | A | 142 | 42.727 | 10.756 | 13.154 | 1.00 | 17.89 A |
| ATOM | 582 | CB | PHE | A | 142 | 44.115 | 10.645 | 13.793 | 1.00 | 17.57 A |
| ATOM | 583 | CC | PHE | A | 142 | 44.240 | 11.371 | 15.103 | 1.00 | 18.74 A |
| ATOM | 584 | CD1 | PHE | A | 142 | 44.559 | 12.726 | 15.135 | 1.00 | 17.77 A |
| ATOM | 585 | CD2 | PHE | A | 142 | 43.997 | 10.711 | 16.304 | 1.00 | 18.74 A |
| ATOM | 586 | CE1 | PHE | A | 142 | 44.632 | 13.417 | 16.347 | 1.00 | 15.77 A |
| ATOM | 587 | CE2 | PHE | A | 142 | 44.065 | 11.393 | 17.522 | 1.00 | 17.56 A |
| ATOM | 588 | CZ | PHE | A | 142 | 44.383 | 12.747 | 17.542 | 1.00 | 17.14 A |
| ATOM | 589 | C | PHE | A | 142 | 42.793 | 10.231 | 11.729 | 1.00 | 19.12 A |
| ATOM | 590 | O | PHE | A | 142 | 42.659 | 9.030 | 11.504 | 1.00 | 20.01 A |
| ATOM | 591 | N | VAL | A | 143 | 42.978 | 11.135 | 10.769 | 1.00 | 18.72 A |
| ATOM | 592 | CA | VAL | A | 143 | 43.102 | 10.735 | 9.371 | 1.00 | 18.52 A |
| ATOM | 593 | CB | VAL | A | 143 | 43.294 | 11.961 | 8.440 | 1.00 | 20.66 A |
| ATOM | 594 | Cd | VAL | A | 143 | 43.843 | 11.521 | 7.080 | 1.00 | 21.29 A |
| ATOM | 595 | CC2 | VAL | A | 143 | 41.958 | 12.673 | 8.252 | 1.00 | 22.97 A |
| ATOM | 596 | C | VAL | A | 143 | 44.342 | 9.865 | 9.330 | 1.00 | 18.68 A |
| ATOM | 597 | O | VAL | A | 143 | 45.355 | 10.199 | 9.943 | 1.00 | 18.42 A |
| ATOM | 598 | N | LYS | A | 144 | 44.259 | 8.745 | 8.623 | 1.00 | 18.30 A |
| ATOM | 599 | CA | LYS | A | 144 | 45.384 | 7.824 | 8.535 | 1.00 | 18.78 A |
| ATOM | 600 | CB | LYS | A | 144 | 44.889 | 6.373 | 8.608 | 1.00 | 22.27 A |
| ATOM | 601 | CC | LYS | A | 144 | 46.017 | 5.340 | 8.557 | 1.00 | 29.72 A |
| ATOM | 602 | CD | LYS | A | 144 | 45.491 | 3.912 | 8.674 | 1.00 | 34.16 A |
| ATOM | 603 | CE | LYS | A | 144 | 46.631 | 2.896 | 8.577 | 1.00 | 37.67 A |
| ATOM | 604 | NZ | LYS | A | 144 | 46.138 | 1.484 | 8.629 | 1.00 | 39.02 A |
| ATOM | 605 | C | LYS | A | 144 | 46.192 | 8.002 | 7.261 | 1.00 | 18.53 A |
| ATOM | 606 | O | LYS | A | 144 | 45.643 | 8.314 | 6.200 | 1.00 | 18.18 A |
| ATOM | 607 | N | LEU | A | 145 | 47.502 | 7.816 | 7.385 | 1.00 | 16.79 A |
| ATOM | 608 | CA | LEU | A | 145 | 48.411 | 7.900 | 6.251 | 1.00 | 17.45 A |
| ATOM | 609 | CB | LEU | | 145 | 49.686 | 8.653 | 6.641 | 0.50 | 18.82 AC1 |
| ATOM | 610 | CO | LEU | | 145 | 50.734 | 8.902 | 5.549 | 0.50 | 20.23 AC1 |
| ATOM | 611 | CD1 | LEU | | 145 | 51.836 | 9.799 | 6.093 | 0.50 | 18.83 AC1 |
| ATOM | 612 | CD2 | LEU | | 145 | 51.317 | 7.581 | 5.069 | 0.50 | 19.79 AC1 |
| ATOM | 613 | C | LEU | A | 145 | 48.739 | 6.450 | 5.907 | 1.00 | 19.19 A |
| ATOM | 614 | O | LEU | A | 145 | 49.451 | 5.772 | 6.659 | 1.00 | 17.36 A |
| ATOM | 615 | N | TYR | A | 146 | 48.215 | 5.972 | 4.782 | 1.00 | 17.28 A |
| ATOM | 616 | CA | TYR | A | 146 | 48.444 | 4.593 | 4.358 | 1.00 | 17.57 A |
| ATOM | 617 | CB | TYR | A | 146 | 47.288 | 4.098 | 3.486 | 1.00 | 17.74 A |
| ATOM | 618 | CO | TYR | A | 146 | 45.981 | 3.926 | 4.214 | 1.00 | 17.50 A |
| ATOM | 619 | CD1 | TYR | A | 146 | 45.099 | 4.995 | 4.377 | 1.00 | 16.50 A |
| ATOM | 620 | CE1 | TYR | A | 146 | 43.881 | 4.827 | 5.039 | 1.00 | 17.10 A |
| ATOM | 621 | CD2 | TYR | A | 146 | 45.620 | 2.686 | 4.735 | 1.00 | 18.28 A |
| ATOM | 622 | CE2 | TYR | A | 146 | 44.411 | 2.506 | 5.399 | 1.00 | 19.84 A |
| ATOM | 623 | CZ | TYR | A | 146 | 43.547 | 3.576 | 5.544 | 1.00 | 17.53 A |
| ATOM | 624 | OH | TYR | A | 146 | 42.342 | 3.376 | 6.169 | 1.00 | 20.67 A |
| ATOM | 625 | C | TYR | A | 146 | 49.735 | 4.376 | 3.582 | 1.00 | 18.72 A |
| ATOM | 626 | O | TYR | A | 146 | 50.382 | 3.338 | 3.715 | 1.00 | 19.51 A |
| ATOM | 627 | N | PHE | A | 147 | 50.110 | 5.350 | 2.765 | 1.00 | 18.09 A |
| ATOM | 628 | CA | PHE | A | 147 | 51.307 | 5.203 | 1.952 | 1.00 | 17.20 A |
| ATOM | 629 | CB | PHE | A | 147 | 51.007 | 4.258 | 0.783 | 1.00 | 16.77 A |
| ATOM | 630 | CO | PHE | A | 147 | 49.835 | 4.699 | −0.070 | 1.00 | 17.75 A |
| ATOM | 631 | CD1 | PHE | A | 147 | 49.967 | 5.752 | −0.975 | 1.00 | 16.58 A |
| ATOM | 632 | CD2 | PHE | A | 147 | 48.595 | 4.075 | 0.053 | 1.00 | 18.07 A |
| ATOM | 633 | CE1 | PHE | A | 147 | 48.886 | 6.178 | −1.742 | 1.00 | 19.62 A |
| ATOM | 634 | CE2 | PHE | A | 147 | 47.503 | 4.492 | −0.710 | 1.00 | 18.56 A |
| ATOM | 635 | CZ | PHE | A | 147 | 47.647 | 5.546 | −1.610 | 1.00 | 19.27 A |
| ATOM | 636 | C | PHE | A | 147 | 51.768 | 6.533 | 1.395 | 1.00 | 17.13 A |
| ATOM | 637 | O | PHE | A | 147 | 51.045 | 7.528 | 1.452 | 1.00 | 14.43 A |
| ATOM | 638 | N | THR | A | 148 | 52.981 | 6.534 | 0.854 | 1.00 | 17.12 A |
| ATOM | 639 | CA | THR | A | 148 | 53.541 | 7.718 | 0.232 | 1.00 | 17.96 A |
| ATOM | 640 | CB | THR | A | 148 | 54.449 | 8.531 | 1.197 | 1.00 | 21.51 A |
| ATOM | 641 | CO1 | THR | A | 148 | 55.605 | 7.760 | 1.537 | 1.00 | 18.83 A |
| ATOM | 642 | CO2 | THR | A | 148 | 53.700 | 8.897 | 2.472 | 1.00 | 19.60 A |
| ATOM | 643 | C | THR | A | 148 | 54.386 | 7.262 | −0.946 | 1.00 | 20.31 A |
| ATOM | 644 | O | THR | A | 148 | 54.860 | 6.124 | −0.991 | 1.00 | 18.94 A |
| ATOM | 645 | N | PHE | A | 149 | 54.543 | 8.149 | −1.916 | 1.00 | 19.16 A |
| ATOM | 646 | CA | PHE | A | 149 | 55.368 | 7.877 | −3.073 | 1.00 | 18.01 A |
| ATOM | 647 | CB | PHE | A | 149 | 54.748 | 6.801 | −3.989 | 1.00 | 17.23 A |
| ATOM | 648 | CO | PHE | A | 149 | 53.389 | 7.144 | −4.544 | 1.00 | 16.88 A |
| ATOM | 649 | CD1 | PHE | A | 149 | 53.262 | 7.888 | −5.712 | 1.00 | 18.58 A |
| ATOM | 650 | CD2 | PHE | A | 149 | 52.235 | 6.668 | −3.927 | 1.00 | 17.31 A |
| ATOM | 651 | CE1 | PHE | A | 149 | 52.007 | 8.149 | −6.267 | 1.00 | 19.26 A |
| ATOM | 652 | CE2 | PHE | A | 149 | 50.972 | 6.923 | −4.470 | 1.00 | 19.17 A |
| ATOM | 653 | CZ | PHE | A | 149 | 50.858 | 7.663 | −5.642 | 1.00 | 19.60 A |

-continued

| | | | | | | | | | | |
|---|---|---|---|---|---|---|---|---|---|---|
| ATOM | 654 | C | PHE | A | 149 | 55.542 | 9.205 | −3.774 | 1.00 | 20.85 A |
| ATOM | 655 | O | PHE | A | 149 | 54.934 | 10.200 | −3.376 | 1.00 | 19.76 A |
| ATOM | 656 | N | OLN | A | 150 | 56.398 | 9.241 | −4.782 | 1.00 | 19.79 A |
| ATOM | 657 | CA | OLN | A | 150 | 56.636 | 10.481 | −5.497 | 1.00 | 24.03 A |
| ATOM | 658 | CB | OLN | A | 150 | 57.659 | 11.347 | −4.739 | 1.00 | 24.45 A |
| ATOM | 659 | CO | OLN | A | 150 | 58.986 | 10.645 | −4.414 | 1.00 | 26.28 A |
| ATOM | 660 | CD | OLN | A | 150 | 59.988 | 11.558 | −3.692 | 1.00 | 29.02 A |
| ATOM | 661 | OE1 | OLN | A | 150 | 60.693 | 12.353 | −4.321 | 1.00 | 27.05 A |
| ATOM | 662 | NE2 | GIN | A | 150 | 60.042 | 11.449 | −2.365 | 1.00 | 26.47 A |
| ATOM | 663 | C | GIN | A | 150 | 57.160 | 10.203 | −6.885 | 1.00 | 23.88 A |
| ATOM | 664 | O | GIN | A | 150 | 57.673 | 9.118 | −7.158 | 1.00 | 24.79 A |
| ATOM | 665 | N | ASP | A | 151 | 56.987 | 11.171 | −7.774 | 1.00 | 25.88 A |
| ATOM | 666 | CA | ASP | A | 151 | 57.527 | 11.047 | −9.117 | 1.00 | 26.49 A |
| ATOM | 667 | CB | ASP | A | 151 | 56.437 | 11.126 | −10.199 | 1.00 | 24.54 A |
| ATOM | 668 | CC | ASP | A | 151 | 55.544 | 12.336 | −10.064 | 1.00 | 24.95 A |
| ATOM | 669 | OD1 | ASP | A | 151 | 56.005 | 13.379 | −9.561 | 1.00 | 22.44 A |
| ATOM | 670 | OD2 | ASP | A | 151 | 54.369 | 12.242 | −10.490 | 1.00 | 25.72 A |
| ATOM | 671 | C | ASP | A | 151 | 58.515 | 12.203 | −9.220 | 1.00 | 28.63 A |
| ATOM | 672 | O | ASP | A | 151 | 58.890 | 12.780 | −8.194 | 1.00 | 27.83 A |
| ATOM | 673 | N | ASP | A | 152 | 58.934 | 12.560 | −10.426 | 1.00 | 29.21 A |
| ATOM | 674 | CA | ASP | A | 152 | 59.907 | 13.636 | −10.562 | 1.00 | 31.88 A |
| ATOM | 675 | CB | ASP | A | 152 | 60.325 | 13.792 | −12.026 | 1.00 | 33.94 A |
| ATOM | 676 | CC | ASP | A | 152 | 61.033 | 12.564 | −12.557 | 1.00 | 38.88 A |
| ATOM | 677 | OD1 | ASP | A | 152 | 61.817 | 11.959 | −11.791 | 1.00 | 39.67 A |
| ATOM | 678 | OD2 | ASP | A | 152 | 60.817 | 12.211 | −13.738 | 1.00 | 41.57 A |
| ATOM | 679 | C | ASP | A | 152 | 59.487 | 14.994 | −10.013 | 1.00 | 30.90 A |
| ATOM | 680 | O | ASP | A | 152 | 60.316 | 15.735 | −9.482 | 1.00 | 31.69 A |
| ATOM | 681 | N | CLU | A | 153 | 58.207 | 15.322 | −10.107 | 1.00 | 29.44 A |
| ATOM | 682 | CA | CLU | A | 153 | 57.767 | 16.632 | −9.646 | 1.00 | 28.69 A |
| ATOM | 683 | CB | CLU | A | 153 | 56.984 | 17.327 | −10.766 | 1.00 | 32.90 A |
| ATOM | 684 | CC | CLU | A | 153 | 57.451 | 16.987 | −12.183 | 1.00 | 40.57 A |
| ATOM | 685 | CD | CLU | A | 153 | 56.920 | 15.643 | −12.675 | 1.00 | 45.78 A |
| ATOM | 686 | OE1 | CLU | A | 153 | 55.682 | 15.482 | −12.760 | 1.00 | 48.91 A |
| ATOM | 687 | 0E2 | CLU | A | 153 | 57.736 | 14.747 | −12.979 | 1.00 | 48.95 A |
| ATOM | 688 | C | CLU | A | 153 | 56.929 | 16.683 | −8.372 | 1.00 | 26.43 A |
| ATOM | 689 | O | CLU | A | 153 | 56.947 | 17.688 | −7.660 | 1.00 | 25.08 A |
| ATOM | 690 | N | LYS | A | 154 | 56.205 | 15.610 | −8.069 | 1.00 | 22.39 A |
| ATOM | 691 | CA | LYS | A | 154 | 55.318 | 15.631 | −6.912 | 1.00 | 21.43 A |
| ATOM | 692 | CB | LYS | A | 154 | 53.861 | 15.628 | −7.398 | 1.00 | 20.33 A |
| ATOM | 693 | CC | LYS | A | 154 | 53.505 | 16.716 | −8.403 | 1.00 | 21.92 A |
| ATOM | 694 | CD | LYS | A | 154 | 52.211 | 16.375 | −9.146 | 1.00 | 19.70 A |
| ATOM | 695 | CE | LYS | A | 154 | 51.775 | 17.503 | −10.077 | 1.00 | 20.04 A |
| ATOM | 696 | NZ | LYS | A | 154 | 50.631 | 17.094 | −10.951 | 1.00 | 19.97 A |
| ATOM | 697 | C | LYS | A | 154 | 55.458 | 14.522 | −5.881 | 1.00 | 20.43 A |
| ATOM | 698 | O | LYS | A | 154 | 55.949 | 13.426 | −6.173 | 1.00 | 21.13 A |
| ATOM | 699 | N | LEU | A | 155 | 54.985 | 14.832 | −4.676 | 1.00 | 19.69 A |
| ATOM | 700 | CA | LEU | A | 155 | 54.950 | 13.900 | −3.553 | 1.00 | 19.10 A |
| ATOM | 701 | CB | LEU | | 155 | 55.362 | 14.588 | −2.252 | 1.00 | 19.65 A |
| ATOM | 702 | CC | LEU | A | 155 | 56.740 | 15.234 | −2.129 | 1.00 | 21.20 A |
| ATOM | 703 | CD1 | LEU | A | 155 | 56.848 | 15.918 | −0.770 | 1.00 | 23.42 A |
| ATOM | 704 | CD2 | LEU | A | 155 | 57.816 | 14.174 | −2.277 | 1.00 | 23.08 A |
| ATOM | 705 | C | LEU | A | 155 | 53.478 | 13.507 | −3.427 | 1.00 | 18.87 A |
| ATOM | 706 | O | LEU | A | 155 | 52.600 | 14.348 | −3.620 | 1.00 | 18.61 A |
| ATOM | 707 | N | TYR | A | 156 | 53.209 | 12.249 | −3.091 | 1.00 | 15.02 A |
| ATOM | 708 | CA | TYR | A | 156 | 51.834 | 11.783 | −2.934 | 1.00 | 16.29 A |
| ATOM | 709 | CB | TYR | A | 156 | 51.470 | 10.769 | −4.029 | 1.00 | 14.20 A |
| ATOM | 710 | CC | TYR | A | 156 | 51.603 | 11.273 | −5.449 | 1.00 | 17.29 A |
| ATOM | 711 | CD1 | TYR | A | 156 | 52.857 | 11.429 | −6.045 | 1.00 | 16.46 A |
| ATOM | 712 | CE1 | TYR | A | 156 | 52.978 | 11.884 | −7.360 | 1.00 | 18.68 A |
| ATOM | 713 | CD2 | TYR | A | 156 | 50.474 | 11.588 | −6.202 | 1.00 | 16.43 A |
| ATOM | 714 | CE2 | TYR | A | 156 | 50.583 | 12.048 | −7.512 | 1.00 | 16.31 A |
| ATOM | 715 | CZ | TYR | A | 156 | 51.835 | 12.192 | −8.083 | 1.00 | 18.17 A |
| ATOM | 716 | OH | TYR | A | 156 | 51.941 | 12.651 | −9.371 | 1.00 | 17.47 A |
| ATOM | 717 | C | TYR | A | 156 | 51.657 | 11.108 | −1.572 | 1.00 | 16.32 A |
| ATOM | 718 | O | TYR | A | 156 | 52.412 | 10.197 | −1.235 | 1.00 | 16.27 A |
| ATOM | 719 | N | PHE | A | 157 | 50.678 | 11.568 | −0.792 | 1.00 | 15.47 A |
| ATOM | 720 | CA | PHE | A | 157 | 50.385 | 10.966 | 0.508 | 1.00 | 16.66 A |
| ATOM | 721 | CB | PHE | A | 157 | 50.324 | 12.014 | 1.629 | 1.00 | 16.91 A |
| ATOM | 722 | CG | PHE | A | 157 | 51.631 | 12.708 | 1.907 | 1.00 | 18.96 A |
| ATOM | 723 | CD1 | PHE | A | 157 | 52.821 | 12.261 | 1.340 | 1.00 | 20.31 A |
| ATOM | 724 | CD2 | PHE | A | 157 | 51.664 | 13.829 | 2.732 | 1.00 | 21.12 A |
| ATOM | 725 | CE1 | PHE | A | 157 | 54.025 | 12.926 | 1.585 | 1.00 | 22.08 A |
| ATOM | 726 | CE2 | PHE | A | 157 | 52.865 | 14.500 | 2.982 | 1.00 | 22.18 A |
| ATOM | 727 | CZ | PHE | A | 157 | 54.045 | 14.045 | 2.405 | 1.00 | 21.27 A |
| ATOM | 728 | C | PHE | A | 157 | 49.016 | 10.308 | 0.404 | 1.00 | 16.52 A |
| ATOM | 729 | O | PHE | A | 157 | 48.029 | 10.979 | 0.110 | 1.00 | 17.32 A |
| ATOM | 730 | N | GLY | A | 158 | 48.953 | 9.002 | 0.644 | 1.00 | 15.97 A |
| ATOM | 731 | CA | GLY | A | 158 | 47.684 | 8.299 | 0.572 | 1.00 | 16.13 A |
| ATOM | 732 | C | GLY | A | 158 | 47.000 | 8.383 | 1.920 | 1.00 | 14.94 A |

-continued

| | | | | | | | | | | |
|---|---|---|---|---|---|---|---|---|---|---|
| ATOM | 733 | O | GLY | A | 158 | 47.445 | 7.756 | 2.879 | 1.00 | 16.28 A |
| ATOM | 734 | N | LEU | A | 159 | 45.915 | 9.145 | 1.989 | 1.00 | 13.50 A |
| ATOM | 735 | CA | LEU | A | 159 | 45.191 | 9.340 | 3.241 | 1.00 | 15.20 A |
| ATOM | 736 | CB | LEU | A | 159 | 45.031 | 10.835 | 3.517 | 1.00 | 14.20 A |
| ATOM | 737 | CG | LEU | A | 159 | 46.270 | 11.726 | 3.385 | 1.00 | 19.00 A |
| ATOM | 738 | CD1 | LEU | A | 159 | 45.847 | 13.188 | 3.477 | 1.00 | 17.12 A |
| ATOM | 739 | CD2 | LEU | A | 159 | 47.275 | 11.390 | 4.471 | 1.00 | 14.71 A |
| ATOM | 740 | C | LEU | A | 159 | 43.809 | 8.716 | 3.232 | 1.00 | 15.53 A |
| ATOM | 741 | O | LEU | A | 159 | 43.232 | 8.472 | 2.177 | 1.00 | 16.05 A |
| ATOM | 742 | N | SER | A | 160 | 43.268 | 8.469 | 4.418 | 1.00 | 15.86 A |
| ATOM | 743 | CA | SER | A | 160 | 41.932 | 7.917 | 4.498 | 1.00 | 19.01 A |
| ATOM | 744 | CB | SER | A | 160 | 41.566 | 7.582 | 5.949 | 1.00 | 22.90 A |
| ATOM | 745 | OG | SER | A | 160 | 41.901 | 8.629 | 6.833 | 1.00 | 24.18 A |
| ATOM | 746 | C | SER | A | 160 | 40.987 | 8.968 | 3.924 | 1.00 | 20.43 A |
| ATOM | 747 | O | SER | A | 160 | 41.213 | 10.173 | 4.062 | 1.00 | 19.96 A |
| ATOM | 748 | N | TYR | A | 161 | 39.945 | 8.508 | 3.250 | 1.00 | 19.20 A |
| ATOM | 749 | CA | TYR | A | 161 | 38.975 | 9.406 | 2.644 | 1.00 | 20.37 A |
| ATOM | 750 | CB | TYR | A | 161 | 38.471 | 8.785 | 1.332 | 1.00 | 20.00 A |
| ATOM | 751 | CG | TYR | A | 161 | 37.314 | 9.502 | 0.666 | 1.00 | 20.72 A |
| ATOM | 752 | CD1 | TYR | A | 161 | 37.222 | 10.895 | 0.682 | 1.00 | 18.22 A |
| ATOM | 753 | CE1 | TYR | A | 161 | 36.180 | 11.557 | 0.029 | 1.00 | 22.24 A |
| ATOM | 754 | CD2 | TYR | A | 161 | 36.333 | 8.784 | −0.020 | 1.00 | 20.53 A |
| ATOM | 755 | CE2 | TYR | A | 161 | 35.287 | 9.436 | −0.678 | 1.00 | 24.24 A |
| ATOM | 756 | CZ | TYR | A | 161 | 35.218 | 10.822 | −0.648 | 1.00 | 22.32 A |
| ATOM | 757 | OH | TYR | A | 161 | 34.194 | 11.471 | −1.298 | 1.00 | 23.03 A |
| ATOM | 758 | C | TYR | A | 161 | 37.812 | 9.681 | 3.598 | 1.00 | 20.14 A |
| ATOM | 759 | O | TYR | A | 161 | 36.959 | 8.819 | 3.810 | 1.00 | 19.53 A |
| ATOM | 760 | N | ALA | A | 162 | 37.791 | 10.880 | 4.178 | 1.00 | 19.92 A |
| ATOM | 761 | CA | ALA | A | 162 | 36.721 | 11.271 | 5.099 | 1.00 | 21.07 A |
| ATOM | 762 | CB | ALA | A | 162 | 37.187 | 12.419 | 6.002 | 1.00 | 19.60 A |
| ATOM | 763 | C | ALA | A | 162 | 35.542 | 11.712 | 4.238 | 1.00 | 22.07 A |
| ATOM | 764 | O | ALA | A | 162 | 35.436 | 12.875 | 3.860 | 1.00 | 20.66 A |
| ATOM | 765 | N | LYS | A | 163 | 34.653 | 10.769 | 3.945 | 1.00 | 23.27 A |
| ATOM | 766 | CA | LYS | A | 163 | 33.503 | 11.017 | 3.080 | 1.00 | 27.12 A |
| ATOM | 767 | CB | LYS | A | 163 | 32.663 | 9.741 | 2.963 | 1.00 | 29.68 A |
| ATOM | 768 | CG | LYS | A | 163 | 33.455 | 8.524 | 2.515 | 1.00 | 37.67 A |
| ATOM | 769 | CD | LYS | A | 163 | 32.556 | 7.310 | 2.321 | 1.00 | 42.24 A |
| ATOM | 770 | CE | LYS | A | 163 | 33.373 | 6.034 | 2.185 | 1.00 | 44.48 A |
| ATOM | 771 | NZ | LYS | A | 163 | 34.143 | 5.735 | 3.430 | 1.00 | 44.88 A |
| ATOM | 772 | C | LYS | A | 163 | 32.581 | 12.186 | 3.411 | 1.00 | 25.78 A |
| ATOM | 773 | O | LYS | A | 163 | 32.103 | 12.863 | 2.506 | 1.00 | 26.53 A |
| ATOM | 774 | N | ASN | A | 164 | 32.327 | 12.441 | 4.689 | 1.00 | 24.57 A |
| ATOM | 775 | CA | ASN | A | 164 | 31.420 | 13.522 | 5.033 | 1.00 | 23.77 A |
| ATOM | 776 | CB | ASN | A | 164 | 30.610 | 13.129 | 6.265 | 1.00 | 25.02 A |
| ATOM | 777 | CG | ASN | A | 164 | 29.537 | 12.101 | 5.932 | 1.00 | 27.54 A |
| ATOM | 778 | OD1 | ASN | A | 164 | 28.772 | 12.281 | 4.983 | 1.00 | 28.79 A |
| ATOM | 779 | ND2 | ASN | A | 164 | 29.475 | 11.024 | 6.704 | 1.00 | 27.13 A |
| ATOM | 780 | C | ASN | A | 164 | 31.999 | 14.931 | 5.169 | 1.00 | 24.43 A |
| ATOM | 781 | O | ASN | A | 164 | 31.306 | 15.856 | 5.589 | 1.00 | 23.98 A |
| ATOM | 782 | N | GLY | A | 165 | 33.262 | 15.097 | 4.795 | 1.00 | 21.56 A |
| ATOM | 783 | CA | GLY | A | 165 | 33.873 | 16.414 | 4.836 | 1.00 | 24.39 A |
| ATOM | 784 | C | GLY | A | 165 | 34.191 | 17.043 | 6.181 | 1.00 | 23.62 A |
| ATOM | 785 | O | GLY | A | 165 | 34.380 | 16.352 | 7.177 | 1.00 | 23.26 A |
| ATOM | 786 | N | GLU | A | 166 | 34.234 | 18.373 | 6.186 | 1.00 | 23.22 A |
| ATOM | 787 | CA | GLU | A | 166 | 34.563 | 19.176 | 7.362 | 1.00 | 24.54 A |
| ATOM | 788 | CB | GLU | A | 166 | 35.055 | 20.558 | 6.913 | 1.00 | 25.04 A |
| ATOM | 789 | CG | GLU | A | 166 | 36.419 | 20.569 | 6.229 | 1.00 | 26.48 A |
| ATOM | 790 | CD | GLU | A | 166 | 36.699 | 21.889 | 5.517 | 1.00 | 30.02 A |
| ATOM | 791 | OE1 | GLU | A | 166 | 36.081 | 22.906 | 5.889 | 1.00 | 29.33 A |
| ATOM | 792 | OE2 | GLU | A | 166 | 37.544 | 21.916 | 4.596 | 1.00 | 30.48 A |
| ATOM | 793 | C | GLU | A | 166 | 33.436 | 19.372 | 8.369 | 1.00 | 24.44 A |
| ATOM | 794 | O | GLU | A | 166 | 32.279 | 19.541 | 8.001 | 1.00 | 22.76 A |
| ATOM | 795 | N | LEU | A | 167 | 33.791 | 19.370 | 9.649 | 1.00 | 22.95 A |
| ATOM | 796 | CA | LEU | A | 167 | 32.813 | 19.581 | 10.707 | 1.00 | 22.26 A |
| ATOM | 797 | CB | LEU | A | 167 | 33.497 | 19.481 | 12.073 | 1.00 | 22.32 A |
| ATOM | 798 | CG | LEU | A | 167 | 32.706 | 19.923 | 13.306 | 1.00 | 22.04 A |
| ATOM | 799 | CD1 | LEU | A | 167 | 31.454 | 19.074 | 13.463 | 1.00 | 19.66 A |
| ATOM | 800 | CD2 | LEU | A | 167 | 33.597 | 19.805 | 14.537 | 1.00 | 21.17 A |
| ATOM | 801 | C | LEU | A | 167 | 32.193 | 20.971 | 10.529 | 1.00 | 23.49 A |
| ATOM | 802 | O | LEU | A | 167 | 31.047 | 21.209 | 10.907 | 1.00 | 23.56 A |
| ATOM | 803 | N | LEU | A | 168 | 32.960 | 21.887 | 9.948 | 1.00 | 24.25 A |
| ATOM | 804 | CA | LEU | A | 168 | 32.473 | 23.245 | 9.722 | 1.00 | 26.64 A |
| ATOM | 805 | CB | LEU | A | 168 | 33.560 | 24.099 | 9.066 | 1.00 | 25.62 A |
| ATOM | 806 | CG | LEU | A | 168 | 33.198 | 25.546 | 8.707 | 1.00 | 27.34 A |
| ATOM | 807 | CD1 | LEU | A | 168 | 32.718 | 26.296 | 9.946 | 1.00 | 26.42 A |
| ATOM | 808 | CD2 | LEU | A | 168 | 34.418 | 26.238 | 8.119 | 1.00 | 26.74 A |
| ATOM | 809 | C | LEU | A | 168 | 31.234 | 23.218 | 8.829 | 1.00 | 27.13 A |
| ATOM | 810 | O | LEU | A | 168 | 30.297 | 23.989 | 9.030 | 1.00 | 26.01 A |
| ATOM | 811 | N | LYS | A | 169 | 31.233 | 22.320 | 7.848 | 1.00 | 26.41 A |

-continued

| | | | | | | | | | | |
|---|---|---|---|---|---|---|---|---|---|---|
| ATOM | 812 | CA | LYS | A | 169 | 30.106 | 22.210 | 6.934 | 1.00 | 27.70 A |
| ATOM | 813 | CB | LYS | A | 169 | 30.324 | 21.064 | 5.945 | 1.00 | 30.49 A |
| ATOM | 814 | CG | LYS | A | 169 | 29.151 | 20.854 | 4.993 | 1.00 | 32.47 A |
| ATOM | 815 | CD | LYS | A | 169 | 29.407 | 19.728 | 3.998 | 1.00 | 35.98 A |
| ATOM | 816 | CE | LYS | A | 169 | 29.462 | 18.372 | 4.683 | 1.00 | 38.53 A |
| ATOM | 817 | NZ | LYS | A | 169 | 29.622 | 17.263 | 3.702 | 1.00 | 41.00 A |
| ATOM | 818 | C | LYS | A | 169 | 28.801 | 21.985 | 7.682 | 1.00 | 28.12 A |
| ATOM | 819 | O | LYS | A | 169 | 27.785 | 22.608 | 7.371 | 1.00 | 28.08 A |
| ATOM | 820 | N | TYR | A | 170 | 28.826 | 21.094 | 8.668 | 1.00 | 26.53 A |
| ATOM | 821 | CA | TYR | A | 170 | 27.624 | 20.791 | 9.434 | 1.00 | 26.95 A |
| ATOM | 822 | CB | TYR | A | 170 | 27.810 | 19.476 | 10.193 | 1.00 | 25.03 A |
| ATOM | 823 | CG | TYR | A | 170 | 27.898 | 18.300 | 9.251 | 1.00 | 26.65 A |
| ATOM | 824 | CD1 | TYR | A | 170 | 26.745 | 17.661 | 8.790 | 1.00 | 28.27 A |
| ATOM | 825 | CE1 | TYR | A | 170 | 26.814 | 16.642 | 7.839 | 1.00 | 26.85 A |
| ATOM | 826 | CD2 | TYR | A | 170 | 29.127 | 17.884 | 8.742 | 1.00 | 27.83 A |
| ATOM | 827 | CE2 | TYR | A | 170 | 29.209 | 16.869 | 7.792 | 1.00 | 27.19 A |
| ATOM | 828 | CZ | TYR | A | 170 | 28.049 | 16.254 | 7.343 | 1.00 | 30.02 A |
| ATOM | 829 | OH | TYR | A | 170 | 28.130 | 15.268 | 6.382 | 1.00 | 29.23 A |
| ATOM | 830 | C | TYR | A | 170 | 27.229 | 21.918 | 10.376 | 1.00 | 27.59 A |
| ATOM | 831 | O | TYR | A | 170 | 26.045 | 22.122 | 10.642 | 1.00 | 29.25 A |
| ATOM | 832 | N | ILE | A | 171 | 28.208 | 22.660 | 10.882 | 1.00 | 28.16 A |
| ATOM | 833 | CA | ILE | A | 171 | 27.883 | 23.770 | 11.763 | 1.00 | 29.03 A |
| ATOM | 834 | CB | ILE | A | 171 | 29.151 | 24.435 | 12.337 | 1.00 | 27.51 A |
| ATOM | 835 | CG2 | ILE | A | 171 | 28.773 | 25.705 | 13.084 | 1.00 | 27.97 A |
| ATOM | 836 | CG1 | ILE | A | 171 | 29.872 | 23.458 | 13.272 | 1.00 | 26.70 A |
| ATOM | 837 | CD1 | ILE | A | 171 | 31.163 | 23.996 | 13.856 | 1.00 | 24.07 A |
| ATOM | 838 | C | ILE | A | 171 | 27.094 | 24.796 | 10.944 | 1.00 | 31.41 A |
| ATOM | 839 | O | ILE | A | 171 | 26.088 | 25.335 | 11.407 | 1.00 | 31.69 A |
| ATOM | 840 | N | ARG | A | 172 | 27.546 | 25.047 | 9.719 | 1.00 | 33.21 A |
| ATOM | 841 | CA | ARG | A | 172 | 26.874 | 26.000 | 8.844 | 1.00 | 36.54 A |
| ATOM | 842 | CB | ARG | A | 172 | 27.734 | 26.314 | 7.616 | 1.00 | 37.73 A |
| ATOM | 843 | CG | ARG | A | 172 | 29.057 | 27.011 | 7.912 | 1.00 | 41.65 A |
| ATOM | 844 | CD | ARG | A | 172 | 29.708 | 27.492 | 6.616 | 1.00 | 45.29 A |
| ATOM | 845 | NE | ARG | A | 172 | 31.037 | 28.070 | 6.812 | 1.00 | 48.51 A |
| ATOM | 846 | CZ | ARG | A | 172 | 31.314 | 29.059 | 7.658 | 1.00 | 51.53 A |
| ATOM | 847 | NH1 | ARG | A | 172 | 30.355 | 29.593 | 8.406 | 1.00 | 53.75 A |
| ATOM | 848 | NH2 | ARG | A | 172 | 32.553 | 29.526 | 7.748 | 1.00 | 51.21 A |
| ATOM | 849 | C | ARG | A | 172 | 25.528 | 25.459 | 8.378 | 1.00 | 37.67 A |
| ATOM | 850 | O | ARG | A | 172 | 24.550 | 26.200 | 8.288 | 1.00 | 39.09 A |
| ATOM | 851 | N | LYS | A | 173 | 25.481 | 24.163 | 8.092 | 1.00 | 38.44 A |
| ATOM | 852 | CA | LYS | A | 173 | 24.259 | 23.528 | 7.619 | 1.00 | 39.25 A |
| ATOM | 853 | CB | LYS | A | 173 | 24.523 | 22.061 | 7.272 | 1.00 | 41.89 A |
| ATOM | 854 | CG | LYS | A | 173 | 23.279 | 21.298 | 6.830 | 1.00 | 45.52 A |
| ATOM | 855 | CD | LYS | A | 173 | 23.557 | 19.808 | 6.653 | 1.00 | 49.60 A |
| ATOM | 856 | CE | LYS | A | 173 | 24.477 | 19.530 | 5.469 | 1.00 | 52.63 A |
| ATOM | 857 | NZ | LYS | A | 173 | 23.855 | 19.894 | 4.160 | 1.00 | 54.61 A |
| ATOM | 858 | C | LYS | A | 173 | 23.089 | 23.608 | 8.595 | 1.00 | 39.30 A |
| ATOM | 859 | O | LYS | A | 173 | 21.981 | 23.960 | 8.201 | 1.00 | 39.62 A |
| ATOM | 860 | N | ILE | A | 174 | 23.320 | 23.282 | 9.863 | 1.00 | 37.96 A |
| ATOM | 861 | CA | ILE | A | 174 | 22.229 | 23.314 | 10.833 | 1.00 | 37.36 A |
| ATOM | 862 | CB | ILE | A | 174 | 22.159 | 21.998 | 11.652 | 1.00 | 37.44 A |
| ATOM | 863 | CG2 | ILE | A | 174 | 22.058 | 20.802 | 10.709 | 1.00 | 38.37 A |
| ATOM | 864 | CG1 | ILE | A | 174 | 23.397 | 21.850 | 12.532 | 1.00 | 37.25 A |
| ATOM | 865 | CD1 | ILE | A | 174 | 23.355 | 20.620 | 13.418 | 1.00 | 36.85 A |
| ATOM | 866 | C | ILE | A | 174 | 22.259 | 24.492 | 11.801 | 1.00 | 36.71 A |
| ATOM | 867 | O | ILE | A | 174 | 21.448 | 24.556 | 12.724 | 1.00 | 38.05 A |
| ATOM | 868 | N | GLY | A | 175 | 23.185 | 25.423 | 11.592 | 1.00 | 35.48 A |
| ATOM | 869 | CA | GLY | A | 175 | 23.265 | 26.585 | 12.462 | 1.00 | 35.29 A |
| ATOM | 870 | C | GLY | A | 175 | 24.053 | 26.360 | 13.737 | 1.00 | 35.06 A |
| ATOM | 871 | O | GLY | A | 175 | 25.066 | 27.019 | 13.970 | 1.00 | 37.46 A |
| ATOM | 872 | N | SER | A | 176 | 23.581 | 25.441 | 14.571 | 1.00 | 33.94 A |
| ATOM | 873 | CA | SER | A | 176 | 24.253 | 25.113 | 15.822 | 1.00 | 32.84 A |
| ATOM | 874 | CB | SER | A | 176 | 23.938 | 26.155 | 16.901 | 1.00 | 33.54 A |
| ATOM | 875 | OG | SER | A | 176 | 22.599 | 26.056 | 17.347 | 1.00 | 34.86 A |
| ATOM | 876 | C | SER | A | 176 | 23.796 | 23.731 | 16.276 | 1.00 | 32.34 A |
| ATOM | 877 | O | SER | A | 176 | 22.726 | 23.263 | 15.884 | 1.00 | 32.82 A |
| ATOM | 878 | N | PHE | A | 177 | 24.609 | 23.085 | 17.103 | 1.00 | 29.39 A |
| ATOM | 879 | CA | PHE | A | 177 | 24.313 | 21.743 | 17.597 | 1.00 | 27.20 A |
| ATOM | 880 | CB | PHE | A | 177 | 25.621 | 20.989 | 17.865 | 1.00 | 26.39 A |
| ATOM | 881 | CG | PHE | A | 177 | 26.372 | 20.585 | 16.622 | 1.00 | 26.18 A |
| ATOM | 882 | CD1 | PHE | A | 177 | 26.210 | 21.277 | 15.426 | 1.00 | 25.30 A |
| ATOM | 883 | CD2 | PHE | A | 177 | 27.266 | 19.516 | 16.662 | 1.00 | 26.05 A |
| ATOM | 884 | CE1 | PHE | A | 177 | 26.923 | 20.912 | 14.290 | 1.00 | 26.59 A |
| ATOM | 885 | CE2 | PHE | A | 177 | 27.986 | 19.143 | 15.532 | 1.00 | 26.06 A |
| ATOM | 886 | CZ | PHE | A | 177 | 27.815 | 19.841 | 14.343 | 1.00 | 25.42 A |
| ATOM | 887 | C | PHE | A | 177 | 23.500 | 21.752 | 18.884 | 1.00 | 27.00 A |
| ATOM | 888 | O | PHE | A | 177 | 23.704 | 22.610 | 19.747 | 1.00 | 26.48 A |
| ATOM | 889 | N | ASP | A | 178 | 22.578 | 20.802 | 19.022 | 1.00 | 26.70 A |
| ATOM | 890 | CA | ASP | A | 178 | 21.816 | 20.729 | 20.260 | 1.00 | 26.35 A |

-continued

| | | | | | | | | | | |
|---|---|---|---|---|---|---|---|---|---|---|
| ATOM | 891 | CB | ASP | A | 178 | 20.621 | 19.773 | 20.142 | 1.00 | 29.90 A |
| ATOM | 892 | CG | ASP | A | 178 | 21.020 | 18.372 | 19.720 | 1.00 | 32.28 A |
| ATOM | 893 | OD1 | ASP | A | 178 | 22.157 | 17.949 | 20.014 | 1.00 | 35.21 A |
| ATOM | 894 | 0D2 | ASP | A | 178 | 20.179 | 17.683 | 19.105 | 1.00 | 34.79 A |
| ATOM | 895 | C | ASP | A | 178 | 22.810 | 20.228 | 21.311 | 1.00 | 25.03 A |
| ATOM | 896 | O | ASP | A | 178 | 23.974 | 19.968 | 20.992 | 1.00 | 21.24 A |
| ATOM | 897 | N | GLU | A | 179 | 22.361 | 20.083 | 22.552 | 1.00 | 23.60 A |
| ATOM | 898 | CA | GLU | A | 179 | 23.247 | 19.644 | 23.619 | 1.00 | 25.18 A |
| ATOM | 899 | CB | GLU | A | 179 | 22.542 | 19.770 | 24.971 | 1.00 | 27.60 A |
| ATOM | 900 | CC | GLU | A | 179 | 23.324 | 19.176 | 26.130 | 1.00 | 32.58 A |
| ATOM | 901 | CD | GLU | A | 179 | 22.997 | 19.845 | 27.449 | 1.00 | 35.82 A |
| ATOM | 902 | OE1 | GLU | A | 179 | 21.825 | 20.224 | 27.645 | 1.00 | 35.95 A |
| ATOM | 903 | OE2 | GLU | A | 179 | 23.912 | 19.984 | 28.291 | 1.00 | 38.19 A |
| ATOM | 904 | C | GLU | A | 179 | 23.808 | 18.235 | 23.450 | 1.00 | 24.08 A |
| ATOM | 905 | O | GLU | A | 179 | 24.977 | 17.989 | 23.756 | 1.00 | 22.79 A |
| ATOM | 906 | N | THR | A | 180 | 22.983 | 17.316 | 22.961 | 1.00 | 23.36 A |
| ATOM | 907 | CA | THR | A | 180 | 23.412 | 15.935 | 22.761 | 1.00 | 22.15 A |
| ATOM | 908 | CB | THR | A | 180 | 22.224 | 15.054 | 22.320 | 1.00 | 23.77 A |
| ATOM | 909 | OG1 | THR | A | 180 | 21.222 | 15.075 | 23.341 | 1.00 | 26.37 A |
| ATOM | 910 | CC2 | THR | A | 180 | 22.670 | 13.616 | 22.088 | 1.00 | 22.66 A |
| ATOM | 911 | C | THR | A | 180 | 24.533 | 15.830 | 21.724 | 1.00 | 22.01 A |
| ATOM | 912 | O | THR | A | 180 | 25.533 | 15.141 | 21.944 | 1.00 | 19.87 A |
| ATOM | 913 | N | CYS | A | 181 | 24.365 | 16.511 | 20.596 | 1.00 | 21.21 A |
| ATOM | 914 | CA | CYS | A | 181 | 25.372 | 16.480 | 19.541 | 1.00 | 22.22 A |
| ATOM | 915 | CB | CYS | A | 181 | 24.800 | 17.065 | 18.250 | 1.00 | 24.62 A |
| ATOM | 916 | SC | CYS | A | 181 | 23.435 | 16.080 | 17.560 | 1.00 | 29.50 A |
| ATOM | 917 | C | CYS | A | 181 | 26.633 | 17.232 | 19.954 | 1.00 | 23.07 A |
| ATOM | 918 | O | CYS | A | 181 | 27.746 | 16.827 | 19.608 | 1.00 | 23.95 A |
| ATOM | 919 | N | THR | A | 182 | 26.463 | 18.325 | 20.695 | 1.00 | 22.76 A |
| ATOM | 920 | CA | THR | A | 182 | 27.606 | 19.103 | 21.161 | 1.00 | 21.49 A |
| ATOM | 921 | CB | THR | A | 182 | 27.167 | 20.346 | 21.978 | 1.00 | 21.37 A |
| ATOM | 922 | OG1 | THR | A | 182 | 26.459 | 21.262 | 21.134 | 1.00 | 22.50 A |
| ATOM | 923 | CG2 | THR | A | 182 | 28.379 | 21.046 | 22.565 | 1.00 | 18.36 A |
| ATOM | 924 | C | THR | A | 182 | 28.454 | 18.215 | 22.071 | 1.00 | 21.48 A |
| ATOM | 925 | O | THR | A | 182 | 29.669 | 18.090 | 21.894 | 1.00 | 19.95 A |
| ATOM | 926 | N | ARC | A | 183 | 27.798 | 17.602 | 23.050 | 1.00 | 18.97 A |
| ATOM | 927 | CA | ARC | A | 183 | 28.468 | 16.723 | 23.996 | 1.00 | 19.39 A |
| ATOM | 928 | CB | ARC | | 183 | 27.455 | 16.140 | 24.984 | 0.50 | 19.46 AC1 |
| ATOM | 929 | CC | ARC | | 183 | 28.030 | 15.062 | 25.887 | 0.50 | 18.77 AC1 |
| ATOM | 930 | CD | ARC | | 183 | 27.021 | 14.571 | 26.925 | 0.50 | 21.19 AC1 |
| ATOM | 931 | NE | ARC | | 183 | 26.605 | 15.642 | 27.824 | 0.50 | 19.46 AC1 |
| ATOM | 932 | CZ | ARC | | 183 | 25.496 | 16.362 | 27.679 | 0.50 | 20.45 AC1 |
| ATOM | 933 | NH1 | ARC | | 183 | 24.672 | 16.123 | 26.666 | 0.50 | 19.81 AC1 |
| ATOM | 934 | NH2 | ARC | | 183 | 25.224 | 17.338 | 28.539 | 0.50 | 17.11 AC1 |
| ATOM | 935 | C | ARC | A | 183 | 29.206 | 15.577 | 23.302 | 1.00 | 20.02 A |
| ATOM | 936 | O | ARC | A | 183 | 30.383 | 15.333 | 23.573 | 1.00 | 19.97 A |
| ATOM | 937 | N | PHE | A | 184 | 28.520 | 14.871 | 22.409 | 1.00 | 19.24 A |
| ATOM | 938 | CA | PHE | A | 184 | 29.144 | 13.746 | 21.722 | 1.00 | 18.04 A |
| ATOM | 939 | CB | PHE | A | 184 | 28.158 | 13.078 | 20.764 | 1.00 | 21.05 A |
| ATOM | 940 | CC | PHE | A | 184 | 28.719 | 11.857 | 20.098 | 1.00 | 22.67 A |
| ATOM | 941 | CD1 | PHE | A | 184 | 28.717 | 10.630 | 20.754 | 1.00 | 22.97 A |
| ATOM | 942 | CD2 | PHE | A | 184 | 29.317 | 11.949 | 18.850 | 1.00 | 19.97 A |
| ATOM | 943 | CE1 | PHE | A | 184 | 29.308 | 9.510 | 20.176 | 1.00 | 23.53 A |
| ATOM | 944 | CE2 | PHE | A | 184 | 29.915 | 10.833 | 18.263 | 1.00 | 24.11 A |
| ATOM | 945 | CZ | PHE | A | 184 | 29.910 | 9.613 | 18.928 | 1.00 | 22.97 A |
| ATOM | 946 | C | PHE | A | 184 | 30.403 | 14.127 | 20.941 | 1.00 | 17.99 A |
| ATOM | 947 | O | PHE | A | 184 | 31.461 | 13.531 | 21.130 | 1.00 | 18.89 A |
| ATOM | 948 | N | TYR | A | 185 | 30.292 | 15.110 | 20.056 | 1.00 | 15.73 A |
| ATOM | 949 | CA | TYR | A | 185 | 31.443 | 15.519 | 19.265 | 1.00 | 15.72 A |
| ATOM | 950 | CB | TYR | A | 185 | 30.992 | 16.413 | 18.111 | 1.00 | 17.33 A |
| ATOM | 951 | CC | TYR | A | 185 | 30.364 | 15.584 | 17.015 | 1.00 | 19.37 A |
| ATOM | 952 | CD1 | TYR | A | 185 | 31.159 | 14.809 | 16.168 | 1.00 | 16.53 A |
| ATOM | 953 | CE1 | TYR | A | 185 | 30.590 | 13.952 | 15.232 | 1.00 | 18.12 A |
| ATOM | 954 | CD2 | TYR | A | 185 | 28.976 | 15.484 | 16.892 | 1.00 | 18.18 A |
| ATOM | 955 | CE2 | TYR | A | 185 | 28.398 | 14.623 | 15.956 | 1.00 | 18.90 A |
| ATOM | 956 | CZ | TYR | A | 185 | 29.211 | 13.861 | 15.133 | 1.00 | 18.41 A |
| ATOM | 957 | OH | TYR | A | 185 | 28.650 | 12.995 | 14.218 | 1.00 | 20.48 A |
| ATOM | 958 | C | TYR | A | 185 | 32.544 | 16.172 | 20.083 | 1.00 | 15.79 A |
| ATOM | 959 | O | TYR | A | 185 | 33.720 | 16.015 | 19.766 | 1.00 | 17.69 A |
| ATOM | 960 | N | THR | A | 186 | 32.176 | 16.887 | 21.142 | 1.00 | 15.68 A |
| ATOM | 961 | CA | THR | A | 186 | 33.184 | 17.504 | 21.997 | 1.00 | 16.03 A |
| ATOM | 962 | CB | THR | A | 186 | 32.559 | 18.403 | 23.094 | 1.00 | 16.62 A |
| ATOM | 963 | OG1 | THR | A | 186 | 31.866 | 19.503 | 22.481 | 1.00 | 14.79 A |
| ATOM | 964 | CO2 | THR | A | 186 | 33.656 | 18.953 | 24.019 | 1.00 | 14.68 A |
| ATOM | 965 | C | THR | A | 186 | 33.954 | 16.375 | 22.680 | 1.00 | 15.59 A |
| ATOM | 966 | O | THR | A | 186 | 35.176 | 16.443 | 22.823 | 1.00 | 13.77 A |
| ATOM | 967 | N | ALA | A | 187 | 33.234 | 15.333 | 23.097 | 1.00 | 14.06 A |
| ATOM | 968 | CA | ALA | A | 187 | 33.869 | 14.196 | 23.757 | 1.00 | 14.74 A |
| ATOM | 969 | CB | ALA | A | 187 | 32.810 | 13.195 | 24.224 | 1.00 | 14.32 A |

-continued

| | | | | | | | | | |
|---|---|---|---|---|---|---|---|---|---|
| ATOM | 970 | C | ALA | A | 187 | 34.875 | 13.509 | 22.821 | 1.00 14.41 A |
| ATOM | 971 | O | ALA | A | 187 | 35.972 | 13.136 | 23.247 | 1.00 15.61 A |
| ATOM | 972 | N | GLU | A | 188 | 34.516 | 13.340 | 21.549 | 1.00 14.01 A |
| ATOM | 973 | CA | GLU | A | 188 | 35.443 | 12.704 | 20.615 | 1.00 13.50 A |
| ATOM | 974 | CB | GLU | A | 188 | 34.782 | 12.449 | 19.251 | 1.00 12.85 A |
| ATOM | 975 | CO | GLU | A | 188 | 33.622 | 11.454 | 19.282 | 1.00 12.71 A |
| ATOM | 976 | CD | GLU | A | 188 | 33.464 | 10.685 | 17.979 | 1.00 15.01 A |
| ATOM | 977 | OE1 | GLU | A | 188 | 33.687 | 11.275 | 16.899 | 1.00 13.21 A |
| ATOM | 978 | OE2 | GLU | A | 188 | 33.110 | 9.484 | 18.031 | 1.00 17.69 A |
| ATOM | 979 | C | GLU | A | 188 | 36.682 | 13.582 | 20.436 | 1.00 13.34 A |
| ATOM | 980 | O | GLU | A | 188 | 37.803 | 13.085 | 20.408 | 1.00 14.69 A |
| ATOM | 981 | N | ILE | A | 189 | 36.486 | 14.893 | 20.326 | 1.00 13.52 A |
| ATOM | 982 | CA | ILE | A | 189 | 37.627 | 15.787 | 20.159 | 1.00 13.35 A |
| ATOM | 983 | CB | ILE | A | 189 | 37.169 | 17.247 | 19.939 | 1.00 13.95 A |
| ATOM | 984 | CO2 | ILE | A | 189 | 38.381 | 18.165 | 19.822 | 1.00 12.47 A |
| ATOM | 985 | CCI | ILE | A | 189 | 36.302 | 17.332 | 18.671 | 1.00 13.44 A |
| ATOM | 986 | CD1 | ILE | A | 189 | 35.588 | 18.664 | 18.491 | 1.00 14.29 A |
| ATOM | 987 | C | ILE | A | 189 | 38.530 | 15.702 | 21.394 | 1.00 14.63 A |
| ATOM | 988 | O | ILE | A | 189 | 39.753 | 15.595 | 21.271 | 1.00 12.97 A |
| ATOM | 989 | N | VAL | A | 190 | 37.927 | 15.751 | 22.582 | 1.00 14.35 A |
| ATOM | 990 | CA | VAL | A | 190 | 38.684 | 15.655 | 23.832 | 1.00 13.22 A |
| ATOM | 991 | CB | VAL | A | 190 | 37.743 | 15.690 | 25.061 | 1.00 14.28 A |
| ATOM | 992 | CCI | VAL | A | 190 | 38.509 | 15.267 | 26.326 | 1.00 15.08 A |
| ATOM | 993 | C02 | VAL | A | 190 | 37.160 | 17.082 | 25.233 | 1.00 12.08 A |
| ATOM | 994 | C | VAL | A | 190 | 39.468 | 14.338 | 23.859 | 1.00 14.61 A |
| ATOM | 995 | O | VAL | A | 190 | 40.634 | 14.304 | 24.250 | 1.00 13.72 A |
| ATOM | 996 | N | SER | A | 191 | 38.825 | 13.254 | 23.432 | 1.00 15.26 A |
| ATOM | 997 | CA | SER | A | 191 | 39.478 | 11.943 | 23.421 | 1.00 16.81 A |
| ATOM | 998 | CB | SER | | 191 | 38.470 | 10.857 | 23.041 | 0.50 16.14 AC1 |
| ATOM | 999 | OG | SER | | 191 | 39.018 | 9.569 | 23.238 | 0.50 16.94 AC1 |
| ATOM | 1000 | C | SER | A | 191 | 40.649 | 11.928 | 22.441 | 1.00 16.58 A |
| ATOM | 1001 | O | SER | A | 191 | 41.697 | 11.335 | 22.713 | 1.00 13.96 A |
| ATOM | 1002 | N | ALA | A | 192 | 40.468 | 12.586 | 21.300 | 1.00 15.26 A |
| ATOM | 1003 | CA | ALA | A | 192 | 41.518 | 12.645 | 20.292 | 1.00 14.37 A |
| ATOM | 1004 | CB | ALA | A | 192 | 40.989 | 13.296 | 19.016 | 1.00 14.43 A |
| ATOM | 1005 | C | ALA | A | 192 | 42.695 | 13.440 | 20.845 | 1.00 16.46 A |
| ATOM | 1006 | O | ALA | A | 192 | 43.851 | 13.038 | 20.697 | 1.00 17.96 A |
| ATOM | 1007 | N | LEU | A | 193 | 42.401 | 14.563 | 21.496 | 1.00 15.02 A |
| ATOM | 1008 | CA | LEU | A | 193 | 43.459 | 15.392 | 22.067 | 1.00 15.42 A |
| ATOM | 1009 | CB | LEU | A | 193 | 42.884 | 16.712 | 22.600 | 1.00 12.88 A |
| ATOM | 1010 | CO | LEU | A | 193 | 42.445 | 17.721 | 21.525 | 1.00 15.97 A |
| ATOM | 1011 | CD1 | LEU | A | 193 | 41.869 | 18.979 | 22.190 | 1.00 13.97 A |
| ATOM | 1012 | CD2 | LEU | A | 193 | 43.642 | 18.088 | 20.655 | 1.00 14.58 A |
| ATOM | 1013 | C | LEU | A | 193 | 44.211 | 14.659 | 23.174 | 1.00 14.49 A |
| ATOM | 1014 | O | LEU | A | 193 | 45.427 | 14.813 | 23.310 | 1.00 16.56 A |
| ATOM | 1015 | N | OLU | A | 194 | 43.500 | 13.870 | 23.975 | 1.00 13.96 A |
| ATOM | 1016 | CA | GLU | A | 194 | 44.179 | 13.123 | 25.032 | 1.00 14.08 A |
| ATOM | 1017 | CB | GLU | A | 194 | 43.190 | 12.295 | 25.857 | 1.00 14.65 A |
| ATOM | 1018 | CC | GLU | A | 194 | 43.882 | 11.301 | 26.789 | 1.00 17.09 A |
| ATOM | 1019 | CD | GLU | A | 194 | 42.924 | 10.592 | 27.730 | 1.00 19.59 A |
| ATOM | 1020 | OE1 | GLU | A | 194 | 41.809 | 10.237 | 27.295 | 1.00 19.25 A |
| ATOM | 1021 | OE2 | GLU | A | 194 | 43.302 | 10.380 | 28.906 | 1.00 20.20 A |
| ATOM | 1022 | C | GLU | A | 194 | 45.208 | 12.199 | 24.386 | 1.00 13.57 A |
| ATOM | 1023 | O | GLU | A | 194 | 46.337 | 12.093 | 24.847 | 1.00 14.23 A |
| ATOM | 1024 | N | TYR | A | 195 | 44.822 | 11.544 | 23.301 | 1.00 14.89 A |
| ATOM | 1025 | CA | TYR | A | 195 | 45.743 | 10.642 | 22.618 | 1.00 16.58 A |
| ATOM | 1026 | CB | TYR | A | 195 | 45.030 | 9.910 | 21.488 | 1.00 17.29 A |
| ATOM | 1027 | CC | TYR | A | 195 | 45.956 | 9.058 | 20.649 | 1.00 17.92 A |
| ATOM | 1028 | CD1 | TYR | A | 195 | 46.347 | 7.788 | 21.077 | 1.00 17.96 A |
| ATOM | 1029 | CE1 | TYR | A | 195 | 47.203 | 6.996 | 20.304 | 1.00 19.77 A |
| ATOM | 1030 | CD2 | TYR | A | 195 | 46.445 | 9.524 | 19.428 | 1.00 16.67 A |
| ATOM | 1031 | CE2 | TYR | A | 195 | 47.299 | 8.744 | 18.650 | 1.00 18.51 A |
| ATOM | 1032 | CZ | TYR | A | 195 | 47.671 | 7.481 | 19.094 | 1.00 20.24 A |
| ATOM | 1033 | OH | TYR | A | 195 | 48.506 | 6.705 | 18.325 | 1.00 21.89 A |
| ATOM | 1034 | C | TYR | A | 195 | 46.917 | 11.419 | 22.035 | 1.00 16.98 A |
| ATOM | 1035 | O | TYR | A | 195 | 48.081 | 11.047 | 22.203 | 1.00 14.61 A |
| ATOM | 1036 | N | LEU | A | 196 | 46.599 | 12.507 | 21.347 | 1.00 16.30 A |
| ATOM | 1037 | CA | LEU | A | 196 | 47.619 | 13.328 | 20.720 | 1.00 18.15 A |
| ATOM | 1038 | CB | LEU | A | 196 | 46.969 | 14.502 | 19.982 | 1.00 18.59 A |
| ATOM | 1039 | CC | LEU | A | 196 | 47.834 | 15.203 | 18.935 | 1.00 22.51 A |
| ATOM | 1040 | CD1 | LEU | A | 196 | 48.222 | 14.206 | 17.841 | 1.00 20.94 A |
| ATOM | 1041 | CD2 | LEU | A | 196 | 47.060 | 16.375 | 18.338 | 1.00 22.98 A |
| ATOM | 1042 | C | LEU | A | 196 | 48.592 | 13.844 | 21.763 | 1.00 17.75 A |
| ATOM | 1043 | O | LEU | A | 196 | 49.801 | 13.644 | 21.649 | 1.00 18.33 A |
| ATOM | 1044 | N | HIS | A | 197 | 48.064 | 14.495 | 22.792 | 1.00 17.12 A |
| ATOM | 1045 | CA | HIS | A | 197 | 48.913 | 15.042 | 23.842 | 1.00 18.47 A |
| ATOM | 1046 | CB | HIS | A | 197 | 48.069 | 15.866 | 24.817 | 1.00 15.90 A |
| ATOM | 1047 | CC | HIS | A | 197 | 47.571 | 17.152 | 24.231 | 1.00 19.15 A |
| ATOM | 1048 | CD2 | HIS | A | 197 | 47.830 | 17.745 | 23.038 | 1.00 18.22 A |

-continued

| | | | | | | | | | | |
|---|---|---|---|---|---|---|---|---|---|---|
| ATOM | 1049 | ND1 | HIS | A | 197 | 46.704 | 17.992 | 24.897 | 1.00 | 17.47 A |
| ATOM | 1050 | CE | HIS | A | 197 | 46.450 | 19.047 | 24.139 | 1.00 | 19.74 A |
| ATOM | 1051 | NE2 | HIS | A | 197 | 47.119 | 18.921 | 23.007 | 1.00 | 15.69 A |
| ATOM | 1052 | C | HIS | A | 197 | 49.696 | 13.958 | 24.572 | 1.00 | 19.40 A |
| ATOM | 1053 | O | HIS | A | 197 | 50.823 | 14.192 | 25.021 | 1.00 | 19.42 A |
| ATOM | 1054 | N | GLY | A | 198 | 49.106 | 12.770 | 24.679 | 1.00 | 18.59 A |
| ATOM | 1055 | CA | GLY | A | 198 | 49.793 | 11.675 | 25.339 | 1.00 | 19.60 A |
| ATOM | 1056 | C | GLY | A | 198 | 51.075 | 11.307 | 24.612 | 1.00 | 21.86 A |
| ATOM | 1057 | O | GLY | A | 198 | 51.963 | 10.682 | 25.186 | 1.00 | 23.09 A |
| ATOM | 1058 | N | LYS | A | 199 | 51.174 | 11.687 | 23.341 | 1.00 | 22.81 A |
| ATOM | 1059 | CA | LYS | A | 199 | 52.368 | 11.401 | 22.549 | 1.00 | 24.43 A |
| ATOM | 1060 | CB | LYS | A | 199 | 51.990 | 10.905 | 21.154 | 1.00 | 26.00 A |
| ATOM | 1061 | CC | LYS | A | 199 | 51.378 | 9.520 | 21.133 | 1.00 | 30.98 A |
| ATOM | 1062 | CD | LYS | A | 199 | 51.291 | 9.002 | 19.708 | 1.00 | 36.85 A |
| ATOM | 1063 | CE | LYS | A | 199 | 50.832 | 7.559 | 19.682 | 1.00 | 40.37 A |
| ATOM | 1064 | NZ | LYS | A | 199 | 51.646 | 6.691 | 20.581 | 1.00 | 43.48 A |
| ATOM | 1065 | C | LYS | A | 199 | 53.253 | 12.631 | 22.414 | 1.00 | 23.88 A |
| ATOM | 1066 | O | LYS | A | 199 | 54.144 | 12.669 | 21.568 | 1.00 | 24.97 A |
| ATOM | 1067 | N | GLY | A | 200 | 52.997 | 13.638 | 23.243 | 1.00 | 24.00 A |
| ATOM | 1068 | CA | GLY | A | 200 | 53.790 | 14.853 | 23.203 | 1.00 | 22.12 A |
| ATOM | 1069 | C | GLY | A | 200 | 53.665 | 15.632 | 21.907 | 1.00 | 22.14 A |
| ATOM | 1070 | O | GLY | A | 200 | 54.632 | 16.231 | 21.439 | 1.00 | 22.41 A |
| ATOM | 1071 | N | ILE | A | 201 | 52.475 | 15.630 | 21.320 | 1.00 | 20.00 A |
| ATOM | 1072 | CA | ILE | A | 201 | 52.252 | 16.355 | 20.080 | 1.00 | 18.93 A |
| ATOM | 1073 | CB | ILE | A | 201 | 51.784 | 15.414 | 18.955 | 1.00 | 19.70 A |
| ATOM | 1074 | CC2 | ILE | A | 201 | 51.414 | 16.226 | 17.716 | 1.00 | 20.12 A |
| ATOM | 1075 | CC1 | ILE | A | 201 | 52.880 | 14.395 | 18.636 | 1.00 | 20.03 A |
| ATOM | 1076 | CD1 | ILE | A | 201 | 52.408 | 13.258 | 17.745 | 1.00 | 22.75 A |
| ATOM | 1077 | C | ILE | A | 201 | 51.193 | 17.425 | 20.270 | 1.00 | 19.87 A |
| ATOM | 1078 | O | ILE | A | 201 | 50.121 | 17.161 | 20.817 | 1.00 | 20.08 A |
| ATOM | 1079 | N | ILE | A | 202 | 51.508 | 18.633 | 19.815 | 1.00 | 19.94 A |
| ATOM | 1080 | CA | ILE | A | 202 | 50.601 | 19.772 | 19.891 | 1.00 | 20.45 A |
| ATOM | 1081 | CB | ILE | A | 202 | 51.352 | 21.040 | 20.356 | 1.00 | 22.21 A |
| ATOM | 1082 | CC2 | ILE | A | 202 | 50.381 | 22.220 | 20.470 | 1.00 | 22.67 A |
| ATOM | 1083 | CC1 | ILE | A | 202 | 52.033 | 20.775 | 21.700 | 1.00 | 24.19 A |
| ATOM | 1084 | CD1 | ILE | A | 202 | 52.914 | 21.920 | 22.169 | 1.00 | 25.39 A |
| ATOM | 1085 | C | ILE | A | 202 | 50.105 | 19.999 | 18.464 | 1.00 | 20.71 A |
| ATOM | 1086 | O | ILE | A | 202 | 50.910 | 20.067 | 17.538 | 1.00 | 19.48 A |
| ATOM | 1087 | N | HIS | A | 203 | 48.795 | 20.108 | 18.270 | 1.00 | 18.65 A |
| ATOM | 1088 | CA | HIS | A | 203 | 48.280 | 20.319 | 16.919 | 1.00 | 18.02 A |
| ATOM | 1089 | CB | HIS | A | 203 | 46.775 | 20.057 | 16.874 | 1.00 | 16.31 A |
| ATOM | 1090 | CC | HIS | A | 203 | 46.199 | 20.136 | 15.495 | 1.00 | 18.36 A |
| ATOM | 1091 | CD2 | HIS | A | 203 | 46.043 | 21.186 | 14.655 | 1.00 | 16.42 A |
| ATOM | 1092 | ND1 | HIS | A | 203 | 45.759 | 19.026 | 14.806 | 1.00 | 19.50 A |
| ATOM | 1093 | CE1 | HIS | A | 203 | 45.359 | 19.389 | 13.600 | 1.00 | 17.64 A |
| ATOM | 1094 | NE2 | HIS | A | 203 | 45.522 | 20.694 | 13.483 | 1.00 | 20.87 A |
| ATOM | 1095 | C | HIS | A | 203 | 48.589 | 21.738 | 16.405 | 1.00 | 18.92 A |
| ATOM | 1096 | O | HIS | A | 203 | 49.073 | 21.906 | 15.282 | 1.00 | 16.21 A |
| ATOM | 1097 | N | ARC | A | 204 | 48.301 | 22.744 | 17.232 | 1.00 | 18.60 A |
| ATOM | 1098 | CA | ARC | A | 204 | 48.552 | 24.157 | 16.914 | 1.00 | 19.81 A |
| ATOM | 1099 | CB | ARC | A | 204 | 49.998 | 24.365 | 16.458 | 1.00 | 21.61 A |
| ATOM | 1100 | CC | ARC | A | 204 | 51.024 | 24.137 | 17.550 | 1.00 | 23.82 A |
| ATOM | 1101 | CD | ARC | A | 204 | 52.323 | 24.870 | 17.252 | 1.00 | 27.62 A |
| ATOM | 1102 | NE | ARC | A | 204 | 52.932 | 24.449 | 15.994 | 1.00 | 29.43 A |
| ATOM | 1103 | CZ | ARC | A | 204 | 54.125 | 24.861 | 15.572 | 1.00 | 33.10 A |
| ATOM | 1104 | NH1 | ARC | A | 204 | 54.835 | 25.706 | 16.311 | 1.00 | 32.12 A |
| ATOM | 1105 | NH2 | ARC | A | 204 | 54.614 | 24.426 | 14.418 | 1.00 | 30.25 A |
| ATOM | 1106 | C | ARC | A | 204 | 47.624 | 24.830 | 15.905 | 1.00 | 20.03 A |
| ATOM | 1107 | O | ARC | A | 204 | 47.711 | 26.038 | 15.698 | 1.00 | 20.88 A |
| ATOM | 1108 | N | ASP | A | 205 | 46.755 | 24.071 | 15.255 | 1.00 | 18.96 A |
| ATOM | 1109 | CA | ASP | A | 205 | 45.828 | 24.692 | 14.325 | 1.00 | 17.90 A |
| ATOM | 1110 | CB | ASP | A | 205 | 46.418 | 24.741 | 12.914 | 1.00 | 18.95 A |
| ATOM | 1111 | CC | ASP | A | 205 | 45.655 | 25.688 | 12.008 | 1.00 | 20.36 A |
| ATOM | 1112 | OD1 | ASP | A | 205 | 44.939 | 26.560 | 12.545 | 1.00 | 20.35 A |
| ATOM | 1113 | OD2 | ASP | A | 205 | 45.772 | 25.573 | 10.771 | 1.00 | 22.49 A |
| ATOM | 1114 | C | ASP | A | 205 | 44.500 | 23.956 | 14.328 | 1.00 | 19.60 A |
| ATOM | 1115 | O | ASP | A | 205 | 43.876 | 23.751 | 13.287 | 1.00 | 21.53 A |
| ATOM | 1116 | N | LEU | A | 206 | 44.063 | 23.569 | 15.521 | 1.00 | 18.53 A |
| ATOM | 1117 | CA | LEU | A | 206 | 42.813 | 22.851 | 15.667 | 1.00 | 19.18 A |
| ATOM | 1118 | CB | LEU | A | 206 | 42.693 | 22.295 | 17.087 | 1.00 | 18.94 A |
| ATOM | 1119 | CC | LEU | A | 206 | 41.511 | 21.358 | 17.346 | 1.00 | 23.10 A |
| ATOM | 1120 | CD1 | LEU | A | 206 | 41.615 | 20.142 | 16.436 | 1.00 | 23.01 A |
| ATOM | 1121 | CD2 | LEU | A | 206 | 41.504 | 20.933 | 18.808 | 1.00 | 22.97 A |
| ATOM | 1122 | C | LEU | A | 206 | 41.639 | 23.772 | 15.361 | 1.00 | 19.05 A |
| ATOM | 1123 | O | LEU | A | 206 | 41.556 | 24.880 | 15.886 | 1.00 | 19.25 A |
| ATOM | 1124 | N | LYS | A | 207 | 40.740 | 23.307 | 14.500 | 1.00 | 17.54 A |
| ATOM | 1125 | CA | LYS | A | 207 | 39.564 | 24.081 | 14.110 | 1.00 | 18.60 A |
| ATOM | 1126 | CB | LYS | A | 207 | 39.980 | 25.248 | 13.196 | 1.00 | 18.98 A |
| ATOM | 1127 | CC | LYS | A | 207 | 40.786 | 24.817 | 11.982 | 1.00 | 18.20 A |

-continued

| | | | | | | | | | |
|---|---|---|---|---|---|---|---|---|---|
| ATOM | 1128 | CD | LYS | A | 207 | 41.246 | 26.000 | 11.139 | 1.00 | 21.42 | A |
| ATOM | 1129 | CE | LYS | A | 207 | 42.223 | 25.537 | 10.062 | 1.00 | 23.21 | A |
| ATOM | 1130 | NZ | LYS | A | 207 | 42.561 | 26.604 | 9.084 | 1.00 | 29.61 | A |
| ATOM | 1131 | C | LYS | A | 207 | 38.566 | 23.181 | 13.388 | 1.00 | 18.18 | A |
| ATOM | 1132 | O | LYS | A | 207 | 38.921 | 22.100 | 12.915 | 1.00 | 18.11 | A |
| ATOM | 1133 | N | PRO | A | 208 | 37.298 | 23.614 | 13.293 | 1.00 | 20.26 | A |
| ATOM | 1134 | CD | PRO | A | 208 | 36.713 | 24.833 | 13.882 | 1.00 | 18.79 | A |
| ATOM | 1135 | CA | PRO | A | 208 | 36.272 | 22.814 | 12.616 | 1.00 | 19.67 | A |
| ATOM | 1136 | CB | PRO | A | 208 | 35.063 | 23.742 | 12.608 | 1.00 | 19.45 | A |
| ATOM | 1137 | CG | PRO | A | 208 | 35.231 | 24.509 | 13.891 | 1.00 | 21.81 | A |
| ATOM | 1138 | C | PRO | A | 208 | 36.674 | 22.372 | 11.209 | 1.00 | 21.04 | A |
| ATOM | 1139 | O | PRO | A | 208 | 36.264 | 21.307 | 10.751 | 1.00 | 21.19 | A |
| ATOM | 1140 | N | GLU | A | 209 | 37.474 | 23.188 | 10.528 | 1.00 | 21.69 | A |
| ATOM | 1141 | CA | GLU | A | 209 | 37.928 | 22.872 | 9.170 | 1.00 | 22.64 | A |
| ATOM | 1142 | CB | GLU | | 209 | 38.644 | 24.084 | 8.558 | 0.50 | 23.65 | AC1 |
| ATOM | 1143 | CG | GLU | | 209 | 39.253 | 23.825 | 7.185 | 0.50 | 27.24 | AC1 |
| ATOM | 1144 | CD | GLU | | 209 | 40.155 | 24.958 | 6.716 | 0.50 | 29.40 | AC1 |
| ATOM | 1145 | OE1 | GLU | | 209 | 39.660 | 26.094 | 6.553 | 0.50 | 29.68 | AC1 |
| ATOM | 1146 | OE2 | GLU | | 209 | 41.363 | 24.711 | 6.511 | 0.50 | 30.07 | AC1 |
| ATOM | 1147 | C | GLU | A | 209 | 38.879 | 21.668 | 9.159 | 1.00 | 22.28 | A |
| ATOM | 1148 | O | GLU | A | 209 | 38.955 | 20.933 | 8.170 | 1.00 | 21.36 | A |
| ATOM | 1149 | N | ASN | A | 210 | 39.600 | 21.490 | 10.263 | 1.00 | 19.90 | A |
| ATOM | 1150 | CA | ASN | A | 210 | 40.574 | 20.412 | 10.436 | 1.00 | 19.44 | A |
| ATOM | 1151 | CB | ASN | A | 210 | 41.744 | 20.912 | 11.287 | 1.00 | 20.07 | A |
| ATOM | 1152 | CG | ASN | A | 210 | 42.746 | 21.698 | 10.479 | 1.00 | 25.77 | A |
| ATOM | 1153 | OD1 | ASN | A | 210 | 43.571 | 22.427 | 11.029 | 1.00 | 26.73 | A |
| ATOM | 1154 | ND2 | ASN | A | 210 | 42.687 | 21.548 | 9.158 | 1.00 | 25.15 | A |
| ATOM | 1155 | C | ASN | A | 210 | 40.005 | 19.151 | 11.078 | 1.00 | 18.63 | A |
| ATOM | 1156 | O | ASN | A | 210 | 40.712 | 18.154 | 11.234 | 1.00 | 18.29 | A |
| ATOM | 1157 | N | ILE | A | 211 | 38.739 | 19.202 | 11.469 | 1.00 | 16.31 | A |
| ATOM | 1158 | CA | ILE | A | 211 | 38.090 | 18.058 | 12.085 | 1.00 | 15.49 | A |
| ATOM | 1159 | CB | ILE | A | 211 | 37.336 | 18.488 | 13.354 | 1.00 | 15.40 | A |
| ATOM | 1160 | CG2 | ILE | A | 211 | 36.582 | 17.311 | 13.950 | 1.00 | 14.59 | A |
| ATOM | 1161 | CG1 | ILE | A | 211 | 38.342 | 19.046 | 14.365 | 1.00 | 15.91 | A |
| ATOM | 1162 | CD1 | ILE | A | 211 | 37.720 | 19.669 | 15.590 | 1.00 | 15.98 | A |
| ATOM | 1163 | C | ILE | A | 211 | 37.131 | 17.485 | 11.059 | 1.00 | 17.26 | A |
| ATOM | 1164 | O | ILE | A | 211 | 35.995 | 17.947 | 10.926 | 1.00 | 16.16 | A |
| ATOM | 1165 | N | LEU | | 212 | 37.599 | 16.486 | 10.317 | 1.00 | 15.97 | A |
| ATOM | 1166 | CA | LEU | A | 212 | 36.784 | 15.875 | 9.274 | 1.00 | 17.08 | A |
| ATOM | 1167 | CB | LEU | A | 212 | 37.685 | 15.249 | 8.202 | 1.00 | 17.78 | A |
| ATOM | 1168 | CG | LEU | A | 212 | 38.785 | 16.157 | 7.640 | 1.00 | 18.92 | A |
| ATOM | 1169 | CD1 | LEU | A | 212 | 39.476 | 15.450 | 6.485 | 1.00 | 22.09 | A |
| ATOM | 1170 | CD2 | LEU | A | 212 | 38.188 | 17.482 | 7.166 | 1.00 | 19.91 | A |
| ATOM | 1171 | C | LEU | A | 212 | 35.843 | 14.825 | 9.837 | 1.00 | 18.35 | A |
| ATOM | 1172 | O | LEU | A | 212 | 35.957 | 14.433 | 11.002 | 1.00 | 19.39 | A |
| ATOM | 1173 | N | LEU | A | 213 | 34.915 | 14.368 | 9.000 | 1.00 | 17.84 | A |
| ATOM | 1174 | CA | LEU | A | 213 | 33.942 | 13.362 | 9.403 | 1.00 | 19.94 | A |
| ATOM | 1175 | CB | LEU | A | 213 | 32.556 | 14.004 | 9.487 | 1.00 | 20.84 | A |
| ATOM | 1176 | CG | LEU | A | 213 | 32.396 | 15.059 | 10.583 | 1.00 | 20.31 | A |
| ATOM | 1177 | CD1 | LEU | A | 213 | 31.124 | 15.837 | 10.367 | 1.00 | 22.75 | A |
| ATOM | 1178 | CD2 | LEU | A | 213 | 32.379 | 14.378 | 11.940 | 1.00 | 23.93 | A |
| ATOM | 1179 | C | LEU | A | 213 | 33.914 | 12.187 | 8.426 | 1.00 | 20.98 | A |
| ATOM | 1180 | O | LEU | A | 213 | 33.743 | 12.379 | 7.218 | 1.00 | 19.55 | A |
| ATOM | 1181 | N | ASN | A | 214 | 34.088 | 10.970 | 8.935 | 1.00 | 20.44 | A |
| ATOM | 1182 | CA | ASN | A | 214 | 34.055 | 9.814 | 8.049 | 1.00 | 23.77 | A |
| ATOM | 1183 | CB | ASN | A | 214 | 34.745 | 8.596 | 8.674 | 1.00 | 25.30 | A |
| ATOM | 1184 | CG | ASN | A | 214 | 34.077 | 8.127 | 9.948 | 1.00 | 32.04 | A |
| ATOM | 1185 | OD1 | ASN | A | 214 | 32.908 | 8.422 | 10.206 | 1.00 | 34.43 | A |
| ATOM | 1186 | ND2 | ASN | A | 214 | 34.818 | 7.369 | 10.752 | 1.00 | 33.85 | A |
| ATOM | 1187 | C | ASN | A | 214 | 32.618 | 9.466 | 7.693 | 1.00 | 24.07 | A |
| ATOM | 1188 | O | ASN | A | 214 | 31.672 | 10.113 | 8.150 | 1.00 | 19.94 | A |
| ATOM | 1189 | N | GLU | A | 215 | 32.459 | 8.433 | 6.879 | 1.00 | 25.77 | A |
| ATOM | 1190 | CA | GLU | A | 215 | 31.138 | 8.003 | 6.445 | 1.00 | 28.69 | A |
| ATOM | 1191 | CB | GLU | A | 215 | 31.275 | 6.796 | 5.513 | 1.00 | 31.98 | A |
| ATOM | 1192 | CG | GLU | A | 215 | 29.970 | 6.334 | 4.896 | 1.00 | 40.22 | A |
| ATOM | 1193 | CD | GLU | A | 215 | 30.182 | 5.312 | 3.795 | 1.00 | 44.27 | A |
| ATOM | 1194 | OE1 | GLU | A | 215 | 30.817 | 4.268 | 4.065 | 1.00 | 46.46 | A |
| ATOM | 1195 | OE2 | GLU | A | 215 | 29.716 | 5.556 | 2.660 | 1.00 | 46.13 | A |
| ATOM | 1196 | C | GLU | A | 215 | 30.188 | 7.673 | 7.601 | 1.00 | 28.41 | A |
| ATOM | 1197 | O | GLU | A | 215 | 28.971 | 7.769 | 7.447 | 1.00 | 28.52 | A |
| ATOM | 1198 | N | ASP | A | 216 | 30.737 | 7.287 | 8.752 | 1.00 | 26.77 | A |
| ATOM | 1199 | CA | ASP | A | 216 | 29.914 | 6.953 | 9.917 | 1.00 | 27.28 | A |
| ATOM | 1200 | CB | ASP | A | 216 | 30.538 | 5.795 | 10.696 | 1.00 | 31.27 | A |
| ATOM | 1201 | CC | ASP | A | 216 | 30.390 | 4.466 | 9.979 | 1.00 | 37.61 | A |
| ATOM | 1202 | OD1 | ASP | A | 216 | 29.274 | 4.170 | 9.499 | 1.00 | 39.45 | A |
| ATOM | 1203 | OD2 | ASP | A | 216 | 31.382 | 3.710 | 9.902 | 1.00 | 41.84 | A |
| ATOM | 1204 | C | ASP | A | 216 | 29.697 | 8.135 | 10.862 | 1.00 | 26.37 | A |
| ATOM | 1205 | O | ASP | A | 216 | 29.136 | 7.984 | 11.950 | 1.00 | 25.73 | A |
| ATOM | 1206 | N | MET | A | 217 | 30.156 | 9.306 | 10.441 | 1.00 | 23.02 | A |

-continued

| | | | | | | | | | | |
|---|---|---|---|---|---|---|---|---|---|---|
| ATOM | 1207 | CA | MET | A | 217 | 30.015 | 10.527 | 11.218 | 1.00 | 21.83 | A |
| ATOM | 1208 | CB | MET | A | 217 | 28.537 | 10.789 | 11.517 | 1.00 | 23.24 | A |
| ATOM | 1209 | CC | MET | A | 217 | 27.742 | 11.186 | 10.274 | 1.00 | 22.98 | A |
| ATOM | 1210 | SD | MET | A | 217 | 28.464 | 12.616 | 9.430 | 1.00 | 27.57 | A |
| ATOM | 1211 | CE | MET | A | 217 | 27.679 | 13.974 | 10.332 | 1.00 | 26.68 | A |
| ATOM | 1212 | C | MET | A | 217 | 30.844 | 10.618 | 12.502 | 1.00 | 21.51 | A |
| ATOM | 1213 | O | MET | A | 217 | 30.474 | 11.323 | 13.440 | 1.00 | 18.62 | A |
| ATOM | 1214 | N | HIS | A | 218 | 31.957 | 9.892 | 12.544 | 1.00 | 20.10 | A |
| ATOM | 1215 | CA | HIS | A | 218 | 32.873 | 9.964 | 13.678 | 1.00 | 19.86 | A |
| ATOM | 1216 | CB | HIS | A | 218 | 33.482 | 8.594 | 13.977 | 1.00 | 20.21 | A |
| ATOM | 1217 | CC | HIS | A | 218 | 32.551 | 7.667 | 14.698 | 1.00 | 22.40 | A |
| ATOM | 1218 | CD2 | HIS | A | 218 | 31.910 | 6.547 | 14.287 | 1.00 | 21.27 | A |
| ATOM | 1219 | ND1 | HIS | A | 218 | 32.177 | 7.863 | 16.011 | 1.00 | 19.59 | A |
| ATOM | 1220 | CE1 | HIS | A | 218 | 31.348 | 6.902 | 16.379 | 1.00 | 21.88 | A |
| ATOM | 1221 | NE2 | HIS | A | 218 | 31.168 | 6.091 | 15.351 | 1.00 | 22.08 | A |
| ATOM | 1222 | C | HIS | A | 218 | 33.947 | 10.921 | 13.172 | 1.00 | 19.10 | A |
| ATOM | 1223 | O | HIS | A | 218 | 34.170 | 11.004 | 11.965 | 1.00 | 20.31 | A |
| ATOM | 1224 | N | ILE | A | 219 | 34.617 | 11.638 | 14.067 | 1.00 | 17.21 | A |
| ATOM | 1225 | CA | ILE | A | 219 | 35.628 | 12.586 | 13.618 | 1.00 | 15.26 | A |
| ATOM | 1226 | CB | ILE | A | 219 | 35.987 | 13.614 | 14.716 | 1.00 | 15.38 | A |
| ATOM | 1227 | CC2 | ILE | A | 219 | 34.722 | 14.305 | 15.221 | 1.00 | 14.58 | A |
| ATOM | 1228 | CC1 | ILE | A | 219 | 36.734 | 12.919 | 15.864 | 1.00 | 14.46 | A |
| ATOM | 1229 | CD1 | ILE | A | 219 | 37.279 | 13.885 | 16.911 | 1.00 | 13.74 | A |
| ATOM | 1230 | C | ILE | A | 219 | 36.929 | 11.944 | 13.161 | 1.00 | 16.21 | A |
| ATOM | 1231 | O | ILE | A | 219 | 37.238 | 10.799 | 13.500 | 1.00 | 15.88 | A |
| ATOM | 1232 | N | GIN | A | 220 | 37.677 | 12.711 | 12.378 | 1.00 | 15.62 | A |
| ATOM | 1233 | CA | GIN | A | 220 | 38.980 | 12.316 | 11.876 | 1.00 | 17.84 | A |
| ATOM | 1234 | CB | GIN | A | 220 | 38.872 | 11.595 | 10.525 | 1.00 | 20.00 | A |
| ATOM | 1235 | CC | CLN | A | 220 | 38.463 | 10.129 | 10.659 | 1.00 | 26.97 | A |
| ATOM | 1236 | CD | CLN | A | 220 | 38.648 | 9.343 | 9.372 | 1.00 | 29.95 | A |
| ATOM | 1237 | OE1 | CLN | A | 220 | 37.968 | 9.590 | 8.373 | 1.00 | 33.12 | A |
| ATOM | 1238 | NE2 | CLN | A | 220 | 39.578 | 8.393 | 9.389 | 1.00 | 30.47 | A |
| ATOM | 1239 | C | CLN | A | 220 | 39.757 | 13.610 | 11.735 | 1.00 | 17.00 | A |
| ATOM | 1240 | O | CLN | A | 220 | 39.609 | 14.339 | 10.751 | 1.00 | 18.27 | A |
| ATOM | 1241 | N | ILE | A | 221 | 40.566 | 13.906 | 12.746 | 1.00 | 14.34 | A |
| ATOM | 1242 | CA | ILE | A | 221 | 41.361 | 15.120 | 12.753 | 1.00 | 14.46 | A |
| ATOM | 1243 | CB | ILE | A | 221 | 41.867 | 15.416 | 14.175 | 1.00 | 12.30 | A |
| ATOM | 1244 | CC2 | ILE | A | 221 | 42.764 | 16.656 | 14.167 | 1.00 | 14.78 | A |
| ATOM | 1245 | Cd | ILE | A | 221 | 40.660 | 15.613 | 15.102 | 1.00 | 13.92 | A |
| ATOM | 1246 | CD1 | ILE | A | 221 | 41.003 | 15.901 | 16.543 | 1.00 | 15.06 | A |
| ATOM | 1247 | C | ILE | A | 221 | 42.536 | 14.996 | 11.783 | 1.00 | 15.44 | A |
| ATOM | 1248 | O | ILE | A | 221 | 43.106 | 13.915 | 11.613 | 1.00 | 13.93 | A |
| ATOM | 1249 | N | THR | A | 222 | 42.877 | 16.101 | 11.127 | 1.00 | 15.36 | A |
| ATOM | 1250 | CA | THR | A | 222 | 43.980 | 16.098 | 10.174 | 1.00 | 17.52 | A |
| ATOM | 1251 | CB | THR | A | 222 | 43.470 | 15.836 | 8.750 | 1.00 | 19.92 | A |
| ATOM | 1252 | OG1 | THR | A | 222 | 44.587 | 15.637 | 7.875 | 1.00 | 18.78 | A |
| ATOM | 1253 | CG2 | THR | A | 222 | 42.630 | 17.018 | 8.257 | 1.00 | 18.16 | A |
| ATOM | 1254 | C | THR | A | 222 | 44.735 | 17.428 | 10.192 | 1.00 | 19.60 | A |
| ATOM | 1255 | O | THR | A | 222 | 44.509 | 18.257 | 11.084 | 1.00 | 18.59 | A |
| ATOM | 1256 | N | ASP | A | 223 | 45.630 | 17.610 | 9.216 | 1.00 | 18.69 | A |
| ATOM | 1257 | CA | ASP | A | 223 | 46.440 | 18.825 | 9.069 | 1.00 | 20.12 | A |
| ATOM | 1258 | CB | ASP | A | 223 | 45.532 | 20.065 | 9.108 | 1.00 | 23.51 | A |
| ATOM | 1259 | CG | ASP | A | 223 | 46.248 | 21.335 | 8.670 | 1.00 | 27.09 | A |
| ATOM | 1260 | OD1 | ASP | A | 223 | 47.283 | 21.227 | 7.975 | 1.00 | 26.28 | A |
| ATOM | 1261 | OD2 | ASP | A | 223 | 45.765 | 22.438 | 9.009 | 1.00 | 26.15 | A |
| ATOM | 1262 | C | ASP | A | 223 | 47.516 | 18.913 | 10.150 | 1.00 | 21.73 | A |
| ATOM | 1263 | O | ASP | A | 223 | 47.439 | 19.751 | 11.055 | 1.00 | 22.76 | A |
| ATOM | 1264 | N | PHE | A | 224 | 48.535 | 18.063 | 10.027 | 1.00 | 20.75 | A |
| ATOM | 1265 | CA | PHE | A | 224 | 49.611 | 17.988 | 11.009 | 1.00 | 20.11 | A |
| ATOM | 1266 | CB | PHE | A | 224 | 49.805 | 16.527 | 11.424 | 1.00 | 20.62 | A |
| ATOM | 1267 | CG | PHE | A | 224 | 48.682 | 15.991 | 12.263 | 1.00 | 21.41 | A |
| ATOM | 1268 | CD1 | PHE | A | 224 | 48.598 | 16.312 | 13.614 | 1.00 | 23.05 | A |
| ATOM | 1269 | CD2 | PHE | A | 224 | 47.681 | 15.212 | 11.693 | 1.00 | 22.27 | A |
| ATOM | 1270 | CE1 | PHE | A | 224 | 47.528 | 15.868 | 14.389 | 1.00 | 23.30 | A |
| ATOM | 1271 | CE2 | PHE | A | 224 | 46.606 | 14.763 | 12.457 | 1.00 | 21.11 | A |
| ATOM | 1272 | CZ | PHE | A | 224 | 46.530 | 15.093 | 13.807 | 1.00 | 22.02 | A |
| ATOM | 1273 | C | PHE | A | 224 | 50.957 | 18.583 | 10.619 | 1.00 | 20.45 | A |
| ATOM | 1274 | O | PHE | A | 224 | 51.905 | 18.547 | 11.407 | 1.00 | 20.73 | A |
| ATOM | 1275 | N | GLY | A | 225 | 51.049 | 19.125 | 9.412 | 1.00 | 22.02 | A |
| ATOM | 1276 | CA | GLY | A | 225 | 52.301 | 19.713 | 8.981 | 1.00 | 22.66 | A |
| ATOM | 1277 | C | GLY | A | 225 | 52.742 | 20.822 | 9.920 | 1.00 | 24.99 | A |
| ATOM | 1278 | O | GLY | A | 225 | 53.939 | 21.041 | 10.122 | 1.00 | 24.52 | A |
| ATOM | 1279 | N | THR | A | 226 | 51.779 | 21.524 | 10.508 | 1.00 | 23.50 | A |
| ATOM | 1280 | CA | THR | A | 226 | 52.106 | 22.613 | 11.416 | 1.00 | 25.16 | A |
| ATOM | 1281 | CB | THR | A | 226 | 51.199 | 23.829 | 11.160 | 1.00 | 24.76 | A |
| ATOM | 1282 | OG1 | THR | A | 226 | 49.831 | 23.410 | 11.113 | 1.00 | 22.68 | A |
| ATOM | 1283 | CG2 | THR | A | 226 | 51.571 | 24.490 | 9.834 | 1.00 | 25.00 | A |
| ATOM | 1284 | C | THR | A | 226 | 52.046 | 22.233 | 12.894 | 1.00 | 25.79 | A |
| ATOM | 1285 | O | THR | A | 226 | 52.019 | 23.100 | 13.768 | 1.00 | 24.54 | A |

-continued

| | | | | | | | | | | |
|---|---|---|---|---|---|---|---|---|---|---|
| ATOM | 1286 | N | ALA | A | 227 | 52.037 | 20.935 | 13.173 | 1.00 | 24.97 A |
| ATOM | 1287 | CA | ALA | A | 227 | 52.004 | 20.475 | 14.550 | 1.00 | 25.49 A |
| ATOM | 1288 | CB | ALA | A | 227 | 51.659 | 18.993 | 14.607 | 1.00 | 22.85 A |
| ATOM | 1289 | C | ALA | A | 227 | 53.384 | 20.715 | 15.149 | 1.00 | 27.70 A |
| ATOM | 1290 | O | ALA | A | 227 | 54.331 | 21.047 | 14.435 | 1.00 | 26.60 A |
| ATOM | 1291 | N | LYS | A | 228 | 53.491 | 20.558 | 16.461 | 1.00 | 28.53 A |
| ATOM | 1292 | CA | LYS | A | 228 | 54.760 | 20.745 | 17.149 | 1.00 | 32.12 A |
| ATOM | 1293 | CB | LYS | A | 228 | 54.699 | 21.974 | 18.054 | 1.00 | 33.81 A |
| ATOM | 1294 | CG | LYS | A | 228 | 56.007 | 22.294 | 18.765 | 1.00 | 41.23 A |
| ATOM | 1295 | CD | LYS | A | 228 | 57.082 | 22.725 | 17.768 | 1.00 | 47.57 A |
| ATOM | 1296 | CE | LYS | A | 228 | 58.401 | 23.056 | 18.462 | 1.00 | 49.82 A |
| ATOM | 1297 | NZ | LYS | A | 228 | 59.459 | 23.425 | 17.480 | 1.00 | 51.49 A |
| ATOM | 1298 | C | LYS | A | 228 | 55.019 | 19.504 | 17.985 | 1.00 | 33.25 A |
| ATOM | 1299 | O | LYS | A | 228 | 54.190 | 19.129 | 18.815 | 1.00 | 33.70 A |
| ATOM | 1300 | N | VAL | A | 229 | 56.159 | 18.860 | 17.756 | 1.00 | 33.64 A |
| ATOM | 1301 | CA | VAL | A | 229 | 56.516 | 17.661 | 18.501 | 1.00 | 34.66 A |
| ATOM | 1302 | CB | VAL | A | 229 | 57.248 | 16.646 | 17.609 | 1.00 | 33.50 A |
| ATOM | 1303 | CG1 | VAL | A | 229 | 57.619 | 15.419 | 18.415 | 1.00 | 32.34 A |
| ATOM | 1304 | CG2 | VAL | A | 229 | 56.370 | 16.264 | 16.436 | 1.00 | 34.25 A |
| ATOM | 1305 | C | VAL | A | 229 | 57.420 | 18.035 | 19.668 | 1.00 | 37.57 A |
| ATOM | 1306 | O | VAL | A | 229 | 58.581 | 18.392 | 19.474 | 1.00 | 35.91 A |
| ATOM | 1307 | N | LEU | A | 230 | 56.877 | 17.948 | 20.878 | 1.00 | 40.57 A |
| ATOM | 1308 | CA | LEU | A | 230 | 57.615 | 18.289 | 22.088 | 1.00 | 46.10 A |
| ATOM | 1309 | CB | LEU | A | 230 | 56.654 | 18.417 | 23.270 | 1.00 | 44.71 A |
| ATOM | 1310 | CG | LEU | A | 230 | 55.627 | 19.545 | 23.207 | 1.00 | 44.50 A |
| ATOM | 1311 | CD1 | LEU | A | 230 | 54.673 | 19.430 | 24.383 | 1.00 | 44.39 A |
| ATOM | 1312 | CD2 | LEU | A | 230 | 56.340 | 20.885 | 23.214 | 1.00 | 44.81 A |
| ATOM | 1313 | C | LEU | A | 230 | 58.695 | 17.279 | 22.440 | 1.00 | 50.42 A |
| ATOM | 1314 | O | LEU | A | 230 | 58.603 | 16.104 | 22.089 | 1.00 | 51.64 A |
| ATOM | 1315 | N | SER | A | 231 | 59.717 | 17.756 | 23.145 | 1.00 | 55.81 A |
| ATOM | 1316 | CA | SER | A | 231 | 60.824 | 16.914 | 23.583 | 1.00 | 61.14 A |
| ATOM | 1317 | CB | SER | A | 231 | 62.077 | 17.200 | 22.750 | 1.00 | 61.27 A |
| ATOM | 1318 | OG | SER | A | 231 | 62.444 | 18.568 | 22.823 | 1.00 | 62.85 A |
| ATOM | 1319 | C | SER | A | 231 | 61.124 | 17.126 | 25.071 | 1.00 | 64.65 A |
| ATOM | 1320 | O | SER | A | 231 | 61.392 | 16.164 | 25.794 | 1.00 | 65.70 A |
| ATOM | 1321 | N | PRO | A | 232 | 61.081 | 18.387 | 25.549 | 1.00 | 67.54 A |
| ATOM | 1322 | CD | PRO | A | 232 | 60.854 | 19.651 | 24.823 | 1.00 | 68.60 A |
| ATOM | 1323 | CA | PRO | A | 232 | 61.358 | 18.655 | 26.966 | 1.00 | 68.74 A |
| ATOM | 1324 | CB | PRO | A | 232 | 61.109 | 20.158 | 27.086 | 1.00 | 68.83 A |
| ATOM | 1325 | CG | PRO | A | 232 | 61.505 | 20.666 | 25.737 | 1.00 | 68.96 A |
| ATOM | 1326 | C | PRO | A | 232 | 60.460 | 17.846 | 27.899 | 1.00 | 69.17 A |
| ATOM | 1327 | O | PRO | A | 232 | 59.335 | 17.494 | 27.541 | 1.00 | 69.94 A |
| ATOM | 1328 | N | ALA | A | 237 | 57.424 | 23.198 | 27.637 | 1.00 | 80.06 A |
| ATOM | 1329 | CA | ALA | A | 237 | 56.783 | 23.047 | 26.335 | 1.00 | 79.29 A |
| ATOM | 1330 | CB | ALA | A | 237 | 55.275 | 22.907 | 26.512 | 1.00 | 78.64 A |
| ATOM | 1331 | C | ALA | A | 237 | 57.092 | 24.239 | 25.433 | 1.00 | 79.07 A |
| ATOM | 1332 | O | ALA | A | 237 | 56.250 | 25.113 | 25.249 | 1.00 | 79.47 A |
| ATOM | 1333 | N | ALA | A | 238 | 58.297 | 24.280 | 24.871 | 1.00 | 78.57 A |
| ATOM | 1334 | CA | ALA | A | 238 | 58.683 | 25.383 | 23.992 | 1.00 | 78.50 A |
| ATOM | 1335 | CB | ALA | A | 238 | 60.186 | 25.347 | 23.728 | 1.00 | 78.50 A |
| ATOM | 1336 | C | ALA | A | 238 | 57.920 | 25.327 | 22.673 | 1.00 | 78.15 A |
| ATOM | 1337 | O | ALA | A | 238 | 57.243 | 24.341 | 22.375 | 1.00 | 77.96 A |
| ATOM | 1338 | N | ALA | A | 239 | 58.027 | 26.393 | 21.887 | 1.00 | 77.28 A |
| ATOM | 1339 | CA | ALA | A | 239 | 57.338 | 26.452 | 20.603 | 1.00 | 76.27 A |
| ATOM | 1340 | CB | ALA | A | 239 | 55.849 | 26.489 | 20.827 | 1.00 | 76.61 A |
| ATOM | 1341 | C | ALA | A | 239 | 57.766 | 27.667 | 19.793 | 1.00 | 75.38 A |
| ATOM | 1342 | O | ALA | A | 239 | 58.955 | 27.955 | 19.700 | 1.00 | 75.89 A |
| ATOM | 1343 | N | ASN | A | 240 | 56.781 | 28.357 | 19.214 | 1.00 | 73.95 A |
| ATOM | 1344 | CA | ASN | A | 240 | 56.967 | 29.553 | 18.389 | 1.00 | 71.07 A |
| ATOM | 1345 | CB | ASN | A | 240 | 58.151 | 30.400 | 18.874 | 1.00 | 71.47 A |
| ATOM | 1346 | CG | ASN | A | 240 | 59.459 | 30.055 | 18.174 | 1.00 | 72.06 A |
| ATOM | 1347 | OD1 | ASN | A | 240 | 59.575 | 30.149 | 16.943 | 1.00 | 72.03 A |
| ATOM | 1348 | ND2 | ASN | A | 240 | 60.470 | 29.665 | 18.964 | 1.00 | 71.91 A |
| ATOM | 1349 | C | ASN | A | 240 | 57.188 | 29.178 | 16.928 | 1.00 | 69.41 A |
| ATOM | 1350 | O | ASN | A | 240 | 57.480 | 28.024 | 16.624 | 1.00 | 70.09 A |
| ATOM | 1351 | N | ALA | A | 241 | 57.055 | 30.165 | 16.038 | 1.00 | 66.62 A |
| ATOM | 1352 | CA | ALA | A | 241 | 57.246 | 30.013 | 14.585 | 1.00 | 63.94 A |
| ATOM | 1353 | C | ALA | A | 241 | 55.952 | 30.080 | 13.772 | 1.00 | 60.63 A |
| ATOM | 1354 | O | ALA | A | 241 | 55.840 | 30.880 | 12.845 | 1.00 | 61.29 A |
| ATOM | 1355 | CB | ALA | A | 241 | 57.979 | 28.704 | 14.246 | 1.00 | 65.23 A |
| ATOM | 1356 | N | PHE | A | 242 | 54.984 | 29.236 | 14.113 | 1.00 | 56.72 A |
| ATOM | 1357 | CA | PHE | A | 242 | 53.712 | 29.196 | 13.394 | 1.00 | 52.53 A |
| ATOM | 1358 | CB | PHE | A | 242 | 53.419 | 27.767 | 12.923 | 1.00 | 49.14 A |
| ATOM | 1359 | CG | PHE | A | 242 | 52.040 | 27.590 | 12.354 | 1.00 | 47.38 A |
| ATOM | 1360 | CD1 | PHE | A | 242 | 51.731 | 28.067 | 11.085 | 1.00 | 47.69 A |
| ATOM | 1361 | CD2 | PHE | A | 242 | 51.038 | 26.975 | 13.102 | 1.00 | 45.45 A |
| ATOM | 1362 | CE1 | PHE | A | 242 | 50.445 | 27.937 | 10.565 | 1.00 | 46.75 A |
| ATOM | 1363 | CE2 | PHE | A | 242 | 49.751 | 26.840 | 12.594 | 1.00 | 45.41 A |
| ATOM | 1364 | CZ | PHE | A | 242 | 49.453 | 27.323 | 11.322 | 1.00 | 46.55 A |

-continued

| | | | | | | | | | | |
|---|---|---|---|---|---|---|---|---|---|---|
| ATOM | 1365 | C | PHE | A | 242 | 52.534 | 29.688 | 14.229 | 1.00 | 50.08 A |
| ATOM | 1366 | O | PHE | A | 242 | 52.502 | 29.505 | 15.444 | 1.00 | 49.86 A |
| ATOM | 1367 | N | VAL | A | 243 | 51.566 | 30.305 | 13.557 | 1.00 | 47.67 A |
| ATOM | 1368 | CA | VAL | A | 243 | 50.355 | 30.809 | 14.200 | 1.00 | 46.21 A |
| ATOM | 1369 | CB | VAL | A | 243 | 50.340 | 32.352 | 14.258 | 1.00 | 47.36 A |
| ATOM | 1370 | CG1 | VAL | A | 243 | 49.012 | 32.844 | 14.825 | 1.00 | 47.54 A |
| ATOM | 1371 | CG2 | VAL | A | 243 | 51.497 | 32.842 | 15.109 | 1.00 | 48.50 A |
| ATOM | 1372 | C | VAL | A | 243 | 49.150 | 30.342 | 13.389 | 1.00 | 44.12 A |
| ATOM | 1373 | O | VAL | A | 243 | 48.956 | 30.765 | 12.247 | 1.00 | 44.46 A |
| ATOM | 1374 | N | GLY | A | 244 | 48.348 | 29.467 | 13.985 | 1.00 | 40.48 A |
| ATOM | 1375 | CA | GLY | A | 244 | 47.176 | 28.941 | 13.306 | 1.00 | 37.65 A |
| ATOM | 1376 | C | GLY | A | 244 | 46.101 | 29.960 | 12.964 | 1.00 | 35.39 A |
| ATOM | 1377 | O | GLY | A | 244 | 46.313 | 31.168 | 13.065 | 1.00 | 35.92 A |
| ATOM | 1378 | N | THR | A | 245 | 44.936 | 29.463 | 12.560 | 1.00 | 33.30 A |
| ATOM | 1379 | CA | THR | A | 245 | 43.813 | 30.312 | 12.184 | 1.00 | 30.20 A |
| ATOM | 1380 | CB | THR | A | 245 | 42.593 | 29.450 | 11.829 | 1.00 | 32.00 A |
| ATOM | 1381 | OG1 | THR | A | 245 | 42.952 | 28.573 | 10.755 | 1.00 | 32.81 A |
| ATOM | 1382 | CG2 | THR | A | 245 | 41.419 | 30.319 | 11.390 | 1.00 | 28.34 A |
| ATOM | 1383 | C | THR | A | 245 | 43.476 | 31.296 | 13.296 | 1.00 | 27.96 A |
| ATOM | 1384 | O | THR | A | 245 | 43.212 | 30.907 | 14.434 | 1.00 | 25.46 A |
| ATOM | 1385 | N | ALA | A | 246 | 43.486 | 32.576 | 12.938 | 1.00 | 25.22 A |
| ATOM | 1386 | CA | ALA | A | 246 | 43.247 | 33.675 | 13.867 | 1.00 | 23.27 A |
| ATOM | 1387 | CB | ALA | A | 246 | 42.956 | 34.955 | 13.082 | 1.00 | 22.94 A |
| ATOM | 1388 | C | ALA | A | 246 | 42.178 | 33.475 | 14.934 | 1.00 | 21.27 A |
| ATOM | 1389 | O | ALA | A | 246 | 42.431 | 33.705 | 16.114 | 1.00 | 20.93 A |
| ATOM | 1390 | N | GLN | A | 247 | 40.988 | 33.047 | 14.536 | 1.00 | 19.67 A |
| ATOM | 1391 | CA | GLN | A | 247 | 39.911 | 32.886 | 15.504 | 1.00 | 20.17 A |
| ATOM | 1392 | CB | GLN | | 247 | 38.608 | 32.535 | 14.779 | 0.50 | 21.89 AC1 |
| ATOM | 1393 | CG | GLN | | 247 | 38.522 | 33.076 | 13.355 | 0.50 | 26.18 AC1 |
| ATOM | 1394 | CD | GLN | | 247 | 37.220 | 33.794 | 13.064 | 0.50 | 27.30 AC1 |
| ATOM | 1395 | OE1 | GLN | | 247 | 36.172 | 33.447 | 13.605 | 0.50 | 30.13 AC1 |
| ATOM | 1396 | NE2 | GLN | | 247 | 37.278 | 34.792 | 12.189 | 0.50 | 28.70 AC1 |
| ATOM | 1397 | C | GLN | A | 247 | 40.181 | 31.849 | 16.595 | 1.00 | 19.43 A |
| ATOM | 1398 | O | GLN | A | 247 | 39.546 | 31.883 | 17.648 | 1.00 | 18.93 A |
| ATOM | 1399 | N | TYR | A | 248 | 41.132 | 30.948 | 16.359 | 1.00 | 18.60 A |
| ATOM | 1400 | CA | TYR | A | 248 | 41.441 | 29.896 | 17.329 | 1.00 | 19.20 A |
| ATOM | 1401 | CB | TYR | A | 248 | 41.333 | 28.529 | 16.642 | 1.00 | 17.53 A |
| ATOM | 1402 | CG | TYR | A | 248 | 40.013 | 28.362 | 15.927 | 1.00 | 19.32 A |
| ATOM | 1403 | CD1 | TYR | A | 248 | 38.859 | 28.010 | 16.625 | 1.00 | 17.69 A |
| ATOM | 1404 | CE1 | TYR | A | 248 | 37.617 | 27.976 | 15.990 | 1.00 | 18.18 A |
| ATOM | 1405 | CD2 | TYR | A | 248 | 39.897 | 28.664 | 14.569 | 1.00 | 16.87 A |
| ATOM | 1406 | CE2 | TYR | A | 248 | 38.665 | 28.635 | 13.924 | 1.00 | 19.17 A |
| ATOM | 1407 | CZ | TYR | A | 248 | 37.527 | 28.295 | 14.643 | 1.00 | 19.46 A |
| ATOM | 1408 | OH | TYR | A | 248 | 36.299 | 28.311 | 14.023 | 1.00 | 18.98 A |
| ATOM | 1409 | C | TYR | A | 248 | 42.810 | 30.039 | 17.993 | 1.00 | 20.42 A |
| ATOM | 1410 | O | TYR | A | 248 | 43.208 | 29.191 | 18.792 | 1.00 | 19.19 A |
| ATOM | 1411 | N | VAL | A | 249 | 43.523 | 31.114 | 17.673 | 1.00 | 20.20 A |
| ATOM | 1412 | CA | VAL | A | 249 | 44.841 | 31.343 | 18.251 | 1.00 | 20.91 A |
| ATOM | 1413 | CB | VAL | A | 249 | 45.542 | 32.532 | 17.570 | 1.00 | 21.18 A |
| ATOM | 1414 | CG1 | VAL | A | 249 | 46.821 | 32.896 | 18.317 | 1.00 | 22.45 A |
| ATOM | 1415 | CG2 | VAL | A | 249 | 45.862 | 32.170 | 16.139 | 1.00 | 24.01 A |
| ATOM | 1416 | C | VAL | A | 249 | 44.764 | 31.606 | 19.750 | 1.00 | 21.52 A |
| ATOM | 1417 | O | VAL | A | 249 | 43.915 | 32.368 | 20.216 | 1.00 | 22.72 A |
| ATOM | 1418 | N | SER | A | 250 | 45.654 | 30.965 | 20.503 | 1.00 | 20.70 A |
| ATOM | 1419 | CA | SER | A | 250 | 45.697 | 31.133 | 21.951 | 1.00 | 21.65 A |
| ATOM | 1420 | CB | SER | A | 250 | 46.370 | 29.919 | 22.613 | 1.00 | 22.02 A |
| ATOM | 1421 | OG | SER | A | 250 | 47.692 | 29.725 | 22.132 | 1.00 | 22.12 A |
| ATOM | 1422 | C | SER | A | 250 | 46.476 | 32.402 | 22.280 | 1.00 | 22.13 A |
| ATOM | 1423 | O | SER | A | 250 | 47.332 | 32.828 | 21.511 | 1.00 | 22.77 A |
| ATOM | 1424 | N | PRO | A | 251 | 46.180 | 33.029 | 23.425 | 1.00 | 22.23 A |
| ATOM | 1425 | CD | PRO | A | 251 | 45.163 | 32.684 | 24.433 | 1.00 | 22.97 A |
| ATOM | 1426 | CA | PRO | A | 251 | 46.893 | 34.254 | 23.800 | 1.00 | 22.52 A |
| ATOM | 1427 | CB | PRO | A | 251 | 46.233 | 34.650 | 25.127 | 1.00 | 23.06 A |
| ATOM | 1428 | CG | PRO | A | 251 | 45.726 | 33.329 | 25.676 | 1.00 | 22.55 A |
| ATOM | 1429 | C | PRO | A | 251 | 48.414 | 34.115 | 23.907 | 1.00 | 22.15 A |
| ATOM | 1430 | O | PRO | A | 251 | 49.143 | 35.047 | 23.563 | 1.00 | 22.62 A |
| ATOM | 1431 | N | GLU | A | 252 | 48.901 | 32.966 | 24.367 | 1.00 | 20.69 A |
| ATOM | 1432 | CA | GLU | A | 252 | 50.347 | 32.772 | 24.500 | 1.00 | 21.40 A |
| ATOM | 1433 | CB | GLU | A | 252 | 50.673 | 31.382 | 25.071 | 1.00 | 20.59 A |
| ATOM | 1434 | CC | GLU | A | 252 | 49.993 | 30.232 | 24.352 | 1.00 | 21.91 A |
| ATOM | 1435 | CD | GLU | A | 252 | 48.691 | 29.822 | 25.014 | 1.00 | 21.51 A |
| ATOM | 1436 | OE1 | GLU | A | 252 | 47.989 | 30.707 | 25.550 | 1.00 | 21.46 A |
| ATOM | 1437 | 0E2 | GLU | A | 252 | 48.367 | 28.613 | 24.993 | 1.00 | 20.23 A |
| ATOM | 1438 | C | GLU | A | 252 | 51.071 | 32.970 | 23.167 | 1.00 | 22.99 A |
| ATOM | 1439 | O | GLU | A | 252 | 52.191 | 33.480 | 23.136 | 1.00 | 23.17 A |
| ATOM | 1440 | N | LEU | A | 253 | 50.441 | 32.576 | 22.064 | 1.00 | 23.00 A |
| ATOM | 1441 | CA | LEU | A | 253 | 51.068 | 32.753 | 20.758 | 1.00 | 25.62 A |
| ATOM | 1442 | CB | LEU | A | 253 | 50.277 | 32.029 | 19.669 | 1.00 | 26.75 A |
| ATOM | 1443 | CC | LEU | A | 253 | 50.743 | 30.620 | 19.296 | 1.00 | 31.87 A |

-continued

| ATOM | 1444 | CD1 | LEU | A | 253 | 50.433 | 29.651 | 20.422 | 1.00 | 31.81 | A |
|------|------|-----|-----|---|-----|--------|--------|--------|------|-------|---|
| ATOM | 1445 | CD2 | LEU | A | 253 | 50.044 | 30.179 | 18.015 | 1.00 | 31.86 | A |
| ATOM | 1446 | C | LEU | A | 253 | 51.201 | 34.228 | 20.371 | 1.00 | 26.94 | A |
| ATOM | 1447 | O | LEU | A | 253 | 52.107 | 34.601 | 19.626 | 1.00 | 27.09 | A |
| ATOM | 1448 | N | LEU | A | 254 | 50.297 | 35.059 | 20.877 | 1.00 | 25.83 | A |
| ATOM | 1449 | CA | LEU | A | 254 | 50.297 | 36.485 | 20.564 | 1.00 | 27.26 | A |
| ATOM | 1450 | CB | LEU | A | 254 | 48.858 | 37.006 | 20.564 | 1.00 | 25.84 | A |
| ATOM | 1451 | CC | LEU | A | 254 | 47.882 | 36.290 | 19.621 | 1.00 | 24.69 | A |
| ATOM | 1452 | CD1 | LEU | A | 254 | 46.459 | 36.724 | 19.932 | 1.00 | 23.64 | A |
| ATOM | 1453 | CD2 | LEU | A | 254 | 48.236 | 36.597 | 18.177 | 1.00 | 24.24 | A |
| ATOM | 1454 | C | LEU | A | 254 | 51.134 | 37.314 | 21.537 | 1.00 | 30.62 | A |
| ATOM | 1455 | O | LEU | A | 254 | 51.633 | 38.383 | 21.187 | 1.00 | 32.35 | A |
| ATOM | 1456 | N | THR | A | 255 | 51.292 | 36.821 | 22.758 | 1.00 | 32.47 | A |
| ATOM | 1457 | CA | THR | A | 255 | 52.056 | 37.547 | 23.759 | 1.00 | 36.70 | A |
| ATOM | 1458 | CB | THR | A | 255 | 51.368 | 37.478 | 25.127 | 1.00 | 34.51 | A |
| ATOM | 1459 | OG1 | THR | A | 255 | 51.188 | 36.106 | 25.494 | 1.00 | 35.49 | A |
| ATOM | 1460 | CC2 | THR | A | 255 | 50.013 | 38.166 | 25.077 | 1.00 | 33.40 | A |
| ATOM | 1461 | C | THR | A | 255 | 53.477 | 37.035 | 23.910 | 1.00 | 40.09 | A |
| ATOM | 1462 | O | THR | A | 255 | 54.430 | 37.793 | 23.772 | 1.00 | 43.69 | A |
| ATOM | 1463 | N | CLU | A | 256 | 53.617 | 35.747 | 24.189 | 1.00 | 44.77 | A |
| ATOM | 1464 | CA | CLU | A | 256 | 54.932 | 35.144 | 24.382 | 1.00 | 49.15 | A |
| ATOM | 1465 | CB | CLU | A | 256 | 54.866 | 34.143 | 25.534 | 1.00 | 51.24 | A |
| ATOM | 1466 | CC | CLU | A | 256 | 54.514 | 34.786 | 26.862 | 1.00 | 56.03 | A |
| ATOM | 1467 | CD | CLU | A | 256 | 54.053 | 33.780 | 27.893 | 1.00 | 58.83 | A |
| ATOM | 1468 | OE1 | CLU | A | 256 | 54.766 | 32.776 | 28.107 | 1.00 | 62.13 | A |
| ATOM | 1469 | OE2 | CLU | A | 256 | 52.979 | 33.996 | 28.494 | 1.00 | 60.34 | A |
| ATOM | 1470 | C | CLU | A | 256 | 55.475 | 34.456 | 23.137 | 1.00 | 50.09 | A |
| ATOM | 1471 | O | CLU | A | 256 | 56.616 | 33.995 | 23.127 | 1.00 | 50.42 | A |
| ATOM | 1472 | N | LYS | A | 257 | 54.658 | 34.389 | 22.090 | 1.00 | 51.21 | A |
| ATOM | 1473 | CA | LYS | A | 257 | 55.064 | 33.746 | 20.845 | 1.00 | 51.22 | A |
| ATOM | 1474 | CB | LYS | A | 257 | 56.244 | 34.502 | 20.227 | 1.00 | 53.28 | A |
| ATOM | 1475 | CC | LYS | A | 257 | 56.558 | 34.125 | 18.790 | 1.00 | 55.19 | A |
| ATOM | 1476 | CD | LYS | A | 257 | 57.709 | 34.961 | 18.253 | 1.00 | 57.52 | A |
| ATOM | 1477 | CE | LYS | A | 257 | 57.952 | 34.694 | 16.777 | 1.00 | 58.52 | A |
| ATOM | 1478 | NZ | LYS | A | 257 | 58.290 | 33.268 | 16.515 | 1.00 | 60.88 | A |
| ATOM | 1479 | C | LYS | A | 257 | 55.467 | 32.302 | 21.138 | 1.00 | 50.74 | A |
| ATOM | 1480 | O | LYS | A | 257 | 56.432 | 31.790 | 20.577 | 1.00 | 52.26 | A |
| ATOM | 1481 | N | SER | A | 258 | 54.721 | 31.654 | 22.027 | 1.00 | 48.07 | A |
| ATOM | 1482 | CA | SER | A | 258 | 54.999 | 30.273 | 22.402 | 1.00 | 46.87 | A |
| ATOM | 1483 | CB | SER | A | 258 | 55.590 | 30.229 | 23.812 | 1.00 | 48.88 | A |
| ATOM | 1484 | OG | SER | A | 258 | 54.741 | 30.892 | 24.734 | 1.00 | 53.14 | A |
| ATOM | 1485 | C | SER | A | 258 | 53.735 | 29.415 | 22.342 | 1.00 | 44.07 | A |
| ATOM | 1486 | O | SER | A | 258 | 52.617 | 29.932 | 22.417 | 1.00 | 44.17 | A |
| ATOM | 1487 | N | ALA | A | 259 | 53.917 | 28.105 | 22.204 | 1.00 | 38.30 | A |
| ATOM | 1488 | CA | ALA | A | 259 | 52.793 | 27.180 | 22.127 | 1.00 | 34.73 | A |
| ATOM | 1489 | CB | ALA | A | 259 | 52.551 | 26.779 | 20.684 | 1.00 | 34.16 | A |
| ATOM | 1490 | C | ALA | A | 259 | 53.042 | 25.940 | 22.977 | 1.00 | 32.34 | A |
| ATOM | 1491 | O | ALA | A | 259 | 54.172 | 25.459 | 23.086 | 1.00 | 31.81 | A |
| ATOM | 1492 | N | CYS | A | 260 | 51.975 | 25.428 | 23.579 | 1.00 | 28.58 | A |
| ATOM | 1493 | CA | CYS | A | 260 | 52.056 | 24.244 | 24.425 | 1.00 | 26.27 | A |
| ATOM | 1494 | CB | CYS | A | 260 | 52.183 | 24.654 | 25.892 | 1.00 | 26.53 | A |
| ATOM | 1495 | SG | CYS | A | 260 | 50.846 | 25.739 | 26.469 | 1.00 | 32.91 | A |
| ATOM | 1496 | C | CYS | A | 260 | 50.786 | 23.435 | 24.224 | 1.00 | 22.83 | A |
| ATOM | 1497 | O | CYS | A | 260 | 49.892 | 23.856 | 23.495 | 1.00 | 22.14 | A |
| ATOM | 1498 | N | LYS | A | 261 | 50.706 | 22.277 | 24.868 | 1.00 | 20.02 | A |
| ATOM | 1499 | CA | LYS | A | 261 | 49.526 | 21.434 | 24.744 | 1.00 | 20.65 | A |
| ATOM | 1500 | CB | LYS | A | 261 | 49.619 | 20.243 | 25.696 | 1.00 | 23.28 | A |
| ATOM | 1501 | CG | LYS | A | 261 | 50.716 | 19.253 | 25.347 | 1.00 | 27.44 | A |
| ATOM | 1502 | CD | LYS | A | 261 | 50.732 | 18.117 | 26.350 | 1.00 | 29.98 | A |
| ATOM | 1503 | CE | LYS | A | 261 | 51.922 | 17.203 | 26.134 | 1.00 | 32.34 | A |
| ATOM | 1504 | NZ | LYS | A | 261 | 51.940 | 16.121 | 27.153 | 1.00 | 33.28 | A |
| ATOM | 1505 | C | LYS | A | 261 | 48.268 | 22.229 | 25.062 | 1.00 | 19.20 | A |
| ATOM | 1506 | O | LYS | A | 261 | 47.253 | 22.092 | 24.387 | 1.00 | 18.08 | A |
| ATOM | 1507 | N | SER | A | 262 | 48.358 | 23.068 | 26.089 | 1.00 | 16.92 | A |
| ATOM | 1508 | CA | SER | A | 262 | 47.235 | 23.883 | 26.534 | 1.00 | 18.13 | A |
| ATOM | 1509 | CB | SER | A | 262 | 47.644 | 24.698 | 27.770 | 1.00 | 18.27 | A |
| ATOM | 1510 | CO | SER | A | 262 | 46.517 | 25.258 | 28.421 | 1.00 | 22.53 | A |
| ATOM | 1511 | C | SER | A | 262 | 46.736 | 24.811 | 25.424 | 1.00 | 16.77 | A |
| ATOM | 1512 | O | SER | A | 262 | 45.591 | 25.254 | 25.450 | 1.00 | 15.69 | A |
| ATOM | 1513 | N | SER | A | 263 | 47.595 | 25.118 | 24.456 | 1.00 | 16.44 | A |
| ATOM | 1514 | CA | SER | A | 263 | 47.175 | 25.970 | 23.347 | 1.00 | 16.89 | A |
| ATOM | 1515 | CB | SER | A | 263 | 48.340 | 26.228 | 22.382 | 1.00 | 18.49 | A |
| ATOM | 1516 | OG | SER | A | 263 | 49.402 | 26.909 | 23.031 | 1.00 | 22.10 | A |
| ATOM | 1517 | C | SER | A | 263 | 46.040 | 25.257 | 22.612 | 1.00 | 17.79 | A |
| ATOM | 1518 | O | SER | A | 263 | 45.099 | 25.898 | 22.148 | 1.00 | 17.57 | A |
| ATOM | 1519 | N | ASP | A | 264 | 46.119 | 23.928 | 22.517 | 1.00 | 16.30 | A |
| ATOM | 1520 | CA | ASP | A | 264 | 45.069 | 23.166 | 21.836 | 1.00 | 16.72 | A |
| ATOM | 1521 | CB | ASP | A | 264 | 45.483 | 21.704 | 21.620 | 1.00 | 15.92 | A |
| ATOM | 1522 | CO | ASP | A | 264 | 46.544 | 21.539 | 20.548 | 1.00 | 17.93 | A |

-continued

| | | | | | | | | | | |
|---|---|---|---|---|---|---|---|---|---|---|
| ATOM | 1523 | OD1 | ASP | A | 264 | 46.642 | 22.412 | 19.661 | 1.00 | 16.78 A |
| ATOM | 1524 | OD2 | ASP | A | 264 | 47.265 | 20.515 | 20.579 | 1.00 | 16.64 A |
| ATOM | 1525 | C | ASP | A | 264 | 43.773 | 23.194 | 22.646 | 1.00 | 17.67 A |
| ATOM | 1526 | O | ASP | A | 264 | 42.681 | 23.197 | 22.076 | 1.00 | 18.27 A |
| ATOM | 1527 | N | LEU | A | 265 | 43.898 | 23.205 | 23.974 | 1.00 | 15.49 A |
| ATOM | 1528 | CA | LEU | A | 265 | 42.730 | 23.232 | 24.849 | 1.00 | 14.75 A |
| ATOM | 1529 | CB | LEU | A | 265 | 43.147 | 23.038 | 26.313 | 1.00 | 11.38 A |
| ATOM | 1530 | CO | LEU | A | 265 | 43.711 | 21.641 | 26.621 | 1.00 | 14.04 A |
| ATOM | 1531 | CD1 | LEU | A | 265 | 44.249 | 21.579 | 28.052 | 1.00 | 13.96 A |
| ATOM | 1532 | CD2 | LEU | A | 265 | 42.619 | 20.603 | 26.416 | 1.00 | 11.62 A |
| ATOM | 1533 | C | LEU | A | 265 | 41.999 | 24.557 | 24.675 | 1.00 | 15.13 A |
| ATOM | 1534 | O | LEU | A | 265 | 40.777 | 24.620 | 24.785 | 1.00 | 16.75 A |
| ATOM | 1535 | N | TRP | A | 266 | 42.746 | 25.622 | 24.405 | 1.00 | 16.08 A |
| ATOM | 1536 | CA | TRP | A | 266 | 42.118 | 26.918 | 24.184 | 1.00 | 16.96 A |
| ATOM | 1537 | CB | TRP | A | 266 | 43.176 | 28.015 | 24.023 | 1.00 | 17.28 A |
| ATOM | 1538 | CO | TRP | A | 266 | 42.618 | 29.326 | 23.521 | 1.00 | 20.54 A |
| ATOM | 1539 | CD2 | TRP | A | 266 | 42.313 | 30.490 | 24.301 | 1.00 | 20.07 A |
| ATOM | 1540 | CE2 | TRP | A | 266 | 41.782 | 31.459 | 23.417 | 1.00 | 20.46 A |
| ATOM | 1541 | CE3 | TRP | A | 266 | 42.435 | 30.810 | 25.660 | 1.00 | 20.68 A |
| ATOM | 1542 | CD1 | TRP | A | 266 | 42.270 | 29.631 | 22.231 | 1.00 | 19.53 A |
| ATOM | 1543 | NE1 | TRP | A | 266 | 41.769 | 30.908 | 22.163 | 1.00 | 19.61 A |
| ATOM | 1544 | CZ2 | TRP | A | 266 | 41.372 | 32.727 | 23.850 | 1.00 | 20.90 A |
| ATOM | 1545 | CZ3 | TRP | A | 266 | 42.026 | 32.073 | 26.091 | 1.00 | 19.45 A |
| ATOM | 1546 | CH2 | TRP | A | 266 | 41.501 | 33.015 | 25.185 | 1.00 | 20.71 A |
| ATOM | 1547 | C | TRP | A | 266 | 41.284 | 26.795 | 22.913 | 1.00 | 17.22 A |
| ATOM | 1548 | O | TRP | A | 266 | 40.139 | 27.240 | 22.863 | 1.00 | 18.03 A |
| ATOM | 1549 | N | ALA | A | 267 | 41.863 | 26.181 | 21.886 | 1.00 | 17.50 A |
| ATOM | 1550 | CA | ALA | A | 267 | 41.155 | 25.990 | 20.626 | 1.00 | 16.16 A |
| ATOM | 1551 | CB | ALA | A | 267 | 42.050 | 25.290 | 19.621 | 1.00 | 14.28 A |
| ATOM | 1552 | C | ALA | A | 267 | 39.901 | 25.159 | 20.891 | 1.00 | 16.28 A |
| ATOM | 1553 | O | ALA | A | 267 | 38.835 | 25.436 | 20.346 | 1.00 | 16.46 A |
| ATOM | 1554 | N | LEU | A | 268 | 40.031 | 24.144 | 21.739 | 1.00 | 16.57 A |
| ATOM | 1555 | CA | LEU | A | 268 | 38.890 | 23.299 | 22.084 | 1.00 | 17.03 A |
| ATOM | 1556 | CB | LEU | A | 268 | 39.292 | 22.260 | 23.139 | 1.00 | 15.35 A |
| ATOM | 1557 | CC | LEU | A | 268 | 38.158 | 21.429 | 23.754 | 1.00 | 19.00 A |
| ATOM | 1558 | CD1 | LEU | A | 268 | 37.505 | 20.578 | 22.678 | 1.00 | 16.17 A |
| ATOM | 1559 | CD2 | LEU | A | 268 | 38.718 | 20.537 | 24.881 | 1.00 | 17.49 A |
| ATOM | 1560 | C | LEU | A | 268 | 37.766 | 24.179 | 22.628 | 1.00 | 15.72 A |
| ATOM | 1561 | O | LEU | A | 268 | 36.603 | 24.031 | 22.247 | 1.00 | 15.28 A |
| ATOM | 1562 | N | GLY | A | 269 | 38.119 | 25.099 | 23.520 | 1.00 | 14.34 A |
| ATOM | 1563 | CA | GLY | A | 269 | 37.124 | 25.989 | 24.092 | 1.00 | 13.39 A |
| ATOM | 1564 | C | GLY | A | 269 | 36.406 | 26.808 | 23.031 | 1.00 | 14.94 A |
| ATOM | 1565 | O | GLY | A | 269 | 35.193 | 27.014 | 23.114 | 1.00 | 14.76 A |
| ATOM | 1566 | N | CYS | A | 270 | 37.146 | 27.279 | 22.030 | 1.00 | 13.86 A |
| ATOM | 1567 | CA | CYS | A | 270 | 36.539 | 28.061 | 20.958 | 1.00 | 16.80 A |
| ATOM | 1568 | CB | CYS | A | 270 | 37.611 | 28.634 | 20.023 | 1.00 | 15.97 A |
| ATOM | 1569 | SQ | CYS | A | 270 | 38.751 | 29.810 | 20.780 | 1.00 | 20.48 A |
| ATOM | 1570 | C | CYS | A | 270 | 35.598 | 27.175 | 20.140 | 1.00 | 17.50 A |
| ATOM | 1571 | O | CYS | A | 270 | 34.516 | 27.604 | 19.741 | 1.00 | 18.38 A |
| ATOM | 1572 | N | ILE | A | 271 | 36.022 | 25.939 | 19.887 | 1.00 | 16.99 A |
| ATOM | 1573 | CA | ILE | A | 271 | 35.221 | 25.004 | 19.104 | 1.00 | 16.66 A |
| ATOM | 1574 | CB | ILE | A | 271 | 36.038 | 23.741 | 18.778 | 1.00 | 16.53 A |
| ATOM | 1575 | CG2 | ILE | A | 271 | 35.155 | 22.694 | 18.102 | 1.00 | 16.34 A |
| ATOM | 1576 | Cd | ILE | A | 271 | 37.222 | 24.129 | 17.882 | 1.00 | 15.59 A |
| ATOM | 1577 | CD1 | ILE | A | 271 | 38.239 | 23.018 | 17.690 | 1.00 | 14.88 A |
| ATOM | 1578 | C | ILE | A | 271 | 33.920 | 24.626 | 19.809 | 1.00 | 16.74 A |
| ATOM | 1579 | O | ILE | A | 271 | 32.865 | 24.576 | 19.179 | 1.00 | 17.12 A |
| ATOM | 1580 | N | ILE | A | 272 | 33.990 | 24.357 | 21.111 | 1.00 | 16.13 A |
| ATOM | 1581 | CA | ILE | A | 272 | 32.785 | 24.021 | 21.862 | 1.00 | 18.30 A |
| ATOM | 1582 | CB | ILE | A | 272 | 33.097 | 23.747 | 23.346 | 1.00 | 17.77 A |
| ATOM | 1583 | CG2 | ILE | A | 272 | 31.796 | 23.666 | 24.152 | 1.00 | 17.96 A |
| ATOM | 1584 | Cd | ILE | A | 272 | 33.877 | 22.437 | 23.481 | 1.00 | 19.55 A |
| ATOM | 1585 | CD1 | ILE | A | 272 | 34.446 | 22.217 | 24.886 | 1.00 | 18.64 A |
| ATOM | 1586 | C | ILE | A | 272 | 31.824 | 25.207 | 21.776 | 1.00 | 19.51 A |
| ATOM | 1587 | O | ILE | A | 272 | 30.624 | 25.037 | 21.554 | 1.00 | 20.44 A |
| ATOM | 1588 | N | TYR | A | 273 | 32.362 | 26.409 | 21.947 | 1.00 | 18.52 A |
| ATOM | 1589 | CA | TYR | A | 273 | 31.553 | 27.615 | 21.881 | 1.00 | 20.48 A |
| ATOM | 1590 | CB | TYR | A | 273 | 32.418 | 28.847 | 22.162 | 1.00 | 18.98 A |
| ATOM | 1591 | Cd | TYR | A | 273 | 31.663 | 30.161 | 22.125 | 1.00 | 20.26 A |
| ATOM | 1592 | CD1 | TYR | A | 273 | 31.229 | 30.709 | 20.916 | 1.00 | 20.67 A |
| ATOM | 1593 | CEl | TYR | A | 273 | 30.536 | 31.917 | 20.880 | 1.00 | 20.98 A |
| ATOM | 1594 | CD2 | TYR | A | 273 | 31.383 | 30.857 | 23.302 | 1.00 | 19.82 A |
| ATOM | 1595 | CE2 | TYR | A | 273 | 30.691 | 32.062 | 23.280 | 1.00 | 20.62 A |
| ATOM | 1596 | CZ | TYR | A | 273 | 30.271 | 32.587 | 22.067 | 1.00 | 21.15 A |
| ATOM | 1597 | OH | TYR | A | 273 | 29.588 | 33.776 | 22.049 | 1.00 | 21.86 A |
| ATOM | 1598 | C | TYR | A | 273 | 30.902 | 27.730 | 20.507 | 1.00 | 21.54 A |
| ATOM | 1599 | O | TYR | A | 273 | 29.719 | 28.049 | 20.401 | 1.00 | 22.80 A |
| ATOM | 1600 | N | GLN | A | 274 | 31.676 | 27.454 | 19.461 | 1.00 | 21.05 A |
| ATOM | 1601 | CA | GLN | A | 274 | 31.176 | 27.538 | 18.095 | 1.00 | 21.48 A |

-continued

| | | | | | | | | | | |
|---|---|---|---|---|---|---|---|---|---|---|
| ATOM | 1602 | CB | GLN | A | 274 | 32.323 | 27.341 | 17.097 | 1.00 | 21.41 A |
| ATOM | 1603 | Cd | GLN | A | 274 | 31.934 | 27.596 | 15.645 | 1.00 | 23.15 A |
| ATOM | 1604 | CD | GLN | A | 274 | 33.131 | 27.588 | 14.706 | 1.00 | 24.80 A |
| ATOM | 1605 | OE1 | GLN | A | 274 | 34.276 | 27.446 | 15.139 | 1.00 | 22.51 A |
| ATOM | 1606 | NE2 | GLN | A | 274 | 32.870 | 27.750 | 13.413 | 1.00 | 22.96 A |
| ATOM | 1607 | C | GLN | A | 274 | 30.076 | 26.517 | 17.828 | 1.00 | 21.51 A |
| ATOM | 1608 | O | GLN | A | 274 | 29.123 | 26.806 | 17.108 | 1.00 | 20.50 A |
| ATOM | 1609 | N | LEU | A | 275 | 30.207 | 25.324 | 18.403 | 1.00 | 21.44 A |
| ATOM | 1610 | CA | LEU | A | 275 | 29.196 | 24.282 | 18.208 | 1.00 | 20.95 A |
| ATOM | 1611 | CB | LEU | A | 275 | 29.645 | 22.958 | 18.846 | 1.00 | 19.11 A |
| ATOM | 1612 | CG | LEU | A | 275 | 30.775 | 22.182 | 18.159 | 1.00 | 21.43 A |
| ATOM | 1613 | CD1 | LEU | A | 275 | 31.118 | 20.936 | 18.963 | 1.00 | 17.64 A |
| ATOM | 1614 | CD2 | LEU | A | 275 | 30.342 | 21.795 | 16.754 | 1.00 | 20.34 A |
| ATOM | 1615 | C | LEU | A | 275 | 27.860 | 24.697 | 18.815 | 1.00 | 21.32 A |
| ATOM | 1616 | O | LEU | A | 275 | 26.802 | 24.461 | 18.229 | 1.00 | 19.75 A |
| ATOM | 1617 | N | VAL | A | 276 | 27.921 | 25.322 | 19.987 | 1.00 | 19.10 A |
| ATOM | 1618 | CA | VAL | A | 276 | 26.724 | 25.750 | 20.702 | 1.00 | 22.47 A |
| ATOM | 1619 | CB | VAL | A | 276 | 27.011 | 25.882 | 22.217 | 1.00 | 20.87 A |
| ATOM | 1620 | CG1 | VAL | A | 276 | 25.742 | 26.291 | 22.957 | 1.00 | 19.68 A |
| ATOM | 1621 | CG2 | VAL | A | 276 | 27.550 | 24.558 | 22.766 | 1.00 | 19.43 A |
| ATOM | 1622 | C | VAL | A | 276 | 26.127 | 27.075 | 20.211 | 1.00 | 23.89 A |
| ATOM | 1623 | O | VAL | A | 276 | 24.910 | 27.199 | 20.070 | 1.00 | 24.90 A |
| ATOM | 1624 | N | ALA | A | 277 | 26.983 | 28.062 | 19.965 | 1.00 | 24.56 A |
| ATOM | 1625 | CA | ALA | A | 277 | 26.533 | 29.374 | 19.518 | 1.00 | 24.72 A |
| ATOM | 1626 | CB | ALA | A | 277 | 27.504 | 30.444 | 19.999 | 1.00 | 24.36 A |
| ATOM | 1627 | C | ALA | A | 277 | 26.378 | 29.458 | 18.005 | 1.00 | 25.76 A |
| ATOM | 1628 | O | ALA | A | 277 | 25.577 | 30.242 | 17.502 | 1.00 | 26.39 A |
| ATOM | 1629 | N | GLY | A | 278 | 27.142 | 28.651 | 17.280 | 1.00 | 25.13 A |
| ATOM | 1630 | CA | GLY | A | 278 | 27.062 | 28.673 | 15.834 | 1.00 | 25.58 A |
| ATOM | 1631 | C | GLY | A | 278 | 28.163 | 29.524 | 15.231 | 1.00 | 26.50 A |
| ATOM | 1632 | O | GLY | A | 278 | 28.374 | 29.510 | 14.015 | 1.00 | 28.17 A |
| ATOM | 1633 | N | LEU | A | 279 | 28.866 | 30.262 | 16.086 | 1.00 | 24.44 A |
| ATOM | 1634 | CA | LEU | A | 279 | 29.962 | 31.130 | 15.656 | 1.00 | 25.21 A |
| ATOM | 1635 | CB | LEU | A | 279 | 29.468 | 32.575 | 15.500 | 1.00 | 25.78 A |
| ATOM | 1636 | CG | LEU | A | 279 | 28.364 | 32.899 | 14.490 | 1.00 | 28.17 A |
| ATOM | 1637 | CD1 | LEU | A | 279 | 27.922 | 34.344 | 14.684 | 1.00 | 26.60 A |
| ATOM | 1638 | CD2 | LEU | A | 279 | 28.862 | 32.670 | 13.071 | 1.00 | 26.52 A |
| ATOM | 1639 | C | LEU | A | 279 | 31.093 | 31.116 | 16.687 | 1.00 | 23.47 A |
| ATOM | 1640 | O | LEU | A | 279 | 30.848 | 30.994 | 17.882 | 1.00 | 24.44 A |
| ATOM | 1641 | N | PRO | A | 280 | 32.349 | 31.239 | 16.236 | 1.00 | 23.35 A |
| ATOM | 1642 | CD | PRO | A | 280 | 32.831 | 31.404 | 14.855 | 1.00 | 22.26 A |
| ATOM | 1643 | CA | PRO | A | 280 | 33.464 | 31.239 | 17.189 | 1.00 | 23.81 A |
| ATOM | 1644 | CB | PRO | A | 280 | 34.692 | 31.293 | 16.282 | 1.00 | 23.24 A |
| ATOM | 1645 | CG | PRO | A | 280 | 34.189 | 32.020 | 15.073 | 1.00 | 24.89 A |
| ATOM | 1646 | C | PRO | A | 280 | 33.353 | 32.444 | 18.137 | 1.00 | 22.69 A |
| ATOM | 1647 | O | PRO | A | 280 | 32.750 | 33.457 | 17.788 | 1.00 | 22.11 A |
| ATOM | 1648 | N | PRO | A | 281 | 33.939 | 32.344 | 19.345 | 1.00 | 23.06 A |
| ATOM | 1649 | CD | PRO | A | 281 | 34.810 | 31.223 | 19.734 | 1.00 | 21.37 A |
| ATOM | 1650 | CA | PRO | A | 281 | 33.935 | 33.375 | 20.395 | 1.00 | 23.67 A |
| ATOM | 1651 | CB | PRO | A | 281 | 34.781 | 32.751 | 21.509 | 1.00 | 24.89 A |
| ATOM | 1652 | CG | PRO | A | 281 | 34.749 | 31.287 | 21.219 | 1.00 | 25.24 A |
| ATOM | 1653 | C | PRO | A | 281 | 34.481 | 34.752 | 20.017 | 1.00 | 23.75 A |
| ATOM | 1654 | O | PRO | A | 281 | 33.869 | 35.781 | 20.317 | 1.00 | 21.02 A |
| ATOM | 1655 | N | PHE | A | 282 | 35.644 | 34.763 | 19.379 | 1.00 | 22.17 A |
| ATOM | 1656 | CA | PHE | A | 282 | 36.293 | 36.007 | 18.998 | 1.00 | 23.16 A |
| ATOM | 1657 | CB | PHE | A | 282 | 37.765 | 35.943 | 19.406 | 1.00 | 21.01 A |
| ATOM | 1658 | CG | PHE | A | 282 | 37.975 | 35.482 | 20.822 | 1.00 | 22.66 A |
| ATOM | 1659 | CD1 | PHE | A | 282 | 37.806 | 36.361 | 21.888 | 1.00 | 20.06 A |
| ATOM | 1660 | CD2 | PHE | A | 282 | 38.291 | 34.151 | 21.093 | 1.00 | 20.72 A |
| ATOM | 1661 | CE1 | PHE | A | 282 | 37.947 | 35.921 | 23.206 | 1.00 | 22.66 A |
| ATOM | 1662 | CE2 | PHE | A | 282 | 38.433 | 33.702 | 22.405 | 1.00 | 20.97 A |
| ATOM | 1663 | CZ | PHE | A | 282 | 38.261 | 34.590 | 23.466 | 1.00 | 19.58 A |
| ATOM | 1664 | C | PHE | A | 282 | 36.169 | 36.263 | 17.503 | 1.00 | 24.39 A |
| ATOM | 1665 | O | PHE | A | 282 | 36.802 | 35.585 | 16.694 | 1.00 | 25.80 A |
| ATOM | 1666 | N | ARC | A | 283 | 35.355 | 37.248 | 17.142 | 1.00 | 24.99 A |
| ATOM | 1667 | CA | ARC | A | 283 | 35.141 | 37.594 | 15.741 | 1.00 | 26.33 A |
| ATOM | 1668 | CB | ARC | A | 283 | 33.721 | 37.209 | 15.316 | 1.00 | 28.91 A |
| ATOM | 1669 | CC | ARC | A | 283 | 33.293 | 35.808 | 15.724 | 1.00 | 30.27 A |
| ATOM | 1670 | CD | ARC | A | 283 | 31.904 | 35.493 | 15.188 | 1.00 | 33.36 A |
| ATOM | 1671 | NE | ARC | A | 283 | 30.890 | 36.392 | 15.733 | 1.00 | 32.76 A |
| ATOM | 1672 | CZ | ARC | A | 283 | 30.372 | 36.287 | 16.952 | 1.00 | 34.79 A |
| ATOM | 1673 | NH1 | ARC | A | 283 | 30.767 | 35.317 | 17.768 | 1.00 | 35.77 A |
| ATOM | 1674 | NH2 | ARC | A | 283 | 29.458 | 37.156 | 17.359 | 1.00 | 36.12 A |
| ATOM | 1675 | C | ARC | A | 283 | 35.328 | 39.096 | 15.544 | 1.00 | 26.47 A |
| ATOM | 1676 | O | ARC | A | 283 | 35.029 | 39.888 | 16.438 | 1.00 | 26.28 A |
| ATOM | 1677 | N | ALA | A | 284 | 35.818 | 39.486 | 14.373 | 1.00 | 26.70 A |
| ATOM | 1678 | CA | ALA | A | 284 | 36.033 | 40.899 | 14.079 | 1.00 | 27.84 A |
| ATOM | 1679 | CB | ALA | A | 284 | 37.188 | 41.442 | 14.914 | 1.00 | 26.24 A |
| ATOM | 1680 | C | ALA | A | 284 | 36.327 | 41.077 | 12.602 | 1.00 | 28.35 A |

-continued

| | | | | | | | | | | |
|---|---|---|---|---|---|---|---|---|---|---|
| ATOM | 1681 | O | ALA | A | 284 | 36.560 | 40.101 | 11.891 | 1.00 | 29.91 A |
| ATOM | 1682 | N | CLY | A | 285 | 36.332 | 42.329 | 12.153 | 1.00 | 29.29 A |
| ATOM | 1683 | CA | CLY | A | 285 | 36.577 | 42.631 | 10.753 | 1.00 | 29.52 A |
| ATOM | 1684 | C | CLY | A | 285 | 37.893 | 42.156 | 10.168 | 1.00 | 30.12 A |
| ATOM | 1685 | O | CLY | A | 285 | 37.974 | 41.862 | 8.976 | 1.00 | 30.60 A |
| ATOM | 1686 | N | ASN | A | 286 | 38.939 | 42.097 | 10.983 | 1.00 | 28.49 A |
| ATOM | 1687 | CA | ASN | A | 286 | 40.231 | 41.644 | 10.489 | 1.00 | 26.71 A |
| ATOM | 1688 | CB | ASN | A | 286 | 41.050 | 42.825 | 9.945 | 1.00 | 26.11 A |
| ATOM | 1689 | CC | ASN | A | 286 | 41.310 | 43.900 | 10.990 | 1.00 | 27.83 A |
| ATOM | 1690 | OD1 | ASN | A | 286 | 41.877 | 43.631 | 12.049 | 1.00 | 27.84 A |
| ATOM | 1691 | ND2 | ASN | A | 286 | 40.908 | 45.131 | 10.685 | 1.00 | 25.95 A |
| ATOM | 1692 | C | ASN | A | 286 | 40.997 | 40.924 | 11.584 | 1.00 | 26.03 A |
| ATOM | 1693 | O | ASN | A | 286 | 40.540 | 40.851 | 12.723 | 1.00 | 25.66 A |
| ATOM | 1694 | N | CLU | A | 287 | 42.162 | 40.391 | 11.239 | 1.00 | 24.81 A |
| ATOM | 1695 | CA | CLU | A | 287 | 42.965 | 39.662 | 12.206 | 1.00 | 27.59 A |
| ATOM | 1696 | CB | CLU | A | 287 | 44.145 | 38.985 | 11.510 | 1.00 | 30.17 A |
| ATOM | 1697 | CC | CLU | A | 287 | 43.776 | 37.632 | 10.931 | 1.00 | 38.21 A |
| ATOM | 1698 | CD | CLU | A | 287 | 44.900 | 36.998 | 10.140 | 1.00 | 41.86 A |
| ATOM | 1699 | OE1 | CLU | A | 287 | 46.061 | 37.036 | 10.608 | 1.00 | 43.08 A |
| ATOM | 1700 | 0E2 | CLU | A | 287 | 44.612 | 36.449 | 9.052 | 1.00 | 45.22 A |
| ATOM | 1701 | C | CLU | A | 287 | 43.459 | 40.485 | 13.383 | 1.00 | 25.05 A |
| ATOM | 1702 | O | CLU | A | 287 | 43.382 | 40.030 | 14.521 | 1.00 | 26.41 A |
| ATOM | 1703 | N | TYR | A | 288 | 43.966 | 41.685 | 13.122 | 1.00 | 23.04 A |
| ATOM | 1704 | CA | TYR | A | 288 | 44.460 | 42.528 | 14.205 | 1.00 | 22.34 A |
| ATOM | 1705 | CB | TYR | A | 288 | 44.867 | 43.913 | 13.691 | 1.00 | 21.07 A |
| ATOM | 1706 | CC | TYR | A | 288 | 45.275 | 44.858 | 14.805 | 1.00 | 21.07 A |
| ATOM | 1707 | CD1 | TYR | A | 288 | 46.533 | 44.762 | 15.405 | 1.00 | 21.23 A |
| ATOM | 1708 | CE1 | TYR | A | 288 | 46.891 | 45.588 | 16.475 | 1.00 | 20.43 A |
| ATOM | 1709 | CD2 | TYR | A | 288 | 44.380 | 45.809 | 15.302 | 1.00 | 22.32 A |
| ATOM | 1710 | CE2 | TYR | A | 288 | 44.725 | 46.637 | 16.373 | 1.00 | 23.28 A |
| ATOM | 1711 | CZ | TYR | A | 288 | 45.981 | 46.518 | 16.953 | 1.00 | 22.96 A |
| ATOM | 1712 | OH | TYR | A | 288 | 46.316 | 47.313 | 18.024 | 1.00 | 23.18 A |
| ATOM | 1713 | C | TYR | A | 288 | 43.402 | 42.698 | 15.288 | 1.00 | 21.38 A |
| ATOM | 1714 | O | TYR | A | 288 | 43.710 | 42.616 | 16.473 | 1.00 | 22.09 A |
| ATOM | 1715 | N | LEU | A | 289 | 42.159 | 42.939 | 14.874 | 1.00 | 21.88 A |
| ATOM | 1716 | CA | LEU | A | 289 | 41.055 | 43.130 | 15.811 | 1.00 | 21.98 A |
| ATOM | 1717 | CB | LEU | A | 289 | 39.821 | 43.673 | 15.078 | 1.00 | 22.90 A |
| ATOM | 1718 | CC | LEU | A | 289 | 39.896 | 45.130 | 14.601 | 1.00 | 26.52 A |
| ATOM | 1719 | CD1 | LEU | A | 289 | 38.706 | 45.436 | 13.696 | 1.00 | 26.55 A |
| ATOM | 1720 | CD2 | LEU | A | 289 | 39.914 | 46.071 | 15.807 | 1.00 | 23.13 A |
| ATOM | 1721 | C | LEU | A | 289 | 40.686 | 41.849 | 16.560 | 1.00 | 21.24 A |
| ATOM | 1722 | O | LEU | A | 289 | 40.256 | 41.897 | 17.715 | 1.00 | 20.72 A |
| ATOM | 1723 | N | ILE | A | 290 | 40.843 | 40.708 | 15.900 | 1.00 | 19.62 A |
| ATOM | 1724 | CA | ILE | A | 290 | 40.538 | 39.433 | 16.533 | 1.00 | 18.54 A |
| ATOM | 1725 | CB | ILE | A | 290 | 40.560 | 38.281 | 15.509 | 1.00 | 18.52 A |
| ATOM | 1726 | C02 | ILE | A | 290 | 40.503 | 36.934 | 16.234 | 1.00 | 17.63 A |
| ATOM | 1727 | CCI | ILE | A | 290 | 39.378 | 38.429 | 14.545 | 1.00 | 18.88 A |
| ATOM | 1728 | CD1 | ILE | A | 290 | 39.421 | 37.483 | 13.357 | 1.00 | 19.81 A |
| ATOM | 1729 | C | ILE | A | 290 | 41.578 | 39.167 | 17.618 | 1.00 | 19.09 A |
| ATOM | 1730 | O | ILE | A | 290 | 41.236 | 38.788 | 18.737 | 1.00 | 18.20 A |
| ATOM | 1731 | N | PHE | A | 291 | 42.849 | 39.376 | 17.286 | 1.00 | 18.76 A |
| ATOM | 1732 | CA | PHE | A | 291 | 43.925 | 39.156 | 18.247 | 1.00 | 20.75 A |
| ATOM | 1733 | CB | PHE | A | 291 | 45.286 | 39.434 | 17.606 | 1.00 | 20.71 A |
| ATOM | 1734 | CC | PHE | A | 291 | 45.644 | 38.480 | 16.503 | 1.00 | 22.92 A |
| ATOM | 1735 | CD1 | PHE | A | 291 | 45.065 | 37.214 | 16.443 | 1.00 | 22.98 A |
| ATOM | 1736 | CD2 | PHE | A | 291 | 46.588 | 38.830 | 15.543 | 1.00 | 22.91 A |
| ATOM | 1737 | CE1 | PHE | A | 291 | 45.423 | 36.310 | 15.440 | 1.00 | 24.51 A |
| ATOM | 1738 | CE2 | PHE | A | 291 | 46.954 | 37.931 | 14.535 | 1.00 | 25.54 A |
| ATOM | 1739 | CZ | PHE | A | 291 | 46.370 | 36.670 | 14.485 | 1.00 | 23.29 A |
| ATOM | 1740 | C | PHE | A | 291 | 43.739 | 40.061 | 19.451 | 1.00 | 21.72 A |
| ATOM | 1741 | O | PHE | A | 291 | 43.992 | 39.671 | 20.593 | 1.00 | 22.32 A |
| ATOM | 1742 | N | GIN | A | 292 | 43.284 | 41.275 | 19.178 | 1.00 | 23.27 A |
| ATOM | 1743 | CA | GIN | A | 292 | 43.055 | 42.264 | 20.216 | 1.00 | 24.01 A |
| ATOM | 1744 | CB | GIN | A | 292 | 42.574 | 43.559 | 19.562 | 1.00 | 25.77 A |
| ATOM | 1745 | CC | GIN | A | 292 | 42.577 | 44.773 | 20.447 | 1.00 | 28.45 A |
| ATOM | 1746 | CD | GIN | A | 292 | 42.469 | 46.057 | 19.638 | 1.00 | 29.83 A |
| ATOM | 1747 | OE1 | GIN | A | 292 | 41.520 | 46.244 | 18.872 | 1.00 | 27.16 A |
| ATOM | 1748 | NE2 | GIN | A | 292 | 43.449 | 46.944 | 19.799 | 1.00 | 27.61 A |
| ATOM | 1749 | C | GIN | A | 292 | 42.018 | 41.733 | 21.204 | 1.00 | 22.97 A |
| ATOM | 1750 | O | GIN | A | 292 | 42.200 | 41.832 | 22.415 | 1.00 | 21.64 A |
| ATOM | 1751 | N | LYS | A | 293 | 40.937 | 41.154 | 20.687 | 1.00 | 21.82 A |
| ATOM | 1752 | CA | LYS | A | 293 | 39.895 | 40.612 | 21.558 | 1.00 | 22.18 A |
| ATOM | 1753 | CB | LYS | A | 293 | 38.664 | 40.223 | 20.740 | 1.00 | 22.69 A |
| ATOM | 1754 | CC | LYS | A | 293 | 37.919 | 41.407 | 20.153 | 1.00 | 25.78 A |
| ATOM | 1755 | CD | LYS | A | 293 | 36.651 | 40.961 | 19.429 | 1.00 | 27.88 A |
| ATOM | 1756 | CE | LYS | A | 293 | 35.857 | 42.161 | 18.926 | 1.00 | 30.85 A |
| ATOM | 1757 | NZ | LYS | A | 293 | 34.612 | 41.750 | 18.214 | 1.00 | 32.98 A |
| ATOM | 1758 | C | LYS | A | 293 | 40.398 | 39.398 | 22.343 | 1.00 | 21.20 A |
| ATOM | 1759 | O | LYS | A | 293 | 40.041 | 39.204 | 23.509 | 1.00 | 22.01 A |

-continued

| ATOM | 1760 | N | ILE | A | 294 | 41.226 | 38.583 | 21.702 | 1.00 | 19.91 | A |
|---|---|---|---|---|---|---|---|---|---|---|---|
| ATOM | 1761 | CA | ILE | A | 294 | 41.774 | 37.394 | 22.347 | 1.00 | 20.28 | A |
| ATOM | 1762 | CB | ILE | A | 294 | 42.631 | 36.575 | 21.349 | 1.00 | 18.98 | A |
| ATOM | 1763 | CC2 | ILE | A | 294 | 43.481 | 35.550 | 22.098 | 1.00 | 17.70 | A |
| ATOM | 1764 | CCl | ILE | A | 294 | 41.716 | 35.897 | 20.318 | 1.00 | 17.93 | A |
| ATOM | 1765 | CD1 | ILE | A | 294 | 42.467 | 35.237 | 19.178 | 1.00 | 16.21 | A |
| ATOM | 1766 | C | ILE | A | 294 | 42.618 | 37.727 | 23.587 | 1.00 | 21.94 | A |
| ATOM | 1767 | O | ILE | A | 294 | 42.366 | 37.199 | 24.673 | 1.00 | 20.86 | A |
| ATOM | 1768 | N | ILE | A | 295 | 43.610 | 38.600 | 23.439 | 1.00 | 21.88 | A |
| ATOM | 1769 | CA | ILE | A | 295 | 44.461 | 38.934 | 24.582 | 1.00 | 24.25 | A |
| ATOM | 1770 | CB | ILE | A | 295 | 45.668 | 39.805 | 24.175 | 1.00 | 23.93 | A |
| ATOM | 1771 | CC2 | ILE | A | 295 | 46.514 | 39.066 | 23.140 | 1.00 | 24.61 | A |
| ATOM | 1772 | CCl | ILE | A | 295 | 45.189 | 41.151 | 23.637 | 1.00 | 24.58 | A |
| ATOM | 1773 | CD1 | ILE | A | 295 | 46.317 | 42.149 | 23.433 | 1.00 | 26.69 | A |
| ATOM | 1774 | C | ILE | A | 295 | 43.720 | 39.636 | 25.717 | 1.00 | 24.80 | A |
| ATOM | 1775 | O | ILE | A | 295 | 44.214 | 39.687 | 26.842 | 1.00 | 24.76 | A |
| ATOM | 1776 | N | LYS | A | 296 | 42.539 | 40.173 | 25.425 | 1.00 | 25.33 | A |
| ATOM | 1777 | CA | LYS | A | 296 | 41.743 | 40.853 | 26.444 | 1.00 | 26.80 | A |
| ATOM | 1778 | CB | LYS | A | 296 | 41.178 | 42.170 | 25.894 | 1.00 | 27.39 | A |
| ATOM | 1779 | CC | LYS | A | 296 | 42.240 | 43.141 | 25.413 | 1.00 | 31.79 | A |
| ATOM | 1780 | CD | LYS | A | 296 | 41.634 | 44.410 | 24.826 | 1.00 | 35.56 | A |
| ATOM | 1781 | CE | LYS | A | 296 | 41.009 | 45.283 | 25.900 | 1.00 | 39.29 | A |
| ATOM | 1782 | NZ | LYS | A | 296 | 40.564 | 46.603 | 25.357 | 1.00 | 41.72 | A |
| ATOM | 1783 | C | LYS | A | 296 | 40.593 | 39.958 | 26.893 | 1.00 | 25.50 | A |
| ATOM | 1784 | O | LYS | A | 296 | 39.770 | 40.361 | 27.713 | 1.00 | 24.02 | A |
| ATOM | 1785 | N | LEU | A | 297 | 40.550 | 38.742 | 26.349 | 1.00 | 25.67 | A |
| ATOM | 1786 | CA | LEU | A | 297 | 39.500 | 37.777 | 26.666 | 1.00 | 25.16 | A |
| ATOM | 1787 | CB | LEU | A | 297 | 39.632 | 37.285 | 28.111 | 1.00 | 24.80 | A |
| ATOM | 1788 | CG | LEU | A | 297 | 38.766 | 36.068 | 28.460 | 1.00 | 26.43 | A |
| ATOM | 1789 | CD1 | LEU | A | 297 | 39.238 | 34.852 | 27.646 | 1.00 | 26.70 | A |
| ATOM | 1790 | CD2 | LEU | A | 297 | 38.856 | 35.777 | 29.951 | 1.00 | 24.84 | A |
| ATOM | 1791 | C | LEU | A | 297 | 38.151 | 38.459 | 26.467 | 1.00 | 25.11 | A |
| ATOM | 1792 | O | LEU | A | 297 | 37.261 | 38.378 | 27.309 | 1.00 | 25.28 | A |
| ATOM | 1793 | N | GLU | A | 298 | 38.007 | 39.127 | 25.331 | 1.00 | 24.98 | A |
| ATOM | 1794 | CA | GLU | A | 298 | 36.786 | 39.847 | 25.023 | 1.00 | 25.31 | A |
| ATOM | 1795 | CB | GLU | A | 298 | 37.143 | 41.139 | 24.291 | 1.00 | 27.13 | A |
| ATOM | 1796 | CG | GLU | A | 298 | 35.991 | 42.092 | 24.108 | 1.00 | 31.28 | A |
| ATOM | 1797 | CD | GLU | A | 298 | 36.419 | 43.362 | 23.410 | 1.00 | 34.40 | A |
| ATOM | 1798 | OE1 | GLU | A | 298 | 37.348 | 44.027 | 23.918 | 1.00 | 35.90 | A |
| ATOM | 1799 | OE2 | GLU | A | 298 | 35.832 | 43.693 | 22.359 | 1.00 | 36.16 | A |
| ATOM | 1800 | C | GLU | A | 298 | 35.766 | 39.057 | 24.207 | 1.00 | 23.79 | A |
| ATOM | 1801 | O | GLU | A | 298 | 35.832 | 39.017 | 22.979 | 1.00 | 24.35 | A |
| ATOM | 1802 | N | TYR | A | 299 | 34.825 | 38.427 | 24.902 | 1.00 | 23.45 | A |
| ATOM | 1803 | CA | TYR | A | 299 | 33.760 | 37.663 | 24.265 | 1.00 | 23.98 | A |
| ATOM | 1804 | CB | TYR | A | 299 | 34.264 | 36.304 | 23.755 | 1.00 | 20.13 | A |
| ATOM | 1805 | CG | TYR | A | 299 | 34.348 | 35.233 | 24.828 | 1.00 | 21.17 | A |
| ATOM | 1806 | CD1 | TYR | A | 299 | 35.336 | 35.279 | 25.810 | 1.00 | 19.32 | A |
| ATOM | 1807 | CEl | TYR | A | 299 | 35.389 | 34.332 | 26.826 | 1.00 | 19.30 | A |
| ATOM | 1808 | CD2 | TYR | A | 299 | 33.410 | 34.201 | 24.888 | 1.00 | 18.96 | A |
| ATOM | 1809 | CE2 | TYR | A | 299 | 33.456 | 33.243 | 25.907 | 1.00 | 19.41 | A |
| ATOM | 1810 | CZ | TYR | A | 299 | 34.449 | 33.321 | 26.870 | 1.00 | 18.79 | A |
| ATOM | 1811 | OH | TYR | A | 299 | 34.511 | 32.401 | 27.881 | 1.00 | 18.77 | A |
| ATOM | 1812 | C | TYR | A | 299 | 32.699 | 37.437 | 25.331 | 1.00 | 25.20 | A |
| ATOM | 1813 | O | TYR | A | 299 | 32.942 | 37.681 | 26.506 | 1.00 | 26.46 | A |
| ATOM | 1814 | N | ASP | A | 300 | 31.522 | 36.981 | 24.927 | 1.00 | 26.94 | A |
| ATOM | 1815 | CA | ASP | A | 300 | 30.467 | 36.710 | 25.891 | 1.00 | 30.60 | A |
| ATOM | 1816 | CB | ASP | A | 300 | 29.665 | 37.981 | 26.179 | 1.00 | 35.86 | A |
| ATOM | 1817 | CG | ASP | A | 300 | 29.228 | 38.687 | 24.923 | 1.00 | 42.04 | A |
| ATOM | 1818 | ODi | ASP | A | 300 | 28.450 | 38.088 | 24.149 | 1.00 | 45.98 | A |
| ATOM | 1819 | 0D2 | ASP | A | 300 | 29.666 | 39.840 | 24.707 | 1.00 | 45.69 | A |
| ATOM | 1820 | C | ASP | A | 300 | 29.564 | 35.608 | 25.363 | 1.00 | 29.26 | A |
| ATOM | 1821 | O | ASP | A | 300 | 29.590 | 35.299 | 24.172 | 1.00 | 28.64 | A |
| ATOM | 1822 | N | PHE | A | 301 | 28.778 | 35.011 | 26.253 | 1.00 | 28.96 | A |
| ATOM | 1823 | CA | PHE | A | 301 | 27.884 | 33.924 | 25.871 | 1.00 | 30.48 | A |
| ATOM | 1824 | CB | PHE | A | 301 | 27.818 | 32.854 | 26.968 | 1.00 | 29.17 | A |
| ATOM | 1825 | CG | PHE | A | 301 | 29.147 | 32.279 | 27.356 | 1.00 | 29.29 | A |
| ATOM | 1826 | CD1 | PHE | A | 301 | 29.978 | 32.949 | 28.245 | 1.00 | 27.31 | A |
| ATOM | 1827 | CD2 | PHE | A | 301 | 29.560 | 31.050 | 26.845 | 1.00 | 27.89 | A |
| ATOM | 1828 | CEl | PHE | A | 301 | 31.205 | 32.403 | 28.625 | 1.00 | 28.83 | A |
| ATOM | 1829 | CE2 | PHE | A | 301 | 30.781 | 30.498 | 27.217 | 1.00 | 28.05 | A |
| ATOM | 1830 | CZ | PHE | A | 301 | 31.605 | 31.175 | 28.110 | 1.00 | 28.27 | A |
| ATOM | 1831 | C | PHE | A | 301 | 26.459 | 34.384 | 25.619 | 1.00 | 32.20 | A |
| ATOM | 1832 | O | PHE | A | 301 | 25.946 | 35.261 | 26.317 | 1.00 | 32.36 | A |
| ATOM | 1833 | N | PRO | A | 302 | 25.798 | 33.804 | 24.607 | 1.00 | 33.29 | A |
| ATOM | 1834 | CD | PRO | A | 302 | 26.313 | 32.943 | 23.529 | 1.00 | 34.04 | A |
| ATOM | 1835 | CA | PRO | A | 302 | 24.415 | 34.199 | 24.341 | 1.00 | 35.24 | A |
| ATOM | 1836 | CB | PRO | A | 302 | 24.144 | 33.608 | 22.959 | 1.00 | 34.01 | A |
| ATOM | 1837 | CG | PRO | A | 302 | 25.041 | 32.413 | 22.921 | 1.00 | 35.48 | A |
| ATOM | 1838 | C | PRO | A | 302 | 23.567 | 33.561 | 25.444 | 1.00 | 37.39 | A |

-continued

| | | | | | | | | | | |
|---|---|---|---|---|---|---|---|---|---|---|
| ATOM | 1839 | O | PRO | A | 302 | 23.935 | 32.518 | 25.986 | 1.00 | 38.49 A |
| ATOM | 1840 | N | ALA | A | 303 | 22.447 | 34.188 | 25.783 | 1.00 | 39.36 A |
| ATOM | 1841 | CA | ALA | A | 303 | 21.572 | 33.692 | 26.843 | 1.00 | 40.65 A |
| ATOM | 1842 | CB | ALA | A | 303 | 20.280 | 34.506 | 26.862 | 1.00 | 41.66 A |
| ATOM | 1843 | C | ALA | A | 303 | 21.238 | 32.197 | 26.814 | 1.00 | 41.25 A |
| ATOM | 1844 | O | ALA | A | 303 | 21.253 | 31.537 | 27.854 | 1.00 | 43.16 A |
| ATOM | 1845 | N | ALA | A | 304 | 20.945 | 31.665 | 25.631 | 1.00 | 41.04 A |
| ATOM | 1846 | CA | ALA | A | 304 | 20.569 | 30.258 | 25.480 | 1.00 | 40.66 A |
| ATOM | 1847 | CB | ALA | A | 304 | 20.121 | 30.004 | 24.040 | 1.00 | 41.36 A |
| ATOM | 1848 | C | ALA | A | 304 | 21.628 | 29.223 | 25.876 | 1.00 | 39.61 A |
| ATOM | 1849 | O | ALA | A | 304 | 21.298 | 28.156 | 26.395 | 1.00 | 40.61 A |
| ATOM | 1850 | N | PHE | A | 305 | 22.891 | 29.543 | 25.617 | 1.00 | 36.21 A |
| ATOM | 1851 | CA | PHE | A | 305 | 24.022 | 28.662 | 25.909 | 1.00 | 32.08 A |
| ATOM | 1852 | CB | PHE | A | 305 | 25.259 | 29.519 | 26.187 | 1.00 | 29.46 A |
| ATOM | 1853 | CG | PHE | A | 305 | 26.536 | 28.917 | 25.690 | 1.00 | 28.15 A |
| ATOM | 1854 | CD1 | PHE | A | 305 | 27.146 | 27.875 | 26.377 | 1.00 | 26.20 A |
| ATOM | 1855 | CD2 | PHE | A | 305 | 27.127 | 29.386 | 24.521 | 1.00 | 27.05 A |
| ATOM | 1856 | CE1 | PHE | A | 305 | 28.330 | 27.308 | 25.908 | 1.00 | 26.92 A |
| ATOM | 1857 | CE2 | PHE | A | 305 | 28.312 | 28.826 | 24.042 | 1.00 | 26.62 A |
| ATOM | 1858 | CZ | PHE | A | 305 | 28.914 | 27.786 | 24.737 | 1.00 | 26.61 A |
| ATOM | 1859 | C | PHE | A | 305 | 23.811 | 27.664 | 27.057 | 1.00 | 30.09 A |
| ATOM | 1860 | O | PHE | A | 305 | 23.518 | 28.051 | 28.187 | 1.00 | 31.51 A |
| ATOM | 1861 | N | PHE | A | 306 | 23.964 | 26.378 | 26.758 | 1.00 | 27.01 A |
| ATOM | 1862 | CA | PHE | A | 306 | 23.801 | 25.334 | 27.769 | 1.00 | 26.30 A |
| ATOM | 1863 | CB | PHE | A | 306 | 24.157 | 23.970 | 27.170 | 1.00 | 25.03 A |
| ATOM | 1864 | CG | PHE | A | 306 | 23.548 | 23.725 | 25.815 | 1.00 | 27.24 A |
| ATOM | 1865 | CD1 | PHE | A | 306 | 22.170 | 23.831 | 25.622 | 1.00 | 28.40 A |
| ATOM | 1866 | CD2 | PHE | A | 306 | 24.350 | 23.386 | 24.728 | 1.00 | 27.84 A |
| ATOM | 1867 | CE1 | PHE | A | 306 | 21.601 | 23.603 | 24.365 | 1.00 | 28.05 A |
| ATOM | 1868 | CE2 | PHE | A | 306 | 23.792 | 23.155 | 23.465 | 1.00 | 28.31 A |
| ATOM | 1869 | CZ | PHE | A | 306 | 22.415 | 23.263 | 23.283 | 1.00 | 28.00 A |
| ATOM | 1870 | C | PHE | A | 306 | 24.711 | 25.652 | 28.961 | 1.00 | 26.23 A |
| ATOM | 1871 | O | PHE | A | 306 | 25.927 | 25.775 | 28.811 | 1.00 | 25.59 A |
| ATOM | 1872 | N | PRO | A | 307 | 24.125 | 25.796 | 30.163 | 1.00 | 26.67 A |
| ATOM | 1873 | CD | PRO | A | 307 | 22.685 | 25.625 | 30.430 | 1.00 | 27.95 A |
| ATOM | 1874 | CA | PRO | A | 307 | 24.842 | 26.110 | 31.405 | 1.00 | 26.59 A |
| ATOM | 1875 | CB | PRO | A | 307 | 23.795 | 25.832 | 32.481 | 1.00 | 26.14 A |
| ATOM | 1876 | CG | PRO | A | 307 | 22.531 | 26.250 | 31.803 | 1.00 | 27.86 A |
| ATOM | 1877 | C | PRO | A | 307 | 26.145 | 25.355 | 31.659 | 1.00 | 25.58 A |
| ATOM | 1878 | O | PRO | A | 307 | 27.189 | 25.964 | 31.900 | 1.00 | 22.65 A |
| ATOM | 1879 | N | LYS | A | 308 | 26.085 | 24.031 | 31.620 | 1.00 | 24.46 A |
| ATOM | 1880 | CA | LYS | A | 308 | 27.274 | 23.232 | 31.867 | 1.00 | 23.91 A |
| ATOM | 1881 | CB | LYS | A | 308 | 26.887 | 21.760 | 32.024 | 1.00 | 23.25 A |
| ATOM | 1882 | CG | LYS | A | 308 | 26.062 | 21.532 | 33.285 | 1.00 | 28.49 A |
| ATOM | 1883 | CD | LYS | A | 308 | 25.618 | 20.093 | 33.466 | 1.00 | 30.17 A |
| ATOM | 1884 | CE | LYS | A | 308 | 24.760 | 19.973 | 34.722 | 1.00 | 33.12 A |
| ATOM | 1885 | NZ | LYS | A | 308 | 24.122 | 18.636 | 34.860 | 1.00 | 34.13 A |
| ATOM | 1886 | C | LYS | A | 308 | 28.314 | 23.426 | 30.769 | 1.00 | 22.84 A |
| ATOM | 1887 | O | LYS | A | 308 | 29.514 | 23.411 | 31.042 | 1.00 | 22.46 A |
| ATOM | 1888 | N | ALA | A | 309 | 27.861 | 23.621 | 29.534 | 1.00 | 21.59 A |
| ATOM | 1889 | CA | ALA | A | 309 | 28.792 | 23.848 | 28.432 | 1.00 | 20.02 A |
| ATOM | 1890 | CB | ALA | A | 309 | 28.056 | 23.856 | 27.106 | 1.00 | 18.80 A |
| ATOM | 1891 | C | ALA | A | 309 | 29.481 | 25.191 | 28.662 | 1.00 | 21.41 A |
| ATOM | 1892 | O | ALA | A | 309 | 30.680 | 25.335 | 28.427 | 1.00 | 21.39 A |
| ATOM | 1893 | N | ARG | A | 310 | 28.717 | 26.179 | 29.121 | 1.00 | 21.39 A |
| ATOM | 1894 | CA | ARG | A | 310 | 29.290 | 27.494 | 29.388 | 1.00 | 22.02 A |
| ATOM | 1895 | CB | ARG | A | 310 | 28.213 | 28.479 | 29.854 | 1.00 | 22.39 A |
| ATOM | 1896 | CG | ARG | A | 310 | 28.806 | 29.756 | 30.436 | 1.00 | 25.30 A |
| ATOM | 1897 | CD | ARG | A | 310 | 27.780 | 30.852 | 30.664 | 1.00 | 28.33 A |
| ATOM | 1898 | NE | ARG | A | 310 | 28.420 | 32.039 | 31.230 | 1.00 | 30.18 A |
| ATOM | 1899 | CZ | ARG | A | 310 | 27.901 | 33.263 | 31.203 | 1.00 | 32.07 A |
| ATOM | 1900 | NH1 | ARG | A | 310 | 26.719 | 33.477 | 30.634 | 1.00 | 31.19 A |
| ATOM | 1901 | NH2 | ARG | A | 310 | 28.567 | 34.277 | 31.742 | 1.00 | 30.49 A |
| ATOM | 1902 | C | ARG | A | 310 | 30.376 | 27.388 | 30.458 | 1.00 | 21.65 A |
| ATOM | 1903 | O | ARG | A | 310 | 31.464 | 27.949 | 30.311 | 1.00 | 20.36 A |
| ATOM | 1904 | N | ASP | A | 311 | 30.074 | 26.677 | 31.541 | 1.00 | 19.57 A |
| ATOM | 1905 | CA | ASP | A | 311 | 31.043 | 26.512 | 32.615 | 1.00 | 20.18 A |
| ATOM | 1906 | CB | ASP | A | 311 | 30.460 | 25.649 | 33.739 | 1.00 | 20.39 A |
| ATOM | 1907 | CG | ASP | A | 311 | 31.439 | 25.446 | 34.881 | 1.00 | 23.35 A |
| ATOM | 1908 | OD1 | ASP | A | 311 | 32.158 | 24.428 | 34.885 | 1.00 | 24.91 A |
| ATOM | 1909 | OD2 | ASP | A | 311 | 31.500 | 26.312 | 35.776 | 1.00 | 26.96 A |
| ATOM | 1910 | C | ASP | A | 311 | 32.322 | 25.877 | 32.073 | 1.00 | 19.73 A |
| ATOM | 1911 | O | ASP | A | 311 | 33.422 | 26.289 | 32.439 | 1.00 | 19.30 A |
| ATOM | 1912 | N | LEU | A | 312 | 32.179 | 24.891 | 31.188 | 1.00 | 16.32 A |
| ATOM | 1913 | CA | LEU | A | 312 | 33.349 | 24.226 | 30.611 | 1.00 | 16.66 A |
| ATOM | 1914 | CB | LEU | A | 312 | 32.927 | 23.035 | 29.744 | 1.00 | 16.12 A |
| ATOM | 1915 | CG | LEU | A | 312 | 34.050 | 22.320 | 28.974 | 1.00 | 14.73 A |
| ATOM | 1916 | CD1 | LEU | A | 312 | 35.192 | 21.935 | 29.912 | 1.00 | 14.56 A |
| ATOM | 1917 | CD2 | LEU | A | 312 | 33.477 | 21.084 | 28.289 | 1.00 | 14.22 A |

-continued

| | | | | | | | | | |
|---|---|---|---|---|---|---|---|---|---|
| ATOM | 1918 | C | LEU | A | 312 | 34.181 | 25.189 | 29.774 | 1.00 | 16.61 | A |
| ATOM | 1919 | O | LEU | A | 312 | 35.402 | 25.241 | 29.910 | 1.00 | 16.20 | A |
| ATOM | 1920 | N | VAL | A | 313 | 33.515 | 25.949 | 28.908 | 1.00 | 16.20 | A |
| ATOM | 1921 | CA | VAL | A | 313 | 34.207 | 26.907 | 28.058 | 1.00 | 15.37 | A |
| ATOM | 1922 | CB | VAL | A | 313 | 33.216 | 27.648 | 27.130 | 1.00 | 16.42 | A |
| ATOM | 1923 | CG1 | VAL | A | 313 | 33.915 | 28.796 | 26.426 | 1.00 | 16.93 | A |
| ATOM | 1924 | CG2 | VAL | A | 313 | 32.644 | 26.672 | 26.103 | 1.00 | 17.88 | A |
| ATOM | 1925 | C | VAL | A | 313 | 34.960 | 27.923 | 28.911 | 1.00 | 17.39 | A |
| ATOM | 1926 | O | VAL | A | 313 | 36.093 | 28.294 | 28.591 | 1.00 | 18.00 | A |
| ATOM | 1927 | N | GLU | A | 314 | 34.342 | 28.364 | 30.004 | 1.00 | 17.61 | A |
| ATOM | 1928 | CA | GLU | A | 314 | 34.986 | 29.331 | 30.885 | 1.00 | 20.43 | A |
| ATOM | 1929 | CB | GLU | A | 314 | 34.009 | 29.816 | 31.959 | 1.00 | 22.14 | A |
| ATOM | 1930 | CG | GLU | A | 314 | 32.800 | 30.550 | 31.396 | 1.00 | 26.52 | A |
| ATOM | 1931 | CD | GLU | A | 314 | 31.852 | 31.025 | 32.478 | 1.00 | 31.26 | A |
| ATOM | 1932 | OE1 | GLU | A | 314 | 31.580 | 30.246 | 33.417 | 1.00 | 33.48 | A |
| ATOM | 1933 | OE2 | GLU | A | 314 | 31.370 | 32.173 | 32.387 | 1.00 | 34.81 | A |
| ATOM | 1934 | C | GLU | A | 314 | 36.217 | 28.721 | 31.539 | 1.00 | 19.15 | A |
| ATOM | 1935 | O | GLU | A | 314 | 37.134 | 29.433 | 31.934 | 1.00 | 21.47 | A |
| ATOM | 1936 | N | LYS | A | 315 | 36.245 | 27.400 | 31.651 | 1.00 | 19.51 | A |
| ATOM | 1937 | CA | LYS | A | 315 | 37.394 | 26.749 | 32.258 | 1.00 | 19.17 | A |
| ATOM | 1938 | CB | LYS | A | 315 | 36.946 | 25.514 | 33.043 | 1.00 | 18.84 | A |
| ATOM | 1939 | CG | LYS | A | 315 | 36.280 | 25.885 | 34.368 | 1.00 | 19.62 | A |
| ATOM | 1940 | CD | LYS | A | 315 | 35.653 | 24.696 | 35.073 | 1.00 | 19.22 | A |
| ATOM | 1941 | CE | LYS | | 315 | 35.070 | 25.095 | 36.427 | 0.50 | 21.00 | AC1 |
| ATOM | 1942 | NZ | LYS | | 315 | 36.119 | 25.552 | 37.381 | 0.50 | 19.53 | AC1 |
| ATOM | 1943 | C | LYS | A | 315 | 38.452 | 26.393 | 31.218 | 1.00 | 18.96 | A |
| ATOM | 1944 | O | LYS | A | 315 | 39.511 | 25.873 | 31.561 | 1.00 | 19.85 | A |
| ATOM | 1945 | N | LEU | A | 316 | 38.164 | 26.691 | 29.950 | 1.00 | 17.08 | A |
| ATOM | 1946 | CA | LEU | A | 316 | 39.102 | 26.429 | 28.854 | 1.00 | 16.41 | A |
| ATOM | 1947 | CB | LEU | A | 316 | 38.414 | 25.636 | 27.738 | 1.00 | 13.81 | A |
| ATOM | 1948 | CG | LEU | A | 316 | 38.028 | 24.201 | 28.115 | 1.00 | 14.39 | A |
| ATOM | 1949 | CD1 | LEU | A | 316 | 37.139 | 23.597 | 27.031 | 1.00 | 12.38 | A |
| ATOM | 1950 | CD2 | LEU | A | 316 | 39.302 | 23.373 | 28.309 | 1.00 | 12.77 | A |
| ATOM | 1951 | C | LEU | A | 316 | 39.652 | 27.743 | 28.290 | 1.00 | 17.12 | A |
| ATOM | 1952 | O | LEU | A | 316 | 40.851 | 27.860 | 28.023 | 1.00 | 16.53 | A |
| ATOM | 1953 | N | LEU | A | 317 | 38.780 | 28.729 | 28.105 | 1.00 | 16.27 | A |
| ATOM | 1954 | CA | LEU | A | 317 | 39.228 | 30.022 | 27.596 | 1.00 | 17.52 | A |
| ATOM | 1955 | CB | LEU | A | 317 | 38.083 | 30.752 | 26.887 | 1.00 | 16.37 | A |
| ATOM | 1956 | CG | LEU | A | 317 | 37.448 | 29.973 | 25.727 | 1.00 | 18.81 | A |
| ATOM | 1957 | CD1 | LEU | A | 317 | 36.415 | 30.851 | 25.018 | 1.00 | 16.47 | A |
| ATOM | 1958 | CD2 | LEU | A | 317 | 38.528 | 29.526 | 24.741 | 1.00 | 17.87 | A |
| ATOM | 1959 | C | LEU | A | 317 | 39.745 | 30.841 | 28.774 | 1.00 | 18.27 | A |
| ATOM | 1960 | O | LEU | A | 317 | 39.078 | 31.753 | 29.273 | 1.00 | 18.58 | A |
| ATOM | 1961 | N | VAL | A | 318 | 40.937 | 30.475 | 29.229 | 1.00 | 18.02 | A |
| ATOM | 1962 | CA | VAL | A | 318 | 41.593 | 31.141 | 30.342 | 1.00 | 18.85 | A |
| ATOM | 1963 | CB | VAL | A | 318 | 41.846 | 30.153 | 31.500 | 1.00 | 19.91 | A |
| ATOM | 1964 | CG1 | VAL | A | 318 | 42.590 | 30.848 | 32.634 | 1.00 | 20.01 | A |
| ATOM | 1965 | CG2 | VAL | A | 318 | 40.520 | 29.584 | 31.990 | 1.00 | 19.44 | A |
| ATOM | 1966 | C | VAL | A | 318 | 42.923 | 31.657 | 29.811 | 1.00 | 19.67 | A |
| ATOM | 1967 | O | VAL | A | 318 | 43.690 | 30.902 | 29.208 | 1.00 | 18.26 | A |
| ATOM | 1968 | N | LEU | A | 319 | 43.197 | 32.939 | 30.028 | 1.00 | 20.07 | A |
| ATOM | 1969 | CA | LEU | A | 319 | 44.436 | 33.533 | 29.538 | 1.00 | 20.98 | A |
| ATOM | 1970 | CB | LEU | A | 319 | 44.521 | 35.002 | 29.968 | 1.00 | 21.64 | A |
| ATOM | 1971 | CG | LEU | A | 319 | 43.418 | 35.908 | 29.408 | 1.00 | 24.38 | A |
| ATOM | 1972 | CD1 | LEU | A | 319 | 43.606 | 37.332 | 29.935 | 1.00 | 23.28 | A |
| ATOM | 1973 | CD2 | LEU | A | 319 | 43.453 | 35.887 | 27.875 | 1.00 | 24.33 | A |
| ATOM | 1974 | C | LEU | A | 319 | 45.680 | 32.774 | 29.994 | 1.00 | 20.38 | A |
| ATOM | 1975 | O | LEU | A | 319 | 46.568 | 32.496 | 29.192 | 1.00 | 21.34 | A |
| ATOM | 1976 | N | ASP | A | 320 | 45.742 | 32.440 | 31.280 | 1.00 | 20.22 | A |
| ATOM | 1977 | CA | ASP | A | 320 | 46.879 | 31.707 | 31.833 | 1.00 | 20.90 | A |
| ATOM | 1978 | CB | ASP | A | 320 | 46.842 | 31.760 | 33.365 | 1.00 | 20.76 | A |
| ATOM | 1979 | CG | ASP | A | 320 | 48.049 | 31.102 | 34.004 | 1.00 | 21.51 | A |
| ATOM | 1980 | OD1 | ASP | A | 320 | 48.669 | 30.226 | 33.367 | 1.00 | 23.46 | A |
| ATOM | 1981 | OD2 | ASP | A | 320 | 48.371 | 31.450 | 35.159 | 1.00 | 23.89 | A |
| ATOM | 1982 | C | ASP | A | 320 | 46.814 | 30.247 | 31.367 | 1.00 | 20.06 | A |
| ATOM | 1983 | O | ASP | A | 320 | 45.988 | 29.476 | 31.840 | 1.00 | 20.54 | A |
| ATOM | 1984 | N | ALA | A | 321 | 47.700 | 29.876 | 30.451 | 1.00 | 20.68 | A |
| ATOM | 1985 | CA | ALA | A | 321 | 47.733 | 28.522 | 29.903 | 1.00 | 22.04 | A |
| ATOM | 1986 | CB | ALA | A | 321 | 48.860 | 28.411 | 28.881 | 1.00 | 20.75 | A |
| ATOM | 1987 | C | ALA | A | 321 | 47.858 | 27.400 | 30.940 | 1.00 | 21.62 | A |
| ATOM | 1988 | O | ALA | A | 321 | 47.482 | 26.259 | 30.665 | 1.00 | 21.99 | A |
| ATOM | 1989 | N | THR | A | 322 | 48.372 | 27.715 | 32.127 | 1.00 | 20.89 | A |
| ATOM | 1990 | CA | THR | A | 322 | 48.531 | 26.698 | 33.167 | 1.00 | 20.82 | A |
| ATOM | 1991 | CB | THR | A | 322 | 49.670 | 27.051 | 34.146 | 1.00 | 19.47 | A |
| ATOM | 1992 | OG1 | THR | A | 322 | 49.341 | 28.253 | 34.848 | 1.00 | 20.19 | A |
| ATOM | 1993 | CG2 | THR | A | 322 | 50.981 | 27.249 | 33.394 | 1.00 | 21.59 | A |
| ATOM | 1994 | C | THR | A | 322 | 47.264 | 26.498 | 33.983 | 1.00 | 19.55 | A |
| ATOM | 1995 | O | THR | A | 322 | 47.235 | 25.673 | 34.894 | 1.00 | 21.13 | A |
| ATOM | 1996 | N | LYS | A | 323 | 46.216 | 27.248 | 33.661 | 1.00 | 19.33 | A |

-continued

| | | | | | | | | | |
|---|---|---|---|---|---|---|---|---|---|
| ATOM | 1997 | CA | LYS | A | 323 | 44.962 | 27.122 | 34.392 | 1.00 | 21.20 A |
| ATOM | 1998 | CB | LYS | A | 323 | 44.580 | 28.460 | 35.030 | 1.00 | 23.75 A |
| ATOM | 1999 | CG | LYS | A | 323 | 45.562 | 28.933 | 36.084 | 1.00 | 28.45 A |
| ATOM | 2000 | CD | LYS | A | 323 | 45.055 | 30.177 | 36.799 | 1.00 | 33.76 A |
| ATOM | 2001 | CE | LYS | A | 323 | 46.087 | 30.678 | 37.802 | 1.00 | 36.15 A |
| ATOM | 2002 | NZ | LYS | A | 323 | 46.532 | 29.569 | 38.693 | 1.00 | 37.34 A |
| ATOM | 2003 | C | LYS | A | 323 | 43.806 | 26.614 | 33.539 | 1.00 | 20.68 A |
| ATOM | 2004 | O | LYS | A | 323 | 42.649 | 26.757 | 33.915 | 1.00 | 20.42 A |
| ATOM | 2005 | N | ARG | A | 324 | 44.114 | 26.019 | 32.392 | 1.00 | 19.97 A |
| ATOM | 2006 | CA | ARG | A | 324 | 43.060 | 25.494 | 31.531 | 1.00 | 17.98 A |
| ATOM | 2007 | CB | ARG | A | 324 | 43.461 | 25.609 | 30.061 | 1.00 | 15.95 A |
| ATOM | 2008 | CG | ARG | A | 324 | 43.534 | 27.050 | 29.603 | 1.00 | 17.34 A |
| ATOM | 2009 | CD | ARG | A | 324 | 43.996 | 27.194 | 28.172 | 1.00 | 19.80 A |
| ATOM | 2010 | NE | ARG | A | 324 | 44.438 | 28.565 | 27.944 | 1.00 | 16.93 A |
| ATOM | 2011 | CZ | ARG | A | 324 | 45.410 | 28.908 | 27.108 | 1.00 | 19.88 A |
| ATOM | 2012 | NH1 | ARG | A | 324 | 46.045 | 27.978 | 26.398 | 1.00 | 14.58 A |
| ATOM | 2013 | NH2 | ARG | A | 324 | 45.774 | 30.181 | 27.015 | 1.00 | 16.51 A |
| ATOM | 2014 | C | ARG | A | 324 | 42.762 | 24.046 | 31.883 | 1.00 | 18.32 A |
| ATOM | 2015 | O | ARG | A | 324 | 43.673 | 23.222 | 32.006 | 1.00 | 18.20 A |
| ATOM | 2016 | N | LEU | A | 325 | 41.479 | 23.748 | 32.055 | 1.00 | 18.32 A |
| ATOM | 2017 | CA | LEU | A | 325 | 41.050 | 22.403 | 32.395 | 1.00 | 17.79 A |
| ATOM | 2018 | CB | LEU | A | 325 | 39.523 | 22.335 | 32.425 | 1.00 | 17.03 A |
| ATOM | 2019 | CG | LEU | A | 325 | 38.896 | 21.125 | 33.116 | 1.00 | 15.91 A |
| ATOM | 2020 | CD1 | LEU | A | 325 | 39.392 | 21.048 | 34.557 | 1.00 | 15.93 A |
| ATOM | 2021 | CD2 | LEU | A | 325 | 37.375 | 21.255 | 33.084 | 1.00 | 16.56 A |
| ATOM | 2022 | C | LEU | A | 325 | 41.599 | 21.433 | 31.356 | 1.00 | 18.68 A |
| ATOM | 2023 | O | LEU | A | 325 | 41.347 | 21.586 | 30.157 | 1.00 | 18.28 A |
| ATOM | 2024 | N | GLY | A | 326 | 42.354 | 20.439 | 31.821 | 1.00 | 18.18 A |
| ATOM | 2025 | CA | GLY | A | 326 | 42.931 | 19.462 | 30.915 | 1.00 | 16.36 A |
| ATOM | 2026 | C | GLY | A | 326 | 44.443 | 19.558 | 30.807 | 1.00 | 19.15 A |
| ATOM | 2027 | O | GLY | A | 326 | 45.093 | 18.592 | 30.404 | 1.00 | 19.52 A |
| ATOM | 2028 | N | CYS | A | 327 | 45.016 | 20.708 | 31.161 | 1.00 | 18.16 A |
| ATOM | 2029 | CA | CYS | A | 327 | 46.463 | 20.867 | 31.075 | 1.00 | 19.30 A |
| ATOM | 2030 | CB | CYS | A | 327 | 46.856 | 22.350 | 31.058 | 1.00 | 20.22 A |
| ATOM | 2031 | SG | CYS | A | 327 | 46.782 | 23.200 | 32.649 | 1.00 | 21.97 A |
| ATOM | 2032 | C | CYS | A | 327 | 47.169 | 20.157 | 32.228 | 1.00 | 20.22 A |
| ATOM | 2033 | O | CYS | A | 327 | 46.561 | 19.828 | 33.246 | 1.00 | 17.92 A |
| ATOM | 2034 | N | GLU | A | 328 | 48.463 | 19.933 | 32.053 | 1.00 | 20.51 A |
| ATOM | 2035 | CA | GLU | A | 328 | 49.274 | 19.244 | 33.042 | 1.00 | 23.34 A |
| ATOM | 2036 | CB | GLU | A | 328 | 50.710 | 19.139 | 32.507 | 1.00 | 28.68 A |
| ATOM | 2037 | CG | GLU | A | 328 | 50.754 | 18.367 | 31.175 | 1.00 | 38.24 A |
| ATOM | 2038 | CD | GLU | A | 328 | 52.067 | 18.500 | 30.414 | 1.00 | 43.23 A |
| ATOM | 2039 | OE1 | GLU | A | 328 | 52.535 | 19.643 | 30.218 | 1.00 | 46.22 A |
| ATOM | 2040 | 0E2 | GLU | A | 328 | 52.618 | 17.459 | 29.991 | 1.00 | 44.90 A |
| ATOM | 2041 | C | GLU | A | 328 | 49.234 | 19.876 | 34.435 | 1.00 | 22.11 A |
| ATOM | 2042 | O | GLU | A | 328 | 49.147 | 19.161 | 35.437 | 1.00 | 20.27 A |
| ATOM | 2043 | N | GLU | A | 329 | 49.276 | 21.204 | 34.506 | 1.00 | 18.40 A |
| ATOM | 2044 | CA | GLU | A | 329 | 49.248 | 21.875 | 35.801 | 1.00 | 20.13 A |
| ATOM | 2045 | CB | GLU | A | 329 | 49.587 | 23.363 | 35.657 | 1.00 | 20.36 A |
| ATOM | 2046 | CG | GLU | A | 329 | 51.014 | 23.651 | 35.190 | 1.00 | 24.05 A |
| ATOM | 2047 | CD | GLU | A | 329 | 51.191 | 23.518 | 33.688 | 1.00 | 25.93 A |
| ATOM | 2048 | OE1 | GLU | A | 329 | 50.213 | 23.154 | 32.995 | 1.00 | 26.61 A |
| ATOM | 2049 | 0E2 | GLU | A | 329 | 52.311 | 23.781 | 33.198 | 1.00 | 27.19 A |
| ATOM | 2050 | C | GLU | A | 329 | 47.890 | 21.718 | 36.480 | 1.00 | 19.36 A |
| ATOM | 2051 | O | GLU | A | 329 | 47.775 | 21.879 | 37.694 | 1.00 | 18.74 A |
| ATOM | 2052 | N | MET | A | 330 | 46.863 | 21.415 | 35.691 | 1.00 | 17.28 A |
| ATOM | 2053 | CA | MET | A | 330 | 45.520 | 21.220 | 36.229 | 1.00 | 16.38 A |
| ATOM | 2054 | CB | MET | A | 330 | 44.474 | 21.833 | 35.294 | 1.00 | 17.65 A |
| ATOM | 2055 | CG | MET | A | 330 | 44.460 | 23.365 | 35.311 | 1.00 | 22.95 A |
| ATOM | 2056 | SD | MET | A | 330 | 44.186 | 24.026 | 36.979 | 1.00 | 26.78 A |
| ATOM | 2057 | CE | MET | A | 330 | 42.435 | 23.712 | 37.186 | 1.00 | 24.69 A |
| ATOM | 2058 | C | MET | A | 330 | 45.257 | 19.730 | 36.422 | 1.00 | 14.30 A |
| ATOM | 2059 | O | MET | A | 330 | 44.127 | 19.304 | 36.629 | 1.00 | 15.39 A |
| ATOM | 2060 | N | GLU | A | 331 | 46.327 | 18.949 | 36.346 | 1.00 | 15.60 A |
| ATOM | 2061 | CA | GLU | A | 331 | 46.289 | 17.501 | 36.531 | 1.00 | 17.08 A |
| ATOM | 2062 | CB | GLU | A | 331 | 45.607 | 17.155 | 37.862 | 1.00 | 17.00 A |
| ATOM | 2063 | CG | GLU | A | 331 | 46.070 | 18.027 | 39.038 | 1.00 | 17.46 A |
| ATOM | 2064 | CD | GLU | A | 331 | 47.591 | 18.179 | 39.145 | 1.00 | 20.16 A |
| ATOM | 2065 | OE1 | GLU | A | 331 | 48.034 | 19.073 | 39.896 | 1.00 | 21.39 A |
| ATOM | 2066 | 0E2 | GLU | A | 331 | 48.345 | 17.420 | 38.500 | 1.00 | 18.87 A |
| ATOM | 2067 | C | GLU | A | 331 | 45.697 | 16.658 | 35.398 | 1.00 | 17.80 A |
| ATOM | 2068 | O | GLU | A | 331 | 45.107 | 15.602 | 35.636 | 1.00 | 20.40 A |
| ATOM | 2069 | N | GLY | A | 332 | 45.844 | 17.133 | 34.167 | 1.00 | 16.23 A |
| ATOM | 2070 | CA | GLY | A | 332 | 45.420 | 16.353 | 33.015 | 1.00 | 14.10 A |
| ATOM | 2071 | C | GLY | A | 332 | 43.982 | 16.154 | 32.596 | 1.00 | 13.54 A |
| ATOM | 2072 | O | GLY | A | 332 | 43.063 | 16.864 | 33.017 | 1.00 | 11.96 A |
| ATOM | 2073 | N | TYR | A | 333 | 43.804 | 15.141 | 31.750 | 1.00 | 14.37 A |
| ATOM | 2074 | CA | TYR | A | 333 | 42.510 | 14.806 | 31.182 | 1.00 | 13.56 A |
| ATOM | 2075 | CB | TYR | A | 333 | 42.722 | 13.892 | 29.968 | 1.00 | 15.00 A |

-continued

| | | | | | | | | | |
|---|---|---|---|---|---|---|---|---|---|
| ATOM | 2076 | CG | TYR | A | 333 | 43.153 | 14.683 | 28.752 | 1.00 | 16.46 | A |
| ATOM | 2077 | CD1 | TYR | A | 333 | 42.206 | 15.172 | 27.849 | 1.00 | 15.29 | A |
| ATOM | 2078 | CE1 | TYR | A | 333 | 42.573 | 16.002 | 26.794 | 1.00 | 13.42 | A |
| ATOM | 2079 | CD2 | TYR | A | 333 | 44.490 | 15.039 | 28.561 | 1.00 | 14.91 | A |
| ATOM | 2080 | CE2 | TYR | A | 333 | 44.872 | 15.877 | 27.499 | 1.00 | 14.87 | A |
| ATOM | 2081 | CZ | TYR | A | 333 | 43.902 | 16.353 | 26.626 | 1.00 | 15.61 | A |
| ATOM | 2082 | OH | TYR | A | 333 | 44.244 | 17.197 | 25.599 | 1.00 | 17.29 | A |
| ATOM | 2083 | C | TYR | A | 333 | 41.470 | 14.230 | 32.127 | 1.00 | 15.23 | A |
| ATOM | 2084 | O | TYR | A | 333 | 40.278 | 14.323 | 31.846 | 1.00 | 16.63 | A |
| ATOM | 2085 | N | GLY | A | 334 | 41.907 | 13.650 | 33.244 | 1.00 | 15.50 | A |
| ATOM | 2086 | CA | GLY | A | 334 | 40.957 | 13.100 | 34.202 | 1.00 | 15.07 | A |
| ATOM | 2087 | C | GLY | A | 334 | 39.925 | 14.146 | 34.616 | 1.00 | 16.40 | A |
| ATOM | 2088 | O | GLY | A | 334 | 38.724 | 13.946 | 34.433 | 1.00 | 15.05 | A |
| ATOM | 2089 | N | PRO | A | 335 | 40.366 | 15.278 | 35.184 | 1.00 | 14.96 | A |
| ATOM | 2090 | CD | PRO | A | 335 | 41.727 | 15.531 | 35.689 | 1.00 | 15.88 | A |
| ATOM | 2091 | CA | PRO | A | 335 | 39.444 | 16.339 | 35.606 | 1.00 | 15.29 | A |
| ATOM | 2092 | CB | PRO | A | 335 | 40.383 | 17.397 | 36.178 | 1.00 | 13.19 | A |
| ATOM | 2093 | CG | PRO | A | 335 | 41.485 | 16.569 | 36.758 | 1.00 | 13.81 | A |
| ATOM | 2094 | C | PRO | A | 335 | 38.594 | 16.877 | 34.448 | 1.00 | 15.84 | A |
| ATOM | 2095 | O | PRO | A | 335 | 37.423 | 17.204 | 34.631 | 1.00 | 14.84 | A |
| ATOM | 2096 | N | LEU | A | 336 | 39.184 | 16.971 | 33.257 | 1.00 | 16.12 | A |
| ATOM | 2097 | CA | LEU | A | 336 | 38.450 | 17.465 | 32.094 | 1.00 | 15.52 | A |
| ATOM | 2098 | CB | LEU | A | 336 | 39.396 | 17.653 | 30.898 | 1.00 | 14.39 | A |
| ATOM | 2099 | CG | LEU | A | 336 | 38.770 | 17.991 | 29.538 | 1.00 | 15.46 | A |
| ATOM | 2100 | CD1 | LEU | A | 336 | 37.836 | 19.182 | 29.662 | 1.00 | 11.25 | A |
| ATOM | 2101 | CD2 | LEU | A | 336 | 39.884 | 18.285 | 28.528 | 1.00 | 14.11 | A |
| ATOM | 2102 | C | LEU | A | 336 | 37.321 | 16.508 | 31.714 | 1.00 | 16.28 | A |
| ATOM | 2103 | O | LEU | A | 336 | 36.176 | 16.921 | 31.540 | 1.00 | 15.51 | A |
| ATOM | 2104 | N | LYS | A | 337 | 37.640 | 15.225 | 31.592 | 1.00 | 17.22 | A |
| ATOM | 2105 | CA | LYS | A | 337 | 36.624 | 14.243 | 31.235 | 1.00 | 17.39 | A |
| ATOM | 2106 | CB | LYS | A | 337 | 37.293 | 12.900 | 30.921 | 1.00 | 17.68 | A |
| ATOM | 2107 | CG | LYS | A | 337 | 38.170 | 12.994 | 29.676 | 1.00 | 22.31 | A |
| ATOM | 2108 | CD | LYS | A | 337 | 39.213 | 11.892 | 29.592 | 1.00 | 24.60 | A |
| ATOM | 2109 | CE | LYS | A | 337 | 38.620 | 10.560 | 29.189 | 1.00 | 24.76 | A |
| ATOM | 2110 | NZ | LYS | A | 337 | 39.710 | 9.560 | 28.997 | 1.00 | 25.05 | A |
| ATOM | 2111 | C | LYS | A | 337 | 35.577 | 14.096 | 32.342 | 1.00 | 17.33 | A |
| ATOM | 2112 | O | LYS | A | 337 | 34.456 | 13.652 | 32.090 | 1.00 | 14.42 | A |
| ATOM | 2113 | N | ALA | A | 338 | 35.928 | 14.500 | 33.559 | 1.00 | 15.83 | A |
| ATOM | 2114 | CA | ALA | A | 338 | 34.989 | 14.395 | 34.674 | 1.00 | 17.52 | A |
| ATOM | 2115 | CB | ALA | A | 338 | 35.749 | 14.167 | 35.980 | 1.00 | 19.68 | A |
| ATOM | 2116 | C | ALA | A | 338 | 34.095 | 15.621 | 34.804 | 1.00 | 18.83 | A |
| ATOM | 2117 | O | ALA | A | 338 | 33.252 | 15.687 | 35.695 | 1.00 | 18.94 | A |
| ATOM | 2118 | N | HIS | A | 339 | 34.262 | 16.596 | 33.918 | 1.00 | 19.42 | A |
| ATOM | 2119 | CA | HIS | A | 339 | 33.438 | 17.796 | 34.004 | 1.00 | 19.28 | A |
| ATOM | 2120 | CB | HIS | A | 339 | 33.865 | 18.819 | 32.949 | 1.00 | 19.20 | A |
| ATOM | 2121 | CG | HIS | A | 339 | 33.163 | 20.134 | 33.074 | 1.00 | 20.26 | A |
| ATOM | 2122 | CD2 | HIS | A | 339 | 33.549 | 21.299 | 33.649 | 1.00 | 18.95 | A |
| ATOM | 2123 | ND1 | HIS | A | 339 | 31.880 | 20.340 | 32.612 | 1.00 | 19.10 | A |
| ATOM | 2124 | CE1 | HIS | A | 339 | 31.506 | 21.576 | 32.896 | 1.00 | 22.19 | A |
| ATOM | 2125 | NE2 | HIS | A | 339 | 32.500 | 22.179 | 33.525 | 1.00 | 21.98 | A |
| ATOM | 2126 | C | HIS | A | 339 | 31.957 | 17.448 | 33.845 | 1.00 | 19.13 | A |
| ATOM | 2127 | O | HIS | A | 339 | 31.597 | 16.576 | 33.061 | 1.00 | 19.52 | A |
| ATOM | 2128 | N | PRO | A | 340 | 31.079 | 18.125 | 34.606 | 1.00 | 19.80 | A |
| ATOM | 2129 | CD | PRO | A | 340 | 31.424 | 19.119 | 35.640 | 1.00 | 19.08 | A |
| ATOM | 2130 | CA | PRO | A | 340 | 29.630 | 17.900 | 34.569 | 1.00 | 20.52 | A |
| ATOM | 2131 | CB | PRO | A | 340 | 29.091 | 19.058 | 35.396 | 1.00 | 20.74 | A |
| ATOM | 2132 | CG | PRO | A | 340 | 30.146 | 19.207 | 36.454 | 1.00 | 19.20 | A |
| ATOM | 2133 | C | PRO | A | 340 | 29.000 | 17.834 | 33.176 | 1.00 | 21.42 | A |
| ATOM | 2134 | O | PRO | A | 340 | 28.049 | 17.088 | 32.955 | 1.00 | 22.48 | A |
| ATOM | 2135 | N | PHE | A | 341 | 29.528 | 18.606 | 32.237 | 1.00 | 21.33 | A |
| ATOM | 2136 | CA | PHE | A | 341 | 28.985 | 18.610 | 30.886 | 1.00 | 21.57 | A |
| ATOM | 2137 | CB | PHE | A | 341 | 29.739 | 19.624 | 30.017 | 1.00 | 21.64 | A |
| ATOM | 2138 | CC | PHE | A | 341 | 29.207 | 19.740 | 28.613 | 1.00 | 23.18 | A |
| ATOM | 2139 | CD1 | PHE | A | 341 | 27.903 | 20.171 | 28.382 | 1.00 | 22.58 | A |
| ATOM | 2140 | CD2 | PHE | A | 341 | 30.013 | 19.431 | 27.522 | 1.00 | 21.95 | A |
| ATOM | 2141 | CE1 | PHE | A | 341 | 27.410 | 20.292 | 27.082 | 1.00 | 23.54 | A |
| ATOM | 2142 | CE2 | PHE | A | 341 | 29.533 | 19.548 | 26.220 | 1.00 | 21.83 | A |
| ATOM | 2143 | CZ | PHE | A | 341 | 28.228 | 19.980 | 25.998 | 1.00 | 23.23 | A |
| ATOM | 2144 | C | PHE | A | 341 | 29.055 | 17.226 | 30.237 | 1.00 | 21.84 | A |
| ATOM | 2145 | O | PHE | A | 341 | 28.232 | 16.896 | 29.389 | 1.00 | 20.37 | A |
| ATOM | 2146 | N | PHE | A | 342 | 30.034 | 16.422 | 30.640 | 1.00 | 20.51 | A |
| ATOM | 2147 | CA | PHE | A | 342 | 30.221 | 15.085 | 30.077 | 1.00 | 23.01 | A |
| ATOM | 2148 | CB | PHE | A | 342 | 31.710 | 14.809 | 29.850 | 1.00 | 18.00 | A |
| ATOM | 2149 | CC | PHE | A | 342 | 32.398 | 15.812 | 28.971 | 1.00 | 17.05 | A |
| ATOM | 2150 | CD1 | PHE | A | 342 | 32.010 | 15.987 | 27.652 | 1.00 | 17.78 | A |
| ATOM | 2151 | CD2 | PHE | A | 342 | 33.487 | 16.534 | 29.450 | 1.00 | 15.72 | A |
| ATOM | 2152 | CE1 | PHE | A | 342 | 32.702 | 16.867 | 26.811 | 1.00 | 18.08 | A |
| ATOM | 2153 | CE2 | PHE | A | 342 | 34.184 | 17.414 | 28.617 | 1.00 | 17.45 | A |
| ATOM | 2154 | CZ | PHE | A | 342 | 33.790 | 17.578 | 27.298 | 1.00 | 16.56 | A |

-continued

| | | | | | | | | | | |
|---|---|---|---|---|---|---|---|---|---|---|
| ATOM | 2155 | C | PHE | A | 342 | 29.679 | 13.972 | 30.976 | 1.00 | 24.95 A |
| ATOM | 2156 | O | PHE | A | 342 | 30.002 | 12.798 | 30.777 | 1.00 | 23.95 A |
| ATOM | 2157 | N | GLU | A | 343 | 28.861 | 14.333 | 31.958 | 1.00 | 27.35 A |
| ATOM | 2158 | CA | GLU | A | 343 | 28.325 | 13.349 | 32.897 | 1.00 | 30.28 A |
| ATOM | 2159 | CB | GLU | A | 343 | 27.187 | 13.964 | 33.716 | 1.00 | 32.20 A |
| ATOM | 2160 | CC | GLU | A | 343 | 26.581 | 12.991 | 34.714 | 1.00 | 39.71 A |
| ATOM | 2161 | CD | GLU | A | 343 | 25.628 | 13.661 | 35.688 | 1.00 | 44.72 A |
| ATOM | 2162 | OE1 | GLU | A | 343 | 24.661 | 14.314 | 35.234 | 1.00 | 47.55 A |
| ATOM | 2163 | 0E2 | GLU | A | 343 | 25.847 | 13.526 | 36.911 | 1.00 | 46.89 A |
| ATOM | 2164 | C | GLU | A | 343 | 27.852 | 12.017 | 32.305 | 1.00 | 28.98 A |
| ATOM | 2165 | O | GLU | A | 343 | 28.225 | 10.952 | 32.800 | 1.00 | 31.73 A |
| ATOM | 2166 | N | SER | A | 344 | 27.037 | 12.067 | 31.258 | 1.00 | 26.09 A |
| ATOM | 2167 | CA | SER | A | 344 | 26.520 | 10.838 | 30.656 | 1.00 | 28.36 A |
| ATOM | 2168 | CB | SER | A | 344 | 25.129 | 11.089 | 30.067 | 1.00 | 28.73 A |
| ATOM | 2169 | OG | SER | A | 344 | 25.203 | 11.942 | 28.940 | 1.00 | 30.91 A |
| ATOM | 2170 | C | SER | A | 344 | 27.407 | 10.214 | 29.577 | 1.00 | 27.66 A |
| ATOM | 2171 | O | SER | A | 344 | 26.987 | 9.281 | 28.900 | 1.00 | 28.66 A |
| ATOM | 2172 | N | VAL | A | 345 | 28.627 | 10.715 | 29.419 | 1.00 | 26.75 A |
| ATOM | 2173 | CA | VAL | A | 345 | 29.534 | 10.183 | 28.402 | 1.00 | 23.44 A |
| ATOM | 2174 | CB | VAL | A | 345 | 30.565 | 11.256 | 27.950 | 1.00 | 23.10 A |
| ATOM | 2175 | CCI | VAL | A | 345 | 31.589 | 10.631 | 26.995 | 1.00 | 22.24 A |
| ATOM | 2176 | CO2 | VAL | A | 345 | 29.854 | 12.418 | 27.275 | 1.00 | 20.05 A |
| ATOM | 2177 | C | VAL | A | 345 | 30.326 | 8.957 | 28.855 | 1.00 | 24.26 A |
| ATOM | 2178 | O | VAL | A | 345 | 30.876 | 8.930 | 29.960 | 1.00 | 22.83 A |
| ATOM | 2179 | N | THR | A | 346 | 30.374 | 7.942 | 27.997 | 1.00 | 21.77 A |
| ATOM | 2180 | CA | THR | A | 346 | 31.153 | 6.740 | 28.272 | 1.00 | 23.70 A |
| ATOM | 2181 | CB | THR | A | 346 | 30.391 | 5.455 | 27.857 | 1.00 | 26.53 A |
| ATOM | 2182 | OG1 | THR | A | 346 | 29.248 | 5.284 | 28.706 | 1.00 | 29.98 A |
| ATOM | 2183 | CO2 | THR | A | 346 | 31.289 | 4.231 | 27.990 | 1.00 | 24.28 A |
| ATOM | 2184 | C | THR | A | 346 | 32.383 | 6.945 | 27.385 | 1.00 | 23.43 A |
| ATOM | 2185 | O | THR | A | 346 | 32.306 | 6.827 | 26.160 | 1.00 | 24.50 A |
| ATOM | 2186 | N | TRP | A | 347 | 33.508 | 7.270 | 28.013 | 1.00 | 22.98 A |
| ATOM | 2187 | CA | TRP | A | 347 | 34.744 | 7.569 | 27.300 | 1.00 | 23.81 A |
| ATOM | 2188 | CB | TRP | A | 347 | 35.683 | 8.352 | 28.219 | 1.00 | 22.54 A |
| ATOM | 2189 | CC | TRP | A | 347 | 35.128 | 9.658 | 28.693 | 1.00 | 20.61 A |
| ATOM | 2190 | CD2 | TRP | A | 347 | 35.257 | 10.927 | 28.040 | 1.00 | 19.11 A |
| ATOM | 2191 | CE2 | TRP | A | 347 | 34.581 | 11.881 | 28.838 | 1.00 | 18.39 A |
| ATOM | 2192 | CE3 | TRP | A | 347 | 35.878 | 11.351 | 26.858 | 1.00 | 18.16 A |
| ATOM | 2193 | CD1 | TRP | A | 347 | 34.397 | 9.883 | 29.828 | 1.00 | 18.35 A |
| ATOM | 2194 | NE1 | TRP | A | 347 | 34.065 | 11.218 | 29.923 | 1.00 | 19.51 A |
| ATOM | 2195 | CZ2 | TRP | A | 347 | 34.510 | 13.234 | 28.491 | 1.00 | 16.88 A |
| ATOM | 2196 | CZ3 | TRP | A | 347 | 35.808 | 12.701 | 26.511 | 1.00 | 17.23 A |
| ATOM | 2197 | CH2 | TRP | A | 347 | 35.127 | 13.624 | 27.327 | 1.00 | 18.16 A |
| ATOM | 2198 | C | TRP | A | 347 | 35.538 | 6.429 | 26.675 | 1.00 | 25.79 A |
| ATOM | 2199 | O | TRP | A | 347 | 36.304 | 6.654 | 25.742 | 1.00 | 24.67 A |
| ATOM | 2200 | N | ALA | A | 348 | 35.360 | 5.215 | 27.183 | 1.00 | 27.10 A |
| ATOM | 2201 | CA | ALA | A | 348 | 36.116 | 4.063 | 26.697 | 1.00 | 27.46 A |
| ATOM | 2202 | CB | ALA | A | 348 | 35.899 | 2.869 | 27.636 | 1.00 | 27.09 A |
| ATOM | 2203 | C | ALA | A | 348 | 35.895 | 3.620 | 25.256 | 1.00 | 27.18 A |
| ATOM | 2204 | O | ALA | A | 348 | 36.830 | 3.148 | 24.613 | 1.00 | 29.41 A |
| ATOM | 2205 | N | ASN | A | 349 | 34.682 | 3.769 | 24.735 | 1.00 | 26.55 A |
| ATOM | 2206 | CA | ASN | A | 349 | 34.418 | 3.310 | 23.375 | 1.00 | 27.28 A |
| ATOM | 2207 | CB | ASN | A | 349 | 33.700 | 1.962 | 23.444 | 1.00 | 29.37 A |
| ATOM | 2208 | CG | ASN | A | 349 | 32.299 | 2.088 | 24.013 | 1.00 | 30.92 A |
| ATOM | 2209 | ODi | ASN | A | 349 | 32.045 | 2.942 | 24.859 | 1.00 | 30.17 A |
| ATOM | 2210 | ND2 | ASN | A | 349 | 31.386 | 1.237 | 23.553 | 1.00 | 33.52 A |
| ATOM | 2211 | C | ASN | A | 349 | 33.599 | 4.265 | 22.509 | 1.00 | 26.47 A |
| ATOM | 2212 | O | ASN | A | 349 | 32.669 | 3.843 | 21.819 | 1.00 | 25.87 A |
| ATOM | 2213 | N | LEU | A | 350 | 33.947 | 5.543 | 22.518 | 1.00 | 24.45 A |
| ATOM | 2214 | CA | LEU | A | 350 | 33.203 | 6.510 | 21.721 | 1.00 | 23.14 A |
| ATOM | 2215 | CB | LEU | A | 350 | 33.837 | 7.898 | 21.848 | 1.00 | 23.22 A |
| ATOM | 2216 | CG | LEU | A | 350 | 33.659 | 8.605 | 23.191 | 1.00 | 21.05 A |
| ATOM | 2217 | CD1 | LEU | A | 350 | 34.646 | 9.756 | 23.293 | 1.00 | 19.36 A |
| ATOM | 2218 | CD2 | LEU | A | 350 | 32.220 | 9.094 | 23.319 | 1.00 | 18.78 A |
| ATOM | 2219 | C | LEU | A | 350 | 33.082 | 6.152 | 20.240 | 1.00 | 22.60 A |
| ATOM | 2220 | O | LEU | A | 350 | 32.011 | 6.296 | 19.650 | 1.00 | 21.15 A |
| ATOM | 2221 | N | HIS | A | 351 | 34.165 | 5.689 | 19.627 | 1.00 | 23.13 A |
| ATOM | 2222 | CA | HIS | A | 351 | 34.089 | 5.387 | 18.204 | 1.00 | 27.83 A |
| ATOM | 2223 | CB | HIS | A | 351 | 35.506 | 5.325 | 17.596 | 1.00 | 29.36 A |
| ATOM | 2224 | CG | HIS | A | 351 | 36.082 | 3.950 | 17.493 | 1.00 | 32.07 A |
| ATOM | 2225 | CD2 | HIS | A | 351 | 36.611 | 3.128 | 18.431 | 1.00 | 32.39 A |
| ATOM | 2226 | ND1 | HIS | A | 351 | 36.197 | 3.285 | 16.291 | 1.00 | 33.02 A |
| ATOM | 2227 | CEl | HIS | A | 351 | 36.775 | 2.113 | 16.493 | 1.00 | 33.58 A |
| ATOM | 2228 | NE2 | HIS | A | 351 | 37.036 | 1.992 | 17.782 | 1.00 | 31.76 A |
| ATOM | 2229 | C | HIS | A | 351 | 33.258 | 4.144 | 17.874 | 1.00 | 28.12 A |
| ATOM | 2230 | O | HIS | A | 351 | 33.015 | 3.847 | 16.707 | 1.00 | 29.49 A |
| ATOM | 2231 | N | GLN | A | 352 | 32.800 | 3.442 | 18.908 | 1.00 | 29.28 A |
| ATOM | 2232 | CA | GLN | A | 352 | 31.963 | 2.255 | 18.726 | 1.00 | 29.67 A |
| ATOM | 2233 | CB | GLN | | 352 | 32.366 | 1.145 | 19.694 | 0.50 | 30.56 AC1 |

-continued

| | | | | | | | | | | |
|---|---|---|---|---|---|---|---|---|---|---|
| ATOM | 2234 | CG | GLN | | 352 | 33.169 | 0.041 | 19.041 | 0.50 | 30.88 AC1 |
| ATOM | 2235 | CD | GLN | | 352 | 34.493 | −0.186 | 19.729 | 0.50 | 31.21 AC1 |
| ATOM | 2236 | OE1 | GLN | | 352 | 34.541 | −0.450 | 20.928 | 0.50 | 30.76 AC1 |
| ATOM | 2237 | NE2 | GLN | | 352 | 35.578 | −0.084 | 18.971 | 0.50 | 32.30 AC1 |
| ATOM | 2238 | C | GLN | A | 352 | 30.504 | 2.638 | 18.963 | 1.00 | 30.42 A |
| ATOM | 2239 | O | GLN | A | 352 | 29.595 | 1.831 | 18.770 | 1.00 | 29.01 A |
| ATOM | 2240 | N | GLN | A | 353 | 30.290 | 3.875 | 19.397 | 1.00 | 27.64 A |
| ATOM | 2241 | CA | GLN | A | 353 | 28.948 | 4.365 | 19.652 | 1.00 | 27.42 A |
| ATOM | 2242 | CB | GLN | A | 353 | 28.977 | 5.401 | 20.775 | 1.00 | 25.77 A |
| ATOM | 2243 | CG | GLN | A | 353 | 29.408 | 4.837 | 22.115 | 1.00 | 27.34 A |
| ATOM | 2244 | CD | GLN | A | 353 | 29.638 | 5.914 | 23.156 | 1.00 | 27.19 A |
| ATOM | 2245 | OE1 | GLN | A | 353 | 28.875 | 6.872 | 23.252 | 1.00 | 28.29 A |
| ATOM | 2246 | NE2 | GLN | A | 353 | 30.687 | 5.753 | 23.951 | 1.00 | 28.79 A |
| ATOM | 2247 | C | GLN | A | 353 | 28.375 | 4.989 | 18.385 | 1.00 | 29.00 A |
| ATOM | 2248 | O | GLN | A | 353 | 29.118 | 5.455 | 17.516 | 1.00 | 29.14 A |
| ATOM | 2249 | N | THR | A | 354 | 27.053 | 4.984 | 18.276 | 1.00 | 27.31 A |
| ATOM | 2250 | CA | THR | A | 354 | 26.390 | 5.568 | 17.119 | 1.00 | 27.85 A |
| ATOM | 2251 | CB | THR | A | 354 | 24.991 | 4.941 | 16.904 | 1.00 | 30.69 A |
| ATOM | 2252 | OG1 | THR | A | 354 | 25.132 | 3.532 | 16.665 | 1.00 | 30.07 A |
| ATOM | 2253 | CG2 | THR | A | 354 | 24.289 | 5.585 | 15.709 | 1.00 | 29.58 A |
| ATOM | 2254 | C | THR | A | 354 | 26.244 | 7.062 | 17.376 | 1.00 | 26.85 A |
| ATOM | 2255 | O | THR | A | 354 | 25.592 | 7.475 | 18.329 | 1.00 | 25.77 A |
| ATOM | 2256 | N | PRO | A | 355 | 26.867 | 7.898 | 16.533 | 1.00 | 27.22 A |
| ATOM | 2257 | CD | PRO | A | 355 | 27.792 | 7.588 | 15.431 | 1.00 | 25.89 A |
| ATOM | 2258 | CA | PRO | A | 355 | 26.763 | 9.346 | 16.734 | 1.00 | 27.23 A |
| ATOM | 2259 | CB | PRO | A | 355 | 27.625 | 9.915 | 15.609 | 1.00 | 24.91 A |
| ATOM | 2260 | CC | PRO | A | 355 | 28.643 | 8.838 | 15.385 | 1.00 | 25.54 A |
| ATOM | 2261 | C | PRO | A | 355 | 25.322 | 9.837 | 16.641 | 1.00 | 28.07 A |
| ATOM | 2262 | O | PRO | A | 355 | 24.548 | 9.364 | 15.810 | 1.00 | 27.24 A |
| ATOM | 2263 | N | PRO | A | 356 | 24.941 | 10.792 | 17.500 | 1.00 | 28.28 A |
| ATOM | 2264 | CD | PRO | A | 356 | 25.752 | 11.560 | 18.462 | 1.00 | 28.31 A |
| ATOM | 2265 | CA | PRO | A | 356 | 23.572 | 11.306 | 17.448 | 1.00 | 28.44 A |
| ATOM | 2266 | CB | PRO | A | 356 | 23.539 | 12.301 | 18.604 | 1.00 | 28.11 A |
| ATOM | 2267 | CC | PRO | A | 356 | 24.946 | 12.832 | 18.612 | 1.00 | 26.86 A |
| ATOM | 2268 | C | PRO | A | 356 | 23.363 | 11.978 | 16.097 | 1.00 | 29.25 A |
| ATOM | 2269 | O | PRO | A | 356 | 24.304 | 12.537 | 15.529 | 1.00 | 27.27 A |
| ATOM | 2270 | N | ALA | A | 357 | 22.143 | 11.910 | 15.575 | 1.00 | 30.45 A |
| ATOM | 2271 | CA | ALA | A | 357 | 21.848 | 12.521 | 14.287 | 1.00 | 32.81 A |
| ATOM | 2272 | CB | ALA | A | 357 | 20.507 | 12.019 | 13.757 | 1.00 | 31.99 A |
| ATOM | 2273 | C | ALA | A | 357 | 21.824 | 14.035 | 14.448 | 1.00 | 35.05 A |
| ATOM | 2274 | O | ALA | A | 357 | 21.194 | 14.561 | 15.369 | 1.00 | 35.04 A |
| ATOM | 2275 | N | LEU | A | 358 | 22.516 | 14.730 | 13.552 | 1.00 | 37.81 A |
| ATOM | 2276 | CA | LEU | A | 358 | 22.578 | 16.185 | 13.597 | 1.00 | 42.15 A |
| ATOM | 2277 | CB | LEU | A | 358 | 23.679 | 16.681 | 12.658 | 1.00 | 39.54 A |
| ATOM | 2278 | CC | LEU | A | 358 | 25.086 | 16.285 | 13.109 | 1.00 | 39.51 A |
| ATOM | 2279 | CD1 | LEU | A | 358 | 26.102 | 16.686 | 12.062 | 1.00 | 39.29 A |
| ATOM | 2280 | CD2 | LEU | A | 358 | 25.395 | 16.953 | 14.445 | 1.00 | 40.01 A |
| ATOM | 2281 | C | LEU | A | 358 | 21.241 | 16.837 | 13.242 | 1.00 | 45.91 A |
| ATOM | 2282 | O | LEU | A | 358 | 20.874 | 16.927 | 12.069 | 1.00 | 45.71 A |
| ATOM | 2283 | N | THR | A | 359 | 20.530 | 17.290 | 14.275 | 1.00 | 50.06 A |
| ATOM | 2284 | CA | THR | A | 359 | 19.223 | 17.939 | 14.140 | 1.00 | 53.73 A |
| ATOM | 2285 | CB | THR | A | 359 | 19.353 | 19.428 | 13.726 | 1.00 | 54.04 A |
| ATOM | 2286 | 001 | THR | A | 359 | 19.995 | 19.521 | 12.448 | 1.00 | 56.35 A |
| ATOM | 2287 | CC2 | THR | A | 359 | 20.158 | 20.204 | 14.763 | 1.00 | 54.32 A |
| ATOM | 2288 | C | THR | A | 359 | 18.309 | 17.236 | 13.139 | 1.00 | 54.47 A |
| ATOM | 2289 | O | THR | A | 359 | 18.483 | 16.016 | 12.930 | 1.00 | 55.90 A |
| ATOM | 2290 | OXT | THR | A | 359 | 17.407 | 17.908 | 12.595 | 1.00 | 56.97 A |
| ATOM | 2291 | OH2 | TIP | S | 1 | 42.566 | 19.118 | 34.302 | 1.00 | 15.09 S |
| ATOM | 2292 | OH2 | TIP | S | 2 | 41.052 | 32.378 | 19.857 | 1.00 | 15.82 S |
| ATOM | 2293 | OH2 | TIP | S | 3 | 37.014 | 33.030 | 17.747 | 1.00 | 16.95 S |
| ATOM | 2294 | OH2 | TIP | S | 5 | 45.353 | 24.370 | 18.152 | 1.00 | 16.85 S |
| ATOM | 2295 | OH2 | TIP | S | 6 | 31.896 | 13.930 | 33.235 | 1.00 | 20.42 S |
| ATOM | 2296 | OH2 | TIP | S | 7 | 50.351 | 22.781 | 28.249 | 1.00 | 21.14 S |
| ATOM | 2297 | OH2 | TIP | S | 8 | 45.246 | −0.589 | −0.734 | 1.00 | 17.74 S |
| ATOM | 2298 | OH2 | TIP | S | 11 | 46.249 | −0.348 | −8.523 | 1.00 | 21.32 S |
| ATOM | 2299 | OH2 | TIP | S | 14 | 45.756 | 11.148 | 29.680 | 1.00 | 21.94 S |
| ATOM | 2300 | OH2 | TIP | S | 15 | 44.273 | 13.157 | 34.592 | 1.00 | 15.61 S |
| ATOM | 2301 | OH2 | TIP | S | 17 | 53.598 | 3.722 | −1.720 | 1.00 | 21.45 S |
| ATOM | 2302 | OH2 | TIP | S | 18 | 46.049 | 13.087 | 31.565 | 1.00 | 20.35 S |
| ATOM | 2303 | OH2 | TIP | S | 19 | 53.422 | 22.401 | −3.280 | 1.00 | 23.26 S |
| ATOM | 2304 | OH2 | TIP | S | 20 | 34.587 | 7.922 | 5.383 | 1.00 | 22.58 S |
| ATOM | 2305 | OH2 | TIP | S | 21 | 45.053 | 27.379 | 19.376 | 1.00 | 29.60 S |
| ATOM | 2306 | OH2 | TIP | S | 23 | 28.899 | 36.416 | 28.633 | 1.00 | 31.68 S |
| ATOM | 2307 | OH2 | TIP | S | 24 | 35.531 | 11.645 | −8.219 | 1.00 | 23.45 S |
| ATOM | 2308 | OH2 | TIP | S | 25 | 47.364 | 28.787 | 19.612 | 1.00 | 23.03 S |
| ATOM | 2309 | OH2 | TIP | S | 27 | 48.859 | 21.588 | 12.634 | 1.00 | 23.76 S |
| ATOM | 2310 | OH2 | TIP | S | 29 | 48.805 | 8.920 | 23.626 | 1.00 | 22.23 S |
| ATOM | 2311 | OH2 | TIP | S | 31 | 48.619 | 7.247 | 10.112 | 1.00 | 21.32 S |
| ATOM | 2312 | OH2 | TIP | S | 34 | 44.824 | 28.720 | 15.621 | 1.00 | 25.27 S |

-continued

| | | | | | | | | | | | |
|---|---|---|---|---|---|---|---|---|---|---|---|
| ATOM | 2313 | OH2 | TIP | S | 35 | 26.030 | 12.634 | 13.407 | 1.00 | 21.61 | S |
| ATOM | 2314 | OH2 | TIP | S | 36 | 50.462 | 19.810 | 40.066 | 1.00 | 25.45 | S |
| ATOM | 2315 | OH2 | TIP | S | 37 | 39.631 | 23.510 | −0.239 | 1.00 | 30.88 | S |
| ATOM | 2316 | OH2 | TIP | S | 40 | 44.734 | 42.655 | 10.346 | 1.00 | 30.84 | S |
| ATOM | 2317 | OH2 | TIP | S | 41 | 54.653 | 3.902 | 1.503 | 1.00 | 27.14 | S |
| ATOM | 2318 | OH2 | TIP | S | 45 | 45.693 | 21.923 | 39.754 | 1.00 | 28.30 | S |
| ATOM | 2319 | OH2 | TIP | S | 47 | 47.820 | 16.413 | 7.805 | 1.00 | 25.73 | S |
| ATOM | 2320 | OH2 | TIP | S | 48 | 50.292 | 31.412 | 29.642 | 1.00 | 32.79 | S |
| ATOM | 2321 | OH2 | TIP | S | 49 | 26.056 | 16.646 | 34.827 | 1.00 | 29.80 | S |
| ATOM | 2322 | OH2 | TIP | S | 52 | 31.714 | 10.996 | 31.855 | 1.00 | 29.15 | S |
| ATOM | 2323 | OH2 | TIP | S | 53 | 46.108 | 23.843 | −4.299 | 1.00 | 24.21 | S |
| ATOM | 2324 | OH2 | TIP | S | 54 | 37.645 | 11.206 | 34.448 | 1.00 | 28.56 | S |
| ATOM | 2325 | OH2 | TIP | S | 55 | 26.371 | 28.513 | 12.142 | 1.00 | 32.08 | S |
| ATOM | 2326 | OH2 | TIP | S | 58 | 33.564 | 19.700 | 3.483 | 1.00 | 28.28 | S |
| ATOM | 2327 | OH2 | TIP | S | 64 | 48.295 | −0.632 | 14.280 | 1.00 | 32.13 | S |
| ATOM | 2328 | OH2 | TIP | S | 65 | 40.064 | 26.036 | 34.324 | 1.00 | 24.17 | S |
| ATOM | 2329 | OH2 | TIP | S | 66 | 29.570 | 3.958 | 14.729 | 1.00 | 28.94 | S |
| ATOM | 2330 | OH2 | TIP | S | 72 | 60.085 | 11.604 | 6.814 | 1.00 | 38.35 | S |
| ATOM | 2331 | OH2 | TIP | S | 73 | 39.203 | 44.403 | 18.686 | 1.00 | 26.61 | S |
| ATOM | 2332 | OH2 | TIP | S | 76 | 47.312 | 12.366 | 27.366 | 1.00 | 28.51 | S |
| ATOM | 2333 | OH2 | TIP | S | 80 | 43.862 | 33.771 | 33.329 | 1.00 | 28.82 | S |
| ATOM | 2334 | OH2 | TIP | S | 81 | 57.890 | 13.106 | 2.128 | 1.00 | 40.62 | S |
| ATOM | 2335 | OH2 | TIP | S | 82 | 41.663 | 34.381 | 32.043 | 1.00 | 19.35 | S |
| ATOM | 2336 | OH2 | TIP | S | 85 | 50.974 | 40.331 | 19.200 | 1.00 | 21.14 | S |
| ATOM | 2337 | OH2 | TIP | S | 88 | 47.925 | −0.832 | −6.556 | 1.00 | 24.11 | S |
| ATOM | 2338 | OH2 | TIP | S | 90 | 27.231 | 28.336 | 33.481 | 1.00 | 27.64 | S |
| ATOM | 2339 | OH2 | TIP | S | 91 | 43.651 | −7.101 | −7.995 | 1.00 | 24.33 | S |
| ATOM | 2340 | OH2 | TIP | S | 92 | 49.325 | 4.387 | 19.370 | 1.00 | 28.02 | S |
| ATOM | 2341 | OH2 | TIP | S | 93 | 46.231 | 11.549 | 33.898 | 1.00 | 29.40 | S |
| ATOM | 2342 | OH2 | TIP | S | 94 | 63.889 | 24.831 | 1.168 | 1.00 | 26.53 | S |
| ATOM | 2343 | OH2 | TIP | S | 96 | 56.396 | 4.952 | −6.749 | 1.00 | 28.00 | S |
| ATOM | 2344 | OH2 | TIP | S | 98 | 35.510 | 27.986 | 11.558 | 1.00 | 29.24 | S |
| ATOM | 2345 | OH2 | TIP | S | 100 | 49.942 | 24.366 | 30.265 | 1.00 | 31.61 | S |
| ATOM | 2346 | OH2 | TIP | S | 101 | 56.121 | 7.113 | −8.298 | 1.00 | 31.57 | S |
| ATOM | 2347 | OH2 | TIP | S | 102 | 58.318 | 19.957 | −8.378 | 1.00 | 26.95 | S |
| ATOM | 2348 | OH2 | TIP | S | 103 | 49.647 | 22.446 | 39.624 | 1.00 | 40.57 | S |
| ATOM | 2349 | OH2 | TIP | S | 104 | 45.359 | 7.052 | 13.052 | 1.00 | 26.27 | S |
| ATOM | 2350 | OH2 | TIP | S | 105 | 37.150 | 32.340 | 32.346 | 1.00 | 34.45 | S |
| ATOM | 2351 | OH2 | TIP | S | 107 | 43.465 | 40.457 | 8.240 | 1.00 | 40.48 | S |
| ATOM | 2352 | OH2 | TIP | S | 119 | 36.644 | 8.257 | 13.418 | 1.00 | 30.70 | S |
| ATOM | 2353 | OH2 | TIP | S | 123 | 41.912 | −8.974 | −8.264 | 1.00 | 26.08 | S |
| ATOM | 2354 | OH2 | TIP | S | 124 | 62.424 | 15.800 | −7.411 | 1.00 | 24.08 | S |
| ATOM | 2355 | OH2 | TIP | S | 126 | 37.266 | 18.656 | −9.097 | 1.00 | 28.99 | S |
| ATOM | 2356 | OH2 | TIP | S | 127 | 43.129 | 26.845 | −14.606 | 1.00 | 25.19 | S |
| ATOM | 2357 | OH2 | TIP | S | 128 | 36.339 | 32.639 | 29.802 | 1.00 | 29.25 | S |
| ATOM | 2358 | OH2 | TIP | S | 130 | 54.051 | 14.561 | 26.498 | 1.00 | 33.93 | S |
| ATOM | 2359 | OH2 | TIP | S | 131 | 41.805 | −4.242 | 5.492 | 1.00 | 33.72 | S |
| ATOM | 2360 | OH2 | TIP | S | 133 | 38.873 | 25.163 | 36.697 | 1.00 | 30.69 | S |
| ATOM | 2361 | OH2 | TIP | S | 134 | 28.777 | 8.553 | 25.307 | 1.00 | 31.43 | S |
| ATOM | 2362 | OH2 | TIP | S | 135 | 53.672 | 10.546 | −12.803 | 1.00 | 33.45 | S |
| ATOM | 2363 | OH2 | TIP | S | 136 | 59.892 | 15.434 | 11.467 | 1.00 | 31.39 | S |
| ATOM | 2364 | OH2 | TIP | S | 137 | 31.040 | 12.361 | 35.470 | 1.00 | 34.07 | S |
| ATOM | 2365 | OH2 | TIP | S | 139 | 33.489 | 14.292 | −0.598 | 1.00 | 40.68 | S |
| ATOM | 2366 | OH2 | TIP | S | 140 | 46.918 | 8.748 | 11.662 | 1.00 | 29.23 | S |
| ATOM | 2367 | OH2 | TIP | S | 141 | 46.297 | −7.287 | −9.196 | 1.00 | 42.20 | S |
| ATOM | 2368 | OH2 | TIP | S | 142 | 58.193 | 6.715 | −4.685 | 1.00 | 35.48 | S |
| ATOM | 2369 | OH2 | TIP | S | 143 | 44.598 | 4.435 | 12.503 | 1.00 | 27.68 | S |
| ATOM | 2370 | OH2 | TIP | S | 144 | 27.003 | 5.999 | 12.450 | 1.00 | 36.30 | S |
| ATOM | 2371 | OH2 | TIP | S | 145 | 43.676 | 32.852 | 35.735 | 1.00 | 35.70 | S |
| ATOM | 2372 | OH2 | TIP | S | 146 | 35.783 | 18.628 | 36.452 | 1.00 | 34.62 | S |
| ATOM | 2373 | OH2 | TIP | S | 147 | 25.402 | 4.058 | 20.638 | 1.00 | 45.03 | S |
| ATOM | 2374 | OH2 | TIP | S | 148 | 45.839 | 35.853 | 33.724 | 1.00 | 35.47 | S |
| ATOM | 2375 | OH2 | TIP | S | 149 | 22.176 | 18.976 | 16.752 | 1.00 | 31.87 | S |
| ATOM | 2376 | OH2 | TIP | S | 150 | 43.986 | 33.179 | 10.162 | 1.00 | 37.70 | S |
| ATOM | 2377 | OH2 | TIP | S | 151 | 50.653 | 20.347 | 42.428 | 1.00 | 35.80 | S |
| ATOM | 2378 | OH2 | TIP | S | 152 | 47.843 | 24.314 | 9.506 | 1.00 | 31.05 | S |
| ATOM | 2379 | OH2 | TIP | S | 153 | 44.693 | 5.273 | −14.175 | 1.00 | 29.90 | S |
| ATOM | 2380 | OH2 | TIP | S | 155 | 26.560 | 36.851 | 31.684 | 1.00 | 49.29 | S |
| ATOM | 2381 | OH2 | TIP | S | 156 | 46.867 | 8.019 | −12.951 | 1.00 | 29.21 | S |
| ATOM | 2382 | OH2 | TIP | S | 157 | 30.432 | 28.741 | 12.438 | 1.00 | 37.76 | S |
| ATOM | 2383 | OH2 | TIP | S | 158 | 41.004 | 20.553 | 6.423 | 1.00 | 39.53 | S |
| ATOM | 2384 | OH2 | TIP | S | 159 | 49.258 | 20.069 | 29.294 | 1.00 | 33.97 | S |
| ATOM | 2385 | OH2 | TIP | S | 160 | 48.082 | 28.459 | 16.489 | 1.00 | 33.10 | S |
| ATOM | 2386 | OH2 | TIP | S | 161 | 47.448 | 18.625 | 27.683 | 1.00 | 34.87 | S |
| ATOM | 2387 | OH2 | TIP | S | 162 | 19.687 | 20.632 | 23.411 | 1.00 | 35.01 | S |
| ATOM | 2388 | OH2 | TIP | S | 163 | 32.402 | −1.266 | 22.443 | 1.00 | 37.26 | S |
| ATOM | 2389 | OH2 | TIP | S | 164 | 39.475 | 33.468 | 33.237 | 1.00 | 35.34 | S |
| ATOM | 2390 | OH2 | TIP | S | 165 | 44.277 | 18.950 | 5.162 | 1.00 | 45.14 | S |
| ATOM | 2391 | OH2 | TIP | S | 166 | 34.797 | 30.523 | 10.736 | 1.00 | 47.55 | S |

-continued

| | | | | | | | | | | |
|---|---|---|---|---|---|---|---|---|---|---|
| ATOM | 2392 | OH2 | TIP | S | 167 | 46.541 | 3.526 | −14.949 | 1.00 | 26.54 S |
| ATOM | 2393 | OH2 | TIP | S | 168 | 36.333 | 16.371 | 1.539 | 1.00 | 38.68 S |
| ATOM | 2394 | OH2 | TIP | S | 169 | 46.761 | 38.936 | 27.403 | 1.00 | 34.66 S |
| ATOM | 2395 | OH2 | TIP | S | 170 | 24.163 | 13.264 | 11.375 | 1.00 | 41.23 S |
| ATOM | 2396 | OH2 | TIP | S | 171 | 48.459 | 15.018 | 31.951 | 1.00 | 38.11 S |
| ATOM | 2397 | OH2 | TIP | S | 172 | 34.261 | 23.193 | 40.004 | 1.00 | 48.96 S |
| ATOM | 2398 | OH2 | TIP | S | 173 | 45.924 | −0.026 | 13.224 | 1.00 | 39.55 S |
| ATOM | 2399 | OH2 | TIP | S | 175 | 41.384 | 37.389 | 32.543 | 1.00 | 40.74 S |
| ATOM | 2400 | OH2 | TIP | S | 177 | 49.394 | 35.312 | 27.150 | 1.00 | 44.33 S |
| ATOM | 2401 | OH2 | TIP | S | 178 | 29.066 | 29.942 | 34.359 | 1.00 | 41.46 S |
| ATOM | 2402 | OH2 | TIP | S | 180 | 49.354 | 19.467 | 7.273 | 1.00 | 34.56 S |
| ATOM | 2403 | OH2 | TIP | S | 181 | 25.298 | 17.029 | 31.863 | 1.00 | 47.74 S |
| ATOM | 2404 | OH2 | TIP | S | 182 | 37.071 | 25.027 | 4.669 | 1.00 | 43.87 S |
| ATOM | 2405 | OH2 | TIP | S | 183 | 22.581 | 7.487 | 18.691 | 1.00 | 41.75 S |
| ATOM | 2406 | OH2 | TIP | S | 184 | 32.269 | 7.011 | −1.891 | 1.00 | 48.84 S |
| ATOM | 2407 | OH2 | TIP | S | 185 | 48.234 | 0.494 | 6.833 | 1.00 | 48.16 S |
| ATOM | 2408 | OH2 | TIP | S | 187 | 20.008 | 14.658 | 19.211 | 1.00 | 45.27 S |
| ATOM | 2409 | OH2 | TIP | S | 188 | 49.341 | 22.698 | 42.272 | 1.00 | 42.20 S |
| ATOM | 2410 | OH2 | TIP | S | 190 | 61.292 | 18.260 | −8.097 | 1.00 | 45.21 S |
| ATOM | 2411 | OH2 | TIP | S | 191 | 28.152 | 10.606 | 2.819 | 1.00 | 40.38 S |
| ATOM | 2412 | OH2 | TIP | S | 192 | 25.626 | 12.619 | 23.191 | 1.00 | 34.27 S |
| ATOM | 2413 | OH2 | TIP | S | 193 | 59.876 | 11.603 | 1.216 | 1.00 | 46.54 S |
| ATOM | 2414 | OH2 | TIP | S | 194 | 57.592 | 21.183 | −10.646 | 1.00 | 45.82 S |
| ATOM | 2415 | OH2 | TIP | S | 195 | 31.509 | 36.649 | 21.499 | 1.00 | 38.73 S |
| ATOM | 2416 | OH2 | TIP | S | 197 | 50.270 | −1.543 | −6.136 | 1.00 | 42.66 S |
| ATOM | 2417 | OH2 | TIP | S | 198 | 24.467 | 8.729 | 13.088 | 1.00 | 42.78 S |
| ATOM | 2418 | OH2 | TIP | S | 199 | 38.098 | 8.699 | 25.759 | 1.00 | 32.80 S |
| ATOM | 2419 | OH2 | TIP | S | 200 | 57.831 | 11.358 | −13.255 | 1.00 | 45.31 S |
| ATOM | 2420 | OH2 | TIP | S | 201 | 23.888 | 22.328 | 30.524 | 1.00 | 37.12 S |
| ATOM | 2421 | OH2 | TIP | S | 202 | 47.691 | 26.068 | 37.666 | 1.00 | 37.92 S |
| ATOM | 2422 | OH2 | TIP | S | 203 | 38.653 | 7.070 | 29.307 | 1.00 | 50.54 S |
| ATOM | 2423 | OH2 | TIP | S | 206 | 44.424 | 27.583 | 2.092 | 1.00 | 53.50 S |
| ATOM | 2424 | OH2 | TIP | S | 212 | 22.258 | 2.296 | 17.948 | 1.00 | 47.38 S |
| ATOM | 2425 | OH2 | TIP | S | 214 | 19.843 | 17.943 | 23.303 | 1.00 | 30.36 S |
| ATOM | 2426 | OH2 | TIP | S | 216 | 27.647 | 11.344 | 24.681 | 1.00 | 31.32 S |
| ATOM | 2427 | OH2 | TIP | S | 217 | 37.953 | 7.817 | −9.284 | 1.00 | 45.97 S |
| ATOM | 2428 | OH2 | TIP | S | 218 | 33.845 | 34.040 | 12.124 | 1.00 | 38.11 S |
| ATOM | 2429 | OH2 | TIP | S | 219 | 58.484 | 15.269 | 13.717 | 1.00 | 38.26 S |
| ATOM | 2430 | OH2 | TIP | S | 220 | 48.526 | 40.920 | 26.583 | 1.00 | 35.23 S |
| ATOM | 2431 | OH2 | TIP | S | 222 | 52.094 | 21.184 | 38.122 | 1.00 | 29.86 S |
| ATOM | 2432 | OH2 | TIP | S | 223 | 36.889 | 5.881 | 3.281 | 1.00 | 37.63 S |
| ATOM | 2433 | OH2 | TIP | S | 224 | 47.642 | −1.401 | −10.684 | 1.00 | 34.89 S |
| ATOM | 2434 | OH2 | TIP | S | 226 | 47.284 | 2.916 | 19.133 | 1.00 | 34.10 S |
| ATOM | 2435 | OH2 | TIP | S | 227 | 42.468 | 4.463 | −15.039 | 1.00 | 37.98 S |
| ATOM | 2436 | OH2 | TIP | S | 228 | 19.169 | 22.832 | 21.831 | 1.00 | 41.57 S |
| ATOM | 2437 | OH2 | TIP | S | 231 | 57.592 | 12.689 | 14.880 | 1.00 | 50.22 S |
| ATOM | 2438 | OH2 | TIP | S | 232 | 27.102 | 9.176 | 5.655 | 1.00 | 40.57 S |
| ATOM | 2439 | OH2 | TIP | S | 233 | 58.618 | 9.072 | −11.925 | 1.00 | 50.71 S |
| ATOM | 2440 | OH2 | TIP | S | 234 | 22.822 | 25.342 | 19.945 | 1.00 | 34.93 S |
| ATOM | 2441 | OH2 | TIP | S | 236 | 24.831 | 32.218 | 28.901 | 1.00 | 37.69 S |
| ATOM | 2442 | OH2 | TIP | S | 237 | 20.045 | 10.774 | 16.992 | 1.00 | 39.57 S |
| ATOM | 2443 | OH2 | TIP | S | 238 | 58.019 | 19.850 | 15.679 | 1.00 | 41.42 S |
| ATOM | 2444 | OH2 | TIP | S | 239 | 19.490 | 20.949 | 26.114 | 1.00 | 34.55 S |
| ATOM | 2445 | OH2 | TIP | S | 240 | 61.187 | 26.377 | 7.346 | 1.00 | 39.68 S |
| ATOM | 2446 | OH2 | TIP | S | 241 | 33.680 | 38.342 | 19.389 | 1.00 | 48.93 S |
| ATOM | 2447 | OH2 | TIP | S | 242 | 51.539 | 31.612 | 10.881 | 1.00 | 55.65 S |
| ATOM | 2448 | OH2 | TIP | S | 244 | 25.872 | 14.431 | 30.404 | 1.00 | 46.69 S |
| ATOM | 2449 | OH2 | TIP | S | 248 | 37.332 | 5.849 | 9.544 | 1.00 | 43.81 S |
| ATOM | 2450 | OH2 | TIP | S | 250 | 39.087 | −1.293 | −9.655 | 1.00 | 42.96 S |
| ATOM | 2451 | OH2 | TIP | S | 258 | 23.938 | 30.000 | 30.010 | 1.00 | 38.89 S |
| ATOM | 2452 | OH2 | TIP | S | 259 | 24.949 | 29.749 | 32.578 | 1.00 | 40.17 S |
| ATOM | 2453 | OH2 | TIP | S | 260 | 32.111 | 17.986 | 1.918 | 1.00 | 48.36 S |
| ATOM | 2454 | OH2 | TIP | S | 266 | 21.404 | 12.876 | 25.603 | 1.00 | 57.17 S |
| ATOM | 2455 | OH2 | TIP | S | 269 | 35.425 | 36.767 | 12.550 | 1.00 | 30.70 S |
| ATOM | 2456 | OH2 | TIP | S | 270 | 52.438 | 25.529 | 30.131 | 1.00 | 44.85 S |
| ATOM | 2457 | OH2 | TIP | S | 271 | 53.299 | 20.156 | 36.003 | 1.00 | 37.15 S |
| ATOM | 2458 | OH2 | TIP | S | 272 | 50.914 | 6.919 | 23.723 | 1.00 | 43.29 S |
| ATOM | 2459 | OH2 | TIP | S | 274 | 31.578 | 30.795 | 11.014 | 1.00 | 50.15 S |
| ATOM | 2460 | OH2 | TIP | S | 275 | 26.341 | 7.243 | 22.447 | 1.00 | 39.40 S |
| ATOM | 2461 | OH2 | TIP | S | 276 | 60.392 | 18.195 | 10.235 | 1.00 | 37.91 S |
| ATOM | 2462 | OH2 | TIP | S | 277 | 47.355 | −9.081 | −10.821 | 1.00 | 48.18 S |
| ATOM | 2463 | OH2 | TIP | S | 279 | 41.304 | 6.175 | −16.647 | 1.00 | 38.12 S |
| ATOM | 2464 | OH2 | TIP | S | 282 | 33.299 | 21.620 | 37.881 | 1.00 | 46.29 S |
| ATOM | 2465 | OH2 | TIP | S | 283 | 56.469 | 26.112 | −8.575 | 1.00 | 43.71 S |
| ATOM | 2466 | OH2 | TIP | S | 287 | 48.382 | 26.573 | 7.246 | 1.00 | 41.43 S |
| ATOM | 2467 | OH2 | TIP | S | 288 | 56.240 | 7.245 | −11.331 | 1.00 | 41.79 S |
| ATOM | 2468 | OH2 | TIP | S | 290 | 49.060 | 14.978 | 28.166 | 1.00 | 37.03 S |
| ATOM | 2469 | OH2 | TIP | S | 291 | 37.095 | 44.270 | 26.442 | 1.00 | 45.08 S |
| ATOM | 2470 | OH2 | TIP | S | 292 | 47.814 | −0.384 | −13.299 | 1.00 | 48.60 S |

-continued

| | | | | | | | | | | |
|---|---|---|---|---|---|---|---|---|---|---|
| ATOM | 2471 | OH2 | TIP | S | 297 | 58.081 | 2.784 | −7.841 | 1.00 | 41.89 S |
| ATOM | 2472 | OH2 | TIP | S | 298 | 36.447 | 45.321 | 18.644 | 1.00 | 54.91 S |
| ATOM | 2473 | OH2 | TIP | S | 299 | 49.029 | 23.328 | 1.767 | 1.00 | 30.55 S |
| ATOM | 2474 | OH2 | TIP | S | 301 | 24.375 | 13.771 | 8.634 | 1.00 | 48.47 S |
| ATOM | 2475 | OH2 | TIP | S | 303 | 47.904 | 36.798 | 28.653 | 1.00 | 35.76 S |
| ATOM | 2476 | OH2 | TIP | S | 305 | 51.156 | 40.821 | 27.172 | 1.00 | 43.59 S |
| ATOM | 2477 | OH2 | TIP | S | 306 | 32.943 | 28.917 | 35.227 | 1.00 | 42.60 S |
| ATOM | 2478 | OH2 | TIP | S | 307 | 58.462 | 28.373 | 6.251 | 1.00 | 46.15 S |
| ATOM | 2479 | OH2 | TIP | S | 308 | 41.964 | 30.940 | 36.712 | 1.00 | 48.26 S |
| ATOM | 2480 | OH2 | TIP | S | 313 | 51.176 | −1.922 | −3.336 | 1.00 | 50.61 S |
| ATOM | 2481 | OH2 | TIP | S | 1001 | 21.319 | 36.868 | 23.805 | 1.00 | 36.97 S |
| ATOM | 2482 | OH2 | TIP | S | 1002 | 48.880 | 32.620 | 27.617 | 1.00 | 44.40 S |
| ATOM | 2483 | OH2 | TIP | S | 1003 | 61.880 | 19.473 | 11.767 | 1.00 | 45.49 S |
| ATOM | 2484 | OH2 | TIP | S | 1004 | 52.770 | 21.424 | 26.815 | 1.00 | 24.43 S |
| ATOM | 2485 | OH2 | TIP | S | 1005 | 35.373 | 29.094 | 36.197 | 1.00 | 35.97 S |
| ATOM | 2486 | OH2 | TIP | S | 1006 | 40.815 | −6.636 | 4.389 | 1.00 | 43.15 S |
| ATOM | 2487 | OH2 | TIP | S | 1007 | 44.953 | 1.286 | 11.272 | 1.00 | 49.45 S |
| ATOM | 2488 | OH2 | TIP | S | 1010 | 21.004 | 16.168 | 27.009 | 1.00 | 48.51 S |
| ATOM | 2489 | OH2 | TIP | S | 1011 | 47.094 | 41.786 | 9.243 | 1.00 | 50.10 S |
| ATOM | 2490 | OH2 | TIP | S | 1012 | 32.479 | 2.978 | 14.158 | 1.00 | 49.47 S |
| ATOM | 2491 | O12 | GLC | G | 1 | 48.557 | 11.372 | −12.279 | 1.00 | 40.72 G |
| ATOM | 2492 | C11 | GLC | G | 1 | 48.836 | 12.133 | −11.097 | 1.00 | 38.05 G |
| ATOM | 2493 | C13 | GLC | G | 1 | 49.266 | 13.554 | −11.476 | 1.00 | 38.09 G |
| ATOM | 2494 | O14 | GLC | G | 1 | 49.559 | 14.299 | −10.292 | 1.00 | 33.99 G |
| ATOM | 2495 | C15 | GLC | G | 1 | 48.150 | 14.257 | −12.257 | 1.00 | 37.32 G |
| ATOM | 2496 | O16 | GLC | G | 1 | 48.574 | 15.582 | −12.604 | 1.00 | 36.74 G |
| ATOM | 2497 | O12 | GLC | G | 2 | 40.114 | −6.634 | −6.562 | 1.00 | 33.52 G |
| ATOM | 2498 | C11 | GLC | G | 2 | 38.967 | −6.592 | −7.404 | 1.00 | 31.05 G |
| ATOM | 2499 | C13 | GLC | G | 2 | 37.712 | −6.417 | −6.552 | 1.00 | 31.56 G |
| ATOM | 2500 | O14 | GLC | G | 2 | 36.554 | −6.406 | −7.389 | 1.00 | 30.70 G |
| ATOM | 2501 | C1S | GLC | G | 2 | 37.792 | −5.109 | −5.761 | 1.00 | 30.03 G |
| ATOM | 2502 | O16 | GLC | G | 2 | 36.609 | −4.961 | −4.975 | 1.00 | 29.66 G |
| ATOM | 2503 | O12 | GLC | G | 3 | 44.030 | 8.243 | −13.470 | 1.00 | 37.90 G |
| ATOM | 2504 | C11 | GLC | G | 3 | 43.950 | 9.648 | −13.690 | 1.00 | 38.47 G |
| ATOM | 2505 | C13 | GLC | G | 3 | 42.747 | 9.974 | −14.579 | 1.00 | 39.52 G |
| ATOM | 2506 | O14 | GLC | G | 3 | 41.551 | 9.526 | −13.942 | 1.00 | 39.39 G |
| ATOM | 2507 | C15 | GLC | G | 3 | 42.878 | 9.280 | −15.934 | 1.00 | 41.43 G |
| ATOM | 2508 | O16 | GLC | G | 3 | 41.736 | 9.613 | −16.731 | 1.00 | 40.78 G |
| ATOM | 2509 | O12 | GLC | G | S | 40.556 | 1.005 | 2.289 | 1.00 | 45.25 G |
| ATOM | 2510 | C11 | GLC | G | S | 40.966 | 2.332 | 1.960 | 1.00 | 40.56 G |
| ATOM | 2511 | C13 | GLC | G | S | 40.187 | 3.327 | 2.814 | 1.00 | 40.36 G |
| ATOM | 2512 | O14 | GLC | G | S | 38.791 | 3.169 | 2.572 | 1.00 | 40.71 G |
| ATOM | 2513 | CiS | GLC | G | S | 40.619 | 4.751 | 2.464 | 1.00 | 40.04 G |
| ATOM | 2514 | O16 | GLC | G | S | 39.885 | 5.681 | 3.256 | 1.00 | 36.89 G |
| ATOM | 2515 | O12 | GLC | G | 6 | 36.951 | 22.702 | 40.046 | 1.00 | 63.04 G |
| ATOM | 2516 | C11 | GLC | G | 6 | 37.592 | 21.583 | 39.422 | 1.00 | 62.46 G |
| ATOM | 2517 | C13 | GLC | G | 6 | 38.104 | 21.978 | 38.030 | 1.00 | 61.14 G |
| ATOM | 2518 | O14 | GLC | G | 6 | 39.034 | 23.054 | 38.168 | 1.00 | 61.72 G |
| ATOM | 2519 | C15 | GLC | G | 6 | 36.948 | 22.429 | 37.126 | 1.00 | 60.51 G |
| ATOM | 2520 | O16 | GLC | G | 6 | 35.992 | 21.372 | 36.960 | 1.00 | 58.61 G |
| ATOM | 2521 | O12 | GLC | G | 7 | 37.316 | 0.281 | 14.299 | 1.00 | 73.45 G |
| ATOM | 2522 | C11 | GLC | G | 7 | 37.655 | −0.758 | 15.222 | 1.00 | 72.78 G |
| ATOM | 2523 | C13 | GLC | G | 7 | 36.592 | −1.856 | 15.157 | 1.00 | 72.98 G |
| ATOM | 2524 | O14 | GLC | G | 7 | 35.320 | −1.299 | 15.498 | 1.00 | 73.88 G |
| ATOM | 2525 | C15 | GLC | G | 7 | 36.924 | −2.989 | 16.134 | 1.00 | 73.66 G |
| ATOM | 2526 | O16 | GLC | G | 7 | 36.972 | −2.493 | 17.478 | 1.00 | 75.38 G |
| ATOM | 2527 | O12 | GLC | G | 8 | 51.921 | 21.898 | 5.908 | 1.00 | 62.51 G |
| ATOM | 2528 | C11 | GLC | G | 8 | 52.447 | 20.871 | 5.063 | 1.00 | 63.42 G |
| ATOM | 2529 | C13 | GLC | G | 8 | 51.476 | 20.597 | 3.908 | 1.00 | 64.28 G |
| ATOM | 2530 | O14 | GLC | G | 8 | 51.297 | 21.794 | 3.150 | 1.00 | 66.28 G |
| ATOM | 2531 | C15 | GLC | G | 8 | 50.121 | 20.137 | 4.448 | 1.00 | 64.49 G |
| ATOM | 2532 | O16 | GLC | G | 8 | 49.233 | 19.886 | 3.357 | 1.00 | 64.01 G |
| ATOM | 2533 | O12 | GLC | G | 10 | 36.044 | 37.499 | 29.523 | 1.00 | 56.89 G |
| ATOM | 2534 | C11 | GLC | G | 10 | 35.164 | 36.645 | 30.259 | 1.00 | 56.97 G |
| ATOM | 2535 | C13 | GLC | G | 10 | 33.849 | 36.489 | 29.494 | 1.00 | 56.11 G |
| ATOM | 2536 | O14 | GLC | G | 10 | 33.248 | 37.772 | 29.308 | 1.00 | 56.44 G |
| ATOM | 2537 | C15 | GLC | G | 10 | 32.900 | 35.580 | 30.277 | 1.00 | 55.84 G |
| ATOM | 2538 | O16 | GLC | G | 10 | 31.674 | 35.442 | 29.557 | 1.00 | 55.39 G |
| ATOM | 2539 | O3G | ATP | N | 1 | 46.280 | 25.658 | 5.170 | 1.00 | 51.49 N |
| ATOM | 2540 | PG | ATP | N | 1 | 46.464 | 25.053 | 3.691 | 1.00 | 52.22 N |
| ATOM | 2541 | O1G | ATP | N | 1 | 47.406 | 23.911 | 3.763 | 1.00 | 51.41 N |
| ATOM | 2542 | O2G | ATP | N | 1 | 46.794 | 26.182 | 2.784 | 1.00 | 52.07 N |
| ATOM | 2543 | O3B | ATP | N | 1 | 44.976 | 24.513 | 3.344 | 1.00 | 51.01 N |
| ATOM | 2544 | PB | ATP | N | 1 | 44.560 | 22.969 | 3.605 | 1.00 | 50.20 N |
| ATOM | 2545 | O1B | ATP | N | 1 | 43.083 | 22.898 | 3.669 | 1.00 | 49.41 N |
| ATOM | 2546 | O2B | ATP | N | 1 | 45.345 | 22.474 | 4.766 | 1.00 | 50.34 N |
| ATOM | 2547 | O3A | ATP | N | 1 | 45.070 | 22.231 | 2.255 | 1.00 | 47.77 N |
| ATOM | 2548 | PA | ATP | N | 1 | 45.075 | 20.613 | 2.121 | 1.00 | 42.84 N |
| ATOM | 2549 | O1A | ATP | N | 1 | 45.547 | 20.291 | 0.754 | 1.00 | 43.81 N |

-continued

| | | | | | | | | | |
|---|---|---|---|---|---|---|---|---|---|
| ATOM | 2550 | O2A | ATP | N | 1 | 45.807 | 20.035 | 3.270 | 1.00 | 45.03 N |
| ATOM | 2551 | O5* | ATP | N | 1 | 43.516 | 20.223 | 2.245 | 1.00 | 41.73 N |
| ATOM | 2552 | C5* | ATP | N | 1 | 42.528 | 20.925 | 1.489 | 1.00 | 37.57 N |
| ATOM | 2553 | C4* | ATP | N | 1 | 41.127 | 20.379 | 1.776 | 1.00 | 39.45 N |
| ATOM | 2554 | O4* | ATP | N | 1 | 40.907 | 19.024 | 1.279 | 1.00 | 37.72 N |
| ATOM | 2555 | C3* | ATP | N | 1 | 40.777 | 20.321 | 3.251 | 1.00 | 38.48 N |
| ATOM | 2556 | O3* | ATP | N | 1 | 40.360 | 21.615 | 3.697 | 1.00 | 40.42 N |
| ATOM | 2557 | C2* | ATP | N | 1 | 39.608 | 19.374 | 3.270 | 1.00 | 37.58 N |
| ATOM | 2558 | O2* | ATP | N | 1 | 38.410 | 20.076 | 2.924 | 1.00 | 35.98 N |
| ATOM | 2559 | C1* | ATP | N | 1 | 39.939 | 18.346 | 2.173 | 1.00 | 35.55 N |
| ATOM | 2560 | N9 | ATP | N | 1 | 40.628 | 17.1S6 | 2.747 | 1.00 | 31.76 N |
| ATOM | 2561 | C8 | ATP | N | 1 | 41.864 | 17.126 | 3.274 | 1.00 | 30.49 N |
| ATOM | 2562 | N7 | ATP | N | 1 | 42.143 | 15.877 | 3.667 | 1.00 | 29.7S N |
| ATOM | 2563 | C5 | ATP | N | 1 | 41.088 | 15.118 | 3.390 | 1.00 | 27.49 N |
| ATOM | 2564 | C4 | ATP | N | 1 | 40.125 | 15.92S | 2.810 | 1.00 | 30.02 N |
| ATOM | 2565 | N3 | ATP | N | 1 | 38.937 | 15.389 | 2.431 | 1.00 | 27.11 N |
| ATOM | 2566 | C2 | ATP | N | 1 | 38.679 | 14.085 | 2.615 | 1.00 | 25.62 N |
| ATOM | 2567 | N1 | ATP | N | 1 | 39.S97 | 13.283 | 3.175 | 1.00 | 21.76 N |
| ATOM | 2568 | C6 | ATP | N | 1 | 40.800 | 13.768 | 3.571 | 1.00 | 23.90 N |
| ATOM | 2569 | N6 | ATP | N | 1 | 41.698 | 12.964 | 4.127 | 1.00 | 21.94 N |
| ATOM | 2570 | S | SO4 | I | 1 | 58.680 | 8.493 | −0.639 | 1.00 | 56.05 I |
| ATOM | 2571 | O1 | SO4 | I | 1 | 57.956 | 7.875 | 0.483 | 1.00 | 58.83 I |
| ATOM | 2572 | O2 | SO4 | I | 1 | 57.886 | 9.607 | −1.188 | 1.00 | 57.04 I |
| ATOM | 2573 | O3 | SO4 | I | 1 | 58.906 | 7.478 | −1.683 | 1.00 | 57.47 I |
| ATOM | 2574 | O4 | SO4 | I | 1 | 59.976 | 9.008 | −0.156 | 1.00 | 57.S1 I |
| ATOM | 2575 | S | SO4 | I | 2 | 39.339 | 4.855 | 7.087 | 1.00 | 84.24 I |
| ATOM | 2576 | O1 | SO4 | I | 2 | 39.390 | 6.175 | 7.711 | 1.00 | 84.02 I |
| ATOM | 2577 | O2 | SO4 | I | 2 | 40.101 | 4.897 | 5.797 | 1.00 | 84.7S I |
| ATOM | 2578 | O3 | SO4 | I | 2 | 37.936 | 4.506 | 6.766 | 1.00 | 84.94 I |
| ATOM | 2579 | O4 | SO4 | I | 2 | 39.931 | 3.842 | 7.9S4 | 1.00 | 84.44 I |
| ATOM | 2580 | S | SO4 | I | 3 | 38.987 | −2.256 | 3.310 | 1.00 | 58.58 I |
| ATOM | 2581 | O1 | SO4 | I | 3 | 37.734 | −1.675 | 3.827 | 1.00 | 59.11 I |
| ATOM | 2582 | O2 | SO4 | I | 3 | 39.460 | −1.4S4 | 2.172 | 1.00 | 59.91 I |
| ATOM | 2583 | O3 | SO4 | I | 3 | 38.743 | −3.640 | 2.866 | 1.00 | 50.97 I |
| ATOM | 2584 | O4 | SO4 | I | 3 | 40.014 | −2.260 | 4.369 | 1.00 | 59.S8 I |
| ATOM | 2585 | S | SO4 | I | 4 | 34.397 | 5.289 | 30.981 | 1.00 | 64.34 I |
| ATOM | 2586 | O1 | SO4 | I | 4 | 33.627 | 6.528 | 30.742 | 1.00 | 60.43 I |
| ATOM | 2587 | O2 | SO4 | I | 4 | 34.337 | 4.427 | 29.782 | 1.00 | 60.11 I |
| ATOM | 2588 | O3 | SO4 | I | 4 | 33.816 | 4.572 | 32.133 | 1.00 | 64.39 I |
| ATOM | 2589 | O4 | SO4 | I | 4 | 35.806 | S.626 | 31.277 | 1.00 | 63.SS I |
| ATOM | 2590 | S | SO4 | I | S | 55.074 | −6.984 | −3.711 | 1.00 | 75.40 I |
| ATOM | 2591 | O1 | SO4 | I | S | 54.657 | −7.S18 | −2.399 | 1.00 | 74.66 I |
| ATOM | 2592 | O2 | SO4 | I | S | 54.209 | −5.84S | −4.06S | 1.00 | 74.96 I |
| ATOM | 2593 | O3 | SO4 | I | S | 54.9S0 | −8.034 | −4.742 | 1.00 | 74.22 I |
| ATOM | 2594 | O4 | SO4 | I | S | 56.477 | −6.532 | −3.633 | 1.00 | 7S.1S I |
| ATOM | 2595 | O2 | PO4 | P | 100 | 57.362 | 24.998 | 13.149 | 1.00 | 66.76 P |
| ATOM | 2596 | O3 | PO4 | P | 100 | 59.399 | 26.166 | 13.761 | 1.00 | 66.89 P |
| ATOM | 2597 | O4 | PO4 | P | 100 | 57.761 | 25.606 | 1S.462 | 1.00 | 67.43 P |
| ATOM | 2598 | O1 | PO4 | P | 100 | 57.264 | 27.325 | 13.818 | 1.00 | 6S.91 P |
| ATOM | 2599 | P | PO4 | P | 100 | 57.947 | 26.025 | 14.048 | 1.00 | 66.69 P |
| ATOM | 2600 | CB | GLU | | 80 | 50.411 | 3.97S | −13.538 | 0.50 | 23.31 AC2 |
| ATOM | 2601 | CG | GLU | | 80 | 51.306 | 4.896 | −14.362 | 0.50 | 24.09 AC2 |
| ATOM | 2602 | CD | GLU | | 80 | 52.180 | 5.798 | −13.409 | 0.50 | 2S.31 AC2 |
| ATOM | 2603 | OE1 | GLU | | 80 | 52.841 | 5.289 | −12.580 | 0.50 | 22.80 AC2 |
| ATOM | 2604 | OE2 | GLU | | 80 | 52.212 | 7.018 | −13.774 | 0.50 | 28.07 AC2 |
| ATOM | 260S | CB | SER | | 105 | 37.582 | −1.281 | −6.192 | 0.502 | 1.16 AC2 |
| ATOM | 2606 | OG | SER | | 105 | 37.127 | −1.871 | −4.988 | 0.502 | 0.42 AC2 |
| ATOM | 2607 | CB | ARG | | 116 | 59.520 | 22.977 | −7.867 | 0.503 | 1.00 AC2 |
| ATOM | 2608 | CG | ARG | | 116 | 60.312 | 24.192 | −8.323 | 0.503 | 2.50 AC2 |
| ATOM | 2609 | CD | ARC | | 116 | 60.266 | 24.349 | −9.838 | 0.503 | 4.11 AC2 |
| ATOM | 2610 | NE | ARC | | 116 | 61.045 | 25.499 | −10.290 | 0.50 | 36.67 AC2 |
| ATOM | 2611 | CZ | ARC | | 116 | 60.729 | 26.766 | −10.035 | 0.50 | 37.26 AC2 |
| ATOM | 2612 | NH1 | ARC | | 116 | 59.642 | 27.053 | −9.331 | 0.50 | 38.99 AC2 |
| ATOM | 2613 | NH2 | ARC | | 116 | 61.503 | 27.746 | −10.479 | 0.50 | 37.83 AC2 |
| ATOM | 2614 | CB | LEU | | 145 | 49.693 | 8.642 | 6.631 | 0.50 | 15.29 AC2 |
| ATOM | 2615 | CC | LEU | | 145 | 50.783 | 8.664 | 5.552 | 0.50 | 14.29 AC2 |
| ATOM | 2616 | CD1 | LEU | | 145 | 50.264 | 9.373 | 4.305 | 0.50 | 8.20 AC2 |
| ATOM | 2617 | CD2 | LEU | | 145 | 52.030 | 9.361 | 6.087 | 0.50 | 10.66 AC2 |
| ATOM | 2618 | CB | ARC | | 183 | 27.455 | 16.155 | 24.989 | 0.50 | 19.21 AC2 |
| ATOM | 2619 | CC | ARC | | 183 | 28.077 | 15.397 | 26.147 | 0.50 | 18.46 AC2 |
| ATOM | 2620 | CD | ARC | | 183 | 27.002 | 14.945 | 27.127 | 0.50 | 19.72 AC2 |
| ATOM | 2621 | NE | ARC | | 183 | 26.016 | 14.086 | 26.478 | 0.50 | 18.79 AC2 |
| ATOM | 2622 | CZ | ARC | | 183 | 24.703 | 14.279 | 26.539 | 0.50 | 18.52 AC2 |
| ATOM | 2623 | NH1 | ARC | | 183 | 24.213 | 15.305 | 27.221 | 0.50 | 15.35 AC2 |
| ATOM | 2624 | NH2 | ARC | | 183 | 23.881 | 13.445 | 25.915 | 0.50 | 17.55 AC2 |
| ATOM | 2625 | CB | SER | | 191 | 38.479 | 10.847 | 23.036 | 0.50 | 16.57 AC2 |
| ATOM | 2626 | OC | SER | | 191 | 37.418 | 10.765 | 23.973 | 0.50 | 18.62 AC2 |
| ATOM | 2627 | CB | CLU | | 209 | 38.645 | 24.079 | 8.551 | 0.50 | 22.02 AC2 |
| ATOM | 2628 | CC | CLU | | 209 | 37.769 | 25.296 | 8.263 | 0.50 | 23.40 AC2 |

-continued

| | | | | | | | | | |
|---|---|---|---|---|---|---|---|---|---|
| ATOM | 2629 | CD | CLU | 209 | 37.513 | 26.175 | 9.483 | 0.50 | 24.27 AC2 |
| ATOM | 2630 | OE1 | CLU | 209 | 37.076 | 27.328 | 9.288 | 0.50 | 25.25 AC2 |
| ATOM | 2631 | OE2 | CLU | 209 | 37.737 | 25.727 | 10.629 | 0.50 | 20.24 AC2 |
| ATOM | 2632 | CB | CLN | 247 | 38.598 | 32.546 | 14.790 | 0.50 | 18.71 AC2 |
| ATOM | 2633 | CC | CLN | 247 | 38.077 | 33.665 | 13.900 | 0.50 | 16.95 AC2 |
| ATOM | 2634 | CD | CLN | 247 | 38.614 | 33.598 | 12.479 | 0.50 | 19.13 AC2 |
| ATOM | 2635 | OE1 | CLN | 247 | 39.763 | 33.221 | 12.246 | 0.50 | 17.24 AC2 |
| ATOM | 2636 | NE2 | CLN | 247 | 37.780 | 33.979 | 11.520 | 0.50 | 19.88 AC2 |
| ATOM | 2637 | CE | LYS | 315 | 34.978 | 25.150 | 36.369 | 0.50 | 20.49 AC2 |
| ATOM | 2638 | NZ | LYS | 315 | 34.183 | 24.074 | 37.023 | 0.50 | 17.05 AC2 |
| ATOM | 2639 | CB | CLN | 352 | 32.365 | 1.170 | 19.731 | 0.50 | 31.10 AC2 |
| ATOM | 2640 | CC | CLN | 352 | 33.833 | 0.778 | 19.683 | 0.50 | 32.11 AC2 |
| ATOM | 2641 | CD | CLN | 352 | 34.190 | 0.027 | 18.419 | 0.50 | 33.04 AC2 |
| ATOM | 2642 | OE1 | CLN | 352 | 33.906 | 0.485 | 17.314 | 0.50 | 34.87 AC2 |
| ATOM | 2643 | NE2 | CLN | 352 | 34.819 | −1.133 | 18.575 | 0.50 | 32.08 AC2 |

Example 3

Co-Ordinates for the PDK1 Fragment without Alternate Side Chains

```
REMARK   coordinates from restrained individual B-factor refinement
REMARK   refinement resolution: 25.0-2.0 A
REMARK   starting   r = 0.1972  free_r = 0.2220
REMARK   final      r = 0.1954  free_r = 0.2224
REMARK   B rmsd for bonded mainchain atoms = 1.501   target = 1.5
REMARK   B rmsd for bonded sidechain atoms = 2.235   target = 2.0
REMARK   B rmsd for angle mainchain atoms = 2.347    target = 2.0
REMARK   B rmsd for angle sidechain atoms = 3.302    target = 2.5
REMARK   rweight = 0.0900 (with wa = 1.29263)
REMARK   target = mlf   steps = 30
REMARK   sg = P3(2)21  a = 123.013  b = 123.013  c = 47.624  alpha = 90  beta = 90  gamma = 120
REMARK   parameter file 1: /dd1/david/projects/PDK1_new/CNS/prot.par
REMARK   parameter file 2: /dd1/david/projects/PDK1_new/CNS/atp.par
REMARK   parameter file 3: CNS_TOPPAR:water_rep.param
REMARK   parameter file 4: CNS_TOPPAR:ion.param
REMARK   parameter file 5: /dd1/david/projects/PDK1_new/CNS/glycerol.par
REMARK   molecular structure file: ../generate/alternate.mtf
REMARK   input coordinates: ../minimize/minimize.pdb
REMARK   reflection file = ../../1/hkl/cns.hkl
REMARK   ncs = none
REMARK   B-correction resolution: 6.0-2.0
REMARK   initial B-factor correction applied to fobs:
REMARK   B11 = −2.766   B22 = −2.766   B33 = 5.532
REMARK   B12 = −0.375   B13 =  0.000   B23 = 0.000
REMARK   B-factor correction applied to coordinate array B: 0.031
REMARK   bulk solvent: density level = 0.378441 e/A^3, B-factor = 52.6885 A^2
REMARK   reflections with |Fobs|/sigma_F < 0.0 rejected
REMARK   reflections with |Fobs| > 10000 * rms(Fobs) rejected
REMARK   theoretical total number of refl. in resol. range:     28210 ( 100.0% )
REMARK   number of unobserved reflections (no entry or |F| = 0):  568 (   2.0% )
REMARK   number of reflections rejected:                            0 (   0.0% )
REMARK   total number of reflections used:                      27642 (  98.0% )
REMARK   number of reflections in working set:                  27063 (  95.9% )
REMARK   number of reflections in test set:                       579 (   2.1% )
CRYST1   123.013   123.013   47.624   90.00   90.00   120.00   P 32 2 1
REMARK   FILENAME = "bindividual.pdb"
REMARK   DATE: 16-Apr-2002 18:31:12       created by user: david
REMARK   VERSION: 1.0
ATOM     1   CB  PRO  A  71  58.912  −7.251  8.216  1.00  67.78  A
ATOM     2   CG  PRO  A  71  59.621  −6.941  9.534  1.00  69.16  A
ATOM     3   C   PRO  A  71  59.493  −6.506  5.894  1.00  67.06  A
ATOM     4   O   PRO  A  71  59.196  −5.318  5.766  1.00  66.66  A
ATOM     5   N   PRO  A  71  60.984  −6.073  7.833  1.00  67.86  A
ATOM     6   CD  PRO  A  71  60.554  −5.762  9.207  1.00  68.24  A
ATOM     7   CA  PRO  A  71  60.040  −7.035  7.217  1.00  67.75  A
ATOM     8   N   PRO  A  72  59.356  −7.385  4.890  1.00  66.32  A
ATOM     9   CD  PRO  A  72  59.712  −8.816  4.898  1.00  67.17  A
ATOM    10   CA  PRO  A  72  58.840  −6.986  3.578  1.00  65.61  A
ATOM    11   CB  PRO  A  72  58.672  −8.321  2.858  1.00  66.47  A
ATOM    12   CG  PRO  A  72  59.796  −9.133  3.419  1.00  67.57  A
ATOM    13   C   PRO  A  72  57.527  −6.208  3.673  1.00  63.94  A
ATOM    14   O   PRO  A  72  56.710  −6.451  4.561  1.00  64.11  A
```

-continued

| | | | | | | | | | | | |
|---|---|---|---|---|---|---|---|---|---|---|---|
| ATOM | 15 | N | ALA | A | 73 | 57.341 | −5.268 | 2.753 | 1.00 | 61.57 | A |
| ATOM | 16 | CA | ALA | A | 73 | 56.133 | −4.454 | 2.708 | 1.00 | 58.74 | A |
| ATOM | 17 | CB | ALA | A | 73 | 56.438 | −3.030 | 3.165 | 1.00 | 58.05 | A |
| ATOM | 18 | C | ALA | A | 73 | 55.626 | −4.448 | 1.271 | 1.00 | 56.78 | A |
| ATOM | 19 | O | ALA | A | 73 | 56.347 | −4.834 | 0.349 | 1.00 | 56.95 | A |
| ATOM | 20 | N | PRO | A | 74 | 54.372 | −4.024 | 1.057 | 1.00 | 54.15 | A |
| ATOM | 21 | CD | PRO | A | 74 | 53.335 | −3.610 | 2.018 | 1.00 | 53.31 | A |
| ATOM | 22 | CA | PRO | A | 74 | 53.856 | −4.003 | −0.314 | 1.00 | 52.54 | A |
| ATOM | 23 | CB | PRO | A | 74 | 52.474 | −3.375 | −0.148 | 1.00 | 52.86 | A |
| ATOM | 24 | CG | PRO | A | 74 | 52.067 | −3.824 | 1.226 | 1.00 | 52.88 | A |
| ATOM | 25 | C | PRO | A | 74 | 54.772 | −3.167 | −1.204 | 1.00 | 50.08 | A |
| ATOM | 26 | O | PRO | A | 74 | 55.559 | −2.361 | −0.708 | 1.00 | 49.96 | A |
| ATOM | 27 | N | ALA | A | 75 | 54.680 | −3.366 | −2.514 | 1.00 | 47.58 | A |
| ATOM | 28 | CA | ALA | A | 75 | 55.503 | −2.602 | −3.446 | 1.00 | 44.69 | A |
| ATOM | 29 | CB | ALA | A | 75 | 55.312 | −3.121 | −4.870 | 1.00 | 46.14 | A |
| ATOM | 30 | C | ALA | A | 75 | 55.100 | −1.134 | −3.371 | 1.00 | 41.55 | A |
| ATOM | 31 | O | ALA | A | 75 | 53.947 | −0.813 | −3.086 | 1.00 | 41.01 | A |
| ATOM | 32 | N | LYS | A | 76 | 56.053 | −0.245 | −3.619 | 1.00 | 38.31 | A |
| ATOM | 33 | CA | LYS | A | 76 | 55.781 | 1.184 | −3.588 | 1.00 | 35.72 | A |
| ATOM | 34 | CB | LYS | A | 76 | 57.053 | 1.957 | −3.930 | 1.00 | 37.70 | A |
| ATOM | 35 | CG | LYS | A | 76 | 57.123 | 3.356 | −3.350 | 1.00 | 40.99 | A |
| ATOM | 36 | CD | LYS | A | 76 | 57.262 | 3.316 | −1.836 | 1.00 | 40.04 | A |
| ATOM | 37 | CE | LYS | A | 76 | 57.511 | 4.705 | −1.277 | 1.00 | 42.08 | A |
| ATOM | 38 | NZ | LYS | A | 76 | 57.681 | 4.695 | 0.202 | 1.00 | 42.99 | A |
| ATOM | 39 | C | LYS | A | 76 | 54.708 | 1.467 | −4.638 | 1.00 | 32.65 | A |
| ATOM | 40 | O | LYS | A | 76 | 54.814 | 1.005 | −5.770 | 1.00 | 31.41 | A |
| ATOM | 41 | N | LYS | A | 77 | 53.668 | 2.207 | −4.270 | 1.00 | 28.59 | A |
| ATOM | 42 | CA | LYS | A | 77 | 52.619 | 2.517 | −5.232 | 1.00 | 25.72 | A |
| ATOM | 43 | CB | LYS | A | 77 | 51.316 | 2.865 | −4.509 | 1.00 | 26.22 | A |
| ATOM | 44 | CG | LYS | A | 77 | 50.796 | 1.731 | −3.631 | 1.00 | 27.15 | A |
| ATOM | 45 | CD | LYS | A | 77 | 49.487 | 2.089 | −2.967 | 1.00 | 26.80 | A |
| ATOM | 46 | CE | LYS | A | 77 | 49.136 | 1.091 | −1.870 | 1.00 | 27.31 | A |
| ATOM | 47 | NZ | LYS | A | 77 | 48.998 | −0.296 | −2.380 | 1.00 | 27.17 | A |
| ATOM | 48 | C | LYS | A | 77 | 53.053 | 3.668 | −6.137 | 1.00 | 24.67 | A |
| ATOM | 49 | O | LYS | A | 77 | 54.010 | 4.377 | −5.829 | 1.00 | 21.60 | A |
| ATOM | 50 | N | ARG | A | 78 | 52.351 | 3.838 | −7.254 | 1.00 | 23.66 | A |
| ATOM | 51 | CA | ARG | A | 78 | 52.662 | 4.897 | −8.211 | 1.00 | 26.14 | A |
| ATOM | 52 | CB | ARG | A | 78 | 53.574 | 4.344 | −9.318 | 1.00 | 28.57 | A |
| ATOM | 53 | CG | ARG | A | 78 | 53.017 | 3.139 | −10.050 | 1.00 | 34.78 | A |
| ATOM | 54 | CD | ARG | A | 78 | 54.092 | 2.465 | −10.896 | 1.00 | 40.96 | A |
| ATOM | 55 | NE | ARG | A | 78 | 53.560 | 1.364 | −11.700 | 1.00 | 48.93 | A |
| ATOM | 56 | CZ | ARG | A | 78 | 52.985 | 0.270 | −11.203 | 1.00 | 52.58 | A |
| ATOM | 57 | NH1 | ARG | A | 78 | 52.860 | 0.113 | −9.889 | 1.00 | 54.60 | A |
| ATOM | 58 | NH2 | ARG | A | 78 | 52.530 | −0.672 | −12.022 | 1.00 | 54.09 | A |
| ATOM | 59 | C | ARG | A | 78 | 51.382 | 5.488 | −8.803 | 1.00 | 23.76 | A |
| ATOM | 60 | O | ARG | A | 78 | 50.311 | 4.888 | −8.706 | 1.00 | 24.25 | A |
| ATOM | 61 | N | PRO | A | 79 | 51.475 | 6.676 | −9.428 | 1.00 | 21.76 | A |
| ATOM | 62 | CD | PRO | A | 79 | 52.691 | 7.475 | −9.668 | 1.00 | 20.82 | A |
| ATOM | 63 | CA | PRO | A | 79 | 50.301 | 7.325 | −10.021 | 1.00 | 21.96 | A |
| ATOM | 64 | CB | PRO | A | 79 | 50.910 | 8.481 | −10.816 | 1.00 | 22.27 | A |
| ATOM | 65 | CG | PRO | A | 79 | 52.124 | 8.831 | −10.014 | 1.00 | 22.12 | A |
| ATOM | 66 | C | PRO | A | 79 | 49.446 | 6.413 | −10.903 | 1.00 | 22.86 | A |
| ATOM | 67 | O | PRO | A | 79 | 48.213 | 6.461 | −10.842 | 1.00 | 20.52 | A |
| ATOM | 68 | N | GLU | A | 80 | 50.103 | 5.586 | −11.714 | 1.00 | 21.87 | A |
| ATOM | 69 | CA | GLU | A | 80 | 49.403 | 4.685 | −12.628 | 1.00 | 22.99 | A |
| ATOM | 70 | CB | GLU | A | 80 | 50.393 | 3.994 | −13.571 | 1.00 | 25.24 | A |
| ATOM | 71 | CG | GLU | A | 80 | 51.230 | 2.907 | −12.925 | 1.00 | 28.75 | A |
| ATOM | 72 | CD | GLU | A | 80 | 52.157 | 2.224 | −13.913 | 1.00 | 31.99 | A |
| ATOM | 73 | OE1 | GLU | A | 80 | 53.072 | 2.897 | −14.433 | 1.00 | 34.34 | A |
| ATOM | 74 | OE2 | GLU | A | 80 | 51.969 | 1.015 | −14.172 | 1.00 | 32.83 | A |
| ATOM | 75 | C | GLU | A | 80 | 48.556 | 3.631 | −11.912 | 1.00 | 22.09 | A |
| ATOM | 76 | O | GLU | A | 80 | 47.692 | 3.013 | −12.530 | 1.00 | 22.37 | A |
| ATOM | 77 | N | ASP | A | 81 | 48.804 | 3.413 | −10.622 | 1.00 | 19.97 | A |
| ATOM | 78 | CA | ASP | A | 81 | 48.026 | 2.423 | −9.874 | 1.00 | 19.93 | A |
| ATOM | 79 | CB | ASP | A | 81 | 48.736 | 2.029 | −8.571 | 1.00 | 21.19 | A |
| ATOM | 80 | CG | ASP | A | 81 | 50.089 | 1.380 | −8.807 | 1.00 | 22.46 | A |
| ATOM | 81 | OD1 | ASP | A | 81 | 50.195 | 0.554 | −9.731 | 1.00 | 24.22 | A |
| ATOM | 82 | OD2 | ASP | A | 81 | 51.043 | 1.685 | −8.058 | 1.00 | 23.33 | A |
| ATOM | 83 | C | ASP | A | 81 | 46.652 | 2.975 | −9.518 | 1.00 | 20.85 | A |
| ATOM | 84 | O | ASP | A | 81 | 45.793 | 2.246 | −9.015 | 1.00 | 19.96 | A |
| ATOM | 85 | N | PHE | A | 82 | 46.445 | 4.258 | −9.804 | 1.00 | 18.91 | A |
| ATOM | 86 | CA | PHE | A | 82 | 45.200 | 4.934 | −9.465 | 1.00 | 19.30 | A |
| ATOM | 87 | CB | PHE | A | 82 | 45.475 | 6.027 | −8.427 | 1.00 | 18.43 | A |
| ATOM | 88 | CG | PHE | A | 82 | 46.134 | 5.531 | −7.175 | 1.00 | 18.01 | A |
| ATOM | 89 | CD1 | PHE | A | 82 | 45.371 | 5.136 | −6.084 | 1.00 | 17.19 | A |
| ATOM | 90 | CD2 | PHE | A | 82 | 47.520 | 5.460 | −7.086 | 1.00 | 18.99 | A |
| ATOM | 91 | CE1 | PHE | A | 82 | 45.977 | 4.676 | −4.918 | 1.00 | 17.12 | A |
| ATOM | 92 | CE2 | PHE | A | 82 | 48.137 | 5.000 | −5.925 | 1.00 | 19.64 | A |
| ATOM | 93 | CZ | PHE | A | 82 | 47.361 | 4.607 | −4.838 | 1.00 | 18.00 | A |

| | | | | | -continued | | | | | |
|---|---|---|---|---|---|---|---|---|---|---|
| ATOM | 94 | C | PHE | A | 82 | 44.476 | 5.596 | −10.621 | 1.00 | 20.81 | A |
| ATOM | 95 | O | PHE | A | 82 | 45.066 | 5.933 | −11.649 | 1.00 | 20.34 | A |
| ATOM | 96 | N | LYS | A | 83 | 43.182 | 5.792 | −10.411 | 1.00 | 19.80 | A |
| ATOM | 97 | CA | LYS | A | 83 | 42.321 | 6.478 | −11.353 | 1.00 | 21.65 | A |
| ATOM | 98 | CB | LYS | A | 83 | 41.096 | 5.625 | −11.687 | 1.00 | 22.02 | A |
| ATOM | 99 | CG | LYS | A | 83 | 40.062 | 6.326 | −12.550 | 1.00 | 28.93 | A |
| ATOM | 100 | CD | LYS | A | 83 | 38.974 | 5.355 | −12.981 | 1.00 | 34.20 | A |
| ATOM | 101 | CE | LYS | A | 83 | 37.909 | 6.042 | −13.824 | 1.00 | 38.10 | A |
| ATOM | 102 | NZ | LYS | A | 83 | 37.179 | 7.086 | −13.043 | 1.00 | 43.33 | A |
| ATOM | 103 | C | LYS | A | 83 | 41.913 | 7.702 | −10.541 | 1.00 | 20.74 | A |
| ATOM | 104 | O | LYS | A | 83 | 41.084 | 7.606 | −9.635 | 1.00 | 20.98 | A |
| ATOM | 105 | N | PHE | A | 84 | 42.513 | 8.848 | −10.835 | 1.00 | 19.99 | A |
| ATOM | 106 | CA | PHE | A | 84 | 42.188 | 10.049 | −10.083 | 1.00 | 18.63 | A |
| ATOM | 107 | CB | PHE | A | 84 | 43.279 | 11.103 | −10.258 | 1.00 | 18.95 | A |
| ATOM | 108 | CG | PHE | A | 84 | 44.571 | 10.741 | −9.587 | 1.00 | 17.68 | A |
| ATOM | 109 | CD1 | PHE | A | 84 | 45.498 | 9.926 | −10.224 | 1.00 | 18.16 | A |
| ATOM | 110 | CD2 | PHE | A | 84 | 44.843 | 11.183 | −8.299 | 1.00 | 19.66 | A |
| ATOM | 111 | CE1 | PHE | A | 84 | 46.676 | 9.556 | −9.589 | 1.00 | 18.09 | A |
| ATOM | 112 | CE2 | PHE | A | 84 | 46.021 | 10.816 | −7.653 | 1.00 | 18.89 | A |
| ATOM | 113 | CZ | PHE | A | 84 | 46.936 | 10.002 | −8.301 | 1.00 | 17.33 | A |
| ATOM | 114 | C | PHE | A | 84 | 40.834 | 10.617 | −10.460 | 1.00 | 19.69 | A |
| ATOM | 115 | O | PHE | A | 84 | 40.391 | 10.489 | −11.601 | 1.00 | 20.72 | A |
| ATOM | 116 | N | GLY | A | 85 | 40.178 | 11.233 | −9.484 | 1.00 | 16.80 | A |
| ATOM | 117 | CA | GLY | A | 85 | 38.872 | 11.810 | −9.716 | 1.00 | 17.73 | A |
| ATOM | 118 | C | GLY | A | 85 | 38.819 | 13.280 | −9.346 | 1.00 | 18.75 | A |
| ATOM | 119 | O | GLY | A | 85 | 39.740 | 14.043 | −9.650 | 1.00 | 18.45 | A |
| ATOM | 120 | N | LYS | A | 86 | 37.753 | 13.673 | −8.659 | 1.00 | 16.00 | A |
| ATOM | 121 | CA | LYS | A | 86 | 37.571 | 15.064 | −8.278 | 1.00 | 18.26 | A |
| ATOM | 122 | CB | LYS | A | 86 | 36.133 | 15.302 | −7.812 | 1.00 | 19.00 | A |
| ATOM | 123 | CG | LYS | A | 86 | 35.793 | 14.660 | −6.481 | 1.00 | 21.55 | A |
| ATOM | 124 | CD | LYS | A | 86 | 34.368 | 14.981 | −6.066 | 1.00 | 26.48 | A |
| ATOM | 125 | CE | LYS | A | 86 | 33.994 | 14.239 | −4.793 | 1.00 | 31.92 | A |
| ATOM | 126 | NZ | LYS | A | 86 | 32.568 | 14.457 | −4.412 | 1.00 | 35.36 | A |
| ATOM | 127 | C | LYS | A | 86 | 38.523 | 15.571 | −7.202 | 1.00 | 18.57 | A |
| ATOM | 128 | O | LYS | A | 86 | 39.045 | 14.807 | −6.385 | 1.00 | 16.77 | A |
| ATOM | 129 | N | ILE | A | 87 | 38.737 | 16.881 | −7.227 | 1.00 | 17.88 | A |
| ATOM | 130 | CA | ILE | A | 87 | 39.577 | 17.554 | −6.256 | 1.00 | 18.26 | A |
| ATOM | 131 | CB | ILE | A | 87 | 39.994 | 18.952 | −6.772 | 1.00 | 19.60 | A |
| ATOM | 132 | CG2 | ILE | A | 87 | 40.593 | 19.786 | −5.628 | 1.00 | 18.73 | A |
| ATOM | 133 | CG1 | ILE | A | 87 | 40.968 | 18.786 | −7.945 | 1.00 | 21.16 | A |
| ATOM | 134 | CD1 | ILE | A | 87 | 41.412 | 20.087 | −8.588 | 1.00 | 25.26 | A |
| ATOM | 135 | C | ILE | A | 87 | 38.731 | 17.709 | −4.997 | 1.00 | 19.67 | A |
| ATOM | 136 | O | ILE | A | 87 | 37.628 | 18.249 | −5.052 | 1.00 | 20.41 | A |
| ATOM | 137 | N | LEU | A | 88 | 39.240 | 17.229 | −3.867 | 1.00 | 19.15 | A |
| ATOM | 138 | CA | LEU | A | 88 | 38.508 | 17.324 | −2.611 | 1.00 | 20.68 | A |
| ATOM | 139 | CB | LEU | A | 88 | 38.870 | 16.151 | −1.700 | 1.00 | 19.97 | A |
| ATOM | 140 | CG | LEU | A | 88 | 38.529 | 14.759 | −2.237 | 1.00 | 19.24 | A |
| ATOM | 141 | CD1 | LEU | A | 88 | 39.090 | 13.692 | −1.311 | 1.00 | 21.41 | A |
| ATOM | 142 | CD2 | LEU | A | 88 | 37.029 | 14.622 | −2.359 | 1.00 | 18.84 | A |
| ATOM | 143 | C | LEU | A | 88 | 38.815 | 18.632 | −1.901 | 1.00 | 23.11 | A |
| ATOM | 144 | O | LEU | A | 88 | 37.999 | 19.146 | −1.139 | 1.00 | 25.10 | A |
| ATOM | 145 | N | GLY | A | 89 | 39.997 | 19.174 | −2.149 | 1.00 | 24.09 | A |
| ATOM | 146 | CA | GLY | A | 89 | 40.367 | 20.418 | −1.507 | 1.00 | 24.27 | A |
| ATOM | 147 | C | GLY | A | 89 | 41.658 | 20.954 | −2.078 | 1.00 | 25.47 | A |
| ATOM | 148 | O | GLY | A | 89 | 42.445 | 20.202 | −2.666 | 1.00 | 22.19 | A |
| ATOM | 149 | N | GLU | A | 90 | 41.870 | 22.254 | −1.906 | 1.00 | 26.22 | A |
| ATOM | 150 | CA | GLU | A | 90 | 43.064 | 22.924 | −2.404 | 1.00 | 29.96 | A |
| ATOM | 151 | CB | GLU | A | 90 | 42.698 | 23.814 | −3.596 | 1.00 | 30.75 | A |
| ATOM | 152 | CG | GLU | A | 90 | 42.267 | 23.038 | −4.831 | 1.00 | 34.32 | A |
| ATOM | 153 | CD | GLU | A | 90 | 41.711 | 23.930 | −5.927 | 1.00 | 38.27 | A |
| ATOM | 154 | OE1 | GLU | A | 90 | 40.590 | 24.456 | −5.764 | 1.00 | 40.57 | A |
| ATOM | 155 | OE2 | GLU | A | 90 | 42.398 | 24.110 | −6.952 | 1.00 | 40.90 | A |
| ATOM | 156 | C | GLU | A | 90 | 43.711 | 23.768 | −1.313 | 1.00 | 30.68 | A |
| ATOM | 157 | O | GLU | A | 90 | 43.049 | 24.574 | −0.668 | 1.00 | 32.83 | A |
| ATOM | 158 | N | GLY | A | 91 | 45.006 | 23.566 | −1.104 | 1.00 | 29.66 | A |
| ATOM | 159 | CA | GLY | A | 91 | 45.724 | 24.332 | −0.104 | 1.00 | 29.40 | A |
| ATOM | 160 | C | GLY | A | 91 | 46.795 | 25.151 | −0.798 | 1.00 | 29.98 | A |
| ATOM | 161 | O | GLY | A | 91 | 46.894 | 25.130 | −2.028 | 1.00 | 28.16 | A |
| ATOM | 162 | N | SER | A | 92 | 47.605 | 25.870 | −0.029 | 1.00 | 28.30 | A |
| ATOM | 163 | CA | SER | A | 92 | 48.653 | 26.681 | −0.633 | 1.00 | 30.50 | A |
| ATOM | 164 | CB | SER | A | 92 | 49.165 | 27.717 | 0.370 | 1.00 | 32.43 | A |
| ATOM | 165 | OG | SER | A | 92 | 49.520 | 27.099 | 1.593 | 1.00 | 40.94 | A |
| ATOM | 166 | C | SER | A | 92 | 49.815 | 25.843 | −1.164 | 1.00 | 29.77 | A |
| ATOM | 167 | O | SER | A | 92 | 50.456 | 26.221 | −2.143 | 1.00 | 30.46 | A |
| ATOM | 168 | N | PHE | A | 93 | 50.087 | 24.703 | −0.536 | 1.00 | 27.65 | A |
| ATOM | 169 | CA | PHE | A | 93 | 51.185 | 23.855 | −0.995 | 1.00 | 26.34 | A |
| ATOM | 170 | CB | PHE | A | 93 | 52.281 | 23.785 | 0.068 | 1.00 | 27.95 | A |
| ATOM | 171 | CG | PHE | A | 93 | 52.861 | 25.117 | 0.406 | 1.00 | 31.06 | A |
| ATOM | 172 | CD1 | PHE | A | 93 | 52.283 | 25.909 | 1.392 | 1.00 | 29.96 | A |

-continued

| | | | | | | | | | | |
|---|---|---|---|---|---|---|---|---|---|---|
| ATOM | 173 | CD2 | PHE | A | 93 | 53.949 | 25.613 | −0.308 | 1.00 | 31.38 | A |
| ATOM | 174 | CE1 | PHE | A | 93 | 52.779 | 27.181 | 1.665 | 1.00 | 32.69 | A |
| ATOM | 175 | CE2 | PHE | A | 93 | 54.452 | 26.883 | −0.044 | 1.00 | 32.63 | A |
| ATOM | 176 | CZ | PHE | A | 93 | 53.864 | 27.670 | 0.945 | 1.00 | 31.81 | A |
| ATOM | 177 | C | PHE | A | 93 | 50.759 | 22.445 | −1.365 | 1.00 | 25.39 | A |
| ATOM | 178 | O | PHE | A | 93 | 51.601 | 21.559 | −1.522 | 1.00 | 24.59 | A |
| ATOM | 179 | N | SER | A | 94 | 49.457 | 22.235 | −1.519 | 1.00 | 23.63 | A |
| ATOM | 180 | CA | SER | A | 94 | 48.965 | 20.912 | −1.860 | 1.00 | 21.43 | A |
| ATOM | 181 | CB | SER | A | 94 | 49.017 | 20.013 | −0.628 | 1.00 | 21.42 | A |
| ATOM | 182 | OG | SER | A | 94 | 48.091 | 20.475 | 0.340 | 1.00 | 21.19 | A |
| ATOM | 183 | C | SER | A | 94 | 47.539 | 20.925 | −2.378 | 1.00 | 19.82 | A |
| ATOM | 184 | O | SER | A | 94 | 46.795 | 21.882 | −2.173 | 1.00 | 18.76 | A |
| ATOM | 185 | N | THR | A | 95 | 47.174 | 19.832 | −3.038 | 1.00 | 19.38 | A |
| ATOM | 186 | CA | THR | A | 95 | 45.840 | 19.637 | −3.580 | 1.00 | 17.98 | A |
| ATOM | 187 | CB | THR | A | 95 | 45.818 | 19.818 | −5.110 | 1.00 | 19.25 | A |
| ATOM | 188 | OG1 | THR | A | 95 | 46.196 | 21.162 | −5.434 | 1.00 | 22.04 | A |
| ATOM | 189 | CG2 | THR | A | 95 | 44.421 | 19.549 | −5.661 | 1.00 | 17.61 | A |
| ATOM | 190 | C | THR | A | 95 | 45.455 | 18.201 | −3.243 | 1.00 | 18.61 | A |
| ATOM | 191 | O | THR | A | 95 | 46.212 | 17.264 | −3.524 | 1.00 | 17.10 | A |
| ATOM | 192 | N | VAL | A | 96 | 44.295 | 18.024 | −2.623 | 1.00 | 16.53 | A |
| ATOM | 193 | CA | VAL | A | 96 | 43.845 | 16.685 | −2.266 | 1.00 | 16.05 | A |
| ATOM | 194 | CB | VAL | A | 96 | 43.170 | 16.672 | −0.886 | 1.00 | 16.32 | A |
| ATOM | 195 | CG1 | VAL | A | 96 | 42.741 | 15.249 | −0.532 | 1.00 | 18.02 | A |
| ATOM | 196 | CG2 | VAL | A | 96 | 44.145 | 17.206 | 0.168 | 1.00 | 16.69 | A |
| ATOM | 197 | C | VAL | A | 96 | 42.875 | 16.207 | −3.335 | 1.00 | 16.42 | A |
| ATOM | 198 | O | VAL | A | 96 | 41.906 | 16.892 | −3.665 | 1.00 | 16.47 | A |
| ATOM | 199 | N | VAL | A | 97 | 43.157 | 15.033 | −3.888 | 1.00 | 16.80 | A |
| ATOM | 200 | CA | VAL | A | 97 | 42.338 | 14.471 | −4.949 | 1.00 | 16.72 | A |
| ATOM | 201 | CB | VAL | A | 97 | 43.153 | 14.354 | −6.255 | 1.00 | 18.43 | A |
| ATOM | 202 | CG1 | VAL | A | 97 | 42.249 | 13.927 | −7.404 | 1.00 | 19.69 | A |
| ATOM | 203 | CG2 | VAL | A | 97 | 43.831 | 15.685 | −6.569 | 1.00 | 17.84 | A |
| ATOM | 204 | C | VAL | A | 97 | 41.812 | 13.091 | −4.583 | 1.00 | 16.77 | A |
| ATOM | 205 | O | VAL | A | 97 | 42.532 | 12.270 | −4.014 | 1.00 | 17.13 | A |
| ATOM | 206 | N | LEU | A | 98 | 40.545 | 12.845 | −4.895 | 1.00 | 16.62 | A |
| ATOM | 207 | CA | LEU | A | 98 | 39.947 | 11.548 | −4.624 | 1.00 | 17.04 | A |
| ATOM | 208 | CB | LEU | A | 98 | 38.424 | 11.633 | −4.743 | 1.00 | 16.89 | A |
| ATOM | 209 | CG | LEU | A | 98 | 37.635 | 10.342 | −4.508 | 1.00 | 19.46 | A |
| ATOM | 210 | CD1 | LEU | A | 98 | 37.990 | 9.762 | −3.146 | 1.00 | 20.07 | A |
| ATOM | 211 | CD2 | LEU | A | 98 | 36.143 | 10.627 | −4.588 | 1.00 | 17.93 | A |
| ATOM | 212 | C | LEU | A | 98 | 40.512 | 10.597 | −5.677 | 1.00 | 17.38 | A |
| ATOM | 213 | O | LEU | A | 98 | 40.527 | 10.920 | −6.863 | 1.00 | 18.60 | A |
| ATOM | 214 | N | ALA | A | 99 | 40.995 | 9.438 | −5.246 | 1.00 | 17.13 | A |
| ATOM | 215 | CA | ALA | A | 99 | 41.570 | 8.466 | −6.168 | 1.00 | 18.42 | A |
| ATOM | 216 | CB | ALA | A | 99 | 43.090 | 8.524 | −6.105 | 1.00 | 14.76 | A |
| ATOM | 217 | C | ALA | A | 99 | 41.102 | 7.055 | −5.848 | 1.00 | 21.40 | A |
| ATOM | 218 | O | ALA | A | 99 | 40.941 | 6.691 | −4.679 | 1.00 | 22.52 | A |
| ATOM | 219 | N | ARG | A | 100 | 40.878 | 6.261 | −6.888 | 1.00 | 19.77 | A |
| ATOM | 220 | CA | ARG | A | 100 | 40.459 | 4.884 | −6.693 | 1.00 | 20.85 | A |
| ATOM | 221 | CB | ARG | A | 100 | 39.202 | 4.585 | −7.518 | 1.00 | 24.22 | A |
| ATOM | 222 | CG | ARG | A | 100 | 38.608 | 3.205 | −7.256 | 1.00 | 31.78 | A |
| ATOM | 223 | CD | ARG | A | 100 | 37.326 | 2.979 | −8.048 | 1.00 | 36.24 | A |
| ATOM | 224 | NE | ARG | A | 100 | 36.213 | 3.818 | −7.594 | 1.00 | 41.40 | A |
| ATOM | 225 | CZ | ARG | A | 100 | 35.566 | 3.662 | −6.439 | 1.00 | 42.05 | A |
| ATOM | 226 | NH1 | ARG | A | 100 | 35.912 | 2.696 | −5.598 | 1.00 | 40.67 | A |
| ATOM | 227 | NH2 | ARG | A | 100 | 34.559 | 4.468 | −6.128 | 1.00 | 43.65 | A |
| ATOM | 228 | C | ARG | A | 100 | 41.613 | 3.985 | −7.129 | 1.00 | 18.63 | A |
| ATOM | 229 | O | ARG | A | 100 | 42.078 | 4.065 | −8.271 | 1.00 | 19.49 | A |
| ATOM | 230 | N | GLU | A | 101 | 42.102 | 3.157 | −6.212 | 1.00 | 16.43 | A |
| ATOM | 231 | CA | GLU | A | 101 | 43.196 | 2.246 | −6.533 | 1.00 | 16.11 | A |
| ATOM | 232 | CB | GLU | A | 101 | 43.774 | 1.637 | −5.248 | 1.00 | 16.79 | A |
| ATOM | 233 | CG | GLU | A | 101 | 44.917 | 0.657 | −5.488 | 1.00 | 16.51 | A |
| ATOM | 234 | CD | GLU | A | 101 | 45.501 | 0.115 | −4.200 | 1.00 | 18.20 | A |
| ATOM | 235 | OE1 | GLU | A | 101 | 44.733 | −0.081 | −3.239 | 1.00 | 18.32 | A |
| ATOM | 236 | OE2 | GLU | A | 101 | 46.725 | −0.132 | −4.150 | 1.00 | 17.14 | A |
| ATOM | 237 | C | GLU | A | 101 | 42.625 | 1.152 | −7.442 | 1.00 | 17.92 | A |
| ATOM | 238 | O | GLU | A | 101 | 41.681 | 0.462 | −7.069 | 1.00 | 18.02 | A |
| ATOM | 239 | N | LEU | A | 102 | 43.198 | 1.002 | −8.632 | 1.00 | 19.06 | A |
| ATOM | 240 | CA | LEU | A | 102 | 42.718 | 0.025 | −9.607 | 1.00 | 20.71 | A |
| ATOM | 241 | CB | LEU | A | 102 | 43.569 | 0.097 | −10.878 | 1.00 | 23.42 | A |
| ATOM | 242 | CG | LEU | A | 102 | 43.531 | 1.426 | −11.642 | 1.00 | 25.30 | A |
| ATOM | 243 | CD1 | LEU | A | 102 | 44.577 | 1.414 | −12.748 | 1.00 | 27.88 | A |
| ATOM | 244 | CD2 | LEU | A | 102 | 42.140 | 1.647 | −12.214 | 1.00 | 26.79 | A |
| ATOM | 245 | C | LEU | A | 102 | 42.671 | −1.418 | −9.125 | 1.00 | 21.62 | A |
| ATOM | 246 | O | LEU | A | 102 | 41.668 | −2.103 | −9.305 | 1.00 | 21.09 | A |
| ATOM | 247 | N | ALA | A | 103 | 43.753 | −1.874 | −8.507 | 1.00 | 19.38 | A |
| ATOM | 248 | CA | ALA | A | 103 | 43.836 | −3.249 | −8.035 | 1.00 | 20.87 | A |
| ATOM | 249 | CB | ALA | A | 103 | 45.284 | −3.571 | −7.671 | 1.00 | 19.23 | A |
| ATOM | 250 | C | ALA | A | 103 | 42.919 | −3.629 | −6.872 | 1.00 | 19.92 | A |
| ATOM | 251 | O | ALA | A | 103 | 42.703 | −4.815 | −6.628 | 1.00 | 20.38 | A |

-continued

| | | | | | | | | | | | |
|---|---|---|---|---|---|---|---|---|---|---|---|
| ATOM | 252 | N | THR | A | 104 | 42.361 | −2.643 | −6.175 | 1.00 | 18.12 | A |
| ATOM | 253 | CA | THR | A | 104 | 41.517 | −2.927 | −5.018 | 1.00 | 17.15 | A |
| ATOM | 254 | CB | THR | A | 104 | 42.212 | −2.484 | −3.717 | 1.00 | 19.54 | A |
| ATOM | 255 | OG1 | THR | A | 104 | 42.456 | −1.070 | −3.773 | 1.00 | 19.26 | A |
| ATOM | 256 | CG2 | THR | A | 104 | 43.536 | −3.219 | −3.529 | 1.00 | 17.02 | A |
| ATOM | 257 | C | THR | A | 104 | 40.159 | −2.247 | −5.026 | 1.00 | 19.44 | A |
| ATOM | 258 | O | THR | A | 104 | 39.259 | −2.648 | −4.285 | 1.00 | 18.70 | A |
| ATOM | 259 | N | SER | A | 105 | 40.034 | −1.207 | −5.847 | 1.00 | 19.65 | A |
| ATOM | 260 | CA | SER | A | 105 | 38.819 | −0.400 | −5.967 | 1.00 | 19.37 | A |
| ATOM | 261 | CB | SER | A | 105 | 37.598 | −1.304 | −6.173 | 1.00 | 21.81 | A |
| ATOM | 262 | OG | SER | A | 105 | 36.431 | −0.539 | −6.412 | 1.00 | 23.01 | A |
| ATOM | 263 | C | SER | A | 105 | 38.644 | 0.447 | −4.701 | 1.00 | 18.99 | A |
| ATOM | 264 | O | SER | A | 105 | 37.602 | 1.070 | −4.488 | 1.00 | 18.66 | A |
| ATOM | 265 | N | ARG | A | 106 | 39.674 | 0.468 | −3.861 | 1.00 | 16.84 | A |
| ATOM | 266 | CA | ARG | A | 106 | 39.655 | 1.267 | −2.634 | 1.00 | 16.21 | A |
| ATOM | 267 | CB | ARG | A | 106 | 40.827 | 0.886 | −1.723 | 1.00 | 16.41 | A |
| ATOM | 268 | CG | ARG | A | 106 | 40.619 | −0.367 | −0.906 | 1.00 | 15.49 | A |
| ATOM | 269 | CD | ARG | A | 106 | 41.887 | −0.755 | −0.170 | 1.00 | 17.43 | A |
| ATOM | 270 | NE | ARG | A | 106 | 41.620 | −1.792 | 0.824 | 1.00 | 20.47 | A |
| ATOM | 271 | CZ | ARG | A | 106 | 42.548 | −2.568 | 1.371 | 1.00 | 20.24 | A |
| ATOM | 272 | NH1 | ARG | A | 106 | 43.821 | −2.433 | 1.017 | 1.00 | 17.80 | A |
| ATOM | 273 | NH2 | ARG | A | 106 | 42.198 | −3.468 | 2.285 | 1.00 | 20.14 | A |
| ATOM | 274 | C | ARG | A | 106 | 39.785 | 2.746 | −2.981 | 1.00 | 17.37 | A |
| ATOM | 275 | O | ARG | A | 106 | 40.514 | 3.103 | −3.902 | 1.00 | 17.75 | A |
| ATOM | 276 | N | GLU | A | 107 | 39.085 | 3.599 | −2.240 | 1.00 | 16.06 | A |
| ATOM | 277 | CA | GLU | A | 107 | 39.156 | 5.039 | −2.461 | 1.00 | 20.80 | A |
| ATOM | 278 | CB | GLU | A | 107 | 37.779 | 5.694 | −2.337 | 1.00 | 22.93 | A |
| ATOM | 279 | CG | GLU | A | 107 | 36.711 | 5.171 | −3.269 | 1.00 | 30.87 | A |
| ATOM | 280 | CD | GLU | A | 107 | 35.431 | 5.975 | −3.148 | 1.00 | 32.40 | A |
| ATOM | 281 | OE1 | GLU | A | 107 | 35.262 | 6.939 | −3.923 | 1.00 | 33.74 | A |
| ATOM | 282 | OE2 | GLU | A | 107 | 34.608 | 5.654 | −2.263 | 1.00 | 36.00 | A |
| ATOM | 283 | C | GLU | A | 107 | 40.053 | 5.678 | −1.410 | 1.00 | 18.93 | A |
| ATOM | 284 | O | GLU | A | 107 | 39.891 | 5.427 | −0.220 | 1.00 | 19.21 | A |
| ATOM | 285 | N | TYR | A | 108 | 40.988 | 6.507 | −1.852 | 1.00 | 16.70 | A |
| ATOM | 286 | CA | TYR | A | 108 | 41.883 | 7.209 | −0.942 | 1.00 | 15.86 | A |
| ATOM | 287 | CB | TYR | A | 108 | 43.325 | 6.728 | −1.104 | 1.00 | 15.30 | A |
| ATOM | 288 | CG | TYR | A | 108 | 43.593 | 5.328 | −0.612 | 1.00 | 16.33 | A |
| ATOM | 289 | CD1 | TYR | A | 108 | 43.765 | 5.066 | 0.746 | 1.00 | 16.36 | A |
| ATOM | 290 | CE1 | TYR | A | 108 | 44.046 | 3.769 | 1.201 | 1.00 | 18.48 | A |
| ATOM | 291 | CD2 | TYR | A | 108 | 43.701 | 4.268 | −1.511 | 1.00 | 13.25 | A |
| ATOM | 292 | CE2 | TYR | A | 108 | 43.980 | 2.981 | −1.075 | 1.00 | 17.28 | A |
| ATOM | 293 | CZ | TYR | A | 108 | 44.152 | 2.736 | 0.276 | 1.00 | 19.17 | A |
| ATOM | 294 | OH | TYR | A | 108 | 44.440 | 1.461 | 0.688 | 1.00 | 19.38 | A |
| ATOM | 295 | C | TYR | A | 108 | 41.850 | 8.687 | −1.292 | 1.00 | 16.80 | A |
| ATOM | 296 | O | TYR | A | 108 | 41.560 | 9.058 | −2.431 | 1.00 | 15.22 | A |
| ATOM | 297 | N | ALA | A | 109 | 42.132 | 9.528 | −0.306 | 1.00 | 14.61 | A |
| ATOM | 298 | CA | ALA | A | 109 | 42.207 | 10.957 | −0.539 | 1.00 | 14.30 | A |
| ATOM | 299 | CB | ALA | A | 109 | 41.671 | 11.726 | 0.661 | 1.00 | 14.78 | A |
| ATOM | 300 | C | ALA | A | 109 | 43.713 | 11.136 | −0.667 | 1.00 | 16.79 | A |
| ATOM | 301 | O | ALA | A | 109 | 44.450 | 10.983 | 0.317 | 1.00 | 16.52 | A |
| ATOM | 302 | N | ILE | A | 110 | 44.182 | 11.410 | −1.881 | 1.00 | 14.80 | A |
| ATOM | 303 | CA | ILE | A | 110 | 45.609 | 11.574 | −2.093 | 1.00 | 15.80 | A |
| ATOM | 304 | CB | ILE | A | 110 | 46.065 | 10.863 | −3.396 | 1.00 | 16.85 | A |
| ATOM | 305 | CG2 | ILE | A | 110 | 47.550 | 11.098 | −3.632 | 1.00 | 16.80 | A |
| ATOM | 306 | CG1 | ILE | A | 110 | 45.774 | 9.358 | −3.284 | 1.00 | 17.76 | A |
| ATOM | 307 | CD1 | ILE | A | 110 | 46.308 | 8.513 | −4.437 | 1.00 | 16.07 | A |
| ATOM | 308 | C | ILE | A | 110 | 46.004 | 13.045 | −2.129 | 1.00 | 17.78 | A |
| ATOM | 309 | O | ILE | A | 110 | 45.534 | 13.813 | −2.976 | 1.00 | 16.24 | A |
| ATOM | 310 | N | LYS | A | 111 | 46.846 | 13.435 | −1.177 | 1.00 | 16.15 | A |
| ATOM | 311 | CA | LYS | A | 111 | 47.326 | 14.808 | −1.100 | 1.00 | 17.20 | A |
| ATOM | 312 | CB | LYS | A | 111 | 47.700 | 15.176 | 0.344 | 1.00 | 17.41 | A |
| ATOM | 313 | CG | LYS | A | 111 | 48.350 | 16.547 | 0.464 | 1.00 | 20.71 | A |
| ATOM | 314 | CD | LYS | A | 111 | 48.585 | 16.971 | 1.910 | 1.00 | 24.25 | A |
| ATOM | 315 | CE | LYS | A | 111 | 47.288 | 17.381 | 2.598 | 1.00 | 29.46 | A |
| ATOM | 316 | NZ | LYS | A | 111 | 47.516 | 17.866 | 4.000 | 1.00 | 30.50 | A |
| ATOM | 317 | C | LYS | A | 111 | 48.551 | 14.890 | −1.994 | 1.00 | 16.41 | A |
| ATOM | 318 | O | LYS | A | 111 | 49.509 | 14.137 | −1.813 | 1.00 | 18.20 | A |
| ATOM | 319 | N | ILE | A | 112 | 48.509 | 15.798 | −2.963 | 1.00 | 15.87 | A |
| ATOM | 320 | CA | ILE | A | 112 | 49.606 | 15.967 | −3.907 | 1.00 | 17.28 | A |
| ATOM | 321 | CB | ILE | A | 112 | 49.079 | 15.911 | −5.358 | 1.00 | 16.43 | A |
| ATOM | 322 | CG2 | ILE | A | 112 | 50.235 | 15.998 | −6.341 | 1.00 | 15.12 | A |
| ATOM | 323 | CG1 | ILE | A | 112 | 48.293 | 14.609 | −5.565 | 1.00 | 16.82 | A |
| ATOM | 324 | CD1 | ILE | A | 112 | 47.580 | 14.511 | −6.904 | 1.00 | 18.47 | A |
| ATOM | 325 | C | ILE | A | 112 | 50.307 | 17.301 | −3.663 | 1.00 | 19.03 | A |
| ATOM | 326 | O | ILE | A | 112 | 49.669 | 18.350 | −3.635 | 1.00 | 19.15 | A |
| ATOM | 327 | N | LEU | A | 113 | 51.622 | 17.245 | −3.472 | 1.00 | 20.22 | A |
| ATOM | 328 | CA | LEU | A | 113 | 52.416 | 18.442 | −3.214 | 1.00 | 22.36 | A |
| ATOM | 329 | CB | LEU | A | 113 | 52.995 | 18.397 | −1.794 | 1.00 | 22.13 | A |
| ATOM | 330 | CG | LEU | A | 113 | 52.042 | 18.063 | −0.646 | 1.00 | 22.46 | A |

-continued

| | | | | | | | | | | | |
|---|---|---|---|---|---|---|---|---|---|---|---|
| ATOM | 331 | CD1 | LEU | A | 113 | 51.866 | 16.557 | −0.553 | 1.00 | 23.81 | A |
| ATOM | 332 | CD2 | LEU | A | 113 | 52.603 | 18.595 | 0.660 | 1.00 | 23.68 | A |
| ATOM | 333 | C | LEU | A | 113 | 53.560 | 18.547 | −4.215 | 1.00 | 23.37 | A |
| ATOM | 334 | O | LEU | A | 113 | 54.300 | 17.586 | −4.424 | 1.00 | 23.11 | A |
| ATOM | 335 | N | GLU | A | 114 | 53.706 | 19.714 | −4.834 | 1.00 | 23.88 | A |
| ATOM | 336 | CA | GLU | A | 114 | 54.771 | 19.920 | −5.806 | 1.00 | 26.00 | A |
| ATOM | 337 | CB | GLU | A | 114 | 54.435 | 21.111 | −6.706 | 1.00 | 27.74 | A |
| ATOM | 338 | CG | GLU | A | 114 | 55.533 | 21.452 | −7.696 | 1.00 | 35.07 | A |
| ATOM | 339 | CD | GLU | A | 114 | 55.220 | 22.696 | −8.497 | 1.00 | 39.24 | A |
| ATOM | 340 | OE1 | GLU | A | 114 | 54.808 | 23.703 | −7.885 | 1.00 | 41.45 | A |
| ATOM | 341 | OE2 | GLU | A | 114 | 55.395 | 22.670 | −9.736 | 1.00 | 44.05 | A |
| ATOM | 342 | C | GLU | A | 114 | 56.087 | 20.163 | −5.067 | 1.00 | 24.37 | A |
| ATOM | 343 | O | GLU | A | 114 | 56.186 | 21.071 | −4.238 | 1.00 | 24.43 | A |
| ATOM | 344 | N | LYS | A | 115 | 57.096 | 19.350 | −5.360 | 1.00 | 24.10 | A |
| ATOM | 345 | CA | LYS | A | 115 | 58.376 | 19.493 | −4.678 | 1.00 | 24.93 | A |
| ATOM | 346 | CB | LYS | A | 115 | 59.339 | 18.373 | −5.103 | 1.00 | 23.72 | A |
| ATOM | 347 | CG | LYS | A | 115 | 59.139 | 17.080 | −4.308 | 1.00 | 23.09 | A |
| ATOM | 348 | CD | LYS | A | 115 | 60.064 | 15.944 | −4.743 | 1.00 | 21.92 | A |
| ATOM | 349 | CE | LYS | A | 115 | 59.691 | 15.400 | −6.117 | 1.00 | 22.42 | A |
| ATOM | 350 | NZ | LYS | A | 115 | 60.447 | 14.150 | −6.448 | 1.00 | 19.71 | A |
| ATOM | 351 | C | LYS | A | 115 | 59.031 | 20.858 | −4.868 | 1.00 | 26.87 | A |
| ATOM | 352 | O | LYS | A | 115 | 59.492 | 21.469 | −3.903 | 1.00 | 26.17 | A |
| ATOM | 353 | N | ARG | A | 116 | 59.058 | 21.348 | −6.102 | 1.00 | 28.73 | A |
| ATOM | 354 | CA | ARG | A | 116 | 59.678 | 22.638 | −6.380 | 1.00 | 29.66 | A |
| ATOM | 355 | CB | ARG | A | 116 | 59.533 | 22.980 | −7.868 | 1.00 | 31.29 | A |
| ATOM | 356 | CG | ARG | A | 116 | 60.047 | 24.361 | −8.267 | 1.00 | 33.19 | A |
| ATOM | 357 | CD | ARG | A | 116 | 61.368 | 24.710 | −7.590 | 1.00 | 35.13 | A |
| ATOM | 358 | NE | ARG | A | 116 | 62.329 | 23.612 | −7.618 | 1.00 | 36.42 | A |
| ATOM | 359 | CZ | ARG | A | 116 | 63.510 | 23.648 | −7.009 | 1.00 | 36.18 | A |
| ATOM | 360 | NH1 | ARG | A | 116 | 63.871 | 24.729 | −6.332 | 1.00 | 36.12 | A |
| ATOM | 361 | NH2 | ARG | A | 116 | 64.324 | 22.602 | −7.067 | 1.00 | 35.77 | A |
| ATOM | 362 | C | ARG | A | 116 | 59.097 | 23.761 | −5.519 | 1.00 | 29.70 | A |
| ATOM | 363 | O | ARG | A | 116 | 59.843 | 24.515 | −4.889 | 1.00 | 29.16 | A |
| ATOM | 364 | N | HIS | A | 117 | 57.773 | 23.862 | −5.472 | 1.00 | 27.22 | A |
| ATOM | 365 | CA | HIS | A | 117 | 57.126 | 24.903 | −4.681 | 1.00 | 26.33 | A |
| ATOM | 366 | CB | HIS | A | 117 | 55.606 | 24.835 | −4.848 | 1.00 | 28.41 | A |
| ATOM | 367 | CG | HIS | A | 117 | 54.881 | 26.005 | −4.258 | 1.00 | 31.82 | A |
| ATOM | 368 | CD2 | HIS | A | 117 | 55.309 | 27.249 | −3.935 | 1.00 | 33.19 | A |
| ATOM | 369 | ND1 | HIS | A | 117 | 53.536 | 25.974 | −3.961 | 1.00 | 34.30 | A |
| ATOM | 370 | CE1 | HIS | A | 117 | 53.165 | 27.148 | −3.480 | 1.00 | 34.58 | A |
| ATOM | 371 | NE2 | HIS | A | 117 | 54.222 | 27.940 | −3.455 | 1.00 | 35.18 | A |
| ATOM | 372 | C | HIS | A | 117 | 57.477 | 24.780 | −3.202 | 1.00 | 26.22 | A |
| ATOM | 373 | O | HIS | A | 117 | 57.737 | 25.776 | −2.534 | 1.00 | 25.67 | A |
| ATOM | 374 | N | ILE | A | 118 | 57.469 | 23.554 | −2.689 | 1.00 | 24.94 | A |
| ATOM | 375 | CA | ILE | A | 118 | 57.792 | 23.315 | −1.285 | 1.00 | 23.94 | A |
| ATOM | 376 | CB | ILE | A | 118 | 57.711 | 21.812 | −0.952 | 1.00 | 23.50 | A |
| ATOM | 377 | CG2 | ILE | A | 118 | 58.374 | 21.533 | 0.389 | 1.00 | 23.76 | A |
| ATOM | 378 | CG1 | ILE | A | 118 | 56.246 | 21.362 | −0.959 | 1.00 | 24.42 | A |
| ATOM | 379 | CD1 | ILE | A | 118 | 56.066 | 19.858 | −0.834 | 1.00 | 28.06 | A |
| ATOM | 380 | C | ILE | A | 118 | 59.195 | 23.821 | −0.958 | 1.00 | 23.78 | A |
| ATOM | 381 | O | ILE | A | 118 | 59.402 | 24.495 | 0.048 | 1.00 | 23.49 | A |
| ATOM | 382 | N | ILE | A | 119 | 60.153 | 23.489 | −1.815 | 1.00 | 23.46 | A |
| ATOM | 383 | CA | ILE | A | 119 | 61.534 | 23.913 | −1.619 | 1.00 | 25.13 | A |
| ATOM | 384 | CB | ILE | A | 119 | 62.467 | 23.250 | −2.664 | 1.00 | 24.25 | A |
| ATOM | 385 | CG2 | ILE | A | 119 | 63.858 | 23.890 | −2.617 | 1.00 | 22.47 | A |
| ATOM | 386 | CG1 | ILE | A | 119 | 62.540 | 21.738 | −2.395 | 1.00 | 25.05 | A |
| ATOM | 387 | CD1 | ILE | A | 119 | 63.327 | 20.945 | −3.439 | 1.00 | 24.62 | A |
| ATOM | 388 | C | ILE | A | 119 | 61.667 | 25.435 | −1.705 | 1.00 | 25.96 | A |
| ATOM | 389 | O | ILE | A | 119 | 62.330 | 26.051 | −0.872 | 1.00 | 24.78 | A |
| ATOM | 390 | N | LYS | A | 120 | 61.028 | 26.039 | −2.704 | 1.00 | 27.67 | A |
| ATOM | 391 | CA | LYS | A | 120 | 61.100 | 27.489 | −2.879 | 1.00 | 30.29 | A |
| ATOM | 392 | CB | LYS | A | 120 | 60.242 | 27.940 | −4.060 | 1.00 | 32.34 | A |
| ATOM | 393 | CG | LYS | A | 120 | 60.674 | 27.407 | −5.409 | 1.00 | 39.30 | A |
| ATOM | 394 | CD | LYS | A | 120 | 59.765 | 27.950 | −6.512 | 1.00 | 45.19 | A |
| ATOM | 395 | CE | LYS | A | 120 | 58.294 | 27.636 | −6.218 | 1.00 | 46.48 | A |
| ATOM | 396 | NZ | LYS | A | 120 | 57.363 | 28.155 | −7.252 | 1.00 | 46.49 | A |
| ATOM | 397 | C | LYS | A | 120 | 60.647 | 28.247 | −1.638 | 1.00 | 30.89 | A |
| ATOM | 398 | O | LYS | A | 120 | 61.303 | 29.198 | −1.217 | 1.00 | 32.48 | A |
| ATOM | 399 | N | GLU | A | 121 | 59.527 | 27.825 | −1.055 | 1.00 | 29.82 | A |
| ATOM | 400 | CA | GLU | A | 121 | 58.986 | 28.488 | 0.128 | 1.00 | 30.33 | A |
| ATOM | 401 | CB | GLU | A | 121 | 57.455 | 28.416 | 0.117 | 1.00 | 33.04 | A |
| ATOM | 402 | CG | GLU | A | 121 | 56.794 | 29.021 | −1.120 | 1.00 | 36.45 | A |
| ATOM | 403 | CD | GLU | A | 121 | 57.221 | 30.456 | −1.373 | 1.00 | 39.88 | A |
| ATOM | 404 | OE1 | GLU | A | 121 | 57.200 | 31.264 | −0.420 | 1.00 | 40.53 | A |
| ATOM | 405 | OE2 | GLU | A | 121 | 57.573 | 30.778 | −2.529 | 1.00 | 43.24 | A |
| ATOM | 406 | C | GLU | A | 121 | 59.511 | 27.930 | 1.451 | 1.00 | 30.37 | A |
| ATOM | 407 | O | GLU | A | 121 | 58.946 | 28.204 | 2.513 | 1.00 | 31.24 | A |
| ATOM | 408 | N | ASN | A | 122 | 60.588 | 27.151 | 1.390 | 1.00 | 29.03 | A |
| ATOM | 409 | CA | ASN | A | 122 | 61.183 | 26.573 | 2.594 | 1.00 | 28.46 | A |

-continued

| | | | | | | | | | | |
|---|---|---|---|---|---|---|---|---|---|---|
| ATOM | 410 | CB | ASN | A | 122 | 61.836 | 27.673 | 3.436 | 1.00 | 31.28 | A |
| ATOM | 411 | CG | ASN | A | 122 | 62.945 | 28.395 | 2.698 | 1.00 | 34.12 | A |
| ATOM | 412 | OD1 | ASN | A | 122 | 62.697 | 29.143 | 1.754 | 1.00 | 35.57 | A |
| ATOM | 413 | ND2 | ASN | A | 122 | 64.181 | 28.169 | 3.127 | 1.00 | 35.73 | A |
| ATOM | 414 | C | ASN | A | 122 | 60.157 | 25.835 | 3.456 | 1.00 | 26.89 | A |
| ATOM | 415 | O | ASN | A | 122 | 60.085 | 26.055 | 4.663 | 1.00 | 27.23 | A |
| ATOM | 416 | N | LYS | A | 123 | 59.375 | 24.955 | 2.842 | 1.00 | 23.99 | A |
| ATOM | 417 | CA | LYS | A | 123 | 58.358 | 24.210 | 3.574 | 1.00 | 22.43 | A |
| ATOM | 418 | CB | LYS | A | 123 | 57.031 | 24.248 | 2.810 | 1.00 | 21.97 | A |
| ATOM | 419 | CG | LYS | A | 123 | 56.475 | 25.645 | 2.599 | 1.00 | 25.68 | A |
| ATOM | 420 | CD | LYS | A | 123 | 56.253 | 26.354 | 3.927 | 1.00 | 27.54 | A |
| ATOM | 421 | CE | LYS | A | 123 | 55.822 | 27.796 | 3.716 | 1.00 | 31.30 | A |
| ATOM | 422 | NZ | LYS | A | 123 | 55.756 | 28.540 | 5.004 | 1.00 | 33.21 | A |
| ATOM | 423 | C | LYS | A | 123 | 58.748 | 22.759 | 3.821 | 1.00 | 22.20 | A |
| ATOM | 424 | O | LYS | A | 123 | 57.924 | 21.960 | 4.264 | 1.00 | 22.50 | A |
| ATOM | 425 | N | VAL | A | 124 | 59.997 | 22.412 | 3.535 | 1.00 | 20.59 | A |
| ATOM | 426 | CA | VAL | A | 124 | 60.439 | 21.039 | 3.730 | 1.00 | 20.25 | A |
| ATOM | 427 | CB | VAL | A | 124 | 61.922 | 20.850 | 3.328 | 1.00 | 19.43 | A |
| ATOM | 428 | CG1 | VAL | A | 124 | 62.346 | 19.407 | 3.573 | 1.00 | 18.69 | A |
| ATOM | 429 | CG2 | VAL | A | 124 | 62.104 | 21.195 | 1.853 | 1.00 | 18.21 | A |
| ATOM | 430 | C | VAL | A | 124 | 60.236 | 20.561 | 5.163 | 1.00 | 19.53 | A |
| ATOM | 431 | O | VAL | A | 124 | 59.841 | 19.418 | 5.385 | 1.00 | 20.02 | A |
| ATOM | 432 | N | PRO | A | 125 | 60.513 | 21.422 | 6.159 | 1.00 | 20.01 | A |
| ATOM | 433 | CD | PRO | A | 125 | 61.178 | 22.738 | 6.118 | 1.00 | 18.69 | A |
| ATOM | 434 | CA | PRO | A | 125 | 60.318 | 20.979 | 7.544 | 1.00 | 19.88 | A |
| ATOM | 435 | CB | PRO | A | 125 | 60.793 | 22.180 | 8.363 | 1.00 | 19.95 | A |
| ATOM | 436 | CG | PRO | A | 125 | 61.839 | 22.805 | 7.479 | 1.00 | 18.85 | A |
| ATOM | 437 | C | PRO | A | 125 | 58.848 | 20.642 | 7.824 | 1.00 | 19.76 | A |
| ATOM | 438 | O | PRO | A | 125 | 58.544 | 19.700 | 8.550 | 1.00 | 16.99 | A |
| ATOM | 439 | N | TYR | A | 126 | 57.947 | 21.418 | 7.235 | 1.00 | 18.98 | A |
| ATOM | 440 | CA | TYR | A | 126 | 56.516 | 21.220 | 7.435 | 1.00 | 21.97 | A |
| ATOM | 441 | CB | TYR | A | 126 | 55.752 | 22.448 | 6.933 | 1.00 | 25.17 | A |
| ATOM | 442 | CG | TYR | A | 126 | 56.040 | 23.690 | 7.748 | 1.00 | 30.98 | A |
| ATOM | 443 | CD1 | TYR | A | 126 | 55.438 | 23.886 | 8.991 | 1.00 | 33.95 | A |
| ATOM | 444 | CE1 | TYR | A | 126 | 55.721 | 25.015 | 9.763 | 1.00 | 36.60 | A |
| ATOM | 445 | CD2 | TYR | A | 126 | 56.938 | 24.657 | 7.292 | 1.00 | 35.43 | A |
| ATOM | 446 | CE2 | TYR | A | 126 | 57.231 | 25.792 | 8.058 | 1.00 | 37.20 | A |
| ATOM | 447 | CZ | TYR | A | 126 | 56.618 | 25.962 | 9.291 | 1.00 | 37.40 | A |
| ATOM | 448 | OH | TYR | A | 126 | 56.903 | 27.073 | 10.052 | 1.00 | 40.85 | A |
| ATOM | 449 | C | TYR | A | 126 | 55.990 | 19.956 | 6.762 | 1.00 | 21.35 | A |
| ATOM | 450 | O | TYR | A | 126 | 55.265 | 19.175 | 7.383 | 1.00 | 20.49 | A |
| ATOM | 451 | N | VAL | A | 127 | 56.354 | 19.746 | 5.501 | 1.00 | 18.16 | A |
| ATOM | 452 | CA | VAL | A | 127 | 55.892 | 18.562 | 4.790 | 1.00 | 17.58 | A |
| ATOM | 453 | CB | VAL | A | 127 | 56.308 | 18.596 | 3.308 | 1.00 | 17.45 | A |
| ATOM | 454 | CG1 | VAL | A | 127 | 55.786 | 17.350 | 2.600 | 1.00 | 17.97 | A |
| ATOM | 455 | CG2 | VAL | A | 127 | 55.751 | 19.850 | 2.641 | 1.00 | 14.90 | A |
| ATOM | 456 | C | VAL | A | 127 | 56.459 | 17.306 | 5.448 | 1.00 | 18.39 | A |
| ATOM | 457 | O | VAL | A | 127 | 55.769 | 16.298 | 5.583 | 1.00 | 18.14 | A |
| ATOM | 458 | N | THR | A | 128 | 57.716 | 17.381 | 5.869 | 1.00 | 17.50 | A |
| ATOM | 459 | CA | THR | A | 128 | 58.375 | 16.260 | 6.530 | 1.00 | 18.54 | A |
| ATOM | 460 | CB | THR | A | 128 | 59.861 | 16.586 | 6.805 | 1.00 | 18.01 | A |
| ATOM | 461 | OG1 | THR | A | 128 | 60.537 | 16.804 | 5.559 | 1.00 | 21.14 | A |
| ATOM | 462 | CG2 | THR | A | 128 | 60.536 | 15.446 | 7.545 | 1.00 | 17.95 | A |
| ATOM | 463 | C | THR | A | 128 | 57.676 | 15.941 | 7.856 | 1.00 | 19.49 | A |
| ATOM | 464 | O | THR | A | 128 | 57.438 | 14.776 | 8.179 | 1.00 | 18.76 | A |
| ATOM | 465 | N | ARG | A | 129 | 57.345 | 16.981 | 8.619 | 1.00 | 19.60 | A |
| ATOM | 466 | CA | ARG | A | 129 | 56.673 | 16.804 | 9.904 | 1.00 | 20.12 | A |
| ATOM | 467 | CB | ARG | A | 129 | 56.534 | 18.144 | 10.621 | 1.00 | 21.33 | A |
| ATOM | 468 | CG | ARG | A | 129 | 55.948 | 18.029 | 12.023 | 1.00 | 28.02 | A |
| ATOM | 469 | CD | ARG | A | 129 | 55.721 | 19.404 | 12.597 | 1.00 | 31.25 | A |
| ATOM | 470 | NE | ARG | A | 129 | 56.940 | 20.205 | 12.560 | 1.00 | 37.78 | A |
| ATOM | 471 | CZ | ARG | A | 129 | 56.962 | 21.524 | 12.391 | 1.00 | 40.10 | A |
| ATOM | 472 | NH1 | ARG | A | 129 | 55.828 | 22.197 | 12.239 | 1.00 | 40.03 | A |
| ATOM | 473 | NH2 | ARG | A | 129 | 58.119 | 22.170 | 12.374 | 1.00 | 44.58 | A |
| ATOM | 474 | C | ARG | A | 129 | 55.288 | 16.186 | 9.729 | 1.00 | 20.08 | A |
| ATOM | 475 | O | ARG | A | 129 | 54.891 | 15.305 | 10.496 | 1.00 | 20.40 | A |
| ATOM | 476 | N | GLU | A | 130 | 54.553 | 16.654 | 8.724 | 1.00 | 18.79 | A |
| ATOM | 477 | CA | GLU | A | 130 | 53.222 | 16.125 | 8.454 | 1.00 | 20.10 | A |
| ATOM | 478 | CB | GLU | A | 130 | 52.638 | 16.749 | 7.183 | 1.00 | 19.92 | A |
| ATOM | 479 | CG | GLU | A | 130 | 51.350 | 16.087 | 6.708 | 1.00 | 27.85 | A |
| ATOM | 480 | CD | GLU | A | 130 | 50.581 | 16.933 | 5.707 | 1.00 | 29.72 | A |
| ATOM | 481 | OE1 | GLU | A | 130 | 51.216 | 17.528 | 4.814 | 1.00 | 33.46 | A |
| ATOM | 482 | OE2 | GLU | A | 130 | 49.339 | 16.996 | 5.807 | 1.00 | 30.74 | A |
| ATOM | 483 | C | GLU | A | 130 | 53.301 | 14.615 | 8.295 | 1.00 | 19.81 | A |
| ATOM | 484 | O | GLU | A | 130 | 52.553 | 13.875 | 8.935 | 1.00 | 18.37 | A |
| ATOM | 485 | N | ARG | A | 131 | 54.219 | 14.162 | 7.447 | 1.00 | 20.41 | A |
| ATOM | 486 | CA | ARG | A | 131 | 54.397 | 12.735 | 7.202 | 1.00 | 22.45 | A |
| ATOM | 487 | CB | ARG | A | 131 | 55.442 | 12.511 | 6.098 | 1.00 | 25.16 | A |
| ATOM | 488 | CG | ARG | A | 131 | 55.742 | 11.043 | 5.840 | 1.00 | 28.75 | A |

-continued

| | | | | | | | | | | |
|---|---|---|---|---|---|---|---|---|---|---|
| ATOM | 489 | CD | ARG | A | 131 | 56.736 | 10.837 | 4.708 | 1.00 | 33.75 | A |
| ATOM | 490 | NE | ARG | A | 131 | 57.020 | 9.415 | 4.520 | 1.00 | 40.07 | A |
| ATOM | 491 | CZ | ARG | A | 131 | 57.756 | 8.915 | 3.532 | 1.00 | 43.07 | A |
| ATOM | 492 | NH1 | ARG | A | 131 | 58.293 | 9.721 | 2.625 | 1.00 | 44.91 | A |
| ATOM | 493 | NH2 | ARG | A | 131 | 57.955 | 7.606 | 3.449 | 1.00 | 44.45 | A |
| ATOM | 494 | C | ARG | A | 131 | 54.820 | 11.982 | 8.466 | 1.00 | 23.24 | A |
| ATOM | 495 | O | ARG | A | 131 | 54.241 | 10.948 | 8.804 | 1.00 | 23.86 | A |
| ATOM | 496 | N | ASP | A | 132 | 55.831 | 12.497 | 9.160 | 1.00 | 21.99 | A |
| ATOM | 497 | CA | ASP | A | 132 | 56.318 | 11.850 | 10.370 | 1.00 | 22.04 | A |
| ATOM | 498 | CB | ASP | A | 132 | 57.570 | 12.564 | 10.888 | 1.00 | 23.72 | A |
| ATOM | 499 | CG | ASP | A | 132 | 58.750 | 12.442 | 9.932 | 1.00 | 27.77 | A |
| ATOM | 500 | OD1 | ASP | A | 132 | 58.681 | 11.620 | 8.989 | 1.00 | 27.34 | A |
| ATOM | 501 | OD2 | ASP | A | 132 | 59.753 | 13.163 | 10.128 | 1.00 | 28.70 | A |
| ATOM | 502 | C | ASP | A | 132 | 55.258 | 11.772 | 11.474 | 1.00 | 21.69 | A |
| ATOM | 503 | O | ASP | A | 132 | 55.077 | 10.723 | 12.092 | 1.00 | 22.75 | A |
| ATOM | 504 | N | VAL | A | 133 | 54.551 | 12.868 | 11.725 | 1.00 | 19.54 | A |
| ATOM | 505 | CA | VAL | A | 133 | 53.525 | 12.843 | 12.759 | 1.00 | 18.52 | A |
| ATOM | 506 | CB | VAL | A | 133 | 52.908 | 14.244 | 12.990 | 1.00 | 19.26 | A |
| ATOM | 507 | CG1 | VAL | A | 133 | 51.708 | 14.135 | 13.918 | 1.00 | 18.79 | A |
| ATOM | 508 | CG2 | VAL | A | 133 | 53.953 | 15.180 | 13.604 | 1.00 | 18.80 | A |
| ATOM | 509 | C | VAL | A | 133 | 52.419 | 11.854 | 12.398 | 1.00 | 19.46 | A |
| ATOM | 510 | O | VAL | A | 133 | 52.073 | 10.991 | 13.200 | 1.00 | 19.94 | A |
| ATOM | 511 | N | MET | A | 134 | 51.878 | 11.957 | 11.187 | 1.00 | 19.15 | A |
| ATOM | 512 | CA | MET | A | 134 | 50.807 | 11.052 | 10.792 | 1.00 | 21.25 | A |
| ATOM | 513 | CB | MET | A | 134 | 50.309 | 11.381 | 9.383 | 1.00 | 17.34 | A |
| ATOM | 514 | CG | MET | A | 134 | 49.615 | 12.730 | 9.302 | 1.00 | 20.00 | A |
| ATOM | 515 | SD | MET | A | 134 | 48.643 | 12.952 | 7.798 | 1.00 | 24.21 | A |
| ATOM | 516 | CE | MET | A | 134 | 47.033 | 12.434 | 8.400 | 1.00 | 23.20 | A |
| ATOM | 517 | C | MET | A | 134 | 51.203 | 9.582 | 10.881 | 1.00 | 22.43 | A |
| ATOM | 518 | O | MET | A | 134 | 50.384 | 8.741 | 11.249 | 1.00 | 23.82 | A |
| ATOM | 519 | N | SER | A | 135 | 52.454 | 9.273 | 10.556 | 1.00 | 23.09 | A |
| ATOM | 520 | CA | SER | A | 135 | 52.939 | 7.895 | 10.615 | 1.00 | 26.13 | A |
| ATOM | 521 | CB | SER | A | 135 | 54.356 | 7.798 | 10.039 | 1.00 | 26.17 | A |
| ATOM | 522 | OG | SER | A | 135 | 54.383 | 8.177 | 8.673 | 1.00 | 31.91 | A |
| ATOM | 523 | C | SER | A | 135 | 52.957 | 7.358 | 12.045 | 1.00 | 26.58 | A |
| ATOM | 524 | O | SER | A | 135 | 52.926 | 6.148 | 12.261 | 1.00 | 26.42 | A |
| ATOM | 525 | N | ARG | A | 136 | 53.014 | 8.261 | 13.018 | 1.00 | 25.65 | A |
| ATOM | 526 | CA | ARG | A | 136 | 53.056 | 7.870 | 14.425 | 1.00 | 27.47 | A |
| ATOM | 527 | CB | ARG | A | 136 | 53.823 | 8.914 | 15.238 | 1.00 | 27.97 | A |
| ATOM | 528 | CG | ARG | A | 136 | 55.283 | 9.082 | 14.857 | 1.00 | 32.00 | A |
| ATOM | 529 | CD | ARG | A | 136 | 55.904 | 10.218 | 15.664 | 1.00 | 33.03 | A |
| ATOM | 530 | NE | ARG | A | 136 | 55.602 | 10.073 | 17.084 | 1.00 | 36.11 | A |
| ATOM | 531 | CZ | ARG | A | 136 | 55.867 | 10.990 | 18.007 | 1.00 | 39.74 | A |
| ATOM | 532 | NH1 | ARG | A | 136 | 56.449 | 12.132 | 17.661 | 1.00 | 40.55 | A |
| ATOM | 533 | NH2 | ARG | A | 136 | 55.540 | 10.769 | 19.276 | 1.00 | 36.72 | A |
| ATOM | 534 | C | ARG | A | 136 | 51.667 | 7.709 | 15.036 | 1.00 | 26.38 | A |
| ATOM | 535 | O | ARG | A | 136 | 51.516 | 7.121 | 16.106 | 1.00 | 27.06 | A |
| ATOM | 536 | N | LEU | A | 137 | 50.655 | 8.235 | 14.360 | 1.00 | 24.77 | A |
| ATOM | 537 | CA | LEU | A | 137 | 49.294 | 8.162 | 14.870 | 1.00 | 24.70 | A |
| ATOM | 538 | CB | LEU | A | 137 | 48.483 | 9.363 | 14.371 | 1.00 | 24.52 | A |
| ATOM | 539 | CG | LEU | A | 137 | 49.050 | 10.760 | 14.662 | 1.00 | 26.67 | A |
| ATOM | 540 | CD1 | LEU | A | 137 | 48.075 | 11.813 | 14.141 | 1.00 | 27.25 | A |
| ATOM | 541 | CD2 | LEU | A | 137 | 49.279 | 10.945 | 16.155 | 1.00 | 27.09 | A |
| ATOM | 542 | C | LEU | A | 137 | 48.592 | 6.868 | 14.473 | 1.00 | 25.20 | A |
| ATOM | 543 | O | LEU | A | 137 | 48.619 | 6.469 | 13.309 | 1.00 | 25.99 | A |
| ATOM | 544 | N | ASP | A | 138 | 47.971 | 6.218 | 15.451 | 1.00 | 21.89 | A |
| ATOM | 545 | CA | ASP | A | 138 | 47.239 | 4.977 | 15.219 | 1.00 | 21.35 | A |
| ATOM | 546 | CB | ASP | A | 138 | 48.124 | 3.761 | 15.523 | 1.00 | 22.14 | A |
| ATOM | 547 | CG | ASP | A | 138 | 47.432 | 2.448 | 15.201 | 1.00 | 24.90 | A |
| ATOM | 548 | OD1 | ASP | A | 138 | 46.631 | 2.423 | 14.241 | 1.00 | 24.78 | A |
| ATOM | 549 | OD2 | ASP | A | 138 | 47.691 | 1.443 | 15.897 | 1.00 | 25.39 | A |
| ATOM | 550 | C | ASP | A | 138 | 46.031 | 4.991 | 16.138 | 1.00 | 20.47 | A |
| ATOM | 551 | O | ASP | A | 138 | 45.967 | 4.248 | 17.118 | 1.00 | 19.06 | A |
| ATOM | 552 | N | HIS | A | 139 | 45.075 | 5.852 | 15.810 | 1.00 | 18.27 | A |
| ATOM | 553 | CA | HIS | A | 139 | 43.869 | 6.016 | 16.606 | 1.00 | 18.21 | A |
| ATOM | 554 | CB | HIS | A | 139 | 44.096 | 7.157 | 17.612 | 1.00 | 15.84 | A |
| ATOM | 555 | CG | HIS | A | 139 | 42.985 | 7.332 | 18.600 | 1.00 | 15.24 | A |
| ATOM | 556 | CD2 | HIS | A | 139 | 42.884 | 6.964 | 19.900 | 1.00 | 13.97 | A |
| ATOM | 557 | ND1 | HIS | A | 139 | 41.791 | 7.943 | 18.280 | 1.00 | 14.74 | A |
| ATOM | 558 | CE1 | HIS | A | 139 | 41.002 | 7.944 | 19.341 | 1.00 | 14.19 | A |
| ATOM | 559 | NE2 | HIS | A | 139 | 41.641 | 7.356 | 20.336 | 1.00 | 14.15 | A |
| ATOM | 560 | C | HIS | A | 139 | 42.715 | 6.330 | 15.654 | 1.00 | 18.50 | A |
| ATOM | 561 | O | HIS | A | 139 | 42.879 | 7.080 | 14.693 | 1.00 | 20.80 | A |
| ATOM | 562 | N | PRO | A | 140 | 41.527 | 5.767 | 15.913 | 1.00 | 18.32 | A |
| ATOM | 563 | CD | PRO | A | 140 | 41.143 | 4.984 | 17.100 | 1.00 | 16.71 | A |
| ATOM | 564 | CA | PRO | A | 140 | 40.367 | 6.001 | 15.048 | 1.00 | 17.43 | A |
| ATOM | 565 | CB | PRO | A | 140 | 39.273 | 5.157 | 15.704 | 1.00 | 16.64 | A |
| ATOM | 566 | CG | PRO | A | 140 | 39.643 | 5.204 | 17.152 | 1.00 | 18.43 | A |
| ATOM | 567 | C | PRO | A | 140 | 39.914 | 7.441 | 14.803 | 1.00 | 18.77 | A |

-continued

| | | | | | | | | | | | |
|---|---|---|---|---|---|---|---|---|---|---|---|
| ATOM | 568 | O | PRO | A | 140 | 39.207 | 7.695 | 13.831 | 1.00 | 19.88 | A |
| ATOM | 569 | N | PHE | A | 141 | 40.301 | 8.381 | 15.664 | 1.00 | 17.14 | A |
| ATOM | 570 | CA | PHE | A | 141 | 39.874 | 9.767 | 15.477 | 1.00 | 16.42 | A |
| ATOM | 571 | CB | PHE | A | 141 | 39.568 | 10.422 | 16.836 | 1.00 | 14.60 | A |
| ATOM | 572 | CG | PHE | A | 141 | 38.386 | 9.817 | 17.556 | 1.00 | 15.26 | A |
| ATOM | 573 | CD1 | PHE | A | 141 | 37.335 | 9.234 | 16.842 | 1.00 | 14.78 | A |
| ATOM | 574 | CD2 | PHE | A | 141 | 38.297 | 9.880 | 18.942 | 1.00 | 13.70 | A |
| ATOM | 575 | CE1 | PHE | A | 141 | 36.215 | 8.727 | 17.502 | 1.00 | 16.94 | A |
| ATOM | 576 | CE2 | PHE | A | 141 | 37.178 | 9.375 | 19.615 | 1.00 | 15.75 | A |
| ATOM | 577 | CZ | PHE | A | 141 | 36.135 | 8.799 | 18.893 | 1.00 | 16.89 | A |
| ATOM | 578 | C | PHE | A | 141 | 40.857 | 10.641 | 14.694 | 1.00 | 16.15 | A |
| ATOM | 579 | O | PHE | A | 141 | 40.799 | 11.871 | 14.761 | 1.00 | 17.35 | A |
| ATOM | 580 | N | PHE | A | 142 | 41.748 | 10.011 | 13.941 | 1.00 | 15.88 | A |
| ATOM | 581 | CA | PHE | A | 142 | 42.727 | 10.756 | 13.154 | 1.00 | 17.89 | A |
| ATOM | 582 | CB | PHE | A | 142 | 44.115 | 10.645 | 13.793 | 1.00 | 17.57 | A |
| ATOM | 583 | CG | PHE | A | 142 | 44.240 | 11.371 | 15.103 | 1.00 | 18.74 | A |
| ATOM | 584 | CD1 | PHE | A | 142 | 44.559 | 12.726 | 15.135 | 1.00 | 17.77 | A |
| ATOM | 585 | CD2 | PHE | A | 142 | 43.997 | 10.711 | 16.304 | 1.00 | 18.74 | A |
| ATOM | 586 | CE1 | PHE | A | 142 | 44.632 | 13.417 | 16.347 | 1.00 | 15.77 | A |
| ATOM | 587 | CE2 | PHE | A | 142 | 44.065 | 11.393 | 17.522 | 1.00 | 17.56 | A |
| ATOM | 588 | CZ | PHE | A | 142 | 44.383 | 12.747 | 17.542 | 1.00 | 17.14 | A |
| ATOM | 589 | C | PHE | A | 142 | 42.793 | 10.231 | 11.729 | 1.00 | 19.12 | A |
| ATOM | 590 | O | PHE | A | 142 | 42.659 | 9.030 | 11.504 | 1.00 | 20.01 | A |
| ATOM | 591 | N | VAL | A | 143 | 42.978 | 11.135 | 10.769 | 1.00 | 18.72 | A |
| ATOM | 592 | CA | VAL | A | 143 | 43.102 | 10.735 | 9.371 | 1.00 | 18.52 | A |
| ATOM | 593 | CB | VAL | A | 143 | 43.294 | 11.961 | 8.440 | 1.00 | 20.66 | A |
| ATOM | 594 | CG1 | VAL | A | 143 | 43.843 | 11.521 | 7.080 | 1.00 | 21.29 | A |
| ATOM | 595 | CG2 | VAL | A | 143 | 41.958 | 12.673 | 8.252 | 1.00 | 22.97 | A |
| ATOM | 596 | C | VAL | A | 143 | 44.342 | 9.865 | 9.330 | 1.00 | 18.68 | A |
| ATOM | 597 | O | VAL | A | 143 | 45.355 | 10.199 | 9.943 | 1.00 | 18.42 | A |
| ATOM | 598 | N | LYS | A | 144 | 44.259 | 8.745 | 8.623 | 1.00 | 18.30 | A |
| ATOM | 599 | CA | LYS | A | 144 | 45.384 | 7.824 | 8.535 | 1.00 | 18.78 | A |
| ATOM | 600 | CB | LYS | A | 144 | 44.889 | 6.373 | 8.608 | 1.00 | 22.27 | A |
| ATOM | 601 | CG | LYS | A | 144 | 46.017 | 5.340 | 8.557 | 1.00 | 29.72 | A |
| ATOM | 602 | CD | LYS | A | 144 | 45.491 | 3.912 | 8.674 | 1.00 | 34.16 | A |
| ATOM | 603 | CE | LYS | A | 144 | 46.631 | 2.896 | 8.577 | 1.00 | 37.67 | A |
| ATOM | 604 | NZ | LYS | A | 144 | 46.138 | 1.484 | 8.629 | 1.00 | 39.02 | A |
| ATOM | 605 | C | LYS | A | 144 | 46.192 | 8.002 | 7.261 | 1.00 | 18.53 | A |
| ATOM | 606 | O | LYS | A | 144 | 45.643 | 8.314 | 6.200 | 1.00 | 18.18 | A |
| ATOM | 607 | N | LEU | A | 145 | 47.502 | 7.816 | 7.385 | 1.00 | 16.79 | A |
| ATOM | 608 | CA | LEU | A | 145 | 48.411 | 7.900 | 6.251 | 1.00 | 17.45 | A |
| ATOM | 609 | CB | LEU | A | 145 | 49.686 | 8.653 | 6.641 | 1.00 | 18.82 | A |
| ATOM | 610 | CG | LEU | A | 145 | 50.734 | 8.902 | 5.549 | 1.00 | 20.23 | A |
| ATOM | 611 | CD1 | LEU | A | 145 | 51.836 | 9.799 | 6.093 | 1.00 | 18.83 | A |
| ATOM | 612 | CD2 | LEU | A | 145 | 51.317 | 7.581 | 5.069 | 1.00 | 19.79 | A |
| ATOM | 613 | C | LEU | A | 145 | 48.739 | 6.450 | 5.907 | 1.00 | 19.19 | A |
| ATOM | 614 | O | LEU | A | 145 | 49.451 | 5.772 | 6.659 | 1.00 | 17.36 | A |
| ATOM | 615 | N | TYR | A | 146 | 48.215 | 5.972 | 4.782 | 1.00 | 17.28 | A |
| ATOM | 616 | CA | TYR | A | 146 | 48.444 | 4.593 | 4.358 | 1.00 | 17.57 | A |
| ATOM | 617 | CB | TYR | A | 146 | 47.288 | 4.098 | 3.486 | 1.00 | 17.74 | A |
| ATOM | 618 | CG | TYR | A | 146 | 45.981 | 3.926 | 4.214 | 1.00 | 17.50 | A |
| ATOM | 619 | CD1 | TYR | A | 146 | 45.099 | 4.995 | 4.377 | 1.00 | 16.50 | A |
| ATOM | 620 | CE1 | TYR | A | 146 | 43.881 | 4.827 | 5.039 | 1.00 | 17.10 | A |
| ATOM | 621 | CD2 | TYR | A | 146 | 45.620 | 2.686 | 4.735 | 1.00 | 18.28 | A |
| ATOM | 622 | CE2 | TYR | A | 146 | 44.411 | 2.506 | 5.399 | 1.00 | 19.84 | A |
| ATOM | 623 | CZ | TYR | A | 146 | 43.547 | 3.576 | 5.544 | 1.00 | 17.53 | A |
| ATOM | 624 | OH | TYR | A | 146 | 42.342 | 3.376 | 6.169 | 1.00 | 20.67 | A |
| ATOM | 625 | C | TYR | A | 146 | 49.735 | 4.376 | 3.582 | 1.00 | 18.72 | A |
| ATOM | 626 | O | TYR | A | 146 | 50.382 | 3.338 | 3.715 | 1.00 | 19.51 | A |
| ATOM | 627 | N | PHE | A | 147 | 50.110 | 5.350 | 2.765 | 1.00 | 18.09 | A |
| ATOM | 628 | CA | PHE | A | 147 | 51.307 | 5.203 | 1.952 | 1.00 | 17.20 | A |
| ATOM | 629 | CB | PHE | A | 147 | 51.007 | 4.258 | 0.783 | 1.00 | 16.77 | A |
| ATOM | 630 | CG | PHE | A | 147 | 49.835 | 4.699 | −0.070 | 1.00 | 17.75 | A |
| ATOM | 631 | CD1 | PHE | A | 147 | 49.967 | 5.752 | −0.975 | 1.00 | 16.58 | A |
| ATOM | 632 | CD2 | PHE | A | 147 | 48.595 | 4.075 | 0.053 | 1.00 | 18.07 | A |
| ATOM | 633 | CE1 | PHE | A | 147 | 48.886 | 6.178 | −1.742 | 1.00 | 19.62 | A |
| ATOM | 634 | CE2 | PHE | A | 147 | 47.503 | 4.492 | −0.710 | 1.00 | 18.56 | A |
| ATOM | 635 | CZ | PHE | A | 147 | 47.647 | 5.546 | −1.610 | 1.00 | 19.27 | A |
| ATOM | 636 | C | PHE | A | 147 | 51.768 | 6.533 | 1.395 | 1.00 | 17.13 | A |
| ATOM | 637 | O | PHE | A | 147 | 51.045 | 7.528 | 1.452 | 1.00 | 14.43 | A |
| ATOM | 638 | N | THR | A | 148 | 52.981 | 6.534 | 0.854 | 1.00 | 17.12 | A |
| ATOM | 639 | CA | THR | A | 148 | 53.541 | 7.718 | 0.232 | 1.00 | 17.96 | A |
| ATOM | 640 | CB | THR | A | 148 | 54.449 | 8.531 | 1.197 | 1.00 | 21.51 | A |
| ATOM | 641 | OG1 | THR | A | 148 | 55.605 | 7.760 | 1.537 | 1.00 | 18.83 | A |
| ATOM | 642 | CG2 | THR | A | 148 | 53.700 | 8.897 | 2.472 | 1.00 | 19.60 | A |
| ATOM | 643 | C | THR | A | 148 | 54.386 | 7.262 | −0.946 | 1.00 | 20.31 | A |
| ATOM | 644 | O | THR | A | 148 | 54.860 | 6.124 | −0.991 | 1.00 | 18.94 | A |
| ATOM | 645 | N | PHE | A | 149 | 54.543 | 8.149 | −1.916 | 1.00 | 19.16 | A |
| ATOM | 646 | CA | PHE | A | 149 | 55.368 | 7.877 | −3.073 | 1.00 | 18.01 | A |

-continued

| | | | | | | | | | | |
|---|---|---|---|---|---|---|---|---|---|---|
| ATOM | 647 | CB | PHE | A | 149 | 54.748 | 6.801 | −3.989 | 1.00 | 17.23 | A |
| ATOM | 648 | CG | PHE | A | 149 | 53.389 | 7.144 | −4.544 | 1.00 | 16.88 | A |
| ATOM | 649 | CD1 | PHE | A | 149 | 53.262 | 7.888 | −5.712 | 1.00 | 18.58 | A |
| ATOM | 650 | CD2 | PHE | A | 149 | 52.235 | 6.668 | −3.927 | 1.00 | 17.31 | A |
| ATOM | 651 | CE1 | PHE | A | 149 | 52.007 | 8.149 | −6.267 | 1.00 | 19.26 | A |
| ATOM | 652 | CE2 | PHE | A | 149 | 50.972 | 6.923 | −4.470 | 1.00 | 19.17 | A |
| ATOM | 653 | CZ | PHE | A | 149 | 50.858 | 7.663 | −5.642 | 1.00 | 19.60 | A |
| ATOM | 654 | C | PHE | A | 149 | 55.542 | 9.205 | −3.774 | 1.00 | 20.85 | A |
| ATOM | 655 | O | PHE | A | 149 | 54.934 | 10.200 | −3.376 | 1.00 | 19.76 | A |
| ATOM | 656 | N | GLN | A | 150 | 56.398 | 9.241 | −4.782 | 1.00 | 19.79 | A |
| ATOM | 657 | CA | GLN | A | 150 | 56.636 | 10.481 | −5.497 | 1.00 | 24.03 | A |
| ATOM | 658 | CB | GLN | A | 150 | 57.659 | 11.347 | −4.739 | 1.00 | 24.45 | A |
| ATOM | 659 | CG | GLN | A | 150 | 58.986 | 10.645 | −4.414 | 1.00 | 26.28 | A |
| ATOM | 660 | CD | GLN | A | 150 | 59.988 | 11.558 | −3.692 | 1.00 | 29.02 | A |
| ATOM | 661 | OE1 | GLN | A | 150 | 60.693 | 12.353 | −4.321 | 1.00 | 27.05 | A |
| ATOM | 662 | NE2 | GLN | A | 150 | 60.042 | 11.449 | −2.365 | 1.00 | 26.47 | A |
| ATOM | 663 | C | GLN | A | 150 | 57.160 | 10.203 | −6.885 | 1.00 | 23.88 | A |
| ATOM | 664 | O | GLN | A | 150 | 57.673 | 9.118 | −7.158 | 1.00 | 24.79 | A |
| ATOM | 665 | N | ASP | A | 151 | 56.987 | 11.171 | −7.774 | 1.00 | 25.88 | A |
| ATOM | 666 | CA | ASP | A | 151 | 57.527 | 11.047 | −9.117 | 1.00 | 26.49 | A |
| ATOM | 667 | CB | ASP | A | 151 | 56.437 | 11.126 | −10.199 | 1.00 | 24.54 | A |
| ATOM | 668 | CG | ASP | A | 151 | 55.544 | 12.336 | −10.064 | 1.00 | 24.95 | A |
| ATOM | 669 | OD1 | ASP | A | 151 | 56.005 | 13.379 | −9.561 | 1.00 | 22.44 | A |
| ATOM | 670 | OD2 | ASP | A | 151 | 54.369 | 12.242 | −10.490 | 1.00 | 25.72 | A |
| ATOM | 671 | C | ASP | A | 151 | 58.515 | 12.203 | −9.220 | 1.00 | 28.63 | A |
| ATOM | 672 | O | ASP | A | 151 | 58.890 | 12.780 | −8.194 | 1.00 | 27.83 | A |
| ATOM | 673 | N | ASP | A | 152 | 58.934 | 12.560 | −10.426 | 1.00 | 29.21 | A |
| ATOM | 674 | CA | ASP | A | 152 | 59.907 | 13.636 | −10.562 | 1.00 | 31.88 | A |
| ATOM | 675 | CB | ASP | A | 152 | 60.325 | 13.792 | −12.026 | 1.00 | 33.94 | A |
| ATOM | 676 | CG | ASP | A | 152 | 61.033 | 12.564 | −12.557 | 1.00 | 38.88 | A |
| ATOM | 677 | OD1 | ASP | A | 152 | 61.817 | 11.959 | −11.791 | 1.00 | 39.67 | A |
| ATOM | 678 | OD2 | ASP | A | 152 | 60.817 | 12.211 | −13.738 | 1.00 | 41.57 | A |
| ATOM | 679 | C | ASP | A | 152 | 59.487 | 14.994 | −10.013 | 1.00 | 30.90 | A |
| ATOM | 680 | O | ASP | A | 152 | 60.316 | 15.735 | −9.482 | 1.00 | 31.69 | A |
| ATOM | 681 | N | GLU | A | 153 | 58.207 | 15.322 | −10.107 | 1.00 | 29.44 | A |
| ATOM | 682 | CA | GLU | A | 153 | 57.767 | 16.632 | −9.646 | 1.00 | 28.69 | A |
| ATOM | 683 | CB | GLU | A | 153 | 56.984 | 17.327 | −10.766 | 1.00 | 32.90 | A |
| ATOM | 684 | CG | GLU | A | 153 | 57.451 | 16.987 | −12.183 | 1.00 | 40.57 | A |
| ATOM | 685 | CD | GLU | A | 153 | 56.920 | 15.643 | −12.675 | 1.00 | 45.78 | A |
| ATOM | 686 | OE1 | GLU | A | 153 | 55.682 | 15.482 | −12.760 | 1.00 | 48.91 | A |
| ATOM | 687 | OE2 | GLU | A | 153 | 57.736 | 14.747 | −12.979 | 1.00 | 48.95 | A |
| ATOM | 688 | C | GLU | A | 153 | 56.929 | 16.683 | −8.372 | 1.00 | 26.43 | A |
| ATOM | 689 | O | GLU | A | 153 | 56.947 | 17.688 | −7.660 | 1.00 | 25.08 | A |
| ATOM | 690 | N | LYS | A | 154 | 56.205 | 15.610 | −8.069 | 1.00 | 22.39 | A |
| ATOM | 691 | CA | LYS | A | 154 | 55.318 | 15.631 | −6.912 | 1.00 | 21.43 | A |
| ATOM | 692 | CB | LYS | A | 154 | 53.861 | 15.628 | −7.398 | 1.00 | 20.33 | A |
| ATOM | 693 | CG | LYS | A | 154 | 53.505 | 16.716 | −8.403 | 1.00 | 21.92 | A |
| ATOM | 694 | CD | LYS | A | 154 | 52.211 | 16.375 | −9.146 | 1.00 | 19.70 | A |
| ATOM | 695 | CE | LYS | A | 154 | 51.775 | 17.503 | −10.077 | 1.00 | 20.04 | A |
| ATOM | 696 | NZ | LYS | A | 154 | 50.631 | 17.094 | −10.951 | 1.00 | 19.97 | A |
| ATOM | 697 | C | LYS | A | 154 | 55.458 | 14.522 | −5.881 | 1.00 | 20.43 | A |
| ATOM | 698 | O | LYS | A | 154 | 55.949 | 13.426 | −6.173 | 1.00 | 21.13 | A |
| ATOM | 699 | N | LEU | A | 155 | 54.985 | 14.832 | −4.676 | 1.00 | 19.69 | A |
| ATOM | 700 | CA | LEU | A | 155 | 54.950 | 13.900 | −3.553 | 1.00 | 19.10 | A |
| ATOM | 701 | CB | LEU | A | 155 | 55.362 | 14.588 | −2.252 | 1.00 | 19.65 | A |
| ATOM | 702 | CG | LEU | A | 155 | 56.740 | 15.234 | −2.129 | 1.00 | 21.20 | A |
| ATOM | 703 | CD1 | LEU | A | 155 | 56.848 | 15.918 | −0.770 | 1.00 | 23.42 | A |
| ATOM | 704 | CD2 | LEU | A | 155 | 57.816 | 14.174 | −2.277 | 1.00 | 23.08 | A |
| ATOM | 705 | C | LEU | A | 155 | 53.478 | 13.507 | −3.427 | 1.00 | 18.87 | A |
| ATOM | 706 | O | LEU | A | 155 | 52.600 | 14.348 | −3.620 | 1.00 | 18.61 | A |
| ATOM | 707 | N | TYR | A | 156 | 53.209 | 12.249 | −3.091 | 1.00 | 15.02 | A |
| ATOM | 708 | CA | TYR | A | 156 | 51.834 | 11.783 | −2.934 | 1.00 | 16.29 | A |
| ATOM | 709 | CB | TYR | A | 156 | 51.470 | 10.769 | −4.029 | 1.00 | 14.20 | A |
| ATOM | 710 | CG | TYR | A | 156 | 51.603 | 11.273 | −5.449 | 1.00 | 17.29 | A |
| ATOM | 711 | CD1 | TYR | A | 156 | 52.857 | 11.429 | −6.045 | 1.00 | 16.46 | A |
| ATOM | 712 | CE1 | TYR | A | 156 | 52.978 | 11.884 | −7.360 | 1.00 | 18.68 | A |
| ATOM | 713 | CD2 | TYR | A | 156 | 50.474 | 11.588 | −6.202 | 1.00 | 16.43 | A |
| ATOM | 714 | CE2 | TYR | A | 156 | 50.583 | 12.048 | −7.512 | 1.00 | 16.31 | A |
| ATOM | 715 | CZ | TYR | A | 156 | 51.835 | 12.192 | −8.083 | 1.00 | 18.17 | A |
| ATOM | 716 | OH | TYR | A | 156 | 51.941 | 12.651 | −9.371 | 1.00 | 17.47 | A |
| ATOM | 717 | C | TYR | A | 156 | 51.657 | 11.108 | −1.572 | 1.00 | 16.32 | A |
| ATOM | 718 | O | TYR | A | 156 | 52.412 | 10.197 | −1.235 | 1.00 | 16.27 | A |
| ATOM | 719 | N | PHE | A | 157 | 50.678 | 11.568 | −0.792 | 1.00 | 15.47 | A |
| ATOM | 720 | CA | PHE | A | 157 | 50.385 | 10.966 | 0.508 | 1.00 | 16.66 | A |
| ATOM | 721 | CB | PHE | A | 157 | 50.324 | 12.014 | 1.629 | 1.00 | 16.91 | A |
| ATOM | 722 | CG | PHE | A | 157 | 51.631 | 12.708 | 1.907 | 1.00 | 18.96 | A |
| ATOM | 723 | CD1 | PHE | A | 157 | 52.821 | 12.261 | 1.340 | 1.00 | 20.31 | A |
| ATOM | 724 | CD2 | PHE | A | 157 | 51.664 | 13.829 | 2.732 | 1.00 | 21.12 | A |
| ATOM | 725 | CE1 | PHE | A | 157 | 54.025 | 12.926 | 1.585 | 1.00 | 22.08 | A |

-continued

| | | | | | | | | | | | |
|---|---|---|---|---|---|---|---|---|---|---|---|
| ATOM | 726 | CE2 | PHE | A | 157 | 52.865 | 14.500 | 2.982 | 1.00 | 22.18 | A |
| ATOM | 727 | CZ | PHE | A | 157 | 54.045 | 14.045 | 2.405 | 1.00 | 21.27 | A |
| ATOM | 728 | C | PHE | A | 157 | 49.016 | 10.308 | 0.404 | 1.00 | 16.52 | A |
| ATOM | 729 | O | PHE | A | 157 | 48.029 | 10.979 | 0.110 | 1.00 | 17.32 | A |
| ATOM | 730 | N | GLY | A | 158 | 48.953 | 9.002 | 0.644 | 1.00 | 15.97 | A |
| ATOM | 731 | CA | GLY | A | 158 | 47.684 | 8.299 | 0.572 | 1.00 | 16.13 | A |
| ATOM | 732 | C | GLY | A | 158 | 47.000 | 8.383 | 1.920 | 1.00 | 14.94 | A |
| ATOM | 733 | O | GLY | A | 158 | 47.445 | 7.756 | 2.879 | 1.00 | 16.28 | A |
| ATOM | 734 | N | LEU | A | 159 | 45.915 | 9.145 | 1.989 | 1.00 | 13.50 | A |
| ATOM | 735 | CA | LEU | A | 159 | 45.191 | 9.340 | 3.241 | 1.00 | 15.20 | A |
| ATOM | 736 | CB | LEU | A | 159 | 45.031 | 10.835 | 3.517 | 1.00 | 14.20 | A |
| ATOM | 737 | CG | LEU | A | 159 | 46.270 | 11.726 | 3.385 | 1.00 | 19.00 | A |
| ATOM | 738 | CD1 | LEU | A | 159 | 45.847 | 13.188 | 3.477 | 1.00 | 17.12 | A |
| ATOM | 739 | CD2 | LEU | A | 159 | 47.275 | 11.390 | 4.471 | 1.00 | 14.71 | A |
| ATOM | 740 | C | LEU | A | 159 | 43.809 | 8.716 | 3.232 | 1.00 | 15.53 | A |
| ATOM | 741 | O | LEU | A | 159 | 43.232 | 8.472 | 2.177 | 1.00 | 16.05 | A |
| ATOM | 742 | N | SER | A | 160 | 43.268 | 8.469 | 4.418 | 1.00 | 15.86 | A |
| ATOM | 743 | CA | SER | A | 160 | 41.932 | 7.917 | 4.498 | 1.00 | 19.01 | A |
| ATOM | 744 | CB | SER | A | 160 | 41.566 | 7.582 | 5.949 | 1.00 | 22.90 | A |
| ATOM | 745 | CG | SER | A | 160 | 41.901 | 8.629 | 6.833 | 1.00 | 24.18 | A |
| ATOM | 746 | C | SER | A | 160 | 40.987 | 8.968 | 3.924 | 1.00 | 20.43 | A |
| ATOM | 747 | O | SER | A | 160 | 41.213 | 10.173 | 4.062 | 1.00 | 19.96 | A |
| ATOM | 748 | N | TYR | A | 161 | 39.945 | 8.508 | 3.250 | 1.00 | 19.20 | A |
| ATOM | 749 | CA | TYR | A | 161 | 38.975 | 9.406 | 2.644 | 1.00 | 20.37 | A |
| ATOM | 750 | CB | TYR | A | 161 | 38.471 | 8.785 | 1.332 | 1.00 | 20.00 | A |
| ATOM | 751 | CG | TYR | A | 161 | 37.314 | 9.502 | 0.666 | 1.00 | 20.72 | A |
| ATOM | 752 | CD1 | TYR | A | 161 | 37.222 | 10.895 | 0.682 | 1.00 | 18.22 | A |
| ATOM | 753 | CE1 | TYR | A | 161 | 36.180 | 11.557 | 0.029 | 1.00 | 22.24 | A |
| ATOM | 754 | CD2 | TYR | A | 161 | 36.333 | 8.784 | −0.020 | 1.00 | 20.53 | A |
| ATOM | 755 | CE2 | TYR | A | 161 | 35.287 | 9.436 | −0.678 | 1.00 | 24.24 | A |
| ATOM | 756 | CZ | TYR | A | 161 | 35.218 | 10.822 | −0.648 | 1.00 | 22.32 | A |
| ATOM | 757 | OH | TYR | A | 161 | 34.194 | 11.471 | −1.298 | 1.00 | 23.03 | A |
| ATOM | 758 | C | TYR | A | 161 | 37.812 | 9.681 | 3.598 | 1.00 | 20.14 | A |
| ATOM | 759 | O | TYR | A | 161 | 36.959 | 8.819 | 3.810 | 1.00 | 19.53 | A |
| ATOM | 760 | N | ALA | A | 162 | 37.791 | 10.880 | 4.178 | 1.00 | 19.92 | A |
| ATOM | 761 | CA | ALA | A | 162 | 36.721 | 11.271 | 5.099 | 1.00 | 21.07 | A |
| ATOM | 762 | CB | ALA | A | 162 | 37.187 | 12.419 | 6.002 | 1.00 | 19.60 | A |
| ATOM | 763 | C | ALA | A | 162 | 35.542 | 11.712 | 4.238 | 1.00 | 22.07 | A |
| ATOM | 764 | O | ALA | A | 162 | 35.436 | 12.875 | 3.860 | 1.00 | 20.66 | A |
| ATOM | 765 | N | LYS | A | 163 | 34.653 | 10.769 | 3.945 | 1.00 | 23.27 | A |
| ATOM | 766 | CA | LYS | A | 163 | 33.503 | 11.017 | 3.080 | 1.00 | 27.12 | A |
| ATOM | 767 | CB | LYS | A | 163 | 32.663 | 9.741 | 2.963 | 1.00 | 29.68 | A |
| ATOM | 768 | CG | LYS | A | 163 | 33.455 | 8.524 | 2.515 | 1.00 | 37.67 | A |
| ATOM | 769 | CD | LYS | A | 163 | 32.556 | 7.310 | 2.321 | 1.00 | 42.24 | A |
| ATOM | 770 | CE | LYS | A | 163 | 33.373 | 6.034 | 2.185 | 1.00 | 44.48 | A |
| ATOM | 771 | NZ | LYS | A | 163 | 34.143 | 5.735 | 3.430 | 1.00 | 44.88 | A |
| ATOM | 772 | C | LYS | A | 163 | 32.581 | 12.186 | 3.411 | 1.00 | 25.78 | A |
| ATOM | 773 | O | LYS | A | 163 | 32.103 | 12.863 | 2.506 | 1.00 | 26.53 | A |
| ATOM | 774 | N | ASN | A | 164 | 32.327 | 12.441 | 4.689 | 1.00 | 24.57 | A |
| ATOM | 775 | CA | ASN | A | 164 | 31.420 | 13.522 | 5.033 | 1.00 | 23.77 | A |
| ATOM | 776 | CB | ASN | A | 164 | 30.610 | 13.129 | 6.265 | 1.00 | 25.02 | A |
| ATOM | 777 | CG | ASN | A | 164 | 29.537 | 12.101 | 5.932 | 1.00 | 27.54 | A |
| ATOM | 778 | OD1 | ASN | A | 164 | 28.772 | 12.281 | 4.983 | 1.00 | 28.79 | A |
| ATOM | 779 | ND2 | ASN | A | 164 | 29.475 | 11.024 | 6.704 | 1.00 | 27.13 | A |
| ATOM | 780 | C | ASN | A | 164 | 31.999 | 14.931 | 5.169 | 1.00 | 24.43 | A |
| ATOM | 781 | O | ASN | A | 164 | 31.306 | 15.856 | 5.589 | 1.00 | 23.98 | A |
| ATOM | 782 | N | GLY | A | 165 | 33.262 | 15.097 | 4.795 | 1.00 | 21.56 | A |
| ATOM | 783 | CA | GLY | A | 165 | 33.873 | 16.414 | 4.836 | 1.00 | 24.39 | A |
| ATOM | 784 | C | GLY | A | 165 | 34.191 | 17.043 | 6.181 | 1.00 | 23.62 | A |
| ATOM | 785 | O | GLY | A | 165 | 34.380 | 16.352 | 7.177 | 1.00 | 23.26 | A |
| ATOM | 786 | N | GLU | A | 166 | 34.234 | 18.373 | 6.186 | 1.00 | 23.22 | A |
| ATOM | 787 | CA | GLU | A | 166 | 34.563 | 19.176 | 7.362 | 1.00 | 24.54 | A |
| ATOM | 788 | CB | GLU | A | 166 | 35.055 | 20.558 | 6.913 | 1.00 | 25.04 | A |
| ATOM | 789 | CG | GLU | A | 166 | 36.419 | 20.569 | 6.229 | 1.00 | 26.48 | A |
| ATOM | 790 | CD | GLU | A | 166 | 36.699 | 21.889 | 5.517 | 1.00 | 30.02 | A |
| ATOM | 791 | OE1 | GLU | A | 166 | 36.081 | 22.906 | 5.889 | 1.00 | 29.33 | A |
| ATOM | 792 | OE2 | GLU | A | 166 | 37.544 | 21.916 | 4.596 | 1.00 | 30.48 | A |
| ATOM | 793 | C | GLU | A | 166 | 33.436 | 19.372 | 8.369 | 1.00 | 24.44 | A |
| ATOM | 794 | O | GLU | A | 166 | 32.279 | 19.541 | 8.001 | 1.00 | 22.76 | A |
| ATOM | 795 | N | LEU | A | 167 | 33.791 | 19.370 | 9.649 | 1.00 | 22.95 | A |
| ATOM | 796 | CA | LEU | A | 167 | 32.813 | 19.581 | 10.707 | 1.00 | 22.26 | A |
| ATOM | 797 | CB | LEU | A | 167 | 33.497 | 19.481 | 12.073 | 1.00 | 22.32 | A |
| ATOM | 798 | CG | LEU | A | 167 | 32.706 | 19.923 | 13.306 | 1.00 | 22.04 | A |
| ATOM | 799 | CD1 | LEU | A | 167 | 31.454 | 19.074 | 13.463 | 1.00 | 19.66 | A |
| ATOM | 800 | CD2 | LEU | A | 167 | 33.597 | 19.805 | 14.537 | 1.00 | 21.17 | A |
| ATOM | 801 | C | LEU | A | 167 | 32.193 | 20.971 | 10.529 | 1.00 | 23.49 | A |
| ATOM | 802 | O | LEU | A | 167 | 31.047 | 21.209 | 10.907 | 1.00 | 23.56 | A |
| ATOM | 803 | N | LEU | A | 168 | 32.960 | 21.887 | 9.948 | 1.00 | 24.25 | A |
| ATOM | 804 | CA | LEU | A | 168 | 32.473 | 23.245 | 9.722 | 1.00 | 26.64 | A |

-continued

| | | | | | | | | | | | |
|---|---|---|---|---|---|---|---|---|---|---|---|
| ATOM | 805 | CB | LEU | A | 168 | 33.560 | 24.099 | 9.066 | 1.00 | 25.62 | A |
| ATOM | 806 | CG | LEU | A | 168 | 33.198 | 25.546 | 8.707 | 1.00 | 27.34 | A |
| ATOM | 807 | CD1 | LEU | A | 168 | 32.718 | 26.296 | 9.946 | 1.00 | 26.42 | A |
| ATOM | 808 | CD2 | LEU | A | 168 | 34.418 | 26.238 | 8.119 | 1.00 | 26.74 | A |
| ATOM | 809 | C | LEU | A | 168 | 31.234 | 23.218 | 8.829 | 1.00 | 27.13 | A |
| ATOM | 810 | O | LEU | A | 168 | 30.297 | 23.989 | 9.030 | 1.00 | 26.01 | A |
| ATOM | 811 | N | LYS | A | 169 | 31.233 | 22.320 | 7.848 | 1.00 | 26.41 | A |
| ATOM | 812 | CA | LYS | A | 169 | 30.106 | 22.210 | 6.934 | 1.00 | 27.70 | A |
| ATOM | 813 | CB | LYS | A | 169 | 30.324 | 21.064 | 5.945 | 1.00 | 30.49 | A |
| ATOM | 814 | CG | LYS | A | 169 | 29.151 | 20.854 | 4.993 | 1.00 | 32.47 | A |
| ATOM | 815 | CD | LYS | A | 169 | 29.407 | 19.728 | 3.998 | 1.00 | 35.98 | A |
| ATOM | 816 | CE | LYS | A | 169 | 29.462 | 18.372 | 4.683 | 1.00 | 38.53 | A |
| ATOM | 817 | NZ | LYS | A | 169 | 29.622 | 17.263 | 3.702 | 1.00 | 41.00 | A |
| ATOM | 818 | C | LYS | A | 169 | 28.801 | 21.985 | 7.682 | 1.00 | 28.12 | A |
| ATOM | 819 | O | LYS | A | 169 | 27.785 | 22.608 | 7.371 | 1.00 | 28.08 | A |
| ATOM | 820 | N | TYR | A | 170 | 28.826 | 21.094 | 8.668 | 1.00 | 26.53 | A |
| ATOM | 821 | CA | TYR | A | 170 | 27.624 | 20.791 | 9.434 | 1.00 | 26.95 | A |
| ATOM | 822 | CB | TYR | A | 170 | 27.810 | 19.476 | 10.193 | 1.00 | 25.03 | A |
| ATOM | 823 | CG | TYR | A | 170 | 27.898 | 18.300 | 9.251 | 1.00 | 26.65 | A |
| ATOM | 824 | CD1 | TYR | A | 170 | 26.745 | 17.661 | 8.790 | 1.00 | 28.27 | A |
| ATOM | 825 | CE1 | TYR | A | 170 | 26.814 | 16.642 | 7.839 | 1.00 | 26.85 | A |
| ATOM | 826 | CD2 | TYR | A | 170 | 29.127 | 17.884 | 8.742 | 1.00 | 27.83 | A |
| ATOM | 827 | CE2 | TYR | A | 170 | 29.209 | 16.869 | 7.792 | 1.00 | 27.19 | A |
| ATOM | 828 | CZ | TYR | A | 170 | 28.049 | 16.254 | 7.343 | 1.00 | 30.02 | A |
| ATOM | 829 | OH | TYR | A | 170 | 28.130 | 15.268 | 6.382 | 1.00 | 29.23 | A |
| ATOM | 830 | C | TYR | A | 170 | 27.229 | 21.918 | 10.376 | 1.00 | 27.59 | A |
| ATOM | 831 | O | TYR | A | 170 | 26.045 | 22.122 | 10.642 | 1.00 | 29.25 | A |
| ATOM | 832 | N | ILE | A | 171 | 28.208 | 22.660 | 10.882 | 1.00 | 28.16 | A |
| ATOM | 833 | CA | ILE | A | 171 | 27.883 | 23.770 | 11.763 | 1.00 | 29.03 | A |
| ATOM | 834 | CB | ILE | A | 171 | 29.151 | 24.435 | 12.337 | 1.00 | 27.51 | A |
| ATOM | 835 | CG2 | ILE | A | 171 | 28.773 | 25.705 | 13.084 | 1.00 | 27.97 | A |
| ATOM | 836 | CG1 | ILE | A | 171 | 29.872 | 23.458 | 13.272 | 1.00 | 26.70 | A |
| ATOM | 837 | CD1 | ILE | A | 171 | 31.163 | 23.996 | 13.856 | 1.00 | 24.07 | A |
| ATOM | 838 | C | ILE | A | 171 | 27.094 | 24.796 | 10.944 | 1.00 | 31.41 | A |
| ATOM | 839 | O | ILE | A | 171 | 26.088 | 25.335 | 11.407 | 1.00 | 31.69 | A |
| ATOM | 840 | N | ARG | A | 172 | 27.546 | 25.047 | 9.719 | 1.00 | 33.21 | A |
| ATOM | 841 | CA | ARG | A | 172 | 26.874 | 26.000 | 8.844 | 1.00 | 36.54 | A |
| ATOM | 842 | CB | ARG | A | 172 | 27.734 | 26.314 | 7.616 | 1.00 | 37.73 | A |
| ATOM | 843 | CG | ARG | A | 172 | 29.057 | 27.011 | 7.912 | 1.00 | 41.65 | A |
| ATOM | 844 | CD | ARG | A | 172 | 29.708 | 27.492 | 6.616 | 1.00 | 45.29 | A |
| ATOM | 845 | NE | ARG | A | 172 | 31.037 | 28.070 | 6.812 | 1.00 | 48.51 | A |
| ATOM | 846 | CZ | ARG | A | 172 | 31.314 | 29.059 | 7.658 | 1.00 | 51.53 | A |
| ATOM | 847 | NH1 | ARG | A | 172 | 30.355 | 29.593 | 8.406 | 1.00 | 53.75 | A |
| ATOM | 848 | NH2 | ARG | A | 172 | 32.553 | 29.526 | 7.748 | 1.00 | 51.21 | A |
| ATOM | 849 | C | ARG | A | 172 | 25.528 | 25.459 | 8.378 | 1.00 | 37.67 | A |
| ATOM | 850 | O | ARG | A | 172 | 24.550 | 26.200 | 8.288 | 1.00 | 39.09 | A |
| ATOM | 851 | N | LYS | A | 173 | 25.481 | 24.163 | 8.092 | 1.00 | 38.44 | A |
| ATOM | 852 | CA | LYS | A | 173 | 24.259 | 23.528 | 7.619 | 1.00 | 39.25 | A |
| ATOM | 853 | CB | LYS | A | 173 | 24.523 | 22.061 | 7.272 | 1.00 | 41.89 | A |
| ATOM | 854 | CG | LYS | A | 173 | 23.279 | 21.298 | 6.830 | 1.00 | 45.52 | A |
| ATOM | 855 | CD | LYS | A | 173 | 23.557 | 19.808 | 6.653 | 1.00 | 49.60 | A |
| ATOM | 856 | CE | LYS | A | 173 | 24.477 | 19.530 | 5.469 | 1.00 | 52.63 | A |
| ATOM | 857 | NZ | LYS | A | 173 | 23.855 | 19.894 | 4.160 | 1.00 | 54.61 | A |
| ATOM | 858 | C | LYS | A | 173 | 23.089 | 23.608 | 8.595 | 1.00 | 39.30 | A |
| ATOM | 859 | O | LYS | A | 173 | 21.981 | 23.960 | 8.201 | 1.00 | 39.62 | A |
| ATOM | 860 | N | ILE | A | 174 | 23.320 | 23.282 | 9.863 | 1.00 | 37.96 | A |
| ATOM | 861 | CA | ILE | A | 174 | 22.229 | 23.314 | 10.833 | 1.00 | 37.36 | A |
| ATOM | 862 | CB | ILE | A | 174 | 22.159 | 21.998 | 11.652 | 1.00 | 37.44 | A |
| ATOM | 863 | CG2 | ILE | A | 174 | 22.058 | 20.802 | 10.709 | 1.00 | 38.37 | A |
| ATOM | 864 | CG1 | ILE | A | 174 | 23.397 | 21.850 | 12.532 | 1.00 | 37.25 | A |
| ATOM | 865 | CD1 | ILE | A | 174 | 23.355 | 20.620 | 13.418 | 1.00 | 36.85 | A |
| ATOM | 866 | C | ILE | A | 174 | 22.259 | 24.492 | 11.801 | 1.00 | 36.71 | A |
| ATOM | 867 | O | ILE | A | 174 | 21.448 | 24.556 | 12.724 | 1.00 | 38.05 | A |
| ATOM | 868 | N | GLY | A | 175 | 23.185 | 25.423 | 11.592 | 1.00 | 35.48 | A |
| ATOM | 869 | CA | GLY | A | 175 | 23.265 | 26.585 | 12.462 | 1.00 | 35.29 | A |
| ATOM | 870 | C | GLY | A | 175 | 24.053 | 26.360 | 13.737 | 1.00 | 35.06 | A |
| ATOM | 871 | O | GLY | A | 175 | 25.066 | 27.019 | 13.970 | 1.00 | 37.46 | A |
| ATOM | 872 | N | SER | A | 176 | 23.581 | 25.441 | 14.571 | 1.00 | 33.94 | A |
| ATOM | 873 | CA | SER | A | 176 | 24.253 | 25.113 | 15.822 | 1.00 | 32.84 | A |
| ATOM | 874 | CB | SER | A | 176 | 23.938 | 26.155 | 16.901 | 1.00 | 33.54 | A |
| ATOM | 875 | OG | SER | A | 176 | 22.599 | 26.056 | 17.347 | 1.00 | 34.86 | A |
| ATOM | 876 | C | SER | A | 176 | 23.796 | 23.731 | 16.276 | 1.00 | 32.34 | A |
| ATOM | 877 | O | SER | A | 176 | 22.726 | 23.263 | 15.884 | 1.00 | 32.82 | A |
| ATOM | 878 | N | PHE | A | 177 | 24.609 | 23.085 | 17.103 | 1.00 | 29.39 | A |
| ATOM | 879 | CA | PHE | A | 177 | 24.313 | 21.743 | 17.597 | 1.00 | 27.20 | A |
| ATOM | 880 | CB | PHE | A | 177 | 25.621 | 20.989 | 17.865 | 1.00 | 26.39 | A |
| ATOM | 881 | CG | PHE | A | 177 | 26.372 | 20.585 | 16.622 | 1.00 | 26.18 | A |
| ATOM | 882 | CD1 | PHE | A | 177 | 26.210 | 21.277 | 15.426 | 1.00 | 25.30 | A |
| ATOM | 883 | CD2 | PHE | A | 177 | 27.266 | 19.516 | 16.662 | 1.00 | 26.05 | A |

-continued

| | | | | | | | | | | |
|---|---|---|---|---|---|---|---|---|---|---|
| ATOM | 884 | CE1 | PHE | A | 177 | 26.923 | 20.912 | 14.290 | 1.00 | 26.59 | A |
| ATOM | 885 | CE2 | PHE | A | 177 | 27.986 | 19.143 | 15.532 | 1.00 | 26.06 | A |
| ATOM | 886 | CZ | PHE | A | 177 | 27.815 | 19.841 | 14.343 | 1.00 | 25.42 | A |
| ATOM | 887 | C | PHE | A | 177 | 23.500 | 21.752 | 18.884 | 1.00 | 27.00 | A |
| ATOM | 888 | O | PHE | A | 177 | 23.704 | 22.610 | 19.747 | 1.00 | 26.48 | A |
| ATOM | 889 | N | ASP | A | 178 | 22.578 | 20.802 | 19.022 | 1.00 | 26.70 | A |
| ATOM | 890 | CA | ASP | A | 178 | 21.816 | 20.729 | 20.260 | 1.00 | 26.35 | A |
| ATOM | 891 | CB | ASP | A | 178 | 20.621 | 19.773 | 20.142 | 1.00 | 29.90 | A |
| ATOM | 892 | CG | ASP | A | 178 | 21.020 | 18.372 | 19.720 | 1.00 | 32.28 | A |
| ATOM | 893 | OD1 | ASP | A | 178 | 22.157 | 17.949 | 20.014 | 1.00 | 35.21 | A |
| ATOM | 894 | OD2 | ASP | A | 178 | 20.179 | 17.683 | 19.105 | 1.00 | 34.79 | A |
| ATOM | 895 | C | ASP | A | 178 | 22.810 | 20.228 | 21.311 | 1.00 | 25.03 | A |
| ATOM | 896 | O | ASP | A | 178 | 23.974 | 19.968 | 20.992 | 1.00 | 21.24 | A |
| ATOM | 897 | N | GLU | A | 179 | 22.361 | 20.083 | 22.552 | 1.00 | 23.60 | A |
| ATOM | 898 | CA | GLU | A | 179 | 23.247 | 19.644 | 23.619 | 1.00 | 25.18 | A |
| ATOM | 899 | CB | GLU | A | 179 | 22.542 | 19.770 | 24.971 | 1.00 | 27.60 | A |
| ATOM | 900 | CG | GLU | A | 179 | 23.324 | 19.176 | 26.130 | 1.00 | 32.58 | A |
| ATOM | 901 | CD | GLU | A | 179 | 22.997 | 19.845 | 27.449 | 1.00 | 35.82 | A |
| ATOM | 902 | OE1 | GLU | A | 179 | 21.825 | 20.224 | 27.645 | 1.00 | 35.95 | A |
| ATOM | 903 | OE2 | GLU | A | 179 | 23.912 | 19.984 | 28.291 | 1.00 | 38.19 | A |
| ATOM | 904 | C | GLU | A | 179 | 23.808 | 18.235 | 23.450 | 1.00 | 24.08 | A |
| ATOM | 905 | O | GLU | A | 179 | 24.977 | 17.989 | 23.756 | 1.00 | 22.79 | A |
| ATOM | 906 | N | THR | A | 180 | 22.983 | 17.316 | 22.961 | 1.00 | 23.36 | A |
| ATOM | 907 | CA | THR | A | 180 | 23.412 | 15.935 | 22.761 | 1.00 | 22.15 | A |
| ATOM | 908 | CB | THR | A | 180 | 22.224 | 15.054 | 22.320 | 1.00 | 23.77 | A |
| ATOM | 909 | OG1 | THR | A | 180 | 21.222 | 15.075 | 23.341 | 1.00 | 26.37 | A |
| ATOM | 910 | CG2 | THR | A | 180 | 22.670 | 13.616 | 22.088 | 1.00 | 22.66 | A |
| ATOM | 911 | C | THR | A | 180 | 24.533 | 15.830 | 21.724 | 1.00 | 22.01 | A |
| ATOM | 912 | O | THR | A | 180 | 25.533 | 15.141 | 21.944 | 1.00 | 19.87 | A |
| ATOM | 913 | N | CYS | A | 181 | 24.365 | 16.511 | 20.596 | 1.00 | 21.21 | A |
| ATOM | 914 | CA | CYS | A | 181 | 25.372 | 16.480 | 19.541 | 1.00 | 22.22 | A |
| ATOM | 915 | CB | CYS | A | 181 | 24.800 | 17.065 | 18.250 | 1.00 | 24.62 | A |
| ATOM | 916 | SG | CYS | A | 181 | 23.435 | 16.080 | 17.560 | 1.00 | 29.50 | A |
| ATOM | 917 | C | CYS | A | 181 | 26.633 | 17.232 | 19.954 | 1.00 | 23.07 | A |
| ATOM | 918 | O | CYS | A | 181 | 27.746 | 16.827 | 19.608 | 1.00 | 23.95 | A |
| ATOM | 919 | N | THR | A | 182 | 26.463 | 18.325 | 20.695 | 1.00 | 22.76 | A |
| ATOM | 920 | CA | THR | A | 182 | 27.606 | 19.103 | 21.161 | 1.00 | 21.49 | A |
| ATOM | 921 | CB | THR | A | 182 | 27.167 | 20.346 | 21.978 | 1.00 | 21.37 | A |
| ATOM | 922 | OG1 | THR | A | 182 | 26.459 | 21.262 | 21.134 | 1.00 | 22.50 | A |
| ATOM | 923 | CG2 | THR | A | 182 | 28.379 | 21.046 | 22.565 | 1.00 | 18.36 | A |
| ATOM | 924 | C | THR | A | 182 | 28.454 | 18.215 | 22.071 | 1.00 | 21.48 | A |
| ATOM | 925 | O | THR | A | 182 | 29.669 | 18.090 | 21.894 | 1.00 | 19.95 | A |
| ATOM | 926 | N | ARG | A | 183 | 27.798 | 17.602 | 23.050 | 1.00 | 18.97 | A |
| ATOM | 927 | CA | ARG | A | 183 | 28.468 | 16.723 | 23.996 | 1.00 | 19.39 | A |
| ATOM | 928 | CB | ARG | A | 183 | 27.455 | 16.140 | 24.984 | 1.00 | 19.46 | A |
| ATOM | 929 | CG | ARG | A | 183 | 28.030 | 15.062 | 25.887 | 1.00 | 18.77 | A |
| ATOM | 930 | CD | ARG | A | 183 | 27.021 | 14.571 | 26.925 | 1.00 | 21.19 | A |
| ATOM | 931 | NE | ARG | A | 183 | 26.605 | 15.642 | 27.824 | 1.00 | 19.46 | A |
| ATOM | 932 | CZ | ARG | A | 183 | 25.496 | 16.362 | 27.679 | 1.00 | 20.45 | A |
| ATOM | 933 | NH1 | ARG | A | 183 | 24.672 | 16.123 | 26.666 | 1.00 | 19.81 | A |
| ATOM | 934 | NH2 | ARG | A | 183 | 25.224 | 17.338 | 28.539 | 1.00 | 17.11 | A |
| ATOM | 935 | C | ARG | A | 183 | 29.206 | 15.577 | 23.302 | 1.00 | 20.02 | A |
| ATOM | 936 | O | ARG | A | 183 | 30.383 | 15.333 | 23.573 | 1.00 | 19.97 | A |
| ATOM | 937 | N | PHE | A | 184 | 28.520 | 14.871 | 22.409 | 1.00 | 19.24 | A |
| ATOM | 938 | CA | PHE | A | 184 | 29.144 | 13.746 | 21.722 | 1.00 | 18.04 | A |
| ATOM | 939 | CB | PHE | A | 184 | 28.158 | 13.078 | 20.764 | 1.00 | 21.05 | A |
| ATOM | 940 | CG | PHE | A | 184 | 28.719 | 11.857 | 20.098 | 1.00 | 22.67 | A |
| ATOM | 941 | CD1 | PHE | A | 184 | 28.717 | 10.630 | 20.754 | 1.00 | 22.97 | A |
| ATOM | 942 | CD2 | PHE | A | 184 | 29.317 | 11.949 | 18.850 | 1.00 | 19.97 | A |
| ATOM | 943 | CE1 | PHE | A | 184 | 29.308 | 9.510 | 20.176 | 1.00 | 23.53 | A |
| ATOM | 944 | CE2 | PHE | A | 184 | 29.915 | 10.833 | 18.263 | 1.00 | 24.11 | A |
| ATOM | 945 | CZ | PHE | A | 184 | 29.910 | 9.613 | 18.928 | 1.00 | 22.97 | A |
| ATOM | 946 | C | PHE | A | 184 | 30.403 | 14.127 | 20.941 | 1.00 | 17.99 | A |
| ATOM | 947 | O | PHE | A | 184 | 31.461 | 13.531 | 21.130 | 1.00 | 18.89 | A |
| ATOM | 948 | N | TYR | A | 185 | 30.292 | 15.110 | 20.056 | 1.00 | 15.73 | A |
| ATOM | 949 | CA | TYR | A | 185 | 31.443 | 15.519 | 19.265 | 1.00 | 15.72 | A |
| ATOM | 950 | CB | TYR | A | 185 | 30.992 | 16.413 | 18.111 | 1.00 | 17.33 | A |
| ATOM | 951 | CG | TYR | A | 185 | 30.364 | 15.584 | 17.015 | 1.00 | 19.37 | A |
| ATOM | 952 | CD1 | TYR | A | 185 | 31.159 | 14.809 | 16.168 | 1.00 | 16.53 | A |
| ATOM | 953 | CE1 | TYR | A | 185 | 30.590 | 13.952 | 15.232 | 1.00 | 18.12 | A |
| ATOM | 954 | CD2 | TYR | A | 185 | 28.976 | 15.484 | 16.892 | 1.00 | 18.18 | A |
| ATOM | 955 | CE2 | TYR | A | 185 | 28.398 | 14.623 | 15.956 | 1.00 | 18.90 | A |
| ATOM | 956 | CZ | TYR | A | 185 | 29.211 | 13.861 | 15.133 | 1.00 | 18.41 | A |
| ATOM | 957 | OH | TYR | A | 185 | 28.650 | 12.995 | 14.218 | 1.00 | 20.48 | A |
| ATOM | 958 | C | TYR | A | 185 | 32.544 | 16.172 | 20.083 | 1.00 | 15.79 | A |
| ATOM | 959 | O | TYR | A | 185 | 33.720 | 16.015 | 19.766 | 1.00 | 17.69 | A |
| ATOM | 960 | N | THR | A | 186 | 32.176 | 16.887 | 21.142 | 1.00 | 15.68 | A |
| ATOM | 961 | CA | THR | A | 186 | 33.184 | 17.504 | 21.997 | 1.00 | 16.03 | A |
| ATOM | 962 | CB | THR | A | 186 | 32.559 | 18.403 | 23.094 | 1.00 | 16.62 | A |

-continued

| | | | | | | | | | | |
|---|---|---|---|---|---|---|---|---|---|---|
| ATOM | 963 | OG1 | THR | A | 186 | 31.866 | 19.503 | 22.481 | 1.00 | 14.79 | A |
| ATOM | 964 | CG2 | THR | A | 186 | 33.656 | 18.953 | 24.019 | 1.00 | 14.68 | A |
| ATOM | 965 | C | THR | A | 186 | 33.954 | 16.375 | 22.680 | 1.00 | 15.59 | A |
| ATOM | 966 | O | THR | A | 186 | 35.176 | 16.443 | 22.823 | 1.00 | 13.77 | A |
| ATOM | 967 | N | ALA | A | 187 | 33.234 | 15.333 | 23.097 | 1.00 | 14.06 | A |
| ATOM | 968 | CA | ALA | A | 187 | 33.869 | 14.196 | 23.757 | 1.00 | 14.74 | A |
| ATOM | 969 | CB | ALA | A | 187 | 32.810 | 13.195 | 24.224 | 1.00 | 14.32 | A |
| ATOM | 970 | C | ALA | A | 187 | 34.875 | 13.509 | 22.821 | 1.00 | 14.41 | A |
| ATOM | 971 | O | ALA | A | 187 | 35.972 | 13.136 | 23.247 | 1.00 | 15.61 | A |
| ATOM | 972 | N | GLU | A | 188 | 34.516 | 13.340 | 21.549 | 1.00 | 14.01 | A |
| ATOM | 973 | CA | GLU | A | 188 | 35.443 | 12.704 | 20.615 | 1.00 | 13.50 | A |
| ATOM | 974 | CB | GLU | A | 188 | 34.782 | 12.449 | 19.251 | 1.00 | 12.85 | A |
| ATOM | 975 | CG | GLU | A | 188 | 33.622 | 11.454 | 19.282 | 1.00 | 12.71 | A |
| ATOM | 976 | CD | GLU | A | 188 | 33.464 | 10.685 | 17.979 | 1.00 | 15.01 | A |
| ATOM | 977 | OE1 | GLU | A | 188 | 33.687 | 11.275 | 16.899 | 1.00 | 13.21 | A |
| ATOM | 978 | OE2 | GLU | A | 188 | 33.110 | 9.484 | 18.031 | 1.00 | 17.69 | A |
| ATOM | 979 | C | GLU | A | 188 | 36.682 | 13.582 | 20.436 | 1.00 | 13.34 | A |
| ATOM | 980 | O | GLU | A | 188 | 37.803 | 13.085 | 20.408 | 1.00 | 14.69 | A |
| ATOM | 981 | N | ILE | A | 189 | 36.486 | 14.893 | 20.326 | 1.00 | 13.52 | A |
| ATOM | 982 | CA | ILE | A | 189 | 37.627 | 15.787 | 20.159 | 1.00 | 13.35 | A |
| ATOM | 983 | CB | ILE | A | 189 | 37.169 | 17.247 | 19.939 | 1.00 | 13.95 | A |
| ATOM | 984 | CG2 | ILE | A | 189 | 38.381 | 18.165 | 19.822 | 1.00 | 12.47 | A |
| ATOM | 985 | CG1 | ILE | A | 189 | 36.302 | 17.332 | 18.671 | 1.00 | 13.44 | A |
| ATOM | 986 | CD1 | ILE | A | 189 | 35.588 | 18.664 | 18.491 | 1.00 | 14.29 | A |
| ATOM | 987 | C | ILE | A | 189 | 38.530 | 15.702 | 21.394 | 1.00 | 14.63 | A |
| ATOM | 988 | O | ILE | A | 189 | 39.753 | 15.595 | 21.271 | 1.00 | 12.97 | A |
| ATOM | 989 | N | VAL | A | 190 | 37.927 | 15.751 | 22.582 | 1.00 | 14.35 | A |
| ATOM | 990 | CA | VAL | A | 190 | 38.684 | 15.655 | 23.832 | 1.00 | 13.22 | A |
| ATOM | 991 | CB | VAL | A | 190 | 37.743 | 15.690 | 25.061 | 1.00 | 14.28 | A |
| ATOM | 992 | CG1 | VAL | A | 190 | 38.509 | 15.267 | 26.326 | 1.00 | 15.08 | A |
| ATOM | 993 | CG2 | VAL | A | 190 | 37.160 | 17.082 | 25.233 | 1.00 | 12.08 | A |
| ATOM | 994 | C | VAL | A | 190 | 39.468 | 14.338 | 23.859 | 1.00 | 14.61 | A |
| ATOM | 995 | O | VAL | A | 190 | 40.634 | 14.304 | 24.250 | 1.00 | 13.72 | A |
| ATOM | 996 | N | SER | A | 191 | 38.825 | 13.254 | 23.432 | 1.00 | 15.26 | A |
| ATOM | 997 | CA | SER | A | 191 | 39.478 | 11.943 | 23.421 | 1.00 | 16.81 | A |
| ATOM | 998 | CB | SER | A | 191 | 38.470 | 10.857 | 23.041 | 1.00 | 16.14 | A |
| ATOM | 999 | OG | SER | A | 191 | 39.018 | 9.569 | 23.238 | 1.00 | 16.94 | A |
| ATOM | 1000 | C | SER | A | 191 | 40.649 | 11.928 | 22.441 | 1.00 | 16.58 | A |
| ATOM | 1001 | O | SER | A | 191 | 41.697 | 11.335 | 22.713 | 1.00 | 13.96 | A |
| ATOM | 1002 | N | ALA | A | 192 | 40.468 | 12.586 | 21.300 | 1.00 | 15.26 | A |
| ATOM | 1003 | CA | ALA | A | 192 | 41.518 | 12.645 | 20.292 | 1.00 | 14.37 | A |
| ATOM | 1004 | CB | ALA | A | 192 | 40.989 | 13.296 | 19.016 | 1.00 | 14.43 | A |
| ATOM | 1005 | C | ALA | A | 192 | 42.695 | 13.440 | 20.845 | 1.00 | 16.46 | A |
| ATOM | 1006 | O | ALA | A | 192 | 43.851 | 13.038 | 20.697 | 1.00 | 17.96 | A |
| ATOM | 1007 | N | LEU | A | 193 | 42.401 | 14.563 | 21.496 | 1.00 | 15.02 | A |
| ATOM | 1008 | CA | LEU | A | 193 | 43.459 | 15.392 | 22.067 | 1.00 | 15.42 | A |
| ATOM | 1009 | CB | LEU | A | 193 | 42.884 | 16.712 | 22.600 | 1.00 | 12.88 | A |
| ATOM | 1010 | CG | LEU | A | 193 | 42.445 | 17.721 | 21.525 | 1.00 | 15.97 | A |
| ATOM | 1011 | CD1 | LEU | A | 193 | 41.869 | 18.979 | 22.190 | 1.00 | 13.97 | A |
| ATOM | 1012 | CD2 | LEU | A | 193 | 43.642 | 18.088 | 20.655 | 1.00 | 14.58 | A |
| ATOM | 1013 | C | LEU | A | 193 | 44.211 | 14.659 | 23.174 | 1.00 | 14.49 | A |
| ATOM | 1014 | O | LEU | A | 193 | 45.427 | 14.813 | 23.310 | 1.00 | 16.56 | A |
| ATOM | 1015 | N | GLU | A | 194 | 43.500 | 13.870 | 23.975 | 1.00 | 13.96 | A |
| ATOM | 1016 | CA | GLU | A | 194 | 44.179 | 13.123 | 25.032 | 1.00 | 14.08 | A |
| ATOM | 1017 | CB | GLU | A | 194 | 43.190 | 12.295 | 25.857 | 1.00 | 14.65 | A |
| ATOM | 1018 | CG | GLU | A | 194 | 43.882 | 11.301 | 26.789 | 1.00 | 17.09 | A |
| ATOM | 1019 | CD | GLU | A | 194 | 42.924 | 10.592 | 27.730 | 1.00 | 19.59 | A |
| ATOM | 1020 | OE1 | GLU | A | 194 | 41.809 | 10.237 | 27.295 | 1.00 | 19.25 | A |
| ATOM | 1021 | OE2 | GLU | A | 194 | 43.302 | 10.380 | 28.906 | 1.00 | 20.20 | A |
| ATOM | 1022 | C | GLU | A | 194 | 45.208 | 12.199 | 24.386 | 1.00 | 13.57 | A |
| ATOM | 1023 | O | GLU | A | 194 | 46.337 | 12.093 | 24.847 | 1.00 | 14.23 | A |
| ATOM | 1024 | N | TYR | A | 195 | 44.822 | 11.544 | 23.301 | 1.00 | 14.89 | A |
| ATOM | 1025 | CA | TYR | A | 195 | 45.743 | 10.642 | 22.618 | 1.00 | 16.58 | A |
| ATOM | 1026 | CB | TYR | A | 195 | 45.030 | 9.910 | 21.488 | 1.00 | 17.29 | A |
| ATOM | 1027 | CG | TYR | A | 195 | 45.956 | 9.058 | 20.649 | 1.00 | 17.92 | A |
| ATOM | 1028 | CD1 | TYR | A | 195 | 46.347 | 7.788 | 21.077 | 1.00 | 17.96 | A |
| ATOM | 1029 | CE1 | TYR | A | 195 | 47.203 | 6.996 | 20.304 | 1.00 | 19.77 | A |
| ATOM | 1030 | CD2 | TYR | A | 195 | 46.445 | 9.524 | 19.428 | 1.00 | 16.67 | A |
| ATOM | 1031 | CE2 | TYR | A | 195 | 47.299 | 8.744 | 18.650 | 1.00 | 18.51 | A |
| ATOM | 1032 | CZ | TYR | A | 195 | 47.671 | 7.481 | 19.094 | 1.00 | 20.24 | A |
| ATOM | 1033 | OH | TYR | A | 195 | 48.506 | 6.705 | 18.325 | 1.00 | 21.89 | A |
| ATOM | 1034 | C | TYR | A | 195 | 46.917 | 11.419 | 22.035 | 1.00 | 16.98 | A |
| ATOM | 1035 | O | TYR | A | 195 | 48.081 | 11.047 | 22.203 | 1.00 | 14.61 | A |
| ATOM | 1036 | N | LEU | A | 196 | 46.599 | 12.507 | 21.347 | 1.00 | 16.30 | A |
| ATOM | 1037 | CA | LEU | A | 196 | 47.619 | 13.328 | 20.720 | 1.00 | 18.15 | A |
| ATOM | 1038 | CB | LEU | A | 196 | 46.969 | 14.502 | 19.982 | 1.00 | 18.59 | A |
| ATOM | 1039 | CG | LEU | A | 196 | 47.834 | 15.203 | 18.935 | 1.00 | 22.51 | A |
| ATOM | 1040 | CD1 | LEU | A | 196 | 48.222 | 14.206 | 17.841 | 1.00 | 20.94 | A |
| ATOM | 1041 | CD2 | LEU | A | 196 | 47.060 | 16.375 | 18.338 | 1.00 | 22.98 | A |

-continued

| | | | | | | | | | | |
|---|---|---|---|---|---|---|---|---|---|---|
| ATOM | 1042 | C | LEU | A | 196 | 48.592 | 13.844 | 21.763 | 1.00 | 17.75 | A |
| ATOM | 1043 | O | LEU | A | 196 | 49.801 | 13.644 | 21.649 | 1.00 | 18.33 | A |
| ATOM | 1044 | N | HIS | A | 197 | 48.064 | 14.495 | 22.792 | 1.00 | 17.12 | A |
| ATOM | 1045 | CA | HIS | A | 197 | 48.913 | 15.042 | 23.842 | 1.00 | 18.47 | A |
| ATOM | 1046 | CB | HIS | A | 197 | 48.069 | 15.866 | 24.817 | 1.00 | 15.90 | A |
| ATOM | 1047 | CG | HIS | A | 197 | 47.571 | 17.152 | 24.231 | 1.00 | 19.15 | A |
| ATOM | 1048 | CD2 | HIS | A | 197 | 47.830 | 17.745 | 23.038 | 1.00 | 18.22 | A |
| ATOM | 1049 | ND1 | HIS | A | 197 | 46.704 | 17.992 | 24.897 | 1.00 | 17.47 | A |
| ATOM | 1050 | CE1 | HIS | A | 197 | 46.450 | 19.047 | 24.139 | 1.00 | 19.74 | A |
| ATOM | 1051 | NE2 | HIS | A | 197 | 47.119 | 18.921 | 23.007 | 1.00 | 15.69 | A |
| ATOM | 1052 | C | HIS | A | 197 | 49.696 | 13.958 | 24.572 | 1.00 | 19.40 | A |
| ATOM | 1053 | O | HIS | A | 197 | 50.823 | 14.192 | 25.021 | 1.00 | 19.42 | A |
| ATOM | 1054 | N | GLY | A | 198 | 49.106 | 12.770 | 24.679 | 1.00 | 18.59 | A |
| ATOM | 1055 | CA | GLY | A | 198 | 49.793 | 11.675 | 25.339 | 1.00 | 19.60 | A |
| ATOM | 1056 | C | GLY | A | 198 | 51.075 | 11.307 | 24.612 | 1.00 | 21.86 | A |
| ATOM | 1057 | O | GLY | A | 198 | 51.963 | 10.682 | 25.186 | 1.00 | 23.09 | A |
| ATOM | 1058 | N | LYS | A | 199 | 51.174 | 11.687 | 23.341 | 1.00 | 22.81 | A |
| ATOM | 1059 | CA | LYS | A | 199 | 52.368 | 11.401 | 22.549 | 1.00 | 24.43 | A |
| ATOM | 1060 | CB | LYS | A | 199 | 51.990 | 10.905 | 21.154 | 1.00 | 26.00 | A |
| ATOM | 1061 | CG | LYS | A | 199 | 51.378 | 9.520 | 21.133 | 1.00 | 30.98 | A |
| ATOM | 1062 | CD | LYS | A | 199 | 51.291 | 9.002 | 19.708 | 1.00 | 36.85 | A |
| ATOM | 1063 | CE | LYS | A | 199 | 50.832 | 7.559 | 19.682 | 1.00 | 40.37 | A |
| ATOM | 1064 | NZ | LYS | A | 199 | 51.646 | 6.691 | 20.581 | 1.00 | 43.48 | A |
| ATOM | 1065 | C | LYS | A | 199 | 53.253 | 12.631 | 22.414 | 1.00 | 23.88 | A |
| ATOM | 1066 | O | LYS | A | 199 | 54.144 | 12.669 | 21.568 | 1.00 | 24.97 | A |
| ATOM | 1067 | N | GLY | A | 200 | 52.997 | 13.638 | 23.243 | 1.00 | 24.00 | A |
| ATOM | 1068 | CA | GLY | A | 200 | 53.790 | 14.853 | 23.203 | 1.00 | 22.12 | A |
| ATOM | 1069 | C | GLY | A | 200 | 53.665 | 15.632 | 21.907 | 1.00 | 22.14 | A |
| ATOM | 1070 | O | GLY | A | 200 | 54.632 | 16.231 | 21.439 | 1.00 | 22.41 | A |
| ATOM | 1071 | N | ILE | A | 201 | 52.475 | 15.630 | 21.320 | 1.00 | 20.00 | A |
| ATOM | 1072 | CA | ILE | A | 201 | 52.252 | 16.355 | 20.080 | 1.00 | 18.93 | A |
| ATOM | 1073 | CB | ILE | A | 201 | 51.784 | 15.414 | 18.955 | 1.00 | 19.70 | A |
| ATOM | 1074 | CG2 | ILE | A | 201 | 51.414 | 16.226 | 17.716 | 1.00 | 20.12 | A |
| ATOM | 1075 | CG1 | ILE | A | 201 | 52.880 | 14.395 | 18.636 | 1.00 | 20.03 | A |
| ATOM | 1076 | CD1 | ILE | A | 201 | 52.408 | 13.258 | 17.745 | 1.00 | 22.75 | A |
| ATOM | 1077 | C | ILE | A | 201 | 51.193 | 17.425 | 20.270 | 1.00 | 19.87 | A |
| ATOM | 1078 | O | ILE | A | 201 | 50.121 | 17.161 | 20.817 | 1.00 | 20.08 | A |
| ATOM | 1079 | N | ILE | A | 202 | 51.508 | 18.633 | 19.815 | 1.00 | 19.94 | A |
| ATOM | 1080 | CA | ILE | A | 202 | 50.601 | 19.772 | 19.891 | 1.00 | 20.45 | A |
| ATOM | 1081 | CB | ILE | A | 202 | 51.352 | 21.040 | 20.356 | 1.00 | 22.21 | A |
| ATOM | 1082 | CG2 | ILE | A | 202 | 50.381 | 22.220 | 20.470 | 1.00 | 22.67 | A |
| ATOM | 1083 | CG1 | ILE | A | 202 | 52.033 | 20.775 | 21.700 | 1.00 | 24.19 | A |
| ATOM | 1084 | CD1 | ILE | A | 202 | 52.914 | 21.920 | 22.169 | 1.00 | 25.39 | A |
| ATOM | 1085 | C | ILE | A | 202 | 50.105 | 19.999 | 18.464 | 1.00 | 20.71 | A |
| ATOM | 1086 | O | ILE | A | 202 | 50.910 | 20.067 | 17.538 | 1.00 | 19.48 | A |
| ATOM | 1087 | N | HIS | A | 203 | 48.795 | 20.108 | 18.270 | 1.00 | 18.65 | A |
| ATOM | 1088 | CA | HIS | A | 203 | 48.280 | 20.319 | 16.919 | 1.00 | 18.02 | A |
| ATOM | 1089 | CB | HIS | A | 203 | 46.775 | 20.057 | 16.874 | 1.00 | 16.31 | A |
| ATOM | 1090 | CG | HIS | A | 203 | 46.199 | 20.136 | 15.495 | 1.00 | 18.36 | A |
| ATOM | 1091 | CD2 | HIS | A | 203 | 46.043 | 21.186 | 14.655 | 1.00 | 16.42 | A |
| ATOM | 1092 | ND1 | HIS | A | 203 | 45.759 | 19.026 | 14.806 | 1.00 | 19.50 | A |
| ATOM | 1093 | CE1 | HIS | A | 203 | 45.359 | 19.389 | 13.600 | 1.00 | 17.64 | A |
| ATOM | 1094 | NE2 | HIS | A | 203 | 45.522 | 20.694 | 13.483 | 1.00 | 20.87 | A |
| ATOM | 1095 | C | HIS | A | 203 | 48.589 | 21.738 | 16.405 | 1.00 | 18.92 | A |
| ATOM | 1096 | O | HIS | A | 203 | 49.073 | 21.906 | 15.282 | 1.00 | 16.21 | A |
| ATOM | 1097 | N | ARG | A | 204 | 48.301 | 22.744 | 17.232 | 1.00 | 18.60 | A |
| ATOM | 1098 | CA | ARG | A | 204 | 48.552 | 24.157 | 16.914 | 1.00 | 19.81 | A |
| ATOM | 1099 | CB | ARG | A | 204 | 49.998 | 24.365 | 16.458 | 1.00 | 21.61 | A |
| ATOM | 1100 | CG | ARG | A | 204 | 51.024 | 24.137 | 17.550 | 1.00 | 23.82 | A |
| ATOM | 1101 | CD | ARG | A | 204 | 52.323 | 24.870 | 17.252 | 1.00 | 27.62 | A |
| ATOM | 1102 | NE | ARG | A | 204 | 52.932 | 24.449 | 15.994 | 1.00 | 29.43 | A |
| ATOM | 1103 | CZ | ARG | A | 204 | 54.125 | 24.861 | 15.572 | 1.00 | 33.10 | A |
| ATOM | 1104 | NH1 | ARG | A | 204 | 54.835 | 25.706 | 16.311 | 1.00 | 32.12 | A |
| ATOM | 1105 | NH2 | ARG | A | 204 | 54.614 | 24.426 | 14.418 | 1.00 | 30.25 | A |
| ATOM | 1106 | C | ARG | A | 204 | 47.624 | 24.830 | 15.905 | 1.00 | 20.03 | A |
| ATOM | 1107 | O | ARG | A | 204 | 47.711 | 26.038 | 15.698 | 1.00 | 20.88 | A |
| ATOM | 1108 | N | ASP | A | 205 | 46.755 | 24.071 | 15.255 | 1.00 | 18.96 | A |
| ATOM | 1109 | CA | ASP | A | 205 | 45.828 | 24.692 | 14.325 | 1.00 | 17.90 | A |
| ATOM | 1110 | CB | ASP | A | 205 | 46.418 | 24.741 | 12.914 | 1.00 | 18.95 | A |
| ATOM | 1111 | CG | ASP | A | 205 | 45.655 | 25.688 | 12.008 | 1.00 | 20.36 | A |
| ATOM | 1112 | OD1 | ASP | A | 205 | 44.939 | 26.560 | 12.545 | 1.00 | 20.35 | A |
| ATOM | 1113 | OD2 | ASP | A | 205 | 45.772 | 25.573 | 10.771 | 1.00 | 22.49 | A |
| ATOM | 1114 | C | ASP | A | 205 | 44.500 | 23.956 | 14.328 | 1.00 | 19.60 | A |
| ATOM | 1115 | O | ASP | A | 205 | 43.876 | 23.751 | 13.287 | 1.00 | 21.53 | A |
| ATOM | 1116 | N | LEU | A | 206 | 44.063 | 23.569 | 15.521 | 1.00 | 18.53 | A |
| ATOM | 1117 | CA | LEU | A | 206 | 42.813 | 22.851 | 15.667 | 1.00 | 19.18 | A |
| ATOM | 1118 | CB | LEU | A | 206 | 42.693 | 22.295 | 17.087 | 1.00 | 18.94 | A |
| ATOM | 1119 | CG | LEU | A | 206 | 41.511 | 21.358 | 17.346 | 1.00 | 23.10 | A |
| ATOM | 1120 | CD1 | LEU | A | 206 | 41.615 | 20.142 | 16.436 | 1.00 | 23.01 | A |

-continued

| | | | | | | | | | | |
|---|---|---|---|---|---|---|---|---|---|---|
| ATOM | 1121 | CD2 | LEU | A | 206 | 41.504 | 20.933 | 18.808 | 1.00 | 22.97 | A |
| ATOM | 1122 | C | LEU | A | 206 | 41.639 | 23.772 | 15.361 | 1.00 | 19.05 | A |
| ATOM | 1123 | O | LEU | A | 206 | 41.556 | 24.880 | 15.886 | 1.00 | 19.25 | A |
| ATOM | 1124 | N | LYS | A | 207 | 40.740 | 23.307 | 14.500 | 1.00 | 17.54 | A |
| ATOM | 1125 | CA | LYS | A | 207 | 39.564 | 24.081 | 14.110 | 1.00 | 18.60 | A |
| ATOM | 1126 | CB | LYS | A | 207 | 39.980 | 25.248 | 13.196 | 1.00 | 18.98 | A |
| ATOM | 1127 | CG | LYS | A | 207 | 40.786 | 24.817 | 11.982 | 1.00 | 18.20 | A |
| ATOM | 1128 | CD | LYS | A | 207 | 41.246 | 26.000 | 11.139 | 1.00 | 21.42 | A |
| ATOM | 1129 | CE | LYS | A | 207 | 42.223 | 25.537 | 10.062 | 1.00 | 23.21 | A |
| ATOM | 1130 | NZ | LYS | A | 207 | 42.561 | 26.604 | 9.084 | 1.00 | 29.61 | A |
| ATOM | 1131 | C | LYS | A | 207 | 38.566 | 23.181 | 13.388 | 1.00 | 18.18 | A |
| ATOM | 1132 | O | LYS | A | 207 | 38.921 | 22.100 | 12.915 | 1.00 | 18.11 | A |
| ATOM | 1133 | N | PRO | A | 208 | 37.298 | 23.614 | 13.293 | 1.00 | 20.26 | A |
| ATOM | 1134 | CD | PRO | A | 208 | 36.713 | 24.833 | 13.882 | 1.00 | 18.79 | A |
| ATOM | 1135 | CA | PRO | A | 208 | 36.272 | 22.814 | 12.616 | 1.00 | 19.67 | A |
| ATOM | 1136 | CB | PRO | A | 208 | 35.063 | 23.742 | 12.608 | 1.00 | 19.45 | A |
| ATOM | 1137 | CG | PRO | A | 208 | 35.231 | 24.509 | 13.891 | 1.00 | 21.81 | A |
| ATOM | 1138 | C | PRO | A | 208 | 36.674 | 22.372 | 11.209 | 1.00 | 21.04 | A |
| ATOM | 1139 | O | PRO | A | 208 | 36.264 | 21.307 | 10.751 | 1.00 | 21.19 | A |
| ATOM | 1140 | N | GLU | A | 209 | 37.474 | 23.188 | 10.528 | 1.00 | 21.69 | A |
| ATOM | 1141 | CA | GLU | A | 209 | 37.928 | 22.872 | 9.170 | 1.00 | 22.64 | A |
| ATOM | 1142 | CB | GLU | A | 209 | 38.644 | 24.084 | 8.558 | 1.00 | 23.65 | A |
| ATOM | 1143 | CG | GLU | A | 209 | 39.253 | 23.825 | 7.185 | 1.00 | 27.24 | A |
| ATOM | 1144 | CD | GLU | A | 209 | 40.155 | 24.958 | 6.716 | 1.00 | 29.40 | A |
| ATOM | 1145 | OE1 | GLU | A | 209 | 39.660 | 26.094 | 6.553 | 1.00 | 29.68 | A |
| ATOM | 1146 | OE2 | GLU | A | 209 | 41.363 | 24.711 | 6.511 | 1.00 | 30.07 | A |
| ATOM | 1147 | C | GLU | A | 209 | 38.879 | 21.668 | 9.159 | 1.00 | 22.28 | A |
| ATOM | 1148 | O | GLU | A | 209 | 38.955 | 20.933 | 8.170 | 1.00 | 21.36 | A |
| ATOM | 1149 | N | ASN | A | 210 | 39.600 | 21.490 | 10.263 | 1.00 | 19.90 | A |
| ATOM | 1150 | CA | ASN | A | 210 | 40.574 | 20.412 | 10.436 | 1.00 | 19.44 | A |
| ATOM | 1151 | CB | ASN | A | 210 | 41.744 | 20.912 | 11.287 | 1.00 | 20.07 | A |
| ATOM | 1152 | CG | ASN | A | 210 | 42.746 | 21.698 | 10.479 | 1.00 | 25.77 | A |
| ATOM | 1153 | OD1 | ASN | A | 210 | 43.571 | 22.427 | 11.029 | 1.00 | 26.73 | A |
| ATOM | 1154 | ND2 | ASN | A | 210 | 42.687 | 21.548 | 9.158 | 1.00 | 25.15 | A |
| ATOM | 1155 | C | ASN | A | 210 | 40.005 | 19.151 | 11.078 | 1.00 | 18.63 | A |
| ATOM | 1156 | O | ASN | A | 210 | 40.712 | 18.154 | 11.234 | 1.00 | 18.29 | A |
| ATOM | 1157 | N | ILE | A | 211 | 38.739 | 19.202 | 11.469 | 1.00 | 16.31 | A |
| ATOM | 1158 | CA | ILE | A | 211 | 38.090 | 18.058 | 12.085 | 1.00 | 15.49 | A |
| ATOM | 1159 | CB | ILE | A | 211 | 37.336 | 18.488 | 13.354 | 1.00 | 15.40 | A |
| ATOM | 1160 | CG2 | ILE | A | 211 | 36.582 | 17.311 | 13.950 | 1.00 | 14.59 | A |
| ATOM | 1161 | CG1 | ILE | A | 211 | 38.342 | 19.046 | 14.365 | 1.00 | 15.91 | A |
| ATOM | 1162 | CD1 | ILE | A | 211 | 37.720 | 19.669 | 15.590 | 1.00 | 15.98 | A |
| ATOM | 1163 | C | ILE | A | 211 | 37.131 | 17.485 | 11.059 | 1.00 | 17.26 | A |
| ATOM | 1164 | O | ILE | A | 211 | 35.995 | 17.947 | 10.926 | 1.00 | 18.16 | A |
| ATOM | 1165 | N | LEU | A | 212 | 37.599 | 16.486 | 10.317 | 1.00 | 15.97 | A |
| ATOM | 1166 | CA | LEU | A | 212 | 36.784 | 15.875 | 9.274 | 1.00 | 17.08 | A |
| ATOM | 1167 | CB | LEU | A | 212 | 37.685 | 15.249 | 8.202 | 1.00 | 17.78 | A |
| ATOM | 1168 | CG | LEU | A | 212 | 38.785 | 16.157 | 7.640 | 1.00 | 18.92 | A |
| ATOM | 1169 | CD1 | LEU | A | 212 | 39.476 | 15.450 | 6.485 | 1.00 | 22.09 | A |
| ATOM | 1170 | CD2 | LEU | A | 212 | 38.188 | 17.482 | 7.166 | 1.00 | 19.91 | A |
| ATOM | 1171 | C | LEU | A | 212 | 35.843 | 14.825 | 9.837 | 1.00 | 18.35 | A |
| ATOM | 1172 | O | LEU | A | 212 | 35.957 | 14.433 | 11.002 | 1.00 | 19.39 | A |
| ATOM | 1173 | N | LEU | A | 213 | 34.915 | 14.368 | 9.000 | 1.00 | 17.84 | A |
| ATOM | 1174 | CA | LEU | A | 213 | 33.942 | 13.362 | 9.403 | 1.00 | 19.94 | A |
| ATOM | 1175 | CB | LEU | A | 213 | 32.556 | 14.004 | 9.487 | 1.00 | 20.84 | A |
| ATOM | 1176 | CG | LEU | A | 213 | 32.396 | 15.059 | 10.583 | 1.00 | 20.31 | A |
| ATOM | 1177 | CD1 | LEU | A | 213 | 31.124 | 15.837 | 10.367 | 1.00 | 22.75 | A |
| ATOM | 1178 | CD2 | LEU | A | 213 | 32.379 | 14.378 | 11.940 | 1.00 | 23.93 | A |
| ATOM | 1179 | C | LEU | A | 213 | 33.914 | 12.187 | 8.426 | 1.00 | 20.98 | A |
| ATOM | 1180 | O | LEU | A | 213 | 33.743 | 12.379 | 7.218 | 1.00 | 19.55 | A |
| ATOM | 1181 | N | ASN | A | 214 | 34.088 | 10.970 | 8.935 | 1.00 | 20.44 | A |
| ATOM | 1182 | CA | ASN | A | 214 | 34.055 | 9.814 | 8.049 | 1.00 | 23.77 | A |
| ATOM | 1183 | CB | ASN | A | 214 | 34.745 | 8.596 | 8.674 | 1.00 | 25.30 | A |
| ATOM | 1184 | CG | ASN | A | 214 | 34.077 | 8.127 | 9.948 | 1.00 | 32.04 | A |
| ATOM | 1185 | OD1 | ASN | A | 214 | 32.908 | 8.422 | 10.206 | 1.00 | 34.43 | A |
| ATOM | 1186 | ND2 | ASN | A | 214 | 34.818 | 7.369 | 10.752 | 1.00 | 33.85 | A |
| ATOM | 1187 | C | ASN | A | 214 | 32.618 | 9.466 | 7.693 | 1.00 | 24.07 | A |
| ATOM | 1188 | O | ASN | A | 214 | 31.672 | 10.113 | 8.150 | 1.00 | 19.94 | A |
| ATOM | 1189 | N | GLU | A | 215 | 32.459 | 8.433 | 6.879 | 1.00 | 25.77 | A |
| ATOM | 1190 | CA | GLU | A | 215 | 31.138 | 8.003 | 6.445 | 1.00 | 28.69 | A |
| ATOM | 1191 | CB | GLU | A | 215 | 31.275 | 6.796 | 5.513 | 1.00 | 31.98 | A |
| ATOM | 1192 | CG | GLU | A | 215 | 29.970 | 6.334 | 4.896 | 1.00 | 40.22 | A |
| ATOM | 1193 | CD | GLU | A | 215 | 30.182 | 5.312 | 3.795 | 1.00 | 44.27 | A |
| ATOM | 1194 | OE1 | GLU | A | 215 | 30.817 | 4.268 | 4.065 | 1.00 | 46.46 | A |
| ATOM | 1195 | OE2 | GLU | A | 215 | 29.716 | 5.556 | 2.660 | 1.00 | 46.13 | A |
| ATOM | 1196 | C | GLU | A | 215 | 30.188 | 7.673 | 7.601 | 1.00 | 28.41 | A |
| ATOM | 1197 | O | GLU | A | 215 | 28.971 | 7.769 | 7.447 | 1.00 | 28.52 | A |
| ATOM | 1198 | N | ASP | A | 216 | 30.737 | 7.287 | 8.752 | 1.00 | 26.77 | A |
| ATOM | 1199 | CA | ASP | A | 216 | 29.914 | 6.953 | 9.917 | 1.00 | 27.28 | A |

-continued

| | | | | | | | | | | |
|---|---|---|---|---|---|---|---|---|---|---|
| ATOM | 1200 | CB | ASP | A | 216 | 30.538 | 5.795 | 10.696 | 1.00 | 31.27 | A |
| ATOM | 1201 | CG | ASP | A | 216 | 30.390 | 4.466 | 9.979 | 1.00 | 37.61 | A |
| ATOM | 1202 | OD1 | ASP | A | 216 | 29.274 | 4.170 | 9.499 | 1.00 | 39.45 | A |
| ATOM | 1203 | OD2 | ASP | A | 216 | 31.382 | 3.710 | 9.902 | 1.00 | 41.84 | A |
| ATOM | 1204 | C | ASP | A | 216 | 29.697 | 8.135 | 10.862 | 1.00 | 26.37 | A |
| ATOM | 1205 | O | ASP | A | 216 | 29.136 | 7.984 | 11.950 | 1.00 | 25.73 | A |
| ATOM | 1206 | N | MET | A | 217 | 30.156 | 9.306 | 10.441 | 1.00 | 23.02 | A |
| ATOM | 1207 | CA | MET | A | 217 | 30.015 | 10.527 | 11.218 | 1.00 | 21.83 | A |
| ATOM | 1208 | CB | MET | A | 217 | 28.537 | 10.789 | 11.517 | 1.00 | 23.24 | A |
| ATOM | 1209 | CG | MET | A | 217 | 27.742 | 11.186 | 10.274 | 1.00 | 22.98 | A |
| ATOM | 1210 | SD | MET | A | 217 | 28.464 | 12.616 | 9.430 | 1.00 | 27.57 | A |
| ATOM | 1211 | CE | MET | A | 217 | 27.679 | 13.974 | 10.332 | 1.00 | 26.68 | A |
| ATOM | 1212 | C | MET | A | 217 | 30.844 | 10.618 | 12.502 | 1.00 | 21.51 | A |
| ATOM | 1213 | O | MET | A | 217 | 30.474 | 11.323 | 13.440 | 1.00 | 18.62 | A |
| ATOM | 1214 | N | HIS | A | 218 | 31.957 | 9.892 | 12.544 | 1.00 | 20.10 | A |
| ATOM | 1215 | CA | HIS | A | 218 | 32.873 | 9.964 | 13.678 | 1.00 | 19.86 | A |
| ATOM | 1216 | CB | HIS | A | 218 | 33.482 | 8.594 | 13.977 | 1.00 | 20.21 | A |
| ATOM | 1217 | CG | HIS | A | 218 | 32.551 | 7.667 | 14.698 | 1.00 | 22.40 | A |
| ATOM | 1218 | CD2 | HIS | A | 218 | 31.910 | 6.547 | 14.287 | 1.00 | 21.27 | A |
| ATOM | 1219 | ND1 | HIS | A | 218 | 32.177 | 7.863 | 16.011 | 1.00 | 19.59 | A |
| ATOM | 1220 | CE1 | HIS | A | 218 | 31.348 | 6.902 | 16.379 | 1.00 | 21.88 | A |
| ATOM | 1221 | NE2 | HIS | A | 218 | 31.168 | 6.091 | 15.351 | 1.00 | 22.08 | A |
| ATOM | 1222 | C | HIS | A | 218 | 33.947 | 10.921 | 13.172 | 1.00 | 19.10 | A |
| ATOM | 1223 | O | HIS | A | 218 | 34.170 | 11.004 | 11.965 | 1.00 | 20.31 | A |
| ATOM | 1224 | N | ILE | A | 219 | 34.617 | 11.638 | 14.067 | 1.00 | 17.21 | A |
| ATOM | 1225 | CA | ILE | A | 219 | 35.628 | 12.586 | 13.618 | 1.00 | 15.26 | A |
| ATOM | 1226 | CB | ILE | A | 219 | 35.987 | 13.614 | 14.716 | 1.00 | 15.38 | A |
| ATOM | 1227 | CG2 | ILE | A | 219 | 34.722 | 14.305 | 15.221 | 1.00 | 14.58 | A |
| ATOM | 1228 | CG1 | ILE | A | 219 | 36.734 | 12.919 | 15.864 | 1.00 | 14.46 | A |
| ATOM | 1229 | CD1 | ILE | A | 219 | 37.279 | 13.885 | 16.911 | 1.00 | 13.74 | A |
| ATOM | 1230 | C | ILE | A | 219 | 36.929 | 11.944 | 13.161 | 1.00 | 16.21 | A |
| ATOM | 1231 | O | ILE | A | 219 | 37.238 | 10.799 | 13.500 | 1.00 | 15.88 | A |
| ATOM | 1232 | N | GLN | A | 220 | 37.677 | 12.711 | 12.378 | 1.00 | 15.62 | A |
| ATOM | 1233 | CA | GLN | A | 220 | 38.980 | 12.316 | 11.876 | 1.00 | 17.84 | A |
| ATOM | 1234 | CB | GLN | A | 220 | 38.872 | 11.595 | 10.525 | 1.00 | 20.00 | A |
| ATOM | 1235 | CG | GLN | A | 220 | 38.463 | 10.129 | 10.659 | 1.00 | 26.97 | A |
| ATOM | 1236 | CD | GLN | A | 220 | 38.648 | 9.343 | 9.372 | 1.00 | 29.95 | A |
| ATOM | 1237 | OE1 | GLN | A | 220 | 37.968 | 9.590 | 8.373 | 1.00 | 33.12 | A |
| ATOM | 1238 | NE2 | GLN | A | 220 | 39.578 | 8.393 | 9.389 | 1.00 | 30.47 | A |
| ATOM | 1239 | C | GLN | A | 220 | 39.757 | 13.610 | 11.735 | 1.00 | 17.00 | A |
| ATOM | 1240 | O | GLN | A | 220 | 39.609 | 14.339 | 10.751 | 1.00 | 18.27 | A |
| ATOM | 1241 | N | ILE | A | 221 | 40.566 | 13.906 | 12.746 | 1.00 | 14.34 | A |
| ATOM | 1242 | CA | ILE | A | 221 | 41.361 | 15.120 | 12.753 | 1.00 | 14.46 | A |
| ATOM | 1243 | CB | ILE | A | 221 | 41.867 | 15.416 | 14.175 | 1.00 | 12.30 | A |
| ATOM | 1244 | CG2 | ILE | A | 221 | 42.764 | 16.656 | 14.167 | 1.00 | 14.78 | A |
| ATOM | 1245 | CG1 | ILE | A | 221 | 40.660 | 15.613 | 15.102 | 1.00 | 13.92 | A |
| ATOM | 1246 | CD1 | ILE | A | 221 | 41.003 | 15.901 | 16.543 | 1.00 | 15.06 | A |
| ATOM | 1247 | C | ILE | A | 221 | 42.536 | 14.996 | 11.783 | 1.00 | 15.44 | A |
| ATOM | 1248 | O | ILE | A | 221 | 43.106 | 13.915 | 11.613 | 1.00 | 13.93 | A |
| ATOM | 1249 | N | THR | A | 222 | 42.877 | 16.101 | 11.127 | 1.00 | 15.36 | A |
| ATOM | 1250 | CA | THR | A | 222 | 43.980 | 16.098 | 10.174 | 1.00 | 17.52 | A |
| ATOM | 1251 | CB | THR | A | 222 | 43.470 | 15.836 | 8.750 | 1.00 | 19.92 | A |
| ATOM | 1252 | OG1 | THR | A | 222 | 44.587 | 15.637 | 7.875 | 1.00 | 18.78 | A |
| ATOM | 1253 | CG2 | THR | A | 222 | 42.630 | 17.018 | 8.257 | 1.00 | 18.16 | A |
| ATOM | 1254 | C | THR | A | 222 | 44.735 | 17.428 | 10.192 | 1.00 | 19.60 | A |
| ATOM | 1255 | O | THR | A | 222 | 44.509 | 18.257 | 11.084 | 1.00 | 18.59 | A |
| ATOM | 1256 | N | ASP | A | 223 | 45.630 | 17.610 | 9.216 | 1.00 | 18.69 | A |
| ATOM | 1257 | CA | ASP | A | 223 | 46.440 | 18.825 | 9.069 | 1.00 | 20.12 | A |
| ATOM | 1258 | CB | ASP | A | 223 | 45.532 | 20.065 | 9.108 | 1.00 | 23.51 | A |
| ATOM | 1259 | CG | ASP | A | 223 | 46.248 | 21.335 | 8.670 | 1.00 | 27.09 | A |
| ATOM | 1260 | OD1 | ASP | A | 223 | 47.283 | 21.227 | 7.975 | 1.00 | 26.28 | A |
| ATOM | 1261 | OD2 | ASP | A | 223 | 45.765 | 22.438 | 9.009 | 1.00 | 26.15 | A |
| ATOM | 1262 | C | ASP | A | 223 | 47.516 | 18.913 | 10.150 | 1.00 | 21.73 | A |
| ATOM | 1263 | O | ASP | A | 223 | 47.439 | 19.751 | 11.055 | 1.00 | 22.76 | A |
| ATOM | 1264 | N | PHE | A | 224 | 48.535 | 18.063 | 10.027 | 1.00 | 20.75 | A |
| ATOM | 1265 | CA | PHE | A | 224 | 49.611 | 17.988 | 11.009 | 1.00 | 20.11 | A |
| ATOM | 1266 | CB | PHE | A | 224 | 49.805 | 16.527 | 11.424 | 1.00 | 20.62 | A |
| ATOM | 1267 | CG | PHE | A | 224 | 48.682 | 15.991 | 12.263 | 1.00 | 21.41 | A |
| ATOM | 1268 | CD1 | PHE | A | 224 | 48.598 | 16.312 | 13.614 | 1.00 | 23.05 | A |
| ATOM | 1269 | CD2 | PHE | A | 224 | 47.681 | 15.212 | 11.693 | 1.00 | 22.27 | A |
| ATOM | 1270 | CE1 | PHE | A | 224 | 47.528 | 15.868 | 14.389 | 1.00 | 23.30 | A |
| ATOM | 1271 | CE2 | PHE | A | 224 | 46.606 | 14.763 | 12.457 | 1.00 | 21.11 | A |
| ATOM | 1272 | CZ | PHE | A | 224 | 46.530 | 15.093 | 13.807 | 1.00 | 22.02 | A |
| ATOM | 1273 | C | PHE | A | 224 | 50.957 | 18.583 | 10.619 | 1.00 | 20.45 | A |
| ATOM | 1274 | O | PHE | A | 224 | 51.905 | 18.547 | 11.407 | 1.00 | 20.73 | A |
| ATOM | 1275 | N | GLY | A | 225 | 51.049 | 19.125 | 9.412 | 1.00 | 22.02 | A |
| ATOM | 1276 | CA | GLY | A | 225 | 52.301 | 19.713 | 8.981 | 1.00 | 22.66 | A |
| ATOM | 1277 | C | GLY | A | 225 | 52.742 | 20.822 | 9.920 | 1.00 | 24.99 | A |
| ATOM | 1278 | O | GLY | A | 225 | 53.939 | 21.041 | 10.122 | 1.00 | 24.52 | A |

-continued

| | | | | | | | | | | | |
|---|---|---|---|---|---|---|---|---|---|---|---|
| ATOM | 1279 | N | THR | A | 226 | 51.779 | 21.524 | 10.508 | 1.00 | 23.50 | A |
| ATOM | 1280 | CA | THR | A | 226 | 52.106 | 22.613 | 11.416 | 1.00 | 25.16 | A |
| ATOM | 1281 | CB | THR | A | 226 | 51.199 | 23.829 | 11.160 | 1.00 | 24.76 | A |
| ATOM | 1282 | OG1 | THR | A | 226 | 49.831 | 23.410 | 11.113 | 1.00 | 22.68 | A |
| ATOM | 1283 | CG2 | THR | A | 226 | 51.571 | 24.490 | 9.834 | 1.00 | 25.00 | A |
| ATOM | 1284 | C | THR | A | 226 | 52.046 | 22.233 | 12.894 | 1.00 | 25.79 | A |
| ATOM | 1285 | O | THR | A | 226 | 52.019 | 23.100 | 13.768 | 1.00 | 24.54 | A |
| ATOM | 1286 | N | ALA | A | 227 | 52.037 | 20.935 | 13.173 | 1.00 | 24.97 | A |
| ATOM | 1287 | CA | ALA | A | 227 | 52.004 | 20.475 | 14.550 | 1.00 | 25.49 | A |
| ATOM | 1288 | CB | ALA | A | 227 | 51.659 | 18.993 | 14.607 | 1.00 | 22.85 | A |
| ATOM | 1289 | C | ALA | A | 227 | 53.384 | 20.715 | 15.149 | 1.00 | 27.70 | A |
| ATOM | 1290 | O | ALA | A | 227 | 54.331 | 21.047 | 14.435 | 1.00 | 26.60 | A |
| ATOM | 1291 | N | LYS | A | 228 | 53.491 | 20.558 | 16.461 | 1.00 | 28.53 | A |
| ATOM | 1292 | CA | LYS | A | 228 | 54.760 | 20.745 | 17.149 | 1.00 | 32.12 | A |
| ATOM | 1293 | CB | LYS | A | 228 | 54.699 | 21.974 | 18.054 | 1.00 | 33.81 | A |
| ATOM | 1294 | CG | LYS | A | 228 | 56.007 | 22.294 | 18.765 | 1.00 | 41.23 | A |
| ATOM | 1295 | CD | LYS | A | 228 | 57.082 | 22.725 | 17.768 | 1.00 | 47.57 | A |
| ATOM | 1296 | CE | LYS | A | 228 | 58.401 | 23.056 | 18.462 | 1.00 | 49.82 | A |
| ATOM | 1297 | NZ | LYS | A | 228 | 59.459 | 23.425 | 17.480 | 1.00 | 51.49 | A |
| ATOM | 1298 | C | LYS | A | 228 | 55.019 | 19.504 | 17.985 | 1.00 | 33.25 | A |
| ATOM | 1299 | O | LYS | A | 228 | 54.190 | 19.129 | 18.815 | 1.00 | 33.70 | A |
| ATOM | 1300 | N | VAL | A | 229 | 56.159 | 18.860 | 17.756 | 1.00 | 33.64 | A |
| ATOM | 1301 | CA | VAL | A | 229 | 56.516 | 17.661 | 18.501 | 1.00 | 34.66 | A |
| ATOM | 1302 | CB | VAL | A | 229 | 57.248 | 16.646 | 17.609 | 1.00 | 33.50 | A |
| ATOM | 1303 | CG1 | VAL | A | 229 | 57.619 | 15.419 | 18.415 | 1.00 | 32.34 | A |
| ATOM | 1304 | CG2 | VAL | A | 229 | 56.370 | 16.264 | 16.436 | 1.00 | 34.25 | A |
| ATOM | 1305 | C | VAL | A | 229 | 57.420 | 18.035 | 19.668 | 1.00 | 37.57 | A |
| ATOM | 1306 | O | VAL | A | 229 | 58.581 | 18.392 | 19.474 | 1.00 | 35.91 | A |
| ATOM | 1307 | N | LEU | A | 230 | 56.877 | 17.948 | 20.878 | 1.00 | 40.57 | A |
| ATOM | 1308 | CA | LEU | A | 230 | 57.615 | 18.289 | 22.088 | 1.00 | 46.10 | A |
| ATOM | 1309 | CB | LEU | A | 230 | 56.654 | 18.417 | 23.270 | 1.00 | 44.71 | A |
| ATOM | 1310 | CG | LEU | A | 230 | 55.627 | 19.545 | 23.207 | 1.00 | 44.50 | A |
| ATOM | 1311 | CD1 | LEU | A | 230 | 54.673 | 19.430 | 24.383 | 1.00 | 44.39 | A |
| ATOM | 1312 | CD2 | LEU | A | 230 | 56.340 | 20.885 | 23.214 | 1.00 | 44.81 | A |
| ATOM | 1313 | C | LEU | A | 230 | 58.695 | 17.279 | 22.440 | 1.00 | 50.42 | A |
| ATOM | 1314 | O | LEU | A | 230 | 58.603 | 16.104 | 22.089 | 1.00 | 51.64 | A |
| ATOM | 1315 | N | SER | A | 231 | 59.717 | 17.756 | 23.145 | 1.00 | 55.81 | A |
| ATOM | 1316 | CA | SER | A | 231 | 60.824 | 16.914 | 23.583 | 1.00 | 61.14 | A |
| ATOM | 1317 | CB | SER | A | 231 | 62.077 | 17.200 | 22.750 | 1.00 | 61.27 | A |
| ATOM | 1318 | OG | SER | A | 231 | 62.444 | 18.568 | 22.823 | 1.00 | 62.85 | A |
| ATOM | 1319 | C | SER | A | 231 | 61.124 | 17.126 | 25.071 | 1.00 | 64.65 | A |
| ATOM | 1320 | O | SER | A | 231 | 61.392 | 16.164 | 25.794 | 1.00 | 65.70 | A |
| ATOM | 1321 | N | PRO | A | 232 | 61.081 | 18.387 | 25.549 | 1.00 | 67.54 | A |
| ATOM | 1322 | CD | PRO | A | 232 | 60.854 | 19.651 | 24.823 | 1.00 | 68.60 | A |
| ATOM | 1323 | CA | PRO | A | 232 | 61.358 | 18.655 | 26.966 | 1.00 | 68.74 | A |
| ATOM | 1324 | CB | PRO | A | 232 | 61.109 | 20.158 | 27.086 | 1.00 | 68.83 | A |
| ATOM | 1325 | CG | PRO | A | 232 | 61.505 | 20.666 | 25.737 | 1.00 | 68.96 | A |
| ATOM | 1326 | C | PRO | A | 232 | 60.460 | 17.846 | 27.899 | 1.00 | 69.17 | A |
| ATOM | 1327 | O | PRO | A | 232 | 59.335 | 17.494 | 27.541 | 1.00 | 69.94 | A |
| ATOM | 1328 | N | ALA | A | 237 | 57.424 | 23.198 | 27.637 | 1.00 | 80.06 | A |
| ATOM | 1329 | CA | ALA | A | 237 | 56.783 | 23.047 | 26.335 | 1.00 | 79.29 | A |
| ATOM | 1330 | CB | ALA | A | 237 | 55.275 | 22.907 | 26.512 | 1.00 | 78.64 | A |
| ATOM | 1331 | C | ALA | A | 237 | 57.092 | 24.239 | 25.433 | 1.00 | 79.07 | A |
| ATOM | 1332 | O | ALA | A | 237 | 56.250 | 25.113 | 25.249 | 1.00 | 79.47 | A |
| ATOM | 1333 | N | ALA | A | 238 | 58.297 | 24.280 | 24.871 | 1.00 | 78.57 | A |
| ATOM | 1334 | CA | ALA | A | 238 | 58.683 | 25.383 | 23.992 | 1.00 | 78.50 | A |
| ATOM | 1335 | CB | ALA | A | 238 | 60.186 | 25.347 | 23.728 | 1.00 | 78.50 | A |
| ATOM | 1336 | C | ALA | A | 238 | 57.920 | 25.327 | 22.673 | 1.00 | 78.15 | A |
| ATOM | 1337 | O | ALA | A | 238 | 57.243 | 24.341 | 22.375 | 1.00 | 77.96 | A |
| ATOM | 1338 | N | ALA | A | 239 | 58.027 | 26.393 | 21.887 | 1.00 | 77.28 | A |
| ATOM | 1339 | CA | ALA | A | 239 | 57.338 | 26.452 | 20.603 | 1.00 | 76.27 | A |
| ATOM | 1340 | CB | ALA | A | 239 | 55.849 | 26.489 | 20.827 | 1.00 | 76.61 | A |
| ATOM | 1341 | C | ALA | A | 239 | 57.766 | 27.667 | 19.793 | 1.00 | 75.38 | A |
| ATOM | 1342 | O | ALA | A | 239 | 58.955 | 27.955 | 19.700 | 1.00 | 75.89 | A |
| ATOM | 1343 | N | ASN | A | 240 | 56.781 | 28.357 | 19.214 | 1.00 | 73.95 | A |
| ATOM | 1344 | CA | ASN | A | 240 | 56.967 | 29.553 | 18.389 | 1.00 | 71.07 | A |
| ATOM | 1345 | CB | ASN | A | 240 | 58.151 | 30.400 | 18.874 | 1.00 | 71.47 | A |
| ATOM | 1346 | CG | ASN | A | 240 | 59.459 | 30.055 | 18.174 | 1.00 | 72.06 | A |
| ATOM | 1347 | OD1 | ASN | A | 240 | 59.575 | 30.149 | 16.943 | 1.00 | 72.03 | A |
| ATOM | 1348 | ND2 | ASN | A | 240 | 60.470 | 29.665 | 18.964 | 1.00 | 71.91 | A |
| ATOM | 1349 | C | ASN | A | 240 | 57.188 | 29.178 | 16.928 | 1.00 | 69.41 | A |
| ATOM | 1350 | O | ASN | A | 240 | 57.480 | 28.024 | 16.624 | 1.00 | 70.09 | A |
| ATOM | 1351 | N | ALA | A | 241 | 57.055 | 30.165 | 16.038 | 1.00 | 66.62 | A |
| ATOM | 1352 | CA | ALA | A | 241 | 57.246 | 30.013 | 14.585 | 1.00 | 63.94 | A |
| ATOM | 1353 | C | ALA | A | 241 | 55.952 | 30.080 | 13.772 | 1.00 | 60.63 | A |
| ATOM | 1354 | O | ALA | A | 241 | 55.840 | 30.880 | 12.845 | 1.00 | 61.29 | A |
| ATOM | 1355 | CB | ALA | A | 241 | 57.979 | 28.704 | 14.246 | 1.00 | 65.23 | A |
| ATOM | 1356 | N | PHE | A | 242 | 54.984 | 29.236 | 14.113 | 1.00 | 56.72 | A |
| ATOM | 1357 | CA | PHE | A | 242 | 53.712 | 29.196 | 13.394 | 1.00 | 52.53 | A |

-continued

| | | | | | | | | | | |
|---|---|---|---|---|---|---|---|---|---|---|
| ATOM | 1358 | CB | PHE | A | 242 | 53.419 | 27.767 | 12.923 | 1.00 | 49.14 | A |
| ATOM | 1359 | CG | PHE | A | 242 | 52.040 | 27.590 | 12.354 | 1.00 | 47.38 | A |
| ATOM | 1360 | CD1 | PHE | A | 242 | 51.731 | 28.067 | 11.085 | 1.00 | 47.69 | A |
| ATOM | 1361 | CD2 | PHE | A | 242 | 51.038 | 26.975 | 13.102 | 1.00 | 45.45 | A |
| ATOM | 1362 | CE1 | PHE | A | 242 | 50.445 | 27.937 | 10.565 | 1.00 | 46.75 | A |
| ATOM | 1363 | CE2 | PHE | A | 242 | 49.751 | 26.840 | 12.594 | 1.00 | 45.41 | A |
| ATOM | 1364 | CZ | PHE | A | 242 | 49.453 | 27.323 | 11.322 | 1.00 | 46.55 | A |
| ATOM | 1365 | C | PHE | A | 242 | 52.534 | 29.688 | 14.229 | 1.00 | 50.08 | A |
| ATOM | 1366 | O | PHE | A | 242 | 52.502 | 29.505 | 15.444 | 1.00 | 49.86 | A |
| ATOM | 1367 | N | VAL | A | 243 | 51.566 | 30.305 | 13.557 | 1.00 | 47.67 | A |
| ATOM | 1368 | CA | VAL | A | 243 | 50.355 | 30.809 | 14.200 | 1.00 | 46.21 | A |
| ATOM | 1369 | CB | VAL | A | 243 | 50.340 | 32.352 | 14.258 | 1.00 | 47.36 | A |
| ATOM | 1370 | CG1 | VAL | A | 243 | 49.012 | 32.844 | 14.825 | 1.00 | 47.54 | A |
| ATOM | 1371 | CG2 | VAL | A | 243 | 51.497 | 32.842 | 15.109 | 1.00 | 48.50 | A |
| ATOM | 1372 | C | VAL | A | 243 | 49.150 | 30.342 | 13.389 | 1.00 | 44.12 | A |
| ATOM | 1373 | O | VAL | A | 243 | 48.956 | 30.765 | 12.247 | 1.00 | 44.46 | A |
| ATOM | 1374 | N | GLY | A | 244 | 48.348 | 29.467 | 13.985 | 1.00 | 40.48 | A |
| ATOM | 1375 | CA | GLY | A | 244 | 47.176 | 28.941 | 13.306 | 1.00 | 37.65 | A |
| ATOM | 1376 | C | GLY | A | 244 | 46.101 | 29.960 | 12.964 | 1.00 | 35.39 | A |
| ATOM | 1377 | O | GLY | A | 244 | 46.313 | 31.168 | 13.065 | 1.00 | 35.92 | A |
| ATOM | 1378 | N | THR | A | 245 | 44.936 | 29.463 | 12.560 | 1.00 | 33.30 | A |
| ATOM | 1379 | CA | THR | A | 245 | 43.813 | 30.312 | 12.184 | 1.00 | 30.20 | A |
| ATOM | 1380 | CB | THR | A | 245 | 42.593 | 29.450 | 11.829 | 1.00 | 32.00 | A |
| ATOM | 1381 | OG1 | THR | A | 245 | 42.952 | 28.573 | 10.755 | 1.00 | 32.81 | A |
| ATOM | 1382 | CG2 | THR | A | 245 | 41.419 | 30.319 | 11.390 | 1.00 | 28.34 | A |
| ATOM | 1383 | C | THR | A | 245 | 43.476 | 31.296 | 13.296 | 1.00 | 27.96 | A |
| ATOM | 1384 | O | THR | A | 245 | 43.212 | 30.907 | 14.434 | 1.00 | 25.46 | A |
| ATOM | 1385 | N | ALA | A | 246 | 43.486 | 32.576 | 12.938 | 1.00 | 25.22 | A |
| ATOM | 1386 | CA | ALA | A | 246 | 43.247 | 33.675 | 13.867 | 1.00 | 23.27 | A |
| ATOM | 1387 | CB | ALA | A | 246 | 42.956 | 34.955 | 13.082 | 1.00 | 22.94 | A |
| ATOM | 1388 | C | ALA | A | 246 | 42.178 | 33.475 | 14.934 | 1.00 | 21.27 | A |
| ATOM | 1389 | O | ALA | A | 246 | 42.431 | 33.705 | 16.114 | 1.00 | 20.93 | A |
| ATOM | 1390 | N | GLN | A | 247 | 40.988 | 33.047 | 14.536 | 1.00 | 19.67 | A |
| ATOM | 1391 | CA | GLN | A | 247 | 39.911 | 32.886 | 15.504 | 1.00 | 20.17 | A |
| ATOM | 1392 | CB | GLN | A | 247 | 38.608 | 32.535 | 14.779 | 1.00 | 21.89 | A |
| ATOM | 1393 | CG | GLN | A | 247 | 38.522 | 33.076 | 13.355 | 1.00 | 26.18 | A |
| ATOM | 1394 | CD | GLN | A | 247 | 37.220 | 33.794 | 13.064 | 1.00 | 27.30 | A |
| ATOM | 1395 | OE1 | GLN | A | 247 | 36.172 | 33.447 | 13.605 | 1.00 | 30.13 | A |
| ATOM | 1396 | NE2 | GLN | A | 247 | 37.278 | 34.792 | 12.189 | 1.00 | 28.70 | A |
| ATOM | 1397 | C | GLN | A | 247 | 40.181 | 31.849 | 16.595 | 1.00 | 19.43 | A |
| ATOM | 1398 | O | GLN | A | 247 | 39.546 | 31.883 | 17.648 | 1.00 | 18.93 | A |
| ATOM | 1399 | N | TYR | A | 248 | 41.132 | 30.948 | 16.359 | 1.00 | 18.60 | A |
| ATOM | 1400 | CA | TYR | A | 248 | 41.441 | 29.896 | 17.329 | 1.00 | 19.20 | A |
| ATOM | 1401 | CB | TYR | A | 248 | 41.333 | 28.529 | 16.642 | 1.00 | 17.53 | A |
| ATOM | 1402 | CG | TYR | A | 248 | 40.013 | 28.362 | 15.927 | 1.00 | 19.32 | A |
| ATOM | 1403 | CD1 | TYR | A | 248 | 38.859 | 28.010 | 16.625 | 1.00 | 17.69 | A |
| ATOM | 1404 | CE1 | TYR | A | 248 | 37.617 | 27.976 | 15.990 | 1.00 | 18.18 | A |
| ATOM | 1405 | CD2 | TYR | A | 248 | 39.897 | 28.664 | 14.569 | 1.00 | 16.87 | A |
| ATOM | 1406 | CE2 | TYR | A | 248 | 38.665 | 28.635 | 13.924 | 1.00 | 19.17 | A |
| ATOM | 1407 | CZ | TYR | A | 248 | 37.527 | 28.295 | 14.643 | 1.00 | 19.46 | A |
| ATOM | 1408 | OH | TYR | A | 248 | 36.299 | 28.311 | 14.023 | 1.00 | 18.98 | A |
| ATOM | 1409 | C | TYR | A | 248 | 42.810 | 30.039 | 17.993 | 1.00 | 20.42 | A |
| ATOM | 1410 | O | TYR | A | 248 | 43.208 | 29.191 | 18.792 | 1.00 | 19.19 | A |
| ATOM | 1411 | N | VAL | A | 249 | 43.523 | 31.114 | 17.673 | 1.00 | 20.20 | A |
| ATOM | 1412 | CA | VAL | A | 249 | 44.841 | 31.343 | 18.251 | 1.00 | 20.91 | A |
| ATOM | 1413 | CB | VAL | A | 249 | 45.542 | 32.532 | 17.570 | 1.00 | 21.18 | A |
| ATOM | 1414 | CG1 | VAL | A | 249 | 46.821 | 32.896 | 18.317 | 1.00 | 22.45 | A |
| ATOM | 1415 | CG2 | VAL | A | 249 | 45.862 | 32.170 | 16.139 | 1.00 | 24.01 | A |
| ATOM | 1416 | C | VAL | A | 249 | 44.764 | 31.606 | 19.750 | 1.00 | 21.52 | A |
| ATOM | 1417 | O | VAL | A | 249 | 43.915 | 32.368 | 20.216 | 1.00 | 22.72 | A |
| ATOM | 1418 | N | SER | A | 250 | 45.654 | 30.965 | 20.503 | 1.00 | 20.70 | A |
| ATOM | 1419 | CA | SER | A | 250 | 45.697 | 31.133 | 21.951 | 1.00 | 21.65 | A |
| ATOM | 1420 | CB | SER | A | 250 | 46.370 | 29.919 | 22.613 | 1.00 | 22.02 | A |
| ATOM | 1421 | OG | SER | A | 250 | 47.692 | 29.725 | 22.132 | 1.00 | 22.12 | A |
| ATOM | 1422 | C | SER | A | 250 | 46.476 | 32.402 | 22.280 | 1.00 | 22.13 | A |
| ATOM | 1423 | O | SER | A | 250 | 47.332 | 32.828 | 21.511 | 1.00 | 22.77 | A |
| ATOM | 1424 | N | PRO | A | 251 | 46.180 | 33.029 | 23.425 | 1.00 | 22.23 | A |
| ATOM | 1425 | CD | PRO | A | 251 | 45.163 | 32.684 | 24.433 | 1.00 | 22.97 | A |
| ATOM | 1426 | CA | PRO | A | 251 | 46.893 | 34.254 | 23.800 | 1.00 | 22.52 | A |
| ATOM | 1427 | CB | PRO | A | 251 | 46.233 | 34.650 | 25.127 | 1.00 | 23.06 | A |
| ATOM | 1428 | CG | PRO | A | 251 | 45.726 | 33.329 | 25.676 | 1.00 | 22.55 | A |
| ATOM | 1429 | C | PRO | A | 251 | 48.414 | 34.115 | 23.907 | 1.00 | 22.15 | A |
| ATOM | 1430 | O | PRO | A | 251 | 49.143 | 35.047 | 23.563 | 1.00 | 22.62 | A |
| ATOM | 1431 | N | GLU | A | 252 | 48.901 | 32.966 | 24.367 | 1.00 | 20.69 | A |
| ATOM | 1432 | CA | GLU | A | 252 | 50.347 | 32.772 | 24.500 | 1.00 | 21.40 | A |
| ATOM | 1433 | CB | GLU | A | 252 | 50.673 | 31.382 | 25.071 | 1.00 | 20.59 | A |
| ATOM | 1434 | CG | GLU | A | 252 | 49.993 | 30.232 | 24.352 | 1.00 | 21.91 | A |
| ATOM | 1435 | CD | GLU | A | 252 | 48.691 | 29.822 | 25.014 | 1.00 | 21.51 | A |
| ATOM | 1436 | OE1 | GLU | A | 252 | 47.989 | 30.707 | 25.550 | 1.00 | 21.46 | A |

|  | -continued | | | | | | | | | |
|---|---|---|---|---|---|---|---|---|---|---|
| ATOM | 1437 | OE2 | GLU | A | 252 | 48.367 | 28.613 | 24.993 | 1.00 | 20.23 | A |
| ATOM | 1438 | C | GLU | A | 252 | 51.071 | 32.970 | 23.167 | 1.00 | 22.99 | A |
| ATOM | 1439 | O | GLU | A | 252 | 52.191 | 33.480 | 23.136 | 1.00 | 23.17 | A |
| ATOM | 1440 | N | LEU | A | 253 | 50.441 | 32.576 | 22.064 | 1.00 | 23.00 | A |
| ATOM | 1441 | CA | LEU | A | 253 | 51.068 | 32.753 | 20.758 | 1.00 | 25.62 | A |
| ATOM | 1442 | CB | LEU | A | 253 | 50.277 | 32.029 | 19.669 | 1.00 | 26.75 | A |
| ATOM | 1443 | CG | LEU | A | 253 | 50.743 | 30.620 | 19.296 | 1.00 | 31.87 | A |
| ATOM | 1444 | CD1 | LEU | A | 253 | 50.433 | 29.651 | 20.422 | 1.00 | 31.81 | A |
| ATOM | 1445 | CD2 | LEU | A | 253 | 50.044 | 30.179 | 18.015 | 1.00 | 31.86 | A |
| ATOM | 1446 | C | LEU | A | 253 | 51.201 | 34.228 | 20.371 | 1.00 | 26.94 | A |
| ATOM | 1447 | O | LEU | A | 253 | 52.107 | 34.601 | 19.626 | 1.00 | 27.09 | A |
| ATOM | 1448 | N | LEU | A | 254 | 50.297 | 35.059 | 20.877 | 1.00 | 25.83 | A |
| ATOM | 1449 | CA | LEU | A | 254 | 50.297 | 36.485 | 20.564 | 1.00 | 27.26 | A |
| ATOM | 1450 | CB | LEU | A | 254 | 48.858 | 37.006 | 20.564 | 1.00 | 25.84 | A |
| ATOM | 1451 | CG | LEU | A | 254 | 47.882 | 36.290 | 19.621 | 1.00 | 24.69 | A |
| ATOM | 1452 | CD1 | LEU | A | 254 | 46.459 | 36.724 | 19.932 | 1.00 | 23.64 | A |
| ATOM | 1453 | CD2 | LEU | A | 254 | 48.236 | 36.597 | 18.177 | 1.00 | 24.24 | A |
| ATOM | 1454 | C | LEU | A | 254 | 51.134 | 37.314 | 21.537 | 1.00 | 30.62 | A |
| ATOM | 1455 | O | LEU | A | 254 | 51.633 | 38.383 | 21.187 | 1.00 | 32.35 | A |
| ATOM | 1456 | N | THR | A | 255 | 51.292 | 36.821 | 22.758 | 1.00 | 32.47 | A |
| ATOM | 1457 | CA | THR | A | 255 | 52.056 | 37.547 | 23.759 | 1.00 | 36.70 | A |
| ATOM | 1458 | CB | THR | A | 255 | 51.368 | 37.478 | 25.127 | 1.00 | 34.51 | A |
| ATOM | 1459 | OG1 | THR | A | 255 | 51.188 | 36.106 | 25.494 | 1.00 | 35.49 | A |
| ATOM | 1460 | CG2 | THR | A | 255 | 50.013 | 38.166 | 25.077 | 1.00 | 33.40 | A |
| ATOM | 1461 | C | THR | A | 255 | 53.477 | 37.035 | 23.910 | 1.00 | 40.09 | A |
| ATOM | 1462 | O | THR | A | 255 | 54.430 | 37.793 | 23.772 | 1.00 | 43.69 | A |
| ATOM | 1463 | N | GLU | A | 256 | 53.617 | 35.747 | 24.189 | 1.00 | 44.77 | A |
| ATOM | 1464 | CA | GLU | A | 256 | 54.932 | 35.144 | 24.382 | 1.00 | 49.15 | A |
| ATOM | 1465 | CB | GLU | A | 256 | 54.866 | 34.143 | 25.534 | 1.00 | 51.24 | A |
| ATOM | 1466 | CG | GLU | A | 256 | 54.514 | 34.786 | 26.862 | 1.00 | 56.03 | A |
| ATOM | 1467 | CD | GLU | A | 256 | 54.053 | 33.780 | 27.893 | 1.00 | 58.83 | A |
| ATOM | 1468 | OE1 | GLU | A | 256 | 54.766 | 32.776 | 28.107 | 1.00 | 62.13 | A |
| ATOM | 1469 | OE2 | GLU | A | 256 | 52.979 | 33.996 | 28.494 | 1.00 | 60.34 | A |
| ATOM | 1470 | C | GLU | A | 256 | 55.475 | 34.456 | 23.137 | 1.00 | 50.09 | A |
| ATOM | 1471 | O | GLU | A | 256 | 56.616 | 33.995 | 23.127 | 1.00 | 50.42 | A |
| ATOM | 1472 | N | LYS | A | 257 | 54.658 | 34.389 | 22.090 | 1.00 | 51.21 | A |
| ATOM | 1473 | CA | LYS | A | 257 | 55.064 | 33.746 | 20.845 | 1.00 | 51.22 | A |
| ATOM | 1474 | CB | LYS | A | 257 | 56.244 | 34.502 | 20.227 | 1.00 | 53.28 | A |
| ATOM | 1475 | CG | LYS | A | 257 | 56.558 | 34.125 | 18.790 | 1.00 | 55.19 | A |
| ATOM | 1476 | CD | LYS | A | 257 | 57.709 | 34.961 | 18.253 | 1.00 | 57.52 | A |
| ATOM | 1477 | CE | LYS | A | 257 | 57.952 | 34.694 | 16.777 | 1.00 | 58.52 | A |
| ATOM | 1478 | NZ | LYS | A | 257 | 58.290 | 33.268 | 16.515 | 1.00 | 60.88 | A |
| ATOM | 1479 | C | LYS | A | 257 | 55.467 | 32.302 | 21.138 | 1.00 | 50.74 | A |
| ATOM | 1480 | O | LYS | A | 257 | 56.432 | 31.790 | 20.577 | 1.00 | 52.26 | A |
| ATOM | 1481 | N | SER | A | 258 | 54.721 | 31.654 | 22.027 | 1.00 | 48.07 | A |
| ATOM | 1482 | CA | SER | A | 258 | 54.999 | 30.273 | 22.402 | 1.00 | 46.87 | A |
| ATOM | 1483 | CB | SER | A | 258 | 55.590 | 30.229 | 23.812 | 1.00 | 48.88 | A |
| ATOM | 1484 | OG | SER | A | 258 | 54.741 | 30.892 | 24.734 | 1.00 | 53.14 | A |
| ATOM | 1485 | C | SER | A | 258 | 53.735 | 29.415 | 22.342 | 1.00 | 44.07 | A |
| ATOM | 1486 | O | SER | A | 258 | 52.617 | 29.932 | 22.417 | 1.00 | 44.17 | A |
| ATOM | 1487 | N | ALA | A | 259 | 53.917 | 28.105 | 22.204 | 1.00 | 38.30 | A |
| ATOM | 1488 | CA | ALA | A | 259 | 52.793 | 27.180 | 22.127 | 1.00 | 34.73 | A |
| ATOM | 1489 | CB | ALA | A | 259 | 52.551 | 26.779 | 20.684 | 1.00 | 34.16 | A |
| ATOM | 1490 | C | ALA | A | 259 | 53.042 | 25.940 | 22.977 | 1.00 | 32.34 | A |
| ATOM | 1491 | O | ALA | A | 259 | 54.172 | 25.459 | 23.086 | 1.00 | 31.81 | A |
| ATOM | 1492 | N | CYS | A | 260 | 51.975 | 25.428 | 23.579 | 1.00 | 28.58 | A |
| ATOM | 1493 | CA | CYS | A | 260 | 52.056 | 24.244 | 24.425 | 1.00 | 26.27 | A |
| ATOM | 1494 | CB | CYS | A | 260 | 52.183 | 24.654 | 25.892 | 1.00 | 26.53 | A |
| ATOM | 1495 | SG | CYS | A | 260 | 50.846 | 25.739 | 26.469 | 1.00 | 32.91 | A |
| ATOM | 1496 | C | CYS | A | 260 | 50.786 | 23.435 | 24.224 | 1.00 | 22.83 | A |
| ATOM | 1497 | O | CYS | A | 260 | 49.892 | 23.856 | 23.495 | 1.00 | 22.14 | A |
| ATOM | 1498 | N | LYS | A | 261 | 50.706 | 22.277 | 24.868 | 1.00 | 20.02 | A |
| ATOM | 1499 | CA | LYS | A | 261 | 49.526 | 21.434 | 24.744 | 1.00 | 20.65 | A |
| ATOM | 1500 | CB | LYS | A | 261 | 49.619 | 20.243 | 25.696 | 1.00 | 23.28 | A |
| ATOM | 1501 | CG | LYS | A | 261 | 50.716 | 19.253 | 25.347 | 1.00 | 27.44 | A |
| ATOM | 1502 | CD | LYS | A | 261 | 50.732 | 18.117 | 26.350 | 1.00 | 29.98 | A |
| ATOM | 1503 | CE | LYS | A | 261 | 51.922 | 17.203 | 26.134 | 1.00 | 32.34 | A |
| ATOM | 1504 | NZ | LYS | A | 261 | 51.940 | 16.121 | 27.153 | 1.00 | 33.28 | A |
| ATOM | 1505 | C | LYS | A | 261 | 48.268 | 22.229 | 25.062 | 1.00 | 19.20 | A |
| ATOM | 1506 | O | LYS | A | 261 | 47.253 | 22.092 | 24.387 | 1.00 | 18.08 | A |
| ATOM | 1507 | N | SER | A | 262 | 48.358 | 23.068 | 26.089 | 1.00 | 16.92 | A |
| ATOM | 1508 | CA | SER | A | 262 | 47.235 | 23.883 | 26.534 | 1.00 | 18.13 | A |
| ATOM | 1509 | CB | SER | A | 262 | 47.644 | 24.698 | 27.770 | 1.00 | 18.27 | A |
| ATOM | 1510 | OG | SER | A | 262 | 46.517 | 25.258 | 28.421 | 1.00 | 22.53 | A |
| ATOM | 1511 | C | SER | A | 262 | 46.736 | 24.811 | 25.424 | 1.00 | 16.77 | A |
| ATOM | 1512 | O | SER | A | 262 | 45.591 | 25.254 | 25.450 | 1.00 | 15.69 | A |
| ATOM | 1513 | N | SER | A | 263 | 47.595 | 25.118 | 24.456 | 1.00 | 16.44 | A |
| ATOM | 1514 | CA | SER | A | 263 | 47.175 | 25.970 | 23.347 | 1.00 | 16.89 | A |
| ATOM | 1515 | CB | SER | A | 263 | 48.340 | 26.228 | 22.382 | 1.00 | 18.49 | A |

-continued

| | | | | | | | | | | | |
|---|---|---|---|---|---|---|---|---|---|---|---|
| ATOM | 1516 | OG | SER | A | 263 | 49.402 | 26.909 | 23.031 | 1.00 | 22.10 | A |
| ATOM | 1517 | C | SER | A | 263 | 46.040 | 25.257 | 22.612 | 1.00 | 17.79 | A |
| ATOM | 1518 | O | SER | A | 263 | 45.099 | 25.898 | 22.148 | 1.00 | 17.57 | A |
| ATOM | 1519 | N | ASP | A | 264 | 46.119 | 23.928 | 22.517 | 1.00 | 16.30 | A |
| ATOM | 1520 | CA | ASP | A | 264 | 45.069 | 23.166 | 21.836 | 1.00 | 16.72 | A |
| ATOM | 1521 | CB | ASP | A | 264 | 45.483 | 21.704 | 21.620 | 1.00 | 15.92 | A |
| ATOM | 1522 | CG | ASP | A | 264 | 46.544 | 21.539 | 20.548 | 1.00 | 17.93 | A |
| ATOM | 1523 | OD1 | ASP | A | 264 | 46.642 | 22.412 | 19.661 | 1.00 | 16.78 | A |
| ATOM | 1524 | OD2 | ASP | A | 264 | 47.265 | 20.515 | 20.579 | 1.00 | 16.64 | A |
| ATOM | 1525 | C | ASP | A | 264 | 43.773 | 23.194 | 22.646 | 1.00 | 17.67 | A |
| ATOM | 1526 | O | ASP | A | 264 | 42.681 | 23.197 | 22.076 | 1.00 | 18.27 | A |
| ATOM | 1527 | N | LEU | A | 265 | 43.898 | 23.205 | 23.974 | 1.00 | 15.49 | A |
| ATOM | 1528 | CA | LEU | A | 265 | 42.730 | 23.232 | 24.849 | 1.00 | 14.75 | A |
| ATOM | 1529 | CB | LEU | A | 265 | 43.147 | 23.038 | 26.313 | 1.00 | 11.38 | A |
| ATOM | 1530 | CG | LEU | A | 265 | 43.711 | 21.641 | 26.621 | 1.00 | 14.04 | A |
| ATOM | 1531 | CD1 | LEU | A | 265 | 44.249 | 21.579 | 28.052 | 1.00 | 13.96 | A |
| ATOM | 1532 | CD2 | LEU | A | 265 | 42.619 | 20.603 | 26.416 | 1.00 | 11.62 | A |
| ATOM | 1533 | C | LEU | A | 265 | 41.999 | 24.557 | 24.675 | 1.00 | 15.13 | A |
| ATOM | 1534 | O | LEU | A | 265 | 40.777 | 24.620 | 24.785 | 1.00 | 16.75 | A |
| ATOM | 1535 | N | TRP | A | 266 | 42.746 | 25.622 | 24.405 | 1.00 | 16.08 | A |
| ATOM | 1536 | CA | TRP | A | 266 | 42.118 | 26.918 | 24.184 | 1.00 | 16.96 | A |
| ATOM | 1537 | CB | TRP | A | 266 | 43.176 | 28.015 | 24.023 | 1.00 | 17.28 | A |
| ATOM | 1538 | CG | TRP | A | 266 | 42.618 | 29.326 | 23.521 | 1.00 | 20.54 | A |
| ATOM | 1539 | CD2 | TRP | A | 266 | 42.313 | 30.490 | 24.301 | 1.00 | 20.07 | A |
| ATOM | 1540 | CE2 | TRP | A | 266 | 41.782 | 31.459 | 23.417 | 1.00 | 20.46 | A |
| ATOM | 1541 | CE3 | TRP | A | 266 | 42.435 | 30.810 | 25.660 | 1.00 | 20.68 | A |
| ATOM | 1542 | CD1 | TRP | A | 266 | 42.270 | 29.631 | 22.231 | 1.00 | 19.53 | A |
| ATOM | 1543 | NE1 | TRP | A | 266 | 41.769 | 30.908 | 22.163 | 1.00 | 19.61 | A |
| ATOM | 1544 | CZ2 | TRP | A | 266 | 41.372 | 32.727 | 23.850 | 1.00 | 20.90 | A |
| ATOM | 1545 | CZ3 | TRP | A | 266 | 42.026 | 32.073 | 26.091 | 1.00 | 19.45 | A |
| ATOM | 1546 | CH2 | TRP | A | 266 | 41.501 | 33.015 | 25.185 | 1.00 | 20.71 | A |
| ATOM | 1547 | C | TRP | A | 266 | 41.284 | 26.795 | 22.913 | 1.00 | 17.22 | A |
| ATOM | 1548 | O | TRP | A | 266 | 40.139 | 27.240 | 22.863 | 1.00 | 18.03 | A |
| ATOM | 1549 | N | ALA | A | 267 | 41.863 | 26.181 | 21.886 | 1.00 | 17.50 | A |
| ATOM | 1550 | CA | ALA | A | 267 | 41.155 | 25.990 | 20.626 | 1.00 | 16.16 | A |
| ATOM | 1551 | CB | ALA | A | 267 | 42.050 | 25.290 | 19.621 | 1.00 | 14.28 | A |
| ATOM | 1552 | C | ALA | A | 267 | 39.901 | 25.159 | 20.891 | 1.00 | 16.28 | A |
| ATOM | 1553 | O | ALA | A | 267 | 38.835 | 25.436 | 20.346 | 1.00 | 16.46 | A |
| ATOM | 1554 | N | LEU | A | 268 | 40.031 | 24.144 | 21.739 | 1.00 | 16.57 | A |
| ATOM | 1555 | CA | LEU | A | 268 | 38.890 | 23.299 | 22.084 | 1.00 | 17.03 | A |
| ATOM | 1556 | CB | LEU | A | 268 | 39.292 | 22.260 | 23.139 | 1.00 | 15.35 | A |
| ATOM | 1557 | CG | LEU | A | 268 | 38.158 | 21.429 | 23.754 | 1.00 | 19.00 | A |
| ATOM | 1558 | CD1 | LEU | A | 268 | 37.505 | 20.578 | 22.678 | 1.00 | 16.17 | A |
| ATOM | 1559 | CD2 | LEU | A | 268 | 38.718 | 20.537 | 24.881 | 1.00 | 17.49 | A |
| ATOM | 1560 | C | LEU | A | 268 | 37.766 | 24.179 | 22.628 | 1.00 | 15.72 | A |
| ATOM | 1561 | O | LEU | A | 268 | 36.603 | 24.031 | 22.247 | 1.00 | 15.28 | A |
| ATOM | 1562 | N | GLY | A | 269 | 38.119 | 25.099 | 23.520 | 1.00 | 14.34 | A |
| ATOM | 1563 | CA | GLY | A | 269 | 37.124 | 25.989 | 24.092 | 1.00 | 13.39 | A |
| ATOM | 1564 | C | GLY | A | 269 | 36.406 | 26.808 | 23.031 | 1.00 | 14.94 | A |
| ATOM | 1565 | O | GLY | A | 269 | 35.193 | 27.014 | 23.114 | 1.00 | 14.76 | A |
| ATOM | 1566 | N | CYS | A | 270 | 37.146 | 27.279 | 22.030 | 1.00 | 13.86 | A |
| ATOM | 1567 | CA | CYS | A | 270 | 36.539 | 28.061 | 20.958 | 1.00 | 16.80 | A |
| ATOM | 1568 | CB | CYS | A | 270 | 37.611 | 28.634 | 20.023 | 1.00 | 15.97 | A |
| ATOM | 1569 | SG | CYS | A | 270 | 38.751 | 29.810 | 20.780 | 1.00 | 20.48 | A |
| ATOM | 1570 | C | CYS | A | 270 | 35.598 | 27.175 | 20.140 | 1.00 | 17.50 | A |
| ATOM | 1571 | O | CYS | A | 270 | 34.516 | 27.604 | 19.741 | 1.00 | 18.38 | A |
| ATOM | 1572 | N | ILE | A | 271 | 36.022 | 25.939 | 19.887 | 1.00 | 16.99 | A |
| ATOM | 1573 | CA | ILE | A | 271 | 35.221 | 25.004 | 19.104 | 1.00 | 16.66 | A |
| ATOM | 1574 | CB | ILE | A | 271 | 36.038 | 23.741 | 18.778 | 1.00 | 16.53 | A |
| ATOM | 1575 | CG2 | ILE | A | 271 | 35.155 | 22.694 | 18.102 | 1.00 | 16.34 | A |
| ATOM | 1576 | CG1 | ILE | A | 271 | 37.222 | 24.129 | 17.882 | 1.00 | 15.59 | A |
| ATOM | 1577 | CD1 | ILE | A | 271 | 38.239 | 23.018 | 17.690 | 1.00 | 14.88 | A |
| ATOM | 1578 | C | ILE | A | 271 | 33.920 | 24.626 | 19.809 | 1.00 | 16.74 | A |
| ATOM | 1579 | O | ILE | A | 271 | 32.865 | 24.576 | 19.179 | 1.00 | 17.12 | A |
| ATOM | 1580 | N | ILE | A | 272 | 33.990 | 24.357 | 21.111 | 1.00 | 16.13 | A |
| ATOM | 1581 | CA | ILE | A | 272 | 32.785 | 24.021 | 21.862 | 1.00 | 18.30 | A |
| ATOM | 1582 | CB | ILE | A | 272 | 33.097 | 23.747 | 23.346 | 1.00 | 17.77 | A |
| ATOM | 1583 | CG2 | ILE | A | 272 | 31.796 | 23.666 | 24.152 | 1.00 | 17.96 | A |
| ATOM | 1584 | CG1 | ILE | A | 272 | 33.877 | 22.437 | 23.481 | 1.00 | 19.55 | A |
| ATOM | 1585 | CD1 | ILE | A | 272 | 34.446 | 22.217 | 24.886 | 1.00 | 18.64 | A |
| ATOM | 1586 | C | ILE | A | 272 | 31.824 | 25.207 | 21.776 | 1.00 | 19.51 | A |
| ATOM | 1587 | O | ILE | A | 272 | 30.624 | 25.037 | 21.554 | 1.00 | 20.44 | A |
| ATOM | 1588 | N | TYR | A | 273 | 32.362 | 26.409 | 21.947 | 1.00 | 18.52 | A |
| ATOM | 1589 | CA | TYR | A | 273 | 31.553 | 27.615 | 21.881 | 1.00 | 20.48 | A |
| ATOM | 1590 | CB | TYR | A | 273 | 32.418 | 28.847 | 22.162 | 1.00 | 18.98 | A |
| ATOM | 1591 | CG | TYR | A | 273 | 31.663 | 30.161 | 22.125 | 1.00 | 20.26 | A |
| ATOM | 1592 | CD1 | TYR | A | 273 | 31.229 | 30.709 | 20.916 | 1.00 | 20.67 | A |
| ATOM | 1593 | CE1 | TYR | A | 273 | 30.536 | 31.917 | 20.880 | 1.00 | 20.98 | A |
| ATOM | 1594 | CD2 | TYR | A | 273 | 31.383 | 30.857 | 23.302 | 1.00 | 19.82 | A |

-continued

| | | | | | | | | | | |
|---|---|---|---|---|---|---|---|---|---|---|
| ATOM | 1595 | CE2 | TYR | A | 273 | 30.691 | 32.062 | 23.280 | 1.00 | 20.62 | A |
| ATOM | 1596 | CZ | TYR | A | 273 | 30.271 | 32.587 | 22.067 | 1.00 | 21.15 | A |
| ATOM | 1597 | OH | TYR | A | 273 | 29.588 | 33.776 | 22.049 | 1.00 | 21.86 | A |
| ATOM | 1598 | C | TYR | A | 273 | 30.902 | 27.730 | 20.507 | 1.00 | 21.54 | A |
| ATOM | 1599 | O | TYR | A | 273 | 29.719 | 28.049 | 20.401 | 1.00 | 22.80 | A |
| ATOM | 1600 | N | GLN | A | 274 | 31.676 | 27.454 | 19.461 | 1.00 | 21.05 | A |
| ATOM | 1601 | CA | GLN | A | 274 | 31.176 | 27.538 | 18.095 | 1.00 | 21.48 | A |
| ATOM | 1602 | CB | GLN | A | 274 | 32.323 | 27.341 | 17.097 | 1.00 | 21.41 | A |
| ATOM | 1603 | CG | GLN | A | 274 | 31.934 | 27.596 | 15.645 | 1.00 | 23.15 | A |
| ATOM | 1604 | CD | GLN | A | 274 | 33.131 | 27.588 | 14.706 | 1.00 | 24.80 | A |
| ATOM | 1605 | OE1 | GLN | A | 274 | 34.276 | 27.446 | 15.139 | 1.00 | 22.51 | A |
| ATOM | 1606 | NE2 | GLN | A | 274 | 32.870 | 27.750 | 13.413 | 1.00 | 22.96 | A |
| ATOM | 1607 | C | GLN | A | 274 | 30.076 | 26.517 | 17.828 | 1.00 | 21.51 | A |
| ATOM | 1608 | O | GLN | A | 274 | 29.123 | 26.806 | 17.108 | 1.00 | 20.50 | A |
| ATOM | 1609 | N | LEU | A | 275 | 30.207 | 25.324 | 18.403 | 1.00 | 21.44 | A |
| ATOM | 1610 | CA | LEU | A | 275 | 29.196 | 24.282 | 18.208 | 1.00 | 20.95 | A |
| ATOM | 1611 | CB | LEU | A | 275 | 29.645 | 22.958 | 18.846 | 1.00 | 19.11 | A |
| ATOM | 1612 | CG | LEU | A | 275 | 30.775 | 22.182 | 18.159 | 1.00 | 21.43 | A |
| ATOM | 1613 | CD1 | LEU | A | 275 | 31.118 | 20.936 | 18.963 | 1.00 | 17.64 | A |
| ATOM | 1614 | CD2 | LEU | A | 275 | 30.342 | 21.795 | 16.754 | 1.00 | 20.34 | A |
| ATOM | 1615 | C | LEU | A | 275 | 27.860 | 24.697 | 18.815 | 1.00 | 21.32 | A |
| ATOM | 1616 | O | LEU | A | 275 | 26.802 | 24.461 | 18.229 | 1.00 | 19.75 | A |
| ATOM | 1617 | N | VAL | A | 276 | 27.921 | 25.322 | 19.987 | 1.00 | 19.10 | A |
| ATOM | 1618 | CA | VAL | A | 276 | 26.724 | 25.750 | 20.702 | 1.00 | 22.47 | A |
| ATOM | 1619 | CB | VAL | A | 276 | 27.011 | 25.882 | 22.217 | 1.00 | 20.87 | A |
| ATOM | 1620 | CG1 | VAL | A | 276 | 25.742 | 26.291 | 22.957 | 1.00 | 19.68 | A |
| ATOM | 1621 | CG2 | VAL | A | 276 | 27.550 | 24.558 | 22.766 | 1.00 | 19.43 | A |
| ATOM | 1622 | C | VAL | A | 276 | 26.127 | 27.075 | 20.211 | 1.00 | 23.89 | A |
| ATOM | 1623 | O | VAL | A | 276 | 24.910 | 27.199 | 20.070 | 1.00 | 24.90 | A |
| ATOM | 1624 | N | ALA | A | 277 | 26.983 | 28.062 | 19.965 | 1.00 | 24.56 | A |
| ATOM | 1625 | CA | ALA | A | 277 | 26.533 | 29.374 | 19.518 | 1.00 | 24.72 | A |
| ATOM | 1626 | CB | ALA | A | 277 | 27.504 | 30.444 | 19.999 | 1.00 | 24.36 | A |
| ATOM | 1627 | C | ALA | A | 277 | 26.378 | 29.458 | 18.005 | 1.00 | 25.76 | A |
| ATOM | 1628 | O | ALA | A | 277 | 25.577 | 30.242 | 17.502 | 1.00 | 26.39 | A |
| ATOM | 1629 | N | GLY | A | 278 | 27.142 | 28.651 | 17.280 | 1.00 | 25.13 | A |
| ATOM | 1630 | CA | GLY | A | 278 | 27.062 | 28.673 | 15.834 | 1.00 | 25.58 | A |
| ATOM | 1631 | C | GLY | A | 278 | 28.163 | 29.524 | 15.231 | 1.00 | 26.50 | A |
| ATOM | 1632 | O | GLY | A | 278 | 28.374 | 29.510 | 14.015 | 1.00 | 28.17 | A |
| ATOM | 1633 | N | LEU | A | 279 | 28.866 | 30.262 | 16.086 | 1.00 | 24.44 | A |
| ATOM | 1634 | CA | LEU | A | 279 | 29.962 | 31.130 | 15.656 | 1.00 | 25.21 | A |
| ATOM | 1635 | CB | LEU | A | 279 | 29.468 | 32.575 | 15.500 | 1.00 | 25.78 | A |
| ATOM | 1636 | CG | LEU | A | 279 | 28.364 | 32.899 | 14.490 | 1.00 | 28.17 | A |
| ATOM | 1637 | CD1 | LEU | A | 279 | 27.922 | 34.344 | 14.684 | 1.00 | 26.60 | A |
| ATOM | 1638 | CD2 | LEU | A | 279 | 28.862 | 32.670 | 13.071 | 1.00 | 26.52 | A |
| ATOM | 1639 | C | LEU | A | 279 | 31.093 | 31.116 | 16.687 | 1.00 | 23.47 | A |
| ATOM | 1640 | O | LEU | A | 279 | 30.848 | 30.994 | 17.882 | 1.00 | 24.44 | A |
| ATOM | 1641 | N | PRO | A | 280 | 32.349 | 31.239 | 16.236 | 1.00 | 23.35 | A |
| ATOM | 1642 | CD | PRO | A | 280 | 32.831 | 31.404 | 14.855 | 1.00 | 22.26 | A |
| ATOM | 1643 | CA | PRO | A | 280 | 33.464 | 31.239 | 17.189 | 1.00 | 23.81 | A |
| ATOM | 1644 | CB | PRO | A | 280 | 34.692 | 31.293 | 16.282 | 1.00 | 23.24 | A |
| ATOM | 1645 | CG | PRO | A | 280 | 34.189 | 32.020 | 15.073 | 1.00 | 24.89 | A |
| ATOM | 1646 | C | PRO | A | 280 | 33.353 | 32.444 | 18.137 | 1.00 | 22.69 | A |
| ATOM | 1647 | O | PRO | A | 280 | 32.750 | 33.457 | 17.788 | 1.00 | 22.11 | A |
| ATOM | 1648 | N | PRO | A | 281 | 33.939 | 32.344 | 19.345 | 1.00 | 23.06 | A |
| ATOM | 1649 | CD | PRO | A | 281 | 34.810 | 31.223 | 19.734 | 1.00 | 21.37 | A |
| ATOM | 1650 | CA | PRO | A | 281 | 33.935 | 33.375 | 20.395 | 1.00 | 23.67 | A |
| ATOM | 1651 | CB | PRO | A | 281 | 34.781 | 32.751 | 21.509 | 1.00 | 24.89 | A |
| ATOM | 1652 | CG | PRO | A | 281 | 34.749 | 31.287 | 21.219 | 1.00 | 25.24 | A |
| ATOM | 1653 | C | PRO | A | 281 | 34.481 | 34.752 | 20.017 | 1.00 | 23.75 | A |
| ATOM | 1654 | O | PRO | A | 281 | 33.869 | 35.781 | 20.317 | 1.00 | 21.02 | A |
| ATOM | 1655 | N | PHE | A | 282 | 35.644 | 34.763 | 19.379 | 1.00 | 22.17 | A |
| ATOM | 1656 | CA | PHE | A | 282 | 36.293 | 36.007 | 18.998 | 1.00 | 23.16 | A |
| ATOM | 1657 | CB | PHE | A | 282 | 37.765 | 35.943 | 19.406 | 1.00 | 21.01 | A |
| ATOM | 1658 | CG | PHE | A | 282 | 37.975 | 35.482 | 20.822 | 1.00 | 22.66 | A |
| ATOM | 1659 | CD1 | PHE | A | 282 | 37.806 | 36.361 | 21.888 | 1.00 | 20.06 | A |
| ATOM | 1660 | CD2 | PHE | A | 282 | 38.291 | 34.151 | 21.093 | 1.00 | 20.72 | A |
| ATOM | 1661 | CE1 | PHE | A | 282 | 37.947 | 35.921 | 23.206 | 1.00 | 22.66 | A |
| ATOM | 1662 | CE2 | PHE | A | 282 | 38.433 | 33.702 | 22.405 | 1.00 | 20.97 | A |
| ATOM | 1663 | CZ | PHE | A | 282 | 38.261 | 34.590 | 23.466 | 1.00 | 19.58 | A |
| ATOM | 1664 | C | PHE | A | 282 | 36.169 | 36.263 | 17.503 | 1.00 | 24.39 | A |
| ATOM | 1665 | O | PHE | A | 282 | 36.802 | 35.585 | 16.694 | 1.00 | 25.80 | A |
| ATOM | 1666 | N | ARG | A | 283 | 35.355 | 37.248 | 17.142 | 1.00 | 24.99 | A |
| ATOM | 1667 | CA | ARG | A | 283 | 35.141 | 37.594 | 15.741 | 1.00 | 26.33 | A |
| ATOM | 1668 | CB | ARG | A | 283 | 33.721 | 37.209 | 15.316 | 1.00 | 28.91 | A |
| ATOM | 1669 | CG | ARG | A | 283 | 33.293 | 35.808 | 15.724 | 1.00 | 30.27 | A |
| ATOM | 1670 | CD | ARG | A | 283 | 31.904 | 35.493 | 15.188 | 1.00 | 33.36 | A |
| ATOM | 1671 | NE | ARG | A | 283 | 30.890 | 36.392 | 15.733 | 1.00 | 32.76 | A |
| ATOM | 1672 | CZ | ARG | A | 283 | 30.372 | 36.287 | 16.952 | 1.00 | 34.79 | A |
| ATOM | 1673 | NH1 | ARG | A | 283 | 30.767 | 35.317 | 17.768 | 1.00 | 35.77 | A |

-continued

| | | | | | | | | | | |
|---|---|---|---|---|---|---|---|---|---|---|
| ATOM | 1674 | NH2 | ARG | A | 283 | 29.458 | 37.156 | 17.359 | 1.00 | 36.12 | A |
| ATOM | 1675 | C | ARG | A | 283 | 35.328 | 39.096 | 15.544 | 1.00 | 26.47 | A |
| ATOM | 1676 | O | ARG | A | 283 | 35.029 | 39.888 | 16.438 | 1.00 | 26.28 | A |
| ATOM | 1677 | N | ALA | A | 284 | 35.818 | 39.486 | 14.373 | 1.00 | 26.70 | A |
| ATOM | 1678 | CA | ALA | A | 284 | 36.033 | 40.899 | 14.079 | 1.00 | 27.84 | A |
| ATOM | 1679 | CB | ALA | A | 284 | 37.188 | 41.442 | 14.914 | 1.00 | 26.24 | A |
| ATOM | 1680 | C | ALA | A | 284 | 36.327 | 41.077 | 12.602 | 1.00 | 28.35 | A |
| ATOM | 1681 | O | ALA | A | 284 | 36.560 | 40.101 | 11.891 | 1.00 | 29.91 | A |
| ATOM | 1682 | N | GLY | A | 285 | 36.332 | 42.329 | 12.153 | 1.00 | 29.29 | A |
| ATOM | 1683 | CA | GLY | A | 285 | 36.577 | 42.631 | 10.753 | 1.00 | 29.52 | A |
| ATOM | 1684 | C | GLY | A | 285 | 37.893 | 42.156 | 10.168 | 1.00 | 30.12 | A |
| ATOM | 1685 | O | GLY | A | 285 | 37.974 | 41.862 | 8.976 | 1.00 | 30.60 | A |
| ATOM | 1686 | N | ASN | A | 286 | 38.939 | 42.097 | 10.983 | 1.00 | 28.49 | A |
| ATOM | 1687 | CA | ASN | A | 286 | 40.231 | 41.644 | 10.489 | 1.00 | 26.71 | A |
| ATOM | 1688 | CB | ASN | A | 286 | 41.050 | 42.825 | 9.945 | 1.00 | 26.11 | A |
| ATOM | 1689 | CG | ASN | A | 286 | 41.310 | 43.900 | 10.990 | 1.00 | 27.83 | A |
| ATOM | 1690 | OD1 | ASN | A | 286 | 41.877 | 43.631 | 12.049 | 1.00 | 27.84 | A |
| ATOM | 1691 | ND2 | ASN | A | 286 | 40.908 | 45.131 | 10.685 | 1.00 | 25.95 | A |
| ATOM | 1692 | C | ASN | A | 286 | 40.997 | 40.924 | 11.584 | 1.00 | 26.03 | A |
| ATOM | 1693 | O | ASN | A | 286 | 40.540 | 40.851 | 12.723 | 1.00 | 25.66 | A |
| ATOM | 1694 | N | GLU | A | 287 | 42.162 | 40.391 | 11.239 | 1.00 | 24.81 | A |
| ATOM | 1695 | CA | GLU | A | 287 | 42.965 | 39.662 | 12.206 | 1.00 | 27.59 | A |
| ATOM | 1696 | CB | GLU | A | 287 | 44.145 | 38.985 | 11.510 | 1.00 | 30.17 | A |
| ATOM | 1697 | CG | GLU | A | 287 | 43.776 | 37.632 | 10.931 | 1.00 | 38.21 | A |
| ATOM | 1698 | CD | GLU | A | 287 | 44.900 | 36.998 | 10.140 | 1.00 | 41.86 | A |
| ATOM | 1699 | OE1 | GLU | A | 287 | 46.061 | 37.036 | 10.608 | 1.00 | 43.08 | A |
| ATOM | 1700 | OE2 | GLU | A | 287 | 44.612 | 36.449 | 9.052 | 1.00 | 45.22 | A |
| ATOM | 1701 | C | GLU | A | 287 | 43.459 | 40.485 | 13.383 | 1.00 | 25.05 | A |
| ATOM | 1702 | O | GLU | A | 287 | 43.382 | 40.030 | 14.521 | 1.00 | 26.41 | A |
| ATOM | 1703 | N | TYR | A | 288 | 43.966 | 41.685 | 13.122 | 1.00 | 23.04 | A |
| ATOM | 1704 | CA | TYR | A | 288 | 44.460 | 42.528 | 14.205 | 1.00 | 22.34 | A |
| ATOM | 1705 | CB | TYR | A | 288 | 44.867 | 43.913 | 13.691 | 1.00 | 21.07 | A |
| ATOM | 1706 | CG | TYR | A | 288 | 45.275 | 44.858 | 14.805 | 1.00 | 21.07 | A |
| ATOM | 1707 | CD1 | TYR | A | 288 | 46.533 | 44.762 | 15.405 | 1.00 | 21.23 | A |
| ATOM | 1708 | CE1 | TYR | A | 288 | 46.891 | 45.588 | 16.475 | 1.00 | 20.43 | A |
| ATOM | 1709 | CD2 | TYR | A | 288 | 44.380 | 45.809 | 15.302 | 1.00 | 22.32 | A |
| ATOM | 1710 | CE2 | TYR | A | 288 | 44.725 | 46.637 | 16.373 | 1.00 | 23.28 | A |
| ATOM | 1711 | CZ | TYR | A | 288 | 45.981 | 46.518 | 16.953 | 1.00 | 22.96 | A |
| ATOM | 1712 | OH | TYR | A | 288 | 46.316 | 47.313 | 18.024 | 1.00 | 23.18 | A |
| ATOM | 1713 | C | TYR | A | 288 | 43.402 | 42.698 | 15.288 | 1.00 | 21.38 | A |
| ATOM | 1714 | O | TYR | A | 288 | 43.710 | 42.616 | 16.473 | 1.00 | 22.09 | A |
| ATOM | 1715 | N | LEU | A | 289 | 42.159 | 42.939 | 14.874 | 1.00 | 21.88 | A |
| ATOM | 1716 | CA | LEU | A | 289 | 41.055 | 43.130 | 15.811 | 1.00 | 21.98 | A |
| ATOM | 1717 | CB | LEU | A | 289 | 39.821 | 43.673 | 15.078 | 1.00 | 22.90 | A |
| ATOM | 1718 | CG | LEU | A | 289 | 39.896 | 45.130 | 14.601 | 1.00 | 26.52 | A |
| ATOM | 1719 | CD1 | LEU | A | 289 | 38.706 | 45.436 | 13.696 | 1.00 | 26.55 | A |
| ATOM | 1720 | CD2 | LEU | A | 289 | 39.914 | 46.071 | 15.807 | 1.00 | 23.13 | A |
| ATOM | 1721 | C | LEU | A | 289 | 40.686 | 41.849 | 16.560 | 1.00 | 21.24 | A |
| ATOM | 1722 | O | LEU | A | 289 | 40.256 | 41.897 | 17.715 | 1.00 | 20.72 | A |
| ATOM | 1723 | N | ILE | A | 290 | 40.843 | 40.708 | 15.900 | 1.00 | 19.62 | A |
| ATOM | 1724 | CA | ILE | A | 290 | 40.538 | 39.433 | 16.533 | 1.00 | 18.54 | A |
| ATOM | 1725 | CB | ILE | A | 290 | 40.560 | 38.281 | 15.509 | 1.00 | 18.52 | A |
| ATOM | 1726 | CG2 | ILE | A | 290 | 40.503 | 36.934 | 16.234 | 1.00 | 17.63 | A |
| ATOM | 1727 | CG1 | ILE | A | 290 | 39.378 | 38.429 | 14.545 | 1.00 | 18.88 | A |
| ATOM | 1728 | CD1 | ILE | A | 290 | 39.421 | 37.483 | 13.357 | 1.00 | 19.81 | A |
| ATOM | 1729 | C | ILE | A | 290 | 41.578 | 39.167 | 17.618 | 1.00 | 19.09 | A |
| ATOM | 1730 | O | ILE | A | 290 | 41.236 | 38.788 | 18.737 | 1.00 | 18.20 | A |
| ATOM | 1731 | N | PHE | A | 291 | 42.849 | 39.376 | 17.286 | 1.00 | 18.76 | A |
| ATOM | 1732 | CA | PHE | A | 291 | 43.925 | 39.156 | 18.247 | 1.00 | 20.75 | A |
| ATOM | 1733 | CB | PHE | A | 291 | 45.286 | 39.434 | 17.606 | 1.00 | 20.71 | A |
| ATOM | 1734 | CG | PHE | A | 291 | 45.644 | 38.480 | 16.503 | 1.00 | 22.92 | A |
| ATOM | 1735 | CD1 | PHE | A | 291 | 45.065 | 37.214 | 16.443 | 1.00 | 22.98 | A |
| ATOM | 1736 | CD2 | PHE | A | 291 | 46.588 | 38.830 | 15.543 | 1.00 | 22.91 | A |
| ATOM | 1737 | CE1 | PHE | A | 291 | 45.423 | 36.310 | 15.440 | 1.00 | 24.51 | A |
| ATOM | 1738 | CE2 | PHE | A | 291 | 46.954 | 37.931 | 14.535 | 1.00 | 25.54 | A |
| ATOM | 1739 | CZ | PHE | A | 291 | 46.370 | 36.670 | 14.485 | 1.00 | 23.29 | A |
| ATOM | 1740 | C | PHE | A | 291 | 43.739 | 40.061 | 19.451 | 1.00 | 21.72 | A |
| ATOM | 1741 | O | PHE | A | 291 | 43.992 | 39.671 | 20.593 | 1.00 | 22.32 | A |
| ATOM | 1742 | N | GLN | A | 292 | 43.284 | 41.275 | 19.178 | 1.00 | 23.27 | A |
| ATOM | 1743 | CA | GLN | A | 292 | 43.055 | 42.264 | 20.216 | 1.00 | 24.01 | A |
| ATOM | 1744 | CB | GLN | A | 292 | 42.574 | 43.559 | 19.562 | 1.00 | 25.77 | A |
| ATOM | 1745 | CG | GLN | A | 292 | 42.577 | 44.773 | 20.447 | 1.00 | 28.45 | A |
| ATOM | 1746 | CD | GLN | A | 292 | 42.469 | 46.057 | 19.638 | 1.00 | 29.83 | A |
| ATOM | 1747 | OE1 | GLN | A | 292 | 41.520 | 46.244 | 18.872 | 1.00 | 27.16 | A |
| ATOM | 1748 | NE2 | GLN | A | 292 | 43.449 | 46.944 | 19.799 | 1.00 | 27.61 | A |
| ATOM | 1749 | C | GLN | A | 292 | 42.018 | 41.733 | 21.204 | 1.00 | 22.97 | A |
| ATOM | 1750 | O | GLN | A | 292 | 42.200 | 41.832 | 22.415 | 1.00 | 21.64 | A |
| ATOM | 1751 | N | LYS | A | 293 | 40.937 | 41.154 | 20.687 | 1.00 | 21.82 | A |
| ATOM | 1752 | CA | LYS | A | 293 | 39.895 | 40.612 | 21.558 | 1.00 | 22.18 | A |

-continued

| | | | | | | | | | | |
|---|---|---|---|---|---|---|---|---|---|---|
| ATOM | 1753 | CB | LYS | A | 293 | 38.664 | 40.223 | 20.740 | 1.00 | 22.69 | A |
| ATOM | 1754 | CG | LYS | A | 293 | 37.919 | 41.407 | 20.153 | 1.00 | 25.78 | A |
| ATOM | 1755 | CD | LYS | A | 293 | 36.651 | 40.961 | 19.429 | 1.00 | 27.88 | A |
| ATOM | 1756 | CE | LYS | A | 293 | 35.857 | 42.161 | 18.926 | 1.00 | 30.85 | A |
| ATOM | 1757 | NZ | LYS | A | 293 | 34.612 | 41.750 | 18.214 | 1.00 | 32.98 | A |
| ATOM | 1758 | C | LYS | A | 293 | 40.398 | 39.398 | 22.343 | 1.00 | 21.20 | A |
| ATOM | 1759 | O | LYS | A | 293 | 40.041 | 39.204 | 23.509 | 1.00 | 22.01 | A |
| ATOM | 1760 | N | ILE | A | 294 | 41.226 | 38.583 | 21.702 | 1.00 | 19.91 | A |
| ATOM | 1761 | CA | ILE | A | 294 | 41.774 | 37.394 | 22.347 | 1.00 | 20.28 | A |
| ATOM | 1762 | CB | ILE | A | 294 | 42.631 | 36.575 | 21.349 | 1.00 | 18.98 | A |
| ATOM | 1763 | CG2 | ILE | A | 294 | 43.481 | 35.550 | 22.098 | 1.00 | 17.70 | A |
| ATOM | 1764 | CG1 | ILE | A | 294 | 41.716 | 35.897 | 20.318 | 1.00 | 17.93 | A |
| ATOM | 1765 | CD1 | ILE | A | 294 | 42.467 | 35.237 | 19.178 | 1.00 | 16.21 | A |
| ATOM | 1766 | C | ILE | A | 294 | 42.618 | 37.727 | 23.587 | 1.00 | 21.94 | A |
| ATOM | 1767 | O | ILE | A | 294 | 42.366 | 37.199 | 24.673 | 1.00 | 20.86 | A |
| ATOM | 1768 | N | ILE | A | 295 | 43.610 | 38.600 | 23.439 | 1.00 | 21.88 | A |
| ATOM | 1769 | CA | ILE | A | 295 | 44.461 | 38.934 | 24.582 | 1.00 | 24.25 | A |
| ATOM | 1770 | CB | ILE | A | 295 | 45.668 | 39.805 | 24.175 | 1.00 | 23.93 | A |
| ATOM | 1771 | CG2 | ILE | A | 295 | 46.514 | 39.066 | 23.140 | 1.00 | 24.61 | A |
| ATOM | 1772 | CG1 | ILE | A | 295 | 45.189 | 41.151 | 23.637 | 1.00 | 24.58 | A |
| ATOM | 1773 | CD1 | ILE | A | 295 | 46.317 | 42.149 | 23.433 | 1.00 | 26.69 | A |
| ATOM | 1774 | C | ILE | A | 295 | 43.720 | 39.636 | 25.717 | 1.00 | 24.80 | A |
| ATOM | 1775 | O | ILE | A | 295 | 44.214 | 39.687 | 26.842 | 1.00 | 24.76 | A |
| ATOM | 1776 | N | LYS | A | 296 | 42.539 | 40.173 | 25.425 | 1.00 | 25.33 | A |
| ATOM | 1777 | CA | LYS | A | 296 | 41.743 | 40.853 | 26.444 | 1.00 | 26.80 | A |
| ATOM | 1778 | CB | LYS | A | 296 | 41.178 | 42.170 | 25.894 | 1.00 | 27.39 | A |
| ATOM | 1779 | CG | LYS | A | 296 | 42.240 | 43.141 | 25.413 | 1.00 | 31.79 | A |
| ATOM | 1780 | CD | LYS | A | 296 | 41.634 | 44.410 | 24.826 | 1.00 | 35.56 | A |
| ATOM | 1781 | CE | LYS | A | 296 | 41.009 | 45.283 | 25.900 | 1.00 | 39.29 | A |
| ATOM | 1782 | NZ | LYS | A | 296 | 40.564 | 46.603 | 25.357 | 1.00 | 41.72 | A |
| ATOM | 1783 | C | LYS | A | 296 | 40.593 | 39.958 | 26.893 | 1.00 | 25.50 | A |
| ATOM | 1784 | O | LYS | A | 296 | 39.770 | 40.361 | 27.713 | 1.00 | 24.02 | A |
| ATOM | 1785 | N | LEU | A | 297 | 40.550 | 38.742 | 26.349 | 1.00 | 25.67 | A |
| ATOM | 1786 | CA | LEU | A | 297 | 39.500 | 37.777 | 26.666 | 1.00 | 25.16 | A |
| ATOM | 1787 | CB | LEU | A | 297 | 39.632 | 37.285 | 28.111 | 1.00 | 24.80 | A |
| ATOM | 1788 | CG | LEU | A | 297 | 38.766 | 36.068 | 28.460 | 1.00 | 26.43 | A |
| ATOM | 1789 | CD1 | LEU | A | 297 | 39.238 | 34.852 | 27.646 | 1.00 | 26.70 | A |
| ATOM | 1790 | CD2 | LEU | A | 297 | 38.856 | 35.777 | 29.951 | 1.00 | 24.84 | A |
| ATOM | 1791 | C | LEU | A | 297 | 38.151 | 38.459 | 26.467 | 1.00 | 25.11 | A |
| ATOM | 1792 | O | LEU | A | 297 | 37.261 | 38.378 | 27.309 | 1.00 | 25.28 | A |
| ATOM | 1793 | N | GLU | A | 298 | 38.007 | 39.127 | 25.331 | 1.00 | 24.98 | A |
| ATOM | 1794 | CA | GLU | A | 298 | 36.786 | 39.847 | 25.023 | 1.00 | 25.31 | A |
| ATOM | 1795 | CB | GLU | A | 298 | 37.143 | 41.139 | 24.291 | 1.00 | 27.13 | A |
| ATOM | 1796 | CG | GLU | A | 298 | 35.991 | 42.092 | 24.108 | 1.00 | 31.28 | A |
| ATOM | 1797 | CD | GLU | A | 298 | 36.419 | 43.362 | 23.410 | 1.00 | 34.40 | A |
| ATOM | 1798 | OE1 | GLU | A | 298 | 37.348 | 44.027 | 23.918 | 1.00 | 35.90 | A |
| ATOM | 1799 | OE2 | GLU | A | 298 | 35.832 | 43.693 | 22.359 | 1.00 | 36.16 | A |
| ATOM | 1800 | C | GLU | A | 298 | 35.766 | 39.057 | 24.207 | 1.00 | 23.79 | A |
| ATOM | 1801 | O | GLU | A | 298 | 35.832 | 39.017 | 22.979 | 1.00 | 24.35 | A |
| ATOM | 1802 | N | TYR | A | 299 | 34.825 | 38.427 | 24.902 | 1.00 | 23.45 | A |
| ATOM | 1803 | CA | TYR | A | 299 | 33.760 | 37.663 | 24.265 | 1.00 | 23.98 | A |
| ATOM | 1804 | CB | TYR | A | 299 | 34.264 | 36.304 | 23.755 | 1.00 | 20.13 | A |
| ATOM | 1805 | CG | TYR | A | 299 | 34.348 | 35.233 | 24.828 | 1.00 | 21.17 | A |
| ATOM | 1806 | CD1 | TYR | A | 299 | 35.336 | 35.279 | 25.810 | 1.00 | 19.32 | A |
| ATOM | 1807 | CE1 | TYR | A | 299 | 35.389 | 34.332 | 26.826 | 1.00 | 19.30 | A |
| ATOM | 1808 | CD2 | TYR | A | 299 | 33.410 | 34.201 | 24.888 | 1.00 | 18.96 | A |
| ATOM | 1809 | CE2 | TYR | A | 299 | 33.456 | 33.243 | 25.907 | 1.00 | 19.41 | A |
| ATOM | 1810 | CZ | TYR | A | 299 | 34.449 | 33.321 | 26.870 | 1.00 | 18.79 | A |
| ATOM | 1811 | OH | TYR | A | 299 | 34.511 | 32.401 | 27.881 | 1.00 | 18.77 | A |
| ATOM | 1812 | C | TYR | A | 299 | 32.699 | 37.437 | 25.331 | 1.00 | 25.20 | A |
| ATOM | 1813 | O | TYR | A | 299 | 32.942 | 37.681 | 26.506 | 1.00 | 26.46 | A |
| ATOM | 1814 | N | ASP | A | 300 | 31.522 | 36.981 | 24.927 | 1.00 | 26.94 | A |
| ATOM | 1815 | CA | ASP | A | 300 | 30.467 | 36.710 | 25.891 | 1.00 | 30.60 | A |
| ATOM | 1816 | CB | ASP | A | 300 | 29.665 | 37.981 | 26.179 | 1.00 | 35.86 | A |
| ATOM | 1817 | CG | ASP | A | 300 | 29.228 | 38.687 | 24.923 | 1.00 | 42.04 | A |
| ATOM | 1818 | OD1 | ASP | A | 300 | 28.450 | 38.088 | 24.149 | 1.00 | 45.98 | A |
| ATOM | 1819 | OD2 | ASP | A | 300 | 29.666 | 39.840 | 24.707 | 1.00 | 45.69 | A |
| ATOM | 1820 | C | ASP | A | 300 | 29.564 | 35.608 | 25.363 | 1.00 | 29.26 | A |
| ATOM | 1821 | O | ASP | A | 300 | 29.590 | 35.299 | 24.172 | 1.00 | 28.64 | A |
| ATOM | 1822 | N | PHE | A | 301 | 28.778 | 35.011 | 26.253 | 1.00 | 28.96 | A |
| ATOM | 1823 | CA | PHE | A | 301 | 27.884 | 33.924 | 25.871 | 1.00 | 30.48 | A |
| ATOM | 1824 | CB | PHE | A | 301 | 27.818 | 32.854 | 26.968 | 1.00 | 29.17 | A |
| ATOM | 1825 | CG | PHE | A | 301 | 29.147 | 32.279 | 27.356 | 1.00 | 29.29 | A |
| ATOM | 1826 | CD1 | PHE | A | 301 | 29.978 | 32.949 | 28.245 | 1.00 | 27.31 | A |
| ATOM | 1827 | CD2 | PHE | A | 301 | 29.560 | 31.050 | 26.845 | 1.00 | 27.89 | A |
| ATOM | 1828 | CE1 | PHE | A | 301 | 31.205 | 32.403 | 28.625 | 1.00 | 28.83 | A |
| ATOM | 1829 | CE2 | PHE | A | 301 | 30.781 | 30.498 | 27.217 | 1.00 | 28.05 | A |
| ATOM | 1830 | CZ | PHE | A | 301 | 31.605 | 31.175 | 28.110 | 1.00 | 28.27 | A |
| ATOM | 1831 | C | PHE | A | 301 | 26.459 | 34.384 | 25.619 | 1.00 | 32.20 | A |

-continued

| | | | | | | | | | | | |
|---|---|---|---|---|---|---|---|---|---|---|---|
| ATOM | 1832 | O | PHE | A | 301 | 25.946 | 35.261 | 26.317 | 1.00 | 32.36 | A |
| ATOM | 1833 | N | PRO | A | 302 | 25.798 | 33.804 | 24.607 | 1.00 | 33.29 | A |
| ATOM | 1834 | CD | PRO | A | 302 | 26.313 | 32.943 | 23.529 | 1.00 | 34.04 | A |
| ATOM | 1835 | CA | PRO | A | 302 | 24.415 | 34.199 | 24.341 | 1.00 | 35.24 | A |
| ATOM | 1836 | CB | PRO | A | 302 | 24.144 | 33.608 | 22.959 | 1.00 | 34.01 | A |
| ATOM | 1837 | CG | PRO | A | 302 | 25.041 | 32.413 | 22.921 | 1.00 | 35.48 | A |
| ATOM | 1838 | C | PRO | A | 302 | 23.567 | 33.561 | 25.444 | 1.00 | 37.39 | A |
| ATOM | 1839 | O | PRO | A | 302 | 23.935 | 32.518 | 25.986 | 1.00 | 38.49 | A |
| ATOM | 1840 | N | ALA | A | 303 | 22.447 | 34.188 | 25.783 | 1.00 | 39.36 | A |
| ATOM | 1841 | CA | ALA | A | 303 | 21.572 | 33.692 | 26.843 | 1.00 | 40.65 | A |
| ATOM | 1842 | CB | ALA | A | 303 | 20.280 | 34.506 | 26.862 | 1.00 | 41.66 | A |
| ATOM | 1843 | C | ALA | A | 303 | 21.238 | 32.197 | 26.814 | 1.00 | 41.25 | A |
| ATOM | 1844 | O | ALA | A | 303 | 21.253 | 31.537 | 27.854 | 1.00 | 43.16 | A |
| ATOM | 1845 | N | ALA | A | 304 | 20.945 | 31.665 | 25.631 | 1.00 | 41.04 | A |
| ATOM | 1846 | CA | ALA | A | 304 | 20.569 | 30.258 | 25.480 | 1.00 | 40.66 | A |
| ATOM | 1847 | CB | ALA | A | 304 | 20.121 | 30.004 | 24.040 | 1.00 | 41.36 | A |
| ATOM | 1848 | C | ALA | A | 304 | 21.628 | 29.223 | 25.876 | 1.00 | 39.61 | A |
| ATOM | 1849 | O | ALA | A | 304 | 21.298 | 28.156 | 26.395 | 1.00 | 40.61 | A |
| ATOM | 1850 | N | PHE | A | 305 | 22.891 | 29.543 | 25.617 | 1.00 | 36.21 | A |
| ATOM | 1851 | CA | PHE | A | 305 | 24.022 | 28.662 | 25.909 | 1.00 | 32.08 | A |
| ATOM | 1852 | CB | PHE | A | 305 | 25.259 | 29.519 | 26.187 | 1.00 | 29.46 | A |
| ATOM | 1853 | CG | PHE | A | 305 | 26.536 | 28.917 | 25.690 | 1.00 | 28.15 | A |
| ATOM | 1854 | CD1 | PHE | A | 305 | 27.146 | 27.875 | 26.377 | 1.00 | 26.20 | A |
| ATOM | 1855 | CD2 | PHE | A | 305 | 27.127 | 29.386 | 24.521 | 1.00 | 27.05 | A |
| ATOM | 1856 | CE1 | PHE | A | 305 | 28.330 | 27.308 | 25.908 | 1.00 | 26.92 | A |
| ATOM | 1857 | CE2 | PHE | A | 305 | 28.312 | 28.826 | 24.042 | 1.00 | 26.62 | A |
| ATOM | 1858 | CZ | PHE | A | 305 | 28.914 | 27.786 | 24.737 | 1.00 | 26.61 | A |
| ATOM | 1859 | C | PHE | A | 305 | 23.811 | 27.664 | 27.057 | 1.00 | 30.09 | A |
| ATOM | 1860 | O | PHE | A | 305 | 23.518 | 28.051 | 28.187 | 1.00 | 31.51 | A |
| ATOM | 1861 | N | PHE | A | 306 | 23.964 | 26.378 | 26.758 | 1.00 | 27.01 | A |
| ATOM | 1862 | CA | PHE | A | 306 | 23.801 | 25.334 | 27.769 | 1.00 | 26.30 | A |
| ATOM | 1863 | CB | PHE | A | 306 | 24.157 | 23.970 | 27.170 | 1.00 | 25.03 | A |
| ATOM | 1864 | CG | PHE | A | 306 | 23.548 | 23.725 | 25.815 | 1.00 | 27.24 | A |
| ATOM | 1865 | CD1 | PHE | A | 306 | 22.170 | 23.831 | 25.622 | 1.00 | 28.40 | A |
| ATOM | 1866 | CD2 | PHE | A | 306 | 24.350 | 23.386 | 24.728 | 1.00 | 27.84 | A |
| ATOM | 1867 | CE1 | PHE | A | 306 | 21.601 | 23.603 | 24.365 | 1.00 | 28.05 | A |
| ATOM | 1868 | CE2 | PHE | A | 306 | 23.792 | 23.155 | 23.465 | 1.00 | 28.31 | A |
| ATOM | 1869 | CZ | PHE | A | 306 | 22.415 | 23.263 | 23.283 | 1.00 | 28.00 | A |
| ATOM | 1870 | C | PHE | A | 306 | 24.711 | 25.652 | 28.961 | 1.00 | 26.23 | A |
| ATOM | 1871 | O | PHE | A | 306 | 25.927 | 25.775 | 28.811 | 1.00 | 25.59 | A |
| ATOM | 1872 | N | PRO | A | 307 | 24.125 | 25.796 | 30.163 | 1.00 | 26.67 | A |
| ATOM | 1873 | CD | PRO | A | 307 | 22.685 | 25.625 | 30.430 | 1.00 | 27.95 | A |
| ATOM | 1874 | CA | PRO | A | 307 | 24.842 | 26.110 | 31.405 | 1.00 | 26.59 | A |
| ATOM | 1875 | CB | PRO | A | 307 | 23.795 | 25.832 | 32.481 | 1.00 | 26.14 | A |
| ATOM | 1876 | CG | PRO | A | 307 | 22.531 | 26.250 | 31.803 | 1.00 | 27.86 | A |
| ATOM | 1877 | C | PRO | A | 307 | 26.145 | 25.355 | 31.659 | 1.00 | 25.58 | A |
| ATOM | 1878 | O | PRO | A | 307 | 27.189 | 25.964 | 31.900 | 1.00 | 22.65 | A |
| ATOM | 1879 | N | LYS | A | 308 | 26.085 | 24.031 | 31.620 | 1.00 | 24.46 | A |
| ATOM | 1880 | CA | LYS | A | 308 | 27.274 | 23.232 | 31.867 | 1.00 | 23.91 | A |
| ATOM | 1881 | CB | LYS | A | 308 | 26.887 | 21.760 | 32.024 | 1.00 | 23.25 | A |
| ATOM | 1882 | CG | LYS | A | 308 | 26.062 | 21.532 | 33.285 | 1.00 | 28.49 | A |
| ATOM | 1883 | CD | LYS | A | 308 | 25.618 | 20.093 | 33.466 | 1.00 | 30.17 | A |
| ATOM | 1884 | CE | LYS | A | 308 | 24.760 | 19.973 | 34.722 | 1.00 | 33.12 | A |
| ATOM | 1885 | NZ | LYS | A | 308 | 24.122 | 18.636 | 34.860 | 1.00 | 34.13 | A |
| ATOM | 1886 | C | LYS | A | 308 | 28.314 | 23.426 | 30.769 | 1.00 | 22.84 | A |
| ATOM | 1887 | O | LYS | A | 308 | 29.514 | 23.411 | 31.042 | 1.00 | 22.46 | A |
| ATOM | 1888 | N | ALA | A | 309 | 27.861 | 23.621 | 29.534 | 1.00 | 21.59 | A |
| ATOM | 1889 | CA | ALA | A | 309 | 28.792 | 23.848 | 28.432 | 1.00 | 20.02 | A |
| ATOM | 1890 | CB | ALA | A | 309 | 28.056 | 23.856 | 27.106 | 1.00 | 18.80 | A |
| ATOM | 1891 | C | ALA | A | 309 | 29.481 | 25.191 | 28.662 | 1.00 | 21.41 | A |
| ATOM | 1892 | O | ALA | A | 309 | 30.680 | 25.335 | 28.427 | 1.00 | 21.39 | A |
| ATOM | 1893 | N | ARG | A | 310 | 28.717 | 26.179 | 29.121 | 1.00 | 21.39 | A |
| ATOM | 1894 | CA | ARG | A | 310 | 29.290 | 27.494 | 29.388 | 1.00 | 22.02 | A |
| ATOM | 1895 | CB | ARG | A | 310 | 28.213 | 28.479 | 29.854 | 1.00 | 22.39 | A |
| ATOM | 1896 | CG | ARG | A | 310 | 28.806 | 29.756 | 30.436 | 1.00 | 25.30 | A |
| ATOM | 1897 | CD | ARG | A | 310 | 27.780 | 30.852 | 30.664 | 1.00 | 28.33 | A |
| ATOM | 1898 | NE | ARG | A | 310 | 28.420 | 32.039 | 31.230 | 1.00 | 30.18 | A |
| ATOM | 1899 | CZ | ARG | A | 310 | 27.901 | 33.263 | 31.203 | 1.00 | 32.07 | A |
| ATOM | 1900 | NH1 | ARG | A | 310 | 26.719 | 33.477 | 30.634 | 1.00 | 31.19 | A |
| ATOM | 1901 | NH2 | ARG | A | 310 | 28.567 | 34.277 | 31.742 | 1.00 | 30.49 | A |
| ATOM | 1902 | C | ARG | A | 310 | 30.376 | 27.388 | 30.458 | 1.00 | 21.65 | A |
| ATOM | 1903 | O | ARG | A | 310 | 31.464 | 27.949 | 30.311 | 1.00 | 20.36 | A |
| ATOM | 1904 | N | ASP | A | 311 | 30.074 | 26.677 | 31.541 | 1.00 | 19.57 | A |
| ATOM | 1905 | CA | ASP | A | 311 | 31.043 | 26.512 | 32.615 | 1.00 | 20.18 | A |
| ATOM | 1906 | CB | ASP | A | 311 | 30.460 | 25.649 | 33.739 | 1.00 | 20.39 | A |
| ATOM | 1907 | CG | ASP | A | 311 | 31.439 | 25.446 | 34.881 | 1.00 | 23.35 | A |
| ATOM | 1908 | OD1 | ASP | A | 311 | 32.158 | 24.428 | 34.885 | 1.00 | 24.91 | A |
| ATOM | 1909 | OD2 | ASP | A | 311 | 31.500 | 26.312 | 35.776 | 1.00 | 26.96 | A |
| ATOM | 1910 | C | ASP | A | 311 | 32.322 | 25.877 | 32.073 | 1.00 | 19.73 | A |

-continued

| | | | | | | | | | | |
|---|---|---|---|---|---|---|---|---|---|---|
| ATOM | 1911 | O | ASP | A | 311 | 33.422 | 26.289 | 32.439 | 1.00 | 19.30 | A |
| ATOM | 1912 | N | LEU | A | 312 | 32.179 | 24.891 | 31.188 | 1.00 | 16.32 | A |
| ATOM | 1913 | CA | LEU | A | 312 | 33.349 | 24.226 | 30.611 | 1.00 | 16.66 | A |
| ATOM | 1914 | CB | LEU | A | 312 | 32.927 | 23.035 | 29.744 | 1.00 | 16.12 | A |
| ATOM | 1915 | CG | LEU | A | 312 | 34.050 | 22.320 | 28.974 | 1.00 | 14.73 | A |
| ATOM | 1916 | CD1 | LEU | A | 312 | 35.192 | 21.935 | 29.912 | 1.00 | 14.56 | A |
| ATOM | 1917 | CD2 | LEU | A | 312 | 33.477 | 21.084 | 28.289 | 1.00 | 14.22 | A |
| ATOM | 1918 | C | LEU | A | 312 | 34.181 | 25.189 | 29.774 | 1.00 | 16.61 | A |
| ATOM | 1919 | O | LEU | A | 312 | 35.402 | 25.241 | 29.910 | 1.00 | 16.20 | A |
| ATOM | 1920 | N | VAL | A | 313 | 33.515 | 25.949 | 28.908 | 1.00 | 16.20 | A |
| ATOM | 1921 | CA | VAL | A | 313 | 34.207 | 26.907 | 28.058 | 1.00 | 15.37 | A |
| ATOM | 1922 | CB | VAL | A | 313 | 33.216 | 27.648 | 27.130 | 1.00 | 16.42 | A |
| ATOM | 1923 | CG1 | VAL | A | 313 | 33.915 | 28.796 | 26.426 | 1.00 | 16.93 | A |
| ATOM | 1924 | CG2 | VAL | A | 313 | 32.644 | 26.672 | 26.103 | 1.00 | 17.88 | A |
| ATOM | 1925 | C | VAL | A | 313 | 34.960 | 27.923 | 28.911 | 1.00 | 17.39 | A |
| ATOM | 1926 | O | VAL | A | 313 | 36.093 | 28.294 | 28.591 | 1.00 | 18.00 | A |
| ATOM | 1927 | N | GLU | A | 314 | 34.342 | 28.364 | 30.004 | 1.00 | 17.61 | A |
| ATOM | 1928 | CA | GLU | A | 314 | 34.986 | 29.331 | 30.885 | 1.00 | 20.43 | A |
| ATOM | 1929 | CB | GLU | A | 314 | 34.009 | 29.816 | 31.959 | 1.00 | 22.14 | A |
| ATOM | 1930 | CG | GLU | A | 314 | 32.800 | 30.550 | 31.396 | 1.00 | 26.52 | A |
| ATOM | 1931 | CD | GLU | A | 314 | 31.852 | 31.025 | 32.478 | 1.00 | 31.26 | A |
| ATOM | 1932 | OE1 | GLU | A | 314 | 31.580 | 30.246 | 33.417 | 1.00 | 33.48 | A |
| ATOM | 1933 | OE2 | GLU | A | 314 | 31.370 | 32.173 | 32.387 | 1.00 | 34.81 | A |
| ATOM | 1934 | C | GLU | A | 314 | 36.217 | 28.721 | 31.539 | 1.00 | 19.15 | A |
| ATOM | 1935 | O | GLU | A | 314 | 37.134 | 29.433 | 31.934 | 1.00 | 21.47 | A |
| ATOM | 1936 | N | LYS | A | 315 | 36.245 | 27.400 | 31.651 | 1.00 | 19.51 | A |
| ATOM | 1937 | CA | LYS | A | 315 | 37.394 | 26.749 | 32.258 | 1.00 | 19.17 | A |
| ATOM | 1938 | CB | LYS | A | 315 | 36.946 | 25.514 | 33.043 | 1.00 | 18.84 | A |
| ATOM | 1939 | CG | LYS | A | 315 | 36.280 | 25.885 | 34.368 | 1.00 | 19.62 | A |
| ATOM | 1940 | CD | LYS | A | 315 | 35.653 | 24.696 | 35.073 | 1.00 | 19.22 | A |
| ATOM | 1941 | CE | LYS | A | 315 | 35.070 | 25.095 | 36.427 | 1.00 | 21.00 | A |
| ATOM | 1942 | NZ | LYS | A | 315 | 36.119 | 25.552 | 37.381 | 1.00 | 19.53 | A |
| ATOM | 1943 | C | LYS | A | 315 | 38.452 | 26.393 | 31.218 | 1.00 | 18.96 | A |
| ATOM | 1944 | O | LYS | A | 315 | 39.511 | 25.873 | 31.561 | 1.00 | 19.85 | A |
| ATOM | 1945 | N | LEU | A | 316 | 38.164 | 26.691 | 29.950 | 1.00 | 17.08 | A |
| ATOM | 1946 | CA | LEU | A | 316 | 39.102 | 26.429 | 28.854 | 1.00 | 16.41 | A |
| ATOM | 1947 | CB | LEU | A | 316 | 38.414 | 25.636 | 27.738 | 1.00 | 13.81 | A |
| ATOM | 1948 | CG | LEU | A | 316 | 38.028 | 24.201 | 28.115 | 1.00 | 14.39 | A |
| ATOM | 1949 | CD1 | LEU | A | 316 | 37.139 | 23.597 | 27.031 | 1.00 | 12.38 | A |
| ATOM | 1950 | CD2 | LEU | A | 316 | 39.302 | 23.373 | 28.309 | 1.00 | 12.77 | A |
| ATOM | 1951 | C | LEU | A | 316 | 39.652 | 27.743 | 28.290 | 1.00 | 17.12 | A |
| ATOM | 1952 | O | LEU | A | 316 | 40.851 | 27.860 | 28.023 | 1.00 | 16.53 | A |
| ATOM | 1953 | N | LEU | A | 317 | 38.780 | 28.729 | 28.105 | 1.00 | 16.27 | A |
| ATOM | 1954 | CA | LEU | A | 317 | 39.228 | 30.022 | 27.596 | 1.00 | 17.52 | A |
| ATOM | 1955 | CB | LEU | A | 317 | 38.083 | 30.752 | 26.887 | 1.00 | 16.37 | A |
| ATOM | 1956 | CG | LEU | A | 317 | 37.448 | 29.973 | 25.727 | 1.00 | 18.81 | A |
| ATOM | 1957 | CD1 | LEU | A | 317 | 36.415 | 30.851 | 25.018 | 1.00 | 16.47 | A |
| ATOM | 1958 | CD2 | LEU | A | 317 | 38.528 | 29.526 | 24.741 | 1.00 | 17.87 | A |
| ATOM | 1959 | C | LEU | A | 317 | 39.745 | 30.841 | 28.774 | 1.00 | 18.27 | A |
| ATOM | 1960 | O | LEU | A | 317 | 39.078 | 31.753 | 29.273 | 1.00 | 18.58 | A |
| ATOM | 1961 | N | VAL | A | 318 | 40.937 | 30.475 | 29.229 | 1.00 | 18.02 | A |
| ATOM | 1962 | CA | VAL | A | 318 | 41.593 | 31.141 | 30.342 | 1.00 | 18.85 | A |
| ATOM | 1963 | CB | VAL | A | 318 | 41.846 | 30.153 | 31.500 | 1.00 | 19.91 | A |
| ATOM | 1964 | CG1 | VAL | A | 318 | 42.590 | 30.848 | 32.634 | 1.00 | 20.01 | A |
| ATOM | 1965 | CG2 | VAL | A | 318 | 40.520 | 29.584 | 31.990 | 1.00 | 19.44 | A |
| ATOM | 1966 | C | VAL | A | 318 | 42.923 | 31.657 | 29.811 | 1.00 | 19.67 | A |
| ATOM | 1967 | O | VAL | A | 318 | 43.690 | 30.902 | 29.208 | 1.00 | 18.26 | A |
| ATOM | 1968 | N | LEU | A | 319 | 43.197 | 32.939 | 30.028 | 1.00 | 20.07 | A |
| ATOM | 1969 | CA | LEU | A | 319 | 44.436 | 33.533 | 29.538 | 1.00 | 20.98 | A |
| ATOM | 1970 | CB | LEU | A | 319 | 44.521 | 35.002 | 29.968 | 1.00 | 21.64 | A |
| ATOM | 1971 | CG | LEU | A | 319 | 43.418 | 35.908 | 29.408 | 1.00 | 24.38 | A |
| ATOM | 1972 | CD1 | LEU | A | 319 | 43.606 | 37.332 | 29.935 | 1.00 | 23.28 | A |
| ATOM | 1973 | CD2 | LEU | A | 319 | 43.453 | 35.887 | 27.875 | 1.00 | 24.33 | A |
| ATOM | 1974 | C | LEU | A | 319 | 45.680 | 32.774 | 29.994 | 1.00 | 20.38 | A |
| ATOM | 1975 | O | LEU | A | 319 | 46.568 | 32.496 | 29.192 | 1.00 | 21.34 | A |
| ATOM | 1976 | N | ASP | A | 320 | 45.742 | 32.440 | 31.280 | 1.00 | 20.22 | A |
| ATOM | 1977 | CA | ASP | A | 320 | 46.879 | 31.707 | 31.833 | 1.00 | 20.90 | A |
| ATOM | 1978 | CB | ASP | A | 320 | 46.842 | 31.760 | 33.365 | 1.00 | 20.76 | A |
| ATOM | 1979 | CG | ASP | A | 320 | 48.049 | 31.102 | 34.004 | 1.00 | 21.51 | A |
| ATOM | 1980 | OD1 | ASP | A | 320 | 48.669 | 30.226 | 33.367 | 1.00 | 23.46 | A |
| ATOM | 1981 | OD2 | ASP | A | 320 | 48.371 | 31.450 | 35.159 | 1.00 | 23.89 | A |
| ATOM | 1982 | C | ASP | A | 320 | 46.814 | 30.247 | 31.367 | 1.00 | 20.06 | A |
| ATOM | 1983 | O | ASP | A | 320 | 45.988 | 29.476 | 31.840 | 1.00 | 20.54 | A |
| ATOM | 1984 | N | ALA | A | 321 | 47.700 | 29.876 | 30.451 | 1.00 | 20.68 | A |
| ATOM | 1985 | CA | ALA | A | 321 | 47.733 | 28.522 | 29.903 | 1.00 | 22.04 | A |
| ATOM | 1986 | CB | ALA | A | 321 | 48.860 | 28.411 | 28.881 | 1.00 | 20.75 | A |
| ATOM | 1987 | C | ALA | A | 321 | 47.858 | 27.400 | 30.940 | 1.00 | 21.62 | A |
| ATOM | 1988 | O | ALA | A | 321 | 47.482 | 26.259 | 30.665 | 1.00 | 21.99 | A |
| ATOM | 1989 | N | THR | A | 322 | 48.372 | 27.715 | 32.127 | 1.00 | 20.89 | A |

-continued

| | | | | | | | | | | |
|---|---|---|---|---|---|---|---|---|---|---|
| ATOM | 1990 | CA | THR | A | 322 | 48.531 | 26.698 | 33.167 | 1.00 | 20.82 | A |
| ATOM | 1991 | CB | THR | A | 322 | 49.670 | 27.051 | 34.146 | 1.00 | 19.47 | A |
| ATOM | 1992 | OG1 | THR | A | 322 | 49.341 | 28.253 | 34.848 | 1.00 | 20.19 | A |
| ATOM | 1993 | CG2 | THR | A | 322 | 50.981 | 27.249 | 33.394 | 1.00 | 21.59 | A |
| ATOM | 1994 | C | THR | A | 322 | 47.264 | 26.498 | 33.983 | 1.00 | 19.55 | A |
| ATOM | 1995 | O | THR | A | 322 | 47.235 | 25.673 | 34.894 | 1.00 | 21.13 | A |
| ATOM | 1996 | N | LYS | A | 323 | 46.216 | 27.248 | 33.661 | 1.00 | 19.33 | A |
| ATOM | 1997 | CA | LYS | A | 323 | 44.962 | 27.122 | 34.392 | 1.00 | 21.20 | A |
| ATOM | 1998 | CB | LYS | A | 323 | 44.580 | 28.460 | 35.030 | 1.00 | 23.75 | A |
| ATOM | 1999 | CG | LYS | A | 323 | 45.562 | 28.933 | 36.084 | 1.00 | 28.45 | A |
| ATOM | 2000 | CD | LYS | A | 323 | 45.055 | 30.177 | 36.799 | 1.00 | 33.76 | A |
| ATOM | 2001 | CE | LYS | A | 323 | 46.087 | 30.678 | 37.802 | 1.00 | 36.15 | A |
| ATOM | 2002 | NZ | LYS | A | 323 | 46.532 | 29.569 | 38.693 | 1.00 | 37.34 | A |
| ATOM | 2003 | C | LYS | A | 323 | 43.806 | 26.614 | 33.539 | 1.00 | 20.68 | A |
| ATOM | 2004 | O | LYS | A | 323 | 42.649 | 26.757 | 33.915 | 1.00 | 20.42 | A |
| ATOM | 2005 | N | ARG | A | 324 | 44.114 | 26.019 | 32.392 | 1.00 | 19.97 | A |
| ATOM | 2006 | CA | ARG | A | 324 | 43.060 | 25.494 | 31.531 | 1.00 | 17.98 | A |
| ATOM | 2007 | CB | ARG | A | 324 | 43.461 | 25.609 | 30.061 | 1.00 | 15.95 | A |
| ATOM | 2008 | CG | ARG | A | 324 | 43.534 | 27.050 | 29.603 | 1.00 | 17.34 | A |
| ATOM | 2009 | CD | ARG | A | 324 | 43.996 | 27.194 | 28.172 | 1.00 | 19.80 | A |
| ATOM | 2010 | NE | ARG | A | 324 | 44.438 | 28.565 | 27.944 | 1.00 | 16.93 | A |
| ATOM | 2011 | CZ | ARG | A | 324 | 45.410 | 28.908 | 27.108 | 1.00 | 19.88 | A |
| ATOM | 2012 | NH1 | ARG | A | 324 | 46.045 | 27.978 | 26.398 | 1.00 | 14.58 | A |
| ATOM | 2013 | NH2 | ARG | A | 324 | 45.774 | 30.181 | 27.015 | 1.00 | 16.51 | A |
| ATOM | 2014 | C | ARG | A | 324 | 42.762 | 24.046 | 31.883 | 1.00 | 18.32 | A |
| ATOM | 2015 | O | ARG | A | 324 | 43.673 | 23.222 | 32.006 | 1.00 | 18.20 | A |
| ATOM | 2016 | N | LEU | A | 325 | 41.479 | 23.748 | 32.055 | 1.00 | 18.32 | A |
| ATOM | 2017 | CA | LEU | A | 325 | 41.050 | 22.403 | 32.395 | 1.00 | 17.79 | A |
| ATOM | 2018 | CB | LEU | A | 325 | 39.523 | 22.335 | 32.425 | 1.00 | 17.03 | A |
| ATOM | 2019 | CG | LEU | A | 325 | 38.896 | 21.125 | 33.116 | 1.00 | 15.91 | A |
| ATOM | 2020 | CD1 | LEU | A | 325 | 39.392 | 21.048 | 34.557 | 1.00 | 15.93 | A |
| ATOM | 2021 | CD2 | LEU | A | 325 | 37.375 | 21.255 | 33.084 | 1.00 | 16.56 | A |
| ATOM | 2022 | C | LEU | A | 325 | 41.599 | 21.433 | 31.356 | 1.00 | 18.68 | A |
| ATOM | 2023 | O | LEU | A | 325 | 41.347 | 21.586 | 30.157 | 1.00 | 18.28 | A |
| ATOM | 2024 | N | GLY | A | 326 | 42.354 | 20.439 | 31.821 | 1.00 | 18.18 | A |
| ATOM | 2025 | CA | GLY | A | 326 | 42.931 | 19.462 | 30.915 | 1.00 | 16.36 | A |
| ATOM | 2026 | C | GLY | A | 326 | 44.443 | 19.558 | 30.807 | 1.00 | 19.15 | A |
| ATOM | 2027 | O | GLY | A | 326 | 45.093 | 18.592 | 30.404 | 1.00 | 19.52 | A |
| ATOM | 2028 | N | CYS | A | 327 | 45.016 | 20.708 | 31.161 | 1.00 | 18.16 | A |
| ATOM | 2029 | CA | CYS | A | 327 | 46.463 | 20.867 | 31.075 | 1.00 | 19.30 | A |
| ATOM | 2030 | CB | CYS | A | 327 | 46.856 | 22.350 | 31.058 | 1.00 | 20.22 | A |
| ATOM | 2031 | SG | CYS | A | 327 | 46.782 | 23.200 | 32.649 | 1.00 | 21.97 | A |
| ATOM | 2032 | C | CYS | A | 327 | 47.169 | 20.157 | 32.228 | 1.00 | 20.22 | A |
| ATOM | 2033 | O | CYS | A | 327 | 46.561 | 19.828 | 33.246 | 1.00 | 17.92 | A |
| ATOM | 2034 | N | GLU | A | 328 | 48.463 | 19.933 | 32.053 | 1.00 | 20.51 | A |
| ATOM | 2035 | CA | GLU | A | 328 | 49.274 | 19.244 | 33.042 | 1.00 | 23.34 | A |
| ATOM | 2036 | CB | GLU | A | 328 | 50.710 | 19.139 | 32.507 | 1.00 | 28.68 | A |
| ATOM | 2037 | CG | GLU | A | 328 | 50.754 | 18.367 | 31.175 | 1.00 | 38.24 | A |
| ATOM | 2038 | CD | GLU | A | 328 | 52.067 | 18.500 | 30.414 | 1.00 | 43.23 | A |
| ATOM | 2039 | OE1 | GLU | A | 328 | 52.535 | 19.643 | 30.218 | 1.00 | 46.22 | A |
| ATOM | 2040 | OE2 | GLU | A | 328 | 52.618 | 17.459 | 29.991 | 1.00 | 44.90 | A |
| ATOM | 2041 | C | GLU | A | 328 | 49.234 | 19.876 | 34.435 | 1.00 | 22.11 | A |
| ATOM | 2042 | O | GLU | A | 328 | 49.147 | 19.161 | 35.437 | 1.00 | 20.27 | A |
| ATOM | 2043 | N | GLU | A | 329 | 49.276 | 21.204 | 34.506 | 1.00 | 18.40 | A |
| ATOM | 2044 | CA | GLU | A | 329 | 49.248 | 21.875 | 35.801 | 1.00 | 20.13 | A |
| ATOM | 2045 | CB | GLU | A | 329 | 49.587 | 23.363 | 35.657 | 1.00 | 20.36 | A |
| ATOM | 2046 | CG | GLU | A | 329 | 51.014 | 23.651 | 35.190 | 1.00 | 24.05 | A |
| ATOM | 2047 | CD | GLU | A | 329 | 51.191 | 23.518 | 33.688 | 1.00 | 25.93 | A |
| ATOM | 2048 | OE1 | GLU | A | 329 | 50.213 | 23.154 | 32.995 | 1.00 | 26.61 | A |
| ATOM | 2049 | OE2 | GLU | A | 329 | 52.311 | 23.781 | 33.198 | 1.00 | 27.19 | A |
| ATOM | 2050 | C | GLU | A | 329 | 47.890 | 21.718 | 36.480 | 1.00 | 19.36 | A |
| ATOM | 2051 | O | GLU | A | 329 | 47.775 | 21.879 | 37.694 | 1.00 | 18.74 | A |
| ATOM | 2052 | N | MET | A | 330 | 46.863 | 21.415 | 35.691 | 1.00 | 17.28 | A |
| ATOM | 2053 | CA | MET | A | 330 | 45.520 | 21.220 | 36.229 | 1.00 | 16.38 | A |
| ATOM | 2054 | CB | MET | A | 330 | 44.474 | 21.833 | 35.294 | 1.00 | 17.65 | A |
| ATOM | 2055 | CG | MET | A | 330 | 44.460 | 23.365 | 35.311 | 1.00 | 22.95 | A |
| ATOM | 2056 | SD | MET | A | 330 | 44.186 | 24.026 | 36.979 | 1.00 | 26.78 | A |
| ATOM | 2057 | CE | MET | A | 330 | 42.435 | 23.712 | 37.186 | 1.00 | 24.69 | A |
| ATOM | 2058 | C | MET | A | 330 | 45.257 | 19.730 | 36.422 | 1.00 | 14.30 | A |
| ATOM | 2059 | O | MET | A | 330 | 44.127 | 19.304 | 36.629 | 1.00 | 15.39 | A |
| ATOM | 2060 | N | GLU | A | 331 | 46.327 | 18.949 | 36.346 | 1.00 | 15.60 | A |
| ATOM | 2061 | CA | GLU | A | 331 | 46.289 | 17.501 | 36.531 | 1.00 | 17.08 | A |
| ATOM | 2062 | CB | GLU | A | 331 | 45.607 | 17.155 | 37.862 | 1.00 | 17.00 | A |
| ATOM | 2063 | CG | GLU | A | 331 | 46.070 | 18.027 | 39.038 | 1.00 | 17.46 | A |
| ATOM | 2064 | CD | GLU | A | 331 | 47.591 | 18.179 | 39.145 | 1.00 | 20.16 | A |
| ATOM | 2065 | OE1 | GLU | A | 331 | 48.034 | 19.073 | 39.896 | 1.00 | 21.39 | A |
| ATOM | 2066 | OE2 | GLU | A | 331 | 48.345 | 17.420 | 38.500 | 1.00 | 18.87 | A |
| ATOM | 2067 | C | GLU | A | 331 | 45.697 | 16.658 | 35.398 | 1.00 | 17.80 | A |
| ATOM | 2068 | O | GLU | A | 331 | 45.107 | 15.602 | 35.636 | 1.00 | 20.40 | A |

-continued

| | | | | | | | | | | |
|---|---|---|---|---|---|---|---|---|---|---|
| ATOM | 2069 | N | GLY | A | 332 | 45.844 | 17.133 | 34.167 | 1.00 | 16.23 | A |
| ATOM | 2070 | CA | GLY | A | 332 | 45.420 | 16.353 | 33.015 | 1.00 | 14.10 | A |
| ATOM | 2071 | C | GLY | A | 332 | 43.982 | 16.154 | 32.596 | 1.00 | 13.54 | A |
| ATOM | 2072 | O | GLY | A | 332 | 43.063 | 16.864 | 33.017 | 1.00 | 11.96 | A |
| ATOM | 2073 | N | TYR | A | 333 | 43.804 | 15.141 | 31.750 | 1.00 | 14.37 | A |
| ATOM | 2074 | CA | TYR | A | 333 | 42.510 | 14.806 | 31.182 | 1.00 | 13.56 | A |
| ATOM | 2075 | CB | TYR | A | 333 | 42.722 | 13.892 | 29.968 | 1.00 | 15.00 | A |
| ATOM | 2076 | CG | TYR | A | 333 | 43.153 | 14.683 | 28.752 | 1.00 | 16.46 | A |
| ATOM | 2077 | CD1 | TYR | A | 333 | 42.206 | 15.172 | 27.849 | 1.00 | 15.29 | A |
| ATOM | 2078 | CE1 | TYR | A | 333 | 42.573 | 16.002 | 26.794 | 1.00 | 13.42 | A |
| ATOM | 2079 | CD2 | TYR | A | 333 | 44.490 | 15.039 | 28.561 | 1.00 | 14.91 | A |
| ATOM | 2080 | CE2 | TYR | A | 333 | 44.872 | 15.877 | 27.499 | 1.00 | 14.87 | A |
| ATOM | 2081 | CZ | TYR | A | 333 | 43.902 | 16.353 | 26.626 | 1.00 | 15.61 | A |
| ATOM | 2082 | OH | TYR | A | 333 | 44.244 | 17.197 | 25.599 | 1.00 | 17.29 | A |
| ATOM | 2083 | C | TYR | A | 333 | 41.470 | 14.230 | 32.127 | 1.00 | 15.23 | A |
| ATOM | 2084 | O | TYR | A | 333 | 40.278 | 14.323 | 31.846 | 1.00 | 16.63 | A |
| ATOM | 2085 | N | GLY | A | 334 | 41.907 | 13.650 | 33.244 | 1.00 | 15.50 | A |
| ATOM | 2086 | CA | GLY | A | 334 | 40.957 | 13.100 | 34.202 | 1.00 | 15.07 | A |
| ATOM | 2087 | C | GLY | A | 334 | 39.925 | 14.146 | 34.616 | 1.00 | 16.40 | A |
| ATOM | 2088 | O | GLY | A | 334 | 38.724 | 13.946 | 34.433 | 1.00 | 15.05 | A |
| ATOM | 2089 | N | PRO | A | 335 | 40.366 | 15.278 | 35.184 | 1.00 | 14.96 | A |
| ATOM | 2090 | CD | PRO | A | 335 | 41.727 | 15.531 | 35.689 | 1.00 | 15.88 | A |
| ATOM | 2091 | CA | PRO | A | 335 | 39.444 | 16.339 | 35.606 | 1.00 | 15.29 | A |
| ATOM | 2092 | CB | PRO | A | 335 | 40.383 | 17.397 | 36.178 | 1.00 | 13.19 | A |
| ATOM | 2093 | CG | PRO | A | 335 | 41.485 | 16.569 | 36.758 | 1.00 | 13.81 | A |
| ATOM | 2094 | C | PRO | A | 335 | 38.594 | 16.877 | 34.448 | 1.00 | 15.84 | A |
| ATOM | 2095 | O | PRO | A | 335 | 37.423 | 17.204 | 34.631 | 1.00 | 14.84 | A |
| ATOM | 2096 | N | LEU | A | 336 | 39.184 | 16.971 | 33.257 | 1.00 | 16.12 | A |
| ATOM | 2097 | CA | LEU | A | 336 | 38.450 | 17.465 | 32.094 | 1.00 | 15.52 | A |
| ATOM | 2098 | CB | LEU | A | 336 | 39.396 | 17.653 | 30.898 | 1.00 | 14.39 | A |
| ATOM | 2099 | CG | LEU | A | 336 | 38.770 | 17.991 | 29.538 | 1.00 | 15.46 | A |
| ATOM | 2100 | CD1 | LEU | A | 336 | 37.836 | 19.182 | 29.662 | 1.00 | 11.25 | A |
| ATOM | 2101 | CD2 | LEU | A | 336 | 39.884 | 18.285 | 28.528 | 1.00 | 14.11 | A |
| ATOM | 2102 | C | LEU | A | 336 | 37.321 | 16.508 | 31.714 | 1.00 | 16.28 | A |
| ATOM | 2103 | O | LEU | A | 336 | 36.176 | 16.921 | 31.540 | 1.00 | 15.51 | A |
| ATOM | 2104 | N | LYS | A | 337 | 37.640 | 15.225 | 31.592 | 1.00 | 17.22 | A |
| ATOM | 2105 | CA | LYS | A | 337 | 36.624 | 14.243 | 31.235 | 1.00 | 17.39 | A |
| ATOM | 2106 | CB | LYS | A | 337 | 37.293 | 12.900 | 30.921 | 1.00 | 17.68 | A |
| ATOM | 2107 | CG | LYS | A | 337 | 38.170 | 12.994 | 29.676 | 1.00 | 22.31 | A |
| ATOM | 2108 | CD | LYS | A | 337 | 39.213 | 11.892 | 29.592 | 1.00 | 24.60 | A |
| ATOM | 2109 | CE | LYS | A | 337 | 38.620 | 10.560 | 29.189 | 1.00 | 24.76 | A |
| ATOM | 2110 | NZ | LYS | A | 337 | 39.710 | 9.560 | 28.997 | 1.00 | 25.05 | A |
| ATOM | 2111 | C | LYS | A | 337 | 35.577 | 14.096 | 32.342 | 1.00 | 17.33 | A |
| ATOM | 2112 | O | LYS | A | 337 | 34.456 | 13.652 | 32.090 | 1.00 | 14.42 | A |
| ATOM | 2113 | N | ALA | A | 338 | 35.928 | 14.500 | 33.559 | 1.00 | 15.83 | A |
| ATOM | 2114 | CA | ALA | A | 338 | 34.989 | 14.395 | 34.674 | 1.00 | 17.52 | A |
| ATOM | 2115 | CB | ALA | A | 338 | 35.749 | 14.167 | 35.980 | 1.00 | 19.68 | A |
| ATOM | 2116 | C | ALA | A | 338 | 34.095 | 15.621 | 34.804 | 1.00 | 18.83 | A |
| ATOM | 2117 | O | ALA | A | 338 | 33.252 | 15.687 | 35.695 | 1.00 | 18.94 | A |
| ATOM | 2118 | N | HIS | A | 339 | 34.262 | 16.596 | 33.918 | 1.00 | 19.42 | A |
| ATOM | 2119 | CA | HIS | A | 339 | 33.438 | 17.796 | 34.004 | 1.00 | 19.28 | A |
| ATOM | 2120 | CB | HIS | A | 339 | 33.865 | 18.819 | 32.949 | 1.00 | 19.20 | A |
| ATOM | 2121 | CG | HIS | A | 339 | 33.163 | 20.134 | 33.074 | 1.00 | 20.26 | A |
| ATOM | 2122 | CD2 | HIS | A | 339 | 33.549 | 21.299 | 33.649 | 1.00 | 18.95 | A |
| ATOM | 2123 | ND1 | HIS | A | 339 | 31.880 | 20.340 | 32.612 | 1.00 | 19.10 | A |
| ATOM | 2124 | CE1 | HIS | A | 339 | 31.506 | 21.576 | 32.896 | 1.00 | 22.19 | A |
| ATOM | 2125 | NE2 | HIS | A | 339 | 32.500 | 22.179 | 33.525 | 1.00 | 21.98 | A |
| ATOM | 2126 | C | HIS | A | 339 | 31.957 | 17.448 | 33.845 | 1.00 | 19.13 | A |
| ATOM | 2127 | O | HIS | A | 339 | 31.597 | 16.576 | 33.061 | 1.00 | 19.52 | A |
| ATOM | 2128 | N | PRO | A | 340 | 31.079 | 18.125 | 34.606 | 1.00 | 19.80 | A |
| ATOM | 2129 | CD | PRO | A | 340 | 31.424 | 19.119 | 35.640 | 1.00 | 19.08 | A |
| ATOM | 2130 | CA | PRO | A | 340 | 29.630 | 17.900 | 34.569 | 1.00 | 20.52 | A |
| ATOM | 2131 | CB | PRO | A | 340 | 29.091 | 19.058 | 35.396 | 1.00 | 20.74 | A |
| ATOM | 2132 | CG | PRO | A | 340 | 30.146 | 19.207 | 36.454 | 1.00 | 19.20 | A |
| ATOM | 2133 | C | PRO | A | 340 | 29.000 | 17.834 | 33.176 | 1.00 | 21.42 | A |
| ATOM | 2134 | O | PRO | A | 340 | 28.049 | 17.088 | 32.955 | 1.00 | 22.48 | A |
| ATOM | 2135 | N | PHE | A | 341 | 29.528 | 18.606 | 32.237 | 1.00 | 21.33 | A |
| ATOM | 2136 | CA | PHE | A | 341 | 28.985 | 18.610 | 30.886 | 1.00 | 21.57 | A |
| ATOM | 2137 | CB | PHE | A | 341 | 29.739 | 19.624 | 30.017 | 1.00 | 21.64 | A |
| ATOM | 2138 | CG | PHE | A | 341 | 29.207 | 19.740 | 28.613 | 1.00 | 23.18 | A |
| ATOM | 2139 | CD1 | PHE | A | 341 | 27.903 | 20.171 | 28.382 | 1.00 | 22.58 | A |
| ATOM | 2140 | CD2 | PHE | A | 341 | 30.013 | 19.431 | 27.522 | 1.00 | 21.95 | A |
| ATOM | 2141 | CE1 | PHE | A | 341 | 27.410 | 20.292 | 27.082 | 1.00 | 23.54 | A |
| ATOM | 2142 | CE2 | PHE | A | 341 | 29.533 | 19.548 | 26.220 | 1.00 | 21.83 | A |
| ATOM | 2143 | CZ | PHE | A | 341 | 28.228 | 19.980 | 25.998 | 1.00 | 23.23 | A |
| ATOM | 2144 | C | PHE | A | 341 | 29.055 | 17.226 | 30.237 | 1.00 | 21.84 | A |
| ATOM | 2145 | O | PHE | A | 341 | 28.232 | 16.896 | 29.389 | 1.00 | 20.37 | A |
| ATOM | 2146 | N | PHE | A | 342 | 30.034 | 16.422 | 30.640 | 1.00 | 20.51 | A |
| ATOM | 2147 | CA | PHE | A | 342 | 30.221 | 15.085 | 30.077 | 1.00 | 23.01 | A |

|      |      |     |     |   | -continued |        |        |        |      |       |   |
|------|------|-----|-----|---|-----|--------|--------|--------|------|-------|---|
| ATOM | 2148 | CB  | PHE | A | 342 | 31.710 | 14.809 | 29.850 | 1.00 | 18.00 | A |
| ATOM | 2149 | CG  | PHE | A | 342 | 32.398 | 15.812 | 28.971 | 1.00 | 17.05 | A |
| ATOM | 2150 | CD1 | PHE | A | 342 | 32.010 | 15.987 | 27.652 | 1.00 | 17.78 | A |
| ATOM | 2151 | CD2 | PHE | A | 342 | 33.487 | 16.534 | 29.450 | 1.00 | 15.72 | A |
| ATOM | 2152 | CE1 | PHE | A | 342 | 32.702 | 16.867 | 26.811 | 1.00 | 18.08 | A |
| ATOM | 2153 | CE2 | PHE | A | 342 | 34.184 | 17.414 | 28.617 | 1.00 | 17.45 | A |
| ATOM | 2154 | CZ  | PHE | A | 342 | 33.790 | 17.578 | 27.298 | 1.00 | 16.56 | A |
| ATOM | 2155 | C   | PHE | A | 342 | 29.679 | 13.972 | 30.976 | 1.00 | 24.95 | A |
| ATOM | 2156 | O   | PHE | A | 342 | 30.002 | 12.798 | 30.777 | 1.00 | 23.95 | A |
| ATOM | 2157 | N   | GLU | A | 343 | 28.861 | 14.333 | 31.958 | 1.00 | 27.35 | A |
| ATOM | 2158 | CA  | GLU | A | 343 | 28.325 | 13.349 | 32.897 | 1.00 | 30.28 | A |
| ATOM | 2159 | CB  | GLU | A | 343 | 27.187 | 13.964 | 33.716 | 1.00 | 32.20 | A |
| ATOM | 2160 | CG  | GLU | A | 343 | 26.581 | 12.991 | 34.714 | 1.00 | 39.71 | A |
| ATOM | 2161 | CD  | GLU | A | 343 | 25.628 | 13.661 | 35.688 | 1.00 | 44.72 | A |
| ATOM | 2162 | OE1 | GLU | A | 343 | 24.661 | 14.314 | 35.234 | 1.00 | 47.55 | A |
| ATOM | 2163 | OE2 | GLU | A | 343 | 25.847 | 13.526 | 36.911 | 1.00 | 46.89 | A |
| ATOM | 2164 | C   | GLU | A | 343 | 27.852 | 12.017 | 32.305 | 1.00 | 28.98 | A |
| ATOM | 2165 | O   | GLU | A | 343 | 28.225 | 10.952 | 32.800 | 1.00 | 31.73 | A |
| ATOM | 2166 | N   | SER | A | 344 | 27.037 | 12.067 | 31.258 | 1.00 | 26.09 | A |
| ATOM | 2167 | CA  | SER | A | 344 | 26.520 | 10.838 | 30.656 | 1.00 | 28.36 | A |
| ATOM | 2168 | CB  | SER | A | 344 | 25.129 | 11.089 | 30.067 | 1.00 | 28.73 | A |
| ATOM | 2169 | OG  | SER | A | 344 | 25.203 | 11.942 | 28.940 | 1.00 | 30.91 | A |
| ATOM | 2170 | C   | SER | A | 344 | 27.407 | 10.214 | 29.577 | 1.00 | 27.66 | A |
| ATOM | 2171 | O   | SER | A | 344 | 26.987 | 9.281  | 28.900 | 1.00 | 28.66 | A |
| ATOM | 2172 | N   | VAL | A | 345 | 28.627 | 10.715 | 29.419 | 1.00 | 26.75 | A |
| ATOM | 2173 | CA  | VAL | A | 345 | 29.534 | 10.183 | 28.402 | 1.00 | 23.44 | A |
| ATOM | 2174 | CB  | VAL | A | 345 | 30.565 | 11.256 | 27.950 | 1.00 | 23.10 | A |
| ATOM | 2175 | CG1 | VAL | A | 345 | 31.589 | 10.631 | 26.995 | 1.00 | 22.24 | A |
| ATOM | 2176 | CG2 | VAL | A | 345 | 29.854 | 12.418 | 27.275 | 1.00 | 20.05 | A |
| ATOM | 2177 | C   | VAL | A | 345 | 30.326 | 8.957  | 28.855 | 1.00 | 24.26 | A |
| ATOM | 2178 | O   | VAL | A | 345 | 30.876 | 8.930  | 29.960 | 1.00 | 22.83 | A |
| ATOM | 2179 | N   | THR | A | 346 | 30.374 | 7.942  | 27.997 | 1.00 | 21.77 | A |
| ATOM | 2180 | CA  | THR | A | 346 | 31.153 | 6.740  | 28.272 | 1.00 | 23.70 | A |
| ATOM | 2181 | CB  | THR | A | 346 | 30.391 | 5.455  | 27.857 | 1.00 | 26.53 | A |
| ATOM | 2182 | OG1 | THR | A | 346 | 29.248 | 5.284  | 28.706 | 1.00 | 29.98 | A |
| ATOM | 2183 | CG2 | THR | A | 346 | 31.289 | 4.231  | 27.990 | 1.00 | 24.28 | A |
| ATOM | 2184 | C   | THR | A | 346 | 32.383 | 6.945  | 27.385 | 1.00 | 23.43 | A |
| ATOM | 2185 | O   | THR | A | 346 | 32.306 | 6.827  | 26.160 | 1.00 | 24.50 | A |
| ATOM | 2186 | N   | TRP | A | 347 | 33.508 | 7.270  | 28.013 | 1.00 | 22.98 | A |
| ATOM | 2187 | CA  | TRP | A | 347 | 34.744 | 7.569  | 27.300 | 1.00 | 23.81 | A |
| ATOM | 2188 | CB  | TRP | A | 347 | 35.683 | 8.352  | 28.219 | 1.00 | 22.54 | A |
| ATOM | 2189 | CG  | TRP | A | 347 | 35.128 | 9.658  | 28.693 | 1.00 | 20.61 | A |
| ATOM | 2190 | CD2 | TRP | A | 347 | 35.257 | 10.927 | 28.040 | 1.00 | 19.11 | A |
| ATOM | 2191 | CE2 | TRP | A | 347 | 34.581 | 11.881 | 28.838 | 1.00 | 18.39 | A |
| ATOM | 2192 | CE3 | TRP | A | 347 | 35.878 | 11.351 | 26.858 | 1.00 | 18.16 | A |
| ATOM | 2193 | CD1 | TRP | A | 347 | 34.397 | 9.883  | 29.828 | 1.00 | 18.35 | A |
| ATOM | 2194 | NE1 | TRP | A | 347 | 34.065 | 11.218 | 29.923 | 1.00 | 19.51 | A |
| ATOM | 2195 | CZ2 | TRP | A | 347 | 34.510 | 13.234 | 28.491 | 1.00 | 16.88 | A |
| ATOM | 2196 | CZ3 | TRP | A | 347 | 35.808 | 12.701 | 26.511 | 1.00 | 17.23 | A |
| ATOM | 2197 | CH2 | TRP | A | 347 | 35.127 | 13.624 | 27.327 | 1.00 | 18.16 | A |
| ATOM | 2198 | C   | TRP | A | 347 | 35.538 | 6.429  | 26.675 | 1.00 | 25.79 | A |
| ATOM | 2199 | O   | TRP | A | 347 | 36.304 | 6.654  | 25.742 | 1.00 | 24.67 | A |
| ATOM | 2200 | N   | ALA | A | 348 | 35.360 | 5.215  | 27.183 | 1.00 | 27.10 | A |
| ATOM | 2201 | CA  | ALA | A | 348 | 36.116 | 4.063  | 26.697 | 1.00 | 27.46 | A |
| ATOM | 2202 | CB  | ALA | A | 348 | 35.899 | 2.869  | 27.636 | 1.00 | 27.09 | A |
| ATOM | 2203 | C   | ALA | A | 348 | 35.895 | 3.620  | 25.256 | 1.00 | 27.18 | A |
| ATOM | 2204 | O   | ALA | A | 348 | 36.830 | 3.148  | 24.613 | 1.00 | 29.41 | A |
| ATOM | 2205 | N   | ASN | A | 349 | 34.682 | 3.769  | 24.735 | 1.00 | 26.55 | A |
| ATOM | 2206 | CA  | ASN | A | 349 | 34.418 | 3.310  | 23.375 | 1.00 | 27.28 | A |
| ATOM | 2207 | CB  | ASN | A | 349 | 33.700 | 1.962  | 23.444 | 1.00 | 29.37 | A |
| ATOM | 2208 | CG  | ASN | A | 349 | 32.299 | 2.088  | 24.013 | 1.00 | 30.92 | A |
| ATOM | 2209 | OD1 | ASN | A | 349 | 32.045 | 2.942  | 24.859 | 1.00 | 30.17 | A |
| ATOM | 2210 | ND2 | ASN | A | 349 | 31.386 | 1.237  | 23.553 | 1.00 | 33.52 | A |
| ATOM | 2211 | C   | ASN | A | 349 | 33.599 | 4.265  | 22.509 | 1.00 | 26.47 | A |
| ATOM | 2212 | O   | ASN | A | 349 | 32.669 | 3.843  | 21.819 | 1.00 | 25.87 | A |
| ATOM | 2213 | N   | LEU | A | 350 | 33.947 | 5.543  | 22.518 | 1.00 | 24.45 | A |
| ATOM | 2214 | CA  | LEU | A | 350 | 33.203 | 6.510  | 21.721 | 1.00 | 23.14 | A |
| ATOM | 2215 | CB  | LEU | A | 350 | 33.837 | 7.898  | 21.848 | 1.00 | 23.22 | A |
| ATOM | 2216 | CG  | LEU | A | 350 | 33.659 | 8.605  | 23.191 | 1.00 | 21.05 | A |
| ATOM | 2217 | CD1 | LEU | A | 350 | 34.646 | 9.756  | 23.293 | 1.00 | 19.36 | A |
| ATOM | 2218 | CD2 | LEU | A | 350 | 32.220 | 9.094  | 23.319 | 1.00 | 18.78 | A |
| ATOM | 2219 | C   | LEU | A | 350 | 33.082 | 6.152  | 20.240 | 1.00 | 22.60 | A |
| ATOM | 2220 | O   | LEU | A | 350 | 32.011 | 6.296  | 19.650 | 1.00 | 21.15 | A |
| ATOM | 2221 | N   | HIS | A | 351 | 34.165 | 5.689  | 19.627 | 1.00 | 23.13 | A |
| ATOM | 2222 | CA  | HIS | A | 351 | 34.089 | 5.387  | 18.204 | 1.00 | 27.83 | A |
| ATOM | 2223 | CB  | HIS | A | 351 | 35.506 | 5.325  | 17.596 | 1.00 | 29.36 | A |
| ATOM | 2224 | CG  | HIS | A | 351 | 36.082 | 3.950  | 17.493 | 1.00 | 32.07 | A |
| ATOM | 2225 | CD2 | HIS | A | 351 | 36.611 | 3.128  | 18.431 | 1.00 | 32.39 | A |
| ATOM | 2226 | ND1 | HIS | A | 351 | 36.197 | 3.285  | 16.291 | 1.00 | 33.02 | A |

-continued

| | | | | | | | | | | |
|---|---|---|---|---|---|---|---|---|---|---|
| ATOM | 2227 | CE1 | HIS | A | 351 | 36.775 | 2.113 | 16.493 | 1.00 | 33.58 | A |
| ATOM | 2228 | NE2 | HIS | A | 351 | 37.036 | 1.992 | 17.782 | 1.00 | 31.76 | A |
| ATOM | 2229 | C | HIS | A | 351 | 33.258 | 4.144 | 17.874 | 1.00 | 28.12 | A |
| ATOM | 2230 | O | HIS | A | 351 | 33.015 | 3.847 | 16.707 | 1.00 | 29.49 | A |
| ATOM | 2231 | N | GLN | A | 352 | 32.800 | 3.442 | 18.908 | 1.00 | 29.28 | A |
| ATOM | 2232 | CA | GLN | A | 352 | 31.963 | 2.255 | 18.726 | 1.00 | 29.67 | A |
| ATOM | 2233 | CB | GLN | A | 352 | 32.366 | 1.145 | 19.694 | 1.00 | 30.56 | A |
| ATOM | 2234 | CG | GLN | A | 352 | 33.169 | 0.041 | 19.041 | 1.00 | 30.88 | A |
| ATOM | 2235 | CD | GLN | A | 352 | 34.493 | −0.186 | 19.729 | 1.00 | 31.21 | A |
| ATOM | 2236 | OE1 | GLN | A | 352 | 34.541 | −0.450 | 20.928 | 1.00 | 30.76 | A |
| ATOM | 2237 | NE2 | GLN | A | 352 | 35.578 | −0.084 | 18.971 | 1.00 | 32.30 | A |
| ATOM | 2238 | C | GLN | A | 352 | 30.504 | 2.638 | 18.963 | 1.00 | 30.42 | A |
| ATOM | 2239 | O | GLN | A | 352 | 29.595 | 1.831 | 18.770 | 1.00 | 29.01 | A |
| ATOM | 2240 | N | GLN | A | 353 | 30.290 | 3.875 | 19.397 | 1.00 | 27.64 | A |
| ATOM | 2241 | CA | GLN | A | 353 | 28.948 | 4.365 | 19.652 | 1.00 | 27.42 | A |
| ATOM | 2242 | CB | GLN | A | 353 | 28.977 | 5.401 | 20.775 | 1.00 | 25.77 | A |
| ATOM | 2243 | CG | GLN | A | 353 | 29.408 | 4.837 | 22.115 | 1.00 | 27.34 | A |
| ATOM | 2244 | CD | GLN | A | 353 | 29.638 | 5.914 | 23.156 | 1.00 | 27.19 | A |
| ATOM | 2245 | OE1 | GLN | A | 353 | 28.875 | 6.872 | 23.252 | 1.00 | 28.29 | A |
| ATOM | 2246 | NE2 | GLN | A | 353 | 30.687 | 5.753 | 23.951 | 1.00 | 28.79 | A |
| ATOM | 2247 | C | GLN | A | 353 | 28.375 | 4.989 | 18.385 | 1.00 | 29.00 | A |
| ATOM | 2248 | O | GLN | A | 353 | 29.118 | 5.455 | 17.516 | 1.00 | 29.14 | A |
| ATOM | 2249 | N | THR | A | 354 | 27.053 | 4.984 | 18.276 | 1.00 | 27.31 | A |
| ATOM | 2250 | CA | THR | A | 354 | 26.390 | 5.568 | 17.119 | 1.00 | 27.85 | A |
| ATOM | 2251 | CB | THR | A | 354 | 24.991 | 4.941 | 16.904 | 1.00 | 30.69 | A |
| ATOM | 2252 | OG1 | THR | A | 354 | 25.132 | 3.532 | 16.665 | 1.00 | 30.07 | A |
| ATOM | 2253 | CG2 | THR | A | 354 | 24.289 | 5.585 | 15.709 | 1.00 | 29.58 | A |
| ATOM | 2254 | C | THR | A | 354 | 26.244 | 7.062 | 17.376 | 1.00 | 26.85 | A |
| ATOM | 2255 | O | THR | A | 354 | 25.592 | 7.475 | 18.329 | 1.00 | 25.77 | A |
| ATOM | 2256 | N | PRO | A | 355 | 26.867 | 7.898 | 16.533 | 1.00 | 27.22 | A |
| ATOM | 2257 | CD | PRO | A | 355 | 27.792 | 7.588 | 15.431 | 1.00 | 25.89 | A |
| ATOM | 2258 | CA | PRO | A | 355 | 26.763 | 9.346 | 16.734 | 1.00 | 27.23 | A |
| ATOM | 2259 | CB | PRO | A | 355 | 27.625 | 9.915 | 15.609 | 1.00 | 24.91 | A |
| ATOM | 2260 | CG | PRO | A | 355 | 28.643 | 8.838 | 15.385 | 1.00 | 25.54 | A |
| ATOM | 2261 | C | PRO | A | 355 | 25.322 | 9.837 | 16.641 | 1.00 | 28.07 | A |
| ATOM | 2262 | O | PRO | A | 355 | 24.548 | 9.364 | 15.810 | 1.00 | 27.24 | A |
| ATOM | 2263 | N | PRO | A | 356 | 24.941 | 10.792 | 17.500 | 1.00 | 28.28 | A |
| ATOM | 2264 | CD | PRO | A | 356 | 25.752 | 11.560 | 18.462 | 1.00 | 28.31 | A |
| ATOM | 2265 | CA | PRO | A | 356 | 23.572 | 11.306 | 17.448 | 1.00 | 28.44 | A |
| ATOM | 2266 | CB | PRO | A | 356 | 23.539 | 12.301 | 18.604 | 1.00 | 28.11 | A |
| ATOM | 2267 | CG | PRO | A | 356 | 24.946 | 12.832 | 18.612 | 1.00 | 26.86 | A |
| ATOM | 2268 | C | PRO | A | 356 | 23.363 | 11.978 | 16.097 | 1.00 | 29.25 | A |
| ATOM | 2269 | O | PRO | A | 356 | 24.304 | 12.537 | 15.529 | 1.00 | 27.27 | A |
| ATOM | 2270 | N | ALA | A | 357 | 22.143 | 11.910 | 15.575 | 1.00 | 30.45 | A |
| ATOM | 2271 | CA | ALA | A | 357 | 21.848 | 12.521 | 14.287 | 1.00 | 32.81 | A |
| ATOM | 2272 | CB | ALA | A | 357 | 20.507 | 12.019 | 13.757 | 1.00 | 31.99 | A |
| ATOM | 2273 | C | ALA | A | 357 | 21.824 | 14.035 | 14.448 | 1.00 | 35.05 | A |
| ATOM | 2274 | O | ALA | A | 357 | 21.194 | 14.561 | 15.369 | 1.00 | 35.04 | A |
| ATOM | 2275 | N | LEU | A | 358 | 22.516 | 14.730 | 13.552 | 1.00 | 37.81 | A |
| ATOM | 2276 | CA | LEU | A | 358 | 22.578 | 16.185 | 13.597 | 1.00 | 42.15 | A |
| ATOM | 2277 | CB | LEU | A | 358 | 23.679 | 16.681 | 12.658 | 1.00 | 39.54 | A |
| ATOM | 2278 | CG | LEU | A | 358 | 25.086 | 16.285 | 13.109 | 1.00 | 39.51 | A |
| ATOM | 2279 | CD1 | LEU | A | 358 | 26.102 | 16.686 | 12.062 | 1.00 | 39.29 | A |
| ATOM | 2280 | CD2 | LEU | A | 358 | 25.395 | 16.953 | 14.445 | 1.00 | 40.01 | A |
| ATOM | 2281 | C | LEU | A | 358 | 21.241 | 16.837 | 13.242 | 1.00 | 45.91 | A |
| ATOM | 2282 | O | LEU | A | 358 | 20.874 | 16.927 | 12.069 | 1.00 | 45.71 | A |
| ATOM | 2283 | N | THR | A | 359 | 20.530 | 17.290 | 14.275 | 1.00 | 50.06 | A |
| ATOM | 2284 | CA | THR | A | 359 | 19.223 | 17.939 | 14.140 | 1.00 | 53.73 | A |
| ATOM | 2285 | CB | THR | A | 359 | 19.353 | 19.428 | 13.726 | 1.00 | 54.04 | A |
| ATOM | 2286 | OG1 | THR | A | 359 | 19.995 | 19.521 | 12.448 | 1.00 | 56.35 | A |
| ATOM | 2287 | CG2 | THR | A | 359 | 20.158 | 20.204 | 14.763 | 1.00 | 54.32 | A |
| ATOM | 2288 | C | THR | A | 359 | 18.309 | 17.236 | 13.139 | 1.00 | 54.47 | A |
| ATOM | 2289 | O | THR | A | 359 | 18.483 | 16.016 | 12.930 | 1.00 | 55.90 | A |
| ATOM | 2290 | OXT | THR | A | 359 | 17.407 | 17.908 | 12.595 | 1.00 | 56.97 | A |
| ATOM | 2291 | OH2 | TIP | S | 1 | 42.566 | 19.118 | 34.302 | 1.00 | 15.09 | S |
| ATOM | 2292 | OH2 | TIP | S | 2 | 41.052 | 32.378 | 19.857 | 1.00 | 15.82 | S |
| ATOM | 2293 | OH2 | TIP | S | 3 | 37.014 | 33.030 | 17.747 | 1.00 | 16.95 | S |
| ATOM | 2294 | OH2 | TIP | S | 5 | 45.353 | 24.370 | 18.152 | 1.00 | 16.85 | S |
| ATOM | 2295 | OH2 | TIP | S | 6 | 31.896 | 13.930 | 33.235 | 1.00 | 20.42 | S |
| ATOM | 2296 | OH2 | TIP | S | 7 | 50.351 | 22.781 | 28.249 | 1.00 | 21.14 | S |
| ATOM | 2297 | OH2 | TIP | S | 8 | 45.246 | −0.589 | −0.734 | 1.00 | 17.74 | S |
| ATOM | 2298 | OH2 | TIP | S | 11 | 46.249 | −0.348 | −8.523 | 1.00 | 21.32 | S |
| ATOM | 2299 | OH2 | TIP | S | 14 | 45.756 | 11.148 | 29.680 | 1.00 | 21.94 | S |
| ATOM | 2300 | OH2 | TIP | S | 15 | 44.273 | 13.157 | 34.592 | 1.00 | 15.61 | S |
| ATOM | 2301 | OH2 | TIP | S | 17 | 53.598 | 3.722 | −1.720 | 1.00 | 21.45 | S |
| ATOM | 2302 | OH2 | TIP | S | 18 | 46.049 | 13.087 | 31.565 | 1.00 | 20.35 | S |
| ATOM | 2303 | OH2 | TIP | S | 19 | 53.422 | 22.401 | −3.280 | 1.00 | 23.26 | S |
| ATOM | 2304 | OH2 | TIP | S | 20 | 34.587 | 7.922 | 5.383 | 1.00 | 22.58 | S |
| ATOM | 2305 | OH2 | TIP | S | 21 | 45.053 | 27.379 | 19.376 | 1.00 | 29.60 | S |

-continued

| ATOM | 2306 | OH2 | TIP | S | 23 | 28.899 | 36.416 | 28.633 | 1.00 | 31.68 | S |
| --- | --- | --- | --- | --- | --- | --- | --- | --- | --- | --- | --- |
| ATOM | 2307 | OH2 | TIP | S | 24 | 35.531 | 11.645 | −8.219 | 1.00 | 23.45 | S |
| ATOM | 2308 | OH2 | TIP | S | 25 | 47.364 | 28.787 | 19.612 | 1.00 | 23.03 | S |
| ATOM | 2309 | OH2 | TIP | S | 27 | 48.859 | 21.588 | 12.634 | 1.00 | 23.76 | S |
| ATOM | 2310 | OH2 | TIP | S | 29 | 48.805 | 8.920 | 23.626 | 1.00 | 22.23 | S |
| ATOM | 2311 | OH2 | TIP | S | 31 | 48.619 | 7.247 | 10.112 | 1.00 | 21.32 | S |
| ATOM | 2312 | OH2 | TIP | S | 34 | 44.824 | 28.720 | 15.621 | 1.00 | 25.27 | S |
| ATOM | 2313 | OH2 | TIP | S | 35 | 26.030 | 12.634 | 13.407 | 1.00 | 21.61 | S |
| ATOM | 2314 | OH2 | TIP | S | 36 | 50.462 | 19.810 | 40.066 | 1.00 | 25.45 | S |
| ATOM | 2315 | OH2 | TIP | S | 37 | 39.631 | 23.510 | −0.239 | 1.00 | 30.88 | S |
| ATOM | 2316 | OH2 | TIP | S | 40 | 44.734 | 42.655 | 10.346 | 1.00 | 30.84 | S |
| ATOM | 2317 | OH2 | TIP | S | 41 | 54.653 | 3.902 | 1.503 | 1.00 | 27.14 | S |
| ATOM | 2318 | OH2 | TIP | S | 45 | 45.693 | 21.923 | 39.754 | 1.00 | 28.30 | S |
| ATOM | 2319 | OH2 | TIP | S | 47 | 47.820 | 16.413 | 7.805 | 1.00 | 25.73 | S |
| ATOM | 2320 | OH2 | TIP | S | 48 | 50.292 | 31.412 | 29.642 | 1.00 | 32.79 | S |
| ATOM | 2321 | OH2 | TIP | S | 49 | 26.056 | 16.646 | 34.827 | 1.00 | 29.80 | S |
| ATOM | 2322 | OH2 | TIP | S | 52 | 31.714 | 10.996 | 31.855 | 1.00 | 29.15 | S |
| ATOM | 2323 | OH2 | TIP | S | 53 | 46.108 | 23.843 | −4.299 | 1.00 | 24.21 | S |
| ATOM | 2324 | OH2 | TIP | S | 54 | 37.645 | 11.206 | 34.448 | 1.00 | 28.56 | S |
| ATOM | 2325 | OH2 | TIP | S | 55 | 26.371 | 28.513 | 12.142 | 1.00 | 32.08 | S |
| ATOM | 2326 | OH2 | TIP | S | 58 | 33.564 | 19.700 | 3.483 | 1.00 | 28.28 | S |
| ATOM | 2327 | OH2 | TIP | S | 64 | 48.295 | −0.632 | 14.280 | 1.00 | 32.13 | S |
| ATOM | 2328 | OH2 | TIP | S | 65 | 40.064 | 26.036 | 34.324 | 1.00 | 24.17 | S |
| ATOM | 2329 | OH2 | TIP | S | 66 | 29.570 | 3.958 | 14.729 | 1.00 | 28.94 | S |
| ATOM | 2330 | OH2 | TIP | S | 72 | 60.085 | 11.604 | 6.814 | 1.00 | 38.35 | S |
| ATOM | 2331 | OH2 | TIP | S | 73 | 39.203 | 44.403 | 18.686 | 1.00 | 26.61 | S |
| ATOM | 2332 | OH2 | TIP | S | 76 | 47.312 | 12.366 | 27.366 | 1.00 | 28.51 | S |
| ATOM | 2333 | OH2 | TIP | S | 80 | 43.862 | 33.771 | 33.329 | 1.00 | 28.82 | S |
| ATOM | 2334 | OH2 | TIP | S | 81 | 57.890 | 13.106 | 2.128 | 1.00 | 40.62 | S |
| ATOM | 2335 | OH2 | TIP | S | 82 | 41.663 | 34.381 | 32.043 | 1.00 | 19.35 | S |
| ATOM | 2336 | OH2 | TIP | S | 85 | 50.974 | 40.331 | 19.200 | 1.00 | 21.14 | S |
| ATOM | 2337 | OH2 | TIP | S | 88 | 47.925 | −0.832 | −6.556 | 1.00 | 24.11 | S |
| ATOM | 2338 | OH2 | TIP | S | 90 | 27.231 | 28.336 | 33.481 | 1.00 | 27.64 | S |
| ATOM | 2339 | OH2 | TIP | S | 91 | 43.651 | −7.101 | −7.995 | 1.00 | 24.33 | S |
| ATOM | 2340 | OH2 | TIP | S | 92 | 49.325 | 4.387 | 19.370 | 1.00 | 28.02 | S |
| ATOM | 2341 | OH2 | TIP | S | 93 | 46.231 | 11.549 | 33.898 | 1.00 | 29.40 | S |
| ATOM | 2342 | OH2 | TIP | S | 94 | 63.889 | 24.831 | 1.168 | 1.00 | 26.53 | S |
| ATOM | 2343 | OH2 | TIP | S | 96 | 56.396 | 4.952 | −6.749 | 1.00 | 28.00 | S |
| ATOM | 2344 | OH2 | TIP | S | 98 | 35.510 | 27.986 | 11.558 | 1.00 | 29.24 | S |
| ATOM | 2345 | OH2 | TIP | S | 100 | 49.942 | 24.366 | 30.265 | 1.00 | 31.61 | S |
| ATOM | 2346 | OH2 | TIP | S | 101 | 56.121 | 7.113 | −8.298 | 1.00 | 31.57 | S |
| ATOM | 2347 | OH2 | TIP | S | 102 | 58.318 | 19.957 | −8.378 | 1.00 | 26.95 | S |
| ATOM | 2348 | OH2 | TIP | S | 103 | 49.647 | 22.446 | 39.624 | 1.00 | 40.57 | S |
| ATOM | 2349 | OH2 | TIP | S | 104 | 45.359 | 7.052 | 13.052 | 1.00 | 26.27 | S |
| ATOM | 2350 | OH2 | TIP | S | 105 | 37.150 | 32.340 | 32.346 | 1.00 | 34.45 | S |
| ATOM | 2351 | OH2 | TIP | S | 107 | 43.465 | 40.457 | 8.240 | 1.00 | 40.48 | S |
| ATOM | 2352 | OH2 | TIP | S | 119 | 36.644 | 8.257 | 13.418 | 1.00 | 30.70 | S |
| ATOM | 2353 | OH2 | TIP | S | 123 | 41.912 | −8.974 | −8.264 | 1.00 | 26.08 | S |
| ATOM | 2354 | OH2 | TIP | S | 124 | 62.424 | 15.800 | −7.411 | 1.00 | 24.08 | S |
| ATOM | 2355 | OH2 | TIP | S | 126 | 37.266 | 18.656 | −9.097 | 1.00 | 28.99 | S |
| ATOM | 2356 | OH2 | TIP | S | 127 | 43.129 | 26.845 | 14.606 | 1.00 | 25.19 | S |
| ATOM | 2357 | OH2 | TIP | S | 128 | 36.339 | 32.639 | 29.802 | 1.00 | 29.25 | S |
| ATOM | 2358 | OH2 | TIP | S | 130 | 54.051 | 14.561 | 26.498 | 1.00 | 33.93 | S |
| ATOM | 2359 | OH2 | TIP | S | 131 | 41.805 | −4.242 | 5.492 | 1.00 | 33.72 | S |
| ATOM | 2360 | OH2 | TIP | S | 133 | 38.873 | 25.163 | 36.697 | 1.00 | 30.69 | S |
| ATOM | 2361 | OH2 | TIP | S | 134 | 28.777 | 8.553 | 25.307 | 1.00 | 31.43 | S |
| ATOM | 2362 | OH2 | TIP | S | 135 | 53.672 | 10.546 | −12.803 | 1.00 | 33.45 | S |
| ATOM | 2363 | OH2 | TIP | S | 136 | 59.892 | 15.434 | 11.467 | 1.00 | 31.39 | S |
| ATOM | 2364 | OH2 | TIP | S | 137 | 31.040 | 12.361 | 35.470 | 1.00 | 34.07 | S |
| ATOM | 2365 | OH2 | TIP | S | 139 | 33.489 | 14.292 | −0.598 | 1.00 | 40.68 | S |
| ATOM | 2366 | OH2 | TIP | S | 140 | 46.918 | 8.748 | 11.662 | 1.00 | 29.23 | S |
| ATOM | 2367 | OH2 | TIP | S | 141 | 46.297 | −7.287 | −9.196 | 1.00 | 42.20 | S |
| ATOM | 2368 | OH2 | TIP | S | 142 | 58.193 | 6.715 | −4.685 | 1.00 | 35.48 | S |
| ATOM | 2369 | OH2 | TIP | S | 143 | 44.598 | 4.435 | 12.503 | 1.00 | 27.68 | S |
| ATOM | 2370 | OH2 | TIP | S | 144 | 27.003 | 5.999 | 12.450 | 1.00 | 36.30 | S |
| ATOM | 2371 | OH2 | TIP | S | 145 | 43.676 | 32.852 | 35.735 | 1.00 | 35.70 | S |
| ATOM | 2372 | OH2 | TIP | S | 146 | 35.783 | 18.628 | 36.452 | 1.00 | 34.62 | S |
| ATOM | 2373 | OH2 | TIP | S | 147 | 25.402 | 4.058 | 20.638 | 1.00 | 45.03 | S |
| ATOM | 2374 | OH2 | TIP | S | 148 | 45.839 | 35.853 | 33.724 | 1.00 | 35.47 | S |
| ATOM | 2375 | OH2 | TIP | S | 149 | 22.176 | 18.976 | 16.752 | 1.00 | 31.87 | S |
| ATOM | 2376 | OH2 | TIP | S | 150 | 43.986 | 33.179 | 10.162 | 1.00 | 37.70 | S |
| ATOM | 2377 | OH2 | TIP | S | 151 | 50.653 | 20.347 | 42.428 | 1.00 | 35.80 | S |
| ATOM | 2378 | OH2 | TIP | S | 152 | 47.843 | 24.314 | 9.506 | 1.00 | 31.05 | S |
| ATOM | 2379 | OH2 | TIP | S | 153 | 44.693 | 5.273 | −14.175 | 1.00 | 29.90 | S |
| ATOM | 2380 | OH2 | TIP | S | 155 | 26.560 | 36.851 | 31.684 | 1.00 | 49.29 | S |
| ATOM | 2381 | OH2 | TIP | S | 156 | 46.867 | 8.019 | −12.951 | 1.00 | 29.21 | S |
| ATOM | 2382 | OH2 | TIP | S | 157 | 30.432 | 28.741 | 12.438 | 1.00 | 37.76 | S |
| ATOM | 2383 | OH2 | TIP | S | 158 | 41.004 | 20.553 | 6.423 | 1.00 | 39.53 | S |
| ATOM | 2384 | OH2 | TIP | S | 159 | 49.258 | 20.069 | 29.294 | 1.00 | 33.97 | S |

-continued

| | | | | | | | | | | |
|---|---|---|---|---|---|---|---|---|---|---|
| ATOM | 2385 | OH2 | TIP | S | 160 | 48.082 | 28.459 | 16.489 | 1.00 | 33.10 | S |
| ATOM | 2386 | OH2 | TIP | S | 161 | 47.448 | 18.625 | 27.683 | 1.00 | 34.87 | S |
| ATOM | 2387 | OH2 | TIP | S | 162 | 19.687 | 20.632 | 23.411 | 1.00 | 35.01 | S |
| ATOM | 2388 | OH2 | TIP | S | 163 | 32.402 | −1.266 | 22.443 | 1.00 | 37.26 | S |
| ATOM | 2389 | OH2 | TIP | S | 164 | 39.475 | 33.468 | 33.237 | 1.00 | 35.34 | S |
| ATOM | 2390 | OH2 | TIP | S | 165 | 44.277 | 18.950 | 5.162 | 1.00 | 45.14 | S |
| ATOM | 2391 | OH2 | TIP | S | 166 | 34.797 | 30.523 | 10.736 | 1.00 | 47.55 | S |
| ATOM | 2392 | OH2 | TIP | S | 167 | 46.541 | 3.526 | −14.949 | 1.00 | 26.54 | S |
| ATOM | 2393 | OH2 | TIP | S | 168 | 36.333 | 16.371 | 1.539 | 1.00 | 38.68 | S |
| ATOM | 2394 | OH2 | TIP | S | 169 | 46.761 | 38.936 | 27.403 | 1.00 | 34.66 | S |
| ATOM | 2395 | OH2 | TIP | S | 170 | 24.163 | 13.264 | 11.375 | 1.00 | 41.23 | S |
| ATOM | 2396 | OH2 | TIP | S | 171 | 48.459 | 15.018 | 31.951 | 1.00 | 38.11 | S |
| ATOM | 2397 | OH2 | TIP | S | 172 | 34.261 | 23.193 | 40.004 | 1.00 | 48.96 | S |
| ATOM | 2398 | OH2 | TIP | S | 173 | 45.924 | −0.026 | 13.224 | 1.00 | 39.55 | S |
| ATOM | 2399 | OH2 | TIP | S | 175 | 41.384 | 37.389 | 32.543 | 1.00 | 40.74 | S |
| ATOM | 2400 | OH2 | TIP | S | 177 | 49.394 | 35.312 | 27.150 | 1.00 | 44.33 | S |
| ATOM | 2401 | OH2 | TIP | S | 178 | 29.066 | 29.942 | 34.359 | 1.00 | 41.46 | S |
| ATOM | 2402 | OH2 | TIP | S | 180 | 49.354 | 19.467 | 7.273 | 1.00 | 34.56 | S |
| ATOM | 2403 | OH2 | TIP | S | 181 | 25.298 | 17.029 | 31.863 | 1.00 | 47.74 | S |
| ATOM | 2404 | OH2 | TIP | S | 182 | 37.071 | 25.027 | 4.669 | 1.00 | 43.87 | S |
| ATOM | 2405 | OH2 | TIP | S | 183 | 22.581 | 7.487 | 18.691 | 1.00 | 41.75 | S |
| ATOM | 2406 | OH2 | TIP | S | 184 | 32.269 | 7.011 | −1.891 | 1.00 | 48.84 | S |
| ATOM | 2407 | OH2 | TIP | S | 185 | 48.234 | 0.494 | 6.833 | 1.00 | 48.16 | S |
| ATOM | 2408 | OH2 | TIP | S | 187 | 20.008 | 14.658 | 19.211 | 1.00 | 45.27 | S |
| ATOM | 2409 | OH2 | TIP | S | 188 | 49.341 | 22.698 | 42.272 | 1.00 | 42.20 | S |
| ATOM | 2410 | OH2 | TIP | S | 190 | 61.292 | 18.260 | −8.097 | 1.00 | 45.21 | S |
| ATOM | 2411 | OH2 | TIP | S | 191 | 28.152 | 10.606 | 2.819 | 1.00 | 40.38 | S |
| ATOM | 2412 | OH2 | TIP | S | 192 | 25.626 | 12.619 | 23.191 | 1.00 | 34.27 | S |
| ATOM | 2413 | OH2 | TIP | S | 193 | 59.876 | 11.603 | 1.216 | 1.00 | 46.54 | S |
| ATOM | 2414 | OH2 | TIP | S | 194 | 57.592 | 21.183 | −10.646 | 1.00 | 45.82 | S |
| ATOM | 2415 | OH2 | TIP | S | 195 | 31.509 | 36.649 | 21.499 | 1.00 | 38.73 | S |
| ATOM | 2416 | OH2 | TIP | S | 197 | 50.270 | −1.543 | −6.136 | 1.00 | 42.66 | S |
| ATOM | 2417 | OH2 | TIP | S | 198 | 24.467 | 8.729 | 13.088 | 1.00 | 42.78 | S |
| ATOM | 2418 | OH2 | TIP | S | 199 | 38.098 | 8.699 | 25.759 | 1.00 | 32.80 | S |
| ATOM | 2419 | OH2 | TIP | S | 200 | 57.831 | 11.358 | −13.255 | 1.00 | 45.31 | S |
| ATOM | 2420 | OH2 | TIP | S | 201 | 23.888 | 22.328 | 30.524 | 1.00 | 37.12 | S |
| ATOM | 2421 | OH2 | TIP | S | 202 | 47.691 | 26.068 | 37.666 | 1.00 | 37.92 | S |
| ATOM | 2422 | OH2 | TIP | S | 203 | 38.653 | 7.070 | 29.307 | 1.00 | 50.54 | S |
| ATOM | 2423 | OH2 | TIP | S | 206 | 44.424 | 27.583 | 2.092 | 1.00 | 53.50 | S |
| ATOM | 2424 | OH2 | TIP | S | 212 | 22.258 | 2.296 | 17.948 | 1.00 | 47.38 | S |
| ATOM | 2425 | OH2 | TIP | S | 214 | 19.843 | 17.943 | 23.303 | 1.00 | 30.36 | S |
| ATOM | 2426 | OH2 | TIP | S | 216 | 27.647 | 11.344 | 24.681 | 1.00 | 31.32 | S |
| ATOM | 2427 | OH2 | TIP | S | 217 | 37.953 | 7.817 | −9.284 | 1.00 | 45.97 | S |
| ATOM | 2428 | OH2 | TIP | S | 218 | 33.845 | 34.040 | 12.124 | 1.00 | 38.11 | S |
| ATOM | 2429 | OH2 | TIP | S | 219 | 58.484 | 15.269 | 13.717 | 1.00 | 38.26 | S |
| ATOM | 2430 | OH2 | TIP | S | 220 | 48.526 | 40.920 | 26.583 | 1.00 | 35.23 | S |
| ATOM | 2431 | OH2 | TIP | S | 222 | 52.094 | 21.184 | 38.122 | 1.00 | 29.86 | S |
| ATOM | 2432 | OH2 | TIP | S | 223 | 36.889 | 5.881 | 3.281 | 1.00 | 37.63 | S |
| ATOM | 2433 | OH2 | TIP | S | 224 | 47.642 | −1.401 | −10.684 | 1.00 | 34.89 | S |
| ATOM | 2434 | OH2 | TIP | S | 226 | 47.284 | 2.916 | 19.133 | 1.00 | 34.10 | S |
| ATOM | 2435 | OH2 | TIP | S | 227 | 42.468 | 4.463 | −15.039 | 1.00 | 37.98 | S |
| ATOM | 2436 | OH2 | TIP | S | 228 | 19.169 | 22.832 | 21.831 | 1.00 | 41.57 | S |
| ATOM | 2437 | OH2 | TIP | S | 231 | 57.592 | 12.689 | 14.880 | 1.00 | 50.22 | S |
| ATOM | 2438 | OH2 | TIP | S | 232 | 27.102 | 9.176 | 5.655 | 1.00 | 40.57 | S |
| ATOM | 2439 | OH2 | TIP | S | 233 | 58.618 | 9.072 | −11.925 | 1.00 | 50.71 | S |
| ATOM | 2440 | OH2 | TIP | S | 234 | 22.822 | 25.342 | 19.945 | 1.00 | 34.93 | S |
| ATOM | 2441 | OH2 | TIP | S | 236 | 24.831 | 32.218 | 28.901 | 1.00 | 37.69 | S |
| ATOM | 2442 | OH2 | TIP | S | 237 | 20.045 | 10.774 | 16.992 | 1.00 | 39.57 | S |
| ATOM | 2443 | OH2 | TIP | S | 238 | 58.019 | 19.850 | 15.679 | 1.00 | 41.42 | S |
| ATOM | 2444 | OH2 | TIP | S | 239 | 19.490 | 20.949 | 26.114 | 1.00 | 34.55 | S |
| ATOM | 2445 | OH2 | TIP | S | 240 | 61.187 | 26.377 | 7.346 | 1.00 | 39.68 | S |
| ATOM | 2446 | OH2 | TIP | S | 241 | 33.680 | 38.342 | 19.389 | 1.00 | 48.93 | S |
| ATOM | 2447 | OH2 | TIP | S | 242 | 51.539 | 31.612 | 10.881 | 1.00 | 55.65 | S |
| ATOM | 2448 | OH2 | TIP | S | 244 | 25.872 | 14.431 | 30.404 | 1.00 | 46.69 | S |
| ATOM | 2449 | OH2 | TIP | S | 248 | 37.332 | 5.849 | 9.544 | 1.00 | 43.81 | S |
| ATOM | 2450 | OH2 | TIP | S | 250 | 39.087 | −1.293 | −9.655 | 1.00 | 42.96 | S |
| ATOM | 2451 | OH2 | TIP | S | 258 | 23.938 | 30.000 | 30.010 | 1.00 | 38.89 | S |
| ATOM | 2452 | OH2 | TIP | S | 259 | 24.949 | 29.749 | 32.578 | 1.00 | 40.17 | S |
| ATOM | 2453 | OH2 | TIP | S | 260 | 32.111 | 17.986 | 1.918 | 1.00 | 48.36 | S |
| ATOM | 2454 | OH2 | TIP | S | 266 | 21.404 | 12.876 | 25.603 | 1.00 | 57.17 | S |
| ATOM | 2455 | OH2 | TIP | S | 269 | 35.425 | 36.767 | 12.550 | 1.00 | 30.70 | S |
| ATOM | 2456 | OH2 | TIP | S | 270 | 52.438 | 25.529 | 30.131 | 1.00 | 44.85 | S |
| ATOM | 2457 | OH2 | TIP | S | 271 | 53.299 | 20.156 | 36.003 | 1.00 | 37.15 | S |
| ATOM | 2458 | OH2 | TIP | S | 272 | 50.914 | 6.919 | 23.723 | 1.00 | 43.29 | S |
| ATOM | 2459 | OH2 | TIP | S | 274 | 31.578 | 30.795 | 11.014 | 1.00 | 50.15 | S |
| ATOM | 2460 | OH2 | TIP | S | 275 | 26.341 | 7.243 | 22.447 | 1.00 | 39.40 | S |
| ATOM | 2461 | OH2 | TIP | S | 276 | 60.392 | 18.195 | 10.235 | 1.00 | 37.91 | S |
| ATOM | 2462 | OH2 | TIP | S | 277 | 47.355 | −9.081 | −10.821 | 1.00 | 48.18 | S |
| ATOM | 2463 | OH2 | TIP | S | 279 | 41.304 | 6.175 | −16.647 | 1.00 | 38.12 | S |

-continued

| | | | | | | | | | | |
|---|---|---|---|---|---|---|---|---|---|---|
| ATOM | 2464 | OH2 | TIP | S | 282 | 33.299 | 21.620 | 37.881 | 1.00 | 46.29 | S |
| ATOM | 2465 | OH2 | TIP | S | 283 | 56.469 | 26.112 | −8.575 | 1.00 | 43.71 | S |
| ATOM | 2466 | OH2 | TIP | S | 287 | 48.382 | 26.573 | 7.246 | 1.00 | 41.43 | S |
| ATOM | 2467 | OH2 | TIP | S | 288 | 56.240 | 7.245 | −11.331 | 1.00 | 41.79 | S |
| ATOM | 2468 | OH2 | TIP | S | 290 | 49.060 | 14.978 | 28.166 | 1.00 | 37.03 | S |
| ATOM | 2469 | OH2 | TIP | S | 291 | 37.095 | 44.270 | 26.442 | 1.00 | 45.08 | S |
| ATOM | 2470 | OH2 | TIP | S | 292 | 47.814 | −0.384 | −13.299 | 1.00 | 48.60 | S |
| ATOM | 2471 | OH2 | TIP | S | 297 | 58.081 | 2.784 | −7.841 | 1.00 | 41.89 | S |
| ATOM | 2472 | OH2 | TIP | S | 298 | 36.447 | 45.321 | 18.644 | 1.00 | 54.91 | S |
| ATOM | 2473 | OH2 | TIP | S | 299 | 49.029 | 23.328 | 1.767 | 1.00 | 30.55 | S |
| ATOM | 2474 | OH2 | TIP | S | 301 | 24.375 | 13.771 | 8.634 | 1.00 | 48.47 | S |
| ATOM | 2475 | OH2 | TIP | S | 303 | 47.904 | 36.798 | 28.653 | 1.00 | 35.76 | S |
| ATOM | 2476 | OH2 | TIP | S | 305 | 51.156 | 40.821 | 27.172 | 1.00 | 43.59 | S |
| ATOM | 2477 | OH2 | TIP | S | 306 | 32.943 | 28.917 | 35.227 | 1.00 | 42.60 | S |
| ATOM | 2478 | OH2 | TIP | S | 307 | 58.462 | 28.373 | 6.251 | 1.00 | 46.15 | S |
| ATOM | 2479 | OH2 | TIP | S | 308 | 41.964 | 30.940 | 36.712 | 1.00 | 48.26 | S |
| ATOM | 2480 | OH2 | TIP | S | 313 | 51.176 | −1.922 | −3.336 | 1.00 | 50.61 | S |
| ATOM | 2481 | OH2 | TIP | S | 1001 | 21.319 | 36.868 | 23.805 | 1.00 | 36.97 | S |
| ATOM | 2482 | OH2 | TIP | S | 1002 | 48.880 | 32.620 | 27.617 | 1.00 | 44.40 | S |
| ATOM | 2483 | OH2 | TIP | S | 1003 | 61.880 | 19.473 | 11.767 | 1.00 | 45.49 | S |
| ATOM | 2484 | OH2 | TIP | S | 1004 | 52.770 | 21.424 | 26.815 | 1.00 | 24.43 | S |
| ATOM | 2485 | OH2 | TIP | S | 1005 | 35.373 | 29.094 | 36.197 | 1.00 | 35.97 | S |
| ATOM | 2486 | OH2 | TIP | S | 1006 | 40.815 | −6.636 | 4.389 | 1.00 | 43.15 | S |
| ATOM | 2487 | OH2 | TIP | S | 1007 | 44.953 | 1.286 | 11.272 | 1.00 | 49.45 | S |
| ATOM | 2488 | OH2 | TIP | S | 1010 | 21.004 | 16.168 | 27.009 | 1.00 | 48.51 | S |
| ATOM | 2489 | OH2 | TIP | S | 1011 | 47.094 | 41.786 | 9.243 | 1.00 | 50.10 | S |
| ATOM | 2490 | OH2 | TIP | S | 1012 | 32.479 | 2.978 | 14.158 | 1.00 | 49.47 | S |
| ATOM | 2491 | O12 | GLC | G | 1 | 48.557 | 11.372 | −12.279 | 1.00 | 40.72 | G |
| ATOM | 2492 | C11 | GLC | G | 1 | 48.836 | 12.133 | −11.097 | 1.00 | 38.05 | G |
| ATOM | 2493 | C13 | GLC | G | 1 | 49.266 | 13.554 | −11.476 | 1.00 | 38.09 | G |
| ATOM | 2494 | O14 | GLC | G | 1 | 49.559 | 14.299 | −10.292 | 1.00 | 33.99 | G |
| ATOM | 2495 | C15 | GLC | G | 1 | 48.150 | 14.257 | −12.257 | 1.00 | 37.32 | G |
| ATOM | 2496 | O16 | GLC | G | 1 | 48.574 | 15.582 | −12.604 | 1.00 | 36.74 | G |
| ATOM | 2497 | O12 | GLC | G | 2 | 40.114 | −6.634 | −6.562 | 1.00 | 33.52 | G |
| ATOM | 2498 | C11 | GLC | G | 2 | 38.967 | −6.592 | −7.404 | 1.00 | 31.05 | G |
| ATOM | 2499 | C13 | GLC | G | 2 | 37.712 | −6.417 | −6.552 | 1.00 | 31.56 | G |
| ATOM | 2500 | O14 | GLC | G | 2 | 36.554 | −6.406 | −7.389 | 1.00 | 30.70 | G |
| ATOM | 2501 | C15 | GLC | G | 2 | 37.792 | −5.109 | −5.761 | 1.00 | 30.03 | G |
| ATOM | 2502 | O16 | GLC | G | 2 | 36.609 | −4.961 | −4.975 | 1.00 | 29.66 | G |
| ATOM | 2503 | O12 | GLC | G | 3 | 44.030 | 8.243 | −13.470 | 1.00 | 37.90 | G |
| ATOM | 2504 | C11 | GLC | G | 3 | 43.950 | 9.648 | −13.690 | 1.00 | 38.47 | G |
| ATOM | 2505 | C13 | GLC | G | 3 | 42.747 | 9.974 | −14.579 | 1.00 | 39.52 | G |
| ATOM | 2506 | O14 | GLC | G | 3 | 41.551 | 9.526 | −13.942 | 1.00 | 39.39 | G |
| ATOM | 2507 | C15 | GLC | G | 3 | 42.878 | 9.280 | −15.934 | 1.00 | 41.43 | G |
| ATOM | 2508 | O16 | GLC | G | 3 | 41.736 | 9.613 | −16.731 | 1.00 | 40.78 | G |
| ATOM | 2509 | O12 | GLC | G | 5 | 40.556 | 1.005 | 2.289 | 1.00 | 45.25 | G |
| ATOM | 2510 | C11 | GLC | G | 5 | 40.966 | 2.332 | 1.960 | 1.00 | 40.56 | G |
| ATOM | 2511 | C13 | GLC | G | 5 | 40.187 | 3.327 | 2.814 | 1.00 | 40.36 | G |
| ATOM | 2512 | O14 | GLC | G | 5 | 38.791 | 3.169 | 2.572 | 1.00 | 40.71 | G |
| ATOM | 2513 | C15 | GLC | G | 5 | 40.619 | 4.751 | 2.464 | 1.00 | 40.04 | G |
| ATOM | 2514 | O16 | GLC | G | 5 | 39.885 | 5.681 | 3.256 | 1.00 | 36.89 | G |
| ATOM | 2515 | O12 | GLC | G | 6 | 36.951 | 22.702 | 40.046 | 1.00 | 63.04 | G |
| ATOM | 2516 | C11 | GLC | G | 6 | 37.592 | 21.583 | 39.422 | 1.00 | 62.46 | G |
| ATOM | 2517 | C13 | GLC | G | 6 | 38.104 | 21.978 | 38.030 | 1.00 | 61.14 | G |
| ATOM | 2518 | O14 | GLC | G | 6 | 39.034 | 23.054 | 38.168 | 1.00 | 61.72 | G |
| ATOM | 2519 | C15 | GLC | G | 6 | 36.948 | 22.429 | 37.126 | 1.00 | 60.51 | G |
| ATOM | 2520 | O16 | GLC | G | 6 | 35.992 | 21.372 | 36.960 | 1.00 | 58.61 | G |
| ATOM | 2521 | O12 | GLC | G | 7 | 37.316 | 0.281 | 14.299 | 1.00 | 73.45 | G |
| ATOM | 2522 | C11 | GLC | G | 7 | 37.655 | −0.758 | 15.222 | 1.00 | 72.78 | G |
| ATOM | 2523 | C13 | GLC | G | 7 | 36.592 | −1.856 | 15.157 | 1.00 | 72.98 | G |
| ATOM | 2524 | O14 | GLC | G | 7 | 35.320 | −1.299 | 15.498 | 1.00 | 73.88 | G |
| ATOM | 2525 | C15 | GLC | G | 7 | 36.924 | −2.989 | 16.134 | 1.00 | 73.66 | G |
| ATOM | 2526 | O16 | GLC | G | 7 | 36.972 | −2.493 | 17.478 | 1.00 | 75.38 | G |
| ATOM | 2527 | O12 | GLC | G | 8 | 51.921 | 21.898 | 5.908 | 1.00 | 62.51 | G |
| ATOM | 2528 | C11 | GLC | G | 8 | 52.447 | 20.871 | 5.063 | 1.00 | 63.42 | G |
| ATOM | 2529 | C13 | GLC | G | 8 | 51.476 | 20.597 | 3.908 | 1.00 | 64.28 | G |
| ATOM | 2530 | O14 | GLC | G | 8 | 51.297 | 21.794 | 3.150 | 1.00 | 66.28 | G |
| ATOM | 2531 | C15 | GLC | G | 8 | 50.121 | 20.137 | 4.448 | 1.00 | 64.49 | G |
| ATOM | 2532 | O16 | GLC | G | 8 | 49.233 | 19.886 | 3.357 | 1.00 | 64.01 | G |
| ATOM | 2533 | O12 | GLC | G | 10 | 36.044 | 37.499 | 29.523 | 1.00 | 56.89 | G |
| ATOM | 2534 | C11 | GLC | G | 10 | 35.164 | 36.645 | 30.259 | 1.00 | 56.97 | G |
| ATOM | 2535 | C13 | GLC | G | 10 | 33.849 | 36.489 | 29.494 | 1.00 | 56.11 | G |
| ATOM | 2536 | O14 | GLC | G | 10 | 33.248 | 37.772 | 29.308 | 1.00 | 56.44 | G |
| ATOM | 2537 | C15 | GLC | G | 10 | 32.900 | 35.580 | 30.277 | 1.00 | 55.84 | G |
| ATOM | 2538 | O16 | GLC | G | 10 | 31.674 | 35.442 | 29.557 | 1.00 | 55.39 | G |
| ATOM | 2539 | O3G | ATP | N | 1 | 46.280 | 25.658 | 5.170 | 1.00 | 51.49 | N |
| ATOM | 2540 | PG | ATP | N | 1 | 46.464 | 25.053 | 3.691 | 1.00 | 52.22 | N |
| ATOM | 2541 | O1G | ATP | N | 1 | 47.406 | 23.911 | 3.763 | 1.00 | 51.41 | N |
| ATOM | 2542 | O2G | ATP | N | 1 | 46.794 | 26.182 | 2.784 | 1.00 | 52.07 | N |

-continued

| ATOM | 2543 | O3B | ATP | N | 1 | 44.976 | 24.513 | 3.344 | 1.00 | 51.01 | N |
|------|------|-----|-----|---|---|--------|--------|-------|------|-------|---|
| ATOM | 2544 | PB | ATP | N | 1 | 44.560 | 22.969 | 3.605 | 1.00 | 50.20 | N |
| ATOM | 2545 | O1B | ATP | N | 1 | 43.083 | 22.898 | 3.669 | 1.00 | 49.41 | N |
| ATOM | 2546 | O2B | ATP | N | 1 | 45.345 | 22.474 | 4.766 | 1.00 | 50.34 | N |
| ATOM | 2547 | O3A | ATP | N | 1 | 45.070 | 22.231 | 2.255 | 1.00 | 47.77 | N |
| ATOM | 2548 | PA | ATP | N | 1 | 45.075 | 20.613 | 2.121 | 1.00 | 42.84 | N |
| ATOM | 2549 | O1A | ATP | N | 1 | 45.547 | 20.291 | 0.754 | 1.00 | 43.81 | N |
| ATOM | 2550 | O2A | ATP | N | 1 | 45.807 | 20.035 | 3.270 | 1.00 | 45.03 | N |
| ATOM | 2551 | O5* | ATP | N | 1 | 43.516 | 20.223 | 2.245 | 1.00 | 41.73 | N |
| ATOM | 2552 | C5* | ATP | N | 1 | 42.528 | 20.925 | 1.489 | 1.00 | 37.57 | N |
| ATOM | 2553 | C4* | ATP | N | 1 | 41.127 | 20.379 | 1.776 | 1.00 | 39.45 | N |
| ATOM | 2554 | O4* | ATP | N | 1 | 40.907 | 19.024 | 1.279 | 1.00 | 37.72 | N |
| ATOM | 2555 | C3* | ATP | N | 1 | 40.777 | 20.321 | 3.251 | 1.00 | 38.48 | N |
| ATOM | 2556 | O3* | ATP | N | 1 | 40.360 | 21.615 | 3.697 | 1.00 | 40.42 | N |
| ATOM | 2557 | C2* | ATP | N | 1 | 39.608 | 19.374 | 3.270 | 1.00 | 37.58 | N |
| ATOM | 2558 | O2* | ATP | N | 1 | 38.410 | 20.076 | 2.924 | 1.00 | 35.98 | N |
| ATOM | 2559 | C1* | ATP | N | 1 | 39.939 | 18.346 | 2.173 | 1.00 | 35.55 | N |
| ATOM | 2560 | N9 | ATP | N | 1 | 40.628 | 17.156 | 2.747 | 1.00 | 31.76 | N |
| ATOM | 2561 | C8 | ATP | N | 1 | 41.864 | 17.126 | 3.274 | 1.00 | 30.49 | N |
| ATOM | 2562 | N7 | ATP | N | 1 | 42.143 | 15.877 | 3.667 | 1.00 | 29.75 | N |
| ATOM | 2563 | C5 | ATP | N | 1 | 41.088 | 15.118 | 3.390 | 1.00 | 27.49 | N |
| ATOM | 2564 | C4 | ATP | N | 1 | 40.125 | 15.925 | 2.810 | 1.00 | 30.02 | N |
| ATOM | 2565 | N3 | ATP | N | 1 | 38.937 | 15.389 | 2.431 | 1.00 | 27.11 | N |
| ATOM | 2566 | C2 | ATP | N | 1 | 38.679 | 14.085 | 2.615 | 1.00 | 25.62 | N |
| ATOM | 2567 | N1 | ATP | N | 1 | 39.597 | 13.283 | 3.175 | 1.00 | 21.76 | N |
| ATOM | 2568 | C6 | ATP | N | 1 | 40.800 | 13.768 | 3.571 | 1.00 | 23.90 | N |
| ATOM | 2569 | N6 | ATP | N | 1 | 41.698 | 12.964 | 4.127 | 1.00 | 21.94 | N |
| ATOM | 2570 | S | SO4 | I | 1 | 58.680 | 8.493 | −0.639 | 1.00 | 56.05 | I |
| ATOM | 2571 | O1 | SO4 | I | 1 | 57.956 | 7.875 | 0.483 | 1.00 | 58.83 | I |
| ATOM | 2572 | O2 | SO4 | I | 1 | 57.886 | 9.607 | −1.188 | 1.00 | 57.04 | I |
| ATOM | 2573 | O3 | SO4 | I | 1 | 58.906 | 7.478 | −1.683 | 1.00 | 57.47 | I |
| ATOM | 2574 | O4 | SO4 | I | 1 | 59.976 | 9.008 | −0.156 | 1.00 | 57.51 | I |
| ATOM | 2575 | S | SO4 | I | 2 | 39.339 | 4.855 | 7.057 | 1.00 | 84.24 | I |
| ATOM | 2576 | O1 | SO4 | I | 2 | 39.390 | 6.175 | 7.711 | 1.00 | 85.02 | I |
| ATOM | 2577 | O2 | SO4 | I | 2 | 40.101 | 4.897 | 5.797 | 1.00 | 84.75 | I |
| ATOM | 2578 | O3 | SO4 | I | 2 | 37.936 | 4.506 | 6.766 | 1.00 | 84.94 | I |
| ATOM | 2579 | O4 | SO4 | I | 2 | 39.931 | 3.842 | 7.954 | 1.00 | 84.44 | I |
| ATOM | 2580 | S | SO4 | I | 3 | 38.987 | −2.256 | 3.310 | 1.00 | 58.58 | I |
| ATOM | 2581 | O1 | SO4 | I | 3 | 37.734 | −1.675 | 3.827 | 1.00 | 59.11 | I |
| ATOM | 2582 | O2 | SO4 | I | 3 | 39.460 | −1.454 | 2.172 | 1.00 | 59.91 | I |
| ATOM | 2583 | O3 | SO4 | I | 3 | 38.743 | −3.640 | 2.866 | 1.00 | 60.97 | I |
| ATOM | 2584 | O4 | SO4 | I | 3 | 40.014 | −2.260 | 4.369 | 1.00 | 59.58 | I |
| ATOM | 2585 | S | SO4 | I | 4 | 34.397 | 5.289 | 30.981 | 1.00 | 64.34 | I |
| ATOM | 2586 | O1 | SO4 | I | 4 | 33.627 | 6.528 | 30.742 | 1.00 | 60.43 | I |
| ATOM | 2587 | O2 | SO4 | I | 4 | 34.337 | 4.427 | 29.782 | 1.00 | 60.11 | I |
| ATOM | 2588 | O3 | SO4 | I | 4 | 33.816 | 4.572 | 32.133 | 1.00 | 64.39 | I |
| ATOM | 2589 | O4 | SO4 | I | 4 | 35.806 | 5.626 | 31.277 | 1.00 | 63.55 | I |
| ATOM | 2590 | S | SO4 | I | 5 | 55.074 | −6.984 | −3.711 | 1.00 | 75.40 | I |
| ATOM | 2591 | O1 | SO4 | I | 5 | 54.657 | −7.518 | −2.399 | 1.00 | 74.66 | I |
| ATOM | 2592 | O2 | SO4 | I | 5 | 54.209 | −5.845 | −4.065 | 1.00 | 74.96 | I |
| ATOM | 2593 | O3 | SO4 | I | 5 | 54.950 | −8.034 | −4.742 | 1.00 | 74.22 | I |
| ATOM | 2594 | O4 | SO4 | I | 5 | 56.477 | −6.532 | −3.633 | 1.00 | 75.15 | I |
| ATOM | 2595 | O2 | PO4 | P | 100 | 57.362 | 24.998 | 13.149 | 1.00 | 66.76 | P |
| ATOM | 2596 | O3 | PO4 | P | 100 | 59.399 | 26.166 | 13.761 | 1.00 | 66.89 | P |
| ATOM | 2597 | O4 | PO4 | P | 100 | 57.761 | 25.606 | 15.462 | 1.00 | 67.43 | P |
| ATOM | 2598 | O1 | PO4 | P | 100 | 57.264 | 27.325 | 13.818 | 1.00 | 65.91 | P |
| ATOM | 2599 | P | PO4 | P | 100 | 57.947 | 26.025 | 14.048 | 1.00 | 66.69 | P |
| END | | | | | | | | | | | |

Example 4

Co-Ordinates for the Dimer of the PDK1 Fragment, without Alternate Side Chains

Chain A is the molecule for which co-ordinates are given in Examples 2 and 3, and chain B is the symmetry-related molecule.

| ATOM | 1 | CB | PRO | A | 71 | 58.912 | −7.251 | 8.216 | 1.00 | 67.78 | A |
|------|---|----|-----|---|----|--------|--------|-------|------|-------|---|
| ATOM | 2 | CG | PRO | A | 71 | 59.621 | −6.941 | 9.534 | 1.00 | 69.16 | A |
| ATOM | 3 | C | PRO | A | 71 | 59.493 | −6.506 | 5.894 | 1.00 | 67.06 | A |
| ATOM | 4 | O | PRO | A | 71 | 59.196 | −5.318 | 5.766 | 1.00 | 66.66 | A |

-continued

| | | | | | | | | | | | |
|---|---|---|---|---|---|---|---|---|---|---|---|
| ATOM | 5 | N | PRO | A | 71 | 60.984 | −6.073 | 7.833 | 1.00 | 67.86 | A |
| ATOM | 6 | CD | PRO | A | 71 | 60.554 | −5.762 | 9.207 | 1.00 | 68.24 | A |
| ATOM | 7 | CA | PRO | A | 71 | 60.040 | −7.035 | 7.217 | 1.00 | 67.75 | A |
| ATOM | 8 | N | PRO | A | 72 | 59.356 | −7.385 | 4.890 | 1.00 | 66.32 | A |
| ATOM | 9 | CD | PRO | A | 72 | 59.712 | −8.816 | 4.898 | 1.00 | 67.17 | A |
| ATOM | 10 | CA | PRO | A | 72 | 58.840 | −6.986 | 3.578 | 1.00 | 65.61 | A |
| ATOM | 11 | CB | PRO | A | 72 | 58.672 | −8.321 | 2.858 | 1.00 | 66.47 | A |
| ATOM | 12 | CG | PRO | A | 72 | 59.796 | −9.133 | 3.419 | 1.00 | 67.57 | A |
| ATOM | 13 | C | PRO | A | 72 | 57.527 | −6.208 | 3.673 | 1.00 | 63.94 | A |
| ATOM | 14 | O | PRO | A | 72 | 56.710 | −6.451 | 4.561 | 1.00 | 64.11 | A |
| ATOM | 15 | N | ALA | A | 73 | 57.341 | −5.268 | 2.753 | 1.00 | 61.57 | A |
| ATOM | 16 | CA | ALA | A | 73 | 56.133 | −4.454 | 2.708 | 1.00 | 58.74 | A |
| ATOM | 17 | CB | ALA | A | 73 | 56.438 | −3.030 | 3.165 | 1.00 | 58.05 | A |
| ATOM | 18 | C | ALA | A | 73 | 55.626 | −4.448 | 1.271 | 1.00 | 56.78 | A |
| ATOM | 19 | O | ALA | A | 73 | 56.347 | −4.834 | 0.349 | 1.00 | 56.95 | A |
| ATOM | 20 | N | PRO | A | 74 | 54.372 | −4.024 | 1.057 | 1.00 | 54.15 | A |
| ATOM | 21 | CD | PRO | A | 74 | 53.335 | −3.610 | 2.018 | 1.00 | 53.31 | A |
| ATOM | 22 | CA | PRO | A | 74 | 53.856 | −4.003 | −0.314 | 1.00 | 52.54 | A |
| ATOM | 23 | CB | PRO | A | 74 | 52.474 | −3.375 | −0.148 | 1.00 | 52.86 | A |
| ATOM | 24 | CG | PRO | A | 74 | 52.067 | −3.824 | 1.226 | 1.00 | 52.88 | A |
| ATOM | 25 | C | PRO | A | 74 | 54.772 | −3.167 | −1.204 | 1.00 | 50.08 | A |
| ATOM | 26 | O | PRO | A | 74 | 55.559 | −2.361 | −0.708 | 1.00 | 49.96 | A |
| ATOM | 27 | N | ALA | A | 75 | 54.680 | −3.366 | −2.514 | 1.00 | 47.58 | A |
| ATOM | 28 | CA | ALA | A | 75 | 55.503 | −2.602 | −3.446 | 1.00 | 44.69 | A |
| ATOM | 29 | CB | ALA | A | 75 | 55.312 | −3.121 | −4.870 | 1.00 | 46.14 | A |
| ATOM | 30 | C | ALA | A | 75 | 55.100 | −1.134 | −3.371 | 1.00 | 41.55 | A |
| ATOM | 31 | O | ALA | A | 75 | 53.947 | −0.813 | −3.086 | 1.00 | 41.01 | A |
| ATOM | 32 | N | LYS | A | 76 | 56.053 | −0.245 | −3.619 | 1.00 | 38.31 | A |
| ATOM | 33 | CA | LYS | A | 76 | 55.781 | 1.184 | −3.588 | 1.00 | 35.72 | A |
| ATOM | 34 | CB | LYS | A | 76 | 57.053 | 1.957 | −3.930 | 1.00 | 37.70 | A |
| ATOM | 35 | CG | LYS | A | 76 | 57.123 | 3.356 | −3.350 | 1.00 | 40.99 | A |
| ATOM | 36 | CD | LYS | A | 76 | 57.262 | 3.316 | −1.836 | 1.00 | 40.04 | A |
| ATOM | 37 | CE | LYS | A | 76 | 57.511 | 4.705 | −1.277 | 1.00 | 42.08 | A |
| ATOM | 38 | NZ | LYS | A | 76 | 57.681 | 4.695 | 0.202 | 1.00 | 42.99 | A |
| ATOM | 39 | C | LYS | A | 76 | 54.708 | 1.467 | −4.638 | 1.00 | 32.65 | A |
| ATOM | 40 | O | LYS | A | 76 | 54.814 | 1.005 | −5.770 | 1.00 | 31.41 | A |
| ATOM | 41 | N | LYS | A | 77 | 53.668 | 2.207 | −4.270 | 1.00 | 28.59 | A |
| ATOM | 42 | CA | LYS | A | 77 | 52.619 | 2.517 | −5.232 | 1.00 | 25.72 | A |
| ATOM | 43 | CB | LYS | A | 77 | 51.316 | 2.865 | −4.509 | 1.00 | 26.22 | A |
| ATOM | 44 | CG | LYS | A | 77 | 50.796 | 1.731 | −3.631 | 1.00 | 27.15 | A |
| ATOM | 45 | CD | LYS | A | 77 | 49.487 | 2.089 | −2.967 | 1.00 | 26.80 | A |
| ATOM | 46 | CE | LYS | A | 77 | 49.136 | 1.091 | −1.870 | 1.00 | 27.31 | A |
| ATOM | 47 | NZ | LYS | A | 77 | 48.998 | −0.296 | −2.380 | 1.00 | 27.17 | A |
| ATOM | 48 | C | LYS | A | 77 | 53.053 | 3.668 | −6.137 | 1.00 | 24.67 | A |
| ATOM | 49 | O | LYS | A | 77 | 54.010 | 4.377 | −5.829 | 1.00 | 21.60 | A |
| ATOM | 50 | N | ARG | A | 78 | 52.351 | 3.838 | −7.254 | 1.00 | 23.66 | A |
| ATOM | 51 | CA | ARG | A | 78 | 52.662 | 4.897 | −8.211 | 1.00 | 26.14 | A |
| ATOM | 52 | CB | ARG | A | 78 | 53.574 | 4.344 | −9.318 | 1.00 | 28.57 | A |
| ATOM | 53 | CG | ARG | A | 78 | 53.017 | 3.139 | −10.050 | 1.00 | 34.78 | A |
| ATOM | 54 | CD | ARG | A | 78 | 54.092 | 2.465 | −10.896 | 1.00 | 40.96 | A |
| ATOM | 55 | NE | ARG | A | 78 | 53.560 | 1.364 | −11.700 | 1.00 | 48.93 | A |
| ATOM | 56 | CZ | ARG | A | 78 | 52.985 | 0.270 | −11.203 | 1.00 | 52.58 | A |
| ATOM | 57 | NH1 | ARG | A | 78 | 52.860 | 0.113 | −9.889 | 1.00 | 54.60 | A |
| ATOM | 58 | NH2 | ARG | A | 78 | 52.530 | −0.672 | −12.022 | 1.00 | 54.09 | A |
| ATOM | 59 | C | ARG | A | 78 | 51.382 | 5.488 | −8.803 | 1.00 | 23.76 | A |
| ATOM | 60 | O | ARG | A | 78 | 50.311 | 4.888 | −8.706 | 1.00 | 24.25 | A |
| ATOM | 61 | N | PRO | A | 79 | 51.475 | 6.676 | −9.428 | 1.00 | 21.76 | A |
| ATOM | 62 | CD | PRO | A | 79 | 52.691 | 7.475 | −9.668 | 1.00 | 20.82 | A |
| ATOM | 63 | CA | PRO | A | 79 | 50.301 | 7.325 | −10.021 | 1.00 | 21.96 | A |
| ATOM | 64 | CB | PRO | A | 79 | 50.910 | 8.481 | −10.816 | 1.00 | 22.27 | A |
| ATOM | 65 | CG | PRO | A | 79 | 52.124 | 8.831 | −10.014 | 1.00 | 22.12 | A |
| ATOM | 66 | C | PRO | A | 79 | 49.446 | 6.413 | −10.903 | 1.00 | 22.86 | A |
| ATOM | 67 | O | PRO | A | 79 | 48.213 | 6.461 | −10.842 | 1.00 | 20.52 | A |
| ATOM | 68 | N | GLU | A | 80 | 50.103 | 5.586 | −11.714 | 1.00 | 21.87 | A |
| ATOM | 69 | CA | GLU | A | 80 | 49.403 | 4.685 | −12.628 | 1.00 | 22.99 | A |
| ATOM | 70 | CB | GLU | A | 80 | 50.393 | 3.994 | −13.571 | 1.00 | 25.24 | A |
| ATOM | 71 | CG | GLU | A | 80 | 51.230 | 2.907 | −12.925 | 1.00 | 28.75 | A |
| ATOM | 72 | CD | GLU | A | 80 | 52.157 | 2.224 | −13.913 | 1.00 | 31.99 | A |
| ATOM | 73 | OE1 | GLU | A | 80 | 53.072 | 2.897 | −14.433 | 1.00 | 34.34 | A |
| ATOM | 74 | OE2 | GLU | A | 80 | 51.969 | 1.015 | −14.172 | 1.00 | 32.83 | A |
| ATOM | 75 | C | GLU | A | 80 | 48.556 | 3.631 | −11.912 | 1.00 | 22.09 | A |
| ATOM | 76 | O | GLU | A | 80 | 47.692 | 3.013 | −12.530 | 1.00 | 22.37 | A |
| ATOM | 77 | N | ASP | A | 81 | 48.804 | 3.413 | −10.622 | 1.00 | 19.97 | A |
| ATOM | 78 | CA | ASP | A | 81 | 48.026 | 2.423 | −9.874 | 1.00 | 19.93 | A |
| ATOM | 79 | CB | ASP | A | 81 | 48.736 | 2.029 | −8.571 | 1.00 | 21.19 | A |
| ATOM | 80 | CG | ASP | A | 81 | 50.089 | 1.380 | −8.807 | 1.00 | 22.46 | A |
| ATOM | 81 | OD1 | ASP | A | 81 | 50.195 | 0.554 | −9.731 | 1.00 | 24.22 | A |
| ATOM | 82 | OD2 | ASP | A | 81 | 51.043 | 1.685 | −8.058 | 1.00 | 23.33 | A |
| ATOM | 83 | C | ASP | A | 81 | 46.652 | 2.975 | −9.518 | 1.00 | 20.85 | A |

-continued

| | | | | | | | | | | | |
|---|---|---|---|---|---|---|---|---|---|---|---|
| ATOM | 84 | O | ASP | A | 81 | 45.793 | 2.246 | −9.015 | 1.00 | 19.96 | A |
| ATOM | 85 | N | PHE | A | 82 | 46.445 | 4.258 | −9.804 | 1.00 | 18.91 | A |
| ATOM | 86 | CA | PHE | A | 82 | 45.200 | 4.934 | −9.465 | 1.00 | 19.30 | A |
| ATOM | 87 | CB | PHE | A | 82 | 45.475 | 6.027 | −8.427 | 1.00 | 18.43 | A |
| ATOM | 88 | CG | PHE | A | 82 | 46.134 | 5.531 | −7.175 | 1.00 | 18.01 | A |
| ATOM | 89 | CD1 | PHE | A | 82 | 45.371 | 5.136 | −6.084 | 1.00 | 17.19 | A |
| ATOM | 90 | CD2 | PHE | A | 82 | 47.520 | 5.460 | −7.086 | 1.00 | 18.99 | A |
| ATOM | 91 | CE1 | PHE | A | 82 | 45.977 | 4.676 | −4.918 | 1.00 | 17.12 | A |
| ATOM | 92 | CE2 | PHE | A | 82 | 48.137 | 5.000 | −5.925 | 1.00 | 19.64 | A |
| ATOM | 93 | CZ | PHE | A | 82 | 47.361 | 4.607 | −4.838 | 1.00 | 18.00 | A |
| ATOM | 94 | C | PHE | A | 82 | 44.476 | 5.596 | −10.621 | 1.00 | 20.81 | A |
| ATOM | 95 | O | PHE | A | 82 | 45.066 | 5.933 | −11.649 | 1.00 | 20.34 | A |
| ATOM | 96 | N | LYS | A | 83 | 43.182 | 5.792 | −10.411 | 1.00 | 19.80 | A |
| ATOM | 97 | CA | LYS | A | 83 | 42.321 | 6.478 | −11.353 | 1.00 | 21.65 | A |
| ATOM | 98 | CB | LYS | A | 83 | 41.096 | 5.625 | −11.687 | 1.00 | 22.02 | A |
| ATOM | 99 | CG | LYS | A | 83 | 40.062 | 6.326 | −12.550 | 1.00 | 28.93 | A |
| ATOM | 100 | CD | LYS | A | 83 | 38.974 | 5.355 | −12.981 | 1.00 | 34.20 | A |
| ATOM | 101 | CE | LYS | A | 83 | 37.909 | 6.042 | −13.824 | 1.00 | 38.10 | A |
| ATOM | 102 | NZ | LYS | A | 83 | 37.179 | 7.086 | −13.043 | 1.00 | 43.33 | A |
| ATOM | 103 | C | LYS | A | 83 | 41.913 | 7.702 | −10.541 | 1.00 | 20.74 | A |
| ATOM | 104 | O | LYS | A | 83 | 41.084 | 7.606 | −9.635 | 1.00 | 20.98 | A |
| ATOM | 105 | N | PHE | A | 84 | 42.513 | 8.848 | −10.835 | 1.00 | 19.99 | A |
| ATOM | 106 | CA | PHE | A | 84 | 42.188 | 10.049 | −10.083 | 1.00 | 18.63 | A |
| ATOM | 107 | CB | PHE | A | 84 | 43.279 | 11.103 | −10.258 | 1.00 | 18.95 | A |
| ATOM | 108 | CG | PHE | A | 84 | 44.571 | 10.741 | −9.587 | 1.00 | 17.68 | A |
| ATOM | 109 | CD1 | PHE | A | 84 | 45.498 | 9.926 | −10.224 | 1.00 | 18.16 | A |
| ATOM | 110 | CD2 | PHE | A | 84 | 44.843 | 11.183 | −8.299 | 1.00 | 19.66 | A |
| ATOM | 111 | CE1 | PHE | A | 84 | 46.676 | 9.556 | −9.589 | 1.00 | 18.09 | A |
| ATOM | 112 | CE2 | PHE | A | 84 | 46.021 | 10.816 | −7.653 | 1.00 | 18.89 | A |
| ATOM | 113 | CZ | PHE | A | 84 | 46.936 | 10.002 | −8.301 | 1.00 | 17.33 | A |
| ATOM | 114 | C | PHE | A | 84 | 40.834 | 10.617 | −10.460 | 1.00 | 19.69 | A |
| ATOM | 115 | O | PHE | A | 84 | 40.391 | 10.489 | −11.601 | 1.00 | 20.72 | A |
| ATOM | 116 | N | GLY | A | 85 | 40.178 | 11.233 | −9.484 | 1.00 | 16.80 | A |
| ATOM | 117 | CA | GLY | A | 85 | 38.872 | 11.810 | −9.716 | 1.00 | 17.73 | A |
| ATOM | 118 | C | GLY | A | 85 | 38.819 | 13.280 | −9.346 | 1.00 | 18.75 | A |
| ATOM | 119 | O | GLY | A | 85 | 39.740 | 14.043 | −9.650 | 1.00 | 18.45 | A |
| ATOM | 120 | N | LYS | A | 86 | 37.753 | 13.673 | −8.659 | 1.00 | 16.00 | A |
| ATOM | 121 | CA | LYS | A | 86 | 37.571 | 15.064 | −8.278 | 1.00 | 18.26 | A |
| ATOM | 122 | CB | LYS | A | 86 | 36.133 | 15.302 | −7.812 | 1.00 | 19.00 | A |
| ATOM | 123 | CG | LYS | A | 86 | 35.793 | 14.660 | −6.481 | 1.00 | 21.55 | A |
| ATOM | 124 | CD | LYS | A | 86 | 34.368 | 14.981 | −6.066 | 1.00 | 26.48 | A |
| ATOM | 125 | CE | LYS | A | 86 | 33.994 | 14.239 | −4.793 | 1.00 | 31.92 | A |
| ATOM | 126 | NZ | LYS | A | 86 | 32.568 | 14.457 | −4.412 | 1.00 | 35.36 | A |
| ATOM | 127 | C | LYS | A | 86 | 38.523 | 15.571 | −7.202 | 1.00 | 18.57 | A |
| ATOM | 128 | O | LYS | A | 86 | 39.045 | 14.807 | −6.385 | 1.00 | 16.77 | A |
| ATOM | 129 | N | ILE | A | 87 | 38.737 | 16.881 | −7.227 | 1.00 | 17.88 | A |
| ATOM | 130 | CA | ILE | A | 87 | 39.577 | 17.554 | −6.256 | 1.00 | 18.26 | A |
| ATOM | 131 | CB | ILE | A | 87 | 39.994 | 18.952 | −6.772 | 1.00 | 19.60 | A |
| ATOM | 132 | CG2 | ILE | A | 87 | 40.593 | 19.786 | −5.628 | 1.00 | 18.73 | A |
| ATOM | 133 | CG1 | ILE | A | 87 | 40.968 | 18.786 | −7.945 | 1.00 | 21.16 | A |
| ATOM | 134 | CD1 | ILE | A | 87 | 41.412 | 20.087 | −8.588 | 1.00 | 25.26 | A |
| ATOM | 135 | C | ILE | A | 87 | 38.731 | 17.709 | −4.997 | 1.00 | 19.67 | A |
| ATOM | 136 | O | ILE | A | 87 | 37.628 | 18.249 | −5.052 | 1.00 | 20.41 | A |
| ATOM | 137 | N | LEU | A | 88 | 39.240 | 17.229 | −3.867 | 1.00 | 19.15 | A |
| ATOM | 138 | CA | LEU | A | 88 | 38.508 | 17.324 | −2.611 | 1.00 | 20.68 | A |
| ATOM | 139 | CB | LEU | A | 88 | 38.870 | 16.151 | −1.700 | 1.00 | 19.97 | A |
| ATOM | 140 | CG | LEU | A | 88 | 38.529 | 14.759 | −2.237 | 1.00 | 19.24 | A |
| ATOM | 141 | CD1 | LEU | A | 88 | 39.090 | 13.692 | −1.311 | 1.00 | 21.41 | A |
| ATOM | 142 | CD2 | LEU | A | 88 | 37.029 | 14.622 | −2.359 | 1.00 | 18.84 | A |
| ATOM | 143 | C | LEU | A | 88 | 38.815 | 18.632 | −1.901 | 1.00 | 23.11 | A |
| ATOM | 144 | O | LEU | A | 88 | 37.999 | 19.146 | −1.139 | 1.00 | 25.10 | A |
| ATOM | 145 | N | GLY | A | 89 | 39.997 | 19.174 | −2.149 | 1.00 | 24.09 | A |
| ATOM | 146 | CA | GLY | A | 89 | 40.367 | 20.418 | −1.507 | 1.00 | 24.27 | A |
| ATOM | 147 | C | GLY | A | 89 | 41.658 | 20.954 | −2.078 | 1.00 | 25.47 | A |
| ATOM | 148 | O | GLY | A | 89 | 42.445 | 20.202 | −2.666 | 1.00 | 22.19 | A |
| ATOM | 149 | N | GLU | A | 90 | 41.870 | 22.254 | −1.906 | 1.00 | 26.22 | A |
| ATOM | 150 | CA | GLU | A | 90 | 43.064 | 22.924 | −2.404 | 1.00 | 29.96 | A |
| ATOM | 151 | CB | GLU | A | 90 | 42.698 | 23.814 | −3.596 | 1.00 | 30.75 | A |
| ATOM | 152 | CG | GLU | A | 90 | 42.267 | 23.038 | −4.831 | 1.00 | 34.32 | A |
| ATOM | 153 | CD | GLU | A | 90 | 41.711 | 23.930 | −5.927 | 1.00 | 38.27 | A |
| ATOM | 154 | OE1 | GLU | A | 90 | 40.590 | 24.456 | −5.764 | 1.00 | 40.57 | A |
| ATOM | 155 | OE2 | GLU | A | 90 | 42.398 | 24.110 | −6.952 | 1.00 | 40.90 | A |
| ATOM | 156 | C | GLU | A | 90 | 43.711 | 23.768 | −1.313 | 1.00 | 30.68 | A |
| ATOM | 157 | O | GLU | A | 90 | 43.049 | 24.574 | −0.668 | 1.00 | 32.83 | A |
| ATOM | 158 | N | GLY | A | 91 | 45.006 | 23.566 | −1.104 | 1.00 | 29.66 | A |
| ATOM | 159 | CA | GLY | A | 91 | 45.724 | 24.332 | −0.104 | 1.00 | 29.40 | A |
| ATOM | 160 | C | GLY | A | 91 | 46.795 | 25.151 | −0.798 | 1.00 | 29.98 | A |
| ATOM | 161 | O | GLY | A | 91 | 46.894 | 25.130 | −2.028 | 1.00 | 28.16 | A |
| ATOM | 162 | N | SER | A | 92 | 47.605 | 25.870 | −0.029 | 1.00 | 28.30 | A |

| | | | | | -continued | | | | | |
|---|---|---|---|---|---|---|---|---|---|---|
| ATOM | 163 | CA | SER | A | 92 | 48.653 | 26.681 | −0.633 | 1.00 | 30.50 | A |
| ATOM | 164 | CB | SER | A | 92 | 49.165 | 27.717 | 0.370 | 1.00 | 32.43 | A |
| ATOM | 165 | OG | SER | A | 92 | 49.520 | 27.099 | 1.593 | 1.00 | 40.94 | A |
| ATOM | 166 | C | SER | A | 92 | 49.815 | 25.843 | −1.164 | 1.00 | 29.77 | A |
| ATOM | 167 | O | SER | A | 92 | 50.456 | 26.221 | −2.143 | 1.00 | 30.46 | A |
| ATOM | 168 | N | PHE | A | 93 | 50.087 | 24.703 | −0.536 | 1.00 | 27.65 | A |
| ATOM | 169 | CA | PHE | A | 93 | 51.185 | 23.855 | −0.995 | 1.00 | 26.34 | A |
| ATOM | 170 | CB | PHE | A | 93 | 52.281 | 23.785 | 0.068 | 1.00 | 27.95 | A |
| ATOM | 171 | CG | PHE | A | 93 | 52.861 | 25.117 | 0.406 | 1.00 | 31.06 | A |
| ATOM | 172 | CD1 | PHE | A | 93 | 52.283 | 25.909 | 1.392 | 1.00 | 29.96 | A |
| ATOM | 173 | CD2 | PHE | A | 93 | 53.949 | 25.613 | −0.308 | 1.00 | 31.38 | A |
| ATOM | 174 | CE1 | PHE | A | 93 | 52.779 | 27.181 | 1.665 | 1.00 | 32.69 | A |
| ATOM | 175 | CE2 | PHE | A | 93 | 54.452 | 26.883 | −0.044 | 1.00 | 32.63 | A |
| ATOM | 176 | CZ | PHE | A | 93 | 53.864 | 27.670 | 0.945 | 1.00 | 31.81 | A |
| ATOM | 177 | C | PHE | A | 93 | 50.759 | 22.445 | −1.365 | 1.00 | 25.39 | A |
| ATOM | 178 | O | PHE | A | 93 | 51.601 | 21.559 | −1.522 | 1.00 | 24.59 | A |
| ATOM | 179 | N | SER | A | 94 | 49.457 | 22.235 | −1.519 | 1.00 | 23.63 | A |
| ATOM | 180 | CA | SER | A | 94 | 48.965 | 20.912 | −1.860 | 1.00 | 21.43 | A |
| ATOM | 181 | CB | SER | A | 94 | 49.017 | 20.013 | −0.628 | 1.00 | 21.42 | A |
| ATOM | 182 | OG | SER | A | 94 | 48.091 | 20.475 | 0.340 | 1.00 | 21.19 | A |
| ATOM | 183 | C | SER | A | 94 | 47.539 | 20.925 | −2.378 | 1.00 | 19.82 | A |
| ATOM | 184 | O | SER | A | 94 | 46.795 | 21.882 | −2.173 | 1.00 | 18.76 | A |
| ATOM | 185 | N | THR | A | 95 | 47.174 | 19.832 | −3.038 | 1.00 | 19.38 | A |
| ATOM | 186 | CA | THR | A | 95 | 45.840 | 19.637 | −3.580 | 1.00 | 17.98 | A |
| ATOM | 187 | CB | THR | A | 95 | 45.818 | 19.818 | −5.110 | 1.00 | 19.25 | A |
| ATOM | 188 | OG1 | THR | A | 95 | 46.196 | 21.162 | −5.434 | 1.00 | 22.04 | A |
| ATOM | 189 | CG2 | THR | A | 95 | 44.421 | 19.549 | −5.661 | 1.00 | 17.61 | A |
| ATOM | 190 | C | THR | A | 95 | 45.455 | 18.201 | −3.243 | 1.00 | 18.61 | A |
| ATOM | 191 | O | THR | A | 95 | 46.212 | 17.264 | −3.524 | 1.00 | 17.10 | A |
| ATOM | 192 | N | VAL | A | 96 | 44.295 | 18.024 | −2.623 | 1.00 | 16.53 | A |
| ATOM | 193 | CA | VAL | A | 96 | 43.845 | 16.685 | −2.266 | 1.00 | 16.05 | A |
| ATOM | 194 | CB | VAL | A | 96 | 43.170 | 16.672 | −0.886 | 1.00 | 16.32 | A |
| ATOM | 195 | CG1 | VAL | A | 96 | 42.741 | 15.249 | −0.532 | 1.00 | 18.02 | A |
| ATOM | 196 | CG2 | VAL | A | 96 | 44.145 | 17.206 | 0.168 | 1.00 | 16.69 | A |
| ATOM | 197 | C | VAL | A | 96 | 42.875 | 16.207 | −3.335 | 1.00 | 16.42 | A |
| ATOM | 198 | O | VAL | A | 96 | 41.906 | 16.892 | −3.665 | 1.00 | 16.47 | A |
| ATOM | 199 | N | VAL | A | 97 | 43.157 | 15.033 | −3.888 | 1.00 | 16.80 | A |
| ATOM | 200 | CA | VAL | A | 97 | 42.338 | 14.471 | −4.949 | 1.00 | 16.72 | A |
| ATOM | 201 | CB | VAL | A | 97 | 43.153 | 14.354 | −6.255 | 1.00 | 18.43 | A |
| ATOM | 202 | CG1 | VAL | A | 97 | 42.249 | 13.927 | −7.404 | 1.00 | 19.69 | A |
| ATOM | 203 | CG2 | VAL | A | 97 | 43.831 | 15.685 | −6.569 | 1.00 | 17.84 | A |
| ATOM | 204 | C | VAL | A | 97 | 41.812 | 13.091 | −4.583 | 1.00 | 16.77 | A |
| ATOM | 205 | O | VAL | A | 97 | 42.532 | 12.270 | −4.014 | 1.00 | 17.13 | A |
| ATOM | 206 | N | LEU | A | 98 | 40.545 | 12.845 | −4.895 | 1.00 | 16.62 | A |
| ATOM | 207 | CA | LEU | A | 98 | 39.947 | 11.548 | −4.624 | 1.00 | 17.04 | A |
| ATOM | 208 | CB | LEU | A | 98 | 38.424 | 11.633 | −4.743 | 1.00 | 16.89 | A |
| ATOM | 209 | CG | LEU | A | 98 | 37.635 | 10.342 | −4.508 | 1.00 | 19.46 | A |
| ATOM | 210 | CD1 | LEU | A | 98 | 37.990 | 9.762 | −3.146 | 1.00 | 20.07 | A |
| ATOM | 211 | CD2 | LEU | A | 98 | 36.143 | 10.627 | −4.588 | 1.00 | 17.93 | A |
| ATOM | 212 | C | LEU | A | 98 | 40.512 | 10.597 | −5.677 | 1.00 | 17.38 | A |
| ATOM | 213 | O | LEU | A | 98 | 40.527 | 10.920 | −6.863 | 1.00 | 18.60 | A |
| ATOM | 214 | N | ALA | A | 99 | 40.995 | 9.438 | −5.246 | 1.00 | 17.13 | A |
| ATOM | 215 | CA | ALA | A | 99 | 41.570 | 8.466 | −6.168 | 1.00 | 18.42 | A |
| ATOM | 216 | CB | ALA | A | 99 | 43.090 | 8.524 | −6.105 | 1.00 | 14.76 | A |
| ATOM | 217 | C | ALA | A | 99 | 41.102 | 7.055 | −5.848 | 1.00 | 21.40 | A |
| ATOM | 218 | O | ALA | A | 99 | 40.941 | 6.691 | −4.679 | 1.00 | 22.52 | A |
| ATOM | 219 | N | ARG | A | 100 | 40.878 | 6.261 | −6.888 | 1.00 | 19.77 | A |
| ATOM | 220 | CA | ARG | A | 100 | 40.459 | 4.884 | −6.693 | 1.00 | 20.85 | A |
| ATOM | 221 | CB | ARG | A | 100 | 39.202 | 4.585 | −7.518 | 1.00 | 24.22 | A |
| ATOM | 222 | CG | ARG | A | 100 | 38.608 | 3.205 | −7.256 | 1.00 | 31.78 | A |
| ATOM | 223 | CD | ARG | A | 100 | 37.326 | 2.979 | −8.048 | 1.00 | 36.24 | A |
| ATOM | 224 | NE | ARG | A | 100 | 36.213 | 3.818 | −7.594 | 1.00 | 41.40 | A |
| ATOM | 225 | CZ | ARG | A | 100 | 35.566 | 3.662 | −6.439 | 1.00 | 42.05 | A |
| ATOM | 226 | NH1 | ARG | A | 100 | 35.912 | 2.696 | −5.598 | 1.00 | 40.67 | A |
| ATOM | 227 | NH2 | ARG | A | 100 | 34.559 | 4.468 | −6.128 | 1.00 | 43.65 | A |
| ATOM | 228 | C | ARG | A | 100 | 41.613 | 3.985 | −7.129 | 1.00 | 18.63 | A |
| ATOM | 229 | O | ARG | A | 100 | 42.078 | 4.065 | −8.271 | 1.00 | 19.49 | A |
| ATOM | 230 | N | GLU | A | 101 | 42.102 | 3.157 | −6.212 | 1.00 | 16.43 | A |
| ATOM | 231 | CA | GLU | A | 101 | 43.196 | 2.246 | −6.533 | 1.00 | 16.11 | A |
| ATOM | 232 | CB | GLU | A | 101 | 43.774 | 1.637 | −5.248 | 1.00 | 16.79 | A |
| ATOM | 233 | CG | GLU | A | 101 | 44.917 | 0.657 | −5.488 | 1.00 | 16.51 | A |
| ATOM | 234 | CD | GLU | A | 101 | 45.501 | 0.115 | −4.200 | 1.00 | 18.20 | A |
| ATOM | 235 | OE1 | GLU | A | 101 | 44.733 | −0.081 | −3.239 | 1.00 | 18.32 | A |
| ATOM | 236 | OE2 | GLU | A | 101 | 46.725 | −0.132 | −4.150 | 1.00 | 17.14 | A |
| ATOM | 237 | C | GLU | A | 101 | 42.625 | 1.152 | −7.442 | 1.00 | 17.92 | A |
| ATOM | 238 | O | GLU | A | 101 | 41.681 | 0.462 | −7.069 | 1.00 | 18.02 | A |
| ATOM | 239 | N | LEU | A | 102 | 43.198 | 1.002 | −8.632 | 1.00 | 19.06 | A |
| ATOM | 240 | CA | LEU | A | 102 | 42.718 | 0.025 | −9.607 | 1.00 | 20.71 | A |
| ATOM | 241 | CB | LEU | A | 102 | 43.569 | 0.097 | −10.878 | 1.00 | 23.42 | A |

-continued

| | | | | | | | | | | | |
|---|---|---|---|---|---|---|---|---|---|---|---|
| ATOM | 242 | CG | LEU | A | 102 | 43.531 | 1.426 | −11.642 | 1.00 | 25.30 | A |
| ATOM | 243 | CD1 | LEU | A | 102 | 44.577 | 1.414 | −12.748 | 1.00 | 27.88 | A |
| ATOM | 244 | CD2 | LEU | A | 102 | 42.140 | 1.647 | −12.214 | 1.00 | 26.79 | A |
| ATOM | 245 | C | LEU | A | 102 | 42.671 | −1.418 | −9.125 | 1.00 | 21.62 | A |
| ATOM | 246 | O | LEU | A | 102 | 41.668 | −2.103 | −9.305 | 1.00 | 21.09 | A |
| ATOM | 247 | N | ALA | A | 103 | 43.753 | −1.874 | −8.507 | 1.00 | 19.38 | A |
| ATOM | 248 | CA | ALA | A | 103 | 43.836 | −3.249 | −8.035 | 1.00 | 20.87 | A |
| ATOM | 249 | CB | ALA | A | 103 | 45.284 | −3.571 | −7.671 | 1.00 | 19.23 | A |
| ATOM | 250 | C | ALA | A | 103 | 42.919 | −3.629 | −6.872 | 1.00 | 19.92 | A |
| ATOM | 251 | O | ALA | A | 103 | 42.703 | −4.815 | −6.628 | 1.00 | 20.38 | A |
| ATOM | 252 | N | THR | A | 104 | 42.361 | −2.643 | −6.175 | 1.00 | 18.12 | A |
| ATOM | 253 | CA | THR | A | 104 | 41.517 | −2.927 | −5.018 | 1.00 | 17.15 | A |
| ATOM | 254 | CB | THR | A | 104 | 42.212 | −2.484 | −3.717 | 1.00 | 19.54 | A |
| ATOM | 255 | OG1 | THR | A | 104 | 42.456 | −1.070 | −3.773 | 1.00 | 19.26 | A |
| ATOM | 256 | CG2 | THR | A | 104 | 43.536 | −3.219 | −3.529 | 1.00 | 17.02 | A |
| ATOM | 257 | C | THR | A | 104 | 40.159 | −2.247 | −5.026 | 1.00 | 19.44 | A |
| ATOM | 258 | O | THR | A | 104 | 39.259 | −2.648 | −4.285 | 1.00 | 18.70 | A |
| ATOM | 259 | N | SER | A | 105 | 40.034 | −1.207 | −5.847 | 1.00 | 19.65 | A |
| ATOM | 260 | CA | SER | A | 105 | 38.819 | −0.400 | −5.967 | 1.00 | 19.37 | A |
| ATOM | 261 | CB | SER | A | 105 | 37.598 | −1.304 | −6.173 | 1.00 | 21.81 | A |
| ATOM | 262 | OG | SER | A | 105 | 36.431 | −0.539 | −6.412 | 1.00 | 23.01 | A |
| ATOM | 263 | C | SER | A | 105 | 38.644 | 0.447 | −4.701 | 1.00 | 18.99 | A |
| ATOM | 264 | O | SER | A | 105 | 37.602 | 1.070 | −4.488 | 1.00 | 18.66 | A |
| ATOM | 265 | N | ARG | A | 106 | 39.674 | 0.468 | −3.861 | 1.00 | 16.84 | A |
| ATOM | 266 | CA | ARG | A | 106 | 39.655 | 1.267 | −2.634 | 1.00 | 16.21 | A |
| ATOM | 267 | CB | ARG | A | 106 | 40.827 | 0.886 | −1.723 | 1.00 | 16.41 | A |
| ATOM | 268 | CG | ARG | A | 106 | 40.619 | −0.367 | −0.906 | 1.00 | 15.49 | A |
| ATOM | 269 | CD | ARG | A | 106 | 41.887 | −0.755 | −0.170 | 1.00 | 17.43 | A |
| ATOM | 270 | NE | ARG | A | 106 | 41.620 | −1.792 | 0.824 | 1.00 | 20.47 | A |
| ATOM | 271 | CZ | ARG | A | 106 | 42.548 | −2.568 | 1.371 | 1.00 | 20.24 | A |
| ATOM | 272 | NH1 | ARG | A | 106 | 43.821 | −2.433 | 1.017 | 1.00 | 17.80 | A |
| ATOM | 273 | NH2 | ARG | A | 106 | 42.198 | −3.468 | 2.285 | 1.00 | 20.14 | A |
| ATOM | 274 | C | ARG | A | 106 | 39.785 | 2.746 | −2.981 | 1.00 | 17.37 | A |
| ATOM | 275 | O | ARG | A | 106 | 40.514 | 3.103 | −3.902 | 1.00 | 17.75 | A |
| ATOM | 276 | N | GLU | A | 107 | 39.085 | 3.599 | −2.240 | 1.00 | 16.06 | A |
| ATOM | 277 | CA | GLU | A | 107 | 39.156 | 5.039 | −2.461 | 1.00 | 20.80 | A |
| ATOM | 278 | CB | GLU | A | 107 | 37.779 | 5.694 | −2.337 | 1.00 | 22.93 | A |
| ATOM | 279 | CG | GLU | A | 107 | 36.711 | 5.171 | −3.269 | 1.00 | 30.87 | A |
| ATOM | 280 | CD | GLU | A | 107 | 35.431 | 5.975 | −3.148 | 1.00 | 32.40 | A |
| ATOM | 281 | OE1 | GLU | A | 107 | 35.262 | 6.939 | −3.923 | 1.00 | 33.74 | A |
| ATOM | 282 | OE2 | GLU | A | 107 | 34.608 | 5.654 | −2.263 | 1.00 | 36.00 | A |
| ATOM | 283 | C | GLU | A | 107 | 40.053 | 5.678 | −1.410 | 1.00 | 18.93 | A |
| ATOM | 284 | O | GLU | A | 107 | 39.891 | 5.427 | −0.220 | 1.00 | 19.21 | A |
| ATOM | 285 | N | TYR | A | 108 | 40.988 | 6.507 | −1.852 | 1.00 | 16.70 | A |
| ATOM | 286 | CA | TYR | A | 108 | 41.883 | 7.209 | −0.942 | 1.00 | 15.86 | A |
| ATOM | 287 | CB | TYR | A | 108 | 43.325 | 6.728 | −1.104 | 1.00 | 15.30 | A |
| ATOM | 288 | CG | TYR | A | 108 | 43.593 | 5.328 | −0.612 | 1.00 | 16.33 | A |
| ATOM | 289 | CD1 | TYR | A | 108 | 43.765 | 5.066 | 0.746 | 1.00 | 16.36 | A |
| ATOM | 290 | CE1 | TYR | A | 108 | 44.046 | 3.769 | 1.201 | 1.00 | 18.48 | A |
| ATOM | 291 | CD2 | TYR | A | 108 | 43.701 | 4.268 | −1.511 | 1.00 | 13.25 | A |
| ATOM | 292 | CE2 | TYR | A | 108 | 43.980 | 2.981 | −1.075 | 1.00 | 17.28 | A |
| ATOM | 293 | CZ | TYR | A | 108 | 44.152 | 2.736 | 0.276 | 1.00 | 19.17 | A |
| ATOM | 294 | OH | TYR | A | 108 | 44.440 | 1.461 | 0.688 | 1.00 | 19.38 | A |
| ATOM | 295 | C | TYR | A | 108 | 41.850 | 8.687 | −1.292 | 1.00 | 16.80 | A |
| ATOM | 296 | O | TYR | A | 108 | 41.560 | 9.058 | −2.431 | 1.00 | 15.22 | A |
| ATOM | 297 | N | ALA | A | 109 | 42.132 | 9.528 | −0.306 | 1.00 | 14.61 | A |
| ATOM | 298 | CA | ALA | A | 109 | 42.207 | 10.957 | −0.539 | 1.00 | 14.30 | A |
| ATOM | 299 | CB | ALA | A | 109 | 41.671 | 11.726 | 0.661 | 1.00 | 14.78 | A |
| ATOM | 300 | C | ALA | A | 109 | 43.713 | 11.136 | −0.667 | 1.00 | 16.79 | A |
| ATOM | 301 | O | ALA | A | 109 | 44.450 | 10.983 | 0.317 | 1.00 | 16.52 | A |
| ATOM | 302 | N | ILE | A | 110 | 44.182 | 11.410 | −1.881 | 1.00 | 14.80 | A |
| ATOM | 303 | CA | ILE | A | 110 | 45.609 | 11.574 | −2.093 | 1.00 | 15.80 | A |
| ATOM | 304 | CB | ILE | A | 110 | 46.065 | 10.863 | −3.396 | 1.00 | 16.85 | A |
| ATOM | 305 | CG2 | ILE | A | 110 | 47.550 | 11.098 | −3.632 | 1.00 | 16.80 | A |
| ATOM | 306 | CG1 | ILE | A | 110 | 45.774 | 9.358 | −3.284 | 1.00 | 17.76 | A |
| ATOM | 307 | CD1 | ILE | A | 110 | 46.308 | 8.513 | −4.437 | 1.00 | 16.07 | A |
| ATOM | 308 | C | ILE | A | 110 | 46.004 | 13.045 | −2.129 | 1.00 | 17.78 | A |
| ATOM | 309 | O | ILE | A | 110 | 45.534 | 13.813 | −2.976 | 1.00 | 16.24 | A |
| ATOM | 310 | N | LYS | A | 111 | 46.846 | 13.435 | −1.177 | 1.00 | 16.15 | A |
| ATOM | 311 | CA | LYS | A | 111 | 47.326 | 14.808 | −1.100 | 1.00 | 17.20 | A |
| ATOM | 312 | CB | LYS | A | 111 | 47.700 | 15.176 | 0.344 | 1.00 | 17.41 | A |
| ATOM | 313 | CG | LYS | A | 111 | 48.350 | 16.547 | 0.464 | 1.00 | 20.71 | A |
| ATOM | 314 | CD | LYS | A | 111 | 48.585 | 16.971 | 1.910 | 1.00 | 24.25 | A |
| ATOM | 315 | CE | LYS | A | 111 | 47.288 | 17.381 | 2.598 | 1.00 | 29.46 | A |
| ATOM | 316 | NZ | LYS | A | 111 | 47.516 | 17.866 | 4.000 | 1.00 | 30.50 | A |
| ATOM | 317 | C | LYS | A | 111 | 48.551 | 14.890 | −1.994 | 1.00 | 16.41 | A |
| ATOM | 318 | O | LYS | A | 111 | 49.509 | 14.137 | −1.813 | 1.00 | 18.20 | A |
| ATOM | 319 | N | ILE | A | 112 | 48.509 | 15.798 | −2.963 | 1.00 | 15.87 | A |
| ATOM | 320 | CA | ILE | A | 112 | 49.606 | 15.967 | −3.907 | 1.00 | 17.28 | A |

-continued

| | | | | | | | | | | |
|---|---|---|---|---|---|---|---|---|---|---|
| ATOM | 321 | CB | ILE | A | 112 | 49.079 | 15.911 | −5.358 | 1.00 | 16.43 | A |
| ATOM | 322 | CG2 | ILE | A | 112 | 50.235 | 15.998 | −6.341 | 1.00 | 15.12 | A |
| ATOM | 323 | CG1 | ILE | A | 112 | 48.293 | 14.609 | −5.565 | 1.00 | 16.82 | A |
| ATOM | 324 | CD1 | ILE | A | 112 | 47.580 | 14.511 | −6.904 | 1.00 | 18.47 | A |
| ATOM | 325 | C | ILE | A | 112 | 50.307 | 17.301 | −3.663 | 1.00 | 19.03 | A |
| ATOM | 326 | O | ILE | A | 112 | 49.669 | 18.350 | −3.635 | 1.00 | 19.15 | A |
| ATOM | 327 | N | LEU | A | 113 | 51.622 | 17.245 | −3.472 | 1.00 | 20.22 | A |
| ATOM | 328 | CA | LEU | A | 113 | 52.416 | 18.442 | −3.214 | 1.00 | 22.36 | A |
| ATOM | 329 | CB | LEU | A | 113 | 52.995 | 18.397 | −1.794 | 1.00 | 22.13 | A |
| ATOM | 330 | CG | LEU | A | 113 | 52.042 | 18.063 | −0.646 | 1.00 | 22.46 | A |
| ATOM | 331 | CD1 | LEU | A | 113 | 51.866 | 16.557 | −0.553 | 1.00 | 23.81 | A |
| ATOM | 332 | CD2 | LEU | A | 113 | 52.603 | 18.595 | 0.660 | 1.00 | 23.68 | A |
| ATOM | 333 | C | LEU | A | 113 | 53.560 | 18.547 | −4.215 | 1.00 | 23.37 | A |
| ATOM | 334 | O | LEU | A | 113 | 54.300 | 17.586 | −4.424 | 1.00 | 23.11 | A |
| ATOM | 335 | N | GLU | A | 114 | 53.706 | 19.714 | −4.834 | 1.00 | 23.88 | A |
| ATOM | 336 | CA | GLU | A | 114 | 54.771 | 19.920 | −5.806 | 1.00 | 26.00 | A |
| ATOM | 337 | CB | GLU | A | 114 | 54.435 | 21.111 | −6.706 | 1.00 | 27.74 | A |
| ATOM | 338 | CG | GLU | A | 114 | 55.533 | 21.452 | −7.696 | 1.00 | 35.07 | A |
| ATOM | 339 | CD | GLU | A | 114 | 55.220 | 22.696 | −8.497 | 1.00 | 39.24 | A |
| ATOM | 340 | OE1 | GLU | A | 114 | 54.808 | 23.703 | −7.885 | 1.00 | 41.45 | A |
| ATOM | 341 | OE2 | GLU | A | 114 | 55.395 | 22.670 | −9.736 | 1.00 | 44.05 | A |
| ATOM | 342 | C | GLU | A | 114 | 56.087 | 20.163 | −5.067 | 1.00 | 24.37 | A |
| ATOM | 343 | O | GLU | A | 114 | 56.186 | 21.071 | −4.238 | 1.00 | 24.43 | A |
| ATOM | 344 | N | LYS | A | 115 | 57.096 | 19.350 | −5.360 | 1.00 | 24.10 | A |
| ATOM | 345 | CA | LYS | A | 115 | 58.376 | 19.493 | −4.678 | 1.00 | 24.93 | A |
| ATOM | 346 | CB | LYS | A | 115 | 59.339 | 18.373 | −5.103 | 1.00 | 23.72 | A |
| ATOM | 347 | CG | LYS | A | 115 | 59.139 | 17.080 | −4.308 | 1.00 | 23.09 | A |
| ATOM | 348 | CD | LYS | A | 115 | 60.064 | 15.944 | −4.743 | 1.00 | 21.92 | A |
| ATOM | 349 | CE | LYS | A | 115 | 59.691 | 15.400 | −6.117 | 1.00 | 22.42 | A |
| ATOM | 350 | NZ | LYS | A | 115 | 60.447 | 14.150 | −6.448 | 1.00 | 19.71 | A |
| ATOM | 351 | C | LYS | A | 115 | 59.031 | 20.858 | −4.868 | 1.00 | 26.87 | A |
| ATOM | 352 | O | LYS | A | 115 | 59.492 | 21.469 | −3.903 | 1.00 | 26.17 | A |
| ATOM | 353 | N | ARG | A | 116 | 59.058 | 21.348 | −6.102 | 1.00 | 28.73 | A |
| ATOM | 354 | CA | ARG | A | 116 | 59.678 | 22.638 | −6.380 | 1.00 | 29.66 | A |
| ATOM | 355 | CB | ARG | A | 116 | 59.533 | 22.980 | −7.868 | 1.00 | 31.29 | A |
| ATOM | 356 | CG | ARG | A | 116 | 60.047 | 24.361 | −8.267 | 1.00 | 33.19 | A |
| ATOM | 357 | CD | ARG | A | 116 | 61.368 | 24.710 | −7.590 | 1.00 | 35.13 | A |
| ATOM | 358 | NE | ARG | A | 116 | 62.329 | 23.612 | −7.618 | 1.00 | 36.42 | A |
| ATOM | 359 | CZ | ARG | A | 116 | 63.510 | 23.648 | −7.009 | 1.00 | 36.18 | A |
| ATOM | 360 | NH1 | ARG | A | 116 | 63.871 | 24.729 | −6.332 | 1.00 | 36.12 | A |
| ATOM | 361 | NH2 | ARG | A | 116 | 64.324 | 22.602 | −7.067 | 1.00 | 35.77 | A |
| ATOM | 362 | C | ARG | A | 116 | 59.097 | 23.761 | −5.519 | 1.00 | 29.70 | A |
| ATOM | 363 | O | ARG | A | 116 | 59.843 | 24.515 | −4.889 | 1.00 | 29.16 | A |
| ATOM | 364 | N | HIS | A | 117 | 57.773 | 23.862 | −5.472 | 1.00 | 27.22 | A |
| ATOM | 365 | CA | HIS | A | 117 | 57.126 | 24.903 | −4.681 | 1.00 | 26.33 | A |
| ATOM | 366 | CB | HIS | A | 117 | 55.606 | 24.835 | −4.848 | 1.00 | 28.41 | A |
| ATOM | 367 | CG | HIS | A | 117 | 54.881 | 26.005 | −4.258 | 1.00 | 31.82 | A |
| ATOM | 368 | CD2 | HIS | A | 117 | 55.309 | 27.249 | −3.935 | 1.00 | 33.19 | A |
| ATOM | 369 | ND1 | HIS | A | 117 | 53.536 | 25.974 | −3.961 | 1.00 | 34.30 | A |
| ATOM | 370 | CE1 | HIS | A | 117 | 53.165 | 27.148 | −3.480 | 1.00 | 34.58 | A |
| ATOM | 371 | NE2 | HIS | A | 117 | 54.222 | 27.940 | −3.455 | 1.00 | 35.18 | A |
| ATOM | 372 | C | HIS | A | 117 | 57.477 | 24.780 | −3.202 | 1.00 | 26.22 | A |
| ATOM | 373 | O | HIS | A | 117 | 57.737 | 25.776 | −2.534 | 1.00 | 25.67 | A |
| ATOM | 374 | N | ILE | A | 118 | 57.469 | 23.554 | −2.689 | 1.00 | 24.94 | A |
| ATOM | 375 | CA | ILE | A | 118 | 57.792 | 23.315 | −1.285 | 1.00 | 23.94 | A |
| ATOM | 376 | CB | ILE | A | 118 | 57.711 | 21.812 | −0.952 | 1.00 | 23.50 | A |
| ATOM | 377 | CG2 | ILE | A | 118 | 58.374 | 21.533 | 0.389 | 1.00 | 23.76 | A |
| ATOM | 378 | CG1 | ILE | A | 118 | 56.246 | 21.362 | −0.959 | 1.00 | 24.42 | A |
| ATOM | 379 | CD1 | ILE | A | 118 | 56.066 | 19.858 | −0.834 | 1.00 | 28.06 | A |
| ATOM | 380 | C | ILE | A | 118 | 59.195 | 23.821 | −0.958 | 1.00 | 23.78 | A |
| ATOM | 381 | O | ILE | A | 118 | 59.402 | 24.495 | 0.048 | 1.00 | 23.49 | A |
| ATOM | 382 | N | ILE | A | 119 | 60.153 | 23.489 | −1.815 | 1.00 | 23.46 | A |
| ATOM | 383 | CA | ILE | A | 119 | 61.534 | 23.913 | −1.619 | 1.00 | 25.13 | A |
| ATOM | 384 | CB | ILE | A | 119 | 62.467 | 23.250 | −2.664 | 1.00 | 24.25 | A |
| ATOM | 385 | CG2 | ILE | A | 119 | 63.858 | 23.890 | −2.617 | 1.00 | 22.47 | A |
| ATOM | 386 | CG1 | ILE | A | 119 | 62.540 | 21.738 | −2.395 | 1.00 | 25.05 | A |
| ATOM | 387 | CD1 | ILE | A | 119 | 63.327 | 20.945 | −3.439 | 1.00 | 24.62 | A |
| ATOM | 388 | C | ILE | A | 119 | 61.667 | 25.435 | −1.705 | 1.00 | 25.96 | A |
| ATOM | 389 | O | ILE | A | 119 | 62.330 | 26.051 | −0.872 | 1.00 | 24.78 | A |
| ATOM | 390 | N | LYS | A | 120 | 61.028 | 26.039 | −2.704 | 1.00 | 27.67 | A |
| ATOM | 391 | CA | LYS | A | 120 | 61.100 | 27.489 | −2.879 | 1.00 | 30.29 | A |
| ATOM | 392 | CB | LYS | A | 120 | 60.242 | 27.940 | −4.060 | 1.00 | 32.34 | A |
| ATOM | 393 | CG | LYS | A | 120 | 60.674 | 27.407 | −5.409 | 1.00 | 39.30 | A |
| ATOM | 394 | CD | LYS | A | 120 | 59.765 | 27.950 | −6.512 | 1.00 | 45.19 | A |
| ATOM | 395 | CE | LYS | A | 120 | 58.294 | 27.636 | −6.218 | 1.00 | 46.48 | A |
| ATOM | 396 | NZ | LYS | A | 120 | 57.363 | 28.155 | −7.252 | 1.00 | 46.49 | A |
| ATOM | 397 | C | LYS | A | 120 | 60.647 | 28.247 | −1.638 | 1.00 | 30.89 | A |
| ATOM | 398 | O | LYS | A | 120 | 61.303 | 29.198 | −1.217 | 1.00 | 32.48 | A |
| ATOM | 399 | N | GLU | A | 121 | 59.527 | 27.825 | −1.055 | 1.00 | 29.82 | A |

-continued

| | | | | | | | | | | | |
|---|---|---|---|---|---|---|---|---|---|---|---|
| ATOM | 400 | CA | GLU | A | 121 | 58.986 | 28.488 | 0.128 | 1.00 | 30.33 | A |
| ATOM | 401 | CB | GLU | A | 121 | 57.455 | 28.416 | 0.117 | 1.00 | 33.04 | A |
| ATOM | 402 | CG | GLU | A | 121 | 56.794 | 29.021 | −1.120 | 1.00 | 36.45 | A |
| ATOM | 403 | CD | GLU | A | 121 | 57.221 | 30.456 | −1.373 | 1.00 | 39.88 | A |
| ATOM | 404 | OE1 | GLU | A | 121 | 57.200 | 31.264 | −0.420 | 1.00 | 40.53 | A |
| ATOM | 405 | OE2 | GLU | A | 121 | 57.573 | 30.778 | −2.529 | 1.00 | 43.24 | A |
| ATOM | 406 | C | GLU | A | 121 | 59.511 | 27.930 | 1.451 | 1.00 | 30.37 | A |
| ATOM | 407 | O | GLU | A | 121 | 58.946 | 28.204 | 2.513 | 1.00 | 31.24 | A |
| ATOM | 408 | N | ASN | A | 122 | 60.588 | 27.151 | 1.390 | 1.00 | 29.03 | A |
| ATOM | 409 | CA | ASN | A | 122 | 61.183 | 26.573 | 2.594 | 1.00 | 28.46 | A |
| ATOM | 410 | CB | ASN | A | 122 | 61.836 | 27.673 | 3.436 | 1.00 | 31.28 | A |
| ATOM | 411 | CG | ASN | A | 122 | 62.945 | 28.395 | 2.698 | 1.00 | 34.12 | A |
| ATOM | 412 | OD1 | ASN | A | 122 | 62.697 | 29.143 | 1.754 | 1.00 | 35.57 | A |
| ATOM | 413 | ND2 | ASN | A | 122 | 64.181 | 28.169 | 3.127 | 1.00 | 35.73 | A |
| ATOM | 414 | C | ASN | A | 122 | 60.157 | 25.835 | 3.456 | 1.00 | 26.89 | A |
| ATOM | 415 | O | ASN | A | 122 | 60.085 | 26.055 | 4.663 | 1.00 | 27.23 | A |
| ATOM | 416 | N | LYS | A | 123 | 59.375 | 24.955 | 2.842 | 1.00 | 23.99 | A |
| ATOM | 417 | CA | LYS | A | 123 | 58.358 | 24.210 | 3.574 | 1.00 | 22.43 | A |
| ATOM | 418 | CB | LYS | A | 123 | 57.031 | 24.248 | 2.810 | 1.00 | 21.97 | A |
| ATOM | 419 | CG | LYS | A | 123 | 56.475 | 25.645 | 2.599 | 1.00 | 25.68 | A |
| ATOM | 420 | CD | LYS | A | 123 | 56.253 | 26.354 | 3.927 | 1.00 | 27.54 | A |
| ATOM | 421 | CE | LYS | A | 123 | 55.822 | 27.796 | 3.716 | 1.00 | 31.30 | A |
| ATOM | 422 | NZ | LYS | A | 123 | 55.756 | 28.540 | 5.004 | 1.00 | 33.21 | A |
| ATOM | 423 | C | LYS | A | 123 | 58.748 | 22.759 | 3.821 | 1.00 | 22.20 | A |
| ATOM | 424 | O | LYS | A | 123 | 57.924 | 21.960 | 4.264 | 1.00 | 22.50 | A |
| ATOM | 425 | N | VAL | A | 124 | 59.997 | 22.412 | 3.535 | 1.00 | 20.59 | A |
| ATOM | 426 | CA | VAL | A | 124 | 60.439 | 21.039 | 3.730 | 1.00 | 20.25 | A |
| ATOM | 427 | CB | VAL | A | 124 | 61.922 | 20.850 | 3.328 | 1.00 | 19.43 | A |
| ATOM | 428 | CG1 | VAL | A | 124 | 62.346 | 19.407 | 3.573 | 1.00 | 18.69 | A |
| ATOM | 429 | CG2 | VAL | A | 124 | 62.104 | 21.195 | 1.853 | 1.00 | 18.21 | A |
| ATOM | 430 | C | VAL | A | 124 | 60.236 | 20.561 | 5.163 | 1.00 | 19.53 | A |
| ATOM | 431 | O | VAL | A | 124 | 59.841 | 19.418 | 5.385 | 1.00 | 20.02 | A |
| ATOM | 432 | N | PRO | A | 125 | 60.513 | 21.422 | 6.159 | 1.00 | 20.01 | A |
| ATOM | 433 | CD | PRO | A | 125 | 61.178 | 22.738 | 6.118 | 1.00 | 18.69 | A |
| ATOM | 434 | CA | PRO | A | 125 | 60.318 | 20.979 | 7.544 | 1.00 | 19.88 | A |
| ATOM | 435 | CB | PRO | A | 125 | 60.793 | 22.180 | 8.363 | 1.00 | 19.95 | A |
| ATOM | 436 | CG | PRO | A | 125 | 61.839 | 22.805 | 7.479 | 1.00 | 18.85 | A |
| ATOM | 437 | C | PRO | A | 125 | 58.848 | 20.642 | 7.824 | 1.00 | 19.76 | A |
| ATOM | 438 | O | PRO | A | 125 | 58.544 | 19.700 | 8.550 | 1.00 | 16.99 | A |
| ATOM | 439 | N | TYR | A | 126 | 57.947 | 21.418 | 7.235 | 1.00 | 18.98 | A |
| ATOM | 440 | CA | TYR | A | 126 | 56.516 | 21.220 | 7.435 | 1.00 | 21.97 | A |
| ATOM | 441 | CB | TYR | A | 126 | 55.752 | 22.448 | 6.933 | 1.00 | 25.17 | A |
| ATOM | 442 | CG | TYR | A | 126 | 56.040 | 23.690 | 7.748 | 1.00 | 30.98 | A |
| ATOM | 443 | CD1 | TYR | A | 126 | 55.438 | 23.886 | 8.991 | 1.00 | 33.95 | A |
| ATOM | 444 | CE1 | TYR | A | 126 | 55.721 | 25.015 | 9.763 | 1.00 | 36.60 | A |
| ATOM | 445 | CD2 | TYR | A | 126 | 56.938 | 24.657 | 7.292 | 1.00 | 35.43 | A |
| ATOM | 446 | CE2 | TYR | A | 126 | 57.231 | 25.792 | 8.058 | 1.00 | 37.20 | A |
| ATOM | 447 | CZ | TYR | A | 126 | 56.618 | 25.962 | 9.291 | 1.00 | 37.40 | A |
| ATOM | 448 | OH | TYR | A | 126 | 56.903 | 27.073 | 10.052 | 1.00 | 40.85 | A |
| ATOM | 449 | C | TYR | A | 126 | 55.990 | 19.956 | 6.762 | 1.00 | 21.35 | A |
| ATOM | 450 | O | TYR | A | 126 | 55.265 | 19.175 | 7.383 | 1.00 | 20.49 | A |
| ATOM | 451 | N | VAL | A | 127 | 56.354 | 19.746 | 5.501 | 1.00 | 18.16 | A |
| ATOM | 452 | CA | VAL | A | 127 | 55.892 | 18.562 | 4.790 | 1.00 | 17.58 | A |
| ATOM | 453 | CB | VAL | A | 127 | 56.308 | 18.596 | 3.308 | 1.00 | 17.45 | A |
| ATOM | 454 | CG1 | VAL | A | 127 | 55.786 | 17.350 | 2.600 | 1.00 | 17.97 | A |
| ATOM | 455 | CG2 | VAL | A | 127 | 55.751 | 19.850 | 2.641 | 1.00 | 14.90 | A |
| ATOM | 456 | C | VAL | A | 127 | 56.459 | 17.306 | 5.448 | 1.00 | 18.39 | A |
| ATOM | 457 | O | VAL | A | 127 | 55.769 | 16.298 | 5.583 | 1.00 | 18.14 | A |
| ATOM | 458 | N | THR | A | 128 | 57.716 | 17.381 | 5.869 | 1.00 | 17.50 | A |
| ATOM | 459 | CA | THR | A | 128 | 58.375 | 16.260 | 6.530 | 1.00 | 18.54 | A |
| ATOM | 460 | CB | THR | A | 128 | 59.861 | 16.586 | 6.805 | 1.00 | 18.01 | A |
| ATOM | 461 | OG1 | THR | A | 128 | 60.537 | 16.804 | 5.559 | 1.00 | 21.14 | A |
| ATOM | 462 | CG2 | THR | A | 128 | 60.536 | 15.446 | 7.545 | 1.00 | 17.95 | A |
| ATOM | 463 | C | THR | A | 128 | 57.676 | 15.941 | 7.856 | 1.00 | 19.49 | A |
| ATOM | 464 | O | THR | A | 128 | 57.438 | 14.776 | 8.179 | 1.00 | 18.76 | A |
| ATOM | 465 | N | ARG | A | 129 | 57.345 | 16.981 | 8.619 | 1.00 | 19.60 | A |
| ATOM | 466 | CA | ARG | A | 129 | 56.673 | 16.804 | 9.904 | 1.00 | 20.12 | A |
| ATOM | 467 | CB | ARG | A | 129 | 56.534 | 18.144 | 10.621 | 1.00 | 21.33 | A |
| ATOM | 468 | CG | ARG | A | 129 | 55.948 | 18.029 | 12.023 | 1.00 | 28.02 | A |
| ATOM | 469 | CD | ARG | A | 129 | 55.721 | 19.404 | 12.597 | 1.00 | 31.25 | A |
| ATOM | 470 | NE | ARG | A | 129 | 56.940 | 20.205 | 12.560 | 1.00 | 37.78 | A |
| ATOM | 471 | CZ | ARG | A | 129 | 56.962 | 21.524 | 12.391 | 1.00 | 40.10 | A |
| ATOM | 472 | NH1 | ARG | A | 129 | 55.828 | 22.197 | 12.239 | 1.00 | 40.03 | A |
| ATOM | 473 | NH2 | ARG | A | 129 | 58.119 | 22.170 | 12.374 | 1.00 | 44.58 | A |
| ATOM | 474 | C | ARG | A | 129 | 55.288 | 16.186 | 9.729 | 1.00 | 20.08 | A |
| ATOM | 475 | O | ARG | A | 129 | 54.891 | 15.305 | 10.496 | 1.00 | 20.40 | A |
| ATOM | 476 | N | GLU | A | 130 | 54.553 | 16.654 | 8.724 | 1.00 | 18.79 | A |
| ATOM | 477 | CA | GLU | A | 130 | 53.222 | 16.125 | 8.454 | 1.00 | 20.10 | A |
| ATOM | 478 | CB | GLU | A | 130 | 52.638 | 16.749 | 7.183 | 1.00 | 19.92 | A |

|      |     |     |     |   |     |        |        |        |      |       |   |
|------|-----|-----|-----|---|-----|--------|--------|--------|------|-------|---|
| ATOM | 479 | CG  | GLU | A | 130 | 51.350 | 16.087 | 6.708  | 1.00 | 27.85 | A |
| ATOM | 480 | CD  | GLU | A | 130 | 50.581 | 16.933 | 5.707  | 1.00 | 29.72 | A |
| ATOM | 481 | OE1 | GLU | A | 130 | 51.216 | 17.528 | 4.814  | 1.00 | 33.46 | A |
| ATOM | 482 | OE2 | GLU | A | 130 | 49.339 | 16.996 | 5.807  | 1.00 | 30.74 | A |
| ATOM | 483 | C   | GLU | A | 130 | 53.301 | 14.615 | 8.295  | 1.00 | 19.81 | A |
| ATOM | 484 | O   | GLU | A | 130 | 52.553 | 13.875 | 8.935  | 1.00 | 18.37 | A |
| ATOM | 485 | N   | ARG | A | 131 | 54.219 | 14.162 | 7.447  | 1.00 | 20.41 | A |
| ATOM | 486 | CA  | ARG | A | 131 | 54.397 | 12.735 | 7.202  | 1.00 | 22.45 | A |
| ATOM | 487 | CB  | ARG | A | 131 | 55.442 | 12.511 | 6.098  | 1.00 | 25.16 | A |
| ATOM | 488 | CG  | ARG | A | 131 | 55.742 | 11.043 | 5.840  | 1.00 | 28.75 | A |
| ATOM | 489 | CD  | ARG | A | 131 | 56.736 | 10.837 | 4.708  | 1.00 | 33.75 | A |
| ATOM | 490 | NE  | ARG | A | 131 | 57.020 | 9.415  | 4.520  | 1.00 | 40.07 | A |
| ATOM | 491 | CZ  | ARG | A | 131 | 57.756 | 8.915  | 3.532  | 1.00 | 43.07 | A |
| ATOM | 492 | NH1 | ARG | A | 131 | 58.293 | 9.721  | 2.625  | 1.00 | 44.91 | A |
| ATOM | 493 | NH2 | ARG | A | 131 | 57.955 | 7.606  | 3.449  | 1.00 | 44.45 | A |
| ATOM | 494 | C   | ARG | A | 131 | 54.820 | 11.982 | 8.466  | 1.00 | 23.24 | A |
| ATOM | 495 | O   | ARG | A | 131 | 54.241 | 10.948 | 8.804  | 1.00 | 23.86 | A |
| ATOM | 496 | N   | ASP | A | 132 | 55.831 | 12.497 | 9.160  | 1.00 | 21.99 | A |
| ATOM | 497 | CA  | ASP | A | 132 | 56.318 | 11.850 | 10.370 | 1.00 | 22.04 | A |
| ATOM | 498 | CB  | ASP | A | 132 | 57.570 | 12.564 | 10.888 | 1.00 | 23.72 | A |
| ATOM | 499 | CG  | ASP | A | 132 | 58.750 | 12.442 | 9.932  | 1.00 | 27.77 | A |
| ATOM | 500 | OD1 | ASP | A | 132 | 58.681 | 11.620 | 8.989  | 1.00 | 27.34 | A |
| ATOM | 501 | OD2 | ASP | A | 132 | 59.753 | 13.163 | 10.128 | 1.00 | 28.70 | A |
| ATOM | 502 | C   | ASP | A | 132 | 55.258 | 11.772 | 11.474 | 1.00 | 21.69 | A |
| ATOM | 503 | O   | ASP | A | 132 | 55.077 | 10.723 | 12.092 | 1.00 | 22.75 | A |
| ATOM | 504 | N   | VAL | A | 133 | 54.551 | 12.868 | 11.725 | 1.00 | 19.54 | A |
| ATOM | 505 | CA  | VAL | A | 133 | 53.525 | 12.843 | 12.759 | 1.00 | 18.52 | A |
| ATOM | 506 | CB  | VAL | A | 133 | 52.908 | 14.244 | 12.990 | 1.00 | 19.26 | A |
| ATOM | 507 | CG1 | VAL | A | 133 | 51.708 | 14.135 | 13.918 | 1.00 | 18.79 | A |
| ATOM | 508 | CG2 | VAL | A | 133 | 53.953 | 15.180 | 13.604 | 1.00 | 18.80 | A |
| ATOM | 509 | C   | VAL | A | 133 | 52.419 | 11.854 | 12.398 | 1.00 | 19.46 | A |
| ATOM | 510 | O   | VAL | A | 133 | 52.073 | 10.991 | 13.200 | 1.00 | 19.94 | A |
| ATOM | 511 | N   | MET | A | 134 | 51.878 | 11.957 | 11.187 | 1.00 | 19.15 | A |
| ATOM | 512 | CA  | MET | A | 134 | 50.807 | 11.052 | 10.792 | 1.00 | 21.25 | A |
| ATOM | 513 | CB  | MET | A | 134 | 50.309 | 11.381 | 9.383  | 1.00 | 17.34 | A |
| ATOM | 514 | CG  | MET | A | 134 | 49.615 | 12.730 | 9.302  | 1.00 | 20.00 | A |
| ATOM | 515 | SD  | MET | A | 134 | 48.643 | 12.952 | 7.798  | 1.00 | 24.21 | A |
| ATOM | 516 | CE  | MET | A | 134 | 47.033 | 12.434 | 8.400  | 1.00 | 23.20 | A |
| ATOM | 517 | C   | MET | A | 134 | 51.203 | 9.582  | 10.881 | 1.00 | 22.43 | A |
| ATOM | 518 | O   | MET | A | 134 | 50.384 | 8.741  | 11.249 | 1.00 | 23.82 | A |
| ATOM | 519 | N   | SER | A | 135 | 52.454 | 9.273  | 10.556 | 1.00 | 23.09 | A |
| ATOM | 520 | CA  | SER | A | 135 | 52.939 | 7.895  | 10.615 | 1.00 | 26.13 | A |
| ATOM | 521 | CB  | SER | A | 135 | 54.356 | 7.798  | 10.039 | 1.00 | 26.17 | A |
| ATOM | 522 | OG  | SER | A | 135 | 54.383 | 8.177  | 8.673  | 1.00 | 31.91 | A |
| ATOM | 523 | C   | SER | A | 135 | 52.957 | 7.358  | 12.045 | 1.00 | 26.58 | A |
| ATOM | 524 | O   | SER | A | 135 | 52.926 | 6.148  | 12.261 | 1.00 | 26.42 | A |
| ATOM | 525 | N   | ARG | A | 136 | 53.014 | 8.261  | 13.018 | 1.00 | 25.65 | A |
| ATOM | 526 | CA  | ARG | A | 136 | 53.056 | 7.870  | 14.425 | 1.00 | 27.47 | A |
| ATOM | 527 | CB  | ARG | A | 136 | 53.823 | 8.914  | 15.238 | 1.00 | 27.97 | A |
| ATOM | 528 | CG  | ARG | A | 136 | 55.283 | 9.082  | 14.857 | 1.00 | 32.00 | A |
| ATOM | 529 | CD  | ARG | A | 136 | 55.904 | 10.218 | 15.664 | 1.00 | 33.03 | A |
| ATOM | 530 | NE  | ARG | A | 136 | 55.602 | 10.073 | 17.084 | 1.00 | 36.11 | A |
| ATOM | 531 | CZ  | ARG | A | 136 | 55.867 | 10.990 | 18.007 | 1.00 | 39.74 | A |
| ATOM | 532 | NH1 | ARG | A | 136 | 56.449 | 12.132 | 17.661 | 1.00 | 40.55 | A |
| ATOM | 533 | NH2 | ARG | A | 136 | 55.540 | 10.769 | 19.276 | 1.00 | 36.72 | A |
| ATOM | 534 | C   | ARG | A | 136 | 51.667 | 7.709  | 15.036 | 1.00 | 26.38 | A |
| ATOM | 535 | O   | ARG | A | 136 | 51.516 | 7.121  | 16.106 | 1.00 | 27.06 | A |
| ATOM | 536 | N   | LEU | A | 137 | 50.655 | 8.235  | 14.360 | 1.00 | 24.77 | A |
| ATOM | 537 | CA  | LEU | A | 137 | 49.294 | 8.162  | 14.870 | 1.00 | 24.70 | A |
| ATOM | 538 | CB  | LEU | A | 137 | 48.483 | 9.363  | 14.371 | 1.00 | 24.52 | A |
| ATOM | 539 | CG  | LEU | A | 137 | 49.050 | 10.760 | 14.662 | 1.00 | 26.67 | A |
| ATOM | 540 | CD1 | LEU | A | 137 | 48.075 | 11.813 | 14.141 | 1.00 | 27.25 | A |
| ATOM | 541 | CD2 | LEU | A | 137 | 49.279 | 10.945 | 16.155 | 1.00 | 27.09 | A |
| ATOM | 542 | C   | LEU | A | 137 | 48.592 | 6.868  | 14.473 | 1.00 | 25.20 | A |
| ATOM | 543 | O   | LEU | A | 137 | 48.619 | 6.469  | 13.309 | 1.00 | 25.99 | A |
| ATOM | 544 | N   | ASP | A | 138 | 47.971 | 6.218  | 15.451 | 1.00 | 21.89 | A |
| ATOM | 545 | CA  | ASP | A | 138 | 47.239 | 4.977  | 15.219 | 1.00 | 21.35 | A |
| ATOM | 546 | CB  | ASP | A | 138 | 48.124 | 3.761  | 15.523 | 1.00 | 22.14 | A |
| ATOM | 547 | CG  | ASP | A | 138 | 47.432 | 2.448  | 15.201 | 1.00 | 24.90 | A |
| ATOM | 548 | OD1 | ASP | A | 138 | 46.631 | 2.423  | 14.241 | 1.00 | 24.78 | A |
| ATOM | 549 | OD2 | ASP | A | 138 | 47.691 | 1.443  | 15.897 | 1.00 | 25.39 | A |
| ATOM | 550 | C   | ASP | A | 138 | 46.031 | 4.991  | 16.138 | 1.00 | 20.47 | A |
| ATOM | 551 | O   | ASP | A | 138 | 45.967 | 4.248  | 17.118 | 1.00 | 19.06 | A |
| ATOM | 552 | N   | HIS | A | 139 | 45.075 | 5.852  | 15.810 | 1.00 | 18.27 | A |
| ATOM | 553 | CA  | HIS | A | 139 | 43.869 | 6.016  | 16.606 | 1.00 | 18.21 | A |
| ATOM | 554 | CB  | HIS | A | 139 | 44.096 | 7.157  | 17.612 | 1.00 | 15.84 | A |
| ATOM | 555 | CG  | HIS | A | 139 | 42.985 | 7.332  | 18.600 | 1.00 | 15.24 | A |
| ATOM | 556 | CD2 | HIS | A | 139 | 42.884 | 6.964  | 19.900 | 1.00 | 13.97 | A |
| ATOM | 557 | ND1 | HIS | A | 139 | 41.791 | 7.943  | 18.280 | 1.00 | 14.74 | A |

-continued

| ATOM | 558 | CE1 | HIS | A | 139 | 41.002 | 7.944 | 19.341 | 1.00 | 14.19 | A |
|------|-----|-----|-----|---|-----|--------|-------|--------|------|-------|---|
| ATOM | 559 | NE2 | HIS | A | 139 | 41.641 | 7.356 | 20.336 | 1.00 | 14.15 | A |
| ATOM | 560 | C | HIS | A | 139 | 42.715 | 6.330 | 15.654 | 1.00 | 18.50 | A |
| ATOM | 561 | O | HIS | A | 139 | 42.879 | 7.080 | 14.693 | 1.00 | 20.80 | A |
| ATOM | 562 | N | PRO | A | 140 | 41.527 | 5.767 | 15.913 | 1.00 | 18.32 | A |
| ATOM | 563 | CD | PRO | A | 140 | 41.143 | 4.984 | 17.100 | 1.00 | 16.71 | A |
| ATOM | 564 | CA | PRO | A | 140 | 40.367 | 6.001 | 15.048 | 1.00 | 17.43 | A |
| ATOM | 565 | CB | PRO | A | 140 | 39.273 | 5.157 | 15.704 | 1.00 | 16.64 | A |
| ATOM | 566 | CG | PRO | A | 140 | 39.643 | 5.204 | 17.152 | 1.00 | 18.43 | A |
| ATOM | 567 | C | PRO | A | 140 | 39.914 | 7.441 | 14.803 | 1.00 | 18.77 | A |
| ATOM | 568 | O | PRO | A | 140 | 39.207 | 7.695 | 13.831 | 1.00 | 19.88 | A |
| ATOM | 569 | N | PHE | A | 141 | 40.301 | 8.381 | 15.664 | 1.00 | 17.14 | A |
| ATOM | 570 | CA | PHE | A | 141 | 39.874 | 9.767 | 15.477 | 1.00 | 16.42 | A |
| ATOM | 571 | CB | PHE | A | 141 | 39.568 | 10.422 | 16.836 | 1.00 | 14.60 | A |
| ATOM | 572 | CG | PHE | A | 141 | 38.386 | 9.817 | 17.556 | 1.00 | 15.26 | A |
| ATOM | 573 | CD1 | PHE | A | 141 | 37.335 | 9.234 | 16.842 | 1.00 | 14.78 | A |
| ATOM | 574 | CD2 | PHE | A | 141 | 38.297 | 9.880 | 18.942 | 1.00 | 13.70 | A |
| ATOM | 575 | CE1 | PHE | A | 141 | 36.215 | 8.727 | 17.502 | 1.00 | 16.94 | A |
| ATOM | 576 | CE2 | PHE | A | 141 | 37.178 | 9.375 | 19.615 | 1.00 | 15.75 | A |
| ATOM | 577 | CZ | PHE | A | 141 | 36.135 | 8.799 | 18.893 | 1.00 | 16.89 | A |
| ATOM | 578 | C | PHE | A | 141 | 40.857 | 10.641 | 14.694 | 1.00 | 16.15 | A |
| ATOM | 579 | O | PHE | A | 141 | 40.799 | 11.871 | 14.761 | 1.00 | 17.35 | A |
| ATOM | 580 | N | PHE | A | 142 | 41.748 | 10.011 | 13.941 | 1.00 | 15.88 | A |
| ATOM | 581 | CA | PHE | A | 142 | 42.727 | 10.756 | 13.154 | 1.00 | 17.89 | A |
| ATOM | 582 | CB | PHE | A | 142 | 44.115 | 10.645 | 13.793 | 1.00 | 17.57 | A |
| ATOM | 583 | CG | PHE | A | 142 | 44.240 | 11.371 | 15.103 | 1.00 | 18.74 | A |
| ATOM | 584 | CD1 | PHE | A | 142 | 44.559 | 12.726 | 15.135 | 1.00 | 17.77 | A |
| ATOM | 585 | CD2 | PHE | A | 142 | 43.997 | 10.711 | 16.304 | 1.00 | 18.74 | A |
| ATOM | 586 | CE1 | PHE | A | 142 | 44.632 | 13.417 | 16.347 | 1.00 | 15.77 | A |
| ATOM | 587 | CE2 | PHE | A | 142 | 44.065 | 11.393 | 17.522 | 1.00 | 17.56 | A |
| ATOM | 588 | CZ | PHE | A | 142 | 44.383 | 12.747 | 17.542 | 1.00 | 17.14 | A |
| ATOM | 589 | C | PHE | A | 142 | 42.793 | 10.231 | 11.729 | 1.00 | 19.12 | A |
| ATOM | 590 | O | PHE | A | 142 | 42.659 | 9.030 | 11.504 | 1.00 | 20.01 | A |
| ATOM | 591 | N | VAL | A | 143 | 42.978 | 11.135 | 10.769 | 1.00 | 18.72 | A |
| ATOM | 592 | CA | VAL | A | 143 | 43.102 | 10.735 | 9.371 | 1.00 | 18.52 | A |
| ATOM | 593 | CB | VAL | A | 143 | 43.294 | 11.961 | 8.440 | 1.00 | 20.66 | A |
| ATOM | 594 | CG1 | VAL | A | 143 | 43.843 | 11.521 | 7.080 | 1.00 | 21.29 | A |
| ATOM | 595 | CG2 | VAL | A | 143 | 41.958 | 12.673 | 8.252 | 1.00 | 22.97 | A |
| ATOM | 596 | C | VAL | A | 143 | 44.342 | 9.865 | 9.330 | 1.00 | 18.68 | A |
| ATOM | 597 | O | VAL | A | 143 | 45.355 | 10.199 | 9.943 | 1.00 | 18.42 | A |
| ATOM | 598 | N | LYS | A | 144 | 44.259 | 8.745 | 8.623 | 1.00 | 18.30 | A |
| ATOM | 599 | CA | LYS | A | 144 | 45.384 | 7.824 | 8.535 | 1.00 | 18.78 | A |
| ATOM | 600 | CB | LYS | A | 144 | 44.889 | 6.373 | 8.608 | 1.00 | 22.27 | A |
| ATOM | 601 | CG | LYS | A | 144 | 46.017 | 5.340 | 8.557 | 1.00 | 29.72 | A |
| ATOM | 602 | CD | LYS | A | 144 | 45.491 | 3.912 | 8.674 | 1.00 | 34.16 | A |
| ATOM | 603 | CE | LYS | A | 144 | 46.631 | 2.896 | 8.577 | 1.00 | 37.67 | A |
| ATOM | 604 | NZ | LYS | A | 144 | 46.138 | 1.484 | 8.629 | 1.00 | 39.02 | A |
| ATOM | 605 | C | LYS | A | 144 | 46.192 | 8.002 | 7.261 | 1.00 | 18.53 | A |
| ATOM | 606 | O | LYS | A | 144 | 45.643 | 8.314 | 6.200 | 1.00 | 18.18 | A |
| ATOM | 607 | N | LEU | A | 145 | 47.502 | 7.816 | 7.385 | 1.00 | 16.79 | A |
| ATOM | 608 | CA | LEU | A | 145 | 48.411 | 7.900 | 6.251 | 1.00 | 17.45 | A |
| ATOM | 609 | CB | LEU | A | 145 | 49.686 | 8.653 | 6.641 | 1.00 | 18.82 | A |
| ATOM | 610 | CG | LEU | A | 145 | 50.734 | 8.902 | 5.549 | 1.00 | 20.23 | A |
| ATOM | 611 | CD1 | LEU | A | 145 | 51.836 | 9.799 | 6.093 | 1.00 | 18.83 | A |
| ATOM | 612 | CD2 | LEU | A | 145 | 51.317 | 7.581 | 5.069 | 1.00 | 19.79 | A |
| ATOM | 613 | C | LEU | A | 145 | 48.739 | 6.450 | 5.907 | 1.00 | 19.19 | A |
| ATOM | 614 | O | LEU | A | 145 | 49.451 | 5.772 | 6.659 | 1.00 | 17.36 | A |
| ATOM | 615 | N | TYR | A | 146 | 48.215 | 5.972 | 4.782 | 1.00 | 17.28 | A |
| ATOM | 616 | CA | TYR | A | 146 | 48.444 | 4.593 | 4.358 | 1.00 | 17.57 | A |
| ATOM | 617 | CB | TYR | A | 146 | 47.288 | 4.098 | 3.486 | 1.00 | 17.74 | A |
| ATOM | 618 | CG | TYR | A | 146 | 45.981 | 3.926 | 4.214 | 1.00 | 17.50 | A |
| ATOM | 619 | CD1 | TYR | A | 146 | 45.099 | 4.995 | 4.377 | 1.00 | 16.50 | A |
| ATOM | 620 | CE1 | TYR | A | 146 | 43.881 | 4.827 | 5.039 | 1.00 | 17.10 | A |
| ATOM | 621 | CD2 | TYR | A | 146 | 45.620 | 2.686 | 4.735 | 1.00 | 18.28 | A |
| ATOM | 622 | CE2 | TYR | A | 146 | 44.411 | 2.506 | 5.399 | 1.00 | 19.84 | A |
| ATOM | 623 | CZ | TYR | A | 146 | 43.547 | 3.576 | 5.544 | 1.00 | 17.53 | A |
| ATOM | 624 | OH | TYR | A | 146 | 42.342 | 3.376 | 6.169 | 1.00 | 20.67 | A |
| ATOM | 625 | C | TYR | A | 146 | 49.735 | 4.376 | 3.582 | 1.00 | 18.72 | A |
| ATOM | 626 | O | TYR | A | 146 | 50.382 | 3.338 | 3.715 | 1.00 | 19.51 | A |
| ATOM | 627 | N | PHE | A | 147 | 50.110 | 5.350 | 2.765 | 1.00 | 18.09 | A |
| ATOM | 628 | CA | PHE | A | 147 | 51.307 | 5.203 | 1.952 | 1.00 | 17.20 | A |
| ATOM | 629 | CB | PHE | A | 147 | 51.007 | 4.258 | 0.783 | 1.00 | 16.77 | A |
| ATOM | 630 | CG | PHE | A | 147 | 49.835 | 4.699 | −0.070 | 1.00 | 17.75 | A |
| ATOM | 631 | CD1 | PHE | A | 147 | 49.967 | 5.752 | −0.975 | 1.00 | 16.58 | A |
| ATOM | 632 | CD2 | PHE | A | 147 | 48.595 | 4.075 | 0.053 | 1.00 | 18.07 | A |
| ATOM | 633 | CE1 | PHE | A | 147 | 48.886 | 6.178 | −1.742 | 1.00 | 19.62 | A |
| ATOM | 634 | CE2 | PHE | A | 147 | 47.503 | 4.492 | −0.710 | 1.00 | 18.56 | A |
| ATOM | 635 | CZ | PHE | A | 147 | 47.647 | 5.546 | −1.610 | 1.00 | 19.27 | A |
| ATOM | 636 | C | PHE | A | 147 | 51.768 | 6.533 | 1.395 | 1.00 | 17.13 | A |

-continued

| | | | | | | | | | | |
|---|---|---|---|---|---|---|---|---|---|---|
| ATOM | 637 | O | PHE | A | 147 | 51.045 | 7.528 | 1.452 | 1.00 | 14.43 | A |
| ATOM | 638 | N | THR | A | 148 | 52.981 | 6.534 | 0.854 | 1.00 | 17.12 | A |
| ATOM | 639 | CA | THR | A | 148 | 53.541 | 7.718 | 0.232 | 1.00 | 17.96 | A |
| ATOM | 640 | CB | THR | A | 148 | 54.449 | 8.531 | 1.197 | 1.00 | 21.51 | A |
| ATOM | 641 | OG1 | THR | A | 148 | 55.605 | 7.760 | 1.537 | 1.00 | 18.83 | A |
| ATOM | 642 | CG2 | THR | A | 148 | 53.700 | 8.897 | 2.472 | 1.00 | 19.60 | A |
| ATOM | 643 | C | THR | A | 148 | 54.386 | 7.262 | −0.946 | 1.00 | 20.31 | A |
| ATOM | 644 | O | THR | A | 148 | 54.860 | 6.124 | −0.991 | 1.00 | 18.94 | A |
| ATOM | 645 | N | PHE | A | 149 | 54.543 | 8.149 | −1.916 | 1.00 | 19.16 | A |
| ATOM | 646 | CA | PHE | A | 149 | 55.368 | 7.877 | −3.073 | 1.00 | 18.01 | A |
| ATOM | 647 | CB | PHE | A | 149 | 54.748 | 6.801 | −3.989 | 1.00 | 17.23 | A |
| ATOM | 648 | CG | PHE | A | 149 | 53.389 | 7.144 | −4.544 | 1.00 | 16.88 | A |
| ATOM | 649 | CD1 | PHE | A | 149 | 53.262 | 7.888 | −5.712 | 1.00 | 18.58 | A |
| ATOM | 650 | CD2 | PHE | A | 149 | 52.235 | 6.668 | −3.927 | 1.00 | 17.31 | A |
| ATOM | 651 | CE1 | PHE | A | 149 | 52.007 | 8.149 | −6.267 | 1.00 | 19.26 | A |
| ATOM | 652 | CE2 | PHE | A | 149 | 50.972 | 6.923 | −4.470 | 1.00 | 19.17 | A |
| ATOM | 653 | CZ | PHE | A | 149 | 50.858 | 7.663 | −5.642 | 1.00 | 19.60 | A |
| ATOM | 654 | C | PHE | A | 149 | 55.542 | 9.205 | −3.774 | 1.00 | 20.85 | A |
| ATOM | 655 | O | PHE | A | 149 | 54.934 | 10.200 | −3.376 | 1.00 | 19.76 | A |
| ATOM | 656 | N | GLN | A | 150 | 56.398 | 9.241 | −4.782 | 1.00 | 19.79 | A |
| ATOM | 657 | CA | GLN | A | 150 | 56.636 | 10.481 | −5.497 | 1.00 | 24.03 | A |
| ATOM | 658 | CB | GLN | A | 150 | 57.659 | 11.347 | −4.739 | 1.00 | 24.45 | A |
| ATOM | 659 | CG | GLN | A | 150 | 58.986 | 10.645 | −4.414 | 1.00 | 26.28 | A |
| ATOM | 660 | CD | GLN | A | 150 | 59.988 | 11.558 | −3.692 | 1.00 | 29.02 | A |
| ATOM | 661 | OE1 | GLN | A | 150 | 60.693 | 12.353 | −4.321 | 1.00 | 27.05 | A |
| ATOM | 662 | NE2 | GLN | A | 150 | 60.042 | 11.449 | −2.365 | 1.00 | 26.47 | A |
| ATOM | 663 | C | GLN | A | 150 | 57.160 | 10.203 | −6.885 | 1.00 | 23.88 | A |
| ATOM | 664 | O | GLN | A | 150 | 57.673 | 9.118 | −7.158 | 1.00 | 24.79 | A |
| ATOM | 665 | N | ASP | A | 151 | 56.987 | 11.171 | −7.774 | 1.00 | 25.88 | A |
| ATOM | 666 | CA | ASP | A | 151 | 57.527 | 11.047 | −9.117 | 1.00 | 26.49 | A |
| ATOM | 667 | CB | ASP | A | 151 | 56.437 | 11.126 | −10.199 | 1.00 | 24.54 | A |
| ATOM | 668 | CG | ASP | A | 151 | 55.544 | 12.336 | −10.064 | 1.00 | 24.95 | A |
| ATOM | 669 | OD1 | ASP | A | 151 | 56.005 | 13.379 | −9.561 | 1.00 | 22.44 | A |
| ATOM | 670 | OD2 | ASP | A | 151 | 54.369 | 12.242 | −10.490 | 1.00 | 25.72 | A |
| ATOM | 671 | C | ASP | A | 151 | 58.515 | 12.203 | −9.220 | 1.00 | 28.63 | A |
| ATOM | 672 | O | ASP | A | 151 | 58.890 | 12.780 | −8.194 | 1.00 | 27.83 | A |
| ATOM | 673 | N | ASP | A | 152 | 58.934 | 12.560 | −10.426 | 1.00 | 29.21 | A |
| ATOM | 674 | CA | ASP | A | 152 | 59.907 | 13.636 | −10.562 | 1.00 | 31.88 | A |
| ATOM | 675 | CB | ASP | A | 152 | 60.325 | 13.792 | −12.026 | 1.00 | 33.94 | A |
| ATOM | 676 | CG | ASP | A | 152 | 61.033 | 12.564 | −12.557 | 1.00 | 38.88 | A |
| ATOM | 677 | OD1 | ASP | A | 152 | 61.817 | 11.959 | −11.791 | 1.00 | 39.67 | A |
| ATOM | 678 | OD2 | ASP | A | 152 | 60.817 | 12.211 | −13.738 | 1.00 | 41.57 | A |
| ATOM | 679 | C | ASP | A | 152 | 59.487 | 14.994 | −10.013 | 1.00 | 30.90 | A |
| ATOM | 680 | O | ASP | A | 152 | 60.316 | 15.735 | −9.482 | 1.00 | 31.69 | A |
| ATOM | 681 | N | GLU | A | 153 | 58.207 | 15.322 | −10.107 | 1.00 | 29.44 | A |
| ATOM | 682 | CA | GLU | A | 153 | 57.767 | 16.632 | −9.646 | 1.00 | 28.69 | A |
| ATOM | 683 | CB | GLU | A | 153 | 56.984 | 17.327 | −10.766 | 1.00 | 32.90 | A |
| ATOM | 684 | CG | GLU | A | 153 | 57.451 | 16.987 | −12.183 | 1.00 | 40.57 | A |
| ATOM | 685 | CD | GLU | A | 153 | 56.920 | 15.643 | −12.675 | 1.00 | 45.78 | A |
| ATOM | 686 | OE1 | GLU | A | 153 | 55.682 | 15.482 | −12.760 | 1.00 | 48.91 | A |
| ATOM | 687 | OE2 | GLU | A | 153 | 57.736 | 14.747 | −12.979 | 1.00 | 48.95 | A |
| ATOM | 688 | C | GLU | A | 153 | 56.929 | 16.683 | −8.372 | 1.00 | 26.43 | A |
| ATOM | 689 | O | GLU | A | 153 | 56.947 | 17.688 | −7.660 | 1.00 | 25.08 | A |
| ATOM | 690 | N | LYS | A | 154 | 56.205 | 15.610 | −8.069 | 1.00 | 22.39 | A |
| ATOM | 691 | CA | LYS | A | 154 | 55.318 | 15.631 | −6.912 | 1.00 | 21.43 | A |
| ATOM | 692 | CB | LYS | A | 154 | 53.861 | 15.628 | −7.398 | 1.00 | 20.33 | A |
| ATOM | 693 | CG | LYS | A | 154 | 53.505 | 16.716 | −8.403 | 1.00 | 21.92 | A |
| ATOM | 694 | CD | LYS | A | 154 | 52.211 | 16.375 | −9.146 | 1.00 | 19.70 | A |
| ATOM | 695 | CE | LYS | A | 154 | 51.775 | 17.503 | −10.077 | 1.00 | 20.04 | A |
| ATOM | 696 | NZ | LYS | A | 154 | 50.631 | 17.094 | −10.951 | 1.00 | 19.97 | A |
| ATOM | 697 | C | LYS | A | 154 | 55.458 | 14.522 | −5.881 | 1.00 | 20.43 | A |
| ATOM | 698 | O | LYS | A | 154 | 55.949 | 13.426 | −6.173 | 1.00 | 21.13 | A |
| ATOM | 699 | N | LEU | A | 155 | 54.985 | 14.832 | −4.676 | 1.00 | 19.69 | A |
| ATOM | 700 | CA | LEU | A | 155 | 54.950 | 13.900 | −3.553 | 1.00 | 19.10 | A |
| ATOM | 701 | CB | LEU | A | 155 | 55.362 | 14.588 | −2.252 | 1.00 | 19.65 | A |
| ATOM | 702 | CG | LEU | A | 155 | 56.740 | 15.234 | −2.129 | 1.00 | 21.20 | A |
| ATOM | 703 | CD1 | LEU | A | 155 | 56.848 | 15.918 | −0.770 | 1.00 | 23.42 | A |
| ATOM | 704 | CD2 | LEU | A | 155 | 57.816 | 14.174 | −2.277 | 1.00 | 23.08 | A |
| ATOM | 705 | C | LEU | A | 155 | 53.478 | 13.507 | −3.427 | 1.00 | 18.87 | A |
| ATOM | 706 | O | LEU | A | 155 | 52.600 | 14.348 | −3.620 | 1.00 | 18.61 | A |
| ATOM | 707 | N | TYR | A | 156 | 53.209 | 12.249 | −3.091 | 1.00 | 15.02 | A |
| ATOM | 708 | CA | TYR | A | 156 | 51.834 | 11.783 | −2.934 | 1.00 | 16.29 | A |
| ATOM | 709 | CB | TYR | A | 156 | 51.470 | 10.769 | −4.029 | 1.00 | 14.20 | A |
| ATOM | 710 | CG | TYR | A | 156 | 51.603 | 11.273 | −5.449 | 1.00 | 17.29 | A |
| ATOM | 711 | CD1 | TYR | A | 156 | 52.857 | 11.429 | −6.045 | 1.00 | 16.46 | A |
| ATOM | 712 | CE1 | TYR | A | 156 | 52.978 | 11.884 | −7.360 | 1.00 | 18.68 | A |
| ATOM | 713 | CD2 | TYR | A | 156 | 50.474 | 11.588 | −6.202 | 1.00 | 16.43 | A |
| ATOM | 714 | CE2 | TYR | A | 156 | 50.583 | 12.048 | −7.512 | 1.00 | 16.31 | A |
| ATOM | 715 | CZ | TYR | A | 156 | 51.835 | 12.192 | −8.083 | 1.00 | 18.17 | A |

-continued

| | | | | | | | | | | | |
|---|---|---|---|---|---|---|---|---|---|---|---|
| ATOM | 716 | OH | TYR | A | 156 | 51.941 | 12.651 | −9.371 | 1.00 | 17.47 | A |
| ATOM | 717 | C | TYR | A | 156 | 51.657 | 11.108 | −1.572 | 1.00 | 16.32 | A |
| ATOM | 718 | O | TYR | A | 156 | 52.412 | 10.197 | −1.235 | 1.00 | 16.27 | A |
| ATOM | 719 | N | PHE | A | 157 | 50.678 | 11.568 | −0.792 | 1.00 | 15.47 | A |
| ATOM | 720 | CA | PHE | A | 157 | 50.385 | 10.966 | 0.508 | 1.00 | 16.66 | A |
| ATOM | 721 | CB | PHE | A | 157 | 50.324 | 12.014 | 1.629 | 1.00 | 16.91 | A |
| ATOM | 722 | CG | PHE | A | 157 | 51.631 | 12.708 | 1.907 | 1.00 | 18.96 | A |
| ATOM | 723 | CD1 | PHE | A | 157 | 52.821 | 12.261 | 1.340 | 1.00 | 20.31 | A |
| ATOM | 724 | CD2 | PHE | A | 157 | 51.664 | 13.829 | 2.732 | 1.00 | 21.12 | A |
| ATOM | 725 | CE1 | PHE | A | 157 | 54.025 | 12.926 | 1.585 | 1.00 | 22.08 | A |
| ATOM | 726 | CE2 | PHE | A | 157 | 52.865 | 14.500 | 2.982 | 1.00 | 22.18 | A |
| ATOM | 727 | CZ | PHE | A | 157 | 54.045 | 14.045 | 2.405 | 1.00 | 21.27 | A |
| ATOM | 728 | C | PHE | A | 157 | 49.016 | 10.308 | 0.404 | 1.00 | 16.52 | A |
| ATOM | 729 | O | PHE | A | 157 | 48.029 | 10.979 | 0.110 | 1.00 | 17.32 | A |
| ATOM | 730 | N | GLY | A | 158 | 48.953 | 9.002 | 0.644 | 1.00 | 15.97 | A |
| ATOM | 731 | CA | GLY | A | 158 | 47.684 | 8.299 | 0.572 | 1.00 | 16.13 | A |
| ATOM | 732 | C | GLY | A | 158 | 47.000 | 8.383 | 1.920 | 1.00 | 14.94 | A |
| ATOM | 733 | O | GLY | A | 158 | 47.445 | 7.756 | 2.879 | 1.00 | 16.28 | A |
| ATOM | 734 | N | LEU | A | 159 | 45.915 | 9.145 | 1.989 | 1.00 | 13.50 | A |
| ATOM | 735 | CA | LEU | A | 159 | 45.191 | 9.340 | 3.241 | 1.00 | 15.20 | A |
| ATOM | 736 | CB | LEU | A | 159 | 45.031 | 10.835 | 3.517 | 1.00 | 14.20 | A |
| ATOM | 737 | CG | LEU | A | 159 | 46.270 | 11.726 | 3.385 | 1.00 | 19.00 | A |
| ATOM | 738 | CD1 | LEU | A | 159 | 45.847 | 13.188 | 3.477 | 1.00 | 17.12 | A |
| ATOM | 739 | CD2 | LEU | A | 159 | 47.275 | 11.390 | 4.471 | 1.00 | 14.71 | A |
| ATOM | 740 | C | LEU | A | 159 | 43.809 | 8.716 | 3.232 | 1.00 | 15.53 | A |
| ATOM | 741 | O | LEU | A | 159 | 43.232 | 8.472 | 2.177 | 1.00 | 16.05 | A |
| ATOM | 742 | N | SER | A | 160 | 43.268 | 8.469 | 4.418 | 1.00 | 15.86 | A |
| ATOM | 743 | CA | SER | A | 160 | 41.932 | 7.917 | 4.498 | 1.00 | 19.01 | A |
| ATOM | 744 | CB | SER | A | 160 | 41.566 | 7.582 | 5.949 | 1.00 | 22.90 | A |
| ATOM | 745 | OG | SER | A | 160 | 41.901 | 8.629 | 6.833 | 1.00 | 24.18 | A |
| ATOM | 746 | C | SER | A | 160 | 40.987 | 8.968 | 3.924 | 1.00 | 20.43 | A |
| ATOM | 747 | O | SER | A | 160 | 41.213 | 10.173 | 4.062 | 1.00 | 19.96 | A |
| ATOM | 748 | N | TYR | A | 161 | 39.945 | 8.508 | 3.250 | 1.00 | 19.20 | A |
| ATOM | 749 | CA | TYR | A | 161 | 38.975 | 9.406 | 2.644 | 1.00 | 20.37 | A |
| ATOM | 750 | CB | TYR | A | 161 | 38.471 | 8.785 | 1.332 | 1.00 | 20.00 | A |
| ATOM | 751 | CG | TYR | A | 161 | 37.314 | 9.502 | 0.666 | 1.00 | 20.72 | A |
| ATOM | 752 | CD1 | TYR | A | 161 | 37.222 | 10.895 | 0.682 | 1.00 | 18.22 | A |
| ATOM | 753 | CE1 | TYR | A | 161 | 36.180 | 11.557 | 0.029 | 1.00 | 22.24 | A |
| ATOM | 754 | CD2 | TYR | A | 161 | 36.333 | 8.784 | −0.020 | 1.00 | 20.53 | A |
| ATOM | 755 | CE2 | TYR | A | 161 | 35.287 | 9.436 | −0.678 | 1.00 | 24.24 | A |
| ATOM | 756 | CZ | TYR | A | 161 | 35.218 | 10.822 | −0.648 | 1.00 | 22.32 | A |
| ATOM | 757 | OH | TYR | A | 161 | 34.194 | 11.471 | −1.298 | 1.00 | 23.03 | A |
| ATOM | 758 | C | TYR | A | 161 | 37.812 | 9.681 | 3.598 | 1.00 | 20.14 | A |
| ATOM | 759 | O | TYR | A | 161 | 36.959 | 8.819 | 3.810 | 1.00 | 19.53 | A |
| ATOM | 760 | N | ALA | A | 162 | 37.791 | 10.880 | 4.178 | 1.00 | 19.92 | A |
| ATOM | 761 | CA | ALA | A | 162 | 36.721 | 11.271 | 5.099 | 1.00 | 21.07 | A |
| ATOM | 762 | CB | ALA | A | 162 | 37.187 | 12.419 | 6.002 | 1.00 | 19.60 | A |
| ATOM | 763 | C | ALA | A | 162 | 35.542 | 11.712 | 4.238 | 1.00 | 22.07 | A |
| ATOM | 764 | O | ALA | A | 162 | 35.436 | 12.875 | 3.860 | 1.00 | 20.66 | A |
| ATOM | 765 | N | LYS | A | 163 | 34.653 | 10.769 | 3.945 | 1.00 | 23.27 | A |
| ATOM | 766 | CA | LYS | A | 163 | 33.503 | 11.017 | 3.080 | 1.00 | 27.12 | A |
| ATOM | 767 | CB | LYS | A | 163 | 32.663 | 9.741 | 2.963 | 1.00 | 29.68 | A |
| ATOM | 768 | CG | LYS | A | 163 | 33.455 | 8.524 | 2.515 | 1.00 | 37.67 | A |
| ATOM | 769 | CD | LYS | A | 163 | 32.556 | 7.310 | 2.321 | 1.00 | 42.24 | A |
| ATOM | 770 | CE | LYS | A | 163 | 33.373 | 6.034 | 2.185 | 1.00 | 44.48 | A |
| ATOM | 771 | NZ | LYS | A | 163 | 34.143 | 5.735 | 3.430 | 1.00 | 44.88 | A |
| ATOM | 772 | C | LYS | A | 163 | 32.581 | 12.186 | 3.411 | 1.00 | 25.78 | A |
| ATOM | 773 | O | LYS | A | 163 | 32.103 | 12.863 | 2.506 | 1.00 | 26.53 | A |
| ATOM | 774 | N | ASN | A | 164 | 32.327 | 12.441 | 4.689 | 1.00 | 24.57 | A |
| ATOM | 775 | CA | ASN | A | 164 | 31.420 | 13.522 | 5.033 | 1.00 | 23.77 | A |
| ATOM | 776 | CB | ASN | A | 164 | 30.610 | 13.129 | 6.265 | 1.00 | 25.02 | A |
| ATOM | 777 | CG | ASN | A | 164 | 29.537 | 12.101 | 5.932 | 1.00 | 27.54 | A |
| ATOM | 778 | OD1 | ASN | A | 164 | 28.772 | 12.281 | 4.983 | 1.00 | 28.79 | A |
| ATOM | 779 | ND2 | ASN | A | 164 | 29.475 | 11.024 | 6.704 | 1.00 | 27.13 | A |
| ATOM | 780 | C | ASN | A | 164 | 31.999 | 14.931 | 5.169 | 1.00 | 24.43 | A |
| ATOM | 781 | O | ASN | A | 164 | 31.306 | 15.856 | 5.589 | 1.00 | 23.98 | A |
| ATOM | 782 | N | GLY | A | 165 | 33.262 | 15.097 | 4.795 | 1.00 | 21.56 | A |
| ATOM | 783 | CA | GLY | A | 165 | 33.873 | 16.414 | 4.836 | 1.00 | 24.39 | A |
| ATOM | 784 | C | GLY | A | 165 | 34.191 | 17.043 | 6.181 | 1.00 | 23.62 | A |
| ATOM | 785 | O | GLY | A | 165 | 34.380 | 16.352 | 7.177 | 1.00 | 23.26 | A |
| ATOM | 786 | N | GLU | A | 166 | 34.234 | 18.373 | 6.186 | 1.00 | 23.22 | A |
| ATOM | 787 | CA | GLU | A | 166 | 34.563 | 19.176 | 7.362 | 1.00 | 24.54 | A |
| ATOM | 788 | CB | GLU | A | 166 | 35.055 | 20.558 | 6.913 | 1.00 | 25.04 | A |
| ATOM | 789 | CG | GLU | A | 166 | 36.419 | 20.569 | 6.229 | 1.00 | 26.48 | A |
| ATOM | 790 | CD | GLU | A | 166 | 36.699 | 21.889 | 5.517 | 1.00 | 30.02 | A |
| ATOM | 791 | OE1 | GLU | A | 166 | 36.081 | 22.906 | 5.889 | 1.00 | 29.33 | A |
| ATOM | 792 | OE2 | GLU | A | 166 | 37.544 | 21.916 | 4.596 | 1.00 | 30.48 | A |
| ATOM | 793 | C | GLU | A | 166 | 33.436 | 19.372 | 8.369 | 1.00 | 24.44 | A |
| ATOM | 794 | O | GLU | A | 166 | 32.279 | 19.541 | 8.001 | 1.00 | 22.76 | A |

-continued

| | | | | | | | | | | | |
|---|---|---|---|---|---|---|---|---|---|---|---|
| ATOM | 795 | N | LEU | A | 167 | 33.791 | 19.370 | 9.649 | 1.00 | 22.95 | A |
| ATOM | 796 | CA | LEU | A | 167 | 32.813 | 19.581 | 10.707 | 1.00 | 22.26 | A |
| ATOM | 797 | CB | LEU | A | 167 | 33.497 | 19.481 | 12.073 | 1.00 | 22.32 | A |
| ATOM | 798 | CG | LEU | A | 167 | 32.706 | 19.923 | 13.306 | 1.00 | 22.04 | A |
| ATOM | 799 | CD1 | LEU | A | 167 | 31.454 | 19.074 | 13.463 | 1.00 | 19.66 | A |
| ATOM | 800 | CD2 | LEU | A | 167 | 33.597 | 19.805 | 14.537 | 1.00 | 21.17 | A |
| ATOM | 801 | C | LEU | A | 167 | 32.193 | 20.971 | 10.529 | 1.00 | 23.49 | A |
| ATOM | 802 | O | LEU | A | 167 | 31.047 | 21.209 | 10.907 | 1.00 | 23.56 | A |
| ATOM | 803 | N | LEU | A | 168 | 32.960 | 21.887 | 9.948 | 1.00 | 24.25 | A |
| ATOM | 804 | CA | LEU | A | 168 | 32.473 | 23.245 | 9.722 | 1.00 | 26.64 | A |
| ATOM | 805 | CB | LEU | A | 168 | 33.560 | 24.099 | 9.066 | 1.00 | 25.62 | A |
| ATOM | 806 | CG | LEU | A | 168 | 33.198 | 25.546 | 8.707 | 1.00 | 27.34 | A |
| ATOM | 807 | CD1 | LEU | A | 168 | 32.718 | 26.296 | 9.946 | 1.00 | 26.42 | A |
| ATOM | 808 | CD2 | LEU | A | 168 | 34.418 | 26.238 | 8.119 | 1.00 | 26.74 | A |
| ATOM | 809 | C | LEU | A | 168 | 31.234 | 23.218 | 8.829 | 1.00 | 27.13 | A |
| ATOM | 810 | O | LEU | A | 168 | 30.297 | 23.989 | 9.030 | 1.00 | 26.01 | A |
| ATOM | 811 | N | LYS | A | 169 | 31.233 | 22.320 | 7.848 | 1.00 | 26.41 | A |
| ATOM | 812 | CA | LYS | A | 169 | 30.106 | 22.210 | 6.934 | 1.00 | 27.70 | A |
| ATOM | 813 | CB | LYS | A | 169 | 30.324 | 21.064 | 5.945 | 1.00 | 30.49 | A |
| ATOM | 814 | CG | LYS | A | 169 | 29.151 | 20.854 | 4.993 | 1.00 | 32.47 | A |
| ATOM | 815 | CD | LYS | A | 169 | 29.407 | 19.728 | 3.998 | 1.00 | 35.98 | A |
| ATOM | 816 | CE | LYS | A | 169 | 29.462 | 18.372 | 4.683 | 1.00 | 38.53 | A |
| ATOM | 817 | NZ | LYS | A | 169 | 29.622 | 17.263 | 3.702 | 1.00 | 41.00 | A |
| ATOM | 818 | C | LYS | A | 169 | 28.801 | 21.985 | 7.682 | 1.00 | 28.12 | A |
| ATOM | 819 | O | LYS | A | 169 | 27.785 | 22.608 | 7.371 | 1.00 | 28.08 | A |
| ATOM | 820 | N | TYR | A | 170 | 28.826 | 21.094 | 8.668 | 1.00 | 26.53 | A |
| ATOM | 821 | CA | TYR | A | 170 | 27.624 | 20.791 | 9.434 | 1.00 | 26.95 | A |
| ATOM | 822 | CB | TYR | A | 170 | 27.810 | 19.476 | 10.193 | 1.00 | 25.03 | A |
| ATOM | 823 | CG | TYR | A | 170 | 27.898 | 18.300 | 9.251 | 1.00 | 26.65 | A |
| ATOM | 824 | CD1 | TYR | A | 170 | 26.745 | 17.661 | 8.790 | 1.00 | 28.27 | A |
| ATOM | 825 | CE1 | TYR | A | 170 | 26.814 | 16.642 | 7.839 | 1.00 | 26.85 | A |
| ATOM | 826 | CD2 | TYR | A | 170 | 29.127 | 17.884 | 8.742 | 1.00 | 27.83 | A |
| ATOM | 827 | CE2 | TYR | A | 170 | 29.209 | 16.869 | 7.792 | 1.00 | 27.19 | A |
| ATOM | 828 | CZ | TYR | A | 170 | 28.049 | 16.254 | 7.343 | 1.00 | 30.02 | A |
| ATOM | 829 | OH | TYR | A | 170 | 28.130 | 15.268 | 6.382 | 1.00 | 29.23 | A |
| ATOM | 830 | C | TYR | A | 170 | 27.229 | 21.918 | 10.376 | 1.00 | 27.59 | A |
| ATOM | 831 | O | TYR | A | 170 | 26.045 | 22.122 | 10.642 | 1.00 | 29.25 | A |
| ATOM | 832 | N | ILE | A | 171 | 28.208 | 22.660 | 10.882 | 1.00 | 28.16 | A |
| ATOM | 833 | CA | ILE | A | 171 | 27.883 | 23.770 | 11.763 | 1.00 | 29.03 | A |
| ATOM | 834 | CB | ILE | A | 171 | 29.151 | 24.435 | 12.337 | 1.00 | 27.51 | A |
| ATOM | 835 | CG2 | ILE | A | 171 | 28.773 | 25.705 | 13.084 | 1.00 | 27.97 | A |
| ATOM | 836 | CG1 | ILE | A | 171 | 29.872 | 23.458 | 13.272 | 1.00 | 26.70 | A |
| ATOM | 837 | CD1 | ILE | A | 171 | 31.163 | 23.996 | 13.856 | 1.00 | 24.07 | A |
| ATOM | 838 | C | ILE | A | 171 | 27.094 | 24.796 | 10.944 | 1.00 | 31.41 | A |
| ATOM | 839 | O | ILE | A | 171 | 26.088 | 25.335 | 11.407 | 1.00 | 31.69 | A |
| ATOM | 840 | N | ARG | A | 172 | 27.546 | 25.047 | 9.719 | 1.00 | 33.21 | A |
| ATOM | 841 | CA | ARG | A | 172 | 26.874 | 26.000 | 8.844 | 1.00 | 36.54 | A |
| ATOM | 842 | CB | ARG | A | 172 | 27.734 | 26.314 | 7.616 | 1.00 | 37.73 | A |
| ATOM | 843 | CG | ARG | A | 172 | 29.057 | 27.011 | 7.912 | 1.00 | 41.65 | A |
| ATOM | 844 | CD | ARG | A | 172 | 29.708 | 27.492 | 6.616 | 1.00 | 45.29 | A |
| ATOM | 845 | NE | ARG | A | 172 | 31.037 | 28.070 | 6.812 | 1.00 | 48.51 | A |
| ATOM | 846 | CZ | ARG | A | 172 | 31.314 | 29.059 | 7.658 | 1.00 | 51.53 | A |
| ATOM | 847 | NH1 | ARG | A | 172 | 30.355 | 29.593 | 8.406 | 1.00 | 53.75 | A |
| ATOM | 848 | NH2 | ARG | A | 172 | 32.553 | 29.526 | 7.748 | 1.00 | 51.21 | A |
| ATOM | 849 | C | ARG | A | 172 | 25.528 | 25.459 | 8.378 | 1.00 | 37.67 | A |
| ATOM | 850 | O | ARG | A | 172 | 24.550 | 26.200 | 8.288 | 1.00 | 39.09 | A |
| ATOM | 851 | N | LYS | A | 173 | 25.481 | 24.163 | 8.092 | 1.00 | 38.44 | A |
| ATOM | 852 | CA | LYS | A | 173 | 24.259 | 23.528 | 7.619 | 1.00 | 39.25 | A |
| ATOM | 853 | CB | LYS | A | 173 | 24.523 | 22.061 | 7.272 | 1.00 | 41.89 | A |
| ATOM | 854 | CG | LYS | A | 173 | 23.279 | 21.298 | 6.830 | 1.00 | 45.52 | A |
| ATOM | 855 | CD | LYS | A | 173 | 23.557 | 19.808 | 6.653 | 1.00 | 49.60 | A |
| ATOM | 856 | CE | LYS | A | 173 | 24.477 | 19.530 | 5.469 | 1.00 | 52.63 | A |
| ATOM | 857 | NZ | LYS | A | 173 | 23.855 | 19.894 | 4.160 | 1.00 | 54.61 | A |
| ATOM | 858 | C | LYS | A | 173 | 23.089 | 23.608 | 8.595 | 1.00 | 39.30 | A |
| ATOM | 859 | O | LYS | A | 173 | 21.981 | 23.960 | 8.201 | 1.00 | 39.62 | A |
| ATOM | 860 | N | ILE | A | 174 | 23.320 | 23.282 | 9.863 | 1.00 | 37.96 | A |
| ATOM | 861 | CA | ILE | A | 174 | 22.229 | 23.314 | 10.833 | 1.00 | 37.36 | A |
| ATOM | 862 | CB | ILE | A | 174 | 22.159 | 21.998 | 11.652 | 1.00 | 37.44 | A |
| ATOM | 863 | CG2 | ILE | A | 174 | 22.058 | 20.802 | 10.709 | 1.00 | 38.37 | A |
| ATOM | 864 | CG1 | ILE | A | 174 | 23.397 | 21.850 | 12.532 | 1.00 | 37.25 | A |
| ATOM | 865 | CD1 | ILE | A | 174 | 23.355 | 20.620 | 13.418 | 1.00 | 36.85 | A |
| ATOM | 866 | C | ILE | A | 174 | 22.259 | 24.492 | 11.801 | 1.00 | 36.71 | A |
| ATOM | 867 | O | ILE | A | 174 | 21.448 | 24.556 | 12.724 | 1.00 | 38.05 | A |
| ATOM | 868 | N | GLY | A | 175 | 23.185 | 25.423 | 11.592 | 1.00 | 35.48 | A |
| ATOM | 869 | CA | GLY | A | 175 | 23.265 | 26.585 | 12.462 | 1.00 | 35.29 | A |
| ATOM | 870 | C | GLY | A | 175 | 24.053 | 26.360 | 13.737 | 1.00 | 35.06 | A |
| ATOM | 871 | O | GLY | A | 175 | 25.066 | 27.019 | 13.970 | 1.00 | 37.46 | A |
| ATOM | 872 | N | SER | A | 176 | 23.581 | 25.441 | 14.571 | 1.00 | 33.94 | A |
| ATOM | 873 | CA | SER | A | 176 | 24.253 | 25.113 | 15.822 | 1.00 | 32.84 | A |

-continued

| | | | | | | | | | | |
|---|---|---|---|---|---|---|---|---|---|---|
| ATOM | 874 | CB | SER | A | 176 | 23.938 | 26.155 | 16.901 | 1.00 | 33.54 | A |
| ATOM | 875 | OG | SER | A | 176 | 22.599 | 26.056 | 17.347 | 1.00 | 34.86 | A |
| ATOM | 876 | C | SER | A | 176 | 23.796 | 23.731 | 16.276 | 1.00 | 32.34 | A |
| ATOM | 877 | O | SER | A | 176 | 22.726 | 23.263 | 15.884 | 1.00 | 32.82 | A |
| ATOM | 878 | N | PHE | A | 177 | 24.609 | 23.085 | 17.103 | 1.00 | 29.39 | A |
| ATOM | 879 | CA | PHE | A | 177 | 24.313 | 21.743 | 17.597 | 1.00 | 27.20 | A |
| ATOM | 880 | CB | PHE | A | 177 | 25.621 | 20.989 | 17.865 | 1.00 | 26.39 | A |
| ATOM | 881 | CG | PHE | A | 177 | 26.372 | 20.585 | 16.622 | 1.00 | 26.18 | A |
| ATOM | 882 | CD1 | PHE | A | 177 | 26.210 | 21.277 | 15.426 | 1.00 | 25.30 | A |
| ATOM | 883 | CD2 | PHE | A | 177 | 27.266 | 19.516 | 16.662 | 1.00 | 26.05 | A |
| ATOM | 884 | CE1 | PHE | A | 177 | 26.923 | 20.912 | 14.290 | 1.00 | 26.59 | A |
| ATOM | 885 | CE2 | PHE | A | 177 | 27.986 | 19.143 | 15.532 | 1.00 | 26.06 | A |
| ATOM | 886 | CZ | PHE | A | 177 | 27.815 | 19.841 | 14.343 | 1.00 | 25.42 | A |
| ATOM | 887 | C | PHE | A | 177 | 23.500 | 21.752 | 18.884 | 1.00 | 27.00 | A |
| ATOM | 888 | O | PHE | A | 177 | 23.704 | 22.610 | 19.747 | 1.00 | 26.48 | A |
| ATOM | 889 | N | ASP | A | 178 | 22.578 | 20.802 | 19.022 | 1.00 | 26.70 | A |
| ATOM | 890 | CA | ASP | A | 178 | 21.816 | 20.729 | 20.260 | 1.00 | 26.35 | A |
| ATOM | 891 | CB | ASP | A | 178 | 20.621 | 19.773 | 20.142 | 1.00 | 29.90 | A |
| ATOM | 892 | CG | ASP | A | 178 | 21.020 | 18.372 | 19.720 | 1.00 | 32.28 | A |
| ATOM | 893 | OD1 | ASP | A | 178 | 22.157 | 17.949 | 20.014 | 1.00 | 35.21 | A |
| ATOM | 894 | OD2 | ASP | A | 178 | 20.179 | 17.683 | 19.105 | 1.00 | 34.79 | A |
| ATOM | 895 | C | ASP | A | 178 | 22.810 | 20.228 | 21.311 | 1.00 | 25.03 | A |
| ATOM | 896 | O | ASP | A | 178 | 23.974 | 19.968 | 20.992 | 1.00 | 21.24 | A |
| ATOM | 897 | N | GLU | A | 179 | 22.361 | 20.083 | 22.552 | 1.00 | 23.60 | A |
| ATOM | 898 | CA | GLU | A | 179 | 23.247 | 19.644 | 23.619 | 1.00 | 25.18 | A |
| ATOM | 899 | CB | GLU | A | 179 | 22.542 | 19.770 | 24.971 | 1.00 | 27.60 | A |
| ATOM | 900 | CG | GLU | A | 179 | 23.324 | 19.176 | 26.130 | 1.00 | 32.58 | A |
| ATOM | 901 | CD | GLU | A | 179 | 22.997 | 19.845 | 27.449 | 1.00 | 35.82 | A |
| ATOM | 902 | OE1 | GLU | A | 179 | 21.825 | 20.224 | 27.645 | 1.00 | 35.95 | A |
| ATOM | 903 | OE2 | GLU | A | 179 | 23.912 | 19.984 | 28.291 | 1.00 | 38.19 | A |
| ATOM | 904 | C | GLU | A | 179 | 23.808 | 18.235 | 23.450 | 1.00 | 24.08 | A |
| ATOM | 905 | O | GLU | A | 179 | 24.977 | 17.989 | 23.756 | 1.00 | 22.79 | A |
| ATOM | 906 | N | THR | A | 180 | 22.983 | 17.316 | 22.961 | 1.00 | 23.36 | A |
| ATOM | 907 | CA | THR | A | 180 | 23.412 | 15.935 | 22.761 | 1.00 | 22.15 | A |
| ATOM | 908 | CB | THR | A | 180 | 22.224 | 15.054 | 22.320 | 1.00 | 23.77 | A |
| ATOM | 909 | OG1 | THR | A | 180 | 21.222 | 15.075 | 23.341 | 1.00 | 26.37 | A |
| ATOM | 910 | CG2 | THR | A | 180 | 22.670 | 13.616 | 22.088 | 1.00 | 22.66 | A |
| ATOM | 911 | C | THR | A | 180 | 24.533 | 15.830 | 21.724 | 1.00 | 22.01 | A |
| ATOM | 912 | O | THR | A | 180 | 25.533 | 15.141 | 21.944 | 1.00 | 19.87 | A |
| ATOM | 913 | N | CYS | A | 181 | 24.365 | 16.511 | 20.596 | 1.00 | 21.21 | A |
| ATOM | 914 | CA | CYS | A | 181 | 25.372 | 16.480 | 19.541 | 1.00 | 22.22 | A |
| ATOM | 915 | CB | CYS | A | 181 | 24.800 | 17.065 | 18.250 | 1.00 | 24.62 | A |
| ATOM | 916 | SG | CYS | A | 181 | 23.435 | 16.080 | 17.560 | 1.00 | 29.50 | A |
| ATOM | 917 | C | CYS | A | 181 | 26.633 | 17.232 | 19.954 | 1.00 | 23.07 | A |
| ATOM | 918 | O | CYS | A | 181 | 27.746 | 16.827 | 19.608 | 1.00 | 23.95 | A |
| ATOM | 919 | N | THR | A | 182 | 26.463 | 18.325 | 20.695 | 1.00 | 22.76 | A |
| ATOM | 920 | CA | THR | A | 182 | 27.606 | 19.103 | 21.161 | 1.00 | 21.49 | A |
| ATOM | 921 | CB | THR | A | 182 | 27.167 | 20.346 | 21.978 | 1.00 | 21.37 | A |
| ATOM | 922 | OG1 | THR | A | 182 | 26.459 | 21.262 | 21.134 | 1.00 | 22.50 | A |
| ATOM | 923 | CG2 | THR | A | 182 | 28.379 | 21.046 | 22.565 | 1.00 | 18.36 | A |
| ATOM | 924 | C | THR | A | 182 | 28.454 | 18.215 | 22.071 | 1.00 | 21.48 | A |
| ATOM | 925 | O | THR | A | 182 | 29.669 | 18.090 | 21.894 | 1.00 | 19.95 | A |
| ATOM | 926 | N | ARG | A | 183 | 27.798 | 17.602 | 23.050 | 1.00 | 18.97 | A |
| ATOM | 927 | CA | ARG | A | 183 | 28.468 | 16.723 | 23.996 | 1.00 | 19.39 | A |
| ATOM | 928 | CB | ARG | A | 183 | 27.455 | 16.140 | 24.984 | 1.00 | 19.46 | A |
| ATOM | 929 | CG | ARG | A | 183 | 28.030 | 15.062 | 25.887 | 1.00 | 18.77 | A |
| ATOM | 930 | CD | ARG | A | 183 | 27.021 | 14.571 | 26.925 | 1.00 | 21.19 | A |
| ATOM | 931 | NE | ARG | A | 183 | 26.605 | 15.642 | 27.824 | 1.00 | 19.46 | A |
| ATOM | 932 | CZ | ARG | A | 183 | 25.496 | 16.362 | 27.679 | 1.00 | 20.45 | A |
| ATOM | 933 | NH1 | ARG | A | 183 | 24.672 | 16.123 | 26.666 | 1.00 | 19.81 | A |
| ATOM | 934 | NH2 | ARG | A | 183 | 25.224 | 17.338 | 28.539 | 1.00 | 17.11 | A |
| ATOM | 935 | C | ARG | A | 183 | 29.206 | 15.577 | 23.302 | 1.00 | 20.02 | A |
| ATOM | 936 | O | ARG | A | 183 | 30.383 | 15.333 | 23.573 | 1.00 | 19.97 | A |
| ATOM | 937 | N | PHE | A | 184 | 28.520 | 14.871 | 22.409 | 1.00 | 19.24 | A |
| ATOM | 938 | CA | PHE | A | 184 | 29.144 | 13.746 | 21.722 | 1.00 | 18.04 | A |
| ATOM | 939 | CB | PHE | A | 184 | 28.158 | 13.078 | 20.764 | 1.00 | 21.05 | A |
| ATOM | 940 | CG | PHE | A | 184 | 28.719 | 11.857 | 20.098 | 1.00 | 22.67 | A |
| ATOM | 941 | CD1 | PHE | A | 184 | 28.717 | 10.630 | 20.754 | 1.00 | 22.97 | A |
| ATOM | 942 | CD2 | PHE | A | 184 | 29.317 | 11.949 | 18.850 | 1.00 | 19.97 | A |
| ATOM | 943 | CE1 | PHE | A | 184 | 29.308 | 9.510 | 20.176 | 1.00 | 23.53 | A |
| ATOM | 944 | CE2 | PHE | A | 184 | 29.915 | 10.833 | 18.263 | 1.00 | 24.11 | A |
| ATOM | 945 | CZ | PHE | A | 184 | 29.910 | 9.613 | 18.928 | 1.00 | 22.97 | A |
| ATOM | 946 | C | PHE | A | 184 | 30.403 | 14.127 | 20.941 | 1.00 | 17.99 | A |
| ATOM | 947 | O | PHE | A | 184 | 31.461 | 13.531 | 21.130 | 1.00 | 18.89 | A |
| ATOM | 948 | N | TYR | A | 185 | 30.292 | 15.110 | 20.056 | 1.00 | 15.73 | A |
| ATOM | 949 | CA | TYR | A | 185 | 31.443 | 15.519 | 19.265 | 1.00 | 15.72 | A |
| ATOM | 950 | CB | TYR | A | 185 | 30.992 | 16.413 | 18.111 | 1.00 | 17.33 | A |
| ATOM | 951 | CG | TYR | A | 185 | 30.364 | 15.584 | 17.015 | 1.00 | 19.37 | A |
| ATOM | 952 | CD1 | TYR | A | 185 | 31.159 | 14.809 | 16.168 | 1.00 | 16.53 | A |

-continued

| | | | | | | | | | | |
|---|---|---|---|---|---|---|---|---|---|---|
| ATOM | 953 | CE1 | TYR | A | 185 | 30.590 | 13.952 | 15.232 | 1.00 | 18.12 | A |
| ATOM | 954 | CD2 | TYR | A | 185 | 28.976 | 15.484 | 16.892 | 1.00 | 18.18 | A |
| ATOM | 955 | CE2 | TYR | A | 185 | 28.398 | 14.623 | 15.956 | 1.00 | 18.90 | A |
| ATOM | 956 | CZ | TYR | A | 185 | 29.211 | 13.861 | 15.133 | 1.00 | 18.41 | A |
| ATOM | 957 | OH | TYR | A | 185 | 28.650 | 12.995 | 14.218 | 1.00 | 20.48 | A |
| ATOM | 958 | C | TYR | A | 185 | 32.544 | 16.172 | 20.083 | 1.00 | 15.79 | A |
| ATOM | 959 | O | TYR | A | 185 | 33.720 | 16.015 | 19.766 | 1.00 | 17.69 | A |
| ATOM | 960 | N | THR | A | 186 | 32.176 | 16.887 | 21.142 | 1.00 | 15.68 | A |
| ATOM | 961 | CA | THR | A | 186 | 33.184 | 17.504 | 21.997 | 1.00 | 16.03 | A |
| ATOM | 962 | CB | THR | A | 186 | 32.559 | 18.403 | 23.094 | 1.00 | 16.62 | A |
| ATOM | 963 | OG1 | THR | A | 186 | 31.866 | 19.503 | 22.481 | 1.00 | 14.79 | A |
| ATOM | 964 | CG2 | THR | A | 186 | 33.656 | 18.953 | 24.019 | 1.00 | 14.68 | A |
| ATOM | 965 | C | THR | A | 186 | 33.954 | 16.375 | 22.680 | 1.00 | 15.59 | A |
| ATOM | 966 | O | THR | A | 186 | 35.176 | 16.443 | 22.823 | 1.00 | 13.77 | A |
| ATOM | 967 | N | ALA | A | 187 | 33.234 | 15.333 | 23.097 | 1.00 | 14.06 | A |
| ATOM | 968 | CA | ALA | A | 187 | 33.869 | 14.196 | 23.757 | 1.00 | 14.74 | A |
| ATOM | 969 | CB | ALA | A | 187 | 32.810 | 13.195 | 24.224 | 1.00 | 14.32 | A |
| ATOM | 970 | C | ALA | A | 187 | 34.875 | 13.509 | 22.821 | 1.00 | 14.41 | A |
| ATOM | 971 | O | ALA | A | 187 | 35.972 | 13.136 | 23.247 | 1.00 | 15.61 | A |
| ATOM | 972 | N | GLU | A | 188 | 34.516 | 13.340 | 21.549 | 1.00 | 14.01 | A |
| ATOM | 973 | CA | GLU | A | 188 | 35.443 | 12.704 | 20.615 | 1.00 | 13.50 | A |
| ATOM | 974 | CB | GLU | A | 188 | 34.782 | 12.449 | 19.251 | 1.00 | 12.85 | A |
| ATOM | 975 | CG | GLU | A | 188 | 33.622 | 11.454 | 19.282 | 1.00 | 12.71 | A |
| ATOM | 976 | CD | GLU | A | 188 | 33.464 | 10.685 | 17.979 | 1.00 | 15.01 | A |
| ATOM | 977 | OE1 | GLU | A | 188 | 33.687 | 11.275 | 16.899 | 1.00 | 13.21 | A |
| ATOM | 978 | OE2 | GLU | A | 188 | 33.110 | 9.484 | 18.031 | 1.00 | 17.69 | A |
| ATOM | 979 | C | GLU | A | 188 | 36.682 | 13.582 | 20.436 | 1.00 | 13.34 | A |
| ATOM | 980 | O | GLU | A | 188 | 37.803 | 13.085 | 20.408 | 1.00 | 14.69 | A |
| ATOM | 981 | N | ILE | A | 189 | 36.486 | 14.893 | 20.326 | 1.00 | 13.52 | A |
| ATOM | 982 | CA | ILE | A | 189 | 37.627 | 15.787 | 20.159 | 1.00 | 13.35 | A |
| ATOM | 983 | CB | ILE | A | 189 | 37.169 | 17.247 | 19.939 | 1.00 | 13.95 | A |
| ATOM | 984 | CG2 | ILE | A | 189 | 38.381 | 18.165 | 19.822 | 1.00 | 12.47 | A |
| ATOM | 985 | CG1 | ILE | A | 189 | 36.302 | 17.332 | 18.671 | 1.00 | 13.44 | A |
| ATOM | 986 | CD1 | ILE | A | 189 | 35.588 | 18.664 | 18.491 | 1.00 | 14.29 | A |
| ATOM | 987 | C | ILE | A | 189 | 38.530 | 15.702 | 21.394 | 1.00 | 14.63 | A |
| ATOM | 988 | O | ILE | A | 189 | 39.753 | 15.595 | 21.271 | 1.00 | 12.97 | A |
| ATOM | 989 | N | VAL | A | 190 | 37.927 | 15.751 | 22.582 | 1.00 | 14.35 | A |
| ATOM | 990 | CA | VAL | A | 190 | 38.684 | 15.655 | 23.832 | 1.00 | 13.22 | A |
| ATOM | 991 | CB | VAL | A | 190 | 37.743 | 15.690 | 25.061 | 1.00 | 14.28 | A |
| ATOM | 992 | CG1 | VAL | A | 190 | 38.509 | 15.267 | 26.326 | 1.00 | 15.08 | A |
| ATOM | 993 | CG2 | VAL | A | 190 | 37.160 | 17.082 | 25.233 | 1.00 | 12.08 | A |
| ATOM | 994 | C | VAL | A | 190 | 39.468 | 14.338 | 23.859 | 1.00 | 14.61 | A |
| ATOM | 995 | O | VAL | A | 190 | 40.634 | 14.304 | 24.250 | 1.00 | 13.72 | A |
| ATOM | 996 | N | SER | A | 191 | 38.825 | 13.254 | 23.432 | 1.00 | 15.26 | A |
| ATOM | 997 | CA | SER | A | 191 | 39.478 | 11.943 | 23.421 | 1.00 | 16.81 | A |
| ATOM | 998 | CB | SER | A | 191 | 38.470 | 10.857 | 23.041 | 1.00 | 16.14 | A |
| ATOM | 999 | OG | SER | A | 191 | 39.018 | 9.569 | 23.238 | 1.00 | 16.94 | A |
| ATOM | 1000 | C | SER | A | 191 | 40.649 | 11.928 | 22.441 | 1.00 | 16.58 | A |
| ATOM | 1001 | O | SER | A | 191 | 41.697 | 11.335 | 22.713 | 1.00 | 13.96 | A |
| ATOM | 1002 | N | ALA | A | 192 | 40.468 | 12.586 | 21.300 | 1.00 | 15.26 | A |
| ATOM | 1003 | CA | ALA | A | 192 | 41.518 | 12.645 | 20.292 | 1.00 | 14.37 | A |
| ATOM | 1004 | CB | ALA | A | 192 | 40.989 | 13.296 | 19.016 | 1.00 | 14.43 | A |
| ATOM | 1005 | C | ALA | A | 192 | 42.695 | 13.440 | 20.845 | 1.00 | 16.46 | A |
| ATOM | 1006 | O | ALA | A | 192 | 43.851 | 13.038 | 20.697 | 1.00 | 17.96 | A |
| ATOM | 1007 | N | LEU | A | 193 | 42.401 | 14.563 | 21.496 | 1.00 | 15.02 | A |
| ATOM | 1008 | CA | LEU | A | 193 | 43.459 | 15.392 | 22.067 | 1.00 | 15.42 | A |
| ATOM | 1009 | CB | LEU | A | 193 | 42.884 | 16.712 | 22.600 | 1.00 | 12.88 | A |
| ATOM | 1010 | CG | LEU | A | 193 | 42.445 | 17.721 | 21.525 | 1.00 | 15.97 | A |
| ATOM | 1011 | CD1 | LEU | A | 193 | 41.869 | 18.979 | 22.190 | 1.00 | 13.97 | A |
| ATOM | 1012 | CD2 | LEU | A | 193 | 43.642 | 18.088 | 20.655 | 1.00 | 14.58 | A |
| ATOM | 1013 | C | LEU | A | 193 | 44.211 | 14.659 | 23.174 | 1.00 | 14.49 | A |
| ATOM | 1014 | O | LEU | A | 193 | 45.427 | 14.813 | 23.310 | 1.00 | 16.56 | A |
| ATOM | 1015 | N | GLU | A | 194 | 43.500 | 13.870 | 23.975 | 1.00 | 13.96 | A |
| ATOM | 1016 | CA | GLU | A | 194 | 44.179 | 13.123 | 25.032 | 1.00 | 14.08 | A |
| ATOM | 1017 | CB | GLU | A | 194 | 43.190 | 12.295 | 25.857 | 1.00 | 14.65 | A |
| ATOM | 1018 | CG | GLU | A | 194 | 43.882 | 11.301 | 26.789 | 1.00 | 17.09 | A |
| ATOM | 1019 | CD | GLU | A | 194 | 42.924 | 10.592 | 27.730 | 1.00 | 19.59 | A |
| ATOM | 1020 | OE1 | GLU | A | 194 | 41.809 | 10.237 | 27.295 | 1.00 | 19.25 | A |
| ATOM | 1021 | OE2 | GLU | A | 194 | 43.302 | 10.380 | 28.906 | 1.00 | 20.20 | A |
| ATOM | 1022 | C | GLU | A | 194 | 45.208 | 12.199 | 24.386 | 1.00 | 13.57 | A |
| ATOM | 1023 | O | GLU | A | 194 | 46.337 | 12.093 | 24.847 | 1.00 | 14.23 | A |
| ATOM | 1024 | N | TYR | A | 195 | 44.822 | 11.544 | 23.301 | 1.00 | 14.89 | A |
| ATOM | 1025 | CA | TYR | A | 195 | 45.743 | 10.642 | 22.618 | 1.00 | 16.58 | A |
| ATOM | 1026 | CB | TYR | A | 195 | 45.030 | 9.910 | 21.488 | 1.00 | 17.29 | A |
| ATOM | 1027 | CG | TYR | A | 195 | 45.956 | 9.058 | 20.649 | 1.00 | 17.92 | A |
| ATOM | 1028 | CD1 | TYR | A | 195 | 46.347 | 7.788 | 21.077 | 1.00 | 17.96 | A |
| ATOM | 1029 | CE1 | TYR | A | 195 | 47.203 | 6.996 | 20.304 | 1.00 | 19.77 | A |
| ATOM | 1030 | CD2 | TYR | A | 195 | 46.445 | 9.524 | 19.428 | 1.00 | 16.67 | A |
| ATOM | 1031 | CE2 | TYR | A | 195 | 47.299 | 8.744 | 18.650 | 1.00 | 18.51 | A |

| | | | | -continued | | | | | | |
|---|---|---|---|---|---|---|---|---|---|---|
| ATOM | 1032 | CZ | TYR | A | 195 | 47.671 | 7.481 | 19.094 | 1.00 | 20.24 | A |
| ATOM | 1033 | OH | TYR | A | 195 | 48.506 | 6.705 | 18.325 | 1.00 | 21.89 | A |
| ATOM | 1034 | C | TYR | A | 195 | 46.917 | 11.419 | 22.035 | 1.00 | 16.98 | A |
| ATOM | 1035 | O | TYR | A | 195 | 48.081 | 11.047 | 22.203 | 1.00 | 14.61 | A |
| ATOM | 1036 | N | LEU | A | 196 | 46.599 | 12.507 | 21.347 | 1.00 | 16.30 | A |
| ATOM | 1037 | CA | LEU | A | 196 | 47.619 | 13.328 | 20.720 | 1.00 | 18.15 | A |
| ATOM | 1038 | CB | LEU | A | 196 | 46.969 | 14.502 | 19.982 | 1.00 | 18.59 | A |
| ATOM | 1039 | CG | LEU | A | 196 | 47.834 | 15.203 | 18.935 | 1.00 | 22.51 | A |
| ATOM | 1040 | CD1 | LEU | A | 196 | 48.222 | 14.206 | 17.841 | 1.00 | 20.94 | A |
| ATOM | 1041 | CD2 | LEU | A | 196 | 47.060 | 16.375 | 18.338 | 1.00 | 22.98 | A |
| ATOM | 1042 | C | LEU | A | 196 | 48.592 | 13.844 | 21.763 | 1.00 | 17.75 | A |
| ATOM | 1043 | O | LEU | A | 196 | 49.801 | 13.644 | 21.649 | 1.00 | 18.33 | A |
| ATOM | 1044 | N | HIS | A | 197 | 48.064 | 14.495 | 22.792 | 1.00 | 17.12 | A |
| ATOM | 1045 | CA | HIS | A | 197 | 48.913 | 15.042 | 23.842 | 1.00 | 18.47 | A |
| ATOM | 1046 | CB | HIS | A | 197 | 48.069 | 15.866 | 24.817 | 1.00 | 15.90 | A |
| ATOM | 1047 | CG | HIS | A | 197 | 47.571 | 17.152 | 24.231 | 1.00 | 19.15 | A |
| ATOM | 1048 | CD2 | HIS | A | 197 | 47.830 | 17.745 | 23.038 | 1.00 | 18.22 | A |
| ATOM | 1049 | ND1 | HIS | A | 197 | 46.704 | 17.992 | 24.897 | 1.00 | 17.47 | A |
| ATOM | 1050 | CE1 | HIS | A | 197 | 46.450 | 19.047 | 24.139 | 1.00 | 19.74 | A |
| ATOM | 1051 | NE2 | HIS | A | 197 | 47.119 | 18.921 | 23.007 | 1.00 | 15.69 | A |
| ATOM | 1052 | C | HIS | A | 197 | 49.696 | 13.958 | 24.572 | 1.00 | 19.40 | A |
| ATOM | 1053 | O | HIS | A | 197 | 50.823 | 14.192 | 25.021 | 1.00 | 19.42 | A |
| ATOM | 1054 | N | GLY | A | 198 | 49.106 | 12.770 | 24.679 | 1.00 | 18.59 | A |
| ATOM | 1055 | CA | GLY | A | 198 | 49.793 | 11.675 | 25.339 | 1.00 | 19.60 | A |
| ATOM | 1056 | C | GLY | A | 198 | 51.075 | 11.307 | 24.612 | 1.00 | 21.86 | A |
| ATOM | 1057 | O | GLY | A | 198 | 51.963 | 10.682 | 25.186 | 1.00 | 23.09 | A |
| ATOM | 1058 | N | LYS | A | 199 | 51.174 | 11.687 | 23.341 | 1.00 | 22.81 | A |
| ATOM | 1059 | CA | LYS | A | 199 | 52.368 | 11.401 | 22.549 | 1.00 | 24.43 | A |
| ATOM | 1060 | CB | LYS | A | 199 | 51.990 | 10.905 | 21.154 | 1.00 | 26.00 | A |
| ATOM | 1061 | CG | LYS | A | 199 | 51.378 | 9.520 | 21.133 | 1.00 | 30.98 | A |
| ATOM | 1062 | CD | LYS | A | 199 | 51.291 | 9.002 | 19.708 | 1.00 | 36.85 | A |
| ATOM | 1063 | CE | LYS | A | 199 | 50.832 | 7.559 | 19.682 | 1.00 | 40.37 | A |
| ATOM | 1064 | NZ | LYS | A | 199 | 51.646 | 6.691 | 20.581 | 1.00 | 43.48 | A |
| ATOM | 1065 | C | LYS | A | 199 | 53.253 | 12.631 | 22.414 | 1.00 | 23.88 | A |
| ATOM | 1066 | O | LYS | A | 199 | 54.144 | 12.669 | 21.568 | 1.00 | 24.97 | A |
| ATOM | 1067 | N | GLY | A | 200 | 52.997 | 13.638 | 23.243 | 1.00 | 24.00 | A |
| ATOM | 1068 | CA | GLY | A | 200 | 53.790 | 14.853 | 23.203 | 1.00 | 22.12 | A |
| ATOM | 1069 | C | GLY | A | 200 | 53.665 | 15.632 | 21.907 | 1.00 | 22.14 | A |
| ATOM | 1070 | O | GLY | A | 200 | 54.632 | 16.231 | 21.439 | 1.00 | 22.41 | A |
| ATOM | 1071 | N | ILE | A | 201 | 52.475 | 15.630 | 21.320 | 1.00 | 20.00 | A |
| ATOM | 1072 | CA | ILE | A | 201 | 52.252 | 16.355 | 20.080 | 1.00 | 18.93 | A |
| ATOM | 1073 | CB | ILE | A | 201 | 51.784 | 15.414 | 18.955 | 1.00 | 19.70 | A |
| ATOM | 1074 | CG2 | ILE | A | 201 | 51.414 | 16.226 | 17.716 | 1.00 | 20.12 | A |
| ATOM | 1075 | CG1 | ILE | A | 201 | 52.880 | 14.395 | 18.636 | 1.00 | 20.03 | A |
| ATOM | 1076 | CD1 | ILE | A | 201 | 52.408 | 13.258 | 17.745 | 1.00 | 22.75 | A |
| ATOM | 1077 | C | ILE | A | 201 | 51.193 | 17.425 | 20.270 | 1.00 | 19.87 | A |
| ATOM | 1078 | O | ILE | A | 201 | 50.121 | 17.161 | 20.817 | 1.00 | 20.08 | A |
| ATOM | 1079 | N | ILE | A | 202 | 51.508 | 18.633 | 19.815 | 1.00 | 19.94 | A |
| ATOM | 1080 | CA | ILE | A | 202 | 50.601 | 19.772 | 19.891 | 1.00 | 20.45 | A |
| ATOM | 1081 | CB | ILE | A | 202 | 51.352 | 21.040 | 20.356 | 1.00 | 22.21 | A |
| ATOM | 1082 | CG2 | ILE | A | 202 | 50.381 | 22.220 | 20.470 | 1.00 | 22.67 | A |
| ATOM | 1083 | CG1 | ILE | A | 202 | 52.033 | 20.775 | 21.700 | 1.00 | 24.19 | A |
| ATOM | 1084 | CD1 | ILE | A | 202 | 52.914 | 21.920 | 22.169 | 1.00 | 25.39 | A |
| ATOM | 1085 | C | ILE | A | 202 | 50.105 | 19.999 | 18.464 | 1.00 | 20.71 | A |
| ATOM | 1086 | O | ILE | A | 202 | 50.910 | 20.067 | 17.538 | 1.00 | 19.48 | A |
| ATOM | 1087 | N | HIS | A | 203 | 48.795 | 20.108 | 18.270 | 1.00 | 18.65 | A |
| ATOM | 1088 | CA | HIS | A | 203 | 48.280 | 20.319 | 16.919 | 1.00 | 18.02 | A |
| ATOM | 1089 | CB | HIS | A | 203 | 46.775 | 20.057 | 16.874 | 1.00 | 16.31 | A |
| ATOM | 1090 | CG | HIS | A | 203 | 46.199 | 20.136 | 15.495 | 1.00 | 18.36 | A |
| ATOM | 1091 | CD2 | HIS | A | 203 | 46.043 | 21.186 | 14.655 | 1.00 | 16.42 | A |
| ATOM | 1092 | ND1 | HIS | A | 203 | 45.759 | 19.026 | 14.806 | 1.00 | 19.50 | A |
| ATOM | 1093 | CE1 | HIS | A | 203 | 45.359 | 19.389 | 13.600 | 1.00 | 17.64 | A |
| ATOM | 1094 | NE2 | HIS | A | 203 | 45.522 | 20.694 | 13.483 | 1.00 | 20.87 | A |
| ATOM | 1095 | C | HIS | A | 203 | 48.589 | 21.738 | 16.405 | 1.00 | 18.92 | A |
| ATOM | 1096 | O | HIS | A | 203 | 49.073 | 21.906 | 15.282 | 1.00 | 16.21 | A |
| ATOM | 1097 | N | ARG | A | 204 | 48.301 | 22.744 | 17.232 | 1.00 | 18.60 | A |
| ATOM | 1098 | CA | ARG | A | 204 | 48.552 | 24.157 | 16.914 | 1.00 | 19.81 | A |
| ATOM | 1099 | CB | ARG | A | 204 | 49.998 | 24.365 | 16.458 | 1.00 | 21.61 | A |
| ATOM | 1100 | CG | ARG | A | 204 | 51.024 | 24.137 | 17.550 | 1.00 | 23.82 | A |
| ATOM | 1101 | CD | ARG | A | 204 | 52.323 | 24.870 | 17.252 | 1.00 | 27.62 | A |
| ATOM | 1102 | NE | ARG | A | 204 | 52.932 | 24.449 | 15.994 | 1.00 | 29.43 | A |
| ATOM | 1103 | CZ | ARG | A | 204 | 54.125 | 24.861 | 15.572 | 1.00 | 33.10 | A |
| ATOM | 1104 | NH1 | ARG | A | 204 | 54.835 | 25.706 | 16.311 | 1.00 | 32.12 | A |
| ATOM | 1105 | NH2 | ARG | A | 204 | 54.614 | 24.426 | 14.418 | 1.00 | 30.25 | A |
| ATOM | 1106 | C | ARG | A | 204 | 47.624 | 24.830 | 15.905 | 1.00 | 20.03 | A |
| ATOM | 1107 | O | ARG | A | 204 | 47.711 | 26.038 | 15.698 | 1.00 | 20.88 | A |
| ATOM | 1108 | N | ASP | A | 205 | 46.755 | 24.071 | 15.255 | 1.00 | 18.96 | A |
| ATOM | 1109 | CA | ASP | A | 205 | 45.828 | 24.692 | 14.325 | 1.00 | 17.90 | A |
| ATOM | 1110 | CB | ASP | A | 205 | 46.418 | 24.741 | 12.914 | 1.00 | 18.95 | A |

-continued

| | | | | | | | | | | |
|---|---|---|---|---|---|---|---|---|---|---|
| ATOM | 1111 | CG | ASP | A | 205 | 45.655 | 25.688 | 12.008 | 1.00 | 20.36 | A |
| ATOM | 1112 | OD1 | ASP | A | 205 | 44.939 | 26.560 | 12.545 | 1.00 | 20.35 | A |
| ATOM | 1113 | OD2 | ASP | A | 205 | 45.772 | 25.573 | 10.771 | 1.00 | 22.49 | A |
| ATOM | 1114 | C | ASP | A | 205 | 44.500 | 23.956 | 14.328 | 1.00 | 19.60 | A |
| ATOM | 1115 | O | ASP | A | 205 | 43.876 | 23.751 | 13.287 | 1.00 | 21.53 | A |
| ATOM | 1116 | N | LEU | A | 206 | 44.063 | 23.569 | 15.521 | 1.00 | 18.53 | A |
| ATOM | 1117 | CA | LEU | A | 206 | 42.813 | 22.851 | 15.667 | 1.00 | 19.18 | A |
| ATOM | 1118 | CB | LEU | A | 206 | 42.693 | 22.295 | 17.087 | 1.00 | 18.94 | A |
| ATOM | 1119 | CG | LEU | A | 206 | 41.511 | 21.358 | 17.346 | 1.00 | 23.10 | A |
| ATOM | 1120 | CD1 | LEU | A | 206 | 41.615 | 20.142 | 16.436 | 1.00 | 23.01 | A |
| ATOM | 1121 | CD2 | LEU | A | 206 | 41.504 | 20.933 | 18.808 | 1.00 | 22.97 | A |
| ATOM | 1122 | C | LEU | A | 206 | 41.639 | 23.772 | 15.361 | 1.00 | 19.05 | A |
| ATOM | 1123 | O | LEU | A | 206 | 41.556 | 24.880 | 15.886 | 1.00 | 19.25 | A |
| ATOM | 1124 | N | LYS | A | 207 | 40.740 | 23.307 | 14.500 | 1.00 | 17.54 | A |
| ATOM | 1125 | CA | LYS | A | 207 | 39.564 | 24.081 | 14.110 | 1.00 | 18.60 | A |
| ATOM | 1126 | CB | LYS | A | 207 | 39.980 | 25.248 | 13.196 | 1.00 | 18.98 | A |
| ATOM | 1127 | CG | LYS | A | 207 | 40.786 | 24.817 | 11.982 | 1.00 | 18.20 | A |
| ATOM | 1128 | CD | LYS | A | 207 | 41.246 | 26.000 | 11.139 | 1.00 | 21.42 | A |
| ATOM | 1129 | CE | LYS | A | 207 | 42.223 | 25.537 | 10.062 | 1.00 | 23.21 | A |
| ATOM | 1130 | NZ | LYS | A | 207 | 42.561 | 26.604 | 9.084 | 1.00 | 29.61 | A |
| ATOM | 1131 | C | LYS | A | 207 | 38.566 | 23.181 | 13.388 | 1.00 | 18.18 | A |
| ATOM | 1132 | O | LYS | A | 207 | 38.921 | 22.100 | 12.915 | 1.00 | 18.11 | A |
| ATOM | 1133 | N | PRO | A | 208 | 37.298 | 23.614 | 13.293 | 1.00 | 20.26 | A |
| ATOM | 1134 | CD | PRO | A | 208 | 36.713 | 24.833 | 13.882 | 1.00 | 18.79 | A |
| ATOM | 1135 | CA | PRO | A | 208 | 36.272 | 22.814 | 12.616 | 1.00 | 19.67 | A |
| ATOM | 1136 | CB | PRO | A | 208 | 35.063 | 23.742 | 12.608 | 1.00 | 19.45 | A |
| ATOM | 1137 | CG | PRO | A | 208 | 35.231 | 24.509 | 13.891 | 1.00 | 21.81 | A |
| ATOM | 1138 | C | PRO | A | 208 | 36.674 | 22.372 | 11.209 | 1.00 | 21.04 | A |
| ATOM | 1139 | O | PRO | A | 208 | 36.264 | 21.307 | 10.751 | 1.00 | 21.19 | A |
| ATOM | 1140 | N | GLU | A | 209 | 37.474 | 23.188 | 10.528 | 1.00 | 21.69 | A |
| ATOM | 1141 | CA | GLU | A | 209 | 37.928 | 22.872 | 9.170 | 1.00 | 22.64 | A |
| ATOM | 1142 | CB | GLU | A | 209 | 38.644 | 24.084 | 8.558 | 1.00 | 23.65 | A |
| ATOM | 1143 | CG | GLU | A | 209 | 39.253 | 23.825 | 7.185 | 1.00 | 27.24 | A |
| ATOM | 1144 | CD | GLU | A | 209 | 40.155 | 24.958 | 6.716 | 1.00 | 29.40 | A |
| ATOM | 1145 | OE1 | GLU | A | 209 | 39.660 | 26.094 | 6.553 | 1.00 | 29.68 | A |
| ATOM | 1146 | OE2 | GLU | A | 209 | 41.363 | 24.711 | 6.511 | 1.00 | 30.07 | A |
| ATOM | 1147 | C | GLU | A | 209 | 38.879 | 21.668 | 9.159 | 1.00 | 22.28 | A |
| ATOM | 1148 | O | GLU | A | 209 | 38.955 | 20.933 | 8.170 | 1.00 | 21.36 | A |
| ATOM | 1149 | N | ASN | A | 210 | 39.600 | 21.490 | 10.263 | 1.00 | 19.90 | A |
| ATOM | 1150 | CA | ASN | A | 210 | 40.574 | 20.412 | 10.436 | 1.00 | 19.44 | A |
| ATOM | 1151 | CB | ASN | A | 210 | 41.744 | 20.912 | 11.287 | 1.00 | 20.07 | A |
| ATOM | 1152 | CG | ASN | A | 210 | 42.746 | 21.698 | 10.479 | 1.00 | 25.77 | A |
| ATOM | 1153 | OD1 | ASN | A | 210 | 43.571 | 22.427 | 11.029 | 1.00 | 26.73 | A |
| ATOM | 1154 | ND2 | ASN | A | 210 | 42.687 | 21.548 | 9.158 | 1.00 | 25.15 | A |
| ATOM | 1155 | C | ASN | A | 210 | 40.005 | 19.151 | 11.078 | 1.00 | 18.63 | A |
| ATOM | 1156 | O | ASN | A | 210 | 40.712 | 18.154 | 11.234 | 1.00 | 18.29 | A |
| ATOM | 1157 | N | ILE | A | 211 | 38.739 | 19.202 | 11.469 | 1.00 | 16.31 | A |
| ATOM | 1158 | CA | ILE | A | 211 | 38.090 | 18.058 | 12.085 | 1.00 | 15.49 | A |
| ATOM | 1159 | CB | ILE | A | 211 | 37.336 | 18.488 | 13.354 | 1.00 | 15.40 | A |
| ATOM | 1160 | CG2 | ILE | A | 211 | 36.582 | 17.311 | 13.950 | 1.00 | 14.59 | A |
| ATOM | 1161 | CG1 | ILE | A | 211 | 38.342 | 19.046 | 14.365 | 1.00 | 15.91 | A |
| ATOM | 1162 | CD1 | ILE | A | 211 | 37.720 | 19.669 | 15.590 | 1.00 | 15.98 | A |
| ATOM | 1163 | C | ILE | A | 211 | 37.131 | 17.485 | 11.059 | 1.00 | 17.26 | A |
| ATOM | 1164 | O | ILE | A | 211 | 35.995 | 17.947 | 10.926 | 1.00 | 18.16 | A |
| ATOM | 1165 | N | LEU | A | 212 | 37.599 | 16.486 | 10.317 | 1.00 | 15.97 | A |
| ATOM | 1166 | CA | LEU | A | 212 | 36.784 | 15.875 | 9.274 | 1.00 | 17.08 | A |
| ATOM | 1167 | CB | LEU | A | 212 | 37.685 | 15.249 | 8.202 | 1.00 | 17.78 | A |
| ATOM | 1168 | CG | LEU | A | 212 | 38.785 | 16.157 | 7.640 | 1.00 | 18.92 | A |
| ATOM | 1169 | CD1 | LEU | A | 212 | 39.476 | 15.450 | 6.485 | 1.00 | 22.09 | A |
| ATOM | 1170 | CD2 | LEU | A | 212 | 38.188 | 17.482 | 7.166 | 1.00 | 19.91 | A |
| ATOM | 1171 | C | LEU | A | 212 | 35.843 | 14.825 | 9.837 | 1.00 | 18.35 | A |
| ATOM | 1172 | O | LEU | A | 212 | 35.957 | 14.433 | 11.002 | 1.00 | 19.39 | A |
| ATOM | 1173 | N | LEU | A | 213 | 34.915 | 14.368 | 9.000 | 1.00 | 17.84 | A |
| ATOM | 1174 | CA | LEU | A | 213 | 33.942 | 13.362 | 9.403 | 1.00 | 19.94 | A |
| ATOM | 1175 | CB | LEU | A | 213 | 32.556 | 14.004 | 9.487 | 1.00 | 20.84 | A |
| ATOM | 1176 | CG | LEU | A | 213 | 32.396 | 15.059 | 10.583 | 1.00 | 20.31 | A |
| ATOM | 1177 | CD1 | LEU | A | 213 | 31.124 | 15.837 | 10.367 | 1.00 | 22.75 | A |
| ATOM | 1178 | CD2 | LEU | A | 213 | 32.379 | 14.378 | 11.940 | 1.00 | 23.93 | A |
| ATOM | 1179 | C | LEU | A | 213 | 33.914 | 12.187 | 8.426 | 1.00 | 20.98 | A |
| ATOM | 1180 | O | LEU | A | 213 | 33.743 | 12.379 | 7.218 | 1.00 | 19.55 | A |
| ATOM | 1181 | N | ASN | A | 214 | 34.088 | 10.970 | 8.935 | 1.00 | 20.44 | A |
| ATOM | 1182 | CA | ASN | A | 214 | 34.055 | 9.814 | 8.049 | 1.00 | 23.77 | A |
| ATOM | 1183 | CB | ASN | A | 214 | 34.745 | 8.596 | 8.674 | 1.00 | 25.30 | A |
| ATOM | 1184 | CG | ASN | A | 214 | 34.077 | 8.127 | 9.948 | 1.00 | 32.04 | A |
| ATOM | 1185 | OD1 | ASN | A | 214 | 32.908 | 8.422 | 10.206 | 1.00 | 34.43 | A |
| ATOM | 1186 | ND2 | ASN | A | 214 | 34.818 | 7.369 | 10.752 | 1.00 | 33.85 | A |
| ATOM | 1187 | C | ASN | A | 214 | 32.618 | 9.466 | 7.693 | 1.00 | 24.07 | A |
| ATOM | 1188 | O | ASN | A | 214 | 31.672 | 10.113 | 8.150 | 1.00 | 19.94 | A |
| ATOM | 1189 | N | GLU | A | 215 | 32.459 | 8.433 | 6.879 | 1.00 | 25.77 | A |

-continued

| | | | | | | | | | | | |
|---|---|---|---|---|---|---|---|---|---|---|---|
| ATOM | 1190 | CA | GLU | A | 215 | 31.138 | 8.003 | 6.445 | 1.00 | 28.69 | A |
| ATOM | 1191 | CB | GLU | A | 215 | 31.275 | 6.796 | 5.513 | 1.00 | 31.98 | A |
| ATOM | 1192 | CG | GLU | A | 215 | 29.970 | 6.334 | 4.896 | 1.00 | 40.22 | A |
| ATOM | 1193 | CD | GLU | A | 215 | 30.182 | 5.312 | 3.795 | 1.00 | 44.27 | A |
| ATOM | 1194 | OE1 | GLU | A | 215 | 30.817 | 4.268 | 4.065 | 1.00 | 46.46 | A |
| ATOM | 1195 | OE2 | GLU | A | 215 | 29.716 | 5.556 | 2.660 | 1.00 | 46.13 | A |
| ATOM | 1196 | C | GLU | A | 215 | 30.188 | 7.673 | 7.601 | 1.00 | 28.41 | A |
| ATOM | 1197 | O | GLU | A | 215 | 28.971 | 7.769 | 7.447 | 1.00 | 28.52 | A |
| ATOM | 1198 | N | ASP | A | 216 | 30.737 | 7.287 | 8.752 | 1.00 | 26.77 | A |
| ATOM | 1199 | CA | ASP | A | 216 | 29.914 | 6.953 | 9.917 | 1.00 | 27.28 | A |
| ATOM | 1200 | CB | ASP | A | 216 | 30.538 | 5.795 | 10.696 | 1.00 | 31.27 | A |
| ATOM | 1201 | CG | ASP | A | 216 | 30.390 | 4.466 | 9.979 | 1.00 | 37.61 | A |
| ATOM | 1202 | OD1 | ASP | A | 216 | 29.274 | 4.170 | 9.499 | 1.00 | 39.45 | A |
| ATOM | 1203 | OD2 | ASP | A | 216 | 31.382 | 3.710 | 9.902 | 1.00 | 41.84 | A |
| ATOM | 1204 | C | ASP | A | 216 | 29.697 | 8.135 | 10.862 | 1.00 | 26.37 | A |
| ATOM | 1205 | O | ASP | A | 216 | 29.136 | 7.984 | 11.950 | 1.00 | 25.73 | A |
| ATOM | 1206 | N | MET | A | 217 | 30.156 | 9.306 | 10.441 | 1.00 | 23.02 | A |
| ATOM | 1207 | CA | MET | A | 217 | 30.015 | 10.527 | 11.218 | 1.00 | 21.83 | A |
| ATOM | 1208 | CB | MET | A | 217 | 28.537 | 10.789 | 11.517 | 1.00 | 23.24 | A |
| ATOM | 1209 | CG | MET | A | 217 | 27.742 | 11.186 | 10.274 | 1.00 | 22.98 | A |
| ATOM | 1210 | SD | MET | A | 217 | 28.464 | 12.616 | 9.430 | 1.00 | 27.57 | A |
| ATOM | 1211 | CE | MET | A | 217 | 27.679 | 13.974 | 10.332 | 1.00 | 26.68 | A |
| ATOM | 1212 | C | MET | A | 217 | 30.844 | 10.618 | 12.502 | 1.00 | 21.51 | A |
| ATOM | 1213 | O | MET | A | 217 | 30.474 | 11.323 | 13.440 | 1.00 | 18.62 | A |
| ATOM | 1214 | N | HIS | A | 218 | 31.957 | 9.892 | 12.544 | 1.00 | 20.10 | A |
| ATOM | 1215 | CA | HIS | A | 218 | 32.873 | 9.964 | 13.678 | 1.00 | 19.86 | A |
| ATOM | 1216 | CB | HIS | A | 218 | 33.482 | 8.594 | 13.977 | 1.00 | 20.21 | A |
| ATOM | 1217 | CG | HIS | A | 218 | 32.551 | 7.667 | 14.698 | 1.00 | 22.40 | A |
| ATOM | 1218 | CD2 | HIS | A | 218 | 31.910 | 6.547 | 14.287 | 1.00 | 21.27 | A |
| ATOM | 1219 | ND1 | HIS | A | 218 | 32.177 | 7.863 | 16.011 | 1.00 | 19.59 | A |
| ATOM | 1220 | CE1 | HIS | A | 218 | 31.348 | 6.902 | 16.379 | 1.00 | 21.88 | A |
| ATOM | 1221 | NE2 | HIS | A | 218 | 31.168 | 6.091 | 15.351 | 1.00 | 22.08 | A |
| ATOM | 1222 | C | HIS | A | 218 | 33.947 | 10.921 | 13.172 | 1.00 | 19.10 | A |
| ATOM | 1223 | O | HIS | A | 218 | 34.1701 | 11.004 | 11.965 | 1.00 | 20.31 | A |
| ATOM | 1224 | N | ILE | A | 219 | 34.617 | 11.638 | 14.067 | 1.00 | 17.21 | A |
| ATOM | 1225 | CA | ILE | A | 219 | 35.628 | 12.586 | 13.618 | 1.00 | 15.26 | A |
| ATOM | 1226 | CB | ILE | A | 219 | 35.987 | 13.614 | 14.716 | 1.00 | 15.38 | A |
| ATOM | 1227 | CG2 | ILE | A | 219 | 34.722 | 14.305 | 15.221 | 1.00 | 14.58 | A |
| ATOM | 1228 | CG1 | ILE | A | 219 | 36.734 | 12.919 | 15.864 | 1.00 | 14.46 | A |
| ATOM | 1229 | CD1 | ILE | A | 219 | 37.279 | 13.885 | 16.911 | 1.00 | 13.74 | A |
| ATOM | 1230 | C | ILE | A | 219 | 36.929 | 11.944 | 13.161 | 1.00 | 16.21 | A |
| ATOM | 1231 | O | ILE | A | 219 | 37.238 | 10.799 | 13.500 | 1.00 | 15.88 | A |
| ATOM | 1232 | N | GLN | A | 220 | 37.677 | 12.711 | 12.378 | 1.00 | 15.62 | A |
| ATOM | 1233 | CA | GLN | A | 220 | 38.980 | 12.316 | 11.876 | 1.00 | 17.84 | A |
| ATOM | 1234 | CB | GLN | A | 220 | 38.872 | 11.595 | 10.525 | 1.00 | 20.00 | A |
| ATOM | 1235 | CG | GLN | A | 220 | 38.463 | 10.129 | 10.659 | 1.00 | 26.97 | A |
| ATOM | 1236 | CD | GLN | A | 220 | 38.648 | 9.343 | 9.372 | 1.00 | 29.95 | A |
| ATOM | 1237 | OE1 | GLN | A | 220 | 37.968 | 9.590 | 8.373 | 1.00 | 33.12 | A |
| ATOM | 1238 | NE2 | GLN | A | 220 | 39.578 | 8.393 | 9.389 | 1.00 | 30.47 | A |
| ATOM | 1239 | C | GLN | A | 220 | 39.757 | 13.610 | 11.735 | 1.00 | 17.00 | A |
| ATOM | 1240 | O | GLN | A | 220 | 39.609 | 14.339 | 10.751 | 1.00 | 18.27 | A |
| ATOM | 1241 | N | ILE | A | 221 | 40.566 | 13.906 | 12.746 | 1.00 | 14.34 | A |
| ATOM | 1242 | CA | ILE | A | 221 | 41.361 | 15.120 | 12.753 | 1.00 | 14.46 | A |
| ATOM | 1243 | CB | ILE | A | 221 | 41.867 | 15.416 | 14.175 | 1.00 | 12.30 | A |
| ATOM | 1244 | CG2 | ILE | A | 221 | 42.764 | 16.656 | 14.167 | 1.00 | 14.78 | A |
| ATOM | 1245 | CG1 | ILE | A | 221 | 40.660 | 15.613 | 15.102 | 1.00 | 13.92 | A |
| ATOM | 1246 | CD1 | ILE | A | 221 | 41.003 | 15.901 | 16.543 | 1.00 | 15.06 | A |
| ATOM | 1247 | C | ILE | A | 221 | 42.536 | 14.996 | 11.783 | 1.00 | 15.44 | A |
| ATOM | 1248 | O | ILE | A | 221 | 43.106 | 13.915 | 11.613 | 1.00 | 13.93 | A |
| ATOM | 1249 | N | THR | A | 222 | 42.877 | 16.101 | 11.127 | 1.00 | 15.36 | A |
| ATOM | 1250 | CA | THR | A | 222 | 43.980 | 16.098 | 10.174 | 1.00 | 17.52 | A |
| ATOM | 1251 | CB | THR | A | 222 | 43.470 | 15.836 | 8.750 | 1.00 | 19.92 | A |
| ATOM | 1252 | OG1 | THR | A | 222 | 44.587 | 15.637 | 7.875 | 1.00 | 18.78 | A |
| ATOM | 1253 | CG2 | THR | A | 222 | 42.630 | 17.018 | 8.257 | 1.00 | 18.16 | A |
| ATOM | 1254 | C | THR | A | 222 | 44.735 | 17.428 | 10.192 | 1.00 | 19.60 | A |
| ATOM | 1255 | O | THR | A | 222 | 44.509 | 18.257 | 11.084 | 1.00 | 18.59 | A |
| ATOM | 1256 | N | ASP | A | 223 | 45.630 | 17.610 | 9.216 | 1.00 | 18.69 | A |
| ATOM | 1257 | CA | ASP | A | 223 | 46.440 | 18.825 | 9.069 | 1.00 | 20.12 | A |
| ATOM | 1258 | CB | ASP | A | 223 | 45.532 | 20.065 | 9.108 | 1.00 | 23.51 | A |
| ATOM | 1259 | CG | ASP | A | 223 | 46.248 | 21.335 | 8.670 | 1.00 | 27.09 | A |
| ATOM | 1260 | OD1 | ASP | A | 223 | 47.283 | 21.227 | 7.975 | 1.00 | 26.28 | A |
| ATOM | 1261 | OD2 | ASP | A | 223 | 45.765 | 22.438 | 9.009 | 1.00 | 26.15 | A |
| ATOM | 1262 | C | ASP | A | 223 | 47.516 | 18.913 | 10.150 | 1.00 | 21.73 | A |
| ATOM | 1263 | O | ASP | A | 223 | 47.439 | 19.751 | 11.055 | 1.00 | 22.76 | A |
| ATOM | 1264 | N | PHE | A | 224 | 48.535 | 18.063 | 10.027 | 1.00 | 20.75 | A |
| ATOM | 1265 | CA | PHE | A | 224 | 49.611 | 17.988 | 11.009 | 1.00 | 20.11 | A |
| ATOM | 1266 | CB | PHE | A | 224 | 49.805 | 16.527 | 11.424 | 1.00 | 20.62 | A |
| ATOM | 1267 | CG | PHE | A | 224 | 48.682 | 15.991 | 12.263 | 1.00 | 21.41 | A |
| ATOM | 1268 | CD1 | PHE | A | 224 | 48.598 | 16.312 | 13.614 | 1.00 | 23.05 | A |

-continued

| | | | | | | | | | | |
|---|---|---|---|---|---|---|---|---|---|---|
| ATOM | 1269 | CD2 | PHE | A | 224 | 47.681 | 15.212 | 11.693 | 1.00 | 22.27 | A |
| ATOM | 1270 | CE1 | PHE | A | 224 | 47.528 | 15.868 | 14.389 | 1.00 | 23.30 | A |
| ATOM | 1271 | CE2 | PHE | A | 224 | 46.606 | 14.763 | 12.457 | 1.00 | 21.11 | A |
| ATOM | 1272 | CZ | PHE | A | 224 | 46.530 | 15.093 | 13.807 | 1.00 | 22.02 | A |
| ATOM | 1273 | C | PHE | A | 224 | 50.957 | 18.583 | 10.619 | 1.00 | 20.45 | A |
| ATOM | 1274 | O | PHE | A | 224 | 51.905 | 18.547 | 11.407 | 1.00 | 20.73 | A |
| ATOM | 1275 | N | GLY | A | 225 | 51.049 | 19.125 | 9.412 | 1.00 | 22.02 | A |
| ATOM | 1276 | CA | GLY | A | 225 | 52.301 | 19.713 | 8.981 | 1.00 | 22.66 | A |
| ATOM | 1277 | C | GLY | A | 225 | 52.742 | 20.822 | 9.920 | 1.00 | 24.99 | A |
| ATOM | 1278 | O | GLY | A | 225 | 53.939 | 21.041 | 10.122 | 1.00 | 24.52 | A |
| ATOM | 1279 | N | THR | A | 226 | 51.779 | 21.524 | 10.508 | 1.00 | 23.50 | A |
| ATOM | 1280 | CA | THR | A | 226 | 52.106 | 22.613 | 11.416 | 1.00 | 25.16 | A |
| ATOM | 1281 | CB | THR | A | 226 | 51.199 | 23.829 | 11.160 | 1.00 | 24.76 | A |
| ATOM | 1282 | OG1 | THR | A | 226 | 49.831 | 23.410 | 11.113 | 1.00 | 22.68 | A |
| ATOM | 1283 | CG2 | THR | A | 226 | 51.571 | 24.490 | 9.834 | 1.00 | 25.00 | A |
| ATOM | 1284 | C | THR | A | 226 | 52.046 | 22.233 | 12.894 | 1.00 | 25.79 | A |
| ATOM | 1285 | O | THR | A | 226 | 52.019 | 23.100 | 13.768 | 1.00 | 24.54 | A |
| ATOM | 1286 | N | ALA | A | 227 | 52.037 | 20.935 | 13.173 | 1.00 | 24.97 | A |
| ATOM | 1287 | CA | ALA | A | 227 | 52.004 | 20.475 | 14.550 | 1.00 | 25.49 | A |
| ATOM | 1288 | CB | ALA | A | 227 | 51.659 | 18.993 | 14.607 | 1.00 | 22.85 | A |
| ATOM | 1289 | C | ALA | A | 227 | 53.384 | 20.715 | 15.149 | 1.00 | 27.70 | A |
| ATOM | 1290 | O | ALA | A | 227 | 54.331 | 21.047 | 14.435 | 1.00 | 26.60 | A |
| ATOM | 1291 | N | LYS | A | 228 | 53.491 | 20.558 | 16.461 | 1.00 | 28.53 | A |
| ATOM | 1292 | CA | LYS | A | 228 | 54.760 | 20.745 | 17.149 | 1.00 | 32.12 | A |
| ATOM | 1293 | CB | LYS | A | 228 | 54.699 | 21.974 | 18.054 | 1.00 | 33.81 | A |
| ATOM | 1294 | CG | LYS | A | 228 | 56.007 | 22.294 | 18.765 | 1.00 | 41.23 | A |
| ATOM | 1295 | CD | LYS | A | 228 | 57.082 | 22.725 | 17.768 | 1.00 | 47.57 | A |
| ATOM | 1296 | CE | LYS | A | 228 | 58.401 | 23.056 | 18.462 | 1.00 | 49.82 | A |
| ATOM | 1297 | NZ | LYS | A | 228 | 59.459 | 23.425 | 17.480 | 1.00 | 51.49 | A |
| ATOM | 1298 | C | LYS | A | 228 | 55.019 | 19.504 | 17.985 | 1.00 | 33.25 | A |
| ATOM | 1299 | O | LYS | A | 228 | 54.190 | 19.129 | 18.815 | 1.00 | 33.70 | A |
| ATOM | 1300 | N | VAL | A | 229 | 56.159 | 18.860 | 17.756 | 1.00 | 33.64 | A |
| ATOM | 1301 | CA | VAL | A | 229 | 56.516 | 17.661 | 18.501 | 1.00 | 34.66 | A |
| ATOM | 1302 | CB | VAL | A | 229 | 57.248 | 16.646 | 17.609 | 1.00 | 33.50 | A |
| ATOM | 1303 | CG1 | VAL | A | 229 | 57.619 | 15.419 | 18.415 | 1.00 | 32.34 | A |
| ATOM | 1304 | CG2 | VAL | A | 229 | 56.370 | 16.264 | 16.436 | 1.00 | 34.25 | A |
| ATOM | 1305 | C | VAL | A | 229 | 57.420 | 18.035 | 19.668 | 1.00 | 37.57 | A |
| ATOM | 1306 | O | VAL | A | 229 | 58.581 | 18.392 | 19.474 | 1.00 | 35.91 | A |
| ATOM | 1307 | N | LEU | A | 230 | 56.877 | 17.948 | 20.878 | 1.00 | 40.57 | A |
| ATOM | 1308 | CA | LEU | A | 230 | 57.615 | 18.289 | 22.088 | 1.00 | 46.10 | A |
| ATOM | 1309 | CB | LEU | A | 230 | 56.654 | 18.417 | 23.270 | 1.00 | 44.71 | A |
| ATOM | 1310 | CG | LEU | A | 230 | 55.627 | 19.545 | 23.207 | 1.00 | 44.50 | A |
| ATOM | 1311 | CD1 | LEU | A | 230 | 54.673 | 19.430 | 24.383 | 1.00 | 44.39 | A |
| ATOM | 1312 | CD2 | LEU | A | 230 | 56.340 | 20.885 | 23.214 | 1.00 | 44.81 | A |
| ATOM | 1313 | C | LEU | A | 230 | 58.695 | 17.279 | 22.440 | 1.00 | 50.42 | A |
| ATOM | 1314 | O | LEU | A | 230 | 58.603 | 16.104 | 22.089 | 1.00 | 51.64 | A |
| ATOM | 1315 | N | SER | A | 231 | 59.717 | 17.756 | 23.145 | 1.00 | 55.81 | A |
| ATOM | 1316 | CA | SER | A | 231 | 60.824 | 16.914 | 23.583 | 1.00 | 61.14 | A |
| ATOM | 1317 | CB | SER | A | 231 | 62.077 | 17.200 | 22.750 | 1.00 | 61.27 | A |
| ATOM | 1318 | OG | SER | A | 231 | 62.444 | 18.568 | 22.823 | 1.00 | 62.85 | A |
| ATOM | 1319 | C | SER | A | 231 | 61.124 | 17.126 | 25.071 | 1.00 | 64.65 | A |
| ATOM | 1320 | O | SER | A | 231 | 61.392 | 16.164 | 25.794 | 1.00 | 65.70 | A |
| ATOM | 1321 | N | PRO | A | 232 | 61.081 | 18.387 | 25.549 | 1.00 | 67.54 | A |
| ATOM | 1322 | CD | PRO | A | 232 | 60.854 | 19.651 | 24.823 | 1.00 | 68.60 | A |
| ATOM | 1323 | CA | PRO | A | 232 | 61.358 | 18.655 | 26.966 | 1.00 | 68.74 | A |
| ATOM | 1324 | CB | PRO | A | 232 | 61.109 | 20.158 | 27.086 | 1.00 | 68.83 | A |
| ATOM | 1325 | CG | PRO | A | 232 | 61.505 | 20.666 | 25.737 | 1.00 | 68.96 | A |
| ATOM | 1326 | C | PRO | A | 232 | 60.460 | 17.846 | 27.899 | 1.00 | 69.17 | A |
| ATOM | 1327 | O | PRO | A | 232 | 59.335 | 17.494 | 27.541 | 1.00 | 69.94 | A |
| ATOM | 1328 | N | ALA | A | 237 | 57.424 | 23.198 | 27.637 | 1.00 | 80.06 | A |
| ATOM | 1329 | CA | ALA | A | 237 | 56.783 | 23.047 | 26.335 | 1.00 | 79.29 | A |
| ATOM | 1330 | CB | ALA | A | 237 | 55.275 | 22.907 | 26.512 | 1.00 | 78.64 | A |
| ATOM | 1331 | C | ALA | A | 237 | 57.092 | 24.239 | 25.433 | 1.00 | 79.07 | A |
| ATOM | 1332 | O | ALA | A | 237 | 56.250 | 25.113 | 25.249 | 1.00 | 79.47 | A |
| ATOM | 1333 | N | ALA | A | 238 | 58.297 | 24.280 | 24.871 | 1.00 | 78.57 | A |
| ATOM | 1334 | CA | ALA | A | 238 | 58.683 | 25.383 | 23.992 | 1.00 | 78.50 | A |
| ATOM | 1335 | CB | ALA | A | 238 | 60.186 | 25.347 | 23.728 | 1.00 | 78.50 | A |
| ATOM | 1336 | C | ALA | A | 238 | 57.920 | 25.327 | 22.673 | 1.00 | 78.15 | A |
| ATOM | 1337 | O | ALA | A | 238 | 57.243 | 24.341 | 22.375 | 1.00 | 77.96 | A |
| ATOM | 1338 | N | ALA | A | 239 | 58.027 | 26.393 | 21.887 | 1.00 | 77.28 | A |
| ATOM | 1339 | CA | ALA | A | 239 | 57.338 | 26.452 | 20.603 | 1.00 | 76.27 | A |
| ATOM | 1340 | CB | ALA | A | 239 | 55.849 | 26.489 | 20.827 | 1.00 | 76.61 | A |
| ATOM | 1341 | C | ALA | A | 239 | 57.766 | 27.667 | 19.793 | 1.00 | 75.38 | A |
| ATOM | 1342 | O | ALA | A | 239 | 58.955 | 27.955 | 19.700 | 1.00 | 75.89 | A |
| ATOM | 1343 | N | ASN | A | 240 | 56.781 | 28.357 | 19.214 | 1.00 | 73.95 | A |
| ATOM | 1344 | CA | ASN | A | 240 | 56.967 | 29.553 | 18.389 | 1.00 | 71.07 | A |
| ATOM | 1345 | CB | ASN | A | 240 | 58.151 | 30.400 | 18.874 | 1.00 | 71.47 | A |
| ATOM | 1346 | CG | ASN | A | 240 | 59.459 | 30.055 | 18.174 | 1.00 | 72.06 | A |
| ATOM | 1347 | OD1 | ASN | A | 240 | 59.575 | 30.149 | 16.943 | 1.00 | 72.03 | A |

-continued

| | | | | | | | | | | |
|---|---|---|---|---|---|---|---|---|---|---|
| ATOM | 1348 | ND2 | ASN | A | 240 | 60.470 | 29.665 | 18.964 | 1.00 | 71.91 | A |
| ATOM | 1349 | C | ASN | A | 240 | 57.188 | 29.178 | 16.928 | 1.00 | 69.41 | A |
| ATOM | 1350 | O | ASN | A | 240 | 57.480 | 28.024 | 16.624 | 1.00 | 70.09 | A |
| ATOM | 1351 | N | ALA | A | 241 | 57.055 | 30.165 | 16.038 | 1.00 | 66.62 | A |
| ATOM | 1352 | CA | ALA | A | 241 | 57.246 | 30.013 | 14.585 | 1.00 | 63.94 | A |
| ATOM | 1353 | C | ALA | A | 241 | 55.952 | 30.080 | 13.772 | 1.00 | 60.63 | A |
| ATOM | 1354 | O | ALA | A | 241 | 55.840 | 30.880 | 12.845 | 1.00 | 61.29 | A |
| ATOM | 1355 | CB | ALA | A | 241 | 57.979 | 28.704 | 14.246 | 1.00 | 65.23 | A |
| ATOM | 1356 | N | PHE | A | 242 | 54.984 | 29.236 | 14.113 | 1.00 | 56.72 | A |
| ATOM | 1357 | CA | PHE | A | 242 | 53.712 | 29.196 | 13.394 | 1.00 | 52.53 | A |
| ATOM | 1358 | CB | PHE | A | 242 | 53.419 | 27.767 | 12.923 | 1.00 | 49.14 | A |
| ATOM | 1359 | CG | PHE | A | 242 | 52.040 | 27.590 | 12.354 | 1.00 | 47.38 | A |
| ATOM | 1360 | CD1 | PHE | A | 242 | 51.731 | 28.067 | 11.085 | 1.00 | 47.69 | A |
| ATOM | 1361 | CD2 | PHE | A | 242 | 51.038 | 26.975 | 13.102 | 1.00 | 45.45 | A |
| ATOM | 1362 | CE1 | PHE | A | 242 | 50.445 | 27.937 | 10.565 | 1.00 | 46.75 | A |
| ATOM | 1363 | CE2 | PHE | A | 242 | 49.751 | 26.840 | 12.594 | 1.00 | 45.41 | A |
| ATOM | 1364 | CZ | PHE | A | 242 | 49.453 | 27.323 | 11.322 | 1.00 | 46.55 | A |
| ATOM | 1365 | C | PHE | A | 242 | 52.534 | 29.688 | 14.229 | 1.00 | 50.08 | A |
| ATOM | 1366 | O | PHE | A | 242 | 52.502 | 29.505 | 15.444 | 1.00 | 49.86 | A |
| ATOM | 1367 | N | VAL | A | 243 | 51.566 | 30.305 | 13.557 | 1.00 | 47.67 | A |
| ATOM | 1368 | CA | VAL | A | 243 | 50.355 | 30.809 | 14.200 | 1.00 | 46.21 | A |
| ATOM | 1369 | CB | VAL | A | 243 | 50.340 | 32.352 | 14.258 | 1.00 | 47.36 | A |
| ATOM | 1370 | CG1 | VAL | A | 243 | 49.012 | 32.844 | 14.825 | 1.00 | 47.54 | A |
| ATOM | 1371 | CG2 | VAL | A | 243 | 51.497 | 32.842 | 15.109 | 1.00 | 48.50 | A |
| ATOM | 1372 | C | VAL | A | 243 | 49.150 | 30.342 | 13.389 | 1.00 | 44.12 | A |
| ATOM | 1373 | O | VAL | A | 243 | 48.956 | 30.765 | 12.247 | 1.00 | 44.46 | A |
| ATOM | 1374 | N | GLY | A | 244 | 48.348 | 29.467 | 13.985 | 1.00 | 40.48 | A |
| ATOM | 1375 | CA | GLY | A | 244 | 47.176 | 28.941 | 13.306 | 1.00 | 37.65 | A |
| ATOM | 1376 | C | GLY | A | 244 | 46.101 | 29.960 | 12.964 | 1.00 | 35.39 | A |
| ATOM | 1377 | O | GLY | A | 244 | 46.313 | 31.168 | 13.065 | 1.00 | 35.92 | A |
| ATOM | 1378 | N | THR | A | 245 | 44.936 | 29.463 | 12.560 | 1.00 | 33.30 | A |
| ATOM | 1379 | CA | THR | A | 245 | 43.813 | 30.312 | 12.184 | 1.00 | 30.20 | A |
| ATOM | 1380 | CB | THR | A | 245 | 42.593 | 29.450 | 11.829 | 1.00 | 32.00 | A |
| ATOM | 1381 | OG1 | THR | A | 245 | 42.952 | 28.573 | 10.755 | 1.00 | 32.81 | A |
| ATOM | 1382 | CG2 | THR | A | 245 | 41.419 | 30.319 | 11.390 | 1.00 | 28.34 | A |
| ATOM | 1383 | C | THR | A | 245 | 43.476 | 31.296 | 13.296 | 1.00 | 27.96 | A |
| ATOM | 1384 | O | THR | A | 245 | 43.212 | 30.907 | 14.434 | 1.00 | 25.46 | A |
| ATOM | 1385 | N | ALA | A | 246 | 43.486 | 32.576 | 12.938 | 1.00 | 25.22 | A |
| ATOM | 1386 | CA | ALA | A | 246 | 43.247 | 33.675 | 13.867 | 1.00 | 23.27 | A |
| ATOM | 1387 | CB | ALA | A | 246 | 42.956 | 34.955 | 13.082 | 1.00 | 22.94 | A |
| ATOM | 1388 | C | ALA | A | 246 | 42.178 | 33.475 | 14.934 | 1.00 | 21.27 | A |
| ATOM | 1389 | O | ALA | A | 246 | 42.431 | 33.705 | 16.114 | 1.00 | 20.93 | A |
| ATOM | 1390 | N | GLN | A | 247 | 40.988 | 33.047 | 14.536 | 1.00 | 19.67 | A |
| ATOM | 1391 | CA | GLN | A | 247 | 39.911 | 32.886 | 15.504 | 1.00 | 20.17 | A |
| ATOM | 1392 | CB | GLN | A | 247 | 38.608 | 32.535 | 14.779 | 1.00 | 21.89 | A |
| ATOM | 1393 | CG | GLN | A | 247 | 38.522 | 33.076 | 13.355 | 1.00 | 26.18 | A |
| ATOM | 1394 | CD | GLN | A | 247 | 37.220 | 33.794 | 13.064 | 1.00 | 27.30 | A |
| ATOM | 1395 | OE1 | GLN | A | 247 | 36.172 | 33.447 | 13.605 | 1.00 | 30.13 | A |
| ATOM | 1396 | NE2 | GLN | A | 247 | 37.278 | 34.792 | 12.189 | 1.00 | 28.70 | A |
| ATOM | 1397 | C | GLN | A | 247 | 40.181 | 31.849 | 16.595 | 1.00 | 19.43 | A |
| ATOM | 1398 | O | GLN | A | 247 | 39.546 | 31.883 | 17.648 | 1.00 | 18.93 | A |
| ATOM | 1399 | N | TYR | A | 248 | 41.132 | 30.948 | 16.359 | 1.00 | 18.60 | A |
| ATOM | 1400 | CA | TYR | A | 248 | 41.441 | 29.896 | 17.329 | 1.00 | 19.20 | A |
| ATOM | 1401 | CB | TYR | A | 248 | 41.333 | 28.529 | 16.642 | 1.00 | 17.53 | A |
| ATOM | 1402 | CG | TYR | A | 248 | 40.013 | 28.362 | 15.927 | 1.00 | 19.32 | A |
| ATOM | 1403 | CD1 | TYR | A | 248 | 38.859 | 28.010 | 16.625 | 1.00 | 17.69 | A |
| ATOM | 1404 | CE1 | TYR | A | 248 | 37.617 | 27.976 | 15.990 | 1.00 | 18.18 | A |
| ATOM | 1405 | CD2 | TYR | A | 248 | 39.897 | 28.664 | 14.569 | 1.00 | 16.87 | A |
| ATOM | 1406 | CE2 | TYR | A | 248 | 38.665 | 28.635 | 13.924 | 1.00 | 19.17 | A |
| ATOM | 1407 | CZ | TYR | A | 248 | 37.527 | 28.295 | 14.643 | 1.00 | 19.46 | A |
| ATOM | 1408 | OH | TYR | A | 248 | 36.299 | 28.311 | 14.023 | 1.00 | 18.98 | A |
| ATOM | 1409 | C | TYR | A | 248 | 42.810 | 30.039 | 17.993 | 1.00 | 20.42 | A |
| ATOM | 1410 | O | TYR | A | 248 | 43.208 | 29.191 | 18.792 | 1.00 | 19.19 | A |
| ATOM | 1411 | N | VAL | A | 249 | 43.523 | 31.114 | 17.673 | 1.00 | 20.20 | A |
| ATOM | 1412 | CA | VAL | A | 249 | 44.841 | 31.343 | 18.251 | 1.00 | 20.91 | A |
| ATOM | 1413 | CB | VAL | A | 249 | 45.542 | 32.532 | 17.570 | 1.00 | 21.18 | A |
| ATOM | 1414 | CG1 | VAL | A | 249 | 46.821 | 32.896 | 18.317 | 1.00 | 22.45 | A |
| ATOM | 1415 | CG2 | VAL | A | 249 | 45.862 | 32.170 | 16.139 | 1.00 | 24.01 | A |
| ATOM | 1416 | C | VAL | A | 249 | 44.764 | 31.606 | 19.750 | 1.00 | 21.52 | A |
| ATOM | 1417 | O | VAL | A | 249 | 43.915 | 32.368 | 20.216 | 1.00 | 22.72 | A |
| ATOM | 1418 | N | SER | A | 250 | 45.654 | 30.965 | 20.503 | 1.00 | 20.70 | A |
| ATOM | 1419 | CA | SER | A | 250 | 45.697 | 31.133 | 21.951 | 1.00 | 21.65 | A |
| ATOM | 1420 | CB | SER | A | 250 | 46.370 | 29.919 | 22.613 | 1.00 | 22.02 | A |
| ATOM | 1421 | OG | SER | A | 250 | 47.692 | 29.725 | 22.132 | 1.00 | 22.12 | A |
| ATOM | 1422 | C | SER | A | 250 | 46.476 | 32.402 | 22.280 | 1.00 | 22.13 | A |
| ATOM | 1423 | O | SER | A | 250 | 47.332 | 32.828 | 21.511 | 1.00 | 22.77 | A |
| ATOM | 1424 | N | PRO | A | 251 | 46.180 | 33.029 | 23.425 | 1.00 | 22.23 | A |
| ATOM | 1425 | CD | PRO | A | 251 | 45.163 | 32.684 | 24.433 | 1.00 | 22.97 | A |
| ATOM | 1426 | CA | PRO | A | 251 | 46.893 | 34.254 | 23.800 | 1.00 | 22.52 | A |

-continued

| | | | | | | | | | | |
|---|---|---|---|---|---|---|---|---|---|---|
| ATOM | 1427 | CB | PRO | A | 251 | 46.233 | 34.650 | 25.127 | 1.00 | 23.06 | A |
| ATOM | 1428 | CG | PRO | A | 251 | 45.726 | 33.329 | 25.676 | 1.00 | 22.55 | A |
| ATOM | 1429 | C | PRO | A | 251 | 48.414 | 34.115 | 23.907 | 1.00 | 22.15 | A |
| ATOM | 1430 | O | PRO | A | 251 | 49.143 | 35.047 | 23.563 | 1.00 | 22.62 | A |
| ATOM | 1431 | N | GLU | A | 252 | 48.901 | 32.966 | 24.367 | 1.00 | 20.69 | A |
| ATOM | 1432 | CA | GLU | A | 252 | 50.347 | 32.772 | 24.500 | 1.00 | 21.40 | A |
| ATOM | 1433 | CB | GLU | A | 252 | 50.673 | 31.382 | 25.071 | 1.00 | 20.59 | A |
| ATOM | 1434 | CG | GLU | A | 252 | 49.993 | 30.232 | 24.352 | 1.00 | 21.91 | A |
| ATOM | 1435 | CD | GLU | A | 252 | 48.691 | 29.822 | 25.014 | 1.00 | 21.51 | A |
| ATOM | 1436 | OE1 | GLU | A | 252 | 47.989 | 30.707 | 25.550 | 1.00 | 21.46 | A |
| ATOM | 1437 | OE2 | GLU | A | 252 | 48.367 | 28.613 | 24.993 | 1.00 | 20.23 | A |
| ATOM | 1438 | C | GLU | A | 252 | 51.071 | 32.970 | 23.167 | 1.00 | 22.99 | A |
| ATOM | 1439 | O | GLU | A | 252 | 52.191 | 33.480 | 23.136 | 1.00 | 23.17 | A |
| ATOM | 1440 | N | LEU | A | 253 | 50.441 | 32.576 | 22.064 | 1.00 | 23.00 | A |
| ATOM | 1441 | CA | LEU | A | 253 | 51.068 | 32.753 | 20.758 | 1.00 | 25.62 | A |
| ATOM | 1442 | CB | LEU | A | 253 | 50.277 | 32.029 | 19.669 | 1.00 | 26.75 | A |
| ATOM | 1443 | CG | LEU | A | 253 | 50.743 | 30.620 | 19.296 | 1.00 | 31.87 | A |
| ATOM | 1444 | CD1 | LEU | A | 253 | 50.433 | 29.651 | 20.422 | 1.00 | 31.81 | A |
| ATOM | 1445 | CD2 | LEU | A | 253 | 50.044 | 30.179 | 18.015 | 1.00 | 31.86 | A |
| ATOM | 1446 | C | LEU | A | 253 | 51.201 | 34.228 | 20.371 | 1.00 | 26.94 | A |
| ATOM | 1447 | O | LEU | A | 253 | 52.107 | 34.601 | 19.626 | 1.00 | 27.09 | A |
| ATOM | 1448 | N | LEU | A | 254 | 50.297 | 35.059 | 20.877 | 1.00 | 25.83 | A |
| ATOM | 1449 | CA | LEU | A | 254 | 50.297 | 36.485 | 20.564 | 1.00 | 27.26 | A |
| ATOM | 1450 | CB | LEU | A | 254 | 48.858 | 37.006 | 20.564 | 1.00 | 25.84 | A |
| ATOM | 1451 | CG | LEU | A | 254 | 47.882 | 36.290 | 19.621 | 1.00 | 24.69 | A |
| ATOM | 1452 | CD1 | LEU | A | 254 | 46.459 | 36.724 | 19.932 | 1.00 | 23.64 | A |
| ATOM | 1453 | CD2 | LEU | A | 254 | 48.236 | 36.597 | 18.177 | 1.00 | 24.24 | A |
| ATOM | 1454 | C | LEU | A | 254 | 51.134 | 37.314 | 21.537 | 1.00 | 30.62 | A |
| ATOM | 1455 | O | LEU | A | 254 | 51.633 | 38.383 | 21.187 | 1.00 | 32.35 | A |
| ATOM | 1456 | N | THR | A | 255 | 51.292 | 36.821 | 22.758 | 1.00 | 32.47 | A |
| ATOM | 1457 | CA | THR | A | 255 | 52.056 | 37.547 | 23.759 | 1.00 | 36.70 | A |
| ATOM | 1458 | CB | THR | A | 255 | 51.368 | 37.478 | 25.127 | 1.00 | 34.51 | A |
| ATOM | 1459 | OG1 | THR | A | 255 | 51.188 | 36.106 | 25.494 | 1.00 | 35.49 | A |
| ATOM | 1460 | CG2 | THR | A | 255 | 50.013 | 38.166 | 25.077 | 1.00 | 33.40 | A |
| ATOM | 1461 | C | THR | A | 255 | 53.477 | 37.035 | 23.910 | 1.00 | 40.09 | A |
| ATOM | 1462 | O | THR | A | 255 | 54.430 | 37.793 | 23.772 | 1.00 | 43.69 | A |
| ATOM | 1463 | N | GLU | A | 256 | 53.617 | 35.747 | 24.189 | 1.00 | 44.77 | A |
| ATOM | 1464 | CA | GLU | A | 256 | 54.932 | 35.144 | 24.382 | 1.00 | 49.15 | A |
| ATOM | 1465 | CB | GLU | A | 256 | 54.866 | 34.143 | 25.534 | 1.00 | 51.24 | A |
| ATOM | 1466 | CG | GLU | A | 256 | 54.514 | 34.786 | 26.862 | 1.00 | 56.03 | A |
| ATOM | 1467 | CD | GLU | A | 256 | 54.053 | 33.780 | 27.893 | 1.00 | 58.83 | A |
| ATOM | 1468 | OE1 | GLU | A | 256 | 54.766 | 32.776 | 28.107 | 1.00 | 62.13 | A |
| ATOM | 1469 | OE2 | GLU | A | 256 | 52.979 | 33.996 | 28.494 | 1.00 | 60.34 | A |
| ATOM | 1470 | C | GLU | A | 256 | 55.475 | 34.456 | 23.137 | 1.00 | 50.09 | A |
| ATOM | 1471 | O | GLU | A | 256 | 56.616 | 33.995 | 23.127 | 1.00 | 50.42 | A |
| ATOM | 1472 | N | LYS | A | 257 | 54.658 | 34.389 | 22.090 | 1.00 | 51.21 | A |
| ATOM | 1473 | CA | LYS | A | 257 | 55.064 | 33.746 | 20.845 | 1.00 | 51.22 | A |
| ATOM | 1474 | CB | LYS | A | 257 | 56.244 | 34.502 | 20.227 | 1.00 | 53.28 | A |
| ATOM | 1475 | CG | LYS | A | 257 | 56.558 | 34.125 | 18.790 | 1.00 | 55.19 | A |
| ATOM | 1476 | CD | LYS | A | 257 | 57.709 | 34.961 | 18.253 | 1.00 | 57.52 | A |
| ATOM | 1477 | CE | LYS | A | 257 | 57.952 | 34.694 | 16.777 | 1.00 | 58.52 | A |
| ATOM | 1478 | NZ | LYS | A | 257 | 58.290 | 33.268 | 16.515 | 1.00 | 60.88 | A |
| ATOM | 1479 | C | LYS | A | 257 | 55.467 | 32.302 | 21.138 | 1.00 | 50.74 | A |
| ATOM | 1480 | O | LYS | A | 257 | 56.432 | 31.790 | 20.577 | 1.00 | 52.26 | A |
| ATOM | 1481 | N | SER | A | 258 | 54.721 | 31.654 | 22.027 | 1.00 | 48.07 | A |
| ATOM | 1482 | CA | SER | A | 258 | 54.999 | 30.273 | 22.402 | 1.00 | 46.87 | A |
| ATOM | 1483 | CB | SER | A | 258 | 55.590 | 30.229 | 23.812 | 1.00 | 48.88 | A |
| ATOM | 1484 | OG | SER | A | 258 | 54.741 | 30.892 | 24.734 | 1.00 | 53.14 | A |
| ATOM | 1485 | C | SER | A | 258 | 53.735 | 29.415 | 22.342 | 1.00 | 44.07 | A |
| ATOM | 1486 | O | SER | A | 258 | 52.617 | 29.932 | 22.417 | 1.00 | 44.17 | A |
| ATOM | 1487 | N | ALA | A | 259 | 53.917 | 28.105 | 22.204 | 1.00 | 38.30 | A |
| ATOM | 1488 | CA | ALA | A | 259 | 52.793 | 27.180 | 22.127 | 1.00 | 34.73 | A |
| ATOM | 1489 | CB | ALA | A | 259 | 52.551 | 26.779 | 20.684 | 1.00 | 34.16 | A |
| ATOM | 1490 | C | ALA | A | 259 | 53.042 | 25.940 | 22.977 | 1.00 | 32.34 | A |
| ATOM | 1491 | O | ALA | A | 259 | 54.172 | 25.459 | 23.086 | 1.00 | 31.81 | A |
| ATOM | 1492 | N | CYS | A | 260 | 51.975 | 25.428 | 23.579 | 1.00 | 28.58 | A |
| ATOM | 1493 | CA | CYS | A | 260 | 52.056 | 24.244 | 24.425 | 1.00 | 26.27 | A |
| ATOM | 1494 | CB | CYS | A | 260 | 52.183 | 24.654 | 25.892 | 1.00 | 26.53 | A |
| ATOM | 1495 | SG | CYS | A | 260 | 50.846 | 25.739 | 26.469 | 1.00 | 32.91 | A |
| ATOM | 1496 | C | CYS | A | 260 | 50.786 | 23.435 | 24.224 | 1.00 | 22.83 | A |
| ATOM | 1497 | O | CYS | A | 260 | 49.892 | 23.856 | 23.495 | 1.00 | 22.14 | A |
| ATOM | 1498 | N | LYS | A | 261 | 50.706 | 22.277 | 24.868 | 1.00 | 20.02 | A |
| ATOM | 1499 | CA | LYS | A | 261 | 49.526 | 21.434 | 24.744 | 1.00 | 20.65 | A |
| ATOM | 1500 | CB | LYS | A | 261 | 49.619 | 20.243 | 25.696 | 1.00 | 23.28 | A |
| ATOM | 1501 | CG | LYS | A | 261 | 50.716 | 19.253 | 25.347 | 1.00 | 27.44 | A |
| ATOM | 1502 | CD | LYS | A | 261 | 50.732 | 18.117 | 26.350 | 1.00 | 29.98 | A |
| ATOM | 1503 | CE | LYS | A | 261 | 51.922 | 17.203 | 26.134 | 1.00 | 32.34 | A |
| ATOM | 1504 | NZ | LYS | A | 261 | 51.940 | 16.121 | 27.153 | 1.00 | 33.28 | A |
| ATOM | 1505 | C | LYS | A | 261 | 48.268 | 22.229 | 25.062 | 1.00 | 19.20 | A |

-continued

| | | | | | | | | | | | |
|---|---|---|---|---|---|---|---|---|---|---|---|
| ATOM | 1506 | O | LYS | A | 261 | 47.253 | 22.092 | 24.387 | 1.00 | 18.08 | A |
| ATOM | 1507 | N | SER | A | 262 | 48.358 | 23.068 | 26.089 | 1.00 | 16.92 | A |
| ATOM | 1508 | CA | SER | A | 262 | 47.235 | 23.883 | 26.534 | 1.00 | 18.13 | A |
| ATOM | 1509 | CB | SER | A | 262 | 47.644 | 24.698 | 27.770 | 1.00 | 18.27 | A |
| ATOM | 1510 | OG | SER | A | 262 | 46.517 | 25.258 | 28.421 | 1.00 | 22.53 | A |
| ATOM | 1511 | C | SER | A | 262 | 46.736 | 24.811 | 25.424 | 1.00 | 16.77 | A |
| ATOM | 1512 | O | SER | A | 262 | 45.591 | 25.254 | 25.450 | 1.00 | 15.69 | A |
| ATOM | 1513 | N | SER | A | 263 | 47.595 | 25.118 | 24.456 | 1.00 | 16.44 | A |
| ATOM | 1514 | CA | SER | A | 263 | 47.175 | 25.970 | 23.347 | 1.00 | 16.89 | A |
| ATOM | 1515 | CB | SER | A | 263 | 48.340 | 26.228 | 22.382 | 1.00 | 18.49 | A |
| ATOM | 1516 | OG | SER | A | 263 | 49.402 | 26.909 | 23.031 | 1.00 | 22.10 | A |
| ATOM | 1517 | C | SER | A | 263 | 46.040 | 25.257 | 22.612 | 1.00 | 17.79 | A |
| ATOM | 1518 | O | SER | A | 263 | 45.099 | 25.898 | 22.148 | 1.00 | 17.57 | A |
| ATOM | 1519 | N | ASP | A | 264 | 46.119 | 23.928 | 22.517 | 1.00 | 16.30 | A |
| ATOM | 1520 | CA | ASP | A | 264 | 45.069 | 23.166 | 21.836 | 1.00 | 16.72 | A |
| ATOM | 1521 | CB | ASP | A | 264 | 45.483 | 21.704 | 21.620 | 1.00 | 15.92 | A |
| ATOM | 1522 | CG | ASP | A | 264 | 46.544 | 21.539 | 20.548 | 1.00 | 17.93 | A |
| ATOM | 1523 | OD1 | ASP | A | 264 | 46.642 | 22.412 | 19.661 | 1.00 | 16.78 | A |
| ATOM | 1524 | OD2 | ASP | A | 264 | 47.265 | 20.515 | 20.579 | 1.00 | 16.64 | A |
| ATOM | 1525 | C | ASP | A | 264 | 43.773 | 23.194 | 22.646 | 1.00 | 17.67 | A |
| ATOM | 1526 | O | ASP | A | 264 | 42.681 | 23.197 | 22.076 | 1.00 | 18.27 | A |
| ATOM | 1527 | N | LEU | A | 265 | 43.898 | 23.205 | 23.974 | 1.00 | 15.49 | A |
| ATOM | 1528 | CA | LEU | A | 265 | 42.730 | 23.232 | 24.849 | 1.00 | 14.75 | A |
| ATOM | 1529 | CB | LEU | A | 265 | 43.147 | 23.038 | 26.313 | 1.00 | 11.38 | A |
| ATOM | 1530 | CG | LEU | A | 265 | 43.711 | 21.641 | 26.621 | 1.00 | 14.04 | A |
| ATOM | 1531 | CD1 | LEU | A | 265 | 44.249 | 21.579 | 28.052 | 1.00 | 13.96 | A |
| ATOM | 1532 | CD2 | LEU | A | 265 | 42.619 | 20.603 | 26.416 | 1.00 | 11.62 | A |
| ATOM | 1533 | C | LEU | A | 265 | 41.999 | 24.557 | 24.675 | 1.00 | 15.13 | A |
| ATOM | 1534 | O | LEU | A | 265 | 40.777 | 24.620 | 24.785 | 1.00 | 16.75 | A |
| ATOM | 1535 | N | TRP | A | 266 | 42.746 | 25.622 | 24.405 | 1.00 | 16.08 | A |
| ATOM | 1536 | CA | TRP | A | 266 | 42.118 | 26.918 | 24.184 | 1.00 | 16.96 | A |
| ATOM | 1537 | CB | TRP | A | 266 | 43.176 | 28.015 | 24.023 | 1.00 | 17.28 | A |
| ATOM | 1538 | CG | TRP | A | 266 | 42.618 | 29.326 | 23.521 | 1.00 | 20.54 | A |
| ATOM | 1539 | CD2 | TRP | A | 266 | 42.313 | 30.490 | 24.301 | 1.00 | 20.07 | A |
| ATOM | 1540 | CE2 | TRP | A | 266 | 41.782 | 31.459 | 23.417 | 1.00 | 20.46 | A |
| ATOM | 1541 | CE3 | TRP | A | 266 | 42.435 | 30.810 | 25.660 | 1.00 | 20.68 | A |
| ATOM | 1542 | CD1 | TRP | A | 266 | 42.270 | 29.631 | 22.231 | 1.00 | 19.53 | A |
| ATOM | 1543 | NE1 | TRP | A | 266 | 41.769 | 30.908 | 22.163 | 1.00 | 19.61 | A |
| ATOM | 1544 | CZ2 | TRP | A | 266 | 41.372 | 32.727 | 23.850 | 1.00 | 20.90 | A |
| ATOM | 1545 | CZ3 | TRP | A | 266 | 42.026 | 32.073 | 26.091 | 1.00 | 19.45 | A |
| ATOM | 1546 | CH2 | TRP | A | 266 | 41.501 | 33.015 | 25.185 | 1.00 | 20.71 | A |
| ATOM | 1547 | C | TRP | A | 266 | 41.284 | 26.795 | 22.913 | 1.00 | 17.22 | A |
| ATOM | 1548 | O | TRP | A | 266 | 40.139 | 27.240 | 22.863 | 1.00 | 18.03 | A |
| ATOM | 1549 | N | ALA | A | 267 | 41.863 | 26.181 | 21.886 | 1.00 | 17.50 | A |
| ATOM | 1550 | CA | ALA | A | 267 | 41.155 | 25.990 | 20.626 | 1.00 | 16.16 | A |
| ATOM | 1551 | CB | ALA | A | 267 | 42.050 | 25.290 | 19.621 | 1.00 | 14.28 | A |
| ATOM | 1552 | C | ALA | A | 267 | 39.901 | 25.159 | 20.891 | 1.00 | 16.28 | A |
| ATOM | 1553 | O | ALA | A | 267 | 38.835 | 25.436 | 20.346 | 1.00 | 16.46 | A |
| ATOM | 1554 | N | LEU | A | 268 | 40.031 | 24.144 | 21.739 | 1.00 | 16.57 | A |
| ATOM | 1555 | CA | LEU | A | 268 | 38.890 | 23.299 | 22.084 | 1.00 | 17.03 | A |
| ATOM | 1556 | CB | LEU | A | 268 | 39.292 | 22.260 | 23.139 | 1.00 | 15.35 | A |
| ATOM | 1557 | CG | LEU | A | 268 | 38.158 | 21.429 | 23.754 | 1.00 | 19.00 | A |
| ATOM | 1558 | CD1 | LEU | A | 268 | 37.505 | 20.578 | 22.678 | 1.00 | 16.17 | A |
| ATOM | 1559 | CD2 | LEU | A | 268 | 38.718 | 20.537 | 24.881 | 1.00 | 17.49 | A |
| ATOM | 1560 | C | LEU | A | 268 | 37.766 | 24.179 | 22.628 | 1.00 | 15.72 | A |
| ATOM | 1561 | O | LEU | A | 268 | 36.603 | 24.031 | 22.247 | 1.00 | 15.28 | A |
| ATOM | 1562 | N | GLY | A | 269 | 38.119 | 25.099 | 23.520 | 1.00 | 14.34 | A |
| ATOM | 1563 | CA | GLY | A | 269 | 37.124 | 25.989 | 24.092 | 1.00 | 13.39 | A |
| ATOM | 1564 | C | GLY | A | 269 | 36.406 | 26.808 | 23.031 | 1.00 | 14.94 | A |
| ATOM | 1565 | O | GLY | A | 269 | 35.193 | 27.014 | 23.114 | 1.00 | 14.76 | A |
| ATOM | 1566 | N | CYS | A | 270 | 37.146 | 27.279 | 22.030 | 1.00 | 13.86 | A |
| ATOM | 1567 | CA | CYS | A | 270 | 36.539 | 28.061 | 20.958 | 1.00 | 16.80 | A |
| ATOM | 1568 | CB | CYS | A | 270 | 37.611 | 28.634 | 20.023 | 1.00 | 15.97 | A |
| ATOM | 1569 | SG | CYS | A | 270 | 38.751 | 29.810 | 20.780 | 1.00 | 20.48 | A |
| ATOM | 1570 | C | CYS | A | 270 | 35.598 | 27.175 | 20.140 | 1.00 | 17.50 | A |
| ATOM | 1571 | O | CYS | A | 270 | 34.516 | 27.604 | 19.741 | 1.00 | 18.38 | A |
| ATOM | 1572 | N | ILE | A | 271 | 36.022 | 25.939 | 19.887 | 1.00 | 16.99 | A |
| ATOM | 1573 | CA | ILE | A | 271 | 35.221 | 25.004 | 19.104 | 1.00 | 16.66 | A |
| ATOM | 1574 | CB | ILE | A | 271 | 36.038 | 23.741 | 18.778 | 1.00 | 16.53 | A |
| ATOM | 1575 | CG2 | ILE | A | 271 | 35.155 | 22.694 | 18.102 | 1.00 | 16.34 | A |
| ATOM | 1576 | CG1 | ILE | A | 271 | 37.222 | 24.129 | 17.882 | 1.00 | 15.59 | A |
| ATOM | 1577 | CD1 | ILE | A | 271 | 38.239 | 23.018 | 17.690 | 1.00 | 14.88 | A |
| ATOM | 1578 | C | ILE | A | 271 | 33.920 | 24.626 | 19.809 | 1.00 | 16.74 | A |
| ATOM | 1579 | O | ILE | A | 271 | 32.865 | 24.576 | 19.179 | 1.00 | 17.12 | A |
| ATOM | 1580 | N | ILE | A | 272 | 33.990 | 24.357 | 21.111 | 1.00 | 16.13 | A |
| ATOM | 1581 | CA | ILE | A | 272 | 32.785 | 24.021 | 21.862 | 1.00 | 18.30 | A |
| ATOM | 1582 | CB | ILE | A | 272 | 33.097 | 23.747 | 23.346 | 1.00 | 17.77 | A |
| ATOM | 1583 | CG2 | ILE | A | 272 | 31.796 | 23.666 | 24.152 | 1.00 | 17.96 | A |
| ATOM | 1584 | CG1 | ILE | A | 272 | 33.877 | 22.437 | 23.481 | 1.00 | 19.55 | A |

-continued

| | | | | | | | | | | |
|---|---|---|---|---|---|---|---|---|---|---|
| ATOM | 1585 | CD1 | ILE | A | 272 | 34.446 | 22.217 | 24.886 | 1.00 | 18.64 | A |
| ATOM | 1586 | C | ILE | A | 272 | 31.824 | 25.207 | 21.776 | 1.00 | 19.51 | A |
| ATOM | 1587 | O | ILE | A | 272 | 30.624 | 25.037 | 21.554 | 1.00 | 20.44 | A |
| ATOM | 1588 | N | TYR | A | 273 | 32.362 | 26.409 | 21.947 | 1.00 | 18.52 | A |
| ATOM | 1589 | CA | TYR | A | 273 | 31.553 | 27.615 | 21.881 | 1.00 | 20.48 | A |
| ATOM | 1590 | CB | TYR | A | 273 | 32.418 | 28.847 | 22.162 | 1.00 | 18.98 | A |
| ATOM | 1591 | CG | TYR | A | 273 | 31.663 | 30.161 | 22.125 | 1.00 | 20.26 | A |
| ATOM | 1592 | CD1 | TYR | A | 273 | 31.229 | 30.709 | 20.916 | 1.00 | 20.67 | A |
| ATOM | 1593 | CE1 | TYR | A | 273 | 30.536 | 31.917 | 20.880 | 1.00 | 20.98 | A |
| ATOM | 1594 | CD2 | TYR | A | 273 | 31.383 | 30.857 | 23.302 | 1.00 | 19.82 | A |
| ATOM | 1595 | CE2 | TYR | A | 273 | 30.691 | 32.062 | 23.280 | 1.00 | 20.62 | A |
| ATOM | 1596 | CZ | TYR | A | 273 | 30.271 | 32.587 | 22.067 | 1.00 | 21.15 | A |
| ATOM | 1597 | OH | TYR | A | 273 | 29.588 | 33.776 | 22.049 | 1.00 | 21.86 | A |
| ATOM | 1598 | C | TYR | A | 273 | 30.902 | 27.730 | 20.507 | 1.00 | 21.54 | A |
| ATOM | 1599 | O | TYR | A | 273 | 29.719 | 28.049 | 20.401 | 1.00 | 22.80 | A |
| ATOM | 1600 | N | GLN | A | 274 | 31.676 | 27.454 | 19.461 | 1.00 | 21.05 | A |
| ATOM | 1601 | CA | GLN | A | 274 | 31.176 | 27.538 | 18.095 | 1.00 | 21.48 | A |
| ATOM | 1602 | CB | GLN | A | 274 | 32.323 | 27.341 | 17.097 | 1.00 | 21.41 | A |
| ATOM | 1603 | CG | GLN | A | 274 | 31.934 | 27.596 | 15.645 | 1.00 | 23.15 | A |
| ATOM | 1604 | CD | GLN | A | 274 | 33.131 | 27.588 | 14.706 | 1.00 | 24.80 | A |
| ATOM | 1605 | OE1 | GLN | A | 274 | 34.276 | 27.446 | 15.139 | 1.00 | 22.51 | A |
| ATOM | 1606 | NE2 | GLN | A | 274 | 32.870 | 27.750 | 13.413 | 1.00 | 22.96 | A |
| ATOM | 1607 | C | GLN | A | 274 | 30.076 | 26.517 | 17.828 | 1.00 | 21.51 | A |
| ATOM | 1608 | O | GLN | A | 274 | 29.123 | 26.806 | 17.108 | 1.00 | 20.50 | A |
| ATOM | 1609 | N | LEU | A | 275 | 30.207 | 25.324 | 18.403 | 1.00 | 21.44 | A |
| ATOM | 1610 | CA | LEU | A | 275 | 29.196 | 24.282 | 18.208 | 1.00 | 20.95 | A |
| ATOM | 1611 | CB | LEU | A | 275 | 29.645 | 22.958 | 18.846 | 1.00 | 19.11 | A |
| ATOM | 1612 | CG | LEU | A | 275 | 30.775 | 22.182 | 18.159 | 1.00 | 21.43 | A |
| ATOM | 1613 | CD1 | LEU | A | 275 | 31.118 | 20.936 | 18.963 | 1.00 | 17.64 | A |
| ATOM | 1614 | CD2 | LEU | A | 275 | 30.342 | 21.795 | 16.754 | 1.00 | 20.34 | A |
| ATOM | 1615 | C | LEU | A | 275 | 27.860 | 24.697 | 18.815 | 1.00 | 21.32 | A |
| ATOM | 1616 | O | LEU | A | 275 | 26.802 | 24.461 | 18.229 | 1.00 | 19.75 | A |
| ATOM | 1617 | N | VAL | A | 276 | 27.921 | 25.322 | 19.987 | 1.00 | 19.10 | A |
| ATOM | 1618 | CA | VAL | A | 276 | 26.724 | 25.750 | 20.702 | 1.00 | 22.47 | A |
| ATOM | 1619 | CB | VAL | A | 276 | 27.011 | 25.882 | 22.217 | 1.00 | 20.87 | A |
| ATOM | 1620 | CG1 | VAL | A | 276 | 25.742 | 26.291 | 22.957 | 1.00 | 19.68 | A |
| ATOM | 1621 | CG2 | VAL | A | 276 | 27.550 | 24.558 | 22.766 | 1.00 | 19.43 | A |
| ATOM | 1622 | C | VAL | A | 276 | 26.127 | 27.075 | 20.211 | 1.00 | 23.89 | A |
| ATOM | 1623 | O | VAL | A | 276 | 24.910 | 27.199 | 20.070 | 1.00 | 24.90 | A |
| ATOM | 1624 | N | ALA | A | 277 | 26.983 | 28.062 | 19.965 | 1.00 | 24.56 | A |
| ATOM | 1625 | CA | ALA | A | 277 | 26.533 | 29.374 | 19.518 | 1.00 | 24.72 | A |
| ATOM | 1626 | CB | ALA | A | 277 | 27.504 | 30.444 | 19.999 | 1.00 | 24.36 | A |
| ATOM | 1627 | C | ALA | A | 277 | 26.378 | 29.458 | 18.005 | 1.00 | 25.76 | A |
| ATOM | 1628 | O | ALA | A | 277 | 25.577 | 30.242 | 17.502 | 1.00 | 26.39 | A |
| ATOM | 1629 | N | GLY | A | 278 | 27.142 | 28.651 | 17.280 | 1.00 | 25.13 | A |
| ATOM | 1630 | CA | GLY | A | 278 | 27.062 | 28.673 | 15.834 | 1.00 | 25.58 | A |
| ATOM | 1631 | C | GLY | A | 278 | 28.163 | 29.524 | 15.231 | 1.00 | 26.50 | A |
| ATOM | 1632 | O | GLY | A | 278 | 28.374 | 29.510 | 14.015 | 1.00 | 28.17 | A |
| ATOM | 1633 | N | LEU | A | 279 | 28.866 | 30.262 | 16.086 | 1.00 | 24.44 | A |
| ATOM | 1634 | CA | LEU | A | 279 | 29.962 | 31.130 | 15.656 | 1.00 | 25.21 | A |
| ATOM | 1635 | CB | LEU | A | 279 | 29.468 | 32.575 | 15.500 | 1.00 | 25.78 | A |
| ATOM | 1636 | CG | LEU | A | 279 | 28.364 | 32.899 | 14.490 | 1.00 | 28.17 | A |
| ATOM | 1637 | CD1 | LEU | A | 279 | 27.922 | 34.344 | 14.684 | 1.00 | 26.60 | A |
| ATOM | 1638 | CD2 | LEU | A | 279 | 28.862 | 32.670 | 13.071 | 1.00 | 26.52 | A |
| ATOM | 1639 | C | LEU | A | 279 | 31.093 | 31.116 | 16.687 | 1.00 | 23.47 | A |
| ATOM | 1640 | O | LEU | A | 279 | 30.848 | 30.994 | 17.882 | 1.00 | 24.44 | A |
| ATOM | 1641 | N | PRO | A | 280 | 32.349 | 31.239 | 16.236 | 1.00 | 23.35 | A |
| ATOM | 1642 | CD | PRO | A | 280 | 32.831 | 31.404 | 14.855 | 1.00 | 22.26 | A |
| ATOM | 1643 | CA | PRO | A | 280 | 33.464 | 31.239 | 17.189 | 1.00 | 23.81 | A |
| ATOM | 1644 | CB | PRO | A | 280 | 34.692 | 31.293 | 16.282 | 1.00 | 23.24 | A |
| ATOM | 1645 | CG | PRO | A | 280 | 34.189 | 32.020 | 15.073 | 1.00 | 24.89 | A |
| ATOM | 1646 | C | PRO | A | 280 | 33.353 | 32.444 | 18.137 | 1.00 | 22.69 | A |
| ATOM | 1647 | O | PRO | A | 280 | 32.750 | 33.457 | 17.788 | 1.00 | 22.11 | A |
| ATOM | 1648 | N | PRO | A | 281 | 33.939 | 32.344 | 19.345 | 1.00 | 23.06 | A |
| ATOM | 1649 | CD | PRO | A | 281 | 34.810 | 31.223 | 19.734 | 1.00 | 21.37 | A |
| ATOM | 1650 | CA | PRO | A | 281 | 33.935 | 33.375 | 20.395 | 1.00 | 23.67 | A |
| ATOM | 1651 | CB | PRO | A | 281 | 34.781 | 32.751 | 21.509 | 1.00 | 24.89 | A |
| ATOM | 1652 | CG | PRO | A | 281 | 34.749 | 31.287 | 21.219 | 1.00 | 25.24 | A |
| ATOM | 1653 | C | PRO | A | 281 | 34.481 | 34.752 | 20.017 | 1.00 | 23.75 | A |
| ATOM | 1654 | O | PRO | A | 281 | 33.869 | 35.781 | 20.317 | 1.00 | 21.02 | A |
| ATOM | 1655 | N | PHE | A | 282 | 35.644 | 34.763 | 19.379 | 1.00 | 22.17 | A |
| ATOM | 1656 | CA | PHE | A | 282 | 36.293 | 36.007 | 18.998 | 1.00 | 23.16 | A |
| ATOM | 1657 | CB | PHE | A | 282 | 37.765 | 35.943 | 19.406 | 1.00 | 21.01 | A |
| ATOM | 1658 | CG | PHE | A | 282 | 37.975 | 35.482 | 20.822 | 1.00 | 22.66 | A |
| ATOM | 1659 | CD1 | PHE | A | 282 | 37.806 | 36.361 | 21.888 | 1.00 | 20.06 | A |
| ATOM | 1660 | CD2 | PHE | A | 282 | 38.291 | 34.151 | 21.093 | 1.00 | 20.72 | A |
| ATOM | 1661 | CE1 | PHE | A | 282 | 37.947 | 35.921 | 23.206 | 1.00 | 22.66 | A |
| ATOM | 1662 | CE2 | PHE | A | 282 | 38.433 | 33.702 | 22.405 | 1.00 | 20.97 | A |
| ATOM | 1663 | CZ | PHE | A | 282 | 38.261 | 34.590 | 23.466 | 1.00 | 19.58 | A |

|      |      |     |     |   |     |        |        |        |      |       |   |
|------|------|-----|-----|---|-----|--------|--------|--------|------|-------|---|
| ATOM | 1664 | C   | PHE | A | 282 | 36.169 | 36.263 | 17.503 | 1.00 | 24.39 | A |
| ATOM | 1665 | O   | PHE | A | 282 | 36.802 | 35.585 | 16.694 | 1.00 | 25.80 | A |
| ATOM | 1666 | N   | ARG | A | 283 | 35.355 | 37.248 | 17.142 | 1.00 | 24.99 | A |
| ATOM | 1667 | CA  | ARG | A | 283 | 35.141 | 37.594 | 15.741 | 1.00 | 26.33 | A |
| ATOM | 1668 | CB  | ARG | A | 283 | 33.721 | 37.209 | 15.316 | 1.00 | 28.91 | A |
| ATOM | 1669 | CG  | ARG | A | 283 | 33.293 | 35.808 | 15.724 | 1.00 | 30.27 | A |
| ATOM | 1670 | CD  | ARG | A | 283 | 31.904 | 35.493 | 15.188 | 1.00 | 33.36 | A |
| ATOM | 1671 | NE  | ARG | A | 283 | 30.890 | 36.392 | 15.733 | 1.00 | 32.76 | A |
| ATOM | 1672 | CZ  | ARG | A | 283 | 30.372 | 36.287 | 16.952 | 1.00 | 34.79 | A |
| ATOM | 1673 | NH1 | ARG | A | 283 | 30.767 | 35.317 | 17.768 | 1.00 | 35.77 | A |
| ATOM | 1674 | NH2 | ARG | A | 283 | 29.458 | 37.156 | 17.359 | 1.00 | 36.12 | A |
| ATOM | 1675 | C   | ARG | A | 283 | 35.328 | 39.096 | 15.544 | 1.00 | 26.47 | A |
| ATOM | 1676 | O   | ARG | A | 283 | 35.029 | 39.888 | 16.438 | 1.00 | 26.28 | A |
| ATOM | 1677 | N   | ALA | A | 284 | 35.818 | 39.486 | 14.373 | 1.00 | 26.70 | A |
| ATOM | 1678 | CA  | ALA | A | 284 | 36.033 | 40.899 | 14.079 | 1.00 | 27.84 | A |
| ATOM | 1679 | CB  | ALA | A | 284 | 37.188 | 41.442 | 14.914 | 1.00 | 26.24 | A |
| ATOM | 1680 | C   | ALA | A | 284 | 36.327 | 41.077 | 12.602 | 1.00 | 28.35 | A |
| ATOM | 1681 | O   | ALA | A | 284 | 36.560 | 40.101 | 11.891 | 1.00 | 29.91 | A |
| ATOM | 1682 | N   | GLY | A | 285 | 36.332 | 42.329 | 12.153 | 1.00 | 29.29 | A |
| ATOM | 1683 | CA  | GLY | A | 285 | 36.577 | 42.631 | 10.753 | 1.00 | 29.52 | A |
| ATOM | 1684 | C   | GLY | A | 285 | 37.893 | 42.156 | 10.168 | 1.00 | 30.12 | A |
| ATOM | 1685 | O   | GLY | A | 285 | 37.974 | 41.862 |  8.976 | 1.00 | 30.60 | A |
| ATOM | 1686 | N   | ASN | A | 286 | 38.939 | 42.097 | 10.983 | 1.00 | 28.49 | A |
| ATOM | 1687 | CA  | ASN | A | 286 | 40.231 | 41.644 | 10.489 | 1.00 | 26.71 | A |
| ATOM | 1688 | CB  | ASN | A | 286 | 41.050 | 42.825 |  9.945 | 1.00 | 26.11 | A |
| ATOM | 1689 | CG  | ASN | A | 286 | 41.310 | 43.900 | 10.990 | 1.00 | 27.83 | A |
| ATOM | 1690 | OD1 | ASN | A | 286 | 41.877 | 43.631 | 12.049 | 1.00 | 27.84 | A |
| ATOM | 1691 | ND2 | ASN | A | 286 | 40.908 | 45.131 | 10.685 | 1.00 | 25.95 | A |
| ATOM | 1692 | C   | ASN | A | 286 | 40.997 | 40.924 | 11.584 | 1.00 | 26.03 | A |
| ATOM | 1693 | O   | ASN | A | 286 | 40.540 | 40.851 | 12.723 | 1.00 | 25.66 | A |
| ATOM | 1694 | N   | GLU | A | 287 | 42.162 | 40.391 | 11.239 | 1.00 | 24.81 | A |
| ATOM | 1695 | CA  | GLU | A | 287 | 42.965 | 39.662 | 12.206 | 1.00 | 27.59 | A |
| ATOM | 1696 | CB  | GLU | A | 287 | 44.145 | 38.985 | 11.510 | 1.00 | 30.17 | A |
| ATOM | 1697 | CG  | GLU | A | 287 | 43.776 | 37.632 | 10.931 | 1.00 | 38.21 | A |
| ATOM | 1698 | CD  | GLU | A | 287 | 44.900 | 36.998 | 10.140 | 1.00 | 41.86 | A |
| ATOM | 1699 | OE1 | GLU | A | 287 | 46.061 | 37.036 | 10.608 | 1.00 | 43.08 | A |
| ATOM | 1700 | OE2 | GLU | A | 287 | 44.612 | 36.449 |  9.052 | 1.00 | 45.22 | A |
| ATOM | 1701 | C   | GLU | A | 287 | 43.459 | 40.485 | 13.383 | 1.00 | 25.05 | A |
| ATOM | 1702 | O   | GLU | A | 287 | 43.382 | 40.030 | 14.521 | 1.00 | 26.41 | A |
| ATOM | 1703 | N   | TYR | A | 288 | 43.966 | 41.685 | 13.122 | 1.00 | 23.04 | A |
| ATOM | 1704 | CA  | TYR | A | 288 | 44.460 | 42.528 | 14.205 | 1.00 | 22.34 | A |
| ATOM | 1705 | CB  | TYR | A | 288 | 44.867 | 43.913 | 13.691 | 1.00 | 21.07 | A |
| ATOM | 1706 | CG  | TYR | A | 288 | 45.275 | 44.858 | 14.805 | 1.00 | 21.07 | A |
| ATOM | 1707 | CD1 | TYR | A | 288 | 46.533 | 44.762 | 15.405 | 1.00 | 21.23 | A |
| ATOM | 1708 | CE1 | TYR | A | 288 | 46.891 | 45.588 | 16.475 | 1.00 | 20.43 | A |
| ATOM | 1709 | CD2 | TYR | A | 288 | 44.380 | 45.809 | 15.302 | 1.00 | 22.32 | A |
| ATOM | 1710 | CE2 | TYR | A | 288 | 44.725 | 46.637 | 16.373 | 1.00 | 23.28 | A |
| ATOM | 1711 | CZ  | TYR | A | 288 | 45.981 | 46.518 | 16.953 | 1.00 | 22.96 | A |
| ATOM | 1712 | OH  | TYR | A | 288 | 46.316 | 47.313 | 18.024 | 1.00 | 23.18 | A |
| ATOM | 1713 | C   | TYR | A | 288 | 43.402 | 42.698 | 15.288 | 1.00 | 21.38 | A |
| ATOM | 1714 | O   | TYR | A | 288 | 43.710 | 42.616 | 16.473 | 1.00 | 22.09 | A |
| ATOM | 1715 | N   | LEU | A | 289 | 42.159 | 42.939 | 14.874 | 1.00 | 21.88 | A |
| ATOM | 1716 | CA  | LEU | A | 289 | 41.055 | 43.130 | 15.811 | 1.00 | 21.98 | A |
| ATOM | 1717 | CB  | LEU | A | 289 | 39.821 | 43.673 | 15.078 | 1.00 | 22.90 | A |
| ATOM | 1718 | CG  | LEU | A | 289 | 39.896 | 45.130 | 14.601 | 1.00 | 26.52 | A |
| ATOM | 1719 | CD1 | LEU | A | 289 | 38.706 | 45.436 | 13.696 | 1.00 | 26.55 | A |
| ATOM | 1720 | CD2 | LEU | A | 289 | 39.914 | 46.071 | 15.807 | 1.00 | 23.13 | A |
| ATOM | 1721 | C   | LEU | A | 289 | 40.686 | 41.849 | 16.560 | 1.00 | 21.24 | A |
| ATOM | 1722 | O   | LEU | A | 289 | 40.256 | 41.897 | 17.715 | 1.00 | 20.72 | A |
| ATOM | 1723 | N   | ILE | A | 290 | 40.843 | 40.708 | 15.900 | 1.00 | 19.62 | A |
| ATOM | 1724 | CA  | ILE | A | 290 | 40.538 | 39.433 | 16.533 | 1.00 | 18.54 | A |
| ATOM | 1725 | CB  | ILE | A | 290 | 40.560 | 38.281 | 15.509 | 1.00 | 18.52 | A |
| ATOM | 1726 | CG2 | ILE | A | 290 | 40.503 | 36.934 | 16.234 | 1.00 | 17.63 | A |
| ATOM | 1727 | CG1 | ILE | A | 290 | 39.378 | 38.429 | 14.545 | 1.00 | 18.88 | A |
| ATOM | 1728 | CD1 | ILE | A | 290 | 39.421 | 37.483 | 13.357 | 1.00 | 19.81 | A |
| ATOM | 1729 | C   | ILE | A | 290 | 41.578 | 39.167 | 17.618 | 1.00 | 19.09 | A |
| ATOM | 1730 | O   | ILE | A | 290 | 41.236 | 38.788 | 18.737 | 1.00 | 18.20 | A |
| ATOM | 1731 | N   | PHE | A | 291 | 42.849 | 39.376 | 17.286 | 1.00 | 18.76 | A |
| ATOM | 1732 | CA  | PHE | A | 291 | 43.925 | 39.156 | 18.247 | 1.00 | 20.75 | A |
| ATOM | 1733 | CB  | PHE | A | 291 | 45.286 | 39.434 | 17.606 | 1.00 | 20.71 | A |
| ATOM | 1734 | CG  | PHE | A | 291 | 45.644 | 38.480 | 16.503 | 1.00 | 22.92 | A |
| ATOM | 1735 | CD1 | PHE | A | 291 | 45.065 | 37.214 | 16.443 | 1.00 | 22.98 | A |
| ATOM | 1736 | CD2 | PHE | A | 291 | 46.588 | 38.830 | 15.543 | 1.00 | 22.91 | A |
| ATOM | 1737 | CE1 | PHE | A | 291 | 45.423 | 36.310 | 15.440 | 1.00 | 24.51 | A |
| ATOM | 1738 | CE2 | PHE | A | 291 | 46.954 | 37.931 | 14.535 | 1.00 | 25.54 | A |
| ATOM | 1739 | CZ  | PHE | A | 291 | 46.370 | 36.670 | 14.485 | 1.00 | 23.29 | A |
| ATOM | 1740 | C   | PHE | A | 291 | 43.739 | 40.061 | 19.451 | 1.00 | 21.72 | A |
| ATOM | 1741 | O   | PHE | A | 291 | 43.992 | 39.671 | 20.593 | 1.00 | 22.32 | A |
| ATOM | 1742 | N   | GLN | A | 292 | 43.284 | 41.275 | 19.178 | 1.00 | 23.27 | A |

-continued

| | | | | | | | | | | |
|---|---|---|---|---|---|---|---|---|---|---|
| ATOM | 1743 | CA | GLN | A | 292 | 43.055 | 42.264 | 20.216 | 1.00 | 24.01 | A |
| ATOM | 1744 | CB | GLN | A | 292 | 42.574 | 43.559 | 19.562 | 1.00 | 25.77 | A |
| ATOM | 1745 | CG | GLN | A | 292 | 42.577 | 44.773 | 20.447 | 1.00 | 28.45 | A |
| ATOM | 1746 | CD | GLN | A | 292 | 42.469 | 46.057 | 19.638 | 1.00 | 29.83 | A |
| ATOM | 1747 | OE1 | GLN | A | 292 | 41.520 | 46.244 | 18.872 | 1.00 | 27.16 | A |
| ATOM | 1748 | NE2 | GLN | A | 292 | 43.449 | 46.944 | 19.799 | 1.00 | 27.61 | A |
| ATOM | 1749 | C | GLN | A | 292 | 42.018 | 41.733 | 21.204 | 1.00 | 22.97 | A |
| ATOM | 1750 | O | GLN | A | 292 | 42.200 | 41.832 | 22.415 | 1.00 | 21.64 | A |
| ATOM | 1751 | N | LYS | A | 293 | 40.937 | 41.154 | 20.687 | 1.00 | 21.82 | A |
| ATOM | 1752 | CA | LYS | A | 293 | 39.895 | 40.612 | 21.558 | 1.00 | 22.18 | A |
| ATOM | 1753 | CB | LYS | A | 293 | 38.664 | 40.223 | 20.740 | 1.00 | 22.69 | A |
| ATOM | 1754 | CG | LYS | A | 293 | 37.919 | 41.407 | 20.153 | 1.00 | 25.78 | A |
| ATOM | 1755 | CD | LYS | A | 293 | 36.651 | 40.961 | 19.429 | 1.00 | 27.88 | A |
| ATOM | 1756 | CE | LYS | A | 293 | 35.857 | 42.161 | 18.926 | 1.00 | 30.85 | A |
| ATOM | 1757 | NZ | LYS | A | 293 | 34.612 | 41.750 | 18.214 | 1.00 | 32.98 | A |
| ATOM | 1758 | C | LYS | A | 293 | 40.398 | 39.398 | 22.343 | 1.00 | 21.20 | A |
| ATOM | 1759 | O | LYS | A | 293 | 40.041 | 39.204 | 23.509 | 1.00 | 22.01 | A |
| ATOM | 1760 | N | ILE | A | 294 | 41.226 | 38.583 | 21.702 | 1.00 | 19.91 | A |
| ATOM | 1761 | CA | ILE | A | 294 | 41.774 | 37.394 | 22.347 | 1.00 | 20.28 | A |
| ATOM | 1762 | CB | ILE | A | 294 | 42.631 | 36.575 | 21.349 | 1.00 | 18.98 | A |
| ATOM | 1763 | CG2 | ILE | A | 294 | 43.481 | 35.550 | 22.098 | 1.00 | 17.70 | A |
| ATOM | 1764 | CG1 | ILE | A | 294 | 41.716 | 35.897 | 20.318 | 1.00 | 17.93 | A |
| ATOM | 1765 | CD1 | ILE | A | 294 | 42.467 | 35.237 | 19.178 | 1.00 | 16.21 | A |
| ATOM | 1766 | C | ILE | A | 294 | 42.618 | 37.727 | 23.587 | 1.00 | 21.94 | A |
| ATOM | 1767 | O | ILE | A | 294 | 42.366 | 37.199 | 24.673 | 1.00 | 20.86 | A |
| ATOM | 1768 | N | ILE | A | 295 | 43.610 | 38.600 | 23.439 | 1.00 | 21.88 | A |
| ATOM | 1769 | CA | ILE | A | 295 | 44.461 | 38.934 | 24.582 | 1.00 | 24.25 | A |
| ATOM | 1770 | CB | ILE | A | 295 | 45.668 | 39.805 | 24.175 | 1.00 | 23.93 | A |
| ATOM | 1771 | CG2 | ILE | A | 295 | 46.514 | 39.066 | 23.140 | 1.00 | 24.61 | A |
| ATOM | 1772 | CG1 | ILE | A | 295 | 45.189 | 41.151 | 23.637 | 1.00 | 24.58 | A |
| ATOM | 1773 | CD1 | ILE | A | 295 | 46.317 | 42.149 | 23.433 | 1.00 | 26.69 | A |
| ATOM | 1774 | C | ILE | A | 295 | 43.720 | 39.636 | 25.717 | 1.00 | 24.80 | A |
| ATOM | 1775 | O | ILE | A | 295 | 44.214 | 39.687 | 26.842 | 1.00 | 24.76 | A |
| ATOM | 1776 | N | LYS | A | 296 | 42.539 | 40.173 | 25.425 | 1.00 | 25.33 | A |
| ATOM | 1777 | CA | LYS | A | 296 | 41.743 | 40.853 | 26.444 | 1.00 | 26.80 | A |
| ATOM | 1778 | CB | LYS | A | 296 | 41.178 | 42.170 | 25.894 | 1.00 | 27.39 | A |
| ATOM | 1779 | CG | LYS | A | 296 | 42.240 | 43.141 | 25.413 | 1.00 | 31.79 | A |
| ATOM | 1780 | CD | LYS | A | 296 | 41.634 | 44.410 | 24.826 | 1.00 | 35.56 | A |
| ATOM | 1781 | CE | LYS | A | 296 | 41.009 | 45.283 | 25.900 | 1.00 | 39.29 | A |
| ATOM | 1782 | NZ | LYS | A | 296 | 40.564 | 46.603 | 25.357 | 1.00 | 41.72 | A |
| ATOM | 1783 | C | LYS | A | 296 | 40.593 | 39.958 | 26.893 | 1.00 | 25.50 | A |
| ATOM | 1784 | O | LYS | A | 296 | 39.770 | 40.361 | 27.713 | 1.00 | 24.02 | A |
| ATOM | 1785 | N | LEU | A | 297 | 40.550 | 38.742 | 26.349 | 1.00 | 25.67 | A |
| ATOM | 1786 | CA | LEU | A | 297 | 39.500 | 37.777 | 26.666 | 1.00 | 25.16 | A |
| ATOM | 1787 | CB | LEU | A | 297 | 39.632 | 37.285 | 28.111 | 1.00 | 24.80 | A |
| ATOM | 1788 | CG | LEU | A | 297 | 38.766 | 36.068 | 28.460 | 1.00 | 26.43 | A |
| ATOM | 1789 | CD1 | LEU | A | 297 | 39.238 | 34.852 | 27.646 | 1.00 | 26.70 | A |
| ATOM | 1790 | CD2 | LEU | A | 297 | 38.856 | 35.777 | 29.951 | 1.00 | 24.84 | A |
| ATOM | 1791 | C | LEU | A | 297 | 38.151 | 38.459 | 26.467 | 1.00 | 25.11 | A |
| ATOM | 1792 | O | LEU | A | 297 | 37.261 | 38.378 | 27.309 | 1.00 | 25.28 | A |
| ATOM | 1793 | N | GLU | A | 298 | 38.007 | 39.127 | 25.331 | 1.00 | 24.98 | A |
| ATOM | 1794 | CA | GLU | A | 298 | 36.786 | 39.847 | 25.023 | 1.00 | 25.31 | A |
| ATOM | 1795 | CB | GLU | A | 298 | 37.143 | 41.139 | 24.291 | 1.00 | 27.13 | A |
| ATOM | 1796 | CG | GLU | A | 298 | 35.991 | 42.092 | 24.108 | 1.00 | 31.28 | A |
| ATOM | 1797 | CD | GLU | A | 298 | 36.419 | 43.362 | 23.410 | 1.00 | 34.40 | A |
| ATOM | 1798 | OE1 | GLU | A | 298 | 37.348 | 44.027 | 23.918 | 1.00 | 35.90 | A |
| ATOM | 1799 | OE2 | GLU | A | 298 | 35.832 | 43.693 | 22.359 | 1.00 | 36.16 | A |
| ATOM | 1800 | C | GLU | A | 298 | 35.766 | 39.057 | 24.207 | 1.00 | 23.79 | A |
| ATOM | 1801 | O | GLU | A | 298 | 35.832 | 39.017 | 22.979 | 1.00 | 24.35 | A |
| ATOM | 1802 | N | TYR | A | 299 | 34.825 | 38.427 | 24.902 | 1.00 | 23.45 | A |
| ATOM | 1803 | CA | TYR | A | 299 | 33.760 | 37.663 | 24.265 | 1.00 | 23.98 | A |
| ATOM | 1804 | CB | TYR | A | 299 | 34.264 | 36.304 | 23.755 | 1.00 | 20.13 | A |
| ATOM | 1805 | CG | TYR | A | 299 | 34.348 | 35.233 | 24.828 | 1.00 | 21.17 | A |
| ATOM | 1806 | CD1 | TYR | A | 299 | 35.336 | 35.279 | 25.810 | 1.00 | 19.32 | A |
| ATOM | 1807 | CE1 | TYR | A | 299 | 35.389 | 34.332 | 26.826 | 1.00 | 19.30 | A |
| ATOM | 1808 | CD2 | TYR | A | 299 | 33.410 | 34.201 | 24.888 | 1.00 | 18.96 | A |
| ATOM | 1809 | CE2 | TYR | A | 299 | 33.456 | 33.243 | 25.907 | 1.00 | 19.41 | A |
| ATOM | 1810 | CZ | TYR | A | 299 | 34.449 | 33.321 | 26.870 | 1.00 | 18.79 | A |
| ATOM | 1811 | OH | TYR | A | 299 | 34.511 | 32.401 | 27.881 | 1.00 | 18.77 | A |
| ATOM | 1812 | C | TYR | A | 299 | 32.699 | 37.437 | 25.331 | 1.00 | 25.20 | A |
| ATOM | 1813 | O | TYR | A | 299 | 32.942 | 37.681 | 26.506 | 1.00 | 26.46 | A |
| ATOM | 1814 | N | ASP | A | 300 | 31.522 | 36.981 | 24.927 | 1.00 | 26.94 | A |
| ATOM | 1815 | CA | ASP | A | 300 | 30.467 | 36.710 | 25.891 | 1.00 | 30.60 | A |
| ATOM | 1816 | CB | ASP | A | 300 | 29.665 | 37.981 | 26.179 | 1.00 | 35.86 | A |
| ATOM | 1817 | CG | ASP | A | 300 | 29.228 | 38.687 | 24.923 | 1.00 | 42.04 | A |
| ATOM | 1818 | OD1 | ASP | A | 300 | 28.450 | 38.088 | 24.149 | 1.00 | 45.98 | A |
| ATOM | 1819 | OD2 | ASP | A | 300 | 29.666 | 39.840 | 24.707 | 1.00 | 45.69 | A |
| ATOM | 1820 | C | ASP | A | 300 | 29.564 | 35.608 | 25.363 | 1.00 | 29.26 | A |
| ATOM | 1821 | O | ASP | A | 300 | 29.590 | 35.299 | 24.172 | 1.00 | 28.64 | A |

-continued

| | | | | | | | | | | | |
|---|---|---|---|---|---|---|---|---|---|---|---|
| ATOM | 1822 | N   | PHE | A | 301 | 28.778 | 35.011 | 26.253 | 1.00 | 28.96 | A |
| ATOM | 1823 | CA  | PHE | A | 301 | 27.884 | 33.924 | 25.871 | 1.00 | 30.48 | A |
| ATOM | 1824 | CB  | PHE | A | 301 | 27.818 | 32.854 | 26.968 | 1.00 | 29.17 | A |
| ATOM | 1825 | CG  | PHE | A | 301 | 29.147 | 32.279 | 27.356 | 1.00 | 29.29 | A |
| ATOM | 1826 | CD1 | PHE | A | 301 | 29.978 | 32.949 | 28.245 | 1.00 | 27.31 | A |
| ATOM | 1827 | CD2 | PHE | A | 301 | 29.560 | 31.050 | 26.845 | 1.00 | 27.89 | A |
| ATOM | 1828 | CE1 | PHE | A | 301 | 31.205 | 32.403 | 28.625 | 1.00 | 28.83 | A |
| ATOM | 1829 | CE2 | PHE | A | 301 | 30.781 | 30.498 | 27.217 | 1.00 | 28.05 | A |
| ATOM | 1830 | CZ  | PHE | A | 301 | 31.605 | 31.175 | 28.110 | 1.00 | 28.27 | A |
| ATOM | 1831 | C   | PHE | A | 301 | 26.459 | 34.384 | 25.619 | 1.00 | 32.20 | A |
| ATOM | 1832 | O   | PHE | A | 301 | 25.946 | 35.261 | 26.317 | 1.00 | 32.36 | A |
| ATOM | 1833 | N   | PRO | A | 302 | 25.798 | 33.804 | 24.607 | 1.00 | 33.29 | A |
| ATOM | 1834 | CD  | PRO | A | 302 | 26.313 | 32.943 | 23.529 | 1.00 | 34.04 | A |
| ATOM | 1835 | CA  | PRO | A | 302 | 24.415 | 34.199 | 24.341 | 1.00 | 35.24 | A |
| ATOM | 1836 | CB  | PRO | A | 302 | 24.144 | 33.608 | 22.959 | 1.00 | 34.01 | A |
| ATOM | 1837 | CG  | PRO | A | 302 | 25.041 | 32.413 | 22.921 | 1.00 | 35.48 | A |
| ATOM | 1838 | C   | PRO | A | 302 | 23.567 | 33.561 | 25.444 | 1.00 | 37.39 | A |
| ATOM | 1839 | O   | PRO | A | 302 | 23.935 | 32.518 | 25.986 | 1.00 | 38.49 | A |
| ATOM | 1840 | N   | ALA | A | 303 | 22.447 | 34.188 | 25.783 | 1.00 | 39.36 | A |
| ATOM | 1841 | CA  | ALA | A | 303 | 21.572 | 33.692 | 26.843 | 1.00 | 40.65 | A |
| ATOM | 1842 | CB  | ALA | A | 303 | 20.280 | 34.506 | 26.862 | 1.00 | 41.66 | A |
| ATOM | 1843 | C   | ALA | A | 303 | 21.238 | 32.197 | 26.814 | 1.00 | 41.25 | A |
| ATOM | 1844 | O   | ALA | A | 303 | 21.253 | 31.537 | 27.854 | 1.00 | 43.16 | A |
| ATOM | 1845 | N   | ALA | A | 304 | 20.945 | 31.665 | 25.631 | 1.00 | 41.04 | A |
| ATOM | 1846 | CA  | ALA | A | 304 | 20.569 | 30.258 | 25.480 | 1.00 | 40.66 | A |
| ATOM | 1847 | CB  | ALA | A | 304 | 20.121 | 30.004 | 24.040 | 1.00 | 41.36 | A |
| ATOM | 1848 | C   | ALA | A | 304 | 21.628 | 29.223 | 25.876 | 1.00 | 39.61 | A |
| ATOM | 1849 | O   | ALA | A | 304 | 21.298 | 28.156 | 26.395 | 1.00 | 40.61 | A |
| ATOM | 1850 | N   | PHE | A | 305 | 22.891 | 29.543 | 25.617 | 1.00 | 36.21 | A |
| ATOM | 1851 | CA  | PHE | A | 305 | 24.022 | 28.662 | 25.909 | 1.00 | 32.08 | A |
| ATOM | 1852 | CB  | PHE | A | 305 | 25.259 | 29.519 | 26.187 | 1.00 | 29.46 | A |
| ATOM | 1853 | CG  | PHE | A | 305 | 26.536 | 28.917 | 25.690 | 1.00 | 28.15 | A |
| ATOM | 1854 | CD1 | PHE | A | 305 | 27.146 | 27.875 | 26.377 | 1.00 | 26.20 | A |
| ATOM | 1855 | CD2 | PHE | A | 305 | 27.127 | 29.386 | 24.521 | 1.00 | 27.05 | A |
| ATOM | 1856 | CE1 | PHE | A | 305 | 28.330 | 27.308 | 25.908 | 1.00 | 26.92 | A |
| ATOM | 1857 | CE2 | PHE | A | 305 | 28.312 | 28.826 | 24.042 | 1.00 | 26.62 | A |
| ATOM | 1858 | CZ  | PHE | A | 305 | 28.914 | 27.786 | 24.737 | 1.00 | 26.61 | A |
| ATOM | 1859 | C   | PHE | A | 305 | 23.811 | 27.664 | 27.057 | 1.00 | 30.09 | A |
| ATOM | 1860 | O   | PHE | A | 305 | 23.518 | 28.051 | 28.187 | 1.00 | 31.51 | A |
| ATOM | 1861 | N   | PHE | A | 306 | 23.964 | 26.378 | 26.758 | 1.00 | 27.01 | A |
| ATOM | 1862 | CA  | PHE | A | 306 | 23.801 | 25.334 | 27.769 | 1.00 | 26.30 | A |
| ATOM | 1863 | CB  | PHE | A | 306 | 24.157 | 23.970 | 27.170 | 1.00 | 25.03 | A |
| ATOM | 1864 | CG  | PHE | A | 306 | 23.548 | 23.725 | 25.815 | 1.00 | 27.24 | A |
| ATOM | 1865 | CD1 | PHE | A | 306 | 22.170 | 23.831 | 25.622 | 1.00 | 28.40 | A |
| ATOM | 1866 | CD2 | PHE | A | 306 | 24.350 | 23.386 | 24.728 | 1.00 | 27.84 | A |
| ATOM | 1867 | CE1 | PHE | A | 306 | 21.601 | 23.603 | 24.365 | 1.00 | 28.05 | A |
| ATOM | 1868 | CE2 | PHE | A | 306 | 23.792 | 23.155 | 23.465 | 1.00 | 28.31 | A |
| ATOM | 1869 | CZ  | PHE | A | 306 | 22.415 | 23.263 | 23.283 | 1.00 | 28.00 | A |
| ATOM | 1870 | C   | PHE | A | 306 | 24.711 | 25.652 | 28.961 | 1.00 | 26.23 | A |
| ATOM | 1871 | O   | PHE | A | 306 | 25.927 | 25.775 | 28.811 | 1.00 | 25.59 | A |
| ATOM | 1872 | N   | PRO | A | 307 | 24.125 | 25.796 | 30.163 | 1.00 | 26.67 | A |
| ATOM | 1873 | CD  | PRO | A | 307 | 22.685 | 25.625 | 30.430 | 1.00 | 27.95 | A |
| ATOM | 1874 | CA  | PRO | A | 307 | 24.842 | 26.110 | 31.405 | 1.00 | 26.59 | A |
| ATOM | 1875 | CB  | PRO | A | 307 | 23.795 | 25.832 | 32.481 | 1.00 | 26.14 | A |
| ATOM | 1876 | CG  | PRO | A | 307 | 22.531 | 26.250 | 31.803 | 1.00 | 27.86 | A |
| ATOM | 1877 | C   | PRO | A | 307 | 26.145 | 25.355 | 31.659 | 1.00 | 25.58 | A |
| ATOM | 1878 | O   | PRO | A | 307 | 27.189 | 25.964 | 31.900 | 1.00 | 22.65 | A |
| ATOM | 1879 | N   | LYS | A | 308 | 26.085 | 24.031 | 31.620 | 1.00 | 24.46 | A |
| ATOM | 1880 | CA  | LYS | A | 308 | 27.274 | 23.232 | 31.867 | 1.00 | 23.91 | A |
| ATOM | 1881 | CB  | LYS | A | 308 | 26.887 | 21.760 | 32.024 | 1.00 | 23.25 | A |
| ATOM | 1882 | CG  | LYS | A | 308 | 26.062 | 21.532 | 33.285 | 1.00 | 28.49 | A |
| ATOM | 1883 | CD  | LYS | A | 308 | 25.618 | 20.093 | 33.466 | 1.00 | 30.17 | A |
| ATOM | 1884 | CE  | LYS | A | 308 | 24.760 | 19.973 | 34.722 | 1.00 | 33.12 | A |
| ATOM | 1885 | NZ  | LYS | A | 308 | 24.122 | 18.636 | 34.860 | 1.00 | 34.13 | A |
| ATOM | 1886 | C   | LYS | A | 308 | 28.314 | 23.426 | 30.769 | 1.00 | 22.84 | A |
| ATOM | 1887 | O   | LYS | A | 308 | 29.514 | 23.411 | 31.042 | 1.00 | 22.46 | A |
| ATOM | 1888 | N   | ALA | A | 309 | 27.861 | 23.621 | 29.534 | 1.00 | 21.59 | A |
| ATOM | 1889 | CA  | ALA | A | 309 | 28.792 | 23.848 | 28.432 | 1.00 | 20.02 | A |
| ATOM | 1890 | CB  | ALA | A | 309 | 28.056 | 23.856 | 27.106 | 1.00 | 18.80 | A |
| ATOM | 1891 | C   | ALA | A | 309 | 29.481 | 25.191 | 28.662 | 1.00 | 21.41 | A |
| ATOM | 1892 | O   | ALA | A | 309 | 30.680 | 25.335 | 28.427 | 1.00 | 21.39 | A |
| ATOM | 1893 | N   | ARG | A | 310 | 28.717 | 26.179 | 29.121 | 1.00 | 21.39 | A |
| ATOM | 1894 | CA  | ARG | A | 310 | 29.290 | 27.494 | 29.388 | 1.00 | 22.02 | A |
| ATOM | 1895 | CB  | ARG | A | 310 | 28.213 | 28.479 | 29.854 | 1.00 | 22.39 | A |
| ATOM | 1896 | CG  | ARG | A | 310 | 28.806 | 29.756 | 30.436 | 1.00 | 25.30 | A |
| ATOM | 1897 | CD  | ARG | A | 310 | 27.780 | 30.852 | 30.664 | 1.00 | 28.33 | A |
| ATOM | 1898 | NE  | ARG | A | 310 | 28.420 | 32.039 | 31.230 | 1.00 | 30.18 | A |
| ATOM | 1899 | CZ  | ARG | A | 310 | 27.901 | 33.263 | 31.203 | 1.00 | 32.07 | A |
| ATOM | 1900 | NH1 | ARG | A | 310 | 26.719 | 33.477 | 30.634 | 1.00 | 31.19 | A |

-continued

| | | | | | | | | | | |
|---|---|---|---|---|---|---|---|---|---|---|
| ATOM | 1901 | NH2 | ARG | A | 310 | 28.567 | 34.277 | 31.742 | 1.00 | 30.49 | A |
| ATOM | 1902 | C | ARG | A | 310 | 30.376 | 27.388 | 30.458 | 1.00 | 21.65 | A |
| ATOM | 1903 | O | ARG | A | 310 | 31.464 | 27.949 | 30.311 | 1.00 | 20.36 | A |
| ATOM | 1904 | N | ASP | A | 311 | 30.074 | 26.677 | 31.541 | 1.00 | 19.57 | A |
| ATOM | 1905 | CA | ASP | A | 311 | 31.043 | 26.512 | 32.615 | 1.00 | 20.18 | A |
| ATOM | 1906 | CB | ASP | A | 311 | 30.460 | 25.649 | 33.739 | 1.00 | 20.39 | A |
| ATOM | 1907 | CG | ASP | A | 311 | 31.439 | 25.446 | 34.881 | 1.00 | 23.35 | A |
| ATOM | 1908 | OD1 | ASP | A | 311 | 32.158 | 24.428 | 34.885 | 1.00 | 24.91 | A |
| ATOM | 1909 | OD2 | ASP | A | 311 | 31.500 | 26.312 | 35.776 | 1.00 | 26.96 | A |
| ATOM | 1910 | C | ASP | A | 311 | 32.322 | 25.877 | 32.073 | 1.00 | 19.73 | A |
| ATOM | 1911 | O | ASP | A | 311 | 33.422 | 26.289 | 32.439 | 1.00 | 19.30 | A |
| ATOM | 1912 | N | LEU | A | 312 | 32.179 | 24.891 | 31.188 | 1.00 | 16.32 | A |
| ATOM | 1913 | CA | LEU | A | 312 | 33.349 | 24.226 | 30.611 | 1.00 | 16.66 | A |
| ATOM | 1914 | CB | LEU | A | 312 | 32.927 | 23.035 | 29.744 | 1.00 | 16.12 | A |
| ATOM | 1915 | CG | LEU | A | 312 | 34.050 | 22.320 | 28.974 | 1.00 | 14.73 | A |
| ATOM | 1916 | CD1 | LEU | A | 312 | 35.192 | 21.935 | 29.912 | 1.00 | 14.56 | A |
| ATOM | 1917 | CD2 | LEU | A | 312 | 33.477 | 21.084 | 28.289 | 1.00 | 14.22 | A |
| ATOM | 1918 | C | LEU | A | 312 | 34.181 | 25.189 | 29.774 | 1.00 | 16.61 | A |
| ATOM | 1919 | O | LEU | A | 312 | 35.402 | 25.241 | 29.910 | 1.00 | 16.20 | A |
| ATOM | 1920 | N | VAL | A | 313 | 33.515 | 25.949 | 28.908 | 1.00 | 16.20 | A |
| ATOM | 1921 | CA | VAL | A | 313 | 34.207 | 26.907 | 28.058 | 1.00 | 15.37 | A |
| ATOM | 1922 | CB | VAL | A | 313 | 33.216 | 27.648 | 27.130 | 1.00 | 16.42 | A |
| ATOM | 1923 | CG1 | VAL | A | 313 | 33.915 | 28.796 | 26.426 | 1.00 | 16.93 | A |
| ATOM | 1924 | CG2 | VAL | A | 313 | 32.644 | 26.672 | 26.103 | 1.00 | 17.88 | A |
| ATOM | 1925 | C | VAL | A | 313 | 34.960 | 27.923 | 28.911 | 1.00 | 17.39 | A |
| ATOM | 1926 | O | VAL | A | 313 | 36.093 | 28.294 | 28.591 | 1.00 | 18.00 | A |
| ATOM | 1927 | N | GLU | A | 314 | 34.342 | 28.364 | 30.004 | 1.00 | 17.61 | A |
| ATOM | 1928 | CA | GLU | A | 314 | 34.986 | 29.331 | 30.885 | 1.00 | 20.43 | A |
| ATOM | 1929 | CB | GLU | A | 314 | 34.009 | 29.816 | 31.959 | 1.00 | 22.14 | A |
| ATOM | 1930 | CG | GLU | A | 314 | 32.800 | 30.550 | 31.396 | 1.00 | 26.52 | A |
| ATOM | 1931 | CD | GLU | A | 314 | 31.852 | 31.025 | 32.478 | 1.00 | 31.26 | A |
| ATOM | 1932 | OE1 | GLU | A | 314 | 31.580 | 30.246 | 33.417 | 1.00 | 33.48 | A |
| ATOM | 1933 | OE2 | GLU | A | 314 | 31.370 | 32.173 | 32.387 | 1.00 | 34.81 | A |
| ATOM | 1934 | C | GLU | A | 314 | 36.217 | 28.721 | 31.539 | 1.00 | 19.15 | A |
| ATOM | 1935 | O | GLU | A | 314 | 37.134 | 29.433 | 31.934 | 1.00 | 21.47 | A |
| ATOM | 1936 | N | LYS | A | 315 | 36.245 | 27.400 | 31.651 | 1.00 | 19.51 | A |
| ATOM | 1937 | CA | LYS | A | 315 | 37.394 | 26.749 | 32.258 | 1.00 | 19.17 | A |
| ATOM | 1938 | CB | LYS | A | 315 | 36.946 | 25.514 | 33.043 | 1.00 | 18.84 | A |
| ATOM | 1939 | CG | LYS | A | 315 | 36.280 | 25.885 | 34.368 | 1.00 | 19.62 | A |
| ATOM | 1940 | CD | LYS | A | 315 | 35.653 | 24.696 | 35.073 | 1.00 | 19.22 | A |
| ATOM | 1941 | CE | LYS | A | 315 | 35.070 | 25.095 | 36.427 | 1.00 | 21.00 | A |
| ATOM | 1942 | NZ | LYS | A | 315 | 36.119 | 25.552 | 37.381 | 1.00 | 19.53 | A |
| ATOM | 1943 | C | LYS | A | 315 | 38.452 | 26.393 | 31.218 | 1.00 | 18.96 | A |
| ATOM | 1944 | O | LYS | A | 315 | 39.511 | 25.873 | 31.561 | 1.00 | 19.85 | A |
| ATOM | 1945 | N | LEU | A | 316 | 38.164 | 26.691 | 29.950 | 1.00 | 17.08 | A |
| ATOM | 1946 | CA | LEU | A | 316 | 39.102 | 26.429 | 28.854 | 1.00 | 16.41 | A |
| ATOM | 1947 | CB | LEU | A | 316 | 38.414 | 25.636 | 27.738 | 1.00 | 13.81 | A |
| ATOM | 1948 | CG | LEU | A | 316 | 38.028 | 24.201 | 28.115 | 1.00 | 14.39 | A |
| ATOM | 1949 | CD1 | LEU | A | 316 | 37.139 | 23.597 | 27.031 | 1.00 | 12.38 | A |
| ATOM | 1950 | CD2 | LEU | A | 316 | 39.302 | 23.373 | 28.309 | 1.00 | 12.77 | A |
| ATOM | 1951 | C | LEU | A | 316 | 39.652 | 27.743 | 28.290 | 1.00 | 17.12 | A |
| ATOM | 1952 | O | LEU | A | 316 | 40.851 | 27.860 | 28.023 | 1.00 | 16.53 | A |
| ATOM | 1953 | N | LEU | A | 317 | 38.780 | 28.729 | 28.105 | 1.00 | 16.27 | A |
| ATOM | 1954 | CA | LEU | A | 317 | 39.228 | 30.022 | 27.596 | 1.00 | 17.52 | A |
| ATOM | 1955 | CB | LEU | A | 317 | 38.083 | 30.752 | 26.887 | 1.00 | 16.37 | A |
| ATOM | 1956 | CG | LEU | A | 317 | 37.448 | 29.973 | 25.727 | 1.00 | 18.81 | A |
| ATOM | 1957 | CD1 | LEU | A | 317 | 36.415 | 30.851 | 25.018 | 1.00 | 16.47 | A |
| ATOM | 1958 | CD2 | LEU | A | 317 | 38.528 | 29.526 | 24.741 | 1.00 | 17.87 | A |
| ATOM | 1959 | C | LEU | A | 317 | 39.745 | 30.841 | 28.774 | 1.00 | 18.27 | A |
| ATOM | 1960 | O | LEU | A | 317 | 39.078 | 31.753 | 29.273 | 1.00 | 18.58 | A |
| ATOM | 1961 | N | VAL | A | 318 | 40.937 | 30.475 | 29.229 | 1.00 | 18.02 | A |
| ATOM | 1962 | CA | VAL | A | 318 | 41.593 | 31.141 | 30.342 | 1.00 | 18.85 | A |
| ATOM | 1963 | CB | VAL | A | 318 | 41.846 | 30.153 | 31.500 | 1.00 | 19.91 | A |
| ATOM | 1964 | CG1 | VAL | A | 318 | 42.590 | 30.848 | 32.634 | 1.00 | 20.01 | A |
| ATOM | 1965 | CG2 | VAL | A | 318 | 40.520 | 29.584 | 31.990 | 1.00 | 19.44 | A |
| ATOM | 1966 | C | VAL | A | 318 | 42.923 | 31.657 | 29.811 | 1.00 | 19.67 | A |
| ATOM | 1967 | O | VAL | A | 318 | 43.690 | 30.902 | 29.208 | 1.00 | 18.26 | A |
| ATOM | 1968 | N | LEU | A | 319 | 43.197 | 32.939 | 30.028 | 1.00 | 20.07 | A |
| ATOM | 1969 | CA | LEU | A | 319 | 44.436 | 33.533 | 29.538 | 1.00 | 20.98 | A |
| ATOM | 1970 | CB | LEU | A | 319 | 44.521 | 35.002 | 29.968 | 1.00 | 21.64 | A |
| ATOM | 1971 | CG | LEU | A | 319 | 43.418 | 35.908 | 29.408 | 1.00 | 24.38 | A |
| ATOM | 1972 | CD1 | LEU | A | 319 | 43.606 | 37.332 | 29.935 | 1.00 | 23.28 | A |
| ATOM | 1973 | CD2 | LEU | A | 319 | 43.453 | 35.887 | 27.875 | 1.00 | 24.33 | A |
| ATOM | 1974 | C | LEU | A | 319 | 45.680 | 32.774 | 29.994 | 1.00 | 20.38 | A |
| ATOM | 1975 | O | LEU | A | 319 | 46.568 | 32.496 | 29.192 | 1.00 | 21.34 | A |
| ATOM | 1976 | N | ASP | A | 320 | 45.742 | 32.440 | 31.280 | 1.00 | 20.22 | A |
| ATOM | 1977 | CA | ASP | A | 320 | 46.879 | 31.707 | 31.833 | 1.00 | 20.90 | A |
| ATOM | 1978 | CB | ASP | A | 320 | 46.842 | 31.760 | 33.365 | 1.00 | 20.76 | A |
| ATOM | 1979 | CG | ASP | A | 320 | 48.049 | 31.102 | 34.004 | 1.00 | 21.51 | A |

-continued

| | | | | | | | | | | |
|---|---|---|---|---|---|---|---|---|---|---|
| ATOM | 1980 | OD1 | ASP | A | 320 | 48.669 | 30.226 | 33.367 | 1.00 | 23.46 | A |
| ATOM | 1981 | OD2 | ASP | A | 320 | 48.371 | 31.450 | 35.159 | 1.00 | 23.89 | A |
| ATOM | 1982 | C | ASP | A | 320 | 46.814 | 30.247 | 31.367 | 1.00 | 20.06 | A |
| ATOM | 1983 | O | ASP | A | 320 | 45.988 | 29.476 | 31.840 | 1.00 | 20.54 | A |
| ATOM | 1984 | N | ALA | A | 321 | 47.700 | 29.876 | 30.451 | 1.00 | 20.68 | A |
| ATOM | 1985 | CA | ALA | A | 321 | 47.733 | 28.522 | 29.903 | 1.00 | 22.04 | A |
| ATOM | 1986 | CB | ALA | A | 321 | 48.860 | 28.411 | 28.881 | 1.00 | 20.75 | A |
| ATOM | 1987 | C | ALA | A | 321 | 47.858 | 27.400 | 30.940 | 1.00 | 21.62 | A |
| ATOM | 1988 | O | ALA | A | 321 | 47.482 | 26.259 | 30.665 | 1.00 | 21.99 | A |
| ATOM | 1989 | N | THR | A | 322 | 48.372 | 27.715 | 32.127 | 1.00 | 20.89 | A |
| ATOM | 1990 | CA | THR | A | 322 | 48.531 | 26.698 | 33.167 | 1.00 | 20.82 | A |
| ATOM | 1991 | CB | THR | A | 322 | 49.670 | 27.051 | 34.146 | 1.00 | 19.47 | A |
| ATOM | 1992 | OG1 | THR | A | 322 | 49.341 | 28.253 | 34.848 | 1.00 | 20.19 | A |
| ATOM | 1993 | CG2 | THR | A | 322 | 50.981 | 27.249 | 33.394 | 1.00 | 21.59 | A |
| ATOM | 1994 | C | THR | A | 322 | 47.264 | 26.498 | 33.983 | 1.00 | 19.55 | A |
| ATOM | 1995 | O | THR | A | 322 | 47.235 | 25.673 | 34.894 | 1.00 | 21.13 | A |
| ATOM | 1996 | N | LYS | A | 323 | 46.216 | 27.248 | 33.661 | 1.00 | 19.33 | A |
| ATOM | 1997 | CA | LYS | A | 323 | 44.962 | 27.122 | 34.392 | 1.00 | 21.20 | A |
| ATOM | 1998 | CB | LYS | A | 323 | 44.580 | 28.460 | 35.030 | 1.00 | 23.75 | A |
| ATOM | 1999 | CG | LYS | A | 323 | 45.562 | 28.933 | 36.084 | 1.00 | 28.45 | A |
| ATOM | 2000 | CD | LYS | A | 323 | 45.055 | 30.177 | 36.799 | 1.00 | 33.76 | A |
| ATOM | 2001 | CE | LYS | A | 323 | 46.087 | 30.678 | 37.802 | 1.00 | 36.15 | A |
| ATOM | 2002 | NZ | LYS | A | 323 | 46.532 | 29.569 | 38.693 | 1.00 | 37.34 | A |
| ATOM | 2003 | C | LYS | A | 323 | 43.806 | 26.614 | 33.539 | 1.00 | 20.68 | A |
| ATOM | 2004 | O | LYS | A | 323 | 42.649 | 26.757 | 33.915 | 1.00 | 20.42 | A |
| ATOM | 2005 | N | ARG | A | 324 | 44.114 | 26.019 | 32.392 | 1.00 | 19.97 | A |
| ATOM | 2006 | CA | ARG | A | 324 | 43.060 | 25.494 | 31.531 | 1.00 | 17.98 | A |
| ATOM | 2007 | CB | ARG | A | 324 | 43.461 | 25.609 | 30.061 | 1.00 | 15.95 | A |
| ATOM | 2008 | CG | ARG | A | 324 | 43.534 | 27.050 | 29.603 | 1.00 | 17.34 | A |
| ATOM | 2009 | CD | ARG | A | 324 | 43.996 | 27.194 | 28.172 | 1.00 | 19.80 | A |
| ATOM | 2010 | NE | ARG | A | 324 | 44.438 | 28.565 | 27.944 | 1.00 | 16.93 | A |
| ATOM | 2011 | CZ | ARG | A | 324 | 45.410 | 28.908 | 27.108 | 1.00 | 19.88 | A |
| ATOM | 2012 | NH1 | ARG | A | 324 | 46.045 | 27.978 | 26.398 | 1.00 | 14.58 | A |
| ATOM | 2013 | NH2 | ARG | A | 324 | 45.774 | 30.181 | 27.015 | 1.00 | 16.51 | A |
| ATOM | 2014 | C | ARG | A | 324 | 42.762 | 24.046 | 31.883 | 1.00 | 18.32 | A |
| ATOM | 2015 | O | ARG | A | 324 | 43.673 | 23.222 | 32.006 | 1.00 | 18.20 | A |
| ATOM | 2016 | N | LEU | A | 325 | 41.479 | 23.748 | 32.055 | 1.00 | 18.32 | A |
| ATOM | 2017 | CA | LEU | A | 325 | 41.050 | 22.403 | 32.395 | 1.00 | 17.79 | A |
| ATOM | 2018 | CB | LEU | A | 325 | 39.523 | 22.335 | 32.425 | 1.00 | 17.03 | A |
| ATOM | 2019 | CG | LEU | A | 325 | 38.896 | 21.125 | 33.116 | 1.00 | 15.91 | A |
| ATOM | 2020 | CD1 | LEU | A | 325 | 39.392 | 21.048 | 34.557 | 1.00 | 15.93 | A |
| ATOM | 2021 | CD2 | LEU | A | 325 | 37.375 | 21.255 | 33.084 | 1.00 | 16.56 | A |
| ATOM | 2022 | C | LEU | A | 325 | 41.599 | 21.433 | 31.356 | 1.00 | 18.68 | A |
| ATOM | 2023 | O | LEU | A | 325 | 41.347 | 21.586 | 30.157 | 1.00 | 18.28 | A |
| ATOM | 2024 | N | GLY | A | 326 | 42.354 | 20.439 | 31.821 | 1.00 | 18.18 | A |
| ATOM | 2025 | CA | GLY | A | 326 | 42.931 | 19.462 | 30.915 | 1.00 | 16.36 | A |
| ATOM | 2026 | C | GLY | A | 326 | 44.443 | 19.558 | 30.807 | 1.00 | 19.15 | A |
| ATOM | 2027 | O | GLY | A | 326 | 45.093 | 18.592 | 30.404 | 1.00 | 19.52 | A |
| ATOM | 2028 | N | CYS | A | 327 | 45.016 | 20.708 | 31.161 | 1.00 | 18.16 | A |
| ATOM | 2029 | CA | CYS | A | 327 | 46.463 | 20.867 | 31.075 | 1.00 | 19.30 | A |
| ATOM | 2030 | CB | CYS | A | 327 | 46.856 | 22.350 | 31.058 | 1.00 | 20.22 | A |
| ATOM | 2031 | SG | CYS | A | 327 | 46.782 | 23.200 | 32.649 | 1.00 | 21.97 | A |
| ATOM | 2032 | C | CYS | A | 327 | 47.169 | 20.157 | 32.228 | 1.00 | 20.22 | A |
| ATOM | 2033 | O | CYS | A | 327 | 46.561 | 19.828 | 33.246 | 1.00 | 17.92 | A |
| ATOM | 2034 | N | GLU | A | 328 | 48.463 | 19.933 | 32.053 | 1.00 | 20.51 | A |
| ATOM | 2035 | CA | GLU | A | 328 | 49.274 | 19.244 | 33.042 | 1.00 | 23.34 | A |
| ATOM | 2036 | CB | GLU | A | 328 | 50.710 | 19.139 | 32.507 | 1.00 | 28.68 | A |
| ATOM | 2037 | CG | GLU | A | 328 | 50.754 | 18.367 | 31.175 | 1.00 | 38.24 | A |
| ATOM | 2038 | CD | GLU | A | 328 | 52.067 | 18.500 | 30.414 | 1.00 | 43.23 | A |
| ATOM | 2039 | OE1 | GLU | A | 328 | 52.535 | 19.643 | 30.218 | 1.00 | 46.22 | A |
| ATOM | 2040 | OE2 | GLU | A | 328 | 52.618 | 17.459 | 29.991 | 1.00 | 44.90 | A |
| ATOM | 2041 | C | GLU | A | 328 | 49.234 | 19.876 | 34.435 | 1.00 | 22.11 | A |
| ATOM | 2042 | O | GLU | A | 328 | 49.147 | 19.161 | 35.437 | 1.00 | 20.27 | A |
| ATOM | 2043 | N | GLU | A | 329 | 49.276 | 21.204 | 34.506 | 1.00 | 18.40 | A |
| ATOM | 2044 | CA | GLU | A | 329 | 49.248 | 21.875 | 35.801 | 1.00 | 20.13 | A |
| ATOM | 2045 | CB | GLU | A | 329 | 49.587 | 23.363 | 35.657 | 1.00 | 20.36 | A |
| ATOM | 2046 | CG | GLU | A | 329 | 51.014 | 23.651 | 35.190 | 1.00 | 24.05 | A |
| ATOM | 2047 | CD | GLU | A | 329 | 51.191 | 23.518 | 33.688 | 1.00 | 25.93 | A |
| ATOM | 2048 | OE1 | GLU | A | 329 | 50.213 | 23.154 | 32.995 | 1.00 | 26.61 | A |
| ATOM | 2049 | OE2 | GLU | A | 329 | 52.311 | 23.781 | 33.198 | 1.00 | 27.19 | A |
| ATOM | 2050 | C | GLU | A | 329 | 47.890 | 21.718 | 36.480 | 1.00 | 19.36 | A |
| ATOM | 2051 | O | GLU | A | 329 | 47.775 | 21.879 | 37.694 | 1.00 | 18.74 | A |
| ATOM | 2052 | N | MET | A | 330 | 46.863 | 21.415 | 35.691 | 1.00 | 17.28 | A |
| ATOM | 2053 | CA | MET | A | 330 | 45.520 | 21.220 | 36.229 | 1.00 | 16.38 | A |
| ATOM | 2054 | CB | MET | A | 330 | 44.474 | 21.833 | 35.294 | 1.00 | 17.65 | A |
| ATOM | 2055 | CG | MET | A | 330 | 44.460 | 23.365 | 35.311 | 1.00 | 22.95 | A |
| ATOM | 2056 | SD | MET | A | 330 | 44.186 | 24.026 | 36.979 | 1.00 | 26.78 | A |
| ATOM | 2057 | CZ | MET | A | 330 | 42.435 | 23.712 | 37.186 | 1.00 | 24.69 | A |
| ATOM | 2058 | C | MET | A | 330 | 45.257 | 19.730 | 36.422 | 1.00 | 14.30 | A |

-continued

| | | | | | | | | | | | |
|---|---|---|---|---|---|---|---|---|---|---|---|
| ATOM | 2059 | O | MET | A | 330 | 44.127 | 19.304 | 36.629 | 1.00 | 15.39 | A |
| ATOM | 2060 | N | GLU | A | 331 | 46.327 | 18.949 | 36.346 | 1.00 | 15.60 | A |
| ATOM | 2061 | CA | GLU | A | 331 | 46.289 | 17.501 | 36.531 | 1.00 | 17.08 | A |
| ATOM | 2062 | CB | GLU | A | 331 | 45.607 | 17.155 | 37.862 | 1.00 | 17.00 | A |
| ATOM | 2063 | CG | GLU | A | 331 | 46.070 | 18.027 | 39.038 | 1.00 | 17.46 | A |
| ATOM | 2064 | CD | GLU | A | 331 | 47.591 | 18.179 | 39.145 | 1.00 | 20.16 | A |
| ATOM | 2065 | OE1 | GLU | A | 331 | 48.034 | 19.073 | 39.896 | 1.00 | 21.39 | A |
| ATOM | 2066 | OE2 | GLU | A | 331 | 48.345 | 17.420 | 38.500 | 1.00 | 18.87 | A |
| ATOM | 2067 | C | GLU | A | 331 | 45.697 | 16.658 | 35.398 | 1.00 | 17.80 | A |
| ATOM | 2068 | O | GLU | A | 331 | 45.107 | 15.602 | 35.636 | 1.00 | 20.40 | A |
| ATOM | 2069 | N | GLY | A | 332 | 45.844 | 17.133 | 34.167 | 1.00 | 16.23 | A |
| ATOM | 2070 | CA | GLY | A | 332 | 45.420 | 16.353 | 33.015 | 1.00 | 14.10 | A |
| ATOM | 2071 | C | GLY | A | 332 | 43.982 | 16.154 | 32.596 | 1.00 | 13.54 | A |
| ATOM | 2072 | O | GLY | A | 332 | 43.063 | 16.864 | 33.017 | 1.00 | 11.96 | A |
| ATOM | 2073 | N | TYR | A | 333 | 43.804 | 15.141 | 31.750 | 1.00 | 14.37 | A |
| ATOM | 2074 | CA | TYR | A | 333 | 42.510 | 14.806 | 31.182 | 1.00 | 13.56 | A |
| ATOM | 2075 | CB | TYR | A | 333 | 42.722 | 13.892 | 29.968 | 1.00 | 15.00 | A |
| ATOM | 2076 | CG | TYR | A | 333 | 43.153 | 14.683 | 28.752 | 1.00 | 16.46 | A |
| ATOM | 2077 | CD1 | TYR | A | 333 | 42.206 | 15.172 | 27.849 | 1.00 | 15.29 | A |
| ATOM | 2078 | CE1 | TYR | A | 333 | 42.573 | 16.002 | 26.794 | 1.00 | 13.42 | A |
| ATOM | 2079 | CD2 | TYR | A | 333 | 44.490 | 15.039 | 28.561 | 1.00 | 14.91 | A |
| ATOM | 2080 | CE2 | TYR | A | 333 | 44.872 | 15.877 | 27.499 | 1.00 | 14.87 | A |
| ATOM | 2081 | CZ | TYR | A | 333 | 43.902 | 16.353 | 26.626 | 1.00 | 15.61 | A |
| ATOM | 2082 | OH | TYR | A | 333 | 44.244 | 17.197 | 25.599 | 1.00 | 17.29 | A |
| ATOM | 2083 | C | TYR | A | 333 | 41.470 | 14.230 | 32.127 | 1.00 | 15.23 | A |
| ATOM | 2084 | O | TYR | A | 333 | 40.278 | 14.323 | 31.846 | 1.00 | 16.63 | A |
| ATOM | 2085 | N | GLY | A | 334 | 41.907 | 13.650 | 33.244 | 1.00 | 15.50 | A |
| ATOM | 2086 | CA | GLY | A | 334 | 40.957 | 13.100 | 34.202 | 1.00 | 15.07 | A |
| ATOM | 2087 | C | GLY | A | 334 | 39.925 | 14.146 | 34.616 | 1.00 | 16.40 | A |
| ATOM | 2088 | O | GLY | A | 334 | 38.724 | 13.946 | 34.433 | 1.00 | 15.05 | A |
| ATOM | 2089 | N | PRO | A | 335 | 40.366 | 15.278 | 35.184 | 1.00 | 14.96 | A |
| ATOM | 2090 | CD | PRO | A | 335 | 41.727 | 15.531 | 35.689 | 1.00 | 15.88 | A |
| ATOM | 2091 | CA | PRO | A | 335 | 39.444 | 16.339 | 35.606 | 1.00 | 15.29 | A |
| ATOM | 2092 | CB | PRO | A | 335 | 40.383 | 17.397 | 36.178 | 1.00 | 13.19 | A |
| ATOM | 2093 | CG | PRO | A | 335 | 41.485 | 16.569 | 36.758 | 1.00 | 13.81 | A |
| ATOM | 2094 | C | PRO | A | 335 | 38.594 | 16.877 | 34.448 | 1.00 | 15.84 | A |
| ATOM | 2095 | O | PRO | A | 335 | 37.423 | 17.204 | 34.631 | 1.00 | 14.84 | A |
| ATOM | 2096 | N | LEU | A | 336 | 39.184 | 16.971 | 33.257 | 1.00 | 16.12 | A |
| ATOM | 2097 | CA | LEU | A | 336 | 38.450 | 17.465 | 32.094 | 1.00 | 15.52 | A |
| ATOM | 2098 | CB | LEU | A | 336 | 39.396 | 17.653 | 30.898 | 1.00 | 14.39 | A |
| ATOM | 2099 | CG | LEU | A | 336 | 38.770 | 17.991 | 29.538 | 1.00 | 15.46 | A |
| ATOM | 2100 | CD1 | LEU | A | 336 | 37.836 | 19.182 | 29.662 | 1.00 | 11.25 | A |
| ATOM | 2101 | CD2 | LEU | A | 336 | 39.884 | 18.285 | 28.528 | 1.00 | 14.11 | A |
| ATOM | 2102 | C | LEU | A | 336 | 37.321 | 16.508 | 31.714 | 1.00 | 16.28 | A |
| ATOM | 2103 | O | LEU | A | 336 | 36.176 | 16.921 | 31.540 | 1.00 | 15.51 | A |
| ATOM | 2104 | N | LYS | A | 337 | 37.640 | 15.225 | 31.592 | 1.00 | 17.22 | A |
| ATOM | 2105 | CA | LYS | A | 337 | 36.624 | 14.243 | 31.235 | 1.00 | 17.39 | A |
| ATOM | 2106 | CB | LYS | A | 337 | 37.293 | 12.900 | 30.921 | 1.00 | 17.68 | A |
| ATOM | 2107 | CG | LYS | A | 337 | 38.170 | 12.994 | 29.676 | 1.00 | 22.31 | A |
| ATOM | 2108 | CD | LYS | A | 337 | 39.213 | 11.892 | 29.592 | 1.00 | 24.60 | A |
| ATOM | 2109 | CE | LYS | A | 337 | 38.620 | 10.560 | 29.189 | 1.00 | 24.76 | A |
| ATOM | 2110 | NZ | LYS | A | 337 | 39.710 | 9.560 | 28.997 | 1.00 | 25.05 | A |
| ATOM | 2111 | C | LYS | A | 337 | 35.577 | 14.096 | 32.342 | 1.00 | 17.33 | A |
| ATOM | 2112 | O | LYS | A | 337 | 34.456 | 13.652 | 32.090 | 1.00 | 14.42 | A |
| ATOM | 2113 | N | ALA | A | 338 | 35.928 | 14.500 | 33.559 | 1.00 | 15.83 | A |
| ATOM | 2114 | CA | ALA | A | 338 | 34.989 | 14.395 | 34.674 | 1.00 | 17.52 | A |
| ATOM | 2115 | CB | ALA | A | 338 | 35.749 | 14.167 | 35.980 | 1.00 | 19.68 | A |
| ATOM | 2116 | C | ALA | A | 338 | 34.095 | 15.621 | 34.804 | 1.00 | 18.83 | A |
| ATOM | 2117 | O | ALA | A | 338 | 33.252 | 15.687 | 35.695 | 1.00 | 18.94 | A |
| ATOM | 2118 | N | HIS | A | 339 | 34.262 | 16.596 | 33.918 | 1.00 | 19.42 | A |
| ATOM | 2119 | CA | HIS | A | 339 | 33.438 | 17.796 | 34.004 | 1.00 | 19.28 | A |
| ATOM | 2120 | CB | HIS | A | 339 | 33.865 | 18.819 | 32.949 | 1.00 | 19.20 | A |
| ATOM | 2121 | CG | HIS | A | 339 | 33.163 | 20.134 | 33.074 | 1.00 | 20.26 | A |
| ATOM | 2122 | CD2 | HIS | A | 339 | 33.549 | 21.299 | 33.649 | 1.00 | 18.95 | A |
| ATOM | 2123 | ND1 | HIS | A | 339 | 31.880 | 20.340 | 32.612 | 1.00 | 19.10 | A |
| ATOM | 2124 | CE1 | HIS | A | 339 | 31.506 | 21.576 | 32.896 | 1.00 | 22.19 | A |
| ATOM | 2125 | NE2 | HIS | A | 339 | 32.500 | 22.179 | 33.525 | 1.00 | 21.98 | A |
| ATOM | 2126 | C | HIS | A | 339 | 31.957 | 17.448 | 33.845 | 1.00 | 19.13 | A |
| ATOM | 2127 | O | HIS | A | 339 | 31.597 | 16.576 | 33.061 | 1.00 | 19.52 | A |
| ATOM | 2128 | N | PRO | A | 340 | 31.079 | 18.125 | 34.606 | 1.00 | 19.80 | A |
| ATOM | 2129 | CD | PRO | A | 340 | 31.424 | 19.119 | 35.640 | 1.00 | 19.08 | A |
| ATOM | 2130 | CA | PRO | A | 340 | 29.630 | 17.900 | 34.569 | 1.00 | 20.52 | A |
| ATOM | 2131 | CB | PRO | A | 340 | 29.091 | 19.058 | 35.396 | 1.00 | 20.74 | A |
| ATOM | 2132 | CG | PRO | A | 340 | 30.146 | 19.207 | 36.454 | 1.00 | 19.20 | A |
| ATOM | 2133 | C | PRO | A | 340 | 29.000 | 17.834 | 33.176 | 1.00 | 21.42 | A |
| ATOM | 2134 | O | PRO | A | 340 | 28.049 | 17.088 | 32.955 | 1.00 | 22.48 | A |
| ATOM | 2135 | N | PHE | A | 341 | 29.528 | 18.606 | 32.237 | 1.00 | 21.33 | A |
| ATOM | 2136 | CA | PHE | A | 341 | 28.985 | 18.610 | 30.886 | 1.00 | 21.57 | A |
| ATOM | 2137 | CB | PHE | A | 341 | 29.739 | 19.624 | 30.017 | 1.00 | 21.64 | A |

-continued

| | | | | | | | | | | |
|---|---|---|---|---|---|---|---|---|---|---|
| ATOM | 2138 | CG | PHE | A | 341 | 29.207 | 19.740 | 28.613 | 1.00 | 23.18 | A |
| ATOM | 2139 | CD1 | PHE | A | 341 | 27.903 | 20.171 | 28.382 | 1.00 | 22.58 | A |
| ATOM | 2140 | CD2 | PHE | A | 341 | 30.013 | 19.431 | 27.522 | 1.00 | 21.95 | A |
| ATOM | 2141 | CE1 | PHE | A | 341 | 27.410 | 20.292 | 27.082 | 1.00 | 23.54 | A |
| ATOM | 2142 | CE2 | PHE | A | 341 | 29.533 | 19.548 | 26.220 | 1.00 | 21.83 | A |
| ATOM | 2143 | CZ | PHE | A | 341 | 28.228 | 19.980 | 25.998 | 1.00 | 23.23 | A |
| ATOM | 2144 | C | PHE | A | 341 | 29.055 | 17.226 | 30.237 | 1.00 | 21.84 | A |
| ATOM | 2145 | O | PHE | A | 341 | 28.232 | 16.896 | 29.389 | 1.00 | 20.37 | A |
| ATOM | 2146 | N | PHE | A | 342 | 30.034 | 16.422 | 30.640 | 1.00 | 20.51 | A |
| ATOM | 2147 | CA | PHE | A | 342 | 30.221 | 15.085 | 30.077 | 1.00 | 23.01 | A |
| ATOM | 2148 | CB | PHE | A | 342 | 31.710 | 14.809 | 29.850 | 1.00 | 18.00 | A |
| ATOM | 2149 | CG | PHE | A | 342 | 32.398 | 15.812 | 28.971 | 1.00 | 17.05 | A |
| ATOM | 2150 | CD1 | PHE | A | 342 | 32.010 | 15.987 | 27.652 | 1.00 | 17.78 | A |
| ATOM | 2151 | CD2 | PHE | A | 342 | 33.487 | 16.534 | 29.450 | 1.00 | 15.72 | A |
| ATOM | 2152 | CE1 | PHE | A | 342 | 32.702 | 16.867 | 26.811 | 1.00 | 18.08 | A |
| ATOM | 2153 | CE2 | PHE | A | 342 | 34.184 | 17.414 | 28.617 | 1.00 | 17.45 | A |
| ATOM | 2154 | CZ | PHE | A | 342 | 33.790 | 17.578 | 27.298 | 1.00 | 16.56 | A |
| ATOM | 2155 | C | PHE | A | 342 | 29.679 | 13.972 | 30.976 | 1.00 | 24.95 | A |
| ATOM | 2156 | O | PHE | A | 342 | 30.002 | 12.798 | 30.777 | 1.00 | 23.95 | A |
| ATOM | 2157 | N | GLU | A | 343 | 28.861 | 14.333 | 31.958 | 1.00 | 27.35 | A |
| ATOM | 2158 | CA | GLU | A | 343 | 28.325 | 13.349 | 32.897 | 1.00 | 30.28 | A |
| ATOM | 2159 | CB | GLU | A | 343 | 27.187 | 13.964 | 33.716 | 1.00 | 32.20 | A |
| ATOM | 2160 | CG | GLU | A | 343 | 26.581 | 12.991 | 34.714 | 1.00 | 39.71 | A |
| ATOM | 2161 | CD | GLU | A | 343 | 25.628 | 13.661 | 35.688 | 1.00 | 44.72 | A |
| ATOM | 2162 | OE1 | GLU | A | 343 | 24.661 | 14.314 | 35.234 | 1.00 | 47.55 | A |
| ATOM | 2163 | OE2 | GLU | A | 343 | 25.847 | 13.526 | 36.911 | 1.00 | 46.89 | A |
| ATOM | 2164 | C | GLU | A | 343 | 27.852 | 12.017 | 32.305 | 1.00 | 28.98 | A |
| ATOM | 2165 | O | GLU | A | 343 | 28.225 | 10.952 | 32.800 | 1.00 | 31.73 | A |
| ATOM | 2166 | N | SER | A | 344 | 27.037 | 12.067 | 31.258 | 1.00 | 26.09 | A |
| ATOM | 2167 | CA | SER | A | 344 | 26.520 | 10.838 | 30.656 | 1.00 | 28.36 | A |
| ATOM | 2168 | CB | SER | A | 344 | 25.129 | 11.089 | 30.067 | 1.00 | 28.73 | A |
| ATOM | 2169 | OG | SER | A | 344 | 25.203 | 11.942 | 28.940 | 1.00 | 30.91 | A |
| ATOM | 2170 | C | SER | A | 344 | 27.407 | 10.214 | 29.577 | 1.00 | 27.66 | A |
| ATOM | 2171 | O | SER | A | 344 | 26.987 | 9.281 | 28.900 | 1.00 | 28.66 | A |
| ATOM | 2172 | N | VAL | A | 345 | 28.627 | 10.715 | 29.419 | 1.00 | 26.75 | A |
| ATOM | 2173 | CA | VAL | A | 345 | 29.534 | 10.183 | 28.402 | 1.00 | 23.44 | A |
| ATOM | 2174 | CB | VAL | A | 345 | 30.565 | 11.256 | 27.950 | 1.00 | 23.10 | A |
| ATOM | 2175 | CG1 | VAL | A | 345 | 31.589 | 10.631 | 26.995 | 1.00 | 22.24 | A |
| ATOM | 2176 | CG2 | VAL | A | 345 | 29.854 | 12.418 | 27.275 | 1.00 | 20.05 | A |
| ATOM | 2177 | C | VAL | A | 345 | 30.326 | 8.957 | 28.855 | 1.00 | 24.26 | A |
| ATOM | 2178 | O | VAL | A | 345 | 30.876 | 8.930 | 29.960 | 1.00 | 22.83 | A |
| ATOM | 2179 | N | THR | A | 346 | 30.374 | 7.942 | 27.997 | 1.00 | 21.77 | A |
| ATOM | 2180 | CA | THR | A | 346 | 31.153 | 6.740 | 28.272 | 1.00 | 23.70 | A |
| ATOM | 2181 | CB | THR | A | 346 | 30.391 | 5.455 | 27.857 | 1.00 | 26.53 | A |
| ATOM | 2182 | OG1 | THR | A | 346 | 29.248 | 5.284 | 28.706 | 1.00 | 29.98 | A |
| ATOM | 2183 | CG2 | THR | A | 346 | 31.289 | 4.231 | 27.990 | 1.00 | 24.28 | A |
| ATOM | 2184 | C | THR | A | 346 | 32.383 | 6.945 | 27.385 | 1.00 | 23.43 | A |
| ATOM | 2185 | O | THR | A | 346 | 32.306 | 6.827 | 26.160 | 1.00 | 24.50 | A |
| ATOM | 2186 | N | TRP | A | 347 | 33.508 | 7.270 | 28.013 | 1.00 | 22.98 | A |
| ATOM | 2187 | CA | TRP | A | 347 | 34.744 | 7.569 | 27.300 | 1.00 | 23.81 | A |
| ATOM | 2188 | CB | TRP | A | 347 | 35.683 | 8.352 | 28.219 | 1.00 | 22.54 | A |
| ATOM | 2189 | CG | TRP | A | 347 | 35.128 | 9.658 | 28.693 | 1.00 | 20.61 | A |
| ATOM | 2190 | CD2 | TRP | A | 347 | 35.257 | 10.927 | 28.040 | 1.00 | 19.11 | A |
| ATOM | 2191 | CE2 | TRP | A | 347 | 34.581 | 11.881 | 28.838 | 1.00 | 18.39 | A |
| ATOM | 2192 | CE3 | TRP | A | 347 | 35.878 | 11.351 | 26.858 | 1.00 | 18.16 | A |
| ATOM | 2193 | CD1 | TRP | A | 347 | 34.397 | 9.883 | 29.828 | 1.00 | 18.35 | A |
| ATOM | 2194 | NE1 | TRP | A | 347 | 34.065 | 11.218 | 29.923 | 1.00 | 19.51 | A |
| ATOM | 2195 | CZ2 | TRP | A | 347 | 34.510 | 13.234 | 28.491 | 1.00 | 16.88 | A |
| ATOM | 2196 | CZ3 | TRP | A | 347 | 35.808 | 12.701 | 26.511 | 1.00 | 17.23 | A |
| ATOM | 2197 | CH2 | TRP | A | 347 | 35.127 | 13.624 | 27.327 | 1.00 | 18.16 | A |
| ATOM | 2198 | C | TRP | A | 347 | 35.538 | 6.429 | 26.675 | 1.00 | 25.79 | A |
| ATOM | 2199 | O | TRP | A | 347 | 36.304 | 6.654 | 25.742 | 1.00 | 24.67 | A |
| ATOM | 2200 | N | ALA | A | 348 | 35.360 | 5.215 | 27.183 | 1.00 | 27.10 | A |
| ATOM | 2201 | CA | ALA | A | 348 | 36.116 | 4.063 | 26.697 | 1.00 | 27.46 | A |
| ATOM | 2202 | CB | ALA | A | 348 | 35.899 | 2.869 | 27.636 | 1.00 | 27.09 | A |
| ATOM | 2203 | C | ALA | A | 348 | 35.895 | 3.620 | 25.256 | 1.00 | 27.18 | A |
| ATOM | 2204 | O | ALA | A | 348 | 36.830 | 3.148 | 24.613 | 1.00 | 29.41 | A |
| ATOM | 2205 | N | ASN | A | 349 | 34.682 | 3.769 | 24.735 | 1.00 | 26.55 | A |
| ATOM | 2206 | CA | ASN | A | 349 | 34.418 | 3.310 | 23.375 | 1.00 | 27.28 | A |
| ATOM | 2207 | CB | ASN | A | 349 | 33.700 | 1.962 | 23.444 | 1.00 | 29.37 | A |
| ATOM | 2208 | CG | ASN | A | 349 | 32.299 | 2.088 | 24.013 | 1.00 | 30.92 | A |
| ATOM | 2209 | OD1 | ASN | A | 349 | 32.045 | 2.942 | 24.859 | 1.00 | 30.17 | A |
| ATOM | 2210 | ND2 | ASN | A | 349 | 31.386 | 1.237 | 23.553 | 1.00 | 33.52 | A |
| ATOM | 2211 | C | ASN | A | 349 | 33.599 | 4.265 | 22.509 | 1.00 | 26.47 | A |
| ATOM | 2212 | O | ASN | A | 349 | 32.669 | 3.843 | 21.819 | 1.00 | 25.87 | A |
| ATOM | 2213 | N | LEU | A | 350 | 33.947 | 5.543 | 22.518 | 1.00 | 24.45 | A |
| ATOM | 2214 | CA | LEU | A | 350 | 33.203 | 6.510 | 21.721 | 1.00 | 23.14 | A |
| ATOM | 2215 | CB | LEU | A | 350 | 33.837 | 7.898 | 21.848 | 1.00 | 23.22 | A |
| ATOM | 2216 | CG | LEU | A | 350 | 33.659 | 8.605 | 23.191 | 1.00 | 21.05 | A |

-continued

| | | | | | | | | | | |
|---|---|---|---|---|---|---|---|---|---|---|
| ATOM | 2217 | CD1 | LEU | A | 350 | 34.646 | 9.756 | 23.293 | 1.00 | 19.36 | A |
| ATOM | 2218 | CD2 | LEU | A | 350 | 32.220 | 9.094 | 23.319 | 1.00 | 18.78 | A |
| ATOM | 2219 | C | LEU | A | 350 | 33.082 | 6.152 | 20.240 | 1.00 | 22.60 | A |
| ATOM | 2220 | O | LEU | A | 350 | 32.011 | 6.296 | 19.650 | 1.00 | 21.15 | A |
| ATOM | 2221 | N | HIS | A | 351 | 34.165 | 5.689 | 19.627 | 1.00 | 23.13 | A |
| ATOM | 2222 | CA | HIS | A | 351 | 34.089 | 5.387 | 18.204 | 1.00 | 27.83 | A |
| ATOM | 2223 | CB | HIS | A | 351 | 35.506 | 5.325 | 17.596 | 1.00 | 29.36 | A |
| ATOM | 2224 | CG | HIS | A | 351 | 36.082 | 3.950 | 17.493 | 1.00 | 32.07 | A |
| ATOM | 2225 | CD2 | HIS | A | 351 | 36.611 | 3.128 | 18.431 | 1.00 | 32.39 | A |
| ATOM | 2226 | ND1 | HIS | A | 351 | 36.197 | 3.285 | 16.291 | 1.00 | 33.02 | A |
| ATOM | 2227 | CE1 | HIS | A | 351 | 36.775 | 2.113 | 16.493 | 1.00 | 33.58 | A |
| ATOM | 2228 | NE2 | HIS | A | 351 | 37.036 | 1.992 | 17.782 | 1.00 | 31.76 | A |
| ATOM | 2229 | C | HIS | A | 351 | 33.258 | 4.144 | 17.874 | 1.00 | 28.12 | A |
| ATOM | 2230 | O | HIS | A | 351 | 33.015 | 3.847 | 16.707 | 1.00 | 29.49 | A |
| ATOM | 2231 | N | GLN | A | 352 | 32.800 | 3.442 | 18.908 | 1.00 | 29.28 | A |
| ATOM | 2232 | CA | GLN | A | 352 | 31.963 | 2.255 | 18.726 | 1.00 | 29.67 | A |
| ATOM | 2233 | CB | GLN | A | 352 | 32.366 | 1.145 | 19.694 | 1.00 | 30.56 | A |
| ATOM | 2234 | CG | GLN | A | 352 | 33.169 | 0.041 | 19.041 | 1.00 | 30.88 | A |
| ATOM | 2235 | CD | GLN | A | 352 | 34.493 | −0.186 | 19.729 | 1.00 | 31.21 | A |
| ATOM | 2236 | OE1 | GLN | A | 352 | 34.541 | −0.450 | 20.928 | 1.00 | 30.76 | A |
| ATOM | 2237 | NE2 | GLN | A | 352 | 35.578 | −0.084 | 18.971 | 1.00 | 32.30 | A |
| ATOM | 2238 | C | GLN | A | 352 | 30.504 | 2.638 | 18.963 | 1.00 | 30.42 | A |
| ATOM | 2239 | O | GLN | A | 352 | 29.595 | 1.831 | 18.770 | 1.00 | 29.01 | A |
| ATOM | 2240 | N | GLN | A | 353 | 30.290 | 3.875 | 19.397 | 1.00 | 27.64 | A |
| ATOM | 2241 | CA | GLN | A | 353 | 28.948 | 4.365 | 19.652 | 1.00 | 27.42 | A |
| ATOM | 2242 | CB | GLN | A | 353 | 28.977 | 5.401 | 20.775 | 1.00 | 25.77 | A |
| ATOM | 2243 | CG | GLN | A | 353 | 29.408 | 4.837 | 22.115 | 1.00 | 27.34 | A |
| ATOM | 2244 | CD | GLN | A | 353 | 29.638 | 5.914 | 23.156 | 1.00 | 27.19 | A |
| ATOM | 2245 | OE1 | GLN | A | 353 | 28.875 | 6.872 | 23.252 | 1.00 | 28.29 | A |
| ATOM | 2246 | NE2 | GLN | A | 353 | 30.687 | 5.753 | 23.951 | 1.00 | 28.79 | A |
| ATOM | 2247 | C | GLN | A | 353 | 28.375 | 4.989 | 18.385 | 1.00 | 29.00 | A |
| ATOM | 2248 | O | GLN | A | 353 | 29.118 | 5.455 | 17.516 | 1.00 | 29.14 | A |
| ATOM | 2249 | N | THR | A | 354 | 27.053 | 4.984 | 18.276 | 1.00 | 27.31 | A |
| ATOM | 2250 | CA | THR | A | 354 | 26.390 | 5.568 | 17.119 | 1.00 | 27.85 | A |
| ATOM | 2251 | CB | THR | A | 354 | 24.991 | 4.941 | 16.904 | 1.00 | 30.69 | A |
| ATOM | 2252 | OG1 | THR | A | 354 | 25.132 | 3.532 | 16.665 | 1.00 | 30.07 | A |
| ATOM | 2253 | CG2 | THR | A | 354 | 24.289 | 5.585 | 15.709 | 1.00 | 29.58 | A |
| ATOM | 2254 | C | THR | A | 354 | 26.244 | 7.062 | 17.376 | 1.00 | 26.85 | A |
| ATOM | 2255 | O | THR | A | 354 | 25.592 | 7.475 | 18.329 | 1.00 | 25.77 | A |
| ATOM | 2256 | N | PRO | A | 355 | 26.867 | 7.898 | 16.533 | 1.00 | 27.22 | A |
| ATOM | 2257 | CD | PRO | A | 355 | 27.792 | 7.588 | 15.431 | 1.00 | 25.89 | A |
| ATOM | 2258 | CA | PRO | A | 355 | 26.763 | 9.346 | 16.734 | 1.00 | 27.23 | A |
| ATOM | 2259 | CB | PRO | A | 355 | 27.625 | 9.915 | 15.609 | 1.00 | 24.91 | A |
| ATOM | 2260 | CG | PRO | A | 355 | 28.643 | 8.838 | 15.385 | 1.00 | 25.54 | A |
| ATOM | 2261 | C | PRO | A | 355 | 25.322 | 9.837 | 16.641 | 1.00 | 28.07 | A |
| ATOM | 2262 | O | PRO | A | 355 | 24.548 | 9.364 | 15.810 | 1.00 | 27.24 | A |
| ATOM | 2263 | N | PRO | A | 356 | 24.941 | 10.792 | 17.500 | 1.00 | 28.28 | A |
| ATOM | 2264 | CD | PRO | A | 356 | 25.752 | 11.560 | 18.462 | 1.00 | 28.31 | A |
| ATOM | 2265 | CA | PRO | A | 356 | 23.572 | 11.306 | 17.448 | 1.00 | 28.44 | A |
| ATOM | 2266 | CB | PRO | A | 356 | 23.539 | 12.301 | 18.604 | 1.00 | 28.11 | A |
| ATOM | 2267 | CG | PRO | A | 356 | 24.946 | 12.832 | 18.612 | 1.00 | 26.86 | A |
| ATOM | 2268 | C | PRO | A | 356 | 23.363 | 11.978 | 16.097 | 1.00 | 29.25 | A |
| ATOM | 2269 | O | PRO | A | 356 | 24.304 | 12.537 | 15.529 | 1.00 | 27.27 | A |
| ATOM | 2270 | N | ALA | A | 357 | 22.143 | 11.910 | 15.575 | 1.00 | 30.45 | A |
| ATOM | 2271 | CA | ALA | A | 357 | 21.848 | 12.521 | 14.287 | 1.00 | 32.81 | A |
| ATOM | 2272 | CB | ALA | A | 357 | 20.507 | 12.019 | 13.757 | 1.00 | 31.99 | A |
| ATOM | 2273 | C | ALA | A | 357 | 21.824 | 14.035 | 14.448 | 1.00 | 35.05 | A |
| ATOM | 2274 | O | ALA | A | 357 | 21.194 | 14.561 | 15.369 | 1.00 | 35.04 | A |
| ATOM | 2275 | N | LEU | A | 358 | 22.516 | 14.730 | 13.552 | 1.00 | 37.81 | A |
| ATOM | 2276 | CA | LEU | A | 358 | 22.578 | 16.185 | 13.597 | 1.00 | 42.15 | A |
| ATOM | 2277 | CB | LEU | A | 358 | 23.679 | 16.681 | 12.658 | 1.00 | 39.54 | A |
| ATOM | 2278 | CG | LEU | A | 358 | 25.086 | 16.285 | 13.109 | 1.00 | 39.51 | A |
| ATOM | 2279 | CD1 | LEU | A | 358 | 26.102 | 16.686 | 12.062 | 1.00 | 39.29 | A |
| ATOM | 2280 | CD2 | LEU | A | 358 | 25.395 | 16.953 | 14.445 | 1.00 | 40.01 | A |
| ATOM | 2281 | C | LEU | A | 358 | 21.241 | 16.837 | 13.242 | 1.00 | 45.91 | A |
| ATOM | 2282 | O | LEU | A | 358 | 20.874 | 16.927 | 12.069 | 1.00 | 45.71 | A |
| ATOM | 2283 | N | THR | A | 359 | 20.530 | 17.290 | 14.275 | 1.00 | 50.06 | A |
| ATOM | 2284 | CA | THR | A | 359 | 19.223 | 17.939 | 14.140 | 1.00 | 53.73 | A |
| ATOM | 2285 | CB | THR | A | 359 | 19.353 | 19.428 | 13.726 | 1.00 | 54.04 | A |
| ATOM | 2286 | OG1 | THR | A | 359 | 19.995 | 19.521 | 12.448 | 1.00 | 56.35 | A |
| ATOM | 2287 | CG2 | THR | A | 359 | 20.158 | 20.204 | 14.763 | 1.00 | 54.32 | A |
| ATOM | 2288 | C | THR | A | 359 | 18.309 | 17.236 | 13.139 | 1.00 | 54.47 | A |
| ATOM | 2289 | O | THR | A | 359 | 18.483 | 16.016 | 12.930 | 1.00 | 55.90 | A |
| ATOM | 2290 | OXT | THR | A | 359 | 17.407 | 17.908 | 12.595 | 1.00 | 56.97 | A |
| TER | | | | | | | | | | | |
| ATOM | 1 | CB | PRO | B | 71 | 99.838 | 54.646 | −7.659 | 1.00 | 20.00 | 6 |
| ATOM | 2 | CG | PRO | B | 71 | 99.216 | 55.105 | −6.341 | 1.00 | 20.00 | 6 |
| ATOM | 3 | C | PRO | B | 71 | 98.903 | 54.776 | −9.981 | 1.00 | 20.00 | 6 |
| ATOM | 4 | O | PRO | B | 71 | 98.022 | 53.925 | −10.109 | 1.00 | 20.00 | 8 |

-continued

| | | | | | | | | | | |
|---|---|---|---|---|---|---|---|---|---|---|
| ATOM | 5 | N | PRO | B | 71 | 97.782 | 55.851 | −8.042 | 1.00 | 20.00 | 7 |
| ATOM | 6 | CD | PRO | B | 71 | 97.728 | 55.323 | −6.668 | 1.00 | 20.00 | 6 |
| ATOM | 7 | CA | PRO | B | 71 | 99.087 | 55.515 | −8.658 | 1.00 | 20.00 | 6 |
| ATOM | 8 | N | PRO | B | 72 | 99.732 | 55.097 | −10.985 | 1.00 | 20.00 | 7 |
| ATOM | 9 | CD | PRO | B | 72 | 100.794 | 56.121 | −10.977 | 1.00 | 20.00 | 6 |
| ATOM | 10 | CA | PRO | B | 72 | 99.645 | 54.451 | −12.297 | 1.00 | 20.00 | 6 |
| ATOM | 11 | CB | PRO | B | 72 | 100.885 | 54.973 | −13.017 | 1.00 | 20.00 | 6 |
| ATOM | 12 | CG | PRO | B | 72 | 101.026 | 56.352 | −12.456 | 1.00 | 20.00 | 6 |
| ATOM | 13 | C | PRO | B | 72 | 99.627 | 52.924 | −12.202 | 1.00 | 20.00 | 6 |
| ATOM | 14 | O | PRO | B | 72 | 100.246 | 52.338 | −11.314 | 1.00 | 20.00 | 8 |
| ATOM | 15 | N | ALA | B | 73 | 98.906 | 52.293 | −13.122 | 1.00 | 20.00 | 7 |
| ATOM | 16 | CA | ALA | B | 73 | 98.805 | 50.840 | −13.167 | 1.00 | 20.00 | 6 |
| ATOM | 17 | CB | ALA | B | 73 | 97.420 | 50.392 | −12.710 | 1.00 | 20.00 | 6 |
| ATOM | 18 | C | ALA | B | 73 | 99.053 | 50.398 | −14.604 | 1.00 | 20.00 | 6 |
| ATOM | 19 | O | ALA | B | 73 | 99.027 | 51.215 | −15.526 | 1.00 | 20.00 | 8 |
| ATOM | 20 | N | PRO | B | 74 | 99.313 | 49.100 | −14.818 | 1.00 | 20.00 | 7 |
| ATOM | 21 | CD | PRO | B | 74 | 99.473 | 47.995 | −13.857 | 1.00 | 20.00 | 6 |
| ATOM | 22 | CA | PRO | B | 74 | 99.553 | 48.642 | −16.189 | 1.00 | 20.00 | 6 |
| ATOM | 23 | CB | PRO | B | 74 | 99.700 | 47.132 | −16.023 | 1.00 | 20.00 | 6 |
| ATOM | 24 | CG | PRO | B | 74 | 100.292 | 47.004 | −14.649 | 1.00 | 20.00 | 6 |
| ATOM | 25 | C | PRO | B | 74 | 98.371 | 49.018 | −17.079 | 1.00 | 20.00 | 6 |
| ATOM | 26 | O | PRO | B | 74 | 97.279 | 49.296 | −16.583 | 1.00 | 20.00 | 8 |
| ATOM | 27 | N | ALA | B | 75 | 98.589 | 49.037 | −18.389 | 1.00 | 20.00 | 7 |
| ATOM | 28 | CA | ALA | B | 75 | 97.516 | 49.368 | −19.321 | 1.00 | 20.00 | 6 |
| ATOM | 29 | CB | ALA | B | 75 | 98.061 | 49.462 | −20.745 | 1.00 | 20.00 | 6 |
| ATOM | 30 | C | ALA | B | 75 | 96.446 | 48.285 | −19.246 | 1.00 | 20.00 | 6 |
| ATOM | 31 | O | ALA | B | 75 | 96.745 | 47.126 | −18.961 | 1.00 | 20.00 | 8 |
| ATOM | 32 | N | LYS | B | 76 | 95.200 | 48.666 | −19.494 | 1.00 | 20.00 | 7 |
| ATOM | 33 | CA | LYS | B | 76 | 94.098 | 47.716 | −19.463 | 1.00 | 20.00 | 6 |
| ATOM | 34 | CB | LYS | B | 76 | 92.793 | 48.431 | −19.805 | 1.00 | 20.00 | 6 |
| ATOM | 35 | CG | LYS | B | 76 | 91.546 | 47.792 | −19.225 | 1.00 | 20.00 | 6 |
| ATOM | 36 | CD | LYS | B | 76 | 91.511 | 47.932 | −17.711 | 1.00 | 20.00 | 6 |
| ATOM | 37 | CZ | LYS | B | 76 | 90.184 | 47.454 | −17.152 | 1.00 | 20.00 | 6 |
| ATOM | 38 | NZ | LYS | B | 76 | 90.108 | 47.606 | −15.673 | 1.00 | 20.00 | 7 |
| ATOM | 39 | C | LYS | B | 76 | 94.389 | 46.645 | −20.513 | 1.00 | 20.00 | 6 |
| ATOM | 40 | O | LYS | B | 76 | 94.736 | 46.968 | −21.645 | 1.00 | 20.00 | 8 |
| ATOM | 41 | N | LYS | B | 77 | 94.269 | 45.374 | −20.145 | 1.00 | 20.00 | 7 |
| ATOM | 42 | CA | LYS | B | 77 | 94.525 | 44.311 | −21.107 | 1.00 | 20.00 | 6 |
| ATOM | 43 | CB | LYS | B | 77 | 94.875 | 43.008 | −20.384 | 1.00 | 20.00 | 6 |
| ATOM | 44 | CG | LYS | B | 77 | 96.117 | 43.125 | −19.506 | 1.00 | 20.00 | 6 |
| ATOM | 45 | CD | LYS | B | 77 | 96.461 | 41.812 | −18.842 | 1.00 | 20.00 | 6 |
| ATOM | 46 | CE | LYS | B | 77 | 97.501 | 42.008 | −17.745 | 1.00 | 20.00 | 6 |
| ATOM | 47 | NZ | LYS | B | 77 | 98.771 | 42.582 | −18.255 | 1.00 | 20.00 | 7 |
| ATOM | 48 | C | LYS | B | 77 | 93.311 | 44.111 | −22.012 | 1.00 | 20.00 | 6 |
| ATOM | 49 | O | LYS | B | 77 | 92.218 | 44.585 | −21.704 | 1.00 | 20.00 | 8 |
| ATOM | 50 | N | ARG | B | 78 | 93.514 | 43.418 | −23.129 | 1.00 | 20.00 | 7 |
| ATOM | 51 | CA | ARG | B | 78 | 92.442 | 43.158 | −24.086 | 1.00 | 20.00 | 6 |
| ATOM | 52 | CB | ARG | B | 78 | 92.465 | 44.224 | −25.193 | 1.00 | 20.00 | 6 |
| ATOM | 53 | CG | ARG | B | 78 | 93.787 | 44.344 | −25.925 | 1.00 | 20.00 | 6 |
| ATOM | 54 | CD | ARG | B | 78 | 93.833 | 45.612 | −26.771 | 1.00 | 20.00 | 6 |
| ATOM | 55 | NE | ARG | B | 78 | 95.052 | 45.702 | −27.575 | 1.00 | 20.00 | 7 |
| ATOM | 56 | CZ | ARG | B | 78 | 96.287 | 45.751 | −27.078 | 1.00 | 20.00 | 6 |
| ATOM | 57 | NH1 | ARG | B | 78 | 96.486 | 45.721 | −25.764 | 1.00 | 20.00 | 7 |
| ATOM | 58 | NH2 | ARG | B | 78 | 97.330 | 45.828 | −27.897 | 1.00 | 20.00 | 7 |
| ATOM | 59 | C | ARG | B | 78 | 92.570 | 41.754 | −24.678 | 1.00 | 20.00 | 6 |
| ATOM | 60 | O | ARG | B | 78 | 93.625 | 41.126 | −24.581 | 1.00 | 20.00 | 8 |
| ATOM | 61 | N | PRO | B | 79 | 91.494 | 41.240 | −25.303 | 1.00 | 20.00 | 7 |
| ATOM | 62 | CD | PRO | B | 79 | 90.195 | 41.894 | −25.543 | 1.00 | 20.00 | 6 |
| ATOM | 63 | CA | PRO | B | 79 | 91.519 | 39.899 | −25.896 | 1.00 | 20.00 | 6 |
| ATOM | 64 | CB | PRO | B | 79 | 90.214 | 39.848 | −26.691 | 1.00 | 20.00 | 6 |
| ATOM | 65 | CG | PRO | B | 79 | 89.304 | 40.725 | −25.889 | 1.00 | 20.00 | 6 |
| ATOM | 66 | C | PRO | B | 79 | 92.737 | 39.614 | −26.778 | 1.00 | 20.00 | 6 |
| ATOM | 67 | O | PRO | B | 79 | 93.311 | 38.523 | −26.717 | 1.00 | 20.00 | 8 |
| ATOM | 68 | N | GLU | B | 80 | 93.124 | 40.597 | −27.589 | 1.00 | 20.00 | 7 |
| ATOM | 69 | CA | GLU | B | 80 | 94.254 | 40.441 | −28.503 | 1.00 | 20.00 | 6 |
| ATOM | 70 | CB | GLU | B | 80 | 94.358 | 41.644 | −29.446 | 1.00 | 20.00 | 6 |
| ATOM | 71 | CG | GLU | B | 80 | 94.881 | 42.912 | −28.800 | 1.00 | 20.00 | 6 |
| ATOM | 72 | CD | GLU | B | 80 | 95.009 | 44.057 | −29.788 | 1.00 | 20.00 | 6 |
| ATOM | 73 | OE1 | GLU | B | 80 | 93.968 | 44.513 | −30.308 | 1.00 | 20.00 | 8 |
| ATOM | 74 | OE2 | GLU | B | 80 | 96.150 | 44.498 | −30.047 | 1.00 | 20.00 | 8 |
| ATOM | 75 | C | GLU | B | 80 | 95.591 | 40.235 | −27.787 | 1.00 | 20.00 | 6 |
| ATOM | 76 | O | GLU | B | 80 | 96.558 | 39.795 | −28.405 | 1.00 | 20.00 | 8 |
| ATOM | 77 | N | ASP | B | 81 | 95.656 | 40.559 | −26.497 | 1.00 | 20.00 | 7 |
| ATOM | 78 | CA | ASP | B | 81 | 96.902 | 40.380 | −25.749 | 1.00 | 20.00 | 6 |
| ATOM | 79 | CB | ASP | B | 81 | 96.888 | 41.192 | −24.446 | 1.00 | 20.00 | 6 |
| ATOM | 80 | CG | ASP | B | 81 | 96.774 | 42.688 | −24.682 | 1.00 | 20.00 | 6 |
| ATOM | 81 | OD1 | ASP | B | 81 | 97.436 | 43.193 | −25.606 | 1.00 | 20.00 | 8 |
| ATOM | 82 | OD2 | ASP | B | 81 | 96.033 | 43.362 | −23.933 | 1.00 | 20.00 | 8 |
| ATOM | 83 | C | ASP | B | 81 | 97.111 | 38.914 | −25.393 | 1.00 | 20.00 | 6 |

-continued

| | | | | | | | | | | |
|---|---|---|---|---|---|---|---|---|---|---|
| ATOM | 84 | O | ASP | B | 81 | 98.172 | 38.535 | −24.890 | 1.00 | 20.00 | 8 |
| ATOM | 85 | N | PHE | B | 82 | 96.103 | 38.093 | −25.679 | 1.00 | 20.00 | 7 |
| ATOM | 86 | CA | PHE | B | 82 | 96.140 | 36.677 | −25.340 | 1.00 | 20.00 | 6 |
| ATOM | 87 | CB | PHE | B | 82 | 95.056 | 36.369 | −24.302 | 1.00 | 20.00 | 6 |
| ATOM | 88 | CG | PHE | B | 82 | 95.157 | 37.187 | −23.050 | 1.00 | 20.00 | 6 |
| ATOM | 89 | CD1 | PHE | B | 82 | 95.880 | 36.724 | −21.959 | 1.00 | 20.00 | 6 |
| ATOM | 90 | CD2 | PHE | B | 82 | 94.525 | 38.423 | −22.961 | 1.00 | 20.00 | 6 |
| ATOM | 91 | CE1 | PHE | B | 82 | 95.976 | 37.479 | −20.793 | 1.00 | 20.00 | 6 |
| ATOM | 92 | CE2 | PHE | B | 82 | 94.615 | 39.188 | −21.800 | 1.00 | 20.00 | 6 |
| ATOM | 93 | CZ | PHE | B | 82 | 95.343 | 38.712 | −20.713 | 1.00 | 20.00 | 6 |
| ATOM | 94 | C | PHE | B | 82 | 95.929 | 35.719 | −26.496 | 1.00 | 20.00 | 6 |
| ATOM | 95 | O | PHE | B | 82 | 95.342 | 36.061 | −27.524 | 1.00 | 20.00 | 8 |
| ATOM | 96 | N | LYS | B | 83 | 96.406 | 34.500 | −26.286 | 1.00 | 20.00 | 7 |
| ATOM | 97 | CA | LYS | B | 83 | 96.242 | 33.411 | −27.228 | 1.00 | 20.00 | 6 |
| ATOM | 98 | CB | LYS | B | 83 | 97.594 | 32.777 | −27.562 | 1.00 | 20.00 | 6 |
| ATOM | 99 | CG | LYS | B | 83 | 97.503 | 31.531 | −28.425 | 1.00 | 20.00 | 6 |
| ATOM | 100 | CD | LYS | B | 83 | 98.888 | 31.074 | −28.856 | 1.00 | 20.00 | 6 |
| ATOM | 101 | CE | LYS | B | 83 | 98.826 | 29.808 | −29.699 | 1.00 | 20.00 | 6 |
| ATOM | 102 | NZ | LYS | B | 83 | 98.287 | 28.654 | −28.918 | 1.00 | 20.00 | 7 |
| ATOM | 103 | C | LYS | B | 83 | 95.387 | 32.446 | −26.416 | 1.00 | 20.00 | 6 |
| ATOM | 104 | O | LYS | B | 83 | 95.884 | 31.776 | −25.510 | 1.00 | 20.00 | 8 |
| ATOM | 105 | N | PHE | B | 84 | 94.094 | 32.393 | −26.710 | 1.00 | 20.00 | 7 |
| ATOM | 106 | CA | PHE | B | 84 | 93.217 | 31.511 | −25.958 | 1.00 | 20.00 | 6 |
| ATOM | 107 | CB | PHE | B | 84 | 91.758 | 31.928 | −26.133 | 1.00 | 20.00 | 6 |
| ATOM | 108 | CG | PHE | B | 84 | 91.426 | 33.228 | −25.462 | 1.00 | 20.00 | 6 |
| ATOM | 109 | CD1 | PHE | B | 84 | 91.668 | 34.439 | −26.099 | 1.00 | 20.00 | 6 |
| ATOM | 110 | CD2 | PHE | B | 84 | 90.907 | 33.243 | −24.174 | 1.00 | 20.00 | 6 |
| ATOM | 111 | CE1 | PHE | B | 84 | 91.400 | 35.644 | −25.464 | 1.00 | 20.00 | 6 |
| ATOM | 112 | CE2 | PHE | B | 84 | 90.636 | 34.447 | −23.528 | 1.00 | 20.00 | 6 |
| ATOM | 113 | CZ | PHE | B | 84 | 90.884 | 35.646 | −24.176 | 1.00 | 20.00 | 6 |
| ATOM | 114 | C | PHE | B | 84 | 93.402 | 30.054 | −26.335 | 1.00 | 20.00 | 6 |
| ATOM | 115 | O | PHE | B | 84 | 93.734 | 29.734 | −27.476 | 1.00 | 20.00 | 8 |
| ATOM | 116 | N | GLY | B | 85 | 93.196 | 29.178 | −25.359 | 1.00 | 20.00 | 7 |
| ATOM | 117 | CA | GLY | B | 85 | 93.349 | 27.758 | −25.591 | 1.00 | 20.00 | 6 |
| ATOM | 118 | C | GLY | B | 85 | 92.103 | 26.977 | −25.221 | 1.00 | 20.00 | 6 |
| ATOM | 119 | O | GLY | B | 85 | 90.982 | 27.393 | −25.525 | 1.00 | 20.00 | 8 |
| ATOM | 120 | N | LYS | B | 86 | 92.296 | 25.858 | −24.534 | 1.00 | 20.00 | 7 |
| ATOM | 121 | CA | LYS | B | 86 | 91.182 | 25.005 | −24.153 | 1.00 | 20.00 | 6 |
| ATOM | 122 | CB | LYS | B | 86 | 91.695 | 23.640 | −23.687 | 1.00 | 20.00 | 6 |
| ATOM | 123 | CG | LYS | B | 86 | 92.421 | 23.667 | −22.356 | 1.00 | 20.00 | 6 |
| ATOM | 124 | CD | LYS | B | 86 | 92.855 | 22.272 | −21.941 | 1.00 | 20.00 | 6 |
| ATOM | 125 | CE | LYS | B | 86 | 93.685 | 22.319 | −20.668 | 1.00 | 20.00 | 6 |
| ATOM | 126 | NZ | LYS | B | 86 | 94.209 | 20.975 | −20.287 | 1.00 | 20.00 | 7 |
| ATOM | 127 | C | LYS | B | 86 | 90.267 | 25.576 | −23.077 | 1.00 | 20.00 | 6 |
| ATOM | 128 | O | LYS | B | 86 | 90.668 | 26.410 | −22.260 | 1.00 | 20.00 | 8 |
| ATOM | 129 | N | ILE | B | 87 | 89.026 | 25.106 | −23.102 | 1.00 | 20.00 | 7 |
| ATOM | 130 | CA | ILE | B | 87 | 88.023 | 25.497 | −22.131 | 1.00 | 20.00 | 6 |
| ATOM | 131 | CB | ILE | B | 87 | 86.604 | 25.159 | −22.647 | 1.00 | 20.00 | 6 |
| ATOM | 132 | CG2 | ILE | B | 87 | 85.582 | 25.261 | −21.503 | 1.00 | 20.00 | 6 |
| ATOM | 133 | CG1 | ILE | B | 87 | 86.260 | 26.085 | −23.820 | 1.00 | 20.00 | 6 |
| ATOM | 134 | CD1 | ILE | B | 87 | 84.912 | 25.819 | −24.463 | 1.00 | 20.00 | 6 |
| ATOM | 135 | C | ILE | B | 87 | 88.312 | 24.687 | −20.872 | 1.00 | 20.00 | 6 |
| ATOM | 136 | O | ILE | B | 87 | 88.396 | 23.461 | −20.927 | 1.00 | 20.00 | 8 |
| ATOM | 137 | N | LEU | B | 88 | 88.473 | 25.368 | −19.742 | 1.00 | 20.00 | 7 |
| ATOM | 138 | CA | LEU | B | 88 | 88.757 | 24.686 | −18.486 | 1.00 | 20.00 | 6 |
| ATOM | 139 | CB | LEU | B | 88 | 89.592 | 25.586 | −17.575 | 1.00 | 20.00 | 6 |
| ATOM | 140 | CG | LEU | B | 88 | 90.968 | 25.987 | −18.112 | 1.00 | 20.00 | 6 |
| ATOM | 141 | CD1 | LEU | B | 88 | 91.611 | 27.006 | −17.186 | 1.00 | 20.00 | 6 |
| ATOM | 142 | CD2 | LEU | B | 88 | 91.836 | 24.756 | −18.234 | 1.00 | 20.00 | 6 |
| ATOM | 143 | C | LEU | B | 88 | 87.471 | 24.298 | −17.776 | 1.00 | 20.00 | 6 |
| ATOM | 144 | O | LEU | B | 88 | 87.434 | 23.334 | −17.014 | 1.00 | 20.00 | 8 |
| ATOM | 145 | N | GLY | B | 89 | 86.410 | 25.051 | −18.024 | 1.00 | 20.00 | 7 |
| ATOM | 146 | CA | GLY | B | 89 | 85.148 | 24.749 | −17.382 | 1.00 | 20.00 | 6 |
| ATOM | 147 | C | GLY | B | 89 | 84.038 | 25.599 | −17.953 | 1.00 | 20.00 | 6 |
| ATOM | 148 | O | GLY | B | 89 | 84.296 | 26.657 | −18.541 | 1.00 | 20.00 | 8 |
| ATOM | 149 | N | GLU | B | 90 | 82.807 | 25.133 | −17.781 | 1.00 | 20.00 | 7 |
| ATOM | 150 | CA | GLU | B | 90 | 81.629 | 25.832 | −18.279 | 1.00 | 20.00 | 6 |
| ATOM | 151 | CB | GLU | B | 90 | 81.041 | 25.070 | −19.471 | 1.00 | 20.00 | 6 |
| ATOM | 152 | CG | GLU | B | 90 | 81.929 | 25.084 | −20.706 | 1.00 | 20.00 | 6 |
| ATOM | 153 | CD | GLU | B | 90 | 81.434 | 24.157 | −21.802 | 1.00 | 20.00 | 6 |
| ATOM | 154 | OE1 | GLU | B | 90 | 81.539 | 22.923 | −21.639 | 1.00 | 20.00 | 8 |
| ATOM | 155 | OE2 | GLU | B | 90 | 80.935 | 24.662 | −22.827 | 1.00 | 20.00 | 8 |
| ATOM | 156 | C | GLU | B | 90 | 80.575 | 25.970 | −17.188 | 1.00 | 20.00 | 6 |
| ATOM | 157 | O | GLU | B | 90 | 80.208 | 24.994 | −16.543 | 1.00 | 20.00 | 8 |
| ATOM | 158 | N | GLY | B | 91 | 80.103 | 27.193 | −16.979 | 1.00 | 20.00 | 7 |
| ATOM | 159 | CA | GLY | B | 91 | 79.080 | 27.431 | −15.979 | 1.00 | 20.00 | 6 |
| ATOM | 160 | C | GLY | B | 91 | 77.835 | 27.949 | −16.673 | 1.00 | 20.00 | 6 |
| ATOM | 161 | O | GLY | B | 91 | 77.804 | 28.046 | −17.903 | 1.00 | 20.00 | 8 |
| ATOM | 162 | N | SER | B | 92 | 76.808 | 28.291 | −15.904 | 1.00 | 20.00 | 7 |

-continued

| | | | | | | | | | | |
|---|---|---|---|---|---|---|---|---|---|---|
| ATOM | 163 | CA | SER | B | 92 | 75.582 | 28.794 | −16.508 | 1.00 | 20.00 | 6 |
| ATOM | 164 | CB | SER | B | 92 | 74.428 | 28.719 | −15.505 | 1.00 | 20.00 | 6 |
| ATOM | 165 | OG | SER | B | 92 | 74.786 | 29.335 | −14.282 | 1.00 | 20.00 | 8 |
| ATOM | 166 | C | SER | B | 92 | 75.726 | 30.219 | −17.039 | 1.00 | 20.00 | 6 |
| ATOM | 167 | O | SER | B | 92 | 75.078 | 30.585 | −18.018 | 1.00 | 20.00 | 8 |
| ATOM | 168 | N | PHE | B | 93 | 76.578 | 31.025 | −16.411 | 1.00 | 20.00 | 7 |
| ATOM | 169 | CA | PHE | B | 93 | 76.763 | 32.399 | −16.870 | 1.00 | 20.00 | 6 |
| ATOM | 170 | CB | PHE | B | 93 | 76.276 | 33.384 | −15.807 | 1.00 | 20.00 | 6 |
| ATOM | 171 | CG | PHE | B | 93 | 74.832 | 33.220 | −15.469 | 1.00 | 20.00 | 6 |
| ATOM | 172 | CD1 | PHE | B | 93 | 74.435 | 32.323 | −14.483 | 1.00 | 20.00 | 6 |
| ATOM | 173 | CD2 | PHE | B | 93 | 73.859 | 33.914 | −16.183 | 1.00 | 20.00 | 6 |
| ATOM | 174 | CE1 | PHE | B | 93 | 73.086 | 32.117 | −14.210 | 1.00 | 20.00 | 6 |
| ATOM | 175 | CE2 | PHE | B | 93 | 72.507 | 33.715 | −15.919 | 1.00 | 20.00 | 6 |
| ATOM | 176 | CZ | PHE | B | 93 | 72.120 | 32.812 | −14.930 | 1.00 | 20.00 | 6 |
| ATOM | 177 | C | PHE | B | 93 | 78.197 | 32.736 | −17.240 | 1.00 | 20.00 | 6 |
| ATOM | 178 | O | PHE | B | 93 | 78.543 | 33.908 | −17.397 | 1.00 | 20.00 | 8 |
| ATOM | 179 | N | SER | B | 94 | 79.030 | 31.713 | −17.394 | 1.00 | 20.00 | 7 |
| ATOM | 180 | CA | SER | B | 94 | 80.421 | 31.948 | −17.735 | 1.00 | 20.00 | 6 |
| ATOM | 181 | CB | SER | B | 94 | 81.174 | 32.443 | −16.503 | 1.00 | 20.00 | 6 |
| ATOM | 182 | OG | SER | B | 94 | 81.237 | 31.410 | −15.535 | 1.00 | 20.00 | 8 |
| ATOM | 183 | C | SER | B | 94 | 81.123 | 30.707 | −18.253 | 1.00 | 20.00 | 6 |
| ATOM | 184 | O | SER | B | 94 | 80.666 | 29.584 | −18.048 | 1.00 | 20.00 | 8 |
| ATOM | 185 | N | THR | B | 95 | 82.252 | 30.937 | −18.913 | 1.00 | 20.00 | 7 |
| ATOM | 186 | CA | THR | B | 95 | 83.088 | 29.879 | −19.455 | 1.00 | 20.00 | 6 |
| ATOM | 187 | CB | THR | B | 95 | 82.942 | 29.770 | −20.985 | 1.00 | 20.00 | 6 |
| ATOM | 188 | OG1 | THR | B | 95 | 81.589 | 29.425 | −21.309 | 1.00 | 20.00 | 8 |
| ATOM | 189 | CG2 | THR | B | 95 | 83.873 | 28.694 | −21.536 | 1.00 | 20.00 | 6 |
| ATOM | 190 | C | THR | B | 95 | 84.524 | 30.264 | −19.118 | 1.00 | 20.00 | 6 |
| ATOM | 191 | O | THR | B | 95 | 84.957 | 31.388 | −19.399 | 1.00 | 20.00 | 8 |
| ATOM | 192 | N | VAL | B | 96 | 85.257 | 29.348 | −18.498 | 1.00 | 20.00 | 7 |
| ATOM | 193 | CA | VAL | B | 96 | 86.642 | 29.628 | −18.141 | 1.00 | 20.00 | 6 |
| ATOM | 194 | CB | VAL | B | 96 | 86.991 | 29.050 | −16.761 | 1.00 | 20.00 | 6 |
| ATOM | 195 | CG1 | VAL | B | 96 | 88.438 | 29.390 | −16.407 | 1.00 | 20.00 | 6 |
| ATOM | 196 | CG2 | VAL | B | 96 | 86.041 | 29.627 | −15.707 | 1.00 | 20.00 | 6 |
| ATOM | 197 | C | VAL | B | 96 | 87.541 | 29.027 | −19.210 | 1.00 | 20.00 | 6 |
| ATOM | 198 | O | VAL | B | 96 | 87.432 | 27.845 | −19.540 | 1.00 | 20.00 | 8 |
| ATOM | 199 | N | VAL | B | 97 | 88.416 | 29.858 | −19.763 | 1.00 | 20.00 | 7 |
| ATOM | 200 | CA | VAL | B | 97 | 89.312 | 29.430 | −20.824 | 1.00 | 20.00 | 6 |
| ATOM | 201 | CB | VAL | B | 97 | 89.006 | 30.194 | −22.130 | 1.00 | 20.00 | 6 |
| ATOM | 202 | CG1 | VAL | B | 97 | 89.828 | 29.624 | −23.279 | 1.00 | 20.00 | 6 |
| ATOM | 203 | CG2 | VAL | B | 97 | 87.515 | 30.116 | −22.444 | 1.00 | 20.00 | 6 |
| ATOM | 204 | C | VAL | B | 97 | 90.771 | 29.664 | −20.458 | 1.00 | 20.00 | 6 |
| ATOM | 205 | O | VAL | B | 97 | 91.122 | 30.698 | −19.889 | 1.00 | 20.00 | 8 |
| ATOM | 206 | N | LEU | B | 98 | 91.617 | 28.690 | −20.770 | 1.00 | 20.00 | 7 |
| ATOM | 207 | CA | LEU | B | 98 | 93.039 | 28.821 | −20.499 | 1.00 | 20.00 | 6 |
| ATOM | 208 | CB | LEU | B | 98 | 93.727 | 27.459 | −20.618 | 1.00 | 20.00 | 6 |
| ATOM | 209 | CG | LEU | B | 98 | 95.240 | 27.421 | −20.383 | 1.00 | 20.00 | 6 |
| ATOM | 210 | CD1 | LEU | B | 98 | 95.565 | 28.019 | −19.021 | 1.00 | 20.00 | 6 |
| ATOM | 211 | CD2 | LEU | B | 98 | 95.739 | 25.987 | −20.463 | 1.00 | 20.00 | 6 |
| ATOM | 212 | C | LEU | B | 98 | 93.580 | 29.785 | −21.552 | 1.00 | 20.00 | 6 |
| ATOM | 213 | O | LEU | B | 98 | 93.293 | 29.637 | −22.738 | 1.00 | 20.00 | 8 |
| ATOM | 214 | N | ALA | B | 99 | 94.343 | 30.783 | −21.121 | 1.00 | 20.00 | 7 |
| ATOM | 215 | CA | ALA | B | 99 | 94.897 | 31.767 | −22.043 | 1.00 | 20.00 | 6 |
| ATOM | 216 | CB | ALA | B | 99 | 94.087 | 33.055 | −21.980 | 1.00 | 20.00 | 6 |
| ATOM | 217 | C | ALA | B | 99 | 96.353 | 32.067 | −21.723 | 1.00 | 20.00 | 6 |
| ATOM | 218 | O | ALA | B | 99 | 96.748 | 32.110 | −20.554 | 1.00 | 20.00 | 8 |
| ATOM | 219 | N | ARG | B | 100 | 97.152 | 32.270 | −22.763 | 1.00 | 20.00 | 7 |
| ATOM | 220 | CA | ARG | B | 100 | 98.554 | 32.596 | −22.568 | 1.00 | 20.00 | 6 |
| ATOM | 221 | CB | ARG | B | 100 | 99.442 | 31.657 | −23.393 | 1.00 | 20.00 | 6 |
| ATOM | 222 | CG | ARG | B | 100 | 100.934 | 31.833 | −23.131 | 1.00 | 20.00 | 6 |
| ATOM | 223 | CD | ARG | B | 100 | 101.770 | 30.835 | −23.923 | 1.00 | 20.00 | 6 |
| ATOM | 224 | NE | ARG | B | 100 | 101.600 | 29.452 | −23.469 | 1.00 | 20.00 | 7 |
| ATOM | 225 | CZ | ARG | B | 100 | 102.059 | 28.970 | −22.314 | 1.00 | 20.00 | 6 |
| ATOM | 226 | NH1 | ARG | B | 100 | 102.722 | 29.752 | −21.473 | 1.00 | 20.00 | 7 |
| ATOM | 227 | NH2 | ARG | B | 100 | 101.864 | 27.694 | −22.003 | 1.00 | 20.00 | 7 |
| ATOM | 228 | C | ARG | B | 100 | 98.756 | 34.045 | −23.004 | 1.00 | 20.00 | 6 |
| ATOM | 229 | O | ARG | B | 100 | 98.454 | 34.408 | −24.146 | 1.00 | 20.00 | 8 |
| ATOM | 230 | N | GLU | B | 101 | 99.228 | 34.883 | −22.087 | 1.00 | 20.00 | 7 |
| ATOM | 231 | CA | GLU | B | 101 | 99.470 | 36.286 | −22.408 | 1.00 | 20.00 | 6 |
| ATOM | 232 | CB | GLU | B | 101 | 99.709 | 37.091 | −21.123 | 1.00 | 20.00 | 6 |
| ATOM | 233 | CG | GLU | B | 101 | 99.986 | 38.571 | −21.363 | 1.00 | 20.00 | 6 |
| ATOM | 234 | CD | GLU | B | 101 | 100.164 | 39.347 | −20.075 | 1.00 | 20.00 | 6 |
| ATOM | 235 | OE1 | GLU | B | 101 | 100.717 | 38.780 | −19.114 | 1.00 | 20.00 | 8 |
| ATOM | 236 | OE2 | GLU | B | 101 | 99.765 | 40.531 | −20.025 | 1.00 | 20.00 | 8 |
| ATOM | 237 | C | GLU | B | 101 | 100.703 | 36.338 | −23.317 | 1.00 | 20.00 | 6 |
| ATOM | 238 | O | GLU | B | 101 | 101.773 | 35.865 | −22.944 | 1.00 | 20.00 | 8 |
| ATOM | 239 | N | LEU | B | 102 | 100.546 | 36.909 | −24.507 | 1.00 | 20.00 | 7 |
| ATOM | 240 | CA | LEU | B | 102 | 101.632 | 36.982 | −25.482 | 1.00 | 20.00 | 6 |
| ATOM | 241 | CB | LEU | B | 102 | 101.145 | 37.683 | −26.753 | 1.00 | 20.00 | 6 |

| | | | | | | | | | | |
|---|---|---|---|---|---|---|---|---|---|---|
| ATOM | 242 | CG | LEU | B | 102 | 100.013 | 36.985 | −27.517 | 1.00 | 20.00 | 6 |
| ATOM | 243 | CD1 | LEU | B | 102 | 99.500 | 37.897 | −28.623 | 1.00 | 20.00 | 6 |
| ATOM | 244 | CD2 | LEU | B | 102 | 100.517 | 35.670 | −28.089 | 1.00 | 20.00 | 6 |
| ATOM | 245 | C | LEU | B | 102 | 102.906 | 37.663 | −25.000 | 1.00 | 20.00 | 6 |
| ATOM | 246 | O | LEU | B | 102 | 104.000 | 37.137 | −25.180 | 1.00 | 20.00 | 8 |
| ATOM | 247 | N | ALA | B | 103 | 102.760 | 38.828 | −24.382 | 1.00 | 20.00 | 7 |
| ATOM | 248 | CA | ALA | B | 103 | 103.909 | 39.587 | −23.910 | 1.00 | 20.00 | 6 |
| ATOM | 249 | CB | ALA | B | 103 | 103.464 | 41.002 | −23.546 | 1.00 | 20.00 | 6 |
| ATOM | 250 | C | ALA | B | 103 | 104.697 | 38.983 | −22.747 | 1.00 | 20.00 | 6 |
| ATOM | 251 | O | ALA | B | 103 | 105.832 | 39.389 | −22.503 | 1.00 | 20.00 | 8 |
| ATOM | 252 | N | THR | B | 104 | 104.122 | 38.007 | −22.050 | 1.00 | 20.00 | 7 |
| ATOM | 253 | CA | THR | B | 104 | 104.790 | 37.418 | −20.893 | 1.00 | 20.00 | 6 |
| ATOM | 254 | CB | THR | B | 104 | 104.059 | 37.799 | −19.592 | 1.00 | 20.00 | 6 |
| ATOM | 255 | OG1 | THR | B | 104 | 102.712 | 37.303 | −19.648 | 1.00 | 20.00 | 8 |
| ATOM | 256 | CG2 | THR | B | 104 | 104.033 | 39.313 | −19.404 | 1.00 | 20.00 | 6 |
| ATOM | 257 | C | THR | B | 104 | 104.880 | 35.902 | −20.901 | 1.00 | 20.00 | 6 |
| ATOM | 258 | O | THR | B | 104 | 105.677 | 35.323 | −20.160 | 1.00 | 20.00 | 8 |
| ATOM | 259 | N | SER | B | 105 | 104.042 | 35.274 | −21.722 | 1.00 | 20.00 | 7 |
| ATOM | 260 | CA | SER | B | 105 | 103.950 | 33.818 | −21.842 | 1.00 | 20.00 | 6 |
| ATOM | 261 | CB | SER | B | 105 | 105.344 | 33.213 | −22.048 | 1.00 | 20.00 | 6 |
| ATOM | 262 | OG | SER | B | 105 | 105.264 | 31.819 | −22.287 | 1.00 | 20.00 | 8 |
| ATOM | 263 | C | SER | B | 105 | 103.304 | 33.243 | −20.576 | 1.00 | 20.00 | 6 |
| ATOM | 264 | O | SER | B | 105 | 103.286 | 32.029 | −20.363 | 1.00 | 20.00 | 8 |
| ATOM | 265 | N | ARG | B | 106 | 102.771 | 34.124 | −19.736 | 1.00 | 20.00 | 7 |
| ATOM | 266 | CA | ARG | B | 106 | 102.089 | 33.709 | −18.509 | 1.00 | 20.00 | 6 |
| ATOM | 267 | CB | ARG | B | 106 | 101.833 | 34.914 | −17.598 | 1.00 | 20.00 | 6 |
| ATOM | 268 | CG | ARG | B | 106 | 103.022 | 35.361 | −16.781 | 1.00 | 20.00 | 6 |
| ATOM | 269 | CD | ARG | B | 106 | 102.724 | 36.653 | −16.045 | 1.00 | 20.00 | 6 |
| ATOM | 270 | NE | ARG | B | 106 | 103.756 | 36.940 | −15.051 | 1.00 | 20.00 | 7 |
| ATOM | 271 | CZ | ARG | B | 106 | 103.964 | 38.132 | −14.504 | 1.00 | 20.00 | 6 |
| ATOM | 272 | NH1 | ARG | B | 106 | 103.210 | 39.167 | −14.858 | 1.00 | 20.00 | 7 |
| ATOM | 273 | NH2 | ARG | B | 106 | 104.918 | 38.279 | −13.590 | 1.00 | 20.00 | 7 |
| ATOM | 274 | C | ARG | B | 106 | 100.743 | 33.082 | −18.856 | 1.00 | 20.00 | 6 |
| ATOM | 275 | O | ARG | B | 106 | 100.069 | 33.534 | −19.777 | 1.00 | 20.00 | 8 |
| ATOM | 276 | N | GLU | B | 107 | 100.354 | 32.049 | −18.115 | 1.00 | 20.00 | 7 |
| ATOM | 277 | CA | GLU | B | 107 | 99.072 | 31.390 | −18.336 | 1.00 | 20.00 | 6 |
| ATOM | 278 | CB | GLU | B | 107 | 99.193 | 29.870 | −18.212 | 1.00 | 20.00 | 6 |
| ATOM | 279 | CG | GLU | B | 107 | 100.180 | 29.207 | −19.144 | 1.00 | 20.00 | 6 |
| ATOM | 280 | CD | GLU | B | 107 | 100.124 | 27.696 | −19.023 | 1.00 | 20.00 | 6 |
| ATOM | 281 | OE1 | GLU | B | 107 | 99.373 | 27.068 | −19.798 | 1.00 | 20.00 | 8 |
| ATOM | 282 | OE2 | GLU | B | 107 | 100.813 | 27.144 | −18.138 | 1.00 | 20.00 | 8 |
| ATOM | 283 | C | GLU | B | 107 | 98.070 | 31.848 | −17.285 | 1.00 | 20.00 | 6 |
| ATOM | 284 | O | GLU | B | 107 | 98.368 | 31.833 | −16.095 | 1.00 | 20.00 | 8 |
| ATOM | 285 | N | TYR | B | 108 | 96.885 | 32.243 | −17.727 | 1.00 | 20.00 | 7 |
| ATOM | 286 | CA | TYR | B | 108 | 95.829 | 32.667 | −16.817 | 1.00 | 20.00 | 6 |
| ATOM | 287 | CB | TYR | B | 108 | 95.525 | 34.156 | −16.979 | 1.00 | 20.00 | 6 |
| ATOM | 288 | CG | TYR | B | 108 | 96.603 | 35.089 | −16.487 | 1.00 | 20.00 | 6 |
| ATOM | 289 | CD1 | TYR | B | 108 | 96.744 | 35.369 | −15.129 | 1.00 | 20.00 | 6 |
| ATOM | 290 | CE1 | TYR | B | 108 | 97.727 | 36.260 | −14.674 | 1.00 | 20.00 | 6 |
| ATOM | 291 | CD2 | TYR | B | 108 | 97.467 | 35.712 | −17.386 | 1.00 | 20.00 | 6 |
| ATOM | 292 | CE2 | TYR | B | 108 | 98.442 | 36.597 | −16.950 | 1.00 | 20.00 | 6 |
| ATOM | 293 | CZ | TYR | B | 108 | 98.569 | 36.869 | −15.599 | 1.00 | 20.00 | 6 |
| ATOM | 294 | OH | TYR | B | 108 | 99.529 | 37.756 | −15.187 | 1.00 | 20.00 | 8 |
| ATOM | 295 | C | TYR | B | 108 | 94.566 | 31.899 | −17.167 | 1.00 | 20.00 | 6 |
| ATOM | 296 | O | TYR | B | 108 | 94.389 | 31.463 | −18.306 | 1.00 | 20.00 | 8 |
| ATOM | 297 | N | ALA | B | 109 | 93.697 | 31.723 | −16.181 | 1.00 | 20.00 | 7 |
| ATOM | 298 | CA | ALA | B | 109 | 92.421 | 31.073 | −16.414 | 1.00 | 20.00 | 6 |
| ATOM | 299 | CB | ALA | B | 109 | 92.024 | 30.225 | −15.214 | 1.00 | 20.00 | 6 |
| ATOM | 300 | C | ALA | B | 109 | 91.513 | 32.288 | −16.542 | 1.00 | 20.00 | 6 |
| ATOM | 301 | O | ALA | B | 109 | 91.278 | 33.003 | −15.558 | 1.00 | 20.00 | 8 |
| ATOM | 302 | N | ILE | B | 110 | 91.042 | 32.557 | −17.756 | 1.00 | 20.00 | 7 |
| ATOM | 303 | CA | ILE | B | 110 | 90.186 | 33.711 | −17.968 | 1.00 | 20.00 | 6 |
| ATOM | 304 | CB | ILE | B | 110 | 90.574 | 34.462 | −19.271 | 1.00 | 20.00 | 6 |
| ATOM | 305 | CG2 | ILE | B | 110 | 89.628 | 35.630 | −19.507 | 1.00 | 20.00 | 6 |
| ATOM | 306 | CG1 | ILE | B | 110 | 92.023 | 34.962 | −19.159 | 1.00 | 20.00 | 6 |
| ATOM | 307 | CD1 | ILE | B | 110 | 92.487 | 35.847 | −20.312 | 1.00 | 20.00 | 6 |
| ATOM | 308 | C | ILE | B | 110 | 88.715 | 33.318 | −18.004 | 1.00 | 20.00 | 6 |
| ATOM | 309 | O | ILE | B | 110 | 88.285 | 32.527 | −18.851 | 1.00 | 20.00 | 8 |
| ATOM | 310 | N | LYS | B | 111 | 87.956 | 33.852 | −17.052 | 1.00 | 20.00 | 7 |
| ATOM | 311 | CA | LYS | B | 111 | 86.527 | 33.581 | −16.975 | 1.00 | 20.00 | 6 |
| ATOM | 312 | CB | LYS | B | 111 | 86.022 | 33.721 | −15.531 | 1.00 | 20.00 | 6 |
| ATOM | 313 | CG | LYS | B | 111 | 84.509 | 33.598 | −15.411 | 1.00 | 20.00 | 6 |
| ATOM | 314 | CD | LYS | B | 111 | 84.025 | 33.590 | −13.965 | 1.00 | 20.00 | 6 |
| ATOM | 315 | CE | LYS | B | 111 | 84.318 | 32.262 | −13.277 | 1.00 | 20.00 | 6 |
| ATOM | 316 | NZ | LYS | B | 111 | 83.784 | 32.217 | −11.875 | 1.00 | 20.00 | 7 |
| ATOM | 317 | C | LYS | B | 111 | 85.844 | 34.601 | −17.869 | 1.00 | 20.00 | 6 |
| ATOM | 318 | O | LYS | B | 111 | 86.017 | 35.807 | −17.688 | 1.00 | 20.00 | 8 |
| ATOM | 319 | N | ILE | B | 112 | 85.078 | 34.111 | −18.838 | 1.00 | 20.00 | 7 |
| ATOM | 320 | CA | ILE | B | 112 | 84.383 | 34.976 | −19.782 | 1.00 | 20.00 | 6 |

-continued

| | | | | | | | | | | |
|---|---|---|---|---|---|---|---|---|---|---|
| ATOM | 321 | CB | ILE | B | 112 | 84.695 | 34.548 | −21.233 | 1.00 | 20.00 | 6 |
| ATOM | 322 | CG2 | ILE | B | 112 | 84.042 | 35.505 | −22.216 | 1.00 | 20.00 | 6 |
| ATOM | 323 | CG1 | ILE | B | 112 | 86.216 | 34.518 | −21.440 | 1.00 | 20.00 | 6 |
| ATOM | 324 | CD1 | ILE | B | 112 | 86.657 | 33.949 | −22.779 | 1.00 | 20.00 | 6 |
| ATOM | 325 | C | ILE | B | 112 | 82.878 | 34.916 | −19.538 | 1.00 | 20.00 | 6 |
| ATOM | 326 | O | ILE | B | 112 | 82.288 | 33.839 | −19.510 | 1.00 | 20.00 | 8 |
| ATOM | 327 | N | LEU | B | 113 | 82.269 | 36.083 | −19.347 | 1.00 | 20.00 | 7 |
| ATOM | 328 | CA | LEU | B | 113 | 80.835 | 36.172 | −19.089 | 1.00 | 20.00 | 6 |
| ATOM | 329 | CB | LEU | B | 113 | 80.585 | 36.696 | −17.669 | 1.00 | 20.00 | 6 |
| ATOM | 330 | CG | LEU | B | 113 | 81.350 | 36.038 | −16.521 | 1.00 | 20.00 | 6 |
| ATOM | 331 | CD1 | LEU | B | 113 | 82.743 | 36.638 | −16.428 | 1.00 | 20.00 | 6 |
| ATOM | 332 | CD2 | LEU | B | 113 | 80.609 | 36.258 | −15.215 | 1.00 | 20.00 | 6 |
| ATOM | 333 | C | LEU | B | 113 | 80.172 | 37.110 | −20.090 | 1.00 | 20.00 | 6 |
| ATOM | 334 | O | LEU | B | 113 | 80.634 | 38.232 | −20.299 | 1.00 | 20.00 | 8 |
| ATOM | 335 | N | GLU | B | 114 | 79.088 | 36.653 | −20.709 | 1.00 | 20.00 | 7 |
| ATOM | 336 | CA | GLU | B | 114 | 78.377 | 37.472 | −21.681 | 1.00 | 20.00 | 6 |
| ATOM | 337 | CB | GLU | B | 114 | 77.514 | 36.586 | −22.581 | 1.00 | 20.00 | 6 |
| ATOM | 338 | CG | GLU | B | 114 | 76.670 | 37.366 | −23.571 | 1.00 | 20.00 | 6 |
| ATOM | 339 | CD | GLU | B | 114 | 75.749 | 36.473 | −24.372 | 1.00 | 20.00 | 6 |
| ATOM | 340 | OE1 | GLU | B | 114 | 75.083 | 35.613 | −23.760 | 1.00 | 20.00 | 8 |
| ATOM | 341 | OE2 | GLU | B | 114 | 75.684 | 36.638 | −25.611 | 1.00 | 20.00 | 8 |
| ATOM | 342 | C | GLU | B | 114 | 77.509 | 38.491 | −20.942 | 1.00 | 20.00 | 6 |
| ATOM | 343 | O | GLU | B | 114 | 76.673 | 38.122 | −20.113 | 1.00 | 20.00 | 8 |
| ATOM | 344 | N | LYS | B | 115 | 77.709 | 39.771 | −21.235 | 1.00 | 20.00 | 7 |
| ATOM | 345 | CA | LYS | B | 115 | 76.945 | 40.808 | −20.553 | 1.00 | 20.00 | 6 |
| ATOM | 346 | CB | LYS | B | 115 | 77.433 | 42.202 | −20.978 | 1.00 | 20.00 | 6 |
| ATOM | 347 | CG | LYS | B | 115 | 78.653 | 42.675 | −20.183 | 1.00 | 20.00 | 6 |
| ATOM | 348 | CD | LYS | B | 115 | 79.174 | 44.045 | −20.618 | 1.00 | 20.00 | 6 |
| ATOM | 349 | CE | LYS | B | 115 | 79.832 | 43.994 | −21.992 | 1.00 | 20.00 | 6 |
| ATOM | 350 | NZ | LYS | B | 115 | 80.536 | 45.273 | −22.323 | 1.00 | 20.00 | 7 |
| ATOM | 351 | C | LYS | B | 115 | 75.435 | 40.693 | −20.743 | 1.00 | 20.00 | 6 |
| ATOM | 352 | O | LYS | B | 115 | 74.676 | 40.787 | −19.778 | 1.00 | 20.00 | 8 |
| ATOM | 353 | N | ARG | B | 116 | 74.997 | 40.471 | −21.977 | 1.00 | 20.00 | 7 |
| ATOM | 354 | CA | ARG | B | 116 | 73.570 | 40.363 | −22.255 | 1.00 | 20.00 | 6 |
| ATOM | 355 | CB | ARG | B | 116 | 73.346 | 40.066 | −23.743 | 1.00 | 20.00 | 6 |
| ATOM | 356 | CG | ARG | B | 116 | 71.893 | 39.821 | −24.142 | 1.00 | 20.00 | 6 |
| ATOM | 357 | CD | ARG | B | 116 | 70.931 | 40.791 | −23.465 | 1.00 | 20.00 | 6 |
| ATOM | 358 | NE | ARG | B | 116 | 71.401 | 42.172 | −23.493 | 1.00 | 20.00 | 7 |
| ATOM | 359 | CZ | ARG | B | 116 | 70.780 | 43.177 | −22.884 | 1.00 | 20.00 | 6 |
| ATOM | 360 | NH1 | ARG | B | 116 | 69.663 | 42.949 | −22.207 | 1.00 | 20.00 | 7 |
| ATOM | 361 | NH2 | ARG | B | 116 | 71.278 | 44.405 | −22.942 | 1.00 | 20.00 | 7 |
| ATOM | 362 | C | ARG | B | 116 | 72.888 | 39.298 | −21.394 | 1.00 | 20.00 | 6 |
| ATOM | 363 | O | ARG | B | 116 | 71.862 | 39.567 | −20.764 | 1.00 | 20.00 | 8 |
| ATOM | 364 | N | HIS | B | 117 | 73.463 | 38.101 | −21.347 | 1.00 | 20.00 | 7 |
| ATOM | 365 | CA | HIS | B | 117 | 72.885 | 37.020 | −20.556 | 1.00 | 20.00 | 6 |
| ATOM | 366 | CB | HIS | B | 117 | 73.704 | 35.738 | −20.723 | 1.00 | 20.00 | 6 |
| ATOM | 367 | CG | HIS | B | 117 | 73.053 | 34.525 | −20.133 | 1.00 | 20.00 | 6 |
| ATOM | 368 | CD2 | HIS | B | 117 | 71.762 | 34.274 | −19.810 | 1.00 | 20.00 | 6 |
| ATOM | 369 | ND1 | HIS | B | 117 | 73.752 | 33.376 | −19.836 | 1.00 | 20.00 | 7 |
| ATOM | 370 | CE1 | HIS | B | 117 | 72.921 | 32.467 | −19.355 | 1.00 | 20.00 | 6 |
| ATOM | 371 | NE2 | HIS | B | 117 | 71.707 | 32.987 | −19.330 | 1.00 | 20.00 | 7 |
| ATOM | 372 | C | HIS | B | 117 | 72.816 | 37.386 | −19.077 | 1.00 | 20.00 | 6 |
| ATOM | 373 | O | HIS | B | 117 | 71.823 | 37.113 | −18.409 | 1.00 | 20.00 | 8 |
| ATOM | 374 | N | ILE | B | 118 | 73.882 | 37.992 | −18.564 | 1.00 | 20.00 | 7 |
| ATOM | 375 | CA | ILE | B | 118 | 73.927 | 38.391 | −17.160 | 1.00 | 20.00 | 6 |
| ATOM | 376 | CB | ILE | B | 118 | 75.269 | 39.073 | −16.827 | 1.00 | 20.00 | 6 |
| ATOM | 377 | CG2 | ILE | B | 118 | 75.180 | 39.787 | −15.486 | 1.00 | 20.00 | 6 |
| ATOM | 378 | CG1 | ILE | B | 118 | 76.392 | 38.029 | −16.834 | 1.00 | 20.00 | 6 |
| ATOM | 379 | CD1 | ILE | B | 118 | 77.784 | 38.625 | −16.709 | 1.00 | 20.00 | 6 |
| ATOM | 380 | C | ILE | B | 118 | 72.788 | 39.353 | −16.833 | 1.00 | 20.00 | 6 |
| ATOM | 381 | O | ILE | B | 118 | 72.101 | 39.196 | −15.827 | 1.00 | 20.00 | 8 |
| ATOM | 382 | N | ILE | B | 119 | 72.596 | 40.349 | −17.690 | 1.00 | 20.00 | 7 |
| ATOM | 383 | CA | ILE | B | 119 | 71.538 | 41.333 | −17.494 | 1.00 | 20.00 | 6 |
| ATOM | 384 | CB | ILE | B | 119 | 71.646 | 42.473 | −18.539 | 1.00 | 20.00 | 6 |
| ATOM | 385 | CG2 | ILE | B | 119 | 70.396 | 43.357 | −18.492 | 1.00 | 20.00 | 6 |
| ATOM | 386 | CG1 | ILE | B | 119 | 72.919 | 43.292 | −18.270 | 1.00 | 20.00 | 6 |
| ATOM | 387 | CD1 | ILE | B | 119 | 73.212 | 44.370 | −19.314 | 1.00 | 20.00 | 6 |
| ATOM | 388 | C | ILE | B | 119 | 70.154 | 40.687 | −17.580 | 1.00 | 20.00 | 6 |
| ATOM | 389 | O | ILE | B | 119 | 69.289 | 40.953 | −16.747 | 1.00 | 20.00 | 8 |
| ATOM | 390 | N | LYS | B | 120 | 69.950 | 39.832 | −18.579 | 1.00 | 20.00 | 7 |
| ATOM | 391 | CA | LYS | B | 120 | 68.659 | 39.169 | −18.754 | 1.00 | 20.00 | 6 |
| ATOM | 392 | CB | LYS | B | 120 | 68.697 | 38.200 | −19.935 | 1.00 | 20.00 | 6 |
| ATOM | 393 | CG | LYS | B | 120 | 68.942 | 38.841 | −21.284 | 1.00 | 20.00 | 6 |
| ATOM | 394 | CD | LYS | B | 120 | 68.926 | 37.782 | −22.387 | 1.00 | 20.00 | 6 |
| ATOM | 395 | CE | LYS | B | 120 | 69.934 | 36.665 | −22.093 | 1.00 | 20.00 | 6 |
| ATOM | 396 | NZ | LYS | B | 120 | 69.950 | 35.599 | −23.127 | 1.00 | 20.00 | 7 |
| ATOM | 397 | C | LYS | B | 120 | 68.229 | 38.398 | −17.513 | 1.00 | 20.00 | 6 |
| ATOM | 398 | O | LYS | B | 120 | 67.077 | 38.490 | −17.092 | 1.00 | 20.00 | 8 |
| ATOM | 399 | N | GLU | B | 121 | 69.154 | 37.639 | −16.930 | 1.00 | 20.00 | 7 |

-continued

| | | | | | | | | | | |
|---|---|---|---|---|---|---|---|---|---|---|
| ATOM | 400 | CA | GLU | B | 121 | 68.851 | 36.839 | −15.747 | 1.00 | 20.00 | 6 |
| ATOM | 401 | CB | GLU | B | 121 | 69.678 | 35.549 | −15.758 | 1.00 | 20.00 | 6 |
| ATOM | 402 | CG | GLU | B | 121 | 69.485 | 34.674 | −16.995 | 1.00 | 20.00 | 6 |
| ATOM | 403 | CD | GLU | B | 121 | 68.029 | 34.326 | −17.248 | 1.00 | 20.00 | 6 |
| ATOM | 404 | OE1 | GLU | B | 121 | 67.339 | 33.904 | −16.295 | 1.00 | 20.00 | 8 |
| ATOM | 405 | OE2 | GLU | B | 121 | 67.574 | 34.470 | −18.404 | 1.00 | 20.00 | 8 |
| ATOM | 406 | C | GLU | B | 121 | 69.071 | 37.573 | −14.424 | 1.00 | 20.00 | 6 |
| ATOM | 407 | O | GLU | B | 121 | 69.117 | 36.946 | −13.362 | 1.00 | 20.00 | 8 |
| ATOM | 408 | N | ASN | B | 122 | 69.208 | 38.895 | −14.485 | 1.00 | 20.00 | 7 |
| ATOM | 409 | CA | ASN | B | 122 | 69.411 | 39.699 | −13.281 | 1.00 | 20.00 | 6 |
| ATOM | 410 | CB | ASN | B | 122 | 68.132 | 39.715 | −12.439 | 1.00 | 20.00 | 6 |
| ATOM | 411 | CG | ASN | B | 122 | 66.952 | 40.314 | −13.177 | 1.00 | 20.00 | 6 |
| ATOM | 412 | OD1 | ASN | B | 122 | 66.428 | 39.725 | −14.121 | 1.00 | 20.00 | 8 |
| ATOM | 413 | ND2 | ASN | B | 122 | 66.530 | 41.498 | −12.748 | 1.00 | 20.00 | 7 |
| ATOM | 414 | C | ASN | B | 122 | 70.563 | 39.180 | −12.419 | 1.00 | 20.00 | 6 |
| ATOM | 415 | O | ASN | B | 122 | 70.408 | 39.007 | −11.212 | 1.00 | 20.00 | 8 |
| ATOM | 416 | N | LYS | B | 123 | 71.716 | 38.942 | −13.033 | 1.00 | 20.00 | 7 |
| ATOM | 417 | CA | LYS | B | 123 | 72.870 | 38.434 | −12.301 | 1.00 | 20.00 | 6 |
| ATOM | 418 | CB | LYS | B | 123 | 73.500 | 37.266 | −13.065 | 1.00 | 20.00 | 6 |
| ATOM | 419 | CG | LYS | B | 123 | 72.568 | 36.086 | −13.276 | 1.00 | 20.00 | 6 |
| ATOM | 420 | CD | LYS | B | 123 | 72.065 | 35.539 | −11.948 | 1.00 | 20.00 | 6 |
| ATOM | 421 | CE | LYS | B | 123 | 71.032 | 34.445 | −12.159 | 1.00 | 20.00 | 6 |
| ATOM | 422 | NZ | LYS | B | 123 | 70.421 | 34.016 | −10.871 | 1.00 | 20.00 | 7 |
| ATOM | 423 | C | LYS | B | 123 | 73.931 | 39.498 | −12.054 | 1.00 | 20.00 | 6 |
| ATOM | 424 | O | LYS | B | 123 | 75.035 | 39.183 | −11.611 | 1.00 | 20.00 | 8 |
| ATOM | 425 | N | VAL | B | 124 | 73.607 | 40.753 | −12.340 | 1.00 | 20.00 | 7 |
| ATOM | 426 | CA | VAL | B | 124 | 74.575 | 41.822 | −12.145 | 1.00 | 20.00 | 6 |
| ATOM | 427 | CB | VAL | B | 124 | 73.997 | 43.201 | −12.547 | 1.00 | 20.00 | 6 |
| ATOM | 428 | CG1 | VAL | B | 124 | 75.035 | 44.290 | −12.302 | 1.00 | 20.00 | 6 |
| ATOM | 429 | CG2 | VAL | B | 124 | 73.608 | 43.186 | −14.022 | 1.00 | 20.00 | 6 |
| ATOM | 430 | C | VAL | B | 124 | 75.091 | 41.885 | −10.712 | 1.00 | 20.00 | 6 |
| ATOM | 431 | O | VAL | B | 124 | 76.278 | 42.115 | −10.490 | 1.00 | 20.00 | 8 |
| ATOM | 432 | N | PRO | B | 125 | 74.207 | 41.695 | −9.716 | 1.00 | 20.00 | 7 |
| ATOM | 433 | CD | PRO | B | 125 | 72.735 | 41.613 | −9.757 | 1.00 | 20.00 | 6 |
| ATOM | 434 | CA | PRO | B | 125 | 74.688 | 41.747 | −8.331 | 1.00 | 20.00 | 6 |
| ATOM | 435 | CB | PRO | B | 125 | 73.411 | 41.558 | −7.512 | 1.00 | 20.00 | 6 |
| ATOM | 436 | CG | PRO | B | 125 | 72.346 | 42.152 | −8.396 | 1.00 | 20.00 | 6 |
| ATOM | 437 | C | PRO | B | 125 | 75.715 | 40.643 | −8.051 | 1.00 | 20.00 | 6 |
| ATOM | 438 | O | PRO | B | 125 | 76.683 | 40.851 | −7.325 | 1.00 | 20.00 | 8 |
| ATOM | 439 | N | TYR | B | 126 | 75.493 | 39.475 | −8.640 | 1.00 | 20.00 | 7 |
| ATOM | 440 | CA | TYR | B | 126 | 76.380 | 38.334 | −8.440 | 1.00 | 20.00 | 6 |
| ATOM | 441 | CB | TYR | B | 126 | 75.699 | 37.059 | −8.942 | 1.00 | 20.00 | 6 |
| ATOM | 442 | CG | TYR | B | 126 | 74.479 | 36.687 | −8.127 | 1.00 | 20.00 | 6 |
| ATOM | 443 | CD1 | TYR | B | 126 | 74.611 | 36.068 | −6.884 | 1.00 | 20.00 | 6 |
| ATOM | 444 | CE1 | TYR | B | 126 | 73.491 | 35.748 | −6.112 | 1.00 | 20.00 | 6 |
| ATOM | 445 | CD2 | TYR | B | 126 | 73.193 | 36.981 | −8.583 | 1.00 | 20.00 | 6 |
| ATOM | 446 | CE2 | TYR | B | 126 | 72.063 | 36.667 | −7.817 | 1.00 | 20.00 | 6 |
| ATOM | 447 | CZ | TYR | B | 126 | 72.223 | 36.052 | −6.584 | 1.00 | 20.00 | 6 |
| ATOM | 448 | OH | TYR | B | 126 | 71.118 | 35.743 | −5.823 | 1.00 | 20.00 | 8 |
| ATOM | 449 | C | TYR | B | 126 | 77.738 | 38.511 | −9.113 | 1.00 | 20.00 | 6 |
| ATOM | 450 | O | TYR | B | 126 | 78.777 | 38.273 | −8.492 | 1.00 | 20.00 | 8 |
| ATOM | 451 | N | VAL | B | 127 | 77.738 | 38.931 | −10.374 | 1.00 | 20.00 | 7 |
| ATOM | 452 | CA | VAL | B | 127 | 78.994 | 39.123 | −11.085 | 1.00 | 20.00 | 6 |
| ATOM | 453 | CB | VAL | B | 127 | 78.756 | 39.466 | −12.567 | 1.00 | 20.00 | 6 |
| ATOM | 454 | CG1 | VAL | B | 127 | 80.096 | 39.637 | −13.275 | 1.00 | 20.00 | 6 |
| ATOM | 455 | CG2 | VAL | B | 127 | 77.949 | 38.357 | −13.234 | 1.00 | 20.00 | 6 |
| ATOM | 456 | C | VAL | B | 127 | 79.798 | 40.242 | −10.427 | 1.00 | 20.00 | 6 |
| ATOM | 457 | O | VAL | B | 127 | 81.016 | 40.148 | −10.292 | 1.00 | 20.00 | 8 |
| ATOM | 458 | N | THR | B | 128 | 79.105 | 41.293 | −10.006 | 1.00 | 20.00 | 7 |
| ATOM | 459 | CA | THR | B | 128 | 79.746 | 42.424 | −9.345 | 1.00 | 20.00 | 6 |
| ATOM | 460 | CB | THR | B | 128 | 78.721 | 43.548 | −9.070 | 1.00 | 20.00 | 6 |
| ATOM | 461 | OG1 | THR | B | 128 | 78.194 | 44.025 | −10.316 | 1.00 | 20.00 | 8 |
| ATOM | 462 | CG2 | THR | B | 128 | 79.371 | 44.703 | −8.330 | 1.00 | 20.00 | 6 |
| ATOM | 463 | C | THR | B | 128 | 80.372 | 41.979 | −8.019 | 1.00 | 20.00 | 6 |
| ATOM | 464 | O | THR | B | 128 | 81.500 | 42.355 | −7.696 | 1.00 | 20.00 | 8 |
| ATOM | 465 | N | ARG | B | 129 | 79.637 | 41.172 | −7.256 | 1.00 | 20.00 | 7 |
| ATOM | 466 | CA | ARG | B | 129 | 80.126 | 40.678 | −5.971 | 1.00 | 20.00 | 6 |
| ATOM | 467 | CB | ARG | B | 129 | 79.035 | 39.888 | −5.254 | 1.00 | 20.00 | 6 |
| ATOM | 468 | CG | ARG | B | 129 | 79.428 | 39.438 | −3.852 | 1.00 | 20.00 | 6 |
| ATOM | 469 | CD | ARG | B | 129 | 78.351 | 38.554 | −3.278 | 1.00 | 20.00 | 6 |
| ATOM | 470 | NE | ARG | B | 129 | 77.048 | 39.209 | −3.315 | 1.00 | 20.00 | 7 |
| ATOM | 471 | CZ | ARG | B | 129 | 75.894 | 38.569 | −3.484 | 1.00 | 20.00 | 6 |
| ATOM | 472 | NH1 | ARG | B | 129 | 75.878 | 37.250 | −3.636 | 1.00 | 20.00 | 7 |
| ATOM | 473 | NH2 | ARG | B | 129 | 74.756 | 39.248 | −3.501 | 1.00 | 20.00 | 7 |
| ATOM | 474 | C | ARG | B | 129 | 81.354 | 39.788 | −6.146 | 1.00 | 20.00 | 6 |
| ATOM | 475 | O | ARG | B | 129 | 82.315 | 39.885 | −5.379 | 1.00 | 20.00 | 8 |
| ATOM | 476 | N | GLU | B | 130 | 81.316 | 38.917 | −7.151 | 1.00 | 20.00 | 7 |
| ATOM | 477 | CA | GLU | B | 130 | 82.439 | 38.029 | −7.421 | 1.00 | 20.00 | 6 |
| ATOM | 478 | CB | GLU | B | 130 | 82.191 | 37.211 | −8.692 | 1.00 | 20.00 | 6 |

-continued

| | | | | | | | | | |
|---|---|---|---|---|---|---|---|---|---|
| ATOM | 479 | CG | GLU | B | 130 | 83.408 | 36.427 | −9.167 | 1.00 | 20.00 | 6 |
| ATOM | 480 | CD | GLU | B | 130 | 83.060 | 35.338 | −10.168 | 1.00 | 20.00 | 6 |
| ATOM | 481 | OE1 | GLU | B | 130 | 82.227 | 35.590 | −11.061 | 1.00 | 20.00 | 8 |
| ATOM | 482 | OE2 | GLU | B | 130 | 83.626 | 34.231 | −10.068 | 1.00 | 20.00 | 8 |
| ATOM | 483 | C | GLU | B | 130 | 83.708 | 38.853 | −7.580 | 1.00 | 20.00 | 6 |
| ATOM | 484 | O | GLU | B | 130 | 84.723 | 38.575 | −6.940 | 1.00 | 20.00 | 8 |
| ATOM | 485 | N | ARG | B | 131 | 83.641 | 39.874 | −8.428 | 1.00 | 20.00 | 7 |
| ATOM | 486 | CA | ARG | B | 131 | 84.788 | 40.742 | −8.673 | 1.00 | 20.00 | 6 |
| ATOM | 487 | CB | ARG | B | 131 | 84.459 | 41.759 | −9.777 | 1.00 | 20.00 | 6 |
| ATOM | 488 | CG | ARG | B | 131 | 85.580 | 42.753 | −10.035 | 1.00 | 20.00 | 6 |
| ATOM | 489 | CD | ARG | B | 131 | 85.262 | 43.716 | −11.167 | 1.00 | 20.00 | 6 |
| ATOM | 490 | NE | ARG | B | 131 | 86.351 | 44.673 | −11.355 | 1.00 | 20.00 | 7 |
| ATOM | 491 | CZ | ARG | B | 131 | 86.416 | 45.561 | −12.343 | 1.00 | 20.00 | 6 |
| ATOM | 492 | NH1 | ARG | B | 131 | 85.450 | 45.623 | −13.250 | 1.00 | 20.00 | 7 |
| ATOM | 493 | NH2 | ARG | B | 131 | 87.450 | 46.388 | −12.426 | 1.00 | 20.00 | 7 |
| ATOM | 494 | C | ARG | B | 131 | 85.228 | 41.485 | −7.409 | 1.00 | 20.00 | 6 |
| ATOM | 495 | O | ARG | B | 131 | 86.413 | 41.500 | −7.071 | 1.00 | 20.00 | 8 |
| ATOM | 496 | N | ASP | B | 132 | 84.277 | 42.103 | −6.715 | 1.00 | 20.00 | 7 |
| ATOM | 497 | CA | ASP | B | 132 | 84.594 | 42.848 | −5.505 | 1.00 | 20.00 | 6 |
| ATOM | 498 | CB | ASP | B | 132 | 83.350 | 43.575 | −4.987 | 1.00 | 20.00 | 6 |
| ATOM | 499 | CG | ASP | B | 132 | 82.865 | 44.658 | −5.943 | 1.00 | 20.00 | 6 |
| ATOM | 500 | OD1 | ASP | B | 132 | 83.612 | 45.010 | −6.886 | 1.00 | 20.00 | 8 |
| ATOM | 501 | OD2 | ASP | B | 132 | 81.739 | 45.167 | −5.747 | 1.00 | 20.00 | 8 |
| ATOM | 502 | C | ASP | B | 132 | 85.192 | 41.969 | −4.401 | 1.00 | 20.00 | 6 |
| ATOM | 503 | O | ASP | B | 132 | 86.191 | 42.337 | −3.783 | 1.00 | 20.00 | 8 |
| ATOM | 504 | N | VAL | B | 133 | 84.596 | 40.809 | −4.150 | 1.00 | 20.00 | 7 |
| ATOM | 505 | CA | VAL | B | 133 | 85.131 | 39.933 | −3.116 | 1.00 | 20.00 | 6 |
| ATOM | 506 | CB | VAL | B | 133 | 84.226 | 38.698 | −2.885 | 1.00 | 20.00 | 6 |
| ATOM | 507 | CG1 | VAL | B | 133 | 84.920 | 37.713 | −1.957 | 1.00 | 20.00 | 6 |
| ATOM | 508 | CG2 | VAL | B | 133 | 82.893 | 39.135 | −2.271 | 1.00 | 20.00 | 6 |
| ATOM | 509 | C | VAL | B | 133 | 86.540 | 39.470 | −3.477 | 1.00 | 20.00 | 6 |
| ATOM | 510 | O | VAL | B | 133 | 87.460 | 39.602 | −2.675 | 1.00 | 20.00 | 8 |
| ATOM | 511 | N | MET | B | 134 | 86.721 | 38.950 | −4.688 | 1.00 | 20.00 | 7 |
| ATOM | 512 | CA | MET | B | 134 | 88.040 | 38.474 | −5.083 | 1.00 | 20.00 | 6 |
| ATOM | 513 | CB | MET | B | 134 | 88.004 | 37.879 | −6.492 | 1.00 | 20.00 | 6 |
| ATOM | 514 | CG | MET | B | 134 | 87.183 | 36.603 | −6.573 | 1.00 | 20.00 | 6 |
| ATOM | 515 | SD | MET | B | 134 | 87.477 | 35.650 | −8.077 | 1.00 | 20.00 | 16 |
| ATOM | 516 | CE | MET | B | 134 | 88.730 | 34.515 | −7.475 | 1.00 | 20.00 | 6 |
| ATOM | 517 | C | MET | B | 134 | 89.115 | 39.552 | −4.994 | 1.00 | 20.00 | 6 |
| ATOM | 518 | O | MET | B | 134 | 90.253 | 39.264 | −4.626 | 1.00 | 20.00 | 8 |
| ATOM | 519 | N | SER | B | 135 | 88.758 | 40.790 | −5.319 | 1.00 | 20.00 | 7 |
| ATOM | 520 | CA | SER | B | 135 | 89.708 | 41.899 | −5.260 | 1.00 | 20.00 | 6 |
| ATOM | 521 | CB | SER | B | 135 | 89.084 | 43.175 | −5.836 | 1.00 | 20.00 | 6 |
| ATOM | 522 | OG | SER | B | 135 | 88.742 | 43.009 | −7.202 | 1.00 | 20.00 | 8 |
| ATOM | 523 | C | SER | B | 135 | 90.165 | 42.184 | −3.830 | 1.00 | 20.00 | 6 |
| ATOM | 524 | O | SER | B | 135 | 91.228 | 42.762 | −3.614 | 1.00 | 20.00 | 8 |
| ATOM | 525 | N | ARG | B | 136 | 89.354 | 41.782 | −2.857 | 1.00 | 20.00 | 7 |
| ATOM | 526 | CA | ARG | B | 136 | 89.672 | 42.013 | −1.450 | 1.00 | 20.00 | 6 |
| ATOM | 527 | CB | ARG | B | 136 | 88.384 | 42.156 | −0.637 | 1.00 | 20.00 | 6 |
| ATOM | 528 | CG | ARG | B | 136 | 87.509 | 43.336 | −1.018 | 1.00 | 20.00 | 6 |
| ATOM | 529 | CD | ARG | B | 136 | 86.215 | 43.306 | −0.211 | 1.00 | 20.00 | 6 |
| ATOM | 530 | NE | ARG | B | 136 | 86.491 | 43.117 | 1.209 | 1.00 | 20.00 | 7 |
| ATOM | 531 | CZ | ARG | B | 136 | 85.565 | 42.888 | 2.132 | 1.00 | 20.00 | 6 |
| ATOM | 532 | NH1 | ARG | B | 136 | 84.285 | 42.821 | 1.786 | 1.00 | 20.00 | 7 |
| ATOM | 533 | NH2 | ARG | B | 136 | 85.920 | 42.715 | 3.401 | 1.00 | 20.00 | 7 |
| ATOM | 534 | C | ARG | B | 136 | 90.506 | 40.891 | −0.839 | 1.00 | 20.00 | 6 |
| ATOM | 535 | O | ARG | B | 136 | 91.091 | 41.054 | 0.231 | 1.00 | 20.00 | 8 |
| ATOM | 536 | N | LEU | B | 137 | 90.556 | 39.752 | −1.515 | 1.00 | 20.00 | 7 |
| ATOM | 537 | CA | LEU | B | 137 | 91.300 | 38.609 | −1.005 | 1.00 | 20.00 | 6 |
| ATOM | 538 | CB | LEU | B | 137 | 90.665 | 37.307 | −1.504 | 1.00 | 20.00 | 6 |
| ATOM | 539 | CG | LEU | B | 137 | 89.172 | 37.099 | −1.213 | 1.00 | 20.00 | 6 |
| ATOM | 540 | CD1 | LEU | B | 137 | 88.748 | 35.728 | −1.734 | 1.00 | 20.00 | 6 |
| ATOM | 541 | CD2 | LEU | B | 137 | 88.897 | 37.205 | 0.280 | 1.00 | 20.00 | 6 |
| ATOM | 542 | C | LEU | B | 137 | 92.771 | 38.648 | −1.402 | 1.00 | 20.00 | 6 |
| ATOM | 543 | O | LEU | B | 137 | 93.103 | 38.871 | −2.566 | 1.00 | 20.00 | 8 |
| ATOM | 544 | N | ASP | B | 138 | 93.645 | 38.436 | −0.424 | 1.00 | 20.00 | 7 |
| ATOM | 545 | CA | ASP | B | 138 | 95.086 | 38.422 | −0.656 | 1.00 | 20.00 | 6 |
| ATOM | 546 | CB | ASP | B | 138 | 95.696 | 39.797 | −0.352 | 1.00 | 20.00 | 6 |
| ATOM | 547 | CG | ASP | B | 138 | 97.179 | 39.854 | −0.674 | 1.00 | 20.00 | 6 |
| ATOM | 548 | OD1 | ASP | B | 138 | 97.601 | 39.173 | −1.634 | 1.00 | 20.00 | 8 |
| ATOM | 549 | OD2 | ASP | B | 138 | 97.920 | 40.581 | 0.022 | 1.00 | 20.00 | 8 |
| ATOM | 550 | C | ASP | B | 138 | 95.678 | 37.369 | 0.263 | 1.00 | 20.00 | 6 |
| ATOM | 551 | O | ASP | B | 138 | 96.353 | 37.685 | 1.243 | 1.00 | 20.00 | 8 |
| ATOM | 552 | N | HIS | B | 139 | 95.410 | 36.111 | −0.065 | 1.00 | 20.00 | 7 |
| ATOM | 553 | CA | HIS | B | 139 | 95.871 | 34.984 | 0.731 | 1.00 | 20.00 | 6 |
| ATOM | 554 | CB | HIS | B | 139 | 94.769 | 34.610 | 1.737 | 1.00 | 20.00 | 6 |
| ATOM | 555 | CG | HIS | B | 139 | 95.173 | 33.561 | 2.725 | 1.00 | 20.00 | 6 |
| ATOM | 556 | CD2 | HIS | B | 139 | 95.543 | 33.657 | 4.025 | 1.00 | 20.00 | 6 |
| ATOM | 557 | ND1 | HIS | B | 139 | 95.241 | 32.221 | 2.405 | 1.00 | 20.00 | 7 |

-continued

| | | | | | | | | | | |
|---|---|---|---|---|---|---|---|---|---|---|
| ATOM | 558 | CE1 | HIS | B | 139 | 95.635 | 31.537 | 3.466 | 1.00 | 20.00 | 6 |
| ATOM | 559 | NE2 | HIS | B | 139 | 95.825 | 32.385 | 4.461 | 1.00 | 20.00 | 7 |
| ATOM | 560 | C | HIS | B | 139 | 96.176 | 33.828 | −0.221 | 1.00 | 20.00 | 6 |
| ATOM | 561 | O | HIS | B | 139 | 95.444 | 33.595 | −1.182 | 1.00 | 20.00 | 8 |
| ATOM | 562 | N | PRO | B | 140 | 97.257 | 33.080 | 0.038 | 1.00 | 20.00 | 7 |
| ATOM | 563 | CD | PRO | B | 140 | 98.128 | 33.140 | 1.225 | 1.00 | 20.00 | 6 |
| ATOM | 564 | CA | PRO | B | 140 | 97.635 | 31.959 | −0.827 | 1.00 | 20.00 | 6 |
| ATOM | 565 | CB | PRO | B | 140 | 98.913 | 31.433 | −0.171 | 1.00 | 20.00 | 6 |
| ATOM | 566 | CG | PRO | B | 140 | 98.687 | 31.730 | 1.277 | 1.00 | 20.00 | 6 |
| ATOM | 567 | C | PRO | B | 140 | 96.614 | 30.846 | −1.072 | 1.00 | 20.00 | 6 |
| ATOM | 568 | O | PRO | B | 140 | 96.747 | 30.107 | −2.044 | 1.00 | 20.00 | 8 |
| ATOM | 569 | N | PHE | B | 141 | 95.607 | 30.712 | −0.211 | 1.00 | 20.00 | 7 |
| ATOM | 570 | CA | PHE | B | 141 | 94.620 | 29.649 | −0.398 | 1.00 | 20.00 | 6 |
| ATOM | 571 | CB | PHE | B | 141 | 94.206 | 29.056 | 0.961 | 1.00 | 20.00 | 6 |
| ATOM | 572 | CG | PHE | B | 141 | 95.321 | 28.335 | 1.681 | 1.00 | 20.00 | 6 |
| ATOM | 573 | CD1 | PHE | B | 141 | 96.351 | 27.716 | 0.967 | 1.00 | 20.00 | 6 |
| ATOM | 574 | CD2 | PHE | B | 141 | 95.311 | 28.227 | 3.067 | 1.00 | 20.00 | 6 |
| ATOM | 575 | CE1 | PHE | B | 141 | 97.350 | 27.000 | 1.627 | 1.00 | 20.00 | 6 |
| ATOM | 576 | CE2 | PHE | B | 141 | 96.307 | 27.510 | 3.740 | 1.00 | 20.00 | 6 |
| ATOM | 577 | CZ | PHE | B | 141 | 97.328 | 26.895 | 3.018 | 1.00 | 20.00 | 6 |
| ATOM | 578 | C | PHE | B | 141 | 93.371 | 30.063 | −1.181 | 1.00 | 20.00 | 6 |
| ATOM | 579 | O | PHE | B | 141 | 92.335 | 29.398 | −1.114 | 1.00 | 20.00 | 8 |
| ATOM | 580 | N | PHE | B | 142 | 93.471 | 31.150 | −1.934 | 1.00 | 20.00 | 7 |
| ATOM | 581 | CA | PHE | B | 142 | 92.337 | 31.625 | −2.721 | 1.00 | 20.00 | 6 |
| ATOM | 582 | CB | PHE | B | 142 | 91.739 | 32.883 | −2.082 | 1.00 | 20.00 | 6 |
| ATOM | 583 | CG | PHE | B | 142 | 91.048 | 32.628 | −0.772 | 1.00 | 20.00 | 6 |
| ATOM | 584 | CD1 | PHE | B | 142 | 89.715 | 32.227 | −0.740 | 1.00 | 20.00 | 6 |
| ATOM | 585 | CD2 | PHE | B | 142 | 91.741 | 32.747 | 0.429 | 1.00 | 20.00 | 6 |
| ATOM | 586 | CE1 | PHE | B | 142 | 89.080 | 31.944 | 0.472 | 1.00 | 20.00 | 6 |
| ATOM | 587 | CE2 | PHE | B | 142 | 91.116 | 32.465 | 1.647 | 1.00 | 20.00 | 6 |
| ATOM | 588 | CZ | PHE | B | 142 | 89.785 | 32.064 | 1.667 | 1.00 | 20.00 | 6 |
| ATOM | 589 | C | PHE | B | 142 | 92.758 | 31.945 | −4.146 | 1.00 | 20.00 | 6 |
| ATOM | 590 | O | PHE | B | 142 | 93.865 | 32.429 | −4.371 | 1.00 | 20.00 | 8 |
| ATOM | 591 | N | VAL | B | 143 | 91.883 | 31.653 | −5.106 | 1.00 | 20.00 | 7 |
| ATOM | 592 | CA | VAL | B | 143 | 92.167 | 31.960 | −6.504 | 1.00 | 20.00 | 6 |
| ATOM | 593 | CB | VAL | B | 143 | 91.009 | 31.513 | −7.435 | 1.00 | 20.00 | 6 |
| ATOM | 594 | CG1 | VAL | B | 143 | 91.116 | 32.209 | −8.795 | 1.00 | 20.00 | 6 |
| ATOM | 595 | CG2 | VAL | B | 143 | 91.061 | 30.000 | −7.623 | 1.00 | 20.00 | 6 |
| ATOM | 596 | C | VAL | B | 143 | 92.301 | 33.469 | −6.545 | 1.00 | 20.00 | 6 |
| ATOM | 597 | O | VAL | B | 143 | 91.505 | 34.179 | −5.932 | 1.00 | 20.00 | 8 |
| ATOM | 598 | N | LYS | B | 144 | 93.312 | 33.957 | −7.252 | 1.00 | 20.00 | 7 |
| ATOM | 599 | CA | LYS | B | 144 | 93.547 | 35.392 | −7.340 | 1.00 | 20.00 | 6 |
| ATOM | 600 | CB | LYS | B | 144 | 95.051 | 35.689 | −7.267 | 1.00 | 20.00 | 6 |
| ATOM | 601 | CG | LYS | B | 144 | 95.382 | 37.182 | −7.318 | 1.00 | 20.00 | 6 |
| ATOM | 602 | CD | LYS | B | 144 | 96.881 | 37.441 | −7.201 | 1.00 | 20.00 | 6 |
| ATOM | 603 | CE | LYS | B | 144 | 97.191 | 38.936 | −7.298 | 1.00 | 20.00 | 6 |
| ATOM | 604 | NZ | LYS | B | 144 | 98.661 | 39.215 | −7.246 | 1.00 | 20.00 | 7 |
| ATOM | 605 | C | LYS | B | 144 | 92.989 | 36.003 | −8.614 | 1.00 | 20.00 | 6 |
| ATOM | 606 | O | LYS | B | 144 | 92.993 | 35.371 | −9.675 | 1.00 | 20.00 | 8 |
| ATOM | 607 | N | LEU | B | 145 | 92.495 | 37.230 | −8.490 | 1.00 | 20.00 | 7 |
| ATOM | 608 | CA | LEU | B | 145 | 91.968 | 37.975 | −9.624 | 1.00 | 20.00 | 6 |
| ATOM | 609 | CB | LEU | B | 145 | 90.678 | 38.703 | −9.234 | 1.00 | 20.00 | 6 |
| ATOM | 610 | CG | LEU | B | 145 | 89.938 | 39.486 | −10.326 | 1.00 | 20.00 | 6 |
| ATOM | 611 | CD1 | LEU | B | 145 | 88.611 | 39.992 | −9.782 | 1.00 | 20.00 | 6 |
| ATOM | 612 | CD2 | LEU | B | 145 | 90.791 | 40.652 | −10.806 | 1.00 | 20.00 | 6 |
| ATOM | 613 | C | LEU | B | 145 | 93.059 | 38.984 | −9.968 | 1.00 | 20.00 | 6 |
| ATOM | 614 | O | LEU | B | 145 | 93.291 | 39.940 | −9.216 | 1.00 | 20.00 | 8 |
| ATOM | 615 | N | TYR | B | 146 | 93.735 | 38.770 | −11.093 | 1.00 | 20.00 | 7 |
| ATOM | 616 | CA | TYR | B | 146 | 94.815 | 39.657 | −11.517 | 1.00 | 20.00 | 6 |
| ATOM | 617 | CB | TYR | B | 146 | 95.821 | 38.904 | −12.389 | 1.00 | 20.00 | 6 |
| ATOM | 618 | CG | TYR | B | 146 | 96.624 | 37.858 | −11.661 | 1.00 | 20.00 | 6 |
| ATOM | 619 | CD1 | TYR | B | 146 | 96.139 | 36.559 | −11.498 | 1.00 | 20.00 | 6 |
| ATOM | 620 | CE1 | TYR | B | 146 | 96.894 | 35.589 | −10.836 | 1.00 | 20.00 | 6 |
| ATOM | 621 | CD2 | TYR | B | 146 | 97.878 | 38.165 | −11.140 | 1.00 | 20.00 | 6 |
| ATOM | 622 | CE2 | TYR | B | 146 | 98.639 | 37.208 | −10.476 | 1.00 | 20.00 | 6 |
| ATOM | 623 | CZ | TYR | B | 146 | 98.144 | 35.925 | −10.331 | 1.00 | 20.00 | 6 |
| ATOM | 624 | OH | TYR | B | 146 | 98.920 | 34.981 | −9.706 | 1.00 | 20.00 | 8 |
| ATOM | 625 | C | TYR | B | 146 | 94.357 | 40.884 | −12.293 | 1.00 | 20.00 | 6 |
| ATOM | 626 | O | TYR | B | 146 | 94.933 | 41.963 | −12.160 | 1.00 | 20.00 | 8 |
| ATOM | 627 | N | PHE | B | 147 | 93.326 | 40.722 | −13.110 | 1.00 | 20.00 | 7 |
| ATOM | 628 | CA | PHE | B | 147 | 92.855 | 41.832 | −13.923 | 1.00 | 20.00 | 6 |
| ATOM | 629 | CB | PHE | B | 147 | 93.823 | 42.044 | −15.092 | 1.00 | 20.00 | 6 |
| ATOM | 630 | CG | PHE | B | 147 | 94.027 | 40.809 | −15.945 | 1.00 | 20.00 | 6 |
| ATOM | 631 | CD1 | PHE | B | 147 | 93.049 | 40.397 | −16.850 | 1.00 | 20.00 | 6 |
| ATOM | 632 | CD2 | PHE | B | 147 | 95.188 | 40.047 | −15.822 | 1.00 | 20.00 | 6 |
| ATOM | 633 | CE1 | PHE | B | 147 | 93.221 | 39.247 | −17.617 | 1.00 | 20.00 | 6 |
| ATOM | 634 | CE2 | PHE | B | 147 | 95.372 | 38.893 | −16.585 | 1.00 | 20.00 | 6 |
| ATOM | 635 | CZ | PHE | B | 147 | 94.388 | 38.490 | −17.485 | 1.00 | 20.00 | 6 |
| ATOM | 636 | C | PHE | B | 147 | 91.473 | 41.566 | −14.480 | 1.00 | 20.00 | 6 |

-continued

| | | | | | | | | | | |
|---|---|---|---|---|---|---|---|---|---|---|
| ATOM | 637 | O | PHE | B | 147 | 90.972 | 40.442 | −14.423 | 1.00 | 20.00 | 8 |
| ATOM | 638 | N | THR | B | 148 | 90.865 | 42.616 | −15.021 | 1.00 | 20.00 | 7 |
| ATOM | 639 | CA | THR | B | 148 | 89.560 | 42.509 | −15.643 | 1.00 | 20.00 | 6 |
| ATOM | 640 | CB | THR | B | 148 | 88.402 | 42.889 | −14.678 | 1.00 | 20.00 | 6 |
| ATOM | 641 | OG1 | THR | B | 148 | 88.492 | 44.275 | −14.338 | 1.00 | 20.00 | 8 |
| ATOM | 642 | CG2 | THR | B | 148 | 88.460 | 42.057 | −13.403 | 1.00 | 20.00 | 6 |
| ATOM | 643 | C | THR | B | 148 | 89.532 | 43.469 | −16.821 | 1.00 | 20.00 | 6 |
| ATOM | 644 | O | THR | B | 148 | 90.281 | 44.448 | −16.866 | 1.00 | 20.00 | 8 |
| ATOM | 645 | N | PHE | B | 149 | 88.685 | 43.161 | −17.791 | 1.00 | 20.00 | 7 |
| ATOM | 646 | CA | PHE | B | 149 | 88.508 | 44.011 | −18.948 | 1.00 | 20.00 | 6 |
| ATOM | 647 | CB | PHE | B | 149 | 89.750 | 44.013 | −19.864 | 1.00 | 20.00 | 6 |
| ATOM | 648 | CG | PHE | B | 149 | 90.133 | 42.664 | −20.419 | 1.00 | 20.00 | 6 |
| ATOM | 649 | CD1 | PHE | B | 149 | 89.552 | 42.182 | −21.587 | 1.00 | 20.00 | 6 |
| ATOM | 650 | CD2 | PHE | B | 149 | 91.122 | 41.903 | −19.802 | 1.00 | 20.00 | 6 |
| ATOM | 651 | CE1 | PHE | B | 149 | 89.953 | 40.965 | −22.142 | 1.00 | 20.00 | 6 |
| ATOM | 652 | CE2 | PHE | B | 149 | 91.532 | 40.681 | −20.345 | 1.00 | 20.00 | 6 |
| ATOM | 653 | CZ | PHE | B | 149 | 90.948 | 40.213 | −21.517 | 1.00 | 20.00 | 6 |
| ATOM | 654 | C | PHE | B | 149 | 87.271 | 43.498 | −19.649 | 1.00 | 20.00 | 6 |
| ATOM | 655 | O | PHE | B | 149 | 86.714 | 42.474 | −19.251 | 1.00 | 20.00 | 8 |
| ATOM | 656 | N | GLN | B | 150 | 86.812 | 44.221 | −20.657 | 1.00 | 20.00 | 7 |
| ATOM | 657 | CA | GLN | B | 150 | 85.619 | 43.807 | −21.372 | 1.00 | 20.00 | 6 |
| ATOM | 658 | CB | GLN | B | 150 | 84.358 | 44.260 | −20.614 | 1.00 | 20.00 | 6 |
| ATOM | 659 | CG | GLN | B | 150 | 84.302 | 45.761 | −20.289 | 1.00 | 20.00 | 6 |
| ATOM | 660 | CD | GLN | B | 150 | 83.011 | 46.172 | −19.567 | 1.00 | 20.00 | 6 |
| ATOM | 661 | OE1 | GLN | B | 150 | 81.970 | 46.385 | −20.196 | 1.00 | 20.00 | 8 |
| ATOM | 662 | NE2 | GLN | B | 150 | 83.078 | 46.273 | −18.240 | 1.00 | 20.00 | 7 |
| ATOM | 663 | C | GLN | B | 150 | 85.598 | 44.400 | −22.760 | 1.00 | 20.00 | 6 |
| ATOM | 664 | O | GLN | B | 150 | 86.281 | 45.387 | −23.033 | 1.00 | 20.00 | 8 |
| ATOM | 665 | N | ASP | B | 151 | 84.846 | 43.766 | −23.649 | 1.00 | 20.00 | 7 |
| ATOM | 666 | CA | ASP | B | 151 | 84.683 | 44.296 | −24.992 | 1.00 | 20.00 | 6 |
| ATOM | 667 | CB | ASP | B | 151 | 85.160 | 43.312 | −26.074 | 1.00 | 20.00 | 6 |
| ATOM | 668 | CG | ASP | B | 151 | 84.558 | 41.934 | −25.939 | 1.00 | 20.00 | 6 |
| ATOM | 669 | OD1 | ASP | B | 151 | 83.425 | 41.812 | −25.436 | 1.00 | 20.00 | 8 |
| ATOM | 670 | OD2 | ASP | B | 151 | 85.227 | 40.963 | −26.365 | 1.00 | 20.00 | 8 |
| ATOM | 671 | C | ASP | B | 151 | 83.188 | 44.573 | −25.095 | 1.00 | 20.00 | 6 |
| ATOM | 672 | O | ASP | B | 151 | 82.501 | 44.610 | −24.069 | 1.00 | 20.00 | 8 |
| ATOM | 673 | N | ASP | B | 152 | 82.669 | 44.758 | −26.301 | 1.00 | 20.00 | 7 |
| ATOM | 674 | CA | ASP | B | 152 | 81.251 | 45.062 | −26.437 | 1.00 | 20.00 | 6 |
| ATOM | 675 | CB | ASP | B | 152 | 80.907 | 45.346 | −27.901 | 1.00 | 20.00 | 6 |
| ATOM | 676 | CG | ASP | B | 152 | 81.616 | 46.574 | −28.432 | 1.00 | 20.00 | 6 |
| ATOM | 677 | OD1 | ASP | B | 152 | 81.748 | 47.555 | −27.666 | 1.00 | 20.00 | 8 |
| ATOM | 678 | OD2 | ASP | B | 152 | 82.030 | 46.563 | −29.613 | 1.00 | 20.00 | 8 |
| ATOM | 679 | C | ASP | B | 152 | 80.285 | 44.020 | −25.888 | 1.00 | 20.00 | 6 |
| ATOM | 680 | O | ASP | B | 152 | 79.229 | 44.367 | −25.357 | 1.00 | 20.00 | 8 |
| ATOM | 681 | N | GLU | B | 153 | 80.641 | 42.747 | −25.982 | 1.00 | 20.00 | 7 |
| ATOM | 682 | CA | GLU | B | 153 | 79.727 | 41.711 | −25.521 | 1.00 | 20.00 | 6 |
| ATOM | 683 | CB | GLU | B | 153 | 79.516 | 40.685 | −26.641 | 1.00 | 20.00 | 6 |
| ATOM | 684 | CG | GLU | B | 153 | 79.577 | 41.260 | −28.058 | 1.00 | 20.00 | 6 |
| ATOM | 685 | CD | GLU | B | 153 | 81.006 | 41.472 | −28.550 | 1.00 | 20.00 | 6 |
| ATOM | 686 | OE1 | GLU | B | 153 | 81.765 | 40.480 | −28.635 | 1.00 | 20.00 | 8 |
| ATOM | 687 | OE2 | GLU | B | 153 | 81.374 | 42.627 | −28.854 | 1.00 | 20.00 | 8 |
| ATOM | 688 | C | GLU | B | 153 | 80.102 | 40.960 | −24.247 | 1.00 | 20.00 | 6 |
| ATOM | 689 | O | GLU | B | 153 | 79.222 | 40.473 | −23.535 | 1.00 | 20.00 | 8 |
| ATOM | 690 | N | LYS | B | 154 | 81.393 | 40.869 | −23.944 | 1.00 | 20.00 | 7 |
| ATOM | 691 | CA | LYS | B | 154 | 81.818 | 40.091 | −22.787 | 1.00 | 20.00 | 6 |
| ATOM | 692 | CB | LYS | B | 154 | 82.549 | 38.830 | −23.273 | 1.00 | 20.00 | 6 |
| ATOM | 693 | CG | LYS | B | 154 | 81.785 | 37.978 | −24.278 | 1.00 | 20.00 | 6 |
| ATOM | 694 | CD | LYS | B | 154 | 82.727 | 37.028 | −25.021 | 1.00 | 20.00 | 6 |
| ATOM | 695 | CE | LYS | B | 154 | 81.968 | 36.086 | −25.952 | 1.00 | 20.00 | 6 |
| ATOM | 696 | NZ | LYS | B | 154 | 82.894 | 35.300 | −26.826 | 1.00 | 20.00 | 7 |
| ATOM | 697 | C | LYS | B | 154 | 82.709 | 40.767 | −21.756 | 1.00 | 20.00 | 6 |
| ATOM | 698 | O | LYS | B | 154 | 83.412 | 41.740 | −22.048 | 1.00 | 20.00 | 8 |
| ATOM | 699 | N | LEU | B | 155 | 82.677 | 40.202 | −20.551 | 1.00 | 20.00 | 7 |
| ATOM | 700 | CA | LEU | B | 155 | 83.501 | 40.638 | −19.428 | 1.00 | 20.00 | 6 |
| ATOM | 701 | CB | LEU | B | 155 | 82.700 | 40.651 | −18.127 | 1.00 | 20.00 | 6 |
| ATOM | 702 | CG | LEU | B | 155 | 81.451 | 41.521 | −18.004 | 1.00 | 20.00 | 6 |
| ATOM | 703 | CD1 | LEU | B | 155 | 80.805 | 41.273 | −16.645 | 1.00 | 20.00 | 6 |
| ATOM | 704 | CD2 | LEU | B | 155 | 81.831 | 42.983 | −18.152 | 1.00 | 20.00 | 6 |
| ATOM | 705 | C | LEU | B | 155 | 84.578 | 39.559 | −19.302 | 1.00 | 20.00 | 6 |
| ATOM | 706 | O | LEU | B | 155 | 84.288 | 38.379 | −19.495 | 1.00 | 20.00 | 8 |
| ATOM | 707 | N | TYR | B | 156 | 85.802 | 39.956 | −18.966 | 1.00 | 20.00 | 7 |
| ATOM | 708 | CA | TYR | B | 156 | 86.893 | 38.998 | −18.809 | 1.00 | 20.00 | 6 |
| ATOM | 709 | CB | TYR | B | 156 | 87.953 | 39.189 | −19.904 | 1.00 | 20.00 | 6 |
| ATOM | 710 | CG | TYR | B | 156 | 87.450 | 39.053 | −21.324 | 1.00 | 20.00 | 6 |
| ATOM | 711 | CD1 | TYR | B | 156 | 86.688 | 40.061 | −21.920 | 1.00 | 20.00 | 6 |
| ATOM | 712 | CE1 | TYR | B | 156 | 86.233 | 39.938 | −23.235 | 1.00 | 20.00 | 6 |
| ATOM | 713 | CD2 | TYR | B | 156 | 87.741 | 37.917 | −22.077 | 1.00 | 20.00 | 6 |
| ATOM | 714 | CE2 | TYR | B | 156 | 87.288 | 37.782 | −23.387 | 1.00 | 20.00 | 6 |
| ATOM | 715 | CZ | TYR | B | 156 | 86.538 | 38.794 | −23.958 | 1.00 | 20.00 | 6 |

-continued

| ATOM | 716 | OH | TYR | B | 156 | 86.087 | 38.656 | −25.246 | 1.00 | 20.00 | 8 |
| ATOM | 717 | C | TYR | B | 156 | 87.566 | 39.182 | −17.447 | 1.00 | 20.00 | 6 |
| ATOM | 718 | O | TYR | B | 156 | 87.977 | 40.291 | −17.110 | 1.00 | 20.00 | 8 |
| ATOM | 719 | N | PHE | B | 157 | 87.657 | 38.104 | −16.667 | 1.00 | 20.00 | 7 |
| ATOM | 720 | CA | PHE | B | 157 | 88.325 | 38.152 | −15.367 | 1.00 | 20.00 | 6 |
| ATOM | 721 | CB | PHE | B | 157 | 87.448 | 37.575 | −14.246 | 1.00 | 20.00 | 6 |
| ATOM | 722 | CG | PHE | B | 157 | 86.194 | 38.360 | −13.968 | 1.00 | 20.00 | 6 |
| ATOM | 723 | CD1 | PHE | B | 157 | 85.986 | 39.614 | −14.535 | 1.00 | 20.00 | 6 |
| ATOM | 724 | CD2 | PHE | B | 157 | 85.206 | 37.828 | −13.143 | 1.00 | 20.00 | 6 |
| ATOM | 725 | CE1 | PHE | B | 157 | 84.808 | 40.324 | −14.290 | 1.00 | 20.00 | 6 |
| ATOM | 726 | CE2 | PHE | B | 157 | 84.025 | 38.532 | −12.893 | 1.00 | 20.00 | 6 |
| ATOM | 727 | CZ | PHE | B | 157 | 83.829 | 39.782 | −13.470 | 1.00 | 20.00 | 6 |
| ATOM | 728 | C | PHE | B | 157 | 89.579 | 37.295 | −15.471 | 1.00 | 20.00 | 6 |
| ATOM | 729 | O | PHE | B | 157 | 89.492 | 36.105 | −15.765 | 1.00 | 20.00 | 8 |
| ATOM | 730 | N | GLY | B | 158 | 90.742 | 37.893 | −15.231 | 1.00 | 20.00 | 7 |
| ATOM | 731 | CA | GLY | B | 158 | 91.985 | 37.146 | −15.303 | 1.00 | 20.00 | 6 |
| ATOM | 732 | C | GLY | B | 158 | 92.254 | 36.512 | −13.955 | 1.00 | 20.00 | 6 |
| ATOM | 733 | O | GLY | B | 158 | 92.575 | 37.211 | −12.996 | 1.00 | 20.00 | 8 |
| ATOM | 734 | N | LEU | B | 159 | 92.137 | 35.191 | 13.886 | 1.00 | 20.00 | 7 |
| ATOM | 735 | CA | LEU | B | 159 | 92.330 | 34.466 | −12.634 | 1.00 | 20.00 | 6 |
| ATOM | 736 | CB | LEU | B | 159 | 91.116 | 33.580 | −12.358 | 1.00 | 20.00 | 6 |
| ATOM | 737 | CG | LEU | B | 159 | 89.724 | 34.208 | −12.490 | 1.00 | 20.00 | 6 |
| ATOM | 738 | CD1 | LEU | B | 159 | 88.670 | 33.111 | −12.398 | 1.00 | 20.00 | 6 |
| ATOM | 739 | CD2 | LEU | B | 159 | 89.513 | 35.246 | −11.404 | 1.00 | 20.00 | 6 |
| ATOM | 740 | C | LEU | B | 159 | 93.562 | 33.582 | −12.643 | 1.00 | 20.00 | 6 |
| ATOM | 741 | O | LEU | B | 159 | 94.061 | 33.204 | −13.698 | 1.00 | 20.00 | 8 |
| ATOM | 742 | N | SER | B | 160 | 94.046 | 33.237 | −11.457 | 1.00 | 20.00 | 7 |
| ATOM | 743 | CA | SER | B | 160 | 95.192 | 32.356 | −11.377 | 1.00 | 20.00 | 6 |
| ATOM | 744 | CB | SER | B | 160 | 95.665 | 32.206 | −9.926 | 1.00 | 20.00 | 6 |
| ATOM | 745 | OG | SER | B | 160 | 94.591 | 31.973 | '19.042 | 1.00 | 20.00 | 8 |
| ATOM | 746 | C | SER | B | 160 | 94.754 | 31.012 | −11.951 | 1.00 | 20.00 | 6 |
| ATOM | 747 | O | SER | B | 160 | 93.598 | 30.605 | −11.813 | 1.00 | 20.00 | 8 |
| ATOM | 748 | N | TYR | B | 161 | 95.674 | 30.339 | −12.625 | 1.00 | 20.00 | 7 |
| ATOM | 749 | CA | TYR | B | 161 | 95.381 | 29.050 | −13.231 | 1.00 | 20.00 | 6 |
| ATOM | 750 | CB | TYR | B | 161 | 96.170 | 28.924 | −14.543 | 1.00 | 20.00 | 6 |
| ATOM | 751 | CG | TYR | B | 161 | 96.128 | 27.564 | −15.209 | 1.00 | 20.00 | 6 |
| ATOM | 752 | CD1 | TYR | B | 161 | 94.968 | 26.787 | −15.193 | 1.00 | 20.00 | 6 |
| ATOM | 753 | CE1 | TYR | B | 161 | 94.915 | 25.554 | −15.846 | 1.00 | 20.00 | 6 |
| ATOM | 754 | CD2 | TYR | B | 161 | 97.240 | 27.073 | −15.895 | 1.00 | 20.00 | 6 |
| ATOM | 755 | CE2 | TYR | B | 161 | 97.198 | 25.841 | −16.553 | 1.00 | 20.00 | 6 |
| ATOM | 756 | CZ | TYR | B | 161 | 96.033 | 25.088 | −16.523 | 1.00 | 20.00 | 6 |
| ATOM | 757 | OH | TYR | B | 161 | 95.983 | 23.877 | −17.173 | 1.00 | 20.00 | 8 |
| ATOM | 758 | C | TYR | B | 161 | 95.724 | 27.905 | −12.277 | 1.00 | 20.00 | 6 |
| ATOM | 759 | O | TYR | B | 161 | 96.897 | 27.598 | −12.065 | 1.00 | 20.00 | 8 |
| ATOM | 760 | N | ALA | B | 162 | 94.696 | 27.288 | −11.697 | 1.00 | 20.00 | 7 |
| ATOM | 761 | CA | ALA | B | 162 | 94.893 | 26.166 | −10.776 | 1.00 | 20.00 | 6 |
| ATOM | 762 | CB | ALA | B | 162 | 93.666 | 25.995 | −9.873 | 1.00 | 20.00 | 6 |
| ATOM | 763 | C | ALA | B | 162 | 95.100 | 24.924 | −11.637 | 1.00 | 20.00 | 6 |
| ATOM | 764 | O | ALA | B | 162 | 94.146 | 24.251 | −12.015 | 1.00 | 20.00 | 8 |
| ATOM | 765 | N | LYS | B | 163 | 96.361 | 24.626 | −11.930 | 1.00 | 20.00 | 7 |
| ATOM | 766 | CA | LYS | B | 163 | 96.722 | 23.506 | −12.795 | 1.00 | 20.00 | 6 |
| ATOM | 767 | CB | LYS | B | 163 | 98.247 | 23.416 | −12.912 | 1.00 | 20.00 | 6 |
| ATOM | 768 | CG | LYS | B | 163 | 98.904 | 24.711 | −13.360 | 1.00 | 20.00 | 6 |
| ATOM | 769 | CD | LYS | B | 163 | 100.405 | 24.539 | 13.554 | 1.00 | 20.00 | 6 |
| ATOM | 770 | CE | LYS | B | 163 | 101.102 | 25.885 | −13.690 | 1.00 | 20.00 | 6 |
| ATOM | 771 | NZ | LYS | B | 163 | 100.976 | 26.701 | −12.445 | 1.00 | 20.00 | 7 |
| ATOM | 772 | C | LYS | B | 163 | 96.170 | 22.123 | 12.464 | 1.00 | 20.00 | 6 |
| ATOM | 773 | O | LYS | B | 163 | 95.823 | 21.370 | −13.369 | 1.00 | 20.00 | 8 |
| ATOM | 774 | N | ASN | B | 164 | 96.076 | 21.775 | −11.186 | 1.00 | 20.00 | 7 |
| ATOM | 775 | CA | ASN | B | 164 | 95.594 | 20.449 | −10.842 | 1.00 | 20.00 | 6 |
| ATOM | 776 | CB | ASN | B | 164 | 96.339 | 19.944 | −9.610 | 1.00 | 20.00 | 6 |
| ATOM | 777 | CG | ASN | B | 164 | 97.766 | 19.529 | −9.943 | 1.00 | 20.00 | 6 |
| ATOM | 778 | OD1 | ASN | B | 164 | 97.992 | 18.776 | −10.892 | 1.00 | 20.00 | 8 |
| ATOM | 779 | ND2 | ASN | B | 164 | 98.730 | 20.014 | −9.171 | 1.00 | 20.00 | 7 |
| ATOM | 780 | C | ASN | B | 164 | 94.084 | 20.246 | −10.706 | 1.00 | 20.00 | 6 |
| ATOM | 781 | O | ASN | B | 164 | 93.630 | 19.183 | −10.286 | 1.00 | 20.00 | 8 |
| ATOM | 782 | N | GLY | B | 165 | 93.309 | 21.257 | −11.080 | 1.00 | 20.00 | 7 |
| ATOM | 783 | CA | GLY | B | 165 | 91.863 | 21.127 | −11.039 | 1.00 | 20.00 | 6 |
| ATOM | 784 | C | GLY | B | 165 | 91.159 | 21.088 | 9.694 | 1.00 | 20.00 | 6 |
| ATOM | 785 | O | GLY | B | 165 | 91.663 | 21.598 | 8.698 | 1.00 | 20.00 | 8 |
| ATOM | 786 | N | GLU | B | 166 | 89.986 | 20.461 | −9.689 | 1.00 | 20.00 | 7 |
| ATOM | 787 | CA | GLU | B | 166 | 89.126 | 20.344 | −8.513 | 1.00 | 20.00 | 6 |
| ATOM | 788 | CB | GLU | B | 166 | 87.683 | 20.079 | −8.962 | 1.00 | 20.00 | 6 |
| ATOM | 789 | CG | GLU | B | 166 | 86.992 | 21.255 | −9.646 | 1.00 | 20.00 | 6 |
| ATOM | 790 | CD | GLU | B | 166 | 85.709 | 20.837 | −10.358 | 1.00 | 20.00 | 6 |
| ATOM | 791 | OE1 | GLU | B | 166 | 85.137 | 19.794 | −9.986 | 1.00 | 20.00 | 8 |
| ATOM | 792 | OE2 | GLU | B | 166 | 85.263 | 21.556 | −11.279 | 1.00 | 20.00 | 8 |
| ATOM | 793 | C | GLU | B | 166 | 89.520 | 19.270 | −7.506 | 1.00 | 20.00 | 6 |
| ATOM | 794 | O | GLU | B | 166 | 89.952 | 18.184 | −7.874 | 1.00 | 20.00 | 8 |

-continued

| | | | | | | | | | | |
|---|---|---|---|---|---|---|---|---|---|---|
| ATOM | 795 | N | LEU | B | 167 | 89.344 | 19.579 | −6.226 | 1.00 | 20.00 | 7 |
| ATOM | 796 | CA | LEU | B | 167 | 89.651 | 18.626 | −5.168 | 1.00 | 20.00 | 6 |
| ATOM | 797 | CB | LEU | B | 167 | 89.395 | 19.269 | −3.802 | 1.00 | 20.00 | 6 |
| ATOM | 798 | CG | LEU | B | 167 | 89.408 | 18.363 | −2.569 | 1.00 | 20.00 | 6 |
| ATOM | 799 | CD1 | LEU | B | 167 | 90.769 | 17.703 | −2.412 | 1.00 | 20.00 | 6 |
| ATOM | 800 | CD2 | LEU | B | 167 | 89.065 | 19.193 | −1.338 | 1.00 | 20.00 | 6 |
| ATOM | 801 | C | LEU | B | 167 | 88.757 | 17.394 | −5.346 | 1.00 | 20.00 | 6 |
| ATOM | 802 | O | LEU | B | 167 | 89.124 | 16.283 | −4.968 | 1.00 | 20.00 | 8 |
| ATOM | 803 | N | LEU | B | 168 | 87.580 | 17.600 | −5.927 | 1.00 | 20.00 | 7 |
| ATOM | 804 | CA | LEU | B | 168 | 86.647 | 16.500 | −6.153 | 1.00 | 20.00 | 6 |
| ATOM | 805 | CB | LEU | B | 168 | 85.364 | 17.014 | −6.809 | 1.00 | 20.00 | 6 |
| ATOM | 806 | CG | LEU | B | 168 | 84.292 | 15.977 | −7.168 | 1.00 | 20.00 | 6 |
| ATOM | 807 | CD1 | LEU | B | 168 | 83.883 | 15.186 | −5.929 | 1.00 | 20.00 | 6 |
| ATOM | 808 | CD2 | LEU | B | 168 | 83.083 | 16.687 | −7.756 | 1.00 | 20.00 | 6 |
| ATOM | 809 | C | LEU | B | 168 | 87.290 | 15.440 | −7.046 | 1.00 | 20.00 | 6 |
| ATOM | 810 | O | LEU | B | 168 | 87.091 | 14.243 | −6.845 | 1.00 | 20.00 | 8 |
| ATOM | 811 | N | LYS | B | 169 | 88.068 | 15.888 | −8.027 | 1.00 | 20.00 | 7 |
| ATOM | 812 | CA | LYS | B | 169 | 88.727 | 14.967 | −8.941 | 1.00 | 20.00 | 6 |
| ATOM | 813 | CB | LYS | B | 169 | 89.610 | 15.729 | −9.930 | 1.00 | 20.00 | 6 |
| ATOM | 814 | CG | LYS | B | 169 | 90.379 | 14.818 | −10.882 | 1.00 | 20.00 | 6 |
| ATOM | 815 | CD | LYS | B | 169 | 91.226 | 15.603 | −11.877 | 1.00 | 20.00 | 6 |
| ATOM | 816 | CE | LYS | B | 169 | 92.373 | 16.328 | −11.192 | 1.00 | 20.00 | 6 |
| ATOM | 817 | NZ | LYS | B | 169 | 93.253 | 17.021 | −12.173 | 1.00 | 20.00 | 7 |
| ATOM | 818 | C | LYS | B | 169 | 89.574 | 13.949 | −8.193 | 1.00 | 20.00 | 6 |
| ATOM | 819 | O | LYS | B | 169 | 89.543 | 12.758 | −8.504 | 1.00 | 20.00 | 8 |
| ATOM | 820 | N | TYR | B | 170 | 90.334 | 14.417 | −7.207 | 1.00 | 20.00 | 7 |
| ATOM | 821 | CA | TYR | B | 170 | 91.197 | 13.527 | −6.441 | 1.00 | 20.00 | 6 |
| ATOM | 822 | CB | TYR | B | 170 | 92.243 | 14.346 | −5.682 | 1.00 | 20.00 | 6 |
| ATOM | 823 | CG | TYR | B | 170 | 93.217 | 15.010 | −6.624 | 1.00 | 20.00 | 6 |
| ATOM | 824 | CD1 | TYR | B | 170 | 94.347 | 14.331 | −7.085 | 1.00 | 20.00 | 6 |
| ATOM | 825 | CE1 | TYR | B | 170 | 95.195 | 14.900 | −8.036 | 1.00 | 20.00 | 6 |
| ATOM | 826 | CD2 | TYR | B | 170 | 92.963 | 16.282 | −7.133 | 1.00 | 20.00 | 6 |
| ATOM | 827 | CE2 | TYR | B | 170 | 93.801 | 16.861 | −8.083 | 1.00 | 20.00 | 6 |
| ATOM | 828 | CZ | TYR | B | 170 | 94.913 | 16.164 | −8.532 | 1.00 | 20.00 | 6 |
| ATOM | 829 | OH | TYR | B | 170 | 95.727 | 16.727 | −9.493 | 1.00 | 20.00 | 8 |
| ATOM | 830 | C | TYR | B | 170 | 90.419 | 12.622 | −5.499 | 1.00 | 20.00 | 6 |
| ATOM | 831 | O | TYR | B | 170 | 90.834 | 11.494 | −5.233 | 1.00 | 20.00 | 8 |
| ATOM | 832 | N | ILE | B | 171 | 89.287 | 13.098 | −4.993 | 1.00 | 20.00 | 7 |
| ATOM | 833 | CA | ILE | B | 171 | 88.488 | 12.262 | −4.112 | 1.00 | 20.00 | 6 |
| ATOM | 834 | CB | ILE | B | 171 | 87.278 | 13.028 | −3.538 | 1.00 | 20.00 | 6 |
| ATOM | 835 | CG2 | ILE | B | 171 | 86.367 | 12.065 | −2.791 | 1.00 | 20.00 | 6 |
| ATOM | 836 | CG1 | ILE | B | 171 | 87.764 | 14.141 | −2.603 | 1.00 | 20.00 | 6 |
| ATOM | 837 | CD1 | ILE | B | 171 | 86.652 | 14.990 | −2.019 | 1.00 | 20.00 | 6 |
| ATOM | 838 | C | ILE | B | 171 | 87.994 | 11.066 | −4.931 | 1.00 | 20.00 | 6 |
| ATOM | 839 | O | ILE | B | 171 | 88.030 | 9.925 | −4.468 | 1.00 | 20.00 | 8 |
| ATOM | 840 | N | ARG | B | 172 | 87.550 | 11.331 | −6.156 | 1.00 | 20.00 | 7 |
| ATOM | 841 | CA | ARG | B | 172 | 87.061 | 10.273 | −7.031 | 1.00 | 20.00 | 6 |
| ATOM | 842 | CB | ARG | B | 172 | 86.359 | 10.861 | −8.259 | 1.00 | 20.00 | 6 |
| ATOM | 843 | CG | ARG | B | 172 | 85.094 | 11.658 | −7.963 | 1.00 | 20.00 | 6 |
| ATOM | 844 | CD | ARG | B | 172 | 84.352 | 11.981 | −9.259 | 1.00 | 20.00 | 6 |
| ATOM | 845 | NE | ARG | B | 172 | 83.187 | 12.843 | −9.063 | 1.00 | 20.00 | 7 |
| ATOM | 846 | CZ | ARG | B | 172 | 82.192 | 12.589 | −8.217 | 1.00 | 20.00 | 6 |
| ATOM | 847 | NH1 | ARG | B | 172 | 82.209 | 11.491 | −7.469 | 1.00 | 20.00 | 7 |
| ATOM | 848 | NH2 | ARG | B | 172 | 81.168 | 13.428 | −8.127 | 1.00 | 20.00 | 7 |
| ATOM | 849 | C | ARG | B | 172 | 88.202 | 9.378 | −7.497 | 1.00 | 20.00 | 6 |
| ATOM | 850 | O | ARG | B | 172 | 88.050 | 8.160 | −7.587 | 1.00 | 20.00 | 8 |
| ATOM | 851 | N | LYS | B | 173 | 89.348 | 9.985 | −7.783 | 1.00 | 20.00 | 7 |
| ATOM | 852 | CA | LYS | B | 173 | 90.509 | 9.244 | −8.256 | 1.00 | 20.00 | 6 |
| ATOM | 853 | CB | LYS | B | 173 | 91.647 | 10.206 | −8.603 | 1.00 | 20.00 | 6 |
| ATOM | 854 | CG | LYS | B | 173 | 92.930 | 9.511 | −9.045 | 1.00 | 20.00 | 6 |
| ATOM | 855 | CD | LYS | B | 173 | 94.081 | 10.496 | −9.222 | 1.00 | 20.00 | 6 |
| ATOM | 856 | CE | LYS | B | 173 | 93.862 | 11.432 | −10.406 | 1.00 | 20.00 | 6 |
| ATOM | 857 | NZ | LYS | B | 173 | 93.858 | 10.711 | −11.715 | 1.00 | 20.00 | 7 |
| ATOM | 858 | C | LYS | B | 173 | 91.025 | 8.191 | −7.280 | 1.00 | 20.00 | 6 |
| ATOM | 859 | O | LYS | B | 173 | 91.274 | 7.055 | −7.674 | 1.00 | 20.00 | 8 |
| ATOM | 860 | N | ILE | B | 174 | 91.192 | 8.554 | −6.012 | 1.00 | 20.00 | 7 |
| ATOM | 861 | CA | ILE | B | 174 | 91.710 | 7.593 | −5.042 | 1.00 | 20.00 | 6 |
| ATOM | 862 | CB | ILE | B | 174 | 92.884 | 8.191 | −4.223 | 1.00 | 20.00 | 6 |
| ATOM | 863 | CG2 | ILE | B | 174 | 93.970 | 8.701 | −5.166 | 1.00 | 20.00 | 6 |
| ATOM | 864 | CG1 | ILE | B | 174 | 92.394 | 9.337 | −3.343 | 1.00 | 20.00 | 6 |
| ATOM | 865 | CD1 | ILE | B | 174 | 93.480 | 9.916 | −2.457 | 1.00 | 20.00 | 6 |
| ATOM | 866 | C | ILE | B | 174 | 90.674 | 7.030 | −4.074 | 1.00 | 20.00 | 6 |
| ATOM | 867 | O | ILE | B | 174 | 91.025 | 6.296 | −3.151 | 1.00 | 20.00 | 8 |
| ATOM | 868 | N | GLY | B | 175 | 89.405 | 7.367 | −4.283 | 1.00 | 20.00 | 7 |
| ATOM | 869 | CA | GLY | B | 175 | 88.359 | 6.855 | −3.413 | 1.00 | 20.00 | 6 |
| ATOM | 870 | C | GLY | B | 175 | 88.160 | 7.650 | −2.138 | 1.00 | 20.00 | 6 |
| ATOM | 871 | O | GLY | B | 175 | 87.083 | 8.198 | −1.905 | 1.00 | 20.00 | 8 |
| ATOM | 872 | N | SER | B | 176 | 89.192 | 7.701 | −1.304 | 1.00 | 20.00 | 7 |
| ATOM | 873 | CA | SER | B | 176 | 89.140 | 8.447 | −0.053 | 1.00 | 20.00 | 6 |

-continued

| | | | | | | | | | | |
|---|---|---|---|---|---|---|---|---|---|---|
| ATOM | 874 | CB | SER | B | 176 | 88.395 | 7.653 | 1.026 | 1.00 | 20.00 | 6 |
| ATOM | 875 | OG | SER | B | 176 | 89.150 | 6.543 | 1.472 | 1.00 | 20.00 | 8 |
| ATOM | 876 | C | SER | B | 176 | 90.565 | 8.742 | 0.401 | 1.00 | 20.00 | 6 |
| ATOM | 877 | O | SER | B | 176 | 91.506 | 8.049 | 0.009 | 1.00 | 20.00 | 8 |
| ATOM | 878 | N | PHE | B | 177 | 90.718 | 9.769 | 1.228 | 1.00 | 20.00 | 7 |
| ATOM | 879 | CA | PHE | B | 177 | 92.029 | 10.184 | 1.722 | 1.00 | 20.00 | 6 |
| ATOM | 880 | CB | PHE | B | 177 | 92.028 | 11.694 | 1.990 | 1.00 | 20.00 | 6 |
| ATOM | 881 | CG | PHE | B | 177 | 92.002 | 12.546 | 0.747 | 1.00 | 20.00 | 6 |
| ATOM | 882 | CD1 | PHE | B | 177 | 91.484 | 12.060 | −0.449 | 1.00 | 20.00 | 6 |
| ATOM | 883 | CD2 | PHE | B | 177 | 92.481 | 13.855 | 0.787 | 1.00 | 20.00 | 6 |
| ATOM | 884 | CE1 | PHE | B | 177 | 91.443 | 12.860 | −1.585 | 1.00 | 20.00 | 6 |
| ATOM | 885 | CE2 | PHE | B | 177 | 92.444 | 14.665 | −0.343 | 1.00 | 20.00 | 6 |
| ATOM | 886 | CZ | PHE | B | 177 | 91.925 | 14.168 | −1.532 | 1.00 | 20.00 | 6 |
| ATOM | 887 | C | PHE | B | 177 | 92.427 | 9.475 | 3.009 | 1.00 | 20.00 | 6 |
| ATOM | 888 | O | PHE | B | 177 | 91.582 | 9.223 | 3.872 | 1.00 | 20.00 | 8 |
| ATOM | 889 | N | ASP | B | 178 | 93.711 | 9.152 | 3.147 | 1.00 | 20.00 | 7 |
| ATOM | 890 | CA | ASP | B | 178 | 94.155 | 8.529 | 4.385 | 1.00 | 20.00 | 6 |
| ATOM | 891 | CB | ASP | B | 178 | 95.581 | 7.972 | 4.267 | 1.00 | 20.00 | 6 |
| ATOM | 892 | CG | ASP | B | 178 | 96.594 | 9.018 | 3.845 | 1.00 | 20.00 | 6 |
| ATOM | 893 | OD1 | ASP | B | 178 | 96.392 | 10.214 | 4.139 | 1.00 | 20.00 | 8 |
| ATOM | 894 | OD2 | ASP | B | 178 | 97.612 | 8.634 | 3.230 | 1.00 | 20.00 | 8 |
| ATOM | 895 | C | ASP | B | 178 | 94.092 | 9.640 | 5.436 | 1.00 | 20.00 | 6 |
| ATOM | 896 | O | ASP | B | 178 | 93.736 | 10.778 | 5.117 | 1.00 | 20.00 | 8 |
| ATOM | 897 | N | GLU | B | 179 | 94.443 | 9.324 | 6.677 | 1.00 | 20.00 | 7 |
| ATOM | 898 | CA | GLU | B | 179 | 94.380 | 10.311 | 7.744 | 1.00 | 20.00 | 6 |
| ATOM | 899 | CB | GLU | B | 179 | 94.623 | 9.637 | 9.096 | 1.00 | 20.00 | 6 |
| ATOM | 900 | CG | GLU | B | 179 | 94.747 | 10.611 | 10.255 | 1.00 | 20.00 | 6 |
| ATOM | 901 | CD | GLU | B | 179 | 94.331 | 9.994 | 11.574 | 1.00 | 20.00 | 6 |
| ATOM | 902 | OE1 | GLU | B | 179 | 94.589 | 8.789 | 11.770 | 1.00 | 20.00 | 8 |
| ATOM | 903 | OE2 | GLU | B | 179 | 93.753 | 10.717 | 12.416 | 1.00 | 20.00 | 8 |
| ATOM | 904 | C | GLU | B | 179 | 95.320 | 11.501 | 7.575 | 1.00 | 20.00 | 6 |
| ATOM | 905 | O | GLU | B | 179 | 94.948 | 12.636 | 7.881 | 1.00 | 20.00 | 8 |
| ATOM | 906 | N | THR | B | 180 | 96.528 | 11.246 | 7.086 | 1.00 | 20.00 | 7 |
| ATOM | 907 | CA | THR | B | 180 | 97.509 | 12.308 | 6.886 | 1.00 | 20.00 | 6 |
| ATOM | 908 | CB | THR | B | 180 | 98.866 | 11.720 | 6.445 | 1.00 | 20.00 | 6 |
| ATOM | 909 | OG1 | THR | B | 180 | 99.349 | 10.842 | 7.466 | 1.00 | 20.00 | 8 |
| ATOM | 910 | CG2 | THR | B | 180 | 99.888 | 12.825 | 6.213 | 1.00 | 20.00 | 6 |
| ATOM | 911 | C | THR | B | 180 | 97.040 | 13.331 | 5.849 | 1.00 | 20.00 | 6 |
| ATOM | 912 | O | THR | B | 180 | 97.136 | 14.542 | 6.069 | 1.00 | 20.00 | 8 |
| ATOM | 913 | N | CYS | B | 181 | 96.534 | 12.845 | 4.721 | 1.00 | 20.00 | 7 |
| ATOM | 914 | CA | CYS | B | 181 | 96.057 | 13.733 | 3.666 | 1.00 | 20.00 | 6 |
| ATOM | 915 | CB | CYS | B | 181 | 95.836 | 12.945 | 2.375 | 1.00 | 20.00 | 6 |
| ATOM | 916 | SG | CYS | B | 181 | 97.372 | 12.255 | 1.685 | 1.00 | 20.00 | 16 |
| ATOM | 917 | C | CYS | B | 181 | 94.775 | 14.449 | 4.079 | 1.00 | 20.00 | 6 |
| ATOM | 918 | O | CYS | B | 181 | 94.570 | 15.615 | 3.733 | 1.00 | 20.00 | 8 |
| ATOM | 919 | N | THR | B | 182 | 93.914 | 13.755 | 4.820 | 1.00 | 20.00 | 7 |
| ATOM | 920 | CA | THR | B | 182 | 92.669 | 14.356 | 5.286 | 1.00 | 20.00 | 6 |
| ATOM | 921 | CB | THR | B | 182 | 91.812 | 13.354 | 6.103 | 1.00 | 20.00 | 6 |
| ATOM | 922 | OG1 | THR | B | 182 | 91.372 | 12.283 | 5.259 | 1.00 | 20.00 | 8 |
| ATOM | 923 | CG2 | THR | B | 182 | 90.600 | 14.054 | 6.690 | 1.00 | 20.00 | 6 |
| ATOM | 924 | C | THR | B | 182 | 93.014 | 15.535 | 6.196 | 1.00 | 20.00 | 6 |
| ATOM | 925 | O | THR | B | 182 | 92.515 | 16.649 | 6.019 | 1.00 | 20.00 | 8 |
| ATOM | 926 | N | ARG | B | 183 | 93.873 | 15.273 | 7.175 | 1.00 | 20.00 | 7 |
| ATOM | 927 | CA | ARG | B | 183 | 94.299 | 16.293 | 8.121 | 1.00 | 20.00 | 6 |
| ATOM | 928 | CB | ARG | B | 183 | 95.311 | 15.707 | 9.109 | 1.00 | 20.00 | 6 |
| ATOM | 929 | CG | ARG | B | 183 | 95.957 | 16.744 | 10.012 | 1.00 | 20.00 | 6 |
| ATOM | 930 | CD | ARG | B | 183 | 96.886 | 16.116 | 11.050 | 1.00 | 20.00 | 6 |
| ATOM | 931 | NE | ARG | B | 183 | 96.167 | 15.220 | 11.949 | 1.00 | 20.00 | 7 |
| ATOM | 932 | CZ | ARG | B | 183 | 96.098 | 13.900 | 11.804 | 1.00 | 20.00 | 6 |
| ATOM | 933 | NH1 | ARG | B | 183 | 96.717 | 13.306 | 10.791 | 1.00 | 20.00 | 7 |
| ATOM | 934 | NH2 | ARG | B | 183 | 95.389 | 13.176 | 12.664 | 1.00 | 20.00 | 7 |
| ATOM | 935 | C | ARG | B | 183 | 94.923 | 17.505 | 7.427 | 1.00 | 20.00 | 6 |
| ATOM | 936 | O | ARG | B | 183 | 94.545 | 18.646 | 7.698 | 1.00 | 20.00 | 8 |
| ATOM | 937 | N | PHE | B | 184 | 95.877 | 17.264 | 6.534 | 1.00 | 20.00 | 7 |
| ATOM | 938 | CA | PHE | B | 184 | 96.539 | 18.367 | 5.847 | 1.00 | 20.00 | 6 |
| ATOM | 939 | CB | PHE | B | 184 | 97.610 | 17.847 | 4.889 | 1.00 | 20.00 | 6 |
| ATOM | 940 | CG | PHE | B | 184 | 98.387 | 18.943 | 4.223 | 1.00 | 20.00 | 6 |
| ATOM | 941 | CD1 | PHE | B | 184 | 99.451 | 19.555 | 4.879 | 1.00 | 20.00 | 6 |
| ATOM | 942 | CD2 | PHE | B | 184 | 98.009 | 19.415 | 2.975 | 1.00 | 20.00 | 6 |
| ATOM | 943 | CE1 | PHE | B | 184 | 100.125 | 20.627 | 4.301 | 1.00 | 20.00 | 6 |
| ATOM | 944 | CE2 | PHE | B | 184 | 98.676 | 20.491 | 2.388 | 1.00 | 20.00 | 6 |
| ATOM | 945 | CZ | PHE | B | 184 | 99.735 | 21.097 | 3.053 | 1.00 | 20.00 | 6 |
| ATOM | 946 | C | PHE | B | 184 | 95.580 | 19.267 | 5.066 | 1.00 | 20.00 | 6 |
| ATOM | 947 | O | PHE | B | 184 | 95.567 | 20.481 | 5.255 | 1.00 | 20.00 | 8 |
| ATOM | 948 | N | TYR | B | 185 | 94.784 | 18.679 | 4.181 | 1.00 | 20.00 | 7 |
| ATOM | 949 | CA | TYR | B | 185 | 93.854 | 19.471 | 3.390 | 1.00 | 20.00 | 6 |
| ATOM | 950 | CB | TYR | B | 185 | 93.305 | 18.634 | 2.236 | 1.00 | 20.00 | 6 |
| ATOM | 951 | CG | TYR | B | 185 | 94.337 | 18.504 | 1.140 | 1.00 | 20.00 | 6 |
| ATOM | 952 | CD1 | TYR | B | 185 | 94.611 | 19.580 | 0.293 | 1.00 | 20.00 | 6 |

-continued

| | | | | | | | | | | |
|---|---|---|---|---|---|---|---|---|---|---|
| ATOM | 953 | CE1 | TYR | B | 185 | 95.637 | 19.516 | −0.643 | 1.00 | 20.00 | 6 |
| ATOM | 954 | CD2 | TYR | B | 185 | 95.118 | 17.352 | 1.017 | 1.00 | 20.00 | 6 |
| ATOM | 955 | CE2 | TYR | B | 185 | 96.152 | 17.282 | 0.081 | 1.00 | 20.00 | 6 |
| ATOM | 956 | CZ | TYR | B | 185 | 96.405 | 18.367 | −0.742 | 1.00 | 20.00 | 6 |
| ATOM | 957 | OH | TYR | B | 185 | 97.436 | 18.314 | −1.657 | 1.00 | 20.00 | 8 |
| ATOM | 958 | C | TYR | B | 185 | 92.738 | 20.098 | 4.208 | 1.00 | 20.00 | 6 |
| ATOM | 959 | O | TYR | B | 185 | 92.286 | 21.195 | 3.891 | 1.00 | 20.00 | 8 |
| ATOM | 960 | N | THR | B | 186 | 92.303 | 19.422 | 5.267 | 1.00 | 20.00 | 7 |
| ATOM | 961 | CA | THR | B | 186 | 91.265 | 19.987 | 6.122 | 1.00 | 20.00 | 6 |
| ATOM | 962 | CB | THR | B | 186 | 90.799 | 18.996 | 7.219 | 1.00 | 20.00 | 6 |
| ATOM | 96 | OG1 | THR | B | 186 | 90.193 | 17.846 | 6.606 | 1.00 | 20.00 | 8 |
| ATOM | 964 | CG2 | THR | B | 186 | 89.774 | 19.671 | 8.144 | 1.00 | 20.00 | 6 |
| ATOM | 965 | C | THR | B | 186 | 91.858 | 21.218 | 6.805 | 1.00 | 20.00 | 6 |
| ATOM | 966 | O | THR | B | 186 | 91.188 | 22.242 | 6.948 | 1.00 | 20.00 | 8 |
| ATOM | 967 | N | ALA | B | 187 | 93.120 | 21.115 | 7.222 | 1.00 | 20.00 | 7 |
| ATOM | 968 | CA | ALA | B | 187 | 93.787 | 22.234 | 7.882 | 1.00 | 20.00 | 6 |
| ATOM | 969 | CB | ALA | B | 187 | 95.184 | 21.817 | 8.349 | 1.00 | 20.00 | 6 |
| ATOM | 970 | C | ALA | B | 187 | 93.879 | 23.449 | 6.946 | 1.00 | 20.00 | 6 |
| ATOM | 971 | O | ALA | B | 187 | 93.654 | 24.585 | 7.372 | 1.00 | 20.00 | 8 |
| ATOM | 972 | N | GLU | B | 188 | 94.205 | 23.222 | 5.674 | 1.00 | 20.00 | 7 |
| ATOM | 973 | CA | GLU | B | 188 | 94.292 | 24.343 | 4.740 | 1.00 | 20.00 | 6 |
| ATOM | 974 | CB | GLU | B | 188 | 94.843 | 23.898 | 3.376 | 1.00 | 20.00 | 6 |
| ATOM | 975 | CG | GLU | B | 188 | 96.285 | 23.391 | 3.407 | 1.00 | 20.00 | 6 |
| ATOM | 976 | CD | GLU | B | 188 | 97.030 | 23.639 | 2.104 | 1.00 | 20.00 | 6 |
| ATOM | 977 | OE1 | GLU | B | 188 | 96.407 | 23.537 | 1.024 | 1.00 | 20.00 | 8 |
| ATOM | 978 | OE2 | GLU | B | 188 | 98.247 | 23.932 | 2.156 | 1.00 | 20.00 | 8 |
| ATOM | 979 | C | GLU | B | 188 | 92.912 | 24.977 | 4.561 | 1.00 | 20.00 | 6 |
| ATOM | 980 | O | GLU | B | 188 | 92.782 | 26.196 | 4.533 | 1.00 | 20.00 | 8 |
| ATOM | 981 | N | ILE | B | 189 | 91.875 | 24.152 | 4.451 | 1.00 | 20.00 | 7 |
| ATOM | 982 | CA | ILE | B | 189 | 90.530 | 24.693 | 4.284 | 1.00 | 20.00 | 6 |
| ATOM | 983 | CB | ILE | B | 189 | 89.495 | 23.566 | 4.064 | 1.00 | 20.00 | 6 |
| ATOM | 984 | CG2 | ILE | B | 189 | 88.094 | 24.157 | 3.947 | 1.00 | 20.00 | 6 |
| ATOM | 985 | CG1 | ILE | B | 189 | 89.855 | 22.773 | 2.796 | 1.00 | 20.00 | 6 |
| ATOM | 986 | CD1 | ILE | B | 189 | 89.058 | 21.488 | 2.616 | 1.00 | 20.00 | 6 |
| ATOM | 987 | C | ILE | B | 189 | 90.152 | 25.517 | 5.519 | 1.00 | 20.00 | 6 |
| ATOM | 988 | O | ILE | B | 189 | 89.634 | 26.630 | 5.396 | 1.00 | 20.00 | 8 |
| ATOM | 989 | N | VAL | B | 190 | 90.412 | 24.971 | 6.707 | 1.00 | 20.00 | 7 |
| ATOM | 990 | CA | VAL | B | 190 | 90.116 | 25.674 | 7.957 | 1.00 | 20.00 | 6 |
| ATOM | 991 | CB | VAL | B | 190 | 90.557 | 24.842 | 9.186 | 1.00 | 20.00 | 6 |
| ATOM | 992 | CG1 | VAL | B | 190 | 90.540 | 25.717 | 10.451 | 1.00 | 20.00 | 6 |
| ATOM | 993 | CG2 | VAL | B | 190 | 89.643 | 23.641 | 9.358 | 1.00 | 20.00 | 6 |
| ATOM | 994 | C | VAL | B | 190 | 90.865 | 27.012 | 7.984 | 1.00 | 20.00 | 6 |
| ATOM | 995 | O | VAL | B | 190 | 90.311 | 28.039 | 8.375 | 1.00 | 20.00 | 8 |
| ATOM | 996 | N | SER | B | 191 | 92.125 | 26.997 | 7.557 | 1.00 | 20.00 | 7 |
| ATOM | 997 | CA | SER | B | 191 | 92.934 | 28.218 | 7.546 | 1.00 | 20.00 | 6 |
| ATOM | 998 | CB | SER | B | 191 | 94.378 | 27.888 | 7.166 | 1.00 | 20.00 | 6 |
| ATOM | 999 | OG | SER | B | 191 | 95.220 | 29.007 | 7.363 | 1.00 | 20.00 | 8 |
| ATOM | 1000 | C | SER | B | 191 | 92.361 | 29.240 | 6.566 | 1.00 | 20.00 | 6 |
| ATOM | 1001 | O | SER | B | 191 | 92.351 | 30.444 | 6.838 | 1.00 | 20.00 | 8 |
| ATOM | 1002 | N | ALA | B | 192 | 91.882 | 28.754 | 5.425 | 1.00 | 20.00 | 7 |
| ATOM | 1003 | CA | ALA | B | 192 | 91.306 | 29.634 | 4.417 | 1.00 | 20.00 | 6 |
| ATOM | 1004 | CB | ALA | B | 192 | 91.006 | 28.850 | 3.141 | 1.00 | 20.00 | 6 |
| ATOM | 1005 | C | ALA | B | 192 | 90.029 | 30.256 | 4.970 | 1.00 | 20.00 | 6 |
| ATOM | 1006 | O | ALA | B | 192 | 89.799 | 31.458 | 4.822 | 1.00 | 20.00 | 8 |
| ATOM | 1007 | N | LEU | B | 193 | 89.203 | 29.439 | 5.621 | 1.00 | 20.00 | 7 |
| ATOM | 1008 | CA | LEU | B | 193 | 87.957 | 29.941 | 6.192 | 1.00 | 20.00 | 6 |
| ATOM | 1009 | CB | LEU | B | 193 | 87.101 | 28.783 | 6.725 | 1.00 | 20.00 | 6 |
| ATOM | 1010 | CG | LEU | B | 193 | 86.447 | 27.898 | 5.650 | 1.00 | 20.00 | 6 |
| ATOM | 1011 | CD1 | LEU | B | 193 | 85.645 | 26.771 | 6.315 | 1.00 | 20.00 | 6 |
| ATOM | 1012 | CD2 | LEU | B | 193 | 85.530 | 28.752 | 4.780 | 1.00 | 20.00 | 6 |
| ATOM | 1013 | C | LEU | B | 193 | 88.215 | 30.959 | 7.299 | 1.00 | 20.00 | 6 |
| ATOM | 1014 | O | LEU | B | 193 | 87.474 | 31.935 | 7.435 | 1.00 | 20.00 | 8 |
| ATOM | 1015 | N | GLU | B | 194 | 89.254 | 30.738 | 8.100 | 1.00 | 20.00 | 7 |
| ATOM | 1016 | CA | GLU | B | 194 | 89.562 | 31.699 | 9.157 | 1.00 | 20.00 | 6 |
| ATOM | 1017 | CB | GLU | B | 194 | 90.773 | 31.257 | 9.982 | 1.00 | 20.00 | 6 |
| ATOM | 1018 | CG | GLU | B | 194 | 91.288 | 32.353 | 10.914 | 1.00 | 20.00 | 6 |
| ATOM | 1019 | CD | GLU | B | 194 | 92.381 | 31.878 | 11.855 | 1.00 | 20.00 | 6 |
| ATOM | 1020 | OE1 | GLU | B | 194 | 93.246 | 31.090 | 11.420 | 1.00 | 20.00 | 8 |
| ATOM | 1021 | OE2 | GLU | B | 194 | 92.376 | 32.312 | 13.031 | 1.00 | 20.00 | 8 |
| ATOM | 1022 | C | GLU | B | 194 | 89.847 | 33.053 | 8.511 | 1.00 | 20.00 | 6 |
| ATOM | 1023 | O | GLU | B | 194 | 89.375 | 34.083 | 8.972 | 1.00 | 20.00 | 8 |
| ATOM | 1024 | N | TYR | B | 195 | 90.608 | 33.046 | 7.426 | 1.00 | 20.00 | 7 |
| ATOM | 1025 | CA | TYR | B | 195 | 90.928 | 34.294 | 6.743 | 1.00 | 20.00 | 6 |
| ATOM | 1026 | CB | TYR | B | 195 | 91.919 | 34.043 | 5.613 | 1.00 | 20.00 | 6 |
| ATOM | 1027 | CG | TYR | B | 195 | 92.193 | 35.271 | 4.774 | 1.00 | 20.00 | 6 |
| ATOM | 1028 | CD1 | TYR | B | 195 | 93.098 | 36.244 | 5.202 | 1.00 | 20.00 | 6 |
| ATOM | 1029 | CE1 | TYR | B | 195 | 93.356 | 37.382 | 4.429 | 1.00 | 20.00 | 6 |
| ATOM | 1030 | CD2 | TYR | B | 195 | 91.545 | 35.461 | 3.553 | 1.00 | 20.00 | 6 |
| ATOM | 1031 | CE2 | TYR | B | 195 | 91.794 | 36.591 | 2.775 | 1.00 | 20.00 | 6 |

-continued

| | | | | | | | | | | |
|---|---|---|---|---|---|---|---|---|---|---|
| ATOM | 1032 | CZ | TYR | B | 195 | 92.701 | 37.545 | 3.219 | 1.00 | 20.00 | 6 |
| ATOM | 1033 | OH | TYR | B | 195 | 92.956 | 38.656 | 2.450 | 1.00 | 20.00 | 8 |
| ATOM | 1034 | C | TYR | B | 195 | 89.668 | 34.923 | 6.160 | 1.00 | 20.00 | 6 |
| ATOM | 1035 | O | TYR | B | 195 | 89.409 | 36.117 | 6.328 | 1.00 | 20.00 | 8 |
| ATOM | 1036 | N | LEU | B | 196 | 88.885 | 34.103 | 5.472 | 1.00 | 20.00 | 7 |
| ATOM | 1037 | CA | LEU | B | 196 | 87.664 | 34.576 | 4.845 | 1.00 | 20.00 | 6 |
| ATOM | 1038 | CB | LEU | B | 196 | 86.972 | 33.426 | 4.107 | 1.00 | 20.00 | 6 |
| ATOM | 1039 | CG | LEU | B | 196 | 85.933 | 33.824 | 3.060 | 1.00 | 20.00 | 6 |
| ATOM | 1040 | CD1 | LEU | B | 196 | 86.602 | 34.659 | 1.966 | 1.00 | 20.00 | 6 |
| ATOM | 1041 | CD2 | LEU | B | 196 | 85.305 | 32.568 | 2.463 | 1.00 | 20.00 | 6 |
| ATOM | 1042 | C | LEU | B | 196 | 86.731 | 35.161 | 5.888 | 1.00 | 20.00 | 6 |
| ATOM | 1043 | O | LEU | B | 196 | 86.299 | 36.308 | 5.774 | 1.00 | 20.00 | 8 |
| ATOM | 1044 | N | HIS | B | 197 | 86.431 | 34.378 | 6.917 | 1.00 | 20.00 | 7 |
| ATOM | 1045 | CA | HIS | B | 197 | 85.533 | 34.840 | 7.967 | 1.00 | 20.00 | 6 |
| ATOM | 1046 | CB | HIS | B | 197 | 85.241 | 33.697 | 8.942 | 1.00 | 20.00 | 6 |
| ATOM | 1047 | CG | HIS | B | 197 | 84.377 | 32.622 | 8.356 | 1.00 | 20.00 | 6 |
| ATOM | 1048 | CD2 | HIS | B | 197 | 83.734 | 32.550 | 7.163 | 1.00 | 20.00 | 6 |
| ATOM | 1049 | ND1 | HIS | B | 197 | 84.083 | 31.452 | 9.022 | 1.00 | 20.00 | 7 |
| ATOM | 1050 | CE1 | HIS | B | 197 | 83.296 | 30.704 | 8.264 | 1.00 | 20.00 | 6 |
| ATOM | 1051 | NE2 | HIS | B | 197 | 83.071 | 31.346 | 7.132 | 1.00 | 20.00 | 7 |
| ATOM | 1052 | C | HIS | B | 197 | 86.080 | 36.060 | 8.697 | 1.00 | 20.00 | 6 |
| ATOM | 1053 | O | HIS | B | 197 | 85.314 | 36.919 | 9.146 | 1.00 | 20.00 | 8 |
| ATOM | 1054 | N | GLY | B | 198 | 87.404 | 36.143 | 8.804 | 1.00 | 20.00 | 7 |
| ATOM | 1055 | CA | GLY | B | 198 | 88.009 | 37.285 | 9.464 | 1.00 | 20.00 | 6 |
| ATOM | 1056 | C | GLY | B | 198 | 87.687 | 38.580 | 8.737 | 1.00 | 20.00 | 6 |
| ATOM | 1057 | O | GLY | B | 198 | 87.784 | 39.661 | 9.311 | 1.00 | 20.00 | 8 |
| ATOM | 1058 | N | LYS | B | 199 | 87.308 | 38.475 | 7.466 | 1.00 | 20.00 | 7 |
| ATOM | 1059 | CA | LYS | B | 199 | 86.959 | 39.652 | 6.674 | 1.00 | 20.00 | 6 |
| ATOM | 1060 | CB | LYS | B | 199 | 87.577 | 39.573 | 5.279 | 1.00 | 20.00 | 6 |
| ATOM | 1061 | CG | LYS | B | 199 | 89.082 | 39.736 | 5.258 | 1.00 | 20.00 | 6 |
| ATOM | 1062 | CD | LYS | B | 199 | 89.574 | 39.919 | 3.833 | 1.00 | 20.00 | 6 |
| ATOM | 1063 | CE | LYS | B | 199 | 91.054 | 40.243 | 3.807 | 1.00 | 20.00 | 6 |
| ATOM | 1064 | NZ | LYS | B | 199 | 91.398 | 41.382 | 4.706 | 1.00 | 20.00 | 7 |
| ATOM | 1065 | C | LYS | B | 199 | 85.451 | 39.804 | 6.539 | 1.00 | 20.00 | 6 |
| ATOM | 1066 | O | LYS | B | 199 | 84.972 | 40.556 | 5.693 | 1.00 | 20.00 | 8 |
| ATOM | 1067 | N | GLY | B | 200 | 84.707 | 39.079 | 7.368 | 1.00 | 20.00 | 7 |
| ATOM | 1068 | CA | GLY | B | 200 | 83.258 | 39.158 | 7.328 | 1.00 | 20.00 | 6 |
| ATOM | 1069 | C | GLY | B | 200 | 82.646 | 38.660 | 6.032 | 1.00 | 20.00 | 6 |
| ATOM | 1070 | O | GLY | B | 200 | 81.644 | 39.198 | 5.564 | 1.00 | 20.00 | 8 |
| ATOM | 1071 | N | ILE | B | 201 | 83.243 | 37.630 | 5.445 | 1.00 | 20.00 | 7 |
| ATOM | 1072 | CA | ILE | B | 201 | 82.726 | 37.075 | 4.205 | 1.00 | 20.00 | 6 |
| ATOM | 1073 | CB | ILE | B | 201 | 83.775 | 37.140 | 3.080 | 1.00 | 20.00 | 6 |
| ATOM | 1074 | CG2 | ILE | B | 201 | 83.257 | 36.413 | 1.841 | 1.00 | 20.00 | 6 |
| ATOM | 1075 | CG1 | ILE | B | 201 | 84.109 | 38.599 | 2.761 | 1.00 | 20.00 | 6 |
| ATOM | 1076 | CD1 | ILE | B | 201 | 85.330 | 38.758 | 1.870 | 1.00 | 20.00 | 6 |
| ATOM | 1077 | C | ILE | B | 201 | 82.329 | 35.623 | 4.395 | 1.00 | 20.00 | 6 |
| ATOM | 1078 | O | ILE | B | 201 | 83.094 | 34.826 | 4.942 | 1.00 | 20.00 | 8 |
| ATOM | 1079 | N | ILE | B | 202 | 81.125 | 35.291 | 3.940 | 1.00 | 20.00 | 7 |
| ATOM | 1080 | CA | ILE | B | 202 | 80.592 | 33.936 | 4.016 | 1.00 | 20.00 | 6 |
| ATOM | 1081 | CB | ILE | B | 202 | 79.119 | 33.953 | 4.481 | 1.00 | 20.00 | 6 |
| ATOM | 1082 | CG2 | ILE | B | 202 | 78.583 | 32.522 | 4.595 | 1.00 | 20.00 | 6 |
| ATOM | 1083 | CG1 | ILE | B | 202 | 79.008 | 34.675 | 5.825 | 1.00 | 20.00 | 6 |
| ATOM | 1084 | CD1 | ILE | B | 202 | 77.576 | 34.865 | 6.294 | 1.00 | 20.00 | 6 |
| ATOM | 1085 | C | ILE | B | 202 | 80.644 | 33.393 | 2.589 | 1.00 | 20.00 | 6 |
| ATOM | 1086 | O | ILE | B | 202 | 80.182 | 34.056 | 1.663 | 1.00 | 20.00 | 8 |
| ATOM | 1087 | N | HIS | B | 203 | 81.204 | 32.204 | 2.395 | 1.00 | 20.00 | 7 |
| ATOM | 1088 | CA | HIS | B | 203 | 81.279 | 31.652 | 1.044 | 1.00 | 20.00 | 6 |
| ATOM | 1089 | CB | HIS | B | 203 | 82.258 | 30.480 | 0.999 | 1.00 | 20.00 | 6 |
| ATOM | 1090 | CG | HIS | B | 203 | 82.478 | 29.942 | −0.380 | 1.00 | 20.00 | 6 |
| ATOM | 1091 | CD2 | HIS | B | 203 | 81.646 | 29.282 | −1.220 | 1.00 | 20.00 | 6 |
| ATOM | 1092 | ND1 | HIS | B | 203 | 83.659 | 30.116 | −1.069 | 1.00 | 20.00 | 7 |
| ATOM | 1093 | CE1 | HIS | B | 203 | 83.545 | 29.588 | −2.275 | 1.00 | 20.00 | 6 |
| ATOM | 1094 | NE2 | HIS | B | 203 | 82.333 | 29.076 | −2.392 | 1.00 | 20.00 | 7 |
| ATOM | 1095 | C | HIS | B | 203 | 79.896 | 31.211 | 0.530 | 1.00 | 20.00 | 6 |
| ATOM | 1096 | O | HIS | B | 203 | 79.508 | 31.546 | −0.593 | 1.00 | 20.00 | 8 |
| ATOM | 1097 | N | ARG | B | 204 | 79.168 | 30.458 | 1.357 | 1.00 | 20.00 | 7 |
| ATOM | 1098 | CA | ARG | B | 204 | 77.819 | 29.969 | 1.039 | 1.00 | 20.00 | 6 |
| ATOM | 1099 | CB | ARG | B | 204 | 76.916 | 31.117 | 0.583 | 1.00 | 20.00 | 6 |
| ATOM | 1100 | CG | ARG | B | 204 | 76.601 | 32.120 | 1.675 | 1.00 | 20.00 | 6 |
| ATOM | 1101 | CD | ARG | B | 204 | 75.316 | 32.878 | 1.377 | 1.00 | 20.00 | 6 |
| ATOM | 1102 | NE | ARG | B | 204 | 75.376 | 33.616 | 0.119 | 1.00 | 20.00 | 7 |
| ATOM | 1103 | CZ | ARG | B | 204 | 74.423 | 34.443 | −0.303 | 1.00 | 20.00 | 6 |
| ATOM | 1104 | NH1 | ARG | B | 204 | 73.336 | 34.636 | 0.436 | 1.00 | 20.00 | 7 |
| ATOM | 1105 | NH2 | ARG | B | 204 | 74.555 | 35.084 | −1.457 | 1.00 | 20.00 | 7 |
| ATOM | 1106 | C | ARG | B | 204 | 77.700 | 28.829 | 0.030 | 1.00 | 20.00 | 6 |
| ATOM | 1107 | O | ARG | B | 204 | 76.611 | 28.300 | −0.177 | 1.00 | 20.00 | 8 |
| ATOM | 1108 | N | ASP | B | 205 | 78.792 | 28.456 | −0.620 | 1.00 | 20.00 | 7 |
| ATOM | 1109 | CA | ASP | B | 205 | 78.718 | 27.342 | −1.550 | 1.00 | 20.00 | 6 |
| ATOM | 1110 | CB | ASP | B | 205 | 78.380 | 27.829 | −2.961 | 1.00 | 20.00 | 6 |

-continued

| | | | | | | | | | | |
|---|---|---|---|---|---|---|---|---|---|---|
| ATOM | 1111 | CG  | ASP | B | 205 | 77.941 | 26.694 | −3.867 | 1.00 | 20.00 | 6 |
| ATOM | 1112 | OD1 | ASP | B | 205 | 77.544 | 25.638 | −3.330 | 1.00 | 20.00 | 8 |
| ATOM | 1113 | OD2 | ASP | B | 205 | 77.982 | 26.853 | −5.104 | 1.00 | 20.00 | 8 |
| ATOM | 1114 | C   | ASP | B | 205 | 80.019 | 26.560 | −1.547 | 1.00 | 20.00 | 6 |
| ATOM | 1115 | O   | ASP | B | 205 | 80.508 | 26.122 | −2.588 | 1.00 | 20.00 | 8 |
| ATOM | 1116 | N   | LEU | B | 206 | 80.573 | 26.375 | −0.354 | 1.00 | 20.00 | 7 |
| ATOM | 1117 | CA  | LEU | B | 206 | 81.819 | 25.652 | −0.208 | 1.00 | 20.00 | 6 |
| ATOM | 1118 | CB  | LEU | B | 206 | 82.361 | 25.826 | 1.212  | 1.00 | 20.00 | 6 |
| ATOM | 1119 | CG  | LEU | B | 206 | 83.764 | 25.271 | 1.471  | 1.00 | 20.00 | 6 |
| ATOM | 1120 | CD1 | LEU | B | 206 | 84.765 | 25.969 | 0.561  | 1.00 | 20.00 | 6 |
| ATOM | 1121 | CD2 | LEU | B | 206 | 84.135 | 25.477 | 2.933  | 1.00 | 20.00 | 6 |
| ATOM | 1122 | C   | LEU | B | 206 | 81.609 | 24.174 | −0.514 | 1.00 | 20.00 | 6 |
| ATOM | 1123 | O   | LEU | B | 206 | 80.691 | 23.549 | 0.011  | 1.00 | 20.00 | 8 |
| ATOM | 1124 | N   | LYS | B | 207 | 82.461 | 23.628 | −1.375 | 1.00 | 20.00 | 7 |
| ATOM | 1125 | CA  | LYS | B | 207 | 82.379 | 22.223 | −1.765 | 1.00 | 20.00 | 6 |
| ATOM | 1126 | CB  | LYS | B | 207 | 81.160 | 22.000 | −2.679 | 1.00 | 20.00 | 6 |
| ATOM | 1127 | CG  | LYS | B | 207 | 81.130 | 22.913 | −3.893 | 1.00 | 20.00 | 6 |
| ATOM | 1128 | CD  | LYS | B | 207 | 79.876 | 22.720 | −4.736 | 1.00 | 20.00 | 6 |
| ATOM | 1129 | CE  | LYS | B | 207 | 79.788 | 23.797 | −5.813 | 1.00 | 20.00 | 6 |
| ATOM | 1130 | NZ  | LYS | B | 207 | 78.695 | 23.557 | −6.791 | 1.00 | 20.00 | 7 |
| ATOM | 1131 | C   | LYS | B | 207 | 83.657 | 21.808 | −2.487 | 1.00 | 20.00 | 6 |
| ATOM | 1132 | O   | LYS | B | 207 | 84.416 | 22.656 | −2.960 | 1.00 | 20.00 | 8 |
| ATOM | 1133 | N   | PRO | B | 208 | 83.916 | 20.494 | −2.582 | 1.00 | 20.00 | 7 |
| ATOM | 1134 | CD  | PRO | B | 208 | 83.153 | 19.378 | −1.993 | 1.00 | 20.00 | 6 |
| ATOM | 1135 | CA  | PRO | B | 208 | 85.122 | 20.005 | −3.259 | 1.00 | 20.00 | 6 |
| ATOM | 1136 | CB  | PRO | B | 208 | 84.922 | 18.494 | −3.267 | 1.00 | 20.00 | 6 |
| ATOM | 1137 | CG  | PRO | B | 208 | 84.174 | 18.256 | −1.984 | 1.00 | 20.00 | 6 |
| ATOM | 1138 | C   | PRO | B | 208 | 85.303 | 20.574 | −4.666 | 1.00 | 20.00 | 6 |
| ATOM | 1139 | O   | PRO | B | 208 | 86.431 | 20.752 | −5.124 | 1.00 | 20.00 | 8 |
| ATOM | 1140 | N   | GLU | B | 209 | 84.197 | 20.859 | −5.347 | 1.00 | 20.00 | 7 |
| ATOM | 1141 | CA  | GLU | B | 209 | 84.243 | 21.410 | −6.705 | 1.00 | 20.00 | 6 |
| ATOM | 1142 | CB  | GLU | B | 209 | 82.836 | 21.424 | −7.317 | 1.00 | 20.00 | 6 |
| ATOM | 1143 | CG  | GLU | B | 209 | 82.755 | 22.081 | −8.690 | 1.00 | 20.00 | 6 |
| ATOM | 1144 | CD  | GLU | B | 209 | 81.323 | 22.296 | −9.159 | 1.00 | 20.00 | 6 |
| ATOM | 1145 | OE1 | GLU | B | 209 | 80.587 | 21.299 | −9.322 | 1.00 | 20.00 | 8 |
| ATOM | 1146 | OE2 | GLU | B | 209 | 80.933 | 23.465 | −9.364 | 1.00 | 20.00 | 8 |
| ATOM | 1147 | C   | GLU | B | 209 | 84.810 | 22.836 | −6.716 | 1.00 | 20.00 | 6 |
| ATOM | 1148 | O   | GLU | B | 209 | 85.409 | 23.269 | −7.705 | 1.00 | 20.00 | 8 |
| ATOM | 1149 | N   | ASN | B | 210 | 84.604 | 23.549 | −5.612 | 1.00 | 20.00 | 7 |
| ATOM | 1150 | CA  | ASN | B | 210 | 85.051 | 24.932 | −5.439 | 1.00 | 20.00 | 6 |
| ATOM | 1151 | CB  | ASN | B | 210 | 84.033 | 25.695 | −4.588 | 1.00 | 20.00 | 6 |
| ATOM | 1152 | CG  | ASN | B | 210 | 82.851 | 26.170 | −5.396 | 1.00 | 20.00 | 6 |
| ATOM | 1153 | OD1 | ASN | B | 210 | 81.807 | 26.520 | −4.846 | 1.00 | 20.00 | 8 |
| ATOM | 1154 | ND2 | ASN | B | 210 | 83.010 | 26.194 | −6.717 | 1.00 | 20.00 | 7 |
| ATOM | 1155 | C   | ASN | B | 210 | 86.427 | 25.070 | −4.797 | 1.00 | 20.00 | 6 |
| ATOM | 1156 | O   | ASN | B | 210 | 86.937 | 26.181 | −4.641 | 1.00 | 20.00 | 8 |
| ATOM | 1157 | N   | ILE | B | 211 | 87.016 | 23.948 | −4.406 | 1.00 | 20.00 | 7 |
| ATOM | 1158 | CA  | ILE | B | 211 | 88.331 | 23.958 | −3.790 | 1.00 | 20.00 | 6 |
| ATOM | 1159 | CB  | ILE | B | 211 | 88.336 | 23.090 | −2.521 | 1.00 | 20.00 | 6 |
| ATOM | 1160 | CG2 | ILE | B | 211 | 89.732 | 23.025 | −1.925 | 1.00 | 20.00 | 6 |
| ATOM | 1161 | CG1 | ILE | B | 211 | 87.350 | 23.682 | −1.510 | 1.00 | 20.00 | 6 |
| ATOM | 1162 | CD1 | ILE | B | 211 | 87.121 | 22.832 | −0.285 | 1.00 | 20.00 | 6 |
| ATOM | 1163 | C   | ILE | B | 211 | 89.307 | 23.414 | −4.816 | 1.00 | 20.00 | 6 |
| ATOM | 1164 | O   | ILE | B | 211 | 89.475 | 22.199 | −4.949 | 1.00 | 20.00 | 8 |
| ATOM | 1165 | N   | LEU | B | 212 | 89.938 | 24.319 | −5.558 | 1.00 | 20.00 | 7 |
| ATOM | 1166 | CA  | LEU | B | 212 | 90.875 | 23.918 | −6.601 | 1.00 | 20.00 | 6 |
| ATOM | 1167 | CB  | LEU | B | 212 | 90.966 | 25.012 | −7.673 | 1.00 | 20.00 | 6 |
| ATOM | 1168 | CG  | LEU | B | 212 | 89.630 | 25.510 | −8.235 | 1.00 | 20.00 | 6 |
| ATOM | 1169 | CD1 | LEU | B | 212 | 89.896 | 26.462 | −9.390 | 1.00 | 20.00 | 6 |
| ATOM | 1170 | CD2 | LEU | B | 212 | 88.781 | 24.331 | −8.709 | 1.00 | 20.00 | 6 |
| ATOM | 1171 | C   | LEU | B | 212 | 92.254 | 23.628 | −6.038 | 1.00 | 20.00 | 6 |
| ATOM | 1172 | O   | LEU | B | 212 | 92.537 | 23.923 | −4.873 | 1.00 | 20.00 | 8 |
| ATOM | 1173 | N   | LEU | B | 213 | 93.114 | 23.053 | −6.875 | 1.00 | 20.00 | 7 |
| ATOM | 1174 | CA  | LEU | B | 213 | 94.472 | 22.714 | −6.472 | 1.00 | 20.00 | 6 |
| ATOM | 1175 | CB  | LEU | B | 213 | 94.609 | 21.192 | −6.388 | 1.00 | 20.00 | 6 |
| ATOM | 1176 | CG  | LEU | B | 213 | 93.775 | 20.526 | −5.292 | 1.00 | 20.00 | 6 |
| ATOM | 1177 | CD1 | LEU | B | 213 | 93.737 | 19.035 | −5.508 | 1.00 | 20.00 | 6 |
| ATOM | 1178 | CD2 | LEU | B | 213 | 94.374 | 20.852 | −3.935 | 1.00 | 20.00 | 6 |
| ATOM | 1179 | C   | LEU | B | 213 | 95.503 | 23.277 | −7.449 | 1.00 | 20.00 | 6 |
| ATOM | 1180 | O   | LEU | B | 213 | 95.422 | 23.033 | −8.657 | 1.00 | 20.00 | 8 |
| ATOM | 1181 | N   | ASN | B | 214 | 96.470 | 24.036 | −6.940 | 1.00 | 20.00 | 7 |
| ATOM | 1182 | CA  | ASN | B | 214 | 97.488 | 24.585 | −7.826 | 1.00 | 20.00 | 6 |
| ATOM | 1183 | CB  | ASN | B | 214 | 98.198 | 25.792 | −7.201 | 1.00 | 20.00 | 6 |
| ATOM | 1184 | CG  | ASN | B | 214 | 98.938 | 25.448 | −5.927 | 1.00 | 20.00 | 6 |
| ATOM | 1185 | OD1 | ASN | B | 214 | 99.267 | 24.288 | −5.669 | 1.00 | 20.00 | 8 |
| ATOM | 1186 | ND2 | ASN | B | 214 | 99.224 | 26.469 | −5.123 | 1.00 | 20.00 | 7 |
| ATOM | 1187 | C   | ASN | B | 214 | 98.508 | 23.515 | −8.182 | 1.00 | 20.00 | 6 |
| ATOM | 1188 | O   | ASN | B | 214 | 98.420 | 22.372 | −7.725 | 1.00 | 20.00 | 8 |
| ATOM | 1189 | N   | GLU | B | 215 | 99.482 | 23.894 | −8.996 | 1.00 | 20.00 | 7 |

| | | | | | | | | | | |
|---|---|---|---|---|---|---|---|---|---|---|
| ATOM | 1190 | CA | GLU | B | 215 | 100.514 | 22.965 | −9.430 | 1.00 | 20.00 | 6 |
| ATOM | 1191 | CB | GLU | B | 215 | 101.491 | 23.687 | −10.362 | 1.00 | 20.00 | 6 |
| ATOM | 1192 | CG | GLU | B | 215 | 102.544 | 22.788 | −10.979 | 1.00 | 20.00 | 6 |
| ATOM | 1193 | CD | GLU | B | 215 | 103.323 | 23.482 | −12.080 | 1.00 | 20.00 | 6 |
| ATOM | 1194 | OE1 | GLU | B | 215 | 103.909 | 24.554 | −11.810 | 1.00 | 20.00 | 8 |
| ATOM | 1195 | OE2 | GLU | B | 215 | 103.344 | 22.957 | −13.215 | 1.00 | 20.00 | 8 |
| ATOM | 1196 | C | GLU | B | 215 | 101.275 | 22.307 | −8.274 | 1.00 | 20.00 | 6 |
| ATOM | 1197 | O | GLU | B | 215 | 101.801 | 21.205 | −8.428 | 1.00 | 20.00 | 8 |
| ATOM | 1198 | N | ASP | B | 216 | 101.335 | 22.976 | −7.123 | 1.00 | 20.00 | 7 |
| ATOM | 1199 | CA | ASP | B | 216 | 102.036 | 22.430 | −5.958 | 1.00 | 20.00 | 6 |
| ATOM | 1200 | CB | ASP | B | 216 | 102.727 | 23.549 | −5.179 | 1.00 | 20.00 | 6 |
| ATOM | 1201 | CG | ASP | B | 216 | 103.952 | 24.086 | −5.896 | 1.00 | 20.00 | 6 |
| ATOM | 1202 | OD1 | ASP | B | 216 | 104.766 | 23.267 | −6.376 | 1.00 | 20.00 | 8 |
| ATOM | 1203 | OD2 | ASP | B | 216 | 104.110 | 25.323 | −5.973 | 1.00 | 20.00 | 8 |
| ATOM | 1204 | C | ASP | B | 216 | 101.121 | 21.651 | −5.013 | 1.00 | 20.00 | 6 |
| ATOM | 1205 | O | ASP | B | 216 | 101.532 | 21.241 | −3.925 | 1.00 | 20.00 | 8 |
| ATOM | 1206 | N | MET | B | 217 | 99.877 | 21.463 | −5.434 | 1.00 | 20.00 | 7 |
| ATOM | 1207 | CA | MET | B | 217 | 98.890 | 20.730 | −4.657 | 1.00 | 20.00 | 6 |
| ATOM | 1208 | CB | MET | B | 217 | 99.402 | 19.319 | −4.358 | 1.00 | 20.00 | 6 |
| ATOM | 1209 | CG | MET | B | 217 | 99.456 | 18.432 | −5.601 | 1.00 | 20.00 | 6 |
| ATOM | 1210 | SD | MET | B | 217 | 97.857 | 18.342 | −6.445 | 1.00 | 20.00 | 16 |
| ATOM | 1211 | CE | MET | B | 217 | 97.073 | 16.984 | −5.543 | 1.00 | 20.00 | 6 |
| ATOM | 1212 | C | MET | B | 217 | 98.397 | 21.403 | −3.373 | 1.00 | 20.00 | 6 |
| ATOM | 1213 | O | MET | B | 217 | 97.972 | 20.730 | −2.435 | 1.00 | 20.00 | 8 |
| ATOM | 1214 | N | HIS | B | 218 | 98.469 | 22.730 | −3.331 | 1.00 | 20.00 | 7 |
| ATOM | 1215 | CA | HIS | B | 218 | 97.949 | 23.487 | −2.197 | 1.00 | 20.00 | 6 |
| ATOM | 1216 | CB | HIS | B | 218 | 98.831 | 24.700 | −1.898 | 1.00 | 20.00 | 6 |
| ATOM | 1217 | CG | HIS | B | 218 | 100.100 | 24.357 | −1.177 | 1.00 | 20.00 | 6 |
| ATOM | 1218 | CD2 | HIS | B | 218 | 101.390 | 24.362 | −1.588 | 1.00 | 20.00 | 6 |
| ATOM | 1219 | ND1 | HIS | B | 218 | 100.117 | 23.935 | 0.136 | 1.00 | 20.00 | 7 |
| ATOM | 1220 | CE1 | HIS | B | 218 | 101.364 | 23.698 | 0.504 | 1.00 | 20.00 | 6 |
| ATOM | 1221 | NE2 | HIS | B | 218 | 102.156 | 23.947 | −0.524 | 1.00 | 20.00 | 7 |
| ATOM | 1222 | C | HIS | B | 218 | 96.583 | 23.939 | −2.703 | 1.00 | 20.00 | 6 |
| ATOM | 1223 | O | HIS | B | 218 | 96.400 | 24.090 | −3.910 | 1.00 | 20.00 | 8 |
| ATOM | 1224 | N | ILE | B | 219 | 95.628 | 24.160 | −1.808 | 1.00 | 20.00 | 7 |
| ATOM | 1225 | CA | ILE | B | 219 | 94.301 | 24.562 | −2.257 | 1.00 | 20.00 | 6 |
| ATOM | 1226 | CB | ILE | B | 219 | 93.232 | 24.359 | −1.159 | 1.00 | 20.00 | 6 |
| ATOM | 1227 | CG2 | ILE | B | 219 | 93.266 | 22.918 | −0.654 | 1.00 | 20.00 | 6 |
| ATOM | 1228 | CG1 | ILE | B | 219 | 93.460 | 25.353 | −0.011 | 1.00 | 20.00 | 6 |
| ATOM | 1229 | CD1 | ILE | B | 219 | 92.351 | 25.342 | 1.036 | 1.00 | 20.00 | 6 |
| ATOM | 1230 | C | ILE | B | 219 | 94.207 | 26.010 | −2.714 | 1.00 | 20.00 | 6 |
| ATOM | 1231 | O | ILE | B | 219 | 95.044 | 26.850 | −2.375 | 1.00 | 20.00 | 8 |
| ATOM | 1232 | N | GLN | B | 220 | 93.168 | 26.274 | −3.497 | 1.00 | 20.00 | 7 |
| ATOM | 1233 | CA | GLN | B | 220 | 92.859 | 27.600 | −3.999 | 1.00 | 20.00 | 6 |
| ATOM | 1234 | CB | GLN | B | 220 | 93.537 | 27.867 | −5.350 | 1.00 | 20.00 | 6 |
| ATOM | 1235 | CG | GLN | B | 220 | 95.011 | 28.246 | −5.216 | 1.00 | 20.00 | 6 |
| ATOM | 1236 | CD | GLN | B | 220 | 95.599 | 28.799 | −6.503 | 1.00 | 20.00 | 6 |
| ATOM | 1237 | OE1 | GLN | B | 220 | 95.725 | 28.086 | −7.502 | 1.00 | 20.00 | 8 |
| ATOM | 1238 | NE2 | GLN | B | 220 | 95.957 | 30.079 | −6.486 | 1.00 | 20.00 | 7 |
| ATOM | 1239 | C | GLN | B | 220 | 91.350 | 27.626 | −4.140 | 1.00 | 20.00 | 6 |
| ATOM | 1240 | O | GLN | B | 220 | 90.792 | 27.133 | −5.124 | 1.00 | 20.00 | 8 |
| ATOM | 1241 | N | ILE | B | 221 | 90.689 | 28.178 | −3.129 | 1.00 | 20.00 | 7 |
| ATOM | 1242 | CA | ILE | B | 221 | 89.240 | 28.260 | −3.122 | 1.00 | 20.00 | 6 |
| ATOM | 1243 | CB | ILE | B | 221 | 88.731 | 28.550 | −1.700 | 1.00 | 20.00 | 6 |
| ATOM | 1244 | CG2 | ILE | B | 221 | 87.209 | 28.707 | −1.708 | 1.00 | 20.00 | 6 |
| ATOM | 1245 | CG1 | ILE | B | 221 | 89.164 | 27.406 | −0.773 | 1.00 | 20.00 | 6 |
| ATOM | 1246 | CD1 | ILE | B | 221 | 88.743 | 27.559 | 0.668 | 1.00 | 20.00 | 6 |
| ATOM | 1247 | C | ILE | B | 221 | 88.760 | 29.339 | −4.092 | 1.00 | 20.00 | 6 |
| ATOM | 1248 | O | ILE | B | 221 | 89.411 | 30.374 | −4.262 | 1.00 | 20.00 | 8 |
| ATOM | 1249 | N | THR | B | 222 | 87.633 | 29.082 | −4.748 | 1.00 | 20.00 | 7 |
| ATOM | 1250 | CA | THR | B | 222 | 87.084 | 30.039 | −5.701 | 1.00 | 20.00 | 6 |
| ATOM | 1251 | CB | THR | B | 222 | 87.565 | 29.728 | −7.125 | 1.00 | 20.00 | 6 |
| ATOM | 1252 | OG1 | THR | B | 222 | 87.179 | 30.795 | −8.000 | 1.00 | 20.00 | 8 |
| ATOM | 1253 | CG2 | THR | B | 222 | 86.962 | 28.410 | −7.618 | 1.00 | 20.00 | 6 |
| ATOM | 1254 | C | THR | B | 222 | 85.554 | 30.028 | −5.683 | 1.00 | 20.00 | 6 |
| ATOM | 1255 | O | THR | B | 222 | 84.950 | 29.417 | −4.791 | 1.00 | 20.00 | 8 |
| ATOM | 1256 | N | ASP | B | 223 | 84.949 | 30.712 | −6.659 | 1.00 | 20.00 | 7 |
| ATOM | 1257 | CA | ASP | B | 223 | 83.492 | 30.806 | −6.806 | 1.00 | 20.00 | 6 |
| ATOM | 1258 | CB | ASP | B | 223 | 82.872 | 29.399 | −6.767 | 1.00 | 20.00 | 6 |
| ATOM | 1259 | CG | ASP | B | 223 | 81.414 | 29.384 | −7.205 | 1.00 | 20.00 | 6 |
| ATOM | 1260 | OD1 | ASP | B | 223 | 80.990 | 30.335 | −7.900 | 1.00 | 20.00 | 8 |
| ATOM | 1261 | OD2 | ASP | B | 223 | 80.701 | 28.414 | −6.866 | 1.00 | 20.00 | 8 |
| ATOM | 1262 | C | ASP | B | 223 | 82.878 | 31.694 | −5.725 | 1.00 | 20.00 | 6 |
| ATOM | 1263 | O | ASP | B | 223 | 82.191 | 31.208 | −4.820 | 1.00 | 20.00 | 8 |
| ATOM | 1264 | N | PHE | B | 224 | 83.105 | 33.001 | −5.848 | 1.00 | 20.00 | 7 |
| ATOM | 1265 | CA | PHE | B | 224 | 82.632 | 33.970 | −4.866 | 1.00 | 20.00 | 6 |
| ATOM | 1266 | CB | PHE | B | 224 | 83.800 | 34.869 | −4.451 | 1.00 | 20.00 | 6 |
| ATOM | 1267 | CG | PHE | B | 224 | 84.826 | 34.165 | −3.612 | 1.00 | 20.00 | 6 |
| ATOM | 1268 | CD1 | PHE | B | 224 | 84.590 | 33.931 | −2.261 | 1.00 | 20.00 | 6 |

-continued

| | | | | | | | | | |
|---|---|---|---|---|---|---|---|---|---|
| ATOM | 1269 | CD2 | PHE | B | 224 | 86.001 | 33.687 | −4.182 | 1.00 | 20.00 | 6 |
| ATOM | 1270 | CE1 | PHE | B | 224 | 85.509 | 33.227 | −1.486 | 1.00 | 20.00 | 6 |
| ATOM | 1271 | CE2 | PHE | B | 224 | 86.927 | 32.981 | −3.418 | 1.00 | 20.00 | 6 |
| ATOM | 1272 | CZ | PHE | B | 224 | 86.679 | 32.750 | −2.068 | 1.00 | 20.00 | 6 |
| ATOM | 1273 | C | PHE | B | 224 | 81.443 | 34.839 | −5.256 | 1.00 | 20.00 | 6 |
| ATOM | 1274 | O | PHE | B | 224 | 81.001 | 35.678 | −4.468 | 1.00 | 20.00 | 8 |
| ATOM | 1275 | N | GLY | B | 225 | 80.928 | 34.647 | −6.463 | 1.00 | 20.00 | 7 |
| ATOM | 1276 | CA | GLY | B | 225 | 79.793 | 35.438 | −6.894 | 1.00 | 20.00 | 6 |
| ATOM | 1277 | C | GLY | B | 225 | 78.612 | 35.265 | −5.955 | 1.00 | 20.00 | 6 |
| ATOM | 1278 | O | GLY | B | 225 | 77.824 | 36.192 | −5.753 | 1.00 | 20.00 | 8 |
| ATOM | 1279 | N | THR | B | 226 | 78.486 | 34.080 | −5.367 | 1.00 | 20.00 | 7 |
| ATOM | 1280 | CA | THR | B | 226 | 77.379 | 33.819 | −4.459 | 1.00 | 20.00 | 6 |
| ATOM | 1281 | CB | THR | B | 226 | 76.779 | 32.425 | −4.715 | 1.00 | 20.00 | 6 |
| ATOM | 1282 | OG1 | THR | B | 226 | 77.826 | 31.450 | −4.762 | 1.00 | 20.00 | 8 |
| ATOM | 1283 | CG2 | THR | B | 226 | 76.021 | 32.417 | −6.041 | 1.00 | 20.00 | 6 |
| ATOM | 1284 | C | THR | B | 226 | 77.738 | 33.957 | −2.981 | 1.00 | 20.00 | 6 |
| ATOM | 1285 | O | THR | B | 226 | 77.001 | 33.500 | −2.107 | 1.00 | 20.00 | 8 |
| ATOM | 1286 | N | ALA | B | 227 | 78.867 | 34.598 | −2.702 | 1.00 | 20.00 | 7 |
| ATOM | 1287 | CA | ALA | B | 227 | 79.282 | 34.800 | −1.325 | 1.00 | 20.00 | 6 |
| ATOM | 1288 | CB | ALA | B | 227 | 80.738 | 35.242 | −1.268 | 1.00 | 20.00 | 6 |
| ATOM | 1289 | C | ALA | B | 227 | 78.384 | 35.875 | −0.726 | 1.00 | 20.00 | 6 |
| ATOM | 1290 | O | ALA | B | 227 | 77.623 | 36.529 | −1.440 | 1.00 | 20.00 | 8 |
| ATOM | 1291 | N | LYS | B | 228 | 78.467 | 36.046 | 0.586 | 1.00 | 20.00 | 7 |
| ATOM | 1292 | CA | LYS | B | 228 | 77.670 | 37.051 | 1.274 | 1.00 | 20.00 | 6 |
| ATOM | 1293 | CB | LYS | B | 228 | 76.637 | 36.384 | 2.179 | 1.00 | 20.00 | 6 |
| ATOM | 1294 | CG | LYS | B | 228 | 75.705 | 37.357 | 2.890 | 1.00 | 20.00 | 6 |
| ATOM | 1295 | CD | LYS | B | 228 | 74.795 | 38.072 | 1.893 | 1.00 | 20.00 | 6 |
| ATOM | 1296 | CE | LYS | B | 228 | 73.849 | 39.049 | 2.587 | 1.00 | 20.00 | 6 |
| ATOM | 1297 | NZ | LYS | B | 228 | 73.000 | 39.781 | 1.605 | 1.00 | 20.00 | 7 |
| ATOM | 1298 | C | LYS | B | 228 | 78.616 | 37.896 | 2.110 | 1.00 | 20.00 | 6 |
| ATOM | 1299 | O | LYS | B | 228 | 79.355 | 37.366 | 2.940 | 1.00 | 20.00 | 8 |
| ATOM | 1300 | N | VAL | B | 229 | 78.603 | 39.206 | 1.881 | 1.00 | 20.00 | 7 |
| ATOM | 1301 | CA | VAL | B | 229 | 79.463 | 40.114 | 2.626 | 1.00 | 20.00 | 6 |
| ATOM | 1302 | CB | VAL | B | 229 | 79.976 | 41.256 | 1.734 | 1.00 | 20.00 | 6 |
| ATOM | 1303 | CG1 | VAL | B | 229 | 80.853 | 42.191 | 2.540 | 1.00 | 20.00 | 6 |
| ATOM | 1304 | CG2 | VAL | B | 229 | 80.746 | 40.686 | 0.561 | 1.00 | 20.00 | 6 |
| ATOM | 1305 | C | VAL | B | 229 | 78.687 | 40.710 | 3.793 | 1.00 | 20.00 | 6 |
| ATOM | 1306 | O | VAL | B | 229 | 77.798 | 41.537 | 3.599 | 1.00 | 20.00 | 8 |
| ATOM | 1307 | N | LEU | B | 230 | 79.034 | 40.284 | 5.003 | 1.00 | 20.00 | 7 |
| ATOM | 1308 | CA | LEU | B | 230 | 78.370 | 40.752 | 6.213 | 1.00 | 20.00 | 6 |
| ATOM | 1309 | CB | LEU | B | 230 | 78.740 | 39.856 | 7.395 | 1.00 | 20.00 | 6 |
| ATOM | 1310 | CG | LEU | B | 230 | 78.276 | 38.403 | 7.332 | 1.00 | 20.00 | 6 |
| ATOM | 1311 | CD1 | LEU | B | 230 | 78.853 | 37.634 | 8.508 | 1.00 | 20.00 | 6 |
| ATOM | 1312 | CD2 | LEU | B | 230 | 76.760 | 38.350 | 7.339 | 1.00 | 20.00 | 6 |
| ATOM | 1313 | C | LEU | B | 230 | 78.705 | 42.193 | 6.565 | 1.00 | 20.00 | 6 |
| ATOM | 1314 | O | LEU | B | 230 | 79.768 | 42.701 | 6.214 | 1.00 | 20.00 | 8 |
| ATOM | 1315 | N | SER | B | 231 | 77.781 | 42.839 | 7.270 | 1.00 | 20.00 | 7 |
| ATOM | 1316 | CA | SER | B | 231 | 77.957 | 44.219 | 7.708 | 1.00 | 20.00 | 6 |
| ATOM | 1317 | CB | SER | B | 231 | 77.082 | 45.161 | 6.875 | 1.00 | 20.00 | 6 |
| ATOM | 1318 | OG | SER | B | 231 | 75.714 | 44.795 | 6.948 | 1.00 | 20.00 | 8 |
| ATOM | 1319 | C | SER | B | 231 | 77.623 | 44.373 | 9.196 | 1.00 | 20.00 | 6 |
| ATOM | 1320 | O | SER | B | 231 | 78.322 | 45.086 | 9.919 | 1.00 | 20.00 | 8 |
| ATOM | 1321 | N | PRO | B | 232 | 76.553 | 43.705 | 9.674 | 1.00 | 20.00 | 7 |
| ATOM | 1322 | CD | PRO | B | 232 | 75.571 | 42.876 | 8.948 | 1.00 | 20.00 | 6 |
| ATOM | 1323 | CA | PRO | B | 232 | 76.182 | 43.811 | 11.091 | 1.00 | 20.00 | 6 |
| ATOM | 1324 | CB | PRO | B | 232 | 75.005 | 42.844 | 11.211 | 1.00 | 20.00 | 6 |
| ATOM | 1325 | CG | PRO | B | 232 | 74.367 | 42.933 | 9.862 | 1.00 | 20.00 | 6 |
| ATOM | 1326 | C | PRO | B | 232 | 77.332 | 43.438 | 12.024 | 1.00 | 20.00 | 6 |
| ATOM | 1327 | O | PRO | B | 232 | 78.199 | 42.640 | 11.666 | 1.00 | 20.00 | 8 |
| ATOM | 1328 | N | ALA | B | 237 | 74.215 | 38.132 | 11.762 | 1.00 | 20.00 | 7 |
| ATOM | 1329 | CA | ALA | B | 237 | 74.666 | 37.653 | 10.460 | 1.00 | 20.00 | 6 |
| ATOM | 1330 | CB | ALA | B | 237 | 75.541 | 36.417 | 10.637 | 1.00 | 20.00 | 6 |
| ATOM | 1331 | C | ALA | B | 237 | 73.479 | 37.324 | 9.558 | 1.00 | 20.00 | 6 |
| ATOM | 1332 | O | ALA | B | 237 | 73.143 | 36.158 | 9.374 | 1.00 | 20.00 | 8 |
| ATOM | 1333 | N | ALA | B | 238 | 72.841 | 38.347 | 8.996 | 1.00 | 20.00 | 7 |
| ATOM | 1334 | CA | ALA | B | 238 | 71.693 | 38.130 | 8.117 | 1.00 | 20.00 | 6 |
| ATOM | 1335 | CB | ALA | B | 238 | 70.973 | 39.450 | 7.853 | 1.00 | 20.00 | 6 |
| ATOM | 1336 | C | ALA | B | 238 | 72.123 | 37.497 | 6.798 | 1.00 | 20.00 | 6 |
| ATOM | 1337 | O | ALA | B | 238 | 73.315 | 37.404 | 6.500 | 1.00 | 20.00 | 8 |
| ATOM | 1338 | N | ALA | B | 239 | 71.146 | 37.057 | 6.012 | 1.00 | 20.00 | 7 |
| ATOM | 1339 | CA | ALA | B | 239 | 71.439 | 36.431 | 4.728 | 1.00 | 20.00 | 6 |
| ATOM | 1340 | CB | ALA | B | 239 | 72.152 | 35.123 | 4.952 | 1.00 | 20.00 | 6 |
| ATOM | 1341 | C | ALA | B | 239 | 70.173 | 36.194 | 3.918 | 1.00 | 20.00 | 6 |
| ATOM | 1342 | O | ALA | B | 239 | 69.329 | 37.079 | 3.825 | 1.00 | 20.00 | 8 |
| ATOM | 1343 | N | ASN | B | 240 | 70.068 | 34.996 | 3.339 | 1.00 | 20.00 | 7 |
| ATOM | 1344 | CA | ASN | B | 240 | 68.939 | 34.559 | 2.514 | 1.00 | 20.00 | 6 |
| ATOM | 1345 | CB | ASN | B | 240 | 67.614 | 35.160 | 2.999 | 1.00 | 20.00 | 6 |
| ATOM | 1346 | CG | ASN | B | 240 | 67.258 | 36.466 | 2.299 | 1.00 | 20.00 | 6 |
| ATOM | 1347 | OD1 | ASN | B | 240 | 67.119 | 36.519 | 1.068 | 1.00 | 20.00 | 8 |

-continued

| | | | | | | | | | |
|---|---|---|---|---|---|---|---|---|---|
| ATOM | 1348 | ND2 | ASN | B | 240 | 67.091 | 37.536 | 3.089 | 1.00 | 20.00 | 7 |
| ATOM | 1349 | C | ASN | B | 240 | 69.153 | 34.937 | 1.053 | 1.00 | 20.00 | 6 |
| ATOM | 1350 | O | ASN | B | 240 | 70.007 | 35.767 | 0.749 | 1.00 | 20.00 | 8 |
| ATOM | 1351 | N | ALA | B | 241 | 68.365 | 34.329 | 0.163 | 1.00 | 20.00 | 7 |
| ATOM | 1352 | CA | ALA | B | 241 | 68.401 | 34.570 | −1.290 | 1.00 | 20.00 | 6 |
| ATOM | 1353 | C | ALA | B | 241 | 68.990 | 33.416 | −2.103 | 1.00 | 20.00 | 6 |
| ATOM | 1354 | O | ALA | B | 241 | 68.353 | 32.919 | −3.030 | 1.00 | 20.00 | 8 |
| ATOM | 1355 | CB | ALA | B | 241 | 69.168 | 35.859 | −1.629 | 1.00 | 20.00 | 6 |
| ATOM | 1356 | N | PHE | B | 242 | 70.205 | 33.000 | −1.762 | 1.00 | 20.00 | 7 |
| ATOM | 1357 | CA | PHE | B | 242 | 70.875 | 31.918 | −2.481 | 1.00 | 20.00 | 6 |
| ATOM | 1358 | CB | PHE | B | 242 | 72.259 | 32.379 | −2.952 | 1.00 | 20.00 | 6 |
| ATOM | 1359 | CG | PHE | B | 242 | 73.102 | 31.273 | −3.521 | 1.00 | 20.00 | 6 |
| ATOM | 1360 | CD1 | PHE | B | 242 | 72.843 | 30.767 | −4.790 | 1.00 | 20.00 | 6 |
| ATOM | 1361 | CD2 | PHE | B | 242 | 74.136 | 30.713 | −2.773 | 1.00 | 20.00 | 6 |
| ATOM | 1362 | CE1 | PHE | B | 242 | 73.599 | 29.718 | −5.310 | 1.00 | 20.00 | 6 |
| ATOM | 1363 | CE2 | PHE | B | 242 | 74.896 | 29.666 | −3.281 | 1.00 | 20.00 | 6 |
| ATOM | 1364 | CZ | PHE | B | 242 | 74.627 | 29.166 | −4.553 | 1.00 | 20.00 | 6 |
| ATOM | 1365 | C | PHE | B | 242 | 71.038 | 30.652 | −1.646 | 1.00 | 20.00 | 6 |
| ATOM | 1366 | O | PHE | B | 242 | 71.213 | 30.716 | −0.431 | 1.00 | 20.00 | 8 |
| ATOM | 1367 | N | VAL | B | 243 | 70.988 | 29.505 | −2.318 | 1.00 | 20.00 | 7 |
| ATOM | 1368 | CA | VAL | B | 243 | 71.157 | 28.204 | −1.675 | 1.00 | 20.00 | 6 |
| ATOM | 1369 | CB | VAL | B | 243 | 69.828 | 27.420 | −1.617 | 1.00 | 20.00 | 6 |
| ATOM | 1370 | CG1 | VAL | B | 243 | 70.066 | 26.023 | −1.050 | 1.00 | 20.00 | 6 |
| ATOM | 1371 | CG2 | VAL | B | 243 | 68.825 | 28.177 | −0.766 | 1.00 | 20.00 | 6 |
| ATOM | 1372 | C | VAL | B | 243 | 72.164 | 27.394 | −2.486 | 1.00 | 20.00 | 6 |
| ATOM | 1373 | O | VAL | B | 243 | 71.894 | 27.014 | −3.628 | 1.00 | 20.00 | 8 |
| ATOM | 1374 | N | GLY | B | 244 | 73.323 | 27.137 | −1.890 | 1.00 | 20.00 | 7 |
| ATOM | 1375 | CA | GLY | B | 244 | 74.364 | 26.385 | −2.569 | 1.00 | 20.00 | 6 |
| ATOM | 1376 | C | GLY | B | 244 | 74.019 | 24.944 | −2.911 | 1.00 | 20.00 | 6 |
| ATOM | 1377 | O | GLY | B | 244 | 72.867 | 24.524 | −2.810 | 1.00 | 20.00 | 8 |
| ATOM | 1378 | N | THR | B | 245 | 75.032 | 24.184 | −3.315 | 1.00 | 20.00 | 7 |
| ATOM | 1379 | CA | THR | B | 245 | 74.858 | 22.787 | −3.691 | 1.00 | 20.00 | 6 |
| ATOM | 1380 | CB | THR | B | 245 | 76.214 | 22.161 | −4.046 | 1.00 | 20.00 | 6 |
| ATOM | 1381 | OG1 | THR | B | 245 | 76.794 | 22.911 | −5.120 | 1.00 | 20.00 | 8 |
| ATOM | 1382 | CG2 | THR | B | 245 | 76.049 | 20.710 | −4.485 | 1.00 | 20.00 | 6 |
| ATOM | 1383 | C | THR | B | 245 | 74.174 | 22.003 | −2.579 | 1.00 | 20.00 | 6 |
| ATOM | 1384 | O | THR | B | 245 | 74.643 | 21.969 | −1.441 | 1.00 | 20.00 | 8 |
| ATOM | 1385 | N | ALA | B | 246 | 73.061 | 21.372 | −2.937 | 1.00 | 20.00 | 7 |
| ATOM | 1386 | CA | ALA | B | 246 | 72.229 | 20.615 | −2.008 | 1.00 | 20.00 | 6 |
| ATOM | 1387 | CB | ALA | B | 246 | 71.266 | 19.723 | −2.793 | 1.00 | 20.00 | 6 |
| ATOM | 1388 | C | ALA | B | 246 | 72.936 | 19.789 | −0.941 | 1.00 | 20.00 | 6 |
| ATOM | 1389 | O | ALA | B | 246 | 72.611 | 19.894 | 0.239 | 1.00 | 20.00 | 8 |
| ATOM | 1390 | N | GLN | B | 247 | 73.902 | 18.973 | −1.339 | 1.00 | 20.00 | 7 |
| ATOM | 1391 | CA | GLN | B | 247 | 74.580 | 18.121 | −0.371 | 1.00 | 20.00 | 6 |
| ATOM | 1392 | CB | GLN | B | 247 | 75.535 | 17.168 | −1.096 | 1.00 | 20.00 | 6 |
| ATOM | 1393 | CG | GLN | B | 247 | 75.110 | 16.823 | −2.520 | 1.00 | 20.00 | 6 |
| ATOM | 1394 | CD | GLN | B | 247 | 75.139 | 15.336 | −2.811 | 1.00 | 20.00 | 6 |
| ATOM | 1395 | OE1 | GLN | B | 247 | 75.963 | 14.602 | −2.270 | 1.00 | 20.00 | 8 |
| ATOM | 1396 | NE2 | GLN | B | 247 | 74.246 | 14.887 | −3.686 | 1.00 | 20.00 | 7 |
| ATOM | 1397 | C | GLN | B | 247 | 75.343 | 18.873 | 0.720 | 1.00 | 20.00 | 6 |
| ATOM | 1398 | O | GLN | B | 247 | 75.631 | 18.306 | 1.773 | 1.00 | 20.00 | 8 |
| ATOM | 1399 | N | TYR | B | 248 | 75.648 | 20.147 | 0.484 | 1.00 | 20.00 | 7 |
| ATOM | 1400 | CA | TYR | B | 248 | 76.405 | 20.941 | 1.454 | 1.00 | 20.00 | 6 |
| ATOM | 1401 | CB | TYR | B | 248 | 77.642 | 21.531 | 0.767 | 1.00 | 20.00 | 6 |
| ATOM | 1402 | CG | TYR | B | 248 | 78.447 | 20.471 | 0.052 | 1.00 | 20.00 | 6 |
| ATOM | 1403 | CD1 | TYR | B | 248 | 79.329 | 19.648 | 0.750 | 1.00 | 20.00 | 6 |
| ATOM | 1404 | CE1 | TYR | B | 248 | 79.979 | 18.589 | 0.115 | 1.00 | 20.00 | 6 |
| ATOM | 1405 | CD2 | TYR | B | 248 | 78.243 | 20.220 | −1.306 | 1.00 | 20.00 | 6 |
| ATOM | 1406 | CE2 | TYR | B | 248 | 78.884 | 19.167 | −1.951 | 1.00 | 20.00 | 6 |
| ATOM | 1407 | CZ | TYR | B | 248 | 79.748 | 18.352 | −1.232 | 1.00 | 20.00 | 6 |
| ATOM | 1408 | OH | TYR | B | 248 | 80.348 | 17.280 | −1.852 | 1.00 | 20.00 | 8 |
| ATOM | 1409 | C | TYR | B | 248 | 75.596 | 22.055 | 2.118 | 1.00 | 20.00 | 6 |
| ATOM | 1410 | O | TYR | B | 248 | 76.132 | 22.824 | 2.917 | 1.00 | 20.00 | 8 |
| ATOM | 1411 | N | VAL | B | 249 | 74.309 | 22.135 | 1.798 | 1.00 | 20.00 | 7 |
| ATOM | 1412 | CA | VAL | B | 249 | 73.452 | 23.162 | 2.376 | 1.00 | 20.00 | 6 |
| ATOM | 1413 | CB | VAL | B | 249 | 72.071 | 23.174 | 1.695 | 1.00 | 20.00 | 6 |
| ATOM | 1414 | CG1 | VAL | B | 249 | 71.117 | 24.100 | 2.442 | 1.00 | 20.00 | 6 |
| ATOM | 1415 | CG2 | VAL | B | 249 | 72.225 | 23.632 | 0.264 | 1.00 | 20.00 | 6 |
| ATOM | 1416 | C | VAL | B | 249 | 73.262 | 22.964 | 3.875 | 1.00 | 20.00 | 6 |
| ATOM | 1417 | O | VAL | B | 249 | 73.027 | 21.847 | 4.341 | 1.00 | 20.00 | 8 |
| ATOM | 1418 | N | SER | B | 250 | 73.373 | 24.055 | 4.628 | 1.00 | 20.00 | 7 |
| ATOM | 1419 | CA | SER | B | 250 | 73.206 | 24.008 | 6.076 | 1.00 | 20.00 | 6 |
| ATOM | 1420 | CB | SER | B | 250 | 73.921 | 25.198 | 6.738 | 1.00 | 20.00 | 6 |
| ATOM | 1421 | OG | SER | B | 250 | 73.428 | 26.440 | 6.257 | 1.00 | 20.00 | 8 |
| ATOM | 1422 | C | SER | B | 250 | 71.717 | 24.049 | 6.405 | 1.00 | 20.00 | 6 |
| ATOM | 1423 | O | SER | B | 250 | 70.920 | 24.577 | 5.636 | 1.00 | 20.00 | 8 |
| ATOM | 1424 | N | PRO | B | 251 | 71.322 | 23.479 | 7.550 | 1.00 | 20.00 | 7 |
| ATOM | 1425 | CD | PRO | B | 251 | 72.130 | 22.770 | 8.558 | 1.00 | 20.00 | 6 |
| ATOM | 1426 | CA | PRO | B | 251 | 69.905 | 23.484 | 7.925 | 1.00 | 20.00 | 6 |

| | | | | | -continued | | | | | |
|---|---|---|---|---|---|---|---|---|---|---|
| ATOM | 1427 | CB | PRO | B | 251 | 69.892 | 22.714 | 9.252 | 1.00 | 20.00 | 6 |
| ATOM | 1428 | CG | PRO | B | 251 | 71.290 | 22.936 | 9.801 | 1.00 | 20.00 | 6 |
| ATOM | 1429 | C | PRO | B | 251 | 69.265 | 24.870 | 8.032 | 1.00 | 20.00 | 6 |
| ATOM | 1430 | O | PRO | B | 251 | 68.093 | 25.036 | 7.688 | 1.00 | 20.00 | 8 |
| ATOM | 1431 | N | GLU | B | 252 | 70.017 | 25.867 | 8.492 | 1.00 | 20.00 | 7 |
| ATOM | 1432 | CA | GLU | B | 252 | 69.462 | 27.216 | 8.625 | 1.00 | 20.00 | 6 |
| ATOM | 1433 | CB | GLU | B | 252 | 70.503 | 28.193 | 9.196 | 1.00 | 20.00 | 6 |
| ATOM | 1434 | CG | GLU | B | 252 | 71.838 | 28.180 | 8.477 | 1.00 | 20.00 | 6 |
| ATOM | 1435 | CD | GLU | B | 252 | 72.844 | 27.257 | 9.139 | 1.00 | 20.00 | 6 |
| ATOM | 1436 | OE1 | GLU | B | 252 | 72.429 | 26.207 | 9.675 | 1.00 | 20.00 | 8 |
| ATOM | 1437 | OE2 | GLU | B | 252 | 74.053 | 27.581 | 9.118 | 1.00 | 20.00 | 8 |
| ATOM | 1438 | C | GLU | B | 252 | 68.928 | 27.744 | 7.292 | 1.00 | 20.00 | 6 |
| ATOM | 1439 | O | GLU | B | 252 | 67.927 | 28.459 | 7.261 | 1.00 | 20.00 | 8 |
| ATOM | 1440 | N | LEU | B | 253 | 69.584 | 27.395 | 6.189 | 1.00 | 20.00 | 7 |
| ATOM | 1441 | CA | LEU | B | 253 | 69.117 | 27.850 | 4.883 | 1.00 | 20.00 | 6 |
| ATOM | 1442 | CB | LEU | B | 253 | 70.140 | 27.527 | 3.794 | 1.00 | 20.00 | 6 |
| ATOM | 1443 | CG | LEU | B | 253 | 71.127 | 28.635 | 3.421 | 1.00 | 20.00 | 6 |
| ATOM | 1444 | CD1 | LEU | B | 253 | 72.121 | 28.851 | 4.547 | 1.00 | 20.00 | 6 |
| ATOM | 1445 | CD2 | LEU | B | 253 | 71.858 | 28.250 | 2.140 | 1.00 | 20.00 | 6 |
| ATOM | 1446 | C | LEU | B | 253 | 67.774 | 27.227 | 4.496 | 1.00 | 20.00 | 6 |
| ATOM | 1447 | O | LEU | B | 253 | 66.997 | 27.826 | 3.751 | 1.00 | 20.00 | 8 |
| ATOM | 1448 | N | LEU | B | 254 | 67.506 | 26.029 | 5.002 | 1.00 | 20.00 | 7 |
| ATOM | 1449 | CA | LEU | B | 254 | 66.271 | 25.316 | 4.689 | 1.00 | 20.00 | 6 |
| ATOM | 1450 | CB | LEU | B | 254 | 66.539 | 23.809 | 4.689 | 1.00 | 20.00 | 6 |
| ATOM | 1451 | CG | LEU | B | 254 | 67.647 | 23.322 | 3.746 | 1.00 | 20.00 | 6 |
| ATOM | 1452 | CD1 | LEU | B | 254 | 67.983 | 21.873 | 4.057 | 1.00 | 20.00 | 6 |
| ATOM | 1453 | CD2 | LEU | B | 254 | 67.204 | 23.475 | 2.302 | 1.00 | 20.00 | 6 |
| ATOM | 1454 | C | LEU | B | 254 | 65.135 | 25.626 | 5.662 | 1.00 | 20.00 | 6 |
| ATOM | 1455 | O | LEU | B | 254 | 63.959 | 25.524 | 5.312 | 1.00 | 20.00 | 8 |
| ATOM | 1456 | N | THR | B | 255 | 65.483 | 26.010 | 6.883 | 1.00 | 20.00 | 7 |
| ATOM | 1457 | CA | THR | B | 255 | 64.472 | 26.308 | 7.884 | 1.00 | 20.00 | 6 |
| ATOM | 1458 | CB | THR | B | 255 | 64.876 | 25.747 | 9.252 | 1.00 | 20.00 | 6 |
| ATOM | 1459 | OG1 | THR | B | 255 | 66.154 | 26.277 | 9.619 | 1.00 | 20.00 | 8 |
| ATOM | 1460 | CG2 | THR | B | 255 | 64.958 | 24.230 | 9.202 | 1.00 | 20.00 | 6 |
| ATOM | 1461 | C | THR | B | 255 | 64.205 | 27.795 | 8.035 | 1.00 | 20.00 | 6 |
| ATOM | 1462 | O | THR | B | 255 | 63.072 | 28.241 | 7.897 | 1.00 | 20.00 | 8 |
| ATOM | 1463 | N | GLU | B | 256 | 65.250 | 28.560 | 8.314 | 1.00 | 20.00 | 7 |
| ATOM | 1464 | CA | GLU | B | 256 | 65.115 | 30.001 | 8.507 | 1.00 | 20.00 | 6 |
| ATOM | 1465 | CB | GLU | B | 256 | 66.015 | 30.444 | 9.659 | 1.00 | 20.00 | 6 |
| ATOM | 1466 | CG | GLU | B | 256 | 65.634 | 29.818 | 10.987 | 1.00 | 20.00 | 6 |
| ATOM | 1467 | CD | GLU | B | 256 | 66.736 | 29.922 | 12.018 | 1.00 | 20.00 | 6 |
| ATOM | 1468 | OE1 | GLU | B | 256 | 67.249 | 31.041 | 12.232 | 1.00 | 20.00 | 8 |
| ATOM | 1469 | OE2 | GLU | B | 256 | 67.086 | 28.884 | 12.619 | 1.00 | 20.00 | 8 |
| ATOM | 1470 | C | GLU | B | 256 | 65.439 | 30.815 | 7.262 | 1.00 | 20.00 | 6 |
| ATOM | 1471 | O | GLU | B | 256 | 65.268 | 32.034 | 7.252 | 1.00 | 20.00 | 8 |
| ATOM | 1472 | N | LYS | B | 257 | 65.906 | 30.141 | 6.215 | 1.00 | 20.00 | 7 |
| ATOM | 1473 | CA | LYS | B | 257 | 66.260 | 30.814 | 4.970 | 1.00 | 20.00 | 6 |
| ATOM | 1474 | CB | LYS | B | 257 | 65.015 | 31.458 | 4.352 | 1.00 | 20.00 | 6 |
| ATOM | 1475 | CG | LYS | B | 257 | 65.184 | 31.918 | 2.915 | 1.00 | 20.00 | 6 |
| ATOM | 1476 | CD | LYS | B | 257 | 63.885 | 32.497 | 2.378 | 1.00 | 20.00 | 6 |
| ATOM | 1477 | CE | LYS | B | 257 | 63.994 | 32.841 | 0.902 | 1.00 | 20.00 | 6 |
| ATOM | 1478 | NZ | LYS | B | 257 | 65.060 | 33.847 | 0.640 | 1.00 | 20.00 | 7 |
| ATOM | 1479 | C | LYS | B | 257 | 67.309 | 31.885 | 5.263 | 1.00 | 20.00 | 6 |
| ATOM | 1480 | O | LYS | B | 257 | 67.270 | 32.977 | 4.702 | 1.00 | 20.00 | 8 |
| ATOM | 1481 | N | SER | B | 258 | 68.243 | 31.563 | 6.152 | 1.00 | 20.00 | 7 |
| ATOM | 1482 | CA | SER | B | 258 | 69.300 | 32.494 | 6.527 | 1.00 | 20.00 | 6 |
| ATOM | 1483 | CB | SER | B | 258 | 69.043 | 33.028 | 7.937 | 1.00 | 20.00 | 6 |
| ATOM | 1484 | OG | SER | B | 258 | 68.893 | 31.962 | 8.859 | 1.00 | 20.00 | 8 |
| ATOM | 1485 | C | SER | B | 258 | 70.675 | 31.829 | 6.467 | 1.00 | 20.00 | 6 |
| ATOM | 1486 | O | SER | B | 258 | 70.786 | 30.602 | 6.542 | 1.00 | 20.00 | 8 |
| ATOM | 1487 | N | ALA | B | 259 | 71.718 | 32.641 | 6.329 | 1.00 | 20.00 | 7 |
| ATOM | 1488 | CA | ALA | B | 259 | 73.081 | 32.130 | 6.252 | 1.00 | 20.00 | 6 |
| ATOM | 1489 | CB | ALA | B | 259 | 73.549 | 32.121 | 4.809 | 1.00 | 20.00 | 6 |
| ATOM | 1490 | C | ALA | B | 259 | 74.031 | 32.966 | 7.102 | 1.00 | 20.00 | 6 |
| ATOM | 1491 | O | ALA | B | 259 | 73.882 | 34.185 | 7.211 | 1.00 | 20.00 | 8 |
| ATOM | 1492 | N | CYS | B | 260 | 75.008 | 32.298 | 7.704 | 1.00 | 20.00 | 7 |
| ATOM | 1493 | CA | CYS | B | 260 | 75.993 | 32.960 | 8.550 | 1.00 | 20.00 | 6 |
| ATOM | 1494 | CB | CYS | B | 260 | 75.574 | 32.865 | 10.017 | 1.00 | 20.00 | 6 |
| ATOM | 1495 | SG | CYS | B | 260 | 75.303 | 31.165 | 10.594 | 1.00 | 20.00 | 16 |
| ATOM | 1496 | C | GYS | B | 260 | 77.328 | 32.265 | 8.349 | 1.00 | 20.00 | 6 |
| ATOM | 1497 | O | CYS | B | 260 | 77.410 | 31.280 | 7.620 | 1.00 | 20.00 | 8 |
| ATOM | 1498 | N | LYS | B | 261 | 78.371 | 32.775 | 8.993 | 1.00 | 20.00 | 7 |
| ATOM | 1499 | CA | LYS | B | 261 | 79.691 | 32.174 | 8.869 | 1.00 | 20.00 | 6 |
| ATOM | 1500 | CB | LYS | B | 261 | 80.676 | 32.851 | 9.821 | 1.00 | 20.00 | 6 |
| ATOM | 1501 | CG | LYS | B | 261 | 80.985 | 34.296 | 9.472 | 1.00 | 20.00 | 6 |
| ATOM | 1502 | CD | LYS | B | 261 | 81.961 | 34.878 | 10.475 | 1.00 | 20.00 | 6 |
| ATOM | 1503 | CE | LYS | B | 261 | 82.157 | 36.365 | 10.259 | 1.00 | 20.00 | 6 |
| ATOM | 1504 | NZ | LYS | B | 261 | 83.085 | 36.922 | 11.278 | 1.00 | 20.00 | 7 |
| ATOM | 1505 | C | LYS | B | 261 | 79.632 | 30.687 | 9.187 | 1.00 | 20.00 | 6 |

-continued

| | | | | | | | | | | |
|---|---|---|---|---|---|---|---|---|---|---|
| ATOM | 1506 | O | LYS | B | 261 | 80.258 | 29.877 | 8.512 | 1.00 | 20.00 | 8 |
| ATOM | 1507 | N | SER | B | 262 | 78.860 | 30.346 | 10.214 | 1.00 | 20.00 | 7 |
| ATOM | 1508 | CA | SER | B | 262 | 78.716 | 28.966 | 10.659 | 1.00 | 20.00 | 6 |
| ATOM | 1509 | CB | SER | B | 262 | 77.806 | 28.913 | 11.895 | 1.00 | 20.00 | 6 |
| ATOM | 1510 | OG | SER | B | 262 | 77.884 | 27.657 | 12.546 | 1.00 | 20.00 | 8 |
| ATOM | 1511 | C | SER | B | 262 | 78.161 | 28.070 | 9.549 | 1.00 | 20.00 | 6 |
| ATOM | 1512 | O | SER | B | 262 | 78.350 | 26.856 | 9.575 | 1.00 | 20.00 | 8 |
| ATOM | 1513 | N | SER | B | 263 | 77.466 | 28.660 | 8.581 | 1.00 | 20.00 | 7 |
| ATOM | 1514 | CA | SER | B | 263 | 76.938 | 27.870 | 7.472 | 1.00 | 20.00 | 6 |
| ATOM | 1515 | CB | SER | B | 263 | 76.132 | 28.750 | 6.507 | 1.00 | 20.00 | 6 |
| ATOM | 1516 | OG | SER | B | 263 | 75.011 | 29.329 | 7.156 | 1.00 | 20.00 | 8 |
| ATOM | 1517 | C | SER | B | 263 | 78.123 | 27.244 | 6.737 | 1.00 | 20.00 | 6 |
| ATOM | 1518 | O | SER | B | 263 | 78.038 | 26.108 | 6.273 | 1.00 | 20.00 | 8 |
| ATOM | 1519 | N | ASP | B | 264 | 79.234 | 27.977 | 6.642 | 1.00 | 20.00 | 7 |
| ATOM | 1520 | CA | ASP | B | 264 | 80.419 | 27.448 | 5.961 | 1.00 | 20.00 | 6 |
| ATOM | 1521 | CB | ASP | B | 264 | 81.478 | 28.538 | 5.745 | 1.00 | 20.00 | 6 |
| ATOM | 1522 | CG | ASP | B | 264 | 81.091 | 29.539 | 4.673 | 1.00 | 20.00 | 6 |
| ATOM | 1523 | OD1 | ASP | B | 264 | 80.286 | 29.187 | 3.786 | 1.00 | 20.00 | 8 |
| ATOM | 1524 | OD2 | ASP | B | 264 | 81.617 | 30.676 | 4.704 | 1.00 | 20.00 | 8 |
| ATOM | 1525 | C | ASP | B | 264 | 81.043 | 26.312 | 6.771 | 1.00 | 20.00 | 6 |
| ATOM | 1526 | O | ASP | B | 264 | 81.586 | 25.365 | 6.201 | 1.00 | 20.00 | 8 |
| ATOM | 1527 | N | LEU | B | 265 | 80.971 | 26.415 | 8.099 | 1.00 | 20.00 | 7 |
| ATOM | 1528 | CA | LEU | B | 265 | 81.532 | 25.390 | 8.974 | 1.00 | 20.00 | 6 |
| ATOM | 1529 | CB | LEU | B | 265 | 81.491 | 25.848 | 10.438 | 1.00 | 20.00 | 6 |
| ATOM | 1530 | CG | LEU | B | 265 | 82.419 | 27.035 | 10.746 | 1.00 | 20.00 | 6 |
| ATOM | 1531 | CD1 | LEU | B | 265 | 82.204 | 27.532 | 12.177 | 1.00 | 20.00 | 6 |
| ATOM | 1532 | CD2 | LEU | B | 265 | 83.864 | 26.608 | 10.541 | 1.00 | 20.00 | 6 |
| ATOM | 1533 | C | LEU | B | 265 | 80.750 | 24.094 | 8.800 | 1.00 | 20.00 | 6 |
| ATOM | 1534 | O | LEU | B | 265 | 81.306 | 23.004 | 8.910 | 1.00 | 20.00 | 8 |
| ATOM | 1535 | N | TRP | B | 266 | 79.454 | 24.208 | 8.530 | 1.00 | 20.00 | 7 |
| ATOM | 1536 | CA | TRP | B | 266 | 78.646 | 23.017 | 8.309 | 1.00 | 20.00 | 6 |
| ATOM | 1537 | CB | TRP | B | 266 | 77.167 | 23.384 | 8.148 | 1.00 | 20.00 | 6 |
| ATOM | 1538 | CG | TRP | B | 266 | 76.310 | 22.245 | 7.646 | 1.00 | 20.00 | 6 |
| ATOM | 1539 | CD2 | TRP | B | 266 | 75.455 | 21.399 | 8.426 | 1.00 | 20.00 | 6 |
| ATOM | 1540 | CE2 | TRP | B | 266 | 74.881 | 20.455 | 7.542 | 1.00 | 20.00 | 6 |
| ATOM | 1541 | CE3 | TRP | B | 266 | 75.117 | 21.345 | 9.785 | 1.00 | 20.00 | 6 |
| ATOM | 1542 | CD1 | TRP | B | 266 | 76.220 | 21.792 | 6.356 | 1.00 | 20.00 | 6 |
| ATOM | 1543 | NE1 | TRP | B | 266 | 75.365 | 20.719 | 6.288 | 1.00 | 20.00 | 7 |
| ATOM | 1544 | CZ2 | TRP | B | 266 | 73.988 | 19.466 | 7.975 | 1.00 | 20.00 | 6 |
| ATOM | 1545 | CZ3 | TRP | B | 266 | 74.227 | 20.359 | 10.216 | 1.00 | 20.00 | 6 |
| ATOM | 1546 | CH2 | TRP | B | 266 | 73.674 | 19.434 | 9.310 | 1.00 | 20.00 | 6 |
| ATOM | 1547 | C | TRP | B | 266 | 79.169 | 22.356 | 7.038 | 1.00 | 20.00 | 6 |
| ATOM | 1548 | O | TRP | B | 266 | 79.356 | 21.142 | 6.988 | 1.00 | 20.00 | 8 |
| ATOM | 1549 | N | ALA | B | 267 | 79.411 | 23.164 | 6.011 | 1.00 | 20.00 | 7 |
| ATOM | 1550 | CA | ALA | B | 267 | 79.930 | 22.646 | 4.751 | 1.00 | 20.00 | 6 |
| ATOM | 1551 | CB | ALA | B | 267 | 80.089 | 23.772 | 3.746 | 1.00 | 20.00 | 6 |
| ATOM | 1552 | C | ALA | B | 267 | 81.277 | 21.976 | 5.016 | 1.00 | 20.00 | 6 |
| ATOM | 1553 | O | ALA | B | 267 | 81.570 | 20.914 | 4.471 | 1.00 | 20.00 | 8 |
| ATOM | 1554 | N | LEU | B | 268 | 82.091 | 22.596 | 5.864 | 1.00 | 20.00 | 7 |
| ATOM | 1555 | CA | LEU | B | 268 | 83.393 | 22.030 | 6.209 | 1.00 | 20.00 | 6 |
| ATOM | 1556 | CB | LEU | B | 268 | 84.092 | 22.898 | 7.264 | 1.00 | 20.00 | 6 |
| ATOM | 1557 | CG | LEU | B | 268 | 85.379 | 22.332 | 7.879 | 1.00 | 20.00 | 6 |
| ATOM | 1558 | CD1 | LEU | B | 268 | 86.442 | 22.192 | 6.803 | 1.00 | 20.00 | 6 |
| ATOM | 1559 | CD2 | LEU | B | 268 | 85.872 | 23.263 | 9.006 | 1.00 | 20.00 | 6 |
| ATOM | 1560 | C | LEU | B | 268 | 83.193 | 20.617 | 6.753 | 1.00 | 20.00 | 6 |
| ATOM | 1561 | O | LEU | B | 268 | 83.903 | 19.684 | 6.372 | 1.00 | 20.00 | 8 |
| ATOM | 1562 | N | GLY | B | 269 | 82.220 | 20.463 | 7.645 | 1.00 | 20.00 | 7 |
| ATOM | 1563 | CA | GLY | B | 269 | 81.947 | 19.156 | 8.217 | 1.00 | 20.00 | 6 |
| ATOM | 1564 | C | GLY | B | 269 | 81.597 | 18.125 | 7.156 | 1.00 | 20.00 | 6 |
| ATOM | 1565 | O | GLY | B | 269 | 82.025 | 16.971 | 7.239 | 1.00 | 20.00 | 8 |
| ATOM | 1566 | N | CYS | B | 270 | 80.819 | 18.530 | 6.155 | 1.00 | 20.00 | 7 |
| ATOM | 1567 | CA | CYS | B | 270 | 80.445 | 17.613 | 5.083 | 1.00 | 20.00 | 6 |
| ATOM | 1568 | CB | CYS | B | 270 | 79.413 | 18.255 | 4.148 | 1.00 | 20.00 | 6 |
| ATOM | 1569 | SG | CYS | B | 270 | 77.824 | 18.654 | 4.905 | 1.00 | 20.00 | 16 |
| ATOM | 1570 | C | GYS | B | 270 | 81.682 | 17.241 | 4.265 | 1.00 | 20.00 | 6 |
| ATOM | 1571 | O | CYS | B | 270 | 81.852 | 16.090 | 3.866 | 1.00 | 20.00 | 8 |
| ATOM | 1572 | N | ILE | B | 271 | 82.541 | 18.226 | 4.012 | 1.00 | 20.00 | 7 |
| ATOM | 1573 | CA | ILE | B | 271 | 83.751 | 18.000 | 3.229 | 1.00 | 20.00 | 6 |
| ATOM | 1574 | CB | ILE | B | 271 | 84.436 | 19.339 | 2.903 | 1.00 | 20.00 | 6 |
| ATOM | 1575 | CG2 | ILE | B | 271 | 85.784 | 19.098 | 2.227 | 1.00 | 20.00 | 6 |
| ATOM | 1576 | CG1 | ILE | B | 271 | 83.508 | 20.171 | 2.007 | 1.00 | 20.00 | 6 |
| ATOM | 1577 | CD1 | ILE | B | 271 | 83.962 | 21.607 | 1.815 | 1.00 | 20.00 | 6 |
| ATOM | 1578 | C | ILE | B | 271 | 84.729 | 17.063 | 3.934 | 1.00 | 20.00 | 6 |
| ATOM | 1579 | O | ILE | B | 271 | 85.300 | 16.174 | 3.304 | 1.00 | 20.00 | 8 |
| ATOM | 1580 | N | ILE | B | 272 | 84.927 | 17.258 | 5.236 | 1.00 | 20.00 | 7 |
| ATOM | 1581 | CA | ILE | B | 272 | 85.820 | 16.382 | 5.987 | 1.00 | 20.00 | 6 |
| ATOM | 1582 | CB | ILE | B | 272 | 85.902 | 16.790 | 7.471 | 1.00 | 20.00 | 6 |
| ATOM | 1583 | CG2 | ILE | B | 272 | 86.623 | 15.703 | 8.277 | 1.00 | 20.00 | 6 |
| ATOM | 1584 | CG1 | ILE | B | 272 | 86.646 | 18.120 | 7.606 | 1.00 | 20.00 | 6 |

|      | -continued |     |     |   |     |        |        |        |      |       |   |
|------|------|-----|-----|---|-----|--------|--------|--------|------|-------|---|
| ATOM | 1585 | CD1 | ILE | B | 272 | 86.553 | 18.723 | 9.011  | 1.00 | 20.00 | 6 |
| ATOM | 1586 | C   | ILE | B | 272 | 85.274 | 14.957 | 5.901  | 1.00 | 20.00 | 6 |
| ATOM | 1587 | O   | ILE | B | 272 | 86.021 | 14.003 | 5.679  | 1.00 | 20.00 | 8 |
| ATOM | 1588 | N   | TYR | B | 273 | 83.964 | 14.822 | 6.072  | 1.00 | 20.00 | 7 |
| ATOM | 1589 | CA  | TYR | B | 273 | 83.324 | 13.518 | 6.006  | 1.00 | 20.00 | 6 |
| ATOM | 1590 | CB  | TYR | B | 273 | 81.825 | 13.651 | 6.287  | 1.00 | 20.00 | 6 |
| ATOM | 1591 | CG  | TYR | B | 273 | 81.064 | 12.340 | 6.250  | 1.00 | 20.00 | 6 |
| ATOM | 1592 | CD1 | TYR | B | 273 | 80.806 | 11.690 | 5.041  | 1.00 | 20.00 | 6 |
| ATOM | 1593 | CE1 | TYR | B | 273 | 80.107 | 10.486 | 5.005  | 1.00 | 20.00 | 6 |
| ATOM | 1594 | CD2 | TYR | B | 273 | 80.601 | 11.750 | 7.427  | 1.00 | 20.00 | 6 |
| ATOM | 1595 | CE2 | TYR | B | 273 | 79.904 | 10.548 | 7.405  | 1.00 | 20.00 | 6 |
| ATOM | 1596 | CZ  | TYR | B | 273 | 79.659 | 9.922  | 6.192  | 1.00 | 20.00 | 6 |
| ATOM | 1597 | OH  | TYR | B | 273 | 78.971 | 8.736  | 6.174  | 1.00 | 20.00 | 8 |
| ATOM | 1598 | C   | TYR | B | 273 | 83.550 | 12.897 | 4.632  | 1.00 | 20.00 | 6 |
| ATOM | 1599 | O   | TYR | B | 273 | 83.865 | 11.713 | 4.526  | 1.00 | 20.00 | 8 |
| ATOM | 1600 | N   | GLN | B | 274 | 83.402 | 13.705 | 3.586  | 1.00 | 20.00 | 7 |
| ATOM | 1601 | CA  | GLN | B | 274 | 83.579 | 13.230 | 2.220  | 1.00 | 20.00 | 6 |
| ATOM | 1602 | CB  | GLN | B | 274 | 83.176 | 14.322 | 1.222  | 1.00 | 20.00 | 6 |
| ATOM | 1603 | CG  | GLN | B | 274 | 83.149 | 13.857 | −0.230 | 1.00 | 20.00 | 6 |
| ATOM | 1604 | CD  | GLN | B | 274 | 82.558 | 14.898 | −1.169 | 1.00 | 20.00 | 6 |
| ATOM | 1605 | OE1 | GLN | B | 274 | 82.108 | 15.961 | −0.736 | 1.00 | 20.00 | 8 |
| ATOM | 1606 | NE2 | GLN | B | 274 | 82.548 | 14.591 | −2.462 | 1.00 | 20.00 | 7 |
| ATOM | 1607 | C   | GLN | B | 274 | 85.013 | 12.788 | 1.953  | 1.00 | 20.00 | 6 |
| ATOM | 1608 | O   | GLN | B | 274 | 85.239 | 11.818 | 1.233  | 1.00 | 20.00 | 8 |
| ATOM | 1609 | N   | LEU | B | 275 | 85.981 | 13.498 | 2.528  | 1.00 | 20.00 | 7 |
| ATOM | 1610 | CA  | LEU | B | 275 | 87.389 | 13.143 | 2.333  | 1.00 | 20.00 | 6 |
| ATOM | 1611 | CB  | LEU | B | 275 | 88.311 | 14.194 | 2.971  | 1.00 | 20.00 | 6 |
| ATOM | 1612 | CG  | LEU | B | 275 | 88.418 | 15.561 | 2.284  | 1.00 | 20.00 | 6 |
| ATOM | 1613 | CD1 | LEU | B | 275 | 89.325 | 16.481 | 3.088  | 1.00 | 20.00 | 6 |
| ATOM | 1614 | CD2 | LEU | B | 275 | 88.969 | 15.379 | 0.879  | 1.00 | 20.00 | 6 |
| ATOM | 1615 | C   | LEU | B | 275 | 87.697 | 11.779 | 2.940  | 1.00 | 20.00 | 6 |
| ATOM | 1616 | O   | LEU | B | 275 | 88.430 | 10.981 | 2.354  | 1.00 | 20.00 | 8 |
| ATOM | 1617 | N   | VAL | B | 276 | 87.125 | 11.519 | 4.112  | 1.00 | 20.00 | 7 |
| ATOM | 1618 | CA  | VAL | B | 276 | 87.353 | 10.269 | 4.827  | 1.00 | 20.00 | 6 |
| ATOM | 1619 | CB  | VAL | B | 276 | 87.096 | 10.451 | 6.342  | 1.00 | 20.00 | 6 |
| ATOM | 1620 | CG1 | VAL | B | 276 | 87.376 | 9.148  | 7.082  | 1.00 | 20.00 | 6 |
| ATOM | 1621 | CG2 | VAL | B | 276 | 87.973 | 11.580 | 6.891  | 1.00 | 20.00 | 6 |
| ATOM | 1622 | C   | VAL | B | 276 | 86.504 | 9.089  | 4.336  | 1.00 | 20.00 | 6 |
| ATOM | 1623 | O   | VAL | B | 276 | 87.005 | 7.973  | 4.195  | 1.00 | 20.00 | 8 |
| ATOM | 1624 | N   | ALA | B | 277 | 85.222 | 9.337  | 4.090  | 1.00 | 20.00 | 7 |
| ATOM | 1625 | CA  | ALA | B | 277 | 84.310 | 8.291  | 3.643  | 1.00 | 20.00 | 6 |
| ATOM | 1626 | CB  | ALA | B | 277 | 82.898 | 8.597  | 4.124  | 1.00 | 20.00 | 6 |
| ATOM | 1627 | C   | ALA | B | 277 | 84.315 | 8.115  | 2.130  | 1.00 | 20.00 | 6 |
| ATOM | 1628 | O   | ALA | B | 277 | 84.036 | 7.029  | 1.627  | 1.00 | 20.00 | 8 |
| ATOM | 1629 | N   | GLY | B | 278 | 84.632 | 9.180  | 1.405  | 1.00 | 20.00 | 7 |
| ATOM | 1630 | CA  | GLY | B | 278 | 84.653 | 9.099  | −0.041 | 1.00 | 20.00 | 6 |
| ATOM | 1631 | C   | GLY | B | 278 | 83.365 | 9.627  | −0.644 | 1.00 | 20.00 | 6 |
| ATOM | 1632 | O   | GLY | B | 278 | 83.272 | 9.817  | −1.860 | 1.00 | 20.00 | 8 |
| ATOM | 1633 | N   | LEU | B | 279 | 82.375 | 9.867  | 0.211  | 1.00 | 20.00 | 7 |
| ATOM | 1634 | CA  | LEU | B | 279 | 81.075 | 10.382 | −0.219 | 1.00 | 20.00 | 6 |
| ATOM | 1635 | CB  | LEU | B | 279 | 80.070 | 9.232  | −0.375 | 1.00 | 20.00 | 6 |
| ATOM | 1636 | CG  | LEU | B | 279 | 80.342 | 8.114  | −1.385 | 1.00 | 20.00 | 6 |
| ATOM | 1637 | CD1 | LEU | B | 279 | 79.311 | 7.009  | −1.191 | 1.00 | 20.00 | 6 |
| ATOM | 1638 | CD2 | LEU | B | 279 | 80.291 | 8.660  | −2.804 | 1.00 | 20.00 | 6 |
| ATOM | 1639 | C   | LEU | B | 279 | 80.522 | 11.369 | 0.812  | 1.00 | 20.00 | 6 |
| ATOM | 1640 | O   | LEU | B | 279 | 80.750 | 11.218 | 2.007  | 1.00 | 20.00 | 8 |
| ATOM | 1641 | N   | PRO | B | 280 | 79.787 | 12.395 | 0.361  | 1.00 | 20.00 | 7 |
| ATOM | 1642 | CD  | PRO | B | 280 | 79.403 | 12.730 | −1.020 | 1.00 | 20.00 | 6 |
| ATOM | 1643 | CA  | PRO | B | 280 | 79.230 | 13.361 | 1.314  | 1.00 | 20.00 | 6 |
| ATOM | 1644 | CB  | PRO | B | 280 | 78.569 | 14.397 | 0.407  | 1.00 | 20.00 | 6 |
| ATOM | 1645 | CG  | PRO | B | 280 | 78.191 | 13.598 | −0.802 | 1.00 | 20.00 | 6 |
| ATOM | 1646 | C   | PRO | B | 280 | 78.242 | 12.662 | 2.262  | 1.00 | 20.00 | 6 |
| ATOM | 1647 | O   | PRO | B | 280 | 77.666 | 11.633 | 1.913  | 1.00 | 20.00 | 8 |
| ATOM | 1648 | N   | PRO | B | 281 | 78.035 | 13.220 | 3.470  | 1.00 | 20.00 | 7 |
| ATOM | 1649 | CD  | PRO | B | 281 | 78.571 | 14.535 | 3.859  | 1.00 | 20.00 | 6 |
| ATOM | 1650 | CA  | PRO | B | 281 | 77.145 | 12.701 | 4.520  | 1.00 | 20.00 | 6 |
| ATOM | 1651 | CB  | PRO | B | 281 | 77.262 | 13.746 | 5.634  | 1.00 | 20.00 | 6 |
| ATOM | 1652 | CG  | PRO | B | 281 | 78.546 | 14.450 | 5.344  | 1.00 | 20.00 | 6 |
| ATOM | 1653 | C   | PRO | B | 281 | 75.679 | 12.485 | 4.142  | 1.00 | 20.00 | 6 |
| ATOM | 1654 | O   | PRO | B | 281 | 75.094 | 11.441 | 4.442  | 1.00 | 20.00 | 8 |
| ATOM | 1655 | N   | PHE | B | 282 | 75.088 | 13.487 | 3.504  | 1.00 | 20.00 | 7 |
| ATOM | 1656 | CA  | PHE | B | 282 | 73.686 | 13.427 | 3.123  | 1.00 | 20.00 | 6 |
| ATOM | 1657 | CB  | PHE | B | 282 | 73.006 | 14.734 | 3.531  | 1.00 | 20.00 | 6 |
| ATOM | 1658 | CG  | PHE | B | 282 | 73.300 | 15.146 | 4.947  | 1.00 | 20.00 | 6 |
| ATOM | 1659 | CD1 | PHE | B | 282 | 72.624 | 14.560 | 6.013  | 1.00 | 20.00 | 6 |
| ATOM | 1660 | CD2 | PHE | B | 282 | 74.295 | 16.085 | 5.218  | 1.00 | 20.00 | 6 |
| ATOM | 1661 | CE1 | PHE | B | 282 | 72.934 | 14.902 | 7.331  | 1.00 | 20.00 | 6 |
| ATOM | 1662 | CE2 | PHE | B | 282 | 74.613 | 16.433 | 6.530  | 1.00 | 20.00 | 6 |
| ATOM | 1663 | CZ  | PHE | B | 282 | 73.930 | 15.840 | 7.591  | 1.00 | 20.00 | 6 |

|      | -continued |     |     |   |     |        |        |        |      |       |   |
| ---- | ---------- | --- | --- | - | --- | ------ | ------ | ------ | ---- | ----- | - |
| ATOM | 1664 | C   | PHE | B | 282 | 73.527 | 13.191 | 1.628  | 1.00 | 20.00 | 6 |
| ATOM | 1665 | O   | PHE | B | 282 | 73.797 | 14.079 | 0.819  | 1.00 | 20.00 | 8 |
| ATOM | 1666 | N   | ARG | B | 283 | 73.080 | 11.994 | 1.267  | 1.00 | 20.00 | 7 |
| ATOM | 1667 | CA  | ARG | B | 283 | 72.888 | 11.635 | -0.134 | 1.00 | 20.00 | 6 |
| ATOM | 1668 | CB  | ARG | B | 283 | 73.931 | 10.598 | -0.559 | 1.00 | 20.00 | 6 |
| ATOM | 1669 | CG  | ARG | B | 283 | 75.358 | 10.928 | -0.151 | 1.00 | 20.00 | 6 |
| ATOM | 1670 | CD  | ARG | B | 283 | 76.326 | 9.883  | -0.687 | 1.00 | 20.00 | 6 |
| ATOM | 1671 | NE  | ARG | B | 283 | 76.054 | 8.555  | -0.142 | 1.00 | 20.00 | 7 |
| ATOM | 1672 | CZ  | ARG | B | 283 | 76.404 | 8.159  | 1.077  | 1.00 | 20.00 | 6 |
| ATOM | 1673 | NH1 | ARG | B | 283 | 77.047 | 8.986  | 1.893  | 1.00 | 20.00 | 7 |
| ATOM | 1674 | NH2 | ARG | B | 283 | 76.108 | 6.933  | 1.484  | 1.00 | 20.00 | 7 |
| ATOM | 1675 | C   | ARG | B | 283 | 71.493 | 11.046 | -0.331 | 1.00 | 20.00 | 6 |
| ATOM | 1676 | O   | ARG | B | 283 | 70.957 | 10.391 | 0.563  | 1.00 | 20.00 | 8 |
| ATOM | 1677 | N   | ALA | B | 284 | 70.911 | 11.276 | -1.502 | 1.00 | 20.00 | 7 |
| ATOM | 1678 | CA  | ALA | B | 284 | 69.579 | 10.755 | -1.796 | 1.00 | 20.00 | 6 |
| ATOM | 1679 | CB  | ALA | B | 284 | 68.532 | 11.484 | -0.961 | 1.00 | 20.00 | 6 |
| ATOM | 1680 | C   | ALA | B | 284 | 69.278 | 10.921 | -3.273 | 1.00 | 20.00 | 6 |
| ATOM | 1681 | O   | ALA | B | 284 | 70.007 | 11.611 | -3.984 | 1.00 | 20.00 | 8 |
| ATOM | 1682 | N   | GLY | B | 285 | 68.191 | 10.299 | -3.722 | 1.00 | 20.00 | 7 |
| ATOM | 1683 | CA  | GLY | B | 285 | 67.807 | 10.360 | -5.122 | 1.00 | 20.00 | 6 |
| ATOM | 1684 | C   | GLY | B | 285 | 67.561 | 11.737 | -5.707 | 1.00 | 20.00 | 6 |
| ATOM | 1685 | O   | GLY | B | 285 | 67.775 | 11.955 | -6.899 | 1.00 | 20.00 | 8 |
| ATOM | 1686 | N   | ASN | B | 286 | 67.089 | 12.673 | -4.892 | 1.00 | 20.00 | 7 |
| ATOM | 1687 | CA  | ASN | B | 286 | 66.835 | 14.018 | -5.386 | 1.00 | 20.00 | 6 |
| ATOM | 1688 | CB  | ASN | B | 286 | 65.403 | 14.137 | -5.930 | 1.00 | 20.00 | 6 |
| ATOM | 1689 | CG  | ASN | B | 286 | 64.342 | 13.825 | -4.885 | 1.00 | 20.00 | 6 |
| ATOM | 1690 | OD1 | ASN | B | 286 | 64.292 | 14.450 | -3.826 | 1.00 | 20.00 | 8 |
| ATOM | 1691 | ND2 | ASN | B | 286 | 63.477 | 12.861 | -5.190 | 1.00 | 20.00 | 7 |
| ATOM | 1692 | C   | ASN | B | 286 | 67.076 | 15.042 | -4.291 | 1.00 | 20.00 | 6 |
| ATOM | 1693 | O   | ASN | B | 286 | 67.368 | 14.682 | -3.152 | 1.00 | 20.00 | 8 |
| ATOM | 1694 | N   | GLU | B | 287 | 66.955 | 16.317 | -4.636 | 1.00 | 20.00 | 7 |
| ATOM | 1695 | CA  | GLU | B | 287 | 67.185 | 17.377 | -3.669 | 1.00 | 20.00 | 6 |
| ATOM | 1696 | CB  | GLU | B | 287 | 67.181 | 18.738 | -4.365 | 1.00 | 20.00 | 6 |
| ATOM | 1697 | CG  | GLU | B | 287 | 68.537 | 19.095 | -4.944 | 1.00 | 20.00 | 6 |
| ATOM | 1698 | CD  | GLU | B | 287 | 68.524 | 20.385 | -5.735 | 1.00 | 20.00 | 6 |
| ATOM | 1699 | OE1 | GLU | B | 287 | 67.911 | 21.371 | -5.267 | 1.00 | 20.00 | 8 |
| ATOM | 1700 | OE2 | GLU | B | 287 | 69.144 | 20.410 | -6.823 | 1.00 | 20.00 | 8 |
| ATOM | 1701 | C   | GLU | B | 287 | 66.225 | 17.394 | -2.492 | 1.00 | 20.00 | 6 |
| ATOM | 1702 | O   | GLU | B | 287 | 66.658 | 17.554 | -1.354 | 1.00 | 20.00 | 8 |
| ATOM | 1703 | N   | TYR | B | 288 | 64.932 | 17.233 | -2.753 | 1.00 | 20.00 | 7 |
| ATOM | 1704 | CA  | TYR | B | 288 | 63.955 | 17.239 | -1.670 | 1.00 | 20.00 | 6 |
| ATOM | 1705 | CB  | TYR | B | 288 | 62.553 | 16.899 | -2.184 | 1.00 | 20.00 | 6 |
| ATOM | 1706 | CG  | TYR | B | 288 | 61.530 | 16.780 | -1.070 | 1.00 | 20.00 | 6 |
| ATOM | 1707 | CD1 | TYR | B | 288 | 60.984 | 17.917 | -0.470 | 1.00 | 20.00 | 6 |
| ATOM | 1708 | CE1 | TYR | B | 288 | 60.090 | 17.814 | 0.600  | 1.00 | 20.00 | 6 |
| ATOM | 1709 | CD2 | TYR | B | 288 | 61.154 | 15.529 | -0.573 | 1.00 | 20.00 | 6 |
| ATOM | 1710 | CE2 | TYR | B | 288 | 60.265 | 15.414 | 0.498  | 1.00 | 20.00 | 6 |
| ATOM | 1711 | CZ  | TYR | B | 288 | 59.740 | 16.561 | 1.078  | 1.00 | 20.00 | 6 |
| ATOM | 1712 | OH  | TYR | B | 288 | 58.884 | 16.454 | 2.149  | 1.00 | 20.00 | 8 |
| ATOM | 1713 | C   | TYR | B | 288 | 64.337 | 16.238 | -0.587 | 1.00 | 20.00 | 6 |
| ATOM | 1714 | O   | TYR | B | 288 | 64.254 | 16.545 | 0.598  | 1.00 | 20.00 | 8 |
| ATOM | 1715 | N   | LEU | B | 289 | 64.750 | 15.041 | -1.001 | 1.00 | 20.00 | 7 |
| ATOM | 1716 | CA  | LEU | B | 289 | 65.137 | 13.989 | -0.064 | 1.00 | 20.00 | 6 |
| ATOM | 1717 | CB  | LEU | B | 289 | 65.283 | 12.649 | -0.797 | 1.00 | 20.00 | 6 |
| ATOM | 1718 | CG  | LEU | B | 289 | 63.984 | 11.985 | -1.274 | 1.00 | 20.00 | 6 |
| ATOM | 1719 | CD1 | LEU | B | 289 | 64.314 | 10.802 | -2.179 | 1.00 | 20.00 | 6 |
| ATOM | 1720 | CD2 | LEU | B | 289 | 63.160 | 11.530 | -0.068 | 1.00 | 20.00 | 6 |
| ATOM | 1721 | C   | LEU | B | 289 | 66.431 | 14.310 | 0.685  | 1.00 | 20.00 | 6 |
| ATOM | 1722 | O   | LEU | B | 289 | 66.604 | 13.914 | 1.840  | 1.00 | 20.00 | 8 |
| ATOM | 1723 | N   | ILE | B | 290 | 67.340 | 15.017 | 0.025  | 1.00 | 20.00 | 7 |
| ATOM | 1724 | CA  | ILE | B | 290 | 68.597 | 15.390 | 0.658  | 1.00 | 20.00 | 6 |
| ATOM | 1725 | CB  | ILE | B | 290 | 69.583 | 15.985 | -0.366 | 1.00 | 20.00 | 6 |
| ATOM | 1726 | CG2 | ILE | B | 290 | 70.778 | 16.609 | 0.359  | 1.00 | 20.00 | 6 |
| ATOM | 1727 | CG1 | ILE | B | 290 | 70.046 | 14.887 | -1.330 | 1.00 | 20.00 | 6 |
| ATOM | 1728 | CD1 | ILE | B | 290 | 70.844 | 15.398 | -2.518 | 1.00 | 20.00 | 6 |
| ATOM | 1729 | C   | ILE | B | 290 | 68.307 | 16.424 | 1.743  | 1.00 | 20.00 | 6 |
| ATOM | 1730 | O   | ILE | B | 290 | 68.807 | 16.317 | 2.862  | 1.00 | 20.00 | 8 |
| ATOM | 1731 | N   | PHE | B | 291 | 67.491 | 17.420 | 1.411  | 1.00 | 20.00 | 7 |
| ATOM | 1732 | CA  | PHE | B | 291 | 67.143 | 18.462 | 2.372  | 1.00 | 20.00 | 6 |
| ATOM | 1733 | CB  | PHE | B | 291 | 66.222 | 19.502 | 1.731  | 1.00 | 20.00 | 6 |
| ATOM | 1734 | CG  | PHE | B | 291 | 66.869 | 20.289 | 0.628  | 1.00 | 20.00 | 6 |
| ATOM | 1735 | CD1 | PHE | B | 291 | 68.255 | 20.420 | 0.568  | 1.00 | 20.00 | 6 |
| ATOM | 1736 | CD2 | PHE | B | 291 | 66.094 | 20.931 | -0.332 | 1.00 | 20.00 | 6 |
| ATOM | 1737 | CE1 | PHE | B | 291 | 68.859 | 21.182 | -0.435 | 1.00 | 20.00 | 6 |
| ATOM | 1738 | CE2 | PHE | B | 291 | 66.690 | 21.697 | -1.340 | 1.00 | 20.00 | 6 |
| ATOM | 1739 | CZ  | PHE | B | 291 | 68.074 | 21.822 | -1.390 | 1.00 | 20.00 | 6 |
| ATOM | 1740 | C   | PHE | B | 291 | 66.453 | 17.848 | 3.576  | 1.00 | 20.00 | 6 |
| ATOM | 1741 | O   | PHE | B | 291 | 66.664 | 18.262 | 4.718  | 1.00 | 20.00 | 8 |
| ATOM | 1742 | N   | GLN | B | 292 | 65.629 | 16.847 | 3.303  | 1.00 | 20.00 | 7 |

-continued

| | | | | | | | | | | |
|---|---|---|---|---|---|---|---|---|---|---|
| ATOM | 1743 | CA | GLN | B | 292 | 64.887 | 16.154 | 4.341 | 1.00 | 20.00 | 6 |
| ATOM | 1744 | CB | GLN | B | 292 | 64.006 | 15.090 | 3.687 | 1.00 | 20.00 | 6 |
| ATOM | 1745 | CG | GLN | B | 292 | 62.953 | 14.486 | 4.572 | 1.00 | 20.00 | 6 |
| ATOM | 1746 | CD | GLN | B | 292 | 61.895 | 13.750 | 3.763 | 1.00 | 20.00 | 6 |
| ATOM | 1747 | OE1 | GLN | B | 292 | 62.208 | 12.835 | 2.997 | 1.00 | 20.00 | 8 |
| ATOM | 1748 | NE2 | GLN | B | 292 | 60.637 | 14.155 | 3.924 | 1.00 | 20.00 | 7 |
| ATOM | 1749 | C | GLN | B | 292 | 65.865 | 15.522 | 5.329 | 1.00 | 20.00 | 6 |
| ATOM | 1750 | O | GLN | B | 292 | 65.689 | 15.630 | 6.540 | 1.00 | 20.00 | 8 |
| ATOM | 1751 | N | LYS | B | 293 | 66.907 | 14.875 | 4.812 | 1.00 | 20.00 | 7 |
| ATOM | 1752 | CA | LYS | B | 293 | 67.898 | 14.244 | 5.683 | 1.00 | 20.00 | 6 |
| ATOM | 1753 | CB | LYS | B | 293 | 68.850 | 13.372 | 4.865 | 1.00 | 20.00 | 6 |
| ATOM | 1754 | CG | LYS | B | 293 | 68.197 | 12.135 | 4.278 | 1.00 | 20.00 | 6 |
| ATOM | 1755 | CD | LYS | B | 293 | 69.217 | 11.260 | 3.554 | 1.00 | 20.00 | 6 |
| ATOM | 1756 | CE | LYS | B | 293 | 68.575 | 9.972 | 3.051 | 1.00 | 20.00 | 6 |
| ATOM | 1757 | NZ | LYS | B | 293 | 69.553 | 9.099 | 2.339 | 1.00 | 20.00 | 7 |
| ATOM | 1758 | C | LYS | B | 293 | 68.698 | 15.287 | 6.468 | 1.00 | 20.00 | 6 |
| ATOM | 1759 | O | LYS | B | 293 | 69.044 | 15.074 | 7.634 | 1.00 | 20.00 | 8 |
| ATOM | 1760 | N | ILE | B | 294 | 68.989 | 16.411 | 5.827 | 1.00 | 20.00 | 7 |
| ATOM | 1761 | CA | ILE | B | 294 | 69.745 | 17.480 | 6.472 | 1.00 | 20.00 | 6 |
| ATOM | 1762 | CB | ILE | B | 294 | 70.026 | 18.632 | 5.474 | 1.00 | 20.00 | 6 |
| ATOM | 1763 | CG2 | ILE | B | 294 | 70.489 | 19.881 | 6.223 | 1.00 | 20.00 | 6 |
| ATOM | 1764 | CG1 | ILE | B | 294 | 71.070 | 18.178 | 4.443 | 1.00 | 20.00 | 6 |
| ATOM | 1765 | CD1 | ILE | B | 294 | 71.266 | 19.159 | 3.303 | 1.00 | 20.00 | 6 |
| ATOM | 1766 | C | ILE | B | 294 | 69.035 | 18.045 | 7.712 | 1.00 | 20.00 | 6 |
| ATOM | 1767 | O | ILE | B | 294 | 69.618 | 18.091 | 8.798 | 1.00 | 20.00 | 8 |
| ATOM | 1768 | N | ILE | B | 295 | 67.783 | 18.467 | 7.564 | 1.00 | 20.00 | 7 |
| ATOM | 1769 | CA | ILE | B | 295 | 67.068 | 19.037 | 8.707 | 1.00 | 20.00 | 6 |
| ATOM | 1770 | CB | ILE | B | 295 | 65.710 | 19.647 | 8.300 | 1.00 | 20.00 | 6 |
| ATOM | 1771 | CG2 | ILE | B | 295 | 65.927 | 20.749 | 7.265 | 1.00 | 20.00 | 6 |
| ATOM | 1772 | CG1 | ILE | B | 295 | 64.784 | 18.559 | 7.762 | 1.00 | 20.00 | 6 |
| ATOM | 1773 | CD1 | ILE | B | 295 | 63.356 | 19.037 | 7.558 | 1.00 | 20.00 | 6 |
| ATOM | 1774 | C | ILE | B | 295 | 66.831 | 18.045 | 9.842 | 1.00 | 20.00 | 6 |
| ATOM | 1775 | O | ILE | B | 295 | 66.540 | 18.447 | 10.967 | 1.00 | 20.00 | 8 |
| ATOM | 1776 | N | LYS | B | 296 | 66.956 | 16.753 | 9.550 | 1.00 | 20.00 | 7 |
| ATOM | 1777 | CA | LYS | B | 296 | 66.765 | 15.724 | 10.569 | 1.00 | 20.00 | 6 |
| ATOM | 1778 | CB | LYS | B | 296 | 65.907 | 14.576 | 10.019 | 1.00 | 20.00 | 6 |
| ATOM | 1779 | CG | LYS | B | 296 | 64.535 | 15.010 | 9.538 | 1.00 | 20.00 | 6 |
| ATOM | 1780 | CD | LYS | B | 296 | 63.739 | 13.851 | 8.951 | 1.00 | 20.00 | 6 |
| ATOM | 1781 | CE | LYS | B | 296 | 63.296 | 12.873 | 10.025 | 1.00 | 20.00 | 6 |
| ATOM | 1782 | NZ | LYS | B | 296 | 62.375 | 11.828 | 9.482 | 1.00 | 20.00 | 7 |
| ATOM | 1783 | C | LYS | B | 296 | 68.116 | 15.176 | 11.018 | 1.00 | 20.00 | 6 |
| ATOM | 1784 | O | LYS | B | 296 | 68.178 | 14.261 | 11.838 | 1.00 | 20.00 | 8 |
| ATOM | 1785 | N | LEU | B | 297 | 69.190 | 15.746 | 10.474 | 1.00 | 20.00 | 7 |
| ATOM | 1786 | CA | LEU | B | 297 | 70.551 | 15.320 | 10.791 | 1.00 | 20.00 | 6 |
| ATOM | 1787 | CB | LEU | B | 297 | 70.911 | 15.680 | 12.236 | 1.00 | 20.00 | 6 |
| ATOM | 1788 | CG | LEU | B | 297 | 72.398 | 15.538 | 12.585 | 1.00 | 20.00 | 6 |
| ATOM | 1789 | CD1 | LEU | B | 297 | 73.215 | 16.555 | 11.771 | 1.00 | 20.00 | 6 |
| ATOM | 1790 | CD2 | LEU | B | 297 | 72.605 | 15.762 | 14.076 | 1.00 | 20.00 | 6 |
| ATOM | 1791 | C | LEU | B | 297 | 70.635 | 13.810 | 10.592 | 1.00 | 20.00 | 6 |
| ATOM | 1792 | O | LEU | B | 297 | 71.150 | 13.080 | 11.434 | 1.00 | 20.00 | 8 |
| ATOM | 1793 | N | GLU | B | 298 | 70.128 | 13.351 | 9.456 | 1.00 | 20.00 | 7 |
| ATOM | 1794 | CA | GLU | B | 298 | 70.115 | 11.934 | 9.148 | 1.00 | 20.00 | 6 |
| ATOM | 1795 | CB | GLU | B | 298 | 68.817 | 11.597 | 8.416 | 1.00 | 20.00 | 6 |
| ATOM | 1796 | CG | GLU | B | 298 | 68.568 | 10.123 | 8.233 | 1.00 | 20.00 | 6 |
| ATOM | 1797 | CD | GLU | B | 298 | 67.254 | 9.858 | 7.535 | 1.00 | 20.00 | 6 |
| ATOM | 1798 | OE1 | GLU | B | 298 | 66.214 | 10.331 | 8.043 | 1.00 | 20.00 | 8 |
| ATOM | 1799 | OE2 | GLU | B | 298 | 67.261 | 9.185 | 6.484 | 1.00 | 20.00 | 8 |
| ATOM | 1800 | C | GLU | B | 298 | 71.309 | 11.446 | 8.332 | 1.00 | 20.00 | 6 |
| ATOM | 1801 | O | GLU | B | 298 | 71.310 | 11.523 | 7.104 | 1.00 | 20.00 | 8 |
| ATOM | 1802 | N | TYR | B | 299 | 72.325 | 10.946 | 9.027 | 1.00 | 20.00 | 7 |
| ATOM | 1803 | CA | TYR | B | 299 | 73.519 | 10.405 | 8.390 | 1.00 | 20.00 | 6 |
| ATOM | 1804 | CB | TYR | B | 299 | 74.444 | 11.521 | 7.880 | 1.00 | 20.00 | 6 |
| ATOM | 1805 | CG | TYR | B | 299 | 75.330 | 12.130 | 8.953 | 1.00 | 20.00 | 6 |
| ATOM | 1806 | CD1 | TYR | B | 299 | 74.796 | 12.962 | 9.935 | 1.00 | 20.00 | 6 |
| ATOM | 1807 | CE1 | TYR | B | 299 | 75.589 | 13.482 | 10.951 | 1.00 | 20.00 | 6 |
| ATOM | 1808 | CD2 | TYR | B | 299 | 76.692 | 11.833 | 9.013 | 1.00 | 20.00 | 6 |
| ATOM | 1809 | CE2 | TYR | B | 299 | 77.499 | 12.352 | 10.032 | 1.00 | 20.00 | 6 |
| ATOM | 1810 | CZ | TYR | B | 299 | 76.935 | 13.173 | 10.995 | 1.00 | 20.00 | 6 |
| ATOM | 1811 | OH | TYR | B | 299 | 77.701 | 13.687 | 12.006 | 1.00 | 20.00 | 8 |
| ATOM | 1812 | C | TYR | B | 299 | 74.245 | 9.600 | 9.456 | 1.00 | 20.00 | 6 |
| ATOM | 1813 | O | TYR | B | 299 | 73.913 | 9.688 | 10.631 | 1.00 | 20.00 | 8 |
| ATOM | 1814 | N | ASP | B | 300 | 75.229 | 8.808 | 9.052 | 1.00 | 20.00 | 7 |
| ATOM | 1815 | CA | ASP | B | 300 | 75.991 | 8.030 | 10.016 | 1.00 | 20.00 | 6 |
| ATOM | 1816 | CB | ASP | B | 300 | 75.291 | 6.700 | 10.304 | 1.00 | 20.00 | 6 |
| ATOM | 1817 | CG | ASP | B | 300 | 74.898 | 5.968 | 9.048 | 1.00 | 20.00 | 6 |
| ATOM | 1818 | OD1 | ASP | B | 300 | 75.806 | 5.594 | 8.274 | 1.00 | 20.00 | 8 |
| ATOM | 1819 | OD2 | ASP | B | 300 | 73.681 | 5.771 | 8.832 | 1.00 | 20.00 | 8 |
| ATOM | 1820 | C | ASP | B | 300 | 77.397 | 7.799 | 9.488 | 1.00 | 20.00 | 6 |
| ATOM | 1821 | O | ASP | B | 300 | 77.651 | 7.976 | 8.297 | 1.00 | 20.00 | 8 |

-continued

| | | | | | | | | | | |
|---|---|---|---|---|---|---|---|---|---|---|
| ATOM | 1822 | N | PHE | B | 301 | 78.307 | 7.417 | 10.378 | 1.00 | 20.00 | 7 |
| ATOM | 1823 | CA | PHE | B | 301 | 79.695 | 7.186 | 9.996 | 1.00 | 20.00 | 6 |
| ATOM | 1824 | CB | PHE | B | 301 | 80.655 | 7.664 | 11.093 | 1.00 | 20.00 | 6 |
| ATOM | 1825 | CG | PHE | B | 301 | 80.488 | 9.103 | 11.481 | 1.00 | 20.00 | 6 |
| ATOM | 1826 | CD1 | PHE | B | 301 | 79.493 | 9.487 | 12.370 | 1.00 | 20.00 | 6 |
| ATOM | 1827 | CD2 | PHE | B | 301 | 81.346 | 10.075 | 10.970 | 1.00 | 20.00 | 6 |
| ATOM | 1828 | CE1 | PHE | B | 301 | 79.352 | 10.823 | 12.750 | 1.00 | 20.00 | 6 |
| ATOM | 1829 | CE2 | PHE | B | 301 | 81.214 | 11.408 | 11.342 | 1.00 | 20.00 | 6 |
| ATOM | 1830 | CZ | PHE | B | 301 | 80.215 | 11.783 | 12.235 | 1.00 | 20.00 | 6 |
| ATOM | 1831 | C | PHE | B | 301 | 80.009 | 5.722 | 9.744 | 1.00 | 20.00 | 6 |
| ATOM | 1832 | O | PHE | B | 301 | 79.506 | 4.839 | 10.442 | 1.00 | 20.00 | 8 |
| ATOM | 1833 | N | PRO | B | 302 | 80.842 | 5.440 | 8.732 | 1.00 | 20.00 | 7 |
| ATOM | 1834 | CD | PRO | B | 302 | 81.330 | 6.316 | 7.654 | 1.00 | 20.00 | 6 |
| ATOM | 1835 | CA | PRO | B | 302 | 81.191 | 4.044 | 8.466 | 1.00 | 20.00 | 6 |
| ATOM | 1836 | CB | PRO | B | 302 | 81.838 | 4.105 | 7.084 | 1.00 | 20.00 | 6 |
| ATOM | 1837 | CG | PRO | B | 302 | 82.425 | 5.479 | 7.046 | 1.00 | 20.00 | 6 |
| ATOM | 1838 | C | PRO | B | 302 | 82.168 | 3.629 | 9.569 | 1.00 | 20.00 | 6 |
| ATOM | 1839 | O | PRO | B | 302 | 82.887 | 4.469 | 10.111 | 1.00 | 20.00 | 8 |
| ATOM | 1840 | N | ALA | B | 303 | 82.185 | 2.345 | 9.908 | 1.00 | 20.00 | 7 |
| ATOM | 1841 | CA | ALA | B | 303 | 83.052 | 1.836 | 10.968 | 1.00 | 20.00 | 6 |
| ATOM | 1842 | CB | ALA | B | 303 | 82.993 | 0.310 | 10.987 | 1.00 | 20.00 | 6 |
| ATOM | 1843 | C | ALA | B | 303 | 84.513 | 2.294 | 10.939 | 1.00 | 20.00 | 6 |
| ATOM | 1844 | O | ALA | B | 303 | 85.078 | 2.637 | 11.979 | 1.00 | 20.00 | 8 |
| ATOM | 1845 | N | ALA | B | 304 | 85.121 | 2.306 | 9.756 | 1.00 | 20.00 | 7 |
| ATOM | 1846 | CA | ALA | B | 304 | 86.527 | 2.684 | 9.605 | 1.00 | 20.00 | 6 |
| ATOM | 1847 | CB | ALA | B | 304 | 86.971 | 2.423 | 8.165 | 1.00 | 20.00 | 6 |
| ATOM | 1848 | C | ALA | B | 304 | 86.894 | 4.119 | 10.001 | 1.00 | 20.00 | 6 |
| ATOM | 1849 | O | ALA | B | 304 | 87.983 | 4.367 | 10.520 | 1.00 | 20.00 | 8 |
| ATOM | 1850 | N | PHE | B | 305 | 85.985 | 5.053 | 9.742 | 1.00 | 20.00 | 7 |
| ATOM | 1851 | CA | PHE | B | 305 | 86.183 | 6.473 | 10.034 | 1.00 | 20.00 | 6 |
| ATOM | 1852 | CB | PHE | B | 305 | 84.822 | 7.115 | 10.312 | 1.00 | 20.00 | 6 |
| ATOM | 1853 | CG | PHE | B | 305 | 84.705 | 8.522 | 9.815 | 1.00 | 20.00 | 6 |
| ATOM | 1854 | CD1 | PHE | B | 305 | 85.303 | 9.572 | 10.502 | 1.00 | 20.00 | 6 |
| ATOM | 1855 | CD2 | PHE | B | 305 | 84.003 | 8.800 | 8.646 | 1.00 | 20.00 | 6 |
| ATOM | 1856 | CE1 | PHE | B | 305 | 85.202 | 10.881 | 10.033 | 1.00 | 20.00 | 6 |
| ATOM | 1857 | CE2 | PHE | B | 305 | 83.896 | 10.106 | 8.167 | 1.00 | 20.00 | 6 |
| ATOM | 1858 | CZ | PHE | B | 305 | 84.496 | 11.147 | 8.862 | 1.00 | 20.00 | 6 |
| ATOM | 1859 | C | PHE | B | 305 | 87.153 | 6.789 | 11.182 | 1.00 | 20.00 | 6 |
| ATOM | 1860 | O | PHE | B | 305 | 86.964 | 6.342 | 12.312 | 1.00 | 20.00 | 8 |
| ATOM | 1861 | N | PHE | B | 306 | 88.190 | 7.565 | 10.883 | 1.00 | 20.00 | 7 |
| ATOM | 1862 | CA | PHE | B | 306 | 89.176 | 7.945 | 11.894 | 1.00 | 20.00 | 6 |
| ATOM | 1863 | CB | PHE | B | 306 | 90.179 | 8.936 | 11.295 | 1.00 | 20.00 | 6 |
| ATOM | 1864 | CG | PHE | B | 306 | 90.695 | 8.531 | 9.940 | 1.00 | 20.00 | 6 |
| ATOM | 1865 | CD1 | PHE | B | 306 | 91.292 | 7.284 | 9.747 | 1.00 | 20.00 | 6 |
| ATOM | 1866 | CD2 | PHE | B | 306 | 90.588 | 9.395 | 8.853 | 1.00 | 20.00 | 6 |
| ATOM | 1867 | CE1 | PHE | B | 306 | 91.774 | 6.906 | 8.490 | 1.00 | 20.00 | 6 |
| ATOM | 1868 | CE2 | PHE | B | 306 | 91.067 | 9.027 | 7.590 | 1.00 | 20.00 | 6 |
| ATOM | 1869 | CZ | PHE | B | 306 | 91.662 | 7.780 | 7.408 | 1.00 | 20.00 | 6 |
| ATOM | 1870 | C | PHE | B | 306 | 88.445 | 8.575 | 13.086 | 1.00 | 20.00 | 6 |
| ATOM | 1871 | O | PHE | B | 306 | 87.731 | 9.566 | 12.936 | 1.00 | 20.00 | 8 |
| ATOM | 1872 | N | PRO | B | 307 | 88.614 | 7.995 | 14.288 | 1.00 | 20.00 | 7 |
| ATOM | 1873 | CD | PRO | B | 307 | 89.482 | 6.834 | 14.555 | 1.00 | 20.00 | 6 |
| ATOM | 1874 | CA | PRO | B | 307 | 87.983 | 8.459 | 15.530 | 1.00 | 20.00 | 6 |
| ATOM | 1875 | CB | PRO | B | 307 | 88.748 | 7.691 | 16.606 | 1.00 | 20.00 | 6 |
| ATOM | 1876 | CG | PRO | B | 307 | 89.018 | 6.388 | 15.928 | 1.00 | 20.00 | 6 |
| ATOM | 1877 | C | PRO | B | 307 | 87.986 | 9.965 | 15.784 | 1.00 | 20.00 | 6 |
| ATOM | 1878 | O | PRO | B | 307 | 86.936 | 10.565 | 16.025 | 1.00 | 20.00 | 8 |
| ATOM | 1879 | N | LYS | B | 308 | 89.162 | 10.575 | 15.745 | 1.00 | 20.00 | 7 |
| ATOM | 1880 | CA | LYS | B | 308 | 89.260 | 12.004 | 15.992 | 1.00 | 20.00 | 6 |
| ATOM | 1881 | CB | LYS | B | 308 | 90.728 | 12.405 | 16.149 | 1.00 | 20.00 | 6 |
| ATOM | 1882 | CG | LYS | B | 308 | 91.338 | 11.805 | 17.410 | 1.00 | 20.00 | 6 |
| ATOM | 1883 | CD | LYS | B | 308 | 92.806 | 12.140 | 17.591 | 1.00 | 20.00 | 6 |
| ATOM | 1884 | CE | LYS | B | 308 | 93.339 | 11.457 | 18.847 | 1.00 | 20.00 | 6 |
| ATOM | 1885 | NZ | LYS | B | 308 | 94.816 | 11.573 | 18.985 | 1.00 | 20.00 | 7 |
| ATOM | 1886 | C | LYS | B | 308 | 88.572 | 12.808 | 14.894 | 1.00 | 20.00 | 6 |
| ATOM | 1887 | O | LYS | B | 308 | 87.985 | 13.855 | 15.167 | 1.00 | 20.00 | 8 |
| ATOM | 1888 | N | ALA | B | 309 | 88.629 | 12.318 | 13.659 | 1.00 | 20.00 | 7 |
| ATOM | 1889 | CA | ALA | B | 309 | 87.967 | 13.011 | 12.557 | 1.00 | 20.00 | 6 |
| ATOM | 1890 | CB | ALA | B | 309 | 88.328 | 12.369 | 11.231 | 1.00 | 20.00 | 6 |
| ATOM | 1891 | C | ALA | B | 309 | 86.460 | 12.936 | 12.787 | 1.00 | 20.00 | 6 |
| ATOM | 1892 | O | ALA | B | 309 | 85.735 | 13.903 | 12.552 | 1.00 | 20.00 | 8 |
| ATOM | 1893 | N | ARG | B | 310 | 85.986 | 11.780 | 13.246 | 1.00 | 20.00 | 7 |
| ATOM | 1894 | CA | ARG | B | 310 | 84.561 | 11.619 | 13.513 | 1.00 | 20.00 | 6 |
| ATOM | 1895 | CB | ARG | B | 310 | 84.246 | 10.194 | 13.979 | 1.00 | 20.00 | 6 |
| ATOM | 1896 | CG | ARG | B | 310 | 82.844 | 10.069 | 14.561 | 1.00 | 20.00 | 6 |
| ATOM | 1897 | CD | ARG | B | 310 | 82.408 | 8.632 | 14.789 | 1.00 | 20.00 | 6 |
| ATOM | 1898 | NE | ARG | B | 310 | 81.060 | 8.593 | 15.355 | 1.00 | 20.00 | 7 |
| ATOM | 1899 | CZ | ARG | B | 310 | 80.259 | 7.532 | 15.328 | 1.00 | 20.00 | 6 |
| ATOM | 1900 | NH1 | ARG | B | 310 | 80.665 | 6.401 | 14.759 | 1.00 | 20.00 | 7 |

-continued

| | | | | | | | | | | |
|---|---|---|---|---|---|---|---|---|---|---|
| ATOM | 1901 | NH2 | ARG | B | 310 | 79.048 | 7.601 | 15.867 | 1.00 | 20.00 | 7 |
| ATOM | 1902 | C | ARG | B | 310 | 84.110 | 12.613 | 14.583 | 1.00 | 20.00 | 6 |
| ATOM | 1903 | O | ARG | B | 310 | 83.080 | 13.274 | 14.436 | 1.00 | 20.00 | 8 |
| ATOM | 1904 | N | ASP | B | 311 | 84.876 | 12.707 | 15.666 | 1.00 | 20.00 | 7 |
| ATOM | 1905 | CA | ASP | B | 311 | 84.535 | 13.629 | 16.740 | 1.00 | 20.00 | 6 |
| ATOM | 1906 | CB | ASP | B | 311 | 85.574 | 13.555 | 17.864 | 1.00 | 20.00 | 6 |
| ATOM | 1907 | CG | ASP | B | 311 | 85.260 | 14.505 | 19.006 | 1.00 | 20.00 | 6 |
| ATOM | 1908 | OD1 | ASP | B | 311 | 85.782 | 15.636 | 19.010 | 1.00 | 20.00 | 8 |
| ATOM | 1909 | OD2 | ASP | B | 311 | 84.480 | 14.124 | 19.901 | 1.00 | 20.00 | 8 |
| ATOM | 1910 | C | ASP | B | 311 | 84.445 | 15.054 | 16.198 | 1.00 | 20.00 | 6 |
| ATOM | 1911 | O | ASP | B | 311 | 83.539 | 15.800 | 16.564 | 1.00 | 20.00 | 8 |
| ATOM | 1912 | N | LEU | B | 312 | 85.371 | 15.423 | 15.313 | 1.00 | 20.00 | 7 |
| ATOM | 1913 | CA | LEU | B | 312 | 85.362 | 16.769 | 14.736 | 1.00 | 20.00 | 6 |
| ATOM | 1914 | CB | LEU | B | 312 | 86.604 | 16.999 | 13.869 | 1.00 | 20.00 | 6 |
| ATOM | 1915 | CG | LEU | B | 312 | 86.662 | 18.329 | 13.099 | 1.00 | 20.00 | 6 |
| ATOM | 1916 | CD1 | LEU | B | 312 | 86.424 | 19.510 | 14.037 | 1.00 | 20.00 | 6 |
| ATOM | 1917 | CD2 | LEU | B | 312 | 88.018 | 18.450 | 12.414 | 1.00 | 20.00 | 6 |
| ATOM | 1918 | C | LEU | B | 312 | 84.112 | 17.008 | 13.899 | 1.00 | 20.00 | 6 |
| ATOM | 1919 | O | LEU | B | 312 | 83.456 | 18.039 | 14.035 | 1.00 | 20.00 | 8 |
| ATOM | 1920 | N | VAL | B | 313 | 83.786 | 16.051 | 13.033 | 1.00 | 20.00 | 7 |
| ATOM | 1921 | CA | VAL | B | 313 | 82.611 | 16.171 | 12.183 | 1.00 | 20.00 | 6 |
| ATOM | 1922 | CB | VAL | B | 313 | 82.464 | 14.942 | 11.255 | 1.00 | 20.00 | 6 |
| ATOM | 1923 | CG1 | VAL | B | 313 | 81.121 | 14.973 | 10.551 | 1.00 | 20.00 | 6 |
| ATOM | 1924 | CG2 | VAL | B | 313 | 83.595 | 14.935 | 10.228 | 1.00 | 20.00 | 6 |
| ATOM | 1925 | C | VAL | B | 313 | 81.354 | 16.315 | 13.036 | 1.00 | 20.00 | 6 |
| ATOM | 1926 | O | VAL | B | 313 | 80.467 | 17.111 | 12.716 | 1.00 | 20.00 | 8 |
| ATOM | 1927 | N | GLU | B | 314 | 81.282 | 15.559 | 14.129 | 1.00 | 20.00 | 7 |
| ATOM | 1928 | CA | GLU | B | 314 | 80.122 | 15.634 | 15.010 | 1.00 | 20.00 | 6 |
| ATOM | 1929 | CB | GLU | B | 314 | 80.191 | 14.545 | 16.084 | 1.00 | 20.00 | 6 |
| ATOM | 1930 | CG | GLU | B | 314 | 80.160 | 13.131 | 15.521 | 1.00 | 20.00 | 6 |
| ATOM | 1931 | CD | GLU | B | 314 | 80.222 | 12.073 | 16.603 | 1.00 | 20.00 | 6 |
| ATOM | 1932 | OE1 | GLU | B | 314 | 81.033 | 12.227 | 17.542 | 1.00 | 20.00 | 8 |
| ATOM | 1933 | OE2 | GLU | B | 314 | 79.469 | 11.081 | 16.512 | 1.00 | 20.00 | 8 |
| ATOM | 1934 | C | GLU | B | 314 | 80.035 | 17.005 | 15.664 | 1.00 | 20.00 | 6 |
| ATOM | 1935 | O | GLU | B | 314 | 78.960 | 17.443 | 16.059 | 1.00 | 20.00 | 8 |
| ATOM | 1936 | N | LYS | B | 315 | 81.165 | 17.690 | 15.776 | 1.00 | 20.00 | 7 |
| ATOM | 1937 | CA | LYS | B | 315 | 81.154 | 19.010 | 16.383 | 1.00 | 20.00 | 6 |
| ATOM | 1938 | CB | LYS | B | 315 | 82.448 | 19.240 | 17.168 | 1.00 | 20.00 | 6 |
| ATOM | 1939 | CG | LYS | B | 315 | 82.460 | 18.478 | 18.493 | 1.00 | 20.00 | 6 |
| ATOM | 1940 | CD | LYS | B | 315 | 83.803 | 18.529 | 19.198 | 1.00 | 20.00 | 6 |
| ATOM | 1941 | CE | LYS | B | 315 | 83.749 | 17.825 | 20.552 | 1.00 | 20.00 | 6 |
| ATOM | 1942 | NZ | LYS | B | 315 | 82.829 | 18.505 | 21.506 | 1.00 | 20.00 | 7 |
| ATOM | 1943 | C | LYS | B | 315 | 80.934 | 20.104 | 15.343 | 1.00 | 20.00 | 6 |
| ATOM | 1944 | O | LYS | B | 315 | 80.855 | 21.282 | 15.686 | 1.00 | 20.00 | 8 |
| ATOM | 1945 | N | LEU | B | 316 | 80.819 | 19.706 | 14.075 | 1.00 | 20.00 | 7 |
| ATOM | 1946 | CA | LEU | B | 316 | 80.577 | 20.649 | 12.979 | 1.00 | 20.00 | 6 |
| ATOM | 1947 | CB | LEU | B | 316 | 81.608 | 20.450 | 11.863 | 1.00 | 20.00 | 6 |
| ATOM | 1948 | CG | LEU | B | 316 | 83.044 | 20.833 | 12.240 | 1.00 | 20.00 | 6 |
| ATOM | 1949 | CD1 | LEU | B | 316 | 84.011 | 20.365 | 11.156 | 1.00 | 20.00 | 6 |
| ATOM | 1950 | CD2 | LEU | B | 316 | 83.124 | 22.351 | 12.434 | 1.00 | 20.00 | 6 |
| ATOM | 1951 | C | LEU | B | 316 | 79.164 | 20.469 | 12.415 | 1.00 | 20.00 | 6 |
| ATOM | 1952 | O | LEU | B | 316 | 78.464 | 21.448 | 12.148 | 1.00 | 20.00 | 8 |
| ATOM | 1953 | N | LEU | B | 317 | 78.746 | 19.220 | 12.230 | 1.00 | 20.00 | 7 |
| ATOM | 1954 | CA | LEU | B | 317 | 77.403 | 18.962 | 11.721 | 1.00 | 20.00 | 6 |
| ATOM | 1955 | CB | LEU | B | 317 | 77.343 | 17.605 | 11.012 | 1.00 | 20.00 | 6 |
| ATOM | 1956 | CG | LEU | B | 317 | 78.335 | 17.445 | 9.852 | 1.00 | 20.00 | 6 |
| ATOM | 1957 | CD1 | LEU | B | 317 | 78.091 | 16.111 | 9.143 | 1.00 | 20.00 | 6 |
| ATOM | 1958 | CD2 | LEU | B | 317 | 78.182 | 18.603 | 8.866 | 1.00 | 20.00 | 6 |
| ATOM | 1959 | C | LEU | B | 317 | 76.435 | 19.000 | 12.899 | 1.00 | 20.00 | 6 |
| ATOM | 1960 | O | LEU | B | 317 | 75.979 | 17.966 | 13.398 | 1.00 | 20.00 | 8 |
| ATOM | 1961 | N | VAL | B | 318 | 76.156 | 20.215 | 13.354 | 1.00 | 20.00 | 7 |
| ATOM | 1962 | CA | VAL | B | 318 | 75.251 | 20.451 | 14.467 | 1.00 | 20.00 | 6 |
| ATOM | 1963 | CB | VAL | B | 318 | 75.981 | 21.164 | 15.625 | 1.00 | 20.00 | 6 |
| ATOM | 1964 | CG1 | VAL | B | 318 | 75.007 | 21.461 | 16.759 | 1.00 | 20.00 | 6 |
| ATOM | 1965 | CG2 | VAL | B | 318 | 77.136 | 20.300 | 16.115 | 1.00 | 20.00 | 6 |
| ATOM | 1966 | C | VAL | B | 318 | 74.140 | 21.344 | 13.936 | 1.00 | 20.00 | 6 |
| ATOM | 1967 | O | VAL | B | 318 | 74.410 | 22.386 | 13.333 | 1.00 | 20.00 | 8 |
| ATOM | 1968 | N | LEU | B | 319 | 72.892 | 20.941 | 14.153 | 1.00 | 20.00 | 7 |
| ATOM | 1969 | CA | LEU | B | 319 | 71.758 | 21.717 | 13.663 | 1.00 | 20.00 | 6 |
| ATOM | 1970 | CB | LEU | B | 319 | 70.444 | 21.056 | 14.093 | 1.00 | 20.00 | 6 |
| ATOM | 1971 | CG | LEU | B | 319 | 70.211 | 19.647 | 13.533 | 1.00 | 20.00 | 6 |
| ATOM | 1972 | CD1 | LEU | B | 319 | 68.883 | 19.098 | 14.060 | 1.00 | 20.00 | 6 |
| ATOM | 1973 | CD2 | LEU | B | 319 | 70.211 | 19.688 | 12.000 | 1.00 | 20.00 | 6 |
| ATOM | 1974 | C | LEU | B | 319 | 71.794 | 23.173 | 14.119 | 1.00 | 20.00 | 6 |
| ATOM | 1975 | O | LEU | B | 319 | 71.591 | 24.082 | 13.317 | 1.00 | 20.00 | 8 |
| ATOM | 1976 | N | ASP | B | 320 | 72.052 | 23.394 | 15.405 | 1.00 | 20.00 | 7 |
| ATOM | 1977 | CA | ASP | B | 320 | 72.119 | 24.745 | 15.958 | 1.00 | 20.00 | 6 |
| ATOM | 1978 | CB | ASP | B | 320 | 72.091 | 24.687 | 17.490 | 1.00 | 20.00 | 6 |
| ATOM | 1979 | CG | ASP | B | 320 | 72.058 | 26.061 | 18.129 | 1.00 | 20.00 | 6 |

-continued

| | | | | | | | | | | |
|---|---|---|---|---|---|---|---|---|---|---|
| ATOM | 1980 | OD1 | ASP | B | 320 | 72.506 | 27.036 | 17.492 | 1.00 | 20.00 | 8 |
| ATOM | 1981 | OD2 | ASP | B | 320 | 71.595 | 26.166 | 19.284 | 1.00 | 20.00 | 8 |
| ATOM | 1982 | C | ASP | B | 320 | 73.415 | 25.419 | 15.492 | 1.00 | 20.00 | 6 |
| ATOM | 1983 | O | ASP | B | 320 | 74.496 | 25.089 | 15.965 | 1.00 | 20.00 | 8 |
| ATOM | 1984 | N | ALA | B | 321 | 73.294 | 26.372 | 14.576 | 1.00 | 20.00 | 7 |
| ATOM | 1985 | CA | ALA | B | 321 | 74.450 | 27.078 | 14.028 | 1.00 | 20.00 | 6 |
| ATOM | 1986 | CB | ALA | B | 321 | 73.982 | 28.109 | 13.006 | 1.00 | 20.00 | 6 |
| ATOM | 1987 | C | ALA | B | 321 | 75.359 | 27.747 | 15.065 | 1.00 | 20.00 | 6 |
| ATOM | 1988 | O | ALA | B | 321 | 76.535 | 27.992 | 14.790 | 1.00 | 20.00 | 8 |
| ATOM | 1989 | N | THR | B | 322 | 74.829 | 28.035 | 16.252 | 1.00 | 20.00 | 7 |
| ATOM | 1990 | CA | THR | B | 322 | 75.631 | 28.681 | 17.292 | 1.00 | 20.00 | 6 |
| ATOM | 1991 | CB | THR | B | 322 | 74.755 | 29.491 | 18.271 | 1.00 | 20.00 | 6 |
| ATOM | 1992 | OG1 | THR | B | 322 | 73.879 | 28.605 | 18.973 | 1.00 | 20.00 | 8 |
| ATOM | 1993 | CG2 | THR | B | 322 | 73.928 | 30.527 | 17.519 | 1.00 | 20.00 | 6 |
| ATOM | 1994 | C | THR | B | 322 | 76.437 | 27.684 | 18.108 | 1.00 | 20.00 | 6 |
| ATOM | 1995 | O | THR | B | 322 | 77.166 | 28.071 | 19.019 | 1.00 | 20.00 | 8 |
| ATOM | 1996 | N | LYS | B | 323 | 76.312 | 26.401 | 17.786 | 1.00 | 20.00 | 7 |
| ATOM | 1997 | CA | LYS | B | 323 | 77.048 | 25.378 | 18.517 | 1.00 | 20.00 | 6 |
| ATOM | 1998 | CB | LYS | B | 323 | 76.080 | 24.378 | 19.155 | 1.00 | 20.00 | 6 |
| ATOM | 1999 | CG | LYS | B | 323 | 75.180 | 24.992 | 20.209 | 1.00 | 20.00 | 6 |
| ATOM | 2000 | CD | LYS | B | 323 | 74.356 | 23.931 | 20.924 | 1.00 | 20.00 | 6 |
| ATOM | 2001 | CE | LYS | B | 323 | 73.406 | 24.574 | 21.927 | 1.00 | 20.00 | 6 |
| ATOM | 2002 | NZ | LYS | B | 323 | 74.144 | 25.514 | 22.818 | 1.00 | 20.00 | 7 |
| ATOM | 2003 | C | LYS | B | 323 | 78.066 | 24.631 | 17.664 | 1.00 | 20.00 | 6 |
| ATOM | 2004 | O | LYS | B | 323 | 78.520 | 23.557 | 18.040 | 1.00 | 20.00 | 8 |
| ATOM | 2005 | N | ARG | B | 324 | 78.427 | 25.195 | 16.517 | 1.00 | 20.00 | 7 |
| ATOM | 2006 | CA | ARG | B | 324 | 79.408 | 24.545 | 15.656 | 1.00 | 20.00 | 6 |
| ATOM | 2007 | CB | ARG | B | 324 | 79.108 | 24.834 | 14.186 | 1.00 | 20.00 | 6 |
| ATOM | 2008 | CG | ARG | B | 324 | 77.824 | 24.177 | 13.728 | 1.00 | 20.00 | 6 |
| ATOM | 2009 | CD | ARG | B | 324 | 77.468 | 24.505 | 12.297 | 1.00 | 20.00 | 6 |
| ATOM | 2010 | NE | ARG | B | 324 | 76.060 | 24.202 | 12.069 | 1.00 | 20.00 | 7 |
| ATOM | 2011 | CZ | ARG | B | 324 | 75.277 | 24.873 | 11.233 | 1.00 | 20.00 | 6 |
| ATOM | 2012 | NH1 | ARG | B | 324 | 75.764 | 25.888 | 10.523 | 1.00 | 20.00 | 7 |
| ATOM | 2013 | NH2 | ARG | B | 324 | 73.992 | 24.551 | 11.140 | 1.00 | 20.00 | 7 |
| ATOM | 2014 | C | ARG | B | 324 | 80.811 | 25.011 | 16.008 | 1.00 | 20.00 | 6 |
| ATOM | 2015 | O | ARG | B | 324 | 81.070 | 26.212 | 16.131 | 1.00 | 20.00 | 8 |
| ATOM | 2016 | N | LEU | B | 325 | 81.711 | 24.049 | 16.180 | 1.00 | 20.00 | 7 |
| ATOM | 2017 | CA | LEU | B | 325 | 83.090 | 24.350 | 16.520 | 1.00 | 20.00 | 6 |
| ATOM | 2018 | CB | LEU | B | 325 | 83.913 | 23.061 | 16.550 | 1.00 | 20.00 | 6 |
| ATOM | 2019 | CG | LEU | B | 325 | 85.274 | 23.123 | 17.241 | 1.00 | 20.00 | 6 |
| ATOM | 2020 | CD1 | LEU | B | 325 | 85.093 | 23.591 | 18.682 | 1.00 | 20.00 | 6 |
| ATOM | 2021 | CD2 | LEU | B | 325 | 85.922 | 21.741 | 17.209 | 1.00 | 20.00 | 6 |
| ATOM | 2022 | C | LEU | B | 325 | 83.656 | 25.310 | 15.481 | 1.00 | 20.00 | 6 |
| ATOM | 2023 | O | LEU | B | 325 | 83.649 | 25.015 | 14.282 | 1.00 | 20.00 | 8 |
| ATOM | 2024 | N | GLY | B | 326 | 84.139 | 26.461 | 15.946 | 1.00 | 20.00 | 7 |
| ATOM | 2025 | CA | GLY | B | 326 | 84.697 | 27.449 | 15.040 | 1.00 | 20.00 | 6 |
| ATOM | 2026 | C | GLY | B | 326 | 83.857 | 28.711 | 14.932 | 1.00 | 20.00 | 6 |
| ATOM | 2027 | O | GLY | B | 326 | 84.369 | 29.757 | 14.529 | 1.00 | 20.00 | 8 |
| ATOM | 2028 | N | CYS | B | 327 | 82.575 | 28.632 | 15.286 | 1.00 | 20.00 | 7 |
| ATOM | 2029 | CA | CYS | B | 327 | 81.714 | 29.806 | 15.200 | 1.00 | 20.00 | 6 |
| ATOM | 2030 | CB | CYS | B | 327 | 80.233 | 29.404 | 15.183 | 1.00 | 20.00 | 6 |
| ATOM | 2031 | SG | CYS | B | 327 | 79.534 | 28.915 | 16.774 | 1.00 | 20.00 | 16 |
| ATOM | 2032 | C | CYS | B | 327 | 81.976 | 30.772 | 16.353 | 1.00 | 20.00 | 6 |
| ATOM | 2033 | O | CYS | B | 327 | 82.565 | 30.410 | 17.371 | 1.00 | 20.00 | 8 |
| ATOM | 2034 | N | GLU | B | 328 | 81.523 | 32.005 | 16.178 | 1.00 | 20.00 | 7 |
| ATOM | 2035 | CA | GLU | B | 328 | 81.714 | 33.052 | 17.167 | 1.00 | 20.00 | 6 |
| ATOM | 2036 | CB | GLU | B | 328 | 81.087 | 34.348 | 16.632 | 1.00 | 20.00 | 6 |
| ATOM | 2037 | CG | GLU | B | 328 | 81.734 | 34.772 | 15.300 | 1.00 | 20.00 | 6 |
| ATOM | 2038 | CD | GLU | B | 328 | 80.962 | 35.842 | 14.539 | 1.00 | 20.00 | 6 |
| ATOM | 2039 | OE1 | GLU | B | 328 | 79.738 | 35.676 | 14.343 | 1.00 | 20.00 | 8 |
| ATOM | 2040 | OE2 | GLU | B | 328 | 81.588 | 36.840 | 14.116 | 1.00 | 20.00 | 8 |
| ATOM | 2041 | C | GLU | B | 328 | 81.187 | 32.701 | 18.560 | 1.00 | 20.00 | 6 |
| ATOM | 2042 | O | GLU | B | 328 | 81.850 | 32.983 | 19.562 | 1.00 | 20.00 | 8 |
| ATOM | 2043 | N | GLU | B | 329 | 80.016 | 32.073 | 18.631 | 1.00 | 20.00 | 7 |
| ATOM | 2044 | CA | GLU | B | 329 | 79.449 | 31.714 | 19.926 | 1.00 | 20.00 | 6 |
| ATOM | 2045 | CB | GLU | B | 329 | 77.991 | 31.263 | 19.782 | 1.00 | 20.00 | 6 |
| ATOM | 2046 | CG | GLU | B | 329 | 77.028 | 32.355 | 19.315 | 1.00 | 20.00 | 6 |
| ATOM | 2047 | CD | GLU | B | 329 | 77.055 | 32.575 | 17.813 | 1.00 | 20.00 | 6 |
| ATOM | 2048 | OE1 | GLU | B | 329 | 77.859 | 31.910 | 17.120 | 1.00 | 20.00 | 8 |
| ATOM | 2049 | OE2 | GLU | B | 329 | 76.267 | 33.413 | 17.323 | 1.00 | 20.00 | 8 |
| ATOM | 2050 | C | GLU | B | 329 | 80.264 | 30.616 | 20.605 | 1.00 | 20.00 | 6 |
| ATOM | 2051 | O | GLU | B | 329 | 80.182 | 30.436 | 21.819 | 1.00 | 20.00 | 8 |
| ATOM | 2052 | N | MET | B | 330 | 81.040 | 29.878 | 19.816 | 1.00 | 20.00 | 7 |
| ATOM | 2053 | CA | MET | B | 330 | 81.880 | 28.813 | 20.354 | 1.00 | 20.00 | 6 |
| ATOM | 2054 | CB | MET | B | 330 | 81.872 | 27.600 | 19.419 | 1.00 | 20.00 | 6 |
| ATOM | 2055 | CG | MET | B | 330 | 80.552 | 26.822 | 19.436 | 1.00 | 20.00 | 6 |
| ATOM | 2056 | SD | MET | B | 330 | 80.117 | 26.254 | 21.104 | 1.00 | 20.00 | 16 |
| ATOM | 2057 | CE | MET | B | 330 | 81.265 | 24.895 | 21.311 | 1.00 | 20.00 | 6 |
| ATOM | 2058 | C | MET | B | 330 | 83.302 | 29.330 | 20.547 | 1.00 | 20.00 | 6 |

-continued

| | | | | | | | | | | |
|---|---|---|---|---|---|---|---|---|---|---|
| ATOM | 2059 | O | MET | B | 330 | 84.236 | 28.564 | 20.754 | 1.00 | 20.00 | 8 |
| ATOM | 2060 | N | GLU | B | 331 | 83.443 | 30.647 | 20.471 | 1.00 | 20.00 | 7 |
| ATOM | 2061 | CA | GLU | B | 331 | 84.716 | 31.338 | 20.656 | 1.00 | 20.00 | 6 |
| ATOM | 2062 | CB | GLU | B | 331 | 85.357 | 30.921 | 21.987 | 1.00 | 20.00 | 6 |
| ATOM | 2063 | CG | GLU | B | 331 | 84.371 | 30.886 | 23.163 | 1.00 | 20.00 | 6 |
| ATOM | 2064 | CD | GLU | B | 331 | 83.478 | 32.127 | 23.270 | 1.00 | 20.00 | 6 |
| ATOM | 2065 | OE1 | GLU | B | 331 | 82.483 | 32.064 | 24.021 | 1.00 | 20.00 | 8 |
| ATOM | 2066 | OE2 | GLU | B | 331 | 83.759 | 33.159 | 22.625 | 1.00 | 20.00 | 8 |
| ATOM | 2067 | C | GLU | B | 331 | 85.742 | 31.247 | 19.523 | 1.00 | 20.00 | 6 |
| ATOM | 2068 | O | GLU | B | 331 | 86.952 | 31.264 | 19.761 | 1.00 | 20.00 | 8 |
| ATOM | 2069 | N | GLY | B | 332 | 85.257 | 31.137 | 18.292 | 1.00 | 20.00 | 7 |
| ATOM | 2070 | CA | GLY | B | 332 | 86.145 | 31.159 | 17.140 | 1.00 | 20.00 | 6 |
| ATOM | 2071 | C | GLY | B | 332 | 87.036 | 30.014 | 16.721 | 1.00 | 20.00 | 6 |
| ATOM | 2072 | O | GLY | B | 332 | 86.881 | 28.863 | 17.142 | 1.00 | 20.00 | 8 |
| ATOM | 2073 | N | TYR | B | 333 | 88.002 | 30.366 | 15.875 | 1.00 | 20.00 | 7 |
| ATOM | 2074 | CA | TYR | B | 333 | 88.939 | 29.413 | 15.307 | 1.00 | 20.00 | 6 |
| ATOM | 2075 | CB | TYR | B | 333 | 89.625 | 30.053 | 14.093 | 1.00 | 20.00 | 6 |
| ATOM | 2076 | CG | TYR | B | 333 | 88.724 | 30.031 | 12.877 | 1.00 | 20.00 | 6 |
| ATOM | 2077 | CD1 | TYR | B | 333 | 88.774 | 28.966 | 11.974 | 1.00 | 20.00 | 6 |
| ATOM | 2078 | CE1 | TYR | B | 333 | 87.872 | 28.869 | 10.919 | 1.00 | 20.00 | 6 |
| ATOM | 2079 | CD2 | TYR | B | 333 | 87.747 | 31.011 | 12.686 | 1.00 | 20.00 | 6 |
| ATOM | 2080 | CE2 | TYR | B | 333 | 86.831 | 30.923 | 11.624 | 1.00 | 20.00 | 6 |
| ATOM | 2081 | CZ | TYR | B | 333 | 86.903 | 29.845 | 10.751 | 1.00 | 20.00 | 6 |
| ATOM | 2082 | OH | TYR | B | 333 | 86.001 | 29.719 | 9.724 | 1.00 | 20.00 | 8 |
| ATOM | 2083 | C | TYR | B | 333 | 89.958 | 28.800 | 16.252 | 1.00 | 20.00 | 6 |
| ATOM | 2084 | O | TYR | B | 333 | 90.473 | 27.721 | 15.971 | 1.00 | 20.00 | 8 |
| ATOM | 2085 | N | GLY | B | 334 | 90.242 | 29.469 | 17.369 | 1.00 | 20.00 | 7 |
| ATOM | 2086 | CA | GLY | B | 334 | 91.193 | 28.921 | 18.327 | 1.00 | 20.00 | 6 |
| ATOM | 2087 | C | GLY | B | 334 | 90.803 | 27.504 | 18.741 | 1.00 | 20.00 | 6 |
| ATOM | 2088 | O | GLY | B | 334 | 91.577 | 26.564 | 18.558 | 1.00 | 20.00 | 8 |
| ATOM | 2089 | N | PRO | B | 335 | 89.603 | 27.320 | 19.309 | 1.00 | 20.00 | 7 |
| ATOM | 2090 | CD | PRO | B | 335 | 88.703 | 28.372 | 19.814 | 1.00 | 20.00 | 6 |
| ATOM | 2091 | CA | PRO | B | 335 | 89.145 | 25.991 | 19.731 | 1.00 | 20.00 | 6 |
| ATOM | 2092 | CB | PRO | B | 335 | 87.759 | 26.275 | 20.303 | 1.00 | 20.00 | 6 |
| ATOM | 2093 | CG | PRO | B | 335 | 87.925 | 27.644 | 20.883 | 1.00 | 20.00 | 6 |
| ATOM | 2094 | C | PRO | B | 335 | 89.104 | 24.986 | 18.573 | 1.00 | 20.00 | 6 |
| ATOM | 2095 | O | PRO | B | 335 | 89.406 | 23.808 | 18.756 | 1.00 | 20.00 | 8 |
| ATOM | 2096 | N | LEU | B | 336 | 88.727 | 25.450 | 17.382 | 1.00 | 20.00 | 7 |
| ATOM | 2097 | CA | LEU | B | 336 | 88.666 | 24.567 | 16.219 | 1.00 | 20.00 | 6 |
| ATOM | 2098 | CB | LEU | B | 336 | 88.031 | 25.292 | 15.023 | 1.00 | 20.00 | 6 |
| ATOM | 2099 | CG | LEU | B | 336 | 88.051 | 24.581 | 13.663 | 1.00 | 20.00 | 6 |
| ATOM | 2100 | CD1 | LEU | B | 336 | 87.486 | 23.177 | 13.787 | 1.00 | 20.00 | 6 |
| ATOM | 2101 | CD2 | LEU | B | 336 | 87.239 | 25.399 | 12.653 | 1.00 | 20.00 | 6 |
| ATOM | 2102 | C | LEU | B | 336 | 90.060 | 24.068 | 15.839 | 1.00 | 20.00 | 6 |
| ATOM | 2103 | O | LEU | B | 336 | 90.274 | 22.870 | 15.665 | 1.00 | 20.00 | 8 |
| ATOM | 2104 | N | LYS | B | 337 | 91.011 | 24.986 | 15.717 | 1.00 | 20.00 | 7 |
| ATOM | 2105 | CA | LYS | B | 337 | 92.370 | 24.597 | 15.360 | 1.00 | 20.00 | 6 |
| ATOM | 2106 | CB | LYS | B | 337 | 93.198 | 25.848 | 15.046 | 1.00 | 20.00 | 6 |
| ATOM | 2107 | CG | LYS | B | 337 | 92.678 | 26.560 | 13.801 | 1.00 | 20.00 | 6 |
| ATOM | 2108 | CD | LYS | B | 337 | 93.111 | 28.014 | 13.717 | 1.00 | 20.00 | 6 |
| ATOM | 2109 | CE | LYS | B | 337 | 94.561 | 28.167 | 13.314 | 1.00 | 20.00 | 6 |
| ATOM | 2110 | NZ | LYS | B | 337 | 94.882 | 29.611 | 13.122 | 1.00 | 20.00 | 7 |
| ATOM | 2111 | C | LYS | B | 337 | 93.020 | 23.764 | 16.467 | 1.00 | 20.00 | 6 |
| ATOM | 2112 | O | LYS | B | 337 | 93.965 | 23.015 | 16.215 | 1.00 | 20.00 | 8 |
| ATOM | 2113 | N | ALA | B | 338 | 92.495 | 23.866 | 17.684 | 1.00 | 20.00 | 7 |
| ATOM | 2114 | CA | ALA | B | 338 | 93.056 | 23.105 | 18.799 | 1.00 | 20.00 | 6 |
| ATOM | 2115 | CB | ALA | B | 338 | 92.873 | 23.877 | 20.105 | 1.00 | 20.00 | 6 |
| ATOM | 2116 | C | ALA | B | 338 | 92.441 | 21.718 | 18.929 | 1.00 | 20.00 | 6 |
| ATOM | 2117 | O | ALA | B | 338 | 92.805 | 20.955 | 19.820 | 1.00 | 20.00 | 8 |
| ATOM | 2118 | N | HIS | B | 339 | 91.513 | 21.375 | 18.043 | 1.00 | 20.00 | 7 |
| ATOM | 2119 | CA | HIS | B | 339 | 90.886 | 20.061 | 18.129 | 1.00 | 20.00 | 6 |
| ATOM | 2120 | CB | HIS | B | 339 | 89.786 | 19.919 | 17.074 | 1.00 | 20.00 | 6 |
| ATOM | 2121 | CG | HIS | B | 339 | 88.999 | 18.654 | 17.199 | 1.00 | 20.00 | 6 |
| ATOM | 2122 | CD2 | HIS | B | 339 | 87.797 | 18.406 | 17.774 | 1.00 | 20.00 | 6 |
| ATOM | 2123 | ND1 | HIS | B | 339 | 89.462 | 17.440 | 16.737 | 1.00 | 20.00 | 7 |
| ATOM | 2124 | CE1 | HIS | B | 339 | 88.578 | 16.498 | 17.021 | 1.00 | 20.00 | 6 |
| ATOM | 2125 | NE2 | HIS | B | 339 | 87.559 | 17.057 | 17.650 | 1.00 | 20.00 | 7 |
| ATOM | 2126 | C | HIS | B | 339 | 91.928 | 18.952 | 17.970 | 1.00 | 20.00 | 6 |
| ATOM | 2127 | O | HIS | B | 339 | 92.863 | 19.077 | 17.186 | 1.00 | 20.00 | 8 |
| ATOM | 2128 | N | PRO | B | 340 | 91.780 | 17.854 | 18.731 | 1.00 | 20.00 | 7 |
| ATOM | 2129 | CD | PRO | B | 340 | 90.747 | 17.655 | 19.765 | 1.00 | 20.00 | 6 |
| ATOM | 2130 | CA | PRO | B | 340 | 92.700 | 16.711 | 18.694 | 1.00 | 20.00 | 6 |
| ATOM | 2131 | CB | PRO | B | 340 | 91.966 | 15.665 | 19.521 | 1.00 | 20.00 | 6 |
| ATOM | 2132 | CG | PRO | B | 340 | 91.310 | 16.505 | 20.579 | 1.00 | 20.00 | 6 |
| ATOM | 2133 | C | PRO | B | 340 | 93.072 | 16.198 | 17.301 | 1.00 | 20.00 | 6 |
| ATOM | 2134 | O | PRO | B | 340 | 94.193 | 15.748 | 17.080 | 1.00 | 20.00 | 8 |
| ATOM | 2135 | N | PHE | B | 341 | 92.139 | 16.270 | 16.362 | 1.00 | 20.00 | 7 |
| ATOM | 2136 | CA | PHE | B | 341 | 92.407 | 15.797 | 15.011 | 1.00 | 20.00 | 6 |
| ATOM | 2137 | CB | PHE | B | 341 | 91.152 | 15.943 | 14.142 | 1.00 | 20.00 | 6 |

-continued

| | | | | | | | | | | |
|---|---|---|---|---|---|---|---|---|---|---|
| ATOM | 2138 | CG | PHE | B | 341 | 91.317 | 15.424 | 12.738 | 1.00 | 20.00 | 6 |
| ATOM | 2139 | CD1 | PHE | B | 341 | 91.596 | 14.080 | 12.507 | 1.00 | 20.00 | 6 |
| ATOM | 2140 | CD2 | PHE | B | 341 | 91.182 | 16.277 | 11.647 | 1.00 | 20.00 | 6 |
| ATOM | 2141 | CE1 | PHE | B | 341 | 91.738 | 13.592 | 11.207 | 1.00 | 20.00 | 6 |
| ATOM | 2142 | CE2 | PHE | B | 341 | 91.320 | 15.803 | 10.345 | 1.00 | 20.00 | 6 |
| ATOM | 2143 | CZ | PHE | B | 341 | 91.599 | 14.457 | 10.123 | 1.00 | 20.00 | 6 |
| ATOM | 2144 | C | PHE | B | 341 | 93.571 | 16.550 | 14.362 | 1.00 | 20.00 | 6 |
| ATOM | 2145 | O | PHE | B | 341 | 94.268 | 16.002 | 13.514 | 1.00 | 20.00 | 8 |
| ATOM | 2146 | N | PHE | B | 342 | 93.777 | 17.800 | 14.765 | 1.00 | 20.00 | 7 |
| ATOM | 2147 | CA | PHE | B | 342 | 94.842 | 18.630 | 14.202 | 1.00 | 20.00 | 6 |
| ATOM | 2148 | CB | PHE | B | 342 | 94.336 | 20.058 | 13.975 | 1.00 | 20.00 | 6 |
| ATOM | 2149 | CG | PHE | B | 342 | 93.124 | 20.152 | 13.096 | 1.00 | 20.00 | 6 |
| ATOM | 2150 | CD1 | PHE | B | 342 | 93.166 | 19.729 | 11.777 | 1.00 | 20.00 | 6 |
| ATOM | 2151 | CD2 | PHE | B | 342 | 91.954 | 20.734 | 13.575 | 1.00 | 20.00 | 6 |
| ATOM | 2152 | CE1 | PHE | B | 342 | 92.058 | 19.888 | 10.936 | 1.00 | 20.00 | 6 |
| ATOM | 2153 | CE2 | PHE | B | 342 | 90.843 | 20.898 | 12.742 | 1.00 | 20.00 | 6 |
| ATOM | 2154 | CZ | PHE | B | 342 | 90.898 | 20.475 | 11.423 | 1.00 | 20.00 | 6 |
| ATOM | 2155 | C | PHE | B | 342 | 96.077 | 18.718 | 15.101 | 1.00 | 20.00 | 6 |
| ATOM | 2156 | O | PHE | B | 342 | 96.932 | 19.584 | 14.902 | 1.00 | 20.00 | 8 |
| ATOM | 2157 | N | GLU | B | 343 | 96.173 | 17.829 | 16.083 | 1.00 | 20.00 | 7 |
| ATOM | 2158 | CA | GLU | B | 343 | 97.293 | 17.857 | 17.022 | 1.00 | 20.00 | 6 |
| ATOM | 2159 | CB | GLU | B | 343 | 97.330 | 16.564 | 17.841 | 1.00 | 20.00 | 6 |
| ATOM | 2160 | CG | GLU | B | 343 | 98.475 | 16.525 | 18.839 | 1.00 | 20.00 | 6 |
| ATOM | 2161 | CD | GLU | B | 343 | 98.372 | 15.365 | 19.813 | 1.00 | 20.00 | 6 |
| ATOM | 2162 | OE1 | GLU | B | 343 | 98.290 | 14.201 | 19.359 | 1.00 | 20.00 | 8 |
| ATOM | 2163 | OE2 | GLU | B | 343 | 98.379 | 15.622 | 21.036 | 1.00 | 20.00 | 8 |
| ATOM | 2164 | C | GLU | B | 343 | 98.683 | 18.113 | 16.430 | 1.00 | 20.00 | 6 |
| ATOM | 2165 | O | GLU | B | 343 | 99.419 | 18.969 | 16.925 | 1.00 | 20.00 | 8 |
| ATOM | 2166 | N | SER | B | 344 | 99.047 | 17.382 | 15.383 | 1.00 | 20.00 | 7 |
| ATOM | 2167 | CA | SER | B | 344 | 100.370 | 17.549 | 14.781 | 1.00 | 20.00 | 6 |
| ATOM | 2168 | CB | SER | B | 344 | 100.848 | 16.219 | 14.192 | 1.00 | 20.00 | 6 |
| ATOM | 2169 | OG | SER | B | 344 | 100.072 | 15.856 | 13.065 | 1.00 | 20.00 | 8 |
| ATOM | 2170 | C | SER | B | 344 | 100.467 | 18.629 | 13.702 | 1.00 | 20.00 | 6 |
| ATOM | 2171 | O | SER | B | 344 | 101.485 | 18.732 | 13.025 | 1.00 | 20.00 | 8 |
| ATOM | 2172 | N | VAL | B | 345 | 99.423 | 19.435 | 13.544 | 1.00 | 20.00 | 7 |
| ATOM | 2173 | CA | VAL | B | 345 | 99.430 | 20.486 | 12.527 | 1.00 | 20.00 | 6 |
| ATOM | 2174 | CB | VAL | B | 345 | 97.985 | 20.843 | 12.075 | 1.00 | 20.00 | 6 |
| ATOM | 2175 | CG1 | VAL | B | 345 | 98.015 | 22.042 | 11.120 | 1.00 | 20.00 | 6 |
| ATOM | 2176 | CG2 | VAL | B | 345 | 97.335 | 19.646 | 11.400 | 1.00 | 20.00 | 6 |
| ATOM | 2177 | C | VAL | B | 345 | 100.096 | 21.785 | 12.980 | 1.00 | 20.00 | 6 |
| ATOM | 2178 | O | VAL | B | 345 | 99.844 | 22.275 | 14.085 | 1.00 | 20.00 | 8 |
| ATOM | 2179 | N | THR | B | 346 | 100.951 | 22.335 | 12.122 | 1.00 | 20.00 | 7 |
| ATOM | 2180 | CA | THR | B | 346 | 101.602 | 23.610 | 12.397 | 1.00 | 20.00 | 6 |
| ATOM | 2181 | CB | THR | B | 346 | 103.096 | 23.593 | 11.982 | 1.00 | 20.00 | 6 |
| ATOM | 2182 | OG1 | THR | B | 346 | 103.816 | 22.688 | 12.831 | 1.00 | 20.00 | 8 |
| ATOM | 2183 | CG2 | THR | B | 346 | 103.707 | 24.983 | 12.115 | 1.00 | 20.00 | 6 |
| ATOM | 2184 | C | THR | B | 346 | 100.810 | 24.573 | 11.510 | 1.00 | 20.00 | 6 |
| ATOM | 2185 | O | THR | B | 346 | 100.950 | 24.565 | 10.285 | 1.00 | 20.00 | 8 |
| ATOM | 2186 | N | TRP | B | 347 | 99.966 | 25.385 | 12.138 | 1.00 | 20.00 | 7 |
| ATOM | 2187 | CA | TRP | B | 347 | 99.089 | 26.306 | 11.425 | 1.00 | 20.00 | 6 |
| ATOM | 2188 | CB | TRP | B | 347 | 97.941 | 26.727 | 12.344 | 1.00 | 20.00 | 6 |
| ATOM | 2189 | CG | TRP | B | 347 | 97.088 | 25.594 | 12.818 | 1.00 | 20.00 | 6 |
| ATOM | 2190 | CD2 | TRP | B | 347 | 95.924 | 25.071 | 12.165 | 1.00 | 20.00 | 6 |
| ATOM | 2191 | CE2 | TRP | B | 347 | 95.436 | 24.008 | 12.963 | 1.00 | 20.00 | 6 |
| ATOM | 2192 | CE3 | TRP | B | 347 | 95.247 | 25.397 | 10.983 | 1.00 | 20.00 | 6 |
| ATOM | 2193 | CD1 | TRP | B | 347 | 97.259 | 24.848 | 13.953 | 1.00 | 20.00 | 6 |
| ATOM | 2194 | NE1 | TRP | B | 347 | 96.269 | 23.893 | 14.048 | 1.00 | 20.00 | 7 |
| ATOM | 2195 | CZ2 | TRP | B | 347 | 94.300 | 23.270 | 12.616 | 1.00 | 20.00 | 6 |
| ATOM | 2196 | CZ3 | TRP | B | 347 | 94.113 | 24.661 | 10.636 | 1.00 | 20.00 | 6 |
| ATOM | 2197 | CH2 | TRP | B | 347 | 93.654 | 23.610 | 11.452 | 1.00 | 20.00 | 6 |
| ATOM | 2198 | C | TRP | B | 347 | 99.679 | 27.563 | 10.800 | 1.00 | 20.00 | 6 |
| ATOM | 2199 | O | TRP | B | 347 | 99.101 | 28.114 | 9.867 | 1.00 | 20.00 | 8 |
| ATOM | 2200 | N | ALA | B | 348 | 100.820 | 28.016 | 11.308 | 1.00 | 20.00 | 7 |
| ATOM | 2201 | CA | ALA | B | 348 | 101.439 | 29.247 | 10.822 | 1.00 | 20.00 | 6 |
| ATOM | 2202 | CB | ALA | B | 348 | 102.582 | 29.656 | 11.761 | 1.00 | 20.00 | 6 |
| ATOM | 2203 | C | ALA | B | 348 | 101.933 | 29.277 | 9.381 | 1.00 | 20.00 | 6 |
| ATOM | 2204 | O | ALA | B | 348 | 101.874 | 30.323 | 8.738 | 1.00 | 20.00 | 8 |
| ATOM | 2205 | N | ASN | B | 349 | 102.411 | 28.152 | 8.860 | 1.00 | 20.00 | 7 |
| ATOM | 2206 | CA | ASN | B | 349 | 102.940 | 28.153 | 7.500 | 1.00 | 20.00 | 6 |
| ATOM | 2207 | CB | ASN | B | 349 | 104.466 | 28.205 | 7.569 | 1.00 | 20.00 | 6 |
| ATOM | 2208 | CG | ASN | B | 349 | 105.058 | 26.929 | 8.138 | 1.00 | 20.00 | 6 |
| ATOM | 2209 | OD1 | ASN | B | 349 | 104.445 | 26.282 | 8.984 | 1.00 | 20.00 | 8 |
| ATOM | 2210 | ND2 | ASN | B | 349 | 106.251 | 26.563 | 7.678 | 1.00 | 20.00 | 7 |
| ATOM | 2211 | C | ASN | B | 349 | 102.522 | 26.966 | 6.634 | 1.00 | 20.00 | 6 |
| ATOM | 2212 | O | ASN | B | 349 | 103.353 | 26.371 | 5.944 | 1.00 | 20.00 | 8 |
| ATOM | 2213 | N | LEU | B | 350 | 101.242 | 26.628 | 6.643 | 1.00 | 20.00 | 7 |
| ATOM | 2214 | CA | LEU | B | 350 | 100.776 | 25.500 | 5.846 | 1.00 | 20.00 | 6 |
| ATOM | 2215 | CB | LEU | B | 350 | 99.257 | 25.355 | 5.973 | 1.00 | 20.00 | 6 |
| ATOM | 2216 | CG | LEU | B | 350 | 98.734 | 24.848 | 7.316 | 1.00 | 20.00 | 6 |

-continued

| | | | | | | | | | | |
|---|---|---|---|---|---|---|---|---|---|---|
| ATOM | 2217 | CD1 | LEU | B | 350 | 97.244 | 25.127 | 7.418 | 1.00 | 20.00 | 6 |
| ATOM | 2218 | CD2 | LEU | B | 350 | 99.030 | 23.357 | 7.444 | 1.00 | 20.00 | 6 |
| ATOM | 2219 | C | LEU | B | 350 | 101.147 | 25.574 | 4.365 | 1.00 | 20.00 | 6 |
| ATOM | 2220 | O | LEU | B | 350 | 101.557 | 24.575 | 3.775 | 1.00 | 20.00 | 8 |
| ATOM | 2221 | N | HIS | B | 351 | 101.006 | 26.744 | 3.752 | 1.00 | 20.00 | 7 |
| ATOM | 2222 | CA | HIS | B | 351 | 101.305 | 26.829 | 2.329 | 1.00 | 20.00 | 6 |
| ATOM | 2223 | CB | HIS | B | 351 | 100.651 | 28.087 | 1.721 | 1.00 | 20.00 | 6 |
| ATOM | 2224 | CG | HIS | B | 351 | 101.553 | 29.274 | 1.618 | 1.00 | 20.00 | 6 |
| ATOM | 2225 | CD2 | HIS | B | 351 | 102.001 | 30.143 | 2.556 | 1.00 | 20.00 | 6 |
| ATOM | 2226 | ND1 | HIS | B | 351 | 102.072 | 29.706 | 0.416 | 1.00 | 20.00 | 7 |
| ATOM | 2227 | CE1 | HIS | B | 351 | 102.798 | 30.792 | 0.618 | 1.00 | 20.00 | 6 |
| ATOM | 2228 | NE2 | HIS | B | 351 | 102.772 | 31.079 | 1.907 | 1.00 | 20.00 | 7 |
| ATOM | 2229 | C | HIS | B | 351 | 102.797 | 26.731 | 1.999 | 1.00 | 20.00 | 6 |
| ATOM | 2230 | O | HIS | B | 351 | 103.176 | 26.669 | 0.832 | 1.00 | 20.00 | 8 |
| ATOM | 2231 | N | GLN | B | 352 | 103.634 | 26.685 | 3.033 | 1.00 | 20.00 | 7 |
| ATOM | 2232 | CA | GLN | B | 352 | 105.081 | 26.554 | 2.851 | 1.00 | 20.00 | 6 |
| ATOM | 2233 | CB | GLN | B | 352 | 105.841 | 27.458 | 3.819 | 1.00 | 20.00 | 6 |
| ATOM | 2234 | CG | GLN | B | 352 | 106.395 | 28.705 | 3.166 | 1.00 | 20.00 | 6 |
| ATOM | 2235 | CD | GLN | B | 352 | 105.930 | 29.966 | 3.854 | 1.00 | 20.00 | 6 |
| ATOM | 2236 | OE1 | GLN | B | 352 | 106.134 | 30.139 | 5.053 | 1.00 | 20.00 | 8 |
| ATOM | 2237 | NE2 | GLN | B | 352 | 105.299 | 30.854 | 3.096 | 1.00 | 20.00 | 7 |
| ATOM | 2238 | C | GLN | B | 352 | 105.478 | 25.099 | 3.088 | 1.00 | 20.00 | 6 |
| ATOM | 2239 | O | GLN | B | 352 | 106.632 | 24.715 | 2.895 | 1.00 | 20.00 | 8 |
| ATOM | 2240 | N | GLN | B | 353 | 104.514 | 24.295 | 3.522 | 1.00 | 20.00 | 7 |
| ATOM | 2241 | CA | GLN | B | 353 | 104.761 | 22.888 | 3.777 | 1.00 | 20.00 | 6 |
| ATOM | 2242 | CB | GLN | B | 353 | 103.849 | 22.395 | 4.900 | 1.00 | 20.00 | 6 |
| ATOM | 2243 | CG | GLN | B | 353 | 104.122 | 23.050 | 6.240 | 1.00 | 20.00 | 6 |
| ATOM | 2244 | CD | GLN | B | 353 | 103.075 | 22.711 | 7.281 | 1.00 | 20.00 | 6 |
| ATOM | 2245 | OE1 | GLN | B | 353 | 102.627 | 21.571 | 7.377 | 1.00 | 20.00 | 8 |
| ATOM | 2246 | NE2 | GLN | B | 353 | 102.690 | 23.700 | 8.076 | 1.00 | 20.00 | 7 |
| ATOM | 2247 | C | GLN | B | 353 | 104.507 | 22.079 | 2.510 | 1.00 | 20.00 | 6 |
| ATOM | 2248 | O | GLN | B | 353 | 103.732 | 22.490 | 1.641 | 1.00 | 20.00 | 8 |
| ATOM | 2249 | N | THR | B | 354 | 105.172 | 20.937 | 2.401 | 1.00 | 20.00 | 7 |
| ATOM | 2250 | CA | THR | B | 354 | 104.998 | 20.071 | 1.244 | 1.00 | 20.00 | 6 |
| ATOM | 2251 | CB | THR | B | 354 | 106.240 | 19.173 | 1.029 | 1.00 | 20.00 | 6 |
| ATOM | 2252 | OG1 | THR | B | 354 | 107.390 | 19.999 | 0.790 | 1.00 | 20.00 | 8 |
| ATOM | 2253 | CG2 | THR | B | 354 | 106.033 | 18.243 | -0.166 | 1.00 | 20.00 | 6 |
| ATOM | 2254 | C | THR | B | 354 | 103.777 | 19.197 | 1.501 | 1.00 | 20.00 | 6 |
| ATOM | 2255 | O | THR | B | 354 | 103.745 | 18.426 | 2.454 | 1.00 | 20.00 | 8 |
| ATOM | 2256 | N | PRO | B | 355 | 102.741 | 19.319 | 0.658 | 1.00 | 20.00 | 7 |
| ATOM | 2257 | CD | PRO | B | 355 | 102.547 | 20.275 | -0.444 | 1.00 | 20.00 | 6 |
| ATOM | 2258 | CA | PRO | B | 355 | 101.540 | 18.505 | 0.859 | 1.00 | 20.00 | 6 |
| ATOM | 2259 | CB | PRO | B | 355 | 100.616 | 18.967 | -0.266 | 1.00 | 20.00 | 6 |
| ATOM | 2260 | CG | PRO | B | 355 | 101.039 | 20.387 | -0.490 | 1.00 | 20.00 | 6 |
| ATOM | 2261 | C | PRO | B | 355 | 101.835 | 17.011 | 0.766 | 1.00 | 20.00 | 6 |
| ATOM | 2262 | O | PRO | B | 355 | 102.631 | 16.577 | -0.065 | 1.00 | 20.00 | 8 |
| ATOM | 2263 | N | PRO | B | 356 | 101.198 | 16.204 | 1.625 | 1.00 | 20.00 | 7 |
| ATOM | 2264 | CD | PRO | B | 356 | 100.128 | 16.522 | 2.587 | 1.00 | 20.00 | 6 |
| ATOM | 2265 | CA | PRO | B | 356 | 101.438 | 14.761 | 1.573 | 1.00 | 20.00 | 6 |
| ATOM | 2266 | CB | PRO | B | 356 | 100.593 | 14.235 | 2.729 | 1.00 | 20.00 | 6 |
| ATOM | 2267 | CG | PRO | B | 356 | 99.429 | 15.188 | 2.737 | 1.00 | 20.00 | 6 |
| ATOM | 2268 | C | PRO | B | 356 | 100.960 | 14.244 | 0.222 | 1.00 | 20.00 | 6 |
| ATOM | 2269 | O | PRO | B | 356 | 100.005 | 14.779 | -0.346 | 1.00 | 20.00 | 8 |
| ATOM | 2270 | N | ALA | B | 357 | 101.629 | 13.221 | -0.300 | 1.00 | 20.00 | 7 |
| ATOM | 2271 | CA | ALA | B | 357 | 101.247 | 12.660 | -1.588 | 1.00 | 20.00 | 6 |
| ATOM | 2272 | CB | ALA | B | 357 | 102.352 | 11.750 | -2.118 | 1.00 | 20.00 | 6 |
| ATOM | 2273 | C | ALA | B | 357 | 99.948 | 11.883 | -1.427 | 1.00 | 20.00 | 6 |
| ATOM | 2274 | O | ALA | B | 357 | 99.808 | 11.074 | -0.506 | 1.00 | 20.00 | 8 |
| ATOM | 2275 | N | LEU | B | 358 | 99.000 | 12.134 | -2.323 | 1.00 | 20.00 | 7 |
| ATOM | 2276 | CA | LEU | B | 358 | 97.709 | 11.460 | -2.278 | 1.00 | 20.00 | 6 |
| ATOM | 2277 | CB | LEU | B | 358 | 96.729 | 12.166 | -3.217 | 1.00 | 20.00 | 6 |
| ATOM | 2278 | CG | LEU | B | 358 | 96.368 | 13.582 | -2.766 | 1.00 | 20.00 | 6 |
| ATOM | 2279 | CD1 | LEU | B | 358 | 95.513 | 14.262 | -3.813 | 1.00 | 20.00 | 6 |
| ATOM | 2280 | CD2 | LEU | B | 358 | 95.636 | 13.516 | -1.430 | 1.00 | 20.00 | 6 |
| ATOM | 2281 | C | LEU | B | 358 | 97.813 | 9.976 | -2.633 | 1.00 | 20.00 | 6 |
| ATOM | 2282 | O | LEU | B | 358 | 97.918 | 9.614 | -3.806 | 1.00 | 20.00 | 8 |
| ATOM | 2283 | N | THR | B | 359 | 97.776 | 9.134 | -1.600 | 1.00 | 20.00 | 7 |
| ATOM | 2284 | CA | THR | B | 359 | 97.867 | 7.678 | -1.735 | 1.00 | 20.00 | 6 |
| ATOM | 2285 | CB | THR | B | 359 | 96.513 | 7.046 | -2.149 | 1.00 | 20.00 | 6 |
| ATOM | 2286 | OG1 | THR | B | 359 | 96.111 | 7.555 | -3.427 | 1.00 | 20.00 | 8 |
| ATOM | 2287 | CG2 | THR | B | 359 | 95.439 | 7.355 | -1.112 | 1.00 | 20.00 | 6 |
| ATOM | 2288 | C | THR | B | 359 | 98.933 | 7.238 | -2.736 | 1.00 | 20.00 | 6 |
| ATOM | 2289 | O | THR | B | 359 | 99.903 | 7.998 | -2.945 | 1.00 | 20.00 | 8 |
| ATOM | 2290 | OXT | THR | B | 359 | 98.802 | 6.121 | -3.280 | 1.00 | 20.00 | 8 |
| TER | | | | | | | | | | | |
| ATOM | 2291 | OH2 | TIP | S | 1 | 42.566 | 19.118 | 34.302 | 1.00 | 15.09 | S |
| ATOM | 2292 | OH2 | TIP | S | 2 | 41.052 | 32.378 | 19.857 | 1.00 | 15.82 | S |
| ATOM | 2293 | OH2 | TIP | S | 3 | 37.014 | 33.030 | 17.747 | 1.00 | 16.95 | S |
| ATOM | 2294 | OH2 | TIP | S | 5 | 45.353 | 24.370 | 18.152 | 1.00 | 16.85 | S |

-continued

| | | | | | | | | | | |
|---|---|---|---|---|---|---|---|---|---|---|
| ATOM | 2295 | OH2 | TIP | S | 6 | 31.896 | 13.930 | 33.235 | 1.00 | 20.42 | S |
| ATOM | 2296 | OH2 | TIP | S | 7 | 50.351 | 22.781 | 28.249 | 1.00 | 21.14 | S |
| ATOM | 2297 | OH2 | TIP | S | 8 | 45.246 | −0.589 | −0.734 | 1.00 | 17.74 | S |
| ATOM | 2298 | OH2 | TIP | S | 11 | 46.249 | −0.348 | −8.523 | 1.00 | 21.32 | S |
| ATOM | 2299 | OH2 | TIP | S | 14 | 45.756 | 11.148 | 29.680 | 1.00 | 21.94 | S |
| ATOM | 2300 | OH2 | TIP | S | 15 | 44.273 | 13.157 | 34.592 | 1.00 | 15.61 | S |
| ATOM | 2301 | OH2 | TIP | S | 17 | 53.598 | 3.722 | −1.720 | 1.00 | 21.45 | S |
| ATOM | 2302 | OH2 | TIP | S | 18 | 46.049 | 13.087 | 31.565 | 1.00 | 20.35 | S |
| ATOM | 2303 | OH2 | TIP | S | 19 | 53.422 | 22.401 | −3.280 | 1.00 | 23.26 | S |
| ATOM | 2304 | OH2 | TIP | S | 20 | 34.587 | 7.922 | 5.383 | 1.00 | 22.58 | S |
| ATOM | 2305 | OH2 | TIP | S | 21 | 45.053 | 27.379 | 19.376 | 1.00 | 29.60 | S |
| ATOM | 2306 | OH2 | TIP | S | 23 | 28.899 | 36.416 | 28.633 | 1.00 | 31.68 | S |
| ATOM | 2307 | OH2 | TIP | S | 24 | 35.531 | 11.645 | −8.219 | 1.00 | 23.45 | S |
| ATOM | 2308 | OH2 | TIP | S | 25 | 47.364 | 28.787 | 19.612 | 1.00 | 23.03 | S |
| ATOM | 2309 | OH2 | TIP | S | 27 | 48.859 | 21.588 | 12.634 | 1.00 | 23.76 | S |
| ATOM | 2310 | OH2 | TIP | S | 29 | 48.805 | 8.920 | 23.626 | 1.00 | 22.23 | S |
| ATOM | 2311 | OH2 | TIP | S | 31 | 48.619 | 7.247 | 10.112 | 1.00 | 21.32 | S |
| ATOM | 2312 | OH2 | TIP | S | 34 | 44.824 | 28.720 | 15.621 | 1.00 | 25.27 | S |
| ATOM | 2313 | OH2 | TIP | S | 35 | 26.030 | 12.634 | 13.407 | 1.00 | 21.61 | S |
| ATOM | 2314 | OH2 | TIP | S | 36 | 50.462 | 19.810 | 40.066 | 1.00 | 25.45 | S |
| ATOM | 2315 | OH2 | TIP | S | 37 | 39.631 | 23.510 | −0.239 | 1.00 | 30.88 | S |
| ATOM | 2316 | OH2 | TIP | S | 40 | 44.734 | 42.655 | 10.346 | 1.00 | 30.84 | S |
| ATOM | 2317 | OH2 | TIP | S | 41 | 54.653 | 3.902 | 1.503 | 1.00 | 27.14 | S |
| ATOM | 2318 | OH2 | TIP | S | 45 | 45.693 | 21.923 | 39.754 | 1.00 | 28.30 | S |
| ATOM | 2319 | OH2 | TIP | S | 47 | 47.820 | 16.413 | 7.805 | 1.00 | 25.73 | S |
| ATOM | 2320 | OH2 | TIP | S | 48 | 50.292 | 31.412 | 29.642 | 1.00 | 32.79 | S |
| ATOM | 2321 | OH2 | TIP | S | 49 | 26.056 | 16.646 | 34.827 | 1.00 | 29.80 | S |
| ATOM | 2322 | OH2 | TIP | S | 52 | 31.714 | 10.996 | 31.855 | 1.00 | 29.15 | S |
| ATOM | 2323 | OH2 | TIP | S | 53 | 46.108 | 23.843 | −4.299 | 1.00 | 24.21 | S |
| ATOM | 2324 | OH2 | TIP | S | 54 | 37.645 | 11.206 | 34.448 | 1.00 | 28.56 | S |
| ATOM | 2325 | OH2 | TIP | S | 55 | 26.371 | 28.513 | 12.142 | 1.00 | 32.08 | S |
| ATOM | 2326 | OH2 | TIP | S | 58 | 33.564 | 19.700 | 3.483 | 1.00 | 28.28 | S |
| ATOM | 2327 | OH2 | TIP | S | 64 | 48.295 | −0.632 | 14.280 | 1.00 | 32.13 | S |
| ATOM | 2328 | OH2 | TIP | S | 65 | 40.064 | 26.036 | 34.324 | 1.00 | 24.17 | S |
| ATOM | 2329 | OH2 | TIP | S | 66 | 29.570 | 3.958 | 14.729 | 1.00 | 28.94 | S |
| ATOM | 2330 | OH2 | TIP | S | 72 | 60.085 | 11.604 | 6.814 | 1.00 | 38.35 | S |
| ATOM | 2331 | OH2 | TIP | S | 73 | 39.203 | 44.403 | 18.686 | 1.00 | 26.61 | S |
| ATOM | 2332 | OH2 | TIP | S | 76 | 47.312 | 12.366 | 27.366 | 1.00 | 28.51 | S |
| ATOM | 2333 | OH2 | TIP | S | 80 | 43.862 | 33.771 | 33.329 | 1.00 | 28.82 | S |
| ATOM | 2334 | OH2 | TIP | S | 81 | 57.890 | 13.106 | 2.128 | 1.00 | 40.62 | S |
| ATOM | 2335 | OH2 | TIP | S | 82 | 41.663 | 34.381 | 32.043 | 1.00 | 19.35 | S |
| ATOM | 2336 | OH2 | TIP | S | 85 | 50.974 | 40.331 | 19.200 | 1.00 | 21.14 | S |
| ATOM | 2337 | OH2 | TIP | S | 88 | 47.925 | −0.832 | −6.556 | 1.00 | 24.11 | S |
| ATOM | 2338 | OH2 | TIP | S | 90 | 27.231 | 28.336 | 33.481 | 1.00 | 27.64 | S |
| ATOM | 2339 | OH2 | TIP | S | 91 | 43.651 | −7.101 | −7.995 | 1.00 | 24.33 | S |
| ATOM | 2340 | OH2 | TIP | S | 92 | 49.325 | 4.387 | 19.370 | 1.00 | 28.02 | S |
| ATOM | 2341 | OH2 | TIP | S | 93 | 46.231 | 11.549 | 33.898 | 1.00 | 29.40 | S |
| ATOM | 2342 | OH2 | TIP | S | 94 | 63.889 | 24.831 | 1.168 | 1.00 | 26.53 | S |
| ATOM | 2343 | OH2 | TIP | S | 96 | 56.396 | 4.952 | −6.749 | 1.00 | 28.00 | S |
| ATOM | 2344 | OH2 | TIP | S | 98 | 35.510 | 27.986 | 11.558 | 1.00 | 29.24 | S |
| ATOM | 2345 | OH2 | TIP | S | 100 | 49.942 | 24.366 | 30.265 | 1.00 | 31.61 | S |
| ATOM | 2346 | OH2 | TIP | S | 101 | 56.121 | 7.113 | −8.298 | 1.00 | 31.57 | S |
| ATOM | 2347 | OH2 | TIP | S | 102 | 58.318 | 19.957 | −8.378 | 1.00 | 26.95 | S |
| ATOM | 2348 | OH2 | TIP | S | 103 | 49.647 | 22.446 | 39.624 | 1.00 | 40.57 | S |
| ATOM | 2349 | OH2 | TIP | S | 104 | 45.359 | 7.052 | 13.052 | 1.00 | 26.27 | S |
| ATOM | 2350 | OH2 | TIP | S | 105 | 37.150 | 32.340 | 32.346 | 1.00 | 34.45 | S |
| ATOM | 2351 | OH2 | TIP | S | 107 | 43.465 | 40.457 | 8.240 | 1.00 | 40.48 | S |
| ATOM | 2352 | OH2 | TIP | S | 119 | 36.644 | 8.257 | 13.418 | 1.00 | 30.70 | S |
| ATOM | 2353 | OH2 | TIP | S | 123 | 41.912 | −8.974 | −8.264 | 1.00 | 26.08 | S |
| ATOM | 2354 | OH2 | TIP | S | 124 | 62.424 | 15.800 | −7.411 | 1.00 | 24.08 | S |
| ATOM | 2355 | OH2 | TIP | S | 126 | 37.266 | 18.656 | −9.097 | 1.00 | 28.99 | S |
| ATOM | 2356 | OH2 | TIP | S | 127 | 43.129 | 26.845 | 14.606 | 1.00 | 25.19 | S |
| ATOM | 2357 | OH2 | TIP | S | 128 | 36.339 | 32.639 | 29.802 | 1.00 | 29.25 | S |
| ATOM | 2358 | OH2 | TIP | S | 130 | 54.051 | 14.561 | 26.498 | 1.00 | 33.93 | S |
| ATOM | 2359 | OH2 | TIP | S | 131 | 41.805 | −4.242 | 5.492 | 1.00 | 33.72 | S |
| ATOM | 2360 | OH2 | TIP | S | 133 | 38.873 | 25.163 | 36.697 | 1.00 | 30.69 | S |
| ATOM | 2361 | OH2 | TIP | S | 134 | 28.777 | 8.553 | 25.307 | 1.00 | 31.43 | S |
| ATOM | 2362 | OH2 | TIP | S | 135 | 53.672 | 10.546 | −12.803 | 1.00 | 33.45 | S |
| ATOM | 2363 | OH2 | TIP | S | 136 | 59.892 | 15.434 | 11.467 | 1.00 | 31.39 | S |
| ATOM | 2364 | OH2 | TIP | S | 137 | 31.040 | 12.361 | 35.470 | 1.00 | 34.07 | S |
| ATOM | 2365 | OH2 | TIP | S | 139 | 33.489 | 14.292 | −0.598 | 1.00 | 40.68 | S |
| ATOM | 2366 | OH2 | TIP | S | 140 | 46.918 | 8.748 | 11.662 | 1.00 | 29.23 | S |
| ATOM | 2367 | OH2 | TIP | S | 141 | 46.297 | −7.287 | −9.196 | 1.00 | 42.20 | S |
| ATOM | 2368 | OH2 | TIP | S | 142 | 58.193 | 6.715 | −4.685 | 1.00 | 35.48 | S |
| ATOM | 2369 | OH2 | TIP | S | 143 | 44.598 | 4.435 | 12.503 | 1.00 | 27.68 | S |
| ATOM | 2370 | OH2 | TIP | S | 144 | 27.003 | 5.999 | 12.450 | 1.00 | 36.30 | S |
| ATOM | 2371 | OH2 | TIP | S | 145 | 43.676 | 32.852 | 35.735 | 1.00 | 35.70 | S |
| ATOM | 2372 | OH2 | TIP | S | 146 | 35.783 | 18.628 | 36.452 | 1.00 | 34.62 | S |
| ATOM | 2373 | OH2 | TIP | S | 147 | 25.402 | 4.058 | 20.638 | 1.00 | 45.03 | S |

-continued

| | | | | | | | | | | |
|---|---|---|---|---|---|---|---|---|---|---|
| ATOM | 2374 | OH2 | TIP | S | 148 | 45.839 | 35.853 | 33.724 | 1.00 | 35.47 | S |
| ATOM | 2375 | OH2 | TIP | S | 149 | 22.176 | 18.976 | 16.752 | 1.00 | 31.87 | S |
| ATOM | 2376 | OH2 | TIP | S | 150 | 43.986 | 33.179 | 10.162 | 1.00 | 37.70 | S |
| ATOM | 2377 | OH2 | TIP | S | 151 | 50.653 | 20.347 | 42.428 | 1.00 | 35.80 | S |
| ATOM | 2378 | OH2 | TIP | S | 152 | 47.843 | 24.314 | 9.506 | 1.00 | 31.05 | S |
| ATOM | 2379 | OH2 | TIP | S | 153 | 44.693 | 5.273 | −14.175 | 1.00 | 29.90 | S |
| ATOM | 2380 | OH2 | TIP | S | 155 | 26.560 | 36.851 | 31.684 | 1.00 | 49.29 | S |
| ATOM | 2381 | OH2 | TIP | S | 156 | 46.867 | 8.019 | −12.951 | 1.00 | 29.21 | S |
| ATOM | 2382 | OH2 | TIP | S | 157 | 30.432 | 28.741 | 12.438 | 1.00 | 37.76 | S |
| ATOM | 2383 | OH2 | TIP | S | 158 | 41.004 | 20.553 | 6.423 | 1.00 | 39.53 | S |
| ATOM | 2384 | OH2 | TIP | S | 159 | 49.258 | 20.069 | 29.294 | 1.00 | 33.97 | S |
| ATOM | 2385 | OH2 | TIP | S | 160 | 48.082 | 28.459 | 16.489 | 1.00 | 33.10 | S |
| ATOM | 2386 | OH2 | TIP | S | 161 | 47.448 | 18.625 | 27.683 | 1.00 | 34.87 | S |
| ATOM | 2387 | OH2 | TIP | S | 162 | 19.687 | 20.632 | 23.411 | 1.00 | 35.01 | S |
| ATOM | 2388 | OH2 | TIP | S | 163 | 32.402 | −1.266 | 22.443 | 1.00 | 37.26 | S |
| ATOM | 2389 | OH2 | TIP | S | 164 | 39.475 | 33.468 | 33.237 | 1.00 | 35.34 | S |
| ATOM | 2390 | OH2 | TIP | S | 165 | 44.277 | 18.950 | 5.162 | 1.00 | 45.14 | S |
| ATOM | 2391 | OH2 | TIP | S | 166 | 34.797 | 30.523 | 10.736 | 1.00 | 47.55 | S |
| ATOM | 2392 | OH2 | TIP | S | 167 | 46.541 | 3.526 | −14.949 | 1.00 | 26.54 | S |
| ATOM | 2393 | OH2 | TIP | S | 168 | 36.333 | 16.371 | 1.539 | 1.00 | 38.68 | S |
| ATOM | 2394 | OH2 | TIP | S | 169 | 46.761 | 38.936 | 27.403 | 1.00 | 34.66 | S |
| ATOM | 2395 | OH2 | TIP | S | 170 | 24.163 | 13.264 | 11.375 | 1.00 | 41.23 | S |
| ATOM | 2396 | OH2 | TIP | S | 171 | 48.459 | 15.018 | 31.951 | 1.00 | 38.11 | S |
| ATOM | 2397 | OH2 | TIP | S | 172 | 34.261 | 23.193 | 40.004 | 1.00 | 48.96 | S |
| ATOM | 2398 | OH2 | TIP | S | 173 | 45.924 | −0.026 | 13.224 | 1.00 | 39.55 | S |
| ATOM | 2399 | OH2 | TIP | S | 175 | 41.384 | 37.389 | 32.543 | 1.00 | 40.74 | S |
| ATOM | 2400 | OH2 | TIP | S | 177 | 49.394 | 35.312 | 27.150 | 1.00 | 44.33 | S |
| ATOM | 2401 | OH2 | TIP | S | 178 | 29.066 | 29.942 | 34.359 | 1.00 | 41.46 | S |
| ATOM | 2402 | OH2 | TIP | S | 180 | 49.354 | 19.467 | 7.273 | 1.00 | 34.56 | S |
| ATOM | 2403 | OH2 | TIP | S | 181 | 25.298 | 17.029 | 31.863 | 1.00 | 47.74 | S |
| ATOM | 2404 | OH2 | TIP | S | 182 | 37.071 | 25.027 | 4.669 | 1.00 | 43.87 | S |
| ATOM | 2405 | OH2 | TIP | S | 183 | 22.581 | 7.487 | 18.691 | 1.00 | 41.75 | S |
| ATOM | 2406 | OH2 | TIP | S | 184 | 32.269 | 7.011 | −1.891 | 1.00 | 48.84 | S |
| ATOM | 2407 | OH2 | TIP | S | 185 | 48.234 | 0.494 | 6.833 | 1.00 | 48.16 | S |
| ATOM | 2408 | OH2 | TIP | S | 187 | 20.008 | 14.658 | 19.211 | 1.00 | 45.27 | S |
| ATOM | 2409 | OH2 | TIP | S | 188 | 49.341 | 22.698 | 42.272 | 1.00 | 42.20 | S |
| ATOM | 2410 | OH2 | TIP | S | 190 | 61.292 | 18.260 | −8.097 | 1.00 | 45.21 | S |
| ATOM | 2411 | OH2 | TIP | S | 191 | 28.152 | 10.606 | 2.819 | 1.00 | 40.38 | S |
| ATOM | 2412 | OH2 | TIP | S | 192 | 25.626 | 12.619 | 23.191 | 1.00 | 34.27 | S |
| ATOM | 2413 | OH2 | TIP | S | 193 | 59.876 | 11.603 | 1.216 | 1.00 | 46.54 | S |
| ATOM | 2414 | OH2 | TIP | S | 194 | 57.592 | 21.183 | −10.646 | 1.00 | 45.82 | S |
| ATOM | 2415 | OH2 | TIP | S | 195 | 31.509 | 36.649 | 21.499 | 1.00 | 38.73 | S |
| ATOM | 2416 | OH2 | TIP | S | 197 | 50.270 | −1.543 | −6.136 | 1.00 | 42.66 | S |
| ATOM | 2417 | OH2 | TIP | S | 198 | 24.467 | 8.729 | 13.088 | 1.00 | 42.78 | S |
| ATOM | 2418 | OH2 | TIP | S | 199 | 38.098 | 8.699 | 25.759 | 1.00 | 32.80 | S |
| ATOM | 2419 | OH2 | TIP | S | 200 | 57.831 | 11.358 | −13.255 | 1.00 | 45.31 | S |
| ATOM | 2420 | OH2 | TIP | S | 201 | 23.888 | 22.328 | 30.524 | 1.00 | 37.12 | S |
| ATOM | 2421 | OH2 | TIP | S | 202 | 47.691 | 26.068 | 37.666 | 1.00 | 37.92 | S |
| ATOM | 2422 | OH2 | TIP | S | 203 | 38.653 | 7.070 | 29.307 | 1.00 | 50.54 | S |
| ATOM | 2423 | OH2 | TIP | S | 206 | 44.424 | 27.583 | 2.092 | 1.00 | 53.50 | S |
| ATOM | 2424 | OH2 | TIP | S | 212 | 22.258 | 2.296 | 17.948 | 1.00 | 47.38 | S |
| ATOM | 2425 | OH2 | TIP | S | 214 | 19.843 | 17.943 | 23.303 | 1.00 | 30.36 | S |
| ATOM | 2426 | OH2 | TIP | S | 216 | 27.647 | 11.344 | 24.681 | 1.00 | 31.32 | S |
| ATOM | 2427 | OH2 | TIP | S | 217 | 37.953 | 7.817 | −9.284 | 1.00 | 45.97 | S |
| ATOM | 2428 | OH2 | TIP | S | 218 | 33.845 | 34.040 | 12.124 | 1.00 | 38.11 | S |
| ATOM | 2429 | OH2 | TIP | S | 219 | 58.484 | 15.269 | 13.717 | 1.00 | 38.26 | S |
| ATOM | 2430 | OH2 | TIP | S | 220 | 48.526 | 40.920 | 26.583 | 1.00 | 35.23 | S |
| ATOM | 2431 | OH2 | TIP | S | 222 | 52.094 | 21.184 | 38.122 | 1.00 | 29.86 | S |
| ATOM | 2432 | OH2 | TIP | S | 223 | 36.889 | 5.881 | 3.281 | 1.00 | 37.63 | S |
| ATOM | 2433 | OH2 | TIP | S | 224 | 47.642 | −1.401 | −10.684 | 1.00 | 34.89 | S |
| ATOM | 2434 | OH2 | TIP | S | 226 | 47.284 | 2.916 | 19.133 | 1.00 | 34.10 | S |
| ATOM | 2435 | OH2 | TIP | S | 227 | 42.468 | 4.463 | −15.039 | 1.00 | 37.98 | S |
| ATOM | 2436 | OH2 | TIP | S | 228 | 19.169 | 22.832 | 21.831 | 1.00 | 41.57 | S |
| ATOM | 2437 | OH2 | TIP | S | 231 | 57.592 | 12.689 | 14.880 | 1.00 | 50.22 | S |
| ATOM | 2438 | OH2 | TIP | S | 232 | 27.102 | 9.176 | 5.655 | 1.00 | 40.57 | S |
| ATOM | 2439 | OH2 | TIP | S | 233 | 58.618 | 9.072 | −11.925 | 1.00 | 50.71 | S |
| ATOM | 2440 | OH2 | TIP | S | 234 | 22.822 | 25.342 | 19.945 | 1.00 | 34.93 | S |
| ATOM | 2441 | OH2 | TIP | S | 236 | 24.831 | 32.218 | 28.901 | 1.00 | 37.69 | S |
| ATOM | 2442 | OH2 | TIP | S | 237 | 20.045 | 10.774 | 16.992 | 1.00 | 39.57 | S |
| ATOM | 2443 | OH2 | TIP | S | 238 | 58.019 | 19.850 | 15.679 | 1.00 | 41.42 | S |
| ATOM | 2444 | OH2 | TIP | S | 239 | 19.490 | 20.949 | 26.114 | 1.00 | 34.55 | S |
| ATOM | 2445 | OH2 | TIP | S | 240 | 61.187 | 26.377 | 7.346 | 1.00 | 39.68 | S |
| ATOM | 2446 | OH2 | TIP | S | 241 | 33.680 | 38.342 | 19.389 | 1.00 | 48.93 | S |
| ATOM | 2447 | OH2 | TIP | S | 242 | 51.539 | 31.612 | 10.881 | 1.00 | 55.65 | S |
| ATOM | 2448 | OH2 | TIP | S | 244 | 25.872 | 14.431 | 30.404 | 1.00 | 46.69 | S |
| ATOM | 2449 | OH2 | TIP | S | 248 | 37.332 | 5.849 | 9.544 | 1.00 | 43.81 | S |
| ATOM | 2450 | OH2 | TIP | S | 250 | 39.087 | −1.293 | −9.655 | 1.00 | 42.96 | S |
| ATOM | 2451 | OH2 | TIP | S | 258 | 23.938 | 30.000 | 30.010 | 1.00 | 38.89 | S |
| ATOM | 2452 | OH2 | TIP | S | 259 | 24.949 | 29.749 | 32.578 | 1.00 | 40.17 | S |

-continued

| | | | | | | | | | | |
|---|---|---|---|---|---|---|---|---|---|---|
| ATOM | 2453 | OH2 | TIP | S | 260 | 32.111 | 17.986 | 1.918 | 1.00 | 48.36 | S |
| ATOM | 2454 | OH2 | TIP | S | 266 | 21.404 | 12.876 | 25.603 | 1.00 | 57.17 | S |
| ATOM | 2455 | OH2 | TIP | S | 269 | 35.425 | 36.767 | 12.550 | 1.00 | 30.70 | S |
| ATOM | 2456 | OH2 | TIP | S | 270 | 52.438 | 25.529 | 30.131 | 1.00 | 44.85 | S |
| ATOM | 2457 | OH2 | TIP | S | 271 | 53.299 | 20.156 | 36.003 | 1.00 | 37.15 | S |
| ATOM | 2458 | OH2 | TIP | S | 272 | 50.914 | 6.919 | 23.723 | 1.00 | 43.29 | S |
| ATOM | 2459 | OH2 | TIP | S | 274 | 31.578 | 30.795 | 11.014 | 1.00 | 50.15 | S |
| ATOM | 2460 | OH2 | TIP | S | 275 | 26.341 | 7.243 | 22.447 | 1.00 | 39.40 | S |
| ATOM | 2461 | OH2 | TIP | S | 276 | 60.392 | 18.195 | 10.235 | 1.00 | 37.91 | S |
| ATOM | 2462 | OH2 | TIP | S | 277 | 47.355 | −9.081 | −10.821 | 1.00 | 48.18 | S |
| ATOM | 2463 | OH2 | TIP | S | 279 | 41.304 | 6.175 | −16.647 | 1.00 | 38.12 | S |
| ATOM | 2464 | OH2 | TIP | S | 282 | 33.299 | 21.620 | 37.881 | 1.00 | 46.29 | S |
| ATOM | 2465 | OH2 | TIP | S | 283 | 56.469 | 26.112 | −8.575 | 1.00 | 43.71 | S |
| ATOM | 2466 | OH2 | TIP | S | 287 | 48.382 | 26.573 | 7.246 | 1.00 | 41.43 | S |
| ATOM | 2467 | OH2 | TIP | S | 288 | 56.240 | 7.245 | −11.331 | 1.00 | 41.79 | S |
| ATOM | 2468 | OH2 | TIP | S | 290 | 49.060 | 14.978 | 28.166 | 1.00 | 37.03 | S |
| ATOM | 2469 | OH2 | TIP | S | 291 | 37.095 | 44.270 | 26.442 | 1.00 | 45.08 | S |
| ATOM | 2470 | OH2 | TIP | S | 292 | 47.814 | −0.384 | −13.299 | 1.00 | 48.60 | S |
| ATOM | 2471 | OH2 | TIP | S | 297 | 58.081 | 2.784 | −7.841 | 1.00 | 41.89 | S |
| ATOM | 2472 | OH2 | TIP | S | 298 | 36.447 | 45.321 | 18.644 | 1.00 | 54.91 | S |
| ATOM | 2473 | OH2 | TIP | S | 299 | 49.029 | 23.328 | 1.767 | 1.00 | 30.55 | S |
| ATOM | 2474 | OH2 | TIP | S | 301 | 24.375 | 13.771 | 8.634 | 1.00 | 48.47 | S |
| ATOM | 2475 | OH2 | TIP | S | 303 | 47.904 | 36.798 | 28.653 | 1.00 | 35.76 | S |
| ATOM | 2476 | OH2 | TIP | S | 305 | 51.156 | 40.821 | 27.172 | 1.00 | 43.59 | S |
| ATOM | 2477 | OH2 | TIP | S | 306 | 32.943 | 28.917 | 35.227 | 1.00 | 42.60 | S |
| ATOM | 2478 | OH2 | TIP | S | 307 | 58.462 | 28.373 | 6.251 | 1.00 | 46.15 | S |
| ATOM | 2479 | OH2 | TIP | S | 308 | 41.964 | 30.940 | 36.712 | 1.00 | 48.26 | S |
| ATOM | 2480 | OH2 | TIP | S | 313 | 51.176 | −1.922 | −3.336 | 1.00 | 50.61 | S |
| ATOM | 2481 | OH2 | TIP | S | 1001 | 21.319 | 36.868 | 23.805 | 1.00 | 36.97 | S |
| ATOM | 2482 | OH2 | TIP | S | 1002 | 48.880 | 32.620 | 27.617 | 1.00 | 44.40 | S |
| ATOM | 2483 | OH2 | TIP | S | 1003 | 61.880 | 19.473 | 11.767 | 1.00 | 45.49 | S |
| ATOM | 2484 | OH2 | TIP | S | 1004 | 52.770 | 21.424 | 26.815 | 1.00 | 24.43 | S |
| ATOM | 2485 | OH2 | TIP | S | 1005 | 35.373 | 29.094 | 36.197 | 1.00 | 35.97 | S |
| ATOM | 2486 | OH2 | TIP | S | 1006 | 40.815 | −6.636 | 4.389 | 1.00 | 43.15 | S |
| ATOM | 2487 | OH2 | TIP | S | 1007 | 44.953 | 1.286 | 11.272 | 1.00 | 49.45 | S |
| ATOM | 2488 | OH2 | TIP | S | 1010 | 21.004 | 16.168 | 27.009 | 1.00 | 48.51 | S |
| ATOM | 2489 | OH2 | TIP | S | 1011 | 47.094 | 41.786 | 9.243 | 1.00 | 50.10 | S |
| ATOM | 2490 | OH2 | TIP | S | 1012 | 32.479 | 2.978 | 14.158 | 1.00 | 49.47 | S |
| ATOM | 2491 | O12 | GLC | G | 1 | 48.557 | 11.372 | −12.279 | 1.00 | 40.72 | G |
| ATOM | 2492 | C11 | GLC | G | 1 | 48.836 | 12.133 | −11.097 | 1.00 | 38.05 | G |
| ATOM | 2493 | C13 | GLC | G | 1 | 49.266 | 13.554 | −11.476 | 1.00 | 38.09 | G |
| ATOM | 2494 | O14 | GLC | G | 1 | 49.559 | 14.299 | −10.292 | 1.00 | 33.99 | G |
| ATOM | 2495 | C15 | GLC | G | 1 | 48.150 | 14.257 | −12.257 | 1.00 | 37.32 | G |
| ATOM | 2496 | O16 | GLC | G | 1 | 48.574 | 15.582 | −12.604 | 1.00 | 36.74 | G |
| ATOM | 2497 | O12 | GLC | G | 2 | 40.114 | −6.634 | −6.562 | 1.00 | 33.52 | G |
| ATOM | 2498 | C11 | GLC | G | 2 | 38.967 | −6.592 | −7.404 | 1.00 | 31.05 | G |
| ATOM | 2499 | C13 | GLC | G | 2 | 37.712 | −6.417 | −6.552 | 1.00 | 31.56 | G |
| ATOM | 2500 | O14 | GLC | G | 2 | 36.554 | −6.406 | −7.389 | 1.00 | 30.70 | G |
| ATOM | 2501 | C15 | GLC | G | 2 | 37.792 | −5.109 | −5.761 | 1.00 | 30.03 | G |
| ATOM | 2502 | O16 | GLC | G | 2 | 36.609 | −4.961 | −4.975 | 1.00 | 29.66 | G |
| ATOM | 2503 | O12 | GLC | G | 3 | 44.030 | 8.243 | −13.470 | 1.00 | 37.90 | G |
| ATOM | 2504 | C11 | GLC | G | 3 | 43.950 | 9.648 | −13.690 | 1.00 | 38.47 | G |
| ATOM | 2505 | C13 | GLC | G | 3 | 42.747 | 9.974 | −14.579 | 1.00 | 39.52 | G |
| ATOM | 2506 | O14 | GLC | G | 3 | 41.551 | 9.526 | −13.942 | 1.00 | 39.39 | G |
| ATOM | 2507 | C15 | GLC | G | 3 | 42.878 | 9.280 | −15.934 | 1.00 | 41.43 | G |
| ATOM | 2508 | O16 | GLC | G | 3 | 41.736 | 9.613 | −16.731 | 1.00 | 40.78 | G |
| ATOM | 2509 | O12 | GLC | G | 5 | 40.556 | 1.005 | 2.289 | 1.00 | 45.25 | G |
| ATOM | 2510 | C11 | GLC | G | 5 | 40.966 | 2.332 | 1.960 | 1.00 | 40.56 | G |
| ATOM | 2511 | C13 | GLC | G | 5 | 40.187 | 3.327 | 2.814 | 1.00 | 40.36 | G |
| ATOM | 2512 | O14 | GLC | G | 5 | 38.791 | 3.169 | 2.572 | 1.00 | 40.71 | G |
| ATOM | 2513 | C15 | GLC | G | 5 | 40.619 | 4.751 | 2.464 | 1.00 | 40.04 | G |
| ATOM | 2514 | O16 | GLC | G | 5 | 39.885 | 5.681 | 3.256 | 1.00 | 36.89 | G |
| ATOM | 2515 | O12 | GLC | G | 6 | 36.951 | 22.702 | 40.046 | 1.00 | 63.04 | G |
| ATOM | 2516 | C11 | GLC | G | 6 | 37.592 | 21.583 | 39.422 | 1.00 | 62.46 | G |
| ATOM | 2517 | C13 | GLC | G | 6 | 38.104 | 21.978 | 38.030 | 1.00 | 61.14 | G |
| ATOM | 2518 | O14 | GLC | G | 6 | 39.034 | 23.054 | 38.168 | 1.00 | 61.72 | G |
| ATOM | 2519 | C15 | GLC | G | 6 | 36.948 | 22.429 | 37.126 | 1.00 | 60.51 | G |
| ATOM | 2520 | O16 | GLC | G | 6 | 35.992 | 21.372 | 36.960 | 1.00 | 58.61 | G |
| ATOM | 2521 | O12 | GLC | G | 7 | 37.316 | 0.281 | 14.299 | 1.00 | 73.45 | G |
| ATOM | 2522 | C11 | GLC | G | 7 | 37.655 | −0.758 | 15.222 | 1.00 | 72.78 | G |
| ATOM | 2523 | C13 | GLC | G | 7 | 36.592 | −1.856 | 15.157 | 1.00 | 72.98 | G |
| ATOM | 2524 | O14 | GLC | G | 7 | 35.320 | −1.299 | 15.498 | 1.00 | 73.88 | G |
| ATOM | 2525 | C15 | GLC | G | 7 | 36.924 | −2.989 | 16.134 | 1.00 | 73.66 | G |
| ATOM | 2526 | O16 | GLC | G | 7 | 36.972 | −2.493 | 17.478 | 1.00 | 75.38 | G |
| ATOM | 2527 | O12 | GLC | G | 8 | 51.921 | 21.898 | 5.908 | 1.00 | 62.51 | G |
| ATOM | 2528 | C11 | GLC | G | 8 | 52.447 | 20.871 | 5.063 | 1.00 | 63.42 | G |
| ATOM | 2529 | C13 | GLC | G | 8 | 51.476 | 20.597 | 3.908 | 1.00 | 64.28 | G |
| ATOM | 2530 | O14 | GLC | G | 8 | 51.297 | 21.794 | 3.150 | 1.00 | 66.28 | G |
| ATOM | 2531 | C15 | GLC | G | 8 | 50.121 | 20.137 | 4.448 | 1.00 | 64.49 | G |

-continued

| | | | | | | | | | | |
|---|---|---|---|---|---|---|---|---|---|---|
| ATOM | 2532 | O16 | GLC | G | 8 | 49.233 | 19.886 | 3.357 | 1.00 | 64.01 | G |
| ATOM | 2533 | O12 | GLC | G | 10 | 36.044 | 37.499 | 29.523 | 1.00 | 56.89 | G |
| ATOM | 2534 | C11 | GLC | G | 10 | 35.164 | 36.645 | 30.259 | 1.00 | 56.97 | G |
| ATOM | 2535 | C13 | GLC | G | 10 | 33.849 | 36.489 | 29.494 | 1.00 | 56.11 | G |
| ATOM | 2536 | O14 | GLC | G | 10 | 33.248 | 37.772 | 29.308 | 1.00 | 56.44 | G |
| ATOM | 2537 | C15 | GLC | G | 10 | 32.900 | 35.580 | 30.277 | 1.00 | 55.84 | G |
| ATOM | 2538 | O16 | GLC | G | 10 | 31.674 | 35.442 | 29.557 | 1.00 | 55.39 | G |
| ATOM | 2539 | O3G | ATP | N | 1 | 46.280 | 25.658 | 5.170 | 1.00 | 51.49 | N |
| ATOM | 2540 | PG | ATP | N | 1 | 46.464 | 25.053 | 3.691 | 1.00 | 52.22 | N |
| ATOM | 2541 | O1G | ATP | N | 1 | 47.406 | 23.911 | 3.763 | 1.00 | 51.41 | N |
| ATOM | 2542 | O2G | ATP | N | 1 | 46.794 | 26.182 | 2.784 | 1.00 | 52.07 | N |
| ATOM | 2543 | O3B | ATP | N | 1 | 44.976 | 24.513 | 3.344 | 1.00 | 51.01 | N |
| ATOM | 2544 | PB | ATP | N | 1 | 44.560 | 22.969 | 3.605 | 1.00 | 50.20 | N |
| ATOM | 2545 | O1B | ATP | N | 1 | 43.083 | 22.898 | 3.669 | 1.00 | 49.41 | N |
| ATOM | 2546 | O2B | ATP | N | 1 | 45.345 | 22.474 | 4.766 | 1.00 | 50.34 | N |
| ATOM | 2547 | O3A | ATP | N | 1 | 45.070 | 22.231 | 2.255 | 1.00 | 47.77 | N |
| ATOM | 2548 | PA | ATP | N | 1 | 45.075 | 20.613 | 2.121 | 1.00 | 42.84 | N |
| ATOM | 2549 | O1A | ATP | N | 1 | 45.547 | 20.291 | 0.754 | 1.00 | 43.81 | N |
| ATOM | 2550 | O2A | ATP | N | 1 | 45.807 | 20.035 | 3.270 | 1.00 | 45.03 | N |
| ATOM | 2551 | O5* | ATP | N | 1 | 43.516 | 20.223 | 2.245 | 1.00 | 41.73 | N |
| ATOM | 2552 | C5* | ATP | N | 1 | 42.528 | 20.925 | 1.489 | 1.00 | 37.57 | N |
| ATOM | 2553 | C4* | ATP | N | 1 | 41.127 | 20.379 | 1.776 | 1.00 | 39.45 | N |
| ATOM | 2554 | O4* | ATP | N | 1 | 40.907 | 19.024 | 1.279 | 1.00 | 37.72 | N |
| ATOM | 2555 | C3* | ATP | N | 1 | 40.777 | 20.321 | 3.251 | 1.00 | 38.48 | N |
| ATOM | 2556 | O3* | ATP | N | 1 | 40.360 | 21.615 | 3.697 | 1.00 | 40.42 | N |
| ATOM | 2557 | C2* | ATP | N | 1 | 39.608 | 19.374 | 3.270 | 1.00 | 37.58 | N |
| ATOM | 2558 | O2* | ATP | N | 1 | 38.410 | 20.076 | 2.924 | 1.00 | 35.98 | N |
| ATOM | 2559 | C1* | ATP | N | 1 | 39.939 | 18.346 | 2.173 | 1.00 | 35.55 | N |
| ATOM | 2560 | N9 | ATP | N | 1 | 40.628 | 17.156 | 2.747 | 1.00 | 31.76 | N |
| ATOM | 2561 | C8 | ATP | N | 1 | 41.864 | 17.126 | 3.274 | 1.00 | 30.49 | N |
| ATOM | 2562 | N7 | ATP | N | 1 | 42.143 | 15.877 | 3.667 | 1.00 | 29.75 | N |
| ATOM | 2563 | C5 | ATP | N | 1 | 41.088 | 15.118 | 3.390 | 1.00 | 27.49 | N |
| ATOM | 2564 | C4 | ATP | N | 1 | 40.125 | 15.925 | 2.810 | 1.00 | 30.02 | N |
| ATOM | 2565 | N3 | ATP | N | 1 | 38.937 | 15.389 | 2.431 | 1.00 | 27.11 | N |
| ATOM | 2566 | C2 | ATP | N | 1 | 38.679 | 14.085 | 2.615 | 1.00 | 25.62 | N |
| ATOM | 2567 | N1 | ATP | N | 1 | 39.597 | 13.283 | 3.175 | 1.00 | 21.76 | N |
| ATOM | 2568 | C6 | ATP | N | 1 | 40.800 | 13.768 | 3.571 | 1.00 | 23.90 | N |
| ATOM | 2569 | N6 | ATP | N | 1 | 41.698 | 12.964 | 4.127 | 1.00 | 21.94 | N |
| ATOM | 2570 | S | SO4 | I | 1 | 58.680 | 8.493 | −0.639 | 1.00 | 56.05 | I |
| ATOM | 2571 | O1 | SO4 | I | 1 | 57.956 | 7.875 | 0.483 | 1.00 | 58.83 | I |
| ATOM | 2572 | O2 | SO4 | I | 1 | 57.886 | 9.607 | −1.188 | 1.00 | 57.04 | I |
| ATOM | 2573 | O3 | SO4 | I | 1 | 58.906 | 7.478 | −1.683 | 1.00 | 57.47 | I |
| ATOM | 2574 | O4 | SO4 | I | 1 | 59.976 | 9.008 | −0.156 | 1.00 | 57.51 | I |
| ATOM | 2575 | S | SO4 | I | 2 | 39.339 | 4.855 | 7.057 | 1.00 | 84.24 | I |
| ATOM | 2576 | O1 | SO4 | I | 2 | 39.390 | 6.175 | 7.711 | 1.00 | 85.02 | I |
| ATOM | 2577 | O2 | SO4 | I | 2 | 40.101 | 4.897 | 5.797 | 1.00 | 84.75 | I |
| ATOM | 2578 | O3 | SO4 | I | 2 | 37.936 | 4.506 | 6.766 | 1.00 | 84.94 | I |
| ATOM | 2579 | O4 | SO4 | I | 2 | 39.931 | 3.842 | 7.954 | 1.00 | 84.44 | I |
| ATOM | 2580 | S | SO4 | I | 3 | 38.987 | −2.256 | 3.310 | 1.00 | 58.58 | I |
| ATOM | 2581 | O1 | SO4 | I | 3 | 37.734 | −1.675 | 3.827 | 1.00 | 59.11 | I |
| ATOM | 2582 | O2 | SO4 | I | 3 | 39.460 | −1.454 | 2.172 | 1.00 | 59.91 | I |
| ATOM | 2583 | O3 | SO4 | I | 3 | 38.743 | −3.640 | 2.866 | 1.00 | 60.97 | I |
| ATOM | 2584 | O4 | SO4 | I | 3 | 40.014 | −2.260 | 4.369 | 1.00 | 59.58 | I |
| ATOM | 2585 | S | SO4 | I | 4 | 34.397 | 5.289 | 30.981 | 1.00 | 64.34 | I |
| ATOM | 2586 | O1 | SO4 | I | 4 | 33.627 | 6.528 | 30.742 | 1.00 | 60.43 | I |
| ATOM | 2587 | O2 | SO4 | I | 4 | 34.337 | 4.427 | 29.782 | 1.00 | 60.11 | I |
| ATOM | 2588 | O3 | SO4 | I | 4 | 33.816 | 4.572 | 32.133 | 1.00 | 64.39 | I |
| ATOM | 2589 | O4 | SO4 | I | 4 | 35.806 | 5.626 | 31.277 | 1.00 | 63.55 | I |
| ATOM | 2590 | S | SO4 | I | 5 | 55.074 | −6.984 | −3.711 | 1.00 | 75.40 | I |
| ATOM | 2591 | O1 | SO4 | I | 5 | 54.657 | −7.518 | −2.399 | 1.00 | 74.66 | I |
| ATOM | 2592 | O2 | SO4 | I | 5 | 54.209 | −5.845 | −4.065 | 1.00 | 74.96 | I |
| ATOM | 2593 | O3 | SO4 | I | 5 | 54.950 | −8.034 | −4.742 | 1.00 | 74.22 | I |
| ATOM | 2594 | O4 | SO4 | I | 5 | 56.477 | −6.532 | −3.633 | 1.00 | 75.15 | I |
| ATOM | 2595 | O2 | PO4 | P | 100 | 57.362 | 24.998 | 13.149 | 1.00 | 66.76 | P |
| ATOM | 2596 | O3 | PO4 | P | 100 | 59.399 | 26.166 | 13.761 | 1.00 | 66.89 | P |
| ATOM | 2597 | O4 | PO4 | P | 100 | 57.761 | 25.606 | 15.462 | 1.00 | 67.43 | P |
| ATOM | 2598 | O1 | PO4 | P | 100 | 57.264 | 27.325 | 13.818 | 1.00 | 65.91 | P |
| ATOM | 2599 | P | PO4 | P | 100 | 57.947 | 26.025 | 14.048 | 1.00 | 66.69 | P |
| END | | | | | | | | | | | |

Example 5

PDK1 Fragments

We produced constructs for expression of different forms of PDK1 in bacteria. The constructs were either in TRC vectors, pET-15b vector and pGEX expression vector to enable the expression of GST fused N-terminally to PDK1. PDK1 expressed from pGEX 51-556 (ie residues 51 to 556 of PDK1) was found to be highly degraded.

PDK1 protein was also expressed with N-terminal His tags from vector TRC comprising PDK1 sequences 51-556, 51-404 and 1-360, or pET15b 51-404 and tested for expression levels and activity. The expression was generally low, around 0.2 mg/L culture. The specific activity was lower than the His-tagged 51-556 protein purified from baculovirus cells. In the case of PDK1 51-404 expressed from pET-15b construct the level of expression turned out to be very variable. This was probably due to instability of the plasmid since we produced evidence that after a growth of 0.2 units of absorbance, (as measured in a spectrophotometer at 600 nm wavelength) the cells growing faster in the culture were actually not harbouring the plasmid with ampiciline resistance. The instability of the plasmid can be due to toxicity produced by basal expression of PDK1. Although production in bacteria was the theoretical best expression system to avoid heterogeneity due to the different extent of phosphorylation of the different phosphorylation sites in hPDK1, it was found that the protein was either degraded, expressed to low levels, had 5 times less specific activity, or was possibly toxic.

The His-tagged purified PDK1 51-556 protein obtained from baculovirus expression system was homogeneous as depicted by the appearance of one band after by SDS-PAGE analysis of a sample.

Nevertheless, the analysis after isoelectric focussing revealed a large smear of protein covering several units of pH. This analysis suggested that the protein was not homogeneous in terms of its isoelectric point, possibly due to the number of phosphorylation sites which were not homogeneously phosphorylated. This protein did not crystallise.

We purified to homogeneity a truncated His-Myc tagged PDK1 (51-404) which lacks the N-terminal 50 residues and the C-terminal 152 residues which include the PH domain. This protein, produced by a baculovirus expression system, had similar characteristics to the full length wild type PDK1 in terms of its activity towards the peptide substrate T308tide, its activation by the peptide PIFtide, and the binding to PIFtide (as analysed by BiaCore). The purified protein was screened for crystallisation conditions using Hampton Research kits (144 different conditions). Crystallisation conditions were screened with two concentrations of PDK1, in the presence or absence of PIFtide, Staurosporine, at 20° C. and in the presence of PIFtide at 4° C. No protein crystals were observed after 6 months, suggesting that this construct was not suitable for forming crystals although all other characteristics were similar to wild type protein.

The His-Myc PDK1 51-404 purified protein was also subjected to protease treatments in order to obtain a protease-insensitive molecule for increasing the chances of obtaining a shorter, stable variant of PDK1. Different protease treatments were tested. Treatment with Glu-C produced a polypeptide of approximately 38 KDa which was stable. This PDK1 protein was active and lacked the His-tag and part of the Myc-tag, and possibly part of the C-terminal residues. This protein was also set up for crystallography screenings. Some crystals were obtained using this preparation after 4 months, but they were not followed up.

A protein kinase corresponding to residues PDk1 51-387 was also produced, in an identical vector to that used to produce the protein PDK1 51-359. Interestingly, this protein was similar to wild type and PDK1 51-404, but had extreme problems for concentration using conventional methods. The protein could not be concentrated further than 2.5 mg/ml, and no crystals were obtained using this construct.

The PDK1 protein that finally crystallised is lacking the first 50 aminoacids and was constructed to end at position 359. This protein was stable in the absence of the PH domain and aminoacids that in hPDK1 link the catalytic domain with the PH domain. The construct PDK1 51-359 was also short enough that no other described phosphorylation sites besides activation loop phosphorylation site 241 were present.

Example 6

Structural Basis for UCN-01 Specificity and PDK1 Inhibition

The staurosporine derivative UCN-01 (7-hydroxyl staurosporine) has been reported to be a potent inhibitor for PDK1 and is currently in clinical trials for the treatment of cancer. Here we report the crystal structures of staurosporine and UCN-01 in complex with the kinase domain of PDK1. We show that although staurosporine and UCN-01 interact with the PDK1 active site in an overall similar manner, the UCN-0,7-hydroxyl group, which is not present on staurosporine, generates direct and water-mediated hydrogen bonds with active site residues. Inhibition data from UCN-01 tested against a panel of 29 different kinases show a different pattern of inhibition compared to staurosporine. We discuss how these differences in inhibition could be attributed to specific interactions with the additional 7-hydroxyl-group as well as by the size of the 7-hydroxyl-binding pocket. This information could lead to opportunities for structure-based optimisation of PDK1 inhibitors.

Insulin and growth factor signalling is mediated by the activation of a lipid kinase, phosphatidylinositol-3-kinase (PI3K), which produces the second messenger molecule phosphatidylinositol(3,4,5)trisphosphate (PtdIns(3,4,5)P) [1]. Upon generation of PtdIns(3,4,5)P, 3-Phosphoinositide Dependent protein Kinase-1 (PDK1) and protein kinase B (PKB, also known as Akt) are co-localised at the plasma membrane through interaction of their Pleckstrin Homology (PH) domains with PtdIns(3,4,5)P [2,3]. PDK1 activates PKB by phosphorylation of its T-loop (Thr308 in PKB) [4, 5]. PDK1 also activates other protein kinases related to PKB, including isoforms of p70 ribosomal S6 kinase (S6K) [6], serum and glucocorticoid responsive kinases (SGK) [7] and p90 ribosomal S6 kinase (Rsk) [8]. These kinases lack PH domains and do not bind PtdIns(3,4,5)P3, and are thought to be activated by a different mechanism, in which the substrates require a priming phosphorylation in a conserved hydrophobic motif (HM) at their C-terminus (reviewed in [9]). This phosphorylation creates a docking motif that specifically interacts with a pocket on the N-terminal lobe of the PDK1 kinase domain (termed PDK1 interacting fragment (PIF) pocket) [10,11] bringing PDK1 together with its substrate and enabling PDK1 to phosphorylate these kinases in their T-loop, thereby activating them. A significant number of human cancers possess elevated PtdIns(3,4,5)P levels due to mutations in a number of genes that regulate the production and degradation of this 3-phosphoinositide. One of the most frequently found mutations occurs in the PtdIns(3,4,5)P 3-phosphatase (PTEN) resulting in constitutive activation of PKB and S6K, which are thought to be major contributors to the proliferation and the survival of such tumour cells [12]. Thus, inhibitors of PDK1 have the potential to act as anticancer agents as they would be expected to suppress activation of S6K and PKB and inhibit cell growth and induce apoptosis of cancer cells that possess elevated levels of PtdIns(3,4,5)P.

PDK1 consists of an N-terminal kinase domain and a C-terminal PH-domain [13]. The structure of the PDK1 kinase domain has been solved (see the preceding Examples and [11]) and leads to a definition of the residues lining the ATP binding site and an understanding of the PDK1 activation mechanism. The PIFbinding pocket could be identified, together with a specific pocket for the phosphorylated Ser/Thr residue on the HM of substrate kinases. Staurosporine, a natural product ATP-competitive inhibitor, inhibits many kinases in the low nM range [14], and therefore displays a high cytotoxicity [15]. UCN-01 (7-hydroxyl staurosporine) is a derivative with an additional hydroxyl group on the lactam ring (FIG. 1). It was originally described as a PKC-selective inhibitor isolated from *Streptomyces* sp. cultures [16], although further studies showed it to be more non-specific [14, 17]. UCN-01 potently inhibits the growth and induces apoptosis of many cancer cells and these effects are thought to be unrelated to PKC inhibition [18, 19]. Due to its antitumour activity in vivo and in vitro, UCN-01 is currently undergoing clinical trials with positive effects being reported in the phase 1 studies (reviewed in [19]). Recent reports suggested the cell cycle checkpoint kinase Chk1 [20] and PDK1 [21] may be key targets of UCN-01 in inhibiting the growth of cancer cells, as both kinases are inhibited by UCN-01 in the low nM range.

Here we report the structures of the PDK1 kinase domain in complex with staurosporine and UCN-01, demonstrating the presence of a pocket that accommodates the 7-hydroxyl group of UCN-01. Specificity tests against a panel of 29 kinases shows that although both staurosporine and UCN-01 are relatively non-specific inhibitors, the fingerprint analysis of UCN-01 inhibition with a panel of protein kinases is significantly different from that of staurosporine. We also perform analysis of residues predicted to line the UCN-01 hydroxyl pocket on a number or protein kinases, and propose a general model that could account for the different sensitivity of protein kinases for staurosporine and UCN-01.

Methods

Expression, Purification and Crystallisation

Human PDK1 (residues 51-359) was expressed using a baculovirus mediated infection of the SF21 insect cell line and purified as described in the preceding examples and [11] with the following differences: After elution of the His-tagged protein from the Ni-NTA-agarose beads with 200 mM imidazole, the protein was dialysed against 250 mM NaCl, 25 mM Tris pH 7.5, 1 mM DTT for 3 hours at 4° C. Proteolysis with GST-tagged PreScission protease was performed overnight at 4° C.

For crystals of the PDK1-UCN-01 complex, 100 µl of PDK1 at a concentration of 6.6 mg/ml was mixed with 30 µl UCN-01 (5.3 mM in 50% ethanol) and incubated on ice for 2 hours. The protein was crystallized using sitting drop vapour diffusion. 1.25 µl of protein solution was mixed with 0.25 µl cobaltous chloride hexahydrate (0.1 M) and 1 µl mother liquor, consisting of 2.1 M ammonium sulphate, 0.1 M Tris-HCl pH 8.5. Hexagonal, rod-shaped crystals grew at 20° C. and reached a maximum size of 0.05×0.05×0.3 mm after 7 days. After soaking for 3 seconds in a cryo-protection solution (2.1 M ammonium sulphate, 0.1 M Tris-HCl pH 7.2, 25% glycerol) crystals were frozen in a stream of cold nitrogen.

PDK1 in complex with staurosporine was crystallized using the hanging drop technique. Drops consisted of 1 µl PDK1 at 7.6 mg/ml, 1 µl mother liquor (2.1 M ammonium sulphate, 0.1 M Tris-HCl pH 7.2) and 0.25 µl staurosporine (10 mM in DMSO). Hexagonal shaped crystals suitable for data collection appeared after 6 weeks at 20 C. Crystals were soaked in 1.7 M ammonium sulphate, 0.1 M Tris-HCl pH 7.2, 15% glycerol and frozen in a stream of cold nitrogen.

Data Collection, Structure Solution and Refinement

Figure 8:
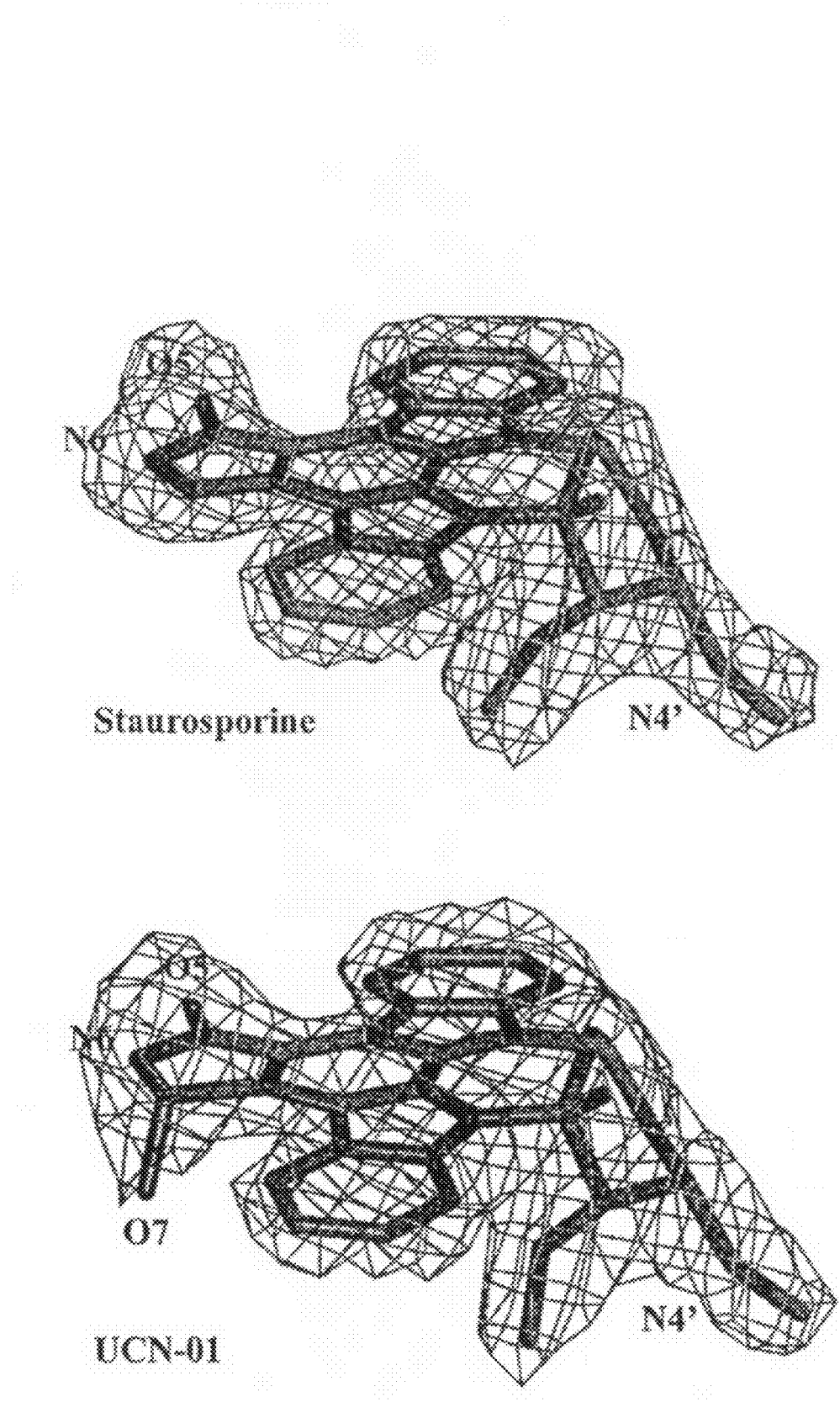
FIG. 8 shows staurosporine and UCN-01 electron density.

Data on the PDK1-staurosporine and PDK1-UCN-01 complexes were collected at the European Synchrotron Radiation Facility (Grenoble, France) beamline ID14-EH4. The temperature of the crystals was maintained at 100 K using a nitrogen cryostream. Data were processed using the HKL package [22] with final statistics shown in Table 3. The structures were solved by rigid body refinement with CNS [23] using the previously determined PDK1 structure (See previous Examples; PDB code 1H1W) [11] as a starting model which resulted in an initial R-factor of 0.306 ($R_{free}$=0.284) for PDK1-staurosporine and 0.299 ($R_{free}$=0.311) for PDK1-UCN-01. Model building with O [24] and iterative refinement in CNS, including solvent molecules and the T-loop phosphorylation site, resulted in final R-factors as shown in Table 3. The ATP binding site showed well-defined density in the unbiased $|F_o|-F_c|$, $\phi_{calc}$ maps for all atoms of staurosporine and UCN-01, including the 7-hydroxyl group (FIG. 8). CNS topologies and coordinates for the inhibitors were generated with PRODRG [25]. No electron density could be observed for residues 51-72 (N-terminus), residues 231-239 (T-loop) and residue 359 (C-terminus) in the PDK1-UCN-01 complex. Residues 51-71 (N-terminus) and 233-238 (T-loop) were disordered in the PDK1-staurosporine complex.

Determination of Inhibition and Specificity

Protein kinase assays: PDK1 was assayed for 10 min at 30° C. in a 50 µl assay mixture in 50 mM Tris pH 7.5, 0.1 mM EGTA, 0.1% 2-mercaptoethanol, containing 100 µM PDK1tide substrate peptide (KTFCGTPEYLAPEVRRE-PRILSEEEQEMFRDFDYIADWC) (SEQ ID NO:112), 10 mM magnesium acetate, 100 µM [$\gamma$-$^{32}$P]ATP (200 cpm/pmole) as described previously [10]. Other protein kinases employed in Table 5, were assayed as described previously [17, 26].

Results & Discussion

Structures of the Staurosporine and UCN-01 Complexes

PDK1 (residues 51-359) was co-crystallized with staurosporine and UCN-01, and synchrotron diffraction data on a thin hexagonal needle were collected to 2.3 Å and 2.5 Å resolution, respectively.

In the unbiased $|F_o|-F_c|$, $\phi_{calc}$ maps well defined (>3.0σ) density could be observed in the ATP binding site of the kinase, covering all staurosporine/UCN-01 atoms including the 7-hydroxyl group (FIG. 8). After initial rounds of protein model building and inclusion of water molecules, the inhibitor molecules were built and refined with full occupancy to average B-factor of 18.5 Å$^2$ (staurosporine) and 17.3 Å$^2$ (UCN-01). Further refinement resulted in a final PDK1-staurosporine model with R=0.218 ($R_{free}$=0.255) and a final PDK1-UCN-01 model with R=0.184 ($R_{free}$=0.257), both with good stereochemistry (Table 3).

The staurosporine molecule is located in the ATP-binding site (which lies between the N-terminal and C-terminal lobes of kinases [27, 28]), at the same position described for the inhibitor in complex with the closely related (38% sequence identity) protein kinase A (PKA, [29], PDB code 1STC) (FIG. 8). Hydrophobic residues on both sides of the ATP binding cleft sandwich the heterocyclic moiety of staurosporine, namely Leu88, Val96, Ala109, Leu98 (small lobe) and Thr222, Leu212 of the larger lobe (FIG. 1).

Similar to the PKA-staurosporine complex, the lactam group mimics the interactions of the adenine base in ATP with the protein backbone, where 2 conserved hydrogen bonds are formed between the lactam-nitrogen N6 in staurosporine (nomenclature according to [30]) and the backbone-oxygen of Ser160, and the lactam-oxygen at the C5 position and the backbone-nitrogen of Ala162 (Table 4). An additional hydrogen bond is mimicked in the staurosporine sugar-moiety, where the methyl-amino group contacts oxygen O 2 of Glu166, similar to the hydrogen bond with the ribose in the PDK1-ATP complex [11], and also the backbone carbonyl of Glu209 (Table 4).

The UCN-01 molecule occupies the same position in the ATP binding site as staurosporine (maximum atomic shift=0.35 Å) (FIG. 9). The same hydrophobic interactions are made to the heterocyclic moiety in the PDK1-staurosporine complex. Hydrogen bonding interactions to the heterocycle and the sugar moiety are also conserved, with similar geometry (Table 4). However, the 7-hydroxyl group of UCN-01 forms several novel hydrogen bonds (FIG. 9, Table 4). It hydrogen bonds directly to Oγ1 of Thr222 (FIG. 9, Table 4). In addition, an ordered water molecule (B-factor=24.0 Å$^2$) is found in a position where it contacts the 7-hydroxyl (distance=3.0 Å, Table 4) and the oxygen Oε1 of Gln220 (distance=2.5 Å) the side chain of which is shifted towards the ligand (1.5 Å for Cδ, rotation of 82° around $\chi_1$) compared to the PDK1-STO complex. However, the water molecule is buried in a predominantly hydrophobic pocket, lined by Val143, Leu212 and Cγ2 of Thr222 (FIG. 9). Val143 also changes its position compared to the PDK1-staurosporine complex (FIG. 9), moving further towards the back of the pocket (shift of 0.7° A for the Cα carbon, and a rotation of 100° around $\chi_1$) and displaces an ordered water molecule present in the PDK1-staurosporine complex (FIG. 9), and also observed in other kinase-staurosporine complexes [31, 30]. These changes result in more space to accommodate the bulky 7-hydroxyl group on UCN-01 as indicated by a 6° A$^3$ increase in ligand volume (calculated with VOIDOO [32]).

Comparison with Chk1-UCN-01

High resolution data for the Chk1 kinase bound to staurosporine and UCN-01 is available (PDB code 1NVQ [30]). In Chk1, Ser147, the equivalent of Thr222 in PDK1, also hydrogen bonds the UCN-01 7-OH directly. In addition, a water mediated network of hydrogen bonds to UCN-01 is observed. However, in Chk1 the water molecule that hydrogen bonds UCN-01 occupies a different position (shifted 5.2 Å compared to the PDK1-UCN-01 complex). Chk1 appears to have a more extended hydrophilic cavity, as there are 2 additional buried water molecules present also in the Chk1-staurosporine complex. The corresponding residue to Gln220 in PDK1 is a Lys (Lys145) in Chk1, which does not interact with the ligand but points away from it.

UCN-01 Inhibition and Specificity

PDK1 inhibition by UCN-01 and staurosporine was measured using kinase assays with P$^{32}$-labelled ATP. PDK1 is inhibited by UCN-01 with an IC$_{50}$ value of 5 nM, and by staurosporine with an IC$_{50}$ of 6.5 nM. As a measure for overall specificity of UCN-01 and staurosporine, the effect of these inhibitors was tested against a panel of 29 protein kinases as described previously [17, 26]. The results are shown in Table 5 as percentage of control activity. These data further confirm that UCN-01 and staurosporine are aspecific inhibitors. UCN-01 at 1 μM concentration reduces the activity of nine kinases in the panel to less than 10%, and of ten others to below 60% of control activity. Staurosporine at 1 μM will inhibit twelve kinases to less than 10% control activity, and another ten to below 60%. Interestingly, however, several of the protein kinases were differentially inhibited by staurosporine and UCN-01 (Table 5). In an attempt to understand these differences the panel of kinases was divided in four distinct classes: (a) similar inhibition, (b) stronger inhibition by staurosporine than by UCN-01, (c) stronger inhibition by UCN-01 than by staurosporine, and (d) no inhibition (Table 5). As the additional 7-hydroxyl group is the only difference in the ligand molecules (FIG. 8), and staurosporine and UCN-01 occupy the same position with similar interactions in the binding site (FIG. 9), the residues contacting the extra hydroxyl group were identified for PDK1 and extracted from a sequence alignment of all protein kinases used in the panel (Table 5). A structure-based sequence alignment of known kinase structures was obtained from [33], which was used to validate the sequence-based sequence alignment (Table 5). The nature of the side chains lining the hydroxyl-pocket could provide a partial explanation for the relative difference between UCN-01 and staurosporine inhibition. Two trends can be observed. For the kinases that are inhibited by UCN-01, there appears to be a preference for a side chain capable of hydrogen bonding the 7-hydroxyl in the hydroxyl-pocket. This is in agreement with the presence of a Thr/Ser residue that hydrogen bonds the 7-hydroxyl in the structures of PDK1 (Thr222) and Chk1 (Ser147) bound to UCN-01. Seven out of ten kinases that are hit equally by staurosporine and UCN-01 (group (a)) appear to have a potential hydrogen bonding residue (Table 5). The kinases that are more potently inhibited by UCN-01 than by staurosporine (group (c)) contain a Thr at the Thr222 equivalent position (Table 5). Five out of nine kinases that are inhibited more potently by staurosporine than by UCN-01 (group (b)) lack a potential hydrogen binding partner in the 7-hydroxyl-pocket (Table 5).

A second trend which appears to determine specificity is the size of the residues lining the hydroxyl-pocket. If the predicted total volume of the residues (calculated with the BL-set of side chain volumes [34]) at the positions indicated in Table 5 is set against the activity in the presence of UCN-01, a correlation coefficient of 0.6 is obtained. This suggests that despite inaccuracies in this approach, such as the absence of structural information on precise side chain conformation and water molecules, a weak correlation between predicted hydroxyl pocket volume and UCN-01 inhibition exists. For instance, PKA contains a possible hydrogen bonding partner for UCN-01 (Thr183), but Met134 in the centre of the hydroxyl pocket may leave no space for the extra hydroxyl group (Table 5). A similar arrangement of residues can be observed for MAPKAP-K2 (Table 5). This size dependency may also play a role for the protein kinases neither hit by staurosporine nor UCN-01. The sequence alignment shows that the Val143 and Thr222 equivalent residues are replaced by bulkier Leu or Ile residues in several of the Mitogen Activated Protein Kinase families (Table 5). To investigate the effect of these bulkier side chains on the hydroxyl pocket, we, starting from the PDK1 crystal structure, replaced residues Val143 with Ile and Thr222 with Leu in standard side chain rotamers (in O [24]), which indeed resulted in van der Waals clashes with C7 of staurosporine (shortest distances: 2.8 Å for Leu222, 3.5 Å for Ile143), and may therefore explain the lack of susceptibility towards UCN-01 in the Mitogen Activated Protein Kinase families. CDK2 is inhibited by both staurosporine and UCN-01 similarly, however this kinase lacks a hydrogen bonding partner for the 7-hydroxyl and contains a bulky Phe (Phe80) at the Leu159 equivalent position. In a superposition of CDK2-staurosporine structure [31] with PDK1-UCN-01 (RMSD=1.3 Å on Cα atoms) staurosporine is seen to be shifted by 1.2 Å out of the potential hydroxyl pocket due to presence of the bulky Phe80. Interaction of the 7-hydroxyl on UCN-01 was described to be water mediated in CDK2 due to the lack of hydrogen bonding residues [35]. This particular example highlights the limitations of the approach described above. Other examples where none of the described effects account for the observed behaviour are AMPK and MSK1. Both MSK1 and SGK1 show the same sequence in their hydroxyl-pocket with Thr406/Thr407, respectively, as potential hydrogen bonding partners, but both were placed in different groups. MSK1 activity is abolished by 1 μM staurosporine, but shows residual activity (11%) with UCN-01. SGK1 activity is at 25% of control activity with 1 μM UCN-01, but twice as high with staurosporine.

Conclusions

UCN-01 was subjected to a specificity analysis against an in-house panel of 29 protein kinases. Contrary to the suggestions of some previous reports, the data show that UCN-01 is not a specific inhibitor as it inhibited more than half of the tested kinases at significant levels. A direct comparison with staurosporine, however, showed a different pattern of inhibition, and was the subject of further analysis. We have reported the crystal structures of PDK1 in complex with the inhibitors staurosporine and UCN-01. Both inhibitors appear to bind to PDK1 in a similar fashion compared to the Chk1-UCN-01 or PKA-staurosporine [29] complex, with additional hydrogen bonding interactions at the UCN-01 7-hydroxyl group. This moiety is hydrogen bonded directly to Thr222 and indirectly via an ordered water molecule to Gln220. A different water-mediated hydrogen bonding network is also observed in other UCN-01 complexes known to date [35, 30], and might serve as a starting point for further structure-based optimisation. The residues around the 7-hydroxyl group ("hydroxyl-pocket") were aligned with known kinase structures and kinases sequences. It is apparent that spatial effects in the identified pocket play a key role in determining UCN-01 inhibition, as does the presence of hydrogen bonding partners for the additional hydroxyl group.

TABLE 3

Details of data collection & structure refinement. Values between brackets are for the highest resolution shell. Crystals were cryo-cooled to 100 K. All measured data were included in structure refinement.

| Dataset | Staurosporine | UCN-01 |
|---|---|---|
| Space group | P3$_2$21 | P3$_2$21 |
| Cell dimensions (Å) | a = 124.17 | a = 123.39 |
|  | b = 124.17 | b = 123.39 |
|  | c = 47.31 | c = 47.12 |
| Resolution range (Å) | 25-2.30 (2.38-2.30) | 25-2.50 (2.59-2.50) |
| # Observed reflections | 31730 (3091) | 68515 (6290) |
| # Unique reflections | 18018 (1794) | 14395 (1430) |
| Redundancy | 1.8 (1.7) | 4.8 (4.4) |
| I/σI | 7.5 (1.8) | 4.5 (2.6) |
| Completeness (%) | 95.8 (95.8) | 100.0 (99.9) |
| $R_{merge}$ | 0.096 (0.505) | 0.167 (0.688) |
| $R_{cryst}$, $R_{free}$ | 0.218, 0.255 | 0.189, 0.257 |
| RMSD from ideal geometry | | |
| Bonds (Å) | 0.007 | 0.009 |
| Angles (°) | 1.7 | 1.8 |
| B-factor RMSD (Å) (bonded, main chain) | 1.5 | 1.4 |
| <B> protein (Å) | 31.5 | 27.3 |
| <B> inhibitor (Å) | 18.5 | 17.4 |

TABLE 4

Hydrogen bonding between inhibitors and PDK1. Hydrogen bonds between PDK1 and UCN-01/staurosporine (STO) were calculated with WHAT IF [36] using the HB2 algorithm [37]. This algorithm gives a 0 (no hydrogen bond) to 1 (optimal hydrogen bond) score to reflect hydrogen bond geometry (HB2 column). Donor-acceptor distances are also listed (D-A).

| Inhibitor | Protein/H$_2$O | UCN-01 D-A (Å) | UCN-01 HB2 | STO D-A (Å) | STO HB2 | Comment |
|---|---|---|---|---|---|---|
| O5 | N-Ala162 | 2.8 | 0.76 | 3.0 | 0.81 | Conserved |
| N6 | O-Ser162 | 2.9 | 0.80 | 3.1 | 0.67 | Conserved |
| N4' | O-Glu209 | 3.2 | 0.68 | 3.1 | 0.39 | Conserved |
| N4' | Oε2-Glu166 | 2.6 | 0.63 | 2.5 | 0.45 | Conserved |
| O7 | Oγ1-Thr222 | 3.0 | 0.56 | | | 7-hydroxyl |
| O7 | H$_2$O | 3.0 | 0.89 | | | Water mediated to (Oε1-Gln220) |

TABLE 5

Comparison of inhibition by UCN-01 vs. staurosporine and hydroxyl pocket-lining residues. The indicated protein kinases were assayed at 0.1 mM ATP as described previously [17, 26], in the absence or presence of 1 μM staurosporine (STO) or UCN-01. Results are presented as percentage of kinase activity compared to that in control incubations. The activity results displayed in the two columns are an average of a triplicate determination. Abbreviations not defined in main text: ROCKII, Rho-dependent protein kinase-II; AMPK, AMP-activated protein kinase; MKK1, MAP-kinase kinase-1; PRAK, p38-regulated/activated protein kinase; PHK, phosphorylase kinase; CK2, Casein kinase-2; CHK1, cell cycle checkpoint kinase-1; DYRK, dual specificity tyrosine phosphorylated and regulated kinase; CSK, C-terminal Src kinase. Residues lining the hydroxyl pocket are shown in the last five columns, as derived from a multiple sequence alignment with T-Coffee [38].

| Kinase | STO | UCN-01 | | | | | |
|---|---|---|---|---|---|---|---|
| Both STO and UCN-01 inhibit | | | | | | | |
| PDK1 | 5 ± 1 | 0 ± 1 | Met134 | Val143 | Leu159 | Gln220 | Thr222 |
| CHK1 (1NVQ [30]) | 3 ± 1 | 1 ± 0 | Ile | Val | Leu | Lys145 | Ser147 |
| PKCα | 8 ± 2 | 1 ± 0 | Leu | Thr | Met | Lys | Ala |
| AMPK | 0 ± 0 | 1 ± 1 | Leu | Ile | Met | Lys | Ala |
| PHOS.KINASE (1PHK [39]) | 2 ± 3 | 1 ± 2 | Leu | Ile | Phe | Lys | Thr |

TABLE 5-continued

Comparison of inhibition by UCN-01 vs. staurosporine and hydroxyl pocket-lining residues.
The indicated protein kinases were assayed at 0.1 mM ATP as described previously [17, 26], in the absence or presence of 1 μM staurosporine (STO) or UCN-01. Results are presented as percentage of kinase activity compared to that in control incubations. The activity results displayed in the two columns are an average of a triplicate determination. Abbreviations not defined in main text: ROCKII, Rho-dependent protein kinase-II; AMPK, AMP-activated protein kinase; MKK1, MAP-kinase kinase-1; PRAK, p38-regulated/activated protein kinase; PHK, phosphorylase kinase; CK2, Casein kinase-2; CHK1, cell cycle checkpoint kinase-1; DYRK, dual specificity tyrosine phosphorylated and regulated kinase; CSK, C-terminal Src kinase. Residues lining the hydroxyl pocket are shown in the last five columns, as derived from a multiple sequence alignment with T-Coffee [38].

| Kinase | STO | UCN-01 | | | | | |
|---|---|---|---|---|---|---|---|
| Lck (1QPJ [40]) | 0 ± 0 | 3 ± 1 | Met | Val | Thr | Lys | Ala |
| CDK2/cyclin A (1AQ1 [31]) | 12 ± 12 | 8 ± 0 | Leu | Val | Phe80 | Lys | Ala |
| PKBΔPH (1O6K [41]) | 8 ± 2 | 9 ± 1 | Leu | Thr | Met | Lys | Thr |
| ROCK-II | 9 ± 5 | 13 ± 2 | Met | Val | Met | Lys | Ala |
| S6K1 | 24 ± 8 | 21 ± 4 | Leu | Val | Leu | Lys | Thr |
| GSK3β (1I09 [42]) | 29 ± 6 | 25 ± 5 | Met | Val | Leu | Lys | Cys |
| STO inhibits stronger than UCN-01 | | | | | | | |
| MSK1 | 1 ± 0 | 11 ± 0 | Leu | Val | Leu | Val | Thr406 |
| DYRK1α | 2 ± 2 | 15 ± 2 | Leu | Met | Phe | Lys | Val |
| PKA (1STC [29]) | 4 ± 1 | 27 ± 2 | Leu | Val | Met134 | Gln | Thr183 |
| MKK1 | 5 ± 8 | 53 ± 1 | Leu | Val | Met | Lys | Cys |
| MAPKAP-K2 | 23 ± 1 | 60 ± 1 | His | Val | Met | Lys | Thr |
| CSK (1BYG [43]) | 25 ± 8 | 58 ± 3 | Met | Val | Thr | Lys | Ser |
| SAPK3/p38γ (1CM8 [44]) | 37 ± 0 | 94 ± 8 | Leu | Ile | Met | Lys | Leu |
| SAPK4/p38δ | 40 ± 5 | 100 ± 7 | Leu | Ile | Met | Lys | Leu |
| PRAK | 48 ± 1 | 89 ± 4 | His | Val | Met | Lys | Cys |
| UCN-01 inhibits stronger than STO | | | | | | | |
| MAPKAP-K1a | 18 ± 10 | 1 ± 1 | Leu | Val | Leu | Lys | Thr341 |
| SGK1 | 51 ± 4 | 22 ± 4 | Leu | Val | Leu | Val | Thr407 |
| Neither UCN-01 nor STO inhibits | | | | | | | |
| MAPK2/ERK2 (1ERK [45]) | 100 ± 4 | 107 ± 5 | Leu | Ile | Gln | Lys | Cys |
| JNKSAPK1c | 91 ± 3 | 112 ± 6 | Met | Ile | Met | Lys | Leu |
| SAPK2α/p38 (1P38 [46]) | 76 ± 4 | 107 ± 5 | Leu | Ile | Thr | Lys | Leu |
| SAPK2β/p38β2 | 84 ± 11 | 106 ± 4 | Leu | Ile | Thr | Arg | Leu |
| CK2 (1F0Q [47]) | 95 ± 4 | 102 ± 11 | Leu | Val | Phe | Arg | Ile |
| CK1 (1CKI [48]) | 95 ± 11 | 96 ± 0 | Tyr | Pro | Met | Tyr | Ile |
| NEK6 | 109 ± 2 | 80 ± 7 | Leu | Ile | Leu | Lys | Gly |

REFERENCES

[1] B. Vanhaesebroeck and D. R. Alessi, The PI3K-PDK1 connection: more than just a road to PKB., *Biochem J*, 346, 561-76 (2000).

[2] R. A. Currie, K. S. Walker, A. Gray, M. Deak, A. Casamayor, C. P. Downes, P. Cohen, D. R. Alessi, and J. Lucocq, Role of phosphatidylinositol 3,4,5-trisphosphate in regulating the activity and localization of 3-phosphoinositide-dependent protein kinase-1, *Biochem. J.*, 337, 575-583 (1999).

[3] D. R. Alessi, Discovery of PDKI, one of the missing links in insulin signal transduction, *Biochem. Soc. Trans.*, 29, 1-14 (2001).

[4] D. P. Brazil and B. A. Hemmings, Ten years of protein kinase B signalling: a hard Akt to follow, *Trends Biochem. Sci.*, 26, 657-664 (2001).

[5] M. P. Scheid and J. R. Woodgett, PKB/AKT: Functional insights from genetic models, *Nat. Rev. Mol. Cell. Biol.*, 2, 760-768 (2001).

[6] N. Pullen, P. B. Dennis, M. Andjelkovic, A. Dufner, S. C. Kozma, B. A. Hemmings, and G. Thomas, Phosphorylation and activation of p70(s6k) by PDK1, *Science*, 279, 707-710 (1998).

[7] F. Lang and P. Cohen, Regulation and physiological roles of serum- and glucocorticoid-induced protein kinase isoforms, *Sci. STKE*, RE17, (2001).

[8] M. Frodin and S. Gammeltoft, Role and regulation of 90 kDa ribosomal S6 kinase (RSK) in signal transduction, *Mol. Cell. Endocrinol.*, 151, 65-77 (1999).

[9] R. M. Biondi and A. R. Nebreda, Signalling specificity of Ser/Thr protein kinases through docking-site-mediated interactions, *Biochem. J.*, 372, 1-13 (2003).

[10] R. M. Biondi, P. C. F. Cheung, A. Casamayor, M. Deak, R. A. Currie, and D. R. Alessi, Identification of a pocket in the PDK1 kinase domain that interacts with PIF and the C-terminal residues of PKA, *Embo J.*, 19, 979-988 (2000).

[11] R. M. Biondi, D. Komander, C. C. Thomas, J. M. Lizcano M. Deak, D. R. Alessi, and D. M. F. van Aalten, High resolution crystal structure of the human PDK1 catalytic domain defines the regulatory phosphopeptide docking site, *EMBO J.*, 21, 4219-4228 (2002).

[12] N. R. Leslie and C. P. Downes, PTEN: The down side of PI 3-kinase signalling, *Cell. Signal.*, 14, 285-295 (2002).

[13] D. R. Alessi, M. Deak, A. Casamayor, F. B. Caudwell, N. Morrice, D. G. Norman, P. Gaffney, C. B. Reese, C. N. MacDougall, D. Harbison, A. Ashworth, and M. Bownes, 3-phosphoinositide-dependent protein kinase-1 (PDK1): structural and functional homology with the *Drosophila* DSTPK61 kinase, *Curr. Biol.*, 7, 776-789 (1997).

[14] U. T. Ruegg and G. M. Burgess, Staurosporine, K-252 and UCN-01-potent but nonspecific inhibitors of protein-kinases, *Trends Pharmacol. Sci.*, 10, 218-220 (1989).

[15] W. T. Couldwell, D. R. Hinton, S. K. He, T. C. Chen, I. Sebat, M. H. Weiss, and R. E. Law, Protein-kinase-C inhibitors induce apoptosis in human-malignant glioma cell-lines, *FEBS Lett.*, 345, 43-46 (1994).

[16] I. Takahashi, Y. Saitoh, M. Yoshida, H. Sano, H. Nakano, M. Morimoto, and T. Tamaoki, Ucn-01 and ucn-02, new selective inhibitors of protein kinase-c 0.2. Purification, physicochemical properties, structural determination and biological-activities, *J. Antibiot.*, 42, 571-576 (1989).

[17] S. P. Davies, H. Reddy, M. Caivano, and P. Cohen, Specificity and mechanism of action of some commonly used protein kinase inhibitors, *Biochem. J.*, 351, 95-105 (2000).

[18] A. Gescher, Staurosporine analogues-pharmacological toys or useful antitumour agents?, *Crit. Rev. Oncol. Hematol.*, 34, 127-133 (2000).

[19] A. M. Senderowicz, The cell cycle as a target for cancer therapy: basic and clinical findings with the small molecule inhibitors flavopiridol and UCN-01., *Oncologist*, 7:3, 9-12 (2002).

[20] P. R. Graves, L. J. Yu, J. K. Schwarz, J. Gales, E. A. Sausville, P. M. O'Connor, and H. Piwnica-Worms, The Chk1 protein kinase and the Cdc25C regulatory pathways are targets of the anticancer agent UCN-01, *J. Biol. Chem.*, 275, 5600-5605 (2000).

[21] S. Sato, N. Fujita, and T. Tsuruo, Interference with PDK1-Akt survival signaling pathway by UCN-01 (7-hydroxystaurosporine), *Oncogene*, 21, 1727-1738 (2002).

[22] Z. Otwinowski and W. Minor, Processing of X-ray diffraction data collected in oscillation mode, *Methods in Enzymology*, 276, 307-326 (1997).

[23] A. T. Brunger, P. D. Adams, G. M. Clore, P. Gros, R. W. Grosse-Kunstleve, J.-S. Jiang, J. Kuszewski, M. Nilges, N. S. Pannu, R. J. Read, L. M. Rice, T. Simonson, and G. L. Warren, Crystallography and NMR system: A new software system for macromolecular structure determination, *Acta Cryst.*, D54, 905-921 (1998).

[24] T. A. Jones, J. Y. Zou, S. W. Cowan, and M. Kjeldgaard, Improved methods for building protein models in electron density maps and the location of errors in these models, *Acta Cryst.*, A47, 110-119 (1991).

[25] D. M. F. van Aalten, R. Bywater, J. B. C. Findlay, M. Hendlich, R. W. W. Hooft, and G. Vriend, PRODRG, a program for generating molecular topologies and unique molecular descriptors from coordinates of small molecules, *J. Comp. Aid. Mol. Des.*, 10, 255-262 (1996).

[26] J. Bain, H. McLauchlan, M. Elliott, and P. Cohen, The specificities of protein kinase inhibitors: an update, *Biochem. J.*, 371, 199-204 (2003).

[27] D. R. Knighton, J. H. Zheng, L. F. Teneyck, V. A. Ashford, N. H. Xuong, S. S. Taylor, and J. M. Sowadski, Crystal-structure of the catalytic subunit of cyclic adenosinemonophosphate dependent protein-kinase, *Science*, 253, 407-414 (1991).

[28] D. A. Johnson, P. Akamine, E. Radzio-Andzelm, Madhusudan, and S. S. Taylor, Dynamics of cAMP-dependent protein kinase, *Chem. Rev.*, 101, 2243-2270 (2001).

[29] L. Prade, R. A. Engh, A. Girod, V. Kinzel, R. Huber, and D. Bossemeyer, Staurosporine-induced conformational changes of cAMP-dependent protein kinase catalytic subunit explain inhibitory potential, *Structure*, 5, 1627-1637 (1997).

[30] B. Zhao, M. J. Bower, P. J. McDevitt, H. Z. Zhao, S. T. Davis, K. O. Johanson, S. M. Green, N. O. Concha, and B. B. S. Zhou, Structural basis for Chk1 inhibition by UCN-01, *J. Biol. Chem.*, 277, 46609-46615 (2002).

[31] A. M. Lawrie, M. E. M. Noble, P. Tunnah, N. R. Brown, L. N. Johnson, and J. A. Endicott, Protein kinase inhibition by staurosporine revealed in details of the molecular interaction with CDK2, *Nat. Struct. Biol.*, 4, 796-801 (1997).

[32] G. J. Kleywegt and T. A. Jones, Detection, delineation, measurement and display of cavities in macromolecular structures, *Acta Cryst.*, D50, 178-185 (1994).

[33] A. Smith, Shindyalovl. N., Veretnik S., Gribskov M., Taylor S. S., TenEyckL. F., and BourneP. E., The protein kinase resource, *Trends Biochem. Sci.*, 22, 444-446 (1997).

[34] J. Tsai, R. Taylor, C. Chothia, and M. Gerstein, The packing density in proteins: Standard radii and volumes, *J. Mol. Biol.*, 290, 253-266 (1999).

[35] M. A. Johnson and B. M. Pinto, Molecular mimicry of carbohydrates by peptides, *Aust. J. Chem.*, 55, 13-25 (2002).

[36] G. Vriend, WHAT IF: a molecular modeling and drug design program, *J. Mol. Graph.*, 8, 52-56 (1990).

[37] R. W. W. Hooft, C. Sander, and G. Vriend, Positioning hydrogen atoms by optimizing hydrogen-bond networks in protein structures, *Proteins*, 26, 363-376 (1996).

[38] C. Notredame, D. G. Higgins, and J. Heringa, T-Coffee: A novel method for fast and accurate multiple sequence alignment, *J. Mol. Biol.*, 302, 205-217 (2000).

[39] D. J. Owen, M. E. M. Noble, E. F. Garman, A. C. Papageorgiou, and L. N. Johnson, 2 structures of the catalytic domain of phosphorylase-kinase—an active protein-kinase complexed with substrate-analog and product, *Structure*, 3, 467-482 (1995).

[40] X. T. Zhu, J. L. Kim, J. R. Newcomb, P. E. Rose, D. R. Stover, L. M. Toledo, H. L. Zhao, and K. A. Morgenstern, Structural analysis of the lymphocyte-specific kinase Lek in complex with non-selective and Src family selective kinase inhibitors, *Struct. Fold. Des.*, 7, 651-661 (1999).

[41] J. Yang, P. Cron, V. M. Good, V. Thompson, B. A. Hemmings, and D. Barford, Crystal structure of an activated Akt/protein kinase B ternary complex with GSK3-peptide and AMP-PNP, *Nat. Struct. Biol.*, 9, 940-944 (2002).

[42] E. ter Haar, J. T. Coll, D. A. Austen, H. M. Hsiao, L. Swenson, and J. Jain, Structure of GSK3 beta reveals a primed phosphorylation mechanism, *Nat. Struct. Biol.*, 8, 593-596 (2001).

[43] M. B. A. C. Lamers, A. A. Antson, R. E. Hubbard, R. K. Scott, and D. H. Williams, Structure of the protein tyrosine kinase domain of C-terminal Src kinase (CSK) in complex with staurosporine, *J. Mol. Biol.*, 285, 713-725 (1999).

[44] S. Bellon, M. J. Fitzgibbon, T. Fox, H. M. Hsiao, and K. P. Wilson, The structure of phosphorylated P38 gamma is monomeric and reveals a conserved activation-loop conformation, *Struct. Fold. Des.*, 7, 1057-1065 (1999).

[45] F. M. Zhang, A. Strand, D. Robbins, M. H. Cobb, and E. J. Goldsmith, Atomic-structure of the map kinase ERK2 at 2.3-angstrom resolution, *Nature*, 367, 704-711 (1994).

[46] Z. L. Wang, P. C. Harkins, R. J. Ulevitch, J. H. Han, M. H. Cobb, and E. J. Goldsmith, The structure of mitogen-activated protein kinase p38 at 2.1 Angstrom resolution, *Proc. Natl. Acad. Sci. USA*, 94, 2327-2332 (1997).

[47] R. Battistutta, S. Sarno, E. DeMoliner, E. Papinutto, G. Zanotti, and L. A. Pinna, The replacement of ATP by the competitive inhibitor emodin induces conformational modifications in the catalytic site of protein kinase CK2, *J. Biol. Chem.*, 275, 29618-29622 (2000).

[48] L. M. Zhai, P. R. Graves, L. C. Robinson, M. Italiano, M. R. Culbertson, J. Rowles, M. H. Cobb, A. A. Depaoliroach, and P. J. Roach, Casein kinase i-gamma subfamily-molecular-cloning, expression, and characterization of 3 mammalian isoforms and complementation of defects in the *saccharomyces*-cerevisiae yck genes, *J. Biol. Chem.*, 270, 12717-12724 (1995).

[49] I. Takahashi, E. Kobayashi, K. Asano, M. Yoshida, and H. Nakano, UCN-01, a selective inhibitor of protein-kinase-c from *streptomyces*, *J. Antibiot.*, 40, 1782-1784 (1987).

Example 7

Co-Ordinates for PDK1 Fragment Co-Crystallised with Staurosporine

```
REMARK coordinates from restrained individual B-factor refinement
REMARK refinement resolution: 25.0 - 2.30 A
REMARK starting r= 0.2196 free_r= 0.2545
REMARK final      r= 0.2182 free_r= 0.2553
REMARK B rmsd for bonded mainchain atoms=  1.536    target= 1.5
REMARK B rmsd for bonded sidechain atoms=  2.154    target= 2.0
REMARK B rmsd for angle mainchain atoms=   2.576    target= 2.0
REMARK B rmsd for angle sidechain atoms=   3.220    target= 2.5
REMARK rweight= 0.1000 (with wa= 2.58634)
REMARK target= mlf  steps= 30
REMARK sg= P3(2)21 a= 124.172 b= 124.172 c= 47.314 alpha= 90 beta= 90
gamma= 120
REMARK parameter file 1    : /dd1/david/projects/MY_CNS/prot.par
REMARK parameter file 2    : /dd1/david/projects/MY_CNS/sto.par
REMARK parameter file 3    : CNS_TOPPAR:water_rep.param
REMARK parameter file 4    : CNS_TOPPAR:ion.param
REMARK parameter file 5    : /dd1/david/projects/MY_CNS/glycerol.par
REMARK molecular structure file: ../generate/alternate.mtf
REMARK input coordinates: ../minimize/minimize.pdb
REMARK reflection file= ../../1/hkl/cns.hkl
REMARK ncs= none
REMARK B-correction resolution: 6.0 - 2.30
REMARK initial B-factor correction applied to fobs :
REMARK B11=  -4.525 B22=  -4.525 B33=   9.049
REMARK B12=  -1.949 B13=   0.000 B23 =  0.000
REMARK B-factor correction applied to coordinate array B:    -0.209
REMARK bulk solvent: density level=0.340909 e/A^3, B-factor=36.8807
A^2
REMARK reflections with |Fobs|/sigma_F < 0.0 rejected
REMARK reflections with |Fobs| > 1000 * rms(Fobs) rejected
REMARK theoretical total number of refl. in resol. range:        18858 (
100.0 % )
REMARK number of unobserved reflections (no entry or |F|=0):       846 (
4.5 % )
REMARK number of reflections rejected:                               0 (
0.0 % )
REMARK total number of reflections used:                         18012 (
95.5 % )
REMARK number of reflections in working set:                     17259 (
91.5 % )
REMARK number of reflections in test set:                          753 (
4.0 % )
CRYST1   124.172  124.172   47.314  90.00  90.00  120.00 P 32 2 1
REMARK FILENAME="bindindividual.pdb"
REMARK DATE:30-Jan-2003   19:44:02             created by user: david
REMARK VERSION:1.0
ATOM    1   CB   PRO  A   72   64.267  -7.345  13.422  1.00  74.69   A
ATOM    2   CG   PRO  A   72   63.278  -8.432  13.027  1.00  74.97   A
ATOM    3   C    PRO  A   72   65.866  -6.007  12.013  1.00  73.72   A
ATOM    4   O    PRO  A   72   66.500  -6.002  10.955  1.00  73.74   A
ATOM    5   N    PRO  A   72   64.256  -7.651  11.034  1.00  74.67   A
ATOM    6   CD   PRO  A   72   63.762  -8.901  11.640  1.00  75.33   A
ATOM    7   CA   PRO  A   72   64.474  -6.639  12.090  1.00  74.30   A
ATOM    8   N    GLN  A   73   66.329  -5.474  13.141  1.00  72.17   A
ATOM    9   CA   GLN  A   73   67.635  -4.829  13.221  1.00  70.49   A
ATOM   10   CB   GLN  A   73   67.570  -3.424  12.611  1.00  69.71   A
ATOM   11   CG   GLN  A   73   66.670  -2.458  13.363  1.00  68.72   A
ATOM   12   CD   GLN  A   73   66.722  -1.054  12.795  0.00  69.01   A
ATOM   13   OE1  GLN  A   73   67.785  -0.435  12.735  0.00  68.92   A
ATOM   14   NE2  GLN  A   73   65.571  -0.541  12.376  0.00  68.92   A
ATOM   15   C    GLN  A   73   68.057  -4.728  14.683  1.00  69.53   A
ATOM   16   O    GLN  A   73   67.267  -5.015  15.585  1.00  69.69   A
ATOM   17   N    PRO  A   74   69.313  -4.321  14.940  1.00  68.34   A
ATOM   18   CD   PRO  A   74   70.411  -4.026  13.999  1.00  67.68   A
ATOM   19   CA   PRO  A   74   69.769  -4.204  16.330  1.00  67.15   A
ATOM   20   CB   PRO  A   74   71.198  -3.675  16.178  1.00  67.56   A
ATOM   21   CG   PRO  A   74   71.635  -4.254  14.855  1.00  67.46   A
ATOM   22   C    PRO  A   74   68.866  -3.240  17.105  1.00  65.27   A
ATOM   23   O    PRO  A   74   68.496  -2.186  16.584  1.00  65.27   A
ATOM   24   N    ARG  A   75   68.506  -3.598  18.337  1.00  62.56   A
ATOM   25   CA   ARG  A   75   67.642  -2.730  19.136  1.00  59.53   A
ATOM   26   CB   ARG  A   75   67.543  -3.228  20.582  1.00  62.40   A
```

-continued

| | | | | | | | | | | | |
|---|---|---|---|---|---|---|---|---|---|---|---|
| ATOM | 27 | CG | ARG | A | 75 | 66.120 | −3.565 | 21.023 | 1.00 | 64.22 | A |
| ATOM | 28 | CD | ARG | A | 75 | 66.020 | −3.746 | 22.537 | 1.00 | 66.65 | A |
| ATOM | 29 | NE | ARG | A | 75 | 64.741 | −4.332 | 22.943 | 1.00 | 68.76 | A |
| ATOM | 30 | CZ | ARG | A | 75 | 64.390 | −4.572 | 24.204 | 1.00 | 70.18 | A |
| ATOM | 31 | NH1 | ARG | A | 75 | 65.218 | −4.272 | 25.197 | 1.00 | 70.31 | A |
| ATOM | 32 | NH2 | ARG | A | 75 | 63.213 | −5.125 | 24.477 | 1.00 | 71.64 | A |
| ATOM | 33 | C | ARG | A | 75 | 68.184 | −1.306 | 19.126 | 1.00 | 55.61 | A |
| ATOM | 34 | O | ARG | A | 75 | 69.386 | −1.082 | 18.961 | 1.00 | 55.58 | A |
| ATOM | 35 | N | LYS | A | 76 | 67.294 | −0.341 | 19.295 | 1.00 | 50.06 | A |
| ATOM | 36 | CA | LYS | A | 76 | 67.704 | 1.050 | 19.297 | 1.00 | 45.50 | A |
| ATOM | 37 | CB | LYS | A | 76 | 66.498 | 1.941 | 19.594 | 1.00 | 45.42 | A |
| ATOM | 38 | CG | LYS | A | 76 | 66.404 | 3.192 | 18.735 | 1.00 | 45.70 | A |
| ATOM | 39 | CD | LYS | A | 76 | 66.329 | 2.829 | 17.257 | 1.00 | 44.53 | A |
| ATOM | 40 | CE | LYS | A | 76 | 66.030 | 4.045 | 16.396 | 1.00 | 44.45 | A |
| ATOM | 41 | NZ | LYS | A | 76 | 66.091 | 3.733 | 14.939 | 1.00 | 43.30 | A |
| ATOM | 42 | C | LYS | A | 76 | 68.783 | 1.251 | 20.359 | 1.00 | 42.73 | A |
| ATOM | 43 | O | LYS | A | 76 | 68.715 | 0.681 | 21.447 | 1.00 | 42.46 | A |
| ATOM | 44 | N | LYS | A | 77 | 69.793 | 2.046 | 20.038 | 1.00 | 39.63 | A |
| ATOM | 45 | CA | LYS | A | 77 | 70.851 | 2.309 | 20.995 | 1.00 | 36.33 | A |
| ATOM | 46 | CB | LYS | A | 77 | 72.139 | 2.670 | 20.267 | 1.00 | 36.33 | A |
| ATOM | 47 | CG | LYS | A | 77 | 72.655 | 1.570 | 19.353 | 1.00 | 36.55 | A |
| ATOM | 48 | CD | LYS | A | 77 | 74.005 | 1.945 | 18.785 | 1.00 | 35.61 | A |
| ATOM | 49 | CE | LYS | A | 77 | 74.491 | 0.932 | 17.766 | 1.00 | 38.34 | A |
| ATOM | 50 | NZ | LYS | A | 77 | 74.706 | −0.419 | 18.354 | 1.00 | 38.65 | A |
| ATOM | 51 | C | LYS | A | 77 | 70.413 | 3.459 | 21.889 | 1.00 | 35.52 | A |
| ATOM | 52 | O | LYS | A | 77 | 69.475 | 4.190 | 21.557 | 1.00 | 32.62 | A |
| ATOM | 53 | N | ARG | A | 78 | 71.097 | 3.608 | 23.020 | 1.00 | 34.95 | A |
| ATOM | 54 | CA | ARG | A | 78 | 70.801 | 4.654 | 23.991 | 1.00 | 33.79 | A |
| ATOM | 55 | CB | ARG | A | 78 | 69.917 | 4.094 | 25.114 | 1.00 | 35.78 | A |
| ATOM | 56 | CG | ARG | A | 78 | 70.211 | 2.652 | 25.483 | 1.00 | 38.18 | A |
| ATOM | 57 | CD | ARG | A | 78 | 69.036 | 2.040 | 26.239 | 1.00 | 38.81 | A |
| ATOM | 58 | NE | ARG | A | 78 | 68.995 | 0.578 | 26.160 | 0.00 | 38.43 | A |
| ATOM | 59 | CZ | ARG | A | 78 | 69.889 | −0.232 | 26.719 | 0.00 | 38.44 | A |
| ATOM | 60 | NH1 | ARG | A | 78 | 70.906 | 0.274 | 27.401 | 0.00 | 38.37 | A |
| ATOM | 61 | NH2 | ARG | A | 78 | 69.760 | −1.549 | 26.610 | 0.00 | 38.37 | A |
| ATOM | 62 | C | ARG | A | 78 | 72.099 | 5.230 | 24.544 | 1.00 | 31.96 | A |
| ATOM | 63 | O | ARG | A | 78 | 73.133 | 4.576 | 24.515 | 1.00 | 32.75 | A |
| ATOM | 64 | N | PRO | A | 79 | 72.060 | 6.470 | 25.055 | 1.00 | 30.51 | A |
| ATOM | 65 | CD | PRO | A | 79 | 70.844 | 7.272 | 25.274 | 1.00 | 27.35 | A |
| ATOM | 66 | CA | PRO | A | 79 | 73.236 | 7.150 | 25.611 | 1.00 | 29.82 | A |
| ATOM | 67 | CB | PRO | A | 79 | 72.626 | 8.326 | 26.365 | 1.00 | 28.52 | A |
| ATOM | 68 | CG | PRO | A | 79 | 71.418 | 8.628 | 25.559 | 1.00 | 29.89 | A |
| ATOM | 69 | C | PRO | A | 79 | 74.129 | 6.298 | 26.510 | 1.00 | 30.92 | A |
| ATOM | 70 | O | PRO | A | 79 | 75.356 | 6.357 | 26.412 | 1.00 | 33.32 | A |
| ATOM | 71 | N | GLU | A | 80 | 73.516 | 5.510 | 27.383 | 1.00 | 29.85 | A |
| ATOM | 72 | CA | GLU | A | 80 | 74.273 | 4.677 | 28.300 | 1.00 | 31.98 | A |
| ATOM | 73 | CB | GLU | A | 80 | 73.327 | 3.941 | 29.242 | 1.00 | 34.31 | A |
| ATOM | 74 | CG | GLU | A | 80 | 72.697 | 2.710 | 28.622 | 1.00 | 41.92 | A |
| ATOM | 75 | CD | GLU | A | 80 | 71.205 | 2.626 | 28.872 | 1.00 | 44.52 | A |
| ATOM | 76 | OE1 | GLU | A | 80 | 70.461 | 3.466 | 28.317 | 1.00 | 46.38 | A |
| ATOM | 77 | OE2 | GLU | A | 80 | 70.780 | 1.721 | 29.625 | 1.00 | 46.03 | A |
| ATOM | 78 | C | GLU | A | 80 | 75.157 | 3.663 | 27.578 | 1.00 | 30.62 | A |
| ATOM | 79 | O | GLU | A | 80 | 76.101 | 3.144 | 28.170 | 1.00 | 30.21 | A |
| ATOM | 80 | N | ASP | A | 81 | 74.859 | 3.378 | 26.312 | 1.00 | 28.14 | A |
| ATOM | 81 | CA | ASP | A | 81 | 75.659 | 2.417 | 25.548 | 1.00 | 27.32 | A |
| ATOM | 82 | CB | ASP | A | 81 | 74.938 | 1.990 | 24.253 | 1.00 | 27.75 | A |
| ATOM | 83 | CG | ASP | A | 81 | 73.612 | 1.275 | 24.512 | 1.00 | 30.45 | A |
| ATOM | 84 | OD1 | ASP | A | 81 | 73.495 | 0.549 | 25.525 | 1.00 | 30.76 | A |
| ATOM | 85 | OD2 | ASP | A | 81 | 72.686 | 1.424 | 23.686 | 1.00 | 30.74 | A |
| ATOM | 86 | C | ASP | A | 81 | 77.026 | 2.990 | 25.166 | 1.00 | 26.35 | A |
| ATOM | 87 | O | ASP | A | 81 | 77.895 | 2.266 | 24.680 | 1.00 | 25.33 | A |
| ATOM | 88 | N | PHE | A | 82 | 77.217 | 4.283 | 25.404 | 1.00 | 24.95 | A |
| ATOM | 89 | CA | PHE | A | 82 | 78.457 | 4.948 | 25.035 | 1.00 | 23.57 | A |
| ATOM | 90 | CB | PHE | A | 82 | 78.168 | 6.040 | 23.991 | 1.00 | 23.02 | A |
| ATOM | 91 | CG | PHE | A | 82 | 77.507 | 5.534 | 22.742 | 1.00 | 23.64 | A |
| ATOM | 92 | CD1 | PHE | A | 82 | 78.270 | 5.059 | 21.680 | 1.00 | 23.15 | A |
| ATOM | 93 | CD2 | PHE | A | 82 | 76.123 | 5.504 | 22.640 | 1.00 | 23.41 | A |
| ATOM | 94 | CE1 | PHE | A | 82 | 77.670 | 4.559 | 20.540 | 1.00 | 23.43 | A |
| ATOM | 95 | CE2 | PHE | A | 82 | 75.504 | 5.003 | 21.498 | 1.00 | 24.29 | A |
| ATOM | 96 | CZ | PHE | A | 82 | 76.283 | 4.527 | 20.444 | 1.00 | 25.15 | A |
| ATOM | 97 | C | PHE | A | 82 | 79.199 | 5.609 | 26.186 | 1.00 | 24.39 | A |
| ATOM | 98 | O | PHE | A | 82 | 78.647 | 5.847 | 27.259 | 1.00 | 22.78 | A |
| ATOM | 99 | N | LYS | A | 83 | 80.471 | 5.896 | 25.932 | 1.00 | 22.40 | A |
| ATOM | 100 | CA | LYS | A | 83 | 81.294 | 6.615 | 26.869 | 1.00 | 23.38 | A |
| ATOM | 101 | CB | LYS | A | 83 | 82.554 | 5.834 | 27.250 | 1.00 | 24.29 | A |
| ATOM | 102 | CG | LYS | A | 83 | 83.453 | 6.594 | 28.227 | 1.00 | 27.32 | A |
| ATOM | 103 | CD | LYS | A | 83 | 84.411 | 5.675 | 28.988 | 1.00 | 31.40 | A |
| ATOM | 104 | CE | LYS | A | 83 | 85.321 | 4.906 | 28.044 | 0.00 | 30.06 | A |
| ATOM | 105 | NZ | LYS | A | 83 | 86.145 | 5.819 | 27.207 | 0.00 | 30.54 | A |

-continued

| | | | | | | | | | | |
|---|---|---|---|---|---|---|---|---|---|---|
| ATOM | 106 | C | LYS | A | 83 | 81.656 | 7.847 | 26.046 | 1.00 | 24.47 | A |
| ATOM | 107 | O | LYS | A | 83 | 82.518 | 7.787 | 25.162 | 1.00 | 26.09 | A |
| ATOM | 108 | N | PHE | A | 84 | 80.965 | 8.951 | 26.309 | 1.00 | 21.59 | A |
| ATOM | 109 | CA | PHE | A | 84 | 81.211 | 10.182 | 25.583 | 1.00 | 21.61 | A |
| ATOM | 110 | CB | PHE | A | 84 | 80.073 | 11.169 | 25.811 | 1.00 | 20.62 | A |
| ATOM | 111 | CG | PHE | A | 84 | 78.794 | 10.757 | 25.159 | 1.00 | 20.05 | A |
| ATOM | 112 | CD1 | PHE | A | 84 | 77.915 | 9.905 | 25.805 | 1.00 | 18.27 | A |
| ATOM | 113 | CD2 | PHE | A | 84 | 78.498 | 11.176 | 23.868 | 1.00 | 19.96 | A |
| ATOM | 114 | CE1 | PHE | A | 84 | 76.764 | 9.473 | 25.183 | 1.00 | 19.47 | A |
| ATOM | 115 | CE2 | PHE | A | 84 | 77.346 | 10.748 | 23.233 | 1.00 | 21.09 | A |
| ATOM | 116 | CZ | PHE | A | 84 | 76.475 | 9.894 | 23.890 | 1.00 | 20.64 | A |
| ATOM | 117 | C | PHE | A | 84 | 82.525 | 10.820 | 25.966 | 1.00 | 22.27 | A |
| ATOM | 118 | O | PHE | A | 84 | 82.900 | 10.822 | 27.129 | 1.00 | 24.09 | A |
| ATOM | 119 | N | GLY | A | 85 | 83.213 | 11.371 | 24.972 | 1.00 | 22.72 | A |
| ATOM | 120 | CA | GLY | A | 85 | 84.496 | 12.007 | 25.203 | 1.00 | 22.66 | A |
| ATOM | 121 | C | GLY | A | 85 | 84.540 | 13.481 | 24.839 | 1.00 | 22.72 | A |
| ATOM | 122 | O | GLY | A | 85 | 83.622 | 14.228 | 25.158 | 1.00 | 22.51 | A |
| ATOM | 123 | N | LYS | A | 86 | 85.608 | 13.894 | 24.162 | 1.00 | 22.49 | A |
| ATOM | 124 | CA | LYS | A | 86 | 85.794 | 15.291 | 23.784 | 1.00 | 22.53 | A |
| ATOM | 125 | CB | LYS | A | 86 | 87.238 | 15.530 | 23.333 | 1.00 | 24.44 | A |
| ATOM | 126 | CG | LYS | A | 86 | 87.617 | 14.804 | 22.051 | 1.00 | 26.94 | A |
| ATOM | 127 | CD | LYS | A | 86 | 89.033 | 15.120 | 21.594 | 1.00 | 29.52 | A |
| ATOM | 128 | CE | LYS | A | 86 | 89.166 | 16.571 | 21.154 | 1.00 | 35.93 | A |
| ATOM | 129 | NZ | LYS | A | 86 | 90.505 | 16.892 | 20.553 | 1.00 | 38.21 | A |
| ATOM | 130 | C | LYS | A | 86 | 84.857 | 15.798 | 22.699 | 1.00 | 23.09 | A |
| ATOM | 131 | O | LYS | A | 86 | 84.295 | 15.032 | 21.923 | 1.00 | 22.85 | A |
| ATOM | 132 | N | ILE | A | 87 | 84.702 | 17.114 | 22.664 | 1.00 | 22.28 | A |
| ATOM | 133 | CA | ILE | A | 87 | 83.867 | 17.780 | 21.683 | 1.00 | 21.22 | A |
| ATOM | 134 | CB | ILE | A | 87 | 83.429 | 19.170 | 22.204 | 1.00 | 22.05 | A |
| ATOM | 135 | CG2 | ILE | A | 87 | 82.792 | 19.993 | 21.076 | 1.00 | 17.65 | A |
| ATOM | 136 | CG1 | ILE | A | 87 | 82.493 | 18.998 | 23.406 | 1.00 | 21.65 | A |
| ATOM | 137 | CD1 | ILE | A | 87 | 82.159 | 20.300 | 24.118 | 1.00 | 18.47 | A |
| ATOM | 138 | C | ILE | A | 87 | 84.707 | 17.963 | 20.418 | 1.00 | 21.83 | A |
| ATOM | 139 | O | ILE | A | 87 | 85.782 | 18.543 | 20.470 | 1.00 | 21.99 | A |
| ATOM | 140 | N | LEU | A | 88 | 84.226 | 17.463 | 19.288 | 1.00 | 22.57 | A |
| ATOM | 141 | CA | LEU | A | 88 | 84.964 | 17.614 | 18.039 | 1.00 | 22.76 | A |
| ATOM | 142 | CB | LEU | A | 88 | 84.586 | 16.515 | 17.044 | 1.00 | 20.65 | A |
| ATOM | 143 | CG | LEU | A | 88 | 84.899 | 15.107 | 17.535 | 1.00 | 20.09 | A |
| ATOM | 144 | CD1 | LEU | A | 88 | 84.455 | 14.082 | 16.502 | 1.00 | 17.42 | A |
| ATOM | 145 | CD2 | LEU | A | 88 | 86.392 | 15.004 | 17.813 | 1.00 | 17.76 | A |
| ATOM | 146 | C | LEU | A | 88 | 84.657 | 18.964 | 17.428 | 1.00 | 23.53 | A |
| ATOM | 147 | O | LEU | A | 88 | 85.512 | 19.577 | 16.794 | 1.00 | 24.73 | A |
| ATOM | 148 | N | GLY | A | 89 | 83.430 | 19.428 | 17.619 | 1.00 | 24.20 | A |
| ATOM | 149 | CA | GLY | A | 89 | 83.057 | 20.710 | 17.062 | 1.00 | 28.57 | A |
| ATOM | 150 | C | GLY | A | 89 | 81.649 | 21.131 | 17.431 | 1.00 | 32.57 | A |
| ATOM | 151 | O | GLY | A | 89 | 80.834 | 20.318 | 17.882 | 1.00 | 32.78 | A |
| ATOM | 152 | N | GLU | A | 90 | 81.363 | 22.412 | 17.224 | 1.00 | 35.17 | A |
| ATOM | 153 | CA | GLU | A | 90 | 80.063 | 22.964 | 17.542 | 1.00 | 39.17 | A |
| ATOM | 154 | CB | GLU | A | 90 | 80.168 | 23.853 | 18.784 | 1.00 | 41.47 | A |
| ATOM | 155 | CG | GLU | A | 90 | 80.112 | 23.061 | 20.082 | 1.00 | 47.18 | A |
| ATOM | 156 | CD | GLU | A | 90 | 80.422 | 23.893 | 21.313 | 1.00 | 50.49 | A |
| ATOM | 157 | OE1 | GLU | A | 90 | 81.610 | 24.228 | 21.526 | 1.00 | 51.41 | A |
| ATOM | 158 | OE2 | GLU | A | 90 | 79.476 | 24.210 | 22.067 | 1.00 | 53.44 | A |
| ATOM | 159 | C | GLU | A | 90 | 79.436 | 23.743 | 16.402 | 1.00 | 40.69 | A |
| ATOM | 160 | O | GLU | A | 90 | 80.110 | 24.185 | 15.471 | 1.00 | 40.64 | A |
| ATOM | 161 | N | GLY | A | 91 | 78.121 | 23.881 | 16.488 | 1.00 | 42.58 | A |
| ATOM | 162 | CA | GLY | A | 91 | 77.363 | 24.618 | 15.503 | 1.00 | 43.40 | A |
| ATOM | 163 | C | GLY | A | 91 | 76.303 | 25.335 | 16.306 | 1.00 | 44.83 | A |
| ATOM | 164 | O | GLY | A | 91 | 76.154 | 25.083 | 17.507 | 1.00 | 43.64 | A |
| ATOM | 165 | N | SER | A | 92 | 75.579 | 26.244 | 15.669 | 1.00 | 47.22 | A |
| ATOM | 166 | CA | SER | A | 92 | 74.522 | 26.969 | 16.366 | 1.00 | 48.94 | A |
| ATOM | 167 | CB | SER | A | 92 | 73.961 | 28.066 | 15.461 | 1.00 | 51.50 | A |
| ATOM | 168 | OG | SER | A | 92 | 73.663 | 27.541 | 14.175 | 1.00 | 54.98 | A |
| ATOM | 169 | C | SER | A | 92 | 73.454 | 25.928 | 16.625 | 1.00 | 47.87 | A |
| ATOM | 170 | O | SER | A | 92 | 72.745 | 25.950 | 17.635 | 1.00 | 47.78 | A |
| ATOM | 171 | N | PHE | A | 93 | 73.392 | 24.994 | 15.689 | 1.00 | 46.49 | A |
| ATOM | 172 | CA | PHE | A | 93 | 72.434 | 23.909 | 15.697 | 1.00 | 46.02 | A |
| ATOM | 173 | CB | PHE | A | 93 | 72.297 | 23.369 | 14.263 | 1.00 | 49.54 | A |
| ATOM | 174 | CG | PHE | A | 93 | 73.588 | 23.398 | 13.459 | 1.00 | 50.29 | A |
| ATOM | 175 | CD1 | PHE | A | 93 | 74.301 | 22.229 | 13.209 | 1.00 | 52.29 | A |
| ATOM | 176 | CD2 | PHE | A | 93 | 74.058 | 24.593 | 12.915 | 1.00 | 51.94 | A |
| ATOM | 177 | CE1 | PHE | A | 93 | 75.459 | 22.245 | 12.424 | 1.00 | 52.28 | A |
| ATOM | 178 | CE2 | PHE | A | 93 | 75.209 | 24.622 | 12.135 | 1.00 | 52.58 | A |
| ATOM | 179 | CZ | PHE | A | 93 | 75.911 | 23.443 | 11.887 | 1.00 | 53.99 | A |
| ATOM | 180 | C | PHE | A | 93 | 72.700 | 22.754 | 16.662 | 1.00 | 43.48 | A |
| ATOM | 181 | O | PHE | A | 93 | 71.772 | 22.245 | 17.292 | 1.00 | 42.15 | A |
| ATOM | 182 | N | SER | A | 94 | 73.955 | 22.343 | 16.796 | 1.00 | 39.99 | A |
| ATOM | 183 | CA | SER | A | 94 | 74.245 | 21.206 | 17.655 | 1.00 | 36.12 | A |
| ATOM | 184 | CB | SER | A | 94 | 73.839 | 19.937 | 16.921 | 1.00 | 38.79 | A |

-continued

| | | | | | | | | | | |
|---|---|---|---|---|---|---|---|---|---|---|
| ATOM | 185 | OG | SER | A | 94 | 74.549 | 19.863 | 15.695 | 1.00 | 40.39 | A |
| ATOM | 186 | C | SER | A | 94 | 75.697 | 21.066 | 18.083 | 1.00 | 32.29 | A |
| ATOM | 187 | O | SER | A | 94 | 76.513 | 21.962 | 17.890 | 1.00 | 30.04 | A |
| ATOM | 188 | N | THR | A | 95 | 76.006 | 19.909 | 18.655 | 1.00 | 28.50 | A |
| ATOM | 189 | CA | THR | A | 95 | 77.350 | 19.614 | 19.116 | 1.00 | 26.86 | A |
| ATOM | 190 | CB | THR | A | 95 | 77.432 | 19.642 | 20.652 | 1.00 | 27.90 | A |
| ATOM | 191 | OG1 | THR | A | 95 | 76.907 | 20.882 | 21.136 | 1.00 | 32.56 | A |
| ATOM | 192 | CG2 | THR | A | 95 | 78.874 | 19.502 | 21.112 | 1.00 | 27.77 | A |
| ATOM | 193 | C | THR | A | 95 | 77.757 | 18.225 | 18.653 | 1.00 | 23.70 | A |
| ATOM | 194 | O | THR | A | 95 | 76.971 | 17.287 | 18.724 | 1.00 | 24.35 | A |
| ATOM | 195 | N | VAL | A | 96 | 78.991 | 18.100 | 18.184 | 1.00 | 22.75 | A |
| ATOM | 196 | CA | VAL | A | 96 | 79.505 | 16.813 | 17.733 | 1.00 | 20.60 | A |
| ATOM | 197 | CB | VAL | A | 96 | 80.139 | 16.909 | 16.336 | 1.00 | 17.79 | A |
| ATOM | 198 | CG1 | VAL | A | 96 | 80.625 | 15.530 | 15.898 | 1.00 | 18.21 | A |
| ATOM | 199 | CG2 | VAL | A | 96 | 79.131 | 17.447 | 15.344 | 1.00 | 13.79 | A |
| ATOM | 200 | C | VAL | A | 96 | 80.566 | 16.351 | 18.716 | 1.00 | 21.23 | A |
| ATOM | 201 | O | VAL | A | 96 | 81.600 | 17.006 | 18.889 | 1.00 | 22.12 | A |
| ATOM | 202 | N | VAL | A | 97 | 80.310 | 15.220 | 19.362 | 1.00 | 22.06 | A |
| ATOM | 203 | CA | VAL | A | 97 | 81.244 | 14.690 | 20.345 | 1.00 | 24.07 | A |
| ATOM | 204 | CB | VAL | A | 97 | 80.592 | 14.680 | 21.743 | 1.00 | 24.91 | A |
| ATOM | 205 | CG1 | VAL | A | 97 | 79.199 | 14.124 | 21.649 | 1.00 | 28.97 | A |
| ATOM | 206 | CG2 | VAL | A | 97 | 81.422 | 13.859 | 22.715 | 1.00 | 27.97 | A |
| ATOM | 207 | C | VAL | A | 97 | 81.748 | 13.298 | 20.002 | 1.00 | 23.47 | A |
| ATOM | 208 | O | VAL | A | 97 | 81.017 | 12.491 | 19.436 | 1.00 | 26.62 | A |
| ATOM | 209 | N | LEU | A | 98 | 83.007 | 13.024 | 20.329 | 1.00 | 22.92 | A |
| ATOM | 210 | CA | LEU | A | 98 | 83.586 | 11.713 | 20.063 | 1.00 | 23.27 | A |
| ATOM | 211 | CB | LEU | A | 98 | 85.117 | 11.777 | 20.110 | 1.00 | 21.94 | A |
| ATOM | 212 | CG | LEU | A | 98 | 85.932 | 10.495 | 19.854 | 1.00 | 22.83 | A |
| ATOM | 213 | CD1 | LEU | A | 98 | 85.606 | 9.924 | 18.486 | 1.00 | 23.24 | A |
| ATOM | 214 | CD2 | LEU | A | 98 | 87.422 | 10.802 | 19.945 | 1.00 | 21.21 | A |
| ATOM | 215 | C | LEU | A | 98 | 83.069 | 10.782 | 21.144 | 1.00 | 23.95 | A |
| ATOM | 216 | O | LEU | A | 98 | 83.143 | 11.099 | 22.322 | 1.00 | 26.02 | A |
| ATOM | 217 | N | ALA | A | 99 | 82.523 | 9.645 | 20.738 | 1.00 | 24.41 | A |
| ATOM | 218 | CA | ALA | A | 99 | 81.999 | 8.677 | 21.686 | 1.00 | 23.76 | A |
| ATOM | 219 | CB | ALA | A | 99 | 80.485 | 8.692 | 21.668 | 1.00 | 20.64 | A |
| ATOM | 220 | C | ALA | A | 99 | 82.502 | 7.282 | 21.357 | 1.00 | 26.42 | A |
| ATOM | 221 | O | ALA | A | 99 | 82.792 | 6.951 | 20.195 | 1.00 | 26.78 | A |
| ATOM | 222 | N | ARG | A | 100 | 82.602 | 6.462 | 22.394 | 1.00 | 26.77 | A |
| ATOM | 223 | CA | ARG | A | 100 | 83.055 | 5.094 | 22.238 | 1.00 | 26.80 | A |
| ATOM | 224 | CB | ARG | A | 100 | 84.362 | 4.897 | 23.001 | 1.00 | 28.29 | A |
| ATOM | 225 | CG | ARG | A | 100 | 84.967 | 3.522 | 22.853 | 1.00 | 33.87 | A |
| ATOM | 226 | CD | ARG | A | 100 | 86.281 | 3.447 | 23.617 | 1.00 | 38.01 | A |
| ATOM | 227 | NE | ARG | A | 100 | 87.337 | 4.240 | 22.983 | 1.00 | 41.22 | A |
| ATOM | 228 | CZ | ARG | A | 100 | 87.932 | 3.917 | 21.837 | 1.00 | 41.46 | A |
| ATOM | 229 | NH1 | ARG | A | 100 | 87.580 | 2.813 | 21.190 | 1.00 | 41.28 | A |
| ATOM | 230 | NH2 | ARG | A | 100 | 88.887 | 4.692 | 21.339 | 1.00 | 43.39 | A |
| ATOM | 231 | C | ARG | A | 100 | 81.970 | 4.167 | 22.770 | 1.00 | 24.32 | A |
| ATOM | 232 | O | ARG | A | 100 | 81.583 | 4.251 | 23.934 | 1.00 | 25.42 | A |
| ATOM | 233 | N | GLU | A | 101 | 81.456 | 3.308 | 21.900 | 1.00 | 22.41 | A |
| ATOM | 234 | CA | GLU | A | 101 | 80.417 | 2.367 | 22.281 | 1.00 | 22.87 | A |
| ATOM | 235 | CB | GLU | A | 101 | 79.787 | 1.775 | 21.025 | 1.00 | 21.96 | A |
| ATOM | 236 | CG | GLU | A | 101 | 78.819 | 0.652 | 21.292 | 1.00 | 24.68 | A |
| ATOM | 237 | CD | GLU | A | 101 | 78.203 | 0.137 | 20.018 | 1.00 | 28.27 | A |
| ATOM | 238 | OE1 | GLU | A | 101 | 78.965 | −0.113 | 19.057 | 1.00 | 28.96 | A |
| ATOM | 239 | OE2 | GLU | A | 101 | 76.963 | −0.022 | 19.971 | 1.00 | 29.77 | A |
| ATOM | 240 | C | GLU | A | 101 | 81.015 | 1.261 | 23.151 | 1.00 | 23.59 | A |
| ATOM | 241 | O | GLU | A | 101 | 81.945 | 0.574 | 22.738 | 1.00 | 24.80 | A |
| ATOM | 242 | N | LEU | A | 102 | 80.475 | 1.088 | 24.351 | 1.00 | 26.09 | A |
| ATOM | 243 | CA | LEU | A | 102 | 80.982 | 0.083 | 25.289 | 1.00 | 28.74 | A |
| ATOM | 244 | CB | LEU | A | 102 | 80.173 | 0.110 | 26.593 | 1.00 | 30.16 | A |
| ATOM | 245 | CG | LEU | A | 102 | 80.347 | 1.308 | 27.532 | 1.00 | 34.19 | A |
| ATOM | 246 | CD1 | LEU | A | 102 | 81.824 | 1.692 | 27.599 | 1.00 | 33.27 | A |
| ATOM | 247 | CD2 | LEU | A | 102 | 79.527 | 2.477 | 27.046 | 1.00 | 34.46 | A |
| ATOM | 248 | C | LEU | A | 102 | 81.042 | −1.359 | 24.791 | 1.00 | 28.32 | A |
| ATOM | 249 | O | LEU | A | 102 | 82.067 | −2.024 | 24.916 | 1.00 | 29.83 | A |
| ATOM | 250 | N | ALA | A | 103 | 79.948 | −1.841 | 24.226 | 1.00 | 27.34 | A |
| ATOM | 251 | CA | ALA | A | 103 | 79.887 | −3.218 | 23.763 | 1.00 | 27.81 | A |
| ATOM | 252 | CB | ALA | A | 103 | 78.466 | −3.549 | 23.367 | 1.00 | 27.48 | A |
| ATOM | 253 | C | ALA | A | 103 | 80.828 | −3.593 | 22.624 | 1.00 | 27.42 | A |
| ATOM | 254 | O | ALA | A | 103 | 81.172 | −4.765 | 22.463 | 1.00 | 28.68 | A |
| ATOM | 255 | N | THR | A | 104 | 81.257 | −2.612 | 21.842 | 1.00 | 24.97 | A |
| ATOM | 256 | CA | THR | A | 104 | 82.105 | −2.907 | 20.695 | 1.00 | 23.79 | A |
| ATOM | 257 | CB | THR | A | 104 | 81.441 | −2.472 | 19.393 | 1.00 | 22.01 | A |
| ATOM | 258 | OG1 | THR | A | 104 | 81.355 | −1.041 | 19.379 | 1.00 | 23.91 | A |
| ATOM | 259 | CG2 | THR | A | 104 | 80.051 | −3.069 | 19.261 | 1.00 | 17.30 | A |
| ATOM | 260 | C | THR | A | 104 | 83.444 | −2.221 | 20.712 | 1.00 | 25.00 | A |
| ATOM | 261 | O | THR | A | 104 | 84.350 | −2.616 | 19.972 | 1.00 | 25.02 | A |
| ATOM | 262 | N | SER | A | 105 | 83.551 | −1.172 | 21.525 | 1.00 | 24.89 | A |
| ATOM | 263 | CA | SER | A | 105 | 84.775 | −0.394 | 21.616 | 1.00 | 24.55 | A |

-continued

| | | | | | | | | | | |
|---|---|---|---|---|---|---|---|---|---|---|
| ATOM | 264 | CB | SER | A | 105 | 85.979 | −1.334 | 21.732 | 1.00 | 26.36 | A |
| ATOM | 265 | OG | SER | A | 105 | 87.143 | −0.621 | 22.090 | 1.00 | 32.45 | A |
| ATOM | 266 | C | SER | A | 105 | 84.916 | 0.514 | 20.374 | 1.00 | 23.38 | A |
| ATOM | 267 | O | SER | A | 105 | 85.931 | 1.175 | 20.188 | 1.00 | 24.92 | A |
| ATOM | 268 | N | ARG | A | 106 | 83.888 | 0.546 | 19.531 | 1.00 | 20.51 | A |
| ATOM | 269 | CA | ARG | A | 106 | 83.906 | 1.372 | 18.323 | 1.00 | 19.31 | A |
| ATOM | 270 | CB | ARG | A | 106 | 82.778 | 0.947 | 17.370 | 1.00 | 19.05 | A |
| ATOM | 271 | CG | ARG | A | 106 | 83.099 | −0.283 | 16.520 | 1.00 | 15.69 | A |
| ATOM | 272 | CD | ARG | A | 106 | 81.853 | −0.804 | 15.832 | 1.00 | 19.45 | A |
| ATOM | 273 | NE | ARG | A | 106 | 82.144 | −1.838 | 14.846 | 1.00 | 20.98 | A |
| ATOM | 274 | CZ | ARG | A | 106 | 81.234 | −2.673 | 14.354 | 1.00 | 21.77 | A |
| ATOM | 275 | NH1 | ARG | A | 106 | 79.974 | −2.599 | 14.768 | 1.00 | 19.65 | A |
| ATOM | 276 | NH2 | ARG | A | 106 | 81.577 | −3.560 | 13.427 | 1.00 | 21.43 | A |
| ATOM | 277 | C | ARG | A | 106 | 83.760 | 2.858 | 18.624 | 1.00 | 17.84 | A |
| ATOM | 278 | O | ARG | A | 106 | 83.022 | 3.234 | 19.525 | 1.00 | 15.87 | A |
| ATOM | 279 | N | GLU | A | 107 | 84.463 | 3.691 | 17.863 | 1.00 | 18.23 | A |
| ATOM | 280 | CA | GLU | A | 107 | 84.395 | 5.144 | 18.039 | 1.00 | 22.75 | A |
| ATOM | 281 | CB | GLU | A | 107 | 85.773 | 5.800 | 17.929 | 1.00 | 23.58 | A |
| ATOM | 282 | CG | GLU | A | 107 | 86.828 | 5.254 | 18.859 | 1.00 | 32.15 | A |
| ATOM | 283 | CD | GLU | A | 107 | 88.066 | 6.131 | 18.878 | 1.00 | 35.04 | A |
| ATOM | 284 | OE1 | GLU | A | 107 | 88.145 | 7.019 | 19.755 | 1.00 | 36.99 | A |
| ATOM | 285 | OE2 | GLU | A | 107 | 88.949 | 5.944 | 18.007 | 1.00 | 37.54 | A |
| ATOM | 286 | C | GLU | A | 107 | 83.514 | 5.787 | 16.982 | 1.00 | 21.00 | A |
| ATOM | 287 | O | GLU | A | 107 | 83.709 | 5.577 | 15.787 | 1.00 | 21.37 | A |
| ATOM | 288 | N | TYR | A | 108 | 82.570 | 6.593 | 17.437 | 1.00 | 19.48 | A |
| ATOM | 289 | CA | TYR | A | 108 | 81.652 | 7.298 | 16.559 | 1.00 | 18.30 | A |
| ATOM | 290 | CB | TYR | A | 108 | 80.228 | 6.791 | 16.754 | 1.00 | 17.52 | A |
| ATOM | 291 | CG | TYR | A | 108 | 79.993 | 5.373 | 16.309 | 1.00 | 22.75 | A |
| ATOM | 292 | CD1 | TYR | A | 108 | 79.727 | 5.075 | 14.972 | 1.00 | 20.94 | A |
| ATOM | 293 | CE1 | TYR | A | 108 | 79.492 | 3.765 | 14.571 | 1.00 | 23.91 | A |
| ATOM | 294 | CD2 | TYR | A | 108 | 80.019 | 4.324 | 17.231 | 1.00 | 19.41 | A |
| ATOM | 295 | CE2 | TYR | A | 108 | 79.788 | 3.026 | 16.845 | 1.00 | 19.33 | A |
| ATOM | 296 | CZ | TYR | A | 108 | 79.527 | 2.744 | 15.521 | 1.00 | 23.13 | A |
| ATOM | 297 | OH | TYR | A | 108 | 79.333 | 1.438 | 15.143 | 1.00 | 23.65 | A |
| ATOM | 298 | C | TYR | A | 108 | 81.660 | 8.777 | 16.906 | 1.00 | 18.00 | A |
| ATOM | 299 | O | TYR | A | 108 | 81.929 | 9.161 | 18.046 | 1.00 | 18.12 | A |
| ATOM | 300 | N | ALA | A | 109 | 81.370 | 9.603 | 15.912 | 1.00 | 17.20 | A |
| ATOM | 301 | CA | ALA | A | 109 | 81.274 | 11.036 | 16.114 | 1.00 | 15.30 | A |
| ATOM | 302 | CB | ALA | A | 109 | 81.853 | 11.784 | 14.928 | 1.00 | 13.44 | A |
| ATOM | 303 | C | ALA | A | 109 | 79.759 | 11.205 | 16.178 | 1.00 | 17.20 | A |
| ATOM | 304 | O | ALA | A | 109 | 79.056 | 11.019 | 15.179 | 1.00 | 17.23 | A |
| ATOM | 305 | N | ILE | A | 110 | 79.250 | 11.522 | 17.362 | 1.00 | 17.40 | A |
| ATOM | 306 | CA | ILE | A | 110 | 77.814 | 11.654 | 17.542 | 1.00 | 17.60 | A |
| ATOM | 307 | CB | ILE | A | 110 | 77.380 | 10.957 | 18.842 | 1.00 | 16.56 | A |
| ATOM | 308 | CG2 | ILE | A | 110 | 75.906 | 11.236 | 19.119 | 1.00 | 14.97 | A |
| ATOM | 309 | CG1 | ILE | A | 110 | 77.672 | 9.453 | 18.728 | 1.00 | 14.02 | A |
| ATOM | 310 | CD1 | ILE | A | 110 | 77.197 | 8.632 | 19.907 | 1.00 | 11.93 | A |
| ATOM | 311 | C | ILE | A | 110 | 77.306 | 13.089 | 17.548 | 1.00 | 19.83 | A |
| ATOM | 312 | O | ILE | A | 110 | 77.690 | 13.892 | 18.396 | 1.00 | 20.84 | A |
| ATOM | 313 | N | LYS | A | 111 | 76.444 | 13.415 | 16.597 | 1.00 | 18.58 | A |
| ATOM | 314 | CA | LYS | A | 111 | 75.902 | 14.761 | 16.551 | 1.00 | 20.88 | A |
| ATOM | 315 | CB | LYS | A | 111 | 75.455 | 15.115 | 15.131 | 1.00 | 21.39 | A |
| ATOM | 316 | CG | LYS | A | 111 | 75.016 | 16.558 | 14.975 | 1.00 | 24.84 | A |
| ATOM | 317 | CD | LYS | A | 111 | 75.005 | 16.971 | 13.516 | 1.00 | 27.43 | A |
| ATOM | 318 | CE | LYS | A | 111 | 74.426 | 18.359 | 13.343 | 1.00 | 28.44 | A |
| ATOM | 319 | NZ | LYS | A | 111 | 74.619 | 18.871 | 11.972 | 1.00 | 28.27 | A |
| ATOM | 320 | C | LYS | A | 111 | 74.724 | 14.819 | 17.507 | 1.00 | 20.66 | A |
| ATOM | 321 | O | LYS | A | 111 | 73.797 | 14.008 | 17.410 | 1.00 | 20.23 | A |
| ATOM | 322 | N | ILE | A | 112 | 74.772 | 15.765 | 18.441 | 1.00 | 20.09 | A |
| ATOM | 323 | CA | ILE | A | 112 | 73.704 | 15.914 | 19.426 | 1.00 | 23.02 | A |
| ATOM | 324 | CB | ILE | A | 112 | 74.261 | 15.882 | 20.863 | 1.00 | 24.20 | A |
| ATOM | 325 | CG2 | ILE | A | 112 | 73.116 | 15.765 | 21.864 | 1.00 | 21.42 | A |
| ATOM | 326 | CG1 | ILE | A | 112 | 75.206 | 14.692 | 21.023 | 1.00 | 24.14 | A |
| ATOM | 327 | CD1 | ILE | A | 112 | 75.893 | 14.634 | 22.375 | 1.00 | 26.83 | A |
| ATOM | 328 | C | ILE | A | 112 | 72.962 | 17.225 | 19.221 | 1.00 | 22.53 | A |
| ATOM | 329 | O | ILE | A | 112 | 73.573 | 18.286 | 19.132 | 1.00 | 21.31 | A |
| ATOM | 330 | N | LEU | A | 113 | 71.641 | 17.138 | 19.150 | 1.00 | 24.04 | A |
| ATOM | 331 | CA | LEU | A | 113 | 70.800 | 18.313 | 18.940 | 1.00 | 25.81 | A |
| ATOM | 332 | CB | LEU | A | 113 | 70.135 | 18.264 | 17.555 | 1.00 | 24.66 | A |
| ATOM | 333 | CG | LEU | A | 113 | 70.988 | 18.095 | 16.295 | 1.00 | 26.73 | A |
| ATOM | 334 | CD1 | LEU | A | 113 | 71.316 | 16.620 | 16.093 | 1.00 | 24.51 | A |
| ATOM | 335 | CD2 | LEU | A | 113 | 70.234 | 18.637 | 15.083 | 1.00 | 26.16 | A |
| ATOM | 336 | C | LEU | A | 113 | 69.702 | 18.400 | 19.994 | 1.00 | 27.62 | A |
| ATOM | 337 | O | LEU | A | 113 | 69.053 | 17.398 | 20.314 | 1.00 | 29.70 | A |
| ATOM | 338 | N | GLU | A | 114 | 69.491 | 19.597 | 20.530 | 1.00 | 29.32 | A |
| ATOM | 339 | CA | GLU | A | 114 | 68.445 | 19.806 | 21.526 | 1.00 | 31.56 | A |
| ATOM | 340 | CB | GLU | A | 114 | 68.775 | 21.020 | 22.391 | 1.00 | 34.85 | A |
| ATOM | 341 | CG | GLU | A | 114 | 67.680 | 21.357 | 23.392 | 1.00 | 42.32 | A |
| ATOM | 342 | CD | GLU | A | 114 | 67.922 | 22.670 | 24.108 | 1.00 | 45.56 | A |

-continued

| | | | | | | | | | | |
|---|---|---|---|---|---|---|---|---|---|---|
| ATOM | 343 | OE1 | GLU | A | 114 | 68.086 | 23.700 | 23.417 | 1.00 | 48.01 | A |
| ATOM | 344 | OE2 | GLU | A | 114 | 67.941 | 22.673 | 25.359 | 1.00 | 48.10 | A |
| ATOM | 345 | C | GLU | A | 114 | 67.107 | 20.036 | 20.816 | 1.00 | 31.02 | A |
| ATOM | 346 | O | GLU | A | 114 | 66.926 | 21.049 | 20.140 | 1.00 | 30.39 | A |
| ATOM | 347 | N | LYS | A | 115 | 66.176 | 19.099 | 20.967 | 1.00 | 30.58 | A |
| ATOM | 348 | CA | LYS | A | 115 | 64.872 | 19.218 | 20.321 | 1.00 | 31.63 | A |
| ATOM | 349 | CB | LYS | A | 115 | 63.964 | 18.049 | 20.734 | 1.00 | 28.91 | A |
| ATOM | 350 | CG | LYS | A | 115 | 64.287 | 16.742 | 20.003 | 1.00 | 28.07 | A |
| ATOM | 351 | CD | LYS | A | 115 | 63.356 | 15.580 | 20.368 | 1.00 | 23.95 | A |
| ATOM | 352 | CE | LYS | A | 115 | 63.713 | 14.960 | 21.707 | 1.00 | 23.89 | A |
| ATOM | 353 | NZ | LYS | A | 115 | 62.860 | 13.782 | 22.020 | 1.00 | 24.15 | A |
| ATOM | 354 | C | LYS | A | 115 | 64.165 | 20.551 | 20.591 | 1.00 | 33.78 | A |
| ATOM | 355 | O | LYS | A | 115 | 63.495 | 21.100 | 19.711 | 1.00 | 33.61 | A |
| ATOM | 356 | N | ARG | A | 116 | 64.325 | 21.076 | 21.801 | 1.00 | 35.55 | A |
| ATOM | 357 | CA | ARG | A | 116 | 63.682 | 22.332 | 22.176 | 1.00 | 38.66 | A |
| ATOM | 358 | CB | ARG | A | 116 | 63.932 | 22.627 | 23.663 | 1.00 | 42.20 | A |
| ATOM | 359 | CG | ARG | A | 116 | 62.949 | 23.603 | 24.302 | 1.00 | 47.35 | A |
| ATOM | 360 | CD | ARG | A | 116 | 63.670 | 24.685 | 25.109 | 1.00 | 52.44 | A |
| ATOM | 361 | NE | ARG | A | 116 | 64.526 | 24.141 | 26.166 | 1.00 | 56.30 | A |
| ATOM | 362 | CZ | ARG | A | 116 | 64.142 | 23.920 | 27.423 | 1.00 | 57.97 | A |
| ATOM | 363 | NH1 | ARG | A | 116 | 62.899 | 24.199 | 27.808 | 1.00 | 58.89 | A |
| ATOM | 364 | NH2 | ARG | A | 116 | 65.006 | 23.420 | 28.300 | 1.00 | 56.55 | A |
| ATOM | 365 | C | ARG | A | 116 | 64.227 | 23.472 | 21.323 | 1.00 | 37.67 | A |
| ATOM | 366 | O | ARG | A | 116 | 63.474 | 24.246 | 20.735 | 1.00 | 36.66 | A |
| ATOM | 367 | N | HIS | A | 117 | 65.550 | 23.555 | 21.259 | 1.00 | 37.78 | A |
| ATOM | 368 | CA | HIS | A | 117 | 66.236 | 24.590 | 20.501 | 1.00 | 35.88 | A |
| ATOM | 369 | CB | HIS | A | 117 | 67.744 | 24.417 | 20.676 | 1.00 | 35.60 | A |
| ATOM | 370 | CG | HIS | A | 117 | 68.560 | 25.532 | 20.101 | 1.00 | 37.06 | A |
| ATOM | 371 | CD2 | HIS | A | 117 | 69.508 | 25.535 | 19.134 | 1.00 | 38.11 | A |
| ATOM | 372 | ND1 | HIS | A | 117 | 68.469 | 26.831 | 20.550 | 1.00 | 37.56 | A |
| ATOM | 373 | CE1 | HIS | A | 117 | 69.325 | 27.587 | 19.886 | 1.00 | 38.35 | A |
| ATOM | 374 | NE2 | HIS | A | 117 | 69.969 | 26.825 | 19.021 | 1.00 | 38.67 | A |
| ATOM | 375 | C | HIS | A | 117 | 65.859 | 24.529 | 19.024 | 1.00 | 34.83 | A |
| ATOM | 376 | O | HIS | A | 117 | 65.600 | 25.554 | 18.398 | 1.00 | 35.80 | A |
| ATOM | 377 | N | ILE | A | 118 | 65.827 | 23.321 | 18.474 | 1.00 | 33.01 | A |
| ATOM | 378 | CA | ILE | A | 118 | 65.483 | 23.122 | 17.071 | 1.00 | 32.12 | A |
| ATOM | 379 | CB | ILE | A | 118 | 65.575 | 21.629 | 16.692 | 1.00 | 33.37 | A |
| ATOM | 380 | CG2 | ILE | A | 118 | 64.968 | 21.398 | 15.312 | 1.00 | 33.44 | A |
| ATOM | 381 | CG1 | ILE | A | 118 | 67.032 | 21.168 | 16.732 | 1.00 | 33.47 | A |
| ATOM | 382 | CD1 | ILE | A | 118 | 67.195 | 19.685 | 16.479 | 1.00 | 35.01 | A |
| ATOM | 383 | C | ILE | A | 118 | 64.066 | 23.603 | 16.760 | 1.00 | 31.17 | A |
| ATOM | 384 | O | ILE | A | 118 | 63.838 | 24.295 | 15.774 | 1.00 | 29.39 | A |
| ATOM | 385 | N | ILE | A | 119 | 63.117 | 23.209 | 17.600 | 1.00 | 31.17 | A |
| ATOM | 386 | CA | ILE | A | 119 | 61.725 | 23.590 | 17.420 | 1.00 | 31.73 | A |
| ATOM | 387 | CB | ILE | A | 119 | 60.841 | 22.896 | 18.473 | 1.00 | 31.45 | A |
| ATOM | 388 | CG2 | ILE | A | 119 | 59.471 | 23.560 | 18.548 | 1.00 | 26.98 | A |
| ATOM | 389 | CG1 | ILE | A | 119 | 60.735 | 21.409 | 18.131 | 1.00 | 27.55 | A |
| ATOM | 390 | CD1 | ILE | A | 119 | 60.092 | 20.574 | 19.205 | 1.00 | 26.52 | A |
| ATOM | 391 | C | ILE | A | 119 | 61.549 | 25.100 | 17.519 | 1.00 | 33.53 | A |
| ATOM | 392 | O | ILE | A | 119 | 60.879 | 25.714 | 16.688 | 1.00 | 32.81 | A |
| ATOM | 393 | N | ALA | A | 120 | 62.165 | 25.691 | 18.535 | 1.00 | 34.30 | A |
| ATOM | 394 | CA | ALA | A | 120 | 62.078 | 27.125 | 18.749 | 1.00 | 34.63 | A |
| ATOM | 395 | CB | ALA | A | 120 | 62.811 | 27.506 | 20.029 | 1.00 | 35.03 | A |
| ATOM | 396 | C | ALA | A | 120 | 62.657 | 27.889 | 17.574 | 1.00 | 35.68 | A |
| ATOM | 397 | O | ALA | A | 120 | 62.141 | 28.938 | 17.195 | 1.00 | 36.85 | A |
| ATOM | 398 | N | GLU | A | 121 | 63.732 | 27.369 | 16.995 | 1.00 | 35.66 | A |
| ATOM | 399 | CA | GLU | A | 121 | 64.375 | 28.041 | 15.870 | 1.00 | 36.43 | A |
| ATOM | 400 | CB | GLU | A | 121 | 65.873 | 27.726 | 15.864 | 1.00 | 40.99 | A |
| ATOM | 401 | CG | GLU | A | 121 | 66.637 | 28.166 | 17.116 | 1.00 | 45.01 | A |
| ATOM | 402 | CD | GLU | A | 121 | 66.844 | 29.676 | 17.205 | 1.00 | 48.12 | A |
| ATOM | 403 | OE1 | GLU | A | 121 | 67.670 | 30.104 | 18.043 | 1.00 | 49.33 | A |
| ATOM | 404 | OE2 | GLU | A | 121 | 66.188 | 30.433 | 16.451 | 1.00 | 49.20 | A |
| ATOM | 405 | C | GLU | A | 121 | 63.780 | 27.670 | 14.512 | 1.00 | 34.98 | A |
| ATOM | 406 | O | GLU | A | 121 | 64.282 | 28.105 | 13.480 | 1.00 | 34.50 | A |
| ATOM | 407 | N | ASN | A | 122 | 62.716 | 26.869 | 14.517 | 1.00 | 33.68 | A |
| ATOM | 408 | CA | ASN | A | 122 | 62.060 | 26.434 | 13.286 | 1.00 | 32.99 | A |
| ATOM | 409 | CB | ASN | A | 122 | 61.492 | 27.639 | 12.530 | 1.00 | 35.58 | A |
| ATOM | 410 | CG | ASN | A | 122 | 60.424 | 28.373 | 13.315 | 1.00 | 38.88 | A |
| ATOM | 411 | OD1 | ASN | A | 122 | 60.717 | 29.154 | 14.227 | 1.00 | 38.30 | A |
| ATOM | 412 | ND2 | ASN | A | 122 | 59.170 | 28.116 | 12.970 | 1.00 | 38.77 | A |
| ATOM | 413 | C | ASN | A | 122 | 63.024 | 25.679 | 12.367 | 1.00 | 31.80 | A |
| ATOM | 414 | O | ASN | A | 122 | 63.095 | 25.957 | 11.172 | 1.00 | 30.78 | A |
| ATOM | 415 | N | LYS | A | 123 | 63.754 | 24.716 | 12.919 | 1.00 | 29.93 | A |
| ATOM | 416 | CA | LYS | A | 123 | 64.717 | 23.966 | 12.120 | 1.00 | 29.87 | A |
| ATOM | 417 | CB | LYS | A | 123 | 66.100 | 24.016 | 12.775 | 1.00 | 30.75 | A |
| ATOM | 418 | CG | LYS | A | 123 | 66.669 | 25.406 | 12.895 | 1.00 | 33.94 | A |
| ATOM | 419 | CD | LYS | A | 123 | 66.810 | 26.049 | 11.527 | 1.00 | 37.59 | A |
| ATOM | 420 | CE | LYS | A | 123 | 67.354 | 27.466 | 11.646 | 1.00 | 39.07 | A |
| ATOM | 421 | NZ | LYS | A | 123 | 67.460 | 28.121 | 10.310 | 1.00 | 41.71 | A |

-continued

| ATOM | 422 | C | LYS | A | 123 | 64.337 | 22.514 | 11.880 | 1.00 | 27.38 | A |
| ATOM | 423 | O | LYS | A | 123 | 65.139 | 21.745 | 11.355 | 1.00 | 24.93 | A |
| ATOM | 424 | N | VAL | A | 124 | 63.124 | 22.132 | 12.260 | 1.00 | 24.22 | A |
| ATOM | 425 | CA | VAL | A | 124 | 62.716 | 20.756 | 12.062 | 1.00 | 22.73 | A |
| ATOM | 426 | CB | VAL | A | 124 | 61.235 | 20.559 | 12.416 | 1.00 | 22.36 | A |
| ATOM | 427 | CG1 | VAL | A | 124 | 60.794 | 19.146 | 12.064 | 1.00 | 22.84 | A |
| ATOM | 428 | CG2 | VAL | A | 124 | 61.031 | 20.802 | 13.905 | 1.00 | 20.63 | A |
| ATOM | 429 | C | VAL | A | 124 | 62.981 | 20.320 | 10.623 | 1.00 | 23.50 | A |
| ATOM | 430 | O | VAL | A | 124 | 63.633 | 19.297 | 10.385 | 1.00 | 21.86 | A |
| ATOM | 431 | N | PRO | A | 125 | 62.512 | 21.109 | 9.639 | 1.00 | 23.91 | A |
| ATOM | 432 | CD | PRO | A | 125 | 61.806 | 22.399 | 9.725 | 1.00 | 24.52 | A |
| ATOM | 433 | CA | PRO | A | 125 | 62.737 | 20.736 | 8.239 | 1.00 | 24.57 | A |
| ATOM | 434 | CB | PRO | A | 125 | 62.147 | 21.914 | 7.464 | 1.00 | 23.69 | A |
| ATOM | 435 | CG | PRO | A | 125 | 61.098 | 22.450 | 8.400 | 1.00 | 25.18 | A |
| ATOM | 436 | C | PRO | A | 125 | 64.217 | 20.520 | 7.923 | 1.00 | 23.84 | A |
| ATOM | 437 | O | PRO | A | 125 | 64.568 | 19.618 | 7.172 | 1.00 | 22.92 | A |
| ATOM | 438 | N | TYR | A | 126 | 65.073 | 21.353 | 8.501 | 1.00 | 24.86 | A |
| ATOM | 439 | CA | TYR | A | 126 | 66.511 | 21.259 | 8.274 | 1.00 | 28.10 | A |
| ATOM | 440 | CB | TYR | A | 126 | 67.202 | 22.494 | 8.859 | 1.00 | 32.76 | A |
| ATOM | 441 | CG | TYR | A | 126 | 66.802 | 23.766 | 8.146 | 1.00 | 39.46 | A |
| ATOM | 442 | CD1 | TYR | A | 126 | 67.466 | 24.179 | 6.987 | 1.00 | 42.04 | A |
| ATOM | 443 | CE1 | TYR | A | 126 | 67.063 | 25.322 | 6.292 | 1.00 | 43.67 | A |
| ATOM | 444 | CD2 | TYR | A | 126 | 65.722 | 24.531 | 8.597 | 1.00 | 42.16 | A |
| ATOM | 445 | CE2 | TYR | A | 126 | 65.309 | 25.673 | 7.909 | 1.00 | 43.70 | A |
| ATOM | 446 | CZ | TYR | A | 126 | 65.983 | 26.062 | 6.758 | 1.00 | 44.51 | A |
| ATOM | 447 | OH | TYR | A | 126 | 65.570 | 27.183 | 6.068 | 1.00 | 45.30 | A |
| ATOM | 448 | C | TYR | A | 126 | 67.115 | 19.984 | 8.852 | 1.00 | 26.14 | A |
| ATOM | 449 | O | TYR | A | 126 | 67.768 | 19.225 | 8.141 | 1.00 | 26.15 | A |
| ATOM | 450 | N | VAL | A | 127 | 66.891 | 19.756 | 10.141 | 1.00 | 24.35 | A |
| ATOM | 451 | CA | VAL | A | 127 | 67.396 | 18.568 | 10.819 | 1.00 | 24.93 | A |
| ATOM | 452 | CB | VAL | A | 127 | 66.956 | 18.568 | 12.296 | 1.00 | 24.24 | A |
| ATOM | 453 | CG1 | VAL | A | 127 | 67.444 | 17.316 | 12.997 | 1.00 | 23.36 | A |
| ATOM | 454 | CG2 | VAL | A | 127 | 67.492 | 19.809 | 12.979 | 1.00 | 21.11 | A |
| ATOM | 455 | C | VAL | A | 127 | 66.894 | 17.290 | 10.130 | 1.00 | 25.81 | A |
| ATOM | 456 | O | VAL | A | 127 | 67.655 | 16.351 | 9.903 | 1.00 | 25.79 | A |
| ATOM | 457 | N | THR | A | 128 | 65.612 | 17.273 | 9.793 | 1.00 | 25.57 | A |
| ATOM | 458 | CA | THR | A | 128 | 64.996 | 16.136 | 9.114 | 1.00 | 26.36 | A |
| ATOM | 459 | CB | THR | A | 128 | 63.486 | 16.384 | 8.908 | 1.00 | 25.21 | A |
| ATOM | 460 | OG1 | THR | A | 128 | 62.827 | 16.390 | 10.181 | 1.00 | 29.29 | A |
| ATOM | 461 | CG2 | THR | A | 128 | 62.883 | 15.317 | 8.043 | 1.00 | 25.73 | A |
| ATOM | 462 | C | THR | A | 128 | 65.640 | 15.898 | 7.748 | 1.00 | 26.97 | A |
| ATOM | 463 | O | THR | A | 128 | 65.929 | 14.760 | 7.366 | 1.00 | 25.68 | A |
| ATOM | 464 | N | ARG | A | 129 | 65.854 | 16.980 | 7.012 | 1.00 | 27.23 | A |
| ATOM | 465 | CA | ARG | A | 129 | 66.462 | 16.897 | 5.692 | 1.00 | 29.37 | A |
| ATOM | 466 | CB | ARG | A | 129 | 66.484 | 18.282 | 5.032 | 1.00 | 32.35 | A |
| ATOM | 467 | CG | ARG | A | 129 | 66.936 | 18.280 | 3.583 | 1.003 | 6.81 | A |
| ATOM | 468 | CD | ARG | A | 129 | 67.208 | 19.693 | 3.064 | 1.00 | 40.45 | A |
| ATOM | 469 | NE | ARG | A | 129 | 66.178 | 20.651 | 3.459 | 1.00 | 44.54 | A |
| ATOM | 470 | CZ | ARG | A | 129 | 64.874 | 20.474 | 3.268 | 1.00 | 48.21 | A |
| ATOM | 471 | NH1 | ARG | A | 129 | 64.431 | 19.366 | 2.681 | 1.00 | 50.01 | A |
| ATOM | 472 | NH2 | ARG | A | 129 | 64.008 | 21.403 | 3.668 | 1.00 | 47.79 | A |
| ATOM | 473 | C | ARG | A | 129 | 67.884 | 16.379 | 5.828 | 1.00 | 28.98 | A |
| ATOM | 474 | O | ARG | A | 129 | 68.316 | 15.532 | 5.054 | 1.00 | 28.26 | A |
| ATOM | 475 | N | GLU | A | 130 | 68.606 | 16.895 | 6.822 | 1.00 | 29.28 | A |
| ATOM | 476 | CA | GLU | A | 130 | 69.988 | 16.490 | 7.057 | 1.00 | 30.58 | A |
| ATOM | 477 | CB | GLU | A | 130 | 70.556 | 17.203 | 8.287 | 1.00 | 34.18 | A |
| ATOM | 478 | CG | GLU | A | 130 | 72.078 | 17.220 | 8.344 | 1.00 | 38.81 | A |
| ATOM | 479 | CD | GLU | A | 130 | 72.633 | 17.650 | 9.702 | 1.00 | 41.66 | A |
| ATOM | 480 | OE1 | GLU | A | 130 | 71.946 | 18.408 | 10.427 | 1.00 | 42.36 | A |
| ATOM | 481 | OE2 | GLU | A | 130 | 73.771 | 17.236 | 10.035 | 1.00 | 42.31 | A |
| ATOM | 482 | C | GLU | A | 130 | 70.063 | 14.984 | 7.273 | 1.00 | 30.12 | A |
| ATOM | 483 | O | GLU | A | 130 | 70.861 | 14.298 | 6.638 | 1.00 | 29.62 | A |
| ATOM | 484 | N | ARG | A | 131 | 69.228 | 14.474 | 8.173 | 1.00 | 29.21 | A |
| ATOM | 485 | CA | ARG | A | 131 | 69.215 | 13.046 | 8.458 | 1.00 | 30.93 | A |
| ATOM | 486 | CB | ARG | A | 131 | 68.241 | 12.724 | 9.601 | 1.00 | 32.88 | A |
| ATOM | 487 | CG | ARG | A | 131 | 68.035 | 11.223 | 9.795 | 1.00 | 36.48 | A |
| ATOM | 488 | CD | ARG | A | 131 | 67.069 | 10.885 | 10.922 | 1.00 | 41.14 | A |
| ATOM | 489 | NE | ARG | A | 131 | 66.859 | 9.440 | 11.012 | 1.00 | 45.98 | A |
| ATOM | 490 | CZ | ARG | A | 131 | 66.167 | 8.833 | 11.974 | 1.00 | 48.77 | A |
| ATOM | 491 | NH1 | ARG | A | 131 | 65.605 | 9.546 | 12.946 | 1.00 | 48.39 | A |
| ATOM | 492 | NH2 | ARG | A | 131 | 66.045 | 7.509 | 11.968 | 1.00 | 48.16 | A |
| ATOM | 493 | C | ARG | A | 131 | 68.836 | 12.226 | 7.224 | 1.00 | 29.97 | A |
| ATOM | 494 | O | ARG | A | 131 | 69.398 | 11.157 | 6.986 | 1.00 | 28.24 | A |
| ATOM | 495 | N | ASP | A | 132 | 67.889 | 12.725 | 6.437 | 1.00 | 28.56 | A |
| ATOM | 496 | CA | ASP | A | 132 | 67.460 | 11.996 | 5.251 | 1.00 | 29.18 | A |
| ATOM | 497 | CB | ASP | A | 132 | 66.160 | 12.583 | 4.710 | 1.00 | 31.39 | A |
| ATOM | 498 | CG | ASP | A | 132 | 65.005 | 12.409 | 5.682 | 1.00 | 38.76 | A |
| ATOM | 499 | OD1 | ASP | A | 132 | 64.892 | 11.319 | 6.283 | 1.00 | 40.09 | A |
| ATOM | 500 | OD2 | ASP | A | 132 | 64.206 | 13.355 | 5.846 | 1.00 | 44.19 | A |

-continued

| | | | | | | | | | | | |
|---|---|---|---|---|---|---|---|---|---|---|---|
| ATOM | 501 | C | ASP | A | 132 | 68.510 | 11.936 | 4.150 | 1.00 | 27.67 | A |
| ATOM | 502 | O | ASP | A | 132 | 68.688 | 10.896 | 3.522 | 1.00 | 27.56 | A |
| ATOM | 503 | N | VAL | A | 133 | 69.200 | 13.044 | 3.909 | 1.00 | 26.09 | A |
| ATOM | 504 | CA | VAL | A | 133 | 70.232 | 13.063 | 2.886 | 1.00 | 25.09 | A |
| ATOM | 505 | CB | VAL | A | 133 | 70.859 | 14.459 | 2.742 | 1.00 | 25.26 | A |
| ATOM | 506 | CG1 | VAL | A | 133 | 72.157 | 14.369 | 1.961 | 1.00 | 24.32 | A |
| ATOM | 507 | CG2 | VAL | A | 133 | 69.890 | 15.390 | 2.029 | 1.00 | 24.76 | A |
| ATOM | 508 | C | VAL | A | 133 | 71.320 | 12.076 | 3.266 | 1.00 | 25.33 | A |
| ATOM | 509 | O | VAL | A | 133 | 71.742 | 11.270 | 2.445 | 1.00 | 23.59 | A |
| ATOM | 510 | N | MET | A | 134 | 71.764 | 12.138 | 4.520 | 1.00 | 26.01 | A |
| ATOM | 511 | CA | MET | A | 134 | 72.812 | 11.243 | 4.995 | 1.00 | 27.63 | A |
| ATOM | 512 | CB | MET | A | 134 | 73.210 | 11.576 | 6.436 | 1.00 | 25.11 | A |
| ATOM | 513 | CG | MET | A | 134 | 74.056 | 12.834 | 6.539 | 1.00 | 27.52 | A |
| ATOM | 514 | SD | MET | A | 134 | 74.875 | 13.035 | 8.132 | 1.00 | 28.28 | A |
| ATOM | 515 | CE | MET | A | 134 | 73.545 | 13.741 | 9.104 | 1.00 | 28.66 | A |
| ATOM | 516 | C | MET | A | 134 | 72.431 | 9.779 | 4.901 | 1.00 | 28.59 | A |
| ATOM | 517 | O | MET | A | 134 | 73.276 | 8.938 | 4.599 | 1.00 | 31.12 | A |
| ATOM | 518 | N | SER | A | 135 | 71.168 | 9.467 | 5.165 | 1.00 | 29.14 | A |
| ATOM | 519 | CA | SER | A | 135 | 70.709 | 8.082 | 5.090 | 1.00 | 31.93 | A |
| ATOM | 520 | CB | SER | A | 135 | 69.261 | 7.966 | 5.558 | 1.00 | 32.44 | A |
| ATOM | 521 | OG | SER | A | 135 | 69.112 | 8.470 | 6.868 | 1.00 | 40.09 | A |
| ATOM | 522 | C | SER | A | 135 | 70.786 | 7.557 | 3.668 | 1.00 | 31.36 | A |
| ATOM | 523 | O | SER | A | 135 | 71.010 | 6.374 | 3.454 | 1.00 | 32.23 | A |
| ATOM | 524 | N | ARG | A | 136 | 70.597 | 8.448 | 2.701 | 1.00 | 31.66 | A |
| ATOM | 525 | CA | ARG | A | 136 | 70.602 | 8.075 | 1.293 | 1.00 | 32.53 | A |
| ATOM | 526 | CB | ARG | A | 136 | 69.798 | 9.095 | 0.491 | 1.00 | 33.51 | A |
| ATOM | 527 | CG | ARG | A | 136 | 68.361 | 9.274 | 0.962 | 1.00 | 38.41 | A |
| ATOM | 528 | CD | ARG | A | 136 | 67.676 | 10.352 | 0.137 | 1.00 | 40.27 | A |
| ATOM | 529 | NE | ARG | A | 136 | 67.850 | 10.090 | −1.288 | 1.00 | 42.75 | A |
| ATOM | 530 | CZ | ARG | A | 136 | 67.560 | 10.953 | −2.253 | 1.00 | 44.58 | A |
| ATOM | 531 | NH1 | ARG | A | 136 | 67.071 | 12.151 | −1.950 | 1.00 | 45.74 | A |
| ATOM | 532 | NH2 | ARG | A | 136 | 67.771 | 10.621 | −3.522 | 1.00 | 43.43 | A |
| ATOM | 533 | C | ARG | A | 136 | 71.985 | 7.946 | 0.670 | 1.00 | 32.09 | A |
| ATOM | 534 | O | ARG | A | 136 | 72.113 | 7.513 | −0.474 | 1.00 | 32.48 | A |
| ATOM | 535 | N | LEU | A | 137 | 73.019 | 8.329 | 1.406 | 1.00 | 30.72 | A |
| ATOM | 536 | CA | LEU | A | 137 | 74.371 | 8.253 | 0.873 | 1.00 | 30.30 | A |
| ATOM | 537 | CB | LEU | A | 137 | 75.167 | 9.508 | 1.262 | 1.00 | 29.84 | A |
| ATOM | 538 | CG | LEU | A | 137 | 74.541 | 10.843 | 0.831 | 1.00 | 30.25 | A |
| ATOM | 539 | CD1 | LEU | A | 137 | 75.488 | 11.963 | 1.154 | 1.00 | 29.16 | A |
| ATOM | 540 | CD2 | LEU | A | 137 | 74.230 | 10.835 | −0.656 | 1.00 | 29.68 | A |
| ATOM | 541 | C | LEU | A | 137 | 75.083 | 7.006 | 1.369 | 1.00 | 29.52 | A |
| ATOM | 542 | O | LEU | A | 137 | 75.033 | 6.684 | 2.553 | 1.00 | 31.12 | A |
| ATOM | 543 | N | ASP | A | 138 | 75.745 | 6.310 | 0.453 | 1.00 | 27.02 | A |
| ATOM | 544 | CA | ASP | A | 138 | 76.467 | 5.087 | 0.773 | 1.00 | 25.70 | A |
| ATOM | 545 | CB | ASP | A | 138 | 75.556 | 3.887 | 0.492 | 1.00 | 29.85 | A |
| ATOM | 546 | CG | ASP | A | 138 | 76.198 | 2.567 | 0.858 | 1.00 | 33.94 | A |
| ATOM | 547 | OD1 | ASP | A | 138 | 76.815 | 2.486 | 1.949 | 1.00 | 34.64 | A |
| ATOM | 548 | OD2 | ASP | A | 138 | 76.074 | 1.610 | 0.058 | 1.00 | 35.28 | A |
| ATOM | 549 | C | ASP | A | 138 | 77.699 | 5.062 | −0.127 | 1.00 | 24.23 | A |
| ATOM | 550 | O | ASP | A | 138 | 77.765 | 4.300 | −1.091 | 1.00 | 24.33 | A |
| ATOM | 551 | N | HIS | A | 139 | 78.672 | 5.904 | 0.209 | 1.00 | 20.89 | A |
| ATOM | 552 | CA | HIS | A | 139 | 79.888 | 6.069 | −0.577 | 1.00 | 19.30 | A |
| ATOM | 553 | CB | HIS | A | 139 | 79.681 | 7.243 | −1.553 | 1.00 | 17.75 | A |
| ATOM | 554 | CG | HIS | A | 139 | 80.774 | 7.410 | −2.564 | 1.00 | 17.45 | A |
| ATOM | 555 | CD2 | HIS | A | 139 | 80.794 | 7.179 | −3.897 | 1.00 | 16.63 | A |
| ATOM | 556 | ND1 | HIS | A | 139 | 82.034 | 7.862 | −2.235 | 1.00 | 20.01 | A |
| ATOM | 557 | CE1 | HIS | A | 139 | 82.784 | 7.901 | −3.322 | 1.00 | 16.89 | A |
| ATOM | 558 | NE2 | HIS | A | 139 | 82.054 | 7.491 | −4.344 | 1.00 | 16.94 | A |
| ATOM | 559 | C | HIS | A | 139 | 81.066 | 6.347 | 0.352 | 1.00 | 19.25 | A |
| ATOM | 560 | O | HIS | A | 139 | 80.914 | 6.990 | 1.388 | 1.00 | 21.17 | A |
| ATOM | 561 | N | PRO | A | 140 | 82.265 | 5.881 | −0.021 | 1.00 | 17.84 | A |
| ATOM | 562 | CD | PRO | A | 140 | 82.575 | 5.120 | −1.243 | 1.00 | 16.07 | A |
| ATOM | 563 | CA | PRO | A | 140 | 83.467 | 6.079 | 0.789 | 1.00 | 18.04 | A |
| ATOM | 564 | CB | PRO | A | 140 | 84.518 | 5.240 | 0.055 | 1.00 | 18.70 | A |
| ATOM | 565 | CG | PRO | A | 140 | 84.061 | 5.315 | −1.365 | 1.00 | 19.17 | A |
| ATOM | 566 | C | PRO | A | 140 | 83.919 | 7.523 | 1.014 | 1.00 | 19.75 | A |
| ATOM | 567 | O | PRO | A | 140 | 84.686 | 7.793 | 1.930 | 1.00 | 21.01 | A |
| ATOM | 568 | N | PHE | A | 141 | 83.460 | 8.457 | 0.192 | 1.00 | 20.21 | A |
| ATOM | 569 | CA | PHE | A | 141 | 83.869 | 9.837 | 0.389 | 1.00 | 20.05 | A |
| ATOM | 570 | CB | PHE | A | 141 | 84.149 | 10.496 | −0.964 | 1.00 | 20.20 | A |
| ATOM | 571 | CG | PHE | A | 141 | 85.333 | 9.909 | 1.686 | 1.00 | 20.95 | A |
| ATOM | 572 | CD1 | PHE | A | 141 | 86.362 | 9.297 | −0.975 | 1.00 | 21.45 | A |
| ATOM | 573 | CD2 | PHE | A | 141 | 85.430 | 9.983 | −3.071 | 1.00 | 20.27 | A |
| ATOM | 574 | CE1 | PHE | A | 141 | 87.476 | 8.765 | −1.635 | 1.00 | 22.05 | A |
| ATOM | 575 | CE2 | PHE | A | 141 | 86.541 | 9.456 | −3.743 | 1.00 | 20.58 | A |
| ATOM | 576 | CZ | PHE | A | 141 | 87.562 | 8.848 | −3.027 | 1.00 | 20.58 | A |
| ATOM | 577 | C | PHE | A | 141 | 82.881 | 10.679 | 1.210 | 1.00 | 18.71 | A |
| ATOM | 578 | O | PHE | A | 141 | 83.015 | 11.897 | 1.300 | 1.00 | 19.78 | A |
| ATOM | 579 | N | PHE | A | 142 | 81.903 | 10.027 | 1.823 | 1.00 | 18.61 | A |

-continued

| | | | | | | | | | | |
|---|---|---|---|---|---|---|---|---|---|---|
| ATOM | 580 | CA | PHE | A | 142 | 80.915 | 10.738 | 2.639 | 1.00 | 19.11 | A |
| ATOM | 581 | CB | PHE | A | 142 | 79.543 | 10.709 | 1.966 | 1.00 | 17.36 | A |
| ATOM | 582 | CG | PHE | A | 142 | 79.458 | 11.565 | 0.750 | 1.00 | 19.19 | A |
| ATOM | 583 | CD1 | PHE | A | 142 | 79.258 | 12.936 | 0.863 | 1.00 | 19.44 | A |
| ATOM | 584 | CD2 | PHE | A | 142 | 79.649 | 11.016 | −0.511 | 1.00 | 18.39 | A |
| ATOM | 585 | CE1 | PHE | A | 142 | 79.254 | 13.759 | −0.268 | 1.00 | 20.66 | A |
| ATOM | 586 | CE2 | PHE | A | 142 | 79.648 | 11.824 | −1.644 | 1.00 | 20.80 | A |
| ATOM | 587 | CZ | PHE | A | 142 | 79.451 | 13.203 | −1.523 | 1.00 | 18.95 | A |
| ATOM | 588 | C | PHE | A | 142 | 80.787 | 10.132 | 4.023 | 1.00 | 18.98 | A |
| ATOM | 589 | O | PHE | A | 142 | 80.735 | 8.918 | 4.168 | 1.00 | 18.39 | A |
| ATOM | 590 | N | VAL | A | 143 | 80.736 | 10.983 | 5.041 | 1.00 | 20.79 | A |
| ATOM | 591 | CA | VAL | A | 143 | 80.578 | 10.499 | 6.401 | 1.00 | 20.94 | A |
| ATOM | 592 | CB | VAL | A | 143 | 80.456 | 11.670 | 7.404 | 1.00 | 21.95 | A |
| ATOM | 593 | CG1 | VAL | A | 143 | 80.081 | 11.145 | 8.783 | 1.00 | 21.30 | A |
| ATOM | 594 | CG2 | VAL | A | 143 | 81.781 | 12.433 | 7.473 | 1.00 | 19.28 | A |
| ATOM | 595 | C | VAL | A | 143 | 79.299 | 9.683 | 6.396 | 1.00 | 21.12 | A |
| ATOM | 596 | O | VAL | A | 143 | 78.280 | 10.124 | 5.895 | 1.00 | 23.63 | A |
| ATOM | 597 | N | LYS | A | 144 | 79.367 | 8.481 | 6.940 | 1.00 | 23.64 | A |
| ATOM | 598 | CA | LYS | A | 144 | 78.221 | 7.582 | 6.990 | 1.00 | 24.47 | A |
| ATOM | 599 | CB | LYS | A | 144 | 78.714 | 6.131 | 6.869 | 1.00 | 25.53 | A |
| ATOM | 600 | CG | LYS | A | 144 | 77.635 | 5.061 | 6.997 | 1.00 | 32.25 | A |
| ATOM | 601 | CD | LYS | A | 144 | 78.240 | 3.660 | 6.870 | 1.00 | 36.07 | A |
| ATOM | 602 | CE | LYS | A | 144 | 77.187 | 2.563 | 7.033 | 1.00 | 38.50 | A |
| ATOM | 603 | NZ | LYS | A | 144 | 77.791 | 1.186 | 7.051 | 1.00 | 41.46 | A |
| ATOM | 604 | C | LYS | A | 144 | 77.418 | 7.744 | 8.275 | 1.00 | 22.60 | A |
| ATOM | 605 | O | LYS | A | 144 | 77.973 | 8.019 | 9.335 | 1.00 | 23.18 | A |
| ATOM | 606 | N | LEU | A | 145 | 76.104 | 7.583 | 8.170 | 1.00 | 21.59 | A |
| ATOM | 607 | CA | LEU | A | 145 | 75.224 | 7.661 | 9.327 | 1.00 | 21.42 | A |
| ATOM | 608 | CB | LEU | | 145 | 73.918 | 8.372 | 8.967 | 0.50 | 21.21 | AC1 |
| ATOM | 609 | CG | LEU | | 145 | 72.843 | 8.332 | 10.060 | 0.50 | 21.32 | AC1 |
| ATOM | 610 | CD1 | LEU | | 145 | 73.356 | 9.036 | 11.309 | 0.50 | 19.59 | AC1 |
| ATOM | 611 | CD2 | LEU | | 145 | 71.569 | 8.994 | 9.559 | 0.50 | 21.45 | AC1 |
| ATOM | 612 | C | LEU | A | 145 | 74.919 | 6.215 | 9.733 | 1.00 | 21.84 | A |
| ATOM | 613 | O | LEU | A | 145 | 74.283 | 5.471 | 8.977 | 1.00 | 19.24 | A |
| ATOM | 614 | N | TYR | A | 146 | 75.363 | 5.816 | 10.921 | 1.00 | 19.77 | A |
| ATOM | 615 | CA | TYR | A | 146 | 75.143 | 4.444 | 11.368 | 1.00 | 19.92 | A |
| ATOM | 616 | CB | TYR | A | 146 | 76.326 | 3.944 | 12.188 | 1.00 | 18.05 | A |
| ATOM | 617 | CG | TYR | A | 146 | 77.601 | 3.803 | 11.415 | 1.00 | 17.64 | A |
| ATOM | 618 | CD1 | TYR | A | 146 | 78.435 | 4.909 | 11.203 | 1.00 | 18.26 | A |
| ATOM | 619 | CE1 | TYR | A | 146 | 79.638 | 4.782 | 10.516 | 1.00 | 17.33 | A |
| ATOM | 620 | CD2 | TYR | A | 146 | 78.000 | 2.560 | 10.910 | 1.00 | 15.57 | A |
| ATOM | 621 | CE2 | TYR | A | 146 | 79.208 | 2.419 | 10.215 | 1.00 | 17.53 | A |
| ATOM | 622 | CZ | TYR | A | 146 | 80.022 | 3.535 | 10.026 | 1.00 | 18.78 | A |
| ATOM | 623 | OH | TYR | A | 146 | 81.224 | 3.413 | 9.369 | 1.00 | 19.47 | A |
| ATOM | 624 | C | TYR | A | 146 | 73.884 | 4.194 | 12.170 | 1.00 | 20.60 | A |
| ATOM | 625 | O | TYR | A | 146 | 73.331 | 3.100 | 12.108 | 1.00 | 21.73 | A |
| ATOM | 626 | N | PHE | A | 147 | 73.431 | 5.192 | 12.921 | 1.00 | 20.92 | A |
| ATOM | 627 | CA | PHE | A | 147 | 72.239 | 5.025 | 13.745 | 1.00 | 22.59 | A |
| ATOM | 628 | CB | PHE | A | 147 | 72.538 | 4.063 | 14.917 | 1.00 | 22.24 | A |
| ATOM | 629 | CG | PHE | A | 147 | 73.708 | 4.488 | 15.770 | 1.00 | 21.88 | A |
| ATOM | 630 | CD1 | PHE | A | 147 | 73.607 | 5.578 | 16.625 | 1.00 | 21.93 | A |
| ATOM | 631 | CD2 | PHE | A | 147 | 74.936 | 3.843 | 15.657 | 1.00 | 21.57 | A |
| ATOM | 632 | CE1 | PHE | A | 147 | 74.715 | 6.025 | 17.352 | 1.00 | 25.21 | A |
| ATOM | 633 | CE2 | PHE | A | 147 | 76.051 | 4.279 | 16.377 | 1.00 | 21.30 | A |
| ATOM | 634 | CZ | PHE | A | 147 | 75.942 | 5.371 | 17.224 | 1.00 | 24.23 | A |
| ATOM | 635 | C | PHE | A | 147 | 71.737 | 6.343 | 14.308 | 1.00 | 23.77 | A |
| ATOM | 636 | O | PHE | A | 147 | 72.448 | 7.352 | 14.307 | 1.00 | 22.91 | A |
| ATOM | 637 | N | THR | A | 148 | 70.501 | 6.324 | 14.791 | 1.00 | 25.15 | A |
| ATOM | 638 | CA | THR | A | 148 | 69.908 | 7.503 | 15.403 | 1.00 | 25.99 | A |
| ATOM | 639 | CB | THR | A | 148 | 68.953 | 8.251 | 14.466 | 1.00 | 27.00 | A |
| ATOM | 640 | OG1 | THR | A | 148 | 67.850 | 7.400 | 14.148 | 1.00 | 27.79 | A |
| ATOM | 641 | CG2 | THR | A | 148 | 69.660 | 8.661 | 13.193 | 1.00 | 26.35 | A |
| ATOM | 642 | C | THR | A | 148 | 69.080 | 7.055 | 16.580 | 1.00 | 26.23 | A |
| ATOM | 643 | O | THR | A | 148 | 68.591 | 5.930 | 16.620 | 1.00 | 26.46 | A |
| ATOM | 644 | N | PHE | A | 149 | 68.942 | 7.943 | 17.550 | 1.00 | 25.72 | A |
| ATOM | 645 | CA | PHE | A | 149 | 68.133 | 7.662 | 18.706 | 1.00 | 25.10 | A |
| ATOM | 646 | CB | PHE | A | 149 | 68.789 | 6.593 | 19.602 | 1.00 | 23.02 | A |
| ATOM | 647 | CG | PHE | A | 149 | 70.088 | 7.011 | 20.231 | 1.00 | 22.26 | A |
| ATOM | 648 | CD1 | PHE | A | 149 | 70.105 | 7.794 | 21.373 | 1.00 | 20.98 | A |
| ATOM | 649 | CD2 | PHE | A | 149 | 71.302 | 6.587 | 19.694 | 1.00 | 21.51 | A |
| ATOM | 650 | CE1 | PHE | A | 149 | 71.312 | 8.151 | 21.976 | 1.00 | 22.36 | A |
| ATOM | 651 | CE2 | PHE | A | 149 | 72.511 | 6.939 | 20.288 | 1.00 | 21.06 | A |
| ATOM | 652 | CZ | PHE | A | 149 | 72.519 | 7.722 | 21.430 | 1.00 | 19.46 | A |
| ATOM | 653 | C | PHE | A | 149 | 67.931 | 8.974 | 19.427 | 1.00 | 27.05 | A |
| ATOM | 654 | O | PHE | A | 149 | 68.565 | 9.974 | 19.096 | 1.00 | 27.03 | A |
| ATOM | 655 | N | GLN | A | 150 | 67.024 | 8.984 | 20.391 | 1.00 | 29.18 | A |
| ATOM | 656 | CA | GLN | A | 150 | 66.757 | 10.198 | 21.133 | 1.00 | 31.94 | A |
| ATOM | 657 | CB | GLN | A | 150 | 65.697 | 11.035 | 20.409 | 1.00 | 32.80 | A |
| ATOM | 658 | CG | GLN | A | 150 | 64.385 | 10.302 | 20.153 | 1.00 | 34.22 | A |

-continued

| | | | | | | | | | | |
|---|---|---|---|---|---|---|---|---|---|---|
| ATOM | 659 | CD | GLN | A | 150 | 63.340 | 11.169 | 19.459 | 1.00 | 36.88 | A |
| ATOM | 660 | OE1 | GLN | A | 150 | 62.630 | 11.959 | 20.098 | 1.00 | 37.60 | A |
| ATOM | 661 | NE2 | GLN | A | 150 | 63.248 | 11.033 | 18.141 | 1.00 | 35.03 | A |
| ATOM | 662 | C | GLN | A | 150 | 66.269 | 9.890 | 22.531 | 1.00 | 32.97 | A |
| ATOM | 663 | O | GLN | A | 150 | 65.857 | 8.768 | 22.825 | 1.00 | 33.19 | A |
| ATOM | 664 | N | ASP | A | 151 | 66.355 | 10.890 | 23.398 | 1.00 | 34.27 | A |
| ATOM | 665 | CA | ASP | A | 151 | 65.847 | 10.771 | 24.753 | 1.00 | 35.77 | A |
| ATOM | 666 | CB | ASP | A | 151 | 66.957 | 10.933 | 25.796 | 1.00 | 35.66 | A |
| ATOM | 667 | CG | ASP | A | 151 | 67.760 | 12.194 | 25.604 | 1.00 | 38.11 | A |
| ATOM | 668 | OD1 | ASP | A | 151 | 67.172 | 13.216 | 25.195 | 1.00 | 39.31 | A |
| ATOM | 669 | OD2 | ASP | A | 151 | 68.982 | 12.167 | 25.879 | 1.00 | 41.03 | A |
| ATOM | 670 | C | ASP | A | 151 | 64.823 | 11.904 | 24.838 | 1.00 | 36.64 | A |
| ATOM | 671 | O | ASP | A | 151 | 64.401 | 12.428 | 23.803 | 1.00 | 36.42 | A |
| ATOM | 672 | N | ASP | A | 152 | 64.427 | 12.301 | 26.041 | 1.00 | 38.18 | A |
| ATOM | 673 | CA | ASP | A | 152 | 63.427 | 13.357 | 26.171 | 1.00 | 39.81 | A |
| ATOM | 674 | CB | ASP | A | 152 | 63.022 | 13.534 | 27.637 | 1.00 | 44.46 | A |
| ATOM | 675 | CG | ASP | A | 152 | 62.291 | 12.324 | 28.186 | 1.00 | 50.02 | A |
| ATOM | 676 | OD1 | ASP | A | 152 | 61.313 | 11.876 | 27.541 | 1.00 | 52.36 | A |
| ATOM | 677 | OD2 | ASP | A | 152 | 62.689 | 11.822 | 29.263 | 1.00 | 52.75 | A |
| ATOM | 678 | C | ASP | A | 152 | 63.822 | 14.709 | 25.594 | 1.00 | 37.45 | A |
| ATOM | 679 | O | ASP | A | 152 | 62.988 | 15.408 | 25.026 | 1.00 | 36.81 | A |
| ATOM | 680 | N | GLU | A | 153 | 65.091 | 15.077 | 25.708 | 1.00 | 35.46 | A |
| ATOM | 681 | CA | GLU | A | 153 | 65.501 | 16.378 | 25.211 | 1.00 | 33.50 | A |
| ATOM | 682 | CB | GLU | A | 153 | 66.132 | 17.174 | 26.354 | 1.00 | 36.16 | A |
| ATOM | 683 | CG | GLU | A | 153 | 65.389 | 17.065 | 27.687 | 1.00 | 37.72 | A |
| ATOM | 684 | CD | GLU | A | 153 | 65.657 | 15.753 | 28.402 | 0.00 | 37.23 | A |
| ATOM | 685 | OE1 | GLU | A | 153 | 65.063 | 15.530 | 29.479 | 0.00 | 37.39 | A |
| ATOM | 686 | OE2 | GLU | A | 153 | 66.464 | 14.947 | 27.893 | 0.00 | 37.39 | A |
| ATOM | 687 | C | GLU | A | 153 | 66.432 | 16.425 | 23.995 | 1.00 | 31.79 | A |
| ATOM | 688 | O | GLU | A | 153 | 66.498 | 17.451 | 23.323 | 1.00 | 30.80 | A |
| ATOM | 689 | N | LYS | A | 154 | 67.131 | 15.334 | 23.691 | 1.00 | 30.35 | A |
| ATOM | 690 | CA | LYS | A | 154 | 68.069 | 15.357 | 22.569 | 1.00 | 28.14 | A |
| ATOM | 691 | CB | LYS | A | 154 | 69.505 | 15.358 | 23.099 | 1.00 | 27.32 | A |
| ATOM | 692 | CG | LYS | A | 154 | 69.853 | 16.503 | 24.026 | 1.00 | 29.91 | A |
| ATOM | 693 | CD | LYS | A | 154 | 71.234 | 16.302 | 24.648 | 1.00 | 30.14 | A |
| ATOM | 694 | CE | LYS | A | 154 | 71.606 | 17.450 | 25.592 | 1.00 | 32.52 | A |
| ATOM | 695 | NZ | LYS | A | 154 | 72.780 | 17.121 | 26.469 | 1.00 | 31.90 | A |
| ATOM | 696 | C | LYS | A | 154 | 67.967 | 14.261 | 21.515 | 1.00 | 26.36 | A |
| ATOM | 697 | O | LYS | A | 154 | 67.517 | 13.145 | 21.781 | 1.00 | 23.71 | A |
| ATOM | 698 | N | LEU | A | 155 | 68.413 | 14.610 | 20.311 | 1.00 | 24.76 | A |
| ATOM | 699 | CA | LEU | A | 155 | 68.462 | 13.691 | 19.178 | 1.00 | 23.29 | A |
| ATOM | 700 | CB | LEU | A | 155 | 68.012 | 14.382 | 17.891 | 1.00 | 22.72 | A |
| ATOM | 701 | CG | LEU | A | 155 | 66.588 | 14.916 | 17.739 | 1.00 | 24.25 | A |
| ATOM | 702 | CD1 | LEU | A | 155 | 66.441 | 15.489 | 16.329 | 1.00 | 24.62 | A |
| ATOM | 703 | CD2 | LEU | A | 155 | 65.576 | 13.798 | 17.965 | 1.00 | 23.10 | A |
| ATOM | 704 | C | LEU | A | 155 | 69.939 | 13.325 | 19.022 | 1.00 | 21.93 | A |
| ATOM | 705 | O | LEU | A | 155 | 70.812 | 14.167 | 19.233 | 1.00 | 20.17 | A |
| ATOM | 706 | N | TYR | A | 156 | 70.227 | 12.088 | 18.647 | 1.00 | 19.72 | A |
| ATOM | 707 | CA | TYR | A | 156 | 71.617 | 11.693 | 18.462 | 1.00 | 20.11 | A |
| ATOM | 708 | CB | TYR | A | 156 | 72.061 | 10.703 | 19.540 | 1.00 | 20.01 | A |
| ATOM | 709 | CG | TYR | A | 156 | 71.885 | 11.172 | 20.963 | 1.00 | 20.98 | A |
| ATOM | 710 | CD1 | TYR | A | 156 | 70.619 | 11.313 | 21.520 | 1.00 | 22.18 | A |
| ATOM | 711 | CE1 | TYR | A | 156 | 70.457 | 11.724 | 22.850 | 1.00 | 25.21 | A |
| ATOM | 712 | CD2 | TYR | A | 156 | 72.991 | 11.449 | 21.762 | 1.00 | 21.38 | A |
| ATOM | 713 | CE2 | TYR | A | 156 | 72.843 | 11.859 | 23.086 | 1.00 | 25.12 | A |
| ATOM | 714 | CZ | TYR | A | 156 | 71.576 | 11.995 | 23.622 | 1.00 | 24.83 | A |
| ATOM | 715 | OH | TYR | A | 156 | 71.431 | 12.410 | 24.923 | 1.00 | 25.97 | A |
| ATOM | 716 | C | TYR | A | 156 | 71.792 | 11.033 | 17.108 | 1.00 | 20.02 | A |
| ATOM | 717 | O | TYR | A | 156 | 70.959 | 10.231 | 16.704 | 1.00 | 22.19 | A |
| ATOM | 718 | N | PHE | A | 157 | 72.860 | 11.385 | 16.399 | 1.00 | 19.17 | A |
| ATOM | 719 | CA | PHE | A | 157 | 73.140 | 10.769 | 15.114 | 1.00 | 18.65 | A |
| ATOM | 720 | CB | PHE | A | 157 | 73.071 | 11.780 | 13.969 | 1.00 | 21.02 | A |
| ATOM | 721 | CG | PHE | A | 157 | 71.719 | 12.411 | 13.791 | 1.00 | 25.64 | A |
| ATOM | 722 | CD1 | PHE | A | 157 | 70.558 | 11.724 | 14.135 | 1.00 | 27.84 | A |
| ATOM | 723 | CD2 | PHE | A | 157 | 71.603 | 13.695 | 13.267 | 1.00 | 27.19 | A |
| ATOM | 724 | CE1 | PHE | A | 157 | 69.301 | 12.310 | 13.964 | 1.00 | 28.87 | A |
| ATOM | 725 | CE2 | PHE | A | 157 | 70.350 | 14.288 | 13.091 | 1.00 | 28.27 | A |
| ATOM | 726 | CZ | PHE | A | 157 | 69.200 | 13.595 | 13.442 | 1.00 | 26.64 | A |
| ATOM | 727 | C | PHE | A | 157 | 74.543 | 10.212 | 15.204 | 1.00 | 19.60 | A |
| ATOM | 728 | O | PHE | A | 157 | 75.489 | 10.952 | 15.467 | 1.00 | 19.26 | A |
| ATOM | 729 | N | GLY | A | 158 | 74.668 | 8.902 | 15.010 | 1.00 | 19.26 | A |
| ATOM | 730 | CA | GLY | A | 158 | 75.972 | 8.265 | 15.063 | 1.00 | 18.63 | A |
| ATOM | 731 | C | GLY | A | 158 | 76.615 | 8.309 | 13.693 | 1.00 | 16.84 | A |
| ATOM | 732 | O | GLY | A | 158 | 76.160 | 7.646 | 12.772 | 1.00 | 15.29 | A |
| ATOM | 733 | N | LEU | A | 159 | 77.677 | 9.096 | 13.567 | 1.00 | 18.10 | A |
| ATOM | 734 | CA | LEU | A | 159 | 78.386 | 9.263 | 12.302 | 1.00 | 17.32 | A |
| ATOM | 735 | CB | LEU | A | 159 | 78.502 | 10.753 | 11.984 | 1.00 | 16.80 | A |
| ATOM | 736 | CG | LEU | A | 159 | 77.161 | 11.485 | 12.068 | 1.00 | 18.21 | A |
| ATOM | 737 | CD1 | LEU | A | 159 | 77.376 | 12.992 | 12.058 | 1.00 | 15.34 | A |

-continued

| ATOM | 738 | CD2 | LEU | A | 159 | 76.280 | 11.036 | 10.906 | 1.00 | 14.27 | A |
|------|-----|-----|-----|---|-----|--------|--------|--------|------|-------|---|
| ATOM | 739 | C | LEU | A | 159 | 79.780 | 8.665 | 12.375 | 1.00 | 18.27 | A |
| ATOM | 740 | O | LEU | A | 159 | 80.338 | 8.518 | 13.465 | 1.00 | 18.92 | A |
| ATOM | 741 | N | SER | A | 160 | 80.343 | 8.320 | 11.220 | 1.00 | 16.88 | A |
| ATOM | 742 | CA | SER | A | 160 | 81.691 | 7.770 | 11.194 | 1.00 | 19.02 | A |
| ATOM | 743 | CB | SER | A | 160 | 82.086 | 7.362 | 9.771 | 1.00 | 20.02 | A |
| ATOM | 744 | OG | SER | A | 160 | 81.866 | 8.421 | 8.864 | 1.00 | 25.88 | A |
| ATOM | 745 | C | SER | A | 160 | 82.655 | 8.831 | 11.724 | 1.00 | 18.34 | A |
| ATOM | 746 | O | SER | A | 160 | 82.413 | 10.032 | 11.588 | 1.00 | 17.84 | A |
| ATOM | 747 | N | TYR | A | 161 | 83.743 | 8.384 | 12.335 | 1.00 | 17.11 | A |
| ATOM | 748 | CA | TYR | A | 161 | 84.723 | 9.300 | 12.901 | 1.00 | 19.21 | A |
| ATOM | 749 | CB | TYR | A | 161 | 85.146 | 8.802 | 14.293 | 1.00 | 19.37 | A |
| ATOM | 750 | CG | TYR | A | 161 | 86.269 | 9.582 | 14.944 | 1.00 | 22.52 | A |
| ATOM | 751 | CD1 | TYR | A | 161 | 86.276 | 10.978 | 14.929 | 1.00 | 21.17 | A |
| ATOM | 752 | CE1 | TYR | A | 161 | 87.283 | 11.703 | 15.559 | 1.00 | 18.10 | A |
| ATOM | 753 | CD2 | TYR | A | 161 | 87.313 | 8.923 | 15.612 | 1.00 | 21.92 | A |
| ATOM | 754 | CE2 | TYR | A | 161 | 88.330 | 9.647 | 16.252 | 1.00 | 20.10 | A |
| ATOM | 755 | CZ | TYR | A | 161 | 88.301 | 11.039 | 16.220 | 1.00 | 20.24 | A |
| ATOM | 756 | OH | TYR | A | 161 | 89.266 | 11.776 | 16.873 | 1.00 | 20.31 | A |
| ATOM | 757 | C | TYR | A | 161 | 85.934 | 9.459 | 11.997 | 1.00 | 20.13 | A |
| ATOM | 758 | O | TYR | A | 161 | 86.621 | 8.491 | 11.675 | 1.00 | 21.97 | A |
| ATOM | 759 | N | ALA | A | 162 | 86.182 | 10.686 | 11.571 | 1.00 | 19.13 | A |
| ATOM | 760 | CA | ALA | A | 162 | 87.320 | 10.969 | 10.717 | 1.00 | 20.60 | A |
| ATOM | 761 | CB | ALA | A | 162 | 86.907 | 11.919 | 9.592 | 1.00 | 21.18 | A |
| ATOM | 762 | C | ALA | A | 162 | 88.375 | 11.617 | 11.604 | 1.00 | 21.36 | A |
| ATOM | 763 | O | ALA | A | 162 | 88.391 | 12.835 | 11.752 | 1.00 | 20.74 | A |
| ATOM | 764 | N | LYS | A | 163 | 89.237 | 10.787 | 12.195 | 1.00 | 21.80 | A |
| ATOM | 765 | CA | LYS | A | 163 | 90.294 | 11.232 | 13.102 | 1.00 | 25.38 | A |
| ATOM | 766 | CB | LYS | A | 163 | 91.315 | 10.109 | 13.332 | 1.00 | 30.51 | A |
| ATOM | 767 | CG | LYS | A | 163 | 90.874 | 8.987 | 14.251 | 1.00 | 38.24 | A |
| ATOM | 768 | CD | LYS | A | 163 | 92.000 | 7.970 | 14.456 | 1.00 | 43.14 | A |
| ATOM | 769 | CE | LYS | A | 163 | 91.556 | 6.794 | 15.342 | 1.00 | 46.63 | A |
| ATOM | 770 | NZ | LYS | A | 163 | 91.252 | 7.200 | 16.752 | 1.00 | 47.21 | A |
| ATOM | 771 | C | LYS | A | 163 | 91.082 | 12.482 | 12.719 | 1.00 | 25.07 | A |
| ATOM | 772 | O | LYS | A | 163 | 91.276 | 13.373 | 13.541 | 1.00 | 25.50 | A |
| ATOM | 773 | N | ASN | A | 164 | 91.540 | 12.549 | 11.477 | 1.00 | 25.06 | A |
| ATOM | 774 | CA | ASN | A | 164 | 92.363 | 13.668 | 11.054 | 1.00 | 26.04 | A |
| ATOM | 775 | CB | ASN | A | 164 | 93.115 | 13.278 | 9.787 | 1.00 | 26.02 | A |
| ATOM | 776 | CG | ASN | A | 164 | 94.062 | 12.120 | 10.033 | 1.00 | 29.07 | A |
| ATOM | 777 | OD1 | ASN | A | 164 | 94.854 | 12.155 | 10.969 | 1.00 | 30.18 | A |
| ATOM | 778 | ND2 | ASN | A | 164 | 93.979 | 11.089 | 9.207 | 1.00 | 32.14 | A |
| ATOM | 779 | C | ASN | A | 164 | 91.725 | 15.040 | 10.915 | 1.00 | 25.35 | A |
| ATOM | 780 | O | ASN | A | 164 | 92.416 | 16.021 | 10.640 | 1.00 | 26.51 | A |
| ATOM | 781 | N | GLY | A | 165 | 90.419 | 15.122 | 11.116 | 1.00 | 23.92 | A |
| ATOM | 782 | CA | GLY | A | 165 | 89.761 | 16.413 | 11.043 | 1.00 | 24.35 | A |
| ATOM | 783 | C | GLY | A | 165 | 89.663 | 17.123 | 9.704 | 1.00 | 23.94 | A |
| ATOM | 784 | O | GLY | A | 165 | 89.632 | 16.501 | 8.643 | 1.00 | 25.49 | A |
| ATOM | 785 | N | GLU | A | 166 | 89.623 | 18.449 | 9.773 | 1.00 | 23.07 | A |
| ATOM | 786 | CA | GLU | A | 166 | 89.467 | 19.301 | 8.602 | 1.00 | 23.26 | A |
| ATOM | 787 | CB | GLU | A | 166 | 89.164 | 20.739 | 9.036 | 1.00 | 23.73 | A |
| ATOM | 788 | CG | GLU | A | 166 | 88.271 | 20.875 | 10.257 | 1.00 | 27.31 | A |
| ATOM | 789 | CD | GLU | A | 166 | 87.812 | 22.302 | 10.474 | 1.00 | 29.74 | A |
| ATOM | 790 | OE1 | GLU | A | 166 | 88.586 | 23.221 | 10.130 | 1.00 | 30.87 | A |
| ATOM | 791 | OE2 | GLU | A | 166 | 86.686 | 22.510 | 10.989 | 1.00 | 29.80 | A |
| ATOM | 792 | C | GLU | A | 166 | 90.612 | 19.354 | 7.602 | 1.00 | 24.47 | A |
| ATOM | 793 | O | GLU | A | 166 | 91.786 | 19.473 | 7.968 | 1.00 | 24.85 | A |
| ATOM | 794 | N | LEU | A | 167 | 90.251 | 19.287 | 6.328 | 1.00 | 23.47 | A |
| ATOM | 795 | CA | LEU | A | 167 | 91.228 | 19.393 | 5.262 | 1.00 | 24.00 | A |
| ATOM | 796 | CB | LEU | A | 167 | 90.528 | 19.369 | 3.901 | 1.00 | 22.48 | A |
| ATOM | 797 | CG | LEU | A | 167 | 91.373 | 19.759 | 2.679 | 1.00 | 23.87 | A |
| ATOM | 798 | CD1 | LEU | A | 167 | 92.583 | 18.846 | 2.563 | 1.00 | 20.03 | A |
| ATOM | 799 | CD2 | LEU | A | 167 | 90.516 | 19.680 | 1.418 | 1.00 | 22.08 | A |
| ATOM | 800 | C | LEU | A | 167 | 91.943 | 20.732 | 5.448 | 1.00 | 24.82 | A |
| ATOM | 801 | O | LEU | A | 167 | 93.138 | 20.858 | 5.165 | 1.00 | 24.59 | A |
| ATOM | 802 | N | LEU | A | 168 | 91.206 | 21.731 | 5.927 | 1.00 | 24.43 | A |
| ATOM | 803 | CA | LEU | A | 168 | 91.784 | 23.055 | 6.150 | 1.00 | 28.25 | A |
| ATOM | 804 | CB | LEU | A | 168 | 90.746 | 24.009 | 6.747 | 1.00 | 27.44 | A |
| ATOM | 805 | CG | LEU | A | 168 | 91.310 | 25.395 | 7.090 | 1.00 | 28.57 | A |
| ATOM | 806 | CD1 | LEU | A | 168 | 91.624 | 26.150 | 5.809 | 1.00 | 28.11 | A |
| ATOM | 807 | CD2 | LEU | A | 168 | 90.312 | 26.174 | 7.921 | 1.00 | 29.97 | A |
| ATOM | 808 | C | LEU | A | 168 | 92.999 | 23.014 | 7.074 | 1.00 | 28.43 | A |
| ATOM | 809 | O | LEU | A | 168 | 93.952 | 23.760 | 6.882 | 1.00 | 30.21 | A |
| ATOM | 810 | N | LYS | A | 169 | 92.958 | 22.152 | 8.081 | 1.00 | 30.23 | A |
| ATOM | 811 | CA | LYS | A | 169 | 94.072 | 22.050 | 9.008 | 1.00 | 33.52 | A |
| ATOM | 812 | CB | LYS | A | 169 | 93.821 | 20.955 | 10.046 | 1.00 | 35.45 | A |
| ATOM | 813 | CG | LYS | A | 169 | 94.972 | 20.784 | 11.033 | 1.00 | 40.43 | A |
| ATOM | 814 | CD | LYS | A | 169 | 94.808 | 19.562 | 11.943 | 1.00 | 41.43 | A |
| ATOM | 815 | CE | LYS | A | 169 | 95.047 | 18.261 | 11.186 | 1.00 | 42.67 | A |
| ATOM | 816 | NZ | LYS | A | 169 | 95.057 | 17.068 | 12.096 | 1.00 | 43.84 | A |

-continued

| ATOM | 817 | C | LYS | A | 169 | 95.329 | 21.718 | 8.228 | 1.00 | 34.58 | A |
|---|---|---|---|---|---|---|---|---|---|---|---|
| ATOM | 818 | O | LYS | A | 169 | 96.377 | 22.333 | 8.421 | 1.00 | 35.58 | A |
| ATOM | 819 | N | TYR | A | 170 | 95.219 | 20.739 | 7.339 | 1.00 | 34.55 | A |
| ATOM | 820 | CA | TYR | A | 170 | 96.357 | 20.328 | 6.539 | 1.00 | 35.07 | A |
| ATOM | 821 | CB | TYR | A | 170 | 96.018 | 19.047 | 5.790 | 1.00 | 35.72 | A |
| ATOM | 822 | CG | TYR | A | 170 | 96.050 | 17.869 | 6.716 | 1.00 | 37.48 | A |
| ATOM | 823 | CD1 | TYR | A | 170 | 97.256 | 17.250 | 7.040 | 1.00 | 39.42 | A |
| ATOM | 824 | CE1 | TYR | A | 170 | 97.313 | 16.230 | 7.987 | 1.00 | 40.93 | A |
| ATOM | 825 | CD2 | TYR | A | 170 | 94.895 | 17.435 | 7.355 | 1.00 | 38.83 | A |
| ATOM | 826 | CE2 | TYR | A | 170 | 94.937 | 16.417 | 8.303 | 1.00 | 41.76 | A |
| ATOM | 827 | CZ | TYR | A | 170 | 96.149 | 15.821 | 8.615 | 1.00 | 42.18 | A |
| ATOM | 828 | OH | TYR | A | 170 | 96.196 | 14.827 | 9.563 | 1.00 | 45.30 | A |
| ATOM | 829 | C | TYR | A | 170 | 96.823 | 21.404 | 5.585 | 1.00 | 35.67 | A |
| ATOM | 830 | O | TYR | A | 170 | 97.999 | 21.465 | 5.248 | 1.00 | 35.28 | A |
| ATOM | 831 | N | ILE | A | 171 | 95.904 | 22.260 | 5.154 | 1.00 | 36.78 | A |
| ATOM | 832 | CA | ILE | A | 171 | 96.272 | 23.333 | 4.252 | 1.00 | 38.95 | A |
| ATOM | 833 | CB | ILE | A | 171 | 95.032 | 24.048 | 3.682 | 1.00 | 39.15 | A |
| ATOM | 834 | CG2 | ILE | A | 171 | 95.452 | 25.329 | 2.960 | 1.00 | 38.11 | A |
| ATOM | 835 | CG1 | ILE | A | 171 | 94.296 | 23.113 | 2.718 | 1.00 | 37.57 | A |
| ATOM | 836 | CD1 | ILE | A | 171 | 93.041 | 23.712 | 2.116 | 1.00 | 37.48 | A |
| ATOM | 837 | C | ILE | A | 171 | 97.146 | 24.338 | 4.990 | 1.00 | 41.33 | A |
| ATOM | 838 | O | ILE | A | 171 | 98.173 | 24.765 | 4.466 | 1.00 | 42.36 | A |
| ATOM | 839 | N | ARG | A | 172 | 96.748 | 24.713 | 6.203 | 1.00 | 42.79 | A |
| ATOM | 840 | CA | ARG | A | 172 | 97.541 | 25.662 | 6.981 | 1.00 | 44.62 | A |
| ATOM | 841 | CB | ARG | A | 172 | 96.809 | 26.103 | 8.253 | 1.00 | 46.82 | A |
| ATOM | 842 | CG | ARG | A | 172 | 95.492 | 26.828 | 8.033 | 1.00 | 50.73 | A |
| ATOM | 843 | CD | ARG | A | 172 | 95.124 | 27.643 | 9.271 | 1.00 | 53.80 | A |
| ATOM | 844 | NE | ARG | A | 172 | 93.747 | 28.136 | 9.247 | 1.00 | 56.88 | A |
| ATOM | 845 | CZ | ARG | A | 172 | 93.183 | 28.766 | 8.218 | 1.00 | 57.65 | A |
| ATOM | 846 | NH1 | ARG | A | 172 | 93.873 | 28.989 | 7.104 | 1.00 | 57.71 | A |
| ATOM | 847 | NH2 | ARG | A | 172 | 91.923 | 29.176 | 8.305 | 1.00 | 56.95 | A |
| ATOM | 848 | C | ARG | A | 172 | 98.856 | 25.015 | 7.383 | 1.00 | 44.41 | A |
| ATOM | 849 | O | ARG | A | 172 | 99.927 | 25.587 | 7.186 | 1.00 | 45.16 | A |
| ATOM | 850 | N | LYS | A | 173 | 98.759 | 23.817 | 7.949 | 1.00 | 44.01 | A |
| ATOM | 851 | CA | LYS | A | 173 | 99.923 | 23.069 | 8.398 | 1.00 | 42.99 | A |
| ATOM | 852 | CB | LYS | A | 173 | 99.538 | 21.616 | 8.667 | 1.00 | 44.20 | A |
| ATOM | 853 | CG | LYS | A | 173 | 100.721 | 20.689 | 8.908 | 1.00 | 45.81 | A |
| ATOM | 854 | CD | LYS | A | 173 | 100.272 | 19.238 | 8.987 | 0.00 | 45.28 | A |
| ATOM | 855 | CE | LYS | A | 173 | 101.457 | 18.296 | 9.120 | 0.00 | 45.43 | A |
| ATOM | 856 | NZ | LYS | A | 173 | 101.028 | 16.870 | 9.146 | 0.00 | 45.35 | A |
| ATOM | 857 | C | LYS | A | 173 | 101.081 | 23.108 | 7.412 | 1.00 | 43.20 | A |
| ATOM | 858 | O | LYS | A | 173 | 102.220 | 23.366 | 7.805 | 1.00 | 43.49 | A |
| ATOM | 859 | N | ILE | A | 174 | 100.802 | 22.867 | 6.133 | 1.00 | 41.97 | A |
| ATOM | 860 | CA | ILE | A | 174 | 101.871 | 22.859 | 5.136 | 1.00 | 40.74 | A |
| ATOM | 861 | CB | ILE | A | 174 | 101.874 | 21.536 | 4.336 | 1.00 | 40.61 | A |
| ATOM | 862 | CG2 | ILE | A | 174 | 101.897 | 20.352 | 5.297 | 1.00 | 41.39 | A |
| ATOM | 863 | CG1 | ILE | A | 174 | 100.638 | 21.448 | 3.442 | 1.00 | 40.75 | A |
| ATOM | 864 | CD1 | ILE | A | 174 | 100.680 | 20.276 | 2.487 | 1.00 | 40.45 | A |
| ATOM | 865 | C | ILE | A | 174 | 101.882 | 24.024 | 4.149 | 1.00 | 39.97 | A |
| ATOM | 866 | O | ILE | A | 174 | 102.675 | 24.033 | 3.209 | 1.00 | 38.15 | A |
| ATOM | 867 | N | GLY | A | 175 | 101.007 | 25.004 | 4.359 | 1.00 | 40.09 | A |
| ATOM | 868 | CA | GLY | A | 175 | 100.969 | 26.156 | 3.473 | 1.00 | 39.94 | A |
| ATOM | 869 | C | GLY | A | 175 | 100.151 | 25.960 | 2.211 | 1.00 | 39.87 | A |
| ATOM | 870 | O | GLY | A | 175 | 99.152 | 26.646 | 2.005 | 1.00 | 40.53 | A |
| ATOM | 871 | N | SER | A | 176 | 100.586 | 25.043 | 1.354 | 1.00 | 39.28 | A |
| ATOM | 872 | CA | SER | A | 176 | 99.871 | 24.747 | 0.122 | 1.00 | 38.77 | A |
| ATOM | 873 | CB | SER | A | 176 | 100.169 | 25.804 | −0.950 | 1.00 | 39.84 | A |
| ATOM | 874 | OG | SER | A | 176 | 101.537 | 25.823 | −1.319 | 1.00 | 43.67 | A |
| ATOM | 875 | C | SER | A | 176 | 100.265 | 23.353 | −0.358 | 1.00 | 38.39 | A |
| ATOM | 876 | O | SER | A | 176 | 101.245 | 22.776 | 0.118 | 1.00 | 39.37 | A |
| ATOM | 877 | N | PHE | A | 177 | 99.491 | 22.811 | −1.289 | 1.00 | 35.85 | A |
| ATOM | 878 | CA | PHE | A | 177 | 99.732 | 21.472 | −1.810 | 1.00 | 32.81 | A |
| ATOM | 879 | CB | PHE | A | 177 | 98.401 | 20.770 | −2.095 | 1.00 | 32.30 | A |
| ATOM | 880 | CG | PHE | A | 177 | 97.645 | 20.344 | −0.867 | 1.00 | 31.20 | A |
| ATOM | 881 | CD1 | PHE | A | 177 | 97.806 | 21.005 | 0.348 | 1.00 | 29.02 | A |
| ATOM | 882 | CD2 | PHE | A | 177 | 96.735 | 19.293 | −0.939 | 1.00 | 30.11 | A |
| ATOM | 883 | CE1 | PHE | A | 177 | 97.076 | 20.628 | 1.468 | 1.00 | 27.07 | A |
| ATOM | 884 | CE2 | PHE | A | 177 | 95.998 | 18.910 | 0.181 | 1.00 | 29.70 | A |
| ATOM | 885 | CZ | PHE | A | 177 | 96.170 | 19.580 | 1.385 | 1.00 | 27.57 | A |
| ATOM | 886 | C | PHE | A | 177 | 100.535 | 21.485 | −3.093 | 1.00 | 33.02 | A |
| ATOM | 887 | O | PHE | A | 177 | 100.386 | 22.381 | −3.927 | 1.00 | 30.75 | A |
| ATOM | 888 | N | ASP | A | 178 | 101.379 | 20.471 | −3.252 | 1.00 | 33.87 | A |
| ATOM | 889 | CA | ASP | A | 178 | 102.184 | 20.329 | −4.454 | 1.00 | 33.45 | A |
| ATOM | 890 | CB | ASP | A | 178 | 103.269 | 19.275 | −4.244 | 1.00 | 35.60 | A |
| ATOM | 891 | CG | ASP | A | 178 | 102.693 | 17.932 | −3.855 | 1.00 | 40.22 | A |
| ATOM | 892 | OD1 | ASP | A | 178 | 101.840 | 17.412 | −4.612 | 1.00 | 42.64 | A |
| ATOM | 893 | OD2 | ASP | A | 178 | 103.079 | 17.398 | −2.793 | 1.00 | 43.32 | A |
| ATOM | 894 | C | ASP | A | 178 | 101.195 | 19.859 | −5.519 | 1.00 | 32.50 | A |
| ATOM | 895 | O | ASP | A | 178 | 99.999 | 19.723 | −5.245 | 1.00 | 30.51 | A |

-continued

| | | | | | | | | | | |
|---|---|---|---|---|---|---|---|---|---|---|
| ATOM | 896 | N | GLU | A | 179 | 101.684 | 19.584 | −6.720 | 1.00 | 31.46 | A |
| ATOM | 897 | CA | GLU | A | 179 | 100.790 | 19.160 | −7.779 | 1.00 | 32.00 | A |
| ATOM | 898 | CB | GLU | A | 179 | 101.480 | 19.291 | −9.138 | 1.00 | 33.70 | A |
| ATOM | 899 | CG | GLU | A | 179 | 100.666 | 18.711 | −10.284 | 1.00 | 38.81 | A |
| ATOM | 900 | CD | GLU | A | 179 | 101.129 | 19.195 | −11.646 | 1.00 | 42.71 | A |
| ATOM | 901 | OE1 | GLU | A | 179 | 102.358 | 19.338 | −11.844 | 1.00 | 43.96 | A |
| ATOM | 902 | OE2 | GLU | A | 179 | 100.261 | 19.422 | −12.523 | 1.00 | 44.44 | A |
| ATOM | 903 | C | GLU | A | 179 | 100.189 | 17.766 | 7.635 | 1.00 | 29.96 | A |
| ATOM | 904 | O | GLU | A | 179 | 99.023 | 17.564 | −7.965 | 1.00 | 27.38 | A |
| ATOM | 905 | N | THR | A | 180 | 100.959 | 16.803 | −7.141 | 1.00 | 30.09 | A |
| ATOM | 906 | CA | THR | A | 180 | 100.429 | 15.448 | −7.007 | 1.00 | 29.75 | A |
| ATOM | 907 | CB | THR | A | 180 | 101.583 | 14.416 | −6.738 | 1.00 | 30.62 | A |
| ATOM | 908 | OG1 | THR | A | 180 | 101.050 | 13.206 | −6.179 | 1.00 | 30.65 | A |
| ATOM | 909 | CG2 | THR | A | 180 | 102.615 | 14.991 | −5.802 | 1.00 | 32.90 | A |
| ATOM | 910 | C | THR | A | 180 | 99.331 | 15.372 | −5.935 | 1.00 | 29.43 | A |
| ATOM | 911 | O | THR | A | 180 | 98.312 | 14.710 | −6.130 | 1.00 | 27.52 | A |
| ATOM | 912 | N | CYS | A | 181 | 99.522 | 16.079 | −4.823 | 1.00 | 29.55 | A |
| ATOM | 913 | CA | CYS | A | 181 | 98.535 | 16.091 | −3.745 | 1.00 | 29.27 | A |
| ATOM | 914 | CB | CYS | A | 181 | 99.156 | 16.681 | −2.480 | 1.00 | 31.47 | A |
| ATOM | 915 | SG | CYS | A | 181 | 100.580 | 15.747 | −1.838 | 1.00 | 39.84 | A |
| ATOM | 916 | C | CYS | A | 181 | 97.271 | 16.879 | −4.126 | 1.00 | 28.16 | A |
| ATOM | 917 | O | CYS | A | 181 | 96.156 | 16.495 | −3.762 | 1.00 | 26.55 | A |
| ATOM | 918 | N | THR | A | 182 | 97.441 | 17.984 | −4.847 | 1.00 | 25.71 | A |
| ATOM | 919 | CA | THR | A | 182 | 96.293 | 18.784 | −5.268 | 1.00 | 24.22 | A |
| ATOM | 920 | CB | THR | A | 182 | 96.714 | 20.043 | −6.066 | 1.00 | 24.45 | A |
| ATOM | 921 | OG1 | THR | A | 182 | 97.515 | 20.901 | −5.241 | 1.00 | 22.57 | A |
| ATOM | 922 | CG2 | THR | A | 182 | 95.483 | 20.809 | −6.537 | 1.00 | 23.42 | A |
| ATOM | 923 | C | THR | A | 182 | 95.447 | 17.915 | −6.184 | 1.00 | 24.78 | A |
| ATOM | 924 | O | THR | A | 182 | 94.227 | 17.812 | −6.020 | 1.00 | 23.72 | A |
| ATOM | 925 | N | ARG | A | 183 | 96.109 | 17.283 | −7.149 | 1.00 | 23.96 | A |
| ATOM | 926 | CA | ARG | A | 183 | 95.422 | 16.419 | −8.096 | 1.00 | 25.38 | A |
| ATOM | 927 | CB | ARG | A | 183 | 96.416 | 15.782 | −9.073 | 1.00 | 24.74 | A |
| ATOM | 928 | CG | ARG | A | 183 | 95.740 | 14.821 | −10.044 | 1.00 | 27.88 | A |
| ATOM | 929 | CD | ARG | A | 183 | 96.704 | 14.244 | −11.070 | 1.00 | 30.56 | A |
| ATOM | 930 | NE | ARG | A | 183 | 97.260 | 15.300 | −11.904 | 1.00 | 34.63 | A |
| ATOM | 931 | CZ | ARG | A | 183 | 98.502 | 15.756 | −11.802 | 1.00 | 33.50 | A |
| ATOM | 932 | NH1 | ARG | A | 183 | 99.328 | 15.234 | −10.903 | 1.00 | 31.79 | A |
| ATOM | 933 | NH2 | ARG | A | 183 | 98.901 | 16.754 | −12.579 | 1.00 | 31.24 | A |
| ATOM | 934 | C | ARG | A | 183 | 94.648 | 15.318 | −7.386 | 1.00 | 24.24 | A |
| ATOM | 935 | O | ARG | A | 183 | 93.466 | 15.099 | −7.659 | 1.00 | 24.95 | A |
| ATOM | 936 | N | PHE | A | 184 | 95.319 | 14.628 | −6.473 | 1.00 | 23.84 | A |
| ATOM | 937 | CA | PHE | A | 184 | 94.689 | 13.541 | −5.742 | 1.00 | 23.63 | A |
| ATOM | 938 | CB | PHE | A | 184 | 95.662 | 12.941 | −4.730 | 1.00 | 25.29 | A |
| ATOM | 939 | CG | PHE | A | 184 | 95.086 | 11.787 | −3.961 | 1.00 | 28.53 | A |
| ATOM | 940 | CD1 | PHE | A | 184 | 94.958 | 10.531 | −4.556 | 1.00 | 30.34 | A |
| ATOM | 941 | CD2 | PHE | A | 184 | 94.620 | 11.964 | −2.663 | 1.00 | 28.04 | A |
| ATOM | 942 | CE1 | PHE | A | 184 | 94.370 | 9.465 | −3.871 | 1.00 | 29.64 | A |
| ATOM | 943 | CE2 | PHE | A | 184 | 94.030 | 10.908 | −1.969 | 1.00 | 30.28 | A |
| ATOM | 944 | CZ | PHE | A | 184 | 93.904 | 9.654 | −2.576 | 1.00 | 29.09 | A |
| ATOM | 945 | C | PHE | A | 184 | 93.431 | 13.977 | −5.003 | 1.00 | 23.55 | A |
| ATOM | 946 | O | PHE | A | 184 | 92.353 | 13.429 | −5.219 | 1.00 | 24.05 | A |
| ATOM | 947 | N | TYR | A | 185 | 93.568 | 14.961 | −4.124 | 1.00 | 22.27 | A |
| ATOM | 948 | CA | TYR | A | 185 | 92.429 | 15.408 | −3.344 | 1.00 | 21.69 | A |
| ATOM | 949 | CB | TYR | A | 185 | 92.925 | 16.295 | −2.200 | 1.00 | 22.66 | A |
| ATOM | 950 | CG | TYR | A | 185 | 93.539 | 15.447 | −1.097 | 1.00 | 25.54 | A |
| ATOM | 951 | CD1 | TYR | A | 185 | 92.738 | 14.614 | −0.314 | 1.00 | 26.51 | A |
| ATOM | 952 | CE1 | TYR | A | 185 | 93.290 | 13.738 | 0.620 | 1.00 | 27.53 | A |
| ATOM | 953 | CD2 | TYR | A | 185 | 94.924 | 15.391 | −0.908 | 1.00 | 28.66 | A |
| ATOM | 954 | CE2 | TYR | A | 185 | 95.496 | 14.514 | 0.032 | 1.00 | 29.09 | A |
| ATOM | 955 | CZ | TYR | A | 185 | 94.667 | 13.688 | 0.790 | 1.00 | 29.75 | A |
| ATOM | 956 | OH | TYR | A | 185 | 95.204 | 12.806 | 1.702 | 1.00 | 29.03 | A |
| ATOM | 957 | C | TYR | A | 185 | 91.316 | 16.058 | −4.167 | 1.00 | 21.02 | A |
| ATOM | 958 | O | TYR | A | 185 | 90.130 | 15.921 | −3.851 | 1.00 | 18.76 | A |
| ATOM | 959 | N | THR | A | 186 | 91.689 | 16.731 | −5.244 | 1.00 | 19.87 | A |
| ATOM | 960 | CA | THR | A | 186 | 90.690 | 17.337 | −6.102 | 1.00 | 18.89 | A |
| ATOM | 961 | CB | THR | A | 186 | 91.344 | 18.170 | −7.200 | 1.00 | 19.73 | A |
| ATOM | 962 | OG1 | THR | A | 186 | 92.115 | 19.218 | −6.603 | 1.00 | 19.38 | A |
| ATOM | 963 | CG2 | THR | A | 186 | 90.282 | 18.765 | −8.125 | 1.00 | 20.16 | A |
| ATOM | 964 | C | THR | A | 186 | 89.905 | 16.201 | −6.753 | 1.00 | 19.05 | A |
| ATOM | 965 | O | THR | A | 186 | 88.675 | 16.244 | −6.855 | 1.00 | 19.38 | A |
| ATOM | 966 | N | ALA | A | 187 | 90.627 | 15.180 | −7.200 | 1.00 | 18.33 | A |
| ATOM | 967 | CA | ALA | A | 187 | 89.984 | 14.043 | −7.841 | 1.00 | 18.09 | A |
| ATOM | 968 | CB | ALA | A | 187 | 91.024 | 13.035 | −8.276 | 1.00 | 19.99 | A |
| ATOM | 969 | C | ALA | A | 187 | 88.986 | 13.402 | −6.886 | 1.00 | 18.07 | A |
| ATOM | 970 | O | ALA | A | 187 | 87.873 | 13.055 | −7.291 | 1.00 | 18.54 | A |
| ATOM | 971 | N | GLU | A | 188 | 89.366 | 13.253 | −5.617 | 1.00 | 16.56 | A |
| ATOM | 972 | CA | GLU | A | 188 | 88.446 | 12.660 | −4.653 | 1.00 | 16.18 | A |
| ATOM | 973 | CB | GLU | A | 188 | 89.099 | 12.495 | −3.280 | 1.00 | 15.52 | A |
| ATOM | 974 | CG | GLU | A | 188 | 90.266 | 11.519 | −3.259 | 1.00 | 20.99 | A |

-continued

| ATOM | 975 | CD | GLU | A | 188 | 90.297 | 10.636 | −2.013 | 1.00 | 22.64 | A |
|---|---|---|---|---|---|---|---|---|---|---|---|
| ATOM | 976 | OE1 | GLU | A | 188 | 90.006 | 11.126 | −0.899 | 1.00 | 22.95 | A |
| ATOM | 977 | OE2 | GLU | A | 188 | 90.629 | 9.439 | −2.149 | 1.00 | 27.37 | A |
| ATOM | 978 | C | GLU | A | 188 | 87.189 | 13.508 | −4.518 | 1.00 | 15.81 | A |
| ATOM | 979 | O | GLU | A | 188 | 86.080 | 12.978 | −4.460 | 1.00 | 15.92 | A |
| ATOM | 980 | N | ILE | A | 189 | 87.364 | 14.825 | −4.483 | 1.00 | 16.14 | A |
| ATOM | 981 | CA | ILE | A | 189 | 86.235 | 15.733 | −4.346 | 1.00 | 16.66 | A |
| ATOM | 982 | CB | ILE | A | 189 | 86.698 | 17.179 | −4.083 | 1.00 | 16.57 | A |
| ATOM | 983 | CG2 | ILE | A | 189 | 85.485 | 18.098 | −3.958 | 1.00 | 14.92 | A |
| ATOM | 984 | CG1 | ILE | A | 189 | 87.502 | 17.235 | −2.784 | 1.00 | 16.19 | A |
| ATOM | 985 | CD1 | ILE | A | 189 | 88.202 | 18.559 | −2.547 | 1.00 | 16.78 | A |
| ATOM | 986 | C | ILE | A | 189 | 85.349 | 15.712 | −5.580 | 1.00 | 16.29 | A |
| ATOM | 987 | O | ILE | A | 189 | 84.123 | 15.667 | −5.471 | 1.00 | 15.80 | A |
| ATOM | 988 | N | VAL | A | 190 | 85.962 | 15.743 | −6.755 | 1.00 | 16.44 | A |
| ATOM | 989 | CA | VAL | A | 190 | 85.186 | 15.704 | −7.985 | 1.00 | 15.98 | A |
| ATOM | 990 | CB | VAL | A | 190 | 86.101 | 15.692 | −9.229 | 1.00 | 17.23 | A |
| ATOM | 991 | CG1 | VAL | A | 190 | 85.280 | 15.380 | −10.488 | 1.00 | 16.01 | A |
| ATOM | 992 | CG2 | VAL | A | 190 | 86.797 | 17.034 | −9.373 | 1.00 | 13.82 | A |
| ATOM | 993 | C | VAL | A | 190 | 84.351 | 14.433 | −7.979 | 1.00 | 16.29 | A |
| ATOM | 994 | O | VAL | A | 190 | 83.140 | 14.462 | −8.194 | 1.00 | 15.64 | A |
| ATOM | 995 | N | SER | A | 191 | 85.011 | 13.312 | −7.723 | 1.00 | 18.94 | A |
| ATOM | 996 | CA | SER | A | 191 | 84.337 | 12.015 | −7.692 | 1.00 | 18.50 | A |
| ATOM | 997 | CB | SER | A | 191 | 85.357 | 10.914 | −7.427 | 1.00 | 19.04 | A |
| ATOM | 998 | OG | SER | A | 191 | 84.712 | 9.680 | −7.206 | 1.00 | 23.87 | A |
| ATOM | 999 | C | SER | A | 191 | 83.233 | 11.961 | −6.642 | 1.00 | 16.85 | A |
| ATOM | 1000 | O | SER | A | 191 | 82.227 | 11.281 | −6.818 | 1.00 | 18.11 | A |
| ATOM | 1001 | N | ALA | A | 192 | 83.419 | 12.671 | −5.540 | 1.00 | 17.37 | A |
| ATOM | 1002 | CA | ALA | A | 192 | 82.395 | 12.687 | −4.501 | 1.00 | 17.10 | A |
| ATOM | 1003 | CB | ALA | A | 192 | 82.947 | 13.302 | −3.222 | 1.00 | 17.08 | A |
| ATOM | 1004 | C | ALA | A | 192 | 81.218 | 13.511 | −5.020 | 1.00 | 18.24 | A |
| ATOM | 1005 | O | ALA | A | 192 | 80.055 | 13.162 | −4.798 | 1.00 | 18.91 | A |
| ATOM | 1006 | N | LEU | A | 193 | 81.524 | 14.597 | −5.725 | 1.00 | 16.53 | A |
| ATOM | 1007 | CA | LEU | A | 193 | 80.483 | 15.453 | −6.270 | 1.00 | 17.25 | A |
| ATOM | 1008 | CB | LEU | A | 193 | 81.091 | 16.750 | −6.826 | 1.00 | 17.70 | A |
| ATOM | 1009 | CG | LEU | A | 193 | 81.537 | 17.738 | −5.732 | 1.00 | 22.88 | A |
| ATOM | 1010 | CD1 | LEU | A | 193 | 82.094 | 19.018 | −6.348 | 1.00 | 22.13 | A |
| ATOM | 1011 | CD2 | LEU | A | 193 | 80.345 | 18.057 | −4.839 | 1.00 | 20.04 | A |
| ATOM | 1012 | C | LEU | A | 193 | 79.664 | 14.737 | −7.343 | 1.00 | 17.26 | A |
| ATOM | 1013 | O | LEU | A | 193 | 78.442 | 14.893 | −7.402 | 1.00 | 15.43 | A |
| ATOM | 1014 | N | GLU | A | 194 | 80.330 | 13.962 | −8.195 | 1.00 | 16.22 | A |
| ATOM | 1015 | CA | GLU | A | 194 | 79.612 | 13.232 | −9.225 | 1.00 | 19.22 | A |
| ATOM | 1016 | CB | GLU | A | 194 | 80.564 | 12.405 | −10.086 | 1.00 | 20.77 | A |
| ATOM | 1017 | CG | GLU | A | 194 | 79.828 | 11.403 | −10.978 | 1.00 | 26.27 | A |
| ATOM | 1018 | CD | GLU | A | 194 | 80.756 | 10.667 | −11.934 | 1.00 | 29.43 | A |
| ATOM | 1019 | OE1 | GLU | A | 194 | 81.840 | 10.222 | −11.489 | 1.00 | 28.21 | A |
| ATOM | 1020 | OE2 | GLU | A | 194 | 80.392 | 10.532 | −13.127 | 1.00 | 31.66 | A |
| ATOM | 1021 | C | GLU | A | 194 | 78.599 | 12.303 | −8.566 | 1.00 | 19.71 | A |
| ATOM | 1022 | O | GLU | A | 194 | 77.466 | 12.159 | −9.027 | 1.00 | 18.40 | A |
| ATOM | 1023 | N | TYR | A | 195 | 79.012 | 11.672 | −7.479 | 1.00 | 19.22 | A |
| ATOM | 1024 | CA | TYR | A | 195 | 78.116 | 10.773 | −6.781 | 1.00 | 19.69 | A |
| ATOM | 1025 | CB | TYR | A | 195 | 78.867 | 10.041 | −5.667 | 1.00 | 21.39 | A |
| ATOM | 1026 | CG | TYR | A | 195 | 77.975 | 9.143 | −4.847 | 1.00 | 22.55 | A |
| ATOM | 1027 | CD1 | TYR | A | 195 | 77.596 | 7.881 | −5.316 | 1.00 | 23.14 | A |
| ATOM | 1028 | CE1 | TYR | A | 195 | 76.743 | 7.065 | −4.577 | 1.00 | 22.98 | A |
| ATOM | 1029 | CD2 | TYR | A | 195 | 77.479 | 9.564 | −3.618 | 1.00 | 21.58 | A |
| ATOM | 1030 | CE2 | TYR | A | 195 | 76.625 | 8.755 | −2.872 | 1.00 | 23.50 | A |
| ATOM | 1031 | CZ | TYR | A | 195 | 76.263 | 7.512 | −3.358 | 1.00 | 23.18 | A |
| ATOM | 1032 | OH | TYR | A | 195 | 75.413 | 6.732 | −2.632 | 1.00 | 24.19 | A |
| ATOM | 1033 | C | TYR | A | 195 | 76.939 | 11.546 | −6.172 | 1.00 | 18.80 | A |
| ATOM | 1034 | O | TYR | A | 195 | 75.782 | 11.164 | −6.337 | 1.00 | 19.89 | A |
| ATOM | 1035 | N | LEU | A | 196 | 77.242 | 12.629 | −5.469 | 1.00 | 15.26 | A |
| ATOM | 1036 | CA | LEU | A | 196 | 76.210 | 13.430 | −4.813 | 1.00 | 16.52 | A |
| ATOM | 1037 | CB | LEU | A | 196 | 76.855 | 14.586 | −4.038 | 1.00 | 15.67 | A |
| ATOM | 1038 | CG | LEU | A | 196 | 75.923 | 15.401 | −3.131 | 1.00 | 19.13 | A |
| ATOM | 1039 | CD1 | LEU | A | 196 | 75.555 | 14.571 | −1.903 | 1.00 | 18.42 | A |
| ATOM | 1040 | CD2 | LEU | A | 196 | 76.604 | 16.681 | −2.689 | 1.00 | 18.50 | A |
| ATOM | 1041 | C | LEU | A | 196 | 75.209 | 13.993 | −5.814 | 1.00 | 18.12 | A |
| ATOM | 1042 | O | LEU | A | 196 | 73.990 | 13.892 | −5.637 | 1.00 | 16.25 | A |
| ATOM | 1043 | N | HIS | A | 197 | 75.732 | 14.592 | −6.875 | 1.00 | 17.99 | A |
| ATOM | 1044 | CA | HIS | A | 197 | 74.873 | 15.171 | −7.878 | 1.00 | 20.69 | A |
| ATOM | 1045 | CB | HIS | A | 197 | 75.715 | 16.004 | −8.832 | 1.00 | 19.71 | A |
| ATOM | 1046 | CG | HIS | A | 197 | 76.292 | 17.224 | −8.190 | 1.00 | 19.55 | A |
| ATOM | 1047 | CD2 | HIS | A | 197 | 76.069 | 17.777 | −6.973 | 1.00 | 18.32 | A |
| ATOM | 1048 | ND1 | HIS | A | 197 | 77.172 | 18.063 | −8.837 | 1.00 | 20.26 | A |
| ATOM | 1049 | CE1 | HIS | A | 197 | 77.463 | 19.084 | −8.049 | 1.00 | 20.73 | A |
| ATOM | 1050 | NE2 | HIS | A | 197 | 76.806 | 18.935 | −6.913 | 1.00 | 19.92 | A |
| ATOM | 1051 | C | HIS | A | 197 | 74.091 | 14.093 | −8.609 | 1.00 | 22.80 | A |
| ATOM | 1052 | O | HIS | A | 197 | 72.974 | 14.328 | −9.068 | 1.00 | 21.91 | A |
| ATOM | 1053 | N | GLY | A | 198 | 74.672 | 12.903 | −8.697 | 1.00 | 23.17 | A |

-continued

| ATOM | 1054 | CA | GLY | A | 198 | 73.990 | 11.815 | −9.366 | 1.00 | 26.22 | A |
| --- | --- | --- | --- | --- | --- | --- | --- | --- | --- | --- | --- |
| ATOM | 1055 | C | GLY | A | 198 | 72.718 | 11.436 | −8.631 | 1.00 | 27.16 | A |
| ATOM | 1056 | O | GLY | A | 198 | 71.837 | 10.787 | −9.185 | 1.00 | 27.89 | A |
| ATOM | 1057 | N | LYS | A | 199 | 72.623 | 11.831 | −7.369 | 1.00 | 27.84 | A |
| ATOM | 1058 | CA | LYS | A | 199 | 71.429 | 11.532 | −6.587 | 1.00 | 28.20 | A |
| ATOM | 1059 | CB | LYS | A | 199 | 71.827 | 10.952 | −5.227 | 1.00 | 29.35 | A |
| ATOM | 1060 | CG | LYS | A | 199 | 72.278 | 9.502 | −5.321 | 1.00 | 32.74 | A |
| ATOM | 1061 | CD | LYS | A | 199 | 72.737 | 8.944 | −3.990 | 1.00 | 38.22 | A |
| ATOM | 1062 | CE | LYS | A | 199 | 72.600 | 7.424 | −3.965 | 1.00 | 41.17 | A |
| ATOM | 1063 | NZ | LYS | A | 199 | 73.173 | 6.779 | −5.185 | 1.00 | 44.70 | A |
| ATOM | 1064 | C | LYS | A | 199 | 70.542 | 12.765 | −6.419 | 1.00 | 26.97 | A |
| ATOM | 1065 | O | LYS | A | 199 | 69.678 | 12.807 | −5.551 | 1.00 | 28.27 | A |
| ATOM | 1066 | N | GLY | A | 200 | 70.759 | 13.762 | −7.269 | 1.00 | 25.62 | A |
| ATOM | 1067 | CA | GLY | A | 200 | 69.963 | 14.972 | −7.222 | 1.00 | 24.75 | A |
| ATOM | 1068 | C | GLY | A | 200 | 70.070 | 15.713 | −5.908 | 1.00 | 25.82 | A |
| ATOM | 1069 | O | GLY | A | 200 | 69.080 | 16.241 | −5.401 | 1.00 | 26.10 | A |
| ATOM | 1070 | N | ILE | A | 201 | 71.275 | 15.759 | −5.353 | 1.00 | 25.31 | A |
| ATOM | 1071 | CA | ILE | A | 201 | 71.490 | 16.440 | −4.089 | 1.00 | 26.11 | A |
| ATOM | 1072 | CB | ILE | A | 201 | 71.886 | 15.438 | −2.983 | 1.00 | 27.58 | A |
| ATOM | 1073 | CG2 | ILE | A | 201 | 72.242 | 16.175 | −1.704 | 1.00 | 27.99 | A |
| ATOM | 1074 | CG1 | ILE | A | 201 | 70.725 | 14.480 | −2.719 | 1.00 | 27.89 | A |
| ATOM | 1075 | CD1 | ILE | A | 201 | 71.068 | 13.366 | −1.746 | 1.00 | 30.62 | A |
| ATOM | 1076 | C | ILE | A | 201 | 72.576 | 17.489 | −4.233 | 1.00 | 25.92 | A |
| ATOM | 1077 | O | ILE | A | 201 | 73.599 | 17.269 | −4.887 | 1.00 | 25.94 | A |
| ATOM | 1078 | N | ILE | A | 202 | 72.337 | 18.640 | −3.627 | 1.00 | 25.04 | A |
| ATOM | 1079 | CA | ILE | A | 202 | 73.289 | 19.733 | −3.680 | 1.00 | 26.57 | A |
| ATOM | 1080 | CB | ILE | A | 202 | 72.640 | 20.990 | −4.286 | 1.00 | 27.69 | A |
| ATOM | 1081 | CG2 | ILE | A | 202 | 73.695 | 22.068 | −4.516 | 1.00 | 30.47 | A |
| ATOM | 1082 | CG1 | ILE | A | 202 | 71.992 | 20.639 | −5.625 | 1.00 | 30.89 | A |
| ATOM | 1083 | CD1 | ILE | A | 202 | 71.083 | 21.736 | −6.178 | 1.00 | 31.79 | A |
| ATOM | 1084 | C | ILE | A | 202 | 73.742 | 20.032 | −2.252 | 1.00 | 26.14 | A |
| ATOM | 1085 | O | ILE | A | 202 | 72.912 | 20.201 | −1.351 | 1.00 | 24.75 | A |
| ATOM | 1086 | N | HIS | A | 203 | 75.054 | 20.075 | −2.042 | 1.00 | 25.17 | A |
| ATOM | 1087 | CA | HIS | A | 203 | 75.585 | 20.362 | −0.717 | 1.00 | 24.36 | A |
| ATOM | 1088 | CB | HIS | A | 203 | 77.095 | 20.131 | −0.677 | 1.00 | 23.06 | A |
| ATOM | 1089 | CG | HIS | A | 203 | 77.680 | 20.268 | 0.694 | 1.00 | 24.09 | A |
| ATOM | 1090 | CD2 | HIS | A | 203 | 77.956 | 21.366 | 1.434 | 1.00 | 22.36 | A |
| ATOM | 1091 | ND1 | HIS | A | 203 | 77.981 | 19.183 | 1.490 | 1.00 | 23.65 | A |
| ATOM | 1092 | CE1 | HIS | A | 203 | 78.418 | 19.607 | 2.661 | 1.00 | 23.87 | A |
| ATOM | 1093 | NE2 | HIS | A | 203 | 78.412 | 20.929 | 2.653 | 1.00 | 25.12 | A |
| ATOM | 1094 | C | HIS | A | 203 | 75.269 | 21.811 | −0.330 | 1.00 | 24.71 | A |
| ATOM | 1095 | O | HIS | A | 203 | 74.633 | 22.055 | 0.693 | 1.00 | 24.27 | A |
| ATOM | 1096 | N | ARG | A | 204 | 75.724 | 22.758 | −1.154 | 1.00 | 25.89 | A |
| ATOM | 1097 | CA | ARG | A | 204 | 75.490 | 24.199 | −0.961 | 1.00 | 25.68 | A |
| ATOM | 1098 | CB | ARG | A | 204 | 74.033 | 24.471 | −0.596 | 1.00 | 25.57 | A |
| ATOM | 1099 | CG | ARG | A | 204 | 73.079 | 24.319 | −1.751 | 1.00 | 29.26 | A |
| ATOM | 1100 | CD | ARG | A | 204 | 71.815 | 25.118 | −1.509 | 1.00 | 29.86 | A |
| ATOM | 1101 | NE | ARG | A | 204 | 71.065 | 24.603 | −0.373 | 1.00 | 33.90 | A |
| ATOM | 1102 | CZ | ARG | A | 204 | 70.021 | 25.219 | 0.170 | 1.00 | 36.01 | A |
| ATOM | 1103 | NH1 | ARG | A | 204 | 69.607 | 26.383 | −0.322 | 1.00 | 37.08 | A |
| ATOM | 1104 | NH2 | ARG | A | 204 | 69.387 | 24.668 | 1.197 | 1.00 | 34.14 | A |
| ATOM | 1105 | C | ARG | A | 204 | 76.373 | 24.935 | 0.034 | 1.00 | 26.91 | A |
| ATOM | 1106 | O | ARG | A | 204 | 76.210 | 26.144 | 0.243 | 1.00 | 26.29 | A |
| ATOM | 1107 | N | ASP | A | 205 | 77.303 | 24.221 | 0.654 | 1.00 | 26.23 | A |
| ATOM | 1108 | CA | ASP | A | 205 | 78.203 | 24.849 | 1.604 | 1.00 | 24.46 | A |
| ATOM | 1109 | CB | ASP | A | 205 | 77.557 | 24.909 | 2.990 | 1.00 | 28.25 | A |
| ATOM | 1110 | CG | ASP | A | 205 | 78.203 | 25.954 | 3.890 | 1.00 | 30.95 | A |
| ATOM | 1111 | OD1 | ASP | A | 205 | 78.872 | 26.862 | 3.354 | 1.00 | 35.13 | A |
| ATOM | 1112 | OD2 | ASP | A | 205 | 78.034 | 25.880 | 5.127 | 1.00 | 33.48 | A |
| ATOM | 1113 | C | ASP | A | 205 | 79.483 | 24.039 | 1.631 | 1.00 | 24.22 | A |
| ATOM | 1114 | O | ASP | A | 205 | 79.998 | 23.676 | 2.685 | 1.00 | 23.62 | A |
| ATOM | 1115 | N | LEU | A | 206 | 79.995 | 23.755 | 0.442 | 1.00 | 23.31 | A |
| ATOM | 1116 | CA | LEU | A | 206 | 81.206 | 22.978 | 0.321 | 1.00 | 24.19 | A |
| ATOM | 1117 | CB | LEU | A | 206 | 81.311 | 22.406 | −1.088 | 1.00 | 24.78 | A |
| ATOM | 1118 | CG | LEU | A | 206 | 82.353 | 21.309 | −1.285 | 1.00 | 25.24 | A |
| ATOM | 1119 | CD1 | LEU | A | 206 | 82.075 | 20.173 | −0.317 | 1.00 | 26.72 | A |
| ATOM | 1120 | CD2 | LEU | A | 206 | 82.298 | 20.808 | −2.720 | 1.00 | 24.32 | A |
| ATOM | 1121 | C | LEU | A | 206 | 82.408 | 23.853 | 0.623 | 1.00 | 24.52 | A |
| ATOM | 1122 | O | LEU | A | 206 | 82.508 | 24.977 | 0.130 | 1.00 | 24.34 | A |
| ATOM | 1123 | N | LYS | A | 207 | 83.328 | 23.330 | 1.424 | 1.00 | 22.98 | A |
| ATOM | 1124 | CA | LYS | A | 207 | 84.517 | 24.083 | 1.796 | 1.00 | 23.05 | A |
| ATOM | 1125 | CB | LYS | A | 207 | 84.113 | 25.305 | 2.629 | 1.00 | 21.18 | A |
| ATOM | 1126 | CG | LYS | A | 207 | 83.278 | 24.948 | 3.830 | 1.00 | 19.29 | A |
| ATOM | 1127 | CD | LYS | A | 207 | 82.775 | 26.179 | 4.568 | 1.00 | 23.68 | A |
| ATOM | 1128 | CE | LYS | A | 207 | 81.913 | 25.781 | 5.767 | 1.00 | 21.99 | A |
| ATOM | 1129 | NZ | LYS | A | 207 | 81.580 | 26.910 | 6.686 | 1.00 | 25.14 | A |
| ATOM | 1130 | C | LYS | A | 207 | 85.444 | 23.183 | 2.602 | 1.00 | 23.54 | A |
| ATOM | 1131 | O | LYS | A | 207 | 85.014 | 22.169 | 3.144 | 1.00 | 26.04 | A |
| ATOM | 1132 | N | PRO | A | 208 | 86.728 | 23.550 | 2.697 | 1.00 | 23.78 | A |

-continued

| ATOM | 1133 | CD | PRO | A | 208 | 87.309 | 24.764 | 2.100 | 1.00 | 21.90 | A |
|------|------|-----|-----|---|-----|--------|--------|-------|------|-------|---|
| ATOM | 1134 | CA | PRO | A | 208 | 87.754 | 22.801 | 3.429 | 1.00 | 23.64 | A |
| ATOM | 1135 | CB | PRO | A | 208 | 88.948 | 23.750 | 3.397 | 1.00 | 22.67 | A |
| ATOM | 1136 | CG | PRO | A | 208 | 88.779 | 24.432 | 2.084 | 1.00 | 23.00 | A |
| ATOM | 1137 | C | PRO | A | 208 | 87.393 | 22.390 | 4.859 | 1.00 | 24.47 | A |
| ATOM | 1138 | O | PRO | A | 208 | 87.890 | 21.378 | 5.358 | 1.00 | 24.20 | A |
| ATOM | 1139 | N | GLU | A | 209 | 86.541 | 23.176 | 5.514 | 1.00 | 25.33 | A |
| ATOM | 1140 | CA | GLU | A | 209 | 86.132 | 22.903 | 6.894 | 1.00 | 26.78 | A |
| ATOM | 1141 | CB | GLU | A | 209 | 85.641 | 24.190 | 7.570 | 1.00 | 27.82 | A |
| ATOM | 1142 | CG | GLU | A | 209 | 86.616 | 25.359 | 7.479 | 1.00 | 34.76 | A |
| ATOM | 1143 | CD | GLU | A | 209 | 86.459 | 26.183 | 6.199 | 1.00 | 39.84 | A |
| ATOM | 1144 | OE1 | GLU | A | 209 | 86.575 | 25.628 | 5.079 | 1.00 | 38.56 | A |
| ATOM | 1145 | OE2 | GLU | A | 209 | 86.219 | 27.405 | 6.322 | 1.00 | 44.97 | A |
| ATOM | 1146 | C | GLU | A | 209 | 85.039 | 21.840 | 6.972 | 1.00 | 26.70 | A |
| ATOM | 1147 | O | GLU | A | 209 | 84.786 | 21.269 | 8.035 | 1.00 | 29.78 | A |
| ATOM | 1148 | N | ASN | A | 210 | 84.395 | 21.583 | 5.841 | 1.00 | 24.55 | A |
| ATOM | 1149 | CA | ASN | A | 210 | 83.339 | 20.587 | 5.751 | 1.00 | 24.33 | A |
| ATOM | 1150 | CB | ASN | A | 210 | 82.195 | 21.105 | 4.866 | 1.00 | 27.29 | A |
| ATOM | 1151 | CG | ASN | A | 210 | 81.225 | 21.998 | 5.622 | 1.00 | 31.63 | A |
| ATOM | 1152 | OD1 | ASN | A | 210 | 80.280 | 22.539 | 5.040 | 1.00 | 35.25 | A |
| ATOM | 1153 | ND2 | ASN | A | 210 | 81.449 | 22.155 | 6.923 | 1.00 | 30.78 | A |
| ATOM | 1154 | C | ASN | A | 210 | 83.885 | 19.289 | 5.158 | 1.00 | 22.61 | A |
| ATOM | 1155 | O | ASN | A | 210 | 83.207 | 18.268 | 5.155 | 1.00 | 19.95 | A |
| ATOM | 1156 | N | ILE | A | 211 | 85.105 | 19.344 | 4.638 | 1.00 | 22.15 | A |
| ATOM | 1157 | CA | ILE | A | 211 | 85.733 | 18.174 | 4.043 | 1.00 | 21.36 | A |
| ATOM | 1158 | CB | ILE | A | 211 | 86.467 | 18.538 | 2.744 | 1.00 | 20.33 | A |
| ATOM | 1159 | CG2 | ILE | A | 211 | 87.167 | 17.315 | 2.180 | 1.00 | 20.04 | A |
| ATOM | 1160 | CG1 | ILE | A | 211 | 85.475 | 19.089 | 1.719 | 1.00 | 19.57 | A |
| ATOM | 1161 | CD1 | ILE | A | 211 | 86.162 | 19.718 | 0.517 | 1.00 | 20.56 | A |
| ATOM | 1162 | C | ILE | A | 211 | 86.733 | 17.629 | 5.048 | 1.00 | 22.45 | A |
| ATOM | 1163 | O | ILE | A | 211 | 87.805 | 18.209 | 5.254 | 1.00 | 21.87 | A |
| ATOM | 1164 | N | LEU | A | 212 | 86.377 | 16.510 | 5.670 | 1.00 | 21.03 | A |
| ATOM | 1165 | CA | LEU | A | 212 | 87.228 | 15.910 | 6.685 | 1.00 | 20.43 | A |
| ATOM | 1166 | CB | LEU | A | 212 | 86.352 | 15.331 | 7.801 | 1.00 | 19.57 | A |
| ATOM | 1167 | CG | LEU | A | 212 | 85.270 | 16.281 | 8.347 | 1.00 | 19.01 | A |
| ATOM | 1168 | CD1 | LEU | A | 212 | 84.543 | 15.613 | 9.494 | 1.00 | 16.54 | A |
| ATOM | 1169 | CD2 | LEU | A | 212 | 85.903 | 17.592 | 8.817 | 1.00 | 19.58 | A |
| ATOM | 1170 | C | LEU | A | 212 | 88.148 | 14.833 | 6.139 | 1.00 | 20.95 | A |
| ATOM | 1171 | O | LEU | A | 212 | 88.034 | 14.420 | 4.983 | 1.00 | 20.16 | A |
| ATOM | 1172 | N | LEU | A | 213 | 89.069 | 14.379 | 6.978 | 1.00 | 21.07 | A |
| ATOM | 1173 | CA | LEU | A | 213 | 89.991 | 13.330 | 6.578 | 1.00 | 21.58 | A |
| ATOM | 1174 | CB | LEU | A | 213 | 91.415 | 13.882 | 6.520 | 1.00 | 21.17 | A |
| ATOM | 1175 | CG | LEU | A | 213 | 91.633 | 14.944 | 5.440 | 1.00 | 21.26 | A |
| ATOM | 1176 | CD1 | LEU | A | 213 | 93.051 | 15.466 | 5.514 | 1.00 | 23.93 | A |
| ATOM | 1177 | CD2 | LEU | A | 213 | 91.378 | 14.335 | 4.070 | 1.00 | 23.36 | A |
| ATOM | 1178 | C | LEU | A | 213 | 89.912 | 12.161 | 7.554 | 1.00 | 22.28 | A |
| ATOM | 1179 | O | LEU | A | 213 | 89.948 | 12.354 | 8.766 | 1.00 | 23.80 | A |
| ATOM | 1180 | N | ASN | A | 214 | 89.786 | 10.949 | 7.025 | 1.00 | 22.96 | A |
| ATOM | 1181 | CA | ASN | A | 214 | 89.718 | 9.766 | 7.872 | 1.00 | 22.83 | A |
| ATOM | 1182 | CB | ASN |   | 214 | 88.997 | 8.647 | 7.103 | 0.50 | 23.75 | AC1 |
| ATOM | 1183 | CG | ASN |   | 214 | 89.144 | 7.286 | 7.756 | 0.50 | 25.62 | AC1 |
| ATOM | 1184 | OD1 | ASN |   | 214 | 90.212 | 6.673 | 7.713 | 0.50 | 25.34 | AC1 |
| ATOM | 1185 | ND2 | ASN |   | 214 | 88.066 | 6.803 | 8.363 | 0.50 | 26.41 | AC1 |
| ATOM | 1186 | C | ASN | A | 214 | 91.151 | 9.354 | 8.228 | 1.00 | 23.68 | A |
| ATOM | 1187 | O | ASN | A | 214 | 92.112 | 9.934 | 7.716 | 1.00 | 20.85 | A |
| ATOM | 1188 | N | GLU | A | 215 | 91.291 | 8.379 | 9.119 | 1.00 | 25.06 | A |
| ATOM | 1189 | CA | GLU | A | 215 | 92.603 | 7.901 | 9.545 | 1.00 | 26.20 | A |
| ATOM | 1190 | CB | GLU | A | 215 | 92.453 | 6.669 | 10.435 | 1.00 | 26.19 | A |
| ATOM | 1191 | CG | GLU | A | 215 | 93.770 | 6.153 | 10.985 | 1.00 | 29.08 | A |
| ATOM | 1192 | CD | GLU | A | 215 | 93.589 | 4.963 | 11.907 | 0.00 | 28.21 | A |
| ATOM | 1193 | OE1 | GLU | A | 215 | 93.064 | 3.927 | 11.449 | 0.00 | 28.42 | A |
| ATOM | 1194 | OE2 | GLU | A | 215 | 93.973 | 5.065 | 13.092 | 0.00 | 28.42 | A |
| ATOM | 1195 | C | GLU | A | 215 | 93.532 | 7.566 | 8.385 | 1.00 | 26.12 | A |
| ATOM | 1196 | O | GLU | A | 215 | 94.746 | 7.743 | 8.487 | 1.00 | 29.48 | A |
| ATOM | 1197 | N | ASP | A | 216 | 92.976 | 7.070 | 7.287 | 1.00 | 25.52 | A |
| ATOM | 1198 | CA | ASP | A | 216 | 93.798 | 6.728 | 6.133 | 1.00 | 25.79 | A |
| ATOM | 1199 | CB | ASP |   | 216 | 93.164 | 5.564 | 5.376 | 0.50 | 27.09 | AC1 |
| ATOM | 1200 | CG | ASP |   | 216 | 93.450 | 4.231 | 6.027 | 0.50 | 29.11 | AC1 |
| ATOM | 1201 | OD1 | ASP |   | 216 | 93.206 | 4.098 | 7.244 | 0.50 | 31.09 | AC1 |
| ATOM | 1202 | OD2 | ASP |   | 216 | 93.921 | 3.315 | 5.320 | 0.50 | 31.52 | AC1 |
| ATOM | 1203 | C | ASP | A | 216 | 94.034 | 7.896 | 5.173 | 1.00 | 24.88 | A |
| ATOM | 1204 | O | ASP | A | 216 | 94.586 | 7.719 | 4.094 | 1.00 | 26.27 | A |
| ATOM | 1205 | N | MET | A | 217 | 93.615 | 9.087 | 5.578 | 1.00 | 25.04 | A |
| ATOM | 1206 | CA | MET | A | 217 | 93.789 | 10.301 | 4.792 | 1.00 | 24.86 | A |
| ATOM | 1207 | CB | MET | A | 217 | 95.270 | 10.503 | 4.454 | 1.00 | 28.81 | A |
| ATOM | 1208 | CG | MET | A | 217 | 96.139 | 10.834 | 5.676 | 1.00 | 29.66 | A |
| ATOM | 1209 | SD | MET | A | 217 | 95.577 | 12.323 | 6.551 | 1.00 | 34.79 | A |
| ATOM | 1210 | CE | MET | A | 217 | 96.130 | 13.598 | 5.411 | 1.00 | 30.61 | A |
| ATOM | 1211 | C | MET | A | 217 | 92.942 | 10.437 | 3.528 | 1.00 | 24.93 | A |

-continued

| ATOM | 1212 | O | MET | A | 217 | 93.277 | 11.215 | 2.629 | 1.00 | 23.08 | A |
| ATOM | 1213 | N | HIS | A | 218 | 91.855 | 9.678 | 3.450 | 1.00 | 21.48 | A |
| ATOM | 1214 | CA | HIS | A | 218 | 90.947 | 9.799 | 2.319 | 1.00 | 21.72 | A |
| ATOM | 1215 | CB | HIS | A | 218 | 90.325 | 8.444 | 1.963 | 1.00 | 21.43 | A |
| ATOM | 1216 | CG | HIS | A | 218 | 91.225 | 7.578 | 1.138 | 1.00 | 24.55 | A |
| ATOM | 1217 | CD2 | HIS | A | 218 | 91.951 | 6.478 | 1.458 | 1.00 | 23.50 | A |
| ATOM | 1218 | ND1 | HIS | A | 218 | 91.522 | 7.860 | −0.179 | 1.00 | 23.64 | A |
| ATOM | 1219 | CE1 | HIS | A | 218 | 92.392 | 6.975 | −0.633 | 1.00 | 21.12 | A |
| ATOM | 1220 | NE2 | HIS | A | 218 | 92.670 | 6.128 | 0.340 | 1.00 | 22.96 | A |
| ATOM | 1221 | C | HIS | A | 218 | 89.891 | 10.785 | 2.812 | 1.00 | 20.49 | A |
| ATOM | 1222 | O | HIS | A | 218 | 89.683 | 10.911 | 4.018 | 1.00 | 20.60 | A |
| ATOM | 1223 | N | ILE | A | 219 | 89.231 | 11.488 | 1.897 | 1.00 | 18.82 | A |
| ATOM | 1224 | CA | ILE | A | 219 | 88.244 | 12.473 | 2.306 | 1.00 | 17.27 | A |
| ATOM | 1225 | CB | ILE | A | 219 | 87.914 | 13.487 | 1.178 | 1.00 | 15.59 | A |
| ATOM | 1226 | CG2 | ILE | A | 219 | 89.175 | 14.201 | 0.718 | 1.00 | 14.62 | A |
| ATOM | 1227 | CG1 | ILE | A | 219 | 87.252 | 12.769 | 0.006 | 1.00 | 16.04 | A |
| ATOM | 1228 | CD1 | ILE | A | 219 | 86.458 | 13.685 | −0.888 | 1.00 | 15.29 | A |
| ATOM | 1229 | C | ILE | A | 219 | 86.934 | 11.885 | 2.772 | 1.00 | 17.64 | A |
| ATOM | 1230 | O | ILE | A | 219 | 86.564 | 10.774 | 2.402 | 1.00 | 18.93 | A |
| ATOM | 1231 | N | GLN | A | 220 | 86.240 | 12.658 | 3.597 | 1.00 | 19.19 | A |
| ATOM | 1232 | CA | GLN | A | 220 | 84.933 | 12.293 | 4.119 | 1.00 | 21.50 | A |
| ATOM | 1233 | CB | GLN | A | 220 | 85.061 | 11.585 | 5.475 | 1.00 | 23.96 | A |
| ATOM | 1234 | CG | GLN | A | 220 | 85.583 | 10.151 | 5.334 | 1.00 | 29.77 | A |
| ATOM | 1235 | CD | GLN | A | 220 | 84.945 | 9.182 | 6.319 | 1.00 | 33.77 | A |
| ATOM | 1236 | OE1 | GLN | A | 220 | 85.257 | 9.188 | 7.513 | 1.00 | 37.87 | A |
| ATOM | 1237 | NE2 | GLN | A | 220 | 84.040 | 8.347 | 5.821 | 1.00 | 34.29 | A |
| ATOM | 1238 | C | GLN | A | 220 | 84.158 | 13.599 | 4.240 | 1.00 | 21.53 | A |
| ATOM | 1239 | O | GLN | A | 220 | 84.367 | 14.393 | 5.166 | 1.00 | 22.54 | A |
| ATOM | 1240 | N | ILE | A | 221 | 83.284 | 13.833 | 3.270 | 1.00 | 19.63 | A |
| ATOM | 1241 | CA | ILE | A | 221 | 82.498 | 15.054 | 3.234 | 1.00 | 19.30 | A |
| ATOM | 1242 | CB | ILE | A | 221 | 82.055 | 15.366 | 1.785 | 1.00 | 20.41 | A |
| ATOM | 1243 | CG2 | ILE | A | 221 | 81.237 | 16.639 | 1.738 | 1.00 | 19.39 | A |
| ATOM | 1244 | CG1 | ILE | A | 221 | 83.290 | 15.524 | 0.900 | 1.00 | 19.44 | A |
| ATOM | 1245 | CD1 | ILE | A | 221 | 82.977 | 15.802 | −0.550 | 1.00 | 17.44 | A |
| ATOM | 1246 | C | ILE | A | 221 | 81.284 | 14.951 | 4.141 | 1.00 | 18.36 | A |
| ATOM | 1247 | O | ILE | A | 221 | 80.627 | 13.911 | 4.204 | 1.00 | 15.98 | A |
| ATOM | 1248 | N | THR | A | 222 | 80.995 | 16.024 | 4.864 | 1.00 | 19.59 | A |
| ATOM | 1249 | CA | THR | A | 222 | 79.844 | 16.008 | 5.753 | 1.00 | 22.76 | A |
| ATOM | 1250 | CB | THR | A | 222 | 80.218 | 15.420 | 7.126 | 1.00 | 23.86 | A |
| ATOM | 1251 | OG1 | THR | A | 222 | 79.019 | 15.145 | 7.863 | 1.00 | 28.20 | A |
| ATOM | 1252 | CG2 | THR | A | 222 | 81.105 | 16.380 | 7.908 | 1.00 | 23.65 | A |
| ATOM | 1253 | C | THR | A | 222 | 79.179 | 17.370 | 5.933 | 1.00 | 23.55 | A |
| ATOM | 1254 | O | THR | A | 222 | 79.505 | 18.334 | 5.229 | 1.00 | 25.65 | A |
| ATOM | 1255 | N | ASP | A | 223 | 78.248 | 17.427 | 6.881 | 1.00 | 24.38 | A |
| ATOM | 1256 | CA | ASP | A | 223 | 77.449 | 18.611 | 7.202 | 1.00 | 25.25 | A |
| ATOM | 1257 | CB | ASP | A | 223 | 78.303 | 19.865 | 7.422 | 1.00 | 26.12 | A |
| ATOM | 1258 | CG | ASP | A | 223 | 77.538 | 20.962 | 8.175 | 1.00 | 29.92 | A |
| ATOM | 1259 | OD1 | ASP | A | 223 | 76.288 | 20.876 | 8.278 | 1.00 | 31.91 | A |
| ATOM | 1260 | OD2 | ASP | A | 223 | 78.177 | 21.911 | 8.671 | 1.00 | 32.94 | A |
| ATOM | 1261 | C | ASP | A | 223 | 76.461 | 18.882 | 6.080 | 1.00 | 25.61 | A |
| ATOM | 1262 | O | ASP | A | 223 | 76.693 | 19.744 | 5.227 | 1.00 | 25.81 | A |
| ATOM | 1263 | N | PHE | A | 224 | 75.358 | 18.139 | 6.098 | 1.00 | 25.18 | A |
| ATOM | 1264 | CA | PHE | A | 224 | 74.310 | 18.266 | 5.096 | 1.00 | 26.75 | A |
| ATOM | 1265 | CB | PHE | A | 224 | 73.860 | 16.879 | 4.635 | 1.00 | 27.24 | A |
| ATOM | 1266 | CG | PHE | A | 224 | 74.857 | 16.189 | 3.753 | 1.00 | 28.10 | A |
| ATOM | 1267 | CD1 | PHE | A | 224 | 74.889 | 16.450 | 2.388 | 1.00 | 29.12 | A |
| ATOM | 1268 | CD2 | PHE | A | 224 | 75.790 | 15.313 | 4.291 | 1.00 | 28.67 | A |
| ATOM | 1269 | CE1 | PHE | A | 224 | 75.841 | 15.847 | 1.567 | 1.00 | 30.28 | A |
| ATOM | 1270 | CE2 | PHE | A | 224 | 76.745 | 14.706 | 3.482 | 1.00 | 31.49 | A |
| ATOM | 1271 | CZ | PHE | A | 224 | 76.770 | 14.973 | 2.117 | 1.00 | 30.54 | A |
| ATOM | 1272 | C | PHE | A | 224 | 73.124 | 19.038 | 5.632 | 1.00 | 27.73 | A |
| ATOM | 1273 | O | PHE | A | 224 | 72.005 | 18.895 | 5.140 | 1.00 | 27.84 | A |
| ATOM | 1274 | N | GLY | A | 225 | 73.378 | 19.862 | 6.643 | 1.00 | 29.36 | A |
| ATOM | 1275 | CA | GLY | A | 225 | 72.319 | 20.656 | 7.235 | 1.00 | 30.10 | A |
| ATOM | 1276 | C | GLY | A | 225 | 71.825 | 21.741 | 6.297 | 1.00 | 31.32 | A |
| ATOM | 1277 | O | GLY | A | 225 | 70.714 | 22.248 | 6.451 | 1.00 | 32.90 | A |
| ATOM | 1278 | N | THR | A | 226 | 72.640 | 22.091 | 5.311 | 1.00 | 29.95 | A |
| ATOM | 1279 | CA | THR | A | 226 | 72.261 | 23.132 | 4.365 | 1.00 | 32.06 | A |
| ATOM | 1280 | CB | THR | A | 226 | 73.381 | 24.167 | 4.226 | 1.00 | 33.35 | A |
| ATOM | 1281 | OG1 | THR | A | 226 | 74.454 | 23.608 | 3.455 | 1.00 | 35.74 | A |
| ATOM | 1282 | CG2 | THR | A | 226 | 73.920 | 24.542 | 5.593 | 1.00 | 34.02 | A |
| ATOM | 1283 | C | THR | A | 226 | 71.979 | 22.551 | 2.983 | 1.00 | 31.11 | A |
| ATOM | 1284 | O | THR | A | 226 | 71.801 | 23.288 | 2.012 | 1.00 | 30.89 | A |
| ATOM | 1285 | N | ALA | A | 227 | 71.938 | 21.230 | 2.899 | 1.00 | 30.02 | A |
| ATOM | 1286 | CA | ALA | A | 227 | 71.714 | 20.566 | 1.624 | 1.00 | 32.20 | A |
| ATOM | 1287 | CB | ALA | A | 227 | 71.906 | 19.057 | 1.770 | 1.00 | 29.19 | A |
| ATOM | 1288 | C | ALA | A | 227 | 70.345 | 20.865 | 1.045 | 1.00 | 32.77 | A |
| ATOM | 1289 | O | ALA | A | 227 | 69.431 | 21.269 | 1.761 | 1.00 | 34.17 | A |
| ATOM | 1290 | N | ALA | A | 228 | 70.229 | 20.684 | −0.266 | 1.00 | 33.18 | A |

-continued

| ATOM | 1291 | CA | ALA | A | 228 | 68.980 | 20.902 | −0.982 | 1.00 | 34.43 | A |
| --- | --- | --- | --- | --- | --- | --- | --- | --- | --- | --- | --- |
| ATOM | 1292 | CB | ALA | A | 228 | 69.079 | 22.146 | −1.861 | 1.00 | 32.03 | A |
| ATOM | 1293 | C | ALA | A | 228 | 68.742 | 19.674 | −1.846 | 1.00 | 35.25 | A |
| ATOM | 1294 | O | ALA | A | 228 | 69.612 | 19.284 | −2.622 | 1.00 | 36.70 | A |
| ATOM | 1295 | N | VAL | A | 229 | 67.578 | 19.056 | −1.698 | 1.00 | 36.21 | A |
| ATOM | 1296 | CA | VAL | A | 229 | 67.246 | 17.876 | −2.488 | 1.00 | 37.95 | A |
| ATOM | 1297 | CB | VAL | A | 229 | 66.438 | 16.857 | −1.674 | 1.00 | 37.37 | A |
| ATOM | 1298 | CG1 | VAL | A | 229 | 66.192 | 15.609 | −2.506 | 1.00 | 35.62 | A |
| ATOM | 1299 | CG2 | VAL | A | 229 | 67.176 | 16.522 | −0.394 | 1.00 | 36.39 | A |
| ATOM | 1300 | C | VAL | A | 229 | 66.393 | 18.341 | −3.649 | 1.00 | 40.15 | A |
| ATOM | 1301 | O | VAL | A | 229 | 65.353 | 18.965 | −3.446 | 1.00 | 39.20 | A |
| ATOM | 1302 | N | LEU | A | 230 | 66.836 | 18.044 | −4.865 | 1.00 | 43.75 | A |
| ATOM | 1303 | CA | LEU | A | 230 | 66.105 | 18.455 | −6.054 | 1.00 | 48.04 | A |
| ATOM | 1304 | CB | LEU | A | 230 | 67.039 | 18.473 | −7.258 | 1.00 | 48.59 | A |
| ATOM | 1305 | CG | LEU | A | 230 | 68.123 | 19.552 | −7.212 | 1.00 | 50.35 | A |
| ATOM | 1306 | CD1 | LEU | A | 230 | 69.118 | 19.312 | −8.326 | 1.00 | 50.62 | A |
| ATOM | 1307 | CD2 | LEU | A | 230 | 67.488 | 20.932 | −7.330 | 1.00 | 50.11 | A |
| ATOM | 1308 | C | LEU | A | 230 | 64.905 | 17.569 | −6.346 | 1.00 | 51.38 | A |
| ATOM | 1309 | O | LEU | A | 230 | 64.929 | 16.364 | −6.095 | 1.00 | 51.84 | A |
| ATOM | 1310 | N | SER | A | 231 | 63.854 | 18.190 | −6.872 | 1.00 | 56.03 | A |
| ATOM | 1311 | CA | SER | A | 231 | 62.616 | 17.502 | −7.224 | 1.00 | 60.24 | A |
| ATOM | 1312 | CB | SER | A | 231 | 61.528 | 17.806 | −6.186 | 1.00 | 60.77 | A |
| ATOM | 1313 | OG | SER | A | 231 | 61.222 | 19.192 | −6.150 | 1.00 | 61.08 | A |
| ATOM | 1314 | C | SER | A | 231 | 62.115 | 17.894 | −8.622 | 1.00 | 62.65 | A |
| ATOM | 1315 | O | SER | A | 231 | 61.527 | 17.068 | −9.326 | 1.00 | 63.42 | A |
| ATOM | 1316 | N | PRO | A | 232 | 62.334 | 19.161 | −9.040 | 1.00 | 64.66 | A |
| ATOM | 1317 | CD | PRO | A | 232 | 62.903 | 20.298 | −8.289 | 1.00 | 64.95 | A |
| ATOM | 1318 | CA | PRO | A | 232 | 61.882 | 19.604 | −10.367 | 1.00 | 65.69 | A |
| ATOM | 1319 | CB | PRO | A | 232 | 62.409 | 21.037 | −10.450 | 1.00 | 65.77 | A |
| ATOM | 1320 | CG | PRO | A | 232 | 62.341 | 21.493 | −9.031 | 1.00 | 65.52 | A |
| ATOM | 1321 | C | PRO | A | 232 | 62.408 | 18.731 | −11.505 | 1.00 | 66.28 | A |
| ATOM | 1322 | O | PRO | A | 232 | 62.858 | 19.241 | −12.532 | 1.00 | 66.55 | A |
| ATOM | 1323 | N | ALA | A | 239 | 65.927 | 26.021 | −3.995 | 1.00 | 92.57 | A |
| ATOM | 1324 | CA | ALA | A | 239 | 67.330 | 26.100 | −3.606 | 1.00 | 92.64 | A |
| ATOM | 1325 | CB | ALA | A | 239 | 68.187 | 25.262 | −4.558 | 1.00 | 92.15 | A |
| ATOM | 1326 | C | ALA | A | 239 | 67.769 | 27.558 | −3.640 | 1.00 | 92.34 | A |
| ATOM | 1327 | O | ALA | A | 239 | 68.683 | 27.930 | −4.373 | 1.00 | 92.47 | A |
| ATOM | 1328 | N | ASN | A | 240 | 67.108 | 28.379 | −2.833 | 1.00 | 91.92 | A |
| ATOM | 1329 | CA | ASN | A | 240 | 67.396 | 29.809 | −2.767 | 1.00 | 91.12 | A |
| ATOM | 1330 | CB | ASN | A | 240 | 66.374 | 30.566 | −3.617 | 1.00 | 92.32 | A |
| ATOM | 1331 | CG | ASN | A | 240 | 64.947 | 30.084 | −3.378 | 1.00 | 93.20 | A |
| ATOM | 1332 | OD1 | ASN | A | 240 | 64.471 | 30.061 | −2.244 | 1.00 | 93.46 | A |
| ATOM | 1333 | ND2 | ASN | A | 240 | 64.261 | 29.697 | −4.452 | 1.00 | 94.00 | A |
| ATOM | 1334 | C | ASN | A | 240 | 67.334 | 30.332 | −1.335 | 1.00 | 89.78 | A |
| ATOM | 1335 | O | ASN | A | 240 | 67.766 | 31.453 | −1.053 | 1.00 | 89.80 | A |
| ATOM | 1336 | N | ALA | A | 241 | 66.787 | 29.515 | −0.441 | 1.00 | 88.16 | A |
| ATOM | 1337 | CA | ALA | A | 241 | 66.624 | 29.891 | 0.955 | 1.00 | 86.55 | A |
| ATOM | 1338 | C | ALA | A | 241 | 67.901 | 29.893 | 1.792 | 1.00 | 84.55 | A |
| ATOM | 1339 | O | ALA | A | 241 | 67.865 | 30.268 | 2.961 | 1.00 | 84.76 | A |
| ATOM | 1340 | CB | ALA | A | 241 | 65.583 | 28.978 | 1.623 | 1.00 | 88.01 | A |
| ATOM | 1341 | N | PHE | A | 242 | 69.028 | 29.494 | 1.216 | 1.00 | 82.28 | A |
| ATOM | 1342 | CA | PHE | A | 242 | 70.264 | 29.483 | 1.993 | 1.00 | 79.83 | A |
| ATOM | 1343 | CB | PHE | A | 242 | 70.718 | 28.046 | 2.282 | 1.00 | 79.60 | A |
| ATOM | 1344 | CG | PHE | A | 242 | 71.980 | 27.962 | 3.100 | 1.00 | 79.10 | A |
| ATOM | 1345 | CD1 | PHE | A | 242 | 72.024 | 28.483 | 4.388 | 1.00 | 79.45 | A |
| ATOM | 1346 | CD2 | PHE | A | 242 | 73.131 | 27.392 | 2.571 | 1.00 | 79.42 | A |
| ATOM | 1347 | CE1 | PHE | A | 242 | 73.202 | 28.442 | 5.143 | 1.00 | 79.29 | A |
| ATOM | 1348 | CE2 | PHE | A | 242 | 74.314 | 27.345 | 3.317 | 1.00 | 80.20 | A |
| ATOM | 1349 | CZ | PHE | A | 242 | 74.348 | 27.872 | 4.605 | 1.00 | 79.98 | A |
| ATOM | 1350 | C | PHE | A | 242 | 71.402 | 30.231 | 1.322 | 1.00 | 77.56 | A |
| ATOM | 1351 | O | PHE | A | 242 | 71.347 | 30.524 | 0.130 | 1.00 | 78.59 | A |
| ATOM | 1352 | N | VAL | A | 243 | 72.440 | 30.529 | 2.098 | 1.00 | 73.76 | A |
| ATOM | 1353 | CA | VAL | A | 243 | 73.595 | 31.238 | 1.579 | 1.00 | 70.34 | A |
| ATOM | 1354 | CB | VAL | A | 243 | 73.864 | 32.515 | 2.405 | 1.00 | 71.71 | A |
| ATOM | 1355 | CG1 | VAL | A | 243 | 75.087 | 33.238 | 1.85 | 91.00 | 71.29 | A |
| ATOM | 1356 | CG2 | VAL | A | 243 | 72.638 | 33.425 | 2.376 | 1.00 | 71.41 | A |
| ATOM | 1357 | C | VAL | A | 243 | 74.851 | 30.362 | 1.581 | 1.00 | 66.69 | A |
| ATOM | 1358 | O | VAL | A | 243 | 75.232 | 29.802 | 0.552 | 1.00 | 66.50 | A |
| ATOM | 1359 | N | GLY | A | 244 | 75.496 | 30.245 | 2.737 | 1.00 | 62.34 | A |
| ATOM | 1360 | CA | GLY | A | 244 | 76.708 | 29.444 | 2.829 | 1.00 | 56.48 | A |
| ATOM | 1361 | C | GLY | A | 244 | 77.889 | 30.327 | 3.168 | 1.00 | 52.17 | A |
| ATOM | 1362 | O | GLY | A | 244 | 77.769 | 31.547 | 3.136 | 1.00 | 52.14 | A |
| ATOM | 1363 | N | THR | A | 245 | 79.031 | 29.733 | 3.490 | 1.00 | 48.25 | A |
| ATOM | 1364 | CA | THR | A | 245 | 80.201 | 30.530 | 3.838 | 1.00 | 44.49 | A |
| ATOM | 1365 | CB | THR | A | 245 | 81.413 | 29.633 | 4.106 | 1.00 | 45.53 | A |
| ATOM | 1366 | OG1 | THR | A | 245 | 80.994 | 28.514 | 4.899 | 1.00 | 45.14 | A |
| ATOM | 1367 | CG2 | THR | A | 245 | 82.486 | 30.403 | 4.873 | 1.00 | 42.13 | A |
| ATOM | 1368 | C | THR | A | 245 | 80.523 | 31.537 | 2.734 | 1.00 | 40.69 | A |
| ATOM | 1369 | O | THR | A | 245 | 80.722 | 31.175 | 1.572 | 1.00 | 38.45 | A |

-continued

| | | | | | | | | | | |
|---|---|---|---|---|---|---|---|---|---|---|
| ATOM | 1370 | N | ALA | A | 246 | 80.570 | 32.804 | 3.127 | 1.00 | 36.53 | A |
| ATOM | 1371 | CA | ALA | A | 246 | 80.816 | 33.915 | 2.219 | 1.00 | 34.68 | A |
| ATOM | 1372 | CB | ALA | A | 246 | 81.106 | 35.186 | 3.023 | 1.00 | 34.13 | A |
| ATOM | 1373 | C | ALA | A | 246 | 81.896 | 33.718 | 1.164 | 1.00 | 33.21 | A |
| ATOM | 1374 | O | ALA | A | 246 | 81.655 | 33.958 | −0.015 | 1.00 | 33.62 | A |
| ATOM | 1375 | N | GLN | A | 247 | 83.082 | 33.281 | 1.567 | 1.00 | 31.02 | A |
| ATOM | 1376 | CA | GLN | A | 247 | 84.151 | 33.112 | 0.595 | 1.00 | 31.05 | A |
| ATOM | 1377 | CB | GLN | A | 247 | 85.476 | 32.814 | 1.310 | 1.00 | 33.25 | A |
| ATOM | 1378 | CG | GLN | A | 247 | 85.921 | 33.931 | 2.253 | 1.00 | 37.08 | A |
| ATOM | 1379 | CD | GLN | A | 247 | 87.378 | 33.831 | 2.665 | 1.00 | 40.56 | A |
| ATOM | 1380 | OE1 | GLN | A | 247 | 88.272 | 34.328 | 1.972 | 1.00 | 41.24 | A |
| ATOM | 1381 | NE2 | GLN | A | 247 | 87.626 | 33.180 | 3.794 | 1.00 | 41.86 | A |
| ATOM | 1382 | C | GLN | A | 247 | 83.895 | 32.069 | −0.488 | 1.00 | 28.53 | A |
| ATOM | 1383 | O | GLN | A | 247 | 84.544 | 32.093 | −1.527 | 1.00 | 27.93 | A |
| ATOM | 1384 | N | TYR | A | 248 | 82.934 | 31.177 | −0.267 | 1.00 | 28.01 | A |
| ATOM | 1385 | CA | TYR | A | 248 | 82.643 | 30.115 | −1.238 | 1.00 | 28.20 | A |
| ATOM | 1386 | CB | TYR | A | 248 | 82.725 | 28.757 | −0.532 | 1.00 | 24.94 | A |
| ATOM | 1387 | CG | TYR | A | 248 | 84.064 | 28.533 | 0.126 | 1.00 | 23.77 | A |
| ATOM | 1388 | CD1 | TYR | A | 248 | 85.153 | 28.073 | −0.611 | 1.00 | 23.01 | A |
| ATOM | 1389 | CE1 | TYR | A | 248 | 86.421 | 27.975 | −0.039 | 1.00 | 24.66 | A |
| ATOM | 1390 | CD2 | TYR | A | 248 | 84.270 | 28.879 | 1.464 | 1.00 | 24.01 | A |
| ATOM | 1391 | CE2 | TYR | A | 248 | 85.535 | 28.785 | 2.050 | 1.00 | 24.49 | A |
| ATOM | 1392 | CZ | TYR | A | 248 | 86.606 | 28.338 | 1.286 | 1.00 | 26.11 | A |
| ATOM | 1393 | OH | TYR | A | 248 | 87.868 | 28.305 | 1.828 | 1.00 | 27.54 | A |
| ATOM | 1394 | C | TYR | A | 248 | 81.301 | 30.249 | −1.961 | 1.00 | 28.78 | A |
| ATOM | 1395 | O | TYR | A | 248 | 80.939 | 29.405 | −2.777 | 1.00 | 30.26 | A |
| ATOM | 1396 | N | VAL | A | 249 | 80.576 | 31.319 | −1.663 | 1.00 | 28.83 | A |
| ATOM | 1397 | CA | VAL | A | 249 | 79.281 | 31.584 | −2.275 | 1.00 | 28.70 | A |
| ATOM | 1398 | CB | VAL | A | 249 | 78.625 | 32.803 | −1.601 | 1.00 | 29.37 | A |
| ATOM | 1399 | CG1 | VAL | A | 249 | 77.333 | 33.163 | −2.297 | 1.00 | 30.56 | A |
| ATOM | 1400 | CG2 | VAL | A | 249 | 78.376 | 32.488 | −0.127 | 1.00 | 31.25 | A |
| ATOM | 1401 | C | VAL | A | 249 | 79.404 | 31.837 | −3.779 | 1.00 | 28.19 | A |
| ATOM | 1402 | O | VAL | A | 249 | 80.335 | 32.497 | −4.231 | 1.00 | 27.69 | A |
| ATOM | 1403 | N | SER | A | 250 | 78.460 | 31.308 | −4.549 | 1.00 | 28.16 | A |
| ATOM | 1404 | CA | SER | A | 250 | 78.476 | 31.481 | −5.993 | 1.00 | 29.05 | A |
| ATOM | 1405 | CB | SER | A | 250 | 77.835 | 30.273 | −6.691 | 1.00 | 31.08 | A |
| ATOM | 1406 | OG | SER | A | 250 | 76.497 | 30.058 | −6.264 | 1.00 | 31.33 | A |
| ATOM | 1407 | C | SER | A | 250 | 77.737 | 32.752 | −6.376 | 1.00 | 29.69 | A |
| ATOM | 1408 | O | SER | A | 250 | 76.820 | 33.191 | −5.685 | 1.00 | 29.14 | A |
| ATOM | 1409 | N | PRO | A | 251 | 78.131 | 33.361 | −7.494 | 1.00 | 29.35 | A |
| ATOM | 1410 | CD | PRO | A | 251 | 79.147 | 32.917 | −8.463 | 1.00 | 29.28 | A |
| ATOM | 1411 | CA | PRO | A | 251 | 77.477 | 34.592 | −7.934 | 1.00 | 30.27 | A |
| ATOM | 1412 | CB | PRO | A | 251 | 78.214 | 34.932 | −9.235 | 1.00 | 29.87 | A |
| ATOM | 1413 | CG | PRO | A | 251 | 78.687 | 33.588 | −9.730 | 1.00 | 30.48 | A |
| ATOM | 1414 | C | PRO | A | 251 | 75.961 | 34.495 | −8.114 | 1.00 | 30.86 | A |
| ATOM | 1415 | O | PRO | A | 251 | 75.246 | 35.442 | −7.801 | 1.00 | 33.28 | A |
| ATOM | 1416 | N | GLU | A | 252 | 75.459 | 33.367 | −8.602 | 1.00 | 30.19 | A |
| ATOM | 1417 | CA | GLU | A | 252 | 74.014 | 33.244 | −8.802 | 1.00 | 30.91 | A |
| ATOM | 1418 | CB | GLU | A | 252 | 73.649 | 31.903 | −9.449 | 1.00 | 30.61 | A |
| ATOM | 1419 | CG | GLU | A | 252 | 74.162 | 30.682 | −8.689 | 1.00 | 33.88 | A |
| ATOM | 1420 | CD | GLU | A | 252 | 75.493 | 30.171 | −9.219 | 1.00 | 32.82 | A |
| ATOM | 1421 | OE1 | GLU | A | 252 | 76.277 | 30.987 | −9.747 | 1.00 | 35.25 | A |
| ATOM | 1422 | OE2 | GLU | A | 252 | 75.756 | 28.956 | −9.095 | 1.00 | 32.14 | A |
| ATOM | 1423 | C | GLU | A | 252 | 73.260 | 33.390 | −7.494 | 1.00 | 32.09 | A |
| ATOM | 1424 | O | GLU | A | 252 | 72.157 | 33.928 | −7.469 | 1.00 | 32.01 | A |
| ATOM | 1425 | N | LEU | A | 253 | 73.852 | 32.900 | −6.408 | 1.00 | 33.87 | A |
| ATOM | 1426 | CA | LEU | A | 253 | 73.230 | 32.988 | −5.096 | 1.00 | 35.16 | A |
| ATOM | 1427 | CB | LEU | A | 253 | 74.031 | 32.183 | −4.078 | 1.00 | 37.63 | A |
| ATOM | 1428 | CG | LEU | A | 253 | 73.371 | 30.937 | −3.479 | 1.00 | 40.98 | A |
| ATOM | 1429 | CD1 | LEU | A | 253 | 74.302 | 30.321 | −2.433 | 1.00 | 42.16 | A |
| ATOM | 1430 | CD2 | LEU | A | 253 | 72.043 | 31.314 | −2.835 | 1.00 | 40.33 | A |
| ATOM | 1431 | C | LEU | A | 253 | 73.148 | 34.445 | −4.640 | 1.00 | 37.20 | A |
| ATOM | 1432 | O | LEU | A | 253 | 72.300 | 34.810 | −3.820 | 1.00 | 37.33 | A |
| ATOM | 1433 | N | LEU | A | 254 | 74.036 | 35.276 | −5.171 | 1.00 | 36.48 | A |
| ATOM | 1434 | CA | LEU | A | 254 | 74.052 | 36.686 | −4.816 | 1.00 | 37.76 | A |
| ATOM | 1435 | CB | LEU | A | 254 | 75.481 | 37.235 | −4.890 | 1.00 | 35.47 | A |
| ATOM | 1436 | CG | LEU | A | 254 | 76.512 | 36.692 | −3.899 | 1.00 | 32.31 | A |
| ATOM | 1437 | CD1 | LEU | A | 254 | 77.839 | 37.416 | −4.108 | 1.00 | 32.18 | A |
| ATOM | 1438 | CD2 | LEU | A | 254 | 76.019 | 36.891 | −2.474 | 1.00 | 29.68 | A |
| ATOM | 1439 | C | LEU | A | 254 | 73.150 | 37.496 | −5.737 | 1.00 | 39.82 | A |
| ATOM | 1440 | O | LEU | A | 254 | 72.772 | 38.615 | −5.409 | 1.00 | 39.15 | A |
| ATOM | 1441 | N | THR | A | 255 | 72.805 | 36.919 | −6.885 | 1.00 | 44.09 | A |
| ATOM | 1442 | CA | THR | A | 255 | 71.959 | 37.594 | −7.865 | 1.00 | 47.95 | A |
| ATOM | 1443 | CB | THR | A | 255 | 72.591 | 37.544 | −9.276 | 1.00 | 48.10 | A |
| ATOM | 1444 | OG1 | THR | A | 255 | 73.924 | 38.072 | −9.227 | 1.00 | 48.96 | A |
| ATOM | 1445 | CG2 | THR | A | 255 | 71.768 | 38.376 | −10.253 | 1.00 | 50.10 | A |
| ATOM | 1446 | C | THR | A | 255 | 70.538 | 37.032 | −7.954 | 1.00 | 49.95 | A |
| ATOM | 1447 | O | THR | A | 255 | 69.631 | 37.537 | −7.300 | 1.00 | 51.66 | A |
| ATOM | 1448 | N | GLU | A | 256 | 70.344 | 35.994 | −8.764 | 1.00 | 52.84 | A |

-continued

| ATOM | 1449 | CA | GLU | A | 256 | 69.018 | 35.395 | −8.939 | 1.00 | 55.77 | A |
| --- | --- | --- | --- | --- | --- | --- | --- | --- | --- | --- | --- |
| ATOM | 1450 | CB | GLU | A | 256 | 69.036 | 34.342 | −10.061 | 1.00 | 55.24 | A |
| ATOM | 1451 | CG | GLU | A | 256 | 70.360 | 34.171 | −10.790 | 0.00 | 55.40 | A |
| ATOM | 1452 | CD | GLU | A | 256 | 70.699 | 35.348 | −11.681 | 0.00 | 55.34 | A |
| ATOM | 1453 | OE1 | GLU | A | 256 | 69.831 | 35.760 | −12.480 | 0.00 | 55.36 | A |
| ATOM | 1454 | OE2 | GLU | A | 256 | 71.837 | 35.852 | −11.593 | 0.00 | 55.36 | A |
| ATOM | 1455 | C | GLU | A | 256 | 68.451 | 34.743 | −7.677 | 1.00 | 57.04 | A |
| ATOM | 1456 | O | GLU | A | 256 | 67.396 | 34.107 | −7.732 | 1.00 | 56.82 | A |
| ATOM | 1457 | N | LYS | A | 257 | 69.137 | 34.911 | −6.549 | 1.00 | 58.87 | A |
| ATOM | 1458 | CA | LYS | A | 257 | 68.711 | 34.308 | −5.286 | 1.00 | 60.38 | A |
| ATOM | 1459 | CB | LYS | A | 257 | 67.607 | 35.151 | −4.623 | 1.00 | 60.84 | A |
| ATOM | 1460 | CG | LYS | A | 257 | 66.327 | 35.322 | −5.430 | 1.00 | 60.71 | A |
| ATOM | 1461 | CD | LYS | A | 257 | 65.352 | 36.261 | −4.731 | 0.00 | 60.78 | A |
| ATOM | 1462 | CE | LYS | A | 257 | 64.943 | 35.734 | −3.363 | 0.00 | 60.77 | A |
| ATOM | 1463 | NZ | LYS | A | 257 | 63.992 | 36.650 | −2.674 | 0.00 | 60.78 | A |
| ATOM | 1464 | C | LYS | A | 257 | 68.227 | 32.878 | −5.546 | 1.00 | 61.40 | A |
| ATOM | 1465 | O | LYS | A | 257 | 67.046 | 32.565 | −5.389 | 1.00 | 61.84 | A |
| ATOM | 1466 | N | SER | A | 258 | 69.160 | 32.020 | −5.958 | 1.00 | 61.26 | A |
| ATOM | 1467 | CA | SER | A | 258 | 68.865 | 30.622 | −6.271 | 1.00 | 61.31 | A |
| ATOM | 1468 | CB | SER | A | 258 | 68.105 | 30.548 | −7.605 | 1.00 | 62.95 | A |
| ATOM | 1469 | OG | SER | A | 258 | 68.707 | 31.374 | −8.596 | 1.00 | 63.22 | A |
| ATOM | 1470 | C | SER | A | 258 | 70.149 | 29.771 | −6.334 | 1.00 | 60.39 | A |
| ATOM | 1471 | O | SER | A | 258 | 71.257 | 30.312 | −6.329 | 1.00 | 60.58 | A |
| ATOM | 1472 | N | ALA | A | 259 | 70.001 | 28.447 | −6.393 | 1.00 | 57.62 | A |
| ATOM | 1473 | CA | ALA | A | 259 | 71.159 | 27.551 | −6.441 | 1.00 | 54.75 | A |
| ATOM | 1474 | CB | ALA | A | 259 | 71.670 | 27.289 | −5.025 | 1.00 | 54.90 | A |
| ATOM | 1475 | C | ALA | A | 259 | 70.890 | 26.218 | −7.147 | 1.00 | 52.13 | A |
| ATOM | 1476 | O | ALA | A | 259 | 69.759 | 25.726 | −7.175 | 1.00 | 51.63 | A |
| ATOM | 1477 | N | CYS | A | 260 | 71.945 | 25.641 | −7.712 | 1.00 | 48.49 | A |
| ATOM | 1478 | CA | CYS | A | 260 | 71.848 | 24.371 | −8.417 | 1.00 | 44.82 | A |
| ATOM | 1479 | CB | CYS | A | 260 | 71.499 | 24.596 | −9.890 | 1.00 | 46.78 | A |
| ATOM | 1480 | SG | CYS | A | 260 | 72.731 | 25.549 | −10.821 | 1.00 | 53.48 | A |
| ATOM | 1481 | C | CYS | A | 260 | 73.176 | 23.643 | −8.310 | 1.00 | 41.48 | A |
| ATOM | 1482 | O | CYS | A | 260 | 74.085 | 24.090 | −7.612 | 1.00 | 41.05 | A |
| ATOM | 1483 | N | LYS | A | 261 | 73.288 | 22.525 | −9.012 | 1.00 | 37.76 | A |
| ATOM | 1484 | CA | LYS | A | 261 | 74.503 | 21.729 | −8.980 | 1.00 | 34.90 | A |
| ATOM | 1485 | CB | LYS | A | 261 | 74.394 | 20.587 | −9.990 | 1.00 | 35.93 | A |
| ATOM | 1486 | CG | LYS | A | 261 | 73.239 | 19.644 | −9.691 | 1.00 | 38.46 | A |
| ATOM | 1487 | CD | LYS | A | 261 | 73.239 | 18.430 | −10.601 | 1.00 | 39.70 | A |
| ATOM | 1488 | CE | LYS | A | 261 | 72.117 | 17.474 | −10.229 | 1.00 | 40.95 | A |
| ATOM | 1489 | NZ | LYS | A | 261 | 72.076 | 16.269 | −11.110 | 1.00 | 41.64 | A |
| ATOM | 1490 | C | LYS | A | 261 | 75.751 | 22.556 | −9.247 | 1.00 | 32.19 | A |
| ATOM | 1491 | O | LYS | A | 261 | 76.780 | 22.366 | −8.595 | 1.00 | 30.08 | A |
| ATOM | 1492 | N | SER | A | 262 | 75.651 | 23.480 | −10.200 | 1.00 | 30.41 | A |
| ATOM | 1493 | CA | SER | A | 262 | 76.771 | 24.337 | −10.556 | 1.00 | 27.88 | A |
| ATOM | 1494 | CB | SER | A | 262 | 76.361 | 25.333 | −11.643 | 1.00 | 29.04 | A |
| ATOM | 1495 | OG | SER | A | 262 | 76.398 | 24.732 | −12.921 | 1.00 | 32.20 | A |
| ATOM | 1496 | C | SER | A | 262 | 77.325 | 25.095 | −9.360 | 1.00 | 27.01 | A |
| ATOM | 1497 | O | SER | A | 262 | 78.515 | 25.403 | −9.320 | 1.00 | 27.37 | A |
| ATOM | 1498 | N | SER | A | 263 | 76.469 | 25.406 | −8.392 | 1.00 | 24.83 | A |
| ATOM | 1499 | CA | SER | A | 263 | 76.924 | 26.115 | −7.201 | 1.00 | 26.29 | A |
| ATOM | 1500 | CB | SER | A | 263 | 75.758 | 26.354 | −6.242 | 1.00 | 26.59 | A |
| ATOM | 1501 | OG | SER | A | 263 | 74.830 | 27.254 | −6.832 | 1.00 | 30.68 | A |
| ATOM | 1502 | C | SER | A | 263 | 78.039 | 25.337 | −6.506 | 1.00 | 25.15 | A |
| ATOM | 503 | O | SER | A | 263 | 79.034 | 25.924 | −6.078 | 1.00 | 25.38 | A |
| ATOM | 1504 | N | ASP | A | 264 | 77.884 | 24.019 | −6.396 | 1.00 | 23.51 | A |
| ATOM | 1505 | CA | ASP | A | 264 | 78.930 | 23.215 | −5.773 | 1.00 | 22.06 | A |
| ATOM | 1506 | CB | ASP | A | 264 | 78.500 | 21.754 | −5.613 | 1.00 | 23.87 | A |
| ATOM | 1507 | CG | ASP | A | 264 | 77.378 | 21.577 | −4.599 | 1.00 | 27.11 | A |
| ATOM | 1508 | OD1 | ASP | A | 264 | 77.276 | 22.402 | −3.662 | 1.00 | 25.60 | A |
| ATOM | 1509 | OD2 | ASP | A | 264 | 76.612 | 20.599 | 4.730 | 1.00 | 26.16 | A |
| ATOM | 1510 | C | ASP | A | 264 | 80.175 | 23.267 | −6.642 | 1.00 | 20.62 | A |
| ATOM | 1511 | O | ASP | A | 264 | 81.289 | 23.339 | −6.129 | 1.00 | 20.01 | A |
| ATOM | 1512 | N | LEU | A | 265 | 79.985 | 23.246 | −7.959 | 1.00 | 18.87 | A |
| ATOM | 1513 | CA | LEU | A | 265 | 81.113 | 23.275 | −8.876 | 1.00 | 20.02 | A |
| ATOM | 1514 | CB | LEU | A | 265 | 80.634 | 23.131 | −10.322 | 1.00 | 19.94 | A |
| ATOM | 1515 | CG | LEU | A | 265 | 80.037 | 21.763 | −10.672 | 1.00 | 21.08 | A |
| ATOM | 1516 | CD1 | LEU | A | 265 | 79.580 | 21.771 | −12.122 | 1.00 | 22.16 | A |
| ATOM | 1517 | CD2 | LEU | A | 265 | 81.077 | 20.659 | −10.449 | 1.00 | 16.76 | A |
| ATOM | 1518 | C | LEU | A | 265 | 81.910 | 24.552 | −8.705 | 1.00 | 20.53 | A |
| ATOM | 1519 | O | LEU | A | 265 | 83.130 | 24.563 | −8.881 | 1.00 | 21.94 | A |
| ATOM | 1520 | N | TRP | A | 266 | 81.221 | 25.633 | −8.361 | 1.00 | 21.74 | A |
| ATOM | 1521 | CA | TRP | A | 266 | 81.897 | 26.899 | −8.138 | 1.00 | 20.89 | A |
| ATOM | 1522 | CB | TRP | A | 266 | 80.879 | 28.031 | −7.960 | 1.00 | 22.97 | A |
| ATOM | 1523 | CG | TRP | A | 266 | 81.477 | 29.309 | −7.411 | 1.00 | 24.01 | A |
| ATOM | 1524 | CD2 | TRP | A | 266 | 81.814 | 30.487 | −8.152 | 1.00 | 23.31 | A |
| ATOM | 1525 | CE2 | TRP | A | 266 | 82.391 | 31.404 | −7.243 | 1.00 | 23.27 | A |
| ATOM | 1526 | CE3 | TRP | A | 266 | 81.689 | 30.858 | −9.497 | 1.00 | 24.79 | A |
| ATOM | 1527 | CD1 | TRP | A | 266 | 81.850 | 29.555 | −6.116 | 1.00 | 24.55 | A |

-continued

| ATOM | 1528 | NE1 | TRP | A | 266 | 82.401 | 30.811 | −6.009 | 1.00 | 23.65 | A |
| ATOM | 1529 | CZ2 | TRP | A | 266 | 82.839 | 32.663 | −7.636 | 1.00 | 22.89 | A |
| ATOM | 1530 | CZ3 | TRP | A | 266 | 82.139 | 32.116 | −9.887 | 1.00 | 23.30 | A |
| ATOM | 1531 | CH2 | TRP | A | 266 | 82.705 | 33.000 | −8.959 | 1.00 | 23.32 | A |
| ATOM | 1532 | C | TRP | A | 266 | 82.739 | 26.735 | −6.877 | 1.00 | 20.30 | A |
| ATOM | 1533 | O | TRP | A | 266 | 83.913 | 27.102 | −6.853 | 1.00 | 20.60 | A |
| ATOM | 1534 | N | ALA | A | 267 | 82.141 | 26.175 | −5.832 | 1.00 | 18.06 | A |
| ATOM | 1535 | CA | ALA | A | 267 | 82.868 | 25.966 | −4.584 | 1.00 | 18.46 | A |
| ATOM | 1536 | CB | ALA | A | 267 | 81.984 | 25.254 | −3.561 | 1.00 | 17.96 | A |
| ATOM | 1537 | C | ALA | A | 267 | 84.112 | 25.132 | −4.877 | 1.00 | 18.05 | A |
| ATOM | 1538 | O | ALA | A | 267 | 85.173 | 25.340 | −4.287 | 1.00 | 17.35 | A |
| ATOM | 1539 | N | LEU | A | 268 | 83.982 | 24.190 | 5.799 | 1.00 | 17.12 | A |
| ATOM | 1540 | CA | LEU | A | 268 | 85.118 | 23.355 | −6.157 | 1.00 | 18.45 | A |
| ATOM | 1541 | CB | LEU | A | 268 | 84.703 | 22.326 | −7.204 | 1.00 | 17.67 | A |
| ATOM | 1542 | CG | LEU | A | 268 | 85.809 | 21.436 | −7.772 | 1.00 | 16.93 | A |
| ATOM | 1543 | CD1 | LEU | A | 268 | 86.333 | 20.495 | −6.704 | 1.00 | 17.10 | A |
| ATOM | 1544 | CD2 | LEU | A | 268 | 85.258 | 20.651 | −8.953 | 1.00 | 13.46 | A |
| ATOM | 1545 | C | LEU | A | 268 | 86.232 | 24.249 | −6.705 | 1.00 | 19.64 | A |
| ATOM | 1546 | O | LEU | A | 268 | 87.389 | 24.129 | −6.306 | 1.00 | 18.99 | A |
| ATOM | 1547 | N | GLY | A | 269 | 85.869 | 25.158 | −7.606 | 1.00 | 19.16 | A |
| ATOM | 1548 | CA | GLY | A | 269 | 86.854 | 26.057 | −8.178 | 1.00 | 18.25 | A |
| ATOM | 1549 | C | GLY | A | 269 | 87.604 | 26.804 | −7.103 | 1.00 | 20.30 | A |
| ATOM | 1550 | O | GLY | A | 269 | 88.825 | 26.960 | −7.178 | 1.00 | 20.24 | A |
| ATOM | 1551 | N | CYS | A | 270 | 86.874 | 27.266 | −6.090 | 1.00 | 20.20 | A |
| ATOM | 1552 | CA | CYS | A | 270 | 87.486 | 27.996 | −4.986 | 1.00 | 20.73 | A |
| ATOM | 1553 | CB | CYS | A | 270 | 86.418 | 28.523 | −4.031 | 1.00 | 21.05 | A |
| ATOM | 1554 | SG | CYS | A | 270 | 85.292 | 29.703 | −4.752 | 1.00 | 23.98 | A |
| ATOM | 1555 | C | CYS | A | 270 | 88.417 | 27.082 | −4.206 | 1.00 | 20.77 | A |
| ATOM | 1556 | O | CYS | A | 270 | 89.550 | 27.449 | −3.878 | 1.00 | 22.00 | A |
| ATOM | 1557 | N | ILE | A | 271 | 87.927 | 25.886 | −3.907 | 1.00 | 19.32 | A |
| ATOM | 1558 | CA | ILE | A | 271 | 88.704 | 24.921 | −3.147 | 1.00 | 18.46 | A |
| ATOM | 1559 | CB | ILE | A | 271 | 87.872 | 23.668 | −2.861 | 1.00 | 15.71 | A |
| ATOM | 1560 | CG2 | ILE | A | 271 | 88.722 | 22.607 | −2.182 | 1.00 | 16.51 | A |
| ATOM | 1561 | CG1 | ILE | A | 271 | 86.688 | 24.051 | −1.974 | 1.00 | 14.97 | A |
| ATOM | 1562 | CD1 | ILE | A | 271 | 85.785 | 22.891 | −1.639 | 1.00 | 17.80 | A |
| ATOM | 1563 | C | ILE | A | 271 | 90.001 | 24.546 | −3.856 | 1.00 | 19.30 | A |
| ATOM | 1564 | O | ILE | A | 271 | 91.062 | 24.532 | −3.242 | 1.00 | 21.30 | A |
| ATOM | 1565 | N | ILE | A | 272 | 89.915 | 24.253 | −5.147 | 1.00 | 20.07 | A |
| ATOM | 1566 | CA | ILE | A | 272 | 91.094 | 23.894 | −5.906 | 1.00 | 21.50 | A |
| ATOM | 1567 | CB | ILE | A | 272 | 90.758 | 23.693 | −7.385 | 1.00 | 22.57 | A |
| ATOM | 1568 | CG2 | ILE | A | 272 | 92.041 | 23.498 | −8.184 | 1.00 | 21.91 | A |
| ATOM | 1569 | CG1 | ILE | A | 272 | 89.818 | 22.495 | −7.542 | 1.00 | 23.57 | A |
| ATOM | 1570 | CD1 | ILE | A | 272 | 89.314 | 22.294 | −8.949 | 1.00 | 24.20 | A |
| ATOM | 1571 | C | ILE | A | 272 | 92.112 | 25.010 | −5.794 | 1.00 | 22.90 | A |
| ATOM | 1572 | O | ILE | A | 272 | 93.287 | 24.783 | −5.507 | 1.00 | 21.82 | A |
| ATOM | 1573 | N | TYR | A | 273 | 91.638 | 26.226 | −6.028 | 1.00 | 24.81 | A |
| ATOM | 1574 | CA | TYR | A | 273 | 92.478 | 27.400 | −5.969 | 1.00 | 25.15 | A |
| ATOM | 1575 | CB | TYR | A | 273 | 91.630 | 28.632 | −6.255 | 1.00 | 26.04 | A |
| ATOM | 1576 | CG | TYR | A | 273 | 92.385 | 29.931 | −6.173 | 1.00 | 27.80 | A |
| ATOM | 1577 | CD1 | TYR | A | 273 | 92.715 | 30.500 | −4.939 | 1.00 | 27.53 | A |
| ATOM | 1578 | CE1 | TYR | A | 273 | 93.405 | 31.708 | −4.870 | 1.00 | 27.30 | A |
| ATOM | 1579 | CD2 | TYR | A | 273 | 92.765 | 30.602 | −7.333 | 1.00 | 27.17 | A |
| ATOM | 1580 | CE2 | TYR | A | 273 | 93.448 | 31.804 | −7.277 | 1.00 | 26.68 | A |
| ATOM | 1581 | CZ | TYR | A | 273 | 93.766 | 32.355 | −6.050 | 1.00 | 28.05 | A |
| ATOM | 1582 | OH | TYR | A | 273 | 94.433 | 33.562 | −6.018 | 1.00 | 30.80 | A |
| ATOM | 1583 | C | TYR | A | 273 | 93.139 | 27.521 | −4.599 | 1.00 | 26.05 | A |
| ATOM | 1584 | O | TYR | A | 273 | 94.310 | 27.889 | −4.489 | 1.00 | 24.45 | A |
| ATOM | 1585 | N | GLN | A | 274 | 92.380 | 27.205 | −3.556 | 1.00 | 25.95 | A |
| ATOM | 1586 | CA | GLN | A | 274 | 92.896 | 27.299 | −2.202 | 1.00 | 25.98 | A |
| ATOM | 1587 | CB | GLN | A | 274 | 91.743 | 27.209 | −1.199 | 1.00 | 25.56 | A |
| ATOM | 1588 | CG | GLN | A | 274 | 92.169 | 27.422 | 0.233 | 1.00 | 25.42 | A |
| ATOM | 1589 | CD | GLN | A | 274 | 90.990 | 27.571 | 1.161 | 1.00 | 28.69 | A |
| ATOM | 1590 | OE1 | GLN | A | 274 | 89.838 | 27.506 | 0.732 | 1.00 | 29.84 | A |
| ATOM | 1591 | NE2 | GLN | A | 274 | 91.267 | 27.774 | 2.445 | 1.00 | 29.83 | A |
| ATOM | 1592 | C | GLN | A | 274 | 93.951 | 26.231 | −1.915 | 1.00 | 25.08 | A |
| ATOM | 1593 | O | GLN | A | 274 | 94.862 | 26.452 | −1.120 | 1.00 | 24.38 | A |
| ATOM | 1594 | N | LEU | A | 275 | 93.838 | 25.081 | −2.567 | 1.00 | 24.42 | A |
| ATOM | 1595 | CA | LEU | A | 275 | 94.813 | 24.006 | −2.369 | 1.00 | 25.43 | A |
| ATOM | 1596 | CB | LEU | A | 275 | 94.335 | 22.713 | −3.035 | 1.00 | 22.95 | A |
| ATOM | 1597 | CG | LEU | A | 275 | 93.193 | 21.959 | −2.354 | 1.00 | 25.67 | A |
| ATOM | 1598 | CD1 | LEU | A | 275 | 92.817 | 20.702 | −3.154 | 1.00 | 22.16 | A |
| ATOM | 1599 | CD2 | LEU | A | 275 | 93.633 | 21.580 | −0.950 | 1.00 | 23.32 | A |
| ATOM | 1600 | C | LEU | A | 275 | 96.171 | 24.376 | −2.948 | 1.00 | 25.40 | A |
| ATOM | 1601 | O | LEU | A | 275 | 97.212 | 24.071 | −2.376 | 1.00 | 25.87 | A |
| ATOM | 1602 | N | VAL | A | 276 | 96.153 | 25.039 | −4.094 | 1.00 | 25.78 | A |
| ATOM | 1603 | CA | VAL | A | 276 | 97.384 | 25.419 | −4.759 | 1.00 | 26.12 | A |
| ATOM | 1604 | CB | VAL | A | 276 | 97.170 | 25.522 | −6.280 | 1.00 | 26.14 | A |
| ATOM | 1605 | CG1 | VAL | A | 276 | 98.492 | 25.783 | −6.962 | 1.00 | 24.46 | A |
| ATOM | 1606 | CG2 | VAL | A | 276 | 96.531 | 24.248 | −6.804 | 1.00 | 22.55 | A |

-continued

| | | | | | | | | | | |
|---|---|---|---|---|---|---|---|---|---|---|
| ATOM | 1607 | C | VAL | A | 276 | 97.990 | 26.735 | −4.275 | 1.00 | 27.83 | A |
| ATOM | 1608 | O | VAL | A | 276 | 99.210 | 26.849 | −4.164 | 1.00 | 29.55 | A |
| ATOM | 1609 | N | ALA | A | 277 | 97.148 | 27.723 | −3.990 | 1.00 | 26.88 | A |
| ATOM | 1610 | CA | ALA | A | 277 | 97.639 | 29.023 | −3.549 | 1.00 | 26.50 | A |
| ATOM | 1611 | CB | ALA | A | 277 | 96.765 | 30.126 | −4.122 | 1.00 | 24.49 | A |
| ATOM | 1612 | C | ALA | A | 277 | 97.740 | 29.175 | −2.035 | 1.00 | 26.79 | A |
| ATOM | 1613 | O | ALA | A | 277 | 98.465 | 30.042 | −1.548 | 1.00 | 28.26 | A |
| ATOM | 1614 | N | GLY | A | 278 | 97.020 | 28.343 | −1.290 | 1.00 | 26.17 | A |
| ATOM | 1615 | CA | GLY | A | 278 | 97.074 | 28.430 | 0.159 | 1.00 | 24.63 | A |
| ATOM | 1616 | C | GLY | A | 278 | 95.971 | 29.272 | 0.780 | 1.00 | 25.52 | A |
| ATOM | 1617 | O | GLY | A | 278 | 95.793 | 29.259 | 1.998 | 1.00 | 27.25 | A |
| ATOM | 1618 | N | LEU | A | 279 | 95.229 | 29.998 | −0.051 | 1.00 | 24.94 | A |
| ATOM | 1619 | CA | LEU | A | 279 | 94.130 | 30.849 | 0.408 | 1.00 | 25.58 | A |
| ATOM | 1620 | CB | LEU | A | 279 | 94.603 | 32.302 | 0.522 | 1.00 | 27.65 | A |
| ATOM | 1621 | CG | LEU | A | 279 | 95.748 | 32.631 | 1.470 | 1.00 | 29.35 | A |
| ATOM | 1622 | CD1 | LEU | A | 279 | 96.365 | 33.958 | 1.075 | 1.00 | 30.47 | A |
| ATOM | 1623 | CD2 | LEU | A | 279 | 95.232 | 32.671 | 2.892 | 1.00 | 29.70 | A |
| ATOM | 1624 | C | LEU | A | 279 | 92.987 | 30.822 | −0.605 | 1.00 | 25.19 | A |
| ATOM | 1625 | O | LEU | A | 279 | 93.201 | 30.525 | −1.781 | 1.00 | 25.34 | A |
| ATOM | 1626 | N | PRO | A | 280 | 91.755 | 31.126 | −0.165 | 1.00 | 23.60 | A |
| ATOM | 1627 | CD | PRO | A | 280 | 91.306 | 31.357 | 1.216 | 1.00 | 22.97 | A |
| ATOM | 1628 | CA | PRO | A | 280 | 90.628 | 31.133 | −1.103 | 1.00 | 23.81 | A |
| ATOM | 1629 | CB | PRO | A | 280 | 89.417 | 31.338 | −0.195 | 1.00 | 25.19 | A |
| ATOM | 1630 | CG | PRO | A | 280 | 89.982 | 32.041 | 1.008 | 1.00 | 25.48 | A |
| ATOM | 1631 | C | PRO | A | 280 | 90.855 | 32.295 | −2.083 | 1.00 | 26.26 | A |
| ATOM | 1632 | O | PRO | A | 280 | 91.632 | 33.207 | −1.792 | 1.00 | 25.42 | A |
| ATOM | 1633 | N | PRO | A | 281 | 90.178 | 32.284 | −3.243 | 1.00 | 26.49 | A |
| ATOM | 1634 | CD | PRO | A | 281 | 89.182 | 31.285 | −3.651 | 1.00 | 27.13 | A |
| ATOM | 1635 | CA | PRO | A | 281 | 90.307 | 33.316 | −4.281 | 1.00 | 27.25 | A |
| ATOM | 1636 | CB | PRO | A | 281 | 89.522 | 32.727 | −5.463 | 1.00 | 26.75 | A |
| ATOM | 1637 | CG | PRO | A | 281 | 89.354 | 31.291 | −5.136 | 1.00 | 25.29 | A |
| ATOM | 1638 | C | PRO | A | 281 | 89.817 | 34.724 | −3.954 | 1.00 | 27.30 | A |
| ATOM | 1639 | O | PRO | A | 281 | 90.497 | 35.709 | −4.238 | 1.00 | 27.67 | A |
| ATOM | 1640 | N | PHE | A | 282 | 88.623 | 34.817 | −3.388 | 1.00 | 27.79 | A |
| ATOM | 1641 | CA | PHE | A | 282 | 88.034 | 36.107 | −3.066 | 1.00 | 28.37 | A |
| ATOM | 1642 | CB | PHE | A | 282 | 86.563 | 36.086 | −3.467 | 1.00 | 27.77 | A |
| ATOM | 1643 | CG | PHE | A | 282 | 86.335 | 35.557 | −4.857 | 1.00 | 29.06 | A |
| ATOM | 1644 | CD1 | PHE | A | 282 | 86.454 | 36.392 | −5.965 | 1.00 | 28.74 | A |
| ATOM | 1645 | CD2 | PHE | A | 282 | 86.077 | 34.207 | −5.063 | 1.00 | 25.80 | A |
| ATOM | 1646 | CE1 | PHE | A | 282 | 86.324 | 35.887 | −7.255 | 1.00 | 28.50 | A |
| ATOM | 1647 | CE2 | PHE | A | 282 | 85.947 | 33.695 | −6.346 | 1.00 | 26.04 | A |
| ATOM | 1648 | CZ | PHE | A | 282 | 86.071 | 34.535 | −7.444 | 1.00 | 28.02 | A |
| ATOM | 1649 | C | PHE | A | 282 | 88.184 | 36.426 | −1.589 | 1.00 | 29.95 | A |
| ATOM | 1650 | O | PHE | A | 282 | 87.600 | 35.763 | −0.741 | 1.00 | 32.95 | A |
| ATOM | 1651 | N | ARG | A | 283 | 88.977 | 37.445 | −1.285 | 1.00 | 32.36 | A |
| ATOM | 1652 | CA | ARG | A | 283 | 89.215 | 37.843 | 0.100 | 1.00 | 33.06 | A |
| ATOM | 1653 | CB | ARG | A | 283 | 90.622 | 37.432 | 0.520 | 1.00 | 33.69 | A |
| ATOM | 1654 | CG | ARG | A | 283 | 90.990 | 36.006 | 0.151 | 1.00 | 36.29 | A |
| ATOM | 1655 | CD | ARG | A | 283 | 92.341 | 35.635 | 0.727 | 1.00 | 38.81 | A |
| ATOM | 1656 | NE | ARG | A | 283 | 93.415 | 36.423 | 0.133 | 1.00 | 41.73 | A |
| ATOM | 1657 | CZ | ARG | A | 283 | 93.783 | 36.338 | −1.142 | 1.00 | 44.14 | A |
| ATOM | 1658 | NH1 | ARG | A | 283 | 93.162 | 35.497 | −1.958 | 1.00 | 45.19 | A |
| ATOM | 1659 | NH2 | ARG | A | 283 | 94.772 | 37.094 | −1.604 | 1.00 | 44.57 | A |
| ATOM | 1660 | C | ARG | A | 283 | 89.065 | 39.353 | 0.267 | 1.00 | 32.44 | A |
| ATOM | 1661 | O | ARG | A | 283 | 89.429 | 40.118 | −0.624 | 1.00 | 31.91 | A |
| ATOM | 1662 | N | ALA | A | 284 | 88.527 | 39.777 | 1.406 | 1.00 | 33.21 | A |
| ATOM | 1663 | CA | ALA | A | 284 | 88.348 | 41.199 | 1.682 | 1.00 | 32.82 | A |
| ATOM | 1664 | CB | ALA | A | 284 | 87.265 | 41.777 | 0.782 | 1.00 | 32.40 | A |
| ATOM | 1665 | C | ALA | A | 284 | 88.004 | 41.445 | 3.147 | 1.00 | 32.98 | A |
| ATOM | 1666 | O | ALA | A | 284 | 87.779 | 40.502 | 3.913 | 1.00 | 32.53 | A |
| ATOM | 1667 | N | GLY | A | 285 | 87.961 | 42.723 | 3.520 | 1.00 | 32.60 | A |
| ATOM | 1668 | CA | GLY | A | 285 | 87.666 | 43.112 | 4.887 | 1.00 | 30.00 | A |
| ATOM | 1669 | C | GLY | A | 285 | 86.355 | 42.637 | 5.486 | 1.00 | 29.37 | A |
| ATOM | 1670 | O | GLY | A | 285 | 86.287 | 42.366 | 6.685 | 1.00 | 29.35 | A |
| ATOM | 1671 | N | ASN | A | 286 | 85.302 | 42.547 | 4.685 | 1.00 | 28.99 | A |
| ATOM | 1672 | CA | ASN | A | 286 | 84.024 | 42.097 | 5.226 | 1.00 | 29.58 | A |
| ATOM | 1673 | CB | ASN | A | 286 | 83.238 | 43.281 | 5.801 | 1.00 | 29.54 | A |
| ATOM | 1674 | CG | ASN | A | 286 | 82.958 | 44.356 | 4.764 | 1.00 | 29.60 | A |
| ATOM | 1675 | OD1 | ASN | A | 286 | 82.350 | 44.092 | 3.720 | 1.00 | 26.48 | A |
| ATOM | 1676 | ND2 | ASN | A | 286 | 83.400 | 45.575 | 5.049 | 1.00 | 25.96 | A |
| ATOM | 1677 | C | ASN | A | 286 | 83.196 | 41.378 | 4.182 | 1.00 | 30.16 | A |
| ATOM | 1678 | O | ASN | A | 286 | 83.551 | 41.357 | 3.004 | 1.00 | 31.70 | A |
| ATOM | 1679 | N | GLU | A | 287 | 82.084 | 40.796 | 4.613 | 1.00 | 31.14 | A |
| ATOM | 1680 | CA | GLU | A | 287 | 81.225 | 40.051 | 3.699 | 1.00 | 32.53 | A |
| ATOM | 1681 | CB | GLU | A | 287 | 79.943 | 39.600 | 4.397 | 1.00 | 35.66 | A |
| ATOM | 1682 | CG | GLU | A | 287 | 80.168 | 38.813 | 5.666 | 1.00 | 43.05 | A |
| ATOM | 1683 | CD | GLU | A | 287 | 79.138 | 37.707 | 5.856 | 1.00 | 47.79 | A |
| ATOM | 1684 | OE1 | GLU | A | 287 | 77.933 | 37.959 | 5.616 | 1.00 | 49.01 | A |
| ATOM | 1685 | OE2 | GLU | A | 287 | 79.539 | 36.588 | 6.256 | 1.00 | 48.82 | A |

-continued

| | | | | | | | | | | |
|---|---|---|---|---|---|---|---|---|---|---|
| ATOM | 1686 | C | GLU | A | 287 | 80.853 | 40.837 | 2.457 | 1.00 | 30.19 | A |
| ATOM | 1687 | O | GLU | A | 287 | 80.986 | 40.332 | 1.343 | 1.00 | 30.33 | A |
| ATOM | 1688 | N | TYR | A | 288 | 80.385 | 42.066 | 2.653 | 1.00 | 29.13 | A |
| ATOM | 1689 | CA | TYR | A | 288 | 79.972 | 42.922 | 1.541 | 1.00 | 27.98 | A |
| ATOM | 1690 | CB | TYR | A | 288 | 79.573 | 44.320 | 2.034 | 1.00 | 26.59 | A |
| ATOM | 1691 | CG | TYR | A | 288 | 79.080 | 45.217 | 0.917 | 1.00 | 26.43 | A |
| ATOM | 1692 | CD1 | TYR | A | 288 | 77.799 | 45.060 | 0.385 | 1.00 | 28.06 | A |
| ATOM | 1693 | CE1 | TYR | A | 288 | 77.350 | 45.854 | −0.675 | 1.00 | 28.72 | A |
| ATOM | 1694 | CD2 | TYR | A | 288 | 79.905 | 46.196 | 0.363 | 1.00 | 27.24 | A |
| ATOM | 1695 | CE2 | TYR | A | 288 | 79.470 | 46.994 | −0.697 | 1.00 | 28.55 | A |
| ATOM | 1696 | CZ | TYR | A | 288 | 78.192 | 46.814 | −1.211 | 1.00 | 29.91 | A |
| ATOM | 1697 | OH | TYR | A | 288 | 77.765 | 47.571 | −2.275 | 1.00 | 30.53 | A |
| ATOM | 1698 | C | TYR | A | 288 | 81.057 | 43.068 | 0.487 | 1.00 | 25.84 | A |
| ATOM | 1699 | O | TYR | A | 288 | 80.790 | 42.940 | −0.701 | 1.00 | 27.88 | A |
| ATOM | 1700 | N | LEU | A | 289 | 82.279 | 43.344 | 0.919 | 1.00 | 24.24 | A |
| ATOM | 1701 | CA | LEU | A | 289 | 83.382 | 43.495 | −0.018 | 1.00 | 26.60 | A |
| ATOM | 1702 | CB | LEU | A | 289 | 84.662 | 43.919 | 0.713 | 1.00 | 25.15 | A |
| ATOM | 1703 | CG | LEU | A | 289 | 85.005 | 45.411 | 0.817 | 1.00 | 27.82 | A |
| ATOM | 1704 | CD1 | LEU | A | 289 | 83.830 | 46.277 | 0.354 | 1.00 | 27.32 | A |
| ATOM | 1705 | CD2 | LEU | A | 289 | 85.404 | 45.727 | 2.251 | 1.00 | 25.62 | A |
| ATOM | 1706 | C | LEU | A | 289 | 83.622 | 42.184 | −0.736 | 1.00 | 27.45 | A |
| ATOM | 1707 | O | LEU | A | 289 | 83.901 | 42.157 | −1.933 | 1.00 | 30.18 | A |
| ATOM | 1708 | N | ILE | A | 290 | 83.520 | 41.093 | 0.009 | 1.00 | 28.11 | A |
| ATOM | 1709 | CA | ILE | A | 290 | 83.726 | 39.770 | −0.551 | 1.00 | 28.84 | A |
| ATOM | 1710 | CB | ILE | A | 290 | 83.565 | 38.710 | 0.545 | 1.00 | 29.67 | A |
| ATOM | 1711 | CG2 | ILE | A | 290 | 83.450 | 37.331 | −0.071 | 1.00 | 31.47 | A |
| ATOM | 1712 | CG1 | ILE | A | 290 | 84.756 | 38.802 | 1.504 | 1.00 | 29.26 | A |
| ATOM | 1713 | CD1 | ILE | A | 290 | 84.604 | 37.995 | 2.779 | 1.00 | 27.48 | A |
| ATOM | 1714 | C | ILE | A | 290 | 82.727 | 39.530 | −1.676 | 1.00 | 27.99 | A |
| ATOM | 1715 | O | ILE | A | 290 | 83.090 | 39.110 | −2.775 | 1.00 | 26.63 | A |
| ATOM | 1716 | N | PHE | A | 291 | 81.464 | 39.824 | −1.406 | 1.00 | 28.54 | A |
| ATOM | 1717 | CA | PHE | A | 291 | 80.432 | 39.638 | −2.407 | 1.00 | 27.14 | A |
| ATOM | 1718 | CB | PHE | A | 291 | 79.066 | 39.945 | −1.807 | 1.00 | 28.37 | A |
| ATOM | 1719 | CG | PHE | A | 291 | 78.674 | 39.024 | −0.688 | 1.00 | 30.37 | A |
| ATOM | 1720 | CD1 | PHE | A | 291 | 79.283 | 37.778 | −0.543 | 1.00 | 30.07 | A |
| ATOM | 1721 | CD2 | PHE | A | 291 | 77.658 | 39.377 | 0.194 | 1.00 | 29.74 | A |
| ATOM | 1722 | CE1 | PHE | A | 291 | 78.885 | 36.897 | 0.463 | 1.00 | 32.11 | A |
| ATOM | 1723 | CE2 | PHE | A | 291 | 77.253 | 38.502 | 1.202 | 1.00 | 32.76 | A |
| ATOM | 1724 | CZ | PHE | A | 291 | 77.867 | 37.259 | 1.336 | 1.00 | 32.01 | A |
| ATOM | 1725 | C | PHE | A | 291 | 80.690 | 40.525 | −3.618 | 1.00 | 27.79 | A |
| ATOM | 1726 | O | PHE | A | 291 | 80.434 | 40.124 | −4.755 | 1.00 | 26.52 | A |
| ATOM | 1727 | N | GLN | A | 292 | 81.200 | 41.730 | −3.384 | 1.00 | 27.05 | A |
| ATOM | 1728 | CA | GLN | A | 292 | 81.478 | 42.613 | −4.503 | 1.00 | 27.48 | A |
| ATOM | 1729 | CB | GLN | A | 292 | 82.072 | 43.945 | −4.037 | 1.00 | 27.80 | A |
| ATOM | 1730 | CG | GLN | A | 292 | 81.041 | 44.984 | −3.651 | 1.00 | 30.50 | A |
| ATOM | 1731 | CD | GLN | A | 292 | 81.630 | 46.381 | −3.565 | 1.00 | 31.30 | A |
| ATOM | 1732 | OE1 | GLN | A | 292 | 82.519 | 46.644 | −2.762 | 1.00 | 33.17 | A |
| ATOM | 1733 | NE2 | GLN | A | 292 | 81.133 | 47.284 | −4.399 | 1.00 | 32.86 | A |
| ATOM | 1734 | C | GLN | A | 292 | 82.442 | 41.934 | −5.460 | 1.00 | 26.82 | A |
| ATOM | 1735 | O | GLN | A | 292 | 82.186 | 41.883 | −6.664 | 1.00 | 28.03 | A |
| ATOM | 1736 | N | LYS | A | 293 | 83.539 | 41.402 | −4.924 | 1.00 | 24.08 | A |
| ATOM | 1737 | CA | LYS | A | 293 | 84.542 | 40.739 | −5.751 | 1.00 | 24.43 | A |
| ATOM | 1738 | CB | LYS | A | 293 | 85.752 | 40.368 | −4.901 | 1.00 | 26.19 | A |
| ATOM | 1739 | CG | LYS | A | 293 | 86.456 | 41.580 | −4.319 | 1.00 | 28.24 | A |
| ATOM | 1740 | CD | LYS | A | 293 | 87.750 | 41.213 | −3.608 | 1.00 | 30.60 | A |
| ATOM | 1741 | CE | LYS | A | 293 | 88.555 | 42.468 | −3.273 | 1.00 | 32.23 | A |
| ATOM | 1742 | NZ | LYS | A | 293 | 89.849 | 42.170 | −2.591 | 1.00 | 32.86 | A |
| ATOM | 1743 | C | LYS | A | 293 | 84.008 | 39.500 | −6.472 | 1.00 | 25.06 | A |
| ATOM | 1744 | O | LYS | A | 293 | 84.350 | 39.236 | −7.628 | 1.00 | 24.96 | A |
| ATOM | 1745 | N | ILE | A | 294 | 83.163 | 38.740 | −5.793 | 1.00 | 24.33 | A |
| ATOM | 1746 | CA | ILE | A | 294 | 82.593 | 37.552 | −6.399 | 1.00 | 24.46 | A |
| ATOM | 1747 | CB | ILE | A | 294 | 81.725 | 36.800 | −5.385 | 1.00 | 22.52 | A |
| ATOM | 1748 | CG2 | ILE | A | 294 | 80.837 | 35.783 | −6.093 | 1.00 | 23.14 | A |
| ATOM | 1749 | CG1 | ILE | A | 294 | 82.632 | 36.141 | −4.345 | 1.00 | 21.54 | A |
| ATOM | 1750 | CD1 | ILE | A | 294 | 81.892 | 35.535 | −3.175 | 1.00 | 19.38 | A |
| ATOM | 1751 | C | ILE | A | 294 | 81.761 | 37.885 | −7.639 | 1.00 | 27.01 | A |
| ATOM | 1752 | O | ILE | A | 294 | 81.967 | 37.303 | −8.704 | 1.00 | 23.93 | A |
| ATOM | 1753 | N | ILE | A | 295 | 80.830 | 38.828 | −7.513 | 1.00 | 29.79 | A |
| ATOM | 1754 | CA | ILE | A | 295 | 79.983 | 39.168 | −8.653 | 1.00 | 32.98 | A |
| ATOM | 1755 | CB | ILE | A | 295 | 78.767 | 40.004 | −8.228 | 1.00 | 33.96 | A |
| ATOM | 1756 | CG2 | ILE | A | 295 | 77.980 | 39.246 | −7.174 | 1.00 | 36.23 | A |
| ATOM | 1757 | CG1 | ILE | A | 295 | 79.216 | 41.358 | −7.682 | 1.00 | 35.79 | A |
| ATOM | 1758 | CD1 | ILE | A | 295 | 78.062 | 42.266 | −7.300 | 1.00 | 37.79 | A |
| ATOM | 1759 | C | ILE | A | 295 | 80.729 | 39.898 | −9.757 | 1.00 | 33.17 | A |
| ATOM | 1760 | O | ILE | A | 295 | 80.212 | 40.066 | −10.862 | 1.00 | 34.06 | A |
| ATOM | 1761 | N | LYS | A | 296 | 81.946 | 40.333 | −9.462 | 1.00 | 33.65 | A |
| ATOM | 1762 | CA | LYS | A | 296 | 82.747 | 41.012 | −10.468 | 1.00 | 34.81 | A |
| ATOM | 1763 | CB | LYS | A | 296 | 83.353 | 42.293 | −9.895 | 1.00 | 38.05 | A |
| ATOM | 1764 | CG | LYS | A | 296 | 82.353 | 43.427 | −9.714 | 1.00 | 40.12 | A |

-continued

| | | | | | | | | | | |
|---|---|---|---|---|---|---|---|---|---|---|
| ATOM | 1765 | CD | LYS | A | 296 | 83.070 | 44.736 | −9.401 | 1.00 | 44.01 | A |
| ATOM | 1766 | CE | LYS | A | 296 | 82.191 | 45.939 | −9.731 | 1.00 | 46.66 | A |
| ATOM | 1767 | NZ | LYS | A | 296 | 82.972 | 47.209 | −9.833 | 1.00 | 47.40 | A |
| ATOM | 1768 | C | LYS | A | 296 | 83.851 | 40.078 | −10.945 | 1.00 | 34.15 | A |
| ATOM | 1769 | O | LYS | A | 296 | 84.622 | 40.415 | −11.847 | 1.00 | 33.48 | A |
| ATOM | 1770 | N | LEU | A | 297 | 83.907 | 38.897 | −10.333 | 1.00 | 33.82 | A |
| ATOM | 1771 | CA | LEU | A | 297 | 84.904 | 37.890 | −10.663 | 1.00 | 32.06 | A |
| ATOM | 1772 | CB | LEU | A | 297 | 84.716 | 37.418 | −12.110 | 1.00 | 32.43 | A |
| ATOM | 1773 | CG | LEU | A | 297 | 85.452 | 36.144 | −12.538 | 1.00 | 33.09 | A |
| ATOM | 1774 | CD1 | LEU | A | 297 | 84.959 | 34.966 | −11.697 | 1.00 | 31.88 | A |
| ATOM | 1775 | CD2 | LEU | A | 297 | 85.206 | 35.875 | −14.025 | 1.00 | 32.51 | A |
| ATOM | 1776 | C | LEU | A | 297 | 86.275 | 38.515 | −10.476 | 1.00 | 32.23 | A |
| ATOM | 1777 | O | LEU | A | 297 | 87.180 | 38.321 | −11.278 | 1.00 | 32.08 | A |
| ATOM | 1778 | N | GLU | A | 298 | 86.424 | 39.267 | −9.395 | 1.00 | 33.56 | A |
| ATOM | 1779 | CA | GLU | A | 298 | 87.682 | 39.936 | −9.110 | 1.00 | 35.66 | A |
| ATOM | 1780 | CB | GLU | A | 298 | 87.405 | 41.274 | −8.428 | 1.00 | 38.03 | A |
| ATOM | 1781 | CG | GLU | A | 298 | 88.641 | 42.125 | −8.236 | 1.00 | 42.97 | A |
| ATOM | 1782 | CD | GLU | A | 298 | 88.383 | 43.313 | −7.338 | 1.00 | 46.19 | A |
| ATOM | 1783 | OE1 | GLU | A | 298 | 87.412 | 44.055 | −7.602 | 1.00 | 48.41 | A |
| ATOM | 1784 | OE2 | GLU | A | 298 | 89.153 | 43.504 | −6.369 | 1.00 | 48.44 | A |
| ATOM | 1785 | C | GLU | A | 298 | 88.644 | 39.117 | −8.245 | 1.00 | 34.35 | A |
| ATOM | 1786 | O | GLU | A | 298 | 88.508 | 39.065 | −7.021 | 1.00 | 35.64 | A |
| ATOM | 1787 | N | TYR | A | 299 | 89.611 | 38.478 | −8.894 | 1.00 | 32.46 | A |
| ATOM | 1788 | CA | TYR | A | 299 | 90.624 | 37.678 | −8.208 | 1.00 | 30.71 | A |
| ATOM | 1789 | CB | TYR | A | 299 | 90.031 | 36.367 | −7.672 | 1.00 | 26.01 | A |
| ATOM | 1790 | CG | TYR | A | 299 | 89.874 | 35.300 | −8.730 | 1.00 | 26.77 | A |
| ATOM | 1791 | CD1 | TYR | A | 299 | 88.871 | 35.390 | −9.699 | 1.00 | 26.60 | A |
| ATOM | 1792 | CE1 | TYR | A | 299 | 88.768 | 34.448 | −10.724 | 1.00 | 26.10 | A |
| ATOM | 1793 | CD2 | TYR | A | 299 | 90.770 | 34.236 | −8.807 | 1.00 | 22.56 | A |
| ATOM | 1794 | CE2 | TYR | A | 299 | 90.677 | 33.291 | −9.822 | 1.00 | 24.59 | A |
| ATOM | 1795 | CZ | TYR | A | 299 | 89.674 | 33.400 | −10.781 | 1.00 | 26.34 | A |
| ATOM | 1796 | OH | TYR | A | 299 | 89.578 | 32.463 | −11.791 | 1.00 | 22.44 | A |
| ATOM | 1797 | C | TYR | A | 299 | 91.720 | 37.374 | −9.229 | 1.00 | 30.95 | A |
| ATOM | 1798 | O | TYR | A | 299 | 91.528 | 37.575 | −10.425 | 1.00 | 28.80 | A |
| ATOM | 1799 | N | ASP | A | 300 | 92.865 | 36.891 | −8.764 | 1.00 | 33.38 | A |
| ATOM | 1800 | CA | ASP | A | 300 | 93.954 | 36.582 | −9.680 | 1.00 | 36.47 | A |
| ATOM | 1801 | CB | ASP | A | 300 | 94.782 | 37.845 | −9.931 | 1.00 | 42.34 | A |
| ATOM | 1802 | CG | ASP | A | 300 | 95.014 | 38.644 | −8.666 | 1.00 | 46.20 | A |
| ATOM | 1803 | OD1 | ASP | A | 300 | 95.607 | 38.085 | −7.719 | 1.00 | 49.27 | A |
| ATOM | 1804 | OD2 | ASP | A | 300 | 94.599 | 39.826 | −8.615 | 1.00 | 49.25 | A |
| ATOM | 1805 | C | ASP | A | 300 | 94.848 | 35.444 | −9.188 | 1.00 | 35.61 | A |
| ATOM | 1806 | O | ASP | A | 300 | 94.857 | 35.113 | −8.002 | 1.00 | 34.48 | A |
| ATOM | 1807 | N | PHE | A | 301 | 95.602 | 34.854 | −10.111 | 1.00 | 35.02 | A |
| ATOM | 1808 | CA | PHE | A | 301 | 96.477 | 33.737 | −9.781 | 1.00 | 35.94 | A |
| ATOM | 1809 | CB | PHE | A | 301 | 96.501 | 32.700 | −10.909 | 1.00 | 34.28 | A |
| ATOM | 1810 | CG | PHE | A | 301 | 95.156 | 32.167 | −11.301 | 1.00 | 32.40 | A |
| ATOM | 1811 | CD1 | PHE | A | 301 | 94.358 | 32.856 | −12.205 | 1.00 | 30.50 | A |
| ATOM | 1812 | CD2 | PHE | A | 301 | 94.708 | 30.947 | −10.803 | 1.00 | 31.83 | A |
| ATOM | 1813 | CE1 | PHE | A | 301 | 93.131 | 32.333 | −12.617 | 1.00 | 31.48 | A |
| ATOM | 1814 | CE2 | PHE | A | 301 | 93.484 | 30.416 | −11.206 | 1.00 | 31.37 | A |
| ATOM | 1815 | CZ | PHE | A | 301 | 92.695 | 31.109 | −12.114 | 1.00 | 31.44 | A |
| ATOM | 1816 | C | PHE | A | 301 | 97.916 | 34.134 | −9.524 | 1.00 | 38.11 | A |
| ATOM | 1817 | O | PHE | A | 301 | 98.458 | 35.010 | −10.196 | 1.00 | 39.06 | A |
| ATOM | 1818 | N | PRO | A | 302 | 98.559 | 33.498 | −8.535 | 1.00 | 40.47 | A |
| ATOM | 1819 | CD | PRO | A | 302 | 98.053 | 32.554 | −7.524 | 1.00 | 41.16 | A |
| ATOM | 1820 | CA | PRO | A | 302 | 99.955 | 33.843 | −8.277 | 1.00 | 41.88 | A |
| ATOM | 1821 | CB | PRO | A | 302 | 100.248 | 33.131 | −6.963 | 1.00 | 42.01 | A |
| ATOM | 1822 | CG | PRO | A | 302 | 99.328 | 31.947 | −7.001 | 1.00 | 41.79 | A |
| ATOM | 1823 | C | PRO | A | 302 | 100.721 | 33.265 | −9.458 | 1.00 | 44.54 | A |
| ATOM | 1824 | O | PRO | A | 302 | 100.263 | 32.305 | −10.082 | 1.00 | 44.30 | A |
| ATOM | 1825 | N | GLU | A | 303 | 101.874 | 33.843 | −9.770 | 1.00 | 47.35 | A |
| ATOM | 1826 | CA | GLU | A | 303 | 102.667 | 33.395 | −10.912 | 1.00 | 50.51 | A |
| ATOM | 1827 | CB | GLU | A | 303 | 103.859 | 34.337 | −11.105 | 1.00 | 53.23 | A |
| ATOM | 1828 | CG | GLU | A | 303 | 104.431 | 34.376 | −12.520 | 1.00 | 56.85 | A |
| ATOM | 1829 | CD | GLU | A | 303 | 103.976 | 35.600 | −13.314 | 1.00 | 59.62 | A |
| ATOM | 1830 | OE1 | GLU | A | 303 | 104.508 | 35.819 | −14.424 | 1.00 | 60.43 | A |
| ATOM | 1831 | OE2 | GLU | A | 303 | 103.088 | 36.341 | −12.834 | 1.00 | 60.45 | A |
| ATOM | 1832 | C | GLU | A | 303 | 103.173 | 31.950 | −10.829 | 1.00 | 50.70 | A |
| ATOM | 1833 | O | GLU | A | 303 | 103.692 | 31.423 | −11.815 | 1.00 | 52.21 | A |
| ATOM | 1834 | N | ALA | A | 304 | 103.018 | 31.309 | −9.672 | 1.00 | 49.61 | A |
| ATOM | 1835 | CA | ALA | A | 304 | 103.495 | 29.933 | −9.488 | 1.00 | 49.10 | A |
| ATOM | 1836 | CB | ALA | A | 304 | 104.077 | 29.779 | −8.082 | 1.00 | 48.82 | A |
| ATOM | 1837 | C | ALA | A | 304 | 102.422 | 28.869 | −9.713 | 1.00 | 47.90 | A |
| ATOM | 1838 | O | ALA | A | 304 | 102.703 | 27.666 | −9.719 | 1.00 | 49.41 | A |
| ATOM | 1839 | N | PHE | A | 305 | 101.192 | 29.322 | −9.899 | 1.00 | 44.69 | A |
| ATOM | 1840 | CA | PHE | A | 305 | 100.053 | 28.440 | −10.089 | 1.00 | 40.05 | A |
| ATOM | 1841 | CB | PHE | A | 305 | 98.809 | 29.301 | −10.299 | 1.00 | 39.69 | A |
| ATOM | 1842 | CG | PHE | A | 305 | 97.568 | 28.729 | −9.697 | 1.00 | 37.21 | A |
| ATOM | 1843 | CD1 | PHE | A | 305 | 96.824 | 27.775 | −10.379 | 1.00 | 35.36 | A |

-continued

| | | | | | | | | | | |
|---|---|---|---|---|---|---|---|---|---|---|
| ATOM | 1844 | CD2 | PHE | A | 305 | 97.133 | 29.157 | −8.445 | 1.00 | 37.52 | A |
| ATOM | 1845 | CE1 | PHE | A | 305 | 95.658 | 27.255 | −9.825 | 1.00 | 34.59 | A |
| ATOM | 1846 | CE2 | PHE | A | 305 | 95.963 | 28.641 | −7.880 | 1.00 | 37.01 | A |
| ATOM | 1847 | CZ | PHE | A | 305 | 95.226 | 27.688 | −8.575 | 1.00 | 35.13 | A |
| ATOM | 1848 | C | PHE | A | 305 | 100.197 | 27.435 | −11.230 | 1.00 | 37.65 | A |
| ATOM | 1849 | O | PHE | A | 305 | 100.364 | 27.814 | −12.389 | 1.00 | 36.24 | A |
| ATOM | 1850 | N | PHE | A | 306 | 100.120 | 26.150 | −10.892 | 1.00 | 35.64 | A |
| ATOM | 1851 | CA | PHE | A | 306 | 100.219 | 25.081 | −11.884 | 1.00 | 32.40 | A |
| ATOM | 1852 | CB | PHE | A | 306 | 99.781 | 23.749 | −11.268 | 1.00 | 29.92 | A |
| ATOM | 1853 | CG | PHE | A | 306 | 100.412 | 23.456 | −9.926 | 1.00 | 28.24 | A |
| ATOM | 1854 | CD1 | PHE | A | 306 | 101.796 | 23.457 | −9.770 | 1.00 | 27.43 | A |
| ATOM | 1855 | CD2 | PHE | A | 306 | 99.617 | 23.173 | −8.816 | 1.00 | 28.59 | A |
| ATOM | 1856 | CE1 | PHE | A | 306 | 102.380 | 23.181 | −8.526 | 1.00 | 29.55 | A |
| ATOM | 1857 | CE2 | PHE | A | 306 | 100.188 | 22.895 | −7.566 | 1.00 | 29.06 | A |
| ATOM | 1858 | CZ | PHE | A | 306 | 101.575 | 22.901 | −7.422 | 1.00 | 29.51 | A |
| ATOM | 1859 | C | PHE | A | 306 | 99.296 | 25.452 | −13.047 | 1.00 | 32.76 | A |
| ATOM | 1860 | O | PHE | A | 306 | 98.087 | 25.625 | −12.861 | 1.00 | 34.51 | A |
| ATOM | 1861 | N | PRO | A | 307 | 99.856 | 25.587 | −14.262 | 1.00 | 31.43 | A |
| ATOM | 1862 | CD | PRO | A | 307 | 101.272 | 25.327 | −14.569 | 1.00 | 30.74 | A |
| ATOM | 1863 | CA | PRO | A | 307 | 99.128 | 25.947 | −15.485 | 1.00 | 29.54 | A |
| ATOM | 1864 | CB | PRO | A | 307 | 100.158 | 25.700 | −16.579 | 1.00 | 29.48 | A |
| ATOM | 1865 | CG | PRO | A | 307 | 101.437 | 26.032 | −15.895 | 1.00 | 30.81 | A |
| ATOM | 1866 | C | PRO | A | 307 | 97.826 | 25.193 | −15.743 | 1.00 | 29.74 | A |
| ATOM | 1867 | O | PRO | A | 307 | 96.795 | 25.804 | −16.022 | 1.00 | 31.08 | A |
| ATOM | 1868 | N | LYS | A | 308 | 97.867 | 23.870 | −15.660 | 1.00 | 28.47 | A |
| ATOM | 1869 | CA | LYS | A | 308 | 96.672 | 23.086 | −15.904 | 1.00 | 27.92 | A |
| ATOM | 1870 | CB | LYS | A | 308 | 97.044 | 21.619 | −16.114 | 1.00 | 28.70 | A |
| ATOM | 1871 | CG | LYS | A | 308 | 97.696 | 21.405 | −17.460 | 1.00 | 30.04 | A |
| ATOM | 1872 | CD | LYS | A | 308 | 98.310 | 20.029 | −17.595 | 1.00 | 33.76 | A |
| ATOM | 1873 | CE | LYS | A | 308 | 99.106 | 19.926 | −18.888 | 1.00 | 33.22 | A |
| ATOM | 1874 | NZ | LYS | A | 308 | 99.897 | 18.663 | −18.948 | 1.00 | 36.67 | A |
| ATOM | 1875 | C | LYS | A | 308 | 95.632 | 23.247 | −14.800 | 1.00 | 26.85 | A |
| ATOM | 1876 | O | LYS | A | 308 | 94.433 | 23.170 | −15.060 | 1.00 | 25.34 | A |
| ATOM | 1877 | N | ALA | A | 309 | 96.084 | 23.480 | −13.574 | 1.00 | 24.70 | A |
| ATOM | 1878 | CA | ALA | A | 309 | 95.145 | 23.685 | −12.486 | 1.00 | 24.41 | A |
| ATOM | 1879 | CB | ALA | A | 309 | 95.855 | 23.652 | −11.146 | 1.00 | 22.65 | A |
| ATOM | 1880 | C | ALA | A | 309 | 94.523 | 25.051 | −12.712 | 1.00 | 26.56 | A |
| ATOM | 1881 | O | ALA | A | 309 | 93.327 | 25.238 | −12.493 | 1.00 | 28.91 | A |
| ATOM | 1882 | N | ARG | A | 310 | 95.335 | 26.011 | −13.149 | 1.00 | 26.94 | A |
| ATOM | 1883 | CA | ARG | A | 310 | 94.830 | 27.354 | −13.402 | 1.00 | 27.56 | A |
| ATOM | 1884 | CB | ARG | A | 310 | 95.961 | 28.289 | −13.864 | 1.00 | 28.69 | A |
| ATOM | 1885 | CG | ARG | A | 310 | 95.438 | 29.584 | −14.480 | 1.00 | 31.42 | A |
| ATOM | 1886 | CD | ARG | A | 310 | 96.482 | 30.676 | −14.634 | 1.00 | 33.72 | A |
| ATOM | 1887 | NE | ARG | A | 310 | 95.881 | 31.868 | −15.233 | 1.00 | 37.73 | A |
| ATOM | 1888 | CZ | ARG | A | 310 | 96.412 | 33.090 | −15.198 | 1.00 | 38.44 | A |
| ATOM | 1889 | NH1 | ARG | A | 310 | 97.572 | 33.297 | −14.588 | 1.00 | 37.72 | A |
| ATOM | 1890 | NH2 | ARG | A | 310 | 95.775 | 34.108 | −15.767 | 1.00 | 37.74 | A |
| ATOM | 1891 | C | ARG | A | 310 | 93.743 | 27.280 | −14.473 | 1.00 | 26.84 | A |
| ATOM | 1892 | O | ARG | A | 310 | 92.678 | 27.880 | −14.344 | 1.00 | 26.39 | A |
| ATOM | 1893 | N | ASP | A | 311 | 94.019 | 26.524 | −15.527 | 1.00 | 26.91 | A |
| ATOM | 1894 | CA | ASP | A | 311 | 93.069 | 26.369 | −16.615 | 1.00 | 28.21 | A |
| ATOM | 1895 | CB | ASP | A | 311 | 93.682 | 25.504 | −17.713 | 1.00 | 30.32 | A |
| ATOM | 1896 | CG | ASP | A | 311 | 92.850 | 25.494 | −18.972 | 1.00 | 35.68 | A |
| ATOM | 1897 | OD1 | ASP | A | 311 | 91.894 | 24.691 | −19.040 | 1.00 | 38.27 | A |
| ATOM | 1898 | OD2 | ASP | A | 311 | 93.145 | 26.302 | −19.888 | 1.00 | 37.07 | A |
| ATOM | 1899 | C | ASP | A | 311 | 91.769 | 25.748 | −16.108 | 1.00 | 27.22 | A |
| ATOM | 1900 | O | ASP | A | 311 | 90.678 | 26.205 | −16.449 | 1.00 | 29.64 | A |
| ATOM | 1901 | N | LEU | A | 312 | 91.886 | 24.715 | −15.285 | 1.00 | 24.32 | A |
| ATOM | 1902 | CA | LEU | A | 312 | 90.708 | 24.062 | −14.728 | 1.00 | 23.48 | A |
| ATOM | 1903 | CB | LEU | A | 312 | 91.118 | 22.838 | −13.892 | 1.00 | 21.65 | A |
| ATOM | 1904 | CG | LEU | A | 312 | 90.067 | 22.228 | −12.945 | 1.00 | 21.40 | A |
| ATOM | 1905 | CD1 | LEU | A | 312 | 88.789 | 21.917 | −13.694 | 1.00 | 16.90 | A |
| ATOM | 1906 | CD2 | LEU | A | 312 | 90.629 | 20.960 | −12.294 | 1.00 | 19.67 | A |
| ATOM | 1907 | C | LEU | A | 312 | 89.899 | 25.039 | −13.871 | 1.00 | 22.73 | A |
| ATOM | 1908 | O | LEU | A | 312 | 88.684 | 25.141 | −14.021 | 1.00 | 22.02 | A |
| ATOM | 1909 | N | VAL | A | 313 | 90.574 | 25.754 | −12.972 | 1.00 | 22.12 | A |
| ATOM | 1910 | CA | VAL | A | 313 | 89.897 | 26.715 | −12.108 | 1.00 | 21.16 | A |
| ATOM | 1911 | CB | VAL | A | 313 | 90.893 | 27.440 | −11.167 | 1.00 | 23.49 | A |
| ATOM | 1912 | CG1 | VAL | A | 313 | 90.221 | 28.679 | −10.534 | 1.00 | 20.45 | A |
| ATOM | 1913 | CG2 | VAL | A | 313 | 91.369 | 26.487 | −10.080 | 1.00 | 21.63 | A |
| ATOM | 1914 | C | VAL | A | 313 | 89.161 | 27.771 | −12.920 | 1.00 | 22.93 | A |
| ATOM | 1915 | O | VAL | A | 313 | 88.051 | 28.168 | −12.566 | 1.00 | 21.46 | A |
| ATOM | 1916 | N | GLU | A | 314 | 89.784 | 28.235 | −14.001 | 1.00 | 23.15 | A |
| ATOM | 1917 | CA | GLU | A | 314 | 89.156 | 29.252 | −14.832 | 1.00 | 25.95 | A |
| ATOM | 1918 | CB | GLU | A | 314 | 90.127 | 29.762 | −15.900 | 1.00 | 28.61 | A |
| ATOM | 1919 | CG | GLU | A | 314 | 91.319 | 30.523 | −15.350 | 1.00 | 32.73 | A |
| ATOM | 1920 | CD | GLU | A | 314 | 92.205 | 31.059 | −16.453 | 1.00 | 35.94 | A |
| ATOM | 1921 | OE1 | GLU | A | 314 | 92.188 | 30.467 | −17.554 | 1.00 | 40.67 | A |
| ATOM | 1922 | OE2 | GLU | A | 314 | 92.923 | 32.059 | −16.225 | 1.00 | 37.73 | A |

-continued

| | | | | | | | | | | |
|---|---|---|---|---|---|---|---|---|---|---|
| ATOM | 1923 | C | GLU | A | 314 | 87.891 | 28.742 | −15.505 | 1.00 | 24.64 | A |
| ATOM | 1924 | O | GLU | A | 314 | 87.030 | 29.528 | −15.892 | 1.00 | 24.01 | A |
| ATOM | 1925 | N | LYS | A | 315 | 87.775 | 27.428 | −15.654 | 1.00 | 23.67 | A |
| ATOM | 1926 | CA | LYS | A | 315 | 86.588 | 26.874 | −16.278 | 1.00 | 23.15 | A |
| ATOM | 1927 | CB | LYS | A | 315 | 86.937 | 25.594 | −17.042 | 1.00 | 24.76 | A |
| ATOM | 1928 | CG | LYS | A | 315 | 87.784 | 25.845 | −18.299 | 1.00 | 22.90 | A |
| ATOM | 1929 | CD | LYS | A | 315 | 88.223 | 24.541 | −18.929 | 1.00 | 23.63 | A |
| ATOM | 1930 | CE | LYS | A | 315 | 89.079 | 24.772 | −20.153 | 1.00 | 23.20 | A |
| ATOM | 1931 | NZ | LYS | A | 315 | 88.332 | 25.582 | −21.142 | 1.00 | 29.09 | A |
| ATOM | 1932 | C | LYS | A | 315 | 85.509 | 26.600 | −15.244 | 1.00 | 23.08 | A |
| ATOM | 1933 | O | LYS | A | 315 | 84.386 | 26.250 | −15.596 | 1.00 | 23.63 | A |
| ATOM | 1934 | N | LEU | A | 316 | 85.852 | 26.773 | −13.969 | 1.00 | 21.74 | A |
| ATOM | 1935 | CA | LEU | A | 316 | 84.910 | 26.547 | −12.876 | 1.00 | 21.89 | A |
| ATOM | 1936 | CB | LEU | A | 316 | 85.569 | 25.738 | −11.760 | 1.00 | 20.54 | A |
| ATOM | 1937 | CG | LEU | A | 316 | 85.841 | 24.269 | −12.090 | 1.00 | 20.69 | A |
| ATOM | 1938 | CD1 | LEU | A | 316 | 86.600 | 23.611 | −10.947 | 1.00 | 17.08 | A |
| ATOM | 1939 | CD2 | LEU | A | 316 | 84.514 | 23.558 | −12.336 | 1.00 | 19.15 | A |
| ATOM | 1940 | C | LEU | A | 316 | 84.404 | 27.860 | −12.312 | 1.00 | 23.66 | A |
| ATOM | 1941 | O | LEU | A | 316 | 83.215 | 28.005 | −12.013 | 1.00 | 25.40 | A |
| ATOM | 1942 | N | LEU | A | 317 | 85.310 | 28.816 | −12.149 | 1.00 | 24.48 | A |
| ATOM | 1943 | CA | LEU | A | 317 | 84.933 | 30.121 | −11.637 | 1.00 | 25.52 | A |
| ATOM | 1944 | CB | LEU | A | 317 | 86.123 | 30.793 | −10.936 | 1.00 | 24.23 | A |
| ATOM | 1945 | CG | LEU | A | 317 | 86.656 | 30.035 | −9.719 | 1.00 | 21.22 | A |
| ATOM | 1946 | CD1 | LEU | A | 317 | 87.718 | 30.859 | −9.015 | 1.00 | 23.73 | A |
| ATOM | 1947 | CD2 | LEU | A | 317 | 85.515 | 29.730 | −8.773 | 1.00 | 21.36 | A |
| ATOM | 1948 | C | LEU | A | 317 | 84.459 | 30.953 | −12.815 | 1.00 | 26.00 | A |
| ATOM | 1949 | O | LEU | A | 317 | 85.148 | 31.856 | −13.286 | 1.00 | 28.02 | A |
| ATOM | 1950 | N | VAL | A | 318 | 83.272 | 30.611 | −13.293 | 1.00 | 27.50 | A |
| ATOM | 1951 | CA | VAL | A | 318 | 82.643 | 31.286 | −14.421 | 1.00 | 28.43 | A |
| ATOM | 1952 | CB | VAL | A | 318 | 82.365 | 30.280 | −15.558 | 1.00 | 28.13 | A |
| ATOM | 1953 | CG1 | VAL | A | 318 | 81.624 | 30.953 | −16.694 | 1.00 | 29.20 | A |
| ATOM | 1954 | CG2 | VAL | A | 318 | 83.677 | 29.689 | −16.045 | 1.00 | 27.12 | A |
| ATOM | 1955 | C | VAL | A | 318 | 81.331 | 31.842 | −13.896 | 1.00 | 29.21 | A |
| ATOM | 1956 | O | VAL | A | 318 | 80.559 | 31.120 | −13.255 | 1.00 | 30.06 | A |
| ATOM | 1957 | N | LEU | A | 319 | 81.082 | 33.121 | −14.150 | 1.00 | 29.94 | A |
| ATOM | 1958 | CA | LEU | A | 319 | 79.858 | 33.758 | −13.671 | 1.00 | 30.57 | A |
| ATOM | 1959 | CB | LEU | A | 319 | 79.808 | 35.214 | −14.133 | 1.00 | 32.89 | A |
| ATOM | 1960 | CG | LEU | A | 319 | 80.908 | 36.115 | −13.553 | 1.00 | 35.26 | A |
| ATOM | 1961 | CD1 | LEU | A | 319 | 80.741 | 37.551 | −14.059 | 1.00 | 34.63 | A |
| ATOM | 1962 | CD2 | LEU | A | 319 | 80.835 | 36.078 | −12.028 | 1.00 | 34.01 | A |
| ATOM | 1963 | C | LEU | A | 319 | 78.598 | 33.029 | −14.117 | 1.00 | 30.01 | A |
| ATOM | 1964 | O | LEU | A | 319 | 77.704 | 32.768 | −13.316 | 1.00 | 30.48 | A |
| ATOM | 1965 | N | ASP | A | 320 | 78.527 | 32.695 | −15.397 | 1.00 | 30.13 | A |
| ATOM | 1966 | CA | ASP | A | 320 | 77.362 | 31.996 | −15.919 | 1.00 | 29.97 | A |
| ATOM | 1967 | CB | ASP | A | 320 | 77.393 | 31.981 | −17.444 | 1.00 | 32.99 | A |
| ATOM | 1968 | CG | ASP | A | 320 | 76.116 | 31.435 | −18.040 | 1.00 | 36.86 | A |
| ATOM | 1969 | OD1 | ASP | A | 320 | 75.495 | 30.548 | −17.412 | 1.00 | 38.81 | A |
| ATOM | 1970 | OD2 | ASP | A | 320 | 75.739 | 31.883 | −19.142 | 1.00 | 38.26 | A |
| ATOM | 1971 | C | ASP | A | 320 | 77.373 | 30.569 | −15.402 | 1.00 | 28.61 | A |
| ATOM | 1972 | O | ASP | A | 320 | 78.244 | 29.786 | −15.758 | 1.00 | 28.87 | A |
| ATOM | 1973 | N | ALA | A | 321 | 76.398 | 30.233 | −14.566 | 1.00 | 28.88 | A |
| ATOM | 1974 | CA | ALA | A | 321 | 76.311 | 28.897 | −13.980 | 1.00 | 28.04 | A |
| ATOM | 1975 | CB | ALA | A | 321 | 75.156 | 28.842 | −12.990 | 1.00 | 25.11 | A |
| ATOM | 1976 | C | ALA | A | 321 | 76.151 | 27.794 | −15.021 | 1.00 | 27.83 | A |
| ATOM | 1977 | O | ALA | A | 321 | 76.500 | 26.643 | −14.773 | 1.00 | 27.26 | A |
| ATOM | 1978 | N | THR | A | 322 | 75.632 | 28.150 | −16.190 | 1.00 | 27.45 | A |
| ATOM | 1979 | CA | THR | A | 322 | 75.413 | 27.167 | −17.243 | 1.00 | 27.18 | A |
| ATOM | 1980 | CB | THR | A | 322 | 74.294 | 27.615 | −18.191 | 1.00 | 26.99 | A |
| ATOM | 1981 | OG1 | THR | A | 322 | 74.739 | 28.753 | −18.940 | 1.00 | 27.15 | A |
| ATOM | 1982 | CG2 | THR | A | 322 | 73.045 | 27.997 | −17.399 | 1.00 | 23.11 | A |
| ATOM | 1983 | C | THR | A | 322 | 76.654 | 26.909 | −18.077 | 1.00 | 28.31 | A |
| ATOM | 1984 | O | THR | A | 322 | 76.605 | 26.133 | −19.027 | 1.00 | 28.80 | A |
| ATOM | 1985 | N | LYS | A | 323 | 77.769 | 27.546 | −17.727 | 1.00 | 28.30 | A |
| ATOM | 1986 | CA | LYS | A | 323 | 78.990 | 27.348 | −18.491 | 1.00 | 28.51 | A |
| ATOM | 1987 | CB | LYS | A | 323 | 79.392 | 28.651 | −19.172 | 1.00 | 30.27 | A |
| ATOM | 1988 | CG | LYS | A | 323 | 78.305 | 29.160 | −20.095 | 1.00 | 35.72 | A |
| ATOM | 1989 | CD | LYS | A | 323 | 78.839 | 30.081 | −21.170 | 1.00 | 37.65 | A |
| ATOM | 1990 | CE | LYS | A | 323 | 77.722 | 30.472 | −22.131 | 1.00 | 39.59 | A |
| ATOM | 1991 | NZ | LYS | A | 323 | 77.088 | 29.263 | −22.733 | 1.00 | 40.41 | A |
| ATOM | 1992 | C | LYS | A | 323 | 80.154 | 26.799 | −17.683 | 1.00 | 28.68 | A |
| ATOM | 1993 | O | LYS | A | 323 | 81.298 | 26.847 | −18.119 | 1.00 | 29.54 | A |
| ATOM | 1994 | N | ARG | A | 324 | 79.866 | 26.271 | −16.503 | 1.00 | 27.43 | A |
| ATOM | 1995 | CA | ARG | A | 324 | 80.921 | 25.709 | −15.684 | 1.00 | 25.01 | A |
| ATOM | 1996 | CB | ARG | A | 324 | 80.559 | 25.800 | −14.205 | 1.00 | 22.81 | A |
| ATOM | 1997 | CG | ARG | A | 324 | 80.489 | 27.223 | −13.715 | 1.00 | 21.68 | A |
| ATOM | 1998 | CD | ARG | A | 324 | 80.036 | 27.315 | −12.277 | 1.00 | 20.65 | A |
| ATOM | 1999 | NE | ARG | A | 324 | 79.655 | 28.689 | −11.971 | 1.00 | 21.18 | A |
| ATOM | 2000 | CZ | ARG | A | 324 | 78.645 | 29.029 | −11.180 | 1.00 | 19.20 | A |
| ATOM | 2001 | NH1 | ARG | A | 324 | 77.909 | 28.093 | −10.598 | 1.00 | 19.05 | A |

-continued

| | | | | | | | | | | |
|---|---|---|---|---|---|---|---|---|---|---|
| ATOM | 2002 | NH2 | ARG | A | 324 | 78.349 | 30.307 | −11.004 | 1.00 | 19.45 | A |
| ATOM | 2003 | C | ARG | A | 324 | 81.161 | 24.264 | −16.073 | 1.00 | 24.64 | A |
| ATOM | 2004 | O | ARG | A | 324 | 80.219 | 23.501 | −16.290 | 1.00 | 23.78 | A |
| ATOM | 2005 | N | LEU | A | 325 | 82.433 | 23.902 | −16.177 | 1.00 | 23.92 | A |
| ATOM | 2006 | CA | LEU | A | 325 | 82.809 | 22.541 | −16.526 | 1.00 | 25.53 | A |
| ATOM | 2007 | CB | LEU | A | 325 | 84.336 | 22.422 | −16.558 | 1.00 | 25.18 | A |
| ATOM | 2008 | CG | LEU | A | 325 | 84.995 | 21.178 | −17.149 | 1.00 | 25.63 | A |
| ATOM | 2009 | CD1 | LEU | A | 325 | 84.541 | 20.949 | −18.590 | 1.00 | 25.39 | A |
| ATOM | 2010 | CD2 | LEU | A | 325 | 86.500 | 21.364 | 17.087 | 1.00 | 23.10 | A |
| ATOM | 2011 | C | LEU | A | 325 | 82.224 | 21.610 | −15.466 | 1.00 | 25.01 | A |
| ATOM | 2012 | O | LEU | A | 325 | 82.449 | 21.809 | −14.278 | 1.00 | 23.81 | A |
| ATOM | 2013 | N | GLY | A | 326 | 81.450 | 20.616 | −15.900 | 1.00 | 26.41 | A |
| ATOM | 2014 | CA | GLY | A | 326 | 80.850 | 19.683 | −14.964 | 1.00 | 26.13 | A |
| ATOM | 2015 | C | GLY | A | 326 | 79.338 | 19.771 | −14.835 | 1.00 | 29.31 | A |
| ATOM | 2016 | O | GLY | A | 326 | 78.697 | 18.795 | −14.444 | 1.00 | 31.67 | A |
| ATOM | 2017 | N | CYS | A | 327 | 78.753 | 20.918 | −15.162 | 1.00 | 29.49 | A |
| ATOM | 2018 | CA | CYS | A | 327 | 77.308 | 21.073 | −15.042 | 1.00 | 31.91 | A |
| ATOM | 2019 | CB | CYS | A | 327 | 76.935 | 22.556 | −14.982 | 1.00 | 31.78 | A |
| ATOM | 2020 | SG | CYS | A | 327 | 77.084 | 23.397 | −16.552 | 1.00 | 38.33 | A |
| ATOM | 2021 | C | CYS | A | 327 | 76.539 | 20.385 | −16.175 | 1.00 | 32.76 | A |
| ATOM | 2022 | O | CYS | A | 327 | 77.096 | 20.069 | −17.228 | 1.00 | 32.18 | A |
| ATOM | 2023 | N | GLU | A | 328 | 75.248 | 20.175 | −15.952 | 1.00 | 33.60 | A |
| ATOM | 2024 | CA | GLU | A | 328 | 74.400 | 19.497 | −16.921 | 1.00 | 36.82 | A |
| ATOM | 2025 | CB | GLU | A | 328 | 72.951 | 19.479 | −16.408 | 1.00 | 41.60 | A |
| ATOM | 2026 | CG | GLU | A | 328 | 72.845 | 19.437 | −14.863 | 1.00 | 48.96 | A |
| ATOM | 2027 | CD | GLU | A | 328 | 72.000 | 18.279 | −14.321 | 1.00 | 51.75 | A |
| ATOM | 2028 | OE1 | GLU | A | 328 | 72.393 | 17.103 | −14.509 | 1.00 | 52.77 | A |
| ATOM | 2029 | OE2 | GLU | A | 328 | 70.948 | 18.550 | −13.696 | 1.00 | 52.29 | A |
| ATOM | 2030 | C | GLU | A | 328 | 74.466 | 20.120 | −18.317 | 1.00 | 35.83 | A |
| ATOM | 2031 | O | GLU | A | 328 | 74.618 | 19.412 | −19.318 | 1.00 | 34.85 | A |
| ATOM | 2032 | N | GLU | A | 329 | 74.370 | 21.443 | −18.378 | 1.00 | 33.75 | A |
| ATOM | 2033 | CA | GLU | A | 329 | 74.399 | 22.146 | −19.650 | 1.00 | 32.37 | A |
| ATOM | 2034 | CB | GLU | A | 329 | 74.153 | 23.640 | −19.439 | 1.00 | 34.70 | A |
| ATOM | 2035 | CG | GLU | A | 329 | 72.898 | 23.972 | −18.640 | 1.00 | 38.53 | A |
| ATOM | 2036 | CD | GLU | A | 329 | 73.017 | 23.589 | −17.172 | 1.00 | 41.60 | A |
| ATOM | 2037 | OE1 | GLU | A | 329 | 74.048 | 23.926 | −16.548 | 1.00 | 44.03 | A |
| ATOM | 2038 | OE2 | GLU | A | 329 | 72.080 | 22.958 | −16.636 | 1.00 | 44.74 | A |
| ATOM | 2039 | C | GLU | A | 329 | 75.711 | 21.947 | −20.399 | 1.00 | 30.96 | A |
| ATOM | 2040 | O | GLU | A | 329 | 75.757 | 22.114 | −21.617 | 1.00 | 28.90 | A |
| ATOM | 2041 | N | MET | A | 330 | 76.773 | 21.605 | −19.673 | 1.00 | 29.20 | A |
| ATOM | 2042 | CA | MET | A | 330 | 78.075 | 21.379 | −20.291 | 1.00 | 27.90 | A |
| ATOM | 2043 | CB | MET | A | 330 | 79.190 | 22.010 | −19.455 | 1.00 | 30.57 | A |
| ATOM | 2044 | CG | MET | A | 330 | 79.189 | 23.536 | −19.446 | 1.00 | 32.33 | A |
| ATOM | 2045 | SD | MET | A | 330 | 79.488 | 24.269 | −21.070 | 1.00 | 36.55 | A |
| ATOM | 2046 | CE | MET | A | 330 | 81.257 | 24.001 | −21.239 | 1.00 | 35.61 | A |
| ATOM | 2047 | C | MET | A | 330 | 78.319 | 19.883 | −20.443 | 1.00 | 27.32 | A |
| ATOM | 2048 | O | MET | A | 330 | 79.452 | 19.436 | −20.606 | 1.00 | 25.82 | A |
| ATOM | 2049 | N | GLU | A | 331 | 77.232 | 19.122 | −20.365 | 1.00 | 25.18 | A |
| ATOM | 2050 | CA | GLU | A | 331 | 77.246 | 17.677 | −20.526 | 1.00 | 24.56 | A |
| ATOM | 2051 | CB | GLU | A | 331 | 77.922 | 17.295 | −21.848 | 1.00 | 23.55 | A |
| ATOM | 2052 | CG | GLU | A | 331 | 77.395 | 18.099 | −23.030 | 1.00 | 25.42 | A |
| ATOM | 2053 | CD | GLU | A | 331 | 75.867 | 18.176 | −23.082 | 1.00 | 28.50 | A |
| ATOM | 2054 | OE1 | GLU | A | 331 | 75.338 | 19.094 | −23.750 | 1.00 | 31.00 | A |
| ATOM | 2055 | OE2 | GLU | A | 331 | 75.190 | 17.323 | −22.467 | 1.00 | 30.18 | A |
| ATOM | 2056 | C | GLU | A | 331 | 77.804 | 16.834 | −19.396 | 1.00 | 24.55 | A |
| ATOM | 2057 | O | GLU | A | 331 | 78.327 | 15.745 | −19.629 | 1.00 | 25.02 | A |
| ATOM | 2058 | N | GLY | A | 332 | 77.692 | 17.339 | −18.172 | 1.00 | 22.83 | A |
| ATOM | 2059 | CA | GLY | A | 332 | 78.098 | 16.564 | −17.017 | 1.00 | 20.57 | A |
| ATOM | 2060 | C | GLY | A | 332 | 79.541 | 16.408 | −16.606 | 1.00 | 20.81 | A |
| ATOM | 2061 | O | GLY | A | 332 | 80.430 | 17.167 | −16.999 | 1.00 | 19.36 | A |
| ATOM | 2062 | N | TYR | A | 333 | 79.753 | 15.374 | −15.801 | 1.00 | 20.19 | A |
| ATOM | 2063 | CA | TYR | A | 333 | 81.053 | 15.056 | −15.243 | 1.00 | 20.12 | A |
| ATOM | 2064 | CB | TYR | A | 333 | 80.860 | 14.127 | −14.052 | 1.00 | 20.05 | A |
| ATOM | 2065 | CG | TYR | A | 333 | 80.483 | 14.902 | −12.828 | 1.00 | 21.40 | A |
| ATOM | 2066 | CD1 | TYR | A | 333 | 81.464 | 15.367 | −11.956 | 1.00 | 22.85 | A |
| ATOM | 2067 | CE1 | TYR | A | 333 | 81.141 | 16.181 | −10.878 | 1.00 | 22.91 | A |
| ATOM | 2068 | CD2 | TYR | A | 333 | 79.160 | 15.266 | −12.590 | 1.00 | 21.24 | A |
| ATOM | 2069 | CE2 | TYR | A | 333 | 78.827 | 16.082 | −11.518 | 1.00 | 22.71 | A |
| ATOM | 2070 | CZ | TYR | A | 333 | 79.827 | 16.535 | −10.670 | 1.00 | 21.44 | A |
| ATOM | 2071 | OH | TYR | A | 333 | 79.522 | 17.358 | −9.621 | 1.00 | 24.72 | A |
| ATOM | 2072 | C | TYR | A | 333 | 82.076 | 14.484 | −16.192 | 1.00 | 20.38 | A |
| ATOM | 2073 | O | TYR | A | 333 | 83.277 | 14.533 | −15.910 | 1.00 | 18.82 | A |
| ATOM | 2074 | N | GLY | A | 334 | 81.610 | 13.942 | −17.313 | 1.00 | 20.41 | A |
| ATOM | 2075 | CA | GLY | A | 334 | 82.534 | 13.378 | −18.280 | 1.00 | 20.48 | A |
| ATOM | 2076 | C | GLY | A | 334 | 83.611 | 14.367 | −18.693 | 1.00 | 20.12 | A |
| ATOM | 2077 | O | GLY | A | 334 | 84.808 | 14.105 | −18.539 | 1.00 | 21.13 | A |
| ATOM | 2078 | N | PRO | A | 335 | 83.216 | 15.524 | −19.230 | 1.00 | 19.75 | A |
| ATOM | 2079 | CD | PRO | A | 335 | 81.872 | 15.899 | −19.699 | 1.00 | 19.25 | A |
| ATOM | 2080 | CA | PRO | A | 335 | 84.218 | 16.512 | −19.644 | 1.00 | 19.66 | A |

| | | | | | | | | | | |
|---|---|---|---|---|---|---|---|---|---|---|
| ATOM | 2081 | CB | PRO | A | 335 | 83.366 | 17.644 | −20.212 | 1.00 | 17.92 | A |
| ATOM | 2082 | CG | PRO | A | 335 | 82.184 | 16.901 | −20.784 | 1.00 | 19.24 | A |
| ATOM | 2083 | C | PRO | A | 335 | 85.115 | 16.967 | −18.495 | 1.00 | 19.62 | A |
| ATOM | 2084 | O | PRO | A | 335 | 86.315 | 17.154 | −18.679 | 1.00 | 21.87 | A |
| ATOM | 2085 | N | LEU | A | 336 | 84.538 | 17.131 | −17.307 | 1.00 | 19.91 | A |
| ATOM | 2086 | CA | LEU | A | 336 | 85.312 | 17.576 | −16.147 | 1.00 | 19.06 | A |
| ATOM | 2087 | CB | LEU | A | 336 | 84.406 | 17.767 | −14.914 | 1.00 | 18.05 | A |
| ATOM | 2088 | CG | LEU | A | 336 | 85.073 | 18.119 | −13.571 | 1.00 | 18.25 | A |
| ATOM | 2089 | CD1 | LEU | A | 336 | 86.049 | 19.280 | −13.746 | 1.00 | 15.57 | A |
| ATOM | 2090 | CD2 | LEU | A | 336 | 84.009 | 18.473 | −12.538 | 1.00 | 15.31 | A |
| ATOM | 2091 | C | LEU | A | 336 | 86.424 | 16.594 | −15.832 | 1.00 | 17.85 | A |
| ATOM | 2092 | O | LEU | A | 336 | 87.582 | 16.986 | −15.690 | 1.00 | 17.14 | A |
| ATOM | 2093 | N | LYS | A | 337 | 86.075 | 15.317 | −15.732 | 1.00 | 17.96 | A |
| ATOM | 2094 | CA | LYS | A | 337 | 87.061 | 14.289 | −15.438 | 1.00 | 19.15 | A |
| ATOM | 2095 | CB | LYS | A | 337 | 86.352 | 12.966 | −15.134 | 1.00 | 21.53 | A |
| ATOM | 2096 | CG | LYS | A | 337 | 85.571 | 13.025 | −13.821 | 1.00 | 25.58 | A |
| ATOM | 2097 | CD | LYS | A | 337 | 84.484 | 11.956 | −13.715 | 1.00 | 26.69 | A |
| ATOM | 2098 | CE | LYS | A | 337 | 85.063 | 10.566 | −13.571 | 1.00 | 29.78 | A |
| ATOM | 2099 | NZ | LYS | A | 337 | 83.979 | 9.552 | −13.368 | 1.00 | 30.74 | A |
| ATOM | 2100 | C | LYS | A | 337 | 88.065 | 14.120 | −16.576 | 1.00 | 21.13 | A |
| ATOM | 2101 | O | LYS | A | 337 | 89.170 | 13.631 | −16.362 | 1.00 | 21.11 | A |
| ATOM | 2102 | N | ALA | A | 338 | 87.697 | 14.549 | −17.780 | 1.00 | 21.55 | A |
| ATOM | 2103 | CA | ALA | A | 338 | 88.600 | 14.426 | −18.922 | 1.00 | 22.23 | A |
| ATOM | 2104 | CB | ALA | A | 338 | 87.802 | 14.368 | −20.221 | 1.00 | 21.66 | A |
| ATOM | 2105 | C | ALA | A | 338 | 89.604 | 15.569 | −18.988 | 1.00 | 23.04 | A |
| ATOM | 2106 | O | ALA | A | 338 | 90.518 | 15.541 | −19.800 | 1.00 | 22.63 | A |
| ATOM | 2107 | N | HIS | A | 339 | 89.447 | 16.570 | −18.131 | 1.00 | 23.26 | A |
| ATOM | 2108 | CA | HIS | A | 339 | 90.362 | 17.705 | −18.148 | 1.00 | 23.33 | A |
| ATOM | 2109 | CB | HIS | A | 339 | 90.017 | 18.680 | −17.027 | 1.00 | 22.99 | A |
| ATOM | 2110 | CG | HIS | A | 339 | 90.696 | 20.004 | −17.156 | 1.00 | 23.43 | A |
| ATOM | 2111 | CD2 | HIS | A | 339 | 90.279 | 21.168 | −17.710 | 1.00 | 24.32 | A |
| ATOM | 2112 | ND1 | HIS | A | 339 | 91.993 | 20.219 | −16.741 | 1.00 | 22.64 | A |
| ATOM | 2113 | CE1 | HIS | A | 339 | 92.346 | 21.459 | −17.036 | 1.00 | 24.03 | A |
| ATOM | 2114 | NE2 | HIS | A | 339 | 91.324 | 22.056 | −17.626 | 1.00 | 23.65 | A |
| ATOM | 2115 | C | HIS | A | 339 | 91.833 | 17.302 | −18.046 | 1.00 | 24.36 | A |
| ATOM | 2116 | O | HIS | A | 339 | 92.186 | 16.376 | −17.317 | 1.00 | 24.27 | A |
| ATOM | 2117 | N | PRO | A | 340 | 92.713 | 17.999 | −18.788 | 1.00 | 25.89 | A |
| ATOM | 2118 | CD | PRO | A | 340 | 92.394 | 19.050 | −19.777 | 1.00 | 26.27 | A |
| ATOM | 2119 | CA | PRO | A | 340 | 94.151 | 17.714 | −18.785 | 1.00 | 26.69 | A |
| ATOM | 2120 | CB | PRO | A | 340 | 94.727 | 18.861 | −19.613 | 1.00 | 26.46 | A |
| ATOM | 2121 | CG | PRO | A | 340 | 93.654 | 19.090 | −20.636 | 1.00 | 25.56 | A |
| ATOM | 2122 | C | PRO | A | 340 | 94.772 | 17.629 | −17.396 | 1.00 | 27.13 | A |
| ATOM | 2123 | O | PRO | A | 340 | 95.686 | 16.841 | −17.167 | 1.00 | 28.89 | A |
| ATOM | 2124 | N | PHE | A | 341 | 94.281 | 18.438 | −16.466 | 1.00 | 26.76 | A |
| ATOM | 2125 | CA | PHE | A | 341 | 94.815 | 18.417 | −15.110 | 1.00 | 25.83 | A |
| ATOM | 2126 | CB | PHE | A | 341 | 94.100 | 19.451 | −14.239 | 1.00 | 24.58 | A |
| ATOM | 2127 | CG | PHE | A | 341 | 94.628 | 19.527 | −12.835 | 1.00 | 23.75 | A |
| ATOM | 2128 | CD1 | PHE | A | 341 | 95.890 | 20.060 | −12.578 | 1.00 | 24.62 | A |
| ATOM | 2129 | CD2 | PHE | A | 341 | 93.867 | 19.066 | −11.765 | 1.00 | 24.82 | A |
| ATOM | 2130 | CE1 | PHE | A | 341 | 96.386 | 20.136 | −11.273 | 1.00 | 23.48 | A |
| ATOM | 2131 | CE2 | PHE | A | 341 | 94.352 | 19.136 | −10.454 | 1.00 | 23.61 | A |
| ATOM | 2132 | CZ | PHE | A | 341 | 95.614 | 19.673 | −10.209 | 1.00 | 23.80 | A |
| ATOM | 2133 | C | PHE | A | 341 | 94.684 | 17.039 | −14.458 | 1.00 | 25.53 | A |
| ATOM | 2134 | O | PHE | A | 341 | 95.453 | 16.698 | −13.572 | 1.00 | 25.60 | A |
| ATOM | 2135 | N | PHE | A | 342 | 93.718 | 16.248 | −14.905 | 1.00 | 26.56 | A |
| ATOM | 2136 | CA | PHE | A | 342 | 93.486 | 14.928 | −14.327 | 1.00 | 28.32 | A |
| ATOM | 2137 | CB | PHE | A | 342 | 91.992 | 14.724 | −14.095 | 1.00 | 25.63 | A |
| ATOM | 2138 | CG | PHE | A | 342 | 91.374 | 15.731 | −13.169 | 1.00 | 24.19 | A |
| ATOM | 2139 | CD1 | PHE | A | 342 | 91.830 | 15.868 | −11.859 | 1.00 | 24.72 | A |
| ATOM | 2140 | CD2 | PHE | A | 342 | 90.285 | 16.492 | −13.579 | 1.00 | 21.46 | A |
| ATOM | 2141 | CE1 | PHE | A | 342 | 91.200 | 16.744 | −10.969 | 1.00 | 22.95 | A |
| ATOM | 2142 | CE2 | PHE | A | 342 | 89.649 | 17.368 | −12.699 | 1.00 | 19.82 | A |
| ATOM | 2143 | CZ | PHE | A | 342 | 90.105 | 17.491 | −11.393 | 1.00 | 20.87 | A |
| ATOM | 2144 | C | PHE | A | 342 | 94.009 | 13.811 | −15.217 | 1.00 | 31.08 | A |
| ATOM | 2145 | O | PHE | A | 342 | 93.655 | 12.643 | −15.047 | 1.00 | 32.72 | A |
| ATOM | 2146 | N | GLU | A | 343 | 94.863 | 14.183 | −16.159 | 1.00 | 33.50 | A |
| ATOM | 2147 | CA | GLU | A | 343 | 95.446 | 13.250 | −17.114 | 1.00 | 36.10 | A |
| ATOM | 2148 | CB | GLU | A | 343 | 96.738 | 13.853 | −17.676 | 1.00 | 38.76 | A |
| ATOM | 2149 | CG | GLU | A | 343 | 96.842 | 13.883 | −19.194 | 1.00 | 44.39 | A |
| ATOM | 2150 | CD | GLU | A | 343 | 96.911 | 15.307 | −19.750 | 1.00 | 48.43 | A |
| ATOM | 2151 | OE1 | GLU | A | 343 | 97.665 | 16.143 | −19.190 | 1.00 | 47.87 | A |
| ATOM | 2152 | OE2 | GLU | A | 343 | 96.217 | 15.587 | −20.755 | 1.00 | 49.34 | A |
| ATOM | 2153 | C | GLU | A | 343 | 95.747 | 11.855 | −16.552 | 1.00 | 35.54 | A |
| ATOM | 2154 | O | GLU | A | 343 | 95.210 | 10.847 | −17.019 | 1.00 | 33.70 | A |
| ATOM | 2155 | N | SER | A | 344 | 96.604 | 11.810 | −15.539 | 1.00 | 34.66 | A |
| ATOM | 2156 | CA | SER | A | 344 | 97.024 | 10.545 | −14.950 | 1.00 | 33.91 | A |
| ATOM | 2157 | CB | SER | A | 344 | 98.421 | 10.712 | −14.360 | 1.00 | 33.13 | A |
| ATOM | 2158 | OG | SER | A | 344 | 98.387 | 11.578 | −13.242 | 1.00 | 30.32 | A |
| ATOM | 2159 | C | SER | A | 344 | 96.116 | 9.927 | −13.886 | 1.00 | 33.50 | A |

-continued

| | | | | | | | | | | |
|---|---|---|---|---|---|---|---|---|---|---|
| ATOM | 2160 | O | SER | A | 344 | 96.510 | 8.962 | −13.234 | 1.00 | 32.98 | A |
| ATOM | 2161 | N | VAL | A | 345 | 94.908 | 10.448 | −13.713 | 1.00 | 31.80 | A |
| ATOM | 2162 | CA | VAL | A | 345 | 94.021 | 9.903 | −12.689 | 1.00 | 31.70 | A |
| ATOM | 2163 | CB | VAL | A | 345 | 93.039 | 10.981 | −12.152 | 1.00 | 31.20 | A |
| ATOM | 2164 | CG1 | VAL | A | 345 | 92.153 | 10.375 | −11.079 | 1.00 | 29.96 | A |
| ATOM | 2165 | CG2 | VAL | A | 345 | 93.799 | 12.176 | −11.601 | 1.00 | 27.23 | A |
| ATOM | 2166 | C | VAL | A | 345 | 93.175 | 8.707 | −13.133 | 1.00 | 32.88 | A |
| ATOM | 2167 | O | VAL | A | 345 | 92.597 | 8.712 | −14.223 | 1.00 | 32.39 | A |
| ATOM | 2168 | N | THR | A | 346 | 93.109 | 7.688 | −12.279 | 1.00 | 31.88 | A |
| ATOM | 2169 | CA | THR | A | 346 | 92.285 | 6.511 | −12.539 | 1.00 | 32.94 | A |
| ATOM | 2170 | CB | THR | A | 346 | 93.007 | 5.209 | −12.149 | 1.00 | 35.61 | A |
| ATOM | 2171 | OG1 | THR | A | 346 | 94.137 | 5.012 | −13.013 | 1.00 | 37.85 | A |
| ATOM | 2172 | CG2 | THR | A | 346 | 92.060 | 4.022 | −12.267 | 1.00 | 32.32 | A |
| ATOM | 2173 | C | THR | A | 346 | 91.051 | 6.700 | −11.658 | 1.00 | 33.08 | A |
| ATOM | 2174 | O | THR | A | 346 | 91.083 | 6.460 | −10.448 | 1.00 | 34.21 | A |
| ATOM | 2175 | N | TRP | A | 347 | 89.964 | 7.142 | −12.274 | 1.00 | 31.78 | A |
| ATOM | 2176 | CA | TRP | A | 347 | 88.741 | 7.427 | −11.549 | 1.00 | 31.53 | A |
| ATOM | 2177 | CB | TRP | A | 347 | 87.769 | 8.171 | −12.463 | 1.00 | 28.28 | A |
| ATOM | 2178 | CG | TRP | A | 347 | 88.303 | 9.476 | −12.937 | 1.00 | 23.66 | A |
| ATOM | 2179 | CD2 | TRP | A | 347 | 88.263 | 10.722 | −12.231 | 1.00 | 23.03 | A |
| ATOM | 2180 | CE2 | TRP | A | 347 | 88.927 | 11.678 | −13.031 | 1.00 | 20.77 | A |
| ATOM | 2181 | CE3 | TRP | A | 347 | 87.731 | 11.121 | −10.999 | 1.00 | 20.57 | A |
| ATOM | 2182 | CD1 | TRP | A | 347 | 88.969 | 9.718 | −14.102 | 1.00 | 21.92 | A |
| ATOM | 2183 | NE1 | TRP | A | 347 | 89.348 | 11.041 | −14.168 | 1.00 | 22.23 | A |
| ATOM | 2184 | CZ2 | TRP | A | 347 | 89.074 | 13.008 | −12.640 | 1.00 | 21.04 | A |
| ATOM | 2185 | CZ3 | TRP | A | 347 | 87.876 | 12.444 | −10.611 | 1.00 | 20.11 | A |
| ATOM | 2186 | CH2 | TRP | A | 347 | 88.544 | 13.372 | −11.430 | 1.00 | 20.44 | A |
| ATOM | 2187 | C | TRP | A | 347 | 88.014 | 6.267 | −10.899 | 1.00 | 34.19 | A |
| ATOM | 2188 | O | TRP | A | 347 | 87.382 | 6.440 | −9.854 | 1.00 | 34.97 | A |
| ATOM | 2189 | N | GLU | A | 348 | 88.108 | 5.089 | −11.502 | 1.00 | 35.77 | A |
| ATOM | 2190 | CA | GLU | A | 348 | 87.405 | 3.913 | −11.000 | 1.00 | 36.41 | A |
| ATOM | 2191 | CB | GLU | A | 348 | 87.600 | 2.740 | −11.977 | 1.00 | 36.95 | A |
| ATOM | 2192 | CG | GLU | A | 348 | 88.990 | 2.626 | −12.588 | 1.00 | 36.86 | A |
| ATOM | 2193 | CD | GLU | A | 348 | 89.173 | 3.510 | −13.812 | 0.00 | 36.91 | A |
| ATOM | 2194 | OE1 | GLU | A | 348 | 89.119 | 4.750 | −13.677 | 0.00 | 36.92 | A |
| ATOM | 2195 | OE2 | GLU | A | 348 | 89.370 | 2.960 | −14.916 | 0.00 | 36.92 | A |
| ATOM | 2196 | C | GLU | A | 348 | 87.668 | 3.435 | −9.563 | 1.00 | 36.38 | A |
| ATOM | 2197 | O | GLU | A | 348 | 86.773 | 2.866 | −8.935 | 1.00 | 38.29 | A |
| ATOM | 2198 | N | ASN | A | 349 | 88.857 | 3.669 | −9.019 | 1.00 | 34.41 | A |
| ATOM | 2199 | CA | ASN | A | 349 | 89.134 | 3.182 | −7.668 | 1.00 | 33.02 | A |
| ATOM | 2200 | CB | ASN | A | 349 | 89.848 | 1.844 | −7.765 | 1.00 | 34.07 | A |
| ATOM | 2201 | CG | ASN | A | 349 | 91.220 | 1.978 | −8.381 | 1.00 | 35.48 | A |
| ATOM | 2202 | OD1 | ASN | A | 349 | 91.409 | 2.742 | −9.324 | 1.00 | 35.13 | A |
| ATOM | 2203 | ND2 | ASN | A | 349 | 92.188 | 1.235 | −7.852 | 1.00 | 38.04 | A |
| ATOM | 2204 | C | ASN | A | 349 | 89.970 | 4.116 | −6.804 | 1.00 | 30.73 | A |
| ATOM | 2205 | O | ASN | A | 349 | 90.878 | 3.672 | −6.106 | 1.00 | 30.66 | A |
| ATOM | 2206 | N | LEU | A | 350 | 89.662 | 5.403 | −6.850 | 1.00 | 28.42 | A |
| ATOM | 2207 | CA | LEU | A | 350 | 90.390 | 6.397 | −6.072 | 1.00 | 27.13 | A |
| ATOM | 2208 | CB | LEU | A | 350 | 89.655 | 7.737 | −6.128 | 1.00 | 25.19 | A |
| ATOM | 2209 | CG | LEU | A | 350 | 89.803 | 8.543 | −7.418 | 1.00 | 25.97 | A |
| ATOM | 2210 | CD1 | LEU | A | 350 | 88.841 | 9.732 | −7.428 | 1.00 | 26.30 | A |
| ATOM | 2211 | CD2 | LEU | A | 350 | 91.242 | 9.014 | −7.521 | 1.00 | 27.40 | A |
| ATOM | 2212 | C | LEU | A | 350 | 90.581 | 5.999 | −4.614 | 1.00 | 26.30 | A |
| ATOM | 2213 | O | LEU | A | 350 | 91.645 | 6.201 | −4.036 | 1.00 | 26.73 | A |
| ATOM | 2214 | N | HIS | A | 351 | 89.547 | 5.424 | −4.024 | 1.00 | 27.16 | A |
| ATOM | 2215 | CA | HIS | A | 351 | 89.593 | 5.044 | −2.622 | 1.00 | 28.60 | A |
| ATOM | 2216 | CB | HIS | A | 351 | 88.184 | 4.748 | −2.124 | 1.00 | 29.94 | A |
| ATOM | 2217 | CG | HIS | A | 351 | 88.111 | 4.503 | −0.653 | 1.00 | 30.99 | A |
| ATOM | 2218 | CD2 | HIS | A | 351 | 88.324 | 5.329 | 0.399 | 1.00 | 31.86 | A |
| ATOM | 2219 | ND1 | HIS | A | 351 | 87.790 | 3.275 | −0.118 | 1.00 | 29.43 | A |
| ATOM | 2220 | CE1 | HIS | A | 351 | 87.804 | 3.356 | 1.202 | 1.00 | 31.81 | A |
| ATOM | 2221 | NE2 | HIS | A | 351 | 88.125 | 4.592 | 1.541 | 1.00 | 32.90 | A |
| ATOM | 2222 | C | HIS | A | 351 | 90.509 | 3.873 | −2.298 | 1.00 | 28.99 | A |
| ATOM | 2223 | O | HIS | A | 351 | 90.875 | 3.677 | −1.141 | 1.00 | 28.53 | A |
| ATOM | 2224 | N | GLN | A | 352 | 90.865 | 3.088 | −3.307 | 1.00 | 30.57 | A |
| ATOM | 2225 | CA | GLN | A | 352 | 91.764 | 1.959 | −3.095 | 1.00 | 33.42 | A |
| ATOM | 2226 | CB | GLN | A | 352 | 91.563 | 0.880 | −4.162 | 1.00 | 35.01 | A |
| ATOM | 2227 | CG | GLN | A | 352 | 90.696 | −0.289 | −3.737 | 1.00 | 37.07 | A |
| ATOM | 2228 | CD | GLN | A | 352 | 89.275 | 0.123 | −3.474 | 1.00 | 39.83 | A |
| ATOM | 2229 | OE1 | GLN | A | 352 | 88.676 | 0.856 | −4.267 | 1.00 | 41.90 | A |
| ATOM | 2230 | NE2 | GLN | A | 352 | 88.712 | −0.351 | −2.365 | 1.00 | 39.86 | A |
| ATOM | 2231 | C | GLN | A | 352 | 93.197 | 2.457 | −3.173 | 1.00 | 33.85 | A |
| ATOM | 2232 | O | GLN | A | 352 | 94.126 | 1.782 | −2.734 | 1.00 | 35.32 | A |
| ATOM | 2233 | N | GLN | A | 353 | 93.368 | 3.647 | −3.734 | 1.00 | 32.53 | A |
| ATOM | 2234 | CA | GLN | A | 353 | 94.693 | 4.216 | −3.886 | 1.00 | 32.78 | A |
| ATOM | 2235 | CB | GLN | A | 353 | 94.666 | 5.298 | −4.965 | 1.00 | 32.07 | A |
| ATOM | 2236 | CG | GLN | A | 353 | 94.373 | 4.739 | −6.345 | 1.00 | 31.94 | A |
| ATOM | 2237 | CD | GLN | A | 353 | 94.206 | 5.819 | −7.382 | 1.00 | 32.50 | A |
| ATOM | 2238 | OE1 | GLN | A | 353 | 95.008 | 6.749 | −7.452 | 1.00 | 35.33 | A |

-continued

| ATOM | 2239 | NE2 | GLN | A | 353 | 93.167 | 5.701 | −8.204 | 1.00 | 31.02 | A |
|------|------|-----|-----|---|-----|--------|-------|--------|------|-------|---|
| ATOM | 2240 | C | GLN | A | 353 | 95.246 | 4.779 | −2.588 | 1.00 | 33.27 | A |
| ATOM | 2241 | O | GLN | A | 353 | 94.494 | 5.209 | −1.717 | 1.00 | 32.38 | A |
| ATOM | 2242 | N | THR | A | 354 | 96.570 | 4.746 | −2.462 | 1.00 | 33.29 | A |
| ATOM | 2243 | CA | THR | A | 354 | 97.239 | 5.267 | −1.280 | 1.00 | 34.35 | A |
| ATOM | 2244 | CB | THR | A | 354 | 98.615 | 4.601 | −1.069 | 1.00 | 35.88 | A |
| ATOM | 2245 | OG1 | THR | A | 354 | 98.430 | 3.232 | −0.690 | 1.00 | 36.70 | A |
| ATOM | 2246 | CG2 | THR | A | 354 | 99.403 | 5.325 | 0.027 | 1.00 | 36.08 | A |
| ATOM | 2247 | C | THR | A | 354 | 97.440 | 6.760 | −1.478 | 1.00 | 33.06 | A |
| ATOM | 2248 | O | THR | A | 354 | 98.120 | 7.181 | −2.403 | 1.00 | 31.33 | A |
| ATOM | 2249 | N | PRO | A | 355 | 96.844 | 7.581 | −0.604 | 1.00 | 33.40 | A |
| ATOM | 2250 | CD | PRO | A | 355 | 96.000 | 7.220 | 0.544 | 1.00 | 31.90 | A |
| ATOM | 2251 | CA | PRO | A | 355 | 96.974 | 9.035 | −0.710 | 1.00 | 34.90 | A |
| ATOM | 2252 | CB | PRO | A | 355 | 96.156 | 9.543 | 0.475 | 1.00 | 33.68 | A |
| ATOM | 2253 | CG | PRO | A | 355 | 95.160 | 8.452 | 0.698 | 1.00 | 33.37 | A |
| ATOM | 2254 | C | PRO | A | 355 | 98.428 | 9.475 | −0.623 | 1.00 | 36.27 | A |
| ATOM | 2255 | O | PRO | A | 355 | 99.196 | 8.960 | 0.191 | 1.00 | 35.70 | A |
| ATOM | 2256 | N | PRO | A | 356 | 98.824 | 10.433 | −1.464 | 1.00 | 37.66 | A |
| ATOM | 2257 | CD | PRO | A | 356 | 98.010 | 11.198 | −2.423 | 1.00 | 38.22 | A |
| ATOM | 2258 | CA | PRO | A | 356 | 100.205 | 10.916 | −1.441 | 1.00 | 39.93 | A |
| ATOM | 2259 | CB | PRO | A | 356 | 100.227 | 11.944 | −2.570 | 1.00 | 38.83 | A |
| ATOM | 2260 | CG | PRO | A | 356 | 98.818 | 12.466 | −2.580 | 1.00 | 38.26 | A |
| ATOM | 2261 | C | PRO | A | 356 | 100.532 | 11.534 | −0.085 | 1.00 | 41.87 | A |
| ATOM | 2262 | O | PRO | A | 356 | 99.696 | 12.209 | 0.506 | 1.00 | 40.91 | A |
| ATOM | 2263 | N | ALA | A | 357 | 101.741 | 11.286 | 0.409 | 1.00 | 46.23 | A |
| ATOM | 2264 | CA | ALA | A | 357 | 102.160 | 11.837 | 1.691 | 1.00 | 51.16 | A |
| ATOM | 2265 | CB | ALA | A | 357 | 103.587 | 11.410 | 2.001 | 1.00 | 49.78 | A |
| ATOM | 2266 | C | ALA | A | 357 | 102.077 | 13.354 | 1.589 | 1.00 | 54.64 | A |
| ATOM | 2267 | O | ALA | A | 357 | 102.591 | 13.942 | 0.637 | 1.00 | 55.14 | A |
| ATOM | 2268 | N | LEU | A | 358 | 101.419 | 13.985 | 2.559 | 1.00 | 58.59 | A |
| ATOM | 2269 | CA | LEU | A | 358 | 101.276 | 15.437 | 2.552 | 1.00 | 62.92 | A |
| ATOM | 2270 | CB | LEU | A | 358 | 100.107 | 15.866 | 3.441 | 1.00 | 62.51 | A |
| ATOM | 2271 | CG | LEU | A | 358 | 98.732 | 15.752 | 2.783 | 1.00 | 63.05 | A |
| ATOM | 2272 | CD1 | LEU | A | 358 | 97.657 | 16.251 | 3.737 | 1.00 | 63.34 | A |
| ATOM | 2273 | CD2 | LEU | A | 358 | 98.721 | 16.570 | 1.494 | 1.00 | 62.56 | A |
| ATOM | 2274 | C | LEU | A | 358 | 102.536 | 16.173 | 2.984 | 1.00 | 65.81 | A |
| ATOM | 2275 | O | LEU | A | 358 | 102.675 | 16.559 | 4.148 | 1.00 | 66.45 | A |
| ATOM | 2276 | N | THR | A | 359 | 103.441 | 16.368 | 2.025 | 1.00 | 69.31 | A |
| ATOM | 2277 | CA | THR | A | 359 | 104.715 | 17.057 | 2.236 | 1.00 | 72.25 | A |
| ATOM | 2278 | CB | THR | A | 359 | 104.519 | 18.594 | 2.271 | 1.00 | 73.17 | A |
| ATOM | 2279 | OG1 | THR | A | 359 | 103.564 | 18.937 | 3.284 | 1.00 | 75.38 | A |
| ATOM | 2280 | CG2 | THR | A | 359 | 104.030 | 19.101 | 0.916 | 1.00 | 72.93 | A |
| ATOM | 2281 | C | THR | A | 359 | 105.468 | 16.627 | 3.497 | 1.00 | 73.76 | A |
| ATOM | 2282 | O | THR | A | 359 | 105.011 | 15.683 | 4.180 | 1.00 | 74.61 | A |
| ATOM | 2283 | OXT | THR | A | 359 | 106.523 | 17.237 | 3.780 | 1.00 | 75.50 | A |
| ATOM | 2284 | OH2 | TIP | S | 1 | 82.965 | 32.402 | −3.946 | 1.00 | 13.32 | S |
| ATOM | 2285 | OH2 | TIP | S | 2 | 91.556 | 13.784 | −17.557 | 1.00 | 22.11 | S |
| ATOM | 2286 | OH2 | TIP | S | 3 | 87.391 | 33.155 | −1.722 | 1.00 | 22.84 | S |
| ATOM | 2287 | OH2 | TIP | S | 4 | 69.033 | 3.499 | 13.879 | 1.00 | 22.91 | S |
| ATOM | 2288 | OH2 | TIP | S | 5 | 81.088 | 19.368 | −18.406 | 1.00 | 24.13 | S |
| ATOM | 2289 | OH2 | TIP | S | 6 | 75.641 | 16.130 | 8.209 | 1.00 | 26.44 | S |
| ATOM | 2290 | OH2 | TIP | S | 7 | 74.760 | 20.961 | 3.347 | 1.00 | 27.74 | S |
| ATOM | 2291 | OH2 | TIP | S | 8 | 75.152 | 6.784 | 5.545 | 1.00 | 22.53 | S |
| ATOM | 2292 | OH2 | TIP | S | 9 | 77.282 | 11.807 | −17.666 | 1.00 | 35.96 | S |
| ATOM | 2293 | OH2 | TIP | S | 10 | 81.785 | 8.968 | −8.072 | 1.00 | 25.44 | S |
| ATOM | 2294 | OH2 | TIP | S | 11 | 78.609 | 24.424 | −2.074 | 1.00 | 22.05 | S |
| ATOM | 2295 | OH2 | TIP | S | 12 | 94.883 | 8.256 | −9.981 | 1.00 | 37.17 | S |
| ATOM | 2296 | OH2 | TIP | S | 13 | 73.164 | 38.970 | −1.072 | 1.00 | 35.95 | S |
| ATOM | 2297 | OH2 | TIP | S | 14 | 78.806 | 27.556 | −3.116 | 1.00 | 39.27 | S |
| ATOM | 2298 | OH2 | TIP | S | 15 | 89.050 | 8.041 | 10.604 | 1.00 | 23.40 | S |
| ATOM | 2299 | OH2 | TIP | S | 16 | 73.265 | 40.376 | −3.301 | 1.00 | 26.94 | S |
| ATOM | 2300 | OH2 | TIP | S | 18 | 84.081 | 33.371 | 4.243 | 1.00 | 30.61 | S |
| ATOM | 2301 | OH2 | TIP | S | 19 | 78.571 | −0.530 | 16.531 | 1.00 | 26.61 | S |
| ATOM | 2302 | OH2 | TIP | S | 21 | 70.088 | 3.703 | 17.559 | 1.00 | 28.94 | S |
| ATOM | 2303 | OH2 | TIP | S | 22 | 79.212 | 13.330 | −18.791 | 1.00 | 26.94 | S |
| ATOM | 2304 | OH2 | TIP | S | 23 | 91.672 | 10.665 | −16.153 | 1.00 | 30.26 | S |
| ATOM | 2305 | OH2 | TIP | S | 25 | 104.173 | 17.689 | −7.204 | 1.00 | 31.65 | S |
| ATOM | 2306 | OH2 | TIP | S | 27 | 87.578 | 18.354 | −20.604 | 1.00 | 25.98 | S |
| ATOM | 2307 | OH2 | TIP | S | 28 | 82.272 | 34.870 | −16.021 | 1.00 | 27.40 | S |
| ATOM | 2308 | OH2 | TIP | S | 29 | 100.496 | 13.074 | −9.812 | 1.00 | 37.92 | S |
| ATOM | 2309 | OH2 | TIP | S | 30 | 65.147 | 10.515 | 28.440 | 1.00 | 40.03 | S |
| ATOM | 2310 | OH2 | TIP | S | 31 | 90.721 | 38.800 | −4.631 | 1.00 | 42.09 | S |
| ATOM | 2311 | OH2 | TIP | S | 32 | 83.367 | 23.841 | 15.654 | 1.00 | 36.15 | S |
| ATOM | 2312 | OH2 | TIP | S | 33 | 87.754 | 11.897 | 23.760 | 1.00 | 26.76 | S |
| ATOM | 2313 | OH2 | TIP | S | 34 | 77.755 | 13.485 | −15.395 | 1.00 | 31.85 | S |
| ATOM | 2314 | OH2 | TIP | S | 35 | 79.767 | 43.115 | 5.371 | 1.00 | 35.26 | S |
| ATOM | 2315 | OH2 | TIP | S | 37 | 80.173 | 32.998 | 6.198 | 1.00 | 40.03 | S |
| ATOM | 2316 | OH2 | TIP | S | 40 | 85.958 | 19.110 | 24.502 | 1.00 | 24.42 | S |
| ATOM | 2317 | OH2 | TIP | S | 42 | 77.719 | −0.391 | 23.732 | 1.00 | 39.71 | S |

-continued

| | | | | | | | | | | |
|---|---|---|---|---|---|---|---|---|---|---|
| ATOM | 2318 | OH2 | TIP | S | 44 | 92.563 | 36.428 | −5.574 | 1.00 | 35.43 | S |
| ATOM | 2319 | OH2 | TIP | S | 45 | 90.942 | 34.092 | 3.570 | 1.00 | 43.64 | S |
| ATOM | 2320 | OH2 | TIP | S | 46 | 74.357 | 32.157 | −13.849 | 1.00 | 33.31 | S |
| ATOM | 2321 | OH2 | TIP | S | 47 | 90.220 | 14.449 | 16.172 | 1.00 | 34.34 | S |
| ATOM | 2322 | OH2 | TIP | S | 48 | 77.876 | 11.229 | −13.863 | 1.00 | 23.53 | S |
| ATOM | 2323 | OH2 | TIP | S | 50 | 76.289 | 12.589 | −11.572 | 1.00 | 37.74 | S |
| ATOM | 2324 | OH2 | TIP | S | 51 | 76.619 | 2.787 | −2.969 | 1.00 | 35.95 | S |
| ATOM | 2325 | OH2 | TIP | S | 52 | 65.118 | 19.629 | 24.370 | 1.00 | 34.85 | S |
| ATOM | 2326 | OH2 | TIP | S | 53 | 99.690 | 31.473 | −13.046 | 1.00 | 48.21 | S |
| ATOM | 2327 | OH2 | TIP | S | 54 | 88.376 | 36.865 | 3.454 | 1.00 | 38.54 | S |
| ATOM | 2328 | OH2 | TIP | S | 57 | 91.236 | 10.819 | 18.279 | 1.00 | 40.76 | S |
| ATOM | 2329 | OH2 | TIP | S | 59 | 100.017 | 21.990 | −14.622 | 1.00 | 41.65 | S |
| ATOM | 2330 | OH2 | TIP | S | 63 | 87.188 | 25.521 | 11.438 | 1.00 | 41.53 | S |
| ATOM | 2331 | OH2 | TIP | S | 65 | 90.264 | 19.625 | 12.286 | 1.00 | 24.22 | S |
| ATOM | 2332 | OH2 | TIP | S | 66 | 83.805 | 26.254 | −18.365 | 1.00 | 37.50 | S |
| ATOM | 2333 | OH2 | TIP | S | 68 | 78.394 | 7.378 | 2.855 | 1.00 | 23.47 | S |
| ATOM | 2334 | OH2 | TIP | S | 74 | 85.541 | 11.500 | −18.436 | 1.00 | 37.35 | S |
| ATOM | 2335 | OH2 | TIP | S | 76 | 98.981 | 8.707 | 2.808 | 1.00 | 47.34 | S |
| ATOM | 2336 | OH2 | TIP | S | 78 | 87.802 | 19.118 | 22.522 | 1.00 | 39.99 | S |
| ATOM | 2337 | OH2 | TIP | S | 80 | 92.438 | 3.105 | 2.517 | 1.00 | 37.27 | S |
| ATOM | 2338 | OH2 | TIP | S | 81 | 75.580 | −0.821 | 22.186 | 1.00 | 36.41 | S |
| ATOM | 2339 | OH2 | TIP | S | 82 | 60.506 | 24.278 | 21.938 | 1.00 | 31.55 | S |
| ATOM | 2340 | OH2 | TIP | S | 83 | 92.298 | 22.520 | −21.183 | 1.00 | 42.32 | S |
| ATOM | 2341 | OH2 | TIP | S | 84 | 74.351 | 4.211 | −3.464 | 1.00 | 32.53 | S |
| ATOM | 2342 | OH2 | TIP | S | 85 | 76.502 | 25.963 | −21.839 | 1.00 | 41.89 | S |
| ATOM | 2343 | OH2 | TIP | S | 86 | 97.965 | 13.142 | 9.216 | 1.00 | 41.76 | S |
| ATOM | 2344 | OH2 | TIP | S | 87 | 78.657 | 4.418 | 3.361 | 1.00 | 35.63 | S |
| ATOM | 2345 | OH2 | TIP | S | 88 | 93.633 | 28.572 | 3.429 | 1.00 | 34.30 | S |
| ATOM | 2346 | OH2 | TIP | S | 89 | 104.691 | 20.306 | −7.235 | 1.00 | 32.75 | S |
| ATOM | 2347 | OH2 | TIP | S | 91 | 98.360 | 16.754 | −15.558 | 1.00 | 37.92 | S |
| ATOM | 2348 | OH2 | TIP | S | 92 | 88.175 | 32.723 | −14.088 | 1.00 | 38.91 | S |
| ATOM | 2349 | OH2 | TIP | S | 93 | 96.974 | 27.936 | −17.613 | 1.00 | 34.47 | S |
| ATOM | 2350 | OH2 | TIP | S | 94 | 85.585 | 22.346 | 15.199 | 1.00 | 41.12 | S |
| ATOM | 2351 | OH2 | TIP | S | 100 | 80.948 | −0.010 | 7.892 | 1.00 | 12.04 | S |
| ATOM | 2352 | OH2 | TIP | S | 101 | 76.653 | 29.202 | −3.527 | 1.00 | 22.10 | S |
| ATOM | 2353 | OH2 | TIP | S | 102 | 74.980 | 8.979 | −7.975 | 1.00 | 21.17 | S |
| ATOM | 2354 | OH2 | TIP | S | 103 | 88.843 | 28.393 | 3.994 | 1.00 | 30.94 | S |
| ATOM | 2355 | OH2 | TIP | S | 105 | 76.862 | 8.067 | 28.490 | 1.00 | 20.20 | S |
| ATOM | 2356 | OH2 | TIP | S | 106 | 66.435 | 30.702 | 8.817 | 1.00 | 35.87 | S |
| ATOM | 2357 | OH2 | TIP | S | 109 | 67.384 | 7.757 | 8.860 | 1.00 | 39.38 | S |
| ATOM | 2358 | OH2 | TIP | S | 110 | 66.852 | 4.666 | 22.301 | 1.00 | 32.75 | S |
| ATOM | 2359 | OH2 | TIP | S | 111 | 72.391 | 2.229 | −3.501 | 1.00 | 51.07 | S |
| ATOM | 2360 | OH2 | TIP | S | 116 | 80.209 | 7.061 | −7.886 | 1.00 | 35.49 | S |
| ATOM | 2361 | OH2 | TIP | S | 121 | 74.466 | 15.313 | −12.357 | 1.00 | 45.36 | S |
| ATOM | 2362 | OH2 | TIP | S | 122 | 79.225 | 28.627 | 0.179 | 1.00 | 30.68 | S |
| ATOM | 2363 | OH2 | TIP | S | 124 | 59.090 | 22.126 | 22.498 | 1.00 | 35.94 | S |
| ATOM | 2364 | OH2 | TIP | S | 126 | 73.715 | 24.448 | −13.973 | 1.00 | 44.35 | S |
| ATOM | 2365 | OH2 | TIP | S | 127 | 105.619 | 22.931 | −11.256 | 1.00 | 43.80 | S |
| ATOM | 2366 | OH2 | TIP | S | 128 | 86.658 | 32.319 | −16.090 | 1.00 | 39.40 | S |
| ATOM | 2367 | OH2 | TIP | S | 129 | 70.750 | 21.709 | −10.875 | 1.00 | 45.74 | S |
| ATOM | 2368 | OH2 | TIP | S | 136 | 77.820 | 12.663 | 6.090 | 1.00 | 47.18 | S |
| ATOM | 2369 | OH2 | TIP | S | 142 | 90.942 | 35.947 | −13.582 | 1.00 | 48.16 | S |
| ATOM | 2370 | OH2 | TIP | S | 146 | 67.351 | 6.830 | 24.075 | 1.00 | 36.66 | S |
| ATOM | 2371 | OH2 | TIP | S | 148 | 98.067 | 12.182 | −7.216 | 1.00 | 38.66 | S |
| ATOM | 2372 | OH2 | TIP | S | 156 | 75.211 | 13.809 | −20.582 | 1.00 | 45.56 | S |
| ATOM | 2373 | OH2 | TIP | S | 158 | 72.261 | 20.575 | 12.175 | 1.00 | 51.45 | S |
| ATOM | 2374 | OH2 | TIP | S | 166 | 77.289 | 42.685 | 7.086 | 1.00 | 42.23 | S |
| ATOM | 2375 | OH2 | TIP | S | 174 | 65.330 | 6.552 | 20.003 | 1.00 | 42.22 | S |
| ATOM | 2376 | OH2 | TIP | S | 176 | 88.027 | 20.872 | −20.665 | 1.00 | 35.09 | S |
| ATOM | 2377 | OH2 | TIP | S | 178 | 99.488 | 29.517 | −16.497 | 1.00 | 44.21 | S |
| ATOM | 2378 | OH2 | TIP | S | 182 | 93.851 | 13.830 | −20.448 | 1.00 | 50.19 | S |
| ATOM | 2379 | OH2 | TIP | S | 192 | 83.811 | 26.388 | 9.460 | 1.00 | 39.52 | S |
| ATOM | 2380 | OH2 | TIP | S | 193 | 91.704 | 42.080 | 2.405 | 1.00 | 40.67 | S |
| ATOM | 2381 | O12 | GLC | G | 1 | 82.624 | 0.887 | 12.473 | 1.00 | 47.94 | G |
| ATOM | 2382 | C11 | GLC | G | 1 | 82.240 | 2.160 | 13.000 | 1.00 | 48.49 | G |
| ATOM | 2383 | C13 | GLC | G | 1 | 83.237 | 3.235 | 12.553 | 1.00 | 46.87 | G |
| ATOM | 2384 | O14 | GLC | G | 1 | 84.544 | 2.903 | 13.022 | 1.00 | 46.62 | G |
| ATOM | 2385 | C15 | GLC | G | 1 | 82.817 | 4.591 | 13.117 | 1.00 | 45.80 | G |
| ATOM | 2386 | O16 | GLC | G | 1 | 83.746 | 5.589 | 12.703 | 1.00 | 43.50 | G |
| ATOM | 2387 | O12 | GLC | G | 5 | 86.722 | −2.593 | 0.107 | 1.00 | 39.62 | G |
| ATOM | 2388 | C11 | GLC | G | 5 | 86.245 | −1.364 | −0.429 | 1.00 | 44.37 | G |
| ATOM | 2389 | C13 | GLC | G | 5 | 86.764 | −0.193 | 0.394 | 1.00 | 44.36 | G |
| ATOM | 2390 | O14 | GLC | G | 5 | 86.355 | −0.326 | 1.761 | 1.00 | 47.64 | G |
| ATOM | 2391 | C15 | GLC | G | 5 | 86.231 | −0.195 | −1.557 | 1.00 | 45.11 | G |
| ATOM | 2392 | O16 | GLC | G | 5 | 86.666 | 1.310 | −1.557 | 1.00 | 42.61 | G |
| ATOM | 2393 | O12 | GLC | G | 8 | 87.512 | 4.414 | −5.278 | 1.00 | 38.37 | G |
| ATOM | 2394 | C11 | GLC | G | 8 | 86.362 | 5.220 | −5.023 | 1.00 | 34.16 | G |
| ATOM | 2395 | C13 | GLC | G | 8 | 85.750 | 5.654 | −6.351 | 1.00 | 35.54 | G |
| ATOM | 2396 | O14 | GLC | G | 8 | 86.717 | 6.392 | −7.111 | 1.00 | 37.03 | G |

-continued

| ATOM | 2397 | C15 | GLC | G | 8 | 84.521 | 6.523 | −6.082 | 1.00 | 35.46 | G |
|---|---|---|---|---|---|---|---|---|---|---|---|
| ATOM | 2398 | O16 | GLC | G | 8 | 83.948 | 6.931 | −7.319 | 1.00 | 33.79 | G |
| ATOM | 2399 | C34 | STO | L | 1 | 82.178 | 19.404 | 9.614 | 1.00 | 23.98 | L |
| ATOM | 2400 | O33 | STO | L | 1 | 83.091 | 19.645 | 10.691 | 1.00 | 24.40 | L |
| ATOM | 2401 | C25 | STO | L | 1 | 82.557 | 20.621 | 11.610 | 1.00 | 19.84 | L |
| ATOM | 2402 | C26 | STO | L | 1 | 83.748 | 21.455 | 12.055 | 1.00 | 20.35 | L |
| ATOM | 2403 | N31 | STO | L | 1 | 84.251 | 22.242 | 10.916 | 1.00 | 22.56 | L |
| ATOM | 2404 | C32 | STO | L | 1 | 83.716 | 23.544 | 10.481 | 1.00 | 20.91 | L |
| ATOM | 2405 | C27 | STO | L | 1 | 84.847 | 20.523 | 12.559 | 1.00 | 19.37 | L |
| ATOM | 2406 | C28 | STO | L | 1 | 84.278 | 19.595 | 13.658 | 1.00 | 18.70 | L |
| ATOM | 2407 | O29 | STO | L | 1 | 82.889 | 19.845 | 13.980 | 1.00 | 20.08 | L |
| ATOM | 2408 | C24 | STO | L | 1 | 81.939 | 19.930 | 12.872 | 1.00 | 21.85 | L |
| ATOM | 2409 | C35 | STO | L | 1 | 80.791 | 20.824 | 13.403 | 1.00 | 20.12 | L |
| ATOM | 2410 | N6 | STO | L | 1 | 81.456 | 18.689 | 12.528 | 1.00 | 19.30 | L |
| ATOM | 2411 | C5 | STO | L | 1 | 80.172 | 18.450 | 12.023 | 1.00 | 16.04 | L |
| ATOM | 2412 | C4 | STO | L | 1 | 79.039 | 19.219 | 11.690 | 1.00 | 14.17 | L |
| ATOM | 2413 | C3 | STO | L | 1 | 77.901 | 18.569 | 11.148 | 1.00 | 14.32 | L |
| ATOM | 2414 | C2 | STO | L | 1 | 77.899 | 17.158 | 10.946 | 1.00 | 14.05 | L |
| ATOM | 2415 | C1 | STO | L | 1 | 79.035 | 16.386 | 11.282 | 1.00 | 13.54 | L |
| ATOM | 2416 | C23 | STO | L | 1 | 80.154 | 17.053 | 11.812 | 1.00 | 16.42 | L |
| ATOM | 2417 | C22 | STO | L | 1 | 81.361 | 16.522 | 12.164 | 1.00 | 17.74 | L |
| ATOM | 2418 | C7 | STO | L | 1 | 82.162 | 17.525 | 12.606 | 1.00 | 18.84 | L |
| ATOM | 2419 | C8 | STO | L | 1 | 83.501 | 17.279 | 12.972 | 1.00 | 18.69 | L |
| ATOM | 2420 | N9 | STO | L | 1 | 84.462 | 18.150 | 13.376 | 1.00 | 19.59 | L |
| ATOM | 2421 | C10 | STO | L | 1 | 85.663 | 17.477 | 13.561 | 1.00 | 19.11 | L |
| ATOM | 2422 | C11 | STO | L | 1 | 86.968 | 17.838 | 13.942 | 1.00 | 16.81 | L |
| ATOM | 2423 | C12 | STO | L | 1 | 87.961 | 16.831 | 14.007 | 1.00 | 20.66 | L |
| ATOM | 2424 | C13 | STO | L | 1 | 87.645 | 15.476 | 13.689 | 1.00 | 20.30 | L |
| ATOM | 2425 | C14 | STO | L | 1 | 86.329 | 15.117 | 13.306 | 1.00 | 19.66 | L |
| ATOM | 2426 | C15 | STO | L | 1 | 85.364 | 16.127 | 13.248 | 1.00 | 18.74 | L |
| ATOM | 2427 | C16 | STO | L | 1 | 84.049 | 16.022 | 12.899 | 1.00 | 19.21 | L |
| ATOM | 2428 | C17 | STO | L | 1 | 83.217 | 14.936 | 12.440 | 1.00 | 18.26 | L |
| ATOM | 2429 | C21 | STO | L | 1 | 81.934 | 15.217 | 12.098 | 1.00 | 17.21 | L |
| ATOM | 2430 | C20 | STO | L | 1 | 81.325 | 14.098 | 11.689 | 1.00 | 17.68 | L |
| ATOM | 2431 | N19 | STO | L | 1 | 82.281 | 13.080 | 11.786 | 1.00 | 13.64 | L |
| ATOM | 2432 | C18 | STO | L | 1 | 83.457 | 13.603 | 12.261 | 1.00 | 16.89 | L |
| ATOM | 2433 | O30 | STO | L | 1 | 84.493 | 12.981 | 12.504 | 1.00 | 15.41 | L |
| ATOM | 2434 | S | SO4 | I | 1 | 64.914 | 7.877 | 16.247 | 1.00 | 82.11 | I |
| ATOM | 2435 | O1 | SO4 | I | 1 | 63.624 | 8.415 | 15.778 | 1.00 | 82.68 | I |
| ATOM | 2436 | O2 | SO4 | I | 1 | 65.841 | 8.992 | 16.520 | 1.00 | 82.73 | I |
| ATOM | 2437 | O3 | SO4 | I | 1 | 65.479 | 7.010 | 15.198 | 1.00 | 83.33 | I |
| ATOM | 2438 | O4 | SO4 | I | 1 | 64.709 | 7.088 | 17.477 | 1.00 | 82.04 | I |
| ATOM | 2439 | S | SO4 | I | 2 | 68.379 | −7.029 | 19.810 | 1.00 | 112.82 | I |
| ATOM | 2440 | O1 | SO4 | I | 2 | 66.992 | −6.526 | 19.786 | 1.00 | 112.60 | I |
| ATOM | 2441 | O2 | SO4 | I | 2 | 68.850 | −7.226 | 18.425 | 1.00 | 112.21 | I |
| ATOM | 2442 | O3 | SO4 | I | 2 | 68.426 | −8.312 | 20.538 | 1.00 | 112.24 | I |
| ATOM | 2443 | O4 | SO4 | I | 2 | 69.249 | −6.051 | 20.491 | 1.00 | 112.72 | I |
| ATOM | 2444 | S | SO4 | I | 3 | 84.927 | −1.874 | 12.302 | 1.00 | 79.99 | I |
| ATOM | 2445 | O1 | SO4 | I | 3 | 84.408 | −1.334 | 13.568 | 1.00 | 79.90 | I |
| ATOM | 2446 | O2 | SO4 | I | 3 | 84.442 | −1.050 | 11.178 | 1.00 | 80.43 | I |
| ATOM | 2447 | O3 | SO4 | I | 3 | 84.453 | −3.263 | 12.131 | 1.00 | 79.92 | I |
| ATOM | 2448 | O4 | SO4 | I | 3 | 86.402 | −1.845 | 12.326 | 1.00 | 80.52 | I |
| ATOM | 2449 | S | SO4 | I | 4 | 80.577 | 9.632 | 30.033 | 1.00 | 98.23 | I |
| ATOM | 2450 | O1 | SO4 | I | 4 | 79.725 | 9.060 | 28.972 | 1.00 | 96.88 | I |
| ATOM | 2451 | O2 | SO4 | I | 4 | 82.000 | 9.461 | 29.683 | 1.00 | 97.80 | I |
| ATOM | 2452 | O3 | SO4 | I | 4 | 80.304 | 8.944 | 31.309 | 1.00 | 98.08 | I |
| ATOM | 2453 | O4 | SO4 | I | 4 | 80.281 | 11.069 | 30.178 | 1.00 | 98.08 | I |
| ATOM | 2454 | S | SO4 | I | 5 | 89.310 | 6.131 | 25.915 | 1.00 | 110.86 | I |
| ATOM | 2455 | O1 | SO4 | I | 5 | 89.025 | 6.456 | 27.331 | 1.00 | 110.48 | I |
| ATOM | 2456 | O2 | SO4 | I | 5 | 88.042 | 6.095 | 25.151 | 1.00 | 110.12 | I |
| ATOM | 2457 | O3 | SO4 | I | 5 | 89.970 | 4.810 | 25.844 | 1.00 | 110.72 | I |
| ATOM | 2458 | O4 | SO4 | I | 5 | 90.205 | 7.155 | 25.330 | 1.00 | 110.02 | I |
| ATOM | 2459 | O2 | PO4 | P | 100 | 64.527 | 26.252 | 2.299 | 1.00 | 88.98 | P |
| ATOM | 2460 | O3 | PO4 | P | 100 | 66.482 | 25.155 | 1.367 | 1.00 | 88.39 | P |
| ATOM | 2461 | O4 | PO4 | P | 100 | 66.688 | 26.504 | 3.376 | 1.00 | 87.87 | P |
| ATOM | 2462 | O1 | PO4 | P | 100 | 66.264 | 27.565 | 1.240 | 1.00 | 88.80 | P |
| ATOM | 2463 | P | PO4 | P | 100 | 65.992 | 26.368 | 2.070 | 1.00 | 88.61 | P |
| ATOM | 2464 | CB | LEU | | 145 | 73.932 | 8.398 | 8.961 | 0.50 | 21.29 | AC2 |
| ATOM | 2465 | CG | LEU | | 145 | 72.901 | 8.606 | 10.076 | 0.50 | 21.65 | AC2 |
| ATOM | 2466 | CD1 | LEU | | 145 | 71.904 | 9.671 | 9.655 | 0.50 | 21.60 | AC2 |
| ATOM | 2467 | CD2 | LEU | | 145 | 72.195 | 7.298 | 10.388 | 0.50 | 19.61 | AC2 |
| ATOM | 2468 | CB | ASN | | 214 | 88.968 | 8.625 | 7.173 | 0.50 | 22.34 | AC2 |
| ATOM | 2469 | CG | ASN | | 214 | 89.705 | 8.084 | 5.975 | 0.50 | 22.01 | AC2 |
| ATOM | 2470 | OD1 | ASN | | 214 | 89.240 | 7.153 | 5.320 | 0.50 | 22.82 | AC2 |
| ATOM | 2471 | ND2 | ASN | | 214 | 90.859 | 8.660 | 5.678 | 0.50 | 22.69 | AC2 |
| ATOM | 2472 | CB | ASP | | 216 | 93.187 | 5.546 | 5.379 | 0.50 | 25.98 | AC2 |
| ATOM | 2473 | CG | ASP | | 216 | 91.789 | 5.828 | 4.895 | 0.50 | 27.09 | AC2 |

-continued

| ATOM | 2474 | OD1 | ASP | | 216 | 91.587 | 6.896 | 4.290 | 0.50 | 28.49 | AC2 |
|---|---|---|---|---|---|---|---|---|---|---|---|
| ATOM | 2475 | OD2 | ASP | | 216 | 90.896 | 4.982 | 5.110 | 0.50 | 28.20 | AC2 |
| END | | | | | | | | | | | |

Example 8

Co-Ordinates for PDK1 Fragment Co-Crystallised with UCN-01

```
REMARK coordinates from restrained individual B-factor refinement
REMARK refinement resolution: 25.0-2.50 A
REMARK starting r= 0.1919 free_r= 0.2582
REMARK final    r= 0.1894 free_r= 0.2567
REMARK B rmsd for bonded mainchain atoms= 1.412 target=1.5
REMARK B rmsd for bonded sidechain atoms=  2.205 target=2.0
REMARK B rmsd for angle mainchain atoms= 2.401 target=2.0
REMARK B rmsd for angle sidechain atoms=  3.256 target=2.5
REMARK rweight= 0.1000 (with wa= 3.1611)
REMARK target= mlf steps= 30
REMARK sg= P3(2)21 a= 123.387 b= 123.387 c= 47.115 alpha= 90 beta= 90 gamma= 120
REMARK parameter file 1 : /ddl/david/refinement/MY_CNS/prot.par
REMARK parameter file 2 : /ddl/david/refinement/MY_CNS/ucn01.par
REMARK parameter file 3 : CNS_TOPPAR:water_rep.param
REMARK parameter file 4 : CNS_TOPPAR:ion.param
REMARK parameter file 5 :
/dd1/david/refinement/MY_CNS/glycerol.par
REMARK molecular structure file: . . /generate/generate.mtf
REMARK input coordinates: . . /minimize/minimize.pdb
REMARK reflection file= . ./. ./. ./data/cns.hkl
REMARK ncs= none
REMARK B-correction resolution: 6.0-2.50
REMARK initial B-factor correction applied to fobs:
REMARK B11= -4.722 B22= 4.722 B33= 9.444
REMARK B12= -3.572 B13= 0.000 B23= 0.000
REMARK B-factor correction applied to coordinate array B: -0.193
REMARK bulk solvent: density level= 0.3837 e/A 3, B-factor=
40.9071 A 2
REMARK reflections with |Fobs|/sigma_F < 0.0 rejected
REMARK reflections with |Fobs| > 10000 * rms(Fobs) rejected
REMARK theoretical total number of refl. in resol. range: 14485
(100.0%)
REMARK number of unobserved reflections (no entry or |F|=0):
101 (0.7%)
REMARK number of reflections rejected: 0 (0.0%)
REMARK total number of reflections used: 14384 (99.3%)
REMARK number of reflections in working set: 13795 (95.2%)
REMARK number of reflections in test set: 589 (4.1%)
CRYST1 123.387 123.387 47.115 90.00 90.00 120.00 P 32 2 1
REMARK FILENAME="bindindividual.pdb"
REMARK DATE:25-Mar-2003 17:21:21 created by user: david
REMARK VERSION:1.0
```

| ATOM | 1 | CB | ALA | A | 73 | 67.051 | −3.293 | 12.591 | 1.00 | 59.77 | A |
|---|---|---|---|---|---|---|---|---|---|---|---|
| ATOM | 2 | C | ALA | A | 73 | 67.941 | −4.753 | 14.416 | 1.00 | 61.14 | A |
| ATOM | 3 | O | ALA | A | 73 | 67.184 | −5.270 | 15.240 | 1.00 | 61.61 | A |
| ATOM | 4 | N | ALA | A | 73 | 66.523 | −5.729 | 12.643 | 1.00 | 58.89 | A |
| ATOM | 5 | CA | ALA | A | 73 | 67.564 | −4.697 | 12.943 | 1.00 | 60.69 | A |
| ATOM | 6 | N | PRO | A | 74 | 69.130 | −4.241 | 14.770 | 1.00 | 61.63 | A |
| ATOM | 7 | CD | PRO | A | 74 | 70.264 | −3.830 | 13.918 | 1.00 | 61.72 | A |
| ATOM | 8 | CA | PRO | A | 74 | 69.514 | −4.278 | 16.187 | 1.00 | 61.34 | A |
| ATOM | 9 | CB | PRO | A | 74 | 70.918 | −3.663 | 16.181 | 1.00 | 61.79 | A |
| ATOM | 10 | CG | PRO | A | 74 | 71.458 | −4.072 | 14.818 | 1.00 | 61.47 | A |
| ATOM | 11 | C | PRO | A | 74 | 68.523 | −3.481 | 17.047 | 1.00 | 60.16 | A |
| ATOM | 12 | O | PRO | A | 74 | 67.625 | −2.817 | 16.519 | 1.00 | 60.77 | A |
| ATOM | 13 | N | ALA | A | 75 | 68.680 | −3.562 | 18.368 | 1.00 | 58.13 | A |
| ATOM | 14 | CA | ALA | A | 75 | 67.815 | −2.828 | 19.292 | 1.00 | 54.74 | A |
| ATOM | 15 | CB | ALA | A | 75 | 68.048 | −3.309 | 20.731 | 1.00 | 54.90 | A |
| ATOM | 16 | C | ALA | A | 75 | 68.175 | −1.349 | 19.177 | 1.00 | 51.85 | A |
| ATOM | 17 | O | ALA | A | 75 | 69.313 | −1.005 | 18.851 | 1.00 | 52.46 | A |
| ATOM | 18 | N | LYS | A | 76 | 67.215 | −0.473 | 19.427 | 1.00 | 46.96 | A |
| ATOM | 19 | CA | LYS | A | 76 | 67.507 | 0.947 | 19.354 | 1.00 | 43.72 | A |
| ATOM | 20 | CB | LYS | A | 76 | 66.270 | 1.756 | 19.744 | 1.00 | 42.81 | A |
| ATOM | 21 | CG | LYS | A | 76 | 66.177 | 3.116 | 19.087 | 1.00 | 41.81 | A |
| ATOM | 22 | CD | LYS | A | 76 | 65.926 | 2.983 | 17.590 | 1.00 | 40.56 | A |

-continued

| | | | | | | | | | | |
|---|---|---|---|---|---|---|---|---|---|---|
| ATOM | 23 | CE | LYS | A | 76 | 65.691 | 4.343 | 16.943 | 1.00 | 42.58 A |
| ATOM | 24 | NZ | LYS | A | 76 | 65.362 | 4.231 | 15.495 | 1.00 | 42.73 A |
| ATOM | 25 | C | LYS | A | 76 | 68.639 | 1.218 | 20.351 | 1.00 | 41.25 A |
| ATOM | 26 | O | LYS | A | 76 | 68.599 | 0.741 | 21.488 | 1.00 | 41.68 A |
| ATOM | 27 | N | LYS | A | 77 | 69.655 | 1.960 | 19.936 | 1.00 | 37.68 A |
| ATOM | 28 | CA | LYS | A | 77 | 70.748 | 2.255 | 20.849 | 1.00 | 35.10 A |
| ATOM | 29 | CB | LYS | A | 77 | 72.016 | 2.619 | 20.074 | 1.00 | 34.13 A |
| ATOM | 30 | CG | LYS | A | 77 | 72.427 | 1.570 | 19.053 | 1.00 | 32.68 A |
| ATOM | 31 | CD | LYS | A | 77 | 73.927 | 1.537 | 18.858 | 1.00 | 33.90 A |
| ATOM | 32 | CE | LYS | A | 77 | 74.366 | 0.471 | 17.849 | 1.00 | 31.40 A |
| ATOM | 33 | NZ | LYS | A | 77 | 73.796 | −0.863 | 18.164 | 1.00 | 34.76 A |
| ATOM | 34 | C | LYS | A | 77 | 70.313 | 3.408 | 21.743 | 1.00 | 34.79 A |
| ATOM | 35 | O | LYS | A | 77 | 69.319 | 4.077 | 21.458 | 1.00 | 34.20 A |
| ATOM | 36 | N | ARG | A | 78 | 71.023 | 3.626 | 22.845 | 1.00 | 34.88 A |
| ATOM | 37 | CA | ARG | A | 78 | 70.687 | 4.723 | 23.759 | 1.00 | 34.62 A |
| ATOM | 38 | CB | ARG | A | 78 | 69.694 | 4.247 | 24.839 | 1.00 | 38.43 A |
| ATOM | 39 | CG | ARG | A | 78 | 70.027 | 2.884 | 25.353 | 1.00 | 42.71 A |
| ATOM | 40 | CD | ARG | A | 78 | 69.355 | 2.424 | 26.625 | 1.00 | 48.52 A |
| ATOM | 41 | NE | ARG | A | 78 | 70.365 | 1.702 | 27.412 | 1.00 | 56.10 A |
| ATOM | 42 | CZ | ARG | A | 78 | 70.428 | 0.355 | 27.518 | 1.00 | 57.88 A |
| ATOM | 43 | NH1 | ARG | A | 78 | 69.519 | −0.397 | 26.838 | 1.00 | 58.45 A |
| ATOM | 44 | NH2 | ARG | A | 78 | 71.335 | −0.195 | 28.369 | 1.00 | 59.23 A |
| ATOM | 45 | C | ARG | A | 78 | 71.967 | 5.330 | 24.382 | 1.00 | 32.26 A |
| ATOM | 46 | O | ARG | A | 78 | 73.066 | 4.777 | 24.278 | 1.00 | 31.42 A |
| ATOM | 47 | N | PRO | A | 79 | 71.844 | 6.509 | 24.997 | 1.00 | 30.46 A |
| ATOM | 48 | CD | PRO | A | 79 | 70.616 | 7.284 | 25.232 | 1.00 | 28.96 A |
| ATOM | 49 | CA | PRO | A | 79 | 72.997 | 7.172 | 25.609 | 1.00 | 30.38 A |
| ATOM | 50 | CB | PRO | A | 79 | 72.350 | 8.303 | 26.405 | 1.00 | 28.86 A |
| ATOM | 51 | CG | PRO | A | 79 | 71.169 | 8.642 | 25.568 | 1.00 | 27.83 A |
| ATOM | 52 | C | PRO | A | 79 | 73.889 | 6.287 | 26.468 | 1.00 | 29.47 A |
| ATOM | 53 | O | PRO | A | 79 | 75.108 | 6.377 | 26.391 | 1.00 | 29.57 A |
| ATOM | 54 | N | GLU | A | 80 | 73.268 | 5.435 | 27.279 | 1.00 | 29.77 A |
| ATOM | 55 | CA | GLU | A | 80 | 73.975 | 4.533 | 28.179 | 1.00 | 29.55 A |
| ATOM | 56 | CB | GLU | A | 80 | 72.980 | 3.768 | 29.043 | 1.00 | 32.88 A |
| ATOM | 57 | CG | GLU | A | 80 | 71.996 | 4.643 | 29.798 | 1.00 | 40.36 A |
| ATOM | 58 | CD | GLU | A | 80 | 71.014 | 5.367 | 28.879 | 1.00 | 44.21 A |
| ATOM | 59 | OE1 | GLU | A | 80 | 70.422 | 4.700 | 28.000 | 1.00 | 46.94 A |
| ATOM | 60 | OE2 | GLU | A | 80 | 70.828 | 6.598 | 29.038 | 1.00 | 45.47 A |
| ATOM | 61 | C | GLU | A | 80 | 74.872 | 3.524 | 27.479 | 1.00 | 28.32 A |
| ATOM | 62 | O | GLU | A | 80 | 75.709 | 2.894 | 28.126 | 1.00 | 28.20 A |
| ATOM | 63 | N | ASP | A | 81 | 74.698 | 3.342 | 26.168 | 1.00 | 26.28 A |
| ATOM | 64 | CA | ASP | A | 81 | 75.528 | 2.384 | 25.441 | 1.00 | 23.59 A |
| ATOM | 65 | CB | ASP | A | 81 | 74.834 | 1.888 | 24.184 | 1.00 | 25.08 A |
| ATOM | 66 | CG | ASP | A | 81 | 73.510 | 1.225 | 24.477 | 1.00 | 28.14 A |
| ATOM | 67 | OD1 | ASP | A | 81 | 73.369 | 0.625 | 25.578 | 1.00 | 29.12 A |
| ATOM | 68 | OD2 | ASP | A | 81 | 72.617 | 1.294 | 23.601 | 1.00 | 28.33 A |
| ATOM | 69 | C | ASP | A | 81 | 76.856 | 2.967 | 25.046 | 1.00 | 23.24 A |
| ATOM | 70 | O | ASP | A | 81 | 77.716 | 2.257 | 24.519 | 1.00 | 24.29 A |
| ATOM | 71 | N | PHE | A | 82 | 77.036 | 4.259 | 25.309 | 1.00 | 21.34 A |
| ATOM | 72 | CA | PHE | A | 82 | 78.272 | 4.930 | 24.946 | 1.00 | 20.86 A |
| ATOM | 73 | CB | PHE | A | 82 | 77.992 | 6.029 | 23.929 | 1.00 | 18.34 A |
| ATOM | 74 | CG | PHE | A | 82 | 77.355 | 5.536 | 22.683 | 1.00 | 19.18 A |
| ATOM | 75 | CD1 | PHE | A | 82 | 78.138 | 5.099 | 21.610 | 1.00 | 19.28 A |
| ATOM | 76 | CD2 | PHE | A | 82 | 75.974 | 5.462 | 22.588 | 1.00 | 17.82 A |
| ATOM | 77 | CE1 | PHE | A | 82 | 77.551 | 4.597 | 20.461 | 1.00 | 17.94 A |
| ATOM | 78 | CE2 | PHE | A | 82 | 75.371 | 4.961 | 21.449 | 1.00 | 19.08 A |
| ATOM | 79 | CZ | PHE | A | 82 | 76.164 | 4.525 | 20.376 | 1.00 | 20.45 A |
| ATOM | 80 | C | PHE | A | 82 | 78.982 | 5.555 | 26.105 | 1.00 | 21.71 A |
| ATOM | 81 | O | PHE | A | 82 | 78.418 | 5.739 | 27.173 | 1.00 | 24.82 A |
| ATOM | 82 | N | LYS | A | 83 | 80.244 | 5.865 | 25.869 | 1.00 | 21.83 A |
| ATOM | 83 | CA | LYS | A | 83 | 81.077 | 6.555 | 26.823 | 1.00 | 22.27 A |
| ATOM | 84 | CB | LYS | A | 83 | 82.327 | 5.750 | 27.148 | 1.00 | 24.03 A |
| ATOM | 85 | CG | LYS | A | 83 | 83.074 | 6.320 | 28.340 | 1.00 | 30.99 A |
| ATOM | 86 | CD | LYS | A | 83 | 84.465 | 6.827 | 27.993 | 1.00 | 35.16 A |
| ATOM | 87 | CE | LYS | A | 83 | 85.465 | 5.683 | 27.945 | 1.00 | 39.06 A |
| ATOM | 88 | NZ | LYS | A | 83 | 85.512 | 4.974 | 29.266 | 1.00 | 41.00 A |
| ATOM | 89 | C | LYS | A | 83 | 81.462 | 7.775 | 25.998 | 1.00 | 22.51 A |
| ATOM | 90 | O | LYS | A | 83 | 82.324 | 7.677 | 25.120 | 1.00 | 23.24 A |
| ATOM | 91 | N | PHE | A | 84 | 80.800 | 8.907 | 26.227 | 1.00 | 20.27 A |
| ATOM | 92 | CA | PHE | A | 84 | 81.118 | 10.098 | 25.454 | 1.00 | 19.31 A |
| ATOM | 93 | CB | PHE | A | 84 | 80.016 | 11.145 | 25.605 | 1.00 | 19.95 A |
| ATOM | 94 | CG | PHE | A | 84 | 78.683 | 10.694 | 25.075 | 1.00 | 20.81 A |
| ATOM | 95 | CD1 | PHE | A | 84 | 77.855 | 9.879 | 25.835 | 1.00 | 21.62 A |
| ATOM | 96 | CD2 | PHE | A | 84 | 78.278 | 11.035 | 23.804 | 1.00 | 20.47 A |
| ATOM | 97 | CE1 | PHE | A | 84 | 76.665 | 9.418 | 25.339 | 1.00 | 19.26 A |
| ATOM | 98 | CE2 | PHE | A | 84 | 77.073 | 10.568 | 23.300 | 1.00 | 18.97 A |
| ATOM | 99 | CZ | PHE | A | 84 | 76.276 | 9.764 | 24.068 | 1.00 | 19.78 A |
| ATOM | 100 | C | PHE | A | 84 | 82.463 | 10.680 | 25.863 | 1.00 | 19.58 A |
| ATOM | 101 | O | PHE | A | 84 | 82.888 | 10.540 | 26.998 | 1.00 | 20.60 A |

-continued

| | | | | | | | | | | |
|---|---|---|---|---|---|---|---|---|---|---|
| ATOM | 102 | N | GLY | A | 85 | 83.141 | 11.307 | 24.913 | 1.00 | 19.33 A |
| ATOM | 103 | CA | GLY | A | 85 | 84.434 | 11.909 | 25.169 | 1.00 | 18.23 A |
| ATOM | 104 | C | GLY | A | 85 | 84.480 | 13.368 | 24.743 | 1.00 | 19.96 A |
| ATOM | 105 | O | GLY | A | 85 | 83.533 | 14.124 | 24.962 | 1.00 | 20.02 A |
| ATOM | 106 | N | LYS | A | 86 | 85.568 | 13.764 | 24.101 | 1.00 | 20.79 A |
| ATOM | 107 | CA | LYS | A | 86 | 85.736 | 15.159 | 23.704 | 1.00 | 22.45 A |
| ATOM | 108 | CB | LYS | A | 86 | 87.168 | 15.400 | 23.210 | 1.00 | 22.06 A |
| ATOM | 109 | CG | LYS | A | 86 | 87.399 | 15.048 | 21.751 | 1.00 | 23.37 A |
| ATOM | 110 | CD | LYS | A | 86 | 88.832 | 14.591 | 21.505 | 1.00 | 26.45 A |
| ATOM | 111 | CE | LYS | A | 86 | 89.451 | 15.275 | 20.294 | 1.00 | 30.25 A |
| ATOM | 112 | NZ | LYS | A | 86 | 89.771 | 16.721 | 20.553 | 1.00 | 33.08 A |
| ATOM | 113 | C | LYS | A | 86 | 84.750 | 15.668 | 22.661 | 1.00 | 21.50 A |
| ATOM | 114 | O | LYS | A | 86 | 84.154 | 14.900 | 21.916 | 1.00 | 21.98 A |
| ATOM | 115 | N | ILE | A | 87 | 84.582 | 16.985 | 22.647 | 1.00 | 20.15 A |
| ATOM | 116 | CA | ILE | A | 87 | 83.712 | 17.661 | 21.705 | 1.00 | 19.38 A |
| ATOM | 117 | CB | ILE | A | 87 | 83.270 | 19.037 | 22.272 | 1.00 | 17.37 A |
| ATOM | 118 | CG2 | ILE | A | 87 | 82.724 | 19.935 | 21.163 | 1.00 | 15.07 A |
| ATOM | 119 | CG1 | ILE | A | 87 | 82.222 | 18.800 | 23.371 | 1.00 | 18.62 A |
| ATOM | 120 | CD1 | ILE | A | 87 | 81.848 | 20.025 | 24.190 | 1.00 | 16.91 A |
| ATOM | 121 | C | ILE | A | 87 | 84.549 | 17.836 | 20.436 | 1.00 | 19.85 A |
| ATOM | 122 | O | ILE | A | 87 | 85.666 | 18.317 | 20.502 | 1.00 | 21.66 A |
| ATOM | 123 | N | LEU | A | 88 | 84.030 | 17.406 | 19.293 | 1.00 | 19.65 A |
| ATOM | 124 | CA | LEU | A | 88 | 84.771 | 17.539 | 18.047 | 1.00 | 20.20 A |
| ATOM | 125 | CB | LEU | A | 88 | 84.423 | 16.405 | 17.078 | 1.00 | 18.76 A |
| ATOM | 126 | CG | LEU | A | 88 | 84.807 | 14.981 | 17.493 | 1.00 | 16.99 A |
| ATOM | 127 | CD1 | LEU | A | 88 | 84.122 | 13.995 | 16.570 | 1.00 | 13.92 A |
| ATOM | 128 | CD2 | LEU | A | 88 | 86.305 | 14.809 | 17.441 | 1.00 | 11.51 A |
| ATOM | 129 | C | LEU | A | 88 | 84.429 | 18.861 | 17.407 | 1.00 | 20.87 A |
| ATOM | 130 | O | LEU | A | 88 | 85.233 | 19.443 | 16.709 | 1.00 | 21.48 A |
| ATOM | 131 | N | GLY | A | 89 | 83.221 | 19.339 | 17.639 | 1.00 | 22.34 A |
| ATOM | 132 | CA | GLY | A | 89 | 82.856 | 20.601 | 17.043 | 1.00 | 25.87 A |
| ATOM | 133 | C | GLY | A | 89 | 81.476 | 21.057 | 17.451 | 1.00 | 29.45 A |
| ATOM | 134 | O | GLY | A | 89 | 80.673 | 20.292 | 17.990 | 1.00 | 29.48 A |
| ATOM | 135 | N | GLU | A | 90 | 81.196 | 22.321 | 17.188 | 1.00 | 32.71 A |
| ATOM | 136 | CA | GLU | A | 90 | 79.904 | 22.864 | 17.530 | 1.00 | 37.61 A |
| ATOM | 137 | CB | GLU | A | 90 | 80.047 | 23.798 | 18.738 | 1.00 | 38.05 A |
| ATOM | 138 | CG | GLU | A | 90 | 80.123 | 22.998 | 20.037 | 1.00 | 42.04 A |
| ATOM | 139 | CD | GLU | A | 90 | 80.463 | 23.813 | 21.270 | 1.00 | 45.47 A |
| ATOM | 140 | OE1 | GLU | A | 90 | 81.662 | 24.137 | 21.477 | 1.00 | 47.26 A |
| ATOM | 141 | OE2 | GLU | A | 90 | 79.524 | 24.119 | 22.041 | 1.00 | 47.39 A |
| ATOM | 142 | C | GLU | A | 90 | 79.277 | 23.565 | 16.349 | 1.00 | 40.01 A |
| ATOM | 143 | O | GLU | A | 90 | 79.972 | 24.148 | 15.518 | 1.00 | 42.05 A |
| ATOM | 144 | N | GLY | A | 91 | 77.962 | 23.440 | 16.240 | 1.00 | 42.05 A |
| ATOM | 145 | CA | GLY | A | 91 | 77.238 | 24.102 | 15.174 | 1.00 | 43.15 A |
| ATOM | 146 | C | GLY | A | 91 | 76.276 | 25.035 | 15.892 | 1.00 | 45.06 A |
| ATOM | 147 | O | GLY | A | 91 | 76.317 | 25.149 | 17.134 | 1.00 | 43.58 A |
| ATOM | 148 | N | SER | A | 92 | 75.408 | 25.699 | 15.136 | 1.00 | 46.66 A |
| ATOM | 149 | CA | SER | A | 92 | 74.430 | 26.606 | 15.742 | 1.00 | 48.21 A |
| ATOM | 150 | CB | SER | A | 92 | 73.754 | 27.462 | 14.660 | 1.00 | 51.13 A |
| ATOM | 151 | CG | SER | A | 92 | 73.601 | 26.741 | 13.439 | 1.00 | 54.79 A |
| ATOM | 152 | C | SER | A | 92 | 73.382 | 25.827 | 16.538 | 1.00 | 47.10 A |
| ATOM | 153 | O | SER | A | 92 | 73.055 | 26.190 | 17.678 | 1.00 | 49.44 A |
| ATOM | 154 | N | PHE | A | 93 | 72.874 | 24.743 | 15.957 | 1.00 | 44.39 A |
| ATOM | 155 | CA | PHE | A | 93 | 71.866 | 23.942 | 16.648 | 1.00 | 41.99 A |
| ATOM | 156 | CB | PHE | A | 93 | 70.617 | 23.798 | 15.780 | 1.00 | 43.92 A |
| ATOM | 157 | CG | PHE | A | 93 | 70.434 | 24.919 | 14.814 | 1.00 | 47.66 A |
| ATOM | 158 | CD1 | PHE | A | 93 | 70.689 | 24.729 | 13.455 | 1.00 | 49.35 A |
| ATOM | 159 | CD2 | PHE | A | 93 | 70.061 | 26.185 | 15.264 | 1.00 | 49.16 A |
| ATOM | 160 | CE1 | PHE | A | 93 | 70.581 | 25.789 | 12.551 | 1.00 | 51.11 A |
| ATOM | 161 | CE2 | PHE | A | 93 | 69.949 | 27.257 | 14.374 | 1.00 | 50.58 A |
| ATOM | 162 | CZ | PHE | A | 93 | 70.209 | 27.062 | 13.014 | 1.00 | 51.37 A |
| ATOM | 163 | C | PHE | A | 93 | 72.352 | 22.555 | 17.028 | 1.00 | 38.35 A |
| ATOM | 164 | O | PHE | A | 93 | 71.532 | 21.670 | 17.257 | 1.00 | 38.33 A |
| ATOM | 165 | N | SER | A | 94 | 73.665 | 22.351 | 17.106 | 1.00 | 33.28 A |
| ATOM | 166 | CA | SER | A | 94 | 74.151 | 21.028 | 17.440 | 1.00 | 29.57 A |
| ATOM | 167 | CB | SER | A | 94 | 73.996 | 20.106 | 16.227 | 1.00 | 30.45 A |
| ATOM | 168 | OG | SER | A | 94 | 75.123 | 20.190 | 15.368 | 1.00 | 30.51 A |
| ATOM | 169 | C | SER | A | 94 | 75.588 | 20.952 | 17.936 | 1.00 | 27.66 A |
| ATOM | 170 | O | SER | A | 94 | 76.369 | 21.893 | 17.803 | 1.00 | 27.25 A |
| ATOM | 171 | N | THR | A | 95 | 75.927 | 19.807 | 18.512 | 1.00 | 25.06 A |
| ATOM | 172 | CA | THR | A | 95 | 77.264 | 19.572 | 19.027 | 1.00 | 23.70 A |
| ATOM | 173 | CB | THR | A | 95 | 77.310 | 19.626 | 20.582 | 1.00 | 24.12 A |
| ATOM | 174 | OG1 | THR | A | 95 | 76.801 | 20.886 | 21.044 | 1.00 | 25.68 A |
| ATOM | 175 | CG2 | THR | A | 95 | 78.731 | 19.458 | 21.073 | 1.00 | 22.92 A |
| ATOM | 176 | C | THR | A | 95 | 77.655 | 18.180 | 18.594 | 1.00 | 22.05 A |
| ATOM | 177 | O | THR | A | 95 | 76.860 | 17.250 | 18.673 | 1.00 | 21.43 A |
| ATOM | 178 | N | VAL | A | 96 | 78.883 | 18.029 | 18.129 | 1.00 | 21.52 A |
| ATOM | 179 | CA | VAL | A | 96 | 79.348 | 16.723 | 17.702 | 1.00 | 19.53 A |
| ATOM | 180 | CB | VAL | A | 96 | 79.980 | 16.818 | 16.316 | 1.00 | 19.24 A |

-continued

| | | | | | | | | | | |
|---|---|---|---|---|---|---|---|---|---|---|
| ATOM | 181 | CG1 | VAL | A | 96 | 80.418 | 15.443 | 15.839 | 1.00 | 17.73 A |
| ATOM | 182 | CG2 | VAL | A | 96 | 78.983 | 17.442 | 15.353 | 1.00 | 18.03 A |
| ATOM | 183 | C | VAL | A | 96 | 80.364 | 16.242 | 18.722 | 1.00 | 19.43 A |
| ATOM | 184 | O | VAL | A | 96 | 81.372 | 16.910 | 18.959 | 1.00 | 19.84 A |
| ATOM | 185 | N | VAL | A | 97 | 80.099 | 15.082 | 19.324 | 1.00 | 17.90 A |
| ATOM | 186 | CA | VAL | A | 97 | 80.989 | 14.532 | 20.341 | 1.00 | 17.32 A |
| ATOM | 187 | CB | VAL | A | 97 | 80.283 | 14.438 | 21.736 | 1.00 | 18.35 A |
| ATOM | 188 | CG1 | VAL | A | 97 | 79.581 | 15.750 | 22.066 | 1.00 | 20.10 A |
| ATOM | 189 | CG2 | VAL | A | 97 | 79.234 | 13.357 | 21.713 | 1.00 | 23.78 A |
| ATOM | 190 | C | VAL | A | 97 | 81.471 | 13.144 | 19.949 | 1.00 | 17.15 A |
| ATOM | 191 | O | VAL | A | 97 | 80.727 | 12.351 | 19.379 | 1.00 | 18.17 A |
| ATOM | 192 | N | LEU | A | 98 | 82.735 | 12.866 | 20.243 | 1.00 | 17.34 A |
| ATOM | 193 | CA | LEU | A | 98 | 83.331 | 11.575 | 19.974 | 1.00 | 17.44 A |
| ATOM | 194 | CB | LEU | A | 98 | 84.853 | 11.689 | 19.990 | 1.00 | 17.84 A |
| ATOM | 195 | CG | LEU | A | 98 | 85.656 | 10.407 | 19.737 | 1.00 | 18.59 A |
| ATOM | 196 | CD1 | LEU | A | 98 | 85.259 | 9.803 | 18.387 | 1.00 | 18.87 A |
| ATOM | 197 | CD2 | LEU | A | 98 | 87.151 | 10.738 | 19.772 | 1.00 | 16.62 A |
| ATOM | 198 | C | LEU | A | 98 | 82.874 | 10.626 | 21.081 | 1.00 | 18.35 A |
| ATOM | 199 | O | LEU | A | 98 | 82.992 | 10.926 | 22.259 | 1.00 | 18.60 A |
| ATOM | 200 | N | ALA | A | 99 | 82.340 | 9.476 | 20.697 | 1.00 | 19.15 A |
| ATOM | 201 | CA | ALA | A | 99 | 81.888 | 8.513 | 21.675 | 1.00 | 19.73 A |
| ATOM | 202 | CB | ALA | A | 99 | 80.383 | 8.534 | 21.759 | 1.00 | 17.97 A |
| ATOM | 203 | C | ALA | A | 99 | 82.360 | 7.117 | 21.317 | 1.00 | 21.86 A |
| ATOM | 204 | O | ALA | A | 99 | 82.502 | 6.766 | 20.131 | 1.00 | 22.18 A |
| ATOM | 205 | N | ARG | A | 100 | 82.631 | 6.324 | 22.345 | 1.00 | 21.93 A |
| ATOM | 206 | CA | ARG | A | 100 | 83.025 | 4.963 | 22.102 | 1.00 | 23.29 A |
| ATOM | 207 | CB | ARG | A | 100 | 84.333 | 4.637 | 22.805 | 1.00 | 25.99 A |
| ATOM | 208 | CG | ARG | A | 100 | 84.870 | 3.271 | 22.388 | 1.00 | 31.56 A |
| ATOM | 209 | CD | ARG | A | 100 | 86.146 | 2.923 | 23.129 | 1.00 | 35.19 A |
| ATOM | 210 | NE | ARG | A | 100 | 87.220 | 3.875 | 22.847 | 1.00 | 37.39 A |
| ATOM | 211 | CZ | ARG | A | 100 | 87.958 | 3.870 | 21.740 | 1.00 | 38.05 A |
| ATOM | 212 | NH1 | ARG | A | 100 | 87.742 | 2.953 | 20.797 | 1.00 | 37.25 A |
| ATOM | 213 | NH2 | ARG | A | 100 | 88.918 | 4.780 | 21.580 | 1.00 | 36.22 A |
| ATOM | 214 | C | ARG | A | 100 | 81.904 | 4.060 | 22.603 | 1.00 | 22.07 A |
| ATOM | 215 | O | ARG | A | 100 | 81.460 | 4.177 | 23.743 | 1.00 | 22.10 A |
| ATOM | 216 | N | GLU | A | 101 | 81.417 | 3.189 | 21.734 | 1.00 | 21.29 A |
| ATOM | 217 | CA | GLU | A | 101 | 80.357 | 2.262 | 22.119 | 1.00 | 22.87 A |
| ATOM | 218 | CB | GLU | A | 101 | 79.747 | 1.631 | 20.867 | 1.00 | 23.10 A |
| ATOM | 219 | CG | GLU | A | 101 | 78.740 | 0.563 | 21.148 | 1.00 | 22.71 A |
| ATOM | 220 | CD | GLU | A | 101 | 78.128 | 0.040 | 19.878 | 1.00 | 23.56 A |
| ATOM | 221 | OE1 | GLU | A | 101 | 78.892 | −0.198 | 18.922 | 1.00 | 21.84 A |
| ATOM | 222 | OE2 | GLU | A | 101 | 76.890 | −0.143 | 19.832 | 1.00 | 26.29 A |
| ATOM | 223 | C | GLU | A | 101 | 80.942 | 1.176 | 23.037 | 1.00 | 21.56 A |
| ATOM | 224 | O | GLU | A | 101 | 81.884 | 0.485 | 22.666 | 1.00 | 20.69 A |
| ATOM | 225 | N | LEU | A | 102 | 80.389 | 1.042 | 24.236 | 1.00 | 21.11 A |
| ATOM | 226 | CA | LEU | A | 102 | 80.874 | 0.057 | 25.204 | 1.00 | 21.54 A |
| ATOM | 227 | CB | LEU | A | 102 | 80.075 | 0.199 | 26.507 | 1.00 | 20.90 A |
| ATOM | 228 | CG | LEU | A | 102 | 80.193 | 1.620 | 27.092 | 1.00 | 22.35 A |
| ATOM | 229 | CD1 | LEU | A | 102 | 79.177 | 1.798 | 28.207 | 1.00 | 20.18 A |
| ATOM | 230 | CD2 | LEU | A | 102 | 81.600 | 1.866 | 27.608 | 1.00 | 17.47 A |
| ATOM | 231 | C | LEU | A | 102 | 80.896 | −1.415 | 24.729 | 1.00 | 20.27 A |
| ATOM | 232 | O | LEU | A | 102 | 81.922 | −2.078 | 24.825 | 1.00 | 21.63 A |
| ATOM | 233 | N | ALA | A | 103 | 79.792 | −1.922 | 24.201 | 1.00 | 18.37 A |
| ATOM | 234 | CA | ALA | A | 103 | 79.757 | −3.307 | 23.731 | 1.00 | 20.54 A |
| ATOM | 235 | CB | ALA | A | 103 | 78.333 | −3.694 | 23.359 | 1.00 | 19.31 A |
| ATOM | 236 | C | ALA | A | 103 | 80.688 | −3.658 | 22.552 | 1.00 | 22.26 A |
| ATOM | 237 | O | ALA | A | 103 | 81.002 | −4.829 | 22.358 | 1.00 | 23.93 A |
| ATOM | 238 | N | THR | A | 104 | 81.141 | −2.677 | 21.775 | 1.00 | 20.79 A |
| ATOM | 239 | CA | THR | A | 104 | 81.972 | −2.999 | 20.622 | 1.00 | 21.40 A |
| ATOM | 240 | CB | THR | A | 104 | 81.279 | −2.632 | 19.326 | 1.00 | 20.97 A |
| ATOM | 241 | OG1 | THR | A | 104 | 81.174 | −1.205 | 19.259 | 1.00 | 23.21 A |
| ATOM | 242 | CG2 | THR | A | 104 | 79.891 | −3.266 | 19.245 | 1.00 | 19.82 A |
| ATOM | 243 | C | THR | A | 104 | 83.304 | −2.300 | 20.569 | 1.00 | 23.57 A |
| ATOM | 244 | O | THR | A | 104 | 84.168 | −2.687 | 19.796 | 1.00 | 23.41 A |
| ATOM | 245 | N | SER | A | 105 | 83.454 | −1.243 | 21.359 | 1.00 | 24.64 A |
| ATOM | 246 | CA | SER | A | 105 | 84.687 | −0.487 | 21.390 | 1.00 | 24.23 A |
| ATOM | 247 | CB | SER | A | 105 | 85.855 | −1.467 | 21.481 | 1.00 | 25.40 A |
| ATOM | 248 | OG | SER | A | 105 | 87.074 | −0.788 | 21.719 | 1.00 | 34.15 A |
| ATOM | 249 | C | SER | A | 105 | 84.819 | 0.454 | 20.163 | 1.00 | 23.42 A |
| ATOM | 250 | O | SER | A | 105 | 85.803 | 1.187 | 20.013 | 1.00 | 23.28 A |
| ATOM | 251 | N | ARG | A | 106 | 83.821 | 0.448 | 19.295 | 1.00 | 21.19 A |
| ATOM | 252 | CA | ARG | A | 106 | 83.850 | 1.323 | 18.115 | 1.00 | 22.25 A |
| ATOM | 253 | CB | ARG | A | 106 | 82.754 | 0.922 | 17.118 | 1.00 | 24.82 A |
| ATOM | 254 | CG | ARG | A | 106 | 83.027 | −0.343 | 16.349 | 1.00 | 25.20 A |
| ATOM | 255 | CD | ARG | A | 106 | 81.740 | −0.942 | 15.884 | 1.00 | 25.19 A |
| ATOM | 256 | NE | ARG | A | 106 | 81.972 | −1.900 | 14.815 | 1.00 | 26.11 A |
| ATOM | 257 | CZ | ARG | A | 106 | 81.042 | −2.707 | 14.322 | 1.00 | 24.24 A |
| ATOM | 258 | NH1 | ARG | A | 106 | 79.805 | −2.677 | 14.818 | 1.00 | 21.06 A |
| ATOM | 259 | NH2 | ARG | A | 106 | 81.351 | −3.513 | 13.315 | 1.00 | 20.25 A |

-continued

| | | | | | | | | | | |
|---|---|---|---|---|---|---|---|---|---|---|
| ATOM | 260 | C | ARG | A | 106 | 83.655 | 2.806 | 18.433 | 1.00 | 19.79 A |
| ATOM | 261 | O | ARG | A | 106 | 82.836 | 3.175 | 19.266 | 1.00 | 18.73 A |
| ATOM | 262 | N | GLU | A | 107 | 84.404 | 3.646 | 17.736 | 1.00 | 19.82 A |
| ATOM | 263 | CA | GLU | A | 107 | 84.294 | 5.086 | 17.903 | 1.00 | 21.14 A |
| ATOM | 264 | CB | GLU | A | 107 | 85.656 | 5.746 | 17.777 | 1.00 | 21.88 A |
| ATOM | 265 | CG | GLU | A | 107 | 86.562 | 5.428 | 18.926 | 1.00 | 26.09 A |
| ATOM | 266 | CD | GLU | A | 107 | 87.916 | 6.043 | 18.746 | 1.00 | 30.29 A |
| ATOM | 267 | OE1 | GLU | A | 107 | 88.212 | 7.057 | 19.434 | 1.00 | 32.48 A |
| ATOM | 268 | OE2 | GLU | A | 107 | 88.678 | 5.512 | 17.901 | 1.00 | 31.98 A |
| ATOM | 269 | C | GLU | A | 107 | 83.358 | 5.693 | 16.870 | 1.00 | 20.50 A |
| ATOM | 270 | O | GLU | A | 107 | 83.474 | 5.429 | 15.676 | 1.00 | 20.70 A |
| ATOM | 271 | N | TYR | A | 108 | 82.415 | 6.498 | 17.347 | 1.00 | 20.38 A |
| ATOM | 272 | CA | TYR | A | 108 | 81.464 | 7.172 | 16.477 | 1.00 | 18.49 A |
| ATOM | 273 | CB | TYR | A | 108 | 80.049 | 6.660 | 16.700 | 1.00 | 17.92 A |
| ATOM | 274 | CG | TYR | A | 108 | 79.828 | 5.247 | 16.238 | 1.00 | 23.37 A |
| ATOM | 275 | CD1 | TYR | A | 108 | 79.598 | 4.964 | 14.886 | 1.00 | 22.79 A |
| ATOM | 276 | CE1 | TYR | A | 108 | 79.357 | 3.648 | 14.458 | 1.00 | 23.56 A |
| ATOM | 277 | CD2 | TYR | A | 108 | 79.820 | 4.180 | 17.154 | 1.00 | 21.34 A |
| ATOM | 278 | CE2 | TYR | A | 108 | 79.583 | 2.873 | 16.740 | 1.00 | 20.43 A |
| ATOM | 279 | CZ | TYR | A | 108 | 79.346 | 2.609 | 15.392 | 1.00 | 23.44 A |
| ATOM | 280 | OH | TYR | A | 108 | 79.061 | 1.321 | 14.972 | 1.00 | 24.10 A |
| ATOM | 281 | C | TYR | A | 108 | 81.478 | 8.635 | 16.828 | 1.00 | 18.53 A |
| ATOM | 282 | O | TYR | A | 108 | 81.778 | 9.011 | 17.971 | 1.00 | 17.37 A |
| ATOM | 283 | N | ALA | A | 109 | 81.169 | 9.453 | 15.829 | 1.00 | 17.24 A |
| ATOM | 284 | CA | ALA | A | 109 | 81.053 | 10.885 | 16.006 | 1.00 | 15.98 A |
| ATOM | 285 | CB | ALA | A | 109 | 81.597 | 11.600 | 14.788 | 1.00 | 15.20 A |
| ATOM | 286 | C | ALA | A | 109 | 79.528 | 11.087 | 16.140 | 1.00 | 15.73 A |
| ATOM | 287 | O | ALA | A | 109 | 78.767 | 10.873 | 15.191 | 1.00 | 15.79 A |
| ATOM | 288 | N | ILE | A | 110 | 79.070 | 11.474 | 17.320 | 1.00 | 14.95 A |
| ATOM | 289 | CA | ILE | A | 110 | 77.636 | 11.636 | 17.511 | 1.00 | 15.99 A |
| ATOM | 290 | CB | ILE | A | 110 | 77.188 | 10.940 | 18.815 | 1.00 | 15.51 A |
| ATOM | 291 | CG2 | ILE | A | 110 | 75.697 | 11.126 | 19.039 | 1.00 | 14.44 A |
| ATOM | 292 | CG1 | ILE | A | 110 | 77.541 | 9.452 | 18.729 | 1.00 | 16.63 A |
| ATOM | 293 | CD1 | ILE | A | 110 | 76.964 | 8.595 | 19.847 | 1.00 | 16.83 A |
| ATOM | 294 | C | ILE | A | 110 | 77.176 | 13.085 | 17.514 | 1.00 | 16.55 A |
| ATOM | 295 | O | ILE | A | 110 | 77.583 | 13.873 | 18.370 | 1.00 | 16.24 A |
| ATOM | 296 | N | LYS | A | 111 | 76.343 | 13.430 | 16.538 | 1.00 | 16.03 A |
| ATOM | 297 | CA | LYS | A | 111 | 75.804 | 14.777 | 16.430 | 1.00 | 18.21 A |
| ATOM | 298 | CB | LYS | A | 111 | 75.341 | 15.065 | 14.997 | 1.00 | 19.36 A |
| ATOM | 299 | CG | LYS | A | 111 | 75.035 | 16.548 | 14.768 | 1.00 | 22.68 A |
| ATOM | 300 | CD | LYS | A | 111 | 74.461 | 16.844 | 13.396 | 1.00 | 23.67 A |
| ATOM | 301 | CE | LYS | A | 111 | 74.876 | 18.222 | 12.930 | 1.00 | 23.18 A |
| ATOM | 302 | NZ | LYS | A | 111 | 73.744 | 18.938 | 12.304 | 1.00 | 28.83 A |
| ATOM | 303 | C | LYS | A | 111 | 74.608 | 14.866 | 17.383 | 1.00 | 17.40 A |
| ATOM | 304 | O | LYS | A | 111 | 73.646 | 14.115 | 17.239 | 1.00 | 18.27 A |
| ATOM | 305 | N | ILE | A | 112 | 74.672 | 15.781 | 18.344 | 1.00 | 15.41 A |
| ATOM | 306 | CA | ILE | A | 112 | 73.609 | 15.938 | 19.331 | 1.00 | 16.56 A |
| ATOM | 307 | CB | ILE | A | 112 | 74.194 | 15.819 | 20.777 | 1.00 | 17.09 A |
| ATOM | 308 | CG2 | ILE | A | 112 | 73.073 | 15.926 | 21.830 | 1.00 | 11.60 A |
| ATOM | 309 | CG1 | ILE | A | 112 | 74.957 | 14.480 | 20.885 | 1.00 | 16.81 A |
| ATOM | 310 | CD1 | ILE | A | 112 | 75.771 | 14.262 | 22.178 | 1.00 | 15.96 A |
| ATOM | 311 | C | ILE | A | 112 | 72.876 | 17.261 | 19.158 | 1.00 | 17.98 A |
| ATOM | 312 | O | ILE | A | 112 | 73.504 | 18.314 | 18.965 | 1.00 | 16.70 A |
| ATOM | 313 | N | LEU | A | 113 | 71.546 | 17.198 | 19.195 | 1.00 | 19.61 A |
| ATOM | 314 | CA | LEU | A | 113 | 70.711 | 18.393 | 19.034 | 1.00 | 21.99 A |
| ATOM | 315 | CB | LEU | A | 113 | 70.058 | 18.434 | 17.641 | 1.00 | 22.17 A |
| ATOM | 316 | CG | LEU | A | 113 | 70.906 | 18.273 | 16.367 | 1.00 | 22.83 A |
| ATOM | 317 | CD1 | LEU | A | 113 | 71.124 | 16.792 | 16.059 | 1.00 | 22.72 A |
| ATOM | 318 | CD2 | LEU | A | 113 | 70.191 | 18.912 | 15.206 | 1.00 | 21.97 A |
| ATOM | 319 | C | LEU | A | 113 | 69.612 | 18.419 | 20.088 | 1.00 | 24.22 A |
| ATOM | 320 | O | LEU | A | 113 | 69.062 | 17.378 | 20.469 | 1.00 | 24.61 A |
| ATOM | 321 | N | GLU | A | 114 | 69.285 | 19.615 | 20.559 | 1.00 | 27.06 A |
| ATOM | 322 | CA | GLU | A | 114 | 68.247 | 19.759 | 21.567 | 1.00 | 28.93 A |
| ATOM | 323 | CB | GLU | A | 114 | 68.586 | 20.926 | 22.488 | 1.00 | 31.39 A |
| ATOM | 324 | CG | GLU | A | 114 | 67.671 | 21.026 | 23.684 | 1.00 | 39.92 A |
| ATOM | 325 | CD | GLU | A | 114 | 67.676 | 22.406 | 24.300 | 1.00 | 45.42 A |
| ATOM | 326 | OE1 | GLU | A | 114 | 67.160 | 23.356 | 23.655 | 1.00 | 46.90 A |
| ATOM | 327 | OE2 | GLU | A | 114 | 68.204 | 22.540 | 25.429 | 1.00 | 50.09 A |
| ATOM | 328 | C | GLU | A | 114 | 66.887 | 19.978 | 20.892 | 1.00 | 29.21 A |
| ATOM | 329 | O | GLU | A | 114 | 66.679 | 20.969 | 20.177 | 1.00 | 29.53 A |
| ATOM | 330 | N | LYS | A | 115 | 65.962 | 19.051 | 21.116 | 1.00 | 28.74 A |
| ATOM | 331 | CA | LYS | A | 115 | 64.642 | 19.152 | 20.507 | 1.00 | 29.44 A |
| ATOM | 332 | CB | LYS | A | 115 | 63.744 | 18.002 | 20.987 | 1.00 | 28.12 A |
| ATOM | 333 | CG | LYS | A | 115 | 63.827 | 16.758 | 20.103 | 1.00 | 28.47 A |
| ATOM | 334 | CD | LYS | A | 115 | 63.026 | 15.571 | 20.639 | 1.00 | 27.07 A |
| ATOM | 335 | CE | LYS | A | 115 | 63.738 | 14.854 | 21.779 | 1.00 | 28.88 A |
| ATOM | 336 | NZ | LYS | A | 115 | 62.963 | 13.672 | 22.282 | 1.00 | 26.42 A |
| ATOM | 337 | C | LYS | A | 115 | 63.947 | 20.502 | 20.724 | 1.00 | 29.72 A |
| ATOM | 338 | O | LYS | A | 115 | 63.310 | 21.025 | 19.799 | 1.00 | 30.03 A |

-continued

| | | | | | | | | | | |
|---|---|---|---|---|---|---|---|---|---|---|
| ATOM | 339 | N | ALA | A | 116 | 64.082 | 21.091 | 21.910 | 1.00 | 28.83 A |
| ATOM | 340 | CA | ALA | A | 116 | 63.407 | 22.365 | 22.159 | 1.00 | 29.91 A |
| ATOM | 341 | CB | ALA | A | 116 | 63.470 | 22.749 | 23.647 | 1.00 | 28.16 A |
| ATOM | 342 | C | ALA | A | 116 | 63.976 | 23.480 | 21.311 | 1.00 | 30.93 A |
| ATOM | 343 | O | ALA | A | 116 | 63.231 | 24.217 | 20.667 | 1.00 | 32.28 A |
| ATOM | 344 | N | HIS | A | 117 | 65.297 | 23.593 | 21.292 | 1.00 | 31.66 A |
| ATOM | 345 | CA | HIS | A | 117 | 65.951 | 24.645 | 20.523 | 1.00 | 32.13 A |
| ATOM | 346 | CB | HIS | A | 117 | 67.472 | 24.571 | 20.728 | 1.00 | 34.12 A |
| ATOM | 347 | CG | HIS | A | 117 | 68.219 | 25.741 | 20.169 | 1.00 | 37.74 A |
| ATOM | 348 | CD2 | HIS | A | 117 | 67.794 | 26.959 | 19.761 | 1.00 | 39.67 A |
| ATOM | 349 | ND1 | HIS | A | 117 | 69.582 | 25.727 | 19.966 | 1.00 | 42.04 A |
| ATOM | 350 | CE1 | HIS | A | 117 | 69.965 | 26.884 | 19.454 | 1.00 | 41.07 A |
| ATOM | 351 | NE2 | HIS | A | 117 | 68.899 | 27.649 | 19.320 | 1.00 | 40.56 A |
| ATOM | 352 | C | HIS | A | 117 | 65.600 | 24.547 | 19.040 | 1.00 | 31.36 A |
| ATOM | 353 | O | HIS | A | 117 | 65.466 | 25.560 | 18.350 | 1.00 | 32.37 A |
| ATOM | 354 | N | ILE | A | 118 | 65.430 | 23.330 | 18.544 | 1.00 | 30.26 A |
| ATOM | 355 | CA | ILE | A | 118 | 65.102 | 23.158 | 17.132 | 1.00 | 29.28 A |
| ATOM | 356 | CB | ILE | A | 118 | 65.266 | 21.696 | 16.712 | 1.00 | 27.64 A |
| ATOM | 357 | CG2 | ILE | A | 118 | 64.560 | 21.439 | 15.401 | 1.00 | 22.46 A |
| ATOM | 358 | CG1 | ILE | A | 118 | 66.756 | 21.371 | 16.642 | 1.00 | 27.22 A |
| ATOM | 359 | CD1 | ILE | A | 118 | 67.036 | 19.917 | 16.437 | 1.00 | 30.51 A |
| ATOM | 360 | C | ILE | A | 118 | 63.688 | 23.618 | 16.816 | 1.00 | 30.41 A |
| ATOM | 361 | O | ILE | A | 118 | 63.444 | 24.251 | 15.785 | 1.00 | 29.55 A |
| ATOM | 362 | N | ILE | A | 119 | 62.756 | 23.291 | 17.705 | 1.00 | 29.59 A |
| ATOM | 363 | CA | ILE | A | 119 | 61.376 | 23.682 | 17.497 | 1.00 | 29.18 A |
| ATOM | 364 | CB | ILE | A | 119 | 60.447 | 22.979 | 18.506 | 1.00 | 27.15 A |
| ATOM | 365 | CG2 | ILE | A | 119 | 59.071 | 23.623 | 18.486 | 1.00 | 22.69 A |
| ATOM | 366 | CG1 | ILE | A | 119 | 60.394 | 21.486 | 18.173 | 1.00 | 23.45 A |
| ATOM | 367 | CD1 | ILE | A | 119 | 59.666 | 20.665 | 19.173 | 1.00 | 19.08 A |
| ATOM | 368 | C | ILE | A | 119 | 61.223 | 25.194 | 17.617 | 1.00 | 30.65 A |
| ATOM | 369 | O | ILE | A | 119 | 60.574 | 25.832 | 16.786 | 1.00 | 30.59 A |
| ATOM | 370 | N | ALA | A | 120 | 61.837 | 25.768 | 18.642 | 1.00 | 31.95 A |
| ATOM | 371 | CA | ALA | A | 120 | 61.752 | 27.205 | 18.848 | 1.00 | 33.69 A |
| ATOM | 372 | CB | ALA | A | 120 | 62.473 | 27.608 | 20.150 | 1.00 | 33.17 A |
| ATOM | 373 | C | ALA | A | 120 | 62.330 | 27.973 | 17.671 | 1.00 | 34.80 A |
| ATOM | 374 | O | ALA | A | 120 | 61.865 | 29.067 | 17.362 | 1.00 | 37.34 A |
| ATOM | 375 | N | GLU | A | 121 | 63.328 | 27.413 | 16.997 | 1.00 | 35.09 A |
| ATOM | 376 | CA | GLU | A | 121 | 63.941 | 28.116 | 15.872 | 1.00 | 35.31 A |
| ATOM | 377 | CB | GLU | A | 121 | 65.453 | 27.927 | 15.933 | 1.00 | 39.72 A |
| ATOM | 378 | CG | GLU | A | 121 | 66.103 | 28.735 | 17.038 | 1.00 | 45.91 A |
| ATOM | 379 | CD | GLU | A | 121 | 65.955 | 30.225 | 16.784 | 1.00 | 49.51 A |
| ATOM | 380 | OE1 | GLU | A | 121 | 66.634 | 30.736 | 15.866 | 1.00 | 52.87 A |
| ATOM | 381 | OE2 | GLU | A | 121 | 65.148 | 30.879 | 17.482 | 1.00 | 51.35 A |
| ATOM | 382 | C | GLU | A | 121 | 63.421 | 27.699 | 14.499 | 1.00 | 34.14 A |
| ATOM | 383 | O | GLU | A | 121 | 63.964 | 28.109 | 13.468 | 1.00 | 31.41 A |
| ATOM | 384 | N | ASN | A | 122 | 62.363 | 26.891 | 14.497 | 1.00 | 33.86 A |
| ATOM | 385 | CA | ASN | A | 122 | 61.771 | 26.367 | 13.266 | 1.00 | 34.00 A |
| ATOM | 386 | CB | ASN | A | 122 | 61.112 | 27.473 | 12.464 | 1.00 | 36.75 A |
| ATOM | 387 | CG | ASN | A | 122 | 59.962 | 28.081 | 13.193 | 1.00 | 39.62 A |
| ATOM | 388 | OD1 | ASN | A | 122 | 60.148 | 28.788 | 14.185 | 1.00 | 39.90 A |
| ATOM | 389 | ND2 | ASN | A | 122 | 58.753 | 27.794 | 12.727 | 1.00 | 41.02 A |
| ATOM | 390 | C | ASN | A | 122 | 62.798 | 25.686 | 12.397 | 1.00 | 31.78 A |
| ATOM | 391 | O | ASN | A | 122 | 62.958 | 26.035 | 11.230 | 1.00 | 32.05 A |
| ATOM | 392 | N | LYS | A | 123 | 63.494 | 24.714 | 12.965 | 1.00 | 28.71 A |
| ATOM | 393 | CA | LYS | A | 123 | 64.508 | 24.008 | 12.217 | 1.00 | 29.39 A |
| ATOM | 394 | CB | LYS | A | 123 | 65.842 | 24.036 | 12.974 | 1.00 | 31.70 A |
| ATOM | 395 | CG | LYS | A | 123 | 66.434 | 25.416 | 13.132 | 1.00 | 33.49 A |
| ATOM | 396 | CD | LYS | A | 123 | 66.612 | 26.076 | 11.763 | 1.00 | 37.43 A |
| ATOM | 397 | CE | LYS | A | 123 | 67.174 | 27.491 | 11.898 | 1.00 | 38.52 A |
| ATOM | 398 | NZ | LYS | A | 123 | 67.337 | 28.176 | 10.582 | 1.00 | 37.85 A |
| ATOM | 399 | C | LYS | A | 123 | 64.116 | 22.572 | 11.931 | 1.00 | 28.30 A |
| ATOM | 400 | O | LYS | A | 123 | 64.867 | 21.844 | 11.289 | 1.00 | 29.68 A |
| ATOM | 401 | N | VAL | A | 124 | 62.944 | 22.162 | 12.404 | 1.00 | 26.80 A |
| ATOM | 402 | CA | VAL | A | 124 | 62.484 | 20.796 | 12.175 | 1.00 | 26.73 A |
| ATOM | 403 | CB | VAL | A | 124 | 61.024 | 20.593 | 12.622 | 1.00 | 26.31 A |
| ATOM | 404 | CG1 | VAL | A | 124 | 60.532 | 19.222 | 12.191 | 1.00 | 25.31 A |
| ATOM | 405 | CG2 | VAL | A | 124 | 60.918 | 20.720 | 14.134 | 1.00 | 26.73 A |
| ATOM | 406 | C | VAL | A | 124 | 62.594 | 20.351 | 10.722 | 1.00 | 27.11 A |
| ATOM | 407 | O | VAL | A | 124 | 62.973 | 19.218 | 10.450 | 1.00 | 29.79 A |
| ATOM | 408 | N | PRO | A | 125 | 62.270 | 21.228 | 9.763 | 1.00 | 27.28 A |
| ATOM | 409 | CD | PRO | A | 125 | 61.610 | 22.544 | 9.818 | 1.00 | 27.49 A |
| ATOM | 410 | CA | PRO | A | 125 | 62.386 | 20.758 | 8.378 | 1.00 | 27.41 A |
| ATOM | 411 | CB | PRO | A | 125 | 61.775 | 21.904 | 7.563 | 1.00 | 26.08 A |
| ATOM | 412 | CG | PRO | A | 125 | 60.821 | 22.546 | 8.524 | 1.00 | 27.54 A |
| ATOM | 413 | C | PRO | A | 125 | 63.837 | 20.506 | 8.006 | 1.00 | 27.90 A |
| ATOM | 414 | O | PRO | A | 125 | 64.162 | 19.572 | 7.260 | 1.00 | 26.27 A |
| ATOM | 415 | N | TYR | A | 126 | 64.703 | 21.350 | 8.550 | 1.00 | 28.64 A |
| ATOM | 416 | CA | TYR | A | 126 | 66.123 | 21.271 | 8.288 | 1.00 | 30.11 A |
| ATOM | 417 | CB | TYR | A | 126 | 66.791 | 22.528 | 8.809 | 1.00 | 36.70 A |

-continued

| | | | | | | | | | | |
|---|---|---|---|---|---|---|---|---|---|---|
| ATOM | 418 | CG | TYR | A | 126 | 66.440 | 23.774 | 8.013 | 1.00 | 44.64 A |
| ATOM | 419 | CD1 | TYR | A | 126 | 66.984 | 23.988 | 6.744 | 1.00 | 47.43 A |
| ATOM | 420 | CE1 | TYR | A | 126 | 66.737 | 25.173 | 6.037 | 1.00 | 50.16 A |
| ATOM | 421 | CD2 | TYR | A | 126 | 65.620 | 24.774 | 8.557 | 1.00 | 47.03 A |
| ATOM | 422 | CE2 | TYR | A | 126 | 65.369 | 25.955 | 7.861 | 1.00 | 49.52 A |
| ATOM | 423 | CZ | TYR | A | 126 | 65.936 | 26.152 | 6.605 | 1.00 | 50.60 A |
| ATOM | 424 | OH | TYR | A | 126 | 65.754 | 27.349 | 5.941 | 1.00 | 52.77 A |
| ATOM | 425 | C | TYR | A | 126 | 66.794 | 20.041 | 8.874 | 1.00 | 28.69 A |
| ATOM | 426 | O | TYR | A | 126 | 67.613 | 19.407 | 8.208 | 1.00 | 28.32 A |
| ATOM | 427 | N | VAL | A | 127 | 66.464 | 19.714 | 10.118 | 1.00 | 25.64 A |
| ATOM | 428 | CA | VAL | A | 127 | 67.033 | 18.550 | 10.766 | 1.00 | 24.89 A |
| ATOM | 429 | CB | VAL | A | 127 | 66.664 | 18.513 | 12.258 | 1.00 | 26.70 A |
| ATOM | 430 | CG1 | VAL | A | 127 | 67.158 | 17.206 | 12.881 | 1.00 | 22.51 A |
| ATOM | 431 | CG2 | VAL | A | 127 | 67.255 | 19.743 | 12.972 | 1.00 | 23.84 A |
| ATOM | 432 | C | VAL | A | 127 | 66.521 | 17.276 | 10.097 | 1.00 | 24.81 A |
| ATOM | 433 | O | VAL | A | 127 | 67.260 | 16.315 | 9.890 | 1.00 | 24.02 A |
| ATOM | 434 | N | THR | A | 128 | 65.245 | 17.290 | 9.755 | 1.00 | 24.02 A |
| ATOM | 435 | CA | THR | A | 128 | 64.608 | 16.164 | 9.088 | 1.00 | 24.59 A |
| ATOM | 436 | CB | THR | A | 128 | 63.123 | 16.471 | 8.843 | 1.00 | 25.38 A |
| ATOM | 437 | CG1 | THR | A | 128 | 62.478 | 16.652 | 10.106 | 1.00 | 25.76 A |
| ATOM | 438 | CG2 | THR | A | 128 | 62.451 | 15.354 | 8.066 | 1.00 | 22.88 A |
| ATOM | 439 | C | THR | A | 128 | 65.266 | 15.875 | 7.744 | 1.00 | 24.53 A |
| ATOM | 440 | O | THR | A | 128 | 65.560 | 14.729 | 7.426 | 1.00 | 25.53 A |
| ATOM | 441 | N | ARG | A | 129 | 65.477 | 16.925 | 6.957 | 1.00 | 24.82 A |
| ATOM | 442 | CA | ARG | A | 129 | 66.099 | 16.812 | 5.646 | 1.00 | 25.49 A |
| ATOM | 443 | CB | ARG | A | 129 | 66.111 | 18.181 | 4.959 | 1.00 | 26.78 A |
| ATOM | 444 | CG | ARG | A | 129 | 66.648 | 18.175 | 3.529 | 1.00 | 32.33 A |
| ATOM | 445 | CD | ARG | A | 129 | 66.579 | 19.563 | 2.878 | 1.00 | 36.93 A |
| ATOM | 446 | NE | ARG | A | 129 | 65.326 | 20.249 | 3.184 | 1.00 | 42.70 A |
| ATOM | 447 | CZ | ARG | A | 129 | 65.254 | 21.462 | 3.730 | 1.00 | 46.67 A |
| ATOM | 448 | NH1 | ARG | A | 129 | 66.366 | 22.128 | 4.018 | 1.00 | 48.50 A |
| ATOM | 449 | NH2 | ARG | A | 129 | 64.073 | 21.997 | 4.027 | 1.00 | 48.90 A |
| ATOM | 450 | C | ARG | A | 129 | 67.532 | 16.296 | 5.801 | 1.00 | 26.46 A |
| ATOM | 451 | O | ARG | A | 129 | 68.002 | 15.456 | 5.020 | 1.00 | 24.76 A |
| ATOM | 452 | N | GLU | A | 130 | 68.216 | 16.795 | 6.825 | 1.00 | 25.56 A |
| ATOM | 453 | CA | GLU | A | 130 | 69.582 | 16.393 | 7.076 | 1.00 | 28.29 A |
| ATOM | 454 | CB | GLU | A | 130 | 70.118 | 17.106 | 8.310 | 1.00 | 27.95 A |
| ATOM | 455 | CG | GLU | A | 130 | 71.591 | 16.875 | 8.539 | 1.00 | 29.48 A |
| ATOM | 456 | CD | GLU | A | 130 | 72.107 | 17.566 | 9.787 | 1.00 | 32.14 A |
| ATOM | 457 | OE1 | GLU | A | 130 | 71.297 | 18.221 | 10.483 | 1.00 | 32.67 A |
| ATOM | 458 | OE2 | GLU | A | 130 | 73.325 | 17.450 | 10.069 | 1.00 | 32.21 A |
| ATOM | 459 | C | GLU | A | 130 | 69.665 | 14.886 | 7.279 | 1.00 | 29.86 A |
| ATOM | 460 | O | GLU | A | 130 | 70.498 | 14.200 | 6.668 | 1.00 | 29.35 A |
| ATOM | 461 | N | ARG | A | 131 | 68.797 | 14.382 | 8.150 | 1.00 | 30.84 A |
| ATOM | 462 | CA | ARG | A | 131 | 68.763 | 12.966 | 8.451 | 1.00 | 31.62 A |
| ATOM | 463 | CB | ARG | A | 131 | 67.786 | 12.684 | 9.598 | 1.00 | 33.12 A |
| ATOM | 464 | CG | ARG | A | 131 | 67.557 | 11.190 | 9.831 | 1.00 | 36.17 A |
| ATOM | 465 | CD | ARG | A | 131 | 66.560 | 10.925 | 10.946 | 1.00 | 41.69 A |
| ATOM | 466 | NE | ARG | A | 131 | 66.330 | 9.492 | 11.166 | 1.00 | 46.62 A |
| ATOM | 467 | CZ | ARG | A | 131 | 65.692 | 8.986 | 12.224 | 1.00 | 48.29 A |
| ATOM | 468 | NH1 | ARG | A | 131 | 65.215 | 9.795 | 13.165 | 1.00 | 49.51 A |
| ATOM | 469 | NH2 | ARG | A | 131 | 65.544 | 7.671 | 12.352 | 1.00 | 48.76 A |
| ATOM | 470 | C | ARG | A | 131 | 68.371 | 12.138 | 7.235 | 1.00 | 30.59 A |
| ATOM | 471 | O | ARG | A | 131 | 68.897 | 11.051 | 7.026 | 1.00 | 29.96 A |
| ATOM | 472 | N | ASP | A | 132 | 67.446 | 12.649 | 6.433 | 1.00 | 29.54 A |
| ATOM | 473 | CA | ASP | A | 132 | 67.000 | 11.913 | 5.259 | 1.00 | 29.40 A |
| ATOM | 474 | CB | ASP | A | 132 | 65.735 | 12.565 | 4.708 | 1.00 | 32.43 A |
| ATOM | 475 | CG | ASP | A | 132 | 64.531 | 12.395 | 5.655 | 1.00 | 38.15 A |
| ATOM | 476 | OD1 | ASP | A | 132 | 64.749 | 12.227 | 6.881 | 1.00 | 40.40 A |
| ATOM | 477 | OD2 | ASP | A | 132 | 63.365 | 12.439 | 5.186 | 1.00 | 41.19 A |
| ATOM | 478 | C | ASP | A | 132 | 68.088 | 11.789 | 4.189 | 1.00 | 27.62 A |
| ATOM | 479 | O | ASP | A | 132 | 68.232 | 10.744 | 3.553 | 1.00 | 26.54 A |
| ATOM | 480 | N | VAL | A | 133 | 68.862 | 12.850 | 4.011 | 1.00 | 25.14 A |
| ATOM | 481 | CA | VAL | A | 133 | 69.939 | 12.857 | 3.044 | 1.00 | 24.12 A |
| ATOM | 482 | CB | VAL | A | 133 | 70.451 | 14.272 | 2.833 | 1.00 | 24.07 A |
| ATOM | 483 | CG1 | VAL | A | 133 | 71.802 | 14.247 | 2.143 | 1.00 | 23.77 A |
| ATOM | 484 | CG2 | VAL | A | 133 | 69.461 | 15.030 | 2.008 | 1.00 | 24.30 A |
| ATOM | 485 | C | VAL | A | 133 | 71.099 | 11.975 | 3.504 | 1.00 | 24.97 A |
| ATOM | 486 | O | VAL | A | 133 | 71.672 | 11.221 | 2.712 | 1.00 | 24.95 A |
| ATOM | 487 | N | MET | A | 134 | 71.458 | 12.074 | 4.779 | 1.00 | 23.41 A |
| ATOM | 488 | CA | MET | A | 134 | 72.539 | 11.255 | 5.268 | 1.00 | 23.12 A |
| ATOM | 489 | CB | MET | A | 134 | 72.932 | 11.653 | 6.683 | 1.00 | 21.12 A |
| ATOM | 490 | CG | MET | A | 134 | 73.608 | 13.005 | 6.759 | 1.00 | 21.21 A |
| ATOM | 491 | SD | MET | A | 134 | 74.530 | 13.204 | 8.291 | 1.00 | 20.52 A |
| ATOM | 492 | CE | MET | A | 134 | 73.172 | 13.347 | 9.534 | 1.00 | 17.71 A |
| ATOM | 493 | C | MET | A | 134 | 72.163 | 9.783 | 5.237 | 1.00 | 24.75 A |
| ATOM | 494 | O | MET | A | 134 | 73.027 | 8.918 | 5.039 | 1.00 | 25.73 A |
| ATOM | 495 | N | SER | A | 135 | 70.885 | 9.474 | 5.425 | 1.00 | 23.96 A |
| ATOM | 496 | CA | SER | A | 135 | 70.484 | 8.064 | 5.408 | 1.00 | 24.82 A |

-continued

| | | | | | | | | | | |
|---|---|---|---|---|---|---|---|---|---|---|
| ATOM | 497 | CB | SER | A | 135 | 69.048 | 7.889 | 5.917 | 1.00 | 24.63 | A |
| ATOM | 498 | OG | SER | A | 135 | 68.139 | 8.496 | 5.015 | 1.00 | 29.80 | A |
| ATOM | 499 | C | SER | A | 135 | 70.585 | 7.479 | 4.003 | 1.00 | 22.35 | A |
| ATOM | 500 | O | SER | A | 135 | 70.534 | 6.274 | 3.829 | 1.00 | 21.60 | A |
| ATOM | 501 | N | ARG | A | 136 | 70.729 | 8.335 | 3.004 | 1.00 | 21.91 | A |
| ATOM | 502 | CA | ARG | A | 136 | 70.815 | 7.858 | 1.631 | 1.00 | 23.76 | A |
| ATOM | 503 | CB | ARG | A | 136 | 69.988 | 8.762 | 0.714 | 1.00 | 25.55 | A |
| ATOM | 504 | CG | ARG | A | 136 | 68.500 | 8.782 | 1.069 | 1.00 | 31.38 | A |
| ATOM | 505 | CD | ARG | A | 136 | 67.764 | 9.897 | 0.332 | 1.00 | 33.65 | A |
| ATOM | 506 | NE | ARG | A | 136 | 68.024 | 9.809 | −1.099 | 1.00 | 38.77 | A |
| ATOM | 507 | CZ | ARG | A | 136 | 67.654 | 10.718 | −1.996 | 1.00 | 41.27 | A |
| ATOM | 508 | NH1 | ARG | A | 136 | 66.988 | 11.806 | −1.604 | 1.00 | 42.53 | A |
| ATOM | 509 | NH2 | ARG | A | 136 | 67.971 | 10.544 | −3.286 | 1.00 | 39.41 | A |
| ATOM | 510 | C | ARG | A | 136 | 72.248 | 7.789 | 1.131 | 1.00 | 22.64 | A |
| ATOM | 511 | O | ARG | A | 136 | 72.520 | 7.268 | 0.052 | 1.00 | 22.43 | A |
| ATOM | 512 | N | LEU | A | 137 | 73.168 | 8.318 | 1.919 | 1.00 | 22.66 | A |
| ATOM | 513 | CA | LEU | A | 137 | 74.568 | 8.307 | 1.535 | 1.00 | 22.60 | A |
| ATOM | 514 | CB | LEU | A | 137 | 75.348 | 9.375 | 2.308 | 1.00 | 20.28 | A |
| ATOM | 515 | CG | LEU | A | 137 | 74.842 | 10.793 | 2.068 | 1.00 | 19.72 | A |
| ATOM | 516 | CD1 | LEU | A | 137 | 75.695 | 11.816 | 2.840 | 1.00 | 17.83 | A |
| ATOM | 517 | CD2 | LEU | A | 137 | 74.855 | 11.062 | 0.564 | 1.00 | 18.39 | A |
| ATOM | 518 | C | LEU | A | 137 | 75.195 | 6.950 | 1.775 | 1.00 | 22.60 | A |
| ATOM | 519 | O | LEU | A | 137 | 75.203 | 6.445 | 2.892 | 1.00 | 23.75 | A |
| ATOM | 520 | N | ASP | A | 138 | 75.723 | 6.371 | 0.710 | 1.00 | 22.09 | A |
| ATOM | 521 | CA | ASP | A | 138 | 76.383 | 5.083 | 0.788 | 1.00 | 22.63 | A |
| ATOM | 522 | CB | ASP | A | 138 | 75.419 | 3.988 | 0.340 | 1.00 | 25.16 | A |
| ATOM | 523 | CG | ASP | A | 138 | 75.976 | 2.622 | 0.582 | 1.00 | 26.26 | A |
| ATOM | 524 | OD1 | ASP | A | 138 | 76.658 | 2.480 | 1.611 | 1.00 | 27.29 | A |
| ATOM | 525 | OD2 | ASP | A | 138 | 75.740 | 1.708 | −0.237 | 1.00 | 30.75 | A |
| ATOM | 526 | C | ASP | A | 138 | 77.617 | 5.112 | −0.124 | 1.00 | 20.82 | A |
| ATOM | 527 | O | ASP | A | 138 | 77.656 | 4.445 | −1.155 | 1.00 | 22.94 | A |
| ATOM | 528 | N | HIS | A | 139 | 78.612 | 5.902 | 0.250 | 1.00 | 16.77 | A |
| ATOM | 529 | CA | HIS | A | 139 | 79.813 | 6.050 | −0.557 | 1.00 | 16.21 | A |
| ATOM | 530 | CB | HIS | A | 139 | 79.614 | 7.180 | −1.583 | 1.00 | 15.30 | A |
| ATOM | 531 | CG | HIS | A | 139 | 80.755 | 7.348 | −2.534 | 1.00 | 16.37 | A |
| ATOM | 532 | CD2 | HIS | A | 139 | 80.853 | 7.087 | −3.860 | 1.00 | 15.32 | A |
| ATOM | 533 | ND1 | HIS | A | 139 | 81.998 | 7.802 | −2.139 | 1.00 | 17.12 | A |
| ATOM | 534 | CE1 | HIS | A | 139 | 82.811 | 7.810 | −3.184 | 1.00 | 15.92 | A |
| ATOM | 535 | NE2 | HIS | A | 139 | 82.140 | 7.380 | −4.238 | 1.00 | 13.96 | A |
| ATOM | 536 | C | HIS | A | 139 | 80.985 | 6.371 | 0.357 | 1.00 | 16.70 | A |
| ATOM | 537 | O | HIS | A | 139 | 80.848 | 7.116 | 1.317 | 1.00 | 16.89 | A |
| ATOM | 538 | N | PRO | A | 140 | 82.164 | 5.823 | 0.056 | 1.00 | 16.94 | A |
| ATOM | 539 | CD | PRO | A | 140 | 82.508 | 4.991 | −1.108 | 1.00 | 17.10 | A |
| ATOM | 540 | CA | PRO | A | 140 | 83.334 | 6.079 | 0.895 | 1.00 | 17.98 | A |
| ATOM | 541 | CB | PRO | A | 140 | 84.390 | 5.163 | 0.291 | 1.00 | 17.03 | A |
| ATOM | 542 | CG | PRO | A | 140 | 84.003 | 5.114 | −1.159 | 1.00 | 18.59 | A |
| ATOM | 543 | C | PRO | A | 140 | 83.822 | 7.528 | 1.070 | 1.00 | 18.59 | A |
| ATOM | 544 | O | PRO | A | 140 | 84.528 | 7.817 | 2.021 | 1.00 | 20.11 | A |
| ATOM | 545 | N | PHE | A | 141 | 83.460 | 8.444 | 0.179 | 1.00 | 19.62 | A |
| ATOM | 546 | CA | PHE | A | 141 | 83.909 | 9.833 | 0.345 | 1.00 | 18.34 | A |
| ATOM | 547 | CB | PHE | A | 141 | 84.223 | 10.474 | −1.010 | 1.00 | 17.53 | A |
| ATOM | 548 | CG | PHE | A | 141 | 85.440 | 9.880 | −1.694 | 1.00 | 17.38 | A |
| ATOM | 549 | CD1 | PHE | A | 141 | 86.450 | 9.275 | −0.938 | 1.00 | 17.01 | A |
| ATOM | 550 | CD2 | PHE | A | 141 | 85.579 | 9.926 | −3.081 | 1.00 | 15.76 | A |
| ATOM | 551 | CE1 | PHE | A | 141 | 87.572 | 8.724 | −1.550 | 1.00 | 16.13 | A |
| ATOM | 552 | CE2 | PHE | A | 141 | 86.707 | 9.375 | −3.708 | 1.00 | 16.99 | A |
| ATOM | 553 | CZ | PHE | A | 141 | 87.705 | 8.772 | −2.938 | 1.00 | 15.01 | A |
| ATOM | 554 | C | PHE | A | 141 | 82.893 | 10.680 | 1.095 | 1.00 | 18.14 | A |
| ATOM | 555 | O | PHE | A | 141 | 83.012 | 11.896 | 1.144 | 1.00 | 20.74 | A |
| ATOM | 556 | N | PHE | A | 142 | 81.901 | 10.037 | 1.697 | 1.00 | 15.85 | A |
| ATOM | 557 | CA | PHE | A | 142 | 80.887 | 10.761 | 2.444 | 1.00 | 15.95 | A |
| ATOM | 558 | CB | PHE | A | 142 | 79.558 | 10.757 | 1.690 | 1.00 | 15.20 | A |
| ATOM | 559 | CG | PHE | A | 142 | 79.507 | 11.721 | 0.542 | 1.00 | 15.62 | A |
| ATOM | 560 | CD1 | PHE | A | 142 | 79.295 | 13.086 | 0.768 | 1.00 | 14.51 | A |
| ATOM | 561 | CD2 | PHE | A | 142 | 79.651 | 11.265 | −0.771 | 1.00 | 12.05 | A |
| ATOM | 562 | CE1 | PHE | A | 142 | 79.222 | 13.991 | −0.291 | 1.00 | 13.97 | A |
| ATOM | 563 | CE2 | PHE | A | 142 | 79.582 | 12.157 | −1.840 | 1.00 | 15.46 | A |
| ATOM | 564 | CZ | PHE | A | 142 | 79.365 | 13.536 | −1.601 | 1.00 | 14.89 | A |
| ATOM | 565 | C | PHE | A | 142 | 80.654 | 10.167 | 3.824 | 1.00 | 15.60 | A |
| ATOM | 566 | O | PHE | A | 142 | 80.886 | 8.986 | 4.061 | 1.00 | 15.39 | A |
| ATOM | 567 | N | VAL | A | 143 | 80.182 | 11.001 | 4.733 | 1.00 | 15.87 | A |
| ATOM | 568 | CA | VAL | A | 143 | 79.878 | 10.564 | 6.075 | 1.00 | 15.04 | A |
| ATOM | 569 | CB | VAL | A | 143 | 79.304 | 11.727 | 6.905 | 1.00 | 15.26 | A |
| ATOM | 570 | CG1 | VAL | A | 143 | 78.012 | 12.231 | 6.276 | 1.00 | 11.03 | A |
| ATOM | 571 | CG2 | VAL | A | 143 | 79.100 | 11.296 | 8.350 | 1.00 | 14.40 | A |
| ATOM | 572 | C | VAL | A | 143 | 78.828 | 9.479 | 5.935 | 1.00 | 15.52 | A |
| ATOM | 573 | O | VAL | A | 143 | 78.076 | 9.453 | 4.963 | 1.00 | 15.45 | A |
| ATOM | 574 | N | LYS | A | 144 | 78.794 | 8.580 | 6.907 | 1.00 | 16.29 | A |
| ATOM | 575 | CA | LYS | A | 144 | 77.848 | 7.482 | 6.933 | 1.00 | 17.45 | A |

-continued

| | | | | | | | | | | |
|---|---|---|---|---|---|---|---|---|---|---|
| ATOM | 576 | CB | LYS | A | 144 | 78.625 | 6.150 | 6.895 | 1.00 | 18.05 A |
| ATOM | 577 | CG | LYS | A | 144 | 77.963 | 4.967 | 7.596 | 1.00 | 24.34 A |
| ATOM | 578 | CD | LYS | A | 144 | 76.922 | 4.263 | 6.752 | 1.00 | 26.35 A |
| ATOM | 579 | CE | LYS | A | 144 | 77.461 | 2.926 | 6.213 | 1.00 | 30.22 A |
| ATOM | 580 | NZ | LYS | A | 144 | 77.576 | 1.882 | 7.271 | 1.00 | 28.27 A |
| ATOM | 581 | C | LYS | A | 144 | 77.024 | 7.626 | 8.222 | 1.00 | 17.39 A |
| ATOM | 582 | O | LYS | A | 144 | 77.565 | 7.913 | 9.284 | 1.00 | 16.92 A |
| ATOM | 583 | N | LEU | A | 145 | 75.711 | 7.458 | 8.116 | 1.00 | 17.41 A |
| ATOM | 584 | CA | LEU | A | 145 | 74.836 | 7.549 | 9.274 | 1.00 | 18.13 A |
| ATOM | 585 | CB | LEU | A | 145 | 73.514 | 8.210 | 8.893 | 1.00 | 18.86 A |
| ATOM | 586 | CG | LEU | A | 145 | 72.612 | 8.850 | 9.964 | 1.00 | 20.13 A |
| ATOM | 587 | CD1 | LEU | A | 145 | 71.157 | 8.607 | 9.582 | 1.00 | 19.48 A |
| ATOM | 588 | CD2 | LEU | A | 145 | 72.900 | 8.311 | 11.331 | 1.00 | 17.86 A |
| ATOM | 589 | C | LEU | A | 145 | 74.559 | 6.113 | 9.689 | 1.00 | 18.85 A |
| ATOM | 590 | O | LEU | A | 145 | 73.905 | 5.379 | 8.954 | 1.00 | 20.15 A |
| ATOM | 591 | N | TYR | A | 146 | 75.030 | 5.713 | 10.867 | 1.00 | 18.09 A |
| ATOM | 592 | CA | TYR | A | 146 | 74.830 | 4.341 | 11.329 | 1.00 | 15.93 A |
| ATOM | 593 | CB | TYR | A | 146 | 76.013 | 3.871 | 12.154 | 1.00 | 14.52 A |
| ATOM | 594 | CG | TYR | A | 146 | 77.295 | 3.776 | 11.390 | 1.00 | 13.98 A |
| ATOM | 595 | CD1 | TYR | A | 146 | 78.093 | 4.907 | 11.193 | 1.00 | 15.01 A |
| ATOM | 596 | CE1 | TYR | A | 146 | 79.329 | 4.815 | 10.548 | 1.00 | 14.94 A |
| ATOM | 597 | CD2 | TYR | A | 146 | 77.752 | 2.541 | 10.912 | 1.00 | 14.36 A |
| ATOM | 598 | CE2 | TYR | A | 146 | 78.984 | 2.426 | 10.266 | 1.00 | 15.47 A |
| ATOM | 599 | CZ | TYR | A | 146 | 79.770 | 3.566 | 10.090 | 1.00 | 15.70 A |
| ATOM | 600 | OH | TYR | A | 146 | 80.999 | 3.473 | 9.491 | 1.00 | 16.29 A |
| ATOM | 601 | C | TYR | A | 146 | 73.591 | 4.135 | 12.154 | 1.00 | 16.74 A |
| ATOM | 602 | O | TYR | A | 146 | 73.004 | 3.050 | 12.132 | 1.00 | 17.63 A |
| ATOM | 603 | N | PHE | A | 147 | 73.198 | 5.158 | 12.901 | 1.00 | 15.90 A |
| ATOM | 604 | CA | PHE | A | 147 | 72.012 | 5.041 | 13.745 | 1.00 | 17.10 A |
| ATOM | 605 | CB | PHE | A | 147 | 72.265 | 4.057 | 14.932 | 1.00 | 14.80 A |
| ATOM | 606 | CG | PHE | A | 147 | 73.509 | 4.366 | 15.747 | 1.00 | 16.36 A |
| ATOM | 607 | CD1 | PHE | A | 147 | 73.526 | 5.427 | 16.657 | 1.00 | 15.38 A |
| ATOM | 608 | CD2 | PHE | A | 147 | 74.701 | 3.663 | 15.514 | 1.00 | 16.83 A |
| ATOM | 609 | CE1 | PHE | A | 147 | 74.709 | 5.801 | 17.314 | 1.00 | 15.96 A |
| ATOM | 610 | CE2 | PHE | A | 147 | 75.907 | 4.024 | 16.163 | 1.00 | 16.65 A |
| ATOM | 611 | CZ | PHE | A | 147 | 75.908 | 5.107 | 17.069 | 1.00 | 16.96 A |
| ATOM | 612 | C | PHE | A | 147 | 71.550 | 6.378 | 14.286 | 1.00 | 17.73 A |
| ATOM | 613 | O | PHE | A | 147 | 72.225 | 7.399 | 14.145 | 1.00 | 18.47 A |
| ATOM | 614 | N | THR | A | 148 | 70.376 | 6.352 | 14.897 | 1.00 | 19.28 A |
| ATOM | 615 | CA | THR | A | 148 | 69.801 | 7.529 | 15.532 | 1.00 | 19.50 A |
| ATOM | 616 | CB | THR | A | 148 | 68.846 | 8.308 | 14.597 | 1.00 | 19.24 A |
| ATOM | 617 | OG1 | THR | A | 148 | 67.722 | 7.485 | 14.271 | 1.00 | 18.29 A |
| ATOM | 618 | CG2 | THR | A | 148 | 69.563 | 8.727 | 13.311 | 1.00 | 18.53 A |
| ATOM | 619 | C | THR | A | 148 | 68.976 | 7.071 | 16.718 | 1.00 | 19.68 A |
| ATOM | 620 | O | THR | A | 148 | 68.556 | 5.915 | 16.802 | 1.00 | 20.20 A |
| ATOM | 621 | N | PHE | A | 149 | 68.765 | 7.975 | 17.653 | 1.00 | 20.20 A |
| ATOM | 622 | CA | PHE | A | 149 | 67.926 | 7.687 | 18.797 | 1.00 | 20.34 A |
| ATOM | 623 | CB | PHE | A | 149 | 68.558 | 6.626 | 19.728 | 1.00 | 19.06 A |
| ATOM | 624 | CG | PHE | A | 149 | 69.932 | 6.961 | 20.216 | 1.00 | 18.27 A |
| ATOM | 625 | CD1 | PHE | A | 149 | 70.114 | 7.745 | 21.357 | 1.00 | 19.90 A |
| ATOM | 626 | CD2 | PHE | A | 149 | 71.049 | 6.467 | 19.559 | 1.00 | 19.21 A |
| ATOM | 627 | CE1 | PHE | A | 149 | 71.387 | 8.028 | 21.840 | 1.00 | 19.04 A |
| ATOM | 628 | CE2 | PHE | A | 149 | 72.341 | 6.741 | 20.025 | 1.00 | 19.95 A |
| ATOM | 629 | CZ | PHE | A | 149 | 72.513 | 7.520 | 21.167 | 1.00 | 21.19 A |
| ATOM | 630 | C | PHE | A | 149 | 67.693 | 9.004 | 19.487 | 1.00 | 20.94 A |
| ATOM | 631 | O | PHE | A | 149 | 68.192 | 10.035 | 19.042 | 1.00 | 17.91 A |
| ATOM | 632 | N | GLN | A | 150 | 66.888 | 8.988 | 20.539 | 1.00 | 25.44 A |
| ATOM | 633 | CA | GLN | A | 150 | 66.609 | 10.212 | 21.279 | 1.00 | 29.09 A |
| ATOM | 634 | CB | GLN | A | 150 | 65.518 | 11.039 | 20.571 | 1.00 | 29.07 A |
| ATOM | 635 | CG | GLN | A | 150 | 64.194 | 10.322 | 20.309 | 1.00 | 31.07 A |
| ATOM | 636 | CD | GLN | A | 150 | 63.150 | 11.227 | 19.609 | 1.00 | 32.52 A |
| ATOM | 637 | OE1 | GLN | A | 150 | 62.503 | 12.075 | 20.243 | 1.00 | 30.50 A |
| ATOM | 638 | NE2 | GLN | A | 150 | 63.009 | 11.056 | 18.294 | 1.00 | 29.34 A |
| ATOM | 639 | C | GLN | A | 150 | 66.190 | 9.927 | 22.707 | 1.00 | 29.59 A |
| ATOM | 640 | O | GLN | A | 150 | 65.738 | 8.832 | 23.018 | 1.00 | 30.34 A |
| ATOM | 641 | N | ASP | A | 151 | 66.407 | 10.892 | 23.590 | 1.00 | 31.52 A |
| ATOM | 642 | CA | ASP | A | 151 | 65.957 | 10.750 | 24.967 | 1.00 | 32.22 A |
| ATOM | 643 | CB | ASP | A | 151 | 67.093 | 10.948 | 25.974 | 1.00 | 31.30 A |
| ATOM | 644 | CG | ASP | A | 151 | 67.832 | 12.246 | 25.790 | 1.00 | 32.39 A |
| ATOM | 645 | OD1 | ASP | A | 151 | 67.241 | 13.217 | 25.263 | 1.00 | 34.30 A |
| ATOM | 646 | OD2 | ASP | A | 151 | 69.011 | 12.290 | 26.195 | 1.00 | 32.02 A |
| ATOM | 647 | C | ASP | A | 151 | 64.914 | 11.858 | 25.063 | 1.00 | 33.56 A |
| ATOM | 648 | O | ASP | A | 151 | 64.495 | 12.387 | 24.033 | 1.00 | 34.76 A |
| ATOM | 649 | N | ASP | A | 152 | 64.498 | 12.239 | 26.261 | 1.00 | 35.00 A |
| ATOM | 650 | CA | ASP | A | 152 | 63.462 | 13.268 | 26.369 | 1.00 | 36.72 A |
| ATOM | 651 | CB | ASP | A | 152 | 63.053 | 13.465 | 27.830 | 1.00 | 38.27 A |
| ATOM | 652 | CG | ASP | A | 152 | 62.237 | 12.312 | 28.351 | 1.00 | 42.45 A |
| ATOM | 653 | OD1 | ASP | A | 152 | 61.377 | 11.824 | 27.579 | 1.00 | 43.52 A |
| ATOM | 654 | OD2 | ASP | A | 152 | 62.444 | 11.900 | 29.519 | 1.00 | 44.28 A |

-continued

| | | | | | | | | | | |
|---|---|---|---|---|---|---|---|---|---|---|
| ATOM | 655 | C | ASP | A | 152 | 63.758 | 14.627 | 25.759 | 1.00 | 36.47 A |
| ATOM | 656 | O | ASP | A | 152 | 62.857 | 15.289 | 25.242 | 1.00 | 36.12 A |
| ATOM | 657 | N | GLU | A | 153 | 65.021 | 15.029 | 25.781 | 1.00 | 36.09 A |
| ATOM | 658 | CA | GLU | A | 153 | 65.358 | 16.343 | 25.292 | 1.00 | 35.16 A |
| ATOM | 659 | CB | GLU | A | 153 | 65.976 | 17.137 | 26.442 | 1.00 | 39.45 A |
| ATOM | 660 | CG | GLU | A | 153 | 65.486 | 16.714 | 27.830 | 1.00 | 45.94 A |
| ATOM | 661 | CD | GLU | A | 153 | 66.383 | 15.652 | 28.468 | 1.00 | 51.78 A |
| ATOM | 662 | OE1 | GLU | A | 153 | 67.563 | 15.977 | 28.746 | 1.00 | 54.51 A |
| ATOM | 663 | OE2 | GLU | A | 153 | 65.924 | 14.500 | 28.689 | 1.00 | 52.47 A |
| ATOM | 664 | C | GLU | A | 153 | 66.258 | 16.455 | 24.073 | 1.00 | 32.91 A |
| ATOM | 665 | O | GLU | A | 153 | 66.304 | 17.524 | 23.457 | 1.00 | 31.19 A |
| ATOM | 666 | N | LYS | A | 154 | 66.959 | 15.376 | 23.710 | 1.00 | 30.19 A |
| ATOM | 667 | CA | LYS | A | 154 | 67.898 | 15.431 | 22.582 | 1.00 | 26.56 A |
| ATOM | 668 | CB | LYS | A | 154 | 69.323 | 15.414 | 23.121 | 1.00 | 24.92 A |
| ATOM | 669 | CG | LYS | A | 154 | 69.630 | 16.551 | 24.041 | 1.00 | 23.66 A |
| ATOM | 670 | CD | LYS | A | 154 | 70.944 | 16.355 | 24.750 | 1.00 | 20.95 A |
| ATOM | 671 | CE | LYS | A | 154 | 71.274 | 17.583 | 25.576 | 1.00 | 18.98 A |
| ATOM | 672 | NZ | LYS | A | 154 | 72.491 | 17.388 | 26.360 | 1.00 | 19.19 A |
| ATOM | 673 | C | LYS | A | 154 | 67.806 | 14.374 | 21.487 | 1.00 | 25.00 A |
| ATOM | 674 | O | LYS | A | 154 | 67.342 | 13.257 | 21.701 | 1.00 | 25.62 A |
| ATOM | 675 | N | LEU | A | 155 | 68.276 | 14.759 | 20.308 | 1.00 | 23.36 A |
| ATOM | 676 | CA | LEU | A | 155 | 68.337 | 13.881 | 19.140 | 1.00 | 22.19 A |
| ATOM | 677 | CB | LEU | A | 155 | 67.946 | 14.624 | 17.864 | 1.00 | 21.64 A |
| ATOM | 678 | CG | LEU | A | 155 | 66.539 | 15.167 | 17.707 | 1.00 | 22.58 A |
| ATOM | 679 | CD1 | LEU | A | 155 | 66.437 | 15.847 | 16.350 | 1.00 | 22.74 A |
| ATOM | 680 | CD2 | LEU | A | 155 | 65.533 | 14.034 | 17.815 | 1.00 | 23.23 A |
| ATOM | 681 | C | LEU | A | 155 | 69.798 | 13.474 | 19.004 | 1.00 | 20.69 A |
| ATOM | 682 | O | LEU | A | 155 | 70.693 | 14.287 | 19.249 | 1.00 | 21.61 A |
| ATOM | 683 | N | TYR | A | 156 | 70.036 | 12.238 | 18.592 | 1.00 | 18.69 A |
| ATOM | 684 | CA | TYR | A | 156 | 71.393 | 11.737 | 18.431 | 1.00 | 18.65 A |
| ATOM | 685 | CB | TYR | A | 156 | 71.690 | 10.661 | 19.489 | 1.00 | 18.51 A |
| ATOM | 686 | CG | TYR | A | 156 | 71.602 | 11.148 | 20.913 | 1.00 | 17.86 A |
| ATOM | 687 | CD1 | TYR | A | 156 | 70.372 | 11.287 | 21.550 | 1.00 | 18.38 A |
| ATOM | 688 | CE1 | TYR | A | 156 | 70.286 | 11.752 | 22.862 | 1.00 | 18.95 A |
| ATOM | 689 | CD2 | TYR | A | 156 | 72.755 | 11.488 | 21.621 | 1.00 | 19.32 A |
| ATOM | 690 | CE2 | TYR | A | 156 | 72.690 | 11.957 | 22.942 | 1.00 | 18.14 A |
| ATOM | 691 | CZ | TYR | A | 156 | 71.449 | 12.086 | 23.551 | 1.00 | 18.56 A |
| ATOM | 692 | OH | TYR | A | 156 | 71.372 | 12.547 | 24.838 | 1.00 | 18.33 A |
| ATOM | 693 | C | TYR | A | 156 | 71.640 | 11.125 | 17.059 | 1.00 | 18.03 A |
| ATOM | 694 | O | TYR | A | 156 | 70.903 | 10.250 | 16.646 | 1.00 | 18.18 A |
| ATOM | 695 | N | PHE | A | 157 | 72.662 | 11.568 | 16.338 | 1.00 | 17.19 A |
| ATOM | 696 | CA | PHE | A | 157 | 72.937 | 10.934 | 15.062 | 1.00 | 17.15 A |
| ATOM | 697 | CB | PHE | A | 157 | 72.980 | 11.951 | 13.918 | 1.00 | 21.54 A |
| ATOM | 698 | CG | PHE | A | 157 | 71.663 | 12.638 | 13.651 | 1.00 | 26.82 A |
| ATOM | 699 | CD1 | PHE | A | 157 | 70.471 | 12.165 | 14.221 | 1.00 | 30.87 A |
| ATOM | 700 | CD2 | PHE | A | 157 | 71.617 | 13.794 | 12.869 | 1.00 | 28.42 A |
| ATOM | 701 | CE1 | PHE | A | 157 | 69.249 | 12.845 | 14.024 | 1.00 | 30.45 A |
| ATOM | 702 | CE2 | PHE | A | 157 | 70.407 | 14.483 | 12.661 | 1.00 | 29.44 A |
| ATOM | 703 | CZ | PHE | A | 157 | 69.224 | 14.008 | 13.243 | 1.00 | 30.41 A |
| ATOM | 704 | C | PHE | A | 157 | 74.286 | 10.244 | 15.184 | 1.00 | 16.38 A |
| ATOM | 705 | O | PHE | A | 157 | 75.256 | 10.883 | 15.527 | 1.00 | 17.91 A |
| ATOM | 706 | N | GLY | A | 158 | 74.347 | 8.942 | 14.919 | 1.00 | 16.20 A |
| ATOM | 707 | CA | GLY | A | 158 | 75.614 | 8.232 | 15.009 | 1.00 | 15.78 A |
| ATOM | 708 | C | GLY | A | 158 | 76.322 | 8.285 | 13.671 | 1.00 | 16.51 A |
| ATOM | 709 | O | GLY | A | 158 | 75.876 | 7.659 | 12.710 | 1.00 | 17.95 A |
| ATOM | 710 | N | LEU | A | 159 | 77.423 | 9.028 | 13.600 | 1.00 | 14.97 A |
| ATOM | 711 | CA | LEU | A | 159 | 78.143 | 9.177 | 12.342 | 1.00 | 15.17 A |
| ATOM | 712 | CB | LEU | A | 159 | 78.264 | 10.669 | 12.012 | 1.00 | 13.14 A |
| ATOM | 713 | CG | LEU | A | 159 | 76.989 | 11.518 | 12.133 | 1.00 | 12.95 A |
| ATOM | 714 | CD1 | LEU | A | 159 | 77.347 | 13.002 | 11.872 | 1.00 | 7.84 A |
| ATOM | 715 | CD2 | LEU | A | 159 | 75.926 | 11.020 | 11.138 | 1.00 | 11.24 A |
| ATOM | 716 | C | LEU | A | 159 | 79.535 | 8.540 | 12.300 | 1.00 | 15.49 A |
| ATOM | 717 | O | LEU | A | 159 | 80.136 | 8.256 | 13.333 | 1.00 | 15.76 A |
| ATOM | 718 | N | SER | A | 160 | 80.051 | 8.313 | 11.097 | 1.00 | 14.32 A |
| ATOM | 719 | CA | SER | A | 160 | 81.389 | 7.759 | 10.984 | 1.00 | 14.68 A |
| ATOM | 720 | CB | SER | A | 160 | 81.699 | 7.386 | 9.529 | 1.00 | 12.79 A |
| ATOM | 721 | OG | SER | A | 160 | 81.395 | 8.432 | 8.626 | 1.00 | 16.15 A |
| ATOM | 722 | C | SER | A | 160 | 82.365 | 8.823 | 11.509 | 1.00 | 15.82 A |
| ATOM | 723 | O | SER | A | 160 | 82.152 | 10.029 | 11.333 | 1.00 | 17.75 A |
| ATOM | 724 | N | TYR | A | 161 | 83.418 | 8.386 | 12.184 | 1.00 | 16.30 A |
| ATOM | 725 | CA | TYR | A | 161 | 84.399 | 9.309 | 12.740 | 1.00 | 17.11 A |
| ATOM | 726 | CB | TYR | A | 161 | 84.863 | 8.785 | 14.100 | 1.00 | 16.09 A |
| ATOM | 727 | CG | TYR | A | 161 | 86.020 | 9.529 | 14.717 | 1.00 | 19.80 A |
| ATOM | 728 | CD1 | TYR | A | 161 | 86.070 | 10.933 | 14.700 | 1.00 | 18.64 A |
| ATOM | 729 | CE1 | TYR | A | 161 | 87.091 | 11.625 | 15.345 | 1.00 | 19.50 A |
| ATOM | 730 | CD2 | TYR | A | 161 | 87.032 | 8.837 | 15.394 | 1.00 | 20.09 A |
| ATOM | 731 | CE2 | TYR | A | 161 | 88.057 | 9.517 | 16.047 | 1.00 | 21.66 A |
| ATOM | 732 | CZ | TYR | A | 161 | 88.085 | 10.918 | 16.022 | 1.00 | 23.52 A |
| ATOM | 733 | OH | TYR | A | 161 | 89.111 | 11.600 | 16.674 | 1.00 | 22.64 A |

-continued

| | | | | | | | | | | |
|---|---|---|---|---|---|---|---|---|---|---|
| ATOM | 734 | C | TYR | A | 161 | 85.594 | 9.495 | 11.815 | 1.00 | 17.86 A |
| ATOM | 735 | O | TYR | A | 161 | 86.269 | 8.527 | 11.459 | 1.00 | 19.30 A |
| ATOM | 736 | N | ALA | A | 162 | 85.854 | 10.736 | 11.418 | 1.00 | 18.22 A |
| ATOM | 737 | CA | ALA | A | 162 | 86.990 | 11.040 | 10.546 | 1.00 | 19.59 A |
| ATOM | 738 | CB | ALA | A | 162 | 86.569 | 12.063 | 9.466 | 1.00 | 19.99 A |
| ATOM | 739 | C | ALA | A | 162 | 88.051 | 11.629 | 11.472 | 1.00 | 19.11 A |
| ATOM | 740 | O | ALA | A | 162 | 88.050 | 12.828 | 11.736 | 1.00 | 18.81 A |
| ATOM | 741 | N | ALA | A | 163 | 88.952 | 10.775 | 11.956 | 1.00 | 18.78 A |
| ATOM | 742 | CA | ALA | A | 163 | 89.994 | 11.165 | 12.918 | 1.00 | 18.84 A |
| ATOM | 743 | CB | ALA | A | 163 | 90.867 | 9.924 | 13.279 | 1.00 | 19.04 A |
| ATOM | 744 | C | ALA | A | 163 | 90.908 | 12.357 | 12.604 | 1.00 | 18.22 A |
| ATOM | 745 | O | ALA | A | 163 | 91.290 | 13.101 | 13.508 | 1.00 | 16.79 A |
| ATOM | 746 | N | ASN | A | 164 | 91.251 | 12.560 | 11.340 | 1.00 | 17.46 A |
| ATOM | 747 | CA | ASN | A | 164 | 92.148 | 13.645 | 11.023 | 1.00 | 17.79 A |
| ATOM | 748 | CB | ASN | A | 164 | 92.990 | 13.270 | 9.803 | 1.00 | 20.45 A |
| ATOM | 749 | CG | ASN | A | 164 | 93.919 | 12.092 | 10.097 | 1.00 | 21.08 A |
| ATOM | 750 | OD1 | ASN | A | 164 | 94.663 | 12.117 | 11.066 | 1.00 | 21.57 A |
| ATOM | 751 | ND2 | ASN | A | 164 | 93.862 | 11.059 | 9.271 | 1.00 | 24.54 A |
| ATOM | 752 | C | ASN | A | 164 | 91.555 | 15.044 | 10.889 | 1.00 | 18.34 A |
| ATOM | 753 | O | ASN | A | 164 | 92.293 | 16.005 | 10.634 | 1.00 | 19.83 A |
| ATOM | 754 | N | GLY | A | 165 | 90.247 | 15.176 | 11.083 | 1.00 | 15.01 A |
| ATOM | 755 | CA | GLY | A | 165 | 89.644 | 16.490 | 11.022 | 1.00 | 15.54 A |
| ATOM | 756 | C | GLY | A | 165 | 89.580 | 17.212 | 9.683 | 1.00 | 17.67 A |
| ATOM | 757 | O | GLY | A | 165 | 89.607 | 16.600 | 8.613 | 1.00 | 19.49 A |
| ATOM | 758 | N | GLU | A | 166 | 89.510 | 18.534 | 9.753 | 1.00 | 17.46 A |
| ATOM | 759 | CA | GLU | A | 166 | 89.378 | 19.379 | 8.577 | 1.00 | 19.26 A |
| ATOM | 760 | CB | GLU | A | 166 | 89.064 | 20.805 | 9.019 | 1.00 | 21.87 A |
| ATOM | 761 | CG | GLU | A | 166 | 88.057 | 20.917 | 10.149 | 1.00 | 24.70 A |
| ATOM | 762 | CD | GLU | A | 166 | 87.723 | 22.359 | 10.477 | 1.00 | 26.05 A |
| ATOM | 763 | OE1 | GLU | A | 166 | 88.469 | 23.251 | 10.001 | 1.00 | 25.93 A |
| ATOM | 764 | OE2 | GLU | A | 166 | 86.726 | 22.598 | 11.213 | 1.00 | 25.24 A |
| ATOM | 765 | C | GLU | A | 166 | 90.538 | 19.441 | 7.592 | 1.00 | 20.11 A |
| ATOM | 766 | O | GLU | A | 166 | 91.707 | 19.501 | 7.978 | 1.00 | 22.88 A |
| ATOM | 767 | N | LEU | A | 167 | 90.195 | 19.443 | 6.312 | 1.00 | 18.72 A |
| ATOM | 768 | CA | LEU | A | 167 | 91.173 | 19.565 | 5.242 | 1.00 | 17.38 A |
| ATOM | 769 | CB | LEU | A | 167 | 90.463 | 19.516 | 3.888 | 1.00 | 15.71 A |
| ATOM | 770 | CG | LEU | A | 167 | 91.238 | 19.817 | 2.601 | 1.00 | 15.42 A |
| ATOM | 771 | CD1 | LEU | A | 167 | 92.242 | 18.704 | 2.343 | 1.00 | 14.98 A |
| ATOM | 772 | CD2 | LEU | A | 167 | 90.265 | 19.947 | 1.416 | 1.00 | 12.32 A |
| ATOM | 773 | C | LEU | A | 167 | 91.817 | 20.940 | 5.438 | 1.00 | 19.75 A |
| ATOM | 774 | O | LEU | A | 167 | 93.030 | 21.103 | 5.266 | 1.00 | 19.61 A |
| ATOM | 775 | N | LEU | A | 168 | 91.001 | 21.928 | 5.812 | 1.00 | 20.53 A |
| ATOM | 776 | CA | LEU | A | 168 | 91.516 | 23.277 | 6.033 | 1.00 | 22.20 A |
| ATOM | 777 | CB | LEU | A | 168 | 90.436 | 24.192 | 6.637 | 1.00 | 20.41 A |
| ATOM | 778 | CG | LEU | A | 168 | 90.923 | 25.611 | 7.024 | 1.00 | 21.71 A |
| ATOM | 779 | CD1 | LEU | A | 168 | 91.275 | 26.413 | 5.768 | 1.00 | 20.09 A |
| ATOM | 780 | CD2 | LEU | A | 168 | 89.837 | 26.341 | 7.797 | 1.00 | 20.84 A |
| ATOM | 781 | C | LEU | A | 168 | 92.731 | 23.245 | 6.968 | 1.00 | 23.07 A |
| ATOM | 782 | O | LEU | A | 168 | 93.636 | 24.054 | 6.838 | 1.00 | 22.18 A |
| ATOM | 783 | N | LYS | A | 169 | 92.742 | 22.305 | 7.905 | 1.00 | 24.67 A |
| ATOM | 784 | CA | LYS | A | 169 | 93.844 | 22.192 | 8.850 | 1.00 | 28.56 A |
| ATOM | 785 | CB | LYS | A | 169 | 93.561 | 21.076 | 9.858 | 1.00 | 31.12 A |
| ATOM | 786 | CG | LYS | A | 169 | 94.615 | 20.933 | 10.938 | 1.00 | 35.60 A |
| ATOM | 787 | CD | LYS | A | 169 | 94.436 | 19.652 | 11.765 | 1.00 | 39.37 A |
| ATOM | 788 | CE | LYS | A | 169 | 94.832 | 18.410 | 10.961 | 1.00 | 42.26 A |
| ATOM | 789 | NZ | LYS | A | 169 | 94.664 | 17.131 | 11.725 | 1.00 | 42.83 A |
| ATOM | 790 | C | LYS | A | 169 | 95.151 | 21.902 | 8.119 | 1.00 | 29.24 A |
| ATOM | 791 | O | LYS | A | 169 | 96.190 | 22.505 | 8.398 | 1.00 | 30.32 A |
| ATOM | 792 | N | TYR | A | 170 | 95.101 | 20.970 | 7.179 | 1.00 | 29.12 A |
| ATOM | 793 | CA | TYR | A | 170 | 96.290 | 20.619 | 6.423 | 1.00 | 28.18 A |
| ATOM | 794 | CB | TYR | A | 170 | 96.037 | 19.344 | 5.637 | 1.00 | 25.30 A |
| ATOM | 795 | CG | TYR | A | 170 | 95.926 | 18.182 | 6.569 | 1.00 | 27.01 A |
| ATOM | 796 | CD1 | TYR | A | 170 | 97.072 | 17.533 | 7.053 | 1.00 | 26.92 A |
| ATOM | 797 | CE1 | TYR | A | 170 | 96.974 | 16.532 | 8.008 | 1.00 | 25.37 A |
| ATOM | 798 | CD2 | TYR | A | 170 | 94.688 | 17.792 | 7.062 | 1.00 | 25.14 A |
| ATOM | 799 | CE2 | TYR | A | 170 | 94.580 | 16.807 | 8.009 | 1.00 | 26.49 A |
| ATOM | 800 | CZ | TYR | A | 170 | 95.720 | 16.179 | 8.484 | 1.00 | 26.98 A |
| ATOM | 801 | OH | TYR | A | 170 | 95.580 | 15.223 | 9.456 | 1.00 | 27.66 A |
| ATOM | 802 | C | TYR | A | 170 | 96.690 | 21.742 | 5.507 | 1.00 | 28.69 A |
| ATOM | 803 | O | TYR | A | 170 | 97.875 | 21.971 | 5.285 | 1.00 | 30.98 A |
| ATOM | 804 | N | ILE | A | 171 | 95.705 | 22.452 | 4.976 | 1.00 | 28.95 A |
| ATOM | 805 | CA | ILE | A | 171 | 96.006 | 23.550 | 4.088 | 1.00 | 29.79 A |
| ATOM | 806 | CB | ILE | A | 171 | 94.721 | 24.233 | 3.579 | 1.00 | 29.29 A |
| ATOM | 807 | CG2 | ILE | A | 171 | 95.082 | 25.439 | 2.714 | 1.00 | 28.21 A |
| ATOM | 808 | CG1 | ILE | A | 171 | 93.906 | 23.227 | 2.747 | 1.00 | 29.66 A |
| ATOM | 809 | CD1 | ILE | A | 171 | 92.567 | 23.754 | 2.224 | 1.00 | 29.13 A |
| ATOM | 810 | C | ILE | A | 171 | 96.897 | 24.536 | 4.833 | 1.00 | 31.13 A |
| ATOM | 811 | O | ILE | A | 171 | 97.925 | 24.956 | 4.300 | 1.00 | 30.93 A |
| ATOM | 812 | N | ARG | A | 172 | 96.525 | 24.862 | 6.075 | 1.00 | 32.00 A |

-continued

| | | | | | | | | | | |
|---|---|---|---|---|---|---|---|---|---|---|
| ATOM | 813 | CA | ARG | A | 172 | 97.294 | 25.789 | 6.903 | 1.00 | 32.60 | A |
| ATOM | 814 | CB | ARG | A | 172 | 96.527 | 26.175 | 8.163 | 1.00 | 32.77 | A |
| ATOM | 815 | CG | ARG | A | 172 | 95.257 | 26.982 | 7.972 | 1.00 | 38.24 | A |
| ATOM | 816 | CD | ARG | A | 172 | 94.853 | 27.602 | 9.335 | 1.00 | 43.47 | A |
| ATOM | 817 | NE | ARG | A | 172 | 93.501 | 28.181 | 9.412 | 1.00 | 46.65 | A |
| ATOM | 818 | CZ | ARG | A | 172 | 92.903 | 28.888 | 8.448 | 1.00 | 47.62 | A |
| ATOM | 819 | NH1 | ARG | A | 172 | 93.517 | 29.115 | 7.287 | 1.00 | 47.16 | A |
| ATOM | 820 | NH2 | ARG | A | 172 | 91.691 | 29.398 | 8.659 | 1.00 | 45.61 | A |
| ATOM | 821 | C | ARG | A | 172 | 98.646 | 25.219 | 7.338 | 1.00 | 32.95 | A |
| ATOM | 822 | O | ARG | A | 172 | 99.644 | 25.920 | 7.311 | 1.00 | 34.27 | A |
| ATOM | 823 | N | ALA | A | 173 | 98.674 | 23.960 | 7.761 | 1.00 | 32.74 | A |
| ATOM | 824 | CA | ALA | A | 173 | 99.912 | 23.341 | 8.209 | 1.00 | 32.81 | A |
| ATOM | 825 | CB | ALA | A | 173 | 99.668 | 21.896 | 8.619 | 1.00 | 32.72 | A |
| ATOM | 826 | C | ALA | A | 173 | 101.005 | 23.400 | 7.152 | 1.00 | 33.67 | A |
| ATOM | 827 | O | ALA | A | 173 | 102.125 | 23.817 | 7.438 | 1.00 | 33.78 | A |
| ATOM | 828 | N | ILE | A | 174 | 100.698 | 22.995 | 5.926 | 1.00 | 33.50 | A |
| ATOM | 829 | CA | ILE | A | 174 | 101.728 | 23.030 | 4.896 | 1.00 | 33.22 | A |
| ATOM | 830 | CB | ILE | A | 174 | 101.731 | 21.736 | 4.043 | 1.00 | 33.98 | A |
| ATOM | 831 | CG2 | ILE | A | 174 | 101.725 | 20.502 | 4.950 | 1.00 | 32.94 | A |
| ATOM | 832 | CG1 | ILE | A | 174 | 100.517 | 21.709 | 3.125 | 1.00 | 33.93 | A |
| ATOM | 833 | CD1 | ILE | A | 174 | 100.602 | 20.631 | 2.080 | 1.00 | 36.79 | A |
| ATOM | 834 | C | ILE | A | 174 | 101.638 | 24.231 | 3.957 | 1.00 | 32.69 | A |
| ATOM | 835 | O | ILE | A | 174 | 102.326 | 24.269 | 2.938 | 1.00 | 33.88 | A |
| ATOM | 836 | N | GLY | A | 175 | 100.792 | 25.204 | 4.287 | 1.00 | 31.76 | A |
| ATOM | 837 | CA | GLY | A | 175 | 100.671 | 26.386 | 3.446 | 1.00 | 32.03 | A |
| ATOM | 838 | C | GLY | A | 175 | 99.838 | 26.223 | 2.184 | 1.00 | 32.77 | A |
| ATOM | 839 | O | GLY | A | 175 | 98.870 | 26.958 | 1.976 | 1.00 | 35.12 | A |
| ATOM | 840 | N | SER | A | 176 | 100.225 | 25.291 | 1.322 | 1.00 | 31.63 | A |
| ATOM | 841 | CA | SER | A | 176 | 99.489 | 25.018 | 0.091 | 1.00 | 31.11 | A |
| ATOM | 842 | CB | SER | A | 176 | 99.810 | 26.040 | -0.996 | 1.00 | 31.54 | A |
| ATOM | 843 | OG | SER | A | 176 | 101.141 | 25.874 | -1.464 | 1.00 | 33.96 | A |
| ATOM | 844 | C | SER | A | 176 | 99.946 | 23.640 | -0.354 | 1.00 | 30.72 | A |
| ATOM | 845 | O | SER | A | 176 | 100.977 | 23.154 | 0.111 | 1.00 | 31.29 | A |
| ATOM | 846 | N | PHE | A | 177 | 99.180 | 23.018 | -1.246 | 1.00 | 28.27 | A |
| ATOM | 847 | CA | PHE | A | 177 | 99.475 | 21.683 | -1.738 | 1.00 | 26.97 | A |
| ATOM | 848 | CB | PHE | A | 177 | 98.169 | 20.948 | -2.060 | 1.00 | 27.18 | A |
| ATOM | 849 | CG | PHE | A | 177 | 97.376 | 20.530 | -0.854 | 1.00 | 27.90 | A |
| ATOM | 850 | CD1 | PHE | A | 177 | 97.551 | 21.155 | 0.379 | 1.00 | 26.91 | A |
| ATOM | 851 | CD2 | PHE | A | 177 | 96.432 | 19.503 | -0.957 | 1.00 | 27.62 | A |
| ATOM | 852 | CE1 | PHE | A | 177 | 96.812 | 20.762 | 1.477 | 1.00 | 26.03 | A |
| ATOM | 853 | CE2 | PHE | A | 177 | 95.684 | 19.106 | 0.144 | 1.00 | 23.95 | A |
| ATOM | 854 | CZ | PHE | A | 177 | 95.873 | 19.730 | 1.357 | 1.00 | 25.81 | A |
| ATOM | 855 | C | PHE | A | 177 | 100.299 | 21.726 | -3.008 | 1.00 | 26.99 | A |
| ATOM | 856 | O | PHE | A | 177 | 100.115 | 22.618 | -3.832 | 1.00 | 27.45 | A |
| ATOM | 857 | N | ASP | A | 178 | 101.200 | 20.762 | -3.179 | 1.00 | 26.09 | A |
| ATOM | 858 | CA | ASP | A | 178 | 101.967 | 20.704 | -4.411 | 1.00 | 26.09 | A |
| ATOM | 859 | CB | ASP | A | 178 | 103.135 | 19.730 | -4.303 | 1.00 | 27.73 | A |
| ATOM | 860 | CG | ASP | A | 178 | 102.689 | 18.318 | -4.023 | 1.00 | 33.79 | A |
| ATOM | 861 | OD1 | ASP | A | 178 | 101.601 | 17.919 | -4.510 | 1.00 | 37.57 | A |
| ATOM | 862 | OD2 | ASP | A | 178 | 103.431 | 17.590 | -3.324 | 1.00 | 35.89 | A |
| ATOM | 863 | C | ASP | A | 178 | 100.955 | 20.202 | -5.443 | 1.00 | 25.72 | A |
| ATOM | 864 | O | ASP | A | 178 | 99.763 | 20.063 | -5.128 | 1.00 | 24.80 | A |
| ATOM | 865 | N | GLU | A | 179 | 101.419 | 19.897 | -6.650 | 1.00 | 24.80 | A |
| ATOM | 866 | CA | GLU | A | 179 | 100.514 | 19.444 | -7.697 | 1.00 | 25.67 | A |
| ATOM | 867 | CB | GLU | A | 179 | 101.187 | 19.554 | -9.052 | 1.00 | 27.44 | A |
| ATOM | 868 | CG | GLU | A | 179 | 100.197 | 19.921 | -10.129 | 1.00 | 31.17 | A |
| ATOM | 869 | CD | GLU | A | 179 | 100.823 | 19.999 | -11.492 | 1.00 | 35.24 | A |
| ATOM | 870 | OE1 | GLU | A | 179 | 102.016 | 20.372 | -11.572 | 1.00 | 35.82 | A |
| ATOM | 871 | OE2 | GLU | A | 179 | 100.116 | 19.707 | -12.488 | 1.00 | 38.12 | A |
| ATOM | 872 | C | GLU | A | 179 | 99.917 | 18.041 | -7.560 | 1.00 | 24.90 | A |
| ATOM | 873 | O | GLU | A | 179 | 98.755 | 17.822 | -7.894 | 1.00 | 23.01 | A |
| ATOM | 874 | N | THR | A | 180 | 100.709 | 17.095 | -7.082 | 1.00 | 24.57 | A |
| ATOM | 875 | CA | THR | A | 180 | 100.240 | 15.723 | -6.923 | 1.00 | 25.53 | A |
| ATOM | 876 | CB | THR | A | 180 | 101.395 | 14.803 | -6.478 | 1.00 | 24.65 | A |
| ATOM | 877 | OG1 | THR | A | 180 | 102.525 | 15.069 | -7.304 | 1.00 | 25.84 | A |
| ATOM | 878 | CG2 | THR | A | 180 | 101.021 | 13.334 | -6.624 | 1.00 | 23.39 | A |
| ATOM | 879 | C | THR | A | 180 | 99.110 | 15.623 | -5.902 | 1.00 | 25.85 | A |
| ATOM | 880 | O | THR | A | 180 | 98.149 | 14.892 | -6.111 | 1.00 | 25.59 | A |
| ATOM | 881 | N | CYS | A | 181 | 99.237 | 16.359 | -4.799 | 1.00 | 25.83 | A |
| ATOM | 882 | CA | CYS | A | 181 | 98.217 | 16.355 | -3.752 | 1.00 | 26.26 | A |
| ATOM | 883 | CB | CYS | A | 181 | 98.778 | 16.939 | -2.451 | 1.00 | 27.81 | A |
| ATOM | 884 | SG | CYS | A | 181 | 100.202 | 16.031 | -1.775 | 1.00 | 32.72 | A |
| ATOM | 885 | C | CYS | A | 181 | 96.963 | 17.127 | -4.169 | 1.00 | 25.20 | A |
| ATOM | 886 | O | CYS | A | 181 | 95.853 | 16.696 | -3.878 | 1.00 | 26.19 | A |
| ATOM | 887 | N | THR | A | 182 | 97.139 | 18.262 | -4.841 | 1.00 | 22.74 | A |
| ATOM | 888 | CA | THR | A | 182 | 96.002 | 19.046 | -5.305 | 1.00 | 21.82 | A |
| ATOM | 889 | CB | THR | A | 182 | 96.453 | 20.308 | -6.103 | 1.00 | 21.81 | A |
| ATOM | 890 | OG1 | THR | A | 182 | 97.258 | 21.161 | -5.276 | 1.00 | 24.55 | A |
| ATOM | 891 | CG2 | THR | A | 182 | 95.252 | 21.080 | -6.593 | 1.00 | 18.62 | A |

-continued

| | | | | | | | | | | |
|---|---|---|---|---|---|---|---|---|---|---|
| ATOM | 892 | C | THR | A | 182 | 95.197 | 18.141 | −6.249 | 1.00 | 23.45 A |
| ATOM | 893 | O | THR | A | 182 | 93.975 | 17.997 | −6.116 | 1.00 | 22.94 A |
| ATOM | 894 | N | ARG | A | 183 | 95.897 | 17.528 | −7.202 | 1.00 | 22.71 A |
| ATOM | 895 | CA | ARG | A | 183 | 95.260 | 16.648 | −8.158 | 1.00 | 23.26 A |
| ATOM | 896 | CB | ARG | A | 183 | 96.285 | 16.118 | −9.171 | 1.00 | 22.46 A |
| ATOM | 897 | CG | ARG | A | 183 | 95.692 | 15.140 | −10.184 | 1.00 | 24.96 A |
| ATOM | 898 | CD | ARG | A | 183 | 96.762 | 14.512 | −11.078 | 1.00 | 27.09 A |
| ATOM | 899 | NE | ARG | A | 183 | 97.372 | 15.577 | −11.849 | 1.00 | 33.02 A |
| ATOM | 900 | CZ | ARG | A | 183 | 98.637 | 15.948 | −11.732 | 1.00 | 33.62 A |
| ATOM | 901 | NH1 | ARG | A | 183 | 99.440 | 15.312 | −10.885 | 1.00 | 32.57 A |
| ATOM | 902 | NH2 | ARG | A | 183 | 99.069 | 17.006 | −12.404 | 1.00 | 33.25 A |
| ATOM | 903 | C | ARG | A | 183 | 94.559 | 15.475 | −7.459 | 1.00 | 22.42 A |
| ATOM | 904 | O | ARG | A | 183 | 93.393 | 15.193 | −7.721 | 1.00 | 21.37 A |
| ATOM | 905 | N | PHE | A | 184 | 95.255 | 14.800 | −6.562 | 1.00 | 21.19 A |
| ATOM | 906 | CA | PHE | A | 184 | 94.630 | 13.673 | −5.888 | 1.00 | 22.20 A |
| ATOM | 907 | CB | PHE | A | 184 | 95.615 | 12.964 | −4.966 | 1.00 | 23.58 A |
| ATOM | 908 | CG | PHE | A | 184 | 95.029 | 11.766 | −4.283 | 1.00 | 25.43 A |
| ATOM | 909 | CD1 | PHE | A | 184 | 94.916 | 10.556 | −4.954 | 1.00 | 25.01 A |
| ATOM | 910 | CD2 | PHE | A | 184 | 94.508 | 11.867 | −2.998 | 1.00 | 24.35 A |
| ATOM | 911 | CE1 | PHE | A | 184 | 94.285 | 9.460 | −4.356 | 1.00 | 23.50 A |
| ATOM | 912 | CE2 | PHE | A | 184 | 93.881 | 10.782 | −2.409 | 1.00 | 24.71 A |
| ATOM | 913 | CZ | PHE | A | 184 | 93.771 | 9.577 | −3.094 | 1.00 | 22.95 A |
| ATOM | 914 | C | PHE | A | 184 | 93.405 | 14.074 | −5.072 | 1.00 | 21.96 A |
| ATOM | 915 | O | PHE | A | 184 | 92.348 | 13.450 | −5.170 | 1.00 | 21.31 A |
| ATOM | 916 | N | TYR | A | 185 | 93.544 | 15.116 | −4.267 | 1.00 | 21.18 A |
| ATOM | 917 | CA | TYR | A | 185 | 92.433 | 15.543 | −3.445 | 1.00 | 20.50 A |
| ATOM | 918 | CB | TYR | A | 185 | 92.956 | 16.425 | −2.313 | 1.00 | 21.33 A |
| ATOM | 919 | CG | TYR | A | 185 | 93.494 | 15.550 | −1.190 | 1.00 | 22.24 A |
| ATOM | 920 | CD1 | TYR | A | 185 | 92.641 | 14.670 | −0.507 | 1.00 | 21.55 A |
| ATOM | 921 | CE1 | TYR | A | 185 | 93.127 | 13.755 | 0.414 | 1.00 | 20.71 A |
| ATOM | 922 | CD2 | TYR | A | 185 | 94.853 | 15.497 | −0.904 | 1.00 | 21.37 A |
| ATOM | 923 | CE2 | TYR | A | 185 | 95.353 | 14.579 | 0.019 | 1.00 | 21.80 A |
| ATOM | 924 | CZ | TYR | A | 185 | 94.486 | 13.705 | 0.670 | 1.00 | 21.18 A |
| ATOM | 925 | OH | TYR | A | 185 | 94.986 | 12.746 | 1.519 | 1.00 | 19.84 A |
| ATOM | 926 | C | TYR | A | 185 | 91.273 | 16.182 | −4.201 | 1.00 | 19.27 A |
| ATOM | 927 | O | TYR | A | 185 | 90.112 | 16.056 | −3.801 | 1.00 | 17.72 A |
| ATOM | 928 | N | THR | A | 186 | 91.576 | 16.834 | −5.314 | 1.00 | 17.25 A |
| ATOM | 929 | CA | THR | A | 186 | 90.527 | 17.433 | −6.110 | 1.00 | 15.61 A |
| ATOM | 930 | CB | THR | A | 186 | 91.097 | 18.366 | −7.188 | 1.00 | 15.69 A |
| ATOM | 931 | OG1 | THR | A | 186 | 91.710 | 19.508 | −6.564 | 1.00 | 16.11 A |
| ATOM | 932 | CG2 | THR | A | 186 | 89.996 | 18.816 | −8.135 | 1.00 | 12.68 A |
| ATOM | 933 | C | THR | A | 186 | 89.756 | 16.302 | −6.785 | 1.00 | 15.75 A |
| ATOM | 934 | O | THR | A | 186 | 88.523 | 16.350 | −6.899 | 1.00 | 16.51 A |
| ATOM | 935 | N | ALA | A | 187 | 90.478 | 15.277 | −7.218 | 1.00 | 14.94 A |
| ATOM | 936 | CA | ALA | A | 187 | 89.841 | 14.136 | −7.868 | 1.00 | 16.15 A |
| ATOM | 937 | CB | ALA | A | 187 | 90.905 | 13.130 | −8.382 | 1.00 | 13.30 A |
| ATOM | 938 | C | ALA | A | 187 | 88.847 | 13.450 | −6.911 | 1.00 | 16.71 A |
| ATOM | 939 | O | ALA | A | 187 | 87.743 | 13.075 | −7.328 | 1.00 | 16.50 A |
| ATOM | 940 | N | GLU | A | 188 | 89.213 | 13.308 | −5.635 | 1.00 | 17.10 A |
| ATOM | 941 | CA | GLU | A | 188 | 88.302 | 12.673 | −4.679 | 1.00 | 17.85 A |
| ATOM | 942 | CB | GLU | A | 188 | 88.953 | 12.514 | −3.302 | 1.00 | 18.83 A |
| ATOM | 943 | CG | GLU | A | 188 | 90.219 | 11.665 | −3.296 | 1.00 | 19.46 A |
| ATOM | 944 | CD | GLU | A | 188 | 90.370 | 10.795 | −2.050 | 1.00 | 20.84 A |
| ATOM | 945 | OE1 | GLU | A | 188 | 90.131 | 11.276 | −0.920 | 1.00 | 21.14 A |
| ATOM | 946 | OE2 | GLU | A | 188 | 90.749 | 9.616 | −2.207 | 1.00 | 23.35 A |
| ATOM | 947 | C | GLU | A | 188 | 87.043 | 13.516 | −4.551 | 1.00 | 17.79 A |
| ATOM | 948 | O | GLU | A | 188 | 85.921 | 13.005 | −4.579 | 1.00 | 18.83 A |
| ATOM | 949 | N | ILE | A | 189 | 87.220 | 14.824 | −4.449 | 1.00 | 17.09 A |
| ATOM | 950 | CA | ILE | A | 189 | 86.060 | 15.688 | −4.312 | 1.00 | 15.61 A |
| ATOM | 951 | CB | ILE | A | 189 | 86.495 | 17.141 | −4.054 | 1.00 | 15.83 A |
| ATOM | 952 | CG2 | ILE | A | 189 | 85.278 | 18.019 | −3.853 | 1.00 | 14.16 A |
| ATOM | 953 | CG1 | ILE | A | 189 | 87.380 | 17.199 | −2.794 | 1.00 | 17.34 A |
| ATOM | 954 | CD1 | ILE | A | 189 | 87.949 | 18.583 | −2.479 | 1.00 | 15.37 A |
| ATOM | 955 | C | ILE | A | 189 | 85.176 | 15.611 | −5.558 | 1.00 | 16.00 A |
| ATOM | 956 | O | ILE | A | 189 | 83.953 | 15.530 | −5.460 | 1.00 | 15.52 A |
| ATOM | 957 | N | VAL | A | 190 | 85.794 | 15.619 | −6.733 | 1.00 | 15.46 A |
| ATOM | 958 | CA | VAL | A | 190 | 85.031 | 15.570 | −7.964 | 1.00 | 15.38 A |
| ATOM | 959 | CB | VAL | A | 190 | 85.975 | 15.641 | −9.181 | 1.00 | 15.37 A |
| ATOM | 960 | CG1 | VAL | A | 190 | 85.273 | 15.168 | −10.447 | 1.00 | 14.43 A |
| ATOM | 961 | CG2 | VAL | A | 190 | 86.454 | 17.056 | −9.350 | 1.00 | 14.03 A |
| ATOM | 962 | C | VAL | A | 190 | 84.228 | 14.279 | −7.987 | 1.00 | 17.35 A |
| ATOM | 963 | O | VAL | A | 190 | 83.016 | 14.281 | −8.258 | 1.00 | 15.96 A |
| ATOM | 964 | N | SER | A | 191 | 84.916 | 13.182 | −7.683 | 1.00 | 17.90 A |
| ATOM | 965 | CA | SER | A | 191 | 84.305 | 11.858 | −7.660 | 1.00 | 17.77 A |
| ATOM | 966 | CB | SER | A | 191 | 85.377 | 10.811 | −7.344 | 1.00 | 18.25 A |
| ATOM | 967 | OG | SER | A | 191 | 84.801 | 9.523 | −7.243 | 1.00 | 21.13 A |
| ATOM | 968 | C | SER | A | 191 | 83.147 | 11.778 | −6.640 | 1.00 | 17.28 A |
| ATOM | 969 | O | SER | A | 191 | 82.153 | 11.095 | −6.865 | 1.00 | 15.44 A |
| ATOM | 970 | N | ALA | A | 192 | 83.291 | 12.490 | −5.525 | 1.00 | 17.27 A |

-continued

| | | | | | | | | | |
|---|---|---|---|---|---|---|---|---|---|
| ATOM | 971 | CA | ALA | A | 192 | 82.267 | 12.529 | −4.485 | 1.00 | 15.98 | A |
| ATOM | 972 | CB | ALA | A | 192 | 82.834 | 13.164 | −3.191 | 1.00 | 14.89 | A |
| ATOM | 973 | C | ALA | A | 192 | 81.078 | 13.336 | −4.988 | 1.00 | 16.44 | A |
| ATOM | 974 | O | ALA | A | 192 | 79.934 | 12.922 | −4.816 | 1.00 | 17.59 | A |
| ATOM | 975 | N | LEU | A | 193 | 81.340 | 14.487 | −5.609 | 1.00 | 16.63 | A |
| ATOM | 976 | CA | LEU | A | 193 | 80.253 | 15.303 | −6.140 | 1.00 | 16.11 | A |
| ATOM | 977 | CB | LEU | A | 193 | 80.769 | 16.632 | −6.688 | 1.00 | 16.40 | A |
| ATOM | 978 | CG | LEU | A | 193 | 81.421 | 17.545 | −5.645 | 1.00 | 18.83 | A |
| ATOM | 979 | CD1 | LEU | A | 193 | 81.779 | 18.885 | −6.276 | 1.00 | 18.24 | A |
| ATOM | 980 | CD2 | LEU | A | 193 | 80.455 | 17.751 | −4.479 | 1.00 | 18.63 | A |
| ATOM | 981 | C | LEU | A | 193 | 79.509 | 14.551 | −7.236 | 1.00 | 16.95 | A |
| ATOM | 982 | O | LEU | A | 193 | 78.286 | 14.623 | −7.325 | 1.00 | 18.76 | A |
| ATOM | 983 | N | GLU | A | 194 | 80.229 | 13.825 | −8.079 | 1.00 | 17.87 | A |
| ATOM | 984 | CA | GLU | A | 194 | 79.539 | 13.082 | −9.124 | 1.00 | 19.66 | A |
| ATOM | 985 | CB | GLU | A | 194 | 80.525 | 12.295 | −9.990 | 1.00 | 21.82 | A |
| ATOM | 986 | CG | GLU | A | 194 | 79.844 | 11.333 | −10.947 | 1.00 | 21.12 | A |
| ATOM | 987 | CD | GLU | A | 194 | 80.831 | 10.513 | −11.758 | 1.00 | 25.70 | A |
| ATOM | 988 | OE1 | GLU | A | 194 | 81.900 | 10.122 | −11.216 | 1.00 | 27.41 | A |
| ATOM | 989 | OE2 | GLU | A | 194 | 80.527 | 10.244 | −12.939 | 1.00 | 26.12 | A |
| ATOM | 990 | C | GLU | A | 194 | 78.546 | 12.123 | −8.479 | 1.00 | 19.58 | A |
| ATOM | 991 | O | GLU | A | 194 | 77.420 | 11.987 | −8.937 | 1.00 | 17.78 | A |
| ATOM | 992 | N | TYR | A | 195 | 78.962 | 11.462 | −7.406 | 1.00 | 19.09 | A |
| ATOM | 993 | CA | TYR | A | 195 | 78.063 | 10.545 | −6.736 | 1.00 | 19.86 | A |
| ATOM | 994 | CB | TYR | A | 195 | 78.807 | 9.740 | −5.673 | 1.00 | 20.01 | A |
| ATOM | 995 | CG | TYR | A | 195 | 77.871 | 8.975 | −4.756 | 1.00 | 20.45 | A |
| ATOM | 996 | CD1 | TYR | A | 195 | 77.329 | 7.748 | −5.142 | 1.00 | 19.40 | A |
| ATOM | 997 | CE1 | TYR | A | 195 | 76.471 | 7.044 | −4.296 | 1.00 | 18.43 | A |
| ATOM | 998 | CD2 | TYR | A | 195 | 77.527 | 9.48 | −3.500 | 1.00 | 20.11 | A |
| ATOM | 999 | CE2 | TYR | A | 195 | 76.678 | 8.79 | −2.652 | 1.00 | 19.96 | A |
| ATOM | 1000 | CZ | TYR | A | 195 | 76.154 | 7.567 | −3.057 | 1.00 | 21.07 | A |
| ATOM | 1001 | OH | TYR | A | 195 | 75.336 | 6.859 | −2.206 | 1.00 | 21.31 | A |
| ATOM | 1002 | C | TYR | A | 195 | 76.914 | 11.295 | −6.060 | 1.00 | 20.00 | A |
| ATOM | 1003 | O | TYR | A | 195 | 75.775 | 10.823 | −6.033 | 1.00 | 21.42 | A |
| ATOM | 1004 | N | LEU | A | 196 | 77.222 | 12.455 | −5.500 | 1.00 | 17.38 | A |
| ATOM | 1005 | CA | LEU | A | 196 | 76.209 | 13.226 | −4.795 | 1.00 | 18.74 | A |
| ATOM | 1006 | CB | LEU | A | 196 | 76.846 | 14.412 | −4.049 | 1.00 | 17.38 | A |
| ATOM | 1007 | CG | LEU | A | 196 | 75.850 | 15.100 | −3.110 | 1.00 | 19.04 | A |
| ATOM | 1008 | CD1 | LEU | A | 196 | 75.423 | 14.093 | −2.061 | 1.00 | 17.66 | A |
| ATOM | 1009 | CD2 | LEU | A | 196 | 76.462 | 16.338 | −2.453 | 1.00 | 19.54 | A |
| ATOM | 1010 | C | LEU | A | 196 | 75.148 | 13.747 | −5.751 | 1.00 | 18.47 | A |
| ATOM | 1011 | O | LEU | A | 196 | 73.944 | 13.608 | −5.523 | 1.00 | 15.05 | A |
| ATOM | 1012 | N | HIS | A | 197 | 75.622 | 14.361 | −6.824 | 1.00 | 18.35 | A |
| ATOM | 1013 | CA | HIS | A | 197 | 74.740 | 14.915 | −7.812 | 1.00 | 20.04 | A |
| ATOM | 1014 | CB | HIS | A | 197 | 75.562 | 15.809 | −8.718 | 1.00 | 20.29 | A |
| ATOM | 1015 | CG | HIS | A | 197 | 76.048 | 17.044 | −8.025 | 1.00 | 21.90 | A |
| ATOM | 1016 | CD2 | HIS | A | 197 | 75.766 | 17.539 | −6.794 | 1.00 | 19.49 | A |
| ATOM | 1017 | ND1 | HIS | A | 197 | 76.892 | 17.956 | −8.621 | 1.00 | 20.69 | A |
| ATOM | 1018 | CE1 | HIS | A | 197 | 77.104 | 18.960 | −7.789 | 1.00 | 20.86 | A |
| ATOM | 1019 | NE2 | HIS | A | 197 | 76.433 | 18.732 | −6.676 | 1.00 | 19.12 | A |
| ATOM | 1020 | C | HIS | A | 197 | 73.950 | 13.858 | −8.587 | 1.00 | 21.27 | A |
| ATOM | 1021 | O | HIS | A | 197 | 72.865 | 14.133 | −9.099 | 1.00 | 21.23 | A |
| ATOM | 1022 | N | GLY | A | 198 | 74.487 | 12.644 | −8.644 | 1.00 | 21.36 | A |
| ATOM | 1023 | CA | GLY | A | 198 | 73.810 | 11.569 | −9.339 | 1.00 | 20.60 | A |
| ATOM | 1024 | C | GLY | A | 198 | 72.528 | 11.203 | −8.632 | 1.00 | 22.72 | A |
| ATOM | 1025 | O | GLY | A | 198 | 71.593 | 10.742 | −9.269 | 1.00 | 22.75 | A |
| ATOM | 1026 | N | LYS | A | 199 | 72.478 | 11.411 | −7.313 | 1.00 | 24.27 | A |
| ATOM | 1027 | CA | LYS | A | 199 | 71.280 | 11.105 | −6.523 | 1.00 | 22.95 | A |
| ATOM | 1028 | CB | LYS | A | 199 | 71.659 | 10.629 | −5.123 | 1.00 | 24.67 | A |
| ATOM | 1029 | CG | LYS | A | 199 | 72.570 | 9.429 | −5.109 | 1.00 | 29.22 | A |
| ATOM | 1030 | CD | LYS | A | 199 | 72.986 | 9.064 | −3.701 | 1.00 | 33.11 | A |
| ATOM | 1031 | CE | LYS | A | 199 | 72.531 | 7.660 | −3.366 | 1.00 | 37.28 | A |
| ATOM | 1032 | NZ | LYS | A | 199 | 72.917 | 6.686 | −4.455 | 1.00 | 38.82 | A |
| ATOM | 1033 | C | LYS | A | 199 | 70.432 | 12.354 | −6.398 | 1.00 | 22.39 | A |
| ATOM | 1034 | O | LYS | A | 199 | 69.558 | 12.431 | −5.542 | 1.00 | 22.53 | A |
| ATOM | 1035 | N | GLY | A | 200 | 70.710 | 13.343 | −7.241 | 1.00 | 21.56 | A |
| ATOM | 1036 | CA | GLY | A | 200 | 69.953 | 14.580 | −7.203 | 1.00 | 22.28 | A |
| ATOM | 1037 | C | GLY | A | 200 | 70.006 | 15.326 | −5.882 | 1.00 | 23.53 | A |
| ATOM | 1038 | O | GLY | A | 200 | 69.017 | 15.930 | −5.461 | 1.00 | 24.83 | A |
| ATOM | 1039 | N | ILE | A | 201 | 71.161 | 15.302 | −5.225 | 1.00 | 22.74 | A |
| ATOM | 1040 | CA | ILE | A | 201 | 71.314 | 15.985 | −3.951 | 1.00 | 22.95 | A |
| ATOM | 1041 | CB | ILE | A | 201 | 71.796 | 15.007 | −2.842 | 1.00 | 22.51 | A |
| ATOM | 1042 | CG2 | ILE | A | 201 | 71.995 | 15.757 | −1.536 | 1.00 | 21.73 | A |
| ATOM | 1043 | CG1 | ILE | A | 201 | 70.788 | 13.876 | −2.638 | 1.00 | 22.48 | A |
| ATOM | 1044 | CD1 | ILE | A | 201 | 71.274 | 12.791 | −1.687 | 1.00 | 17.26 | A |
| ATOM | 1045 | C | ILE | A | 201 | 72.361 | 17.086 | −4.076 | 1.00 | 24.41 | A |
| ATOM | 1046 | O | ILE | A | 201 | 73.387 | 16.904 | −4.737 | 1.00 | 26.41 | A |
| ATOM | 1047 | N | ILE | A | 202 | 72.118 | 18.236 | −3.470 | 1.00 | 23.00 | A |
| ATOM | 1048 | CA | ILE | A | 202 | 73.137 | 19.267 | −3.520 | 1.00 | 24.60 | A |
| ATOM | 1049 | CB | ILE | A | 202 | 72.729 | 20.440 | −4.420 | 1.00 | 26.37 | A |

-continued

| | | | | | | | | | | |
|---|---|---|---|---|---|---|---|---|---|---|
| ATOM | 1050 | CG2 | ILE | A | 202 | 72.503 | 19.934 | −5.829 | 1.00 | 28.52 A |
| ATOM | 1051 | CG1 | ILE | A | 202 | 71.450 | 21.086 | −3.922 | 1.00 | 29.04 A |
| ATOM | 1052 | CD1 | ILE | A | 202 | 70.958 | 22.165 | −4.845 | 1.00 | 32.55 A |
| ATOM | 1053 | C | ILE | A | 202 | 73.482 | 19.732 | −2.105 | 1.00 | 24.36 A |
| ATOM | 1054 | O | ILE | A | 202 | 72.605 | 19.919 | −1.257 | 1.00 | 25.89 A |
| ATOM | 1055 | N | HIS | A | 203 | 74.776 | 19.882 | −1.856 | 1.00 | 22.94 A |
| ATOM | 1056 | CA | HIS | A | 203 | 75.289 | 20.273 | −0.555 | 1.00 | 22.27 A |
| ATOM | 1057 | CB | HIS | A | 203 | 76.800 | 20.010 | −0.526 | 1.00 | 20.00 A |
| ATOM | 1058 | CG | HIS | A | 203 | 77.401 | 20.051 | 0.840 | 1.00 | 18.45 A |
| ATOM | 1059 | CD2 | HIS | A | 203 | 77.865 | 19.060 | 1.640 | 1.00 | 19.77 A |
| ATOM | 1060 | ND1 | HIS | A | 203 | 77.569 | 21.222 | 1.542 | 1.00 | 16.33 A |
| ATOM | 1061 | CE1 | HIS | A | 203 | 78.115 | 20.953 | 2.715 | 1.00 | 17.77 A |
| ATOM | 1062 | NE2 | HIS | A | 203 | 78.306 | 19.650 | 2.800 | 1.00 | 18.48 A |
| ATOM | 1063 | C | HIS | A | 203 | 74.978 | 21.731 | −0.206 | 1.00 | 23.37 A |
| ATOM | 1064 | O | HIS | A | 203 | 74.411 | 22.009 | 0.860 | 1.00 | 22.52 A |
| ATOM | 1065 | N | ARG | A | 204 | 75.361 | 22.648 | −1.101 | 1.00 | 23.22 A |
| ATOM | 1066 | CA | ARG | A | 204 | 75.126 | 24.087 | −0.934 | 1.00 | 23.42 A |
| ATOM | 1067 | CB | ARG | A | 204 | 73.674 | 24.375 | −0.544 | 1.00 | 22.74 A |
| ATOM | 1068 | CG | ARG | A | 204 | 72.663 | 23.966 | −1.561 | 1.00 | 24.57 A |
| ATOM | 1069 | CD | ARG | A | 204 | 71.341 | 24.681 | −1.325 | 1.00 | 26.51 A |
| ATOM | 1070 | NE | ARG | A | 204 | 70.699 | 24.299 | −0.074 | 1.00 | 28.25 A |
| ATOM | 1071 | CZ | ARG | A | 204 | 69.596 | 24.871 | 0.405 | 1.00 | 28.63 A |
| ATOM | 1072 | NH1 | ARG | A | 204 | 69.013 | 25.849 | −0.267 | 1.00 | 28.47 A |
| ATOM | 1073 | NH2 | ARG | A | 204 | 69.086 | 24.472 | 1.563 | 1.00 | 28.55 A |
| ATOM | 1074 | C | ARG | A | 204 | 76.017 | 24.819 | 0.061 | 1.00 | 24.12 A |
| ATOM | 1075 | O | ARG | A | 204 | 75.805 | 26.001 | 0.308 | 1.00 | 26.26 A |
| ATOM | 1076 | N | ASP | A | 205 | 76.990 | 24.135 | 0.654 | 1.00 | 23.05 A |
| ATOM | 1077 | CA | ASP | A | 205 | 77.887 | 24.789 | 1.595 | 1.00 | 20.96 A |
| ATOM | 1078 | CB | ASP | A | 205 | 77.219 | 24.883 | 2.964 | 1.00 | 22.31 A |
| ATOM | 1079 | CG | ASP | A | 205 | 77.964 | 25.801 | 3.914 | 1.00 | 26.08 A |
| ATOM | 1080 | OD1 | ASP | A | 205 | 78.812 | 26.582 | 3.439 | 1.00 | 25.93 A |
| ATOM | 1081 | OD2 | ASP | A | 205 | 77.707 | 25.751 | 5.141 | 1.00 | 29.89 A |
| ATOM | 1082 | C | ASP | A | 205 | 79.210 | 24.020 | 1.662 | 1.00 | 20.46 A |
| ATOM | 1083 | O | ASP | A | 205 | 79.812 | 23.833 | 2.716 | 1.00 | 21.36 A |
| ATOM | 1084 | N | LEU | A | 206 | 79.666 | 23.584 | 0.504 | 1.00 | 18.98 A |
| ATOM | 1085 | CA | LEU | A | 206 | 80.893 | 22.827 | 0.407 | 1.00 | 19.83 A |
| ATOM | 1086 | CB | LEU | A | 206 | 80.983 | 22.229 | −0.994 | 1.00 | 21.73 A |
| ATOM | 1087 | CG | LEU | A | 206 | 82.039 | 21.167 | −1.298 | 1.00 | 24.76 A |
| ATOM | 1088 | CD1 | LEU | A | 206 | 81.818 | 19.943 | −0.401 | 1.00 | 24.95 A |
| ATOM | 1089 | CD2 | LEU | A | 206 | 81.941 | 20.789 | −2.778 | 1.00 | 23.74 A |
| ATOM | 1090 | C | LEU | A | 206 | 82.093 | 23.725 | 0.691 | 1.00 | 20.17 A |
| ATOM | 1091 | O | LEU | A | 206 | 82.162 | 24.857 | 0.200 | 1.00 | 20.92 A |
| ATOM | 1092 | N | LYS | A | 207 | 83.044 | 23.226 | 1.475 | 1.00 | 19.79 A |
| ATOM | 1093 | CA | LYS | A | 207 | 84.233 | 24.004 | 1.821 | 1.00 | 19.45 A |
| ATOM | 1094 | CB | LYS | A | 207 | 83.825 | 25.209 | 2.667 | 1.00 | 17.84 A |
| ATOM | 1095 | CG | LYS | A | 207 | 83.123 | 24.820 | 3.933 | 1.00 | 19.19 A |
| ATOM | 1096 | CD | LYS | A | 207 | 82.331 | 25.969 | 4.500 | 1.00 | 20.50 A |
| ATOM | 1097 | CE | LYS | A | 207 | 81.663 | 25.556 | 5.797 | 1.00 | 22.10 A |
| ATOM | 1098 | NZ | LYS | A | 207 | 80.955 | 26.674 | 6.480 | 1.00 | 22.34 A |
| ATOM | 1099 | C | LYS | A | 207 | 85.241 | 23.130 | 2.565 | 1.00 | 19.59 A |
| ATOM | 1100 | O | LYS | A | 207 | 84.917 | 22.025 | 2.985 | 1.00 | 20.21 A |
| ATOM | 1101 | N | PRO | A | 208 | 86.480 | 23.618 | 2.737 | 1.00 | 19.79 A |
| ATOM | 1102 | CD | PRO | A | 208 | 87.032 | 24.869 | 2.188 | 1.00 | 18.04 A |
| ATOM | 1103 | CA | PRO | A | 208 | 87.526 | 22.853 | 3.428 | 1.00 | 19.22 A |
| ATOM | 1104 | CB | PRO | A | 208 | 88.756 | 23.763 | 3.297 | 1.00 | 19.27 A |
| ATOM | 1105 | CG | PRO | A | 208 | 88.496 | 24.521 | 2.027 | 1.00 | 16.27 A |
| ATOM | 1106 | C | PRO | A | 208 | 87.221 | 22.477 | 4.883 | 1.00 | 20.50 A |
| ATOM | 1107 | O | PRO | A | 208 | 87.791 | 21.511 | 5.411 | 1.00 | 21.44 A |
| ATOM | 1108 | N | GLU | A | 209 | 86.335 | 23.231 | 5.530 | 1.00 | 20.19 A |
| ATOM | 1109 | CA | GLU | A | 209 | 85.956 | 22.976 | 6.927 | 1.00 | 21.25 A |
| ATOM | 1110 | CB | GLU | A | 209 | 85.383 | 24.251 | 7.562 | 1.00 | 21.43 A |
| ATOM | 1111 | CG | GLU | A | 209 | 86.330 | 25.446 | 7.535 | 1.00 | 26.33 A |
| ATOM | 1112 | CD | GLU | A | 209 | 86.203 | 26.315 | 6.270 | 1.00 | 30.17 A |
| ATOM | 1113 | OE1 | GLU | A | 209 | 86.143 | 25.785 | 5.131 | 1.00 | 30.44 A |
| ATOM | 1114 | OE2 | GLU | A | 209 | 86.173 | 27.557 | 6.422 | 1.00 | 33.49 A |
| ATOM | 1115 | C | GLU | A | 209 | 84.920 | 21.839 | 7.040 | 1.00 | 22.45 A |
| ATOM | 1116 | O | GLU | A | 209 | 84.733 | 21.255 | 8.114 | 1.00 | 21.98 A |
| ATOM | 1117 | N | ASN | A | 210 | 84.269 | 21.545 | 5.915 | 1.00 | 22.73 A |
| ATOM | 1118 | CA | ASN | A | 210 | 83.234 | 20.514 | 5.788 | 1.00 | 23.66 A |
| ATOM | 1119 | CB | ASN | A | 210 | 82.102 | 21.013 | 4.882 | 1.00 | 26.67 A |
| ATOM | 1120 | CG | ASN | A | 210 | 81.104 | 21.881 | 5.613 | 1.00 | 33.39 A |
| ATOM | 1121 | OD1 | ASN | A | 210 | 80.223 | 22.481 | 4.988 | 1.00 | 36.52 A |
| ATOM | 1122 | ND2 | ASN | A | 210 | 81.221 | 21.950 | 6.946 | 1.00 | 34.23 A |
| ATOM | 1123 | C | ASN | A | 210 | 83.775 | 19.239 | 5.162 | 1.00 | 21.41 A |
| ATOM | 1124 | O | ASN | A | 210 | 83.067 | 18.244 | 5.081 | 1.00 | 21.16 A |
| ATOM | 1125 | N | ILE | A | 211 | 85.006 | 19.293 | 4.674 | 1.00 | 19.42 A |
| ATOM | 1126 | CA | ILE | A | 211 | 85.619 | 18.141 | 4.029 | 1.00 | 17.43 A |
| ATOM | 1127 | CB | ILE | A | 211 | 86.319 | 18.556 | 2.708 | 1.00 | 14.89 A |
| ATOM | 1128 | CG2 | ILE | A | 211 | 87.046 | 17.349 | 2.096 | 1.00 | 12.68 A |

-continued

| | | | | | | | | | | |
|---|---|---|---|---|---|---|---|---|---|---|
| ATOM | 1129 | CG1 | ILE | A | 211 | 85.277 | 19.157 | 1.736 | 1.00 | 13.30 A |
| ATOM | 1130 | CD1 | ILE | A | 211 | 85.855 | 19.805 | 0.435 | 1.00 | 10.47 A |
| ATOM | 1131 | C | ILE | A | 211 | 86.620 | 17.578 | 5.024 | 1.00 | 17.83 A |
| ATOM | 1132 | O | ILE | A | 211 | 87.685 | 18.151 | 5.241 | 1.00 | 17.76 A |
| ATOM | 1133 | N | LEU | A | 212 | 86.265 | 16.457 | 5.639 | 1.00 | 16.05 A |
| ATOM | 1134 | CA | LEU | A | 212 | 87.121 | 15.871 | 6.656 | 1.00 | 15.84 A |
| ATOM | 1135 | CB | LEU | A | 212 | 86.256 | 15.319 | 7.793 | 1.00 | 14.28 A |
| ATOM | 1136 | CG | LEU | A | 212 | 85.108 | 16.227 | 8.285 | 1.00 | 14.68 A |
| ATOM | 1137 | CD1 | LEU | A | 212 | 84.606 | 15.715 | 9.647 | 1.00 | 11.38 A |
| ATOM | 1138 | CD2 | LEU | A | 212 | 85.579 | 17.685 | 8.422 | 1.00 | 10.88 A |
| ATOM | 1139 | C | LEU | A | 212 | 88.031 | 14.787 | 6.114 | 1.00 | 16.77 A |
| ATOM | 1140 | O | LEU | A | 212 | 87.861 | 14.335 | 4.984 | 1.00 | 16.78 A |
| ATOM | 1141 | N | LEU | A | 213 | 88.999 | 14.374 | 6.925 | 1.00 | 16.47 A |
| ATOM | 1142 | CA | LEU | A | 213 | 89.924 | 13.332 | 6.516 | 1.00 | 17.64 A |
| ATOM | 1143 | CB | LEU | A | 213 | 91.323 | 13.926 | 6.378 | 1.00 | 18.08 A |
| ATOM | 1144 | CG | LEU | A | 213 | 91.367 | 14.880 | 5.176 | 1.00 | 17.92 A |
| ATOM | 1145 | CD1 | LEU | A | 213 | 92.076 | 16.134 | 5.529 | 1.00 | 18.78 A |
| ATOM | 1146 | CD2 | LEU | A | 213 | 92.042 | 14.187 | 4.000 | 1.00 | 17.07 A |
| ATOM | 1147 | C | LEU | A | 213 | 89.919 | 12.147 | 7.473 | 1.00 | 18.68 A |
| ATOM | 1148 | O | LEU | A | 213 | 90.091 | 12.297 | 8.672 | 1.00 | 18.75 A |
| ATOM | 1149 | N | ASN | A | 214 | 89.712 | 10.955 | 6.939 | 1.00 | 21.19 A |
| ATOM | 1150 | CA | ASN | A | 214 | 89.673 | 9.780 | 7.797 | 1.00 | 23.68 A |
| ATOM | 1151 | CB | ASN | A | 214 | 88.864 | 8.657 | 7.122 | 1.00 | 25.68 A |
| ATOM | 1152 | CG | ASN | A | 214 | 89.613 | 7.979 | 6.012 | 1.00 | 31.70 A |
| ATOM | 1153 | OD1 | ASN | A | 214 | 90.680 | 8.426 | 5.590 | 1.00 | 35.54 A |
| ATOM | 1154 | ND2 | ASN | A | 214 | 89.057 | 6.886 | 5.521 | 1.00 | 34.56 A |
| ATOM | 1155 | C | ASN | A | 214 | 91.077 | 9.328 | 8.203 | 1.00 | 22.08 A |
| ATOM | 1156 | O | ASN | A | 214 | 92.056 | 9.972 | 7.864 | 1.00 | 20.25 A |
| ATOM | 1157 | N | ALA | A | 215 | 91.170 | 8.239 | 8.953 | 1.00 | 24.03 A |
| ATOM | 1158 | CA | ALA | A | 215 | 92.464 | 7.738 | 9.420 | 1.00 | 24.26 A |
| ATOM | 1159 | CB | ALA | A | 215 | 92.276 | 6.502 | 10.277 | 1.00 | 21.70 A |
| ATOM | 1160 | C | ALA | A | 215 | 93.421 | 7.426 | 8.296 | 1.00 | 24.90 A |
| ATOM | 1161 | O | ALA | A | 215 | 94.615 | 7.435 | 8.491 | 1.00 | 26.03 A |
| ATOM | 1162 | N | ASP | A | 216 | 92.889 | 7.143 | 7.108 | 1.00 | 25.93 A |
| ATOM | 1163 | CA | ASP | A | 216 | 93.726 | 6.826 | 5.963 | 1.00 | 26.29 A |
| ATOM | 1164 | CB | ASP | A | 216 | 93.048 | 5.773 | 5.091 | 1.00 | 32.31 A |
| ATOM | 1165 | CG | ASP | A | 216 | 92.862 | 4.456 | 5.812 | 1.00 | 38.06 A |
| ATOM | 1166 | OD1 | ASP | A | 216 | 93.780 | 4.043 | 6.559 | 1.00 | 40.03 A |
| ATOM | 1167 | OD2 | ASP | A | 216 | 91.800 | 3.823 | 5.616 | 1.00 | 42.79 A |
| ATOM | 1168 | C | ASP | A | 216 | 94.046 | 8.026 | 5.095 | 1.00 | 23.69 A |
| ATOM | 1169 | O | ASP | A | 216 | 94.717 | 7.899 | 4.085 | 1.00 | 24.38 A |
| ATOM | 1170 | N | MET | A | 217 | 93.546 | 9.187 | 5.478 | 1.00 | 21.45 A |
| ATOM | 1171 | CA | MET | A | 217 | 93.752 | 10.418 | 4.726 | 1.00 | 20.48 A |
| ATOM | 1172 | CB | MET | A | 217 | 95.226 | 10.614 | 4.396 | 1.00 | 21.48 A |
| ATOM | 1173 | CG | MET | A | 217 | 96.081 | 10.894 | 5.629 | 1.00 | 21.46 A |
| ATOM | 1174 | SD | MET | A | 217 | 95.504 | 12.311 | 6.580 | 1.00 | 25.32 A |
| ATOM | 1175 | CE | MET | A | 217 | 96.079 | 13.722 | 5.573 | 1.00 | 24.08 A |
| ATOM | 1176 | C | MET | A | 217 | 92.900 | 10.556 | 3.458 | 1.00 | 19.63 A |
| ATOM | 1177 | O | MET | A | 217 | 93.245 | 11.294 | 2.546 | 1.00 | 19.54 A |
| ATOM | 1178 | N | HIS | A | 218 | 91.794 | 9.824 | 3.405 | 1.00 | 18.82 A |
| ATOM | 1179 | CA | HIS | A | 218 | 90.843 | 9.945 | 2.311 | 1.00 | 18.81 A |
| ATOM | 1180 | CB | HIS | A | 218 | 90.206 | 8.589 | 1.994 | 1.00 | 20.61 A |
| ATOM | 1181 | CG | HIS | A | 218 | 91.097 | 7.666 | 1.218 | 1.00 | 22.68 A |
| ATOM | 1182 | CD2 | HIS | A | 218 | 91.840 | 6.605 | 1.614 | 1.00 | 20.37 A |
| ATOM | 1183 | ND1 | HIS | A | 218 | 91.316 | 7.806 | −0.139 | 1.00 | 21.30 A |
| ATOM | 1184 | CE1 | HIS | A | 218 | 92.153 | 6.867 | −0.541 | 1.00 | 20.75 A |
| ATOM | 1185 | NE2 | HIS | A | 218 | 92.485 | 6.128 | 0.501 | 1.00 | 20.31 A |
| ATOM | 1186 | C | HIS | A | 218 | 89.774 | 10.925 | 2.863 | 1.00 | 18.97 A |
| ATOM | 1187 | O | HIS | A | 218 | 89.534 | 10.965 | 4.083 | 1.00 | 16.48 A |
| ATOM | 1188 | N | ILE | A | 219 | 89.166 | 11.721 | 1.978 | 1.00 | 17.41 A |
| ATOM | 1189 | CA | ILE | A | 219 | 88.165 | 12.702 | 2.387 | 1.00 | 16.48 A |
| ATOM | 1190 | CB | ILE | A | 219 | 87.765 | 13.695 | 1.242 | 1.00 | 13.43 A |
| ATOM | 1191 | CG2 | ILE | A | 219 | 88.984 | 14.404 | 0.698 | 1.00 | 10.66 A |
| ATOM | 1192 | CG1 | ILE | A | 219 | 86.973 | 12.952 | 0.156 | 1.00 | 11.14 A |
| ATOM | 1193 | CD1 | ILE | A | 219 | 86.505 | 13.807 | −0.995 | 1.00 | 4.26 A |
| ATOM | 1194 | C | ILE | A | 219 | 86.875 | 12.067 | 2.864 | 1.00 | 17.14 A |
| ATOM | 1195 | O | ILE | A | 219 | 86.541 | 10.943 | 2.497 | 1.00 | 18.77 A |
| ATOM | 1196 | N | GLN | A | 220 | 86.159 | 12.808 | 3.696 | 1.00 | 17.24 A |
| ATOM | 1197 | CA | GLN | A | 220 | 84.878 | 12.376 | 4.203 | 1.00 | 18.93 A |
| ATOM | 1198 | CB | GLN | A | 220 | 85.002 | 11.756 | 5.604 | 1.00 | 22.02 A |
| ATOM | 1199 | CG | GLN | A | 220 | 83.791 | 10.874 | 5.952 | 1.00 | 26.68 A |
| ATOM | 1200 | CD | GLN | A | 220 | 83.949 | 10.071 | 7.253 | 1.00 | 31.76 A |
| ATOM | 1201 | OE1 | GLN | A | 220 | 83.437 | 10.471 | 8.331 | 1.00 | 27.57 A |
| ATOM | 1202 | NE2 | GLN | A | 220 | 84.667 | 8.930 | 7.161 | 1.00 | 29.97 A |
| ATOM | 1203 | C | GLN | A | 220 | 84.077 | 13.652 | 4.261 | 1.00 | 17.44 A |
| ATOM | 1204 | O | GLN | A | 220 | 84.247 | 14.465 | 5.170 | 1.00 | 17.81 A |
| ATOM | 1205 | N | ILE | A | 221 | 83.229 | 13.852 | 3.263 | 1.00 | 15.69 A |
| ATOM | 1206 | CA | ILE | A | 221 | 82.413 | 15.051 | 3.230 | 1.00 | 16.08 A |
| ATOM | 1207 | CB | ILE | A | 221 | 81.939 | 15.359 | 1.802 | 1.00 | 15.82 A |

|      |      |     |     |   |     |        |        |        |      |       |   |
|------|------|-----|-----|---|-----|--------|--------|--------|------|-------|---|
| ATOM | 1208 | CG2 | ILE | A | 221 | 80.956 | 16.519 | 1.834  | 1.00 | 13.95 | A |
| ATOM | 1209 | CG1 | ILE | A | 221 | 83.163 | 15.627 | 0.899  | 1.00 | 16.66 | A |
| ATOM | 1210 | CD1 | ILE | A | 221 | 82.837 | 16.045 | −0.548 | 1.00 | 13.13 | A |
| ATOM | 1211 | C   | ILE | A | 221 | 81.207 | 14.892 | 4.156  | 1.00 | 16.52 | A |
| ATOM | 1212 | O   | ILE | A | 221 | 80.542 | 13.860 | 4.157  | 1.00 | 16.03 | A |
| ATOM | 1213 | N   | THR | A | 222 | 80.927 | 15.922 | 4.948  | 1.00 | 17.66 | A |
| ATOM | 1214 | CA  | THR | A | 222 | 79.810 | 15.862 | 5.882  | 1.00 | 17.70 | A |
| ATOM | 1215 | CB  | THR | A | 222 | 80.331 | 15.433 | 7.277  | 1.00 | 18.71 | A |
| ATOM | 1216 | OG1 | THR | A | 222 | 79.230 | 15.263 | 8.172  | 1.00 | 16.76 | A |
| ATOM | 1217 | CG2 | THR | A | 222 | 81.319 | 16.470 | 7.825  | 1.00 | 16.79 | A |
| ATOM | 1218 | C   | THR | A | 222 | 79.069 | 17.195 | 5.980  | 1.00 | 17.35 | A |
| ATOM | 1219 | O   | THR | A | 222 | 79.246 | 18.062 | 5.130  | 1.00 | 16.83 | A |
| ATOM | 1220 | N   | ASP | A | 223 | 78.244 | 17.344 | 7.018  | 1.00 | 18.09 | A |
| ATOM | 1221 | CA  | ASP | A | 223 | 77.466 | 18.567 | 7.268  | 1.00 | 19.60 | A |
| ATOM | 1222 | CB  | ASP | A | 223 | 78.403 | 19.778 | 7.311  | 1.00 | 22.73 | A |
| ATOM | 1223 | CG  | ASP | A | 223 | 77.763 | 21.006 | 7.959  | 1.00 | 28.30 | A |
| ATOM | 1224 | OD1 | ASP | A | 223 | 76.565 | 20.931 | 8.335  | 1.00 | 28.17 | A |
| ATOM | 1225 | OD2 | ASP | A | 223 | 78.480 | 22.042 | 8.081  | 1.00 | 30.99 | A |
| ATOM | 1226 | C   | ASP | A | 223 | 76.382 | 18.799 | 6.210  | 1.00 | 19.52 | A |
| ATOM | 1227 | O   | ASP | A | 223 | 76.528 | 19.655 | 5.340  | 1.00 | 19.39 | A |
| ATOM | 1228 | N   | PHE | A | 224 | 75.283 | 18.058 | 6.303  | 1.00 | 18.74 | A |
| ATOM | 1229 | CA  | PHE | A | 224 | 74.213 | 18.168 | 5.321  | 1.00 | 18.81 | A |
| ATOM | 1230 | CB  | PHE | A | 224 | 73.825 | 16.773 | 4.853  | 1.00 | 17.07 | A |
| ATOM | 1231 | CG  | PHE | A | 224 | 74.857 | 16.150 | 3.971  | 1.00 | 17.01 | A |
| ATOM | 1232 | CD1 | PHE | A | 224 | 74.751 | 16.250 | 2.578  | 1.00 | 16.10 | A |
| ATOM | 1233 | CD2 | PHE | A | 224 | 75.982 | 15.543 | 4.521  | 1.00 | 14.00 | A |
| ATOM | 1234 | CE1 | PHE | A | 224 | 75.761 | 15.752 | 1.747  | 1.00 | 15.92 | A |
| ATOM | 1235 | CE2 | PHE | A | 224 | 77.001 | 15.042 | 3.699  | 1.00 | 15.63 | A |
| ATOM | 1236 | CZ  | PHE | A | 224 | 76.889 | 15.147 | 2.309  | 1.00 | 15.79 | A |
| ATOM | 1237 | C   | PHE | A | 224 | 72.997 | 18.932 | 5.775  | 1.00 | 19.88 | A |
| ATOM | 1238 | O   | PHE | A | 224 | 71.961 | 18.922 | 5.115  | 1.00 | 19.36 | A |
| ATOM | 1239 | N   | GLY | A | 225 | 73.135 | 19.599 | 6.911  | 1.00 | 21.38 | A |
| ATOM | 1240 | CA  | GLY | A | 225 | 72.046 | 20.388 | 7.439  | 1.00 | 21.39 | A |
| ATOM | 1241 | C   | GLY | A | 225 | 71.672 | 21.545 | 6.523  | 1.00 | 23.43 | A |
| ATOM | 1242 | O   | GLY | A | 225 | 70.802 | 22.323 | 6.869  | 1.00 | 26.22 | A |
| ATOM | 1243 | N   | THR | A | 226 | 72.311 | 21.692 | 5.370  | 1.00 | 22.15 | A |
| ATOM | 1244 | CA  | THR | A | 226 | 71.930 | 22.784 | 4.492  | 1.00 | 23.85 | A |
| ATOM | 1245 | CB  | THR | A | 226 | 72.986 | 23.946 | 4.465  | 1.00 | 24.65 | A |
| ATOM | 1246 | OG1 | THR | A | 226 | 74.197 | 23.511 | 3.830  | 1.00 | 24.83 | A |
| ATOM | 1247 | CG2 | THR | A | 226 | 73.285 | 24.420 | 5.866  | 1.00 | 23.67 | A |
| ATOM | 1248 | C   | THR | A | 226 | 71.721 | 22.289 | 3.073  | 1.00 | 24.12 | A |
| ATOM | 1249 | O   | THR | A | 226 | 71.646 | 23.079 | 2.129  | 1.00 | 22.82 | A |
| ATOM | 1250 | N   | ALA | A | 227 | 71.620 | 20.976 | 2.935  | 1.00 | 23.84 | A |
| ATOM | 1251 | CA  | ALA | A | 227 | 71.437 | 20.357 | 1.637  | 1.00 | 26.21 | A |
| ATOM | 1252 | CB  | ALA | A | 227 | 71.774 | 18.889 | 1.734  | 1.00 | 24.04 | A |
| ATOM | 1253 | C   | ALA | A | 227 | 70.026 | 20.535 | 1.064  | 1.00 | 28.20 | A |
| ATOM | 1254 | O   | ALA | A | 227 | 69.069 | 20.767 | 1.801  | 1.00 | 29.29 | A |
| ATOM | 1255 | N   | ALA | A | 228 | 69.912 | 20.449 | −0.258 | 1.00 | 28.91 | A |
| ATOM | 1256 | CA  | ALA | A | 228 | 68.623 | 20.554 | −0.928 | 1.00 | 31.02 | A |
| ATOM | 1257 | CB  | ALA | A | 228 | 68.577 | 21.795 | −1.856 | 1.00 | 30.45 | A |
| ATOM | 1258 | C   | ALA | A | 228 | 68.501 | 19.276 | −1.745 | 1.00 | 32.01 | A |
| ATOM | 1259 | O   | ALA | A | 228 | 69.474 | 18.846 | −2.363 | 1.00 | 32.87 | A |
| ATOM | 1260 | N   | VAL | A | 229 | 67.328 | 18.650 | −1.732 | 1.00 | 32.95 | A |
| ATOM | 1261 | CA  | VAL | A | 229 | 67.126 | 17.424 | −2.503 | 1.00 | 34.26 | A |
| ATOM | 1262 | CB  | VAL | A | 229 | 66.468 | 16.347 | −1.657 | 1.00 | 33.02 | A |
| ATOM | 1263 | CG1 | VAL | A | 229 | 66.194 | 15.114 | −2.498 | 1.00 | 33.80 | A |
| ATOM | 1264 | CG2 | VAL | A | 229 | 67.356 | 16.011 | −0.496 | 1.00 | 31.38 | A |
| ATOM | 1265 | C   | VAL | A | 229 | 66.213 | 17.757 | −3.665 | 1.00 | 36.36 | A |
| ATOM | 1266 | O   | VAL | A | 229 | 65.065 | 18.133 | −3.455 | 1.00 | 38.02 | A |
| ATOM | 1267 | N   | LEU | A | 230 | 66.715 | 17.628 | −4.889 | 1.00 | 37.75 | A |
| ATOM | 1268 | CA  | LEU | A | 230 | 65.917 | 17.965 | −6.066 | 1.00 | 39.87 | A |
| ATOM | 1269 | CB  | LEU | A | 230 | 66.741 | 17.775 | −7.335 | 1.00 | 41.23 | A |
| ATOM | 1270 | CG  | LEU | A | 230 | 68.039 | 18.585 | −7.359 | 1.00 | 44.16 | A |
| ATOM | 1271 | CD1 | LEU | A | 230 | 68.843 | 18.208 | −8.599 | 1.00 | 43.48 | A |
| ATOM | 1272 | CD2 | LEU | A | 230 | 67.724 | 20.087 | −7.313 | 1.00 | 42.99 | A |
| ATOM | 1273 | C   | LEU | A | 230 | 64.646 | 17.137 | −6.162 | 1.00 | 40.59 | A |
| ATOM | 1274 | O   | LEU | A | 230 | 64.703 | 15.954 | −6.486 | 1.00 | 41.31 | A |
| ATOM | 1275 | N   | ASN | A | 240 | 65.964 | 27.756 | −2.248 | 1.00 | 83.97 | A |
| ATOM | 1276 | CA  | ASN | A | 240 | 66.331 | 29.165 | −2.370 | 1.00 | 84.48 | A |
| ATOM | 1277 | CB  | ASN | A | 240 | 65.294 | 29.907 | −3.225 | 1.00 | 85.56 | A |
| ATOM | 1278 | CG  | ASN | A | 240 | 63.949 | 30.053 | −2.524 | 1.00 | 86.59 | A |
| ATOM | 1279 | OD1 | ASN | A | 240 | 63.850 | 30.682 | −1.465 | 1.00 | 87.31 | A |
| ATOM | 1280 | ND2 | ASN | A | 240 | 62.904 | 29.473 | −3.115 | 1.00 | 86.14 | A |
| ATOM | 1281 | C   | ASN | A | 240 | 66.433 | 29.828 | −0.994 | 1.00 | 83.85 | A |
| ATOM | 1282 | O   | ASN | A | 240 | 66.898 | 30.963 | −0.862 | 1.00 | 84.11 | A |
| ATOM | 1283 | N   | ALA | A | 241 | 65.997 | 29.096 | 0.023  | 1.00 | 83.19 | A |
| ATOM | 1284 | CA  | ALA | A | 241 | 65.996 | 29.564 | 1.405  | 1.00 | 81.85 | A |
| ATOM | 1285 | C   | ALA | A | 241 | 67.330 | 29.365 | 2.127  | 1.00 | 79.97 | A |
| ATOM | 1286 | O   | ALA | A | 241 | 67.349 | 28.777 | 3.214  | 1.00 | 79.75 | A |

-continued

| | | | | | | | | | | |
|---|---|---|---|---|---|---|---|---|---|---|
| ATOM | 1287 | CB | ALA | A | 241 | 64.894 | 28.825 | 2.183 | 1.00 | 85.17 A |
| ATOM | 1288 | N | PHE | A | 242 | 68.433 | 29.850 | 1.551 | 1.00 | 77.03 A |
| ATOM | 1289 | CA | PHE | A | 242 | 69.737 | 29.680 | 2.197 | 1.00 | 74.85 A |
| ATOM | 1290 | CB | PHE | A | 242 | 69.973 | 28.183 | 2.438 | 1.00 | 73.81 A |
| ATOM | 1291 | CG | PHE | A | 242 | 71.311 | 27.861 | 3.015 | 1.00 | 72.36 A |
| ATOM | 1292 | CD1 | PHE | A | 242 | 71.595 | 28.116 | 4.353 | 1.00 | 72.39 A |
| ATOM | 1293 | CD2 | PHE | A | 242 | 72.297 | 27.312 | 2.210 | 1.00 | 72.03 A |
| ATOM | 1294 | CE1 | PHE | A | 242 | 72.855 | 27.823 | 4.879 | 1.00 | 72.87 A |
| ATOM | 1295 | CE2 | PHE | A | 242 | 73.553 | 27.016 | 2.714 | 1.00 | 72.25 A |
| ATOM | 1296 | CZ | PHE | A | 242 | 73.837 | 27.270 | 4.054 | 1.00 | 72.96 A |
| ATOM | 1297 | C | PHE | A | 242 | 70.951 | 30.283 | 1.462 | 1.00 | 73.13 A |
| ATOM | 1298 | O | PHE | A | 242 | 70.958 | 30.425 | 0.233 | 1.00 | 74.08 A |
| ATOM | 1299 | N | VAL | A | 243 | 71.972 | 30.625 | 2.250 | 1.00 | 69.64 A |
| ATOM | 1300 | CA | VAL | A | 243 | 73.233 | 31.204 | 1.777 | 1.00 | 65.87 A |
| ATOM | 1301 | CB | VAL | A | 243 | 73.207 | 32.765 | 1.834 | 1.00 | 66.73 A |
| ATOM | 1302 | CG1 | VAL | A | 243 | 74.498 | 33.344 | 1.271 | 1.00 | 65.65 A |
| ATOM | 1303 | CG2 | VAL | A | 243 | 72.008 | 33.299 | 1.084 | 1.00 | 66.83 A |
| ATOM | 1304 | C | VAL | A | 243 | 74.349 | 30.708 | 2.703 | 1.00 | 62.21 A |
| ATOM | 1305 | O | VAL | A | 243 | 74.471 | 31.189 | 3.839 | 1.00 | 61.91 A |
| ATOM | 1306 | N | GLY | A | 244 | 75.149 | 29.760 | 2.204 | 1.00 | 57.62 A |
| ATOM | 1307 | CA | GLY | A | 244 | 76.247 | 29.177 | 2.967 | 1.00 | 51.60 A |
| ATOM | 1308 | C | GLY | A | 244 | 77.341 | 30.132 | 3.387 | 1.00 | 46.47 A |
| ATOM | 1309 | O | GLY | A | 244 | 77.063 | 31.261 | 3.757 | 1.00 | 48.62 A |
| ATOM | 1310 | N | THR | A | 245 | 78.588 | 29.686 | 3.325 | 1.00 | 42.06 A |
| ATOM | 1311 | CA | THR | A | 245 | 79.709 | 30.526 | 3.726 | 1.00 | 36.35 A |
| ATOM | 1312 | CB | THR | A | 245 | 80.925 | 29.673 | 4.096 | 1.00 | 35.76 A |
| ATOM | 1313 | OG1 | THR | A | 245 | 80.539 | 28.740 | 5.105 | 1.00 | 31.66 A |
| ATOM | 1314 | CG2 | THR | A | 245 | 82.043 | 30.534 | 4.651 | 1.00 | 33.72 A |
| ATOM | 1315 | C | THR | A | 245 | 80.064 | 31.524 | 2.637 | 1.00 | 34.43 A |
| ATOM | 1316 | O | THR | A | 245 | 80.309 | 31.166 | 1.485 | 1.00 | 33.95 A |
| ATOM | 1317 | N | ALA | A | 246 | 80.087 | 32.787 | 3.034 | 1.00 | 32.72 A |
| ATOM | 1318 | CA | ALA | A | 246 | 80.338 | 33.900 | 2.142 | 1.00 | 30.18 A |
| ATOM | 1319 | CB | ALA | A | 246 | 80.684 | 35.127 | 2.952 | 1.00 | 30.18 A |
| ATOM | 1320 | C | ALA | A | 246 | 81.374 | 33.678 | 1.062 | 1.00 | 29.56 A |
| ATOM | 1321 | O | ALA | A | 246 | 81.099 | 33.895 | -0.113 | 1.00 | 30.00 A |
| ATOM | 1322 | N | GLN | A | 247 | 82.564 | 33.242 | 1.445 | 1.00 | 28.03 A |
| ATOM | 1323 | CA | GLN | A | 247 | 83.623 | 33.030 | 0.468 | 1.00 | 26.97 A |
| ATOM | 1324 | CB | GLN | A | 247 | 84.929 | 32.706 | 1.182 | 1.00 | 28.32 A |
| ATOM | 1325 | CG | GLN | A | 247 | 85.208 | 33.659 | 2.319 | 1.00 | 33.33 A |
| ATOM | 1326 | CD | GLN | A | 247 | 86.600 | 33.522 | 2.863 | 1.00 | 36.16 A |
| ATOM | 1327 | OE1 | GLN | A | 247 | 87.556 | 34.107 | 2.335 | 1.00 | 36.68 A |
| ATOM | 1328 | NE2 | GLN | A | 247 | 86.738 | 32.731 | 3.922 | 1.00 | 39.27 A |
| ATOM | 1329 | C | GLN | A | 247 | 83.355 | 31.968 | -0.583 | 1.00 | 25.04 A |
| ATOM | 1330 | O | GLN | A | 247 | 83.962 | 31.997 | -1.653 | 1.00 | 25.92 A |
| ATOM | 1331 | N | TYR | A | 248 | 82.443 | 31.045 | -0.304 | 1.00 | 22.51 A |
| ATOM | 1332 | CA | TYR | A | 248 | 82.161 | 29.970 | -1.260 | 1.00 | 21.98 A |
| ATOM | 1333 | CB | TYR | A | 248 | 82.273 | 28.613 | -0.541 | 1.00 | 17.74 A |
| ATOM | 1334 | CG | TYR | A | 248 | 83.626 | 28.444 | 0.117 | 1.00 | 14.83 A |
| ATOM | 1335 | CD1 | TYR | A | 248 | 84.736 | 28.063 | -0.630 | 1.00 | 14.53 A |
| ATOM | 1336 | CE1 | TYR | A | 248 | 86.017 | 28.034 | -0.067 | 1.00 | 15.65 A |
| ATOM | 1337 | CD2 | TYR | A | 248 | 83.820 | 28.784 | 1.460 | 1.00 | 13.57 A |
| ATOM | 1338 | CE2 | TYR | A | 248 | 85.086 | 28.757 | 2.039 | 1.00 | 13.28 A |
| ATOM | 1339 | CZ | TYR | A | 248 | 86.192 | 28.386 | 1.271 | 1.00 | 16.78 A |
| ATOM | 1340 | OH | TYR | A | 248 | 87.471 | 28.411 | 1.816 | 1.00 | 15.10 A |
| ATOM | 1341 | C | TYR | A | 248 | 80.827 | 30.091 | -2.005 | 1.00 | 22.23 A |
| ATOM | 1342 | O | TYR | A | 248 | 80.523 | 29.268 | -2.866 | 1.00 | 22.78 A |
| ATOM | 1343 | N | VAL | A | 249 | 80.054 | 31.126 | -1.680 | 1.00 | 21.81 A |
| ATOM | 1344 | CA | VAL | A | 249 | 78.760 | 31.395 | -2.308 | 1.00 | 22.22 A |
| ATOM | 1345 | CB | VAL | A | 249 | 78.077 | 32.634 | -1.640 | 1.00 | 22.82 A |
| ATOM | 1346 | CG1 | VAL | A | 249 | 76.904 | 33.139 | -2.496 | 1.00 | 22.57 A |
| ATOM | 1347 | CG2 | VAL | A | 249 | 77.606 | 32.270 | -0.243 | 1.00 | 22.62 A |
| ATOM | 1348 | C | VAL | A | 249 | 78.878 | 31.666 | -3.818 | 1.00 | 21.92 A |
| ATOM | 1349 | O | VAL | A | 249 | 79.733 | 32.428 | -4.255 | 1.00 | 20.01 A |
| ATOM | 1350 | N | SER | A | 250 | 78.012 | 31.045 | -4.609 | 1.00 | 22.88 A |
| ATOM | 1351 | CA | SER | A | 250 | 78.030 | 31.259 | -6.049 | 1.00 | 24.81 A |
| ATOM | 1352 | CB | SER | A | 250 | 77.357 | 30.105 | -6.792 | 1.00 | 25.82 A |
| ATOM | 1353 | OG | SER | A | 250 | 75.999 | 29.984 | -6.419 | 1.00 | 27.07 A |
| ATOM | 1354 | C | SER | A | 250 | 77.288 | 32.546 | -6.357 | 1.00 | 26.22 A |
| ATOM | 1355 | O | SER | A | 250 | 76.438 | 33.004 | -5.582 | 1.00 | 25.88 A |
| ATOM | 1356 | N | PRO | A | 251 | 77.592 | 33.148 | -7.506 | 1.00 | 26.70 A |
| ATOM | 1357 | CD | PRO | A | 251 | 78.632 | 32.813 | -8.495 | 1.00 | 27.24 A |
| ATOM | 1358 | CA | PRO | A | 251 | 76.908 | 34.393 | -7.847 | 1.00 | 27.08 A |
| ATOM | 1359 | CB | PRO | A | 251 | 77.637 | 34.860 | -9.113 | 1.00 | 25.51 A |
| ATOM | 1360 | CG | PRO | A | 251 | 78.171 | 33.590 | -9.701 | 1.00 | 27.43 A |
| ATOM | 1361 | C | PRO | A | 251 | 75.399 | 34.288 | -8.026 | 1.00 | 28.00 A |
| ATOM | 1362 | O | PRO | A | 251 | 74.684 | 35.218 | -7.678 | 1.00 | 28.30 A |
| ATOM | 1363 | N | GLU | A | 252 | 74.908 | 33.166 | -8.550 | 1.00 | 28.81 A |
| ATOM | 1364 | CA | GLU | A | 252 | 73.469 | 33.012 | -8.768 | 1.00 | 29.67 A |
| ATOM | 1365 | CB | GLU | A | 252 | 73.151 | 31.684 | -9.463 | 1.00 | 29.72 A |

-continued

| | | | | | | | | | | |
|---|---|---|---|---|---|---|---|---|---|---|
| ATOM | 1366 | CG | GLU | A | 252 | 73.698 | 30.453 | −8.740 | 1.00 | 31.04 | A |
| ATOM | 1367 | CD | GLU | A | 252 | 75.106 | 30.075 | −9.191 | 1.00 | 30.61 | A |
| ATOM | 1368 | OE1 | GLU | A | 252 | 75.880 | 30.973 | −9.597 | 1.00 | 30.55 | A |
| ATOM | 1369 | OE2 | GLU | A | 252 | 75.434 | 28.872 | −9.130 | 1.00 | 30.80 | A |
| ATOM | 1370 | C | GLU | A | 252 | 72.709 | 33.083 | −7.462 | 1.00 | 30.83 | A |
| ATOM | 1371 | O | GLU | A | 252 | 71.563 | 33.530 | −7.423 | 1.00 | 31.87 | A |
| ATOM | 1372 | N | LEU | A | 253 | 73.351 | 32.639 | −6.388 | 1.00 | 32.71 | A |
| ATOM | 1373 | CA | LEU | A | 253 | 72.734 | 32.655 | −5.073 | 1.00 | 33.94 | A |
| ATOM | 1374 | CB | LEU | A | 253 | 73.612 | 31.901 | −4.081 | 1.00 | 37.40 | A |
| ATOM | 1375 | CG | LEU | A | 253 | 72.967 | 31.086 | −2.950 | 1.00 | 41.64 | A |
| ATOM | 1376 | CD1 | LEU | A | 253 | 72.067 | 31.925 | −2.048 | 1.00 | 43.86 | A |
| ATOM | 1377 | CD2 | LEU | A | 253 | 72.144 | 30.017 | −3.597 | 1.00 | 45.52 | A |
| ATOM | 1378 | C | LEU | A | 253 | 72.545 | 34.095 | −4.603 | 1.00 | 35.67 | A |
| ATOM | 1379 | O | LEU | A | 253 | 71.589 | 34.392 | −3.897 | 1.00 | 37.48 | A |
| ATOM | 1380 | N | LEU | A | 254 | 73.451 | 34.989 | −4.995 | 1.00 | 36.38 | A |
| ATOM | 1381 | CA | LEU | A | 254 | 73.372 | 36.397 | −4.600 | 1.00 | 36.66 | A |
| ATOM | 1382 | CB | LEU | A | 254 | 74.764 | 37.032 | −4.572 | 1.00 | 33.81 | A |
| ATOM | 1383 | CG | LEU | A | 254 | 75.824 | 36.402 | −3.674 | 1.00 | 33.40 | A |
| ATOM | 1384 | CD1 | LEU | A | 254 | 77.183 | 37.022 | −3.982 | 1.00 | 30.48 | A |
| ATOM | 1385 | CD2 | LEU | A | 254 | 75.440 | 36.574 | −2.208 | 1.00 | 31.43 | A |
| ATOM | 1386 | C | LEU | A | 254 | 72.485 | 37.240 | −5.511 | 1.00 | 38.89 | A |
| ATOM | 1387 | O | LEU | A | 254 | 72.079 | 38.328 | −5.133 | 1.00 | 38.85 | A |
| ATOM | 1388 | N | THR | A | 255 | 72.187 | 36.754 | −6.709 | 1.00 | 42.60 | A |
| ATOM | 1389 | CA | THR | A | 255 | 71.358 | 37.528 | −7.624 | 1.00 | 47.21 | A |
| ATOM | 1390 | CB | THR | A | 255 | 72.102 | 37.847 | −8.941 | 1.00 | 47.08 | A |
| ATOM | 1391 | OG1 | THR | A | 255 | 72.008 | 36.718 | −9.814 | 1.00 | 48.56 | A |
| ATOM | 1392 | CG2 | THR | A | 255 | 73.581 | 38.157 | −8.686 | 1.00 | 45.65 | A |
| ATOM | 1393 | C | THR | A | 255 | 70.044 | 36.848 | −8.009 | 1.00 | 51.00 | A |
| ATOM | 1394 | O | THR | A | 255 | 69.348 | 37.323 | −8.903 | 1.00 | 51.80 | A |
| ATOM | 1395 | N | GLU | A | 256 | 69.696 | 35.745 | −7.353 | 1.00 | 55.01 | A |
| ATOM | 1396 | CA | GLU | A | 256 | 68.450 | 35.044 | −7.683 | 1.00 | 58.97 | A |
| ATOM | 1397 | CB | GLU | A | 256 | 68.679 | 34.057 | −8.832 | 1.00 | 59.81 | A |
| ATOM | 1398 | CG | GLU | A | 256 | 68.922 | 34.707 | −10.181 | 1.00 | 63.59 | A |
| ATOM | 1399 | CD | GLU | A | 256 | 69.343 | 33.707 | −11.240 | 1.00 | 65.64 | A |
| ATOM | 1400 | OE1 | GLU | A | 256 | 68.727 | 32.617 | −11.310 | 1.00 | 67.44 | A |
| ATOM | 1401 | OE2 | GLU | A | 256 | 70.285 | 34.015 | −12.007 | 1.00 | 66.61 | A |
| ATOM | 1402 | C | GLU | A | 256 | 67.859 | 34.279 | −6.512 | 1.00 | 60.83 | A |
| ATOM | 1403 | O | GLU | A | 256 | 66.701 | 33.861 | −6.563 | 1.00 | 61.27 | A |
| ATOM | 1404 | N | ALA | A | 257 | 68.657 | 34.100 | −5.463 | 1.00 | 62.31 | A |
| ATOM | 1405 | CA | ALA | A | 257 | 68.234 | 33.348 | −4.285 | 1.00 | 63.29 | A |
| ATOM | 1406 | CB | ALA | A | 257 | 66.867 | 33.847 | −3.784 | 1.00 | 62.76 | A |
| ATOM | 1407 | C | ALA | A | 257 | 68.157 | 31.860 | −4.651 | 1.00 | 63.64 | A |
| ATOM | 1408 | O | ALA | A | 257 | 67.790 | 31.028 | −3.825 | 1.00 | 64.96 | A |
| ATOM | 1409 | N | SER | A | 258 | 68.523 | 31.532 | −5.888 | 1.00 | 62.79 | A |
| ATOM | 1410 | CA | SER | A | 258 | 68.485 | 30.150 | −6.378 | 1.00 | 62.30 | A |
| ATOM | 1411 | CB | SER | A | 258 | 68.049 | 30.144 | −7.847 | 1.00 | 63.00 | A |
| ATOM | 1412 | OG | SER | A | 258 | 68.762 | 31.129 | −8.582 | 1.00 | 63.40 | A |
| ATOM | 1413 | C | SER | A | 258 | 69.816 | 29.402 | −6.237 | 1.00 | 61.09 | A |
| ATOM | 1414 | O | SER | A | 258 | 70.862 | 30.009 | −6.009 | 1.00 | 62.12 | A |
| ATOM | 1415 | N | ALA | A | 259 | 69.774 | 28.083 | −6.389 | 1.00 | 58.47 | A |
| ATOM | 1416 | CA | ALA | A | 259 | 70.979 | 27.270 | −6.278 | 1.00 | 55.79 | A |
| ATOM | 1417 | CB | ALA | A | 259 | 71.403 | 27.164 | −4.837 | 1.00 | 56.24 | A |
| ATOM | 1418 | C | ALA | A | 259 | 70.738 | 25.886 | −6.842 | 1.00 | 53.38 | A |
| ATOM | 1419 | O | ALA | A | 259 | 69.641 | 25.347 | −6.736 | 1.00 | 54.10 | A |
| ATOM | 1420 | N | CYS | A | 260 | 71.768 | 25.30 | −7.433 | 1.00 | 49.75 | A |
| ATOM | 1421 | CA | CYS | A | 260 | 71.623 | 23.988 | −8.015 | 1.00 | 45.68 | A |
| ATOM | 1422 | CB | CYS | A | 260 | 71.067 | 24.106 | −9.438 | 1.00 | 48.50 | A |
| ATOM | 1423 | SG | CYS | A | 260 | 69.936 | 22.732 | −9.899 | 1.00 | 57.53 | A |
| ATOM | 1424 | C | CYS | A | 260 | 72.980 | 23.318 | −8.022 | 1.00 | 41.30 | A |
| ATOM | 1425 | O | CYS | A | 260 | 73.892 | 23.762 | −7.335 | 1.00 | 39.24 | A |
| ATOM | 1426 | N | LYS | A | 261 | 73.118 | 22.258 | −8.805 | 1.00 | 36.63 | A |
| ATOM | 1427 | CA | LYS | A | 261 | 74.369 | 21.535 | −8.866 | 1.00 | 33.81 | A |
| ATOM | 1428 | CB | LYS | A | 261 | 74.261 | 20.416 | −9.897 | 1.00 | 34.27 | A |
| ATOM | 1429 | CG | LYS | A | 261 | 73.250 | 19.362 | −9.488 | 1.00 | 34.04 | A |
| ATOM | 1430 | CD | LYS | A | 261 | 72.995 | 18.353 | −10.577 | 1.00 | 33.10 | A |
| ATOM | 1431 | CE | LYS | A | 261 | 71.983 | 17.336 | −10.105 | 1.00 | 32.48 | A |
| ATOM | 1432 | NZ | LYS | A | 261 | 71.660 | 16.357 | −11.176 | 1.00 | 33.10 | A |
| ATOM | 1433 | C | LYS | A | 261 | 75.565 | 22.419 | −9.153 | 1.00 | 31.80 | A |
| ATOM | 1434 | O | LYS | A | 261 | 76.636 | 22.214 | −8.589 | 1.00 | 31.89 | A |
| ATOM | 1435 | N | SER | A | 262 | 75.389 | 23.405 | −10.025 | 1.00 | 29.92 | A |
| ATOM | 1436 | CA | SER | A | 262 | 76.477 | 24.314 | −10.354 | 1.00 | 28.19 | A |
| ATOM | 1437 | CB | SER | A | 262 | 76.034 | 25.309 | −11.417 | 1.00 | 29.90 | A |
| ATOM | 1438 | OG | SER | A | 262 | 76.184 | 24.732 | −12.695 | 1.00 | 34.45 | A |
| ATOM | 1439 | C | SER | A | 262 | 77.047 | 25.069 | −9.155 | 1.00 | 25.77 | A |
| ATOM | 1440 | O | SER | A | 262 | 78.225 | 25.405 | −9.146 | 1.00 | 26.59 | A |
| ATOM | 1441 | N | SER | A | 263 | 76.216 | 25.347 | −8.159 | 1.00 | 23.42 | A |
| ATOM | 1442 | CA | SER | A | 263 | 76.663 | 26.040 | −6.953 | 1.00 | 23.04 | A |
| ATOM | 1443 | CB | SER | A | 263 | 75.502 | 26.209 | −5.979 | 1.00 | 24.64 | A |
| ATOM | 1444 | OG | SER | A | 263 | 74.463 | 26.963 | −6.572 | 1.00 | 31.12 | A |

-continued

| ATOM | 1445 | C | SER | A | 263 | 77.777 | 25.233 | −6.283 | 1.00 | 21.37 | A |
|---|---|---|---|---|---|---|---|---|---|---|---|
| ATOM | 1446 | O | SER | A | 263 | 78.745 | 25.803 | −5.788 | 1.00 | 20.74 | A |
| ATOM | 1447 | N | ASP | A | 264 | 77.640 | 23.909 | −6.268 | 1.00 | 19.11 | A |
| ATOM | 1448 | CA | ASP | A | 264 | 78.674 | 23.06 | −5.682 | 1.00 | 19.35 | A |
| ATOM | 1449 | CB | ASP | A | 264 | 78.206 | 21.609 | −5.579 | 1.00 | 18.45 | A |
| ATOM | 1450 | CG | ASP | A | 264 | 77.164 | 21.406 | −4.500 | 1.00 | 19.39 | A |
| ATOM | 1451 | OD1 | ASP | A | 264 | 76.998 | 22.304 | −3.649 | 1.00 | 20.34 | A |
| ATOM | 1452 | OD2 | ASP | A | 264 | 76.522 | 20.338 | −4.488 | 1.00 | 19.48 | A |
| ATOM | 1453 | C | ASP | A | 264 | 79.943 | 23.127 | −6.542 | 1.00 | 19.34 | A |
| ATOM | 1454 | O | ASP | A | 264 | 81.052 | 23.147 | −6.018 | 1.00 | 20.70 | A |
| ATOM | 1455 | N | LEU | A | 265 | 79.772 | 23.16 | −7.864 | 1.00 | 17.68 | A |
| ATOM | 1456 | CA | LEU | A | 265 | 80.898 | 23.23 | −8.774 | 1.00 | 17.42 | A |
| ATOM | 1457 | CB | LEU | A | 265 | 80.406 | 23.058 | −10.208 | 1.00 | 19.36 | A |
| ATOM | 1458 | CG | LEU | A | 265 | 79.683 | 21.717 | −10.453 | 1.00 | 19.53 | A |
| ATOM | 1459 | CD1 | LEU | A | 265 | 79.189 | 21.655 | −11.879 | 1.00 | 17.18 | A |
| ATOM | 1460 | CD2 | LEU | A | 265 | 80.625 | 20.550 | −10.168 | 1.00 | 14.91 | A |
| ATOM | 1461 | C | LEU | A | 265 | 81.619 | 24.566 | −8.600 | 1.00 | 19.06 | A |
| ATOM | 1462 | O | LEU | A | 265 | 82.850 | 24.649 | −8.697 | 1.00 | 18.60 | A |
| ATOM | 1463 | N | TRP | A | 266 | 80.853 | 25.621 | −8.350 | 1.00 | 18.60 | A |
| ATOM | 1464 | CA | TRP | A | 266 | 81.468 | 26.902 | −8.107 | 1.00 | 18.62 | A |
| ATOM | 1465 | CB | TRP | A | 266 | 80.405 | 27.976 | −7.876 | 1.00 | 19.75 | A |
| ATOM | 1466 | CG | TRP | A | 266 | 80.997 | 29.277 | −7.382 | 1.00 | 21.53 | A |
| ATOM | 1467 | CD2 | TRP | A | 266 | 81.357 | 30.420 | −8.174 | 1.00 | 22.40 | A |
| ATOM | 1468 | CE2 | TRP | A | 266 | 81.917 | 31.375 | −7.296 | 1.00 | 22.70 | A |
| ATOM | 1469 | CE3 | TRP | A | 266 | 81.260 | 30.728 | −9.541 | 1.00 | 21.62 | A |
| ATOM | 1470 | CD1 | TRP | A | 266 | 81.344 | 29.582 | −6.094 | 1.00 | 20.15 | A |
| ATOM | 1471 | NE1 | TRP | A | 266 | 81.896 | 30.835 | −6.037 | 1.00 | 20.80 | A |
| ATOM | 1472 | CZ2 | TRP | A | 266 | 82.382 | 32.624 | −7.739 | 1.00 | 22.47 | A |
| ATOM | 1473 | CZ3 | TRP | A | 266 | 81.721 | 31.961 | −9.981 | 1.00 | 22.48 | A |
| ATOM | 1474 | CH2 | TRP | A | 266 | 82.276 | 32.898 | −9.080 | 1.00 | 23.40 | A |
| ATOM | 1475 | C | TRP | A | 266 | 82.338 | 26.734 | −6.857 | 1.00 | 18.89 | A |
| ATOM | 1476 | O | TRP | A | 266 | 83.523 | 27.070 | −6.875 | 1.00 | 20.01 | A |
| ATOM | 1477 | N | ALA | A | 267 | 81.755 | 26.204 | −5.780 | 1.00 | 16.09 | A |
| ATOM | 1478 | CA | ALA | A | 267 | 82.502 | 25.994 | −4.540 | 1.00 | 15.55 | A |
| ATOM | 1479 | CB | ALA | A | 267 | 81.630 | 25.313 | −3.499 | 1.00 | 13.20 | A |
| ATOM | 1480 | C | ALA | A | 267 | 83.738 | 25.145 | −4.813 | 1.00 | 16.44 | A |
| ATOM | 1481 | O | ALA | A | 267 | 84.802 | 25.345 | −4.218 | 1.00 | 17.65 | A |
| ATOM | 1482 | N | LEU | A | 268 | 83.597 | 24.181 | −5.710 | 1.00 | 15.96 | A |
| ATOM | 1483 | CA | LEU | A | 268 | 84.732 | 23.336 | −6.055 | 1.00 | 17.56 | A |
| ATOM | 1484 | CB | LEU | A | 268 | 84.315 | 22.281 | −7.098 | 1.00 | 16.91 | A |
| ATOM | 1485 | CG | LEU | A | 268 | 85.477 | 21.535 | −7.775 | 1.00 | 16.43 | A |
| ATOM | 1486 | CD1 | LEU | A | 268 | 86.214 | 20.697 | −6.766 | 1.00 | 15.17 | A |
| ATOM | 1487 | CD2 | LEU | A | 268 | 84.947 | 20.643 | −8.871 | 1.00 | 17.18 | A |
| ATOM | 1488 | C | LEU | A | 268 | 85.892 | 24.193 | −6.599 | 1.00 | 15.96 | A |
| ATOM | 1489 | O | LEU | A | 268 | 87.032 | 24.040 | −6.178 | 1.00 | 14.54 | A |
| ATOM | 1490 | N | GLY | A | 269 | 85.578 | 25.092 | −7.530 | 1.00 | 17.15 | A |
| ATOM | 1491 | CA | GLY | A | 269 | 86.590 | 25.957 | −8.116 | 1.00 | 18.32 | A |
| ATOM | 1492 | C | GLY | A | 269 | 87.339 | 26.722 | −7.042 | 1.00 | 19.39 | A |
| ATOM | 1493 | O | GLY | A | 269 | 88.579 | 26.777 | −7.042 | 1.00 | 19.66 | A |
| ATOM | 1494 | N | CYS | A | 270 | 86.579 | 27.297 | −6.111 | 1.00 | 17.50 | A |
| ATOM | 1495 | CA | CYS | A | 270 | 87.154 | 28.043 | −5.010 | 1.00 | 17.72 | A |
| ATOM | 1496 | CB | CYS | A | 270 | 86.047 | 28.551 | −4.088 | 1.00 | 18.96 | A |
| ATOM | 1497 | SG | CYS | A | 270 | 84.981 | 29.801 | −4.798 | 1.00 | 19.62 | A |
| ATOM | 1498 | C | CYS | A | 270 | 88.114 | 27.182 | −4.201 | 1.00 | 18.63 | A |
| ATOM | 1499 | O | CYS | A | 270 | 89.213 | 27.612 | −3.850 | 1.00 | 18.78 | A |
| ATOM | 1500 | N | ILE | A | 271 | 87.679 | 25.962 | −3.900 | 1.00 | 20.05 | A |
| ATOM | 1501 | CA | ILE | A | 271 | 88.479 | 25.019 | −3.130 | 1.00 | 20.08 | A |
| ATOM | 1502 | CB | ILE | A | 271 | 87.668 | 23.755 | −2.812 | 1.00 | 20.09 | A |
| ATOM | 1503 | CG2 | ILE | A | 271 | 88.592 | 22.654 | −2.302 | 1.00 | 18.31 | A |
| ATOM | 1504 | CG1 | ILE | A | 271 | 86.558 | 24.104 | −1.810 | 1.00 | 18.38 | A |
| ATOM | 1505 | CD1 | ILE | A | 271 | 85.396 | 23.125 | −1.783 | 1.00 | 14.68 | A |
| ATOM | 1506 | C | ILE | A | 271 | 89.761 | 24.629 | −3.858 | 1.00 | 20.41 | A |
| ATOM | 1507 | O | ILE | A | 271 | 90.826 | 24.548 | −3.234 | 1.00 | 21.81 | A |
| ATOM | 1508 | N | ILE | A | 272 | 89.669 | 24.398 | −5.166 | 1.00 | 18.41 | A |
| ATOM | 1509 | CA | ILE | A | 272 | 90.860 | 24.035 | −5.934 | 1.00 | 19.20 | A |
| ATOM | 1510 | CB | ILE | A | 272 | 90.526 | 23.730 | −7.412 | 1.00 | 20.04 | A |
| ATOM | 1511 | CG2 | ILE | A | 272 | 91.808 | 23.488 | −8.199 | 1.00 | 17.73 | A |
| ATOM | 1512 | CG1 | ILE | A | 272 | 89.602 | 22.523 | −7.513 | 1.00 | 19.47 | A |
| ATOM | 1513 | CD1 | ILE | A | 272 | 89.001 | 22.386 | −8.872 | 1.00 | 20.31 | A |
| ATOM | 1514 | C | ILE | A | 272 | 91.858 | 25.191 | −5.932 | 1.00 | 19.57 | A |
| ATOM | 1515 | O | ILE | A | 272 | 93.061 | 24.978 | −5.884 | 1.00 | 20.97 | A |
| ATOM | 1516 | N | TYR | A | 273 | 91.338 | 26.413 | −6.028 | 1.00 | 19.42 | A |
| ATOM | 1517 | CA | TYR | A | 273 | 92.157 | 27.606 | −6.041 | 1.00 | 18.41 | A |
| ATOM | 1518 | CB | TYR | A | 273 | 91.272 | 28.826 | −6.294 | 1.00 | 18.70 | A |
| ATOM | 1519 | CG | TYR | A | 273 | 91.998 | 30.147 | −6.252 | 1.00 | 19.81 | A |
| ATOM | 1520 | CD1 | TYR | A | 273 | 92.357 | 30.729 | −5.035 | 1.00 | 21.25 | A |
| ATOM | 1521 | CE1 | TYR | A | 273 | 93.072 | 31.936 | −4.990 | 1.00 | 22.12 | A |
| ATOM | 1522 | CD2 | TYR | A | 273 | 92.366 | 30.804 | −7.433 | 1.00 | 20.45 | A |
| ATOM | 1523 | CE2 | TYR | A | 273 | 93.081 | 32.005 | −7.403 | 1.00 | 20.42 | A |

-continued

| | | | | | | | | | | |
|---|---|---|---|---|---|---|---|---|---|---|
| ATOM | 1524 | CZ | TYR | A | 273 | 93.432 | 32.563 | −6.178 | 1.00 | 23.33 A |
| ATOM | 1525 | OH | TYR | A | 273 | 94.159 | 33.731 | −6.138 | 1.00 | 23.26 A |
| ATOM | 1526 | C | TYR | A | 273 | 92.848 | 27.699 | −4.687 | 1.00 | 19.40 A |
| ATOM | 1527 | O | TYR | A | 273 | 94.051 | 27.945 | −4.598 | 1.00 | 19.44 A |
| ATOM | 1528 | N | GLN | A | 274 | 92.079 | 27.471 | −3.632 | 1.00 | 19.53 A |
| ATOM | 1529 | CA | GLN | A | 274 | 92.602 | 27.517 | −2.278 | 1.00 | 21.26 A |
| ATOM | 1530 | CB | GLN | A | 274 | 91.450 | 27.399 | −1.290 | 1.00 | 22.36 A |
| ATOM | 1531 | CG | GLN | A | 274 | 91.838 | 27.629 | 0.142 | 1.00 | 21.87 A |
| ATOM | 1532 | CD | GLN | A | 274 | 90.643 | 27.531 | 1.054 | 1.00 | 23.64 A |
| ATOM | 1533 | OE1 | GLN | A | 274 | 89.499 | 27.479 | 0.585 | 1.00 | 22.12 A |
| ATOM | 1534 | NE2 | GLN | A | 274 | 90.890 | 27.517 | 2.369 | 1.00 | 24.45 A |
| ATOM | 1535 | C | GLN | A | 274 | 93.656 | 26.435 | −1.980 | 1.00 | 22.20 A |
| ATOM | 1536 | O | GLN | A | 274 | 94.549 | 26.652 | −1.160 | 1.00 | 22.03 A |
| ATOM | 1537 | N | LEU | A | 275 | 93.558 | 25.275 | −2.625 | 1.00 | 21.82 A |
| ATOM | 1538 | CA | LEU | A | 275 | 94.550 | 24.223 | −2.385 | 1.00 | 21.95 A |
| ATOM | 1539 | CB | LEU | A | 275 | 94.104 | 22.886 | −3.015 | 1.00 | 19.19 A |
| ATOM | 1540 | CG | LEU | A | 275 | 92.934 | 22.153 | −2.341 | 1.00 | 19.86 A |
| ATOM | 1541 | CD1 | LEU | A | 275 | 92.528 | 20.915 | −3.134 | 1.00 | 19.79 A |
| ATOM | 1542 | CD2 | LEU | A | 275 | 93.333 | 21.757 | −0.938 | 1.00 | 16.56 A |
| ATOM | 1543 | C | LEU | A | 275 | 95.910 | 24.630 | −2.962 | 1.00 | 21.62 A |
| ATOM | 1544 | O | LEU | A | 275 | 96.950 | 24.414 | −2.353 | 1.00 | 21.98 A |
| ATOM | 1545 | N | VAL | A | 276 | 95.884 | 25.239 | −4.137 | 1.00 | 20.54 A |
| ATOM | 1546 | CA | VAL | A | 276 | 97.095 | 25.639 | −4.828 | 1.00 | 21.48 A |
| ATOM | 1547 | CB | VAL | A | 276 | 96.810 | 25.795 | −6.338 | 1.00 | 21.76 A |
| ATOM | 1548 | CG1 | VAL | A | 276 | 98.035 | 26.269 | −7.061 | 1.00 | 20.72 A |
| ATOM | 1549 | CG2 | VAL | A | 276 | 96.332 | 24.479 | −6.908 | 1.00 | 21.98 A |
| ATOM | 1550 | C | VAL | A | 276 | 97.696 | 26.946 | −4.315 | 1.00 | 23.17 A |
| ATOM | 1551 | O | VAL | A | 276 | 98.913 | 27.055 | −4.141 | 1.00 | 24.82 A |
| ATOM | 1552 | N | ALA | A | 277 | 96.837 | 27.934 | −4.085 | 1.00 | 22.20 A |
| ATOM | 1553 | CA | ALA | A | 277 | 97.271 | 29.230 | −3.628 | 1.00 | 19.31 A |
| ATOM | 1554 | CB | ALA | A | 277 | 96.339 | 30.293 | −4.174 | 1.00 | 19.24 A |
| ATOM | 1555 | C | ALA | A | 277 | 97.380 | 29.350 | −2.113 | 1.00 | 20.10 A |
| ATOM | 1556 | O | ALA | A | 277 | 98.096 | 30.222 | −1.622 | 1.00 | 20.73 A |
| ATOM | 1557 | N | GLY | A | 278 | 96.686 | 28.493 | −1.368 | 1.00 | 19.16 A |
| ATOM | 1558 | CA | GLY | A | 278 | 96.748 | 28.579 | 0.084 | 1.00 | 18.62 A |
| ATOM | 1559 | C | GLY | A | 278 | 95.634 | 29.425 | 0.677 | 1.00 | 21.09 A |
| ATOM | 1560 | O | GLY | A | 278 | 95.462 | 29.483 | 1.903 | 1.00 | 20.36 A |
| ATOM | 1561 | N | LEU | A | 279 | 94.865 | 30.084 | −0.190 | 1.00 | 22.58 A |
| ATOM | 1562 | CA | LEU | A | 279 | 93.742 | 30.917 | 0.254 | 1.00 | 24.03 A |
| ATOM | 1563 | CB | LEU | A | 279 | 94.190 | 32.365 | 0.448 | 1.00 | 23.98 A |
| ATOM | 1564 | CG | LEU | A | 279 | 95.322 | 32.744 | 1.396 | 1.00 | 25.93 A |
| ATOM | 1565 | CD1 | LEU | A | 279 | 95.622 | 34.215 | 1.140 | 1.00 | 25.95 A |
| ATOM | 1566 | CD2 | LEU | A | 279 | 94.950 | 32.511 | 2.873 | 1.00 | 24.23 A |
| ATOM | 1567 | C | LEU | A | 279 | 92.575 | 30.940 | −0.735 | 1.00 | 23.96 A |
| ATOM | 1568 | O | LEU | A | 279 | 92.759 | 30.776 | −1.939 | 1.00 | 23.93 A |
| ATOM | 1569 | N | PRO | A | 280 | 91.353 | 31.151 | −0.231 | 1.00 | 24.60 A |
| ATOM | 1570 | CD | PRO | A | 280 | 90.987 | 31.360 | 1.185 | 1.00 | 23.93 A |
| ATOM | 1571 | CA | PRO | A | 280 | 90.177 | 31.208 | −1.109 | 1.00 | 24.56 A |
| ATOM | 1572 | CB | PRO | A | 280 | 89.024 | 31.319 | −0.116 | 1.00 | 24.33 A |
| ATOM | 1573 | CG | PRO | A | 280 | 89.656 | 32.027 | 1.076 | 1.00 | 24.23 A |
| ATOM | 1574 | C | PRO | A | 280 | 90.324 | 32.453 | −2.033 | 1.00 | 25.82 A |
| ATOM | 1575 | O | PRO | A | 280 | 90.892 | 33.458 | −1.632 | 1.00 | 27.28 A |
| ATOM | 1576 | N | PRO | A | 281 | 89.798 | 32.396 | −3.268 | 1.00 | 25.40 A |
| ATOM | 1577 | CD | PRO | A | 281 | 88.807 | 31.385 | −3.660 | 1.00 | 26.04 A |
| ATOM | 1578 | CA | PRO | A | 281 | 89.862 | 33.470 | −4.272 | 1.00 | 24.99 A |
| ATOM | 1579 | CB | PRO | A | 281 | 89.150 | 32.871 | −5.489 | 1.00 | 24.76 A |
| ATOM | 1580 | CG | PRO | A | 281 | 88.882 | 31.442 | −5.137 | 1.00 | 26.48 A |
| ATOM | 1581 | C | PRO | A | 281 | 89.254 | 34.836 | −3.921 | 1.00 | 25.24 A |
| ATOM | 1582 | O | PRO | A | 281 | 89.803 | 35.886 | −4.272 | 1.00 | 25.07 A |
| ATOM | 1583 | N | PHE | A | 282 | 88.103 | 34.821 | −3.264 | 1.00 | 24.47 A |
| ATOM | 1584 | CA | PHE | A | 282 | 87.435 | 36.059 | −2.918 | 1.00 | 24.29 A |
| ATOM | 1585 | CB | PHE | A | 282 | 85.964 | 35.961 | −3.320 | 1.00 | 23.11 A |
| ATOM | 1586 | CG | PHE | A | 282 | 85.759 | 35.596 | −4.774 | 1.00 | 21.99 A |
| ATOM | 1587 | CD1 | PHE | A | 282 | 85.936 | 36.543 | −5.775 | 1.00 | 20.97 A |
| ATOM | 1588 | CD2 | PHE | A | 282 | 85.448 | 34.285 | −5.139 | 1.00 | 21.76 A |
| ATOM | 1589 | CE1 | PHE | A | 282 | 85.812 | 36.194 | −7.124 | 1.00 | 20.59 A |
| ATOM | 1590 | CE2 | PHE | A | 282 | 85.325 | 33.923 | −6.469 | 1.00 | 20.98 A |
| ATOM | 1591 | CZ | PHE | A | 282 | 85.509 | 34.885 | −7.471 | 1.00 | 23.01 A |
| ATOM | 1592 | C | PHE | A | 282 | 87.579 | 36.366 | −1.435 | 1.00 | 25.85 A |
| ATOM | 1593 | O | PHE | A | 282 | 86.963 | 35.707 | −0.596 | 1.00 | 27.04 A |
| ATOM | 1594 | N | ARG | A | 283 | 88.414 | 37.358 | −1.124 | 1.00 | 27.56 A |
| ATOM | 1595 | CA | ARG | A | 283 | 88.676 | 37.784 | 0.260 | 1.00 | 27.41 A |
| ATOM | 1596 | CB | ARG | A | 283 | 90.116 | 37.451 | 0.648 | 1.00 | 28.05 A |
| ATOM | 1597 | CG | ARG | A | 283 | 90.523 | 36.020 | 0.327 | 1.00 | 32.73 A |
| ATOM | 1598 | CD | ARG | A | 283 | 91.944 | 35.722 | 0.788 | 1.00 | 36.54 A |
| ATOM | 1599 | NE | ARG | A | 283 | 92.942 | 36.490 | 0.043 | 1.00 | 39.92 A |
| ATOM | 1600 | CZ | ARG | A | 283 | 93.202 | 36.329 | −1.253 | 1.00 | 42.59 A |
| ATOM | 1601 | NH1 | ARG | A | 283 | 92.544 | 35.421 | −1.961 | 1.00 | 44.54 A |
| ATOM | 1602 | NH2 | ARG | A | 283 | 94.112 | 37.090 | −1.853 | 1.00 | 43.94 A |

-continued

| | | | | | | | | | | |
|---|---|---|---|---|---|---|---|---|---|---|
| ATOM | 1603 | C | ARG | A | 283 | 88.445 | 39.291 | 0.394 | 1.00 | 27.01 A |
| ATOM | 1604 | O | ARG | A | 283 | 88.682 | 40.047 | −0.557 | 1.00 | 26.54 A |
| ATOM | 1605 | N | ALA | A | 284 | 87.977 | 39.724 | 1.568 | 1.00 | 26.05 A |
| ATOM | 1606 | CA | ALA | A | 284 | 87.694 | 41.135 | 1.812 | 1.00 | 23.42 A |
| ATOM | 1607 | CB | ALA | A | 284 | 86.529 | 41.579 | 0.967 | 1.00 | 21.82 A |
| ATOM | 1608 | C | ALA | A | 284 | 87.386 | 41.383 | 3.280 | 1.00 | 24.72 A |
| ATOM | 1609 | O | ALA | A | 284 | 87.193 | 40.440 | 4.048 | 1.00 | 24.83 A |
| ATOM | 1610 | N | GLY | A | 285 | 87.330 | 42.663 | 3.659 | 1.00 | 25.04 A |
| ATOM | 1611 | CA | GLY | A | 285 | 87.055 | 43.039 | 5.035 | 1.00 | 23.67 A |
| ATOM | 1612 | C | GLY | A | 285 | 85.761 | 42.542 | 5.652 | 1.00 | 25.13 A |
| ATOM | 1613 | O | GLY | A | 285 | 85.718 | 42.302 | 6.855 | 1.00 | 26.60 A |
| ATOM | 1614 | N | ASN | A | 286 | 84.700 | 42.399 | 4.862 | 1.00 | 24.84 A |
| ATOM | 1615 | CA | ASN | A | 286 | 83.418 | 41.923 | 5.391 | 1.00 | 23.82 A |
| ATOM | 1616 | CB | ASN | A | 286 | 82.567 | 43.098 | 5.899 | 1.00 | 23.66 A |
| ATOM | 1617 | CG | ASN | A | 286 | 82.362 | 44.190 | 4.843 | 1.00 | 24.14 A |
| ATOM | 1618 | OD1 | ASN | A | 286 | 81.835 | 43.947 | 3.747 | 1.00 | 22.27 A |
| ATOM | 1619 | ND2 | ASN | A | 286 | 82.776 | 45.402 | 5.178 | 1.00 | 24.49 A |
| ATOM | 1620 | C | ASN | A | 286 | 82.672 | 41.185 | 4.296 | 1.00 | 24.75 A |
| ATOM | 1621 | O | ASN | A | 286 | 83.124 | 41.160 | 3.153 | 1.00 | 25.32 A |
| ATOM | 1622 | N | GLU | A | 287 | 81.522 | 40.610 | 4.630 | 1.00 | 26.04 A |
| ATOM | 1623 | CA | GLU | A | 287 | 80.746 | 39.865 | 3.641 | 1.00 | 27.47 A |
| ATOM | 1624 | CB | GLU | A | 287 | 79.549 | 39.175 | 4.287 | 1.00 | 30.33 A |
| ATOM | 1625 | CG | GLU | A | 287 | 79.935 | 38.202 | 5.364 | 1.00 | 36.51 A |
| ATOM | 1626 | CD | GLU | A | 287 | 78.792 | 37.288 | 5.766 | 1.00 | 41.45 A |
| ATOM | 1627 | OE1 | GLU | A | 287 | 77.608 | 37.712 | 5.641 | 1.00 | 43.02 A |
| ATOM | 1628 | OE2 | GLU | A | 287 | 79.092 | 36.155 | 6.222 | 1.00 | 41.33 A |
| ATOM | 1629 | C | GLU | A | 287 | 80.250 | 40.679 | 2.467 | 1.00 | 25.95 A |
| ATOM | 1630 | O | GLU | A | 287 | 80.279 | 40.203 | 1.330 | 1.00 | 25.67 A |
| ATOM | 1631 | N | TYR | A | 288 | 79.772 | 41.893 | 2.730 | 1.00 | 25.20 A |
| ATOM | 1632 | CA | TYR | A | 288 | 79.276 | 42.731 | 1.644 | 1.00 | 22.91 A |
| ATOM | 1633 | CB | TYR | A | 288 | 78.870 | 44.113 | 2.152 | 1.00 | 22.98 A |
| ATOM | 1634 | CG | TYR | A | 288 | 78.459 | 45.068 | 1.038 | 1.00 | 23.01 A |
| ATOM | 1635 | CD1 | TYR | A | 288 | 77.166 | 45.031 | 0.478 | 1.00 | 24.16 A |
| ATOM | 1636 | CE1 | TYR | A | 288 | 76.814 | 45.869 | −0.589 | 1.00 | 22.73 A |
| ATOM | 1637 | CD2 | TYR | A | 288 | 79.376 | 45.965 | 0.508 | 1.00 | 21.34 A |
| ATOM | 1638 | CE2 | TYR | A | 288 | 79.043 | 46.796 | −0.551 | 1.00 | 23.71 A |
| ATOM | 1639 | CZ | TYR | A | 288 | 77.771 | 46.748 | −1.099 | 1.00 | 25.48 A |
| ATOM | 1640 | OH | TYR | A | 288 | 77.490 | 47.571 | −2.172 | 1.00 | 26.98 A |
| ATOM | 1641 | C | TYR | A | 288 | 80.352 | 42.882 | 0.578 | 1.00 | 22.37 A |
| ATOM | 1642 | O | TYR | A | 288 | 80.068 | 42.735 | −0.603 | 1.00 | 22.65 A |
| ATOM | 1643 | N | LEU | A | 289 | 81.590 | 43.155 | 0.993 | 1.00 | 22.04 A |
| ATOM | 1644 | CA | LEU | A | 289 | 82.691 | 43.326 | 0.037 | 1.00 | 23.92 A |
| ATOM | 1645 | CB | LEU | A | 289 | 83.927 | 43.907 | 0.748 | 1.00 | 21.71 A |
| ATOM | 1646 | CG | LEU | A | 289 | 83.661 | 45.326 | 1.298 | 1.00 | 23.89 A |
| ATOM | 1647 | CD1 | LEU | A | 289 | 84.716 | 45.787 | 2.326 | 1.00 | 17.24 A |
| ATOM | 1648 | CD2 | LEU | A | 289 | 83.570 | 46.273 | 0.118 | 1.00 | 19.08 A |
| ATOM | 1649 | C | LEU | A | 289 | 83.050 | 42.025 | −0.693 | 1.00 | 24.50 A |
| ATOM | 1650 | O | LEU | A | 289 | 83.446 | 42.042 | −1.852 | 1.00 | 24.85 A |
| ATOM | 1651 | N | ILE | A | 290 | 82.906 | 40.904 | −0.002 | 1.00 | 24.71 A |
| ATOM | 1652 | CA | ILE | A | 290 | 83.182 | 39.601 | −0.570 | 1.00 | 25.86 A |
| ATOM | 1653 | CB | ILE | A | 290 | 83.131 | 38.521 | 0.528 | 1.00 | 26.67 A |
| ATOM | 1654 | CG2 | ILE | A | 290 | 83.229 | 37.154 | −0.087 | 1.00 | 27.57 A |
| ATOM | 1655 | CG1 | ILE | A | 290 | 84.282 | 38.736 | 1.511 | 1.00 | 28.90 A |
| ATOM | 1656 | CD1 | ILE | A | 290 | 84.173 | 37.928 | 2.798 | 1.00 | 28.83 A |
| ATOM | 1657 | C | ILE | A | 290 | 82.127 | 39.303 | −1.637 | 1.00 | 26.89 A |
| ATOM | 1658 | O | ILE | A | 290 | 82.446 | 38.879 | −2.757 | 1.00 | 26.18 A |
| ATOM | 1659 | N | PHE | A | 291 | 80.864 | 39.531 | −1.294 | 1.00 | 27.48 A |
| ATOM | 1660 | CA | PHE | A | 291 | 79.789 | 39.287 | −2.249 | 1.00 | 28.46 A |
| ATOM | 1661 | CB | PHE | A | 291 | 78.434 | 39.587 | −1.620 | 1.00 | 27.24 A |
| ATOM | 1662 | CG | PHE | A | 291 | 78.079 | 38.664 | −0.496 | 1.00 | 27.02 A |
| ATOM | 1663 | CD1 | PHE | A | 291 | 78.716 | 37.431 | −0.365 | 1.00 | 26.90 A |
| ATOM | 1664 | CD2 | PHE | A | 291 | 77.074 | 38.996 | 0.399 | 1.00 | 25.83 A |
| ATOM | 1665 | CE1 | PHE | A | 291 | 78.353 | 36.545 | 0.637 | 1.00 | 27.02 A |
| ATOM | 1666 | CE2 | PHE | A | 291 | 76.700 | 38.109 | 1.412 | 1.00 | 28.02 A |
| ATOM | 1667 | CZ | PHE | A | 291 | 77.338 | 36.882 | 1.532 | 1.00 | 26.74 A |
| ATOM | 1668 | C | PHE | A | 291 | 79.971 | 40.159 | −3.467 | 1.00 | 29.11 A |
| ATOM | 1669 | O | PHE | A | 291 | 79.595 | 39.787 | −4.584 | 1.00 | 30.18 A |
| ATOM | 1670 | N | GLN | A | 292 | 80.559 | 41.324 | −3.240 | 1.00 | 28.88 A |
| ATOM | 1671 | CA | GLN | A | 292 | 80.783 | 42.280 | −4.304 | 1.00 | 30.00 A |
| ATOM | 1672 | CB | GLN | A | 292 | 81.215 | 43.604 | −3.679 | 1.00 | 32.57 A |
| ATOM | 1673 | CG | GLN | A | 292 | 81.191 | 44.799 | −4.599 | 1.00 | 35.12 A |
| ATOM | 1674 | CD | GLN | A | 292 | 81.208 | 46.113 | −3.817 | 1.00 | 38.65 A |
| ATOM | 1675 | OE1 | GLN | A | 292 | 82.159 | 46.409 | −3.078 | 1.00 | 39.67 A |
| ATOM | 1676 | NE2 | GLN | A | 292 | 80.150 | 46.903 | −3.972 | 1.00 | 38.94 A |
| ATOM | 1677 | C | GLN | A | 292 | 81.822 | 41.755 | −5.296 | 1.00 | 28.96 A |
| ATOM | 1678 | O | GLN | A | 292 | 81.633 | 41.844 | −6.510 | 1.00 | 28.45 A |
| ATOM | 1679 | N | LYS | A | 293 | 82.910 | 41.193 | −4.787 | 1.00 | 26.32 A |
| ATOM | 1680 | CA | LYS | A | 293 | 83.930 | 40.661 | −5.669 | 1.00 | 26.90 A |
| ATOM | 1681 | CB | LYS | A | 293 | 85.174 | 40.319 | −4.858 | 1.00 | 28.03 A |

-continued

| | | | | | | | | | | |
|---|---|---|---|---|---|---|---|---|---|---|
| ATOM | 1682 | CG | LYS | A | 293 | 85.777 | 41.539 | −4.177 | 1.00 | 28.52 A |
| ATOM | 1683 | CD | LYS | A | 293 | 87.065 | 41.208 | −3.482 | 1.00 | 29.14 A |
| ATOM | 1684 | CE | LYS | A | 293 | 87.912 | 42.449 | −3.269 | 1.00 | 30.09 A |
| ATOM | 1685 | NZ | LYS | A | 293 | 89.165 | 42.157 | −2.490 | 1.00 | 30.06 A |
| ATOM | 1686 | C | LYS | A | 293 | 83.414 | 39.432 | −6.434 | 1.00 | 26.13 A |
| ATOM | 1687 | O | LYS | A | 293 | 83.721 | 39.231 | −7.617 | 1.00 | 26.02 A |
| ATOM | 1688 | N | ILE | A | 294 | 82.617 | 38.621 | −5.755 | 1.00 | 24.49 A |
| ATOM | 1689 | CA | ILE | A | 294 | 82.047 | 37.429 | −6.362 | 1.00 | 24.40 A |
| ATOM | 1690 | CB | ILE | A | 294 | 81.168 | 36.680 | −5.340 | 1.00 | 23.24 A |
| ATOM | 1691 | CG2 | ILE | A | 294 | 80.154 | 35.763 | −6.046 | 1.00 | 21.00 A |
| ATOM | 1692 | CG1 | ILE | A | 294 | 82.072 | 35.929 | −4.365 | 1.00 | 19.23 A |
| ATOM | 1693 | CD1 | ILE | A | 294 | 81.388 | 35.559 | −3.067 | 1.00 | 17.91 A |
| ATOM | 1694 | C | ILE | A | 294 | 81.224 | 37.744 | −7.608 | 1.00 | 26.38 A |
| ATOM | 1695 | O | ILE | A | 294 | 81.428 | 37.139 | −8.661 | 1.00 | 25.96 A |
| ATOM | 1696 | N | ILE | A | 295 | 80.303 | 38.694 | −7.505 | 1.00 | 28.38 A |
| ATOM | 1697 | CA | ILE | A | 295 | 79.467 | 39.018 | −8.659 | 1.00 | 31.11 A |
| ATOM | 1698 | CB | ILE | A | 295 | 78.243 | 39.852 | −8.248 | 1.00 | 31.46 A |
| ATOM | 1699 | CG2 | ILE | A | 295 | 77.548 | 39.181 | −7.068 | 1.00 | 32.78 A |
| ATOM | 1700 | CG1 | ILE | A | 295 | 78.669 | 41.268 | −7.871 | 1.00 | 31.79 A |
| ATOM | 1701 | CD1 | ILE | A | 295 | 77.518 | 42.132 | −7.438 | 1.00 | 33.46 A |
| ATOM | 1702 | C | ILE | A | 295 | 80.201 | 39.731 | −9.798 | 1.00 | 31.35 A |
| ATOM | 1703 | O | ILE | A | 295 | 79.709 | 39.784 | −10.930 | 1.00 | 32.03 A |
| ATOM | 1704 | N | LYS | A | 296 | 81.374 | 40.269 | −9.511 | 1.00 | 30.68 A |
| ATOM | 1705 | CA | LYS | A | 296 | 82.129 | 40.937 | −10.552 | 1.00 | 31.64 A |
| ATOM | 1706 | CB | LYS | A | 296 | 82.683 | 42.275 | −10.041 | 1.00 | 32.01 A |
| ATOM | 1707 | CG | LYS | A | 296 | 81.605 | 43.213 | −9.520 | 1.00 | 34.12 A |
| ATOM | 1708 | CD | LYS | A | 296 | 82.184 | 44.441 | −8.841 | 1.00 | 37.38 A |
| ATOM | 1709 | CE | LYS | A | 296 | 82.299 | 45.609 | −9.803 | 1.00 | 40.30 A |
| ATOM | 1710 | NZ | LYS | A | 296 | 82.864 | 46.819 | −9.119 | 1.00 | 42.94 A |
| ATOM | 1711 | C | LYS | A | 296 | 83.258 | 40.010 | −10.966 | 1.00 | 31.87 A |
| ATOM | 1712 | O | LYS | A | 296 | 84.135 | 40.398 | −11.745 | 1.00 | 32.98 A |
| ATOM | 1713 | N | LEU | A | 297 | 83.227 | 38.780 | −10.443 | 1.00 | 30.62 A |
| ATOM | 1714 | CA | LEU | A | 297 | 84.253 | 37.775 | −10.735 | 1.00 | 29.78 A |
| ATOM | 1715 | CB | LEU | A | 297 | 84.100 | 37.253 | −12.169 | 1.00 | 29.42 A |
| ATOM | 1716 | CG | LEU | A | 297 | 84.802 | 35.931 | −12.527 | 1.00 | 29.13 A |
| ATOM | 1717 | CD1 | LEU | A | 297 | 84.142 | 34.776 | −11.783 | 1.00 | 27.91 A |
| ATOM | 1718 | CD2 | LEU | A | 297 | 84.725 | 35.682 | −14.024 | 1.00 | 26.86 A |
| ATOM | 1719 | C | LEU | A | 297 | 85.622 | 38.436 | −10.565 | 1.00 | 29.62 A |
| ATOM | 1720 | O | LEU | A | 297 | 86.489 | 38.333 | −11.419 | 1.00 | 28.99 A |
| ATOM | 1721 | N | GLU | A | 298 | 85.807 | 39.091 | −9.427 | 1.00 | 29.81 A |
| ATOM | 1722 | CA | GLU | A | 298 | 87.027 | 39.826 | −9.143 | 1.00 | 30.88 A |
| ATOM | 1723 | CB | GLU | A | 298 | 86.622 | 41.166 | −8.510 | 1.00 | 33.22 A |
| ATOM | 1724 | CG | GLU | A | 298 | 87.754 | 42.136 | −8.228 | 1.00 | 38.19 A |
| ATOM | 1725 | CD | GLU | A | 298 | 87.317 | 43.274 | −7.303 | 1.00 | 41.34 A |
| ATOM | 1726 | OE1 | GLU | A | 298 | 86.416 | 44.054 | −7.684 | 1.00 | 43.93 A |
| ATOM | 1727 | OE2 | GLU | A | 298 | 87.867 | 43.382 | −6.187 | 1.00 | 43.19 A |
| ATOM | 1728 | C | GLU | A | 298 | 88.071 | 39.110 | −8.269 | 1.00 | 29.28 A |
| ATOM | 1729 | O | GLU | A | 298 | 88.066 | 39.230 | −7.045 | 1.00 | 30.04 A |
| ATOM | 1730 | N | TYR | A | 299 | 88.972 | 38.375 | −8.906 | 1.00 | 26.46 A |
| ATOM | 1731 | CA | TYR | A | 299 | 90.034 | 37.669 | −8.194 | 1.00 | 26.46 A |
| ATOM | 1732 | CB | TYR | A | 299 | 89.548 | 36.315 | −7.640 | 1.00 | 24.23 A |
| ATOM | 1733 | CG | TYR | A | 299 | 89.403 | 35.252 | −8.709 | 1.00 | 23.32 A |
| ATOM | 1734 | CD1 | TYR | A | 299 | 88.369 | 35.318 | −9.653 | 1.00 | 23.42 A |
| ATOM | 1735 | CE1 | TYR | A | 299 | 88.274 | 34.392 | −10.686 | 1.00 | 23.13 A |
| ATOM | 1736 | CD2 | TYR | A | 299 | 90.337 | 34.227 | −8.829 | 1.00 | 21.77 A |
| ATOM | 1737 | CE2 | TYR | A | 299 | 90.250 | 33.292 | −9.864 | 1.00 | 21.81 A |
| ATOM | 1738 | CZ | TYR | A | 299 | 89.214 | 33.379 | −10.784 | 1.00 | 22.35 A |
| ATOM | 1739 | OH | TYR | A | 299 | 89.089 | 32.444 | −11.780 | 1.00 | 21.61 A |
| ATOM | 1740 | C | TYR | A | 299 | 91.102 | 37.416 | −9.245 | 1.00 | 28.31 A |
| ATOM | 1741 | O | TYR | A | 299 | 90.864 | 37.622 | −10.426 | 1.00 | 27.25 A |
| ATOM | 1742 | N | ASP | A | 300 | 92.277 | 36.959 | −8.844 | 1.00 | 30.57 A |
| ATOM | 1743 | CA | ASP | A | 300 | 93.282 | 36.687 | −9.851 | 1.00 | 33.57 A |
| ATOM | 1744 | CB | ASP | A | 300 | 94.012 | 37.980 | −10.193 | 1.00 | 38.77 A |
| ATOM | 1745 | CG | ASP | A | 300 | 94.382 | 38.768 | −8.968 | 1.00 | 43.17 A |
| ATOM | 1746 | OD1 | ASP | A | 300 | 95.245 | 38.283 | −8.197 | 1.00 | 46.59 A |
| ATOM | 1747 | OD2 | ASP | A | 300 | 93.802 | 39.865 | −8.773 | 1.00 | 45.78 A |
| ATOM | 1748 | C | ASP | A | 300 | 94.232 | 35.607 | −9.364 | 1.00 | 33.20 A |
| ATOM | 1749 | O | ASP | A | 300 | 94.311 | 35.354 | −8.169 | 1.00 | 33.46 A |
| ATOM | 1750 | N | PHE | A | 301 | 94.937 | 34.959 | −10.287 | 1.00 | 32.16 A |
| ATOM | 1751 | CA | PHE | A | 301 | 95.853 | 33.892 | −9.910 | 1.00 | 33.41 A |
| ATOM | 1752 | CB | PHE | A | 301 | 95.922 | 32.813 | −11.001 | 1.00 | 32.89 A |
| ATOM | 1753 | CG | PHE | A | 301 | 94.590 | 32.240 | −11.403 | 1.00 | 33.05 A |
| ATOM | 1754 | CD1 | PHE | A | 301 | 93.763 | 32.921 | −12.297 | 1.00 | 31.61 A |
| ATOM | 1755 | CD2 | PHE | A | 301 | 94.171 | 31.006 | −10.905 | 1.00 | 30.94 A |
| ATOM | 1756 | CE1 | PHE | A | 301 | 92.548 | 32.387 | −12.687 | 1.00 | 31.29 A |
| ATOM | 1757 | CE2 | PHE | A | 301 | 92.961 | 30.466 | −11.287 | 1.00 | 31.42 A |
| ATOM | 1758 | CZ | PHE | A | 301 | 92.142 | 31.157 | −12.184 | 1.00 | 32.69 A |
| ATOM | 1759 | C | PHE | A | 301 | 97.287 | 34.359 | −9.649 | 1.00 | 34.23 A |
| ATOM | 1760 | O | PHE | A | 301 | 97.784 | 35.274 | −10.303 | 1.00 | 33.66 A |

-continued

| | | | | | | | | | | |
|---|---|---|---|---|---|---|---|---|---|---|
| ATOM | 1761 | N | PRO | A | 302 | 97.962 | 33.750 | −8.665 | 1.00 | 35.45 A |
| ATOM | 1762 | CD | PRO | A | 302 | 97.426 | 32.932 | −27.564 | 1.00 | 35.55 A |
| ATOM | 1763 | CA | PRO | A | 302 | 99.347 | 34.145 | −8.395 | 1.00 | 35.82 A |
| ATOM | 1764 | CB | PRO | A | 302 | 99.612 | 33.571 | −7.009 | 1.00 | 35.09 A |
| ATOM | 1765 | CG | PRO | A | 302 | 98.682 | 32.401 | −6.933 | 1.00 | 34.93 A |
| ATOM | 1766 | C | PRO | A | 302 | 100.214 | 33.506 | −9.485 | 1.00 | 37.48 A |
| ATOM | 1767 | O | PRO | A | 302 | 99.830 | 32.504 | −10.083 | 1.00 | 37.30 A |
| ATOM | 1768 | N | ALA | A | 303 | 101.370 | 34.100 | −9.744 | 1.00 | 39.16 A |
| ATOM | 1769 | CA | ALA | A | 303 | 102.293 | 33.641 | −10.775 | 1.00 | 39.50 A |
| ATOM | 1770 | CB | ALA | A | 303 | 103.612 | 34.393 | −10.640 | 1.00 | 39.58 A |
| ATOM | 1771 | C | ALA | A | 303 | 102.577 | 32.148 | −10.832 | 1.00 | 41.05 A |
| ATOM | 1772 | O | ALA | A | 303 | 102.642 | 31.569 | −11.920 | 1.00 | 42.39 A |
| ATOM | 1773 | N | ALA | A | 304 | 102.758 | 31.526 | −9.671 | 1.00 | 40.38 A |
| ATOM | 1774 | CA | ALA | A | 304 | 103.099 | 30.105 | −9.614 | 1.00 | 39.93 A |
| ATOM | 1775 | CB | ALA | A | 304 | 103.627 | 29.772 | −8.212 | 1.00 | 41.64 A |
| ATOM | 1776 | C | ALA | A | 304 | 102.025 | 29.089 | −10.002 | 1.00 | 38.27 A |
| ATOM | 1777 | O | ALA | A | 304 | 102.343 | 27.993 | −10.453 | 1.00 | 39.29 A |
| ATOM | 1778 | N | PHE | A | 305 | 100.764 | 29.453 | −9.813 | 1.00 | 35.83 A |
| ATOM | 1779 | CA | PHE | A | 305 | 99.614 | 28.587 | −10.085 | 1.00 | 33.62 A |
| ATOM | 1780 | CB | PHE | A | 305 | 98.376 | 29.475 | −10.278 | 1.00 | 32.70 A |
| ATOM | 1781 | CG | PHE | A | 305 | 97.096 | 28.857 | −9.796 | 1.00 | 31.41 A |
| ATOM | 1782 | CD1 | PHE | A | 305 | 96.422 | 27.915 | −10.574 | 1.00 | 30.30 A |
| ATOM | 1783 | CD2 | PHE | A | 305 | 96.556 | 29.225 | −8.562 | 1.00 | 30.99 A |
| ATOM | 1784 | CE1 | PHE | A | 305 | 95.230 | 27.350 | −10.136 | 1.00 | 29.76 A |
| ATOM | 1785 | CE2 | PHE | A | 305 | 95.352 | 28.663 | −8.105 | 1.00 | 30.08 A |
| ATOM | 1786 | CZ | PHE | A | 305 | 94.689 | 27.725 | −8.897 | 1.00 | 30.22 A |
| ATOM | 1787 | C | PHE | A | 305 | 99.735 | 27.580 | −11.241 | 1.00 | 32.03 A |
| ATOM | 1788 | O | PHE | A | 305 | 99.767 | 27.962 | −12.405 | 1.00 | 32.54 A |
| ATOM | 1789 | N | PHE | A | 306 | 99.781 | 26.290 | −10.914 | 1.00 | 31.58 A |
| ATOM | 1790 | CA | PHE | A | 306 | 99.886 | 25.235 | −11.932 | 1.00 | 30.32 A |
| ATOM | 1791 | CB | PHE | A | 306 | 99.518 | 23.875 | −11.338 | 1.00 | 29.86 A |
| ATOM | 1792 | CG | PHE | A | 306 | 100.087 | 23.639 | −9.971 | 1.00 | 30.29 A |
| ATOM | 1793 | CD1 | PHE | A | 306 | 101.447 | 23.783 | −9.733 | 1.00 | 30.37 A |
| ATOM | 1794 | CD2 | PHE | A | 306 | 99.259 | 23.275 | −8.919 | 1.00 | 30.23 A |
| ATOM | 1795 | CE1 | PHE | A | 306 | 101.975 | 23.570 | −8.465 | 1.00 | 30.98 A |
| ATOM | 1796 | CE2 | PHE | A | 306 | 99.773 | 23.061 | −7.648 | 1.00 | 30.91 A |
| ATOM | 1797 | CZ | PHE | A | 306 | 101.136 | 23.210 | −7.418 | 1.00 | 31.14 A |
| ATOM | 1798 | C | PHE | A | 306 | 98.949 | 25.545 | −13.096 | 1.00 | 29.48 A |
| ATOM | 1799 | O | PHE | A | 306 | 97.738 | 25.631 | −12.920 | 1.00 | 30.39 A |
| ATOM | 1800 | N | PRO | A | 307 | 99.501 | 25.701 | −14.309 | 1.00 | 28.76 A |
| ATOM | 1801 | CD | PRO | A | 307 | 100.934 | 25.575 | −14.635 | 1.00 | 27.67 A |
| ATOM | 1802 | CA | PRO | A | 307 | 98.731 | 26.014 | −15.520 | 1.00 | 27.24 A |
| ATOM | 1803 | CB | PRO | A | 307 | 99.757 | 25.848 | −16.635 | 1.00 | 25.23 A |
| ATOM | 1804 | CG | PRO | A | 307 | 101.010 | 26.262 | −15.978 | 1.00 | 25.61 A |
| ATOM | 1805 | C | PRO | A | 307 | 97.457 | 25.221 | −15.787 | 1.00 | 25.86 A |
| ATOM | 1806 | O | PRO | A | 307 | 96.419 | 25.808 | −16.098 | 1.00 | 24.65 A |
| ATOM | 1807 | N | LYS | A | 308 | 97.521 | 23.901 | −15.682 | 1.00 | 25.13 A |
| ATOM | 1808 | CA | LYS | A | 308 | 96.330 | 23.109 | −15.952 | 1.00 | 24.53 A |
| ATOM | 1809 | CB | LYS | A | 308 | 96.689 | 21.640 | −16.136 | 1.00 | 24.86 A |
| ATOM | 1810 | CG | LYS | A | 308 | 97.361 | 21.413 | −17.490 | 1.00 | 25.50 A |
| ATOM | 1811 | CD | LYS | A | 308 | 97.987 | 20.047 | −17.616 | 1.00 | 27.33 A |
| ATOM | 1812 | CE | LYS | A | 308 | 98.678 | 19.886 | −18.961 | 1.00 | 29.39 A |
| ATOM | 1813 | NZ | LYS | A | 308 | 99.232 | 18.505 | −19.146 | 1.00 | 32.38 A |
| ATOM | 1814 | C | LYS | A | 308 | 95.282 | 23.293 | −14.890 | 1.00 | 24.82 A |
| ATOM | 1815 | O | LYS | A | 308 | 94.085 | 23.281 | −15.193 | 1.00 | 24.89 A |
| ATOM | 1816 | N | ALA | A | 309 | 95.716 | 23.489 | −13.647 | 1.00 | 24.73 A |
| ATOM | 1817 | CA | ALA | A | 309 | 94.758 | 23.716 | −12.573 | 1.00 | 25.03 A |
| ATOM | 1818 | CB | ALA | A | 309 | 95.445 | 23.662 | −11.208 | 1.00 | 24.10 A |
| ATOM | 1819 | C | ALA | A | 309 | 94.140 | 25.094 | −12.816 | 1.00 | 25.34 A |
| ATOM | 1820 | O | ALA | A | 309 | 92.934 | 25.273 | −12.679 | 1.00 | 26.34 A |
| ATOM | 1821 | N | ARG | A | 310 | 94.958 | 26.067 | −13.198 | 1.00 | 26.07 A |
| ATOM | 1822 | CA | ARG | A | 310 | 94.419 | 27.396 | −13.453 | 1.00 | 28.32 A |
| ATOM | 1823 | CB | ARG | A | 310 | 95.513 | 28.359 | −13.908 | 1.00 | 29.31 A |
| ATOM | 1824 | CG | ARG | A | 310 | 94.940 | 29.708 | −14.288 | 1.00 | 31.58 A |
| ATOM | 1825 | CD | ARG | A | 310 | 95.917 | 30.588 | −15.030 | 1.00 | 31.47 A |
| ATOM | 1826 | NE | ARG | A | 310 | 95.275 | 31.825 | −15.473 | 1.00 | 34.52 A |
| ATOM | 1827 | CZ | ARG | A | 310 | 95.771 | 33.050 | −15.276 | 1.00 | 35.51 A |
| ATOM | 1828 | NH1 | ARG | A | 310 | 96.929 | 33.205 | −14.633 | 1.00 | 33.99 A |
| ATOM | 1829 | NH2 | ARG | A | 310 | 95.106 | 34.124 | −15.720 | 1.00 | 32.10 A |
| ATOM | 1830 | C | ARG | A | 310 | 93.331 | 27.348 | −14.521 | 1.00 | 29.03 A |
| ATOM | 1831 | O | ARG | A | 310 | 92.308 | 28.034 | −14.418 | 1.00 | 29.32 A |
| ATOM | 1832 | N | ASP | A | 311 | 93.548 | 26.536 | −15.551 | 1.00 | 29.06 A |
| ATOM | 1833 | CA | ASP | A | 311 | 92.571 | 26.432 | −16.620 | 1.00 | 29.87 A |
| ATOM | 1834 | CB | ASP | A | 311 | 93.156 | 25.636 | −17.776 | 1.00 | 31.71 A |
| ATOM | 1835 | CG | ASP | A | 311 | 92.207 | 25.537 | −18.953 | 1.00 | 34.71 A |
| ATOM | 1836 | OD1 | ASP | A | 311 | 91.288 | 24.690 | −18.912 | 1.00 | 36.90 A |
| ATOM | 1837 | OD2 | ASP | A | 311 | 92.378 | 26.312 | −19.918 | 1.00 | 36.33 A |
| ATOM | 1838 | C | ASP | A | 311 | 91.264 | 25.800 | −16.128 | 1.00 | 29.70 A |
| ATOM | 1839 | O | ASP | A | 311 | 90.169 | 26.238 | −16.513 | 1.00 | 29.95 A |

-continued

| | | | | | | | | | |
|---|---|---|---|---|---|---|---|---|---|
| ATOM | 1840 | N | LEU | A | 312 | 91.383 | 24.778 | −15.282 | 1.00 | 26.64 | A |
| ATOM | 1841 | CA | LEU | A | 312 | 90.215 | 24.112 | −14.715 | 1.00 | 24.92 | A |
| ATOM | 1842 | CB | LEU | A | 312 | 90.645 | 22.911 | −13.869 | 1.00 | 23.93 | A |
| ATOM | 1843 | CG | LEU | A | 312 | 89.504 | 22.112 | −13.227 | 1.00 | 24.48 | A |
| ATOM | 1844 | CD1 | LEU | A | 312 | 88.569 | 21.610 | −14.296 | 1.00 | 25.07 | A |
| ATOM | 1845 | CD2 | LEU | A | 312 | 90.061 | 20.945 | −12.460 | 1.00 | 25.13 | A |
| ATOM | 1846 | C | LEU | A | 312 | 89.412 | 25.095 | −13.841 | 1.00 | 23.85 | A |
| ATOM | 1847 | O | LEU | A | 312 | 88.182 | 25.136 | −13.896 | 1.00 | 21.21 | A |
| ATOM | 1848 | N | VAL | A | 313 | 90.121 | 25.886 | −13.042 | 1.00 | 23.12 | A |
| ATOM | 1849 | CA | VAL | A | 313 | 89.484 | 26.865 | −12.171 | 1.00 | 23.55 | A |
| ATOM | 1850 | CB | VAL | A | 313 | 90.536 | 27.583 | −11.297 | 1.00 | 22.33 | A |
| ATOM | 1851 | CG1 | VAL | A | 313 | 89.898 | 28.752 | −10.559 | 1.00 | 19.05 | A |
| ATOM | 1852 | CG2 | VAL | A | 313 | 91.144 | 26.607 | −10.305 | 1.00 | 19.89 | A |
| ATOM | 1853 | C | VAL | A | 313 | 88.701 | 27.915 | −12.975 | 1.00 | 25.59 | A |
| ATOM | 1854 | O | VAL | A | 313 | 87.590 | 28.305 | −12.605 | 1.00 | 26.57 | A |
| ATOM | 1855 | N | GLU | A | 314 | 89.278 | 28.378 | −14.076 | 1.00 | 26.08 | A |
| ATOM | 1856 | CA | GLU | A | 314 | 88.598 | 29.370 | −14.895 | 1.00 | 26.79 | A |
| ATOM | 1857 | CB | GLU | A | 314 | 89.543 | 29.928 | −15.948 | 1.00 | 27.50 | A |
| ATOM | 1858 | CG | GLU | A | 314 | 90.739 | 30.639 | −15.381 | 1.00 | 32.29 | A |
| ATOM | 1859 | CD | GLU | A | 314 | 91.687 | 31.094 | −16.463 | 1.00 | 35.85 | A |
| ATOM | 1860 | OE1 | GLU | A | 314 | 91.967 | 30.280 | −17.375 | 1.00 | 38.06 | A |
| ATOM | 1861 | OE2 | GLU | A | 314 | 92.157 | 32.257 | −16.399 | 1.00 | 38.48 | A |
| ATOM | 1862 | C | GLU | A | 314 | 87.370 | 28.787 | −15.577 | 1.00 | 26.22 | A |
| ATOM | 1863 | O | GLU | A | 314 | 86.499 | 29.527 | −16.038 | 1.00 | 27.23 | A |
| ATOM | 1864 | N | LYS | A | 315 | 87.300 | 27.464 | −15.662 | 1.00 | 24.74 | A |
| ATOM | 1865 | CA | LYS | A | 315 | 86.151 | 26.832 | −16.294 | 1.00 | 23.60 | A |
| ATOM | 1866 | CB | LYS | A | 315 | 86.578 | 25.584 | −17.073 | 1.00 | 23.69 | A |
| ATOM | 1867 | CG | LYS | A | 315 | 87.393 | 25.865 | −18.344 | 1.00 | 22.41 | A |
| ATOM | 1868 | CD | LYS | A | 315 | 87.825 | 24.545 | −18.968 | 1.00 | 25.68 | A |
| ATOM | 1869 | CE | LYS | A | 315 | 88.768 | 24.695 | −20.155 | 1.00 | 24.86 | A |
| ATOM | 1870 | NZ | LYS | A | 315 | 88.082 | 25.219 | −21.346 | 1.00 | 28.62 | A |
| ATOM | 1871 | C | LYS | A | 315 | 85.119 | 26.471 | −15.230 | 1.00 | 23.42 | A |
| ATOM | 1872 | O | LYS | A | 315 | 84.043 | 25.970 | −15.541 | 1.00 | 25.37 | A |
| ATOM | 1873 | N | LEU | A | 316 | 85.454 | 26.730 | −13.970 | 1.00 | 21.88 | A |
| ATOM | 1874 | CA | LEU | A | 316 | 84.549 | 26.461 | −12.862 | 1.00 | 20.21 | A |
| ATOM | 1875 | CB | LEU | A | 316 | 85.272 | 25.705 | −11.767 | 1.00 | 19.57 | A |
| ATOM | 1876 | CG | LEU | A | 316 | 85.409 | 24.221 | −12.078 | 1.00 | 21.14 | A |
| ATOM | 1877 | CD1 | LEU | A | 316 | 86.272 | 23.552 | −11.009 | 1.00 | 19.21 | A |
| ATOM | 1878 | CD2 | LEU | A | 316 | 84.000 | 23.600 | −12.166 | 1.00 | 18.59 | A |
| ATOM | 1879 | C | LEU | A | 316 | 83.996 | 27.758 | −12.290 | 1.00 | 21.31 | A |
| ATOM | 1880 | O | LEU | A | 316 | 82.811 | 27.848 | −11.955 | 1.00 | 18.79 | A |
| ATOM | 1881 | N | LEU | A | 317 | 84.865 | 28.762 | −12.175 | 1.00 | 20.59 | A |
| ATOM | 1882 | CA | LEU | A | 317 | 84.446 | 30.038 | −11.646 | 1.00 | 21.64 | A |
| ATOM | 1883 | CB | LEU | A | 317 | 85.606 | 30.707 | −10.900 | 1.00 | 21.42 | A |
| ATOM | 1884 | CG | LEU | A | 317 | 86.130 | 29.892 | −9.711 | 1.00 | 21.80 | A |
| ATOM | 1885 | CD1 | LEU | A | 317 | 87.299 | 30.599 | −9.047 | 1.00 | 23.09 | A |
| ATOM | 1886 | CD2 | LEU | A | 317 | 85.031 | 29.688 | −8.724 | 1.00 | 20.34 | A |
| ATOM | 1887 | C | LEU | A | 317 | 83.940 | 30.890 | −12.810 | 1.00 | 23.34 | A |
| ATOM | 1888 | O | LEU | A | 317 | 84.568 | 31.859 | −13.242 | 1.00 | 23.29 | A |
| ATOM | 1889 | N | VAL | A | 318 | 82.786 | 30.485 | −13.324 | 1.00 | 24.06 | A |
| ATOM | 1890 | CA | VAL | A | 318 | 82.135 | 31.161 | −14.436 | 1.00 | 23.46 | A |
| ATOM | 1891 | CB | VAL | A | 318 | 81.829 | 30.150 | −15.547 | 1.00 | 24.32 | A |
| ATOM | 1892 | CG1 | VAL | A | 318 | 81.061 | 30.828 | −16.670 | 1.00 | 22.57 | A |
| ATOM | 1893 | CG2 | VAL | A | 318 | 83.136 | 29.524 | −16.049 | 1.00 | 20.68 | A |
| ATOM | 1894 | C | VAL | A | 318 | 80.838 | 31.765 | −13.918 | 1.00 | 24.59 | A |
| ATOM | 1895 | O | VAL | A | 318 | 80.050 | 31.086 | −13.250 | 1.00 | 24.86 | A |
| ATOM | 1896 | N | LEU | A | 319 | 80.603 | 33.036 | −14.215 | 1.00 | 24.95 | A |
| ATOM | 1897 | CA | LEU | A | 319 | 79.383 | 33.688 | −13.731 | 1.00 | 25.79 | A |
| ATOM | 1898 | CB | LEU | A | 319 | 79.379 | 35.157 | −14.154 | 1.00 | 25.38 | A |
| ATOM | 1899 | CG | LEU | A | 319 | 80.466 | 35.963 | −13.417 | 1.00 | 27.04 | A |
| ATOM | 1900 | CD1 | LEU | A | 319 | 80.452 | 37.421 | −13.869 | 1.00 | 25.54 | A |
| ATOM | 1901 | CD2 | LEU | A | 319 | 80.241 | 35.872 | −11.907 | 1.00 | 23.27 | A |
| ATOM | 1902 | C | LEU | A | 319 | 78.077 | 32.989 | −14.141 | 1.00 | 26.05 | A |
| ATOM | 1903 | O | LEU | A | 319 | 77.171 | 32.819 | −13.319 | 1.00 | 27.69 | A |
| ATOM | 1904 | N | ASP | A | 320 | 77.982 | 32.580 | −15.400 | 1.00 | 25.08 | A |
| ATOM | 1905 | CA | ASP | A | 320 | 76.804 | 31.881 | −15.892 | 1.00 | 24.00 | A |
| ATOM | 1906 | CB | ASP | A | 320 | 76.788 | 31.907 | −17.420 | 1.00 | 24.02 | A |
| ATOM | 1907 | CG | ASP | A | 320 | 75.597 | 31.175 | −17.996 | 1.00 | 27.27 | A |
| ATOM | 1908 | OD1 | ASP | A | 320 | 75.009 | 30.337 | −17.271 | 1.00 | 29.66 | A |
| ATOM | 1909 | OD2 | ASP | A | 320 | 75.253 | 31.417 | −19.175 | 1.00 | 30.03 | A |
| ATOM | 1910 | C | ASP | A | 320 | 76.846 | 30.427 | −15.396 | 1.00 | 24.04 | A |
| ATOM | 1911 | O | ASP | A | 320 | 77.661 | 29.623 | −15.846 | 1.00 | 25.11 | A |
| ATOM | 1912 | N | ALA | A | 321 | 75.940 | 30.094 | −14.489 | 1.00 | 23.73 | A |
| ATOM | 1913 | CA | ALA | A | 321 | 75.867 | 28.770 | −13.887 | 1.00 | 23.58 | A |
| ATOM | 1914 | CB | ALA | A | 321 | 74.710 | 28.720 | −12.916 | 1.00 | 23.62 | A |
| ATOM | 1915 | C | ALA | A | 321 | 75.765 | 27.599 | −14.853 | 1.00 | 24.90 | A |
| ATOM | 1916 | O | ALA | A | 321 | 76.221 | 26.497 | −14.549 | 1.00 | 24.36 | A |
| ATOM | 1917 | N | THR | A | 322 | 75.176 | 27.834 | −16.019 | 1.00 | 25.50 | A |
| ATOM | 1918 | CA | THR | A | 322 | 75.008 | 26.772 | −17.011 | 1.00 | 24.60 | A |

-continued

| | | | | | | | | | | |
|---|---|---|---|---|---|---|---|---|---|---|
| ATOM | 1919 | CB | THR | A | 322 | 73.816 | 27.064 | −17.909 | 1.00 | 23.09 | A |
| ATOM | 1920 | OG1 | THR | A | 322 | 74.079 | 28.263 | −18.646 | 1.00 | 23.74 | A |
| ATOM | 1921 | CG2 | THR | A | 322 | 72.568 | 27.260 | −17.080 | 1.00 | 20.71 | A |
| ATOM | 1922 | C | THR | A | 322 | 76.238 | 26.596 | −17.893 | 1.00 | 25.24 | A |
| ATOM | 1923 | O | THR | A | 322 | 76.221 | 25.807 | −18.832 | 1.00 | 26.45 | A |
| ATOM | 1924 | N | LYS | A | 323 | 77.300 | 27.331 | −17.592 | 1.00 | 25.05 | A |
| ATOM | 1925 | CA | LYS | A | 323 | 78.526 | 27.239 | −18.366 | 1.00 | 26.46 | A |
| ATOM | 1926 | CB | LYS | A | 323 | 78.972 | 28.627 | −18.823 | 1.00 | 28.68 | A |
| ATOM | 1927 | CG | LYS | A | 323 | 78.050 | 29.304 | −19.814 | 1.00 | 31.27 | A |
| ATOM | 1928 | CD | LYS | A | 323 | 78.470 | 29.004 | −21.240 | 1.00 | 34.38 | A |
| ATOM | 1929 | CE | LYS | A | 323 | 77.850 | 29.986 | −22.243 | 1.00 | 35.12 | A |
| ATOM | 1930 | NZ | LYS | A | 323 | 76.363 | 29.936 | −22.251 | 1.00 | 36.71 | A |
| ATOM | 1931 | C | LYS | A | 323 | 79.660 | 26.621 | −17.556 | 1.00 | 26.39 | A |
| ATOM | 1932 | O | LYS | A | 323 | 80.795 | 26.615 | −18.010 | 1.00 | 28.51 | A |
| ATOM | 1933 | N | ARG | A | 324 | 79.372 | 26.114 | −16.360 | 1.00 | 24.50 | A |
| ATOM | 1934 | CA | ARG | A | 324 | 80.429 | 25.524 | −15.543 | 1.00 | 23.37 | A |
| ATOM | 1935 | CB | ARG | A | 324 | 80.087 | 25.633 | −14.049 | 1.00 | 23.41 | A |
| ATOM | 1936 | CG | ARG | A | 324 | 80.233 | 27.034 | −13.520 | 1.00 | 21.60 | A |
| ATOM | 1937 | CD | ARG | A | 324 | 79.594 | 27.220 | −12.173 | 1.00 | 21.55 | A |
| ATOM | 1938 | NE | ARG | A | 324 | 79.245 | 28.624 | −11.986 | 1.00 | 19.69 | A |
| ATOM | 1939 | CZ | ARG | A | 324 | 78.273 | 29.054 | −11.191 | 1.00 | 19.84 | A |
| ATOM | 1940 | NH1 | ARG | A | 324 | 77.555 | 28.183 | −10.496 | 1.00 | 16.83 | A |
| ATOM | 1941 | NH2 | ARG | A | 324 | 77.990 | 30.358 | −11.129 | 1.00 | 21.41 | A |
| ATOM | 1942 | C | ARG | A | 324 | 80.717 | 24.085 | −15.897 | 1.00 | 22.63 | A |
| ATOM | 1943 | O | ARG | A | 324 | 79.798 | 23.280 | −16.058 | 1.00 | 24.44 | A |
| ATOM | 1944 | N | LEU | A | 325 | 82.000 | 23.767 | −16.023 | 1.00 | 20.68 | A |
| ATOM | 1945 | CA | LEU | A | 325 | 82.414 | 22.411 | −16.352 | 1.00 | 20.98 | A |
| ATOM | 1946 | CB | LEU | A | 325 | 83.952 | 22.330 | −16.386 | 1.00 | 20.82 | A |
| ATOM | 1947 | CG | LEU | A | 325 | 84.596 | 21.147 | −17.131 | 1.00 | 23.08 | A |
| ATOM | 1948 | CD1 | LEU | A | 325 | 84.149 | 21.194 | −18.595 | 1.00 | 21.39 | A |
| ATOM | 1949 | CD2 | LEU | A | 325 | 86.132 | 21.173 | −17.038 | 1.00 | 20.00 | A |
| ATOM | 1950 | C | LEU | A | 325 | 81.840 | 21.454 | −15.290 | 1.00 | 20.43 | A |
| ATOM | 1951 | O | LEU | A | 325 | 82.062 | 21.633 | −14.097 | 1.00 | 18.45 | A |
| ATOM | 1952 | N | GLY | A | 326 | 81.076 | 20.456 | −15.725 | 1.00 | 21.33 | A |
| ATOM | 1953 | CA | GLY | A | 326 | 80.501 | 19.513 | −14.778 | 1.00 | 20.60 | A |
| ATOM | 1954 | C | GLY | A | 326 | 78.984 | 19.523 | −14.701 | 1.00 | 22.39 | A |
| ATOM | 1955 | O | GLY | A | 326 | 78.383 | 18.493 | −14.378 | 1.00 | 22.59 | A |
| ATOM | 1956 | N | CYS | A | 327 | 78.358 | 20.664 | −15.009 | 1.00 | 23.36 | A |
| ATOM | 1957 | CA | CYS | A | 327 | 76.896 | 20.771 | −14.963 | 1.00 | 25.18 | A |
| ATOM | 1958 | CB | CYS | A | 327 | 76.453 | 22.246 | −14.889 | 1.00 | 25.79 | A |
| ATOM | 1959 | SG | CYS | A | 327 | 76.742 | 23.237 | −16.364 | 1.00 | 31.42 | A |
| ATOM | 1960 | C | CYS | A | 327 | 76.229 | 20.074 | −16.148 | 1.00 | 24.99 | A |
| ATOM | 1961 | O | CYS | A | 327 | 76.887 | 19.743 | −17.129 | 1.00 | 24.31 | A |
| ATOM | 1962 | N | ALA | A | 328 | 74.923 | 19.847 | −16.040 | 1.00 | 26.34 | A |
| ATOM | 1963 | CA | ALA | A | 328 | 74.157 | 19.172 | −17.094 | 1.00 | 27.51 | A |
| ATOM | 1964 | CB | ALA | A | 328 | 72.703 | 18.949 | −16.629 | 1.00 | 26.81 | A |
| ATOM | 1965 | C | ALA | A | 328 | 74.179 | 19.905 | −18.443 | 1.00 | 28.11 | A |
| ATOM | 1966 | O | ALA | A | 328 | 74.243 | 19.274 | −19.501 | 1.00 | 27.66 | A |
| ATOM | 1967 | N | GLU | A | 329 | 74.144 | 21.231 | −18.418 | 1.00 | 28.05 | A |
| ATOM | 1968 | CA | GLU | A | 329 | 74.172 | 21.973 | −19.668 | 1.00 | 29.54 | A |
| ATOM | 1969 | CB | GLU | A | 329 | 73.915 | 23.458 | −19.428 | 1.00 | 32.18 | A |
| ATOM | 1970 | CG | GLU | A | 329 | 72.539 | 23.783 | −18.863 | 1.00 | 37.89 | A |
| ATOM | 1971 | CD | GLU | A | 329 | 72.418 | 23.503 | −17.374 | 1.00 | 41.37 | A |
| ATOM | 1972 | OE1 | GLU | A | 329 | 73.464 | 23.308 | −16.711 | 1.00 | 43.80 | A |
| ATOM | 1973 | OE2 | GLU | A | 329 | 71.273 | 23.495 | −16.863 | 1.00 | 43.66 | A |
| ATOM | 1974 | C | GLU | A | 329 | 75.514 | 21.807 | −20.377 | 1.00 | 29.08 | A |
| ATOM | 1975 | O | GLU | A | 329 | 75.602 | 21.927 | −21.605 | 1.00 | 27.73 | A |
| ATOM | 1976 | N | MET | A | 330 | 76.559 | 21.540 | −19.598 | 1.00 | 27.54 | A |
| ATOM | 1977 | CA | MET | A | 330 | 77.894 | 21.359 | −20.148 | 1.00 | 25.71 | A |
| ATOM | 1978 | CB | MET | A | 330 | 78.945 | 21.963 | −19.219 | 1.00 | 27.88 | A |
| ATOM | 1979 | CG | MET | A | 330 | 78.964 | 23.489 | −19.209 | 1.00 | 30.29 | A |
| ATOM | 1980 | SD | MET | A | 330 | 79.429 | 24.194 | −20.819 | 1.00 | 34.04 | A |
| ATOM | 1981 | CE | MET | A | 330 | 81.187 | 23.670 | −20.936 | 1.00 | 29.55 | A |
| ATOM | 1982 | C | MET | A | 330 | 78.156 | 19.884 | −20.343 | 1.00 | 24.53 | A |
| ATOM | 1983 | O | MET | A | 330 | 79.290 | 19.473 | −20.575 | 1.00 | 22.65 | A |
| ATOM | 1984 | N | GLU | A | 331 | 77.089 | 19.095 | −20.221 | 1.00 | 22.87 | A |
| ATOM | 1985 | CA | GLU | A | 331 | 77.139 | 17.654 | −20.415 | 1.00 | 21.38 | A |
| ATOM | 1986 | CB | GLU | A | 331 | 77.854 | 17.339 | −21.735 | 1.00 | 22.71 | A |
| ATOM | 1987 | CG | GLU | A | 331 | 76.903 | 16.916 | −22.837 | 1.00 | 23.01 | A |
| ATOM | 1988 | CD | GLU | A | 331 | 75.599 | 17.720 | −22.875 | 1.00 | 24.76 | A |
| ATOM | 1989 | OE1 | GLU | A | 331 | 75.570 | 18.830 | −23.441 | 1.00 | 26.12 | A |
| ATOM | 1990 | OE2 | GLU | A | 331 | 74.588 | 17.230 | −22.337 | 1.00 | 24.22 | A |
| ATOM | 1991 | C | GLU | A | 331 | 77.671 | 16.765 | −19.290 | 1.00 | 21.01 | A |
| ATOM | 1992 | O | GLU | A | 331 | 78.075 | 15.619 | −19.517 | 1.00 | 19.50 | A |
| ATOM | 1993 | N | GLY | A | 332 | 77.675 | 17.284 | −18.071 | 1.00 | 19.73 | A |
| ATOM | 1994 | CA | GLY | A | 332 | 78.056 | 16.445 | −16.954 | 1.00 | 17.80 | A |
| ATOM | 1995 | C | GLY | A | 332 | 79.494 | 16.243 | −16.570 | 1.00 | 17.28 | A |
| ATOM | 1996 | O | GLY | A | 332 | 80.381 | 17.013 | −16.934 | 1.00 | 16.11 | A |
| ATOM | 1997 | N | TYR | A | 333 | 79.701 | 15.151 | −15.842 | 1.00 | 16.52 | A |

|      |      |     |     |     |     |        |        |         |      |       |   |
|------|------|-----|-----|-----|-----|--------|--------|---------|------|-------|---|
| ATOM | 1998 | CA  | TYR | A   | 333 | 80.997 | 14.791 | −15.305 | 1.00 | 16.75 | A |
| ATOM | 1999 | CB  | TYR | A   | 333 | 80.787 | 13.854 | −14.115 | 1.00 | 16.95 | A |
| ATOM | 2000 | CG  | TYR | A   | 333 | 80.369 | 14.624 | −12.893 | 1.00 | 18.08 | A |
| ATOM | 2001 | CD1 | TYR | A   | 333 | 81.332 | 15.207 | −12.059 | 1.00 | 18.77 | A |
| ATOM | 2002 | CE1 | TYR | A   | 333 | 80.971 | 16.035 | −10.982 | 1.00 | 17.69 | A |
| ATOM | 2003 | CD2 | TYR | A   | 333 | 79.021 | 14.877 | −12.620 | 1.00 | 17.08 | A |
| ATOM | 2004 | CE2 | TYR | A   | 333 | 78.646 | 15.713 | −11.538 | 1.00 | 19.05 | A |
| ATOM | 2005 | CZ  | TYR | A   | 333 | 79.640 | 16.287 | −10.728 | 1.00 | 18.04 | A |
| ATOM | 2006 | OH  | TYR | A   | 333 | 79.322 | 17.126 | −9.682  | 1.00 | 18.69 | A |
| ATOM | 2007 | C   | TYR | A   | 333 | 82.051 | 14.240 | −16.238 | 1.00 | 16.78 | A |
| ATOM | 2008 | O   | TYR | A   | 333 | 83.248 | 14.393 | −15.977 | 1.00 | 16.04 | A |
| ATOM | 2009 | N   | GLY | A   | 334 | 81.633 | 13.598 | −17.321 | 1.00 | 16.63 | A |
| ATOM | 2010 | CA  | GLY | A   | 334 | 82.624 | 13.082 | −18.244 | 1.00 | 17.02 | A |
| ATOM | 2011 | C   | GLY | A   | 334 | 83.576 | 14.194 | −18.683 | 1.00 | 17.47 | A |
| ATOM | 2012 | O   | GLY | A   | 334 | 84.802 | 14.063 | −18.562 | 1.00 | 17.18 | A |
| ATOM | 2013 | N   | PRO | A   | 335 | 83.039 | 15.315 | −19.195 | 1.00 | 17.04 | A |
| ATOM | 2014 | CD  | PRO | A   | 335 | 81.650 | 15.611 | −19.590 | 1.00 | 16.18 | A |
| ATOM | 2015 | CA  | PRO | A   | 335 | 83.940 | 16.382 | −19.621 | 1.00 | 17.35 | A |
| ATOM | 2016 | CB  | PRO | A   | 335 | 82.991 | 17.441 | −20.178 | 1.00 | 17.48 | A |
| ATOM | 2017 | CG  | PRO | A   | 335 | 81.857 | 16.605 | −20.713 | 1.00 | 18.64 | A |
| ATOM | 2018 | C   | PRO | A   | 335 | 84.786 | 16.883 | −18.480 | 1.00 | 18.48 | A |
| ATOM | 2019 | O   | PRO | A   | 335 | 85.963 | 17.131 | −18.661 | 1.00 | 20.84 | A |
| ATOM | 2020 | N   | LEU | A   | 336 | 84.204 | 17.034 | −17.299 | 1.00 | 19.46 | A |
| ATOM | 2021 | CA  | LEU | A   | 336 | 84.986 | 17.504 | −16.153 | 1.00 | 19.38 | A |
| ATOM | 2022 | CB  | LEU | A   | 336 | 84.071 | 17.692 | −14.937 | 1.00 | 18.98 | A |
| ATOM | 2023 | CG  | LEU | A   | 336 | 84.765 | 17.982 | −13.604 | 1.00 | 18.01 | A |
| ATOM | 2024 | CD1 | LEU | A   | 336 | 85.534 | 19.289 | −13.690 | 1.00 | 16.66 | A |
| ATOM | 2025 | CD2 | LEU | A   | 336 | 83.724 | 18.055 | −12.491 | 1.00 | 18.81 | A |
| ATOM | 2026 | C   | LEU | A   | 336 | 86.132 | 16.528 | −15.815 | 1.00 | 19.32 | A |
| ATOM | 2027 | O   | LEU | A   | 336 | 87.293 | 16.932 | −15.683 | 1.00 | 18.65 | A |
| ATOM | 2028 | N   | LYS | A   | 337 | 85.808 | 15.244 | −15.688 | 1.00 | 18.38 | A |
| ATOM | 2029 | CA  | LYS | A   | 337 | 86.821 | 14.240 | −15.387 | 1.00 | 18.89 | A |
| ATOM | 2030 | CB  | LYS | A   | 337 | 86.147 | 12.900 | −15.082 | 1.00 | 17.70 | A |
| ATOM | 2031 | CG  | LYS | A   | 337 | 85.460 | 12.933 | −13.727 | 1.00 | 19.89 | A |
| ATOM | 2032 | CD  | LYS | A   | 337 | 84.450 | 11.817 | −13.523 | 1.00 | 22.66 | A |
| ATOM | 2033 | CE  | LYS | A   | 337 | 85.089 | 10.453 | −13.372 | 1.00 | 22.78 | A |
| ATOM | 2034 | NZ  | LYS | A   | 337 | 84.025 | 9.444  | −13.088 | 1.00 | 25.28 | A |
| ATOM | 2035 | C   | LYS | A   | 337 | 87.865 | 14.101 | −16.504 | 1.00 | 20.07 | A |
| ATOM | 2036 | O   | LYS | A   | 337 | 88.996 | 13.671 | −16.254 | 1.00 | 20.47 | A |
| ATOM | 2037 | N   | ALA | A   | 338 | 87.491 | 14.486 | −17.725 | 1.00 | 20.38 | A |
| ATOM | 2038 | CA  | ALA | A   | 338 | 88.393 | 14.441 | −18.876 | 1.00 | 20.65 | A |
| ATOM | 2039 | CB  | ALA | A   | 338 | 87.580 | 14.382 | −20.178 | 1.00 | 20.29 | A |
| ATOM | 2040 | C   | ALA | A   | 338 | 89.357 | 15.636 | −18.933 | 1.00 | 22.18 | A |
| ATOM | 2041 | O   | ALA | A   | 338 | 90.265 | 15.665 | −19.768 | 1.00 | 24.71 | A |
| ATOM | 2042 | N   | HIS | A   | 339 | 89.179 | 16.627 | −18.063 | 1.00 | 21.90 | A |
| ATOM | 2043 | CA  | HIS | A   | 339 | 90.072 | 17.785 | −18.094 | 1.00 | 22.10 | A |
| ATOM | 2044 | CB  | HIS | A   | 339 | 89.711 | 18.762 | −16.989 | 1.00 | 21.35 | A |
| ATOM | 2045 | CG  | HIS | A   | 339 | 90.357 | 20.097 | −17.149 | 1.00 | 20.57 | A |
| ATOM | 2046 | CD2 | HIS | A   | 339 | 89.891 | 21.251 | −17.683 | 1.00 | 19.19 | A |
| ATOM | 2047 | ND1 | HIS | A   | 339 | 91.664 | 20.341 | −16.783 | 1.00 | 20.52 | A |
| ATOM | 2048 | CE1 | HIS | A   | 339 | 91.973 | 21.592 | −17.085 | 1.00 | 22.28 | A |
| ATOM | 2049 | NE2 | HIS | A   | 339 | 90.914 | 22.165 | −17.633 | 1.00 | 21.96 | A |
| ATOM | 2050 | C   | HIS | A   | 339 | 91.555 | 17.404 | −17.963 | 1.00 | 22.78 | A |
| ATOM | 2051 | O   | HIS | A   | 339 | 91.919 | 16.600 | −17.118 | 1.00 | 21.05 | A |
| ATOM | 2052 | N   | PRO | A   | 340 | 92.425 | 17.994 | −18.801 | 1.00 | 24.12 | A |
| ATOM | 2053 | CD  | PRO | A   | 340 | 92.090 | 18.973 | −19.855 | 1.00 | 23.53 | A |
| ATOM | 2054 | CA  | PRO | A   | 340 | 93.872 | 17.724 | −18.795 | 1.00 | 25.11 | A |
| ATOM | 2055 | CB  | PRO | A   | 340 | 94.435 | 18.864 | −19.647 | 1.00 | 22.31 | A |
| ATOM | 2056 | CG  | PRO | A   | 340 | 93.379 | 19.015 | −20.685 | 1.00 | 22.50 | A |
| ATOM | 2057 | C   | PRO | A   | 340 | 94.540 | 17.654 | −17.421 | 1.00 | 25.66 | A |
| ATOM | 2058 | O   | PRO | A   | 340 | 95.523 | 16.951 | −17.237 | 1.00 | 27.43 | A |
| ATOM | 2059 | N   | PHE | A   | 341 | 94.011 | 18.389 | −16.459 | 1.00 | 25.05 | A |
| ATOM | 2060 | CA  | PHE | A   | 341 | 94.596 | 18.399 | −15.139 | 1.00 | 24.88 | A |
| ATOM | 2061 | CB  | PHE | A   | 341 | 93.897 | 19.459 | −14.276 | 1.00 | 24.71 | A |
| ATOM | 2062 | CG  | PHE | A   | 341 | 94.482 | 19.607 | −12.893 | 1.00 | 24.42 | A |
| ATOM | 2063 | CD1 | PHE | A   | 341 | 95.822 | 19.947 | −12.721 | 1.00 | 22.55 | A |
| ATOM | 2064 | CD2 | PHE | A   | 341 | 93.685 | 19.397 | −11.758 | 1.00 | 22.61 | A |
| ATOM | 2065 | CE1 | PHE | A   | 341 | 96.364 | 20.076 | −11.434 | 1.00 | 23.65 | A |
| ATOM | 2066 | CE2 | PHE | A   | 341 | 94.204 | 19.522 | −10.476 | 1.00 | 22.09 | A |
| ATOM | 2067 | CZ  | PHE | A   | 341 | 95.547 | 19.863 | −10.304 | 1.00 | 24.01 | A |
| ATOM | 2068 | C   | PHE | A   | 341 | 94.511 | 17.026 | −14.486 | 1.00 | 25.70 | A |
| ATOM | 2069 | O   | PHE | A   | 341 | 95.363 | 16.665 | −13.680 | 1.00 | 27.11 | A |
| ATOM | 2070 | N   | PHE | A   | 342 | 93.499 | 16.258 | −14.865 | 1.00 | 25.51 | A |
| ATOM | 2071 | CA  | PHE | A   | 342 | 93.262 | 14.929 | −14.318 | 1.00 | 25.34 | A |
| ATOM | 2072 | CB  | PHE | A   | 342 | 91.758 | 14.728 | −14.120 | 1.00 | 21.93 | A |
| ATOM | 2073 | CG  | PHE | A   | 342 | 91.120 | 15.728 | −13.196 | 1.00 | 20.26 | A |
| ATOM | 2074 | CD1 | PHE | A   | 342 | 91.556 | 15.862 | −11.888 | 1.00 | 20.03 | A |
| ATOM | 2075 | CD2 | PHE | A   | 342 | 90.030 | 16.485 | −13.613 | 1.00 | 19.36 | A |
| ATOM | 2076 | CE1 | PHE | A   | 342 | 90.907 | 16.731 | −11.004 | 1.00 | 19.87 | A |

-continued

| | | | | | | | | | | |
|---|---|---|---|---|---|---|---|---|---|---|
| ATOM | 2077 | CE2 | PHE | A | 342 | 89.377 | 17.348 | −12.744 | 1.00 | 18.17 A |
| ATOM | 2078 | CZ | PHE | A | 342 | 89.818 | 17.470 | −11.431 | 1.00 | 19.27 A |
| ATOM | 2079 | C | PHE | A | 342 | 93.805 | 13.815 | −15.214 | 1.00 | 27.64 A |
| ATOM | 2080 | O | PHE | A | 342 | 93.508 | 12.630 | −15.019 | 1.00 | 27.39 A |
| ATOM | 2081 | N | GLU | A | 343 | 94.607 | 14.203 | −16.194 | 1.00 | 31.32 A |
| ATOM | 2082 | CA | GLU | A | 343 | 95.185 | 13.262 | −17.150 | 1.00 | 34.29 A |
| ATOM | 2083 | CB | GLU | A | 343 | 96.320 | 13.950 | −17.889 | 1.00 | 38.36 A |
| ATOM | 2084 | CG | GLU | A | 343 | 96.735 | 13.314 | −19.197 | 1.00 | 45.23 A |
| ATOM | 2085 | CD | GLU | A | 343 | 97.654 | 14.247 | −19.976 | 1.00 | 51.01 A |
| ATOM | 2086 | OE1 | GLU | A | 343 | 98.266 | 13.801 | −20.981 | 1.00 | 51.76 A |
| ATOM | 2087 | OE2 | GLU | A | 343 | 97.755 | 15.439 | −19.568 | 1.00 | 52.42 A |
| ATOM | 2088 | C | GLU | A | 343 | 95.690 | 11.950 | −16.542 | 1.00 | 33.50 A |
| ATOM | 2089 | O | GLU | A | 343 | 95.289 | 10.860 | −16.970 | 1.00 | 33.57 A |
| ATOM | 2090 | N | SER | A | 344 | 96.554 | 12.049 | −15.537 | 1.00 | 31.58 A |
| ATOM | 2091 | CA | SER | A | 344 | 97.117 | 10.857 | −14.906 | 1.00 | 30.38 A |
| ATOM | 2092 | CB | SER | A | 344 | 98.447 | 11.217 | −14.253 | 1.00 | 29.76 A |
| ATOM | 2093 | OG | SER | A | 344 | 98.243 | 11.995 | −13.096 | 1.00 | 30.32 A |
| ATOM | 2094 | C | SER | A | 344 | 96.242 | 10.150 | −13.857 | 1.00 | 30.00 A |
| ATOM | 2095 | O | SER | A | 344 | 96.662 | 9.137 | −13.285 | 1.00 | 31.14 A |
| ATOM | 2096 | N | VAL | A | 345 | 95.046 | 10.679 | −13.606 | 1.00 | 27.28 A |
| ATOM | 2097 | CA | VAL | A | 345 | 94.135 | 10.126 | −12.609 | 1.00 | 25.39 A |
| ATOM | 2098 | CB | VAL | A | 345 | 93.093 | 11.213 | −12.159 | 1.00 | 24.17 A |
| ATOM | 2099 | CG1 | VAL | A | 345 | 91.973 | 10.568 | −11.347 | 1.00 | 19.50 A |
| ATOM | 2100 | CG2 | VAL | A | 345 | 93.779 | 12.321 | −11.363 | 1.00 | 17.85 A |
| ATOM | 2101 | C | VAL | A | 345 | 93.341 | 8.885 | −13.043 | 1.00 | 26.45 A |
| ATOM | 2102 | O | VAL | A | 345 | 92.813 | 8.842 | −14.154 | 1.00 | 27.42 A |
| ATOM | 2103 | N | THR | A | 346 | 93.253 | 7.890 | −12.157 | 1.00 | 26.62 A |
| ATOM | 2104 | CA | THR | A | 346 | 92.451 | 6.680 | −12.406 | 1.00 | 27.91 A |
| ATOM | 2105 | CB | THR | A | 346 | 93.194 | 5.388 | −11.999 | 1.00 | 29.18 A |
| ATOM | 2106 | OG1 | THR | A | 346 | 94.345 | 5.224 | −12.830 | 1.00 | 33.51 A |
| ATOM | 2107 | CG2 | THR | A | 346 | 92.300 | 4.171 | −12.177 | 1.00 | 28.24 A |
| ATOM | 2108 | C | THR | A | 346 | 91.229 | 6.856 | −11.505 | 1.00 | 27.53 A |
| ATOM | 2109 | O | THR | A | 346 | 91.297 | 6.621 | −10.299 | 1.00 | 29.24 A |
| ATOM | 2110 | N | TRP | A | 347 | 90.117 | 7.279 | −12.094 | 1.00 | 27.83 A |
| ATOM | 2111 | CA | TRP | A | 347 | 88.898 | 7.561 | −11.336 | 1.00 | 29.15 A |
| ATOM | 2112 | CB | TRP | A | 347 | 87.878 | 8.278 | −12.224 | 1.00 | 27.12 A |
| ATOM | 2113 | CG | TRP | A | 347 | 88.353 | 9.574 | −12.758 | 1.00 | 25.48 A |
| ATOM | 2114 | CD2 | TRP | A | 347 | 88.252 | 10.853 | −12.118 | 1.00 | 24.27 A |
| ATOM | 2115 | CE2 | TRP | A | 347 | 88.841 | 11.803 | −12.990 | 1.00 | 23.82 A |
| ATOM | 2116 | CE3 | TRP | A | 347 | 87.723 | 11.292 | −10.897 | 1.00 | 22.42 A |
| ATOM | 2117 | CD1 | TRP | A | 347 | 88.984 | 9.788 | −13.952 | 1.00 | 24.47 A |
| ATOM | 2118 | NE1 | TRP | A | 347 | 89.279 | 11.124 | −14.099 | 1.00 | 23.92 A |
| ATOM | 2119 | CZ2 | TRP | A | 347 | 88.913 | 13.169 | −12.678 | 1.00 | 21.68 A |
| ATOM | 2120 | CZ3 | TRP | A | 347 | 87.797 | 12.654 | −10.586 | 1.00 | 24.15 A |
| ATOM | 2121 | CH2 | TRP | A | 347 | 88.391 | 13.575 | −11.480 | 1.00 | 22.35 A |
| ATOM | 2122 | C | TRP | A | 347 | 88.218 | 6.370 | −10.700 | 1.00 | 30.64 A |
| ATOM | 2123 | O | TRP | A | 347 | 87.617 | 6.476 | −9.631 | 1.00 | 31.21 A |
| ATOM | 2124 | N | GLU | A | 348 | 88.318 | 5.242 | −11.376 | 1.00 | 32.16 A |
| ATOM | 2125 | CA | GLU | A | 348 | 87.698 | 4.003 | −10.952 | 1.00 | 34.98 A |
| ATOM | 2126 | CB | GLU | A | 348 | 88.157 | 2.890 | −11.904 | 1.00 | 37.47 A |
| ATOM | 2127 | CG | GLU | A | 348 | 87.815 | 3.125 | −13.419 | 1.00 | 41.39 A |
| ATOM | 2128 | CD | GLU | A | 348 | 88.619 | 4.257 | −14.116 | 1.00 | 41.83 A |
| ATOM | 2129 | OE1 | GLU | A | 348 | 89.828 | 4.408 | −13.841 | 1.00 | 42.27 A |
| ATOM | 2130 | OE2 | GLU | A | 348 | 88.036 | 4.982 | −14.959 | 1.00 | 42.41 A |
| ATOM | 2131 | C | GLU | A | 348 | 87.843 | 3.547 | −9.478 | 1.00 | 34.74 A |
| ATOM | 2132 | O | GLU | A | 348 | 86.866 | 3.111 | −8.869 | 1.00 | 35.95 A |
| ATOM | 2133 | N | ASN | A | 349 | 89.024 | 3.652 | −8.887 | 1.00 | 33.61 A |
| ATOM | 2134 | CA | ASN | A | 349 | 89.189 | 3.179 | −7.507 | 1.00 | 32.34 A |
| ATOM | 2135 | CB | ASN | A | 349 | 89.936 | 1.860 | −7.529 | 1.00 | 33.21 A |
| ATOM | 2136 | CG | ASN | A | 349 | 91.345 | 2.016 | −8.089 | 1.00 | 34.48 A |
| ATOM | 2137 | OD1 | ASN | A | 349 | 91.613 | 2.943 | −8.858 | 1.00 | 32.91 A |
| ATOM | 2138 | ND2 | ASN | A | 349 | 92.247 | 1.110 | −7.712 | 1.00 | 35.85 A |
| ATOM | 2139 | C | ASN | A | 349 | 89.949 | 4.136 | −6.594 | 1.00 | 31.22 A |
| ATOM | 2140 | O | ASN | A | 349 | 90.826 | 3.714 | −5.839 | 1.00 | 31.07 A |
| ATOM | 2141 | N | LEU | A | 350 | 89.611 | 5.416 | −6.646 | 1.00 | 28.54 A |
| ATOM | 2142 | CA | LEU | A | 350 | 90.300 | 6.403 | −5.837 | 1.00 | 26.75 A |
| ATOM | 2143 | CB | LEU | A | 350 | 89.632 | 7.762 | −6.024 | 1.00 | 25.89 A |
| ATOM | 2144 | CG | LEU | A | 350 | 90.095 | 8.558 | −7.239 | 1.00 | 24.21 A |
| ATOM | 2145 | CD1 | LEU | A | 350 | 89.111 | 9.674 | −7.547 | 1.00 | 23.55 A |
| ATOM | 2146 | CD2 | LEU | A | 350 | 91.475 | 9.118 | −6.932 | 1.00 | 23.67 A |
| ATOM | 2147 | C | LEU | A | 350 | 90.440 | 6.102 | −4.345 | 1.00 | 27.67 A |
| ATOM | 2148 | O | LEU | A | 350 | 91.478 | 6.401 | −3.753 | 1.00 | 28.06 A |
| ATOM | 2149 | N | HIS | A | 351 | 89.424 | 5.509 | −3.722 | 1.00 | 27.81 A |
| ATOM | 2150 | CA | HIS | A | 351 | 89.539 | 5.254 | −2.299 | 1.00 | 29.88 A |
| ATOM | 2151 | CB | HIS | A | 351 | 88.144 | 5.197 | −1.646 | 1.00 | 31.47 A |
| ATOM | 2152 | CG | HIS | A | 351 | 87.584 | 3.823 | −1.475 | 1.00 | 32.65 A |
| ATOM | 2153 | CD2 | HIS | A | 351 | 86.926 | 3.009 | −2.338 | 1.00 | 34.75 A |
| ATOM | 2154 | ND1 | HIS | A | 351 | 87.629 | 3.150 | −0.273 | 1.00 | 34.31 A |
| ATOM | 2155 | CE1 | lHIS | A | 351 | 87.022 | 1.981 | −0.402 | 1.00 | 36.41 A |

-continued

| | | | | | | | | | | |
|---|---|---|---|---|---|---|---|---|---|---|
| ATOM | 2156 | NE2 | HIS | A | 351 | 86.586 | 1.871 | −1.644 | 1.00 | 35.36 | A |
| ATOM | 2157 | C | HIS | A | 351 | 90.396 | 4.030 | −1.978 | 1.00 | 30.93 | A |
| ATOM | 2158 | O | HIS | A | 351 | 90.674 | 3.741 | −0.812 | 1.00 | 31.57 | A |
| ATOM | 2159 | N | GLN | A | 352 | 90.842 | 3.337 | −3.022 | 1.00 | 31.09 | A |
| ATOM | 2160 | CA | GLN | A | 352 | 91.709 | 2.177 | −2.864 | 1.00 | 31.86 | A |
| ATOM | 2161 | CB | GLN | A | 352 | 91.482 | 1.187 | −3.992 | 1.00 | 35.63 | A |
| ATOM | 2162 | CG | GLN | A | 352 | 91.038 | 0.141 | −3.497 | 1.00 | 40.62 | A |
| ATOM | 2163 | CD | GLN | A | 352 | 89.739 | 0.036 | −2.766 | 1.00 | 42.39 | A |
| ATOM | 2164 | OE1 | GLN | A | 352 | 88.684 | 0.133 | −3.376 | 1.00 | 44.19 | A |
| ATOM | 2165 | NE2 | GLN | A | 352 | 89.802 | 0.112 | −1.447 | 1.00 | 44.81 | A |
| ATOM | 2166 | C | GLN | A | 352 | 93.167 | 2.626 | −2.907 | 1.00 | 31.39 | A |
| ATOM | 2167 | O | GLN | A | 352 | 94.030 | 2.022 | −2.271 | 1.00 | 31.44 | A |
| ATOM | 2168 | N | GLN | A | 353 | 93.429 | 3.685 | −3.672 | 1.00 | 29.13 | A |
| ATOM | 2169 | CA | GLN | A | 353 | 94.769 | 4.237 | −3.813 | 1.00 | 27.37 | A |
| ATOM | 2170 | CB | GLN | A | 353 | 94.767 | 5.283 | −4.932 | 1.00 | 25.81 | A |
| ATOM | 2171 | CG | GLN | A | 353 | 94.250 | 4.702 | −6.242 | 1.00 | 26.68 | A |
| ATOM | 2172 | CD | GLN | A | 353 | 94.035 | 5.738 | −7.330 | 1.00 | 26.81 | A |
| ATOM | 2173 | OE1 | GLN | A | 353 | 94.792 | 6.709 | −7.435 | 1.00 | 25.21 | A |
| ATOM | 2174 | NE2 | GLN | A | 353 | 93.011 | 5.520 | −8.171 | 1.00 | 24.24 | A |
| ATOM | 2175 | C | GLN | A | 353 | 95.288 | 4.851 | −2.510 | 1.00 | 28.25 | A |
| ATOM | 2176 | O | GLN | A | 353 | 94.511 | 5.245 | −1.633 | 1.00 | 28.38 | A |
| ATOM | 2177 | N | THR | A | 354 | 96.608 | 4.907 | −2.375 | 1.00 | 28.16 | A |
| ATOM | 2178 | CA | THR | A | 354 | 97.220 | 5.489 | −1.193 | 1.00 | 28.54 | A |
| ATOM | 2179 | CB | THR | A | 354 | 98.564 | 4.848 | −0.889 | 1.00 | 29.50 | A |
| ATOM | 2180 | OG1 | THR | A | 354 | 98.354 | 3.459 | −0.624 | 1.00 | 31.62 | A |
| ATOM | 2181 | CG2 | THR | A | 354 | 99.225 | 5.517 | 0.334 | 1.00 | 27.68 | A |
| ATOM | 2182 | C | THR | A | 354 | 97.438 | 6.955 | −1.468 | 1.00 | 27.76 | A |
| ATOM | 2183 | O | THR | A | 354 | 98.062 | 7.307 | −2.453 | 1.00 | 27.12 | A |
| ATOM | 2184 | N | PRO | A | 355 | 96.928 | 7.832 | −0.592 | 1.00 | 28.37 | A |
| ATOM | 2185 | CD | PRO | A | 355 | 96.067 | 7.582 | 0.573 | 1.00 | 27.67 | A |
| ATOM | 2186 | CA | PRO | A | 355 | 97.092 | 9.266 | −0.802 | 1.00 | 28.53 | A |
| ATOM | 2187 | CB | PRO | A | 355 | 96.215 | 9.883 | 0.291 | 1.00 | 28.29 | A |
| ATOM | 2188 | CG | PRO | A | 355 | 95.210 | 8.807 | 0.579 | 1.00 | 28.38 | A |
| ATOM | 2189 | C | PRO | A | 355 | 98.528 | 9.724 | −0.695 | 1.00 | 28.85 | A |
| ATOM | 2190 | O | PRO | A | 355 | 99.290 | 9.232 | 0.139 | 1.00 | 29.42 | A |
| ATOM | 2191 | N | PRO | A | 356 | 98.916 | 10.676 | −1.548 | 1.00 | 28.20 | A |
| ATOM | 2192 | CD | PRO | A | 356 | 98.083 | 11.340 | −2.567 | 1.00 | 27.35 | A |
| ATOM | 2193 | CA | PRO | A | 356 | 100.276 | 11.213 | −1.539 | 1.00 | 28.63 | A |
| ATOM | 2194 | CB | PRO | A | 356 | 100.261 | 12.199 | −2.712 | 1.00 | 29.02 | A |
| ATOM | 2195 | CG | PRO | A | 356 | 98.815 | 12.633 | −2.781 | 1.00 | 27.44 | A |
| ATOM | 2196 | C | PRO | A | 356 | 100.483 | 11.899 | −0.195 | 1.00 | 29.18 | A |
| ATOM | 2197 | O | PRO | A | 356 | 99.543 | 12.505 | 0.331 | 1.00 | 28.80 | A |
| ATOM | 2198 | N | ALA | A | 357 | 101.689 | 11.806 | 0.368 | 1.00 | 29.69 | A |
| ATOM | 2199 | CA | ALA | A | 357 | 101.942 | 12.439 | 1.664 | 1.00 | 31.97 | A |
| ATOM | 2200 | CB | ALA | A | 357 | 103.273 | 11.964 | 2.253 | 1.00 | 29.11 | A |
| ATOM | 2201 | C | ALA | A | 357 | 101.928 | 13.964 | 1.528 | 1.00 | 33.61 | A |
| ATOM | 2202 | O | ALA | A | 357 | 102.371 | 14.507 | 0.520 | 1.00 | 33.81 | A |
| ATOM | 2203 | N | LEU | A | 358 | 101.390 | 14.645 | 2.540 | 1.00 | 36.37 | A |
| ATOM | 2204 | CA | LEU | A | 358 | 101.295 | 16.110 | 2.543 | 1.00 | 38.03 | A |
| ATOM | 2205 | CB | LEU | A | 358 | 99.995 | 16.554 | 3.209 | 1.00 | 36.49 | A |
| ATOM | 2206 | CG | LEU | A | 358 | 98.679 | 16.059 | 2.641 | 1.00 | 35.57 | A |
| ATOM | 2207 | CD1 | LEU | A | 358 | 97.568 | 16.398 | 3.620 | 1.00 | 35.78 | A |
| ATOM | 2208 | CD2 | LEU | A | 358 | 98.443 | 16.689 | 1.278 | 1.00 | 37.10 | A |
| ATOM | 2209 | C | LEU | A | 358 | 102.460 | 16.743 | 3.310 | 1.00 | 39.05 | A |
| ATOM | 2210 | O | LEU | A | 358 | 102.451 | 16.592 | 4.553 | 1.00 | 39.24 | A |
| ATOM | 2211 | OXT | LEU | A | 358 | 103.348 | 17.370 | 2.679 | 1.00 | 40.12 | A |
| ATOM | 2212 | OH2 | TIP | S | 1 | 82.347 | 32.462 | −3.850 | 1.00 | 16.08 | S |
| ATOM | 2213 | OH2 | TIP | S | 4 | 80.761 | 19.051 | −18.244 | 1.00 | 23.37 | S |
| ATOM | 2214 | OH2 | TIP | S | 7 | 79.269 | 13.051 | −18.353 | 1.00 | 22.32 | S |
| ATOM | 2215 | OH2 | TIP | S | 8 | 86.710 | 32.919 | −1.646 | 1.00 | 24.05 | S |
| ATOM | 2216 | OH2 | TIP | S | 9 | 78.564 | −0.823 | 16.465 | 1.00 | 28.00 | S |
| ATOM | 2217 | OH2 | TIP | S | 10 | 75.323 | 16.274 | 8.538 | 1.00 | 18.43 | S |
| ATOM | 2218 | OH2 | TIP | S | 12 | 78.540 | 24.328 | −2.128 | 1.00 | 27.08 | S |
| ATOM | 2219 | OH2 | TIP | S | 13 | 91.533 | 13.928 | −17.231 | 1.00 | 22.56 | S |
| ATOM | 2220 | OH2 | TIP | S | 14 | 77.419 | −0.445 | 24.044 | 1.00 | 23.98 | S |
| ATOM | 2221 | OH2 | TIP | S | 19 | 72.498 | 40.164 | −3.114 | 1.00 | 21.78 | S |
| ATOM | 2222 | OH2 | TIP | S | 20 | 77.303 | 13.198 | −15.393 | 1.00 | 22.49 | S |
| ATOM | 2223 | OH2 | TIP | S | 21 | 75.600 | −1.063 | 22.040 | 1.00 | 24.29 | S |
| ATOM | 2224 | OH2 | TIP | S | 22 | 90.133 | 19.697 | 12.606 | 1.00 | 16.61 | S |
| ATOM | 2225 | OH2 | TIP | S | 24 | 74.810 | 7.002 | 25.700 | 1.00 | 20.66 | S |
| ATOM | 2226 | OH2 | TIP | S | 27 | 74.894 | 8.778 | −8.074 | 1.00 | 23.31 | S |
| ATOM | 2227 | OH2 | TIP | S | 28 | 80.070 | 33.741 | −17.170 | 1.00 | 27.29 | S |
| ATOM | 2228 | OH2 | TIP | S | 31 | 74.744 | 21.007 | 3.348 | 1.00 | 29.98 | S |
| ATOM | 2229 | OH2 | TIP | S | 32 | 97.930 | 12.301 | 2.472 | 1.00 | 16.75 | S |
| ATOM | 2230 | OH2 | TIP | S | 35 | 78.412 | 7.338 | 3.002 | 1.00 | 16.51 | S |
| ATOM | 2231 | OH2 | TIP | S | 36 | 80.172 | 27.171 | 1.300 | 1.00 | 34.66 | S |
| ATOM | 2232 | OH2 | TIP | S | 41 | 69.773 | 3.412 | 17.444 | 1.00 | 24.08 | S |
| ATOM | 2233 | OH2 | TIP | S | 43 | 88.878 | 7.904 | 10.616 | 1.00 | 20.34 | S |
| ATOM | 2234 | OH2 | TIP | S | 44 | 87.375 | 32.487 | −13.928 | 1.00 | 31.99 | S |

-continued

| | | | | | | | | | | |
|---|---|---|---|---|---|---|---|---|---|---|
| ATOM | 2235 | OH2 | TIP | S | 45 | 91.671 | 10.803 | −16.123 | 1.00 | 35.59 S |
| ATOM | 2236 | OH2 | TIP | S | 46 | 87.637 | 11.564 | 23.703 | 1.00 | 22.67 S |
| ATOM | 2237 | OH2 | TIP | S | 48 | 93.353 | 28.739 | 3.547 | 1.00 | 32.79 S |
| ATOM | 2238 | OH2 | TIP | S | 50 | 82.283 | 34.597 | −16.032 | 1.00 | 23.90 S |
| ATOM | 2239 | OH2 | TIP | S | 52 | 81.673 | 8.965 | −8.348 | 1.00 | 27.83 S |
| ATOM | 2240 | OH2 | TIP | S | 55 | 94.012 | 3.488 | 1.399 | 1.00 | 24.78 S |
| ATOM | 2241 | OH2 | TIP | S | 58 | 85.735 | 11.257 | −18.436 | 1.00 | 27.15 S |
| ATOM | 2242 | OH2 | TIP | S | 61 | 79.069 | −4.638 | 12.345 | 1.00 | 21.04 S |
| ATOM | 2243 | OH2 | TIP | S | 64 | 103.981 | 17.563 | −7.228 | 1.00 | 28.86 S |
| ATOM | 2244 | OH2 | TIP | S | 66 | 79.020 | 43.119 | 5.431 | 1.00 | 33.30 S |
| ATOM | 2245 | OH2 | TIP | S | 69 | 88.177 | 36.956 | 3.079 | 1.00 | 30.87 S |
| ATOM | 2246 | OH2 | TIP | S | 75 | 78.707 | 27.486 | −3.439 | 1.00 | 25.25 S |
| ATOM | 2247 | OH2 | TIP | S | 79 | 80.347 | 33.345 | 6.422 | 1.00 | 38.57 S |
| ATOM | 2248 | OH2 | TIP | S | 84 | 64.594 | 19.493 | 24.406 | 1.00 | 26.01 S |
| ATOM | 2249 | OH2 | TIP | S | 98 | 70.215 | 21.980 | 19.413 | 1.00 | 24.75 S |
| ATOM | 2250 | OH2 | TIP | S | 116 | 103.456 | 14.637 | −2.925 | 1.00 | 41.84 S |
| ATOM | 2251 | OH2 | TIP | S | 120 | 97.528 | 14.189 | −14.706 | 1.00 | 43.27 S |
| ATOM | 2252 | OH2 | TIP | S | 128 | 103.602 | 10.418 | −1.388 | 1.00 | 37.07 S |
| ATOM | 2253 | OH2 | TIP | S | 129 | 83.353 | 33.273 | 4.410 | 1.00 | 34.78 S |
| ATOM | 2254 | OH2 | TIP | S | 130 | 74.116 | 4.597 | −3.022 | 1.00 | 27.69 S |
| ATOM | 2255 | OH2 | TIP | S | 131 | 73.104 | −1.689 | 21.760 | 1.00 | 32.76 S |
| ATOM | 2256 | OH2 | TIP | S | 133 | 101.510 | 19.036 | −1.083 | 1.00 | 28.30 S |
| ATOM | 2257 | OH2 | TIP | S | 134 | 65.138 | 6.209 | 20.472 | 1.00 | 27.43 S |
| ATOM | 2258 | OH2 | TIP | S | 135 | 94.509 | 36.623 | −12.734 | 1.00 | 40.27 S |
| ATOM | 2259 | OH2 | TIP | S | 136 | 76.896 | 11.412 | −17.698 | 1.00 | 37.17 S |
| ATOM | 2260 | OH2 | TIP | S | 137 | 97.379 | 7.497 | −6.673 | 1.00 | 41.53 S |
| ATOM | 2261 | OH2 | TIP | S | 138 | 62.239 | 17.934 | 24.368 | 1.00 | 34.35 S |
| ATOM | 2262 | OH2 | TIP | S | 139 | 69.630 | 14.360 | −10.771 | 1.00 | 38.17 S |
| ATOM | 2263 | OH2 | TIP | S | 140 | 84.554 | 44.493 | −2.658 | 1.00 | 24.74 S |
| ATOM | 2264 | OH2 | TIP | S | 141 | 94.631 | 8.129 | −9.752 | 1.00 | 35.45 S |
| ATOM | 2265 | OH2 | TIP | S | 142 | 78.415 | 1.021 | 3.883 | 1.00 | 28.60 S |
| ATOM | 2266 | OH2 | TIP | S | 143 | 99.830 | 12.987 | −10.148 | 1.00 | 35.79 S |
| ATOM | 2267 | OH2 | TIP | S | 144 | 71.235 | 20.688 | 11.365 | 1.00 | 51.52 S |
| ATOM | 2268 | OH2 | TIP | S | 145 | 87.138 | 25.623 | 11.165 | 1.00 | 41.92 S |
| ATOM | 2269 | OH2 | TIP | S | 146 | 60.803 | 15.332 | 23.294 | 1.00 | 32.69 S |
| ATOM | 2270 | OH2 | TIP | S | 148 | 73.970 | 32.165 | −13.455 | 1.00 | 33.99 S |
| ATOM | 2271 | OH2 | TIP | S | 149 | 88.146 | 19.004 | 17.326 | 1.00 | 27.60 S |
| ATOM | 2272 | OH2 | TIP | S | 150 | 90.803 | 9.970 | 18.127 | 1.00 | 35.03 S |
| ATOM | 2273 | OH2 | TIP | S | 153 | 86.261 | 32.393 | −16.403 | 1.00 | 41.89 S |
| ATOM | 2274 | OH2 | TIP | S | 155 | 102.147 | 7.767 | −0.215 | 1.00 | 38.83 S |
| ATOM | 2275 | OH2 | TIP | S | 159 | 95.238 | 0.811 | −7.614 | 1.00 | 47.22 S |
| ATOM | 2276 | OH2 | TIP | S | 163 | 92.356 | 36.543 | −5.580 | 1.00 | 40.19 S |
| ATOM | 2277 | OH2 | TIP | S | 172 | 66.640 | 4.633 | 22.314 | 1.00 | 29.95 S |
| ATOM | 2278 | OH2 | TIP | S | 176 | 99.303 | 9.124 | 3.136 | 1.00 | 37.07 S |
| ATOM | 2279 | OH2 | TIP | S | 184 | 104.566 | 20.517 | −7.318 | 1.00 | 40.83 S |
| ATOM | 2280 | OH2 | TIP | S | 185 | 90.295 | 6.390 | −15.433 | 1.00 | 34.81 S |
| ATOM | 2281 | OH2 | TIP | S | 186 | 82.626 | 12.831 | 8.023 | 1.00 | 23.99 S |
| ATOM | 2282 | OH2 | TIP | S | 187 | 86.159 | 18.737 | 24.618 | 1.00 | 32.12 S |
| ATOM | 2283 | OH2 | TIP | S | 188 | 79.867 | 7.010 | −7.877 | 1.00 | 28.52 S |
| ATOM | 2284 | OH2 | TIP | S | 189 | 88.469 | 4.967 | 1.404 | 1.00 | 45.39 S |
| ATOM | 2285 | OH2 | TIP | S | 190 | 95.628 | 28.435 | −17.705 | 1.00 | 31.73 S |
| ATOM | 2286 | OH2 | TIP | S | 191 | 76.228 | 7.822 | 28.547 | 1.00 | 36.76 S |
| ATOM | 2287 | OH2 | TIP | S | 192 | 85.930 | 8.936 | 23.323 | 1.00 | 31.58 S |
| ATOM | 2288 | OH2 | TIP | S | 193 | 73.669 | 24.555 | −14.317 | 1.00 | 34.12 S |
| ATOM | 2289 | OH2 | TIP | S | 194 | 99.847 | 12.959 | 4.319 | 1.00 | 43.06 S |
| ATOM | 2290 | OH2 | TIP | S | 195 | 76.225 | 28.669 | −3.386 | 1.00 | 38.83 S |
| ATOM | 2291 | OH2 | TIP | S | 197 | 76.955 | 24.214 | 20.057 | 1.00 | 35.16 S |
| ATOM | 2292 | OH2 | TIP | S | 198 | 65.723 | 11.313 | 28.926 | 1.00 | 38.40 S |
| ATOM | 2293 | OH2 | TIP | S | 199 | 88.482 | 28.463 | 4.472 | 1.00 | 29.21 S |
| ATOM | 2294 | OH2 | TIP | S | 200 | 71.017 | 17.440 | −13.980 | 1.00 | 37.15 S |
| ATOM | 2295 | OH2 | TIP | S | 201 | 64.967 | 12.265 | 13.947 | 1.00 | 55.03 S |
| ATOM | 2296 | OH2 | TIP | S | 204 | 99.611 | 22.229 | −14.818 | 1.00 | 46.97 S |
| ATOM | 2297 | OH2 | TIP | S | 205 | 65.422 | −1.944 | 20.970 | 1.00 | 65.13 S |
| ATOM | 2298 | OH2 | TIP | S | 210 | 89.648 | 5.683 | 12.672 | 1.00 | 38.65 S |
| ATOM | 2299 | OH2 | TIP | S | 213 | 80.842 | 40.555 | 7.721 | 1.00 | 37.38 S |
| ATOM | 2300 | OH2 | TIP | S | 214 | 77.452 | 22.142 | 23.411 | 1.00 | 36.35 S |
| ATOM | 2301 | OH2 | TIP | S | 216 | 104.280 | 21.111 | −10.347 | 1.00 | 35.15 S |
| ATOM | 2302 | OH2 | TIP | S | 225 | 84.900 | 44.787 | −5.575 | 1.00 | 36.10 S |
| ATOM | 2303 | OH2 | TIP | S | 230 | 74.759 | 19.808 | 9.165 | 1.00 | 29.67 S |
| ATOM | 2304 | OH2 | TIP | S | 231 | 76.375 | 2.991 | −2.919 | 1.00 | 33.34 S |
| ATOM | 2305 | OH2 | TIP | S | 232 | 97.252 | 36.990 | −15.430 | 1.00 | 39.17 S |
| ATOM | 2306 | OH2 | TIP | S | 233 | 70.180 | 4.692 | 8.907 | 1.00 | 29.97 S |
| ATOM | 2307 | OH2 | TIP | S | 234 | 96.055 | 11.349 | −8.926 | 1.00 | 29.40 S |
| ATOM | 2308 | OH2 | TIP | S | 235 | 70.916 | 31.535 | 4.186 | 1.00 | 53.99 S |
| ATOM | 2309 | OH2 | TIP | S | 236 | 83.279 | 23.905 | 15.245 | 1.00 | 40.79 S |
| ATOM | 2310 | OH2 | TIP | S | 237 | 90.441 | 34.500 | 3.752 | 1.00 | 37.91 S |
| ATOM | 2311 | OH2 | TIP | S | 238 | 74.369 | 15.521 | −11.954 | 1.00 | 36.85 S |
| ATOM | 2312 | OH2 | TIP | S | 239 | 82.630 | 5.971 | 5.382 | 1.00 | 48.63 S |
| ATOM | 2313 | OH2 | TIP | S | 240 | 101.866 | 29.649 | 1.029 | 1.00 | 48.93 S |

-continued

| | | | | | | | | | | |
|---|---|---|---|---|---|---|---|---|---|---|
| ATOM | 2314 | O12 | GLC | G | 2 | 74.980 | 15.310 | 28.834 | 1.00 | 58.25 | G |
| ATOM | 2315 | C11 | GLC | G | 2 | 74.113 | 15.072 | 27.724 | 1.00 | 58.49 | G |
| ATOM | 2316 | C13 | GLC | G | 2 | 74.885 | 14.362 | 26.609 | 1.00 | 58.11 | G |
| ATOM | 2317 | O14 | GLC | G | 2 | 73.990 | 14.120 | 25.524 | 1.00 | 58.57 | G |
| ATOM | 2318 | C15 | GLC | G | 2 | 75.438 | 13.023 | 27.096 | 1.00 | 57.55 | G |
| ATOM | 2319 | O16 | GLC | G | 2 | 74.357 | 12.183 | 27.507 | 1.00 | 57.24 | G |
| ATOM | 2320 | O12 | GLC | G | 3 | 68.191 | 4.312 | 13.268 | 1.00 | 63.76 | G |
| ATOM | 2321 | C11 | GLC | G | 3 | 67.998 | 3.273 | 14.231 | 1.00 | 63.57 | G |
| ATOM | 2322 | C13 | GLC | G | 3 | 69.274 | 2.429 | 14.330 | 1.00 | 64.06 | G |
| ATOM | 2323 | O14 | GLC | G | 3 | 69.570 | 1.858 | 13.049 | 1.00 | 62.75 | G |
| ATOM | 2324 | C15 | GLC | G | 3 | 69.094 | 1.303 | 15.364 | 1.00 | 63.85 | G |
| ATOM | 2325 | O16 | GLC | G | 3 | 68.010 | 0.444 | 14.978 | 1.00 | 65.65 | G |
| ATOM | 2326 | O12 | GLC | G | 4 | 87.921 | 37.473 | −13.378 | 1.00 | 46.73 | G |
| ATOM | 2327 | C11 | GLC | G | 4 | 88.767 | 36.757 | −14.265 | 1.00 | 46.84 | G |
| ATOM | 2328 | C13 | GLC | G | 4 | 90.050 | 36.439 | −13.526 | 1.00 | 46.74 | G |
| ATOM | 2329 | O14 | GLC | G | 4 | 90.660 | 37.648 | −13.104 | 1.00 | 46.91 | G |
| ATOM | 2330 | C15 | GLC | G | 4 | 90.999 | 35.678 | −14.435 | 1.00 | 47.60 | G |
| ATOM | 2331 | O16 | GLC | G | 4 | 92.193 | 35.413 | −13.700 | 1.00 | 50.48 | G |
| ATOM | 2332 | O12 | GLC | G | 6 | 78.608 | 8.519 | 28.683 | 1.00 | 42.02 | G |
| ATOM | 2333 | C11 | GLC | G | 6 | 79.227 | 8.721 | 29.956 | 1.00 | 44.70 | G |
| ATOM | 2334 | C13 | GLC | G | 6 | 80.218 | 9.877 | 29.849 | 1.00 | 45.13 | G |
| ATOM | 2335 | O14 | GLC | G | 6 | 81.208 | 9.537 | 28.896 | 1.00 | 47.43 | G |
| ATOM | 2336 | C15 | GLC | G | 6 | 80.904 | 10.129 | 31.180 | 1.00 | 46.92 | G |
| ATOM | 2337 | O16 | GLC | G | 6 | 81.611 | 8.950 | 31.564 | 1.00 | 49.38 | G |
| ATOM | 2338 | O12 | GLC | G | 8 | 83.278 | 5.163 | 12.485 | 1.00 | 46.74 | G |
| ATOM | 2339 | C11 | GLC | G | 8 | 82.460 | 3.987 | 12.559 | 1.00 | 50.09 | G |
| ATOM | 2340 | C13 | GLC | G | 8 | 83.236 | 2.894 | 13.286 | 1.00 | 50.09 | G |
| ATOM | 2341 | O14 | GLC | G | 8 | 84.408 | 2.621 | 12.529 | 1.00 | 50.75 | G |
| ATOM | 2342 | C15 | GLC | G | 8 | 82.412 | 1.597 | 13.414 | 1.00 | 52.04 | G |
| ATOM | 2343 | O16 | GLC | G | 8 | 82.051 | 1.062 | 12.130 | 1.00 | 53.37 | G |
| ATOM | 2344 | O12 | GLC | G | 10 | 87.146 | 4.682 | −5.006 | 1.00 | 25.46 | G |
| ATOM | 2345 | C11 | GLC | G | 10 | 85.823 | 5.086 | −5.356 | 1.00 | 27.64 | G |
| ATOM | 2346 | C13 | GLC | G | 10 | 85.782 | 5.498 | −6.835 | 1.00 | 30.79 | G |
| ATOM | 2347 | O14 | GLC | G | 10 | 86.689 | 6.600 | −7.069 | 1.00 | 29.47 | G |
| ATOM | 2348 | C15 | GLC | G | 10 | 84.354 | 5.916 | −7.219 | 1.00 | 30.60 | G |
| ATOM | 2349 | O16 | GLC | G | 10 | 83.947 | 7.022 | −6.417 | 1.00 | 31.23 | G |
| ATOM | 2350 | CBI | DRG | L | 1 | 82.223 | 19.878 | 9.473 | 1.00 | 17.56 | L |
| ATOM | 2351 | OBH | DRG | L | 1 | 82.835 | 19.573 | 10.730 | 1.00 | 20.33 | L |
| ATOM | 2352 | CBG | DRG | L | 1 | 82.419 | 20.512 | 11.733 | 1.00 | 17.87 | L |
| ATOM | 2353 | CBF | DRG | L | 1 | 83.661 | 21.291 | 12.177 | 1.00 | 16.47 | L |
| ATOM | 2354 | NBK | DRG | L | 1 | 84.171 | 22.133 | 11.085 | 1.00 | 15.68 | L |
| ATOM | 2355 | CBJ | DRG | L | 1 | 83.683 | 23.479 | 10.751 | 1.00 | 12.47 | L |
| ATOM | 2356 | CBE | DRG | L | 1 | 84.739 | 20.294 | 12.600 | 1.00 | 16.76 | L |
| ATOM | 2357 | CBA | DRG | L | 1 | 84.178 | 19.405 | 13.715 | 1.00 | 18.27 | L |
| ATOM | 2358 | OBB | DRG | L | 1 | 82.790 | 19.632 | 14.017 | 1.00 | 18.03 | L |
| ATOM | 2359 | CBC | DRG | L | 1 | 81.853 | 19.747 | 12.937 | 1.00 | 18.62 | L |
| ATOM | 2360 | CBD | DRG | L | 1 | 80.732 | 20.611 | 13.524 | 1.00 | 14.59 | L |
| ATOM | 2361 | NAW | DRG | L | 1 | 81.398 | 18.547 | 12.551 | 1.00 | 18.60 | L |
| ATOM | 2362 | CAX | DRG | L | 1 | 80.185 | 18.344 | 12.014 | 1.00 | 15.55 | L |
| ATOM | 2363 | CAY | DRG | L | 1 | 79.107 | 19.141 | 11.643 | 1.00 | 13.82 | L |
| ATOM | 2364 | CAZ | DRG | L | 1 | 77.988 | 18.555 | 11.053 | 1.00 | 16.37 | L |
| ATOM | 2365 | CAP | DRG | L | 1 | 77.930 | 17.180 | 10.830 | 1.00 | 15.88 | L |
| ATOM | 2366 | CAO | DRG | L | 1 | 78.999 | 16.366 | 11.196 | 1.00 | 15.07 | L |
| ATOM | 2367 | CAN | DRG | L | 1 | 80.107 | 16.973 | 11.783 | 1.00 | 17.80 | L |
| ATOM | 2368 | CAM | DRG | L | 1 | 81.290 | 16.377 | 12.187 | 1.00 | 19.34 | L |
| ATOM | 2369 | CAH | DRG | L | 1 | 81.811 | 15.087 | 12.083 | 1.00 | 19.93 | L |
| ATOM | 2370 | CAV | DRG | L | 1 | 82.083 | 17.407 | 12.657 | 1.00 | 18.53 | L |
| ATOM | 2371 | CAU | DRG | L | 1 | 83.404 | 17.144 | 13.014 | 1.00 | 18.70 | L |
| ATOM | 2372 | NAT | DRG | L | 1 | 84.365 | 17.964 | 13.438 | 1.00 | 17.82 | L |
| ATOM | 2373 | CAS | DRG | L | 1 | 85.523 | 17.317 | 13.610 | 1.00 | 15.80 | L |
| ATOM | 2374 | CAR | DRG | L | 1 | 86.807 | 17.682 | 14.000 | 1.00 | 14.23 | L |
| ATOM | 2375 | CAQ | DRG | L | 1 | 87.803 | 16.708 | 14.047 | 1.00 | 13.92 | L |
| ATOM | 2376 | CAI | DRG | L | 1 | 87.526 | 15.384 | 13.714 | 1.00 | 16.21 | L |
| ATOM | 2377 | CAJ | DRG | L | 1 | 86.244 | 15.003 | 13.324 | 1.00 | 16.43 | L |
| ATOM | 2378 | CAK | DRG | L | 1 | 85.264 | 15.988 | 13.278 | 1.00 | 17.76 | L |
| ATOM | 2379 | CAL | DRG | L | 1 | 83.932 | 15.867 | 12.904 | 1.00 | 18.99 | L |
| ATOM | 2380 | CAG | DRG | L | 1 | 83.130 | 14.829 | 12.439 | 1.00 | 19.47 | L |
| ATOM | 2381 | CAC | DRG | L | 1 | 83.403 | 13.472 | 12.290 | 1.00 | 18.70 | L |
| ATOM | 2382 | OAB | DRG | L | 1 | 84.471 | 12.895 | 12.480 | 1.00 | 18.10 | L |
| ATOM | 2383 | NAD | DRG | L | 1 | 82.277 | 12.904 | 11.856 | 1.00 | 18.49 | L |
| ATOM | 2384 | CAE | DRG | L | 1 | 81.128 | 13.799 | 11.622 | 1.00 | 20.08 | L |
| ATOM | 2385 | OAF | DRG | L | 1 | 80.902 | 13.891 | 10.214 | 1.00 | 24.92 | L |
| ATOM | 2386 | S | SO4 | I | 1 | 64.638 | 8.174 | 16.414 | 1.00 | 89.13 | I |
| ATOM | 2387 | O1 | SO4 | I | 1 | 65.311 | 9.465 | 16.666 | 1.00 | 88.78 | I |
| ATOM | 2388 | O2 | SO4 | I | 1 | 63.197 | 8.413 | 16.200 | 1.00 | 89.62 | I |
| ATOM | 2389 | O3 | SO4 | I | 1 | 64.827 | 7.262 | 17.566 | 1.00 | 88.49 | I |
| ATOM | 2390 | O4 | SO4 | I | 1 | 65.197 | 7.555 | 15.196 | 1.00 | 89.77 | I |
| ATOM | 2391 | S | SO4 | I | 3 | 84.884 | −1.751 | 12.531 | 1.00 | 81.17 | I |
| ATOM | 2392 | O1 | SO4 | I | 3 | 84.762 | −0.302 | 12.775 | 1.00 | 81.32 | I |

-continued

| ATOM | 2393 | O2 | SO4 | I | 3 | 84.538 | −2.490 | 13.758 | 1.00 | 81.49 | I |
|---|---|---|---|---|---|---|---|---|---|---|---|
| ATOM | 2394 | O3 | SO4 | I | 3 | 86.280 | −2.053 | 12.162 | 1.00 | 81.73 | I |
| ATOM | 2395 | O4 | SO4 | I | 3 | 83.976 | −2.163 | 11.440 | 1.00 | 81.19 | I |
| ATOM | 2396 | S | SO4 | I | 5 | 74.420 | 22.898 | 12.677 | 1.00 | 85.50 | I |
| ATOM | 2397 | O1 | SO4 | I | 5 | 73.256 | 22.153 | 12.161 | 1.00 | 85.36 | I |
| ATOM | 2398 | O2 | SO4 | I | 5 | 75.637 | 22.104 | 12.412 | 1.00 | 84.51 | I |
| ATOM | 2399 | O3 | SO4 | I | 5 | 74.250 | 23.138 | 14.126 | 1.00 | 84.13 | I |
| ATOM | 2400 | O4 | SO4 | I | 5 | 74.527 | 24.202 | 11.997 | 1.00 | 85.44 | I |
| ATOM | 2401 | S | SO4 | I | 6 | 68.798 | 6.993 | −3.457 | 1.00 | 73.84 | I |
| ATOM | 2402 | O1 | SO4 | I | 6 | 68.338 | 7.338 | −4.823 | 1.00 | 72.86 | I |
| ATOM | 2403 | O2 | SO4 | I | 6 | 69.298 | 8.206 | −2.791 | 1.00 | 73.61 | I |
| ATOM | 2404 | O3 | SO4 | I | 6 | 69.888 | 6.003 | −3.540 | 1.00 | 73.52 | I |
| ATOM | 2405 | O4 | SO4 | I | 6 | 67.690 | 6.426 | −2.658 | 1.00 | 73.19 | I |
| ATOM | 2406 | O2 | PO4 | P | 100 | 66.501 | 25.721 | 2.616 | 1.00 | 85.98 | P |
| ATOM | 2407 | O3 | PO4 | P | 100 | 64.376 | 25.028 | 1.654 | 1.00 | 86.96 | P |
| ATOM | 2408 | O4 | PO4 | P | 100 | 65.755 | 26.653 | 0.496 | 1.00 | 86.51 | P |
| ATOM | 2409 | O1 | PO4 | P | 100 | 64.621 | 27.279 | 2.570 | 1.00 | 86.98 | P |
| ATOM | 2410 | P | PO4 | P | 100 | 65.315 | 26.170 | 1.832 | 1.00 | 87.36 | P |
| ATOM | 2411 | S | SO4 | X | 3 | 80.775 | −0.045 | 7.874 | 0.50 | 22.29 | X |
| ATOM | 2412 | O1 | SO4 | X | 3 | 81.160 | 0.521 | 9.176 | 0.50 | 22.30 | X |
| ATOM | 2413 | O2 | SO4 | X | 3 | 81.320 | −1.407 | 7.778 | 0.50 | 22.49 | X |
| ATOM | 2414 | O3 | SO4 | X | 3 | 81.309 | 0.781 | 6.777 | 0.50 | 23.26 | X |
| ATOM | 2415 | O4 | SO4 | X | 3 | 79.305 | −0.088 | 7.772 | 0.50 | 24.36 | X |
| END | | | | | | | | | | | |

The invention claimed is:

1. A method for selecting a compound for modulating the activity of phosphoinositide dependent protein kinase 1 (PDK1), the method comprising:
   [i] generating a three-dimensional structure of the protein kinase catalytic domain of PDK1 as defined by Example 2, 3, 7 or 8;
   [ii] identifying predicted binding region(s): the PDK1 Interacting Fragment (PIF) binding pocket formed by residues including residues Lys115, Ile118, Ile119 on the αB helix, Val124, Val127 on the αC helix, and Leu155 on β-sheet 5 of full length human PDK1 as set forth in SEQ ID NO: 3, the "phosphate binding pocket" formed by residues including residues Lys76, Arg131, Thr148 and Gln150 of full length human PDK1 as set forth in SEQ ID NO: 3, and/or the αC helix formed by residues 123-136 of full length human PDK1 as set forth in SEQ ID NO: 3 in any of the models generated in step [i];
   [iii] modeling a plurality of three-dimensional structures of candidate compounds;
   [iv] comparing said three-dimensional structure of the protein kinase catalytic domain of PDK1 binding regions/pockets as identified in step [ii] with the three-dimensional structure of each of said candidate compounds of step [iii]; and
   [v] selecting one of the candidate compounds as a compound for modulating the activity of phosphoinositide dependent protein kinase 1 (PDK1).

2. The method of claim 1 wherein the three-dimensional structure of at least a part of the protein kinase catalytic domain of PDK1 structure is a three-dimensional structure (or part thereof) determined for a polypeptide consisting of residues 51 to 359 of full length human PDK1 as set forth in SEQ ID NO: 3.

3. The method of claim 2 wherein the three-dimensional structure (or part thereof) is determined for a polypeptide consisting of residues 51 to 359 of full length human PDK1 as set forth in SEQ ID NO: 3 and the amino acid sequence Gly-Pro preceding the methionine corresponding to Met51 of human PDK1.

4. The method of claim 1 wherein the three-dimensional structure of at least a part of the protein kinase catalytic domain of PDK1 structure is a three-dimensional structure (or part thereof) determined for a polypeptide consisting of residues 71 to 359 of full length human PDK1 as set forth in SEQ ID NO: 3 or a fusion thereof.

5. The method of claim 1 wherein the three-dimensional structure of at least a part of the protein kinase catalytic domain of PDK1 structure is obtainable by X-ray analysis of a crystal obtainable using a mother liquor solution comprising ammonium sulphate.

6. The method of claim 5 wherein the mother liquor solution is of pH 7 to 9.

7. The method of claim 6 wherein the mother liquor solution is of pH 8.5.

8. The method of claim 7 wherein the mother liquor solution comprises ATP.

9. The method of claim 1 wherein the compound is for modulating the protein kinase activity of PDK1 towards protein kinase B (PKB) or other pleckstrin homology (PH)-domain-comprising/phosphoinositide-binding substrate of PDK1.

10. The method of claim 1 wherein the compound is for modulating the protein kinase activity of PDK1 towards serum and glucocorticoid stimulated protein kinase (SGK), S6 kinase (S6K) or other substrate of PDK1 whose phosphorylation by PDK1 is promoted by phosphorylation of the substrate on the Ser/Thr of the "hydrophobic motif" FXXFS/TY as set forth in SEQ ID NO: 2.

11. The method of claim 1 further comprising the step of synthesising, purifying and/or formulating the compound.

12. The method of claim 1, wherein the method further comprises:
   designing one or more of said molecules prior to modelling.

13. A method for selecting a compound for modulating the activity of PDK1 Interacting Fragment (PIF) binding pocket containing protein kinase, the method comprising:
   [i] modeling a three-dimensional structure of a plurality of molecules in a computer;
   [ii] generating a three-dimensional structure of the protein kinase catalytic domain of PDK1 as defined by Example 2, 3, 7 or 8;
   [iii] comparing the three-dimensional structure of each of said molecules with the three-dimensional structure of said phosphate binding pocket of human PDK1 and optionally also said hydrophobic pocket of human PDK1;
   [iv] identifying a molecule from the plurality of the modeled molecules which binds to said PIF binding pocket in the position equivalent to a hydrophobic pocket of human PDK1 that is defined by residues including Lys115, Ile118, Ile119, Val124, Val127 and Leu155 of full-length human PDK1 as set forth in SEQ ID NO: 3, and/or a phosphate binding pocket in the position equivalent to the phosphate binding pocket of human PDK1 that is defined by residues including Lys76, Arg131, Thr148 and Gln150 of SEQ ID NO: 3; and
   [v] selecting one of the modeled molecules as said compound based on a predicted ability of the molecule to interact with said phosphate binding pocket of protein kinase or said hydrophobic pocket of protein kinase,
   wherein the three-dimensional structure or a part thereof is determined for a polypeptide comprising residues 51 to 359 of full length human PDK1 as set forth in SEQ ID NO: 3.

14. The method of claim 13, wherein the method further comprises:
   designing one or more of said molecules prior to modelling.

* * * * *